US008013006B2

(12) United States Patent
Karp et al.

(10) Patent No.: US 8,013,006 B2
(45) **Date of Patent: *Sep. 6, 2011**

(54) METHODS FOR TREATING HEPATITIS C

(75) Inventors: Gary Mitchell Karp, Princeton Junction, NJ (US); Peter Seongwoo Hwang, Edison, NJ (US); James Takasugi, Lawrenceville, NJ (US); Hongyu Ren, Dayton, NJ (US); Richard Gerald Wilde, Somerville, NJ (US); Anthony Turpoff, Edison, NJ (US); Alexander Arefolov, Piscataway, NJ (US); Guangming Chen, Bridgewater, NJ (US); Jeffrey Allen Campbell, Bethlehem, PA (US); Christine Espiritu, Highland Park, NJ (US); Concetta Freund, Staten Island, NY (US); Zhengxian Gu, Princeton, NJ (US); Takashi Komatsu, Silver Spring, MD (US)

(73) Assignee: PTC Therapeutics, Inc., South Plainfield, NJ (US)

(*) Notice: Subject to any disclaimer, the term of this patent is extended or adjusted under 35 U.S.C. 154(b) by 1323 days.

This patent is subject to a terminal disclaimer.

(21) Appl. No.: 11/180,961

(22) Filed: Jul. 14, 2005

(65) Prior Publication Data

US 2006/0223863 A1 Oct. 5, 2006
US 2008/0096928 A9 Apr. 24, 2008

Related U.S. Application Data

(60) Provisional application No. 60/587,487, filed on Jul. 14, 2004, provisional application No. 60/634,979, filed on Dec. 13, 2004, provisional application No. 60/645,586, filed on Jan. 24, 2005, provisional application No. 60/665,349, filed on Mar. 28, 2005, provisional application No. 60/675,440, filed on Apr. 28, 2005.

(30) Foreign Application Priority Data

Jul. 14, 2005 (US) ................. PCT/US2005/024881

(51) Int. Cl.
*A01N 43/38* (2006.01)
*A61K 31/405* (2006.01)
*C07D 209/04* (2006.01)

(52) U.S. Cl. ......................... 514/415; 548/469; 548/511

(58) Field of Classification Search .................. 514/415; 548/469, 511
See application file for complete search history.

(56) References Cited

U.S. PATENT DOCUMENTS

| | | | | |
|---|---|---|---|---|
| 4,788,206 | A | 11/1988 | Guthrie et al. | |
| 4,874,756 | A | 10/1989 | Mertens et al. | |
| 5,072,003 | A | 12/1991 | Behrend et al. | |
| 5,190,942 | A | 3/1993 | Poss | |
| 5,215,980 | A | 6/1993 | Jones | |
| 5,217,996 | A | 6/1993 | Ksander | |
| 5,354,759 | A | 10/1994 | Oku et al. | |
| 5,369,120 | A | 11/1994 | Woodruff | |
| 5,413,999 | A | 5/1995 | Vacca et al. | |
| 5,474,994 | A | 12/1995 | Leonardi et al. | |
| 5,527,819 | A | 6/1996 | Williams et al. | |
| 5,559,127 | A | 9/1996 | Hartman et al. | |
| 5,605,896 | A | 2/1997 | Leonardi et al. | |
| 5,633,388 | A | 5/1997 | Diana et al. | |
| 5,639,906 | A | 6/1997 | London et al. | |
| 5,681,954 | A | 10/1997 | Yamamoto et al. | |
| 5,693,643 | A | 12/1997 | Gilbert et al. | |
| 5,714,496 | A | 2/1998 | Brown et al. | |
| 5,880,137 | A | 3/1999 | Miller et al. | |
| 5,922,898 | A | 7/1999 | Miller et al. | |
| 5,958,086 | A | 9/1999 | Adam et al. | |
| 5,977,090 | A | 11/1999 | Slusher et al. | |
| 5,985,910 | A | 11/1999 | Miller et al. | |
| 5,994,378 | A * | 11/1999 | Matsuo et al. | 514/365 |
| 6,030,785 | A | 2/2000 | Katze et al. | |
| 6,057,093 | A | 5/2000 | Han et al. | |
| 6,124,311 | A | 9/2000 | Chandrasekhar et al. | |
| 6,132,966 | A | 10/2000 | Draper | |
| 6,194,599 | B1 | 2/2001 | Miller et al. | |
| 6,221,902 | B1 | 4/2001 | Malamas et al. | |
| 6,326,392 | B1 | 12/2001 | Gast et al. | |
| 6,335,445 | B1 | 1/2002 | Chabrier de Lassauniere et al. | |
| 6,358,992 | B1 | 3/2002 | Pamukcu et al. | |
| 6,376,529 | B1 | 4/2002 | Tang et al. | |
| 6,380,166 | B1 | 4/2002 | Miller et al. | |
| 6,384,022 | B1 | 5/2002 | Jackson et al. | |
| 6,555,555 | B1 | 4/2003 | Konishi et al. | |
| 6,589,570 | B1 | 7/2003 | Thyagarajan | |

(Continued)

FOREIGN PATENT DOCUMENTS

CA 2099060 12/1993

(Continued)

OTHER PUBLICATIONS

Suh et. al., J. Org. Chem., 1965, American Chemical Society, vol. 30, pp. 2253-2259.* Vivona et. al., J. Heterocyclic Chem., 1983, American Chemical Society, vol. 20, No. 4, pp. 931-934.*
Wrobel et. al., Tetrahedron, 1997, Pergamon, vol. 53, No. 15, pp. 5501-5514.*
Wacker et. al., Tetrahedron Letters, 2002, Pergamon, vol. 43, pp. 5189-5191.*
Zhang et. al., CAS STN Abstract, 1988.*

(Continued)

*Primary Examiner* — Sreeni Padmanabhan
*Assistant Examiner* — Sarah Pihonak
(74) *Attorney, Agent, or Firm* — Hoffmann & Baron, LLP

(57) ABSTRACT

In accordance with the present invention, compounds that inhibit viral replication, preferably Hepatitis C Virus (HCV) replication, have been identified, and methods for their use provided. In one aspect of the invention, compounds useful in the treatment or prevention of a viral infection are provided. In another aspect of the invention, compounds useful in the treatment or prevention of HCV infection are provided.

14 Claims, 1 Drawing Sheet

U.S. PATENT DOCUMENTS

| | | | |
|---|---|---|---|
| 6,589,954 | B1 | 7/2003 | Mavunkel et al. |
| 6,685,931 | B1 | 2/2004 | Grint et al. |
| 6,690,975 | B2 | 2/2004 | Yamamoto et al. |
| 6,974,870 | B2 | 12/2005 | Cywin et al. |
| 2002/0055651 | A1 | 5/2002 | Moran et al. |
| 2002/0091116 | A1 | 7/2002 | Zhu et al. |
| 2002/0099054 | A1 | 7/2002 | Conner et al. |
| 2002/0099080 | A1 | 7/2002 | Gagliardi et al. |
| 2002/0103210 | A1 | 8/2002 | Furuya et al. |
| 2002/0143022 | A1 | 10/2002 | Pamukeu et al. |
| 2002/0169101 | A1 | 11/2002 | Gonzalez et al. |
| 2002/0169107 | A1 | 11/2002 | Rajagopalan et al. |
| 2003/0004119 | A1 | 1/2003 | Ganguly et al. |
| 2003/0050320 | A1 | 3/2003 | Hashimoto et al. |
| 2003/0078420 | A1 | 4/2003 | Chabrier de Lassauniere et al. |
| 2003/0096825 | A1 | 5/2003 | Wang et al. |
| 2003/0176433 | A1 | 9/2003 | Beaulieu et al. |
| 2003/0176697 | A1 | 9/2003 | Overman et al. |
| 2003/0199689 | A1 | 10/2003 | Nazare et al. |
| 2003/0220377 | A1 | 11/2003 | Chesworth |
| 2003/0232866 | A1 | 12/2003 | Watterson et al. |
| 2003/0236391 | A1 | 12/2003 | Klunk et al. |
| 2004/0044059 | A1 | 3/2004 | Pinney et al. |
| 2004/0059131 | A1 | 3/2004 | Dell et al. |
| 2004/0067996 | A1 | 4/2004 | Sheppeck |
| 2004/0180945 | A1 | 9/2004 | Artico et al. |
| 2004/0186125 | A1 | 9/2004 | Poupart et al. |
| 2005/0026969 | A1 | 2/2005 | Cheng et al. |
| 2005/0075242 | A1 | 4/2005 | Holtcamp et al. |
| 2005/0075384 | A1 | 4/2005 | Sheppeck et al. |
| 2005/0085529 | A1 | 4/2005 | Brown et al. |
| 2005/0113283 | A1 | 5/2005 | Solow-Cordero et al. |
| 2005/0119318 | A1 | 6/2005 | Hudyma et al. |
| 2005/0123560 | A1 | 6/2005 | Sinnott |
| 2005/0227291 | A1 | 10/2005 | Kinsella |

FOREIGN PATENT DOCUMENTS

| | | | | |
|---|---|---|---|---|
| DE | 258014 | | | 6/1988 |
| DE | 258015 | | | 6/1988 |
| DE | 258016 | | | 6/1988 |
| EP | 0 406 734 | A2 | | 1/1991 |
| EP | 0 414 386 | A1 | | 2/1991 |
| EP | 0 427 225 | A1 | | 5/1991 |
| EP | 0 430 186 | A1 | | 6/1991 |
| EP | 0 436 199 | A1 | | 7/1991 |
| EP | 0 471 372 | A1 | | 2/1992 |
| EP | 470665 | | * | 2/1992 |
| EP | 0 480 204 | A1 | | 4/1992 |
| EP | 0 488 532 | | | 6/1992 |
| EP | 0 548 798 | A1 | | 6/1993 |
| EP | 0 553 682 | A1 | | 8/1993 |
| EP | 0 556 949 | | | 8/1993 |
| EP | 0 558 245 | A1 | | 9/1993 |
| EP | 0 502 424 | B1 | | 1/1994 |
| EP | 0 617 968 | A1 | | 10/1994 |
| EP | 0 622 356 | A1 | | 11/1994 |
| EP | 0 624 584 | A1 | | 11/1994 |
| EP | 0 628 559 | | | 12/1994 |
| EP | 0 630 895 | A1 | | 12/1994 |
| EP | 0 697 172 | | | 2/1996 |
| EP | 0 708 091 | | | 4/1996 |
| EP | 0 716 855 | A2 | | 6/1996 |
| EP | 0 802 183 | | | 10/1997 |
| EP | 0 802 184 | | | 10/1997 |
| EP | 1 118 323 | | | 7/2001 |
| EP | 1 120 114 | | | 8/2001 |
| EP | 1 125 582 | | | 8/2001 |
| EP | 1 149 579 | | | 10/2001 |
| EP | 1 177 787 | | | 2/2002 |
| EP | 1 192 945 | | | 4/2002 |
| EP | 1 199 069 | | | 4/2002 |
| EP | 1 226 823 | | | 7/2002 |
| EP | 1 314 733 | A1 | | 5/2003 |
| EP | 1 457 485 | A1 | | 9/2004 |
| EP | 1 532 980 | | | 5/2005 |
| EP | 1 574 502 | A1 | | 9/2005 |
| GB | 2 282 808 | A | | 4/1995 |
| GB | 2 292 149 | A | | 2/1996 |
| JP | 2002 105081 | | | 4/2002 |
| JP | 2005-194198 | | | 7/2005 |
| WO | WO 92/15579 | | | 9/1992 |
| WO | 93/14758 | | | 8/1993 |
| WO | WO 93/18030 | | | 9/1993 |
| WO | WO 93/18765 | | | 9/1993 |
| WO | WO 93/18766 | | | 9/1993 |
| WO | WO 93/19067 | | | 9/1993 |
| WO | WO 94/04153 | | | 3/1994 |
| WO | WO 94/04535 | | | 3/1994 |
| WO | WO 94/08583 | | | 4/1994 |
| WO | WO 94/08962 | | | 4/1994 |
| WO | WO 94/11378 | | | 5/1994 |
| WO | WO 94/14435 | | | 7/1994 |
| WO | WO 94/14438 | | | 7/1994 |
| WO | WO 94/14763 | | | 7/1994 |
| WO | WO 94/14771 | | | 7/1994 |
| WO | WO 94/26746 | | | 11/1994 |
| WO | WO 95/02583 | | | 1/1995 |
| WO | WO 95/07910 | | | 3/1995 |
| WO | WO 95/14003 | | | 5/1995 |
| WO | WO 95/32710 | | | 12/1995 |
| WO | WO 95/33720 | | | 12/1995 |
| WO | WO 96/10012 | | | 4/1996 |
| WO | 96/16054 | | | 5/1996 |
| WO | WO 96/26207 | | | 8/1996 |
| WO | WO 96/32379 | | | 10/1996 |
| WO | WO 96/40650 | | | 12/1996 |
| WO | WO 96/41800 | | | 12/1996 |
| WO | WO 97/14419 | | | 4/1997 |
| WO | WO 97/45410 | | | 4/1997 |
| WO | WO 98/13044 | | | 4/1998 |
| WO | WO 98/22457 | | | 5/1998 |
| WO | WO 98/25883 | | | 6/1998 |
| WO | 98/48797 | | | 11/1998 |
| WO | WO 99/06836 | | | 2/1999 |
| WO | WO 99/11634 | | | 3/1999 |
| WO | WO 99/13714 | | | 3/1999 |
| WO | WO 99/18096 | | | 4/1999 |
| WO | 99/24027 | | | 5/1999 |
| WO | WO 99/23072 | | | 5/1999 |
| WO | WO 99/26946 | | | 6/1999 |
| WO | WO 99/33849 | | | 7/1999 |
| WO | WO9932482 | | * | 7/1999 |
| WO | 99/43651 | | | 9/1999 |
| WO | WO 99/50237 | | | 10/1999 |
| WO | 99/58520 | | | 11/1999 |
| WO | 99/59581 | | | 11/1999 |
| WO | 99/59969 | | | 11/1999 |
| WO | 99/64415 | | | 12/1999 |
| WO | WO 99/61426 | | | 12/1999 |
| WO | WO 99/64035 | | | 12/1999 |
| WO | WO 00/15645 | | | 3/2000 |
| WO | WO 00/28991 | | | 5/2000 |
| WO | WO 00/29384 | | | 5/2000 |
| WO | WO 00/35886 | | | 6/2000 |
| WO | WO 00/43393 | | | 7/2000 |
| WO | WO 00/61586 | | | 10/2000 |
| WO | WO 00/73269 | A2 | | 12/2000 |
| WO | 01/19839 | | | 3/2001 |
| WO | 01/21609 | | | 3/2001 |
| WO | WO 01/19798 | A2 | | 3/2001 |
| WO | WO 01/21589 | A2 | | 3/2001 |
| WO | 01/23353 | | | 4/2001 |
| WO | WO 01/23390 | A2 | | 4/2001 |
| WO | 01/44182 | | | 6/2001 |
| WO | WO 01/47883 | A1 | | 7/2001 |
| WO | 01/55136 | | | 8/2001 |
| WO | 01/55137 | | | 8/2001 |
| WO | 01/55138 | | | 8/2001 |
| WO | 01/55139 | | | 8/2001 |
| WO | 01/55144 | | | 8/2001 |
| WO | WO 01/55111 | A1 | | 8/2001 |
| WO | WO 01/58859 | A1 | | 8/2001 |
| WO | WO 01/64678 | A2 | | 9/2001 |
| WO | WO 01/68585 | A1 | | 9/2001 |
| WO | WO 01/74773 | A2 | | 10/2001 |
| WO | 01/90105 | | | 11/2001 |

| | | | |
|---|---|---|---|
| WO | WO 01/83451 | A1 | 11/2001 |
| WO | WO 01/85687 | A1 | 11/2001 |
| WO | 02/03975 | | 1/2002 |
| WO | 02/03976 | | 1/2002 |
| WO | 02/03977 | | 1/2002 |
| WO | 02/03986 | | 1/2002 |
| WO | 02/03987 | | 1/2002 |
| WO | 02/03988 | | 1/2002 |
| WO | 02/03989 | | 1/2002 |
| WO | 02/03990 | | 1/2002 |
| WO | 02/03991 | | 1/2002 |
| WO | 02/03992 | | 1/2002 |
| WO | 02/04418 | | 1/2002 |
| WO | WO 02/00651 | A2 | 1/2002 |
| WO | WO 02/06226 | A1 | 1/2002 |
| WO | 02/13802 | | 2/2002 |
| WO | 02/16353 | | 2/2002 |
| WO | WO 02/16333 | A2 | 2/2002 |
| WO | 02/30358 | | 4/2002 |
| WO | WO 02/26696 | A1 | 4/2002 |
| WO | WO 02/26703 | A1 | 4/2002 |
| WO | WO 02/30879 | A2 | 4/2002 |
| WO | 02/36562 | | 5/2002 |
| WO | 02/42292 | | 5/2002 |
| WO | WO 02/36203 | A2 | 5/2002 |
| WO | WO 02/36580 | A2 | 5/2002 |
| WO | WO 02/48099 | A1 | 6/2002 |
| WO | WO 02/051805 | A1 | 7/2002 |
| WO | WO 02/053534 | A1 | 7/2002 |
| WO | WO 02/055496 | A1 | 7/2002 |
| WO | 02/059088 | | 8/2002 |
| WO | 02/059120 | | 8/2002 |
| WO | WO 02/060374 | A2 | 8/2002 |
| WO | WO 02/060447 | A1 | 8/2002 |
| WO | WO 02/066477 | A2 | 8/2002 |
| WO | 02/072549 | | 9/2002 |
| WO | WO 02/070462 | A1 | 9/2002 |
| WO | WO 02/070469 | A2 | 9/2002 |
| WO | WO 02/070510 | A2 | 9/2002 |
| WO | WO 02/074742 | | 9/2002 |
| WO | WO 02/076926 | | 10/2002 |
| WO | WO 02/083134 | A1 | 10/2002 |
| WO | 02/089811 | | 11/2002 |
| WO | WO 02/053565 | A1 | 11/2002 |
| WO | WO 02/096426 | A1 | 12/2002 |
| WO | WO 02/098424 | | 12/2002 |
| WO | WO 03/000254 | A1 | 1/2003 |
| WO | WO 03/000690 | A1 | 1/2003 |
| WO | WO 03/004458 | A1 | 1/2003 |
| WO | WO 03/005025 | A1 | 1/2003 |
| WO | WO 03/006447 | A2 | 1/2003 |
| WO | WO 03/010140 | A2 | 2/2003 |
| WO | WO 03/010141 | A2 | 2/2003 |
| WO | WO 03/022214 | A2 | 3/2003 |
| WO | WO 03/048101 | A1 | 6/2003 |
| WO | WO 03/053359 | A2 | 7/2003 |
| WO | WO 03/053368 | A2 | 7/2003 |
| WO | WO 03/053938 | A1 | 7/2003 |
| WO | WO 03/053941 | A2 | 7/2003 |
| WO | WO 03/055447 | A2 | 7/2003 |
| WO | WO 03/059269 | A2 | 7/2003 |
| WO | WO 03/062392 | A2 | 7/2003 |
| WO | WO 03/064539 | A1 | 8/2003 |
| WO | WO 03/066629 | A2 | 8/2003 |
| WO | WO 03/074047 | A1 | 9/2003 |
| WO | WO 03/082265 | | 10/2003 |
| WO | WO 03/087092 | | 10/2003 |
| WO | 03/091211 | | 11/2003 |
| WO | WO 03/097036 | A1 | 11/2003 |
| WO | 2005/058315 | | 12/2003 |
| WO | WO 03/099276 | A1 | 12/2003 |
| WO | WO 2004/003103 | A1 | 1/2004 |
| WO | 2004/014912 | | 2/2004 |
| WO | WO 2004/012736 | A1 | 2/2004 |
| WO | WO 2004/013135 | | 2/2004 |
| WO | WO 2004/022057 | A1 | 3/2004 |
| WO | WO 2004/024060 | A2 | 3/2004 |
| WO | WO 2004/024655 | A2 | 3/2004 |
| WO | WO 2004/024896 | A2 | 3/2004 |
| WO | WO 2004/030630 | | 4/2004 |
| WO | WO 2004/035047 | A1 | 4/2004 |
| WO | WO 2004/035522 | A1 | 4/2004 |
| WO | WO 2004/035525 | A1 | 4/2004 |
| WO | WO 2004/035571 | | 4/2004 |
| WO | 2004/037788 | | 5/2004 |
| WO | 2004/041256 | | 5/2004 |
| WO | WO 2004/037791 | A1 | 5/2004 |
| WO | WO 2004/041781 | A1 | 5/2004 |
| WO | WO 2004/050035 | A2 | 6/2004 |
| WO | WO 2004/064759 | | 8/2004 |
| WO | WO 2004/064925 | | 8/2004 |
| WO | WO 2004/065367 | | 8/2004 |
| WO | 2004/082638 | | 9/2004 |
| WO | WO 2004/074447 | | 9/2004 |
| WO | WO 2004/083195 | A1 | 9/2004 |
| WO | WO 2004/087714 | A1 | 10/2004 |
| WO | WO 2004/093871 | | 11/2004 |
| WO | WO 2004/093912 | A1 | 11/2004 |
| WO | WO 2004/094409 | | 11/2004 |
| WO | WO 2004/096210 | | 11/2004 |
| WO | WO 2004/099168 | A2 | 11/2004 |
| WO | WO 2004/099170 | A2 | 11/2004 |
| WO | WO 2004/099171 | A2 | 11/2004 |
| WO | WO 2004/099192 | A2 | 11/2004 |
| WO | WO 2004/099239 | A1 | 11/2004 |
| WO | WO 2004/111056 | A2 | 12/2004 |
| WO | WO 2005/003086 | A2 | 1/2005 |
| WO | WO 2005/003131 | A1 | 1/2005 |
| WO | 2005/009389 | | 2/2005 |
| WO | 2005/013976 | | 2/2005 |
| WO | 2005/013977 | | 2/2005 |
| WO | 2005/014000 | | 2/2005 |
| WO | 2005/014045 | | 2/2005 |
| WO | WO 2005/013950 | A2 | 2/2005 |
| WO | WO 2005/014543 | A1 | 2/2005 |
| WO | WO 2005/016862 | A1 | 2/2005 |
| WO | 2005/021505 | | 3/2005 |
| WO | WO 2005/018531 | | 3/2005 |
| WO | WO 2005/020899 | A2 | 3/2005 |
| WO | WO 2005/020921 | A1 | 3/2005 |
| WO | WO 2005/028502 | | 3/2005 |
| WO | WO 2005/034941 | | 4/2005 |
| WO | WO 2005/034943 | | 4/2005 |
| WO | WO 2005/039489 | A2 | 5/2005 |
| WO | WO 2005/042018 | | 5/2005 |
| WO | WO 2005/055940 | A2 | 6/2005 |
| WO | WO 2005/061519 | A1 | 7/2005 |
| WO | WO 2005/062676 | A1 | 7/2005 |
| WO | WO 2005/066180 | A1 | 7/2005 |
| WO | WO 2005/072132 | A2 | 8/2005 |
| WO | WO 2005/076861 | A2 | 8/2005 |
| WO | WO 2005/077122 | A2 | 8/2005 |
| WO | WO 2005/077969 | | 8/2005 |
| WO | 2005/090282 | | 9/2005 |
| WO | WO 2005/080335 | | 9/2005 |
| WO | WO 2005/080388 | A1 | 9/2005 |
| WO | WO 2005/082895 | A1 | 9/2005 |
| WO | WO 2005/082905 | A1 | 9/2005 |
| WO | WO 2005/086754 | A2 | 9/2005 |
| WO | WO 2005/092855 | | 10/2005 |
| WO | 2005/107747 | | 11/2005 |
| WO | 2005/112519 | | 11/2005 |
| WO | 2005/113529 | | 12/2005 |
| WO | 2006/019831 | | 2/2006 |
| WO | 2006/024699 | | 3/2006 |
| WO | 2006/041874 | | 4/2006 |
| WO | 2006/049013 | | 5/2006 |
| WO | 2006/050236 | | 5/2006 |
| WO | 2006/057354 | | 6/2006 |
| WO | 2006/083458 | | 8/2006 |

OTHER PUBLICATIONS

Loudon et. al., Journal of the Chemical Society, Perkins Transactions, 1960, Chemical Society of Great Britain, pp. 3466-3470.*

Watterson et. al., Bioorganic & Medicinal Chemistry Letters, 2003, Elsevier, vol. 13, pp. 1273-1276.*

Tan et. al., Nature Reviews, Drug Discovery, 2002, Nature Publishing Group, vol. 1, pp. 867-881.*

Patent Abstracts of Japan of Publication No. 08183260 Published Jul. 16, 1996.
International Search Report in PCT/US2007/000996 mailed Sep. 19, 2007.
Partial International Search Report in PCT/US2007/000996 mailed Jul. 16, 2007.
Ahlquist et al., "Host Factors in Positive-Strand RNA Virus Genome Replication", *Journal of Virology*, 77(15):8181-8186 (2003).
Almerico et al., "Glycosidopyrroles Part 3. Effect of the Benzocondesnation on Acyclic Derivatives: 1-(2-hydroxyethoxy) Methylindoles as Potential Antiviral Agents", *Il Farmaco*, 53:409-414 (1998).
Almerico et al., "Glycosidopyrroles. part 4. 1-β-D-ribofuranosyl-pyrroles and Indoles as Potential Antiviral agents", *ARKIVOC*, 1(4):486-496 (2000).
Attaby et al., "Synthesis and Antimicrobial Evaluation of Several New Pyridine, Thienopyridine and Pyridothienopyrazole Derivatives", *Phosphorus, Sulfur and Silicon*, 149:49-64 (1999).
Cacchi et al., "2-Aryl and 2-Heteroaryl Indoles from 1-Alkynes and o-lodotrifluoroacetanilide through a Domino Copper-Catalyzed Coupling-Cyclization Process", *Organic Letters*, 5(21):3843-3846 (2003).
Carson et al., "The Synthesis and Properties of 2-p-Dimthylaminophenyl-1,3,3-trimethyl-3H-indolium Salts", *Journal of the Chemical Society*, 5819-5825 (1965).
Chikvaidze et al., "Synthesis and Antimicrobial Activity of New Derivatives of 2-Phenylindone", *Pharmaceutical Chemistry Journal*, 28(10):751-755 (1994).
Dhar et al., "3-Cyanoindole-Based Inhibitors of Inosine Monophosphate Dehydrogenase: Synthesis and Initial Structure-Activity Relationships", *Bioorganic & Medicinal Chemistry Letters*, 13:3557-3560 (2003).
Font et al., "indoles and Pyridazino[4,5-*b*]indoles as Nonnucleoside Analog Inhibitors of HIV-1 Reverse Transcriptase", *Eur J Med Chem*, 30:963-971 (1995).
International Search Report issued in Application No. PCT/US2005/024882.
Patent Abstracts of Japan of vol. 2003, No. 12 J1.
Patent Abstracts of Japan of JP 01273040 A published Oct. 31, 1989.
Patent Abstracts of Japan of JP 06236010 A published Aug. 23, 1994.
Patent Abstracts of Japan of JP 09169729 A published Jun. 30, 1997.
Perola et al., "Successful Virtual Screening of a Chemical Database for Farnesyltransferase Inhibitor Leads", *J. Med. Chem.*, 43:401-408 (2000).
Wang et al., "Alpha Interferon Induces Distinct Translational Control Programs to Suppress Hepatitis C Virus RNA Replication", *Journal of Virology*, 77(7):3898-3912 (2003).
International Search Report for International Application No. PCT/US2005/024881, mailed Feb. 3, 2006.
Al-Omran, STN Accession Number:2000:825367 Document Number:134:131488; Abstract of the Journal of Heterocyclic Chemistry, 37(5):1219-1223 (2000).
Boehm et al., STN Accession Number: 1993:756686 Document Number: 118:233974; Abstract of Pharmazie, 47(12):897-901 (1992).
Dyachenko et at, STN Accession Number: 1996:756686 Document Number: 126:74777; Abstract of Khimiya Geterotsiklicheskikh Soedinenii, 9:1232-1234 (1996).
Elgemeie et al., STN Accession Number: 1994:54466 Document Number: 120:54466; Abstract of Journal of Chemical Research, Synopses, 7:256-257 (1993).
Frolova et al., STN Accession Number: 1996:396582 Document Number: 125:167833; Abstract of Izvestiya Akademii Nauk, Seriya Khimicheskaya, 4:938-942 (1996).
Frolova et al., STN Accession Number: 1997:73192 Document Number:126:131360; Abstract of Izvestiya Akademii Nauk, Seriya Khimicheskaya, 11:2719-2721 (1996).
Leistner et al., STN Accession Number: 1992:235578 Document Number: 116:235578; Abstract of Pharmazie, 47(1):11-14 (1992).
Paronikyan et al., STN Accession Number:1998:173599 Document Number:128:243969, Abstract of Khimiko-Farmatsevticheskii Zhurnal, 31(10):34-36 (1997).
Quintela et al., STN Accession Number: 1999:643470 Document Number: 132:22945; Abstract of Journal of Medicinal Chemistry, 42(22):4720-4724 (1999).
Sharanin et al., STN Accession Number:1985:113330 Document Number: 102:113330, Abstract of Zhumal Organicheskoi Khimii, 20(9):2002-2011 (1984).
Vieweg et al., STN Acession Number: 1993:449330, Document Number: 119:49330, Abstract of Pharmazie, 48(1):26-30 (1993).
Ali et al., "Human La Antigen is Required for the Hepatitis C Virus Internal Ribosome Entry Site-mediated Translation", *J Biol Chem*, 275(36):27531-27540 (2000).
Ali et al., "Interaction of Polypyrimidine Tract-Binding Protein with the 5' Noncoding Region of the Hepatitis C Virus RNA Genome and its Functional Requirement in Internal Initiation of Translation", *J Virol*, 69(10):6367-6375 (1995).
Ali et al., "The La Antigen Binds 5' Noncoding Region of the Hepatitis C Virus RNA in the Context of the Initiator AUG Codon and Stimulates Internal Ribosome Entry Site-Mediated Translation", *Proc Natl Acad Sci USA*, 94:2249-2254 (1997).
Anwar et al., "Demonstration of Functional Requirement of Polypyrimidine Tract-binding Protein by SELEX RNA during Hepatitis C Virus Internal Ribosome Entry Site-mediated Translation Initiation", *J Biol Chem*, 275(44):34231-34235 (2000).
Beales et al., "The Internal Ribosome Entry Site (IRES) of Hepatitis C Virus Visualized by Electron Microscopy", *RNA*, 7:661-670 (2001).
Belsham et al., "A Region of the 5' Noncoding Region of Foot-and-Mouth Disease Virus RNA Directs Efficient Internal Initiation of Protein Synthesis within Cells: Involvement with the Role of L Protease in Translational Control", *J Virol*, 64(11):5389-5395 (1990).
Belsham et al., "Translation Initiation on Picornavirus RNA", p. 869-900, Cold Spring Harbor Laboratory Press, New York (2000).
Blight et al., "Efficient Initiation of HCV RNA Replication in Cell Culture", *Science*, 290:1972-1974 (2000).
Blight et al., "Highly Permissive Cell Lines for Subgenomic and Genomic Hepatitis C Virus RNA Replication", *J Virol*, 76(24):13001-13014 (2002).
Boni et al., "Hepatitis C Virus Core Protein Acts as a *trans*-Modulating Factor on Internal Translation Initiation of the Viral RNA", *J Biol Chem*, 280(18):17737-17748 (2005).
Borovjagin et al., "Pyrimidine Tract Binding Protein Strongly Stimulates in vitro Encephalomyocarditis Virus RNA Translation at the Level of the Preinitiation Complex Formation" *FEBS Lett*, 351:291-302 (1994).
Brown et al., "Secondary Structure of the 5' Nontranslated Regions of Hepatitis C Virus and Pestivirus Genomic RNAs", *Nucleic Acids Res*, 20(19):5041-5045 (1992).
Buck et al., "The Human Immunodeficiency Virus Type 1 *gag* Gene Encodes an Internal Ribosome Entry Site", *J Virol*, 75(1):181-191 (2001).
Bukh et al. "Sequence Analysis of the 5' Noncoding Region of Hepatitis C Virus", *Proc Natl Acad Sci USA*, 89:4942-4946 (1992).
Bukh et al., "Sequence Analysis of the Core Gene of 14 Hepatitis C Virus Genotypes", *Proc Natl Acad Sci USA*, 91:8239-8243 (1994).
Buratti et al., "Functional Analysis of the Interaction Between HCV 5'UTR and Putative Subunits of Eukaryotic Translation Initiation Factor eIF3", *Nucleic Acids Res*, 26(13):3179-3187 (1998).
Chappell et al., "A Mutation in the c-*myc*-IRES Leads to Enhanced Internal Ribosome Entry in Multiple Myeloma: A Novel Mechanism of Oncogene De-Regulation", *Oncogene*, 19:4437-4440 (2000).
Chung et al., "Hepatitis C Virus Replication is Directly Inhibited by IFN-α in a Full-Length Binary Expression System", *Proc Natl Acad Sci USA*, 98(17):9847-9852 (2001).
Coldwell et al., "Initiation of Apaf-1 Translation by Internal Ribosome Entry", *Oncogene*, 19:899-905 (2000).
Créancier et al., "Fibroblast Growth Factor 2 Internal Ribosome Entry Site (IRES) Activity Ex Vivo and in Transgenic Mice Reveals a Stringent Tissue-specific Regulation", *J Cell Biol*, 150(1):275-281 (2000).
Das et al., "Inhibition of Internal Entry Site (IRES)-Mediated Translation by a Small Yeast RNA: a Novel Strategy to Block Hepatitis C Virus Protein Synthesis" *Front Biosci*, (3)d1241-1252 (1998).

Dever, "Gene-Specific Regulation by General Translation Factors", *Cell*, 108:545-556 (2002).
Dumas et al., "A Promoter Activity is Present in the DNA Sequence Corresponding to the Hepatitis C Virus 5' UTR", *Nucleic Acids Res*, 31(4):1275-1281 (2003).
Fukushi et al., "Complete 5' Noncoding Region is Necessary for the Efficient Internal Initiation of Hepatitis C Virus RNA", *Biochem Biophys. Res Commun.*, 199(2):425-432 (1994).
Fukushi et al., "The Sequence Element of the Internal Ribosome Entry Site and a 25-Kilodalton Cellular Protein Contribute to Efficient Internal Initiation of Translation of Hepatitis C Virus RNA", *J Virol*, 71(2):1662-1666 (1997).
Fukushi et al., "Specific Interaction of a 25-Kilodalton Cellular Protein, a 40S Ribosomal Subunit Protein, with the Internal Ribosome Entry Site of Hepatitis C Virus Genome", *Virus Genes*, 19(2):153-161 (1999).
Fukushi et al., "Ribosomal Protein S5 Interacts with the Internal Ribosomal Entry Site of Hepatitis C Virus", *J Biol Chem*, 276(24):20824-20826 (2001).
Funkhouser et al., "Hepatitis A Virus Translation is Rate-Limiting for Virus Replication in MRC-5 Cells", *Virology*, 254:268-278 (1999).
Glass et al., "Identification of the Hepatitis A Virus Internal Ribosome Entry Site: In vivo and in vitro Analysis of Bicistronic RNAs Containing the HAV 5' Noncoding Region", *Virology*, 193:842-852 (1993).
Gordon et al., "A Phase II, 12-Week Study of ISIS 14803, an Antisense Inhibitor of HCV for the Treatment of Chronic Hepatitis C" AASLD Abst., 795, *Hepatology*, 36:362A (2002).
Gosert et al., "Transient Expression of Cellular Polypyrimidine-Tract Binding Protein Stimulates Cap-Independent Translation Directed by Both Picornaviral and Flaviviral Internal Ribosome Entry Sites In Vivo", *Mol Cell Biol*, 20(5):1583-1595 (2000).
Gray et al., "Control of Translation Initiation in Animals", *Annu Rev Cell Dev Biol*, 14:399-458 (1998).
Griffith et al., "An Unusual Internal Ribosome Entry Site in the Herpes Simplex Virus Thymidine Kinase Gene", *Proc Natl Acad Sci USA*, 102(27):9667-72 (2005).
Guo et al., "Effect of Alpha Interferon on the Hepatitis C Virus Replicon", *J Virol*, 75(18):8516-8523 (2001).
Hahm et al., "Heterogeneous Nuclear Ribonucleoprotein L Interacts with the 3' Border of the Internal Ribosomal Entry Site of Hepatitis C Virus", *J Virol*, 72(11):8782-8788 (1998).
Haller et al., "Attenuation Stem-Loop Lesions in the 5' Noncoding Region of Poliovirus RNA: Neuronal Cell-Specific Translation Defects", *J Virol*, 70(3):1467-1474 (1996).
He et al., "The Regulation of Hepatitis C Virus (HCV) Internal Ribosome-Entry Site-Mediated Translation by HCV Replicons and Nonstructural Proteins", *J Gen Virol*, 84:535-543 (2003).
Hellen et al., "Translation of Hepatitis C Virus Rna", *J Viral Hepat*, 6:79-87 (1999).
Hellen et al., "A Cytoplasmic 57-kDa Protein that is Required for Translation of Picornavirus RNA by Internal Ribosomal Entry is Identical to the Nuclear Pyrimidine Tract-Binding Protein", *Proc Natl Acad Sci USA*, 90:7642-7646 (1993).
Hendrix et al., "Direct Observation of Aminoglycoside-RNA Interactions by Surface Plasmon Resonance" *Journal of the American Chemical Society*, 119(16):3641-8 (1997).
Holcik et al., "Functional Characterization of the X-Linked Inhibitor of Apoptosis (XIAP) Internal Ribosome Entry Site Element: Role of La Autoantigen in XIAP Translation", *Mol Cell Biol*, 20(13):4648-4657 (2000).
Holcik et al., "A new Internal-Ribosome-Entry-Site Motif Potentiates XIAP-Mediated Cytoprotection", *Nat Cell Biol*, 1:190-192 (1999).
Honda et al., "A Phylogenetically Conserved Stem-Loop Structure at the 5' Border of the Internal Ribosome Entry Site of Hepatitis C Virus is Required for Cap-Independent Viral Translation", *J Virol*, 73(2):1165-1174 (1999).
Honda et al., "Stability of a Stem-Loop Involving the Initiator AUG Controls the Efficiency of Internal Initiation of Translation on Hepatitis C Virus RNA", *RNA*, 2:955-968 (1996).
Honda et al., "Structural Requirements for Initiation of Translation by Internal Ribosome Entry within Genome-Length Hepatitis C Virus RNA", *Virology*, 222:31-42 (1996).
Honda et al., "Natural Variation in Translational Activities of the 5' Nontranslated RNAs of Hepatitis C Virus Genotypes 1a and 1b: Evidence for a Long- Range RNA-RNA Interaction Outside of the Internal Ribosomal Entry Site", *J Virol*, 73(6):4941-4951 (1999).
Huez et al., "New Vascular Endothelial Growth Factor Isoform Generated by Internal Ribosome Entry Site-Driven CUG Translation Initiation", *Mol Endocrinol.*, 15(12):2197-2210 (2001).
Huez et al., "Two Independent Internal Ribosome Entry Sites Are Involved in Translation Initiation of Vascular Endothelial Growth Factor mRNA", *Mol Cell Biol*, 18(11):6178-6190 (1998).
Ikeda et al., "Selectable Subgenomic and Genome-Length Dicistronic RNAs Derived from an Infectious Molecular Clone of the HCV-N Strain of Hepatitis C Virus Replicate Efficiently in Cultured Huh7 Cells" *J Virol*, 76(6):2997-3006 (2002).
Irvine et al., "MDCK (Madin-Darby Canine Kidney) Cells: A Tool for Membrane Permeability Screening", *J Pharm Sci*, 88(1):28-33 (1999).
Isoyama et al., "Lower Concentration of La Protein Required for Internal Ribosome Entry on Hepatitis C Virus RNA than on Poliovirus RNA", *J Gen Virol*, 80( 9):2319-2327 (1999).
Ito et al., "An Internal Polypyrimidine-Tract-Binding Protein-Binding Site in the Hepatitis C Virus RNA Attenuates Translation, Which is Relieved by the 3'-Untranslated Sequence", *Virology* 254:288-296 (1999).
Jang et al., "A Segment of the 5' Nontranslated Region of Encephalomyocarditis Virus RNA Directs Internal Entry of Ribosomes during In Vitro Translation", *J Virol*, 62(8):2636-2643 (1988).
Jubin et al., "Hepatitis C Virus Internal Ribosome Entry Site (IRES) Stem Loop IIId Contains a Phylogenetically Conserved GGG Triplet Essential for Translation and IRES Folding", *J Virol*, 74(22):10430-10437 (2000).
Kalliampakou et al., "Mutational Analysis of the Apical Region of Domain II of the HCV IRES", *FEBS Lett*, 511:79-84 (2002).
Kaminski et al., "Direct Evidence that Polypyrimidine Tract Binding Protein (PTB) is Essential for Internal Initiation of Translation of Encephalomyocarditis Virus RNA", *RNA*, 1:924-938 (1995).
Kamoshita et al., "Genetic Analysis of Internal Ribosomal Entry Site on Hepatitis C Virus RNA: Implication for Involvement of the Highly Ordered Structure and Cell Type-Specific Transacting Factors", *Virology*, 233:9-18 (1997).
Kato et al., "Hepatitis C Virus NS4A and NS4B Proteins Suppress Translation In Vivo", *J Med Virol*, 66:187-199 (2002).
Kieft et al., "The Hepatitis C Virus Internal Ribosome Entry Site Adopts an Ion-dependent Tertiary Fold", *J Mol Biol*, 292:513-529 (1999).
Kieft et al., "Mechanism of Ribosome Recruitment by Hepatitis C IRES RNA", *RNA*, 7:194-206 (2001).
Klinck et al., "A Potential RNA Drug Target in the Hepatitis C Virus Internal Ribosomal Entry Site", *RNA*, 6:1423-1431 (2000).
Kolupaeva et al., "An Enzymatic Footprinting Analysis of the Interaction of 40S Ribosomal Subunits with the Internal Ribosomal Entry Site of Hepatitis C Virus", *J Virol*, 74(14):6242-6250 (2000).
Kolupaeva et al., "Structural Analysis of the Interaction of the Pyrimidine Tract-Binding Protein with the Internal Ribosomal Entry Site of Encephalomyocarditis Virus and Foot-and-Mouth Disease Virus RNAs", *RNA*, 2:1199-1212(1996).
Kolupaeva et al., "Translation Eukaryotic Initiation Factor 4G Recognizes a Specific Structural Element within the Internal Ribosome Entry Site of Encephalomyocarditis Virus RNA", *J Biol Chem*, 273(29):18599-18604 (1998).
Kozak, "Initiation of Translation in Prokaryotes and Eukaryotes", *Gene*, 234:187-208 (1999).
Krüger et al., "Involvement of Proteasome α-Subunit PSMA7 in Hepatitis C Virus Internal Ribosome Entry Site-Mediated Translation", *Mol Cell Biol*, 21(24): 8357-8364 (2001).
La Monica et al., "Differences in Replication of Attenuated and Neurovirulent Polioviruses in Human Neuroblastoma Cell Line SH-SY5Y", *J Virol*, 63(5):2357-2360 (1989).

Le et al., "Unusual Folding Regions and Ribosome Landing Pad within Hepatitis C Virus and Pestivirus RNAs", *Gene*, 154:137-143 (1995).
Lerat et al., "Cell Type-Specific Enhancement of Hepatitis C Virus Internal Ribosome Entry Site-Directed Translation due to 5' Nontranslated Region Substitutions Selected during Passage of Virus in Lymphoblastoid Cells", *J Virol*, 74(15):7024-7031 (2000).
Li et al., "A Heterocyclic Inhibitor of the Rev-RRE Complex Binds to RRE as a Dimer", *Biochemistry*, 40:1150-1158 (2001).
Li et al., "Amino Acids 1-20 of the Hepatitis C Virus (HCV) Core Protein Specifically Inhibit HCV IRES-Dependent Translation in HepG2 Cells, and Inhibit Both HCV IRES- and Cap-Dependent Translation in HuH7 and CV-1 Cells", *J Gen Virol*, 84:815-825 (2003).
Lipinski, "Drug-Like Properties and the Causes of Poor Solubility and Poor Permeability", *J Pharm Tox Meth*, 44:235-249 (2000).
Llinàs-Brunet, "NS3 Serine Protease Inhibitors as Potential Antiviral Agents for the Treatment of Hepatitis C Virus Infections", The 3rd Internatl Antiviral & Vaccine Discovery & Development Summit, Princeton, NJ (Mar. 13-14, 2002).
Lohmann et al., "Mutations in Hepatitis C Virus RNAs Conferring Cell Culture Adaptation", *J Virol*, 75(3):1437-1449 (2001).
Lohmann et al., "Replication of Subgenomic Hepatitis C Virus RNAs in a Hepatoma Cell Line", *Science*, 285:110-113 (1999).
Lopez et al., "IRES Interaction with Translation Initiation Factors: Functional Characterization of Novel RNA Contacts with eIF3, eIF4B, and eIF4GII", *RNA*, 7:1213-1226 (2001).
Lopez et al., "Interaction of the eIF4G Initiation Factor with the Aphthovirus IRES is Essential for Internal Translation Initiation In Vivo", *RNA*, 6:1380-1392 (2000).
Lu et al., "Poliovirus Chimeras Replicating Under the Translational Control of Genetic Elements of Hepatitis C Virus Reveal Unusual Properties of the Internal Ribosomal Entry Site of Hepatitis C Virus", *Proc Natl Acad Sci USA*, 93:1412-1417 (1996).
Lukavsky et al., "Structures of Two RNA Domains Essential for Hepatitis C Virus Internal Ribosome Entry Site Function", *Nat Struct Bio*, 7(12):1105-1110 (2000).
Lyons et al., "Hepatitis C Virus Internal Ribosome Entry Site RNA Contains a Tertiary Structural Element in a Functional Domain of Stem-Loop II", *Nucleic Acids Res*, 29(12):2535-2541 (2001).
Lukavsky et al., "Structure of HCV IRES Domain II Determined by NMR", *Nat Struct Biol*, 10(12):1033-1038 (2003).
Macejak et al., "Inhibition of Hepatitis C Virus (HCV)-RNA-Dependent Translation and Replication of a Chimeric HCV Poliovirus Using Synthetic Stabilized Ribozymes", *Hepatology*, 31:769-76 (2000).
Macejak et al., "Enhanced Antiviral Effect in Cell Culture of Type 1 Interferon and Ribozymes Targeting HCV RNA", *J Viral Hepatitis*, 8:400-405 (2001).
Macejak et al., "Internal Initiation of Translation Mediated by the 5' Leader of a Cellular mRNA", *Nature*, 353:90-94 (1991).
Major et al., "Hepatitis C Viruses.", p. 1127-1161. In D. Knipe and P. Howley (eds.), Fields Virology, vol. 1, $4^{th}$ Ed. Lippincott Williams and Wilkins, Philadelphia, PA (2001).
Manns et al., "Peginterferon alfa-2b Plus Ribavirin Compared with Interferon Alfa-2b Plus Ribavirin for Initial Treatment of Chronic Hepatitis C: A Randomised Trial", *The Lancet*, 358:958-965 (2001).
Martinez-Salas et al., "Functional Interactions in Internal Translation Initiation Directed by Viral and Cellular IRES Elements", *J Gen Virol*, 82:973-984 (2001).
Mazur et al., "A Thermodynamic and Structural Analysis of DNA Minor-groove Complex Formation", *J Mol Biol*, 300:321-337 (2000).
McHutchison et al., "Combination Therapy With Interferon Plus Ribavirin for the Initial Treatment of Chronic Hepatitis C", *Semin Liver Dis*, 19 Suppl 1:57-65 (1999).
McHutchison et al., "Hepatic HCV RNA Before and After Treatment With Interferon Alone or Combined With Ribavirin", *Hepatology*, 35(3):688-693 (2002).
Meerovitch et al., "A Cellular Protein that Binds to the 5'-Noncoding Region of Poliovirus RNA: Implications for Internal Translation Initiation", *Genes Dev*, 3:1026-1034 (1989).
Meerovitch et al., "La Autoantigen Enhances and Corrects Aberrant Translation of Poliovirus RNA in Reticulocyte Lysate", *J Virol*, 67(7): 3798-3807 (1993).
Mercer et al., "Hepatitis C Virus Replication in Mice with Chimeric Human Livers", *Nature Medicine*, 7(8):927-933 (2001).
Michel et al., "Eukaryotic Initiation Factor 4G-Poly(A) Binding Protein Interaction Is Required for Poly(A) Tail-Mediated Stimulation of Picornavirus Internal Ribosome Entry Segment-Driven Translation but Not for X-Mediated Stimulation of Hepatitis C Virus Translation", *Mol Cell Biol*, 21(13): 4097-4109 (2001).
Mitchell et al., "Protein Factor Requirements of the Apaf-1 Internal Ribosome Entry Segment: Roles of Polypyrimidine Tract Binding Protein and Upstream of N-ras", *Mol Cell Biol*, 21(10):3364-3374 (2001).
Moriguchi, et al., "Simple Method of Calculating Octanol/Water Partition Coefficient", *Chem Pharm Bull*, 40(1):127-130 (1992).
Nanbru et al., "Alternative Translation of the Proto-oncogene c-*myc* by an Internal Ribosome Entry Site", *J Biol Chem*, 272(51):32061-32066 (1997).
Niepmann et al., "Functional Involvement of Polypyrimidine Tract-Binding Protein in Translation Initiation Complexes with the Internal Ribosome Entry Site of Foot-and-Mouth Disease Virus", *J Virol*, 71(11):8330-8339 (1997).
Odreman-Macchioli et al., "Mutational Analysis of the Different Bulge Regions of Hepatitis C Virus Domain II and Their Influence on Internal Ribosome Entry Site Translational Ability", *J Biol Chem*, 276(45):41648-41655 (2001).
Odreman-Macchioli et al., "Influence of Correct Secondary and Tertiary RNA Folding on the Binding of Cellular Factors to the HCV IRES", *Nucleic Acids Res*, 28(4):875-885 (2000).
Ohlmann et al., "An Internal Ribosome Entry Segment Promotes Translation of the Simian Immunodeficiency Virus Genomic RNA", *J Biol Chem*, 275(16):11899-11906 (2000).
Otto et al., "The Pathway of HCV IRES-Mediated Translation Initiation", *Cell*, 119:369-380 (2004).
Pain, "Initiation of Protein Synthesis in Eukaryotic Cells", *Eur J Biochem*, 236:747-771 (1996).
Pelletier et al., "Internal Initiation of Translation of Eukaryotic mRNA Directed by a Sequence Derived from Poliovirus RNA", *Nature*, 334:320-325 (1988).
Pelletier et al., "Internal Binding of Eucaryotic Ribosomes on Poliovirus RNA: Translation in HeLa Cell Extracts", *J Virol*, 63(1):441-444 (1989).
Pestova et al., "Eukaryotic Ribosomes Require Initiation Factors 1 and 1A to Locate Initiation Codons", *Nature* 394:854-859 (1998).
Pestova et al., "A Prokaryotic-Like Mode of Cytoplasmic Eukaryotic Ribosome Binding to the Initiation Codon During Internal Translation Initiation of Hepatitis C and Classical Swine Fever Virus RNAs", *Genes Dev*, 12: 67-83 (1998).
Pestova et al., "Functional Dissection of Eukaryotic Initiation Factor 4F: The 4A Subunit and the Central Domain of the 4G Subunit Are Sufficient to Mediate Internal Entry of 43S Preinitiation Complexes", *Mol Cell Biol*, 16(12):6870-6878 (1996).
Peytou et al., "Synthesis and Antiviral Activity of Ethidium-Arginine Conjugates Directed Against the TAR RNA of HIV-1", *J Med Chem*, 42(20):4042-53 (1999).
Pietschmann et al., "Persistent and Transient Replication of Full-Length Hepatitis C Virus Genomes in Cell Culture", *J Virol*, 76(8):4008-4021 (2002).
Pietschmann et al., "Characterization of Cell Lines Carrying Self-Replicating Hepatitis C Virus RNAs", *J Virol*, 75(3):1252-1264 (2001).
Poole et al, "Pestivirus Translation Initiation Occurs by Internal Ribosome Entry", *Virology*, 206:750-754 (1995).
Pringle, "Virus Taxonomy—1999. The Universal System of Virus Taxonomy, Updated to Include the New Proposals Ratified by the International Committee on Taxonomy of Viruses During 1998", *Arch Virol*, 144/2:421-429 (1999).
Psaridi et al., "Mutational Analysis of a Conserved Tetraloop in the 5' Untranslated Region of Hepatitis C Virus Identifies a Novel RNA Element Essential for the Internal Ribosome Entry Site Function", *FEBS Lett*, 453:49-53 (1999).

Reynolds et al., "Internal Initiation of Translation of Hepatitis C Virus RNA: The Ribosome Entry Site is at the Authentic Initiation Codon", *RNA*, 2:867-878 (1996).
Reynolds et al., "Unique Features of Internal Initiation of Hepatitis C Virus RNA Translation", *EMBO J*, 14(23):6010-6020(1995).
Rijnbrand et al., "Almost the Entire 5' Non-Translated Region of Hepatitis C Virus is Required for Cap-Independent Translation", *FEBS Lett*, 365:115-119 (1995).
Rijnbrand et al., "Internal Ribosome Entry Site-Mediated Translation in Hepatitis C Virus Replication", *Curr Top Microbiol Immunol*, 242:85-116 (2000).
Rijnbrand et al., "The Influence of Downstream Protein-Coding Sequence on Internal Ribosome Entry on Hepatitis C Virus and Other Flavivirus RNAs", *RNA*, 7:585-597 (2001).
Rijnbrand et al., "The Influence of AUG Codons in the Hepatitis C Virus 5' Nontranslated Region on Translation and Mapping of the Translation Initiation Window", *Virology*, 226:47-56 (1996).
Sachs et al., "Starting at the Beginning, Middle, and End: Translation Initiation in Eukaryotes", *Cell*, 89:831-838 (1997).
Saito et al., "Hepatitis C Virus Infection is Associated with the Development of Hepatocellular Carcinoma", *Proc Natl Acad Sci USA*, 87:6547-6549 (1990).
Schultz et al., "Mutations within the 5' Nontranslated RNA of Cell Culture-Adapted Hepatitis A Virus Which Enhance Cap-Independent Translation in Cultured African Green Monkey Kidney Cells", *J Virol*, 70(2):1041-1049 (1996).
Shimazaki et al., "Inhibition of Internal Ribosomal Entry Site-Directed Translation of HCV by Recombinant IFN-α Correlates With a Reduced La Protein", *Hepatology*, 35(1):199-208 (2002).
Simmonds, "Variability of Hepatitis C Virus", *Hepatology*, 21(2):570-583 (1995).
Sinha Roy et al., "Direct Interaction of a Vancomycin Derivative with Bacterial Enzymes Involved in Cell Wall Biosynthesis", *Chem Biol*, 8:1095-1106 (2001).
Sizova et al., "Specific Interaction of Eukaryotic Translation Initiation Factor 3 with the 5' Nontranslated Regions of Hepatitis C Virus and Classical Swine Fever Virus RNAs", *J Virol*, 72(6):4775-4782 (1998).
Smith, "Design of Drugs Through a Consideration of Drug Metabolism and Pharmacokinetics", *Eur J Drug Metab Pharm*, 3:193-199 (1994).
Smith et al., "Variation of the Hepatitis C Virus 5' Non-Coding Region: Implications for Secondary Structure, Virus Detection and Typing", *J Gen Virol*, 76(7):1749-1761 (1995).
Sonenberg et al., "Translational Control of Gene Expression", Cold Spring Harbor. Cold Spring Harbor Laboratory Press, New York (2000).
Spahn et al., "Hepatitis C Virus IRES RNA-Induced Changes in the Conformation of the 40s Ribosomal Subunit", *Science*, 291:1959-1962 (2001).
Spatzenegger et al., "Clinical Importance of Hepatic Cytochrome P450 in Drug Metabolism", *Drug Metab Rev* 27(3):397-417 (1995).
Subkhankulova et al., "Internal Ribosome Entry Segment-Mediated Initiation of c-Myc Protein Synthesis Following Genotoxic Stress", *Biochem J*, 359:183-192 (2001).
Tang et al., "Alterations to Both the Primary and Predicted Secondary Structure of Stem-Loop IIIc of the Hepatitis C Virus 1b 5' Untranslated Region (5'UTR) Lead to Mutants Severely Defective in Translation Which Cannot Be Complemented in *trans* by the Wild-Type 5'UTR Sequence", *J Virol*, 73(3):2359-2364 (1999).
Thiel et al., "Internal Ribosome Entry in the Coding Region of Murine Hepatitis Virus mRNA 5", *J Gen Virol.*, 75(11):3041-3046 (1994).
Tsukiyama-Kohara et al., "Internal Ribosome Entry Site within Hepatitis C Virus RNA", *J Virol*, 66(3):1476-1483 (1992).
Vagner et al., "Alternative Translation of Human Fibroblast Growth Factor 2 mRNA Occurs by Internal Entry of Ribosomes", *Mol Cell Biol*, 15(1):35-44 (1995).
Varaklioti et al., "Mutational Analysis of Two Unstructured Domains of the 5' Untranslated Region of HCV RNA", *Biochem Biophys. Res Commun.*, 253:678-685 (1998).
Wang et al., "An RNA Pseudoknot is an Essential Structural Element of the Internal Ribosome Entry Site Located Within the Hepatitis C Virus 5' Noncoding Region", *RNA*, 1:526-537 (1995).
Wang et al., "Translation of Human Hepatitis C Virus RNA in Cultured Cells is Mediated by an Internal Ribosome-Binding Mechanism", *J Virol*, 67(6):3338-3344 (1993).
Wang et al., "A Conserved Helical Element is Essential for Internal Initiation of Translation of Hepatitis C Virus RNA", *J Virol*, 68(11):7301-7307 (1994).
Wang et al., "Screening poly(dA/dT) cDNAs for Gene Identification", *PNAS USA*, 97(8):4162-7 (2000).
Wang et al., "Core Protein-Coding Sequence, but Not Core Protein, Modulates the Efficiency of Cap-Independent Translation Directed by the Internal Ribosome Entry Site of Hepatitis C Virus", *J Virol*, 74(23):11347-11358 (2000).
Wimmer et al., "Genetics of Poliovirus", *Annu Rev Genet*, 27:353-436 (1993).
Wong et al., "Cost-Effectiveness of 24 or 48 Weeks of Interferon α-2b Alone or With Ribavirin as Initial Treatment of Chronic Hepatitis C", *Am J Gastroenterol*, 95(6):1524-1530 (2000).
Zhao et al., "Genetic Analysis of a Poliovirus/Hepatitis C Virus Chimera: New Structure for Domain II of the Internal Ribosomal Entry Site of Hepatitis C Virus", *J Virol*, 75(8):3719-3730 (2001).
Zhao et al., "Poliovirus/Hepatitis C Virus (Internal Ribosomal Entry Site-Core) Chimeric Viruses: Improved Growth Properties through Modification of a Proteolytic Cleavage Site and Requirement for Core RNA Sequences but Not for Core-Related Polypeptides", *J Virol*, 73(2):1546-1554 (1999).

* cited by examiner

METHODS FOR TREATING HEPATITIS C

CROSS REFERENCE TO RELATED APPLICATIONS

This application claims the benefit of each of U.S. Provisional Application No. 60/587,487, filed Jul. 14, 2004, U.S. Provisional Application No. 60/634,979, filed Dec. 13, 2004, U.S. Provisional Application No. 60/645,586, filed Jan. 24, 2005, U.S. Provisional Application No. 60/665,349, filed Mar. 28, 2005, and U.S. Provisional Application No. 60/675,440, filed Apr. 28, 2005, all of which applications are incorporated herein by reference in their entireties. This application corresponds to International Application PCT/US2005/024881, filed Jul. 14, 2005, which application is herein incorporated by reference in its entirety.

GOVERNMENT SUPPORT

The present invention was made with U.S. Government support under DHHS Grant No. 5R44 AI054029-03. The U.S. Government has certain rights in the invention.

FIELD OF THE INVENTION

The present invention relates to methods for treating Hepatitis C using Indole compounds that modify translational control of Hepatitis C virus.

BACKGROUND OF THE INVENTION

An estimated 170 million people worldwide are reported to be infected with hepatitis C virus (HCV), the causative agent of hepatitis C. Seventy to eighty percent of HCV infections lead to chronic liver infection, which in turn may result in severe liver disease, including liver fibrosis, cirrhosis, and hepatocellular carcinoma (115).

HCV constitutes the *Hepacivirus* genus of the family Flaviviridae (106), and contains a positive-stranded 9.6 kb RNA genome. The features of the HCV genome include a 5'-untranslated region (UTR) that encodes an internal ribosome entry site (IRES) that directs the translation of a single long open reading frame (ORF) encoding a polyprotein of 3,010 amino acids. The HCV ORF is followed by a 3'-UTR of variable length, depending on the HCV variant, that encodes the sequences required for the initiation of antigenomic strand synthesis (79).

The HCV IRES and 3'-UTR both encode regions of RNA structures that are required for genome translation and replication. The HCV polyprotein is posttranslationally processed into at least 10 mature viral proteins, including the structural proteins core (putative nucleocapsid), E1 and E2 and the nonstructural (NS) proteins NS2 to NS5B.

Three distinct elements have been shown to be involved in HCV IRES-mediated translation: (1) integrity of the global structure of HCV IRES, (2) the 3'-terminal region of the HCV genome; and (3) trans-acting cellular factors that interact with the HCV IRES element and assist in translation initiation (35).

The initiation of protein synthesis in eukaryotic cells predominantly follows the 5' cap-dependent, first AUG rule (61). However, an increasing number of viral (6, 12, 28, 31a, 50, 95, 97, 98, 105, 128) and cellular mRNAs (18, 39, 45, 78, 91, 130) have been shown to use an IRES element to direct translation initiation. In 1992, an IRES element was reported in the 5' UTR of the HCV RNA genome (129), indicating that synthesis of the viral protein is initiated in a cap-independent fashion.

A bicistronic expression system can be used to define and evaluate the function of IRES elements. This test system harbors two different reporter genes in which the 5'-proximal reporter gene is expressed by a cap dependent translation mechanism while the second reporter is expressed only if an upstream sequence inserted in the intergenic space contains an IRES sequence element. Using this system, a putative IRES in the HCV 5' UTR was unambiguously demonstrated to function as an IRES involved in translational control of viral proteins (133). In vitro translation, RNA transfection, and mutagenesis studies provided further evidence that the HCV 5' UTR contains an IRES element (23, 41, 42, 108, 129, 132, 133, 134). Both in vitro and cell-based studies demonstrated that the HCV IRES guides cellular translation initiation factors to an internal site of the viral RNA (56, 58, 120), thus functionally demonstrating the HCV IRES activity. Taken together, these results demonstrate that the HCV 5'-UTR contains an IRES element that plays an active and crucial role in the mechanism of internal initiation for HCV protein translation.

The IRES is one of the most conserved regions of the HCV genome, reflecting its essential nature for viral replication and protein synthesis (13, 118, 122). Although both 5' and 3' sequences of the IRES appear to play a role in the control of initiation of translation (42, 109, 110, 113, 136), the minimal sequence requirement for HCV IRES function has been mapped to a region between nucleotides 44-354 (40).

Biochemical probing and computer modeling indicate that the HCV IRES and its 5' sequence is folded into a distinct structure that consists of four major domains and a pseudoknot (11, 42, 122). Domain I contains a small stem-loop structure that does not appear to be a functional part of the IRES element while domains II, III, and IV contain the HCV IRES activity (43, 111). The relationships between secondary and tertiary structures of the HCV IRES and their function have recently been established (5, 55, 56, 99, 124). Both domains II and III consist of multiple stems, loops, and bulges and are important for IRES activity (23, 40, 51, 52, 54, 56, 64, 74, 75, 93, 107, 108, 110, 124, 127, 131, 139). Domain II can induce conformational changes on the ribosome that have been implicated in the decoding process (124). Domain III has the highest degree of structural conservation among the different HCV strains. It comprises the core of the flavivirus IRES and has 6 subdomains (40). Various studies have shown that subdomain IIId forms complex secondary/tertiary structures and is critical for initiation activity (55, 56, 57, 124, 129). Domain IV has one stem-loop that spans the initiation codon and is specific for the HCV IRES (41, 122), but the precise role of domain IV in IRES activity remains controversial (41, 112).

The role of the HCV IRES is to position the translational machinery near an internal initiator codon in the viral mRNA. The translation initiation mechanism of the HCV IRES differs significantly from that of 5'-cap-dependent translation initiation (7, 21, 31, 35, 81, 96, 114, 123). Most cellular capped mRNAs utilize a number of initiation factors (eIFs) that are required for the translation initiation process. The initial steps of the process require proteins that interact with the 5' cap structure and recruit the 40S ribosomal subunit to the cap-proximal region of mRNA. This complex then scans 3' of the cap, until reaching an AUG codon at which translation will initiate (21, 114). However, in the case of HCV, the IRES functionally replaces the 5' cap structure, allowing the 40S ribosomal subunit and eIF3 to bind directly to the RNA.

Subdomain IIId of the HCV IRES harbors the binding site for the 40S ribosomal subunit and the only initiation factors required for translation initiation are eIF2, eIF3, and eIF4E (15, 58, 94, 100, 120, 124).

The polypyrimidine track-binding protein (PTB) and La autoantigen are noncanonical translation initiation factors that bind to and enhance HCV IRES activity (1, 2, 3, 4, 5, 30, 48, 49, 53). PTB, a 57-kDa protein involved in RNA splicing, is also necessary for efficient IRES-mediated translation initiation of picornavirus mRNA, and some cellular mRNAs (10, 11, 36, 53, 59, 89, 92). The La autoantigen, a 52 kDa double-stranded RNA unwinding protein, also increases the activity of poliovirus and cellular IRESs (38, 85, 86). Other cellular factors involved in HCV IRES-mediated translation initiation include proteasome α-subunit PSMA7 (62), ribosomal protein S5 (26), ribosomal protein S9 (24, 25, 100), and hnRNPL (33). However, the role of these RNA-binding proteins in HCV IRES-mediated initiation of translation is unclear. Recently, it was reported that the activity of interferon (IFN) α against HCV replication might target HCV IRES-mediated translation initiation by causing a reduction of La protein levels (117). Thus, an inhibitor that blocks interaction between the IRES and the noncanonical factors might efficiently inhibit HCV replication and lack cytotoxicity.

Currently, only interferon (IFN) α and the nucleoside analogue ribavirin, in combination, are marketed for the treatment of HCV infection. However, these two agents are immunomodulators and have limited efficacy, relatively high toxicity, and high cost (80, 83, 84, 138). Although the treatment outcome is variable among the six major HCV genotypes, only about one-half of all treated patients respond to therapy, suggesting that the virus encodes protein products that may directly or indirectly attenuate the antiviral action of IFN. IFNs are naturally produced in response to virus infection, and cellular exposure to IFN leads to the induced expression of a variety of IFN-stimulated genes (ISGs), many of which have an antiviral function. ISG action can limit virus replication at multiple points within the replicative cycle.

There remains a need for a more effective means of treating patients afflicted with HCV. Specifically, a need exists for novel antiviral drugs that have no cross-resistance with existing treatment modalities, and which demonstrate synergy with other anti-HCV agents. The applicants set out to identify drug candidates that inhibit HCV infection and were successful in identifying Indole compounds that are useful as anti-HCV agents. Without being limited to one theory, it is believed that the compounds of the present invention inhibit IRES-mediated initiation, elongation, and termination, i.e. translation.

The compounds of the present invention are also useful for inhibiting translation of other cap-independent viruses that contain an IRES element. Such viruses include those of the picornavirus genus, such as poliovirus, hepatitis A virus and rhinovirus; those of the coronavirus genus, such as SARS; those of the arbovirus genus; those of the flavivirus genus, such as yellow fever, dengue, and West Nile virus, herpesviruses, such as herpes simplex virus and Kaposi's sarcoma-associated herpesvirus, or any other virus with a similar mode of replication. Furthermore, compounds of the invention are also useful for inhibiting HIV, or any other virus with a similar mode of translation.

All documents referred to herein are incorporated by reference into the present application as though fully set forth herein.

SUMMARY OF THE INVENTION

In accordance with the present invention, compounds that can inhibit HCV replication have been identified. Also in accordance with the present invention, compounds that can inhibit HCV infection have been identified, and methods for their use provided.

In one aspect of the invention, compounds of Formula (I) are provided which are useful in the prevention and/or treatment of HCV infection. Without being limited to one theory, it is believed that the compounds of the present invention inhibit IRES-mediated initiation, elongation and termination, i.e., translation. The compounds of Formula (I) may also be useful for inhibiting and/or treating other viral infections where the virus contains an IRES element. Such viruses include those of the picornavirus genus, such as by way of non-limiting example poliovirus, hepatitis A virus and rhinovirus; those of the coronaviridae genus, such as by way of non-limiting example SARS; those of the arbovirus genus; those of the flavivirus genus, such as by way of non-limiting example yellow fever, dengue, and West Nile virus; herpesviruses, such as by way of non-limiting example herpes simplex virus and Kaposi's sarcoma-associated herpesvirus, or any other virus with a similar mode of replication. Furthermore, compounds of the invention are also useful for inhibiting HIV, or any other virus with a similar mode of translation.

In another aspect of the invention, methods are provided for the prevention and/or treatment of HCV infection.

In yet another aspect of the invention, pharmaceutical compositions comprising the compounds of the invention for the prevention and/or treatment of HCV infection are provided.

In one embodiment, the invention is directed to methods for inhibiting HCV IRES-mediated initiation and translation comprising administering an amount of one or more compound of the invention, effective for inhibiting IRES-mediated initiation and translation, to a subject in need thereof.

CERTAIN EMBODIMENTS

Embodiment 1

A pharmaceutical composition for the prevention or treatment of Hepatitis C viral (HCV) infection comprising a therapeutically effective amount of at least one compound having the following formula:

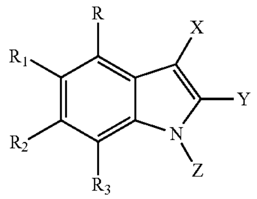

wherein:

X is:
- hydrogen;
- a nitro group;
- a cyano group;
- a —$COR_a$ group, where $R_a$ is:
  - a $C_1$ to $C_6$ alkyl,
  - a $C_6$ to $C_8$ aryl optionally substituted with an alkoxy or a halogen, or
  - a dialkyl-amino;
- a —$COOR_x$ group, where $R_x$ is a $C_1$ to $C_6$ alkyl;
- a formyl group;
- a $C_6$ to $C_8$ aryl optionally substituted with an alkoxy; or
- a 5 or 6-membered heteroaryl optionally substituted with:

a $C_1$ to $C_6$ alkyl,
a $C_6$ to $C_8$ aryl optionally substituted with an alkoxy or one or more halogens, or
a 5 to 6 membered heteroaryl;

Y is:
a hydrogen;
a haloalkyl;
a halogen;
an amino optionally substituted with one or more $C_1$ to $C_6$ alkyls;
a benzofuran;
a benzothiophene;
a dibenzofuran;
a dibenzothiophene;
a benzothiazole;
a naphthalene;
an indole, optionally substituted on the nitrogen with a $C_1$ to $C_6$ alkyl;

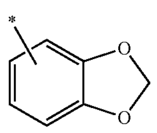
;
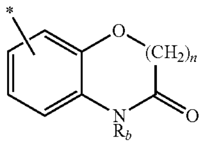
, where $R_b$ is a hydrogen or a $C_1$ to $C_6$ alkyl, and n is 0 or 1;

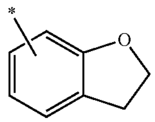
;

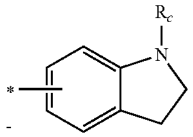
, where $R_c$ is a hydrogen, a —$CONHR_x$, where $R_x$ is as defined above, or an —$SO_2R_x$, where $R_x$ is as defined above; or

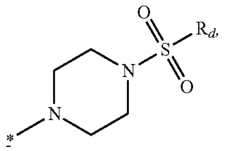

where $R_d$ is a $C_1$ to $C_6$ alkyl or a $C_6$ to $C_8$ aryl;
a —$NHCOR_e$ group, where $R_e$ is:
a $C_1$ to $C_6$ alkyl;
a $C_6$ to $C_8$ aryl optionally substituted with:
a $C_1$ to $C_6$ alkyl,
an alkoxy,
a cyano group, a nitro group, or
a halogen;
a —$NHCOOR_x$ group, where $R_x$ is as defined above;
a —$CH_2O$—$R_f$ group, where $R_f$ is a $C_6$ to $C_8$ aryl;
a —$NR_gR_h$ group, where $R_g$ is a $C_1$ to $C_6$ alkyl or a hydrogen and $R_h$ is a $C_6$ to $C_8$ aryl optionally substituted with an alkoxy;
a $C_1$ to $C_6$ alkyl;
a 5 or 6 membered heteroaryl, optionally substituted with:
a $C_1$ to $C_6$ alkyl, optionally substituted with a $C_6$ to $C_8$ aryl,
a $C_6$ to $C_8$ aryl, optionally substituted with —$COOR_x$, where $R_x$ is as defined above, or
an amino group;
a 5 or 6 membered heterocycle optionally substituted with:
a —$COOR_x$ group, where $R_x$ is as defined above, or
a —$NHCOOR_x$ group, where $R_x$ is as defined above;
a $C_6$ to $C_8$ aryl, optionally substituted with one or more of the following:
an alkoxy, optionally substituted with:
an alkoxy,
a hydroxy,
one or more halogens,
a 5 or 6 membered heterocycle, optionally substituted with:
a $C_1$ to $C_6$ alkyl, or
a hydroxy,
an amino group optionally substituted with one or more $C_1$ to $C_6$ alkyls,
a —$NR_iSO_2R_x$ group, where $R_x$ is as defined above and $R_i$ is:
a hydrogen,
a $C_1$ to $C_6$ alkyl,
a —$COR_x$ group, where $R_x$ is as defined above,
a haloalkyl, or
a haloalkoxy,
a —$NR_jCOR_k$ group, where $R_k$ is:
a $C_1$ to $C_6$ alkyl,
a hydrogen, or
an amino optionally substituted with one or more $C_1$ to $C_6$ alkyls, and $R_j$ is:
a hydrogen,
a $C_1$ to $C_6$ alkyl,
a —$COR_x$ group, where $R_x$ is as defined above,
a haloalkyl, or
a haloalkoxy,
a —$N{=}N^+{=}N^-$ group, or
a —$COR_l$, where $R_l$ is a 5 or 6 membered heterocycle optionally substituted with a hydroxy,
an amino optionally substituted with one or more $C_1$ to $C_6$ alkyls,
a nitro group,
a $C_1$ to $C_6$ alkyl group, optionally substituted with:
a —$NHSO_2R_x$ group, where $R_x$ is as defined above, or
a —$NR_xSO_2R_x$ group, where $R_x$ is as defined above,
a haloalkoxy,
a halogen,
a hydroxy,
a —$COOR_x$ group, where $R_x$ is as defined above,
a —$COR_m$ group, where $R_m$ is:
an amino optionally substituted with one or more $C_1$ to $C_6$ alkyls, where the $C_1$ to $C_6$ alkyls are optionally substituted with:
a hydroxy
a 5 or 6 membered heterocycle,
an amino optionally substituted with one or more $C_1$ to $C_6$ alkyls,
an alkoxy, a 3 to 7 membered heterocycle, optionally substituted with a $C_1$ to $C_6$ alkyl, optionally substituted with a dialkyl-amino, a —$NHR_n$ group, where $R_n$ is:

a —$CH_2CONH_2$, or a $C_6$ to $C_8$ aryl optionally substituted with:

an alkyl, one or more halogens, a nitro group, or one or more alkoxys, a —$NR_oCOR_p$ group, where $R_p$ is:

a $C_1$ to $C_6$ alkyl optionally substituted with:

a halogen, an alkoxy, or a $C_6$ to $C_8$ aryl, a 5 or 6 membered heterocycle, a $C_6$ to $C_8$ aryl, optionally substituted with a halogen, a 5 or 6 membered heteroaryl optionally substituted with one or more $C_1$ to $C_6$ alkyls, a hydrogen,

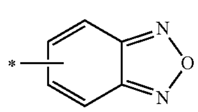

or

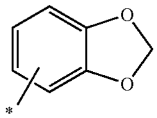

, and where $R_o$ is:

a hydrogen, a $C_1$ to $C_6$ alkyl, a —$COR_x$ group, where $R_x$ is as defined above, a haloalkyl, or a haloalkoxy, a —$NR_qCONR_qR_r$ group, where $R_q$ is:

a hydrogen, a $C_1$ to $C_6$ alkyl, a haloalkyl, a haloalkoxy, or a —$COR_x$ group, where $R_x$ is as defined above, and where $R_r$ is:

a $C_6$ to $C_8$ aryl optionally substituted with:

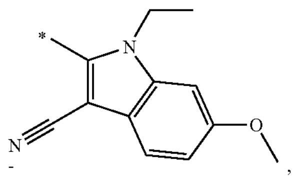

, a $C_1$ to $C_6$ alkyl, a haloalkyl, a —$OR_s$ group, where $R_s$ is a $C_6$ to $C_8$ aryl, or a —$COOR_x$ group, where $R_x$ is as defined above, a $C_1$ to $C_6$ alkyl optionally substituted with one or more of the following:

a halogen, an alkylene, a $C_6$ to $C_8$ aryl, or a —$COOR_x$ group, where $R_x$ is as defined above, a —$COOR_x$ group, where $R_x$ is as defined above, a —$NR_tCOOR_u$ group, where $R_u$ is:

a $C_1$ to $C_{12}$ alkyl, optionally substituted with:

a $C_6$ to $C_8$ aryl optionally substituted with a $C_1$ to $C_6$ alkyl or an alkoxy, an alkylene, an alkoxy, an alkyne, a halogen, or a 5 or 6 membered heterocycle, a $C_6$ to $C_8$ aryl, optionally substituted with:

an alkoxy, a halogen, or a $C_1$ to $C_6$ alkyl, or a 5 or 6 membered heterocycle, and $R_t$ is:

a hydrogen, a $C_1$ to $C_6$ alkyl, a —$COR_x$ group, where $R_x$ is as defined above, a haloalkyl, or a haloalkoxy, a —$NR_vSO_2R_w$ group, where $R_v$ is:

a hydrogen, a —$COR_x$, where $R_x$ is as defined above, or a $C_1$ to $C_6$ alkyl, optionally substituted with:

a halogen, a —$COR_x$ group, where $R_x$ is as defined above, a —$OCOR_x$ group, where $R_x$ is as defined above, a hydroxyl, a hydroxyl, or an alkoxy, and where $R_w$ is:

a $C_1$ to $C_6$ alkyl optionally substituted with:

a halogen, a haloalkyl, a $C_6$ to $C_8$ aryl, or a 5 or 6 membered heterocycle, a $C_2$ to $C_6$ alkylene, an alkyl- or dialkyl-amino optionally substituted with a halogen, a 5 or 6 membered heterocycle, or a 5 or 6 membered heteroaryl optionally substituted with:

a $C_1$ to $C_6$ alkyl, a 5 or 6 membered heterocycle, or

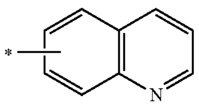

,

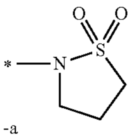

,

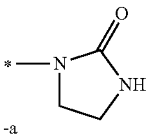

,

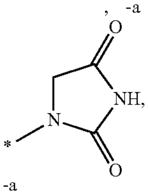

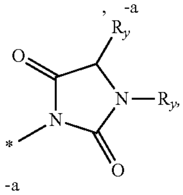

optionally substituted with a $C_1$ to $C_6$ alkyl, where $R_y$ is a $C_1$ to $C_6$ alkyl or hydrogen,

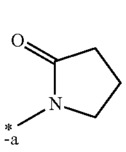
,
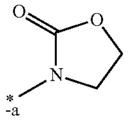
,
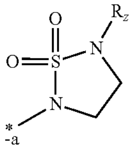
, where $R_z$ is hydrogen or a $C_1$ to $C_6$ alkyl, optionally substituted with a $C_6$ to $C_8$ aryl, a —$SR_x$ group, where $R_x$ is as defined above, a —$SO_2R_{aa}$ group, where $R_{aa}$ is:

- a $C_1$ to $C_6$ alkyl,
- an amino group,
- an alkyl- or dialkyl-amino group optionally substituted with a hydroxy or a —$COOR_x$ group, where $R_x$ is as defined above,
- a 5 or 6 membered heteroaryl, a $C_6$ to $C_8$ aryl, or a —$NHR_{bb}$ group, where $R_{bb}$ is:

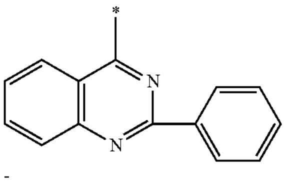
,
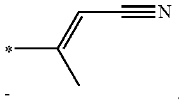
,

- a —C(═S)$NH_2$ group, or
- a —$PO(OR_x)_2$, where $R_x$ is as defined above;

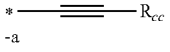

$R_{cc}$ group, where $R_{cc}$ is:

a naphthalene, a 5 or 6 membered heteroaryl, a

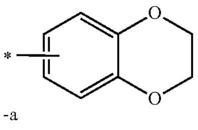
, a $C_6$ to $C_8$ aryl, optionally substituted with one or more of the following:

- an alkoxy,
- an hydroxy,
- a halogen,
- a $C_1$ to $C_6$ alkyl, optionally substituted with a cyano group,
- an amino optionally substituted with one or more $C_1$ to $C_6$ alkyls,
- a —$NHPOR_xR_x$, where $R_x$ is as defined above,
- a —$NR_{ee}CONR_{ff}R_{ff}$ group, where $R_{ee}$ is a hydrogen or a $C_1$ to $C_6$ alkyl, optionally substituted with a halogen, and $R_{ff}$ is:
  - a hydrogen,
  - a haloalkyl,
  - a haloalkoxy,

- a $C_1$ to $C_6$ alkyl, or
  - a —$COR_x$, where $R_x$ is as defined above,
- a —$NR_{gg}COR_{hh}$ group, where $R_{hh}$ is:
  - a hydrogen,
  - a $C_1$ to $C_6$ alkyl optionally substituted with:
    - an alkoxy,
    - a halogen, or
    - an amino optionally substituted with one or more $C_1$ to $C_6$ alkyls,
  - an amino optionally substituted with one or more $C_1$ to $C_6$ alkyls, where the alkyls are optionally substituted with a halogen,
  - a 5 or 6 membered heterocycle,
  - a 5 or 6 membered heteroaryl,
- and $R_{gg}$ is:
  - a hydrogen,
  - a $C_1$ to $C_6$ alkyl,
  - a haloalkyl,
  - a haloalkoxy, or
  - a —$COR_x$ group, where $R_x$ is as defined above,
- a haloalkyl,
- 5 or 6 membered heterocycle groups,
- an amino optionally substituted with one or more $C_1$ to $C_6$ alkyls,
- a —$NR_{ii}SO_2R_x$ group, where $R_x$ is as defined above, and $R_{ii}$ is:
  - a hydrogen,
  - a $C_1$ to $C_6$ alkyl,
  - a haloalkyl,
  - a haloalkoxy,
  - a —$COR_x$ group, where $R_x$ is as defined above;

Z is:

- a hydrogen;
- a $C_1$ to $C_6$ alkyl optionally substituted with:
  - an alkoxy,
  - one or more halogens, or
  - a $C_6$ to $C_8$ aryl;
- a $C_2$ to $C_6$ alkylene;
- a $C_6$ to $C_8$ aryl optionally substituted with an alkoxy or one or more $C_1$ to $C_6$ alkyls;
- a —$COOR_x$ group, where $R_x$ is as defined above; or

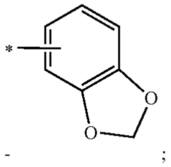
;

R is a hydrogen, a halogen or an alkoxy;

$R_1$ is:

- a hydrogen;
- a hydroxy;
- a halogen;
- a haloalkyl;
- a nitro group;
- a 5 or 6 membered heteroaryl;
- a 5 or 6 membered heterocycle;
- an alkoxy optionally substituted with:
  - one or more halogens,
  - a $C_6$ to $C_8$ aryl, or
  - a 5 or 6 membered heterocycle;
- a $C_6$ to $C_8$ aryl optionally substituted with an alkoxy;
- a —$COR_x$ group, where $R_x$ is as defined above;

a $C_1$ to $C_6$ alkyl optionally substituted with a dialkyl-amino or a 5 or 6 membered heterocycle; or $R_1$ joins together with $R_2$ to form:

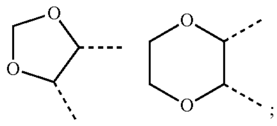

$R_2$ is:

a nitro group;

a hydrogen;

a halogen;

a hydroxy group;

a $C_1$ to $C_6$ alkyl group, optionally substituted with one or more halogens;

an amino group;

an alkoxy group optionally substituted with:

one or more halogens, an —$OCOR_x$ group, where $R_x$ is as defined above, a dialkyl-amino optionally substituted with an alkoxy, a 5 or 6 membered heterocycle group optionally substituted with a $C_1$ to $C_6$ alkyl, a 5 or 6 membered heteroaryl group, or a $C_6$ to $C_8$ aryl group;

a —$COOR_x$ group, where $R_x$ is as defined above;

a haloalkyl;

an amide group optionally substituted with:

a hydroxy group, or a $C_6$ to $C_8$ aryl;

a 5 or 6 membered heteroaryl;

a —$OCOR_x$ group, where $R_x$ is as defined above;

a —$NHCOR_{jj}$ group, where $R_{jj}$ is:

an alkoxy, or an amino optionally substituted with one or more $C_1$ to $C_6$ alkyls;

a —$OR_{kk}$ group, where $R_{kk}$ is a 5 to 6 membered heteroaryl;

a —$NHSO_2R_x$ group, where $R_x$ is as defined above; or $R_2$ joins together with $R_1$ to form:

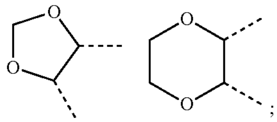

$R_3$ is:

a hydrogen; or

—$CH_2OCOR_x$, and $R_x$ is as defined above;

or a pharmaceutically acceptable salt thereof, a pharmaceutically acceptable excipient, and optionally at least one additional anti-HCV agents.

Embodiment 2

The pharmaceutical composition of Embodiment 1, wherein said optional at least one additional anti-HCV agent is selected from the group consisting of pegylated interferon, un-pegylated interferon, ribavirin or prodrugs or derivatives thereof, a glucosidase inhibitor, a protease inhibitor, a polymerase inhibitor, p7 inhibitors, an entry inhibitor, a fusion inhibitor, an anti-fibrotic, a caspase inhibitor, a drug which targets inosine monophosphate dehydrogenase inhibitors (IMPDH), synthetic thymosin alpha 1, therapeutic vaccines, immunomodulators, a glycosidase inhibitor, a helicase inhibitor, a Toll-like receptor agonist, and combinations thereof.

Embodiment 3

The pharmaceutical composition of Embodiment 1, wherein X is selected from the group consisting of —hydrogen; —a cyano group; and —a —$COR_a$ group, where $R_a$ is: —a $C_1$ to $C_6$ alkyl, or —a dialkyl-amino.

Embodiment 4

The pharmaceutical composition of Embodiment 1, wherein Y is selected from the group consisting of

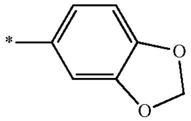
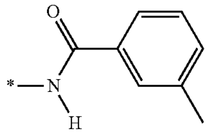
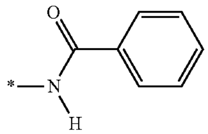
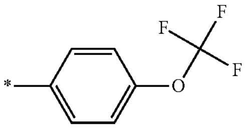
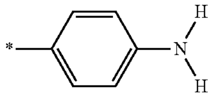
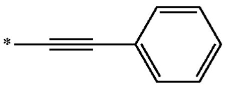
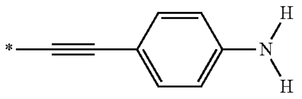
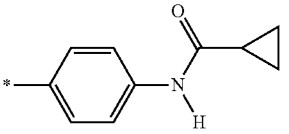
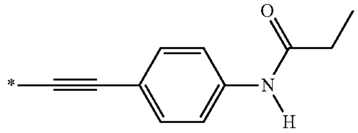
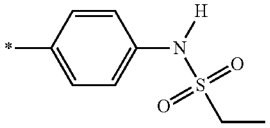
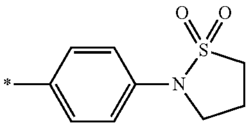
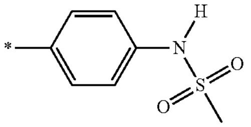
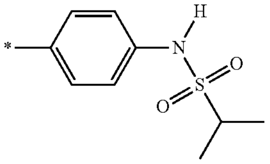
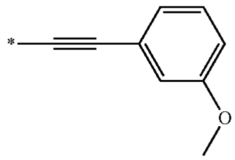
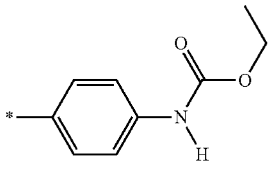

-continued
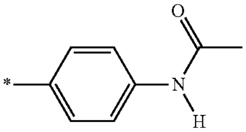
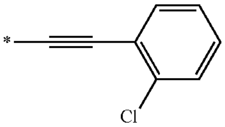
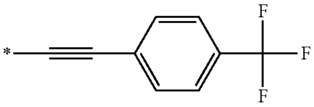
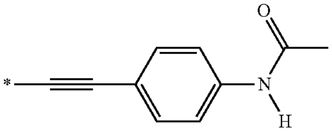
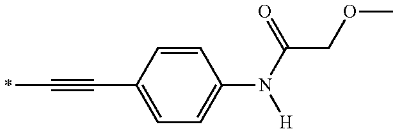
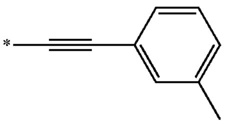
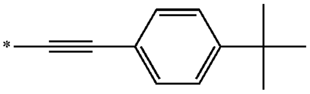
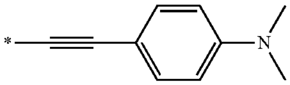
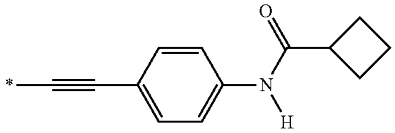
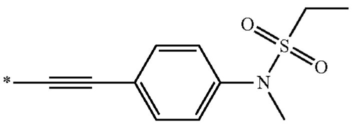
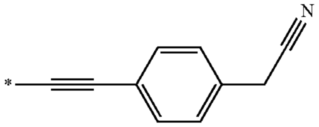
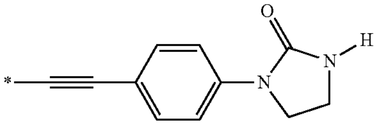
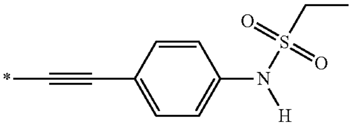
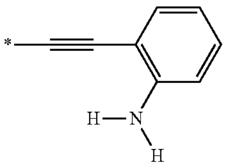
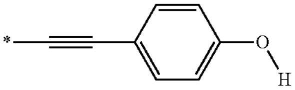
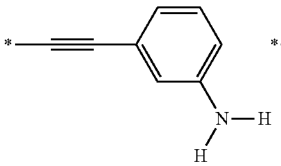
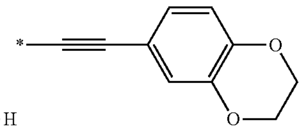
-continued
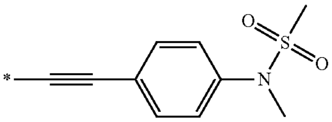
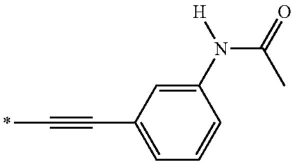
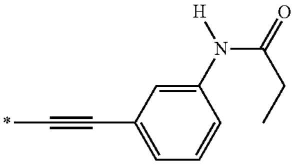
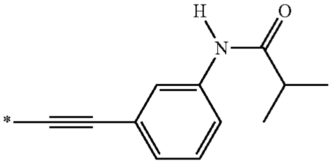
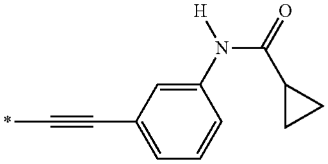
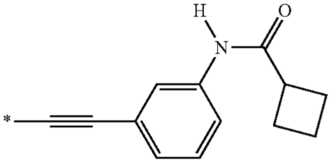
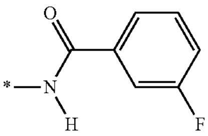
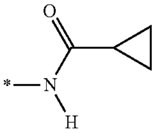
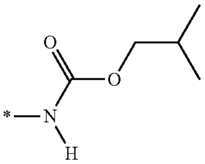
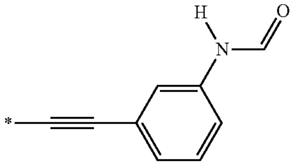
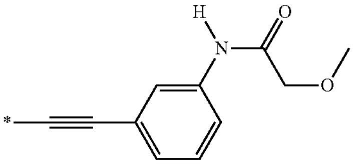
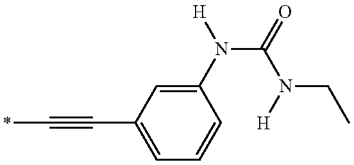

-continued
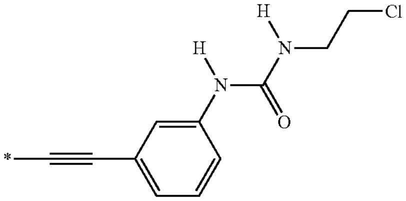
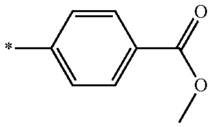
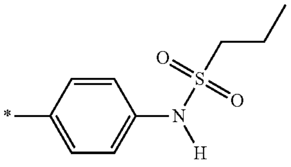
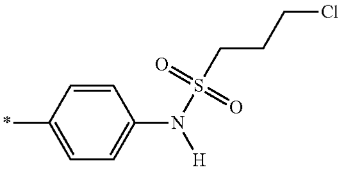
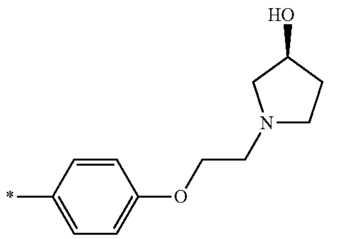
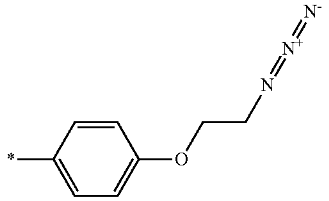
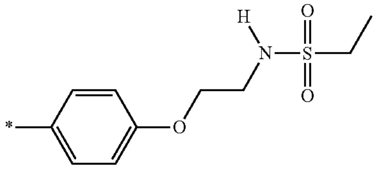
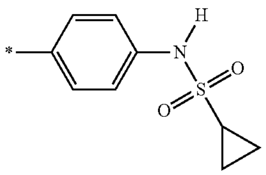
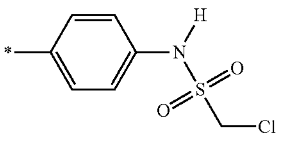
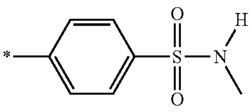
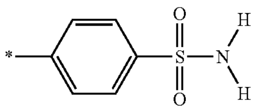
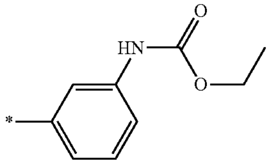
-continued
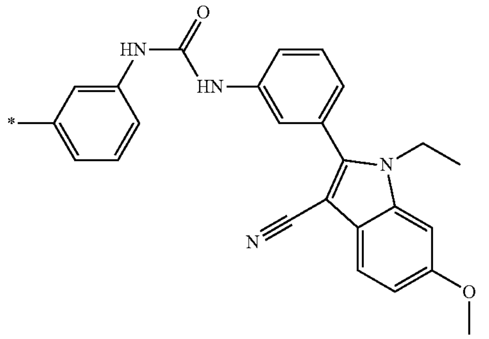
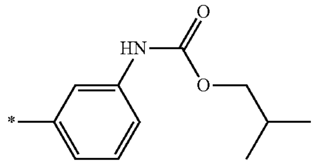
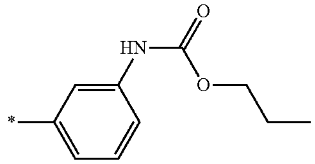
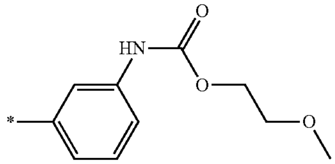
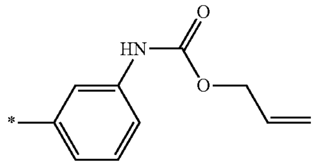
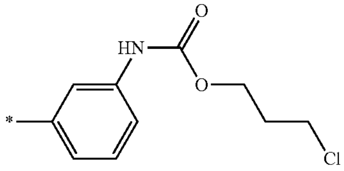
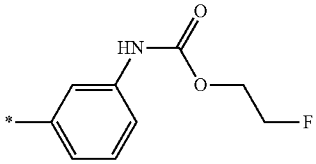
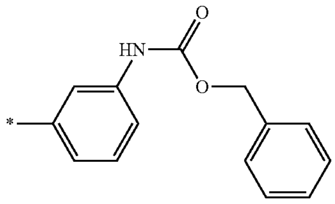
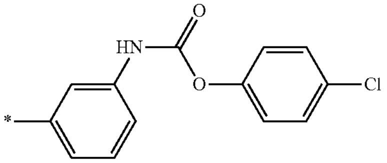

-continued
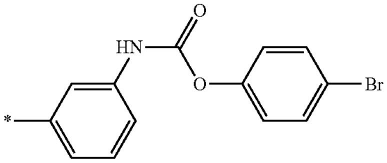
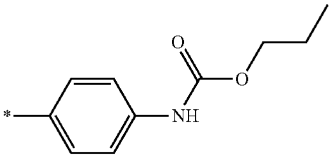
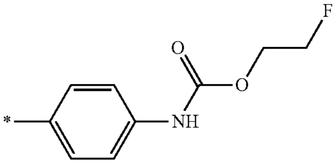
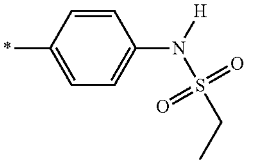
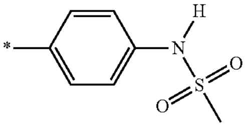
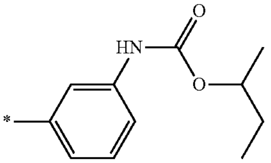
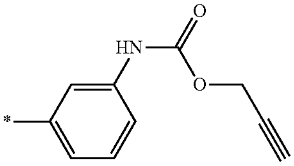
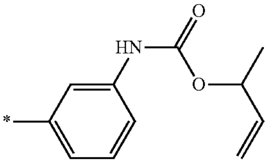
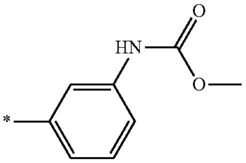
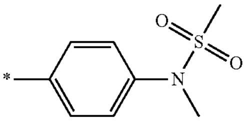
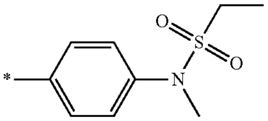
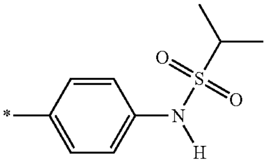
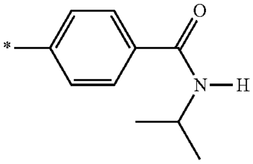
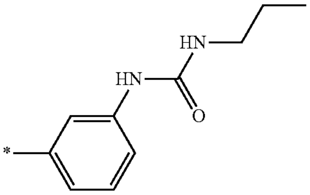
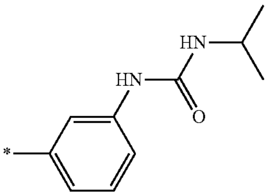
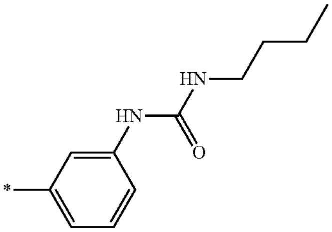
-continued
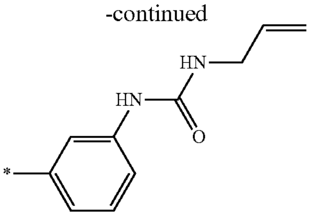
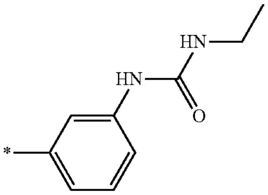
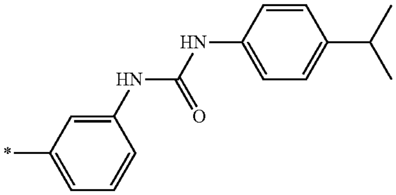
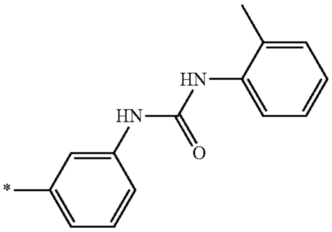
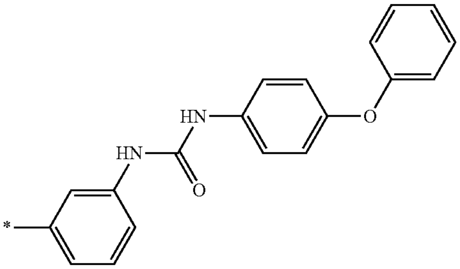
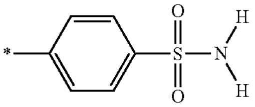
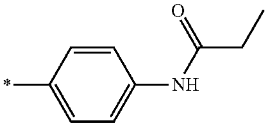
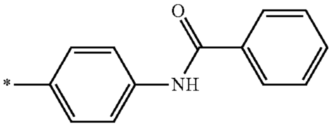
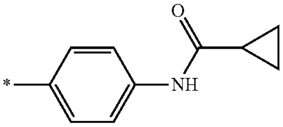
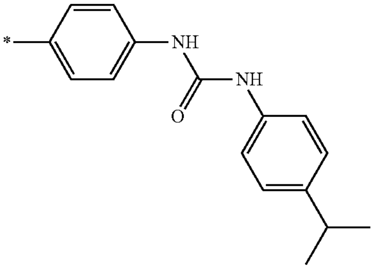

-continued
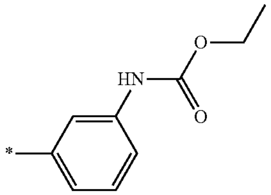
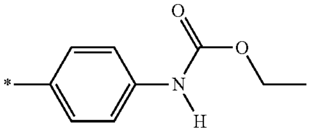
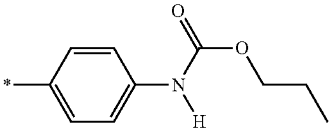
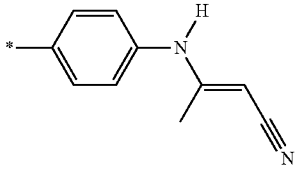
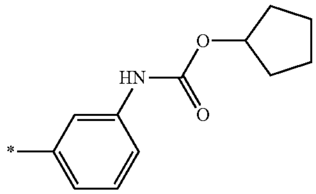
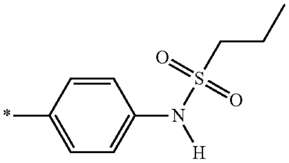
*—I
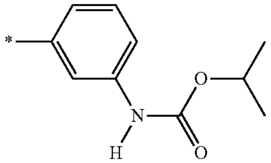
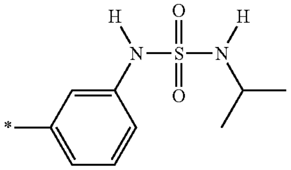
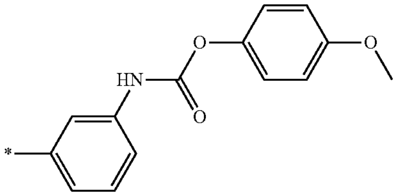
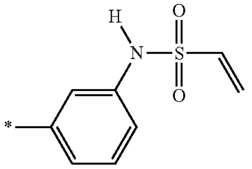
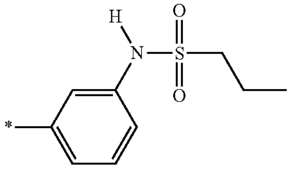
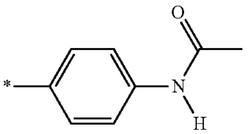
-continued
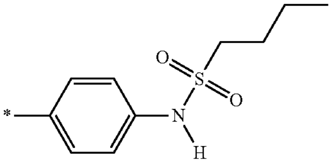
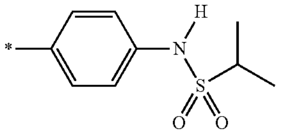
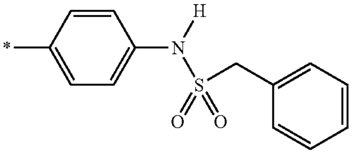
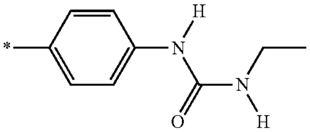
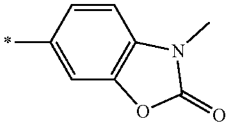
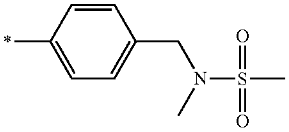
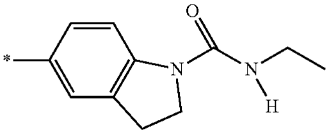
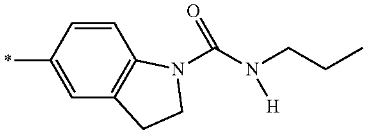
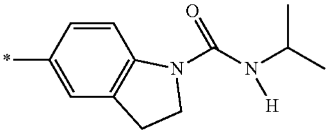
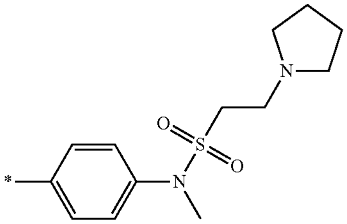
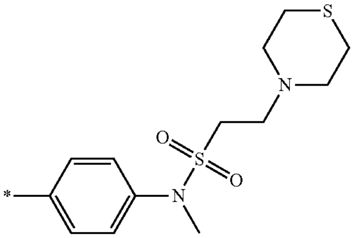
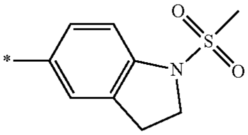
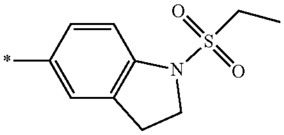

-continued
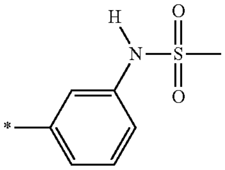
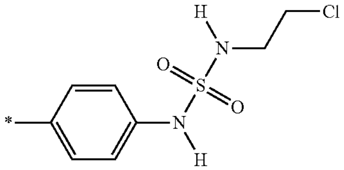
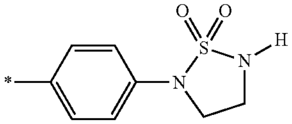
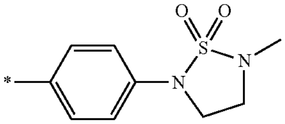
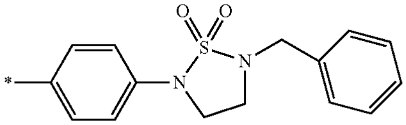
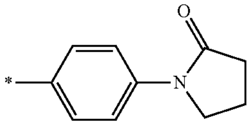
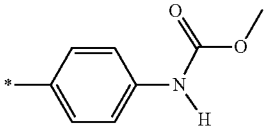
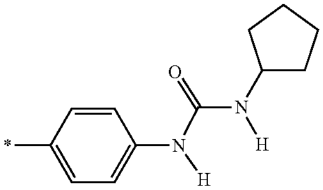
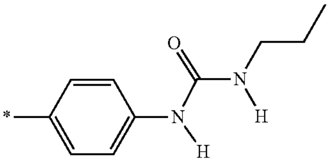
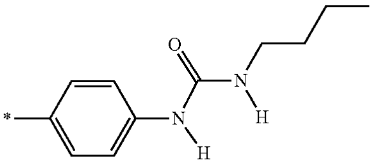
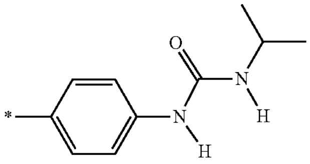
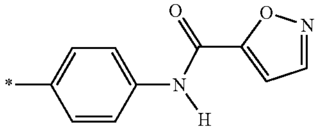
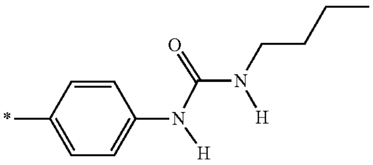
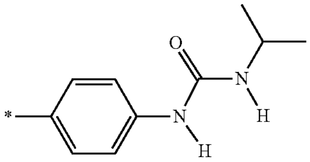
-continued
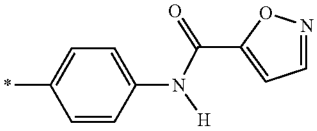
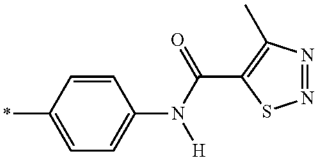
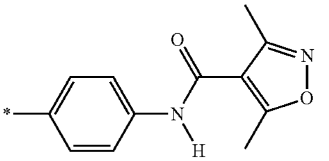
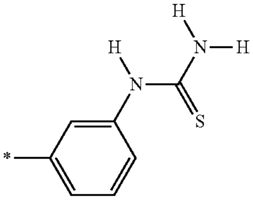
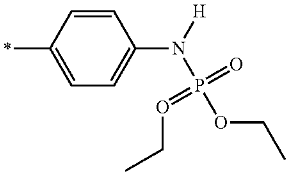
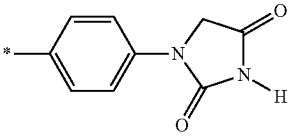
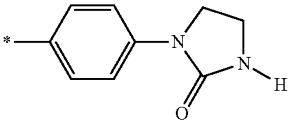
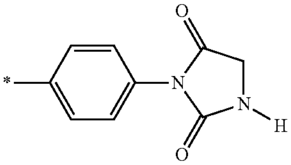
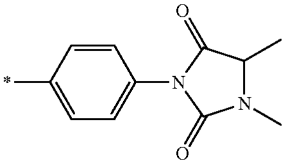
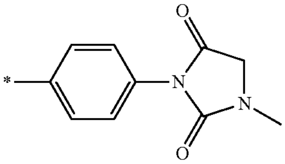
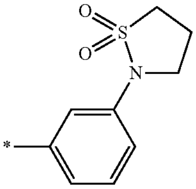
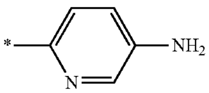

-continued
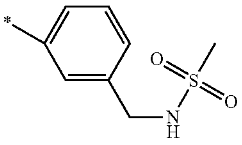
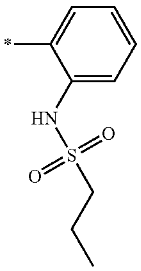
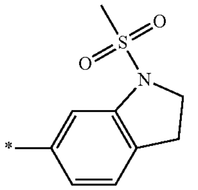
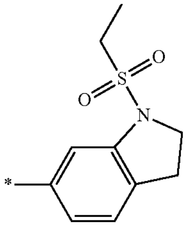
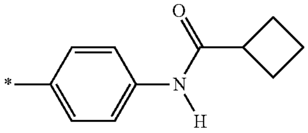
*—H
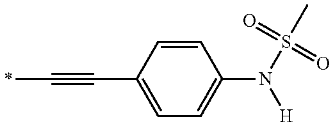
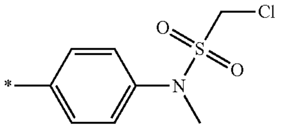
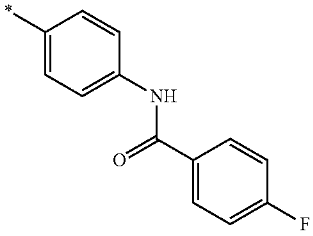
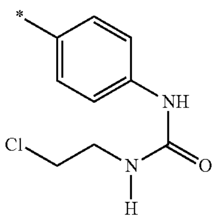
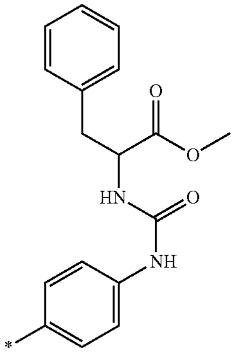
-continued
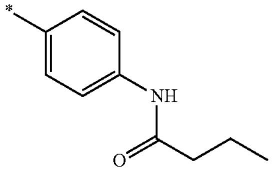
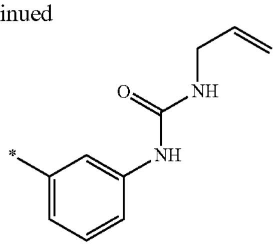
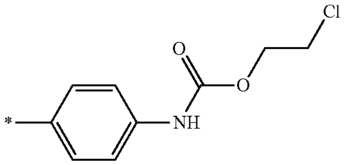
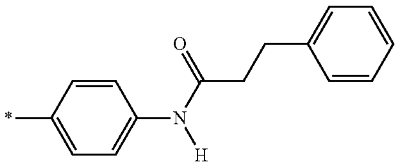
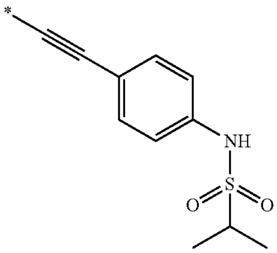
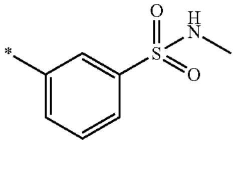
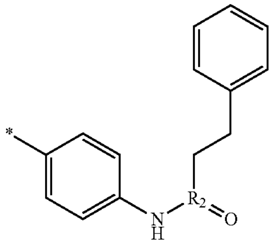
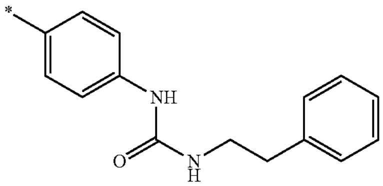
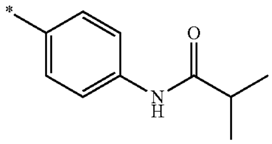
Embodiment 5
The pharmaceutical composition of Embodiment 1, wherein Y is selected from the group consisting of
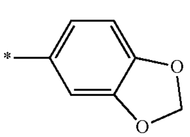
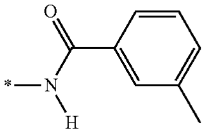

-continued
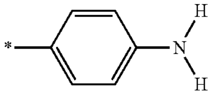
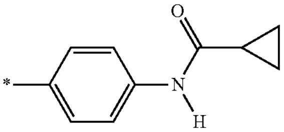
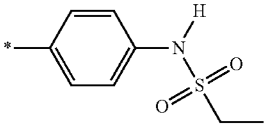
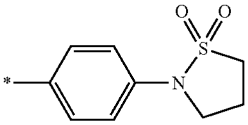
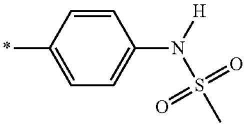
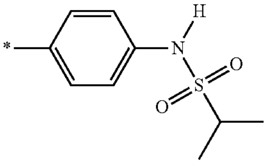
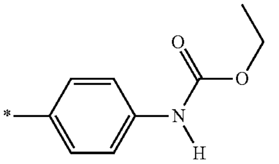
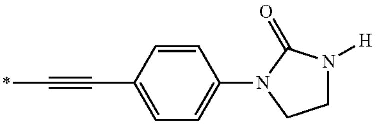
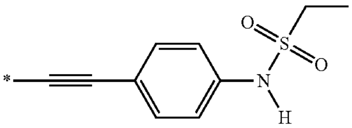
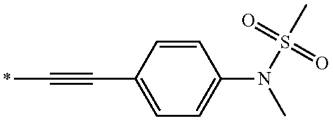
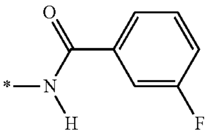
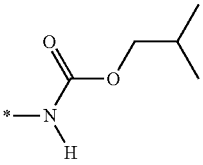
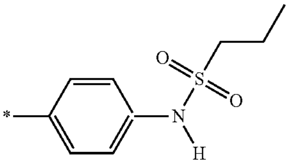
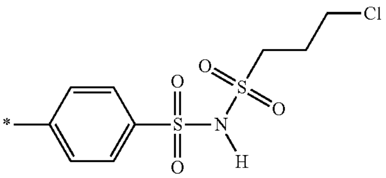
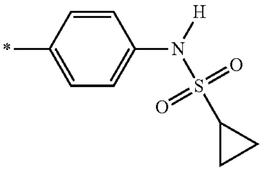
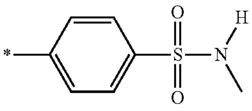
-continued
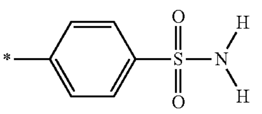
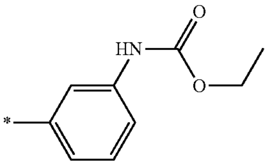
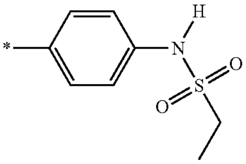
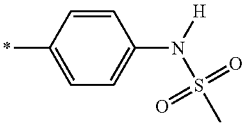
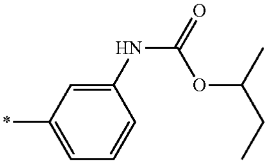
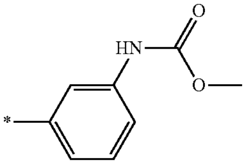
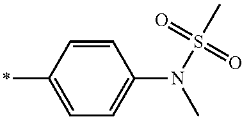
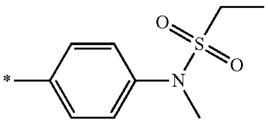
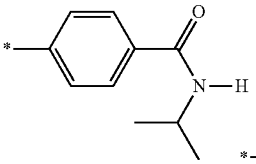
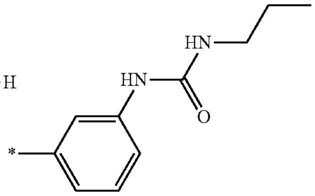
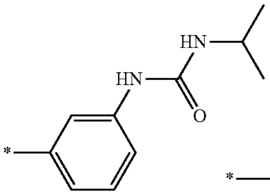
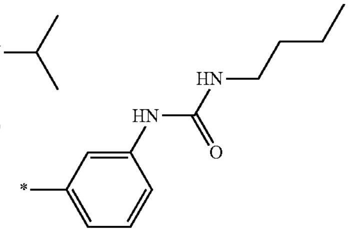
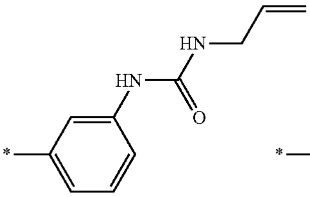
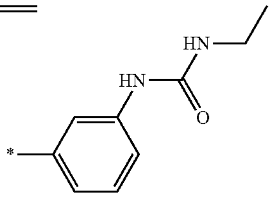
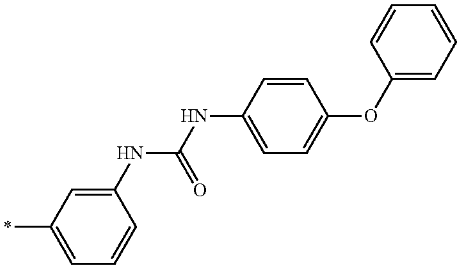
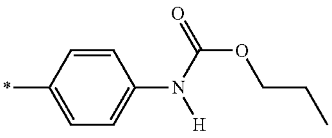
*—I -continued
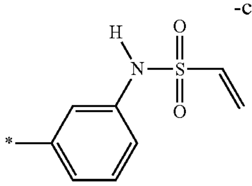
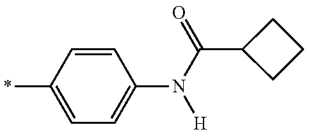
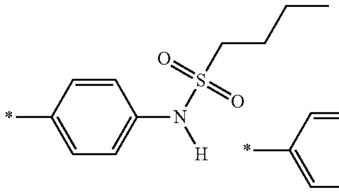
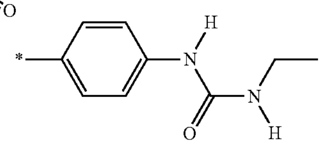
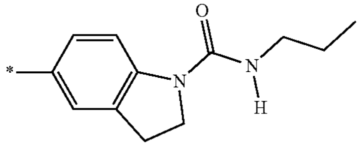
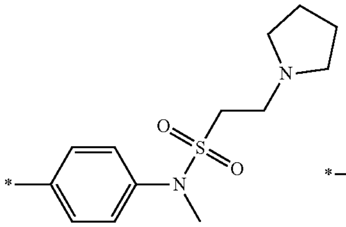
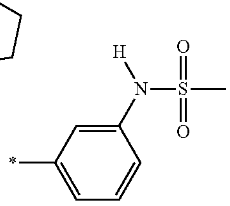
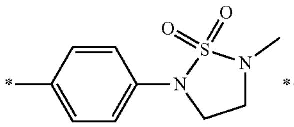
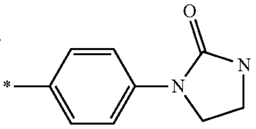
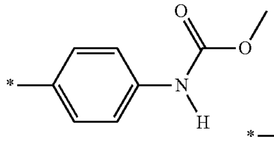
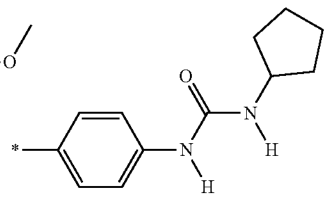
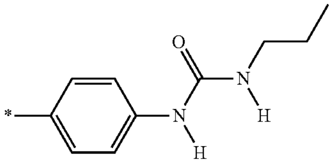
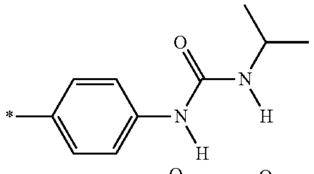
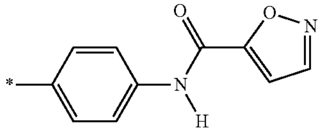
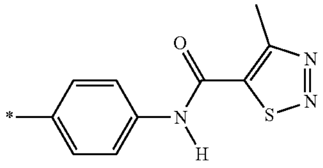
-continued
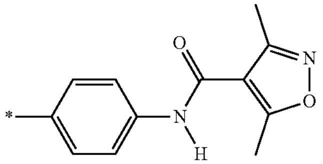
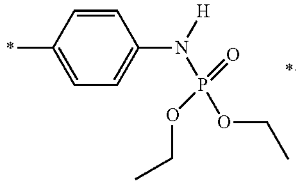
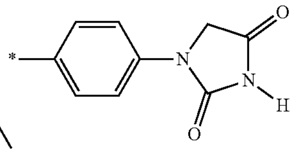
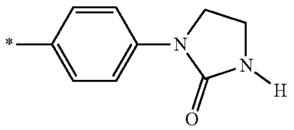
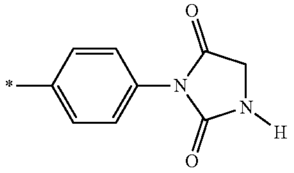
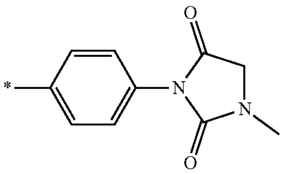
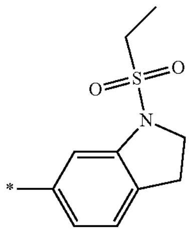
*—H
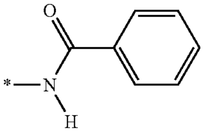
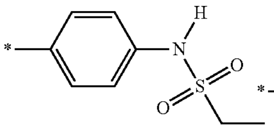
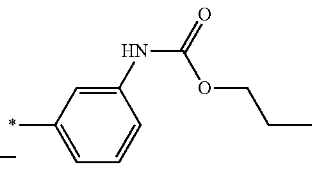
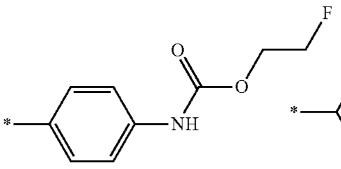
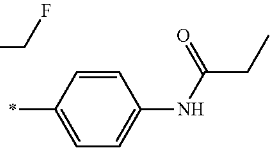
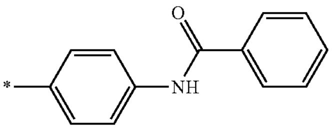
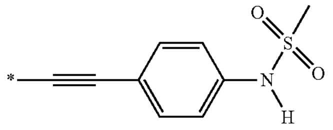

-continued

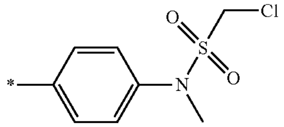
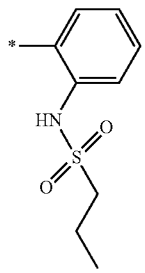
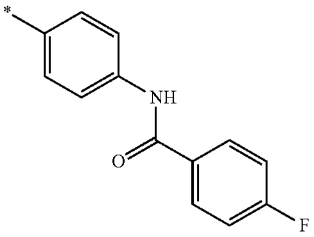
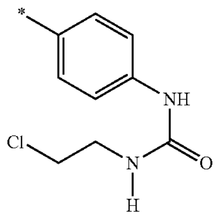
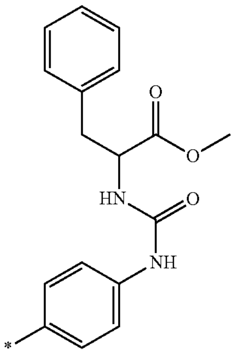
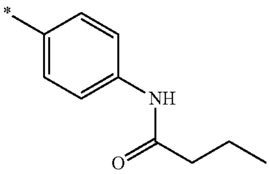
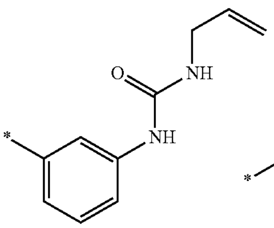
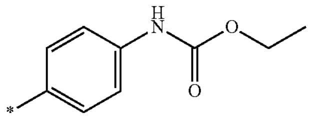
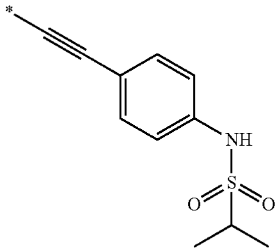
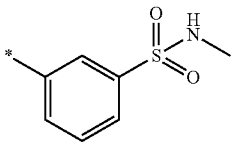
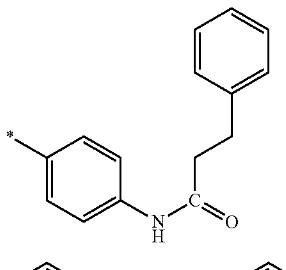
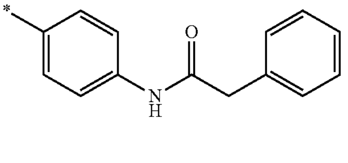

-continued

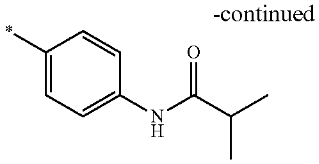
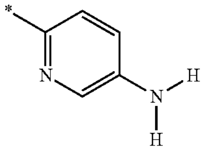
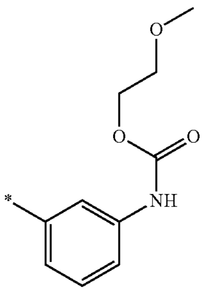
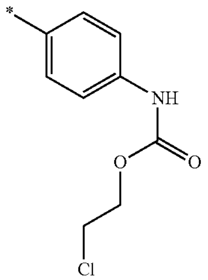
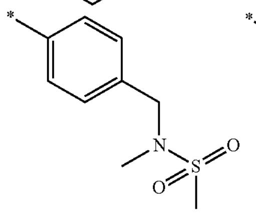
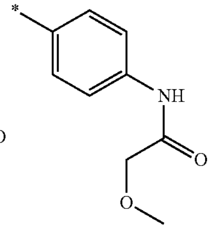
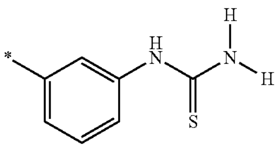
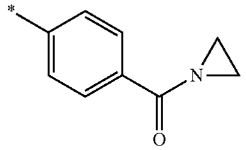
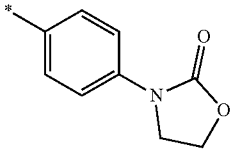

Embodiment 6

The pharmaceutical composition of Embodiment 1, wherein R is a hydrogen.

Embodiment 7

The pharmaceutical composition of Embodiment 1, wherein $R_1$ is selected from the group consisting of a hydrogen, a nitro group, or an alkoxy.

Embodiment 8

The pharmaceutical composition of Embodiment 1, wherein $R_2$ is selected from the group consisting of a hydroxy, a hydrogen, a haloalkyl group, a nitro group, an amide, —CO-$OR_x$ or an alkoxy.

Embodiment 9

The pharmaceutical composition of Embodiment 1, wherein $R_3$ is a hydrogen.

Embodiment 10

The pharmaceutical composition of Embodiment 1, wherein said compound is selected from the compounds of Table A.

Embodiment 11

The pharmaceutical composition of Embodiment 1 wherein said compound is selected from the compounds of Table B or a pharmaceutically acceptable salt thereof and a pharmaceutically acceptable excipient.

Embodiment 12

The pharmaceutical composition of Embodiment 17, wherein said composition further comprises at least one additional anti-HCV agent selected from the group consisting of pegylated interferon, un-pegylated interferon, ribavirin or prodrugs or derivatives thereof, a glucosidase inhibitor, a protease inhibitor, a polymerase inhibitor, p7 inhibitors, an entry inhibitor, a fusion inhibitor, an anti-fibrotic, a caspase inhibitor, a drug which targets inosine monophosphate dehydrogenase inhibitors (IMPDH), synthetic thymosin alpha 1, therapeutic vaccines, immunomodulators, a glycosidase inhibitor, a helicase inhibitor, a Toll-like receptor agonist, and combinations thereof.

Embodiment 13

A method for treating a subject for a Hepatitis C viral (HCV) infection comprising administering to said subject a pharmaceutical composition comprising an HCV inhibitory amount of at least one compound having the following formula:

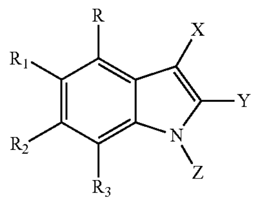

wherein:

X is:

- hydrogen;
- a nitro group;
- a cyano group;
- a —$COR_a$ group, where $R_a$ is:
  - a $C_1$ to $C_6$ alkyl,
  - a $C_6$ to $C_8$ aryl optionally substituted with an alkoxy or a halogen, or
  - a dialkyl-amino;
- a —$COOR_x$ group, where $R_x$ is a $C_1$ to $C_6$ alkyl;
- a formyl group;
- a $C_6$ to $C_8$ aryl optionally substituted with an alkoxy; or
- a 5 or 6-membered heteroaryl optionally substituted with:
  - a $C_1$ to $C_6$ alkyl,
  - a $C_6$ to $C_8$ aryl optionally substituted with an alkoxy or one or more halogens, or
  - a 5 to 6 membered heteroaryl;

Y is:

- a hydrogen;
- a haloalkyl;
- a halogen;
- an amino optionally substituted with one or more $C_1$ to $C_6$ alkyls;
- a benzofuran;
- a benzothiophene;
- a dibenzofuran;
- a dibenzothiophene;
- a benzothiazole;
- a naphthalene;
- an indole, optionally substituted on the nitrogen with a $C_1$ to $C_6$ alkyl;

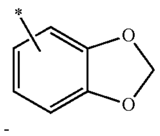 ; 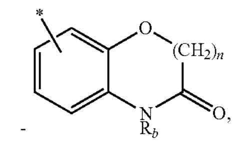

where $R_b$ is a hydrogen or a $C_1$ to $C_6$ alkyl, and n is 0 or 1;

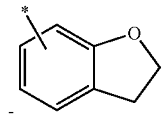 ; 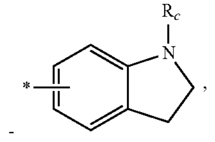

where $R_c$ is a hydrogen, a —$CONHR_x$, where $R_x$ is as defined above, or an —$SO_2R_x$, where $R_x$ is as defined above; or

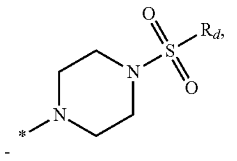

where $R_d$ is a $C_1$ to $C_6$ alkyl or a $C_6$ to $C_8$ aryl;

- a —$NHCOR_e$ group, where $R_e$ is:
  - a $C_1$ to $C_6$ alkyl;
  - a $C_6$ to $C_8$ aryl optionally substituted with:
    - a $C_1$ to $C_6$ alkyl,
    - an alkoxy,
    - a cyano group,
    - a nitro group, or
    - a halogen;
- a —$NHCOOR_x$ group, where $R_x$ is as defined above;
- a —$CH_2O$—$R_f$ group, where $R_f$ is a $C_6$ to $C_8$ aryl;
- a —$NR_gR_h$ group, where $R_g$ is a $C_1$ to $C_6$ alkyl or a hydrogen and $R_h$ is a $C_6$ to $C_8$ aryl optionally substituted with an alkoxy;
- a $C_1$ to $C_6$ alkyl;
- a 5 or 6 membered heteroaryl, optionally substituted with:
  - a $C_1$ to $C_6$ alkyl, optionally substituted with a $C_6$ to $C_8$ aryl,
  - a $C_6$ to $C_8$ aryl, optionally substituted with —$COOR_x$, where $R_x$ is as defined above, or
  - an amino group;
- a 5 or 6 membered heterocycle optionally substituted with:
  - a —$COOR_x$ group, where $R_x$ is as defined above, or
  - a —$NHCOOR_x$ group, where $R_x$ is as defined above;
- a $C_6$ to $C_8$ aryl, optionally substituted with one or more of the following:
  - an alkoxy, optionally substituted with:
    - an alkoxy,
    - a hydroxy, one or more halogens,
a 5 or 6 membered heterocycle, optionally substituted with:
a $C_1$ to $C_6$ alkyl, or
a hydroxy,
an amino group optionally substituted with one or more $C_1$ to $C_6$ alkyls,
a —$NR_iSO_2R_x$ group, where $R_x$ is as defined above and $R_i$ is:
a hydrogen,
a $C_1$ to $C_6$ alkyl,
a —$COR_x$ group, where $R_x$ is as defined above,
a haloalkyl, or
a haloalkoxy,
a —$NR_jCOR_k$ group, where $R_k$ is:
a $C_1$ to $C_6$ alkyl,
a hydrogen, or
an amino optionally substituted with one or more $C_1$ to $C_6$ alkyls,
and $R_j$ is:
a hydrogen,
a $C_1$ to $C_6$ alkyl,
a —$COR_x$ group, where $R_x$ is as defined above,
a haloalkyl, or
a haloalkoxy,
a —$N{=}N^+{=}N^-$ group, or
a —$COR_l$, where $R_l$ is a 5 or 6 membered heterocycle optionally substituted with a hydroxy,
an amino optionally substituted with one or more $C_1$ to $C_6$ alkyls,
a nitro group,
a $C_1$ to $C_6$ alkyl group, optionally substituted with:
a —$NHSO_2R_x$ group, where $R_x$ is as defined above, or
a —$NR_xSO_2R_x$ group, where $R_x$ is as defined above,
a haloalkoxy,
a halogen,
a hydroxy,
a —$COOR_x$ group, where $R_x$ is as defined above,
a —$COR_m$ group, where $R_m$ is:
an amino optionally substituted with one or more $C_1$ to $C_6$ alkyls, where the $C_1$ to $C_6$ alkyls are optionally substituted with:
a hydroxy
a 5 or 6 membered heterocycle,
an amino optionally substituted with one or more $C_1$ to $C_6$ alkyls,
an alkoxy,
a 3 to 7 membered heterocycle, optionally substituted with a $C_1$ to $C_6$ alkyl, optionally substituted with a dialkyl-amino,
a —$NHR_n$ group, where $R_n$ is:
a —$CH_2CONH_2$, or
a $C_6$ to $C_8$ aryl optionally substituted with:
an alkyl,
one or more halogens,
a nitro group, or
one or more alkoxys,
a —$NR_oCOR_p$ group, where $R_p$ is:
a $C_1$ to $C_6$ alkyl optionally substituted with:
a halogen,
an alkoxy, or
a $C_6$ to $C_8$ aryl,
a 5 or 6 membered heterocycle,
a $C_6$ to $C_8$ aryl, optionally substituted with a halogen,
a 5 or 6 membered heteroaryl optionally substituted with one or more $C_1$ to $C_6$ alkyls,
a hydrogen,

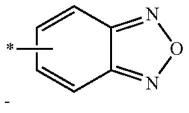
or
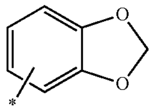
, and where $R_o$ is:
a hydrogen,
a $C_1$ to $C_6$ alkyl,
a —$COR_x$ group, where $R_x$ is as defined above,
a haloalkyl, or
a haloalkoxy,
a —$NR_qCONR_qR_r$ group, where $R_q$ is:
a hydrogen,
a $C_1$ to $C_6$ alkyl,
a haloalkyl,
a haloalkoxy, or
a —$COR_x$ group, where $R_x$ is as defined above,
and where $R_r$ is:
a $C_6$ to $C_8$ aryl optionally substituted with:

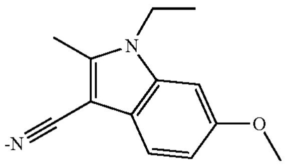
, a $C_1$ to $C_6$ alkyl,
a haloalkyl,
a —$OR_s$ group, where $R_s$ is a $C_6$ to $C_8$ aryl, or
a —$COOR_x$ group, where $R_x$ is as defined above,
a $C_1$ to $C_6$ alkyl optionally substituted with one or more of the following:
a halogen,
an alkylene,
a $C_6$ to $C_8$ aryl, or
a —$COOR_x$ group, where $R_x$ is as defined above,
a —$COOR_x$ group, where $R_x$ is as defined above,
a —$NR_tCOOR_u$ group, where $R_u$ is:
a $C_1$ to $C_{12}$ alkyl, optionally substituted with:
a $C_6$ to $C_8$ aryl optionally substituted with a $C_1$ to $C_6$ alkyl or an alkoxy,
an alkylene,
an alkoxy,
an alkyne,
a halogen, or
a 5 or 6 membered heterocycle,
a $C_6$ to $C_8$ aryl, optionally substituted with:
an alkoxy,
a halogen, or
a $C_1$ to $C_6$ alkyl, or
a 5 or 6 membered heterocycle,
and $R_t$ is:
a hydrogen,
a $C_1$ to $C_6$ alkyl,
a —$COR_x$ group, where $R_x$ is as defined above,
a haloalkyl, or
a haloalkoxy,
a —$NR_vSO_2R_w$ group, where $R_v$ is:
a hydrogen,
a —$COR_x$, where $R_x$ is as defined above, or
a $C_1$ to $C_6$ alkyl, optionally substituted with:
a halogen,
a —$COR_x$ group, where $R_x$ is as defined above, a —$OCOR_x$ group, where $R_x$ is as defined above,
a hydroxyl,
a hydroxyl, or
an alkoxy, and where $R_w$ is:

a $C_1$ to $C_6$ alkyl optionally substituted with:
a halogen,
a haloalkyl,
a $C_6$ to $C_8$ aryl, or
a 5 or 6 membered heterocycle, a $C_2$ to $C_6$ alkylene, an alkyl- or dialkyl-amino optionally substituted with a halogen, a 5 or 6 membered heterocycle, or a 5 or 6 membered heteroaryl optionally substituted with:
a $C_1$ to $C_6$ alkyl,
a 5 or 6 membered heterocycle, or

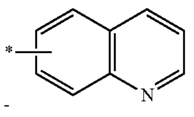
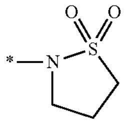,
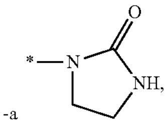
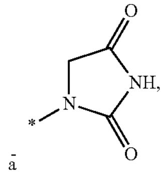
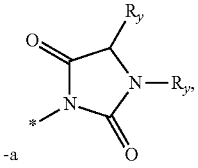

optionally substituted with a $C_1$ to $C_6$ alkyl, where $R_y$ is a $C_1$ to $C_6$ alkyl or hydrogen,

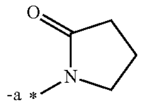,
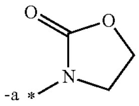,
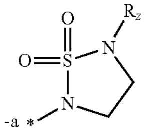, where $R_z$ is hydrogen or a $C_1$ to $C_6$ alkyl, optionally substituted with a $C_6$ to $C_8$ aryl, a —$SR_x$ group, where $R_x$ is as defined above, a —$SO_2R_{aa}$ group, where $R_{aa}$ is:
a $C_1$ to $C_6$ alkyl,
an amino group,
an alkyl- or dialkyl-amino group optionally substituted with a hydroxy or a —$COOR_x$ group, where $R_x$ is as defined above,
a 5 or 6 membered heteroaryl, a $C_6$ to $C_8$ aryl, or a —$NHR_{bb}$ group, where $R_{bb}$ is:

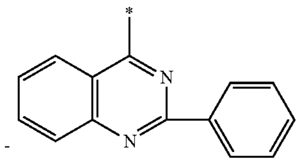,
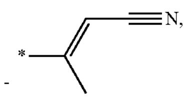

a —$C(=S)NH_2$ group, or a —$PO(OR_x)_2$, where $R_x$ is as defined above;

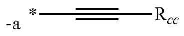

$R_{cc}$ group, where $R_{cc}$ is:
a naphthalene,
a 5 or 6 membered heteroaryl,

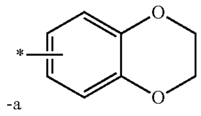, a $C_6$ to $C_8$ aryl, optionally substituted with one or more of the following:
an alkoxy,
an hydroxy,
a halogen,
a $C_1$ to $C_6$ alkyl, optionally substituted with a cyano group,
an amino optionally substituted with one or more $C_1$ to $C_6$ alkyls,
a —$NHPOR_xR_x$, where $R_x$ is as defined above,
a —$NR_{ee}CONR_{ff}R_{ff}$ group, where $R_{ee}$ is a hydrogen or a $C_1$ to $C_6$ alkyl, optionally substituted with a halogen, and $R_{ff}$ is:
a hydrogen,
a haloalkyl,
a haloalkoxy,
a $C_1$ to $C_6$ alkyl, or
a —$COR_x$, where $R_x$ is as defined above,
a —$NR_{gg}COR_{hh}$ group, where $R_{hh}$ is:
a hydrogen,
a $C_1$ to $C_6$ alkyl optionally substituted with:
an alkoxy,
a halogen, or
an amino optionally substituted with one or more $C_1$ to $C_6$ alkyls,
an amino optionally substituted with one or more $C_1$ to $C_6$ alkyls, where the alkyls are optionally substituted with a halogen,
a 5 or 6 membered heterocycle,
a 5 or 6 membered heteroaryl,
and $R_{gg}$ is:
a hydrogen,
a $C_1$ to $C_6$ alkyl,
a haloalkyl,
a haloalkoxy, or
a —$COR_x$ group, where $R_x$ is as defined above,
a haloalkyl,
5 or 6 membered heterocycle groups,
an amino optionally substituted with one or more $C_1$ to $C_6$ alkyls,
a —$NR_{ii}SO_2R_x$ group, where $R_x$ is as defined above, and $R_{ii}$ is:
a hydrogen,
a $C_1$ to $C_6$ alkyl,
a haloalkyl,
a haloalkoxy,
a —$COR_x$ group, where $R_x$ is as defined above;

Z is:

a hydrogen;

a $C_1$ to $C_6$ alkyl optionally substituted with:
an alkoxy,
one or more halogens, or
a $C_6$ to $C_8$ aryl;

a $C_2$ to $C_6$ alkylene;

a $C_6$ to $C_8$ aryl optionally substituted with an alkoxy or one or more $C_1$ to $C_6$ alkyls;

a —$COOR_x$ group, where $R_x$ is as defined above; or

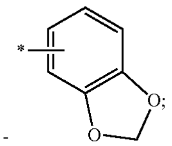

R is a hydrogen, a halogen or an alkoxy;

$R_1$ is:

a hydrogen;

a hydroxy;

a halogen;

a haloalkyl;

a nitro group;

a 5 or 6 membered heteroaryl;

a 5 or 6 membered heterocycle;

an alkoxy optionally substituted with:

one or more halogens, a $C_6$ to $C_8$ aryl, or a 5 or 6 membered heterocycle;

a $C_6$ to $C_8$ aryl optionally substituted with an alkoxy;

a —$COR_x$ group, where $R_x$ is as defined above;

a $C_1$ to $C_6$ alkyl optionally substituted with a dialkyl-amino or a 5 or 6 membered heterocycle; or $R_1$ joins together with $R_2$ to form:

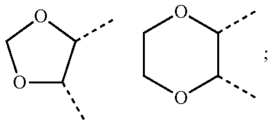

$R_2$ is:

a nitro group;

a hydrogen;

a halogen;

a hydroxy group;

a $C_1$ to $C_6$ alkyl group, optionally substituted with one or more halogens;

an amino group;

an alkoxy group optionally substituted with:

one or more halogens, an —$OCOR_x$ group, where $R_x$ is as defined above, a dialkyl-amino optionally substituted with an alkoxy, a 5 or 6 membered heterocycle group optionally substituted with a $C_1$ to $C_6$ alkyl, a 5 or 6 membered heteroaryl group, or a $C_6$ to $C_8$ aryl group;

a —$COOR_x$ group, where $R_x$ is as defined above;

a haloalkyl;

an amide group optionally substituted with:

a hydroxy group, or a $C_6$ to $C_8$ aryl;

a 5 or 6 membered heteroaryl;

a —$OCOR_x$ group, where $R_x$ is as defined above;

a —$NHCOR_{jj}$ group, where $R_{jj}$ is:

an alkoxy, or an amino optionally substituted with one or more $C_1$ to $C_6$ alkyls;

a —$OR_{kk}$ group, where $R_{kk}$ is a 5 to 6 membered heteroaryl;

a —$NHSO_2R_x$ group, where $R_x$ is as defined above; or $R_2$ joins together with $R_1$ to form:

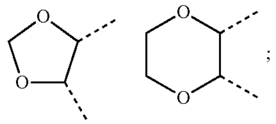

$R_3$ is:

a hydrogen; or

—$CH_2OCOR_x$, and $R_x$ is as defined above;

or a pharmaceutically acceptable salt thereof and a pharmaceutically acceptable excipient.

Embodiment 14

The method of Embodiment 13, wherein said pharmaceutical composition further comprises at least one additional anti-HCV agent.

Embodiment 15

The method of Embodiment 14, wherein said at least one additional anti-HCV agent is selected from the group consisting of pegylated interferon, un-pegylated interferon, ribavirin or prodrugs or derivatives thereof, a glucosidase inhibitor, a protease inhibitor, a polymerase inhibitor, p7 inhibitors, an entry inhibitor, a fusion inhibitor, an anti-fibrotic, a caspase inhibitor, a drug which targets inosine monophosphate dehydrogenase inhibitors (IMPDH), synthetic thymosin alpha 1, therapeutic vaccines, immunomodulators, a glycosidase inhibitor, a helicase inhibitor, a Toll-like receptor agonist, and combinations thereof.

Embodiment 16

The method of Embodiment 13, wherein X is selected from the group consisting of —hydrogen; —a cyano group; and —a —$COR_a$ group, where $R_a$ is: -a $C_1$ to $C_6$ alkyl, or —a dialkyl-amino.

Embodiment 17

The method of Embodiment 13, wherein Y is selected from the group consisting of

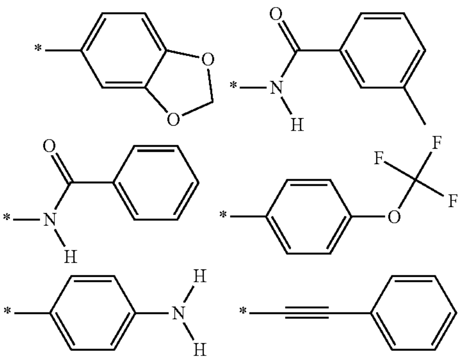

-continued
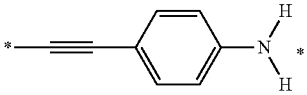
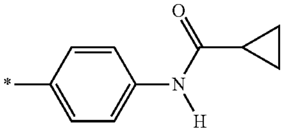
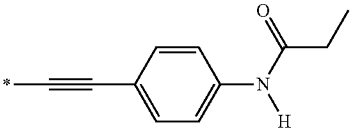
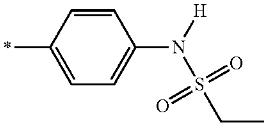
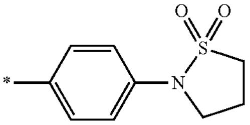
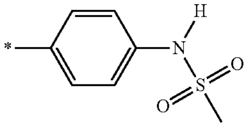
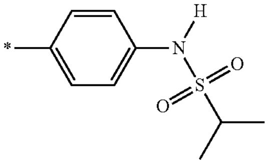
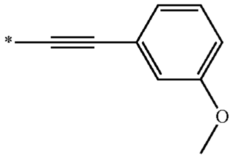
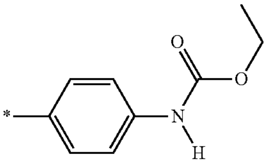
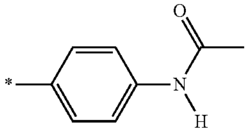
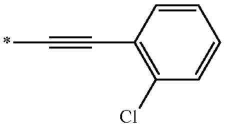
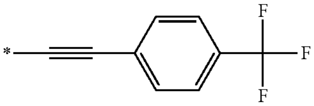
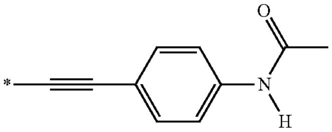
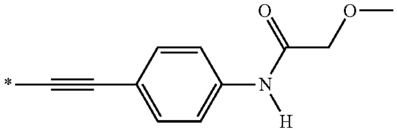
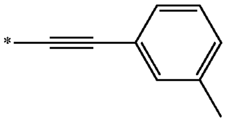
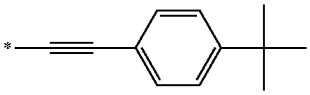
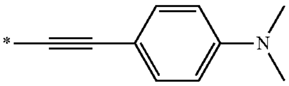
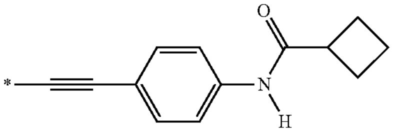
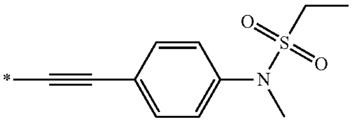
-continued
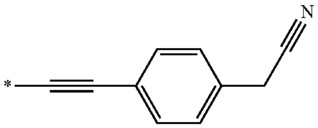
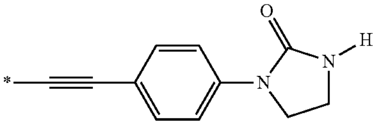
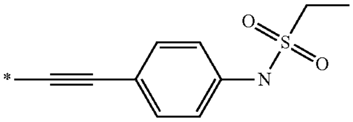
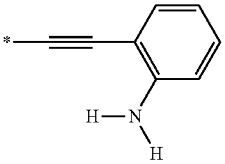
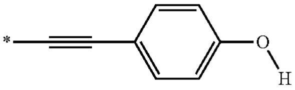
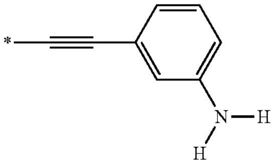
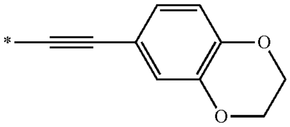
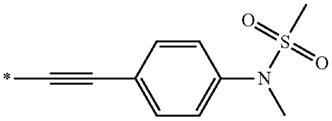
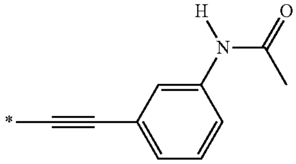
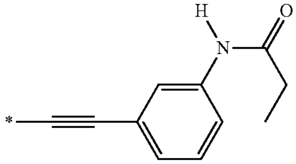
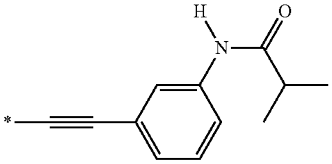
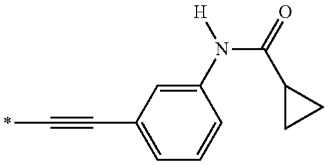
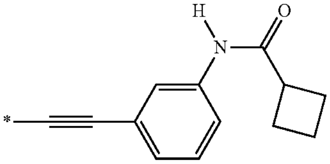
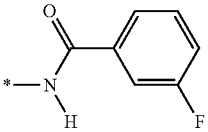

-continued
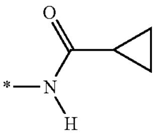
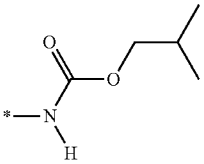
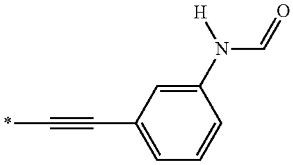
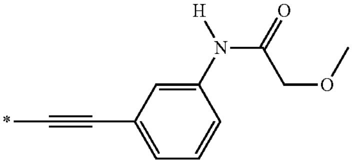
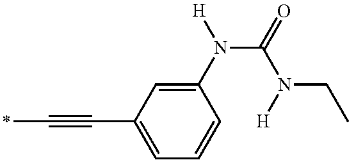
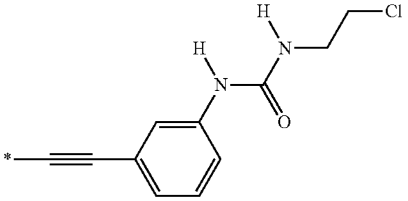
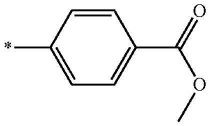
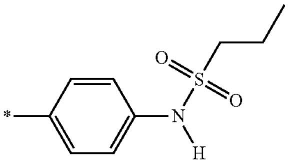
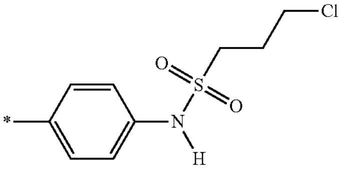
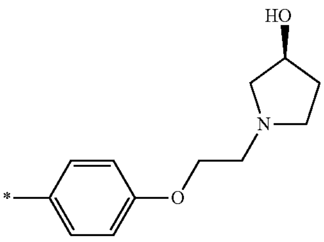
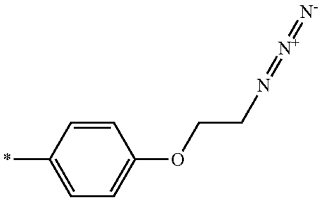
-continued
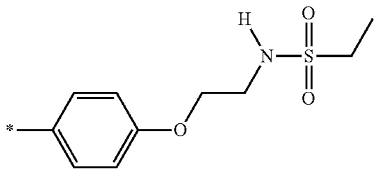
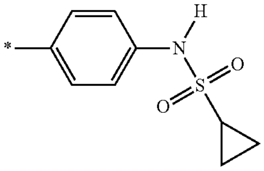
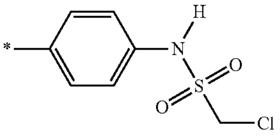
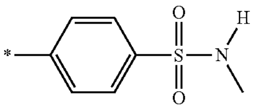
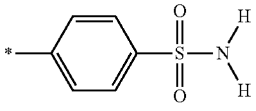
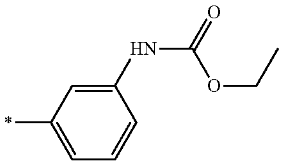
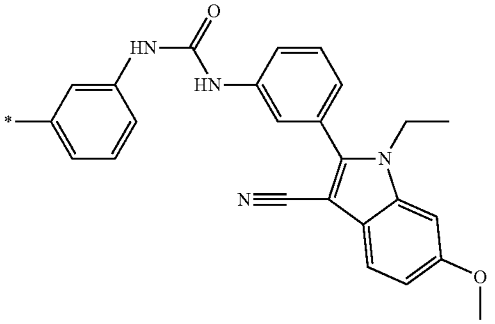
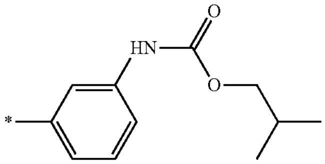
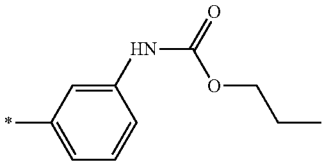
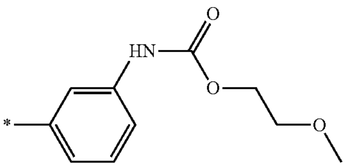
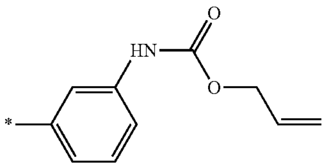

-continued
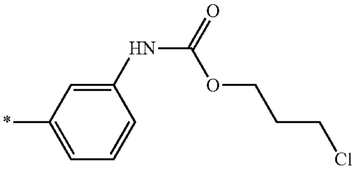
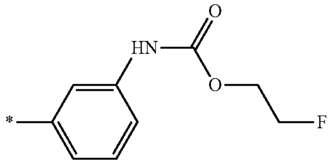
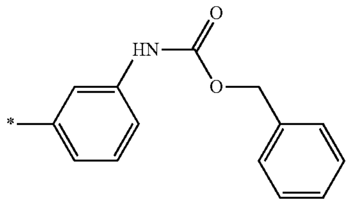
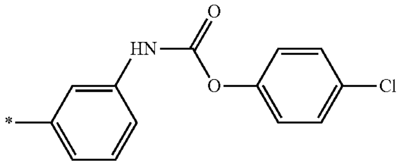
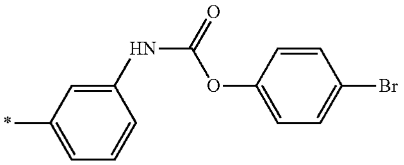
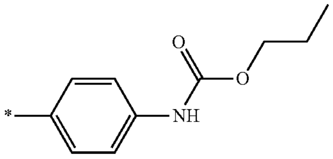
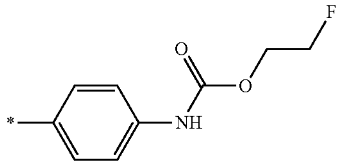
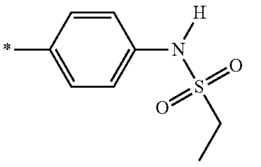
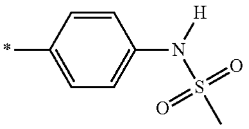
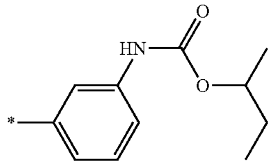
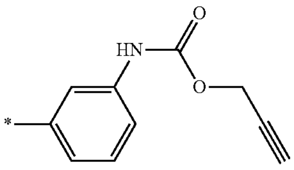
-continued
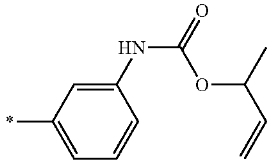
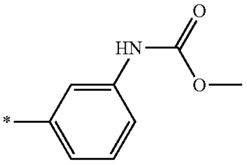
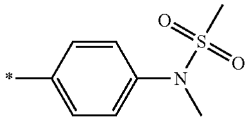
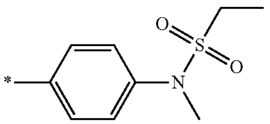
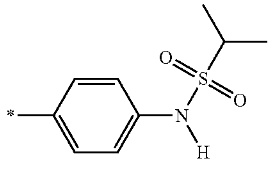
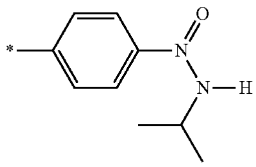
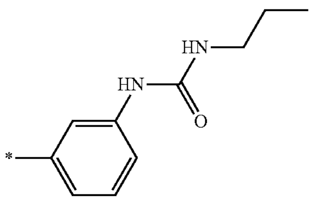
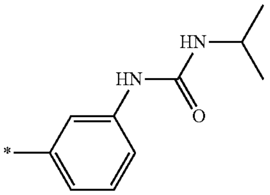
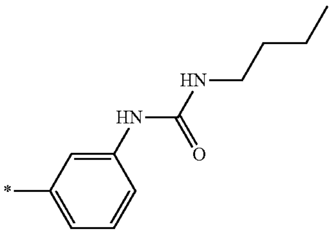
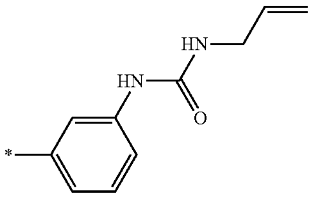
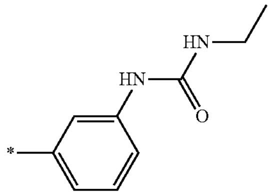
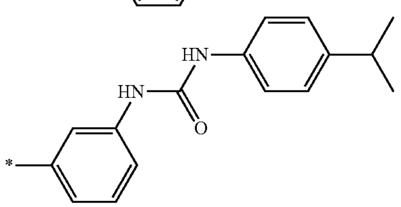
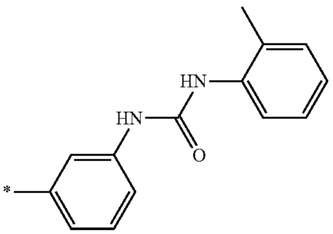

-continued
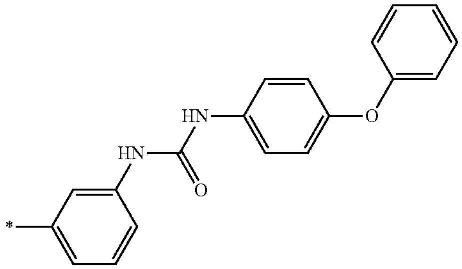
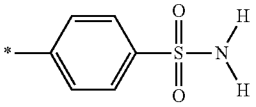
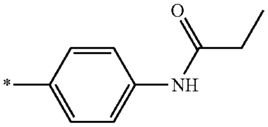
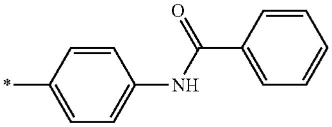
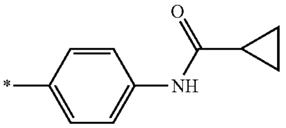
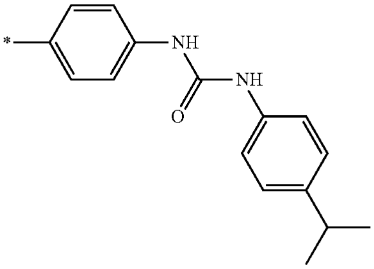
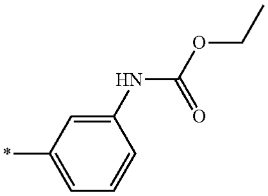
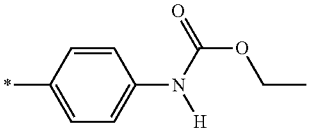
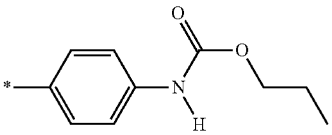
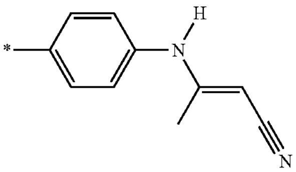
-continued
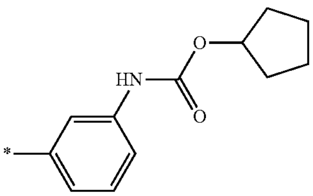
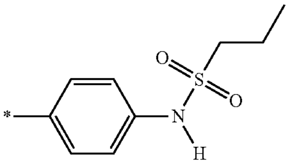
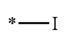
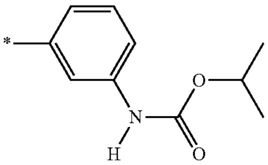
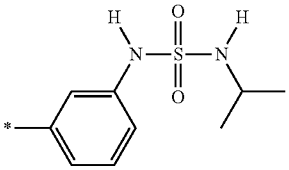
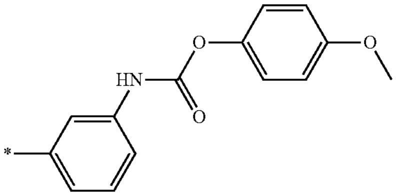
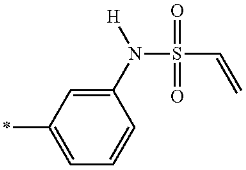
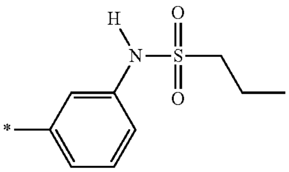
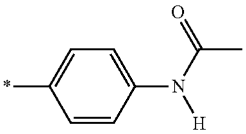
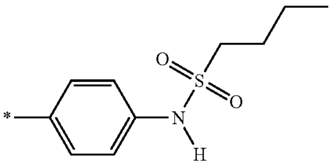
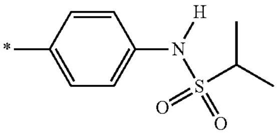
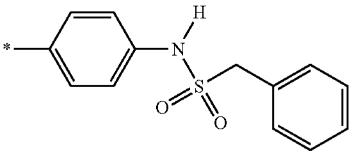
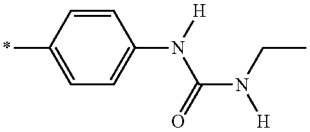
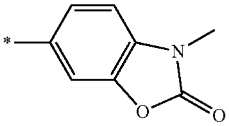

-continued
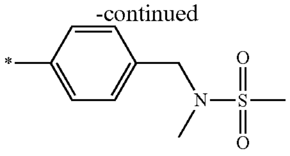
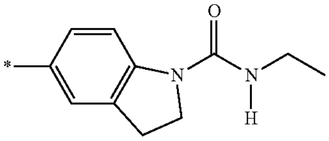
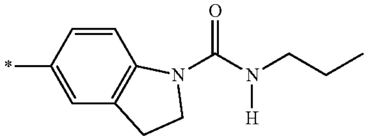
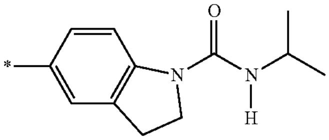
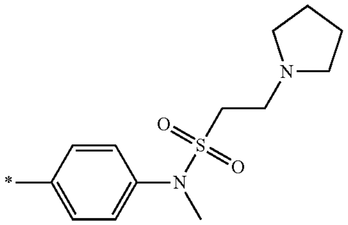
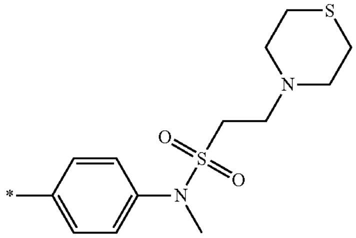
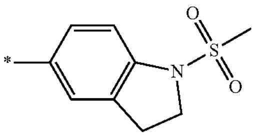
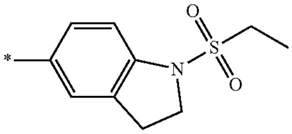
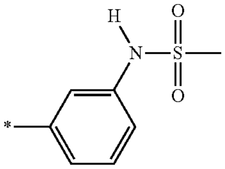
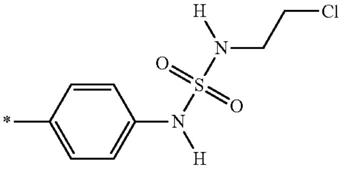
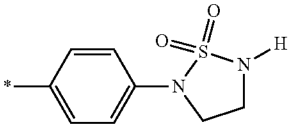
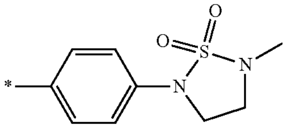
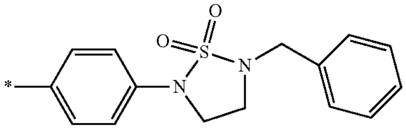
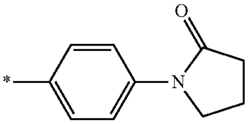
-continued
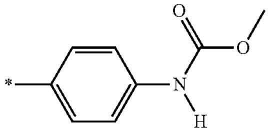
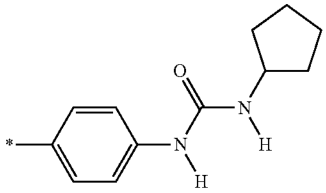
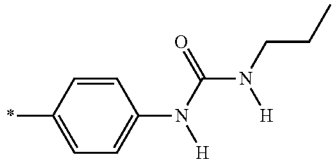
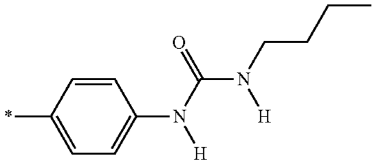
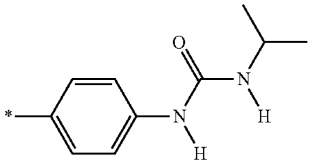
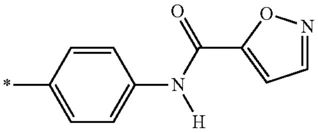
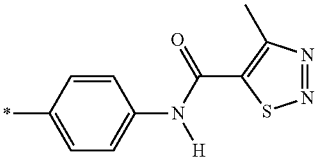
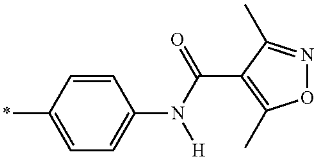
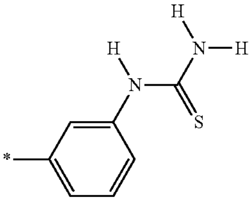
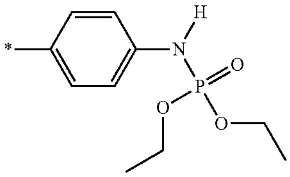
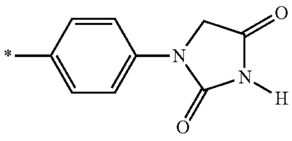
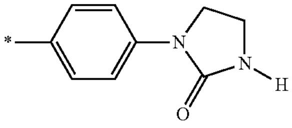

-continued
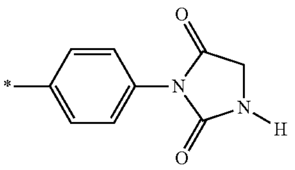
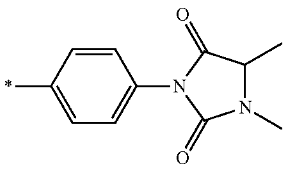
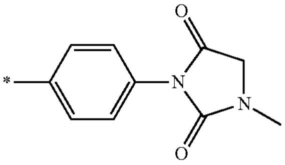
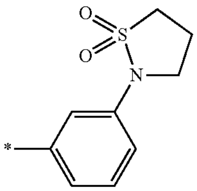
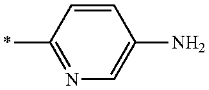
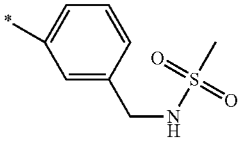
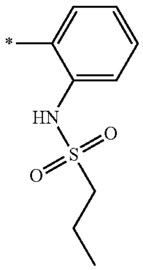
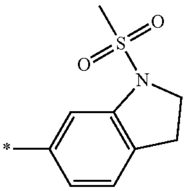
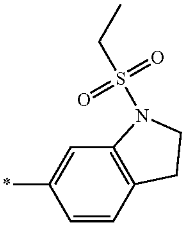
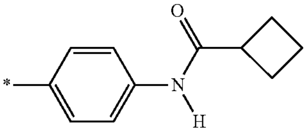
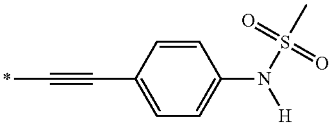
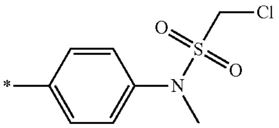
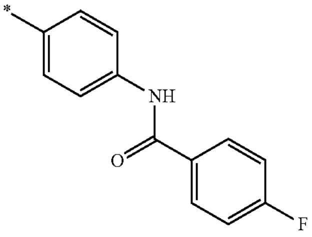
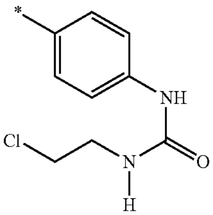
-continued
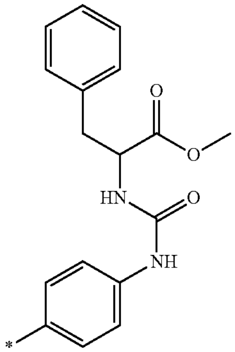
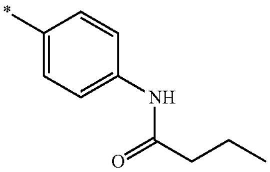
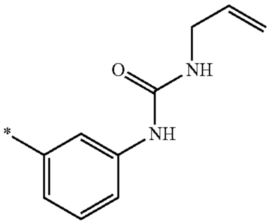
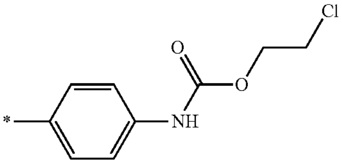
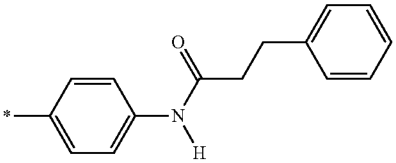
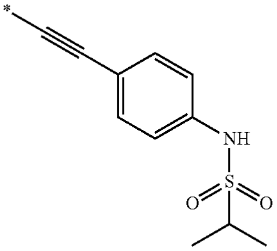
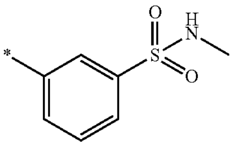
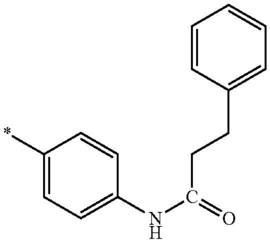
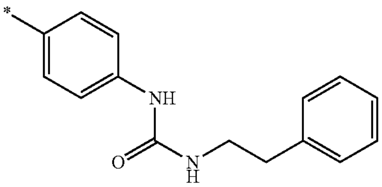

-continued
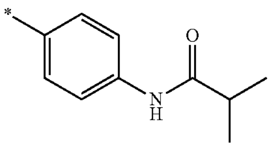
Embodiment 18
The method of Embodiment 13, wherein Y is selected from the group consisting of
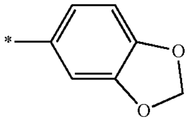
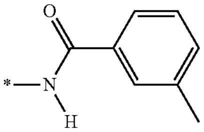
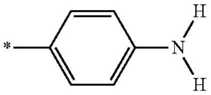
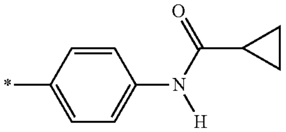
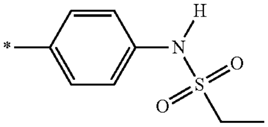
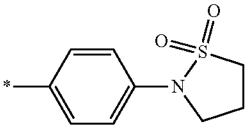
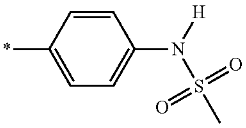
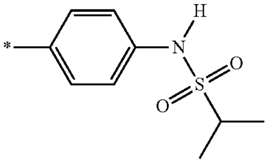
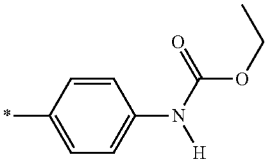
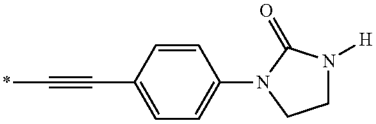
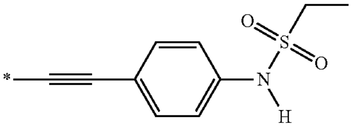
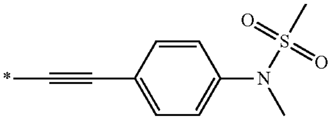
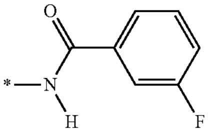
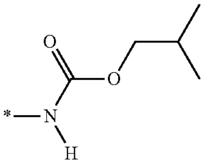
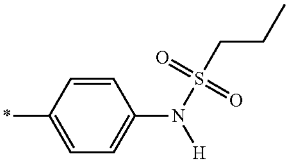
-continued
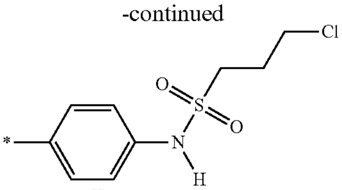
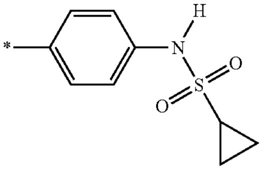
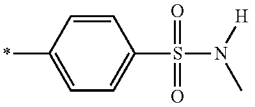
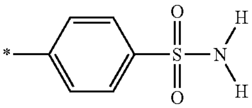
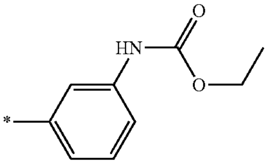
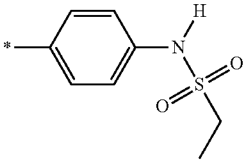
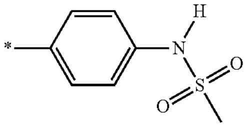
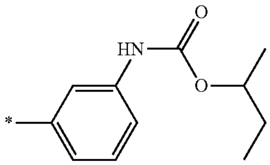
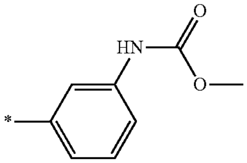
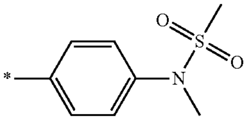
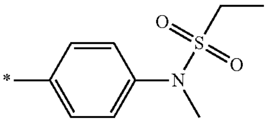
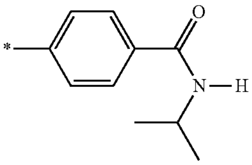
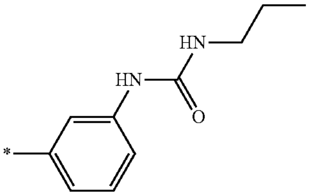
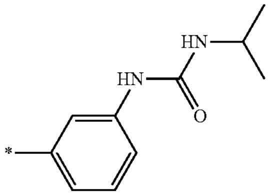
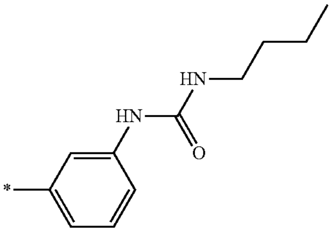

-continued
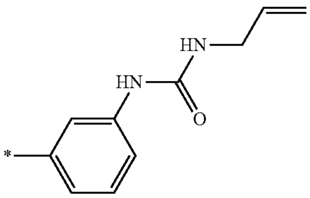
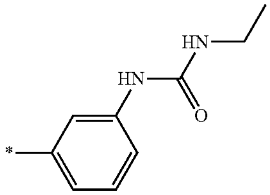
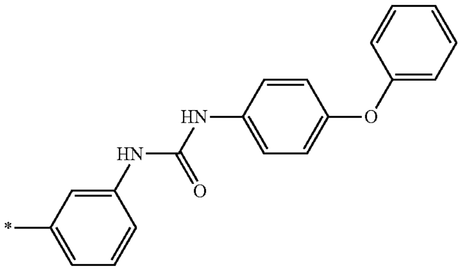
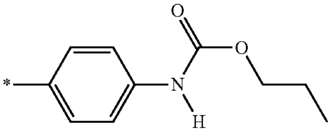
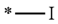
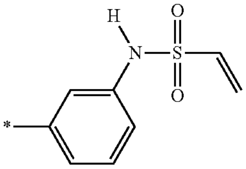
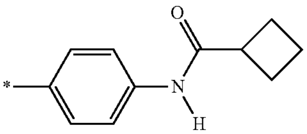
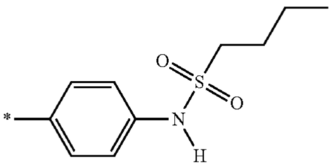
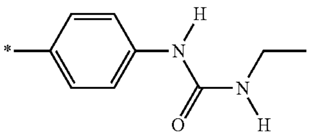
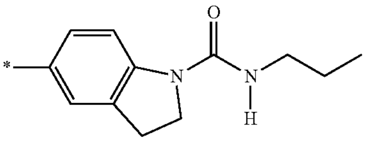
-continued
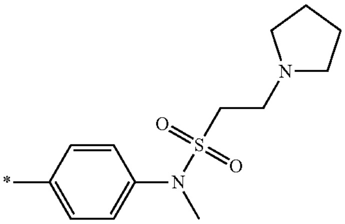
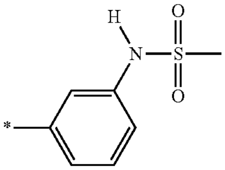
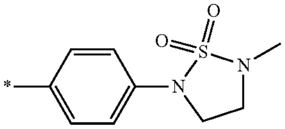
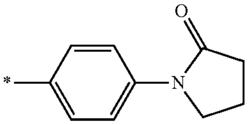
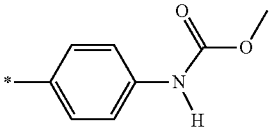
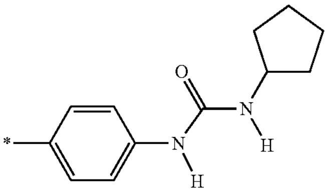
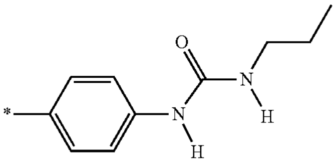
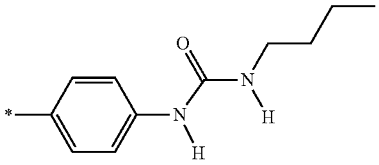
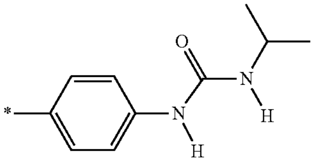
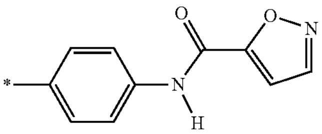
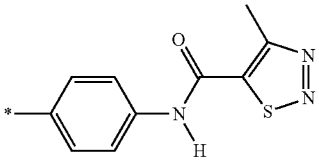
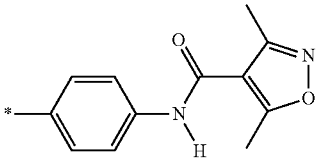

-continued
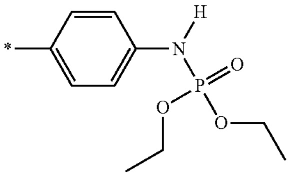
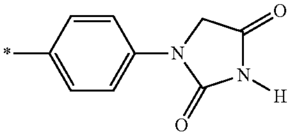
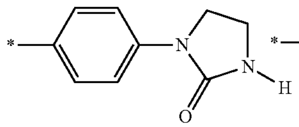
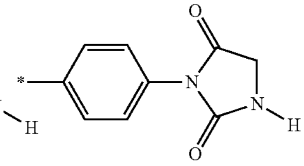
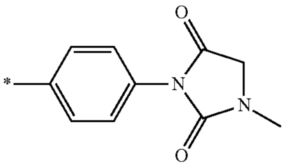
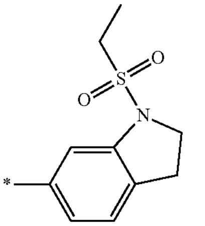
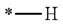
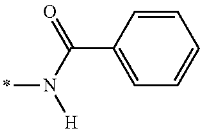
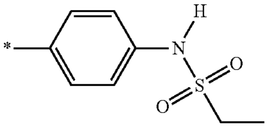
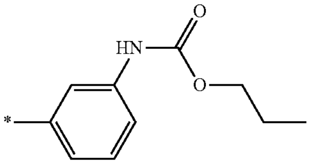
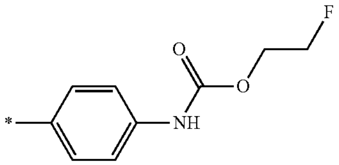
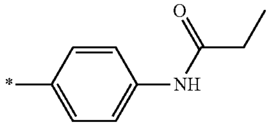
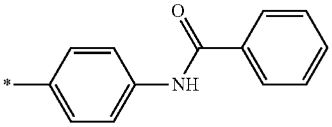
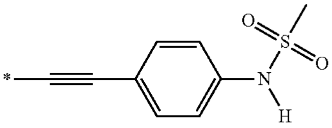
-continued
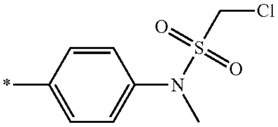
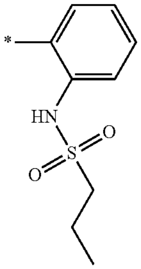
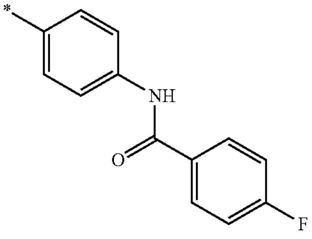
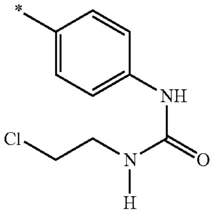
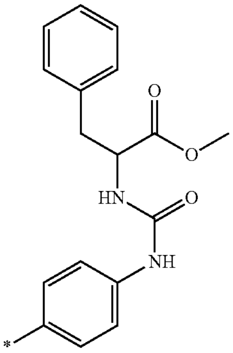
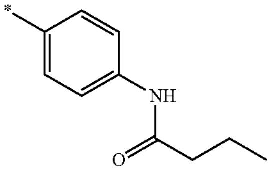
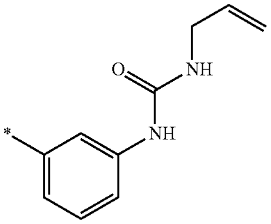
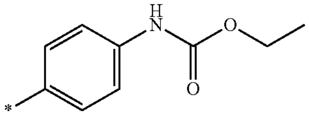
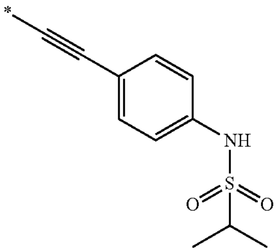
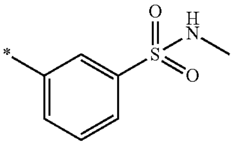
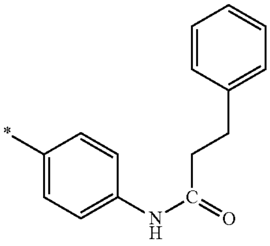

-continued

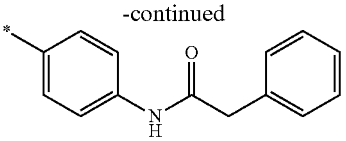

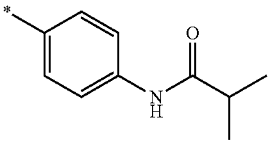

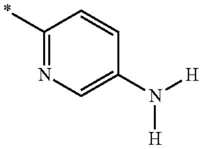

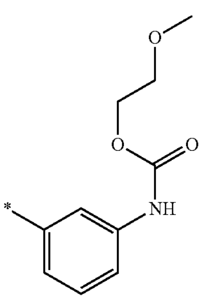

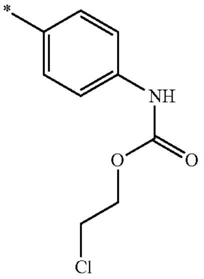

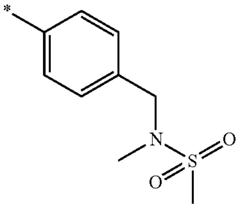

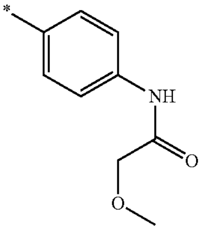

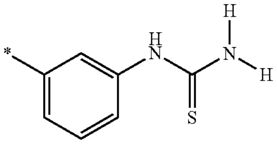

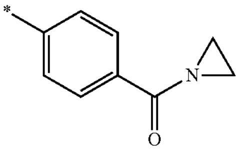

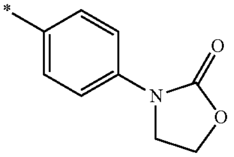

Embodiment 19

The method of Embodiment 13, wherein R is a hydrogen.

Embodiment 20

The method of Embodiment 13, wherein $R_1$ is selected from the group consisting of a hydrogen; —a halogen; —a nitro group; —a 5 or 6 membered heterocycle; —an alkoxy optionally substituted with: —a $C_6$ to $C_8$ aryl; -a $C_6$ to $C_8$ aryl optionally substituted with an alkoxy Embodiment 21

The method of Embodiment 13, wherein $R_2$ is selected from the group consisting of —a nitro group; —a hydrogen; —a halogen; —a hydroxy group; —a $C_1$ to $C_6$ alkyl group, optionally substituted with one or more halogens; —an alkoxy group optionally substituted with: —one or more halogens, —an —$OCOR_x$ group, where $R_x$ is as defined above, —a dialkyl-amino optionally substituted with an alkoxy, —a 5 or 6 membered heterocycle group optionally substituted with a $C_1$ to $C_6$ alkyl, or —a 5 or 6 membered heteroaryl group; —an amide group; and —a —$NHSO_2R_x$ group, where $R_x$ is as defined above Embodiment 22

The method of Embodiment 13, wherein $R_3$ is a hydrogen.

Embodiment 23

The method of Embodiment 13, wherein said compound is selected from the compounds of Table A.

Embodiment 24

The method of Embodiment 13, wherein said compound is selected from the compounds of Table B.

Embodiment 25

A method for treating or preventing infection by a virus in a subject, wherein said virus comprises a internal ribosome entry site (IRES), comprising administering to said subject a pharmaceutical composition comprising a viral inhibitory amount of one or more compound having the following formula:

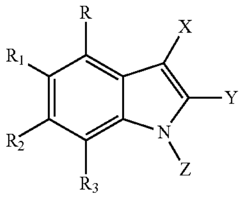

wherein:

X is:
- hydrogen;
- a nitro group;
- a cyano group;
- a —$COR_a$ group, where $R_a$ is:
  - a $C_1$ to $C_6$ alkyl,
  - a $C_6$ to $C_8$ aryl optionally substituted with an alkoxy or a halogen, or
  - a dialkyl-amino;
- a —$COOR_x$ group, where $R_x$ is a $C_1$ to $C_6$ alkyl;
- a formyl group;
- a $C_6$ to $C_8$ aryl optionally substituted with an alkoxy; or
- a 5 or 6-membered heteroaryl optionally substituted with:
  - a $C_1$ to $C_6$ alkyl,
  - a $C_6$ to $C_8$ aryl optionally substituted with an alkoxy or one or more halogens, or
  - a 5 to 6 membered heteroaryl;

Y is:
- a hydrogen;
- a haloalkyl;
- a halogen;
- an amino optionally substituted with one or more $C_1$ to $C_6$ alkyls;
- a benzofuran;
- a benzothiophene;
- a dibenzofuran;
- a dibenzothiophene;
- a benzothiazole;
- a naphthalene;

an indole, optionally substituted on the nitrogen with a $C_1$ to $C_6$ alkyl;

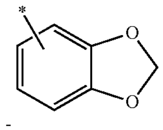
;
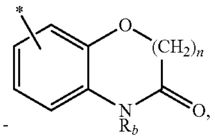

where $R_b$ is a hydrogen or a $C_1$ to $C_6$ alkyl, and n is 0 or 1;

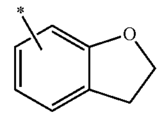
;
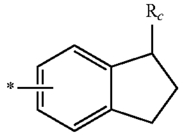
, where $R_c$ is a hydrogen, a —CONHR$_x$, where $R_x$ is as defined above, or an —SO$_2$R$_x$, where $R_x$ is as defined above; or

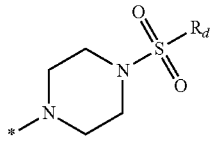
, where $R_d$ is a $C_1$ to $C_6$ alkyl or a $C_6$ to $C_8$ aryl;
a —NHCOR$_e$ group, where $R_e$ is:
a $C_1$ to $C_6$ alkyl;
a $C_6$ to $C_8$ aryl optionally substituted with:
a $C_1$ to $C_6$ alkyl,
an alkoxy,
a cyano group,
a nitro group, or
a halogen;
a —NHCOOR$_x$ group, where $R_x$ is as defined above;
a —CH$_2$O—R$_f$ group, where $R_f$ is a $C_6$ to $C_8$ aryl;
a —NR$_g$R$_h$ group, where $R_g$ is a $C_1$ to $C_6$ alkyl or a hydrogen and $R_h$ is a $C_6$ to $C_8$ aryl optionally substituted with an alkoxy;
a $C_1$ to $C_6$ alkyl;
a 5 or 6 membered heteroaryl, optionally substituted with:
a $C_1$ to $C_6$ alkyl, optionally substituted with a $C_6$ to $C_8$ aryl,
a $C_6$ to $C_8$ aryl, optionally substituted with —COOR$_x$, where $R_x$ is as defined above, or
an amino group;
a 5 or 6 membered heterocycle optionally substituted with:
a —COOR$_x$ group, where $R_x$ is as defined above, or
a —NHCOOR$_x$ group, where $R_x$ is as defined above;
a $C_6$ to $C_8$ aryl, optionally substituted with one or more of the following:
an alkoxy, optionally substituted with:
an alkoxy,
a hydroxy,
one or more halogens,
a 5 or 6 membered heterocycle, optionally substituted with:

a $C_1$ to $C_6$ alkyl, or
a hydroxy,
an amino group optionally substituted with one or more $C_1$ to $C_6$ alkyls,
a —NR$_i$SO$_2$R$_x$ group, where $R_x$ is as defined above and $R_1$ is:
a hydrogen,
a $C_1$ to $C_6$ alkyl,
a —COR$_x$ group, where $R_x$ is as defined above,
a haloalkyl, or
a haloalkoxy,
a —NR$_j$COR$_k$ group, where $R_k$ is:
a $C_1$ to $C_6$ alkyl,
a hydrogen, or
an amino optionally substituted with one or more $C_1$ to $C_6$ alkyls,
and $R_j$ is:
a hydrogen,
a $C_1$ to $C_6$ alkyl,
a —COR$_x$ group, where $R_x$ is as defined above,
a haloalkyl, or
a haloalkoxy,
a —N═N$^+$═N$^-$ group, or
a —COR$_l$, where $R_l$ is a 5 or 6 membered heterocycle optionally substituted with a hydroxy,
an amino optionally substituted with one or more $C_1$ to $C_6$ alkyls,
a nitro group,
a $C_1$ to $C_6$ alkyl group, optionally substituted with:
a —NHSO$_2$R$_x$ group, where $R_x$ is as defined above, or
a —NR$_x$SO$_2$R$_x$ group, where $R_x$ is as defined above,
a haloalkoxy,
a halogen,
a hydroxy,
a —COOR$_x$ group, where $R_x$ is as defined above,
a —COR$_m$ group, where $R_m$ is:
an amino optionally substituted with one or more $C_1$ to $C_6$ alkyls, where the $C_1$ to $C_6$ alkyls are optionally substituted with:
a hydroxy
a 5 or 6 membered heterocycle,
an amino optionally substituted with one or more $C_1$ to $C_6$ alkyls,
an alkoxy,
a 3 to 7 membered heterocycle, optionally substituted with a $C_1$ to $C_6$ alkyl, optionally substituted with a dialkyl-amino,
a —NHR$_n$ group, where $R_n$ is:
a —CH$_2$CONH$_2$, or
a $C_6$ to $C_8$ aryl optionally substituted with:
an alkyl,
one or more halogens,
a nitro group, or
one or more alkoxys,
a —NR$_o$COR$_p$ group, where $R_p$ is:
a $C_1$ to $C_6$ alkyl optionally substituted with:
a halogen,
an alkoxy, or
a $C_6$ to $C_8$ aryl,
a 5 or 6 membered heterocycle,
a $C_6$ to $C_8$ aryl, optionally substituted with a halogen,
a 5 or 6 membered heteroaryl optionally substituted with one or more $C_1$ to $C_6$ alkyls,
a hydrogen,

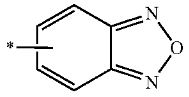

- or 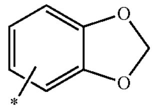 , and where $R_o$ is:
a hydrogen,
a $C_1$ to $C_6$ alkyl,
a —$COR_x$ group, where $R_x$ is as defined above,
a haloalkyl, or
a haloalkoxy,
a —$NR_qCONR_qR_r$ group, where $R_q$ is:
a hydrogen,
a $C_1$ to $C_6$ alkyl,
a haloalkyl,
a haloalkoxy, or
a —$COR_x$ group, where $R_x$ is as defined above,
and where $R_r$ is:
a $C_6$ to $C_8$ aryl optionally substituted with:

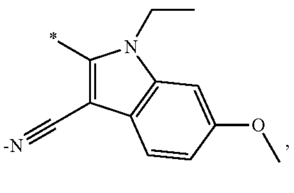 , a $C_1$ to $C_6$ alkyl,
a haloalkyl,
a —$OR_s$ group, where $R_s$ is a $C_6$ to $C_8$ aryl, or
a —$COOR_x$ group, where $R_x$ is as defined above,
a $C_1$ to $C_6$ alkyl optionally substituted with one or more of the following:
a halogen,
an alkylene,
a $C_6$ to $C_8$ aryl, or
a —$COOR_x$ group, where $R_x$ is as defined above,
a —$COOR_x$ group, where $R_x$ is as defined above,
a —$NR_tCOOR_u$ group, where $R_u$ is:
a $C_1$ to $C_{12}$ alkyl, optionally substituted with:
a $C_6$ to $C_8$ aryl optionally substituted with a $C_1$ to $C_6$ alkyl or an alkoxy,
an alkylene,
an alkoxy,
an alkyne,
a halogen, or
a 5 or 6 membered heterocycle,
a $C_6$ to $C_8$ aryl, optionally substituted with:
an alkoxy,
a halogen, or
a $C_1$ to $C_6$ alkyl, or
a 5 or 6 membered heterocycle,
and $R_t$ is:
a hydrogen,
a $C_1$ to $C_6$ alkyl,
a —$COR_x$ group, where $R_x$ is as defined above,
a haloalkyl, or
a haloalkoxy,
a —$NR_vSO_2R_w$ group, where $R_v$ is:
a hydrogen,
a —$COR_x$, where $R_x$ is as defined above, or
a $C_1$ to $C_6$ alkyl, optionally substituted with:
a halogen,
a —$COR_x$ group, where $R_x$ is as defined above,
a —$OCOR_x$ group, where $R_x$ is as defined above,
a hydroxyl,
a hydroxyl, or
an alkoxy,
and where $R_w$ is:
a $C_1$ to $C_6$ alkyl optionally substituted with:
a halogen,
a haloalkyl,
a $C_6$ to $C_8$ aryl, or
a 5 or 6 membered heterocycle,
a $C_2$ to $C_6$ alkylene,
an alkyl- or dialkyl-amino optionally substituted with a halogen,
a 5 or 6 membered heterocycle, or
a 5 or 6 membered heteroaryl optionally substituted with:
a $C_1$ to $C_6$ alkyl,
a 5 or 6 membered heterocycle, or

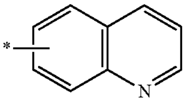 - 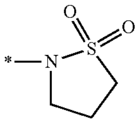 -a , 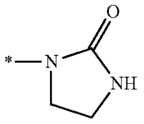 -a ,

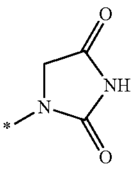 -a , 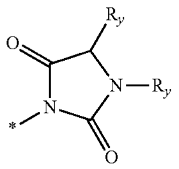 -a , optionally substituted with a $C_1$ to $C_6$ alkyl, where $R_y$ is a $C_1$ to $C_6$ alkyl or hydrogen,

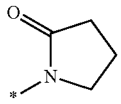 -a , 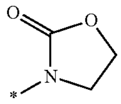 -a , 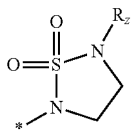 -a , where $R_z$ is hydrogen or a $C_1$ to $C_6$ alkyl, optionally substituted with a $C_6$ to $C_8$ aryl,
a —$SR_x$ group, where $R_x$ is as defined above,
a —$SO_2R_{aa}$ group, where $R_{aa}$ is:
a $C_1$ to $C_6$ alkyl,
an amino group,
an alkyl- or dialkyl-amino group optionally substituted with a hydroxy or a —$COOR_x$ group, where $R_x$ is as defined above,
a 5 or 6 membered heteroaryl,
a $C_6$ to $C_8$ aryl, or
a —$NHR_{bb}$ group, where $R_{bb}$ is:

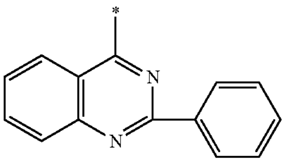
-,

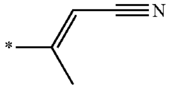
-, a —C(=S)$NH_2$ group, or a —$PO(OR_x)_2$, where $R_x$ is as defined above;

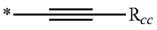
-a $R_{cc}$ group, where $R_{cc}$ is:

a naphthalene, a 5 or 6 membered heteroaryl,

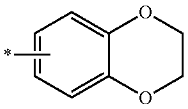
-a , a $C_6$ to $C_8$ aryl, optionally substituted with one or more of the following:

an alkoxy, an hydroxy, a halogen, a $C_1$ to $C_6$ alkyl, optionally substituted with a cyano group, an amino optionally substituted with one or more $C_1$ to $C_6$ alkyls, a —$NHPOR_xR_x$, where $R_x$ is as defined above, a —$NR_{ee}CONR_{ff}R_{ff}$ group, where $R_{ee}$ is a hydrogen or a $C_1$ to $C_6$ alkyl, optionally substituted with a halogen, and $R_{ff}$ is:

a hydrogen, a haloalkyl, a haloalkoxy, a $C_1$ to $C_6$ alkyl, or a —$COR_x$, where $R_x$ is as defined above, a —$NR_{gg}COR_{hh}$ group, where $R_{hh}$ is:

a hydrogen, a $C_1$ to $C_6$ alkyl optionally substituted with:

an alkoxy, a halogen, or an amino optionally substituted with one or more $C_1$ to $C_6$ alkyls, an amino optionally substituted with one or more $C_1$ to $C_6$ alkyls, where the alkyls are optionally substituted with a halogen, a 5 or 6 membered heterocycle, a 5 or 6 membered heteroaryl, and $R_{gg}$ is:

a hydrogen, a $C_1$ to C 6 alkyl, a haloalkyl, a haloalkoxy, or a —$COR_x$ group, where $R_x$ is as defined above, a haloalkyl, 5 or 6 membered heterocycle groups, an amino optionally substituted with one or more $C_1$ to $C_6$ alkyls, a —$NR_{ii}SO_2R_x$ group, where $R_x$ is as defined above, and $R_{ii}$ is:

a hydrogen, a $C_1$ to $C_6$ alkyl, a haloalkyl, a haloalkoxy, a —$COR_x$ group, where $R_x$ is as defined above;

Z is:

a hydrogen;

a $C_1$ to $C_6$ alkyl optionally substituted with:

an alkoxy, one or more halogens, or a $C_6$ to $C_8$ aryl;

a $C_2$ to $C_6$ alkylene;

a $C_6$ to $C_8$ aryl optionally substituted with an alkoxy or one or more $C_1$ to $C_6$ alkyls;

a —$COOR_x$ group, where $R_x$ is as defined above; or

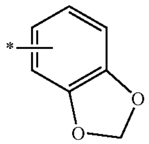
- ;

R is a hydrogen, a halogen or an alkoxy;

$R_1$ is:

a hydrogen;

a hydroxy;

a halogen;

a haloalkyl;

a nitro group;

a 5 or 6 membered heteroaryl;

a 5 or 6 membered heterocycle;

an alkoxy optionally substituted with:

one or more halogens, a $C_6$ to $C_8$ aryl, or a 5 or 6 membered heterocycle;

a $C_6$ to $C_8$ aryl optionally substituted with an alkoxy;

a —$COR_x$ group, where $R_x$ is as defined above;

a $C_1$ to $C_6$ alkyl optionally substituted with a dialkyl-amino or a 5 or 6 membered heterocycle; or $R_1$ joins together with $R_2$ to form:

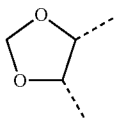
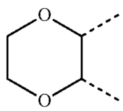
;

$R_2$ is:

a nitro group;

a hydrogen;

a halogen;

a hydroxy group;

a $C_1$ to $C_6$ alkyl group, optionally substituted with one or more halogens;

an amino group;

an alkoxy group optionally substituted with:

one or more halogens, an —$OCOR_x$ group, where $R_x$ is as defined above, a dialkyl-amino optionally substituted with an alkoxy, a 5 or 6 membered heterocycle group optionally substituted with a $C_1$ to $C_6$ alkyl, a 5 or 6 membered heteroaryl group, or a $C_6$ to $C_8$ aryl group;

a —$COOR_x$ group, where $R_x$ is as defined above;

a haloalkyl;

an amide group optionally substituted with:

a hydroxy group, or a $C_6$ to $C_8$ aryl;

a 5 or 6 membered heteroaryl;

a —$OCOR_x$ group, where $R_x$ is as defined above;

a —$NHCOR_{jj}$ group, where $R_{jj}$ is:

an alkoxy, or an amino optionally substituted with one or more $C_1$ to $C_6$ alkyls;

a —$OR_{kk}$ group, where $R_{kk}$ is a 5 to 6 membered heteroaryl;

a —$NHSO_2R_x$ group, where $R_x$ is as defined above; or $R_2$ joins together with $R_1$ to form:

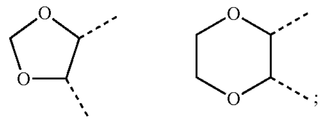

$R_3$ is:

a hydrogen; or

—$CH_2OCOR_x$, and $R_x$ is as defined above;

and/or a pharmaceutically acceptable salt thereof, together with a pharmaceutically acceptable excipient.

Embodiment 33

The method of Embodiment 32 wherein said pharmaceutical composition further comprises at least one additional anti-viral agent.

Embodiment 34

The method of Embodiment 33, wherein said at least one additional anti-viral agent is elected from the group consisting of pegylated interferon, un-pegylated interferon, ribavirin or prodrugs or derivatives thereof, a glucosidase inhibitor, a protease inhibitor, a polymerase inhibitor, p7 inhibitors, an entry inhibitor, a fusion inhibitor, an anti-fibrotic, a caspase inhibitor, a drug which targets inosine monophosphate dehydrogenase inhibitors (IMPDH), synthetic thymosin alpha 1, therapeutic vaccines, immunomodulators, a glycosidase inhibitor, a helicase inhibitor, and a Toll-like receptor agonist.

Embodiment 26

A compound selected from the group consisting of the following:

1

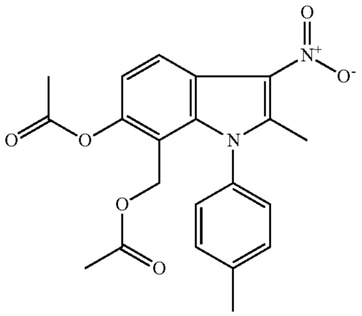

2

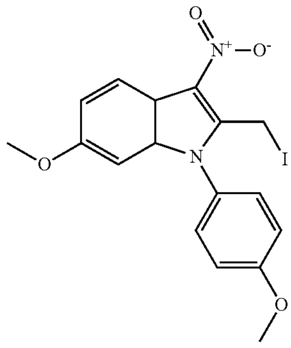

3

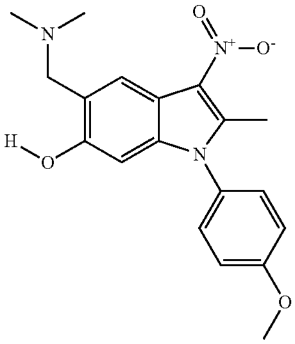

4

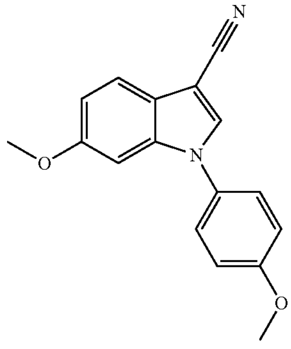

5

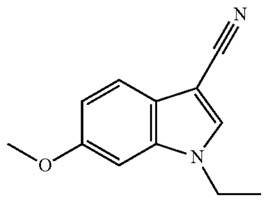

-continued
6
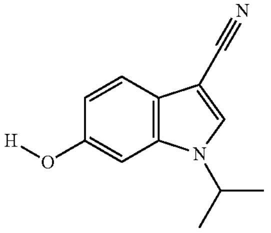
7
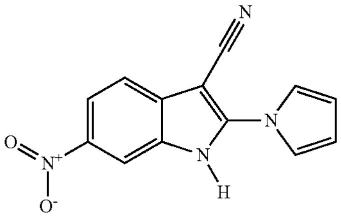
8
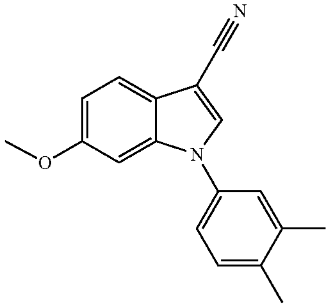
9
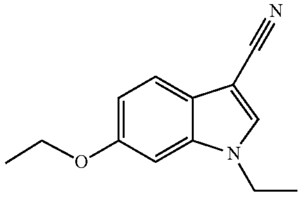
10
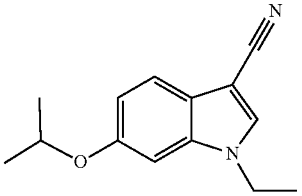
11
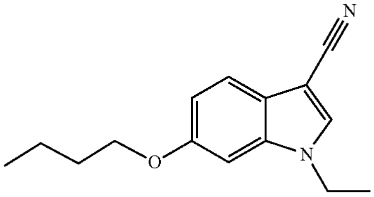
12
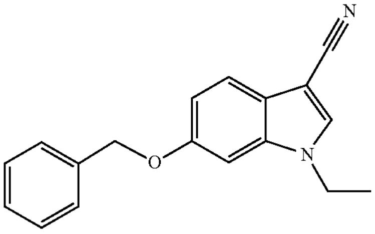
-continued
13
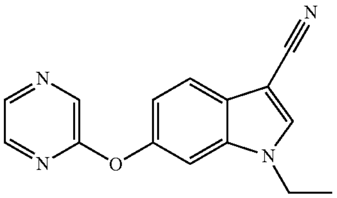
14
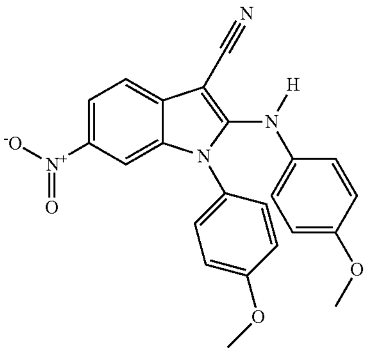
15
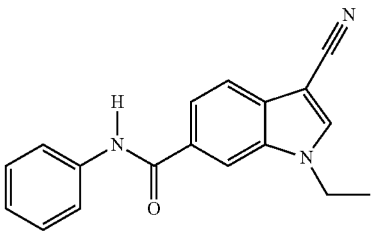
16
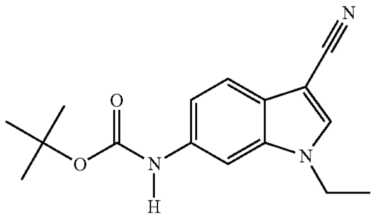
17
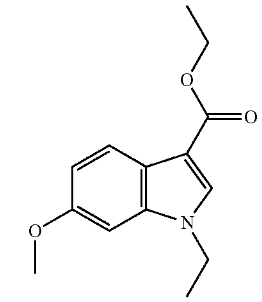
18
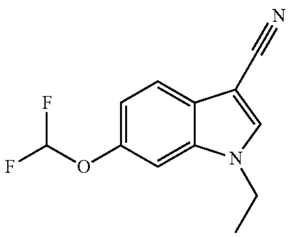

-continued
19
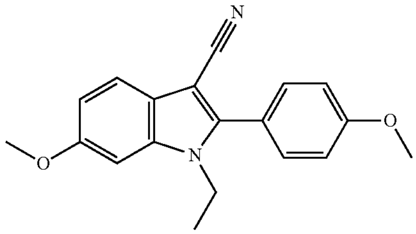
20
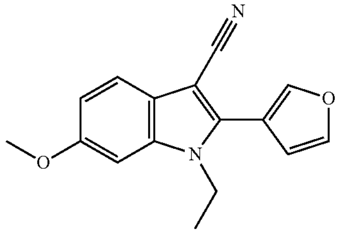
21
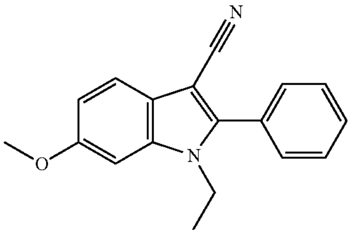
22
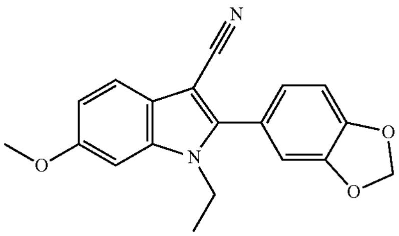
23
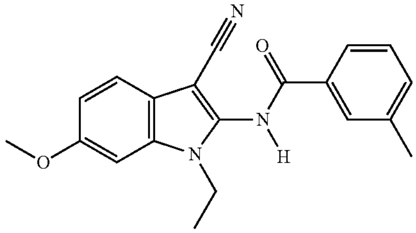
24
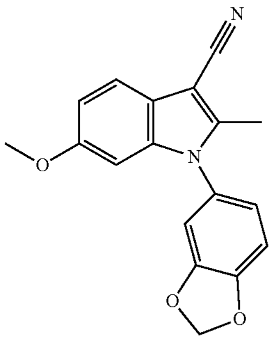
-continued
25
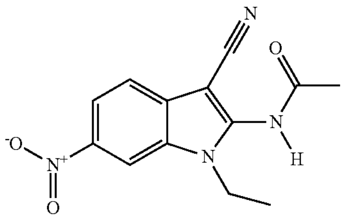
26
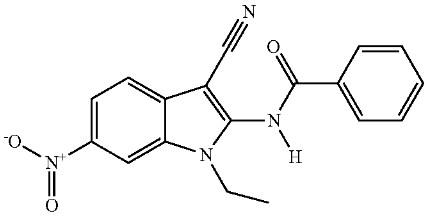
27
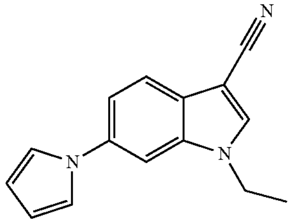
28
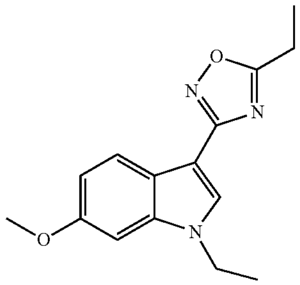
29
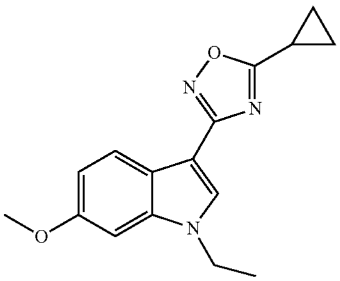
30
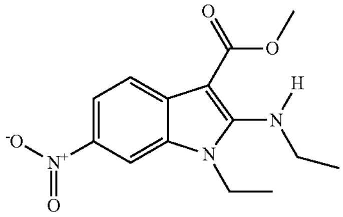

-continued
31
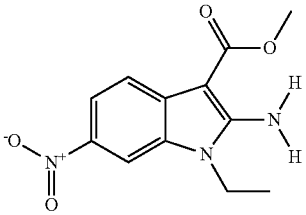
32
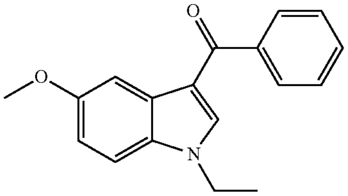
33
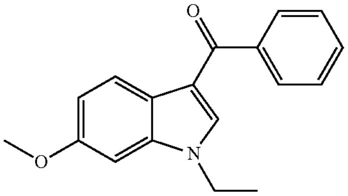
34
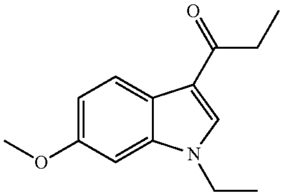
35
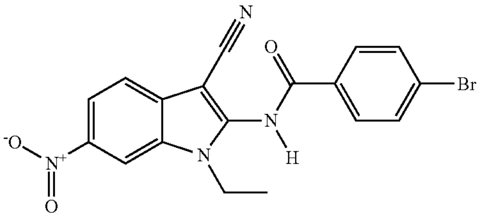
36
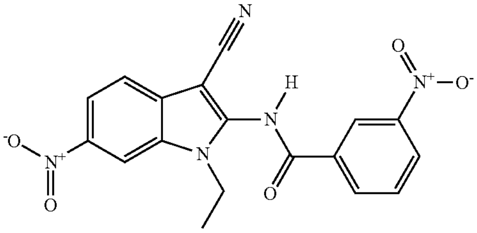
37
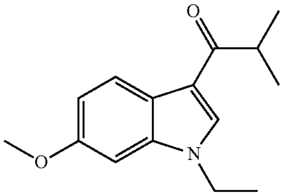
-continued
38
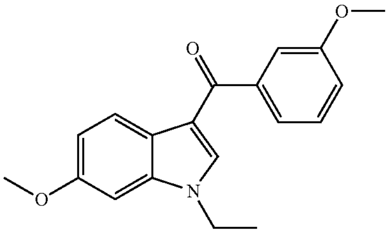
39
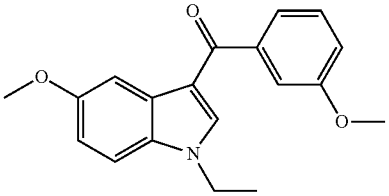
40
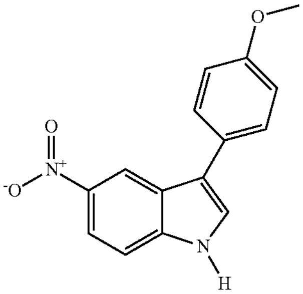
41
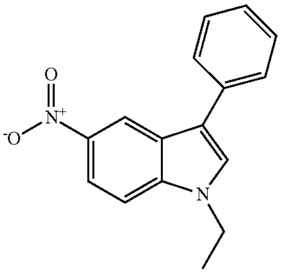
42
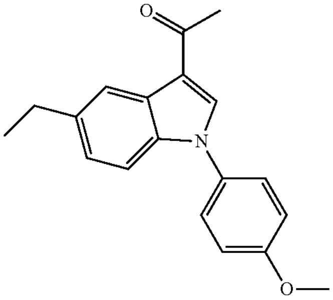
43
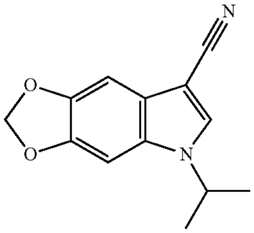

-continued
44
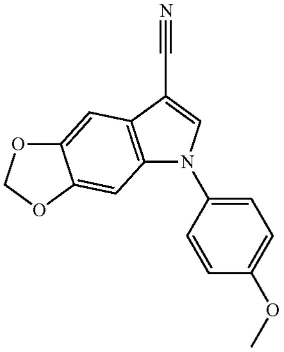
45
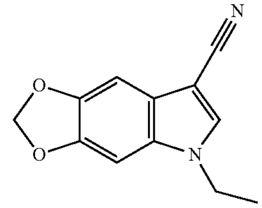
46
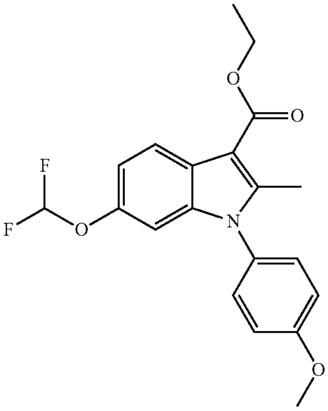
47
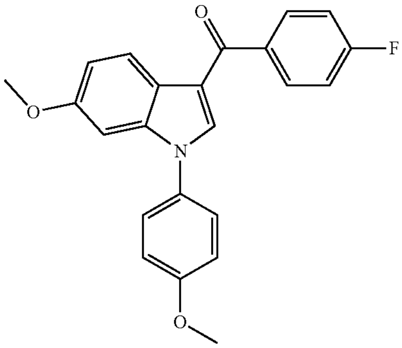
48
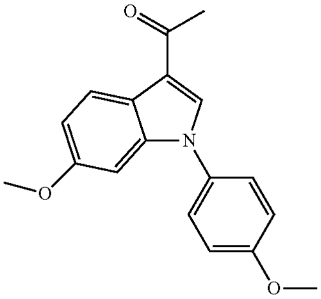
-continued
49
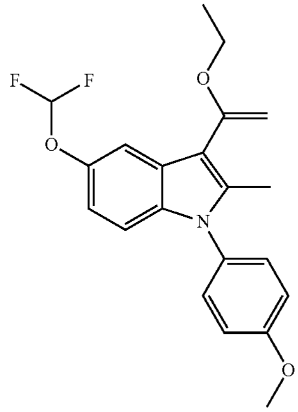
50
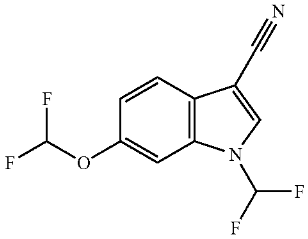
51
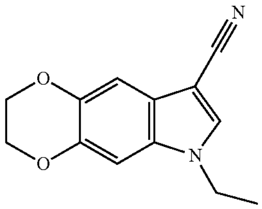
52
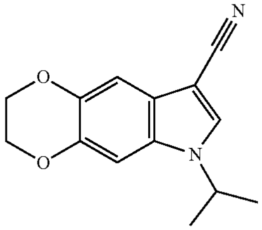
53
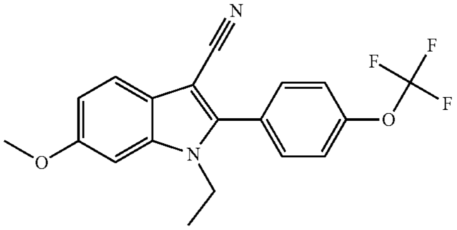
54
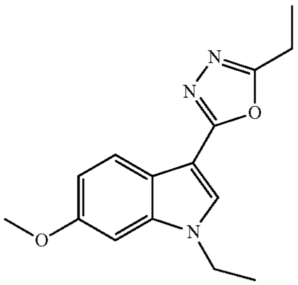

-continued
55
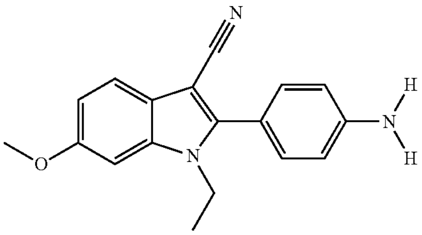
56
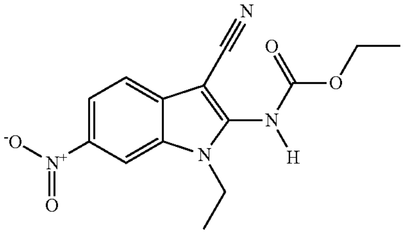
57
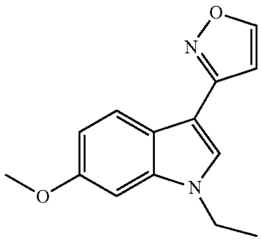
58
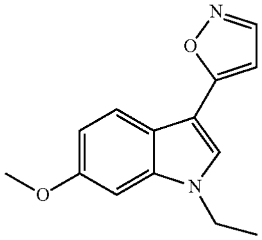
59
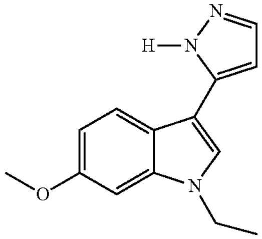
60
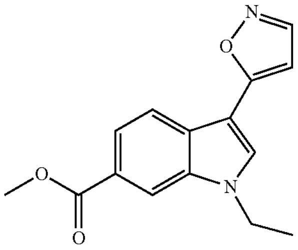
-continued
61
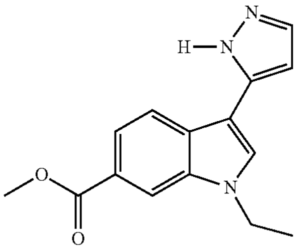
62
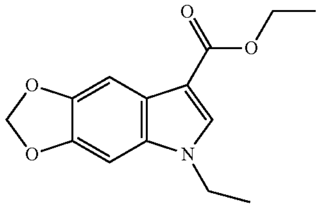
63
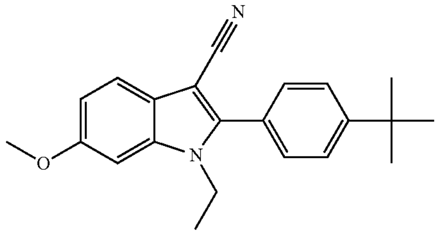
64
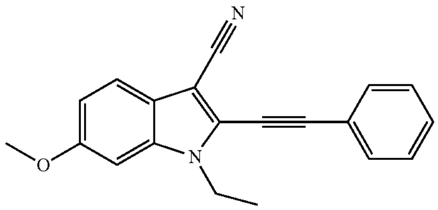
65
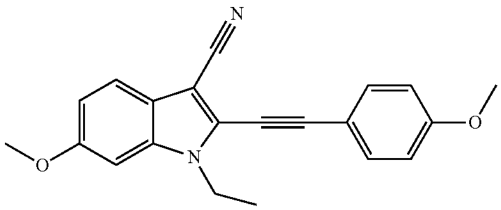
66
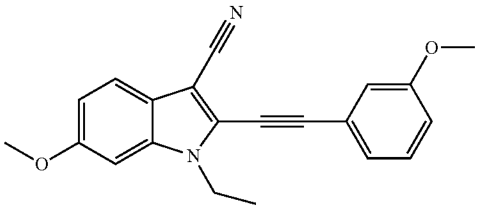
67
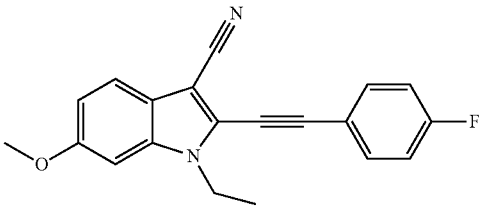

-continued
68
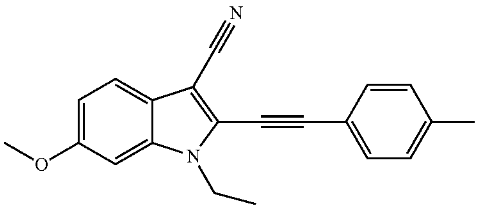
69
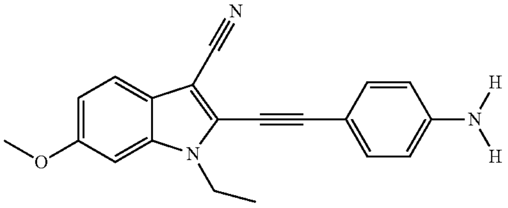
70
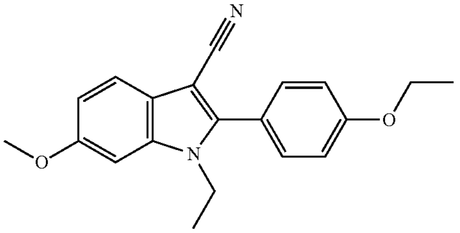
71
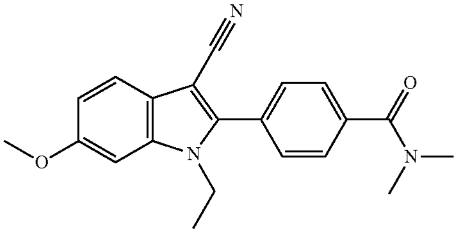
72
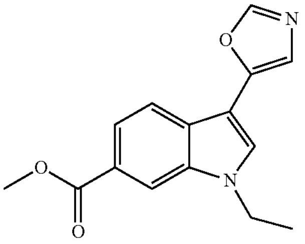
73
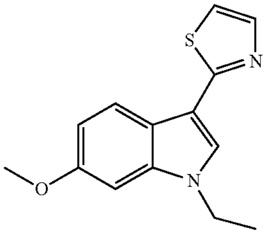
-continued
74
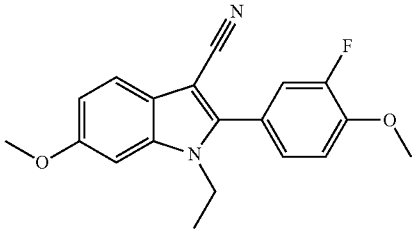
75
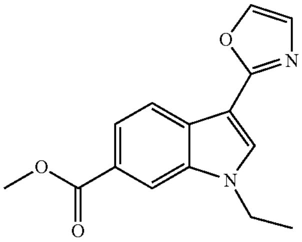
76
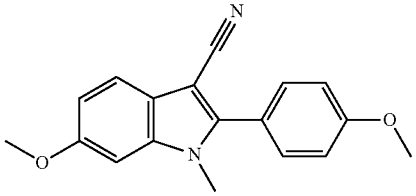
77
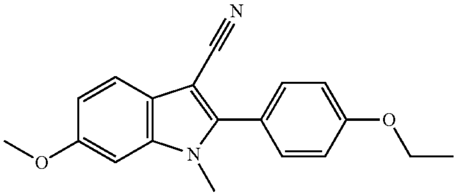
78
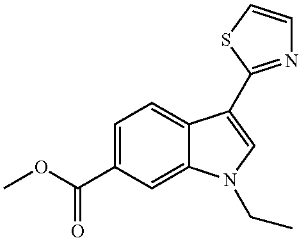
79
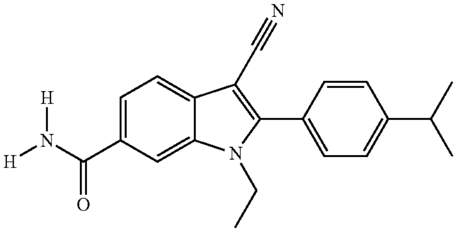
80
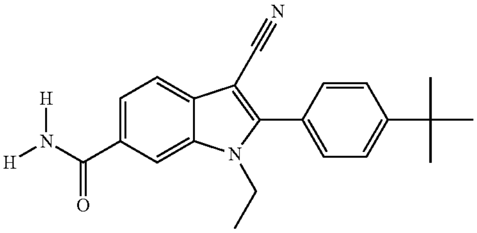

-continued
81
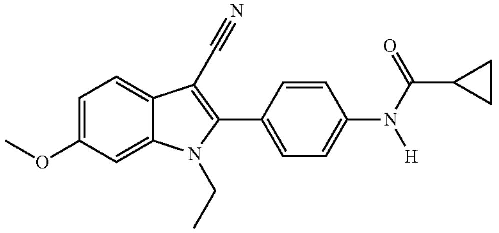
82
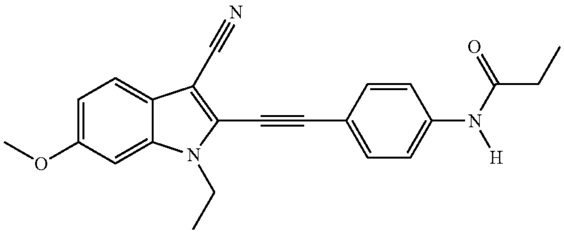
83
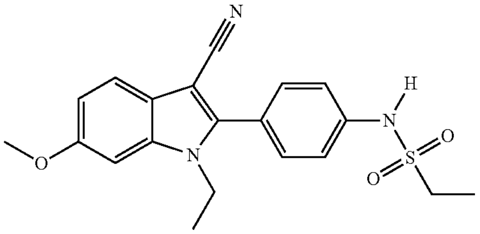
84
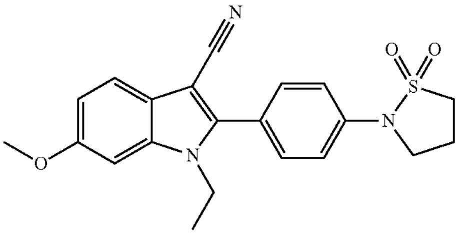
85
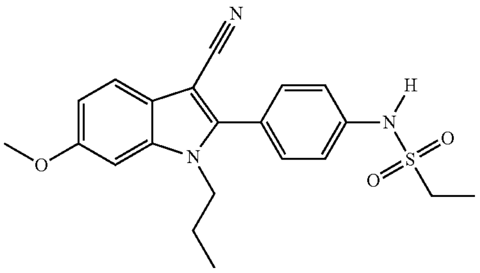
86
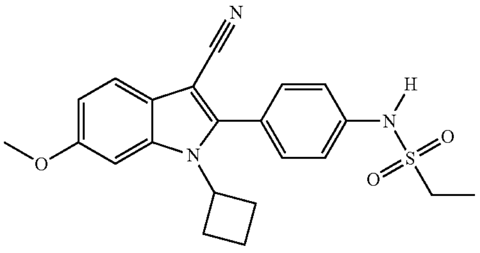
-continued
87
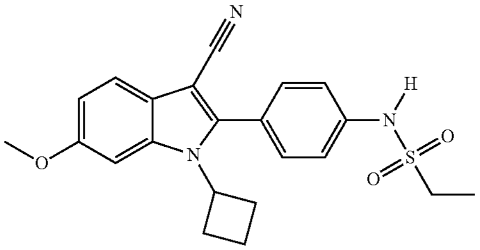
88
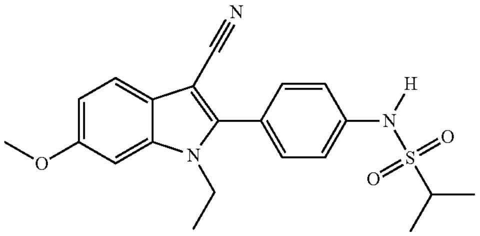
89
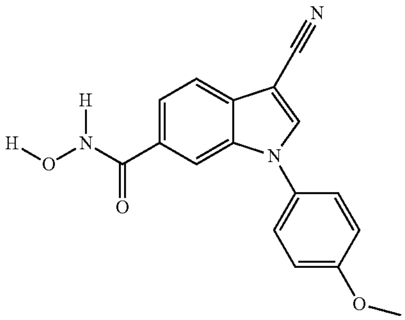
90
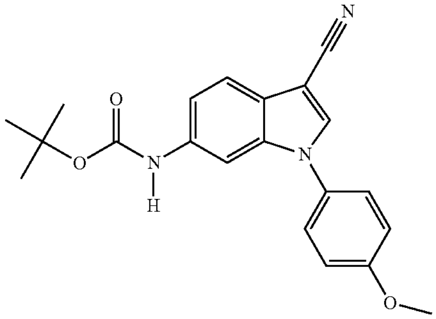
91
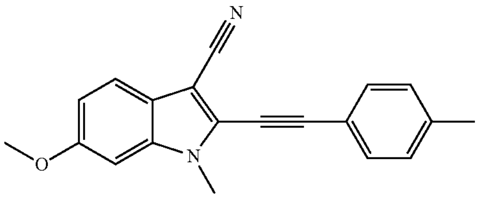
92
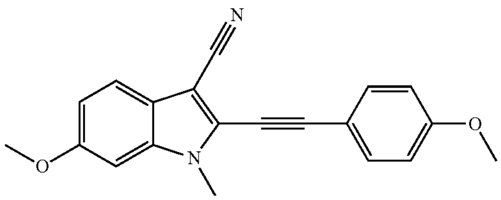

-continued
93
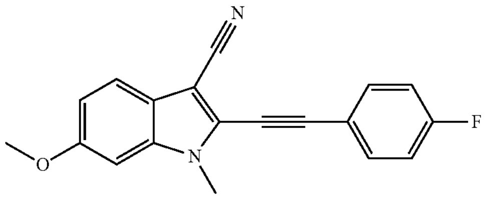
94
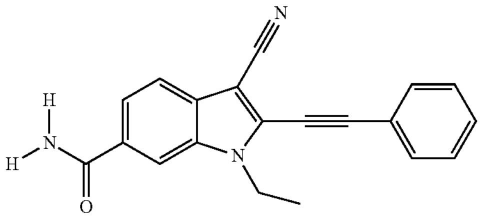
95
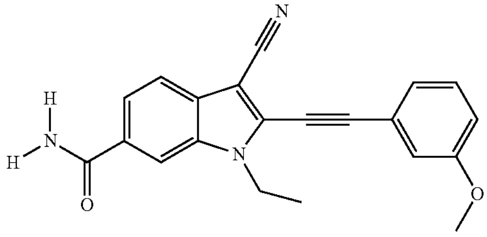
96
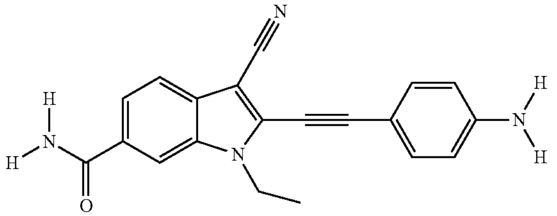
97
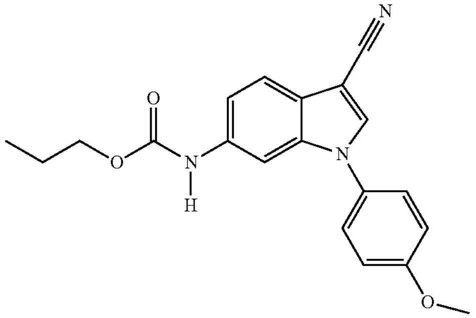
98
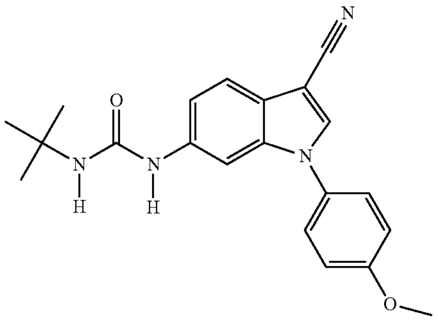
-continued
99
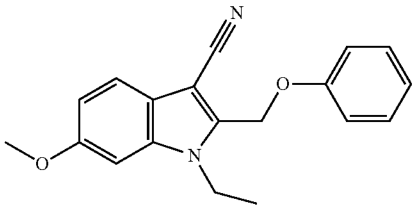
100
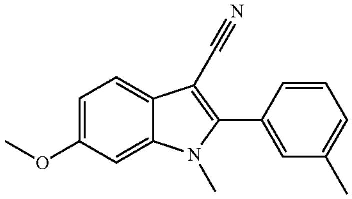
101
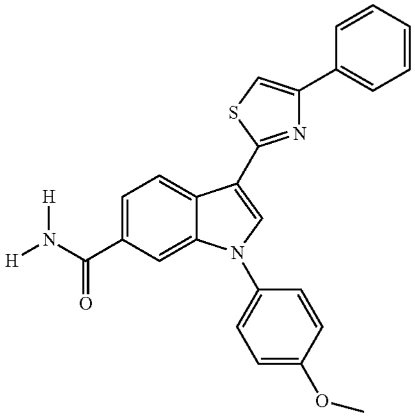
102
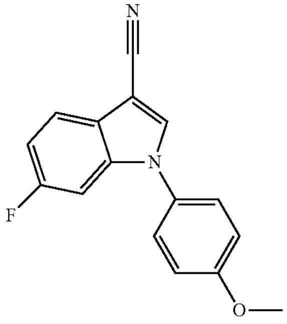
103
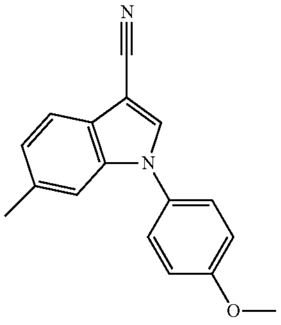

-continued
104
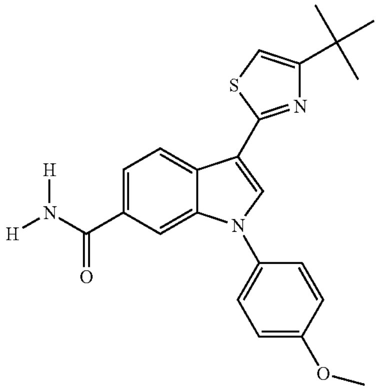
105
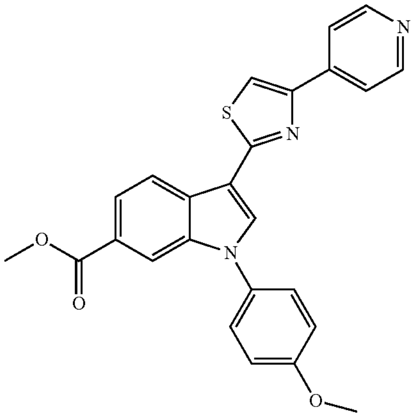
106
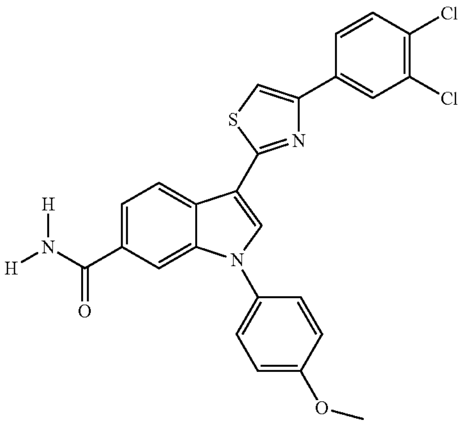
107
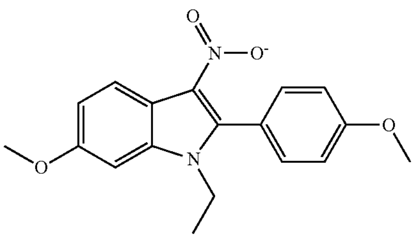
-continued
108
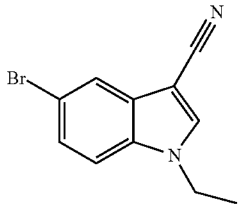
109
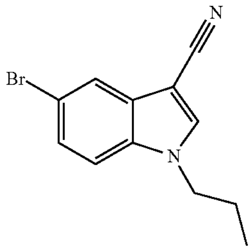
110
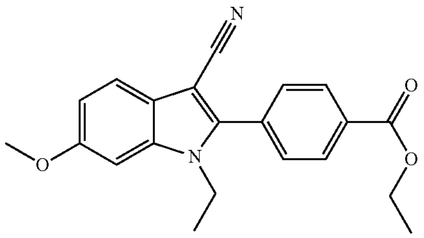
111
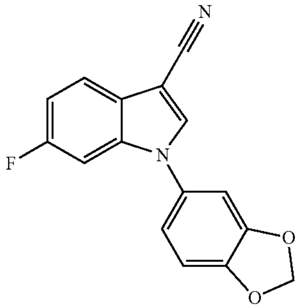
112
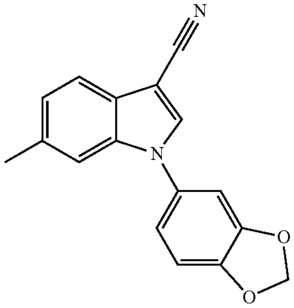
113
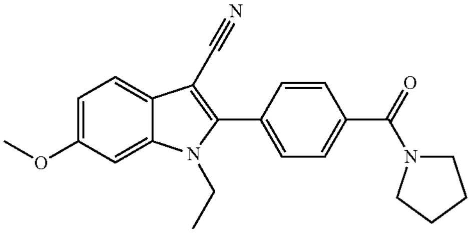

-continued
114
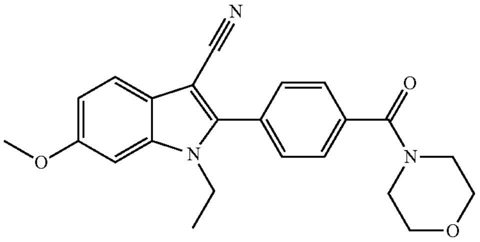
115
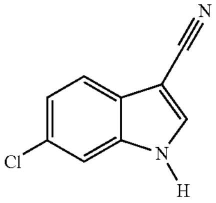
116
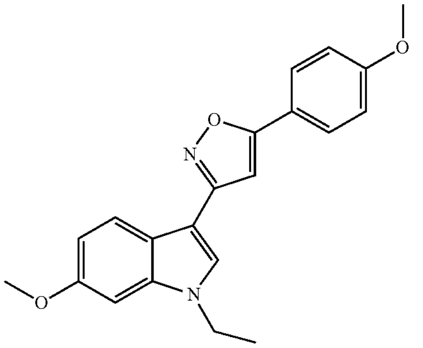
117
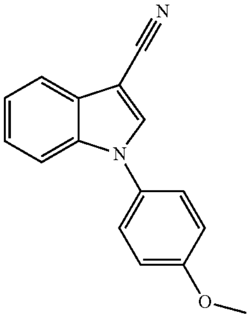
118
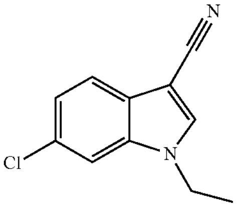
-continued
119
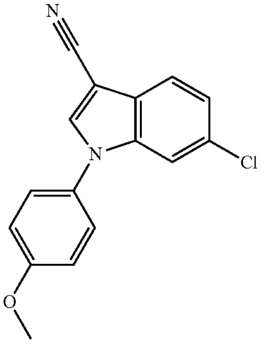
120
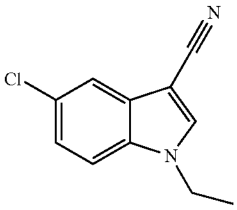
121
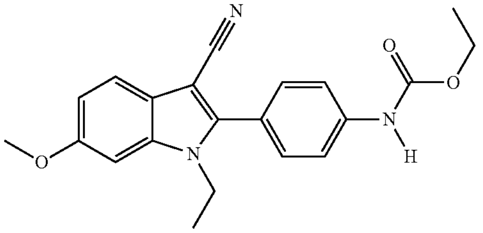
122
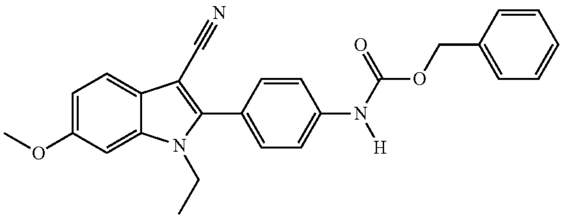
123
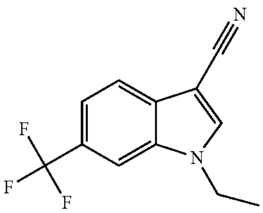
124
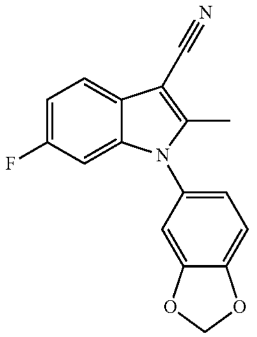

-continued
125
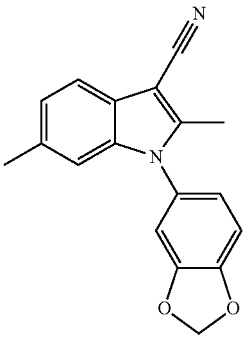
126
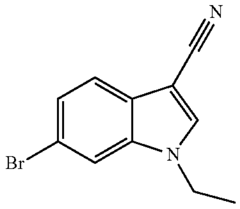
127
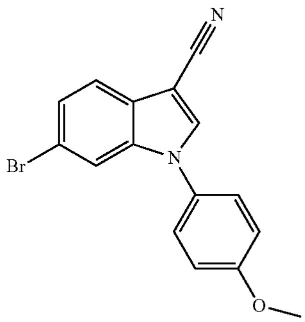
128
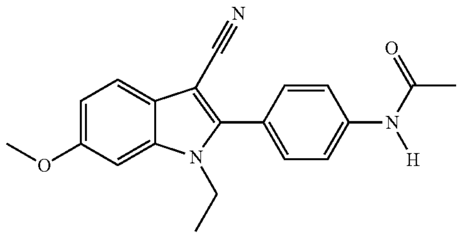
129
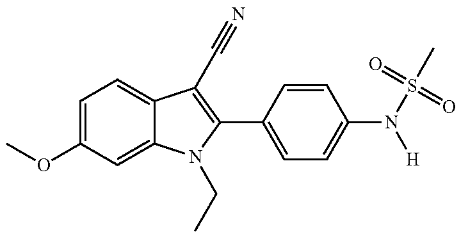
130
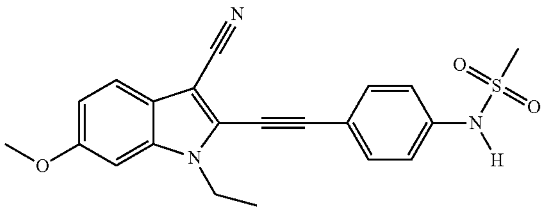
-continued
131
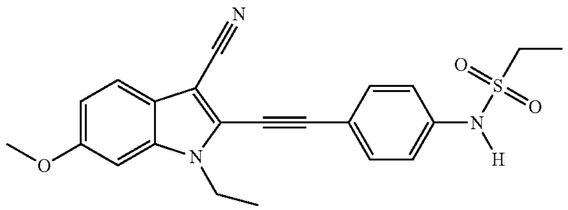
132
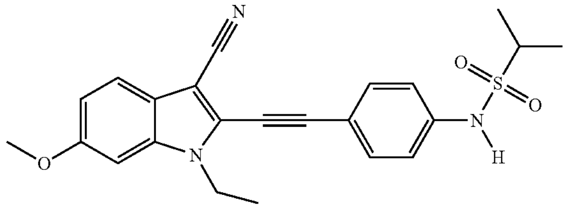
133
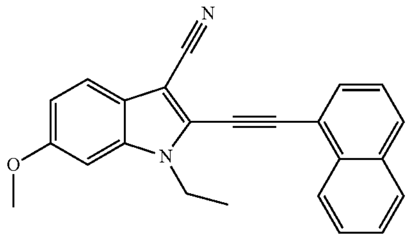
134
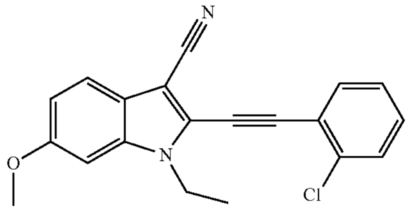
135
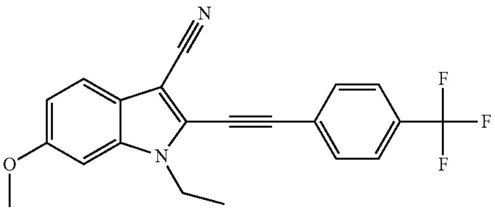
136
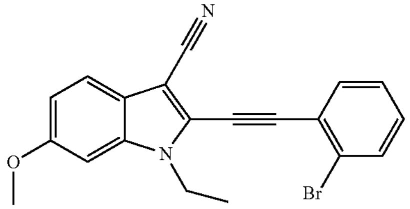
137
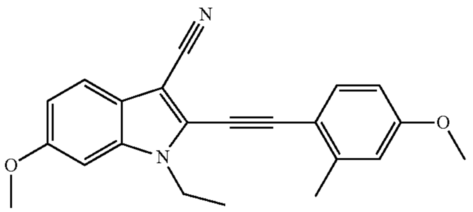

-continued
138
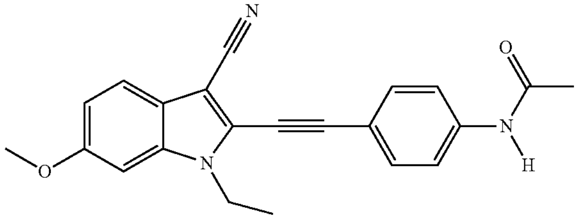
139
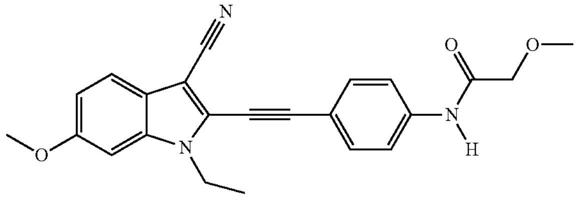
140
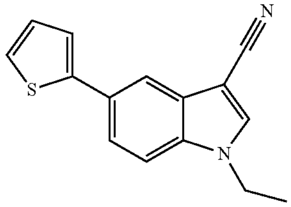
141
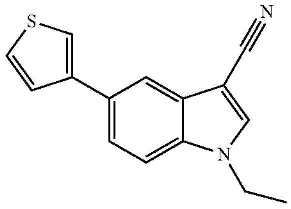
142
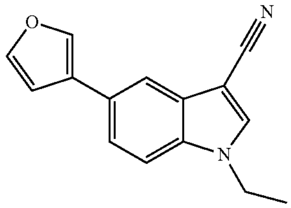
143
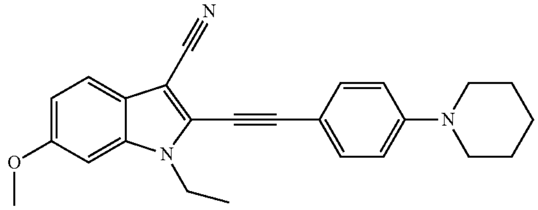
144
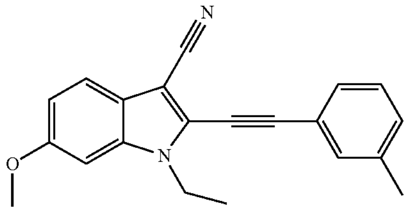
-continued
145
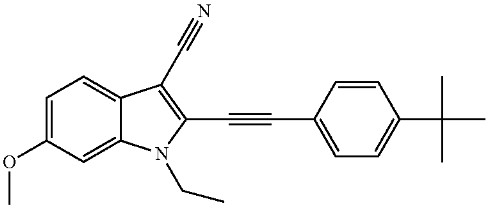
146
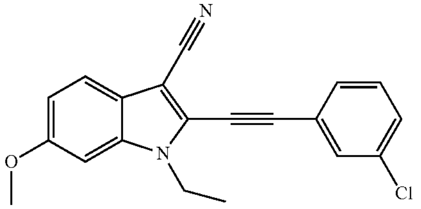
147
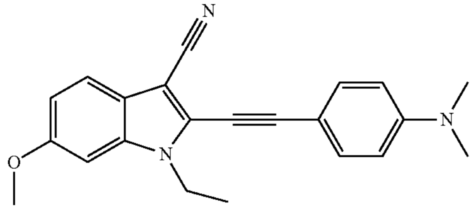
148
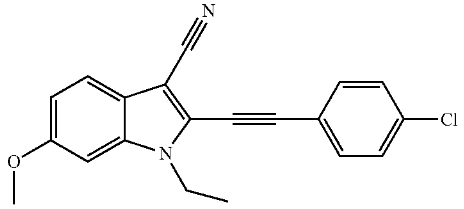
149
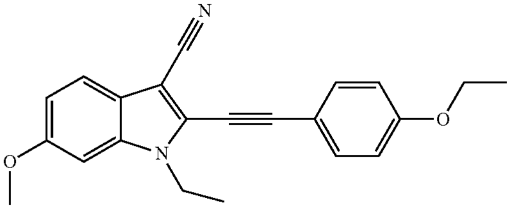
150
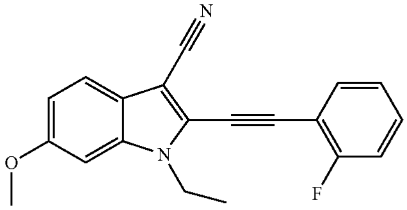
151
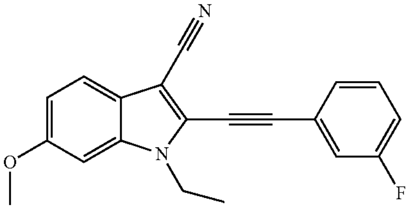

-continued
152
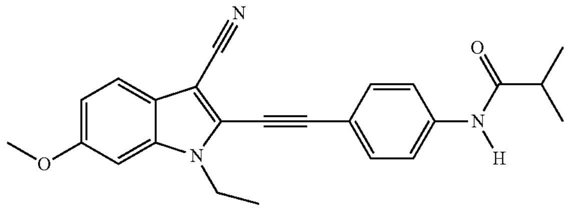
153
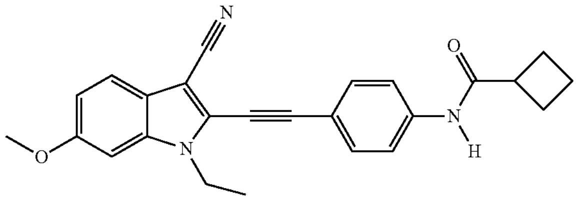
154
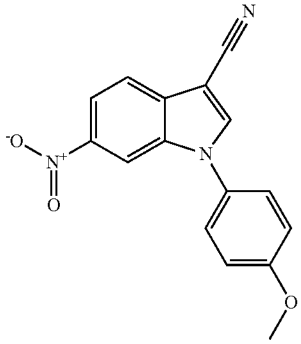
155
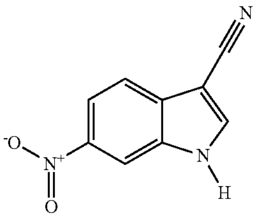
156
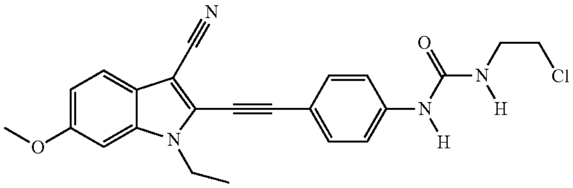
157
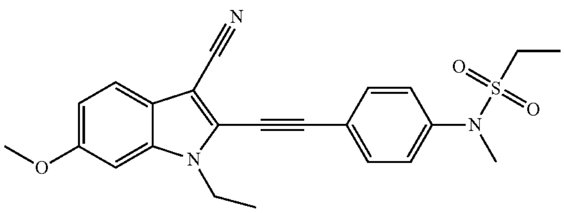
-continued
158
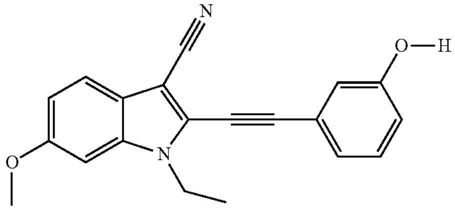
159
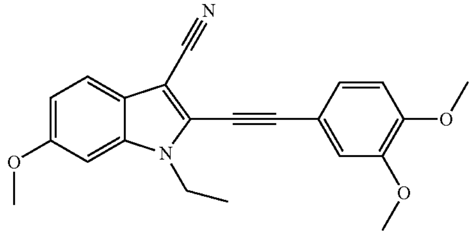
160
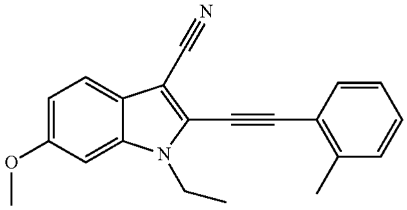
161
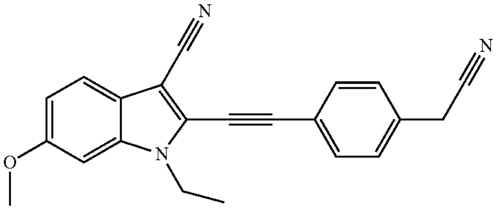
162
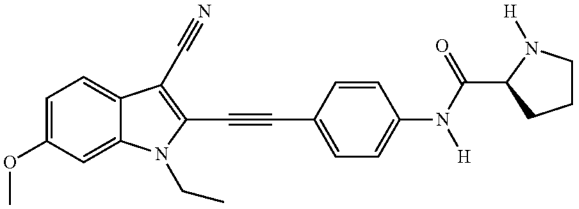
163
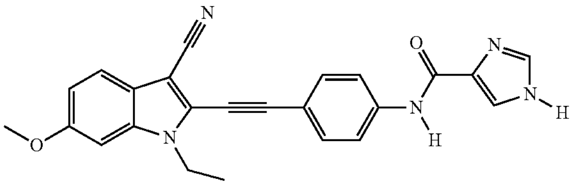
164
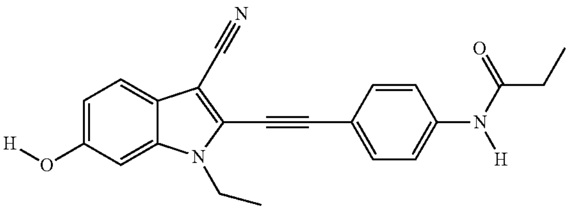

-continued
165
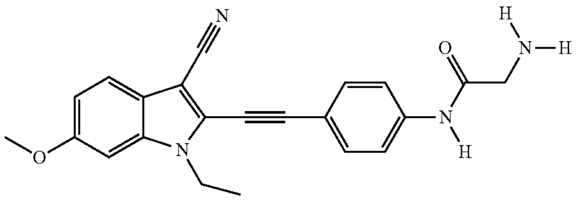
166
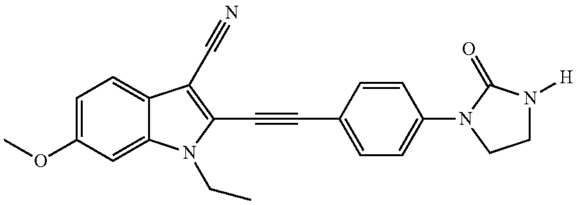
167
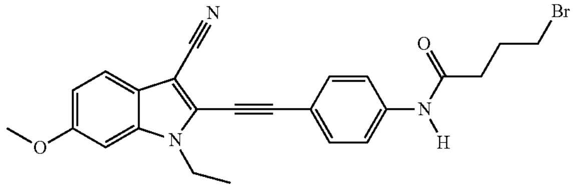
168
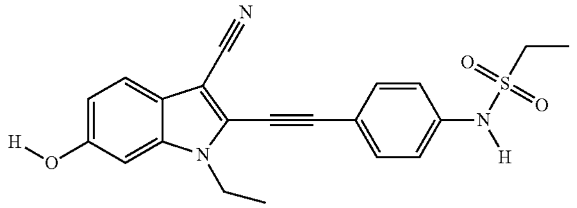
169
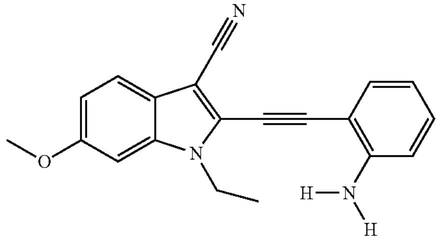
170
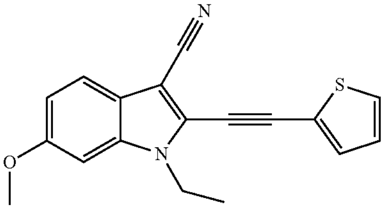
171
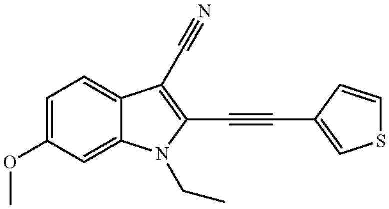
-continued
172
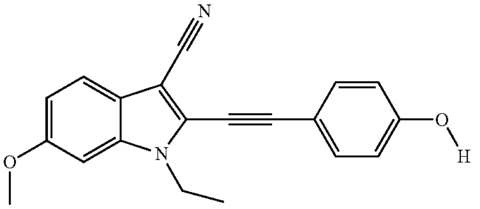
173
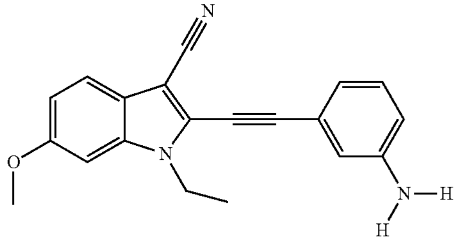
174
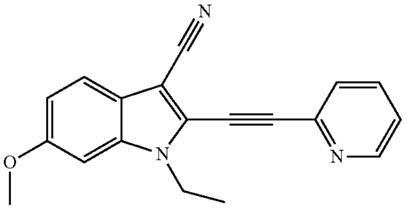
175
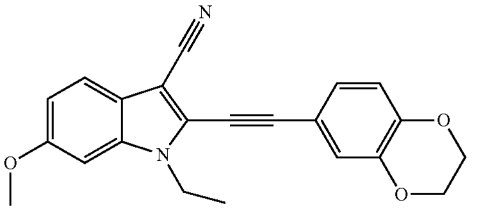
176
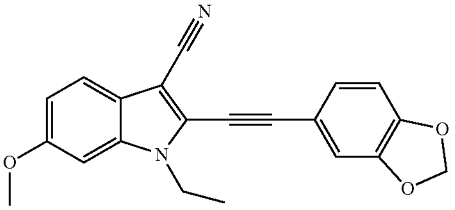
177
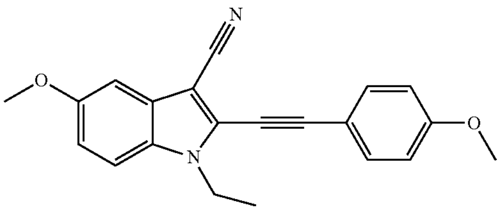
178
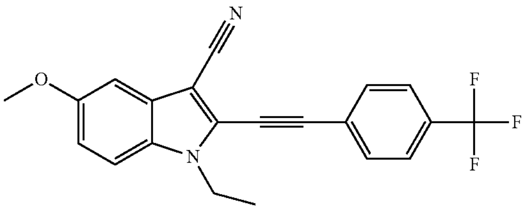

-continued
179
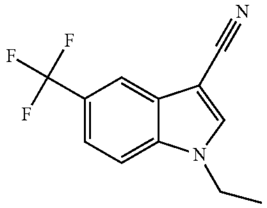
180
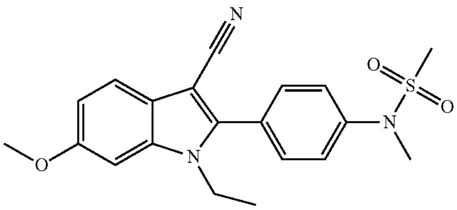
181
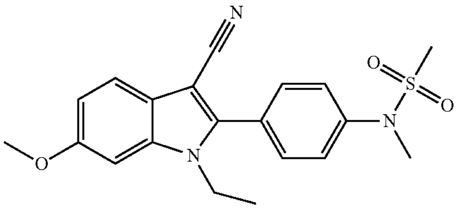
182
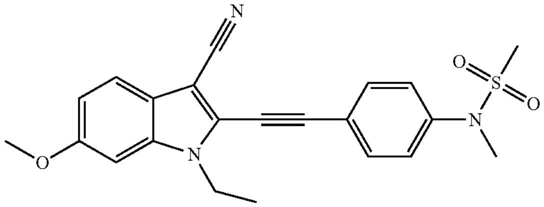
183
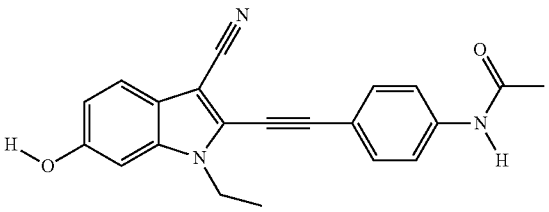
184
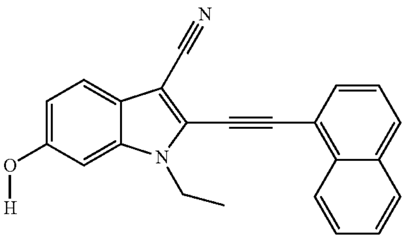
185
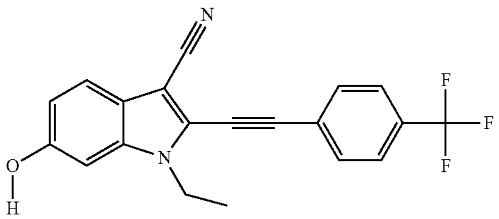
-continued
186
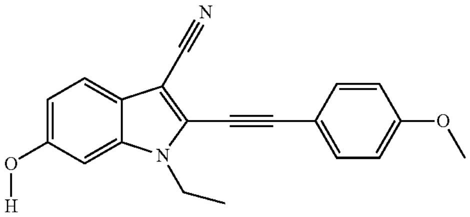
187
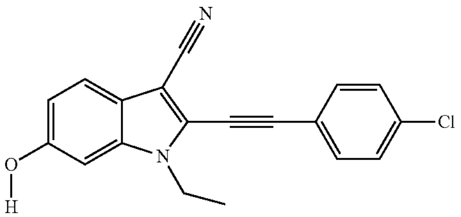
188
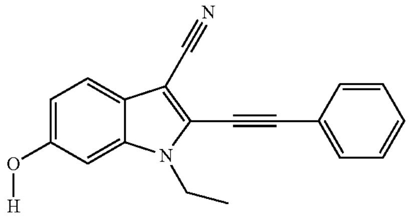
189
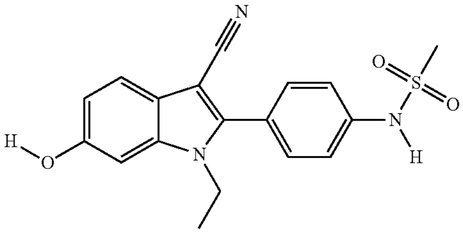
190
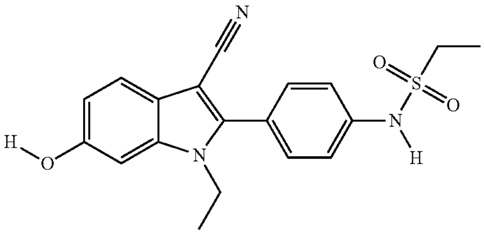
191
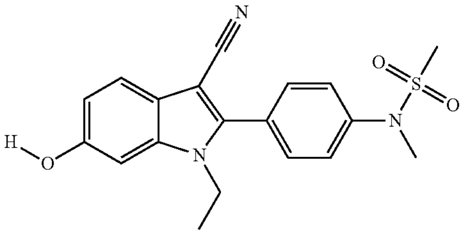
192
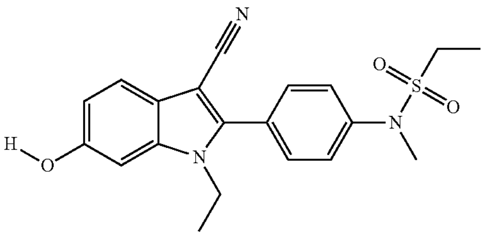

-continued
193
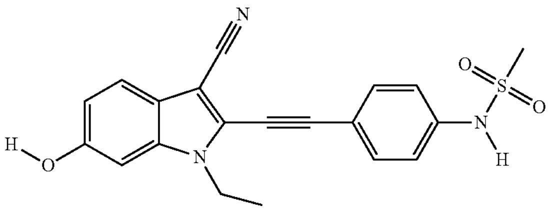
194
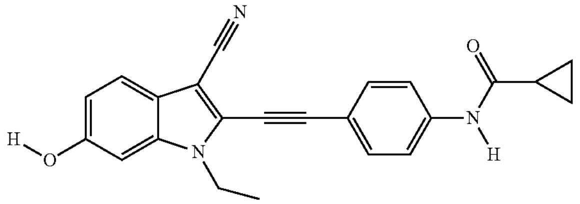
195
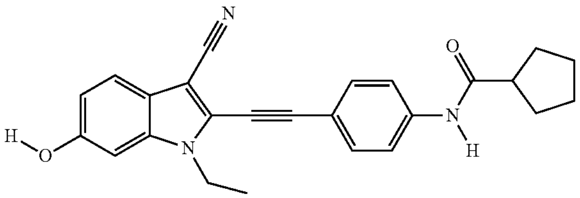
196
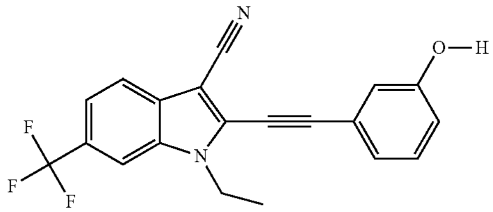
197
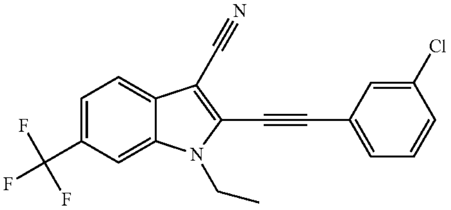
198
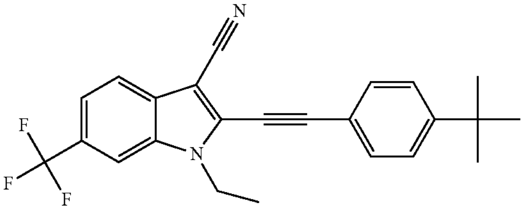
199
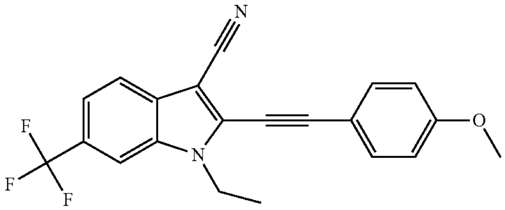
-continued
200
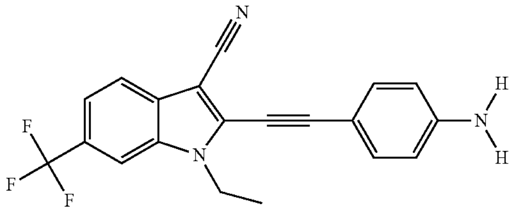
201
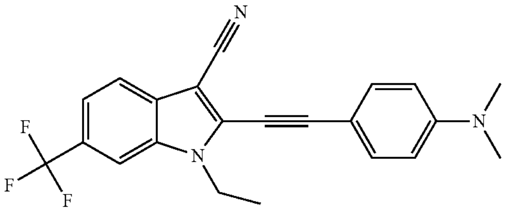
202
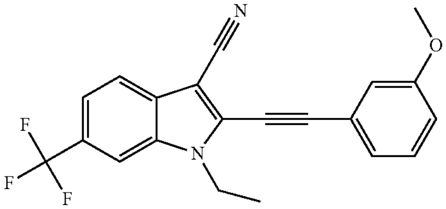
203
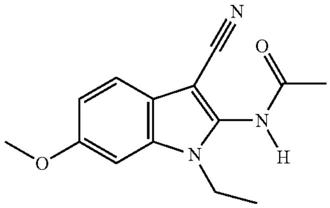
204
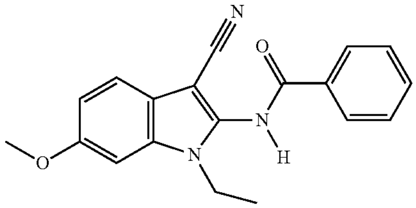
205
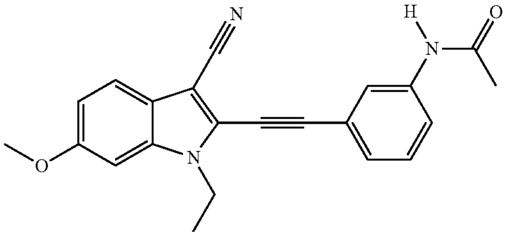
206
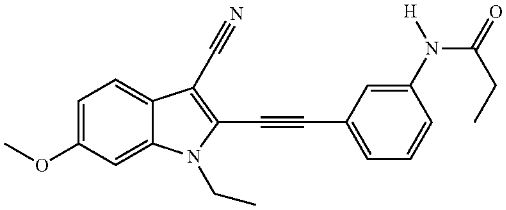

-continued
207
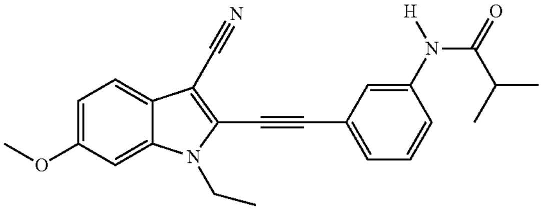
208
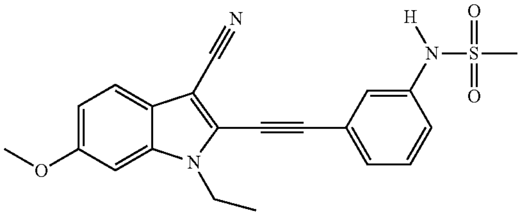
209
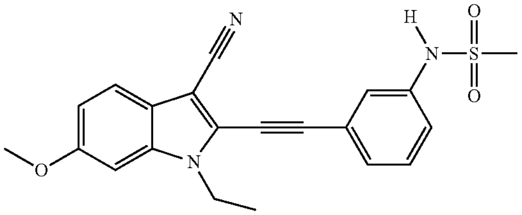
210
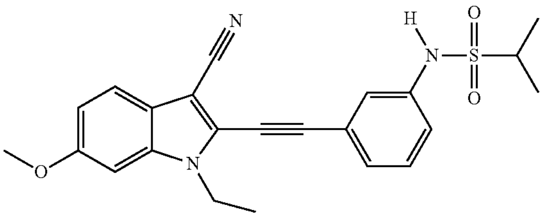
211
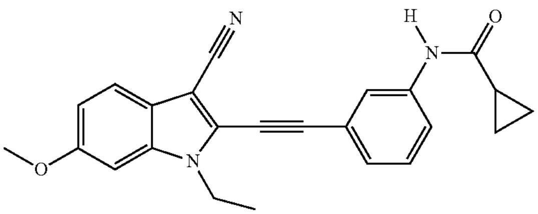
212
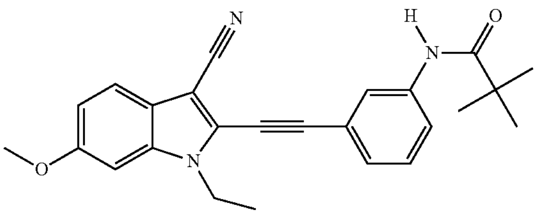
-continued
213
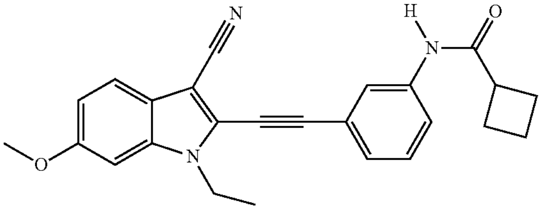
214
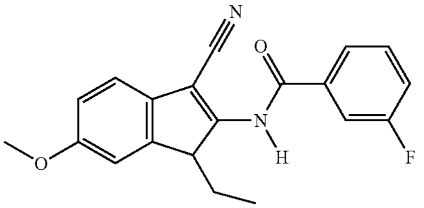
215
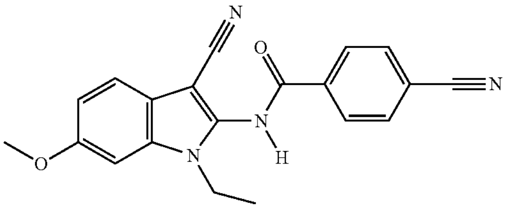
216
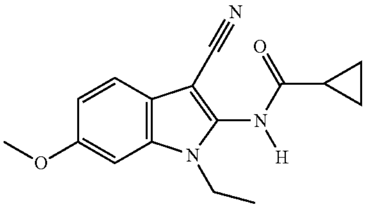
217
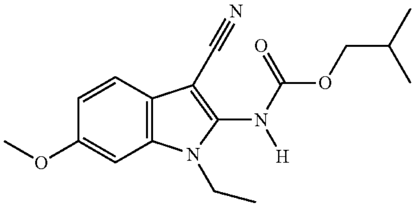
218
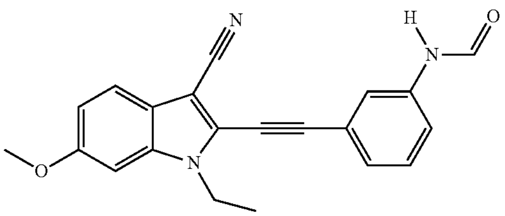
219
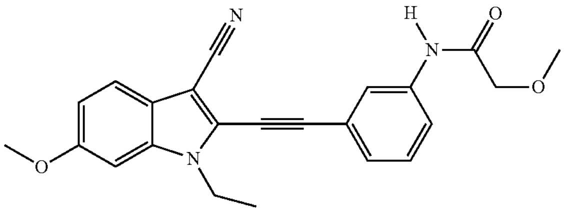

-continued
220
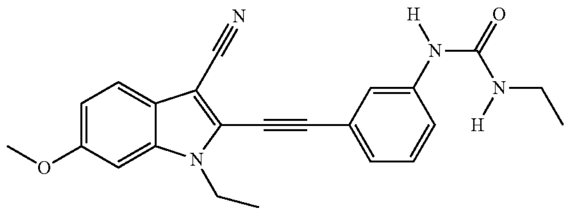
221
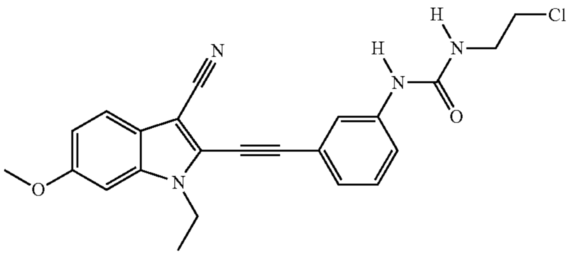
222
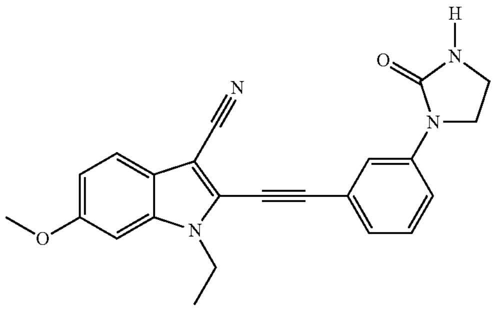
223
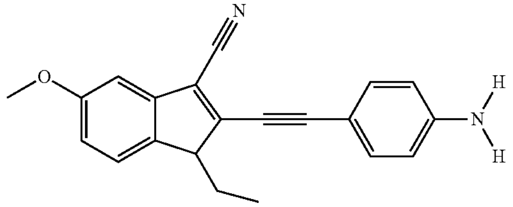
224
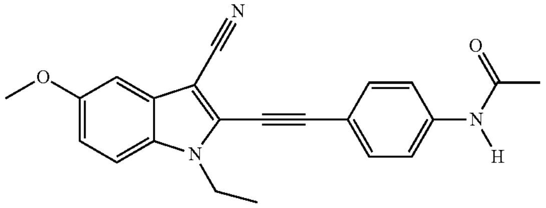
225
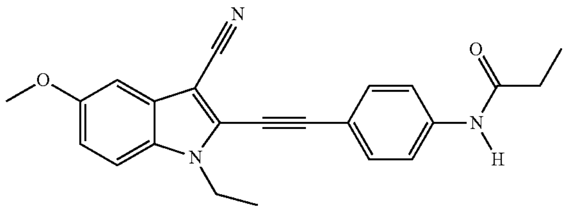
-continued
226
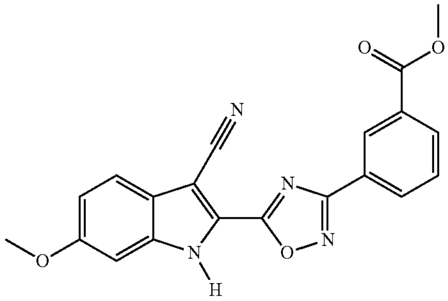
227
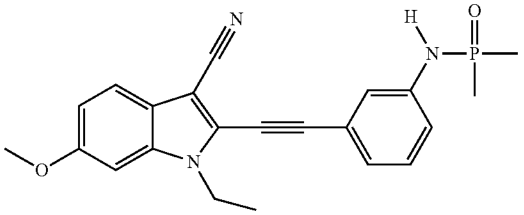
228
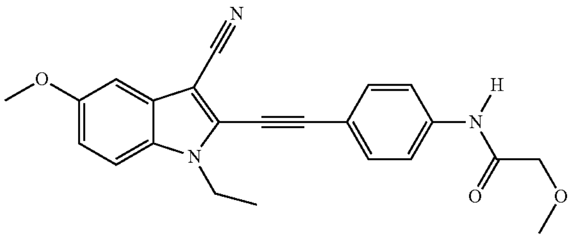
229
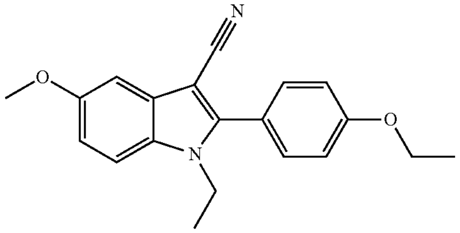
230
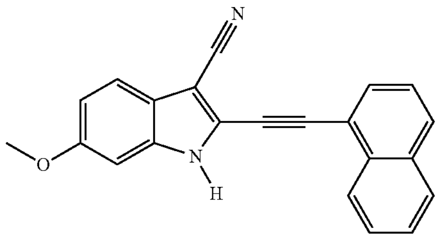
231
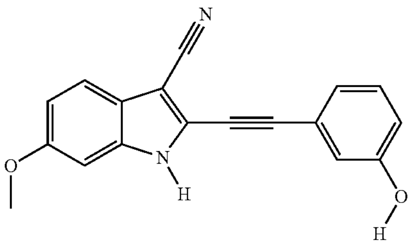

-continued
232
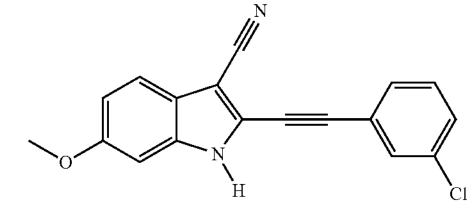
233
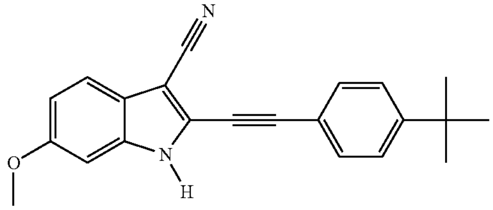
234
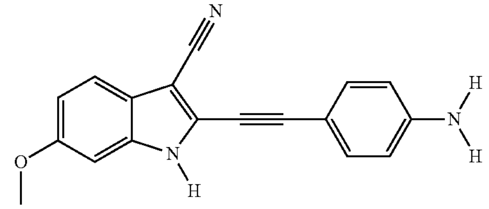
235
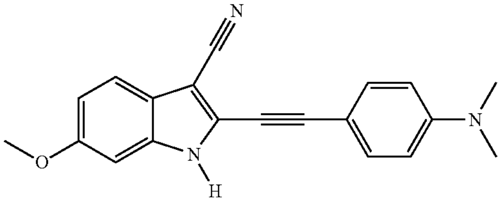
236
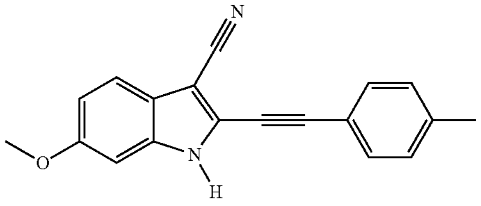
237
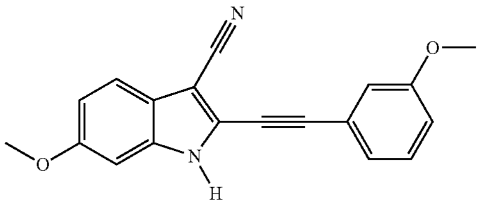
238
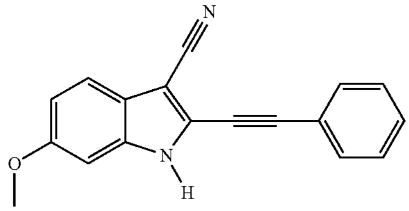
-continued
239
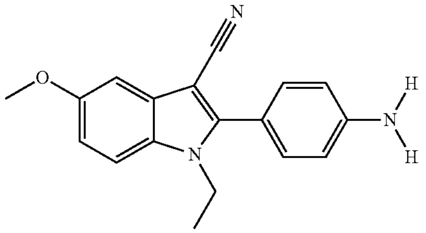
240
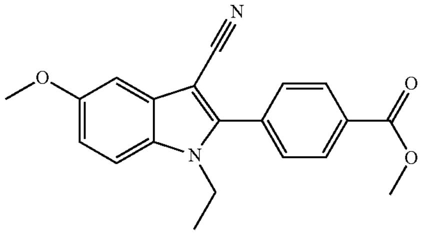
241
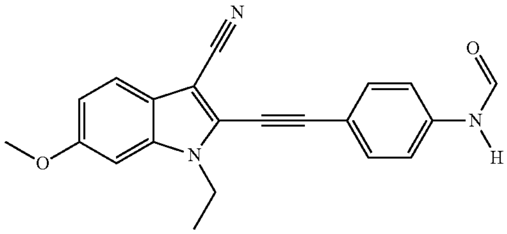
242
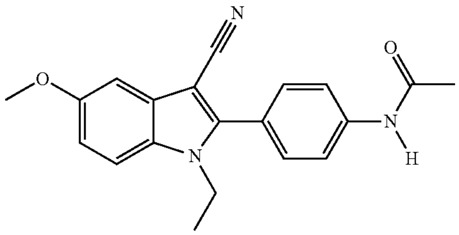
243
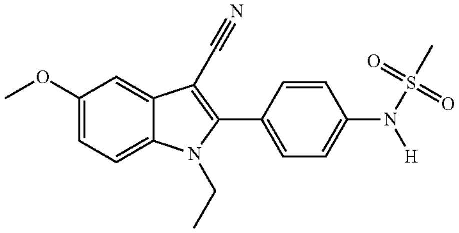
244
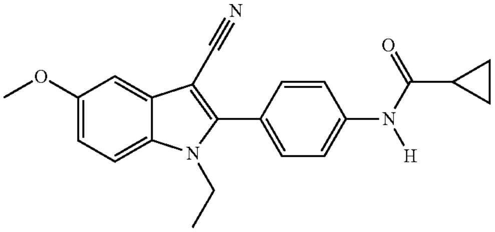

-continued
245
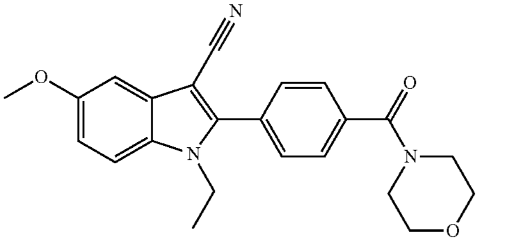
246
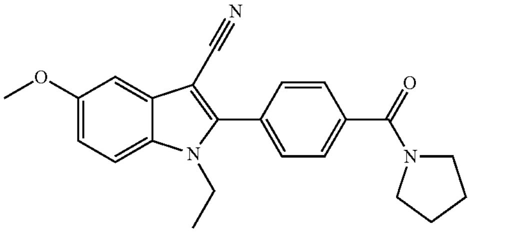
247
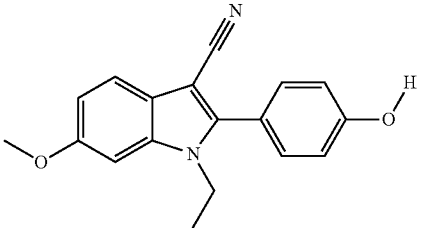
248
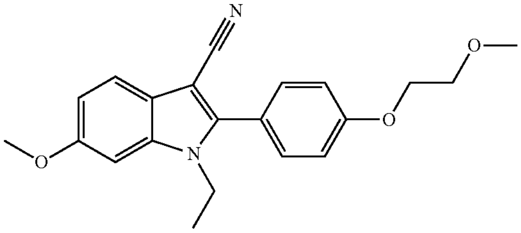
249
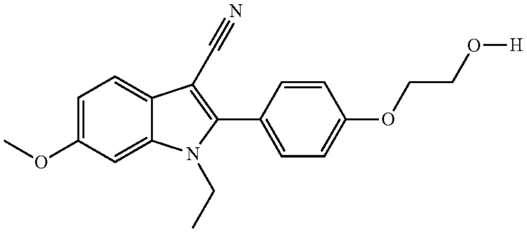
250
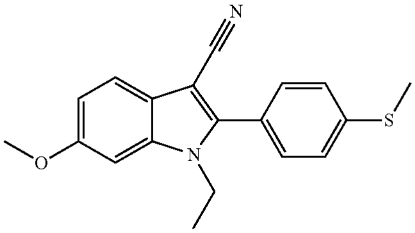
-continued
251
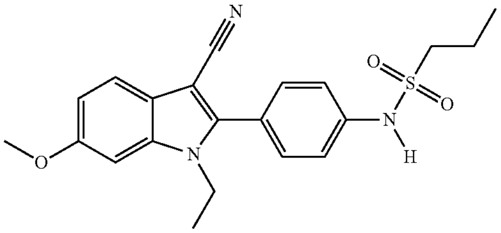
252
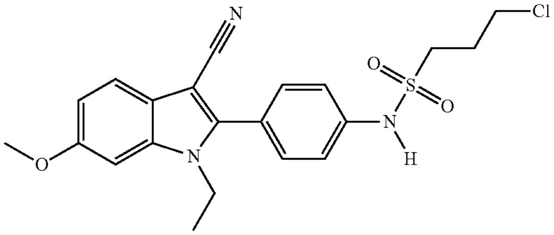
253
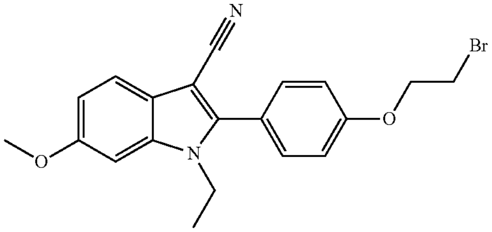
254
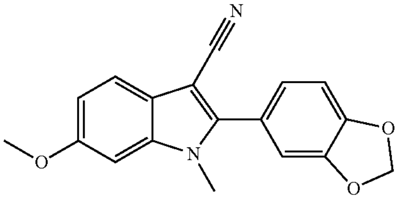
255
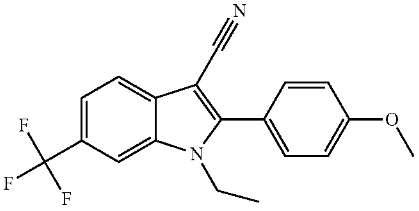
256
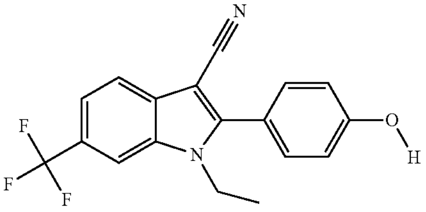
257
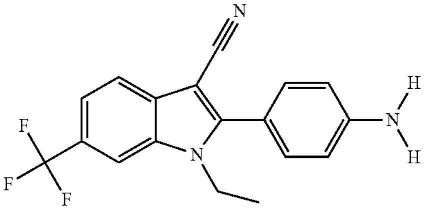

-continued
258
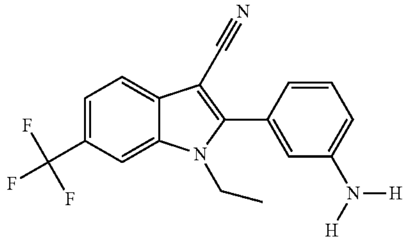
259
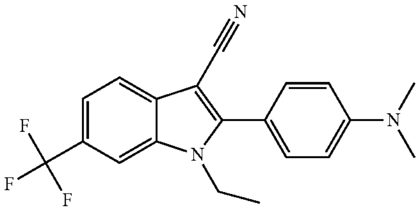
260
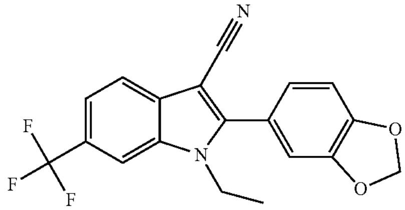
261
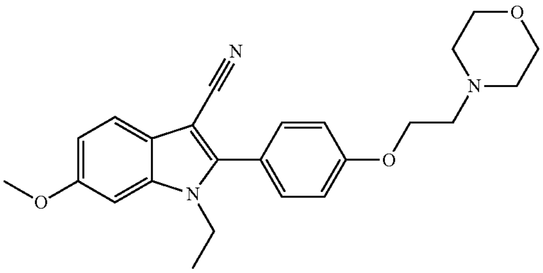
262
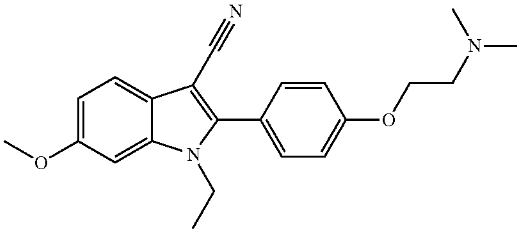
263
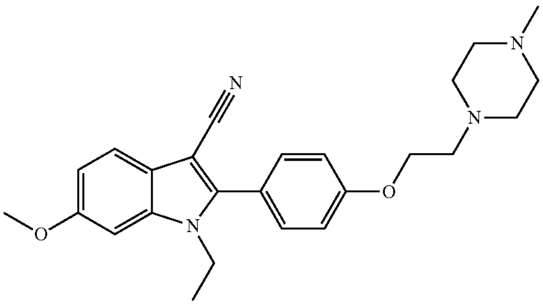
-continued
264
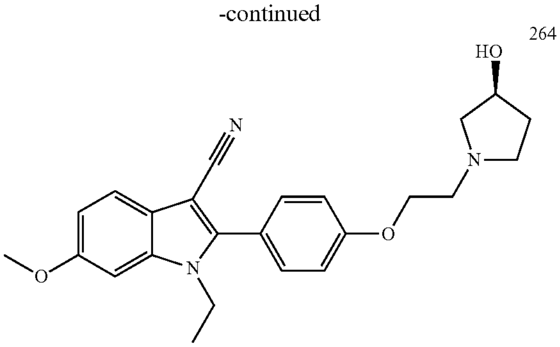
265
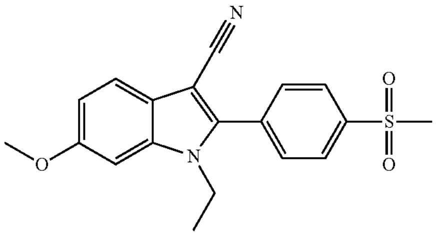
266
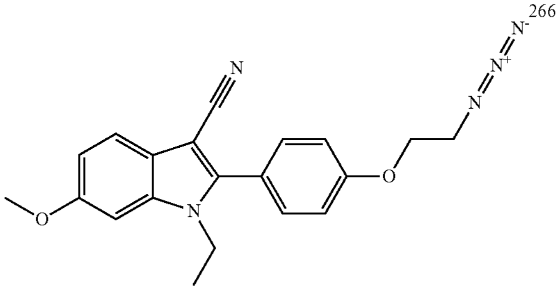
267
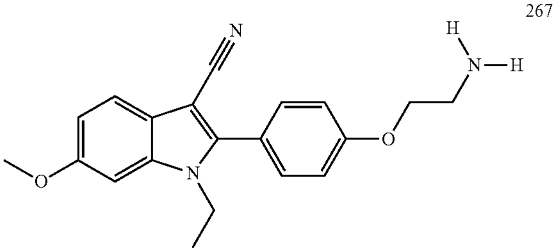
268
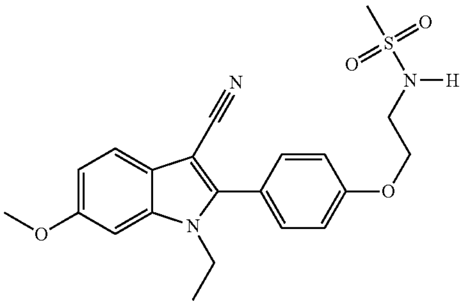
269
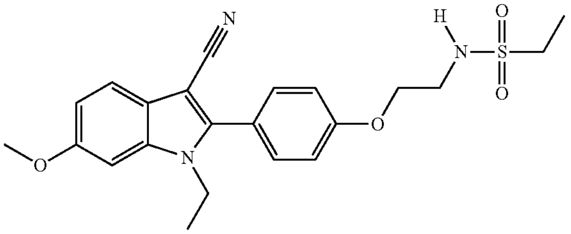

-continued
270
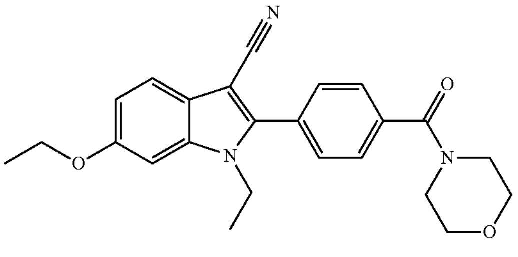
271
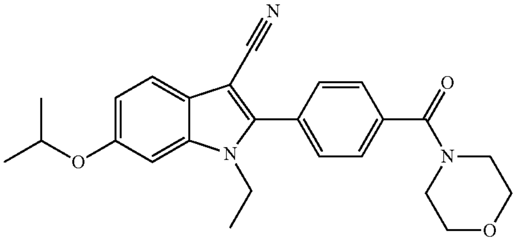
272
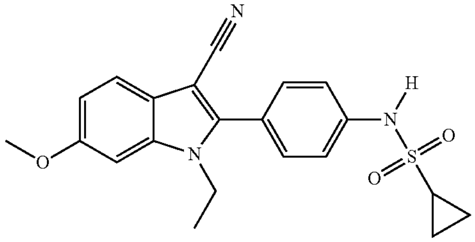
273
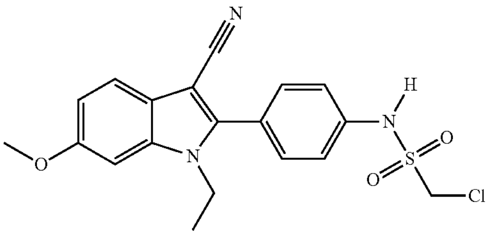
274
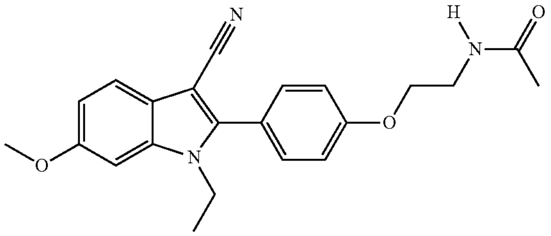
275
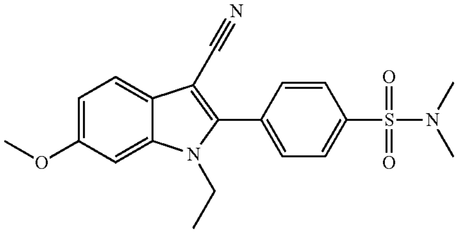
-continued
276
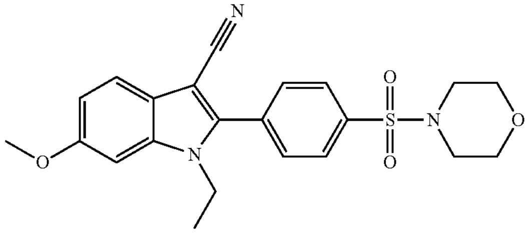
277
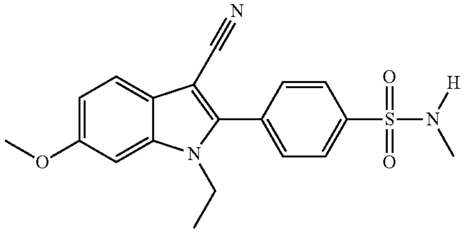
278
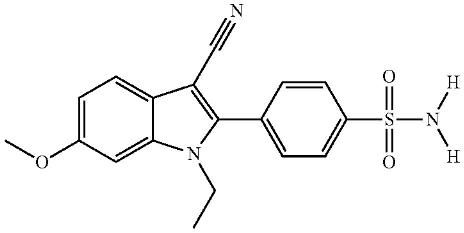
279
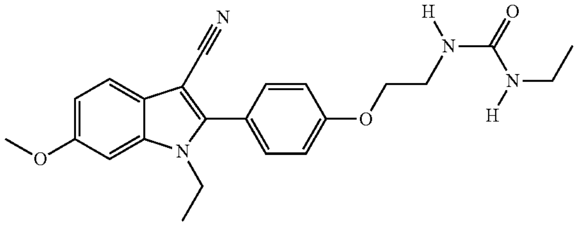
280
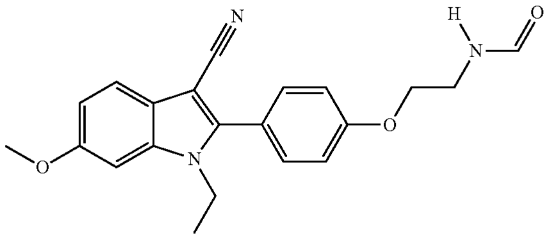
281
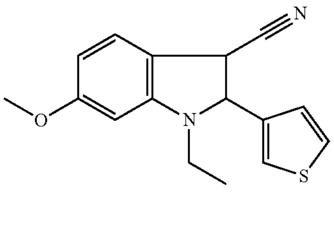

-continued
282
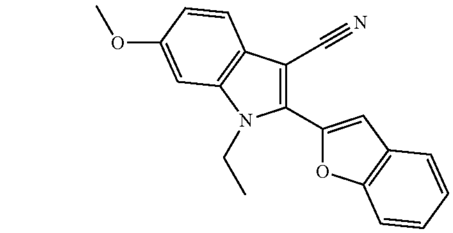
283
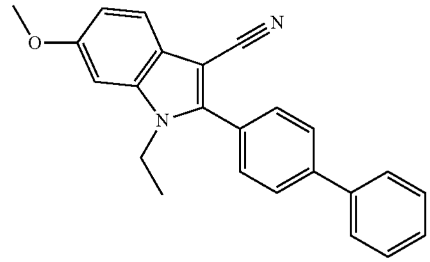
284
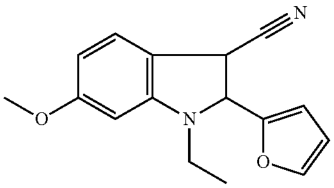
285
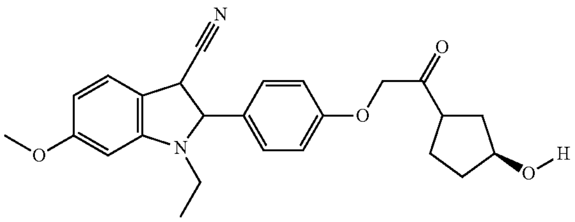
286
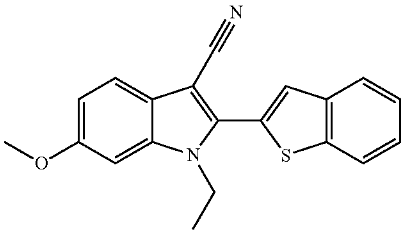
287
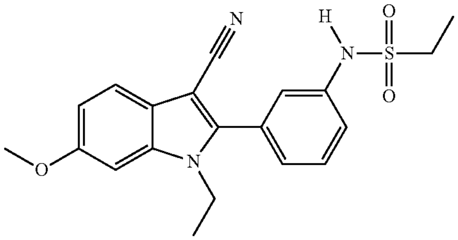
-continued
288
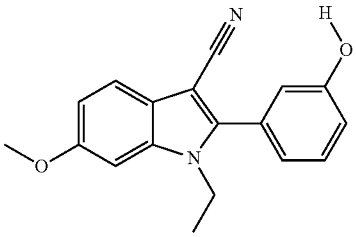
289
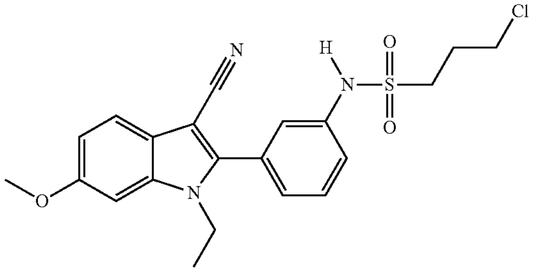
290
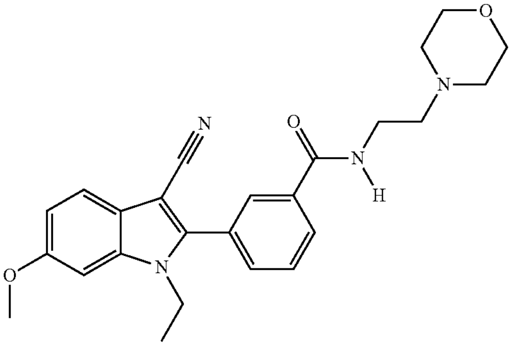
291
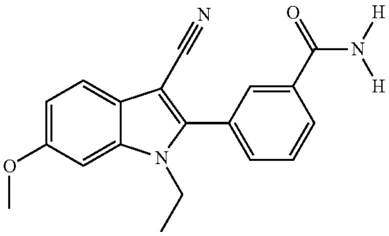
292
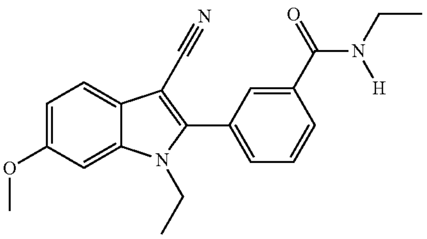
293
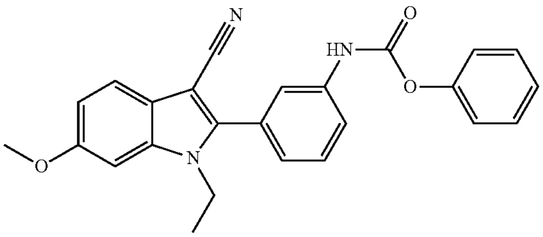

-continued
294
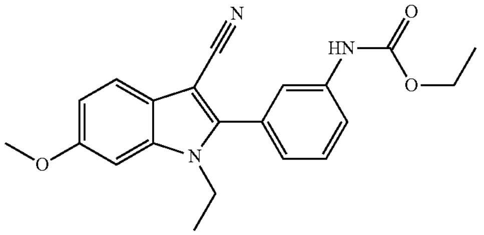
295
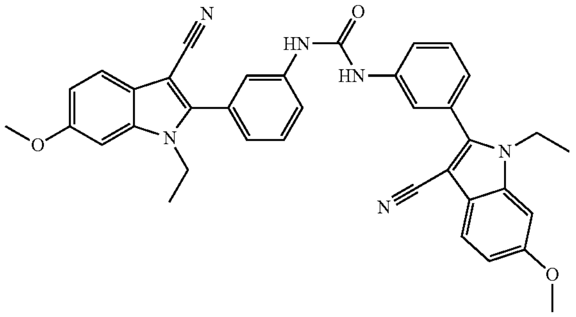
296
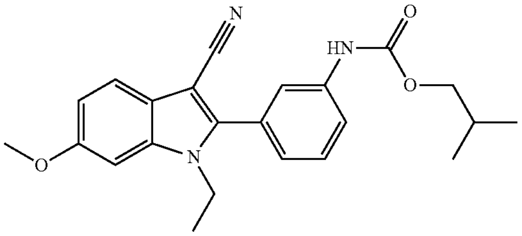
297
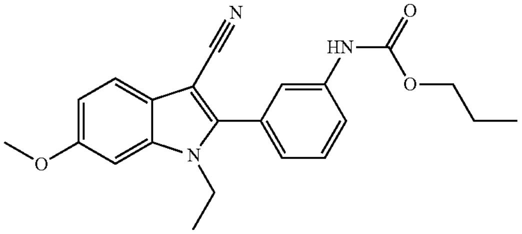
298
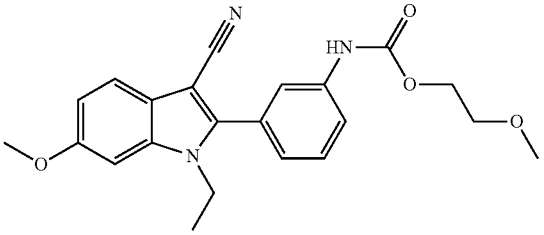
299
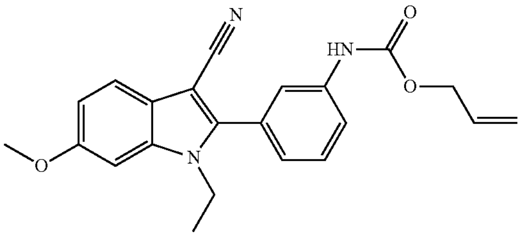
-continued
300
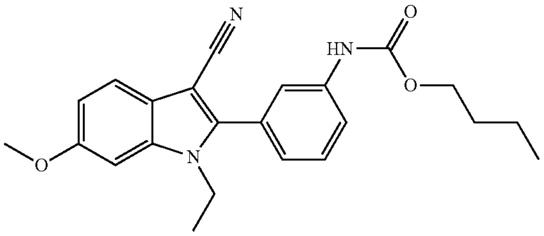
301
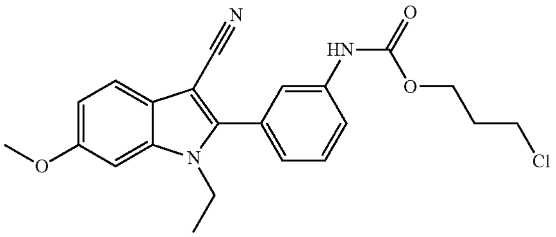
302
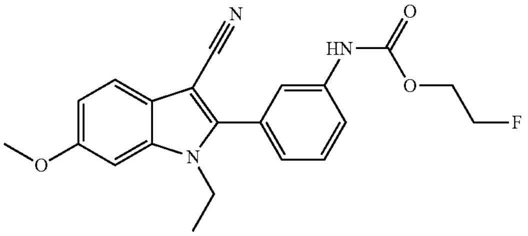
303
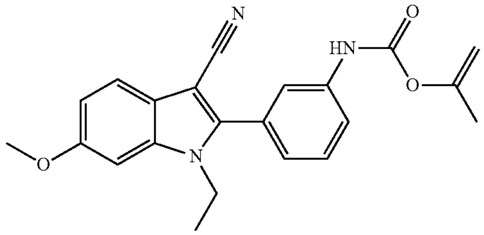
304
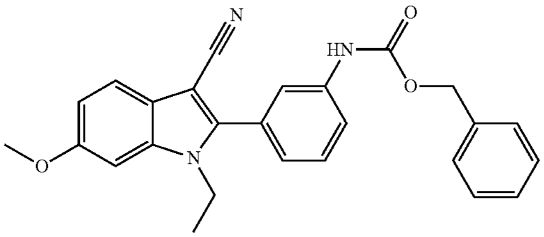
305
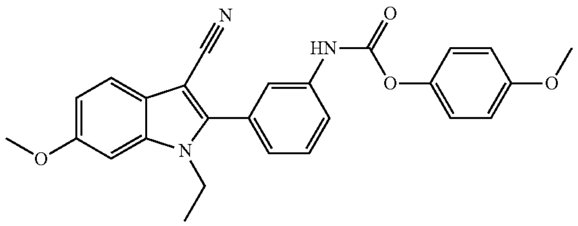

-continued
306
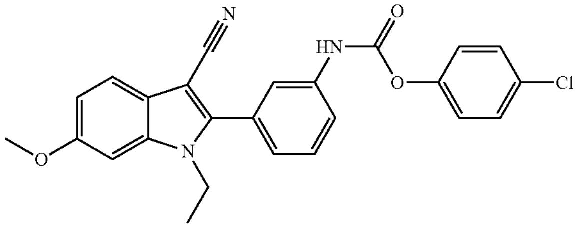
307
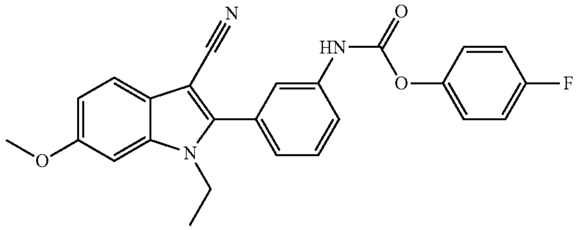
308
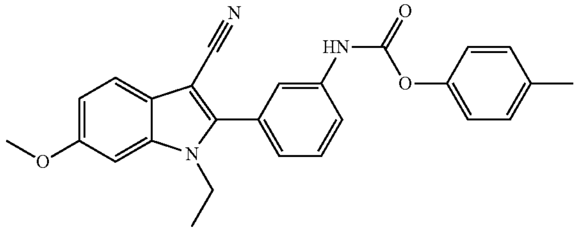
309
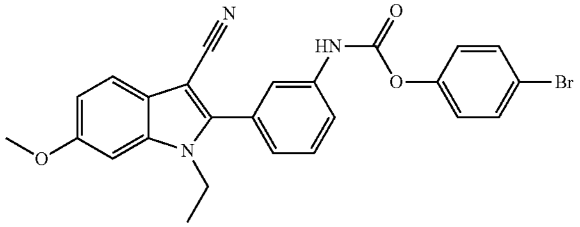
310
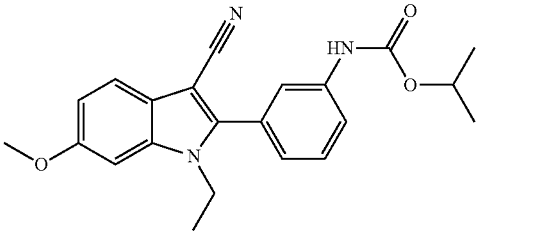
311
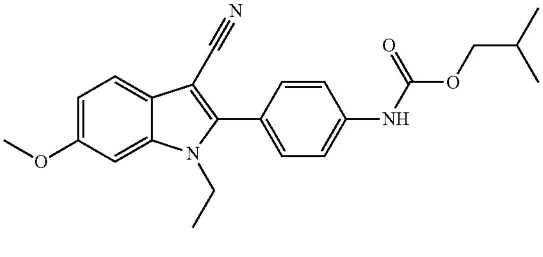
-continued
312
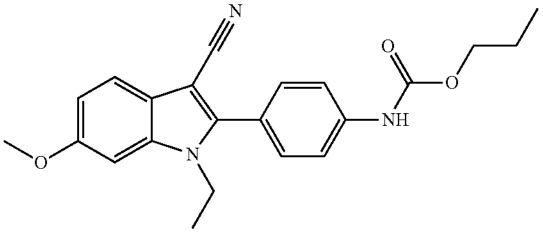
313
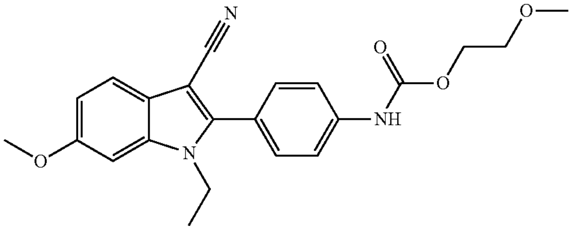
314
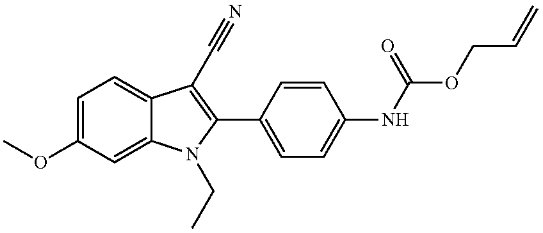
315
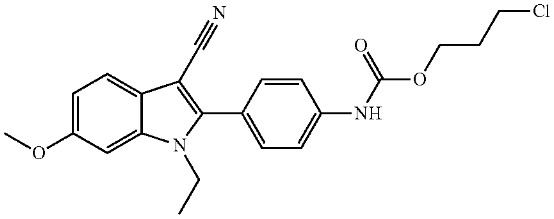
316
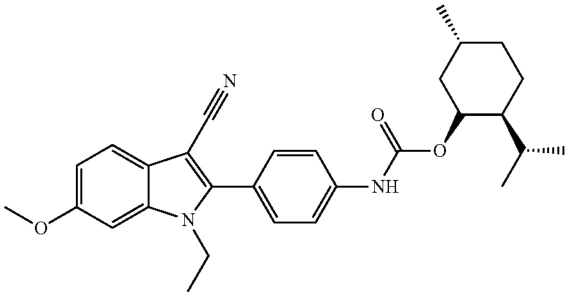
317
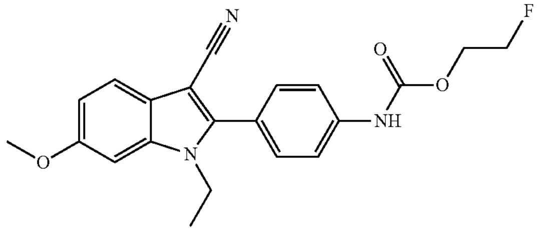

-continued
318
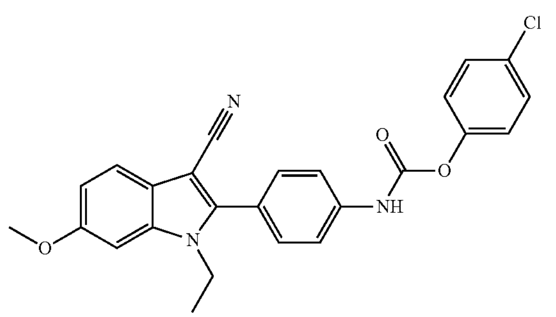
319
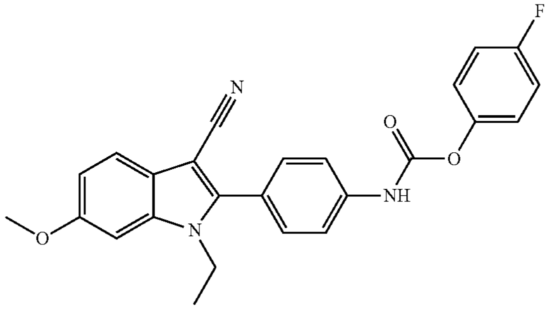
320
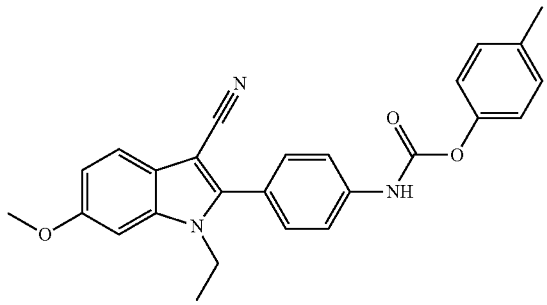
321
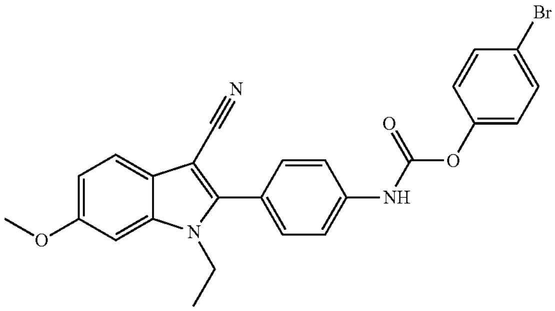
322
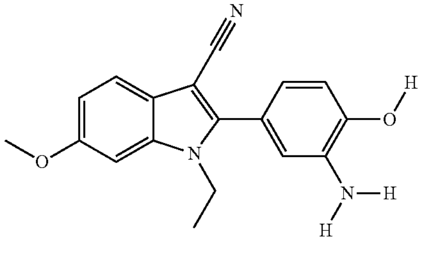
-continued
323
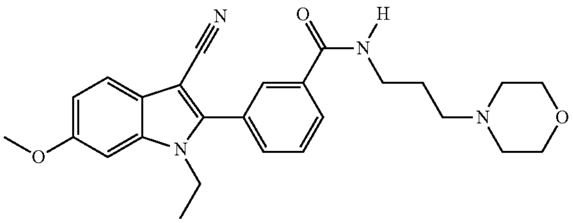
324
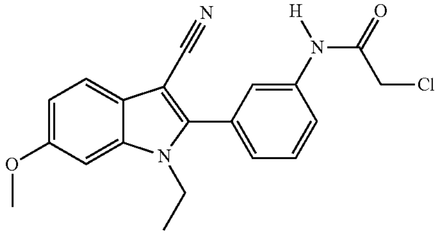
325
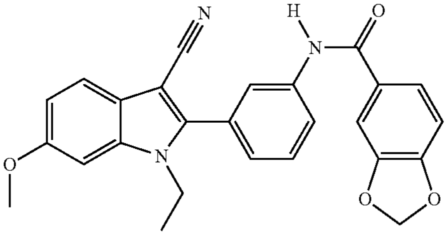
326
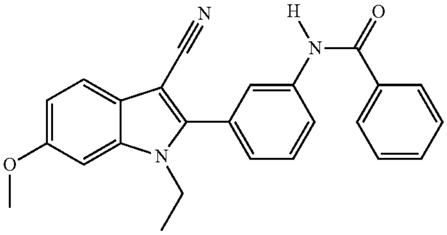
327
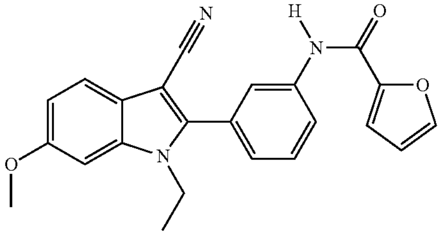
328
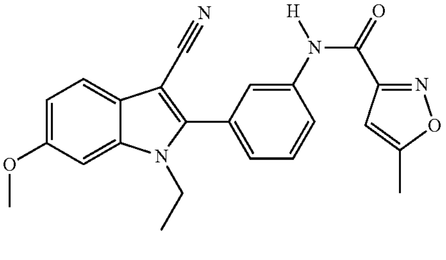

-continued
329
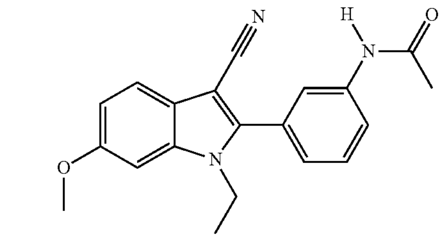
330
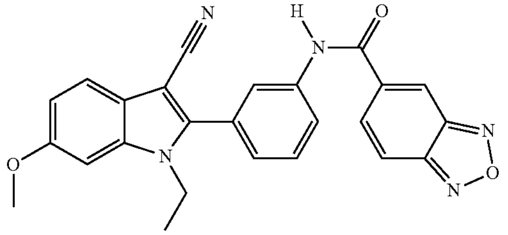
331
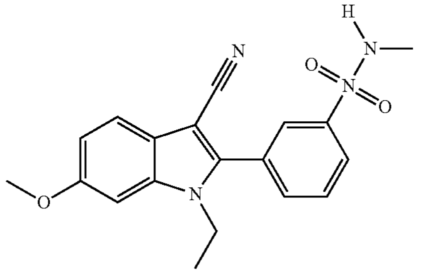
332
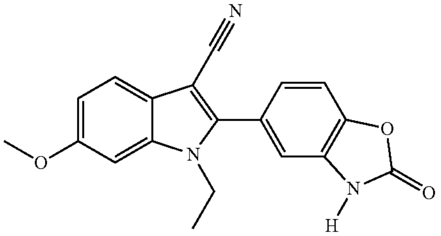
333
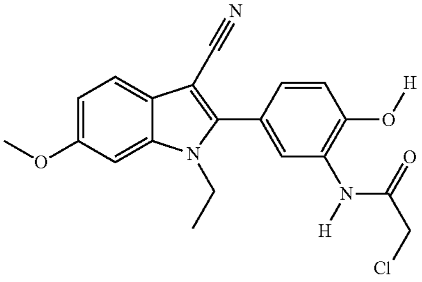
334
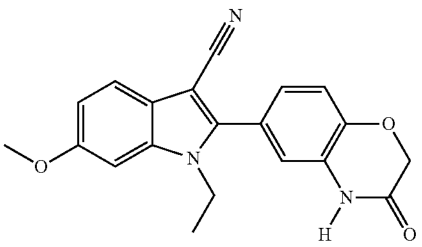
-continued
335
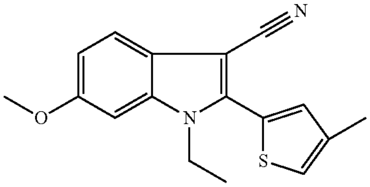
336
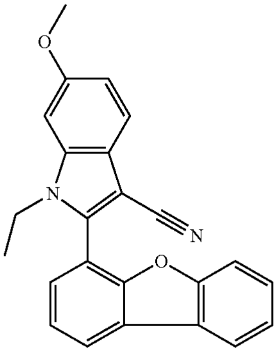
337
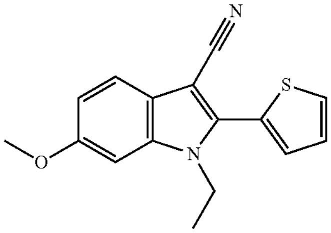
338
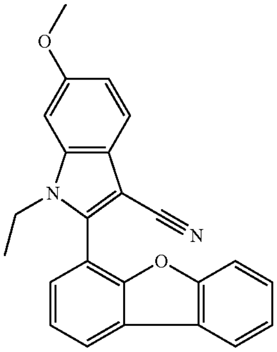
339
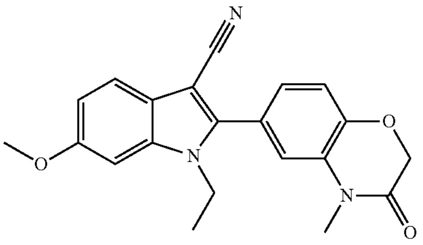
340
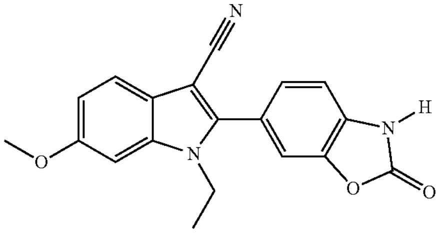

-continued
341
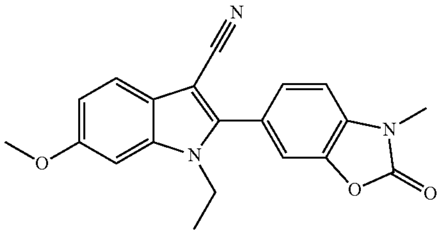
342
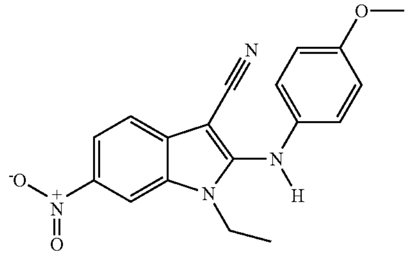
343
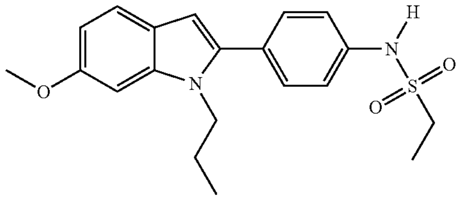
344
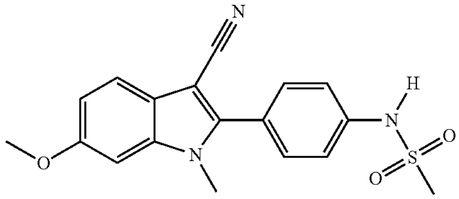
345
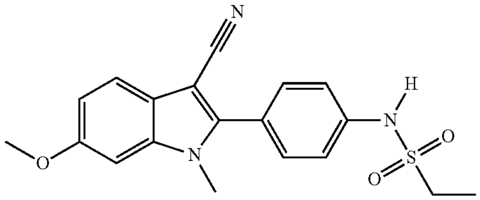
346
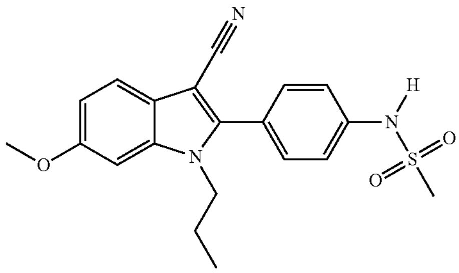
-continued
347
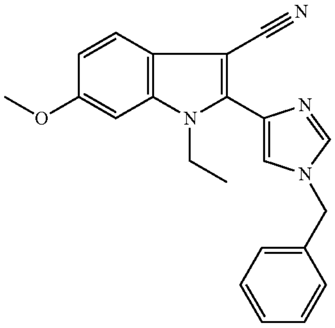
348
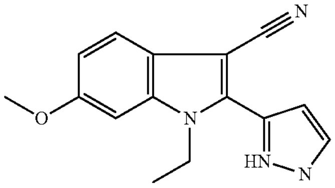
349
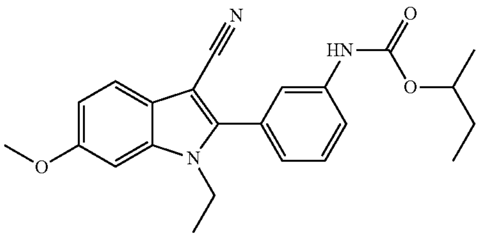
350
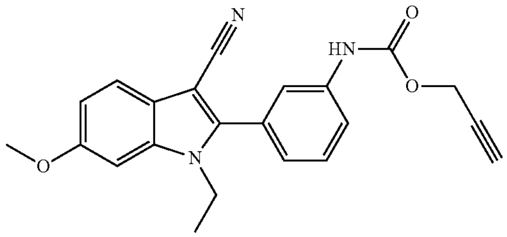
351
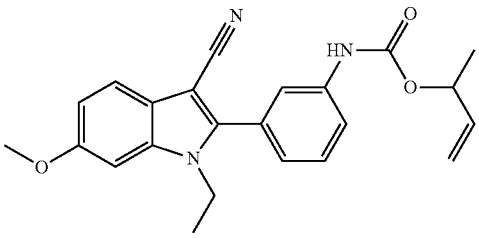
352
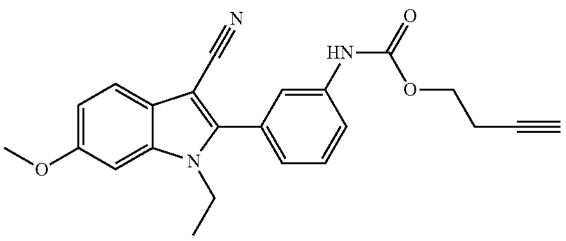

-continued
353
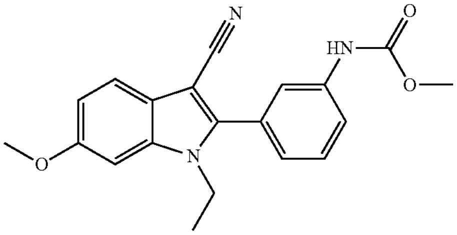
354
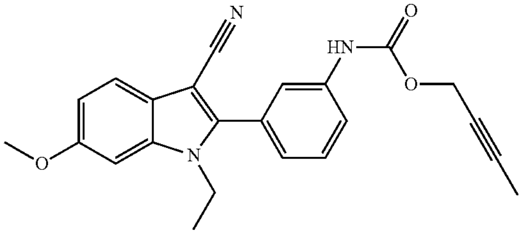
355
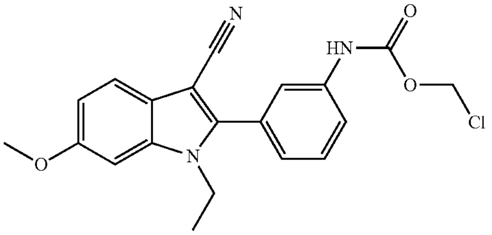
356
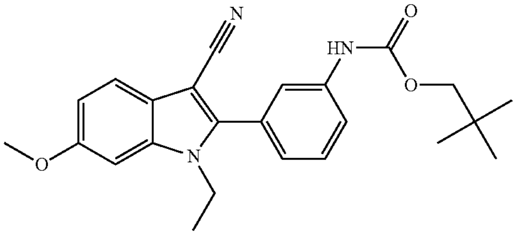
357
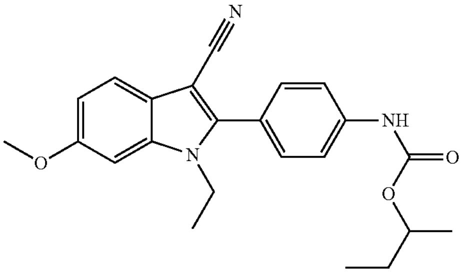
358
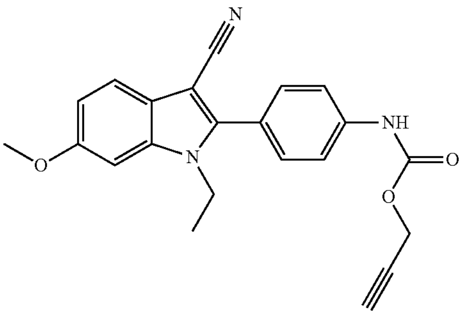
-continued
359
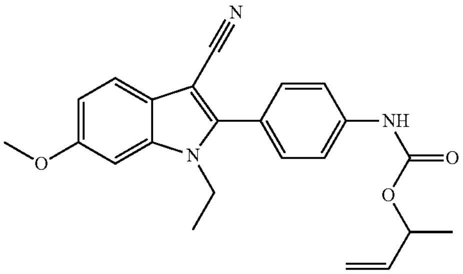
360
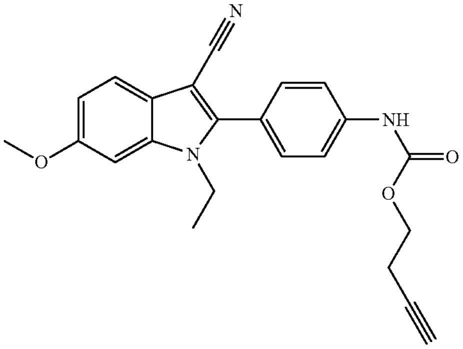
361
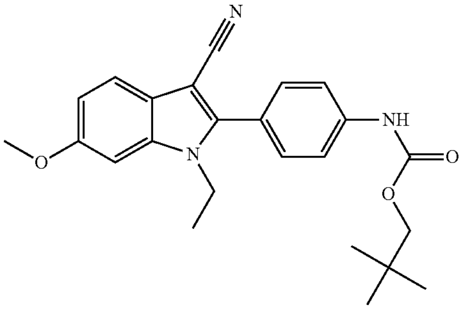
362
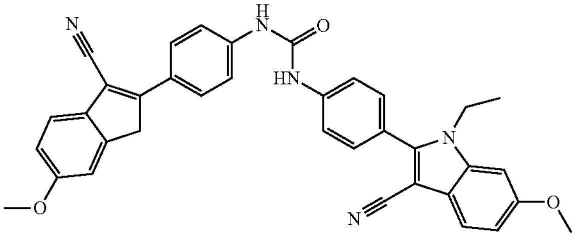
363
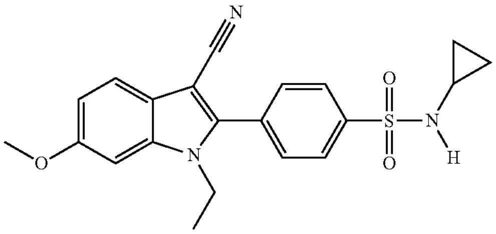

-continued
364
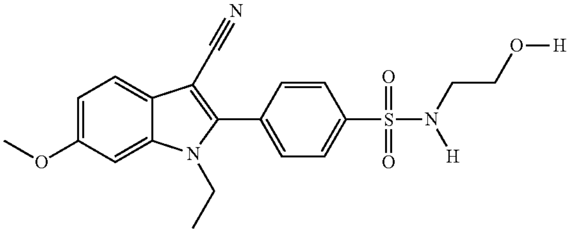
365
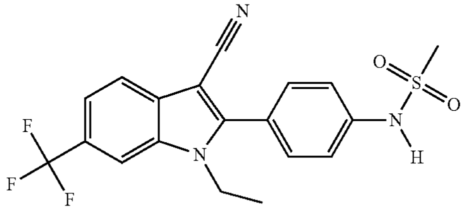
366
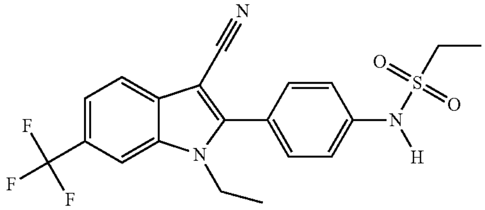
367
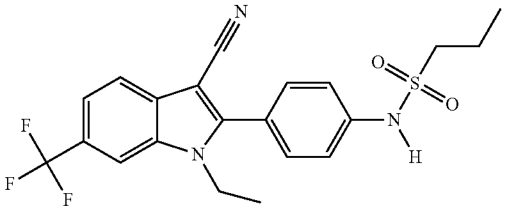
368
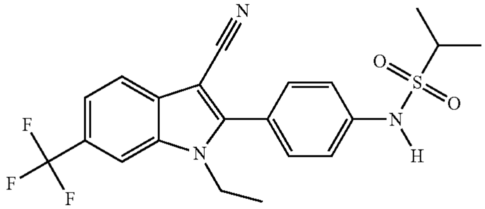
369
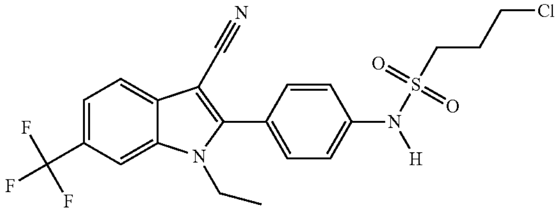
370
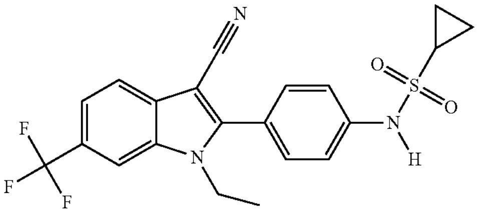
-continued
371
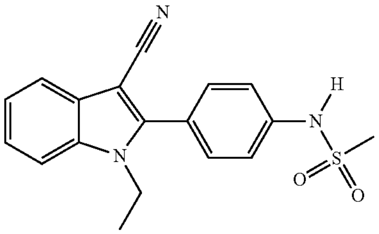
372
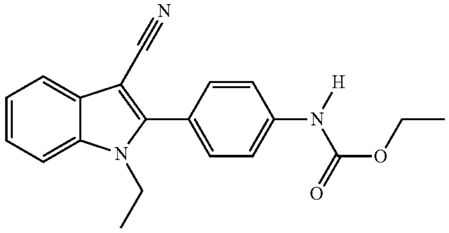
373
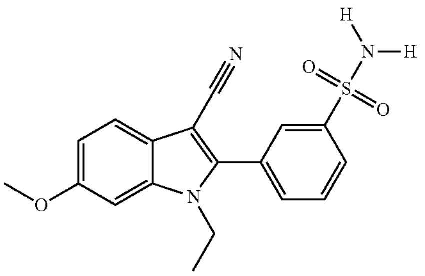
374
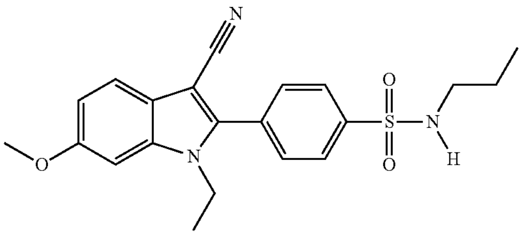
375
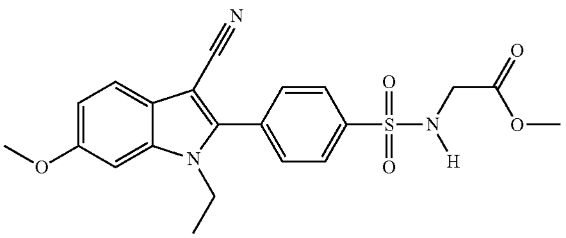
376
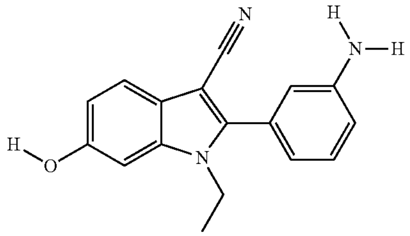

-continued
377
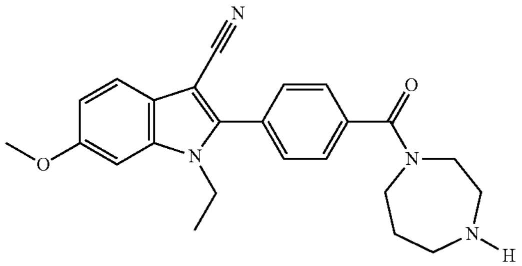
378
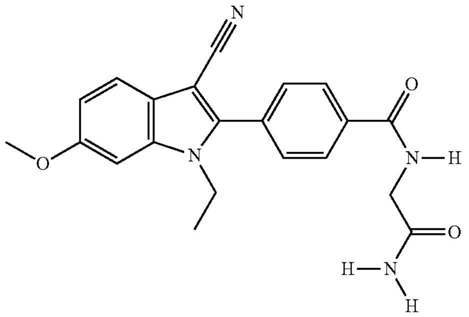
379
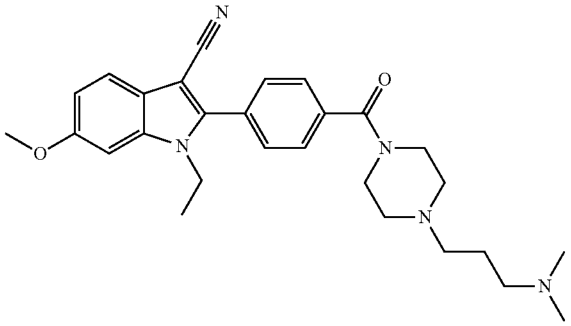
380
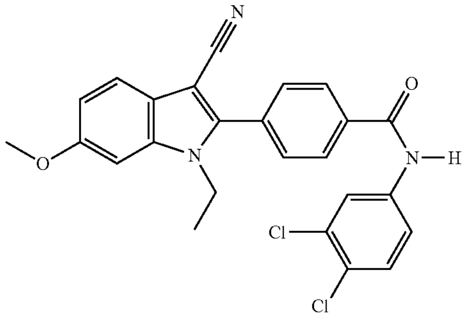
381
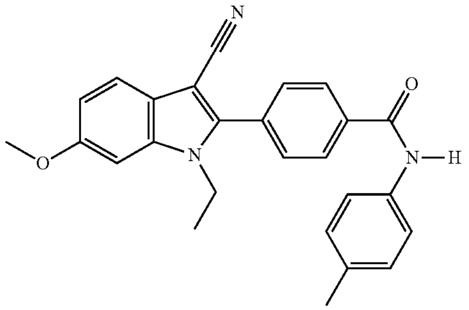
-continued
382
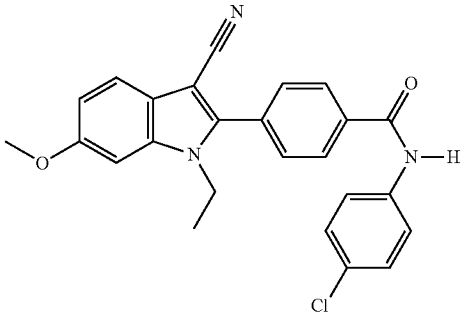
383
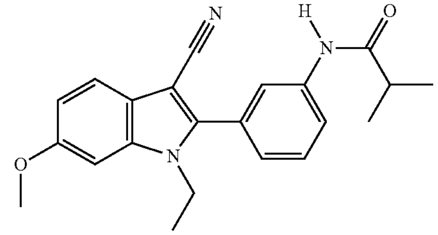
384
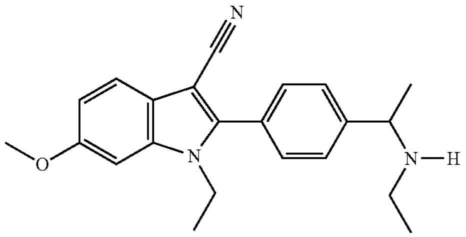
385
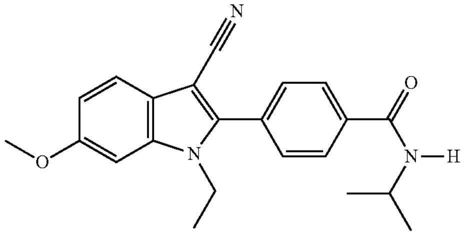
386
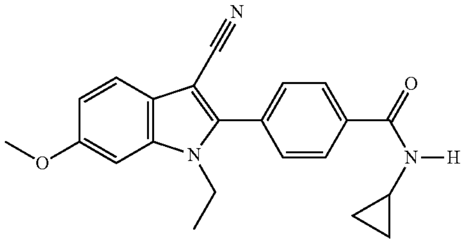
387
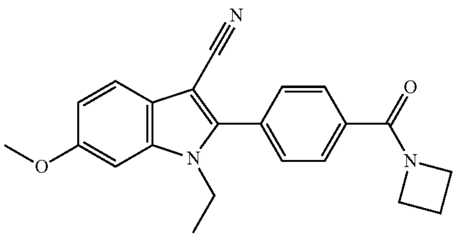

-continued
388
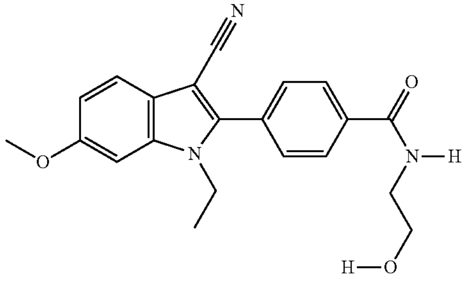
389
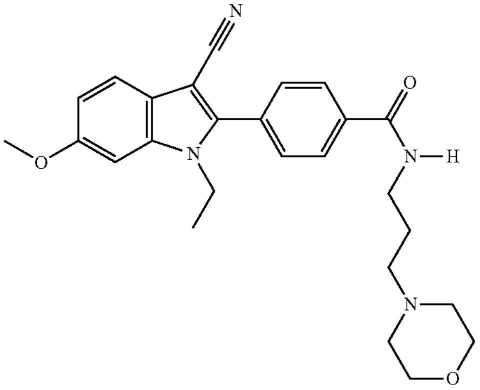
390
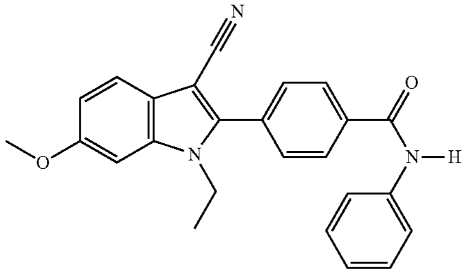
391
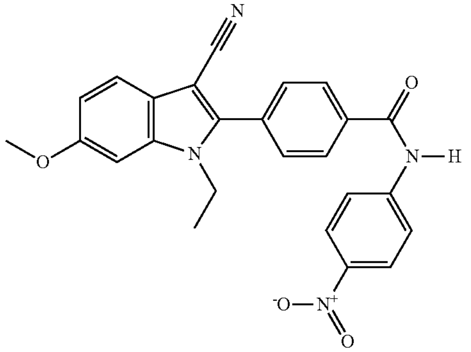
392
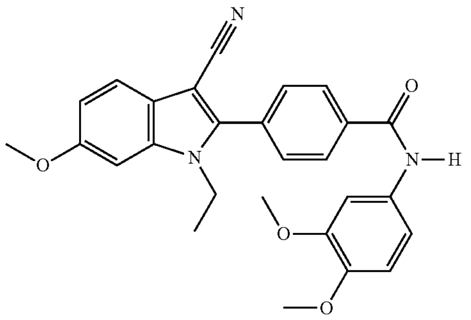
-continued
393
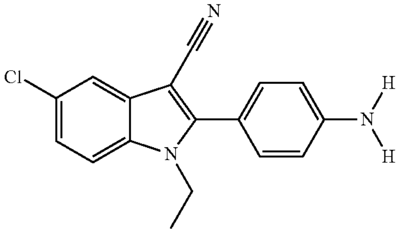
394
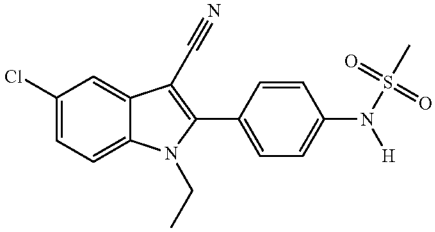
395
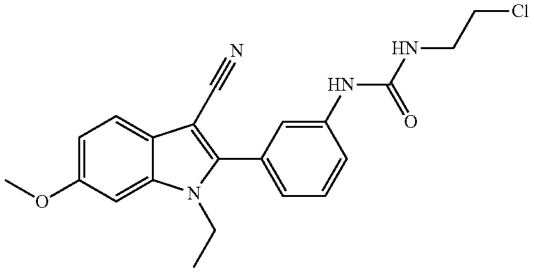
396
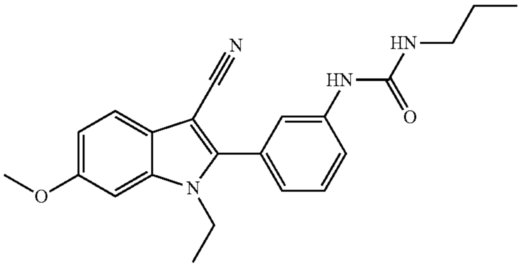
397
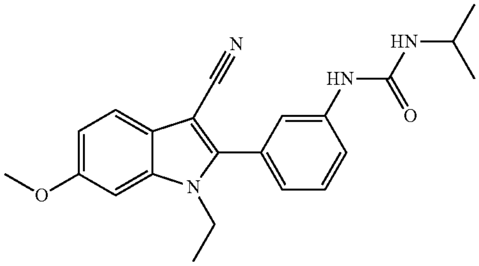
398
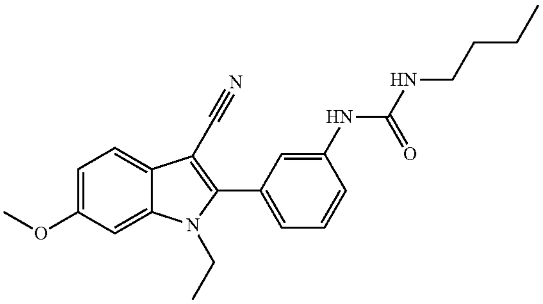

-continued
399
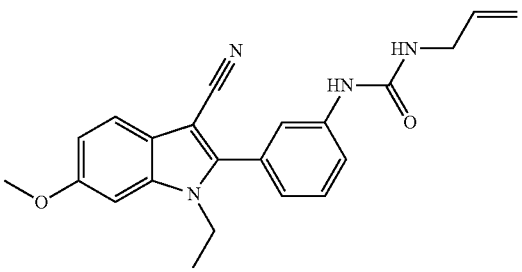
400
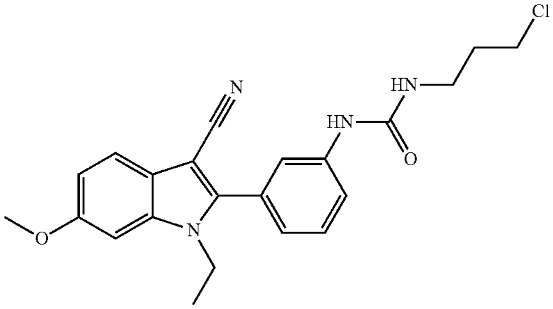
401
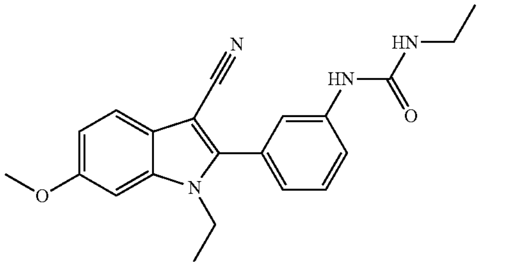
402
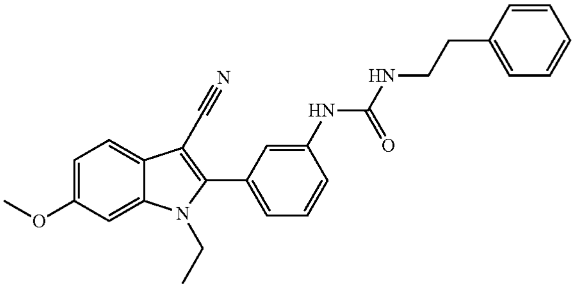
403
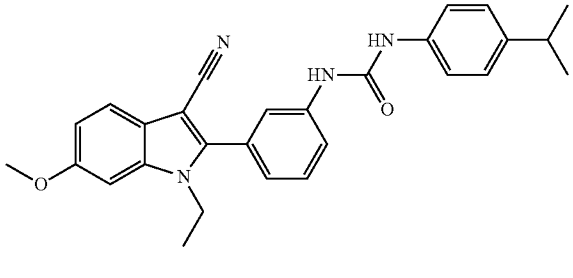
-continued
404
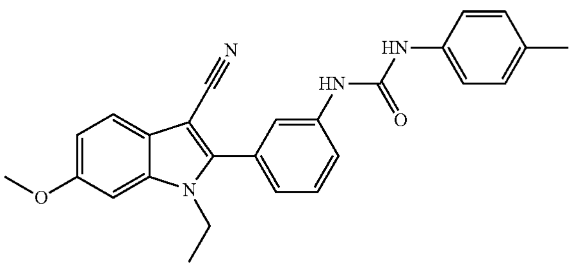
405
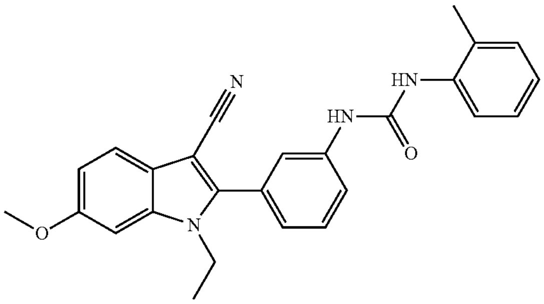
406
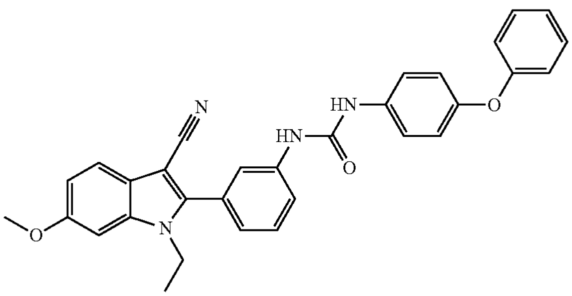
407
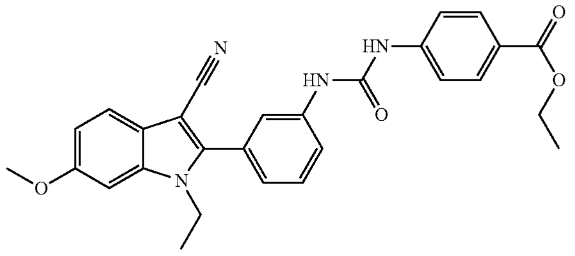
408
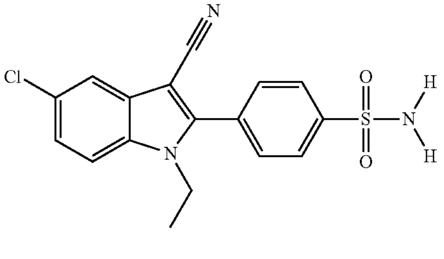

-continued
409
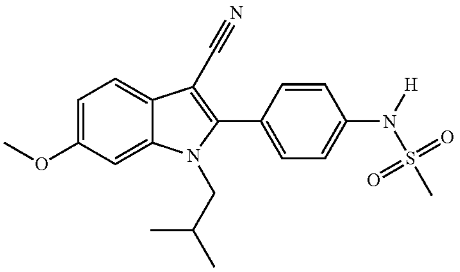
410
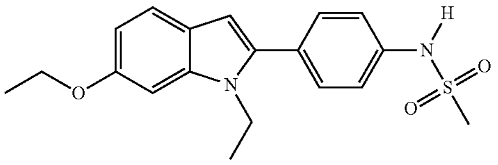
411
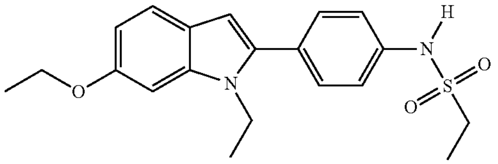
412
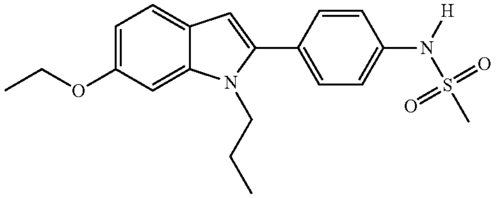
413
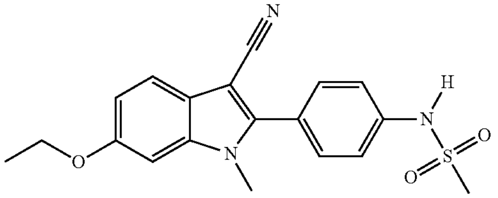
414
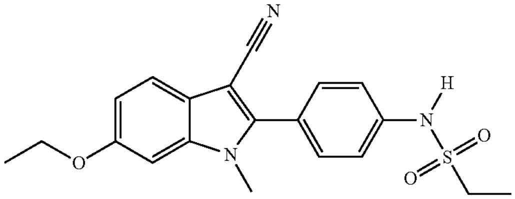
415
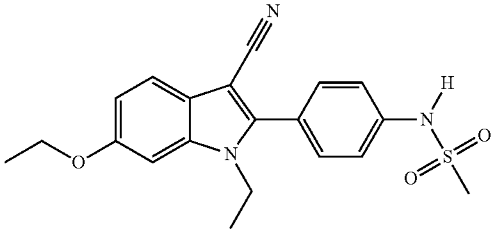
-continued
416
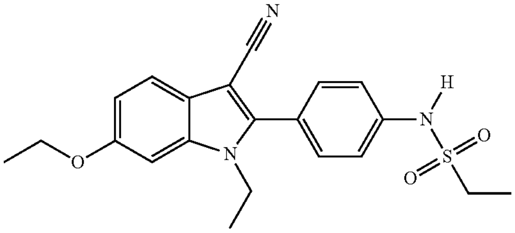
417
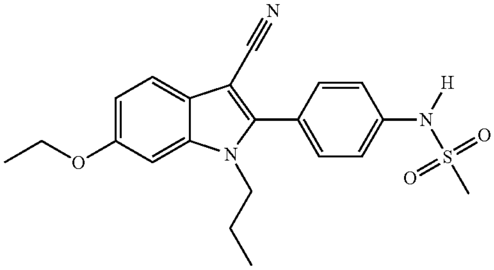
418
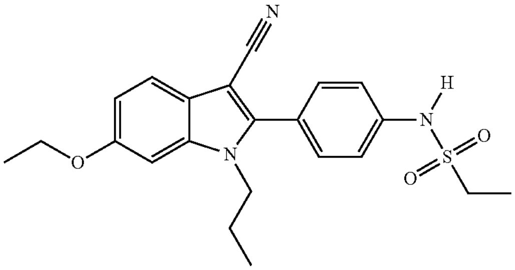
419
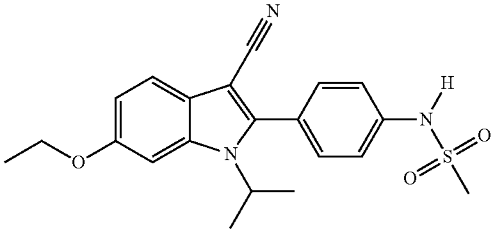
420
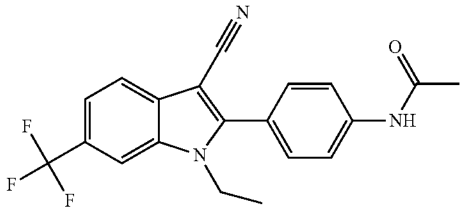
421
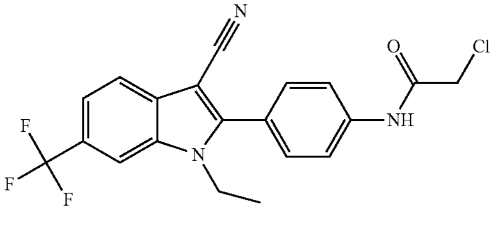

-continued
422
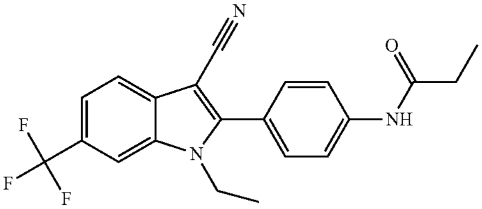
423
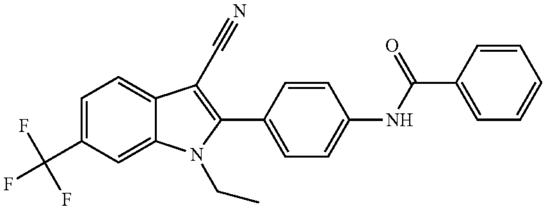
424
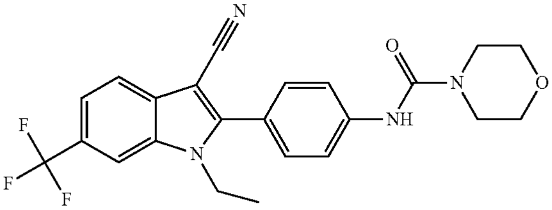
425
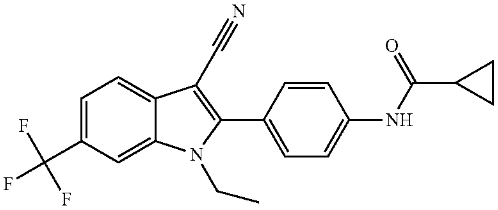
426
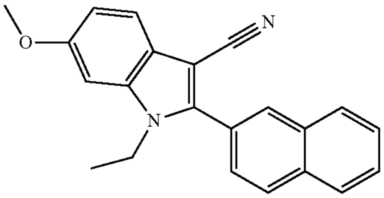
427
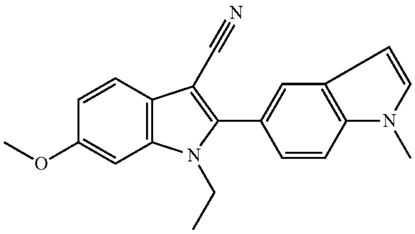
428
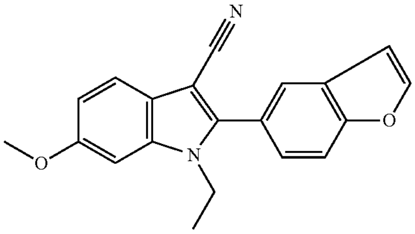
-continued
429
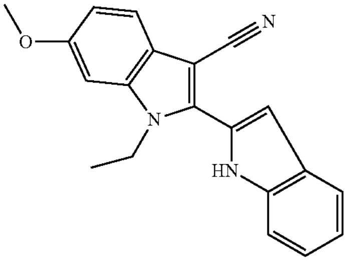
430
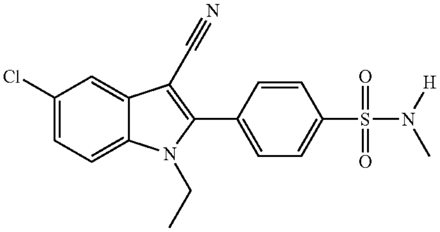
431
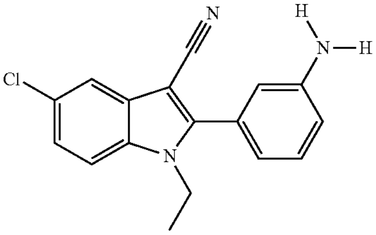
432
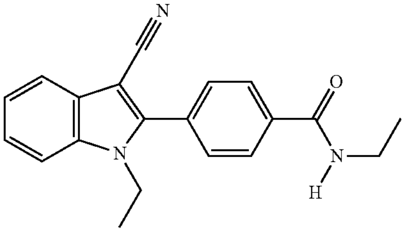
433
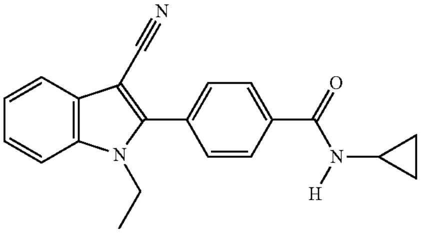
434
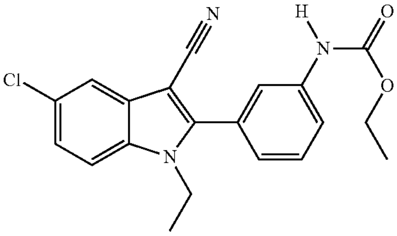

-continued
435
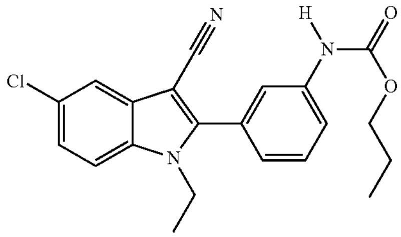
436
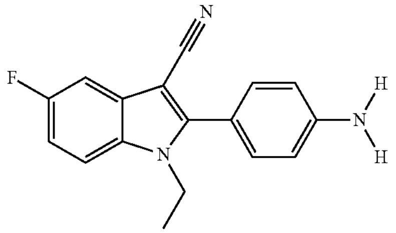
437
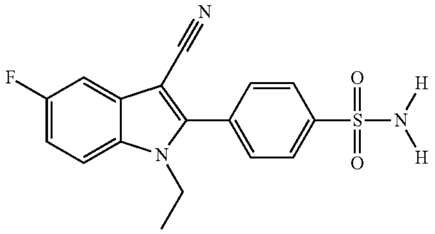
438
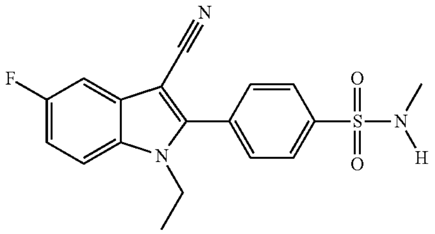
439
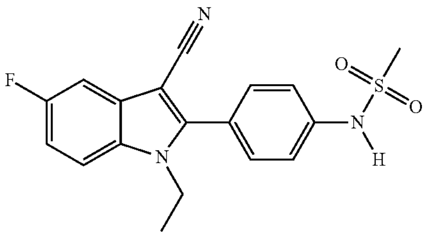
440
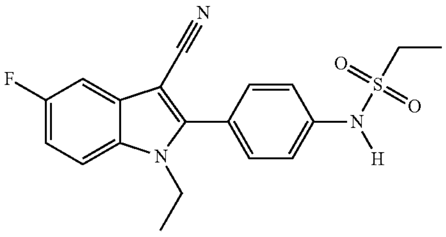
-continued
441
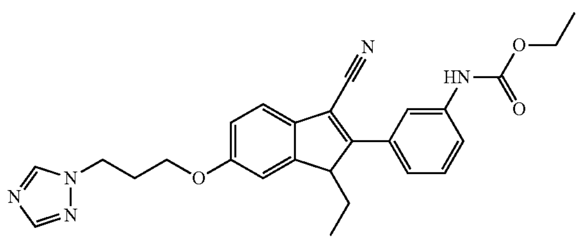
442
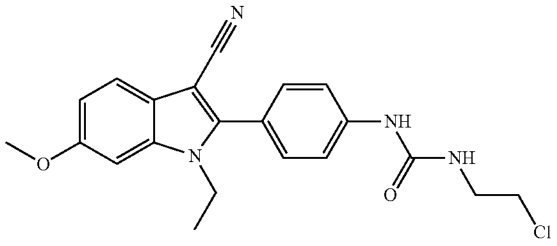
443
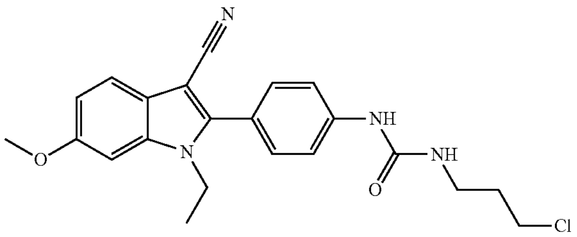
444
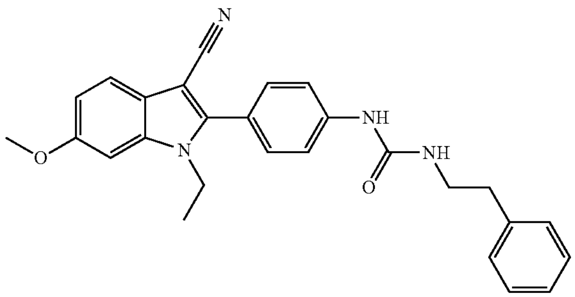
445
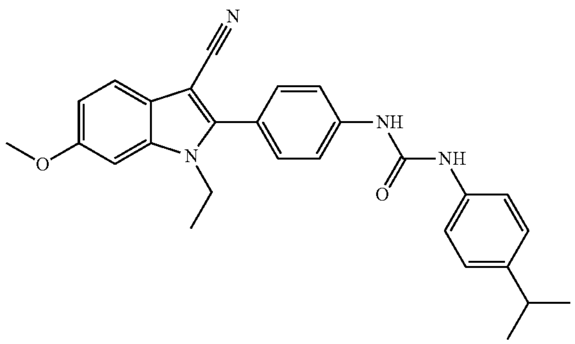

446
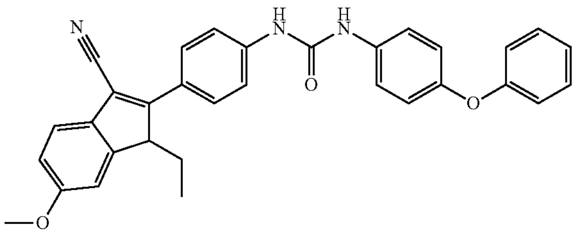
447
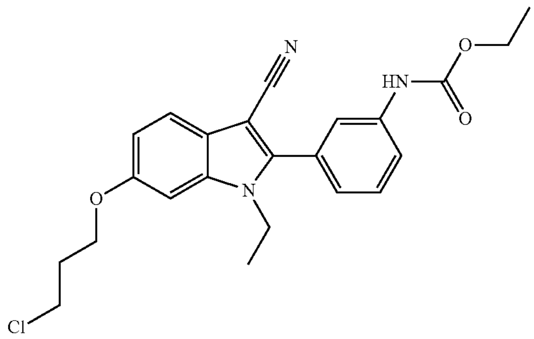
448
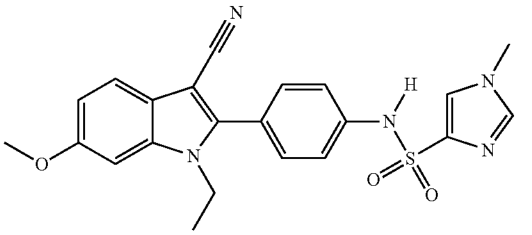
449
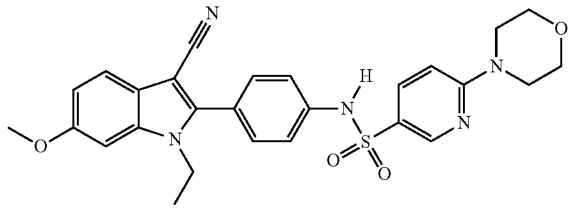
450
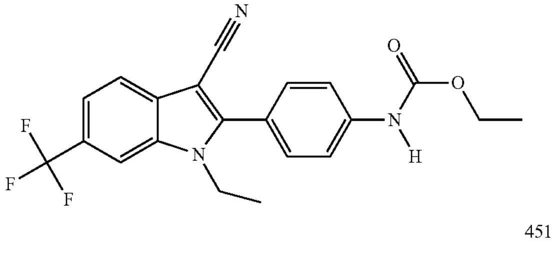
451
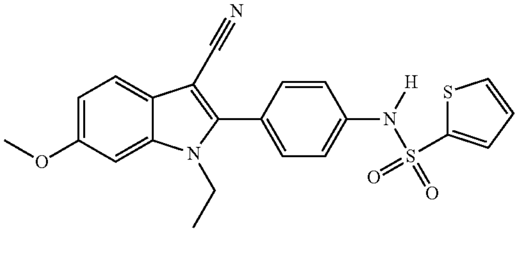
452
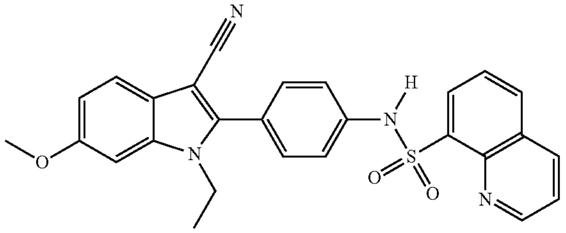
453
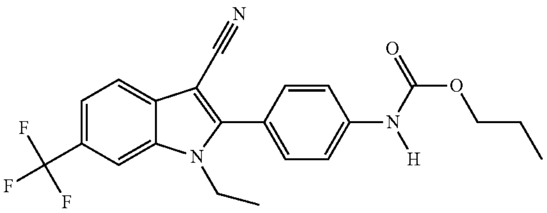
454
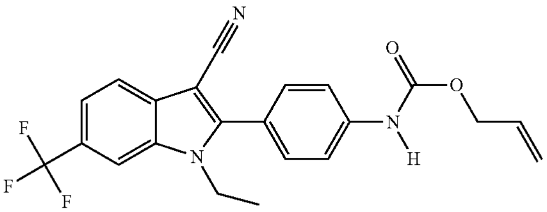
455
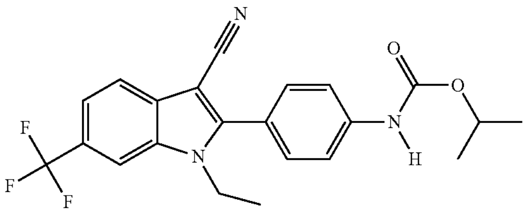
456
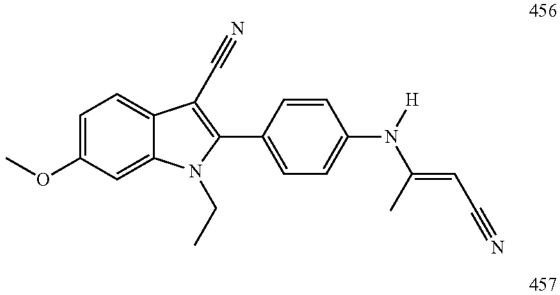
457
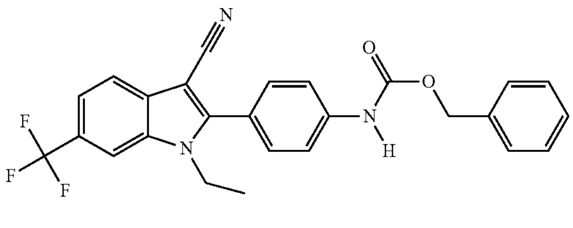

-continued
458
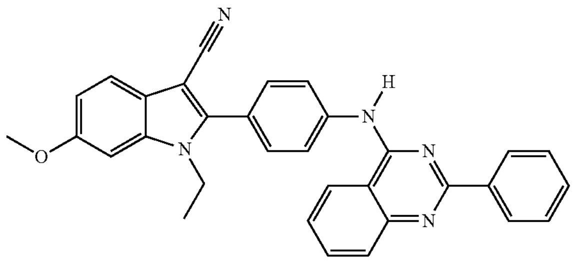
459
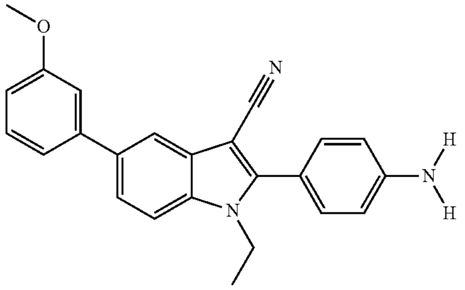
460
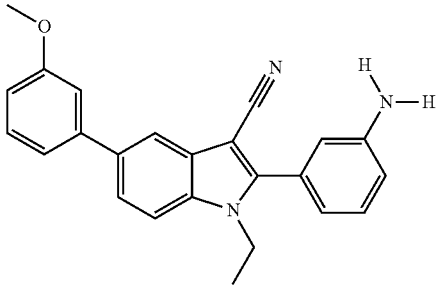
461
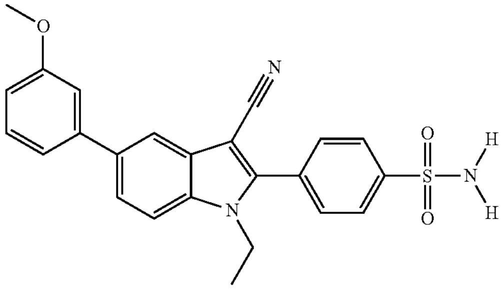
462
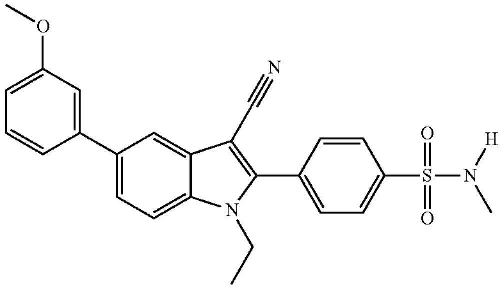
-continued
463
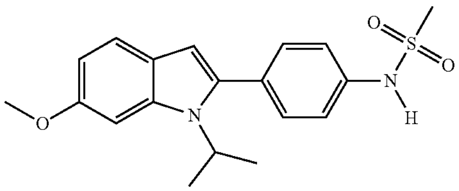
464
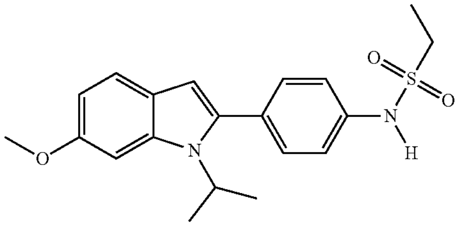
465
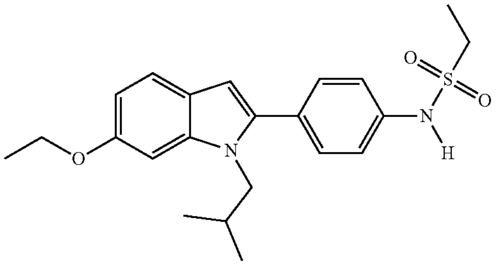
466
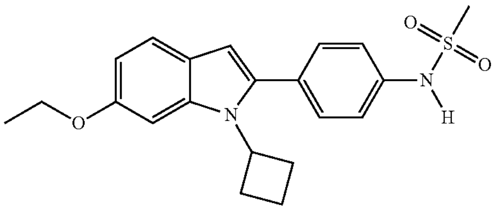
467
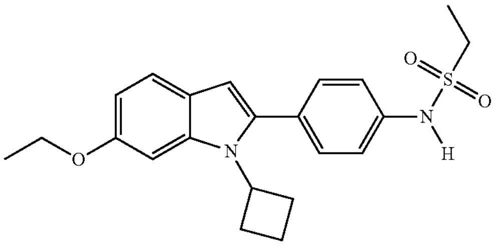
468
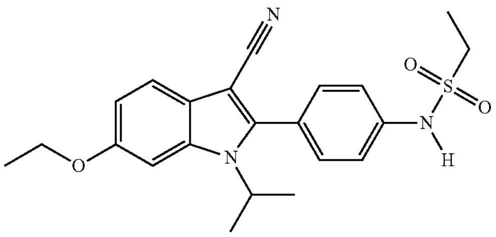

-continued
469
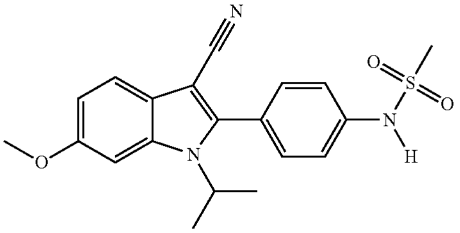
470
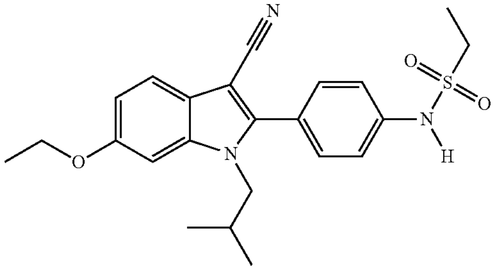
471
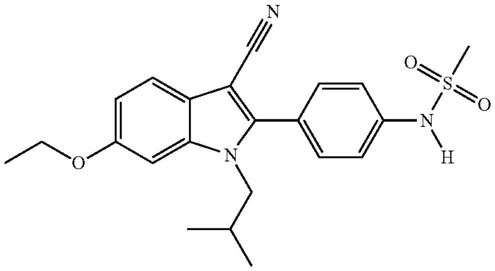
472
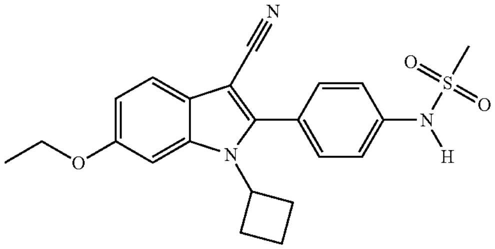
473
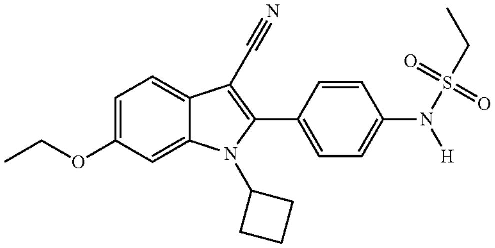
474
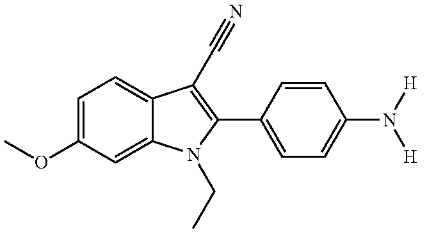
-continued
475
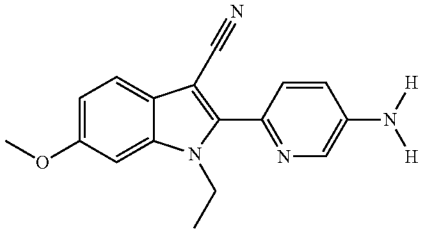
476
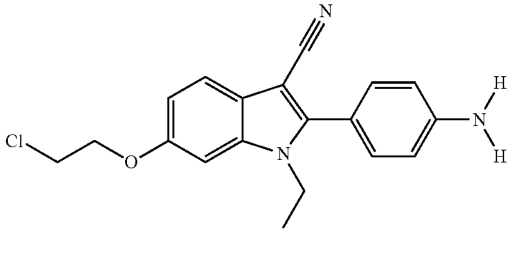
477
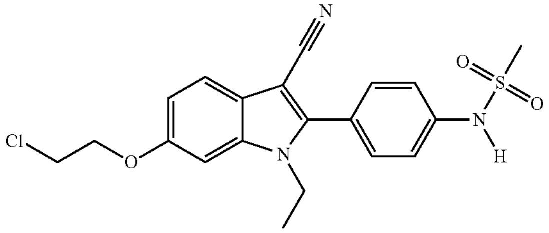
478
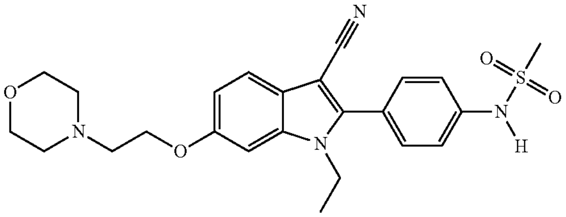
482
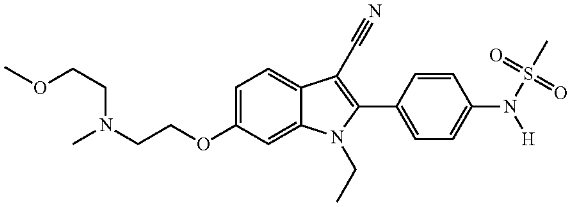
483
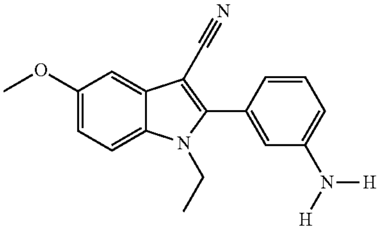

-continued
484
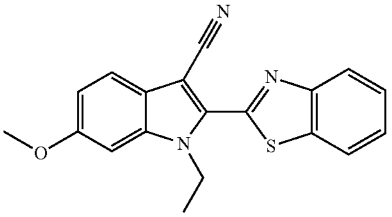
485
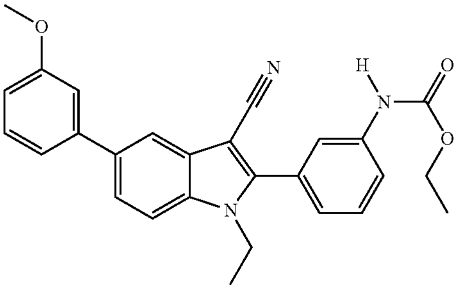
486
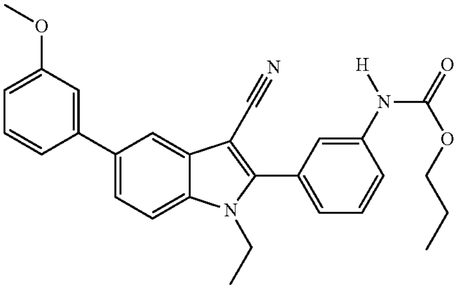
487
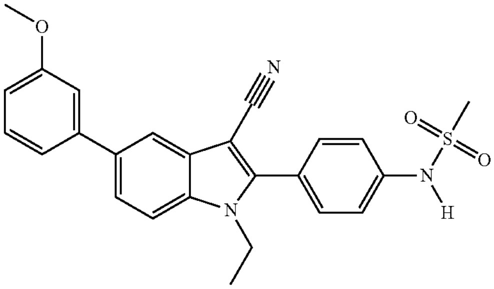
488
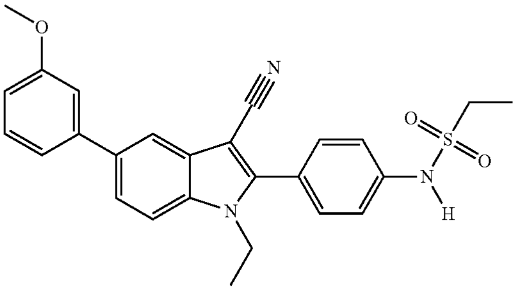
-continued
489
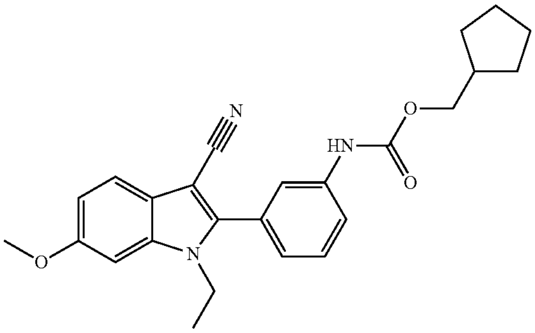
490
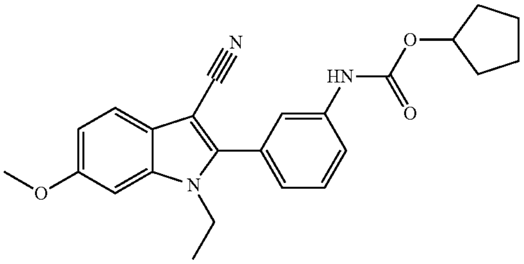
491
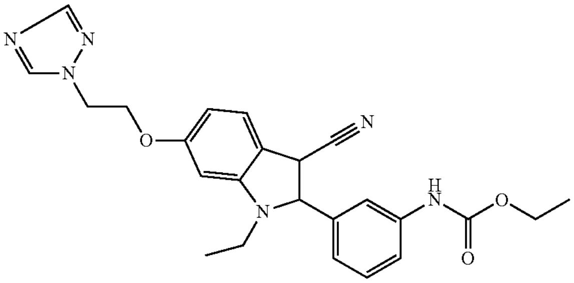
492
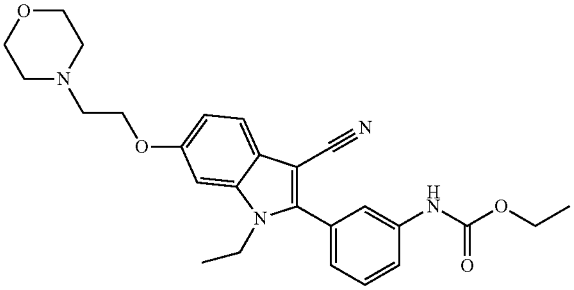

-continued
493
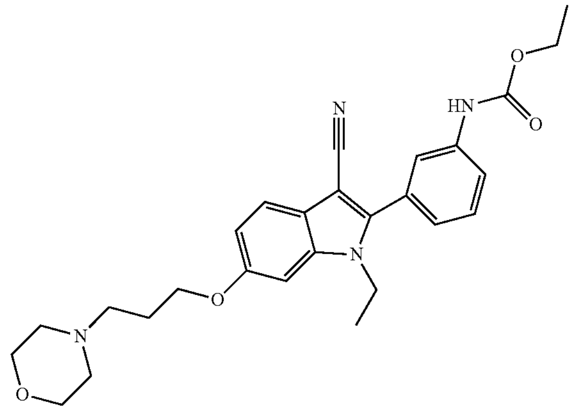
494
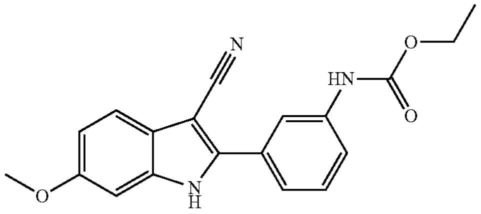
495
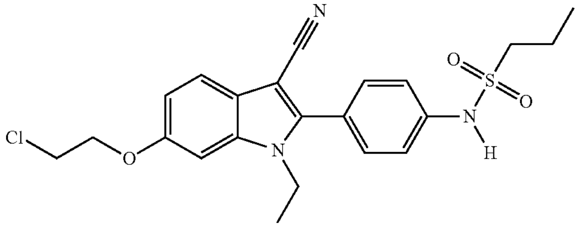
469
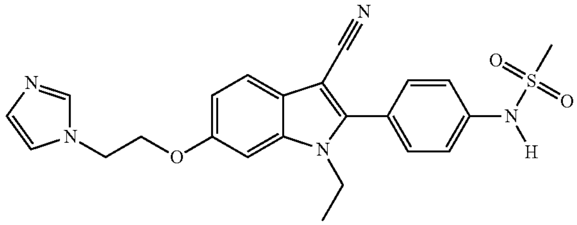
497
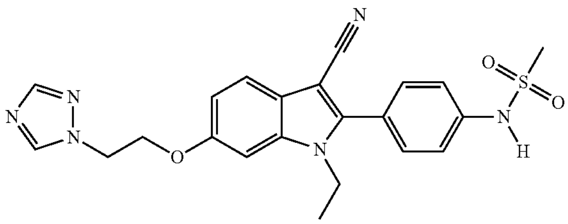
-continued
498
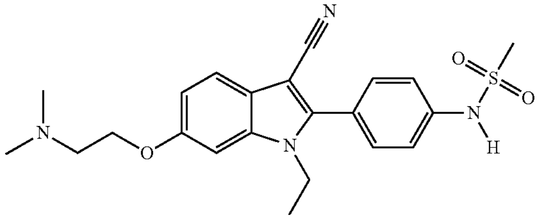
499
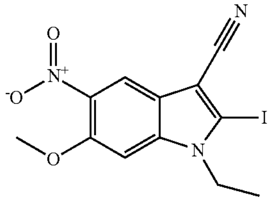
500
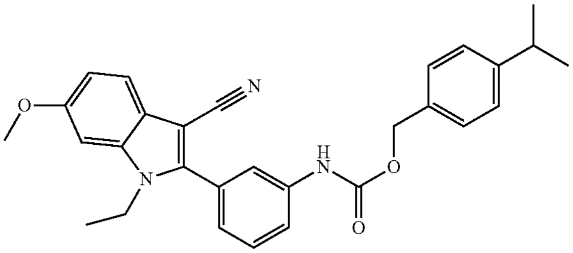
501
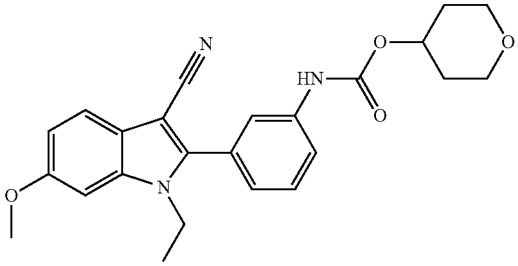
502
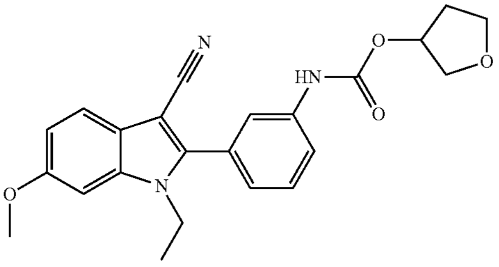
503
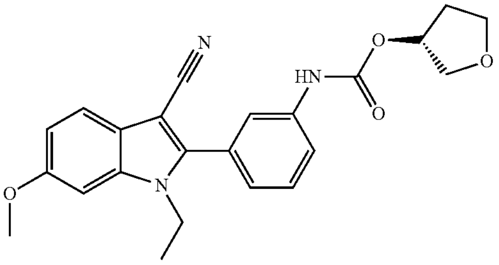

-continued
504
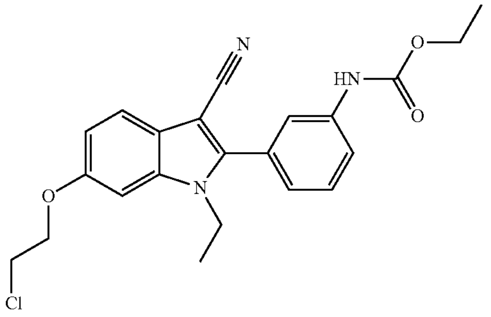
505
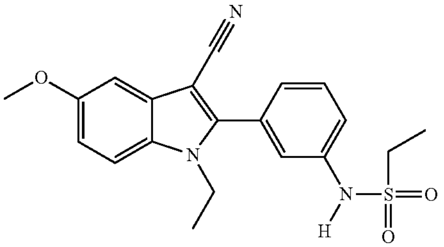
506
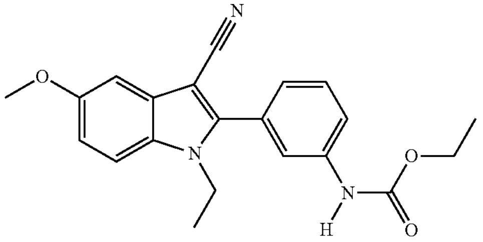
507
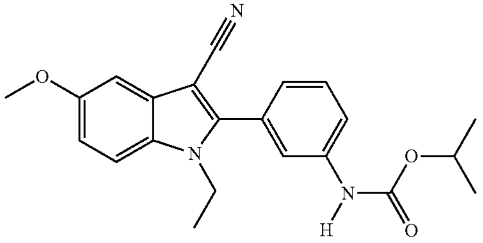
508
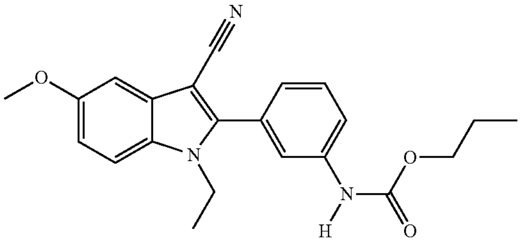
509
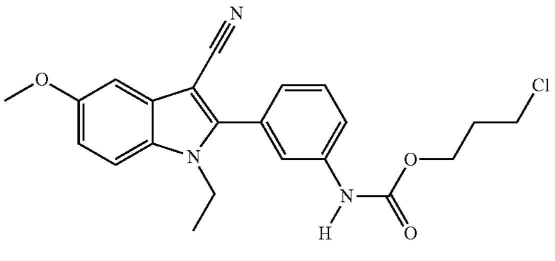
-continued
510
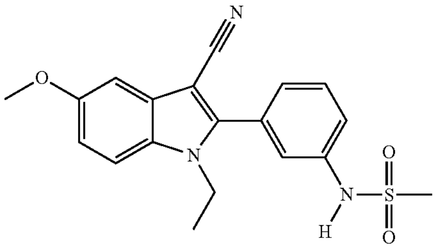
511
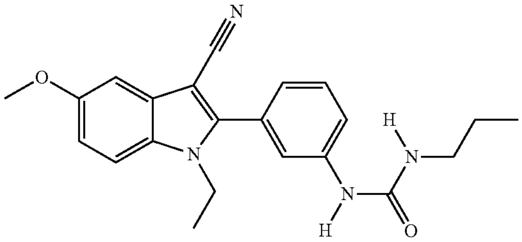
512
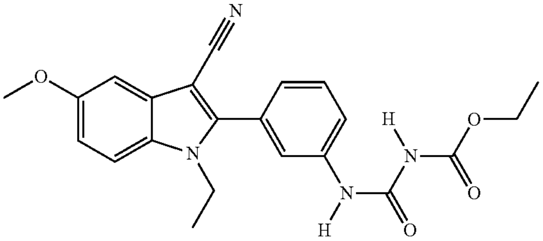
513
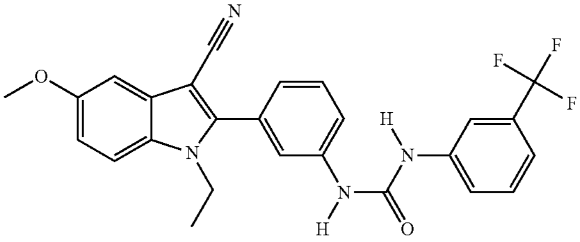
514
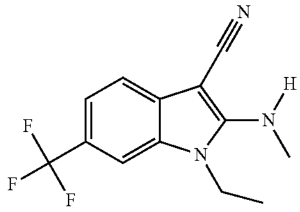
515
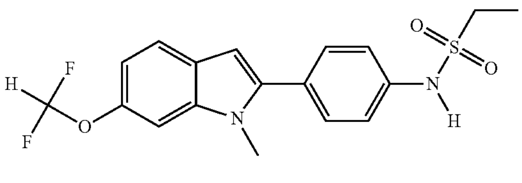

-continued
516
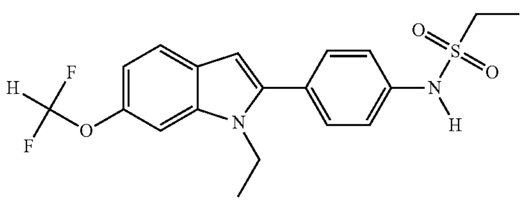
517
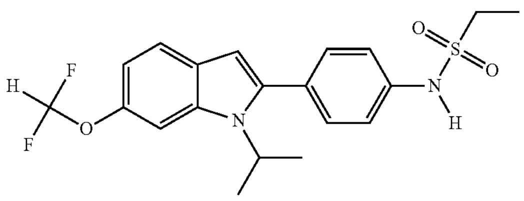
518
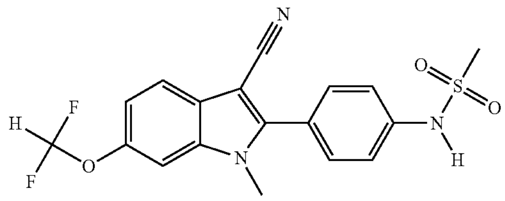
519
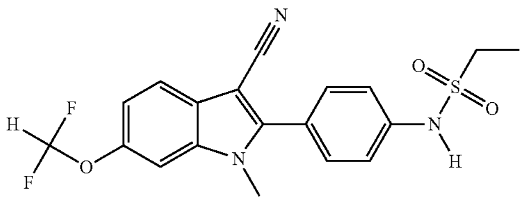
520
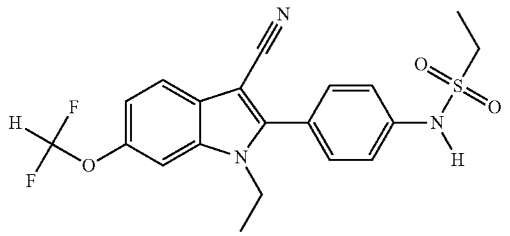
521
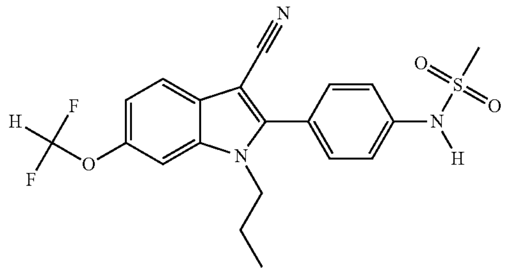
-continued
522
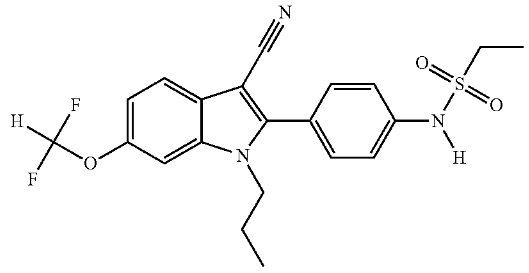
523
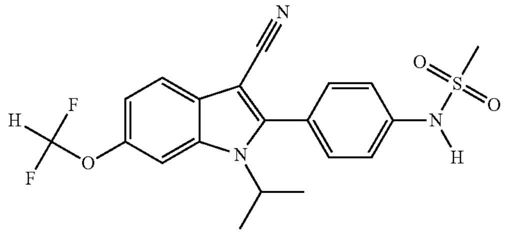
524
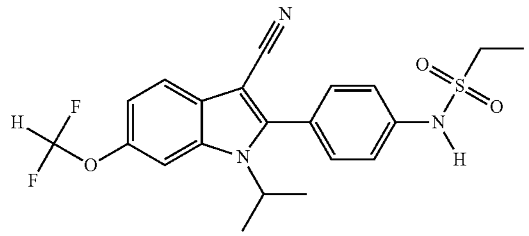
525
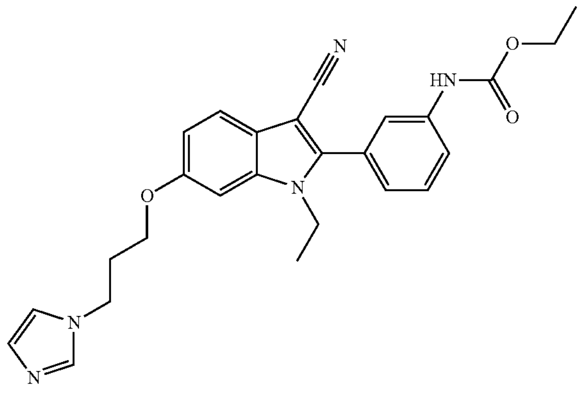
526
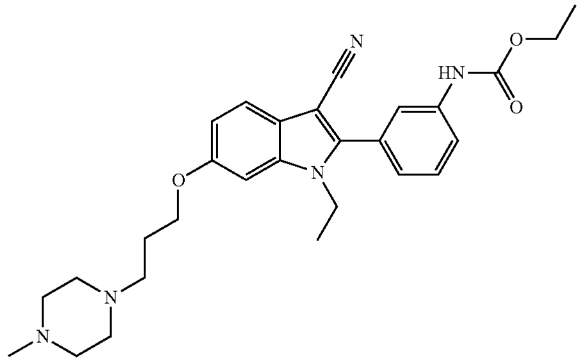

-continued
527
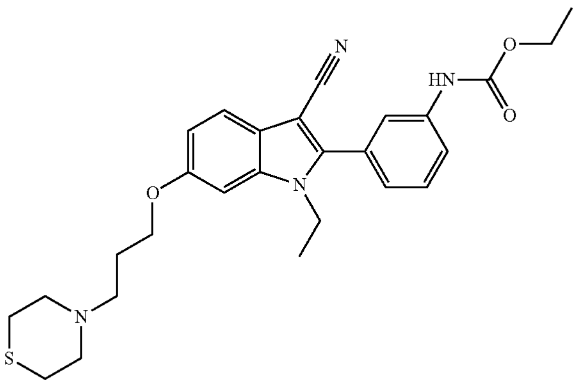
528
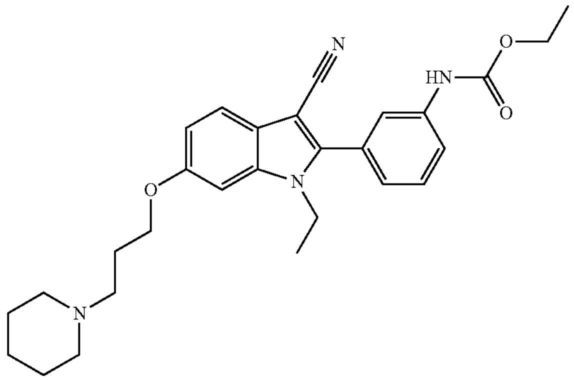
529
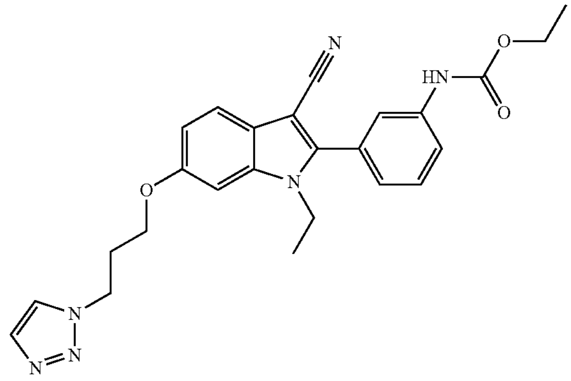
530
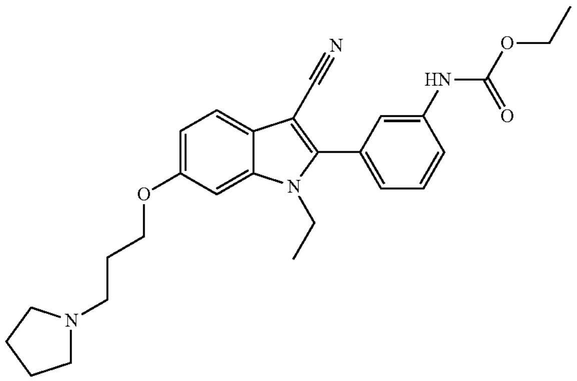
-continued
531
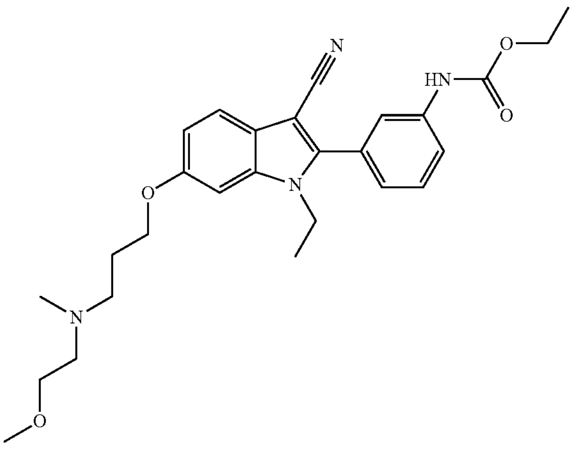
532
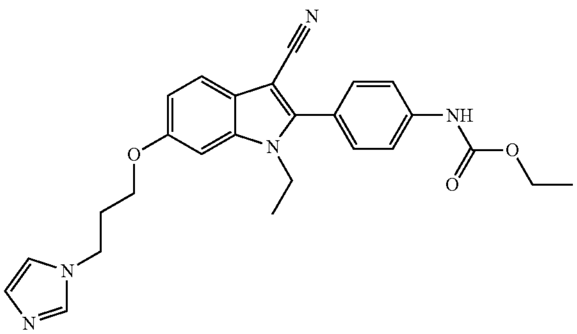
533
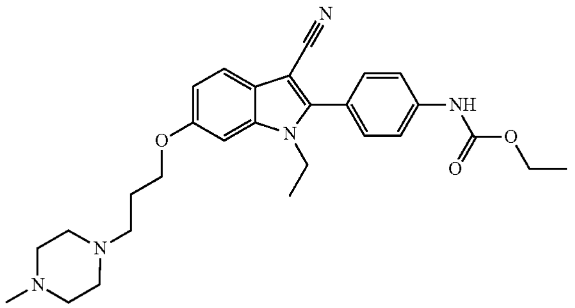
534
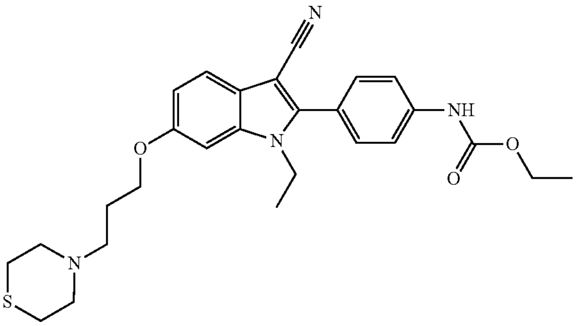

-continued
535
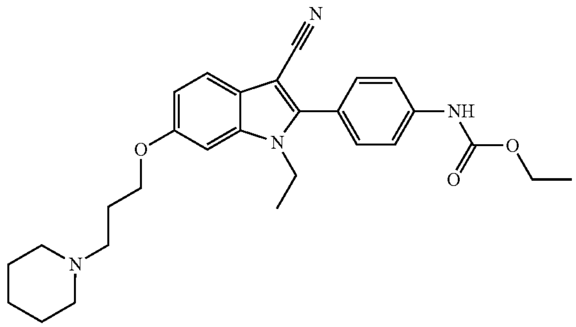
536
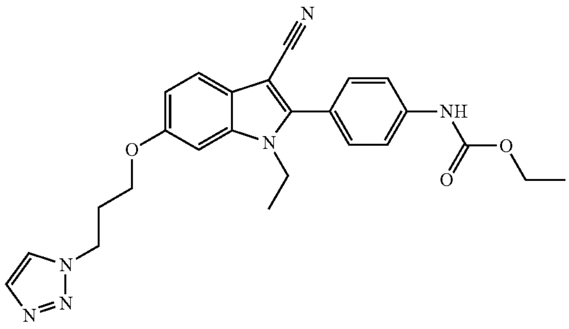
537
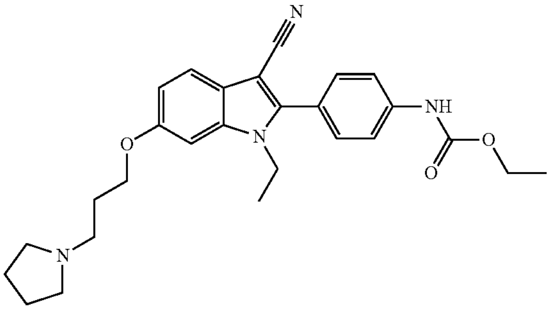
538
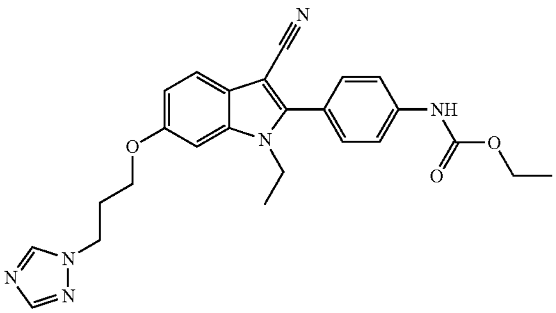
-continued
539
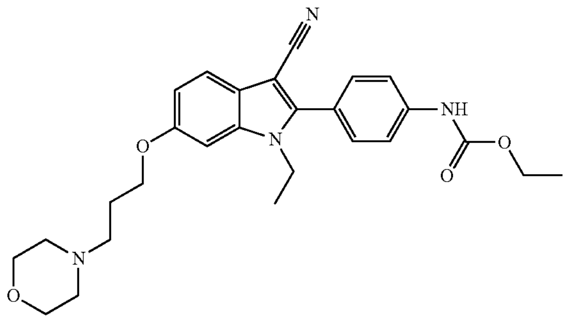
540
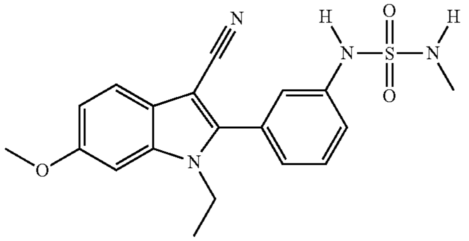
541
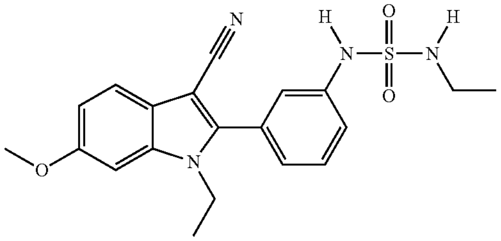
542
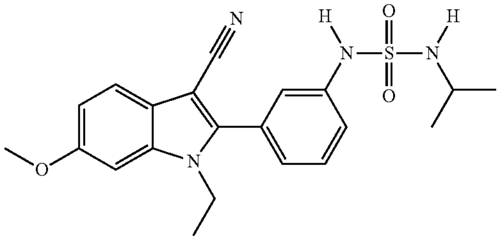
543
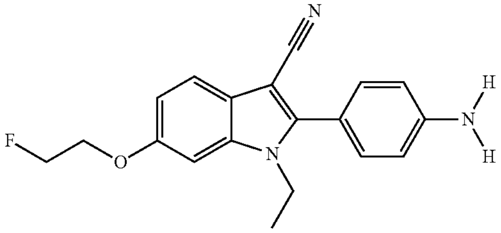
544
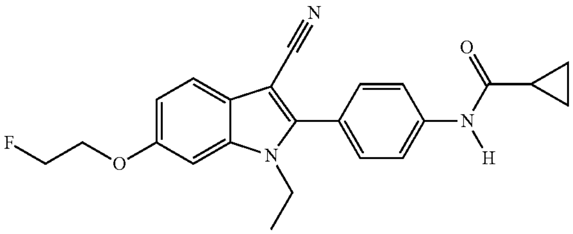

-continued
545
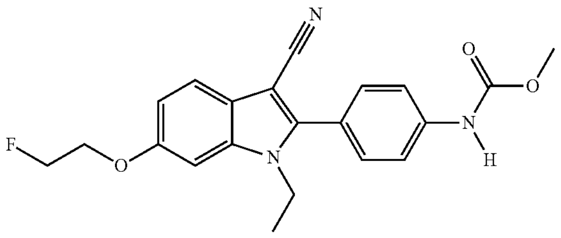
546
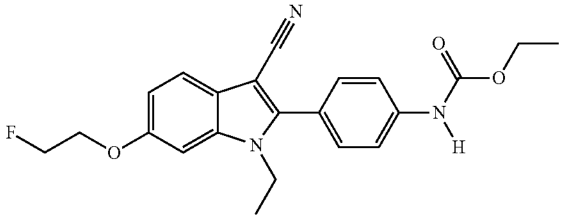
547
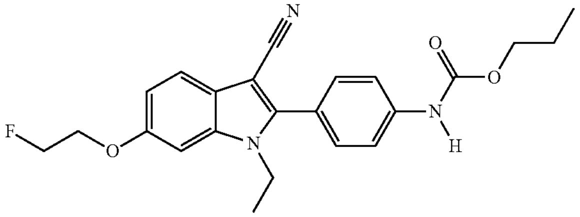
548
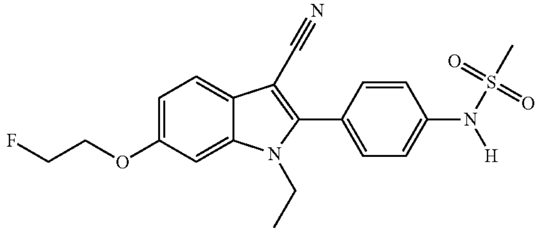
549
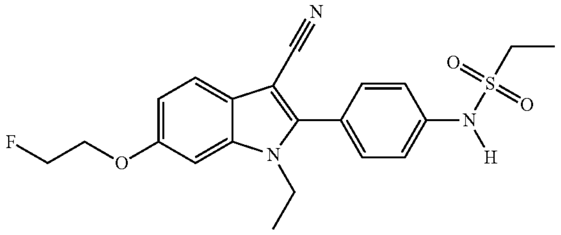
550
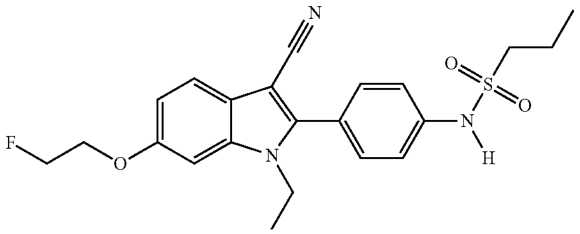
-continued
551
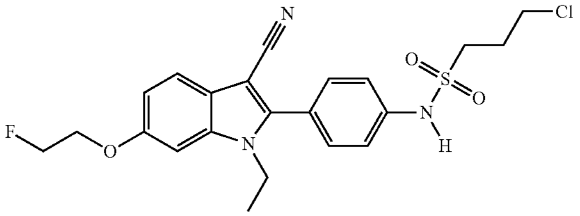
552
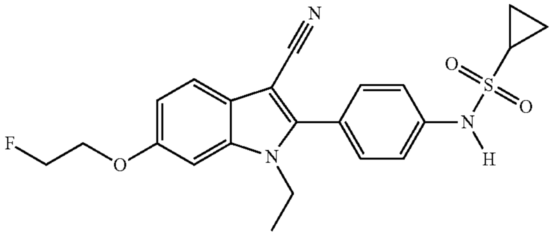
553
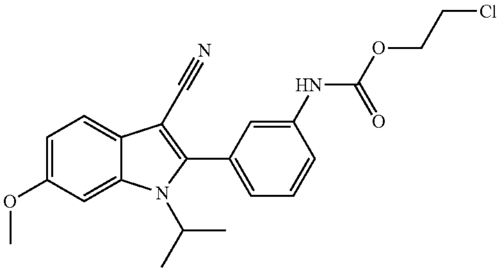
554
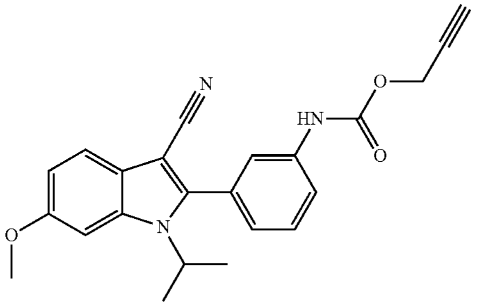
555
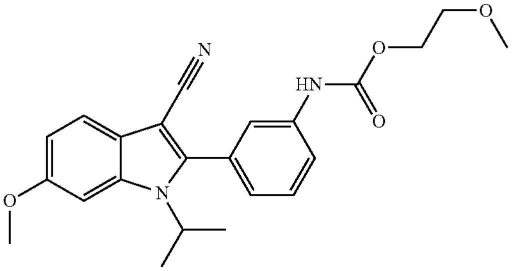

-continued
556
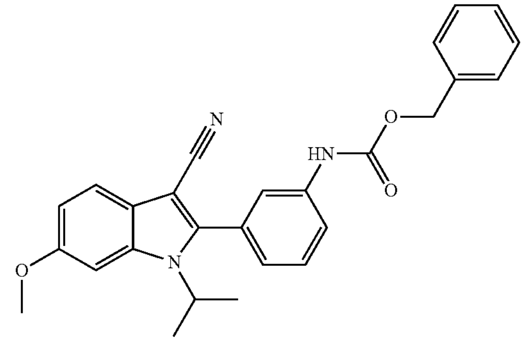
557
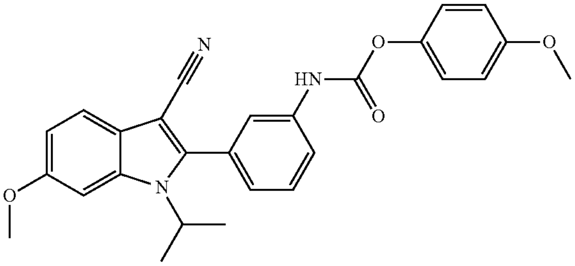
558
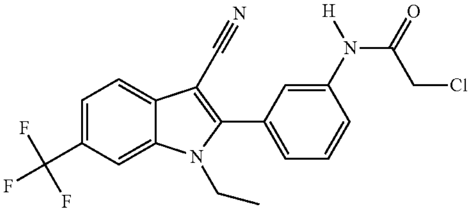
559
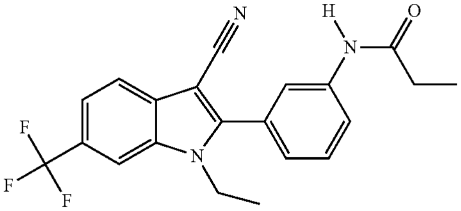
560
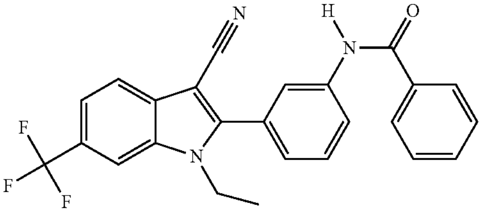
561
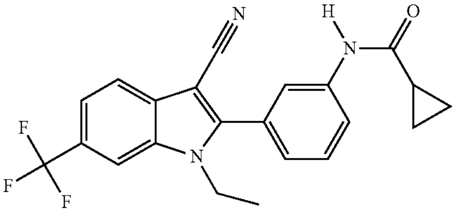
-continued
562
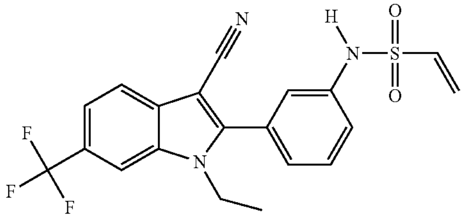
563
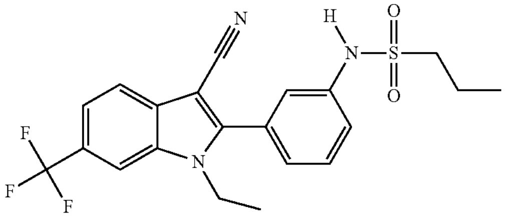
564
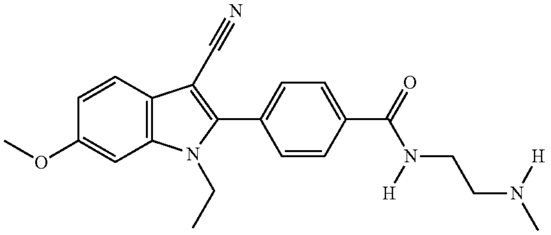
565
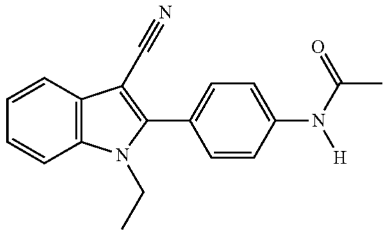
566
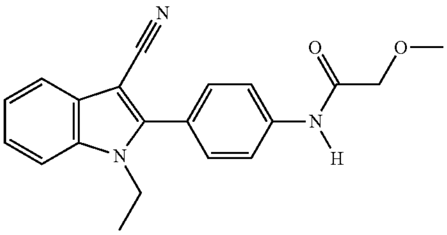
567
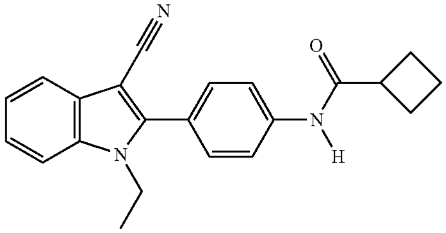

-continued
568
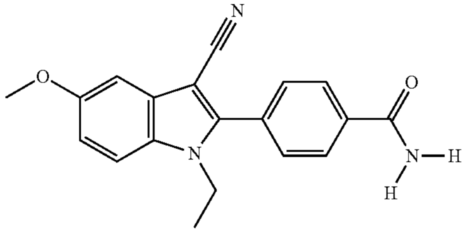
569
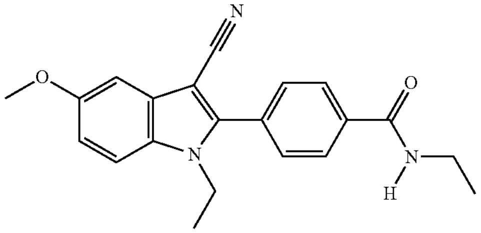
570
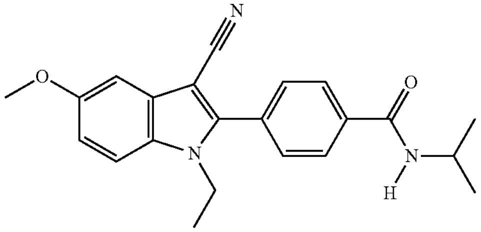
571
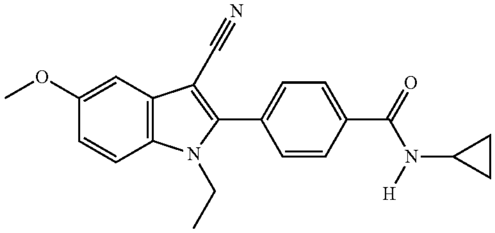
572
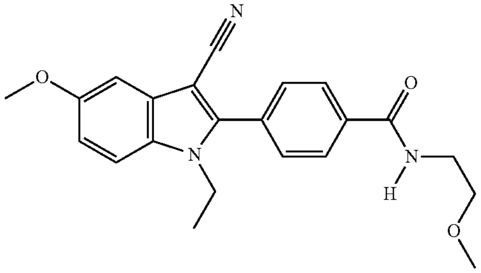
573
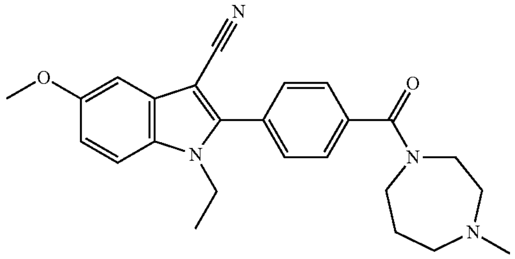
-continued
574
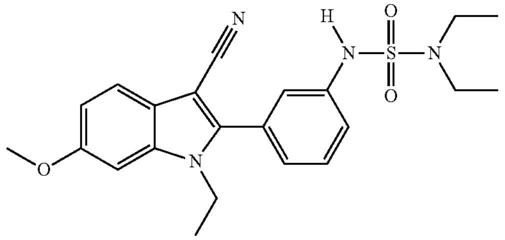
575
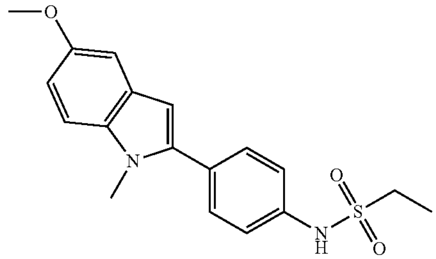
576
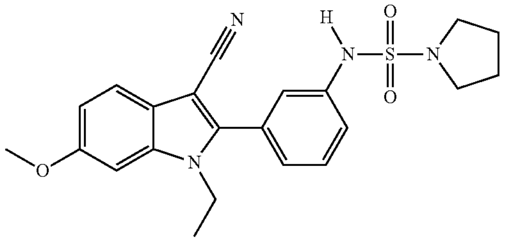
577
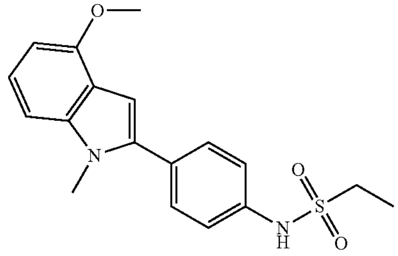
578
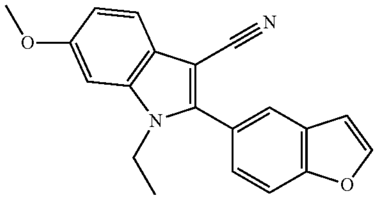
579
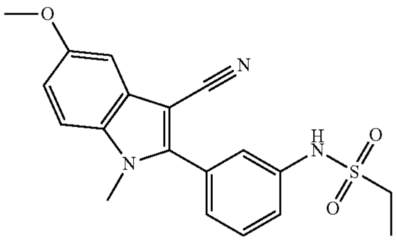

-continued
580
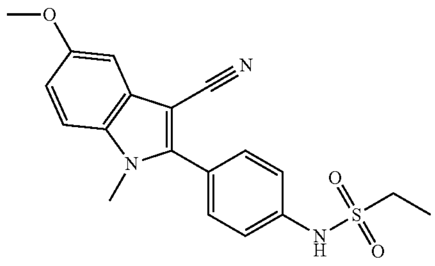
581
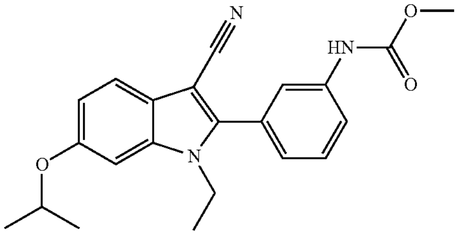
582
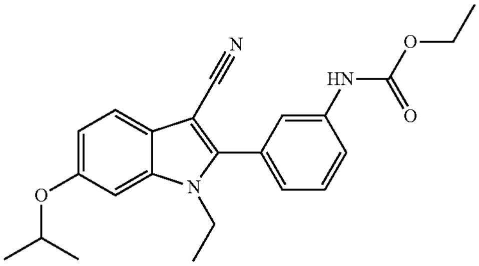
583
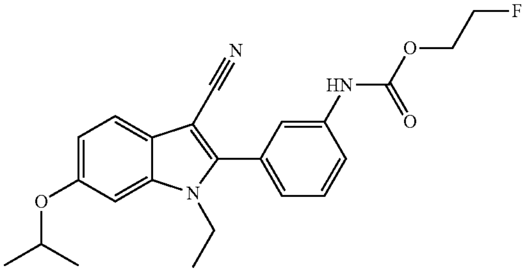
584
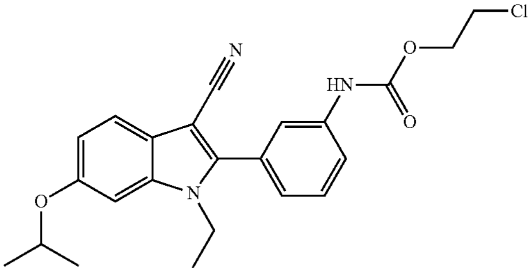
-continued
585
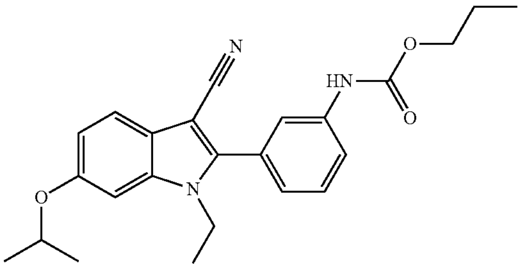
586
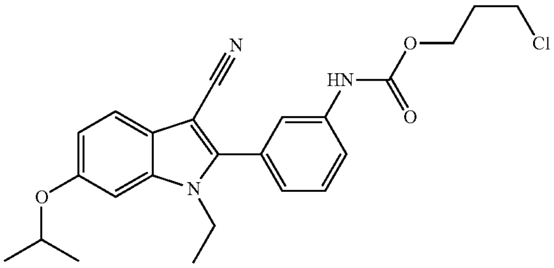
587
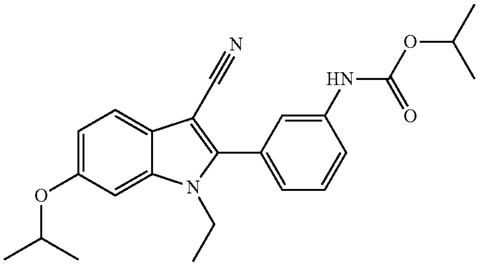
588
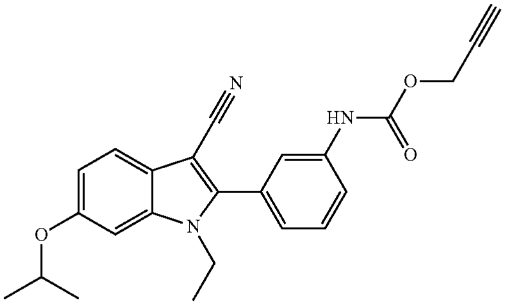
589
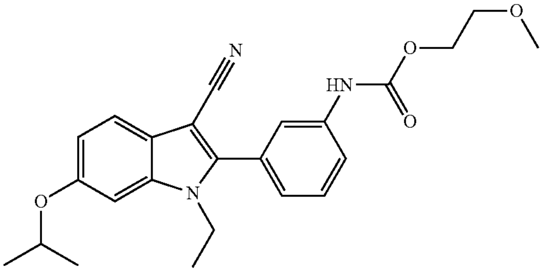

-continued
590
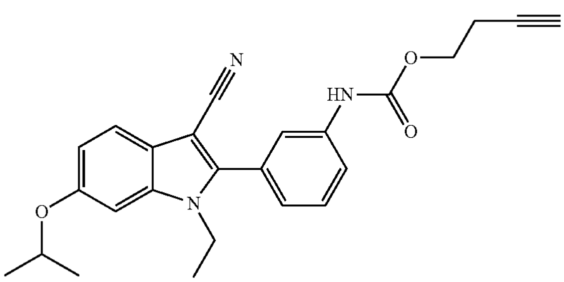
591
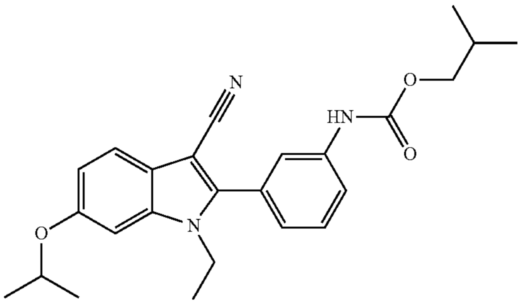
592
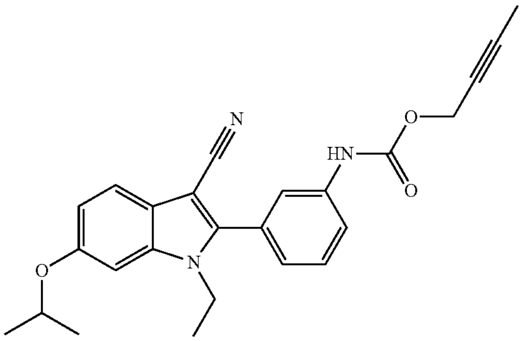
593
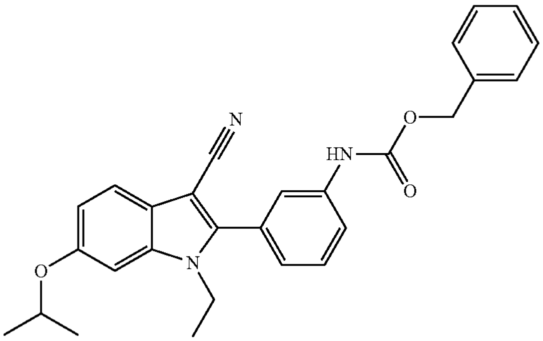
594
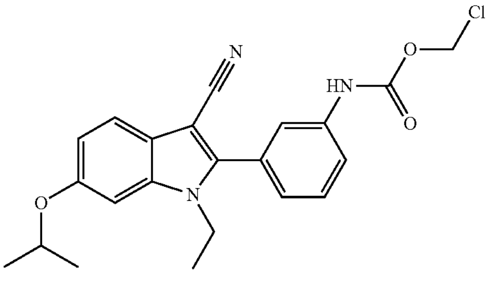
-continued
595
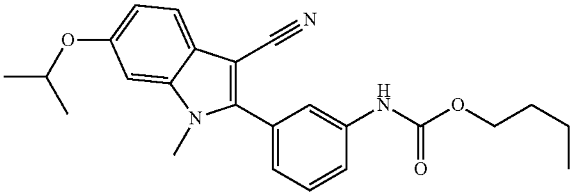
596
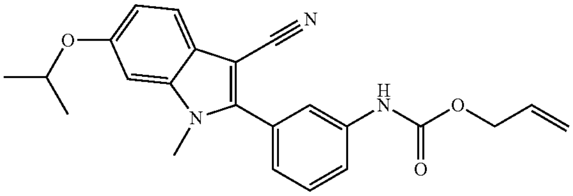
597
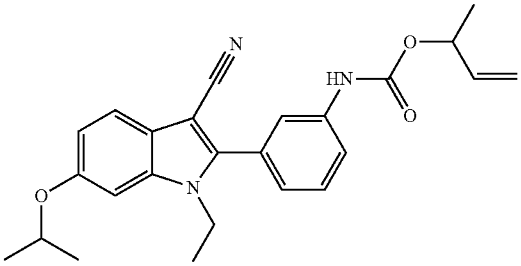
598
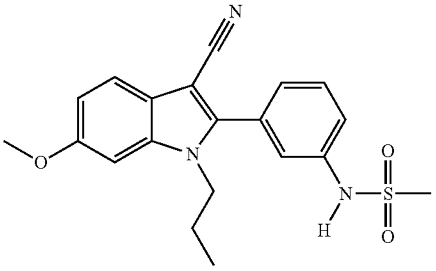
599
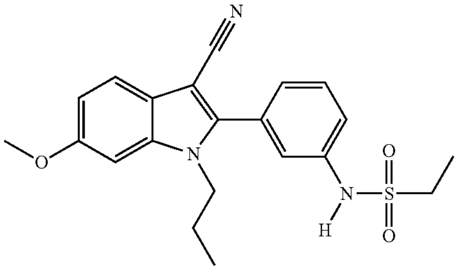
600
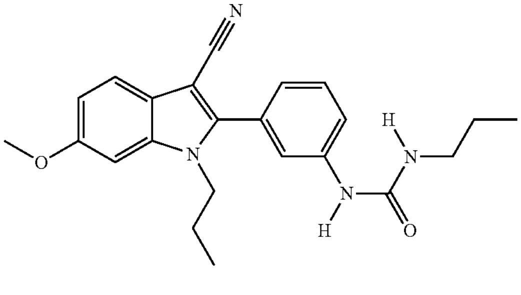

-continued
601
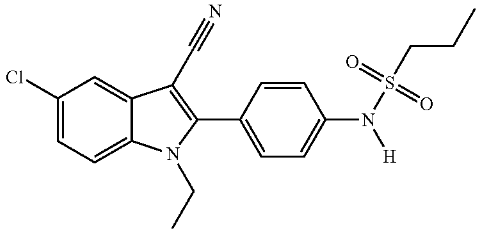
602
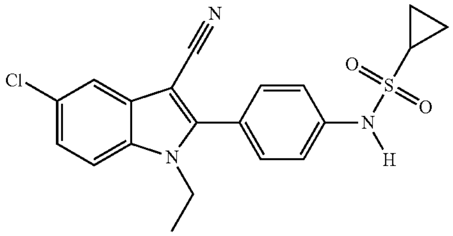
603
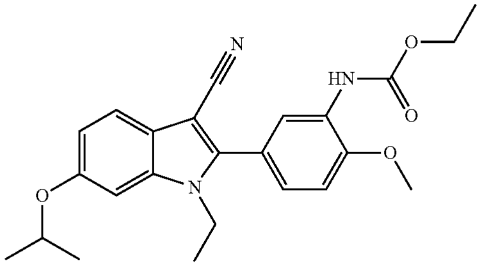
604
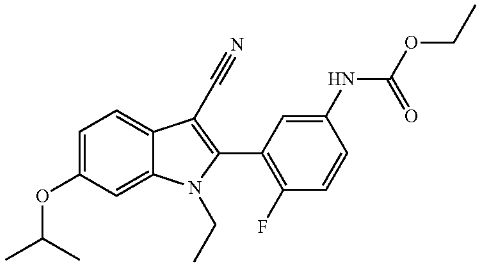
605
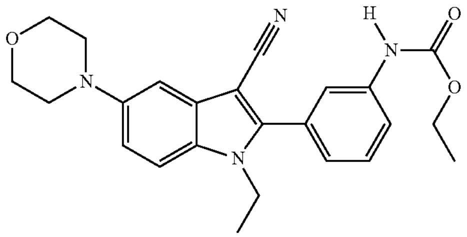
606
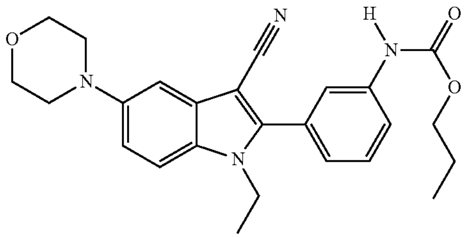
-continued
607
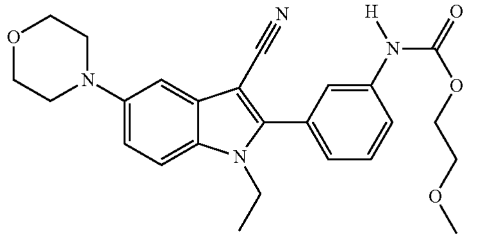
608
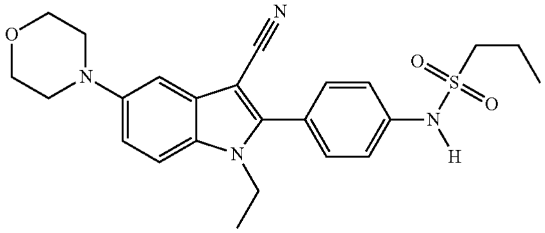
609
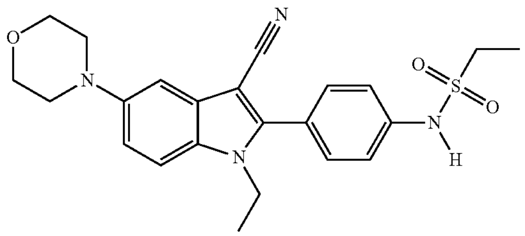
610
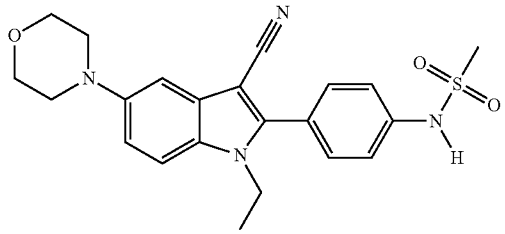
611
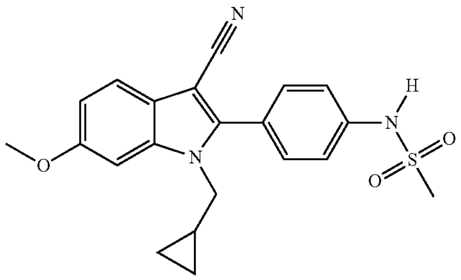
612
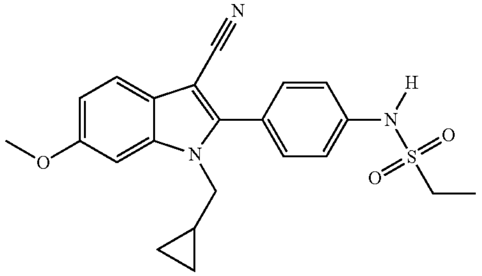

-continued
613
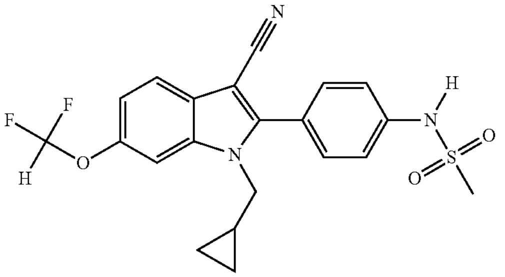
614
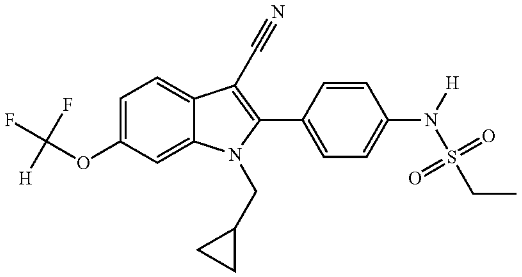
615
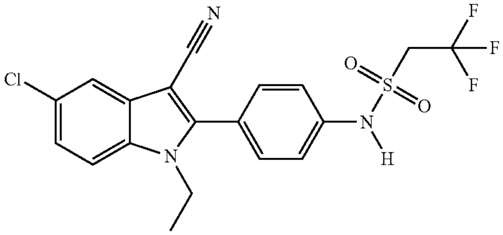
616
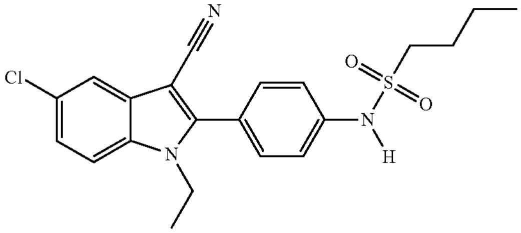
617
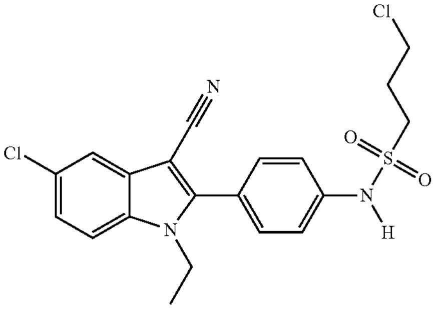
-continued
618
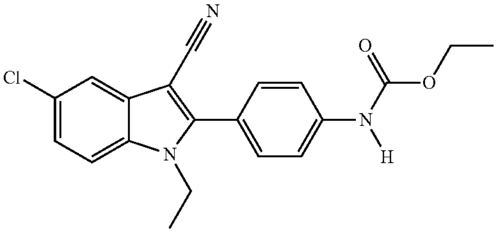
619
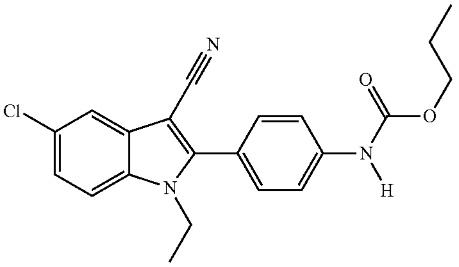
620
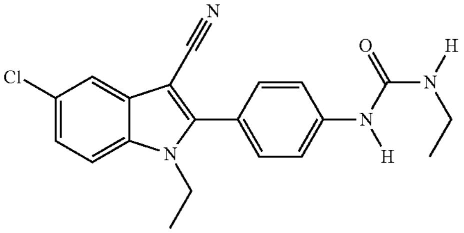
621
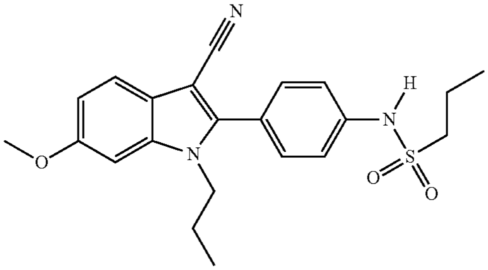
622
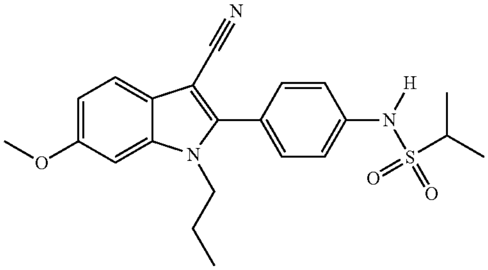
623
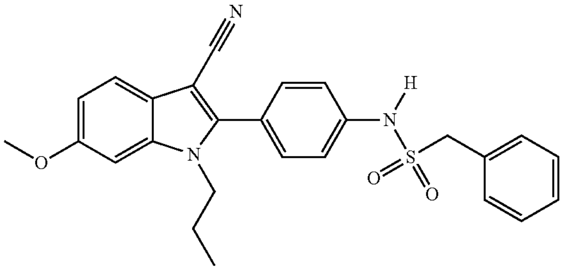

-continued
624
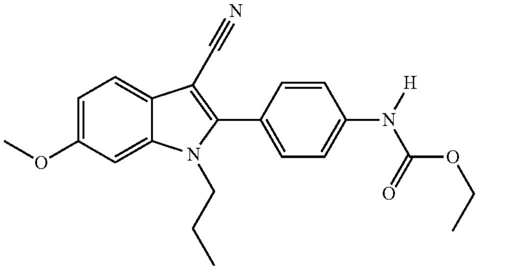
625
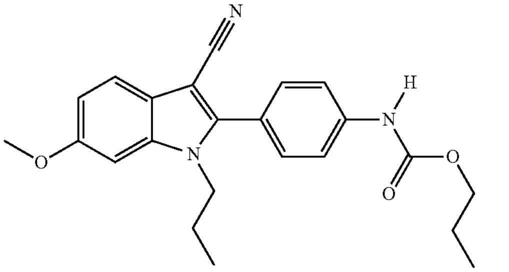
626
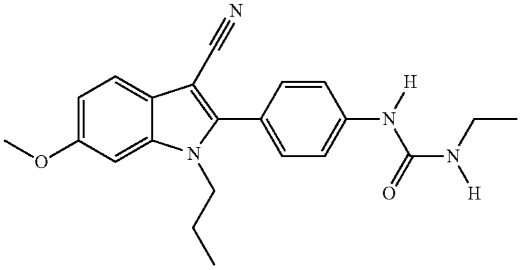
627
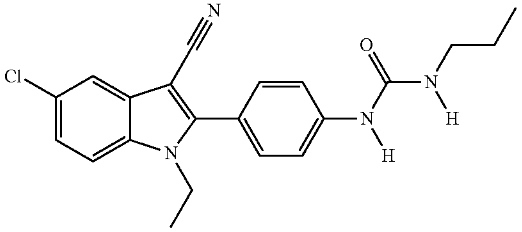
628
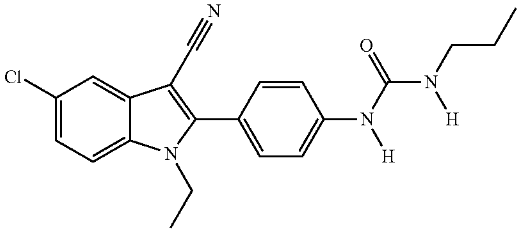
629
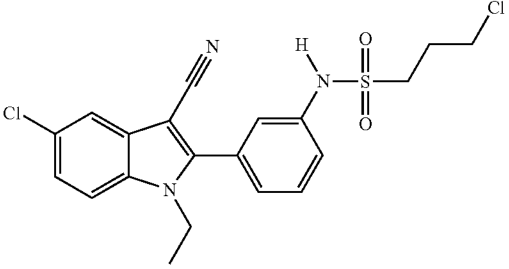
-continued
630
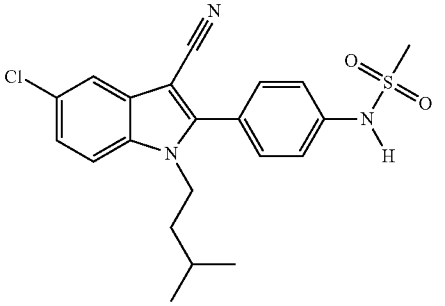
631
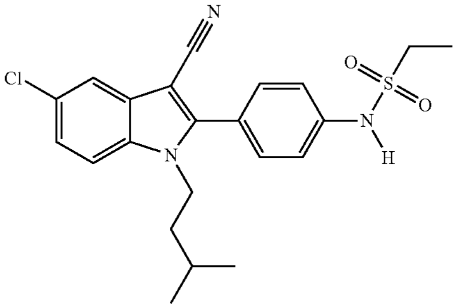
632
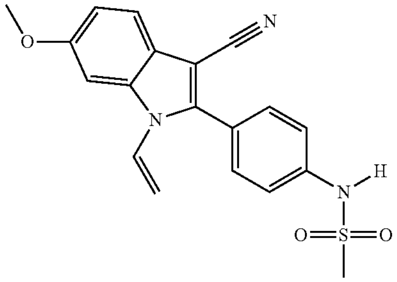
633
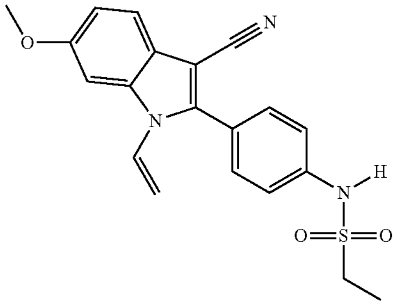
634
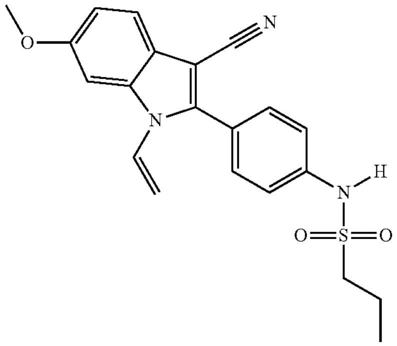

635
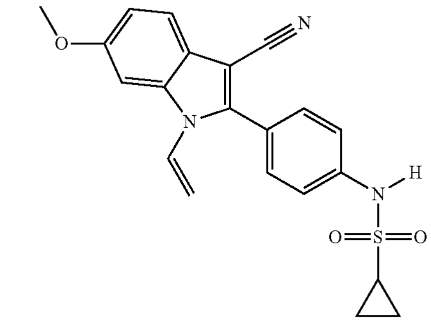
636
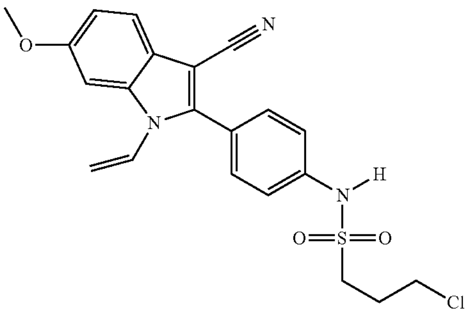
637
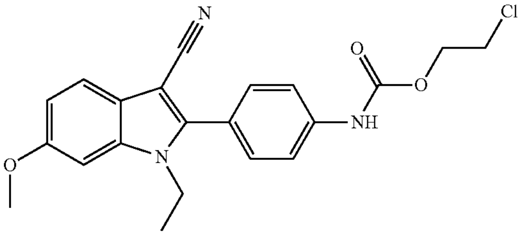
638
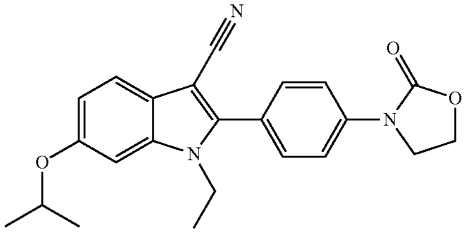
639
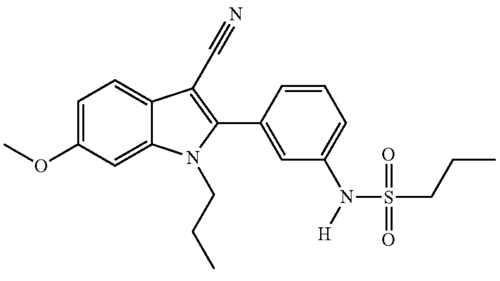
640
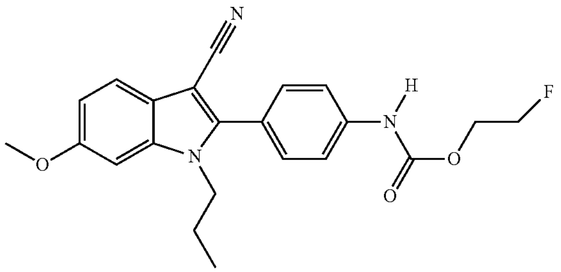
641
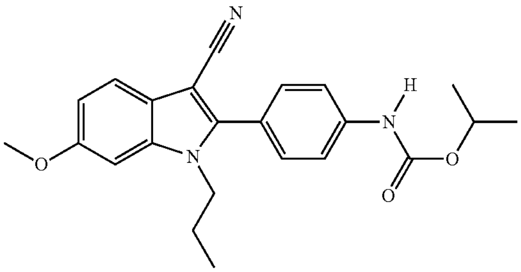
642
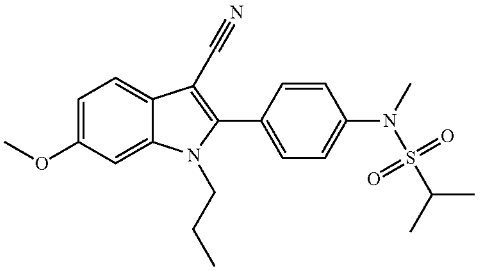
643
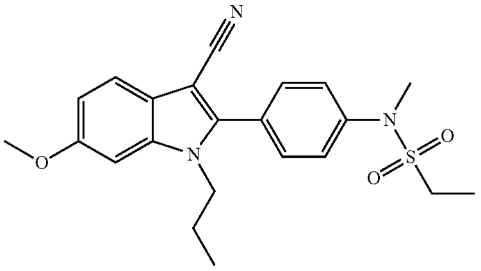
644
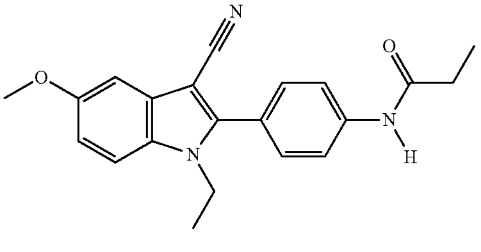

-continued
645
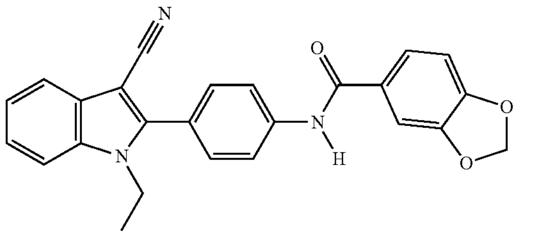
646
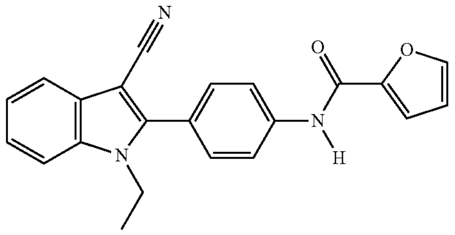
647
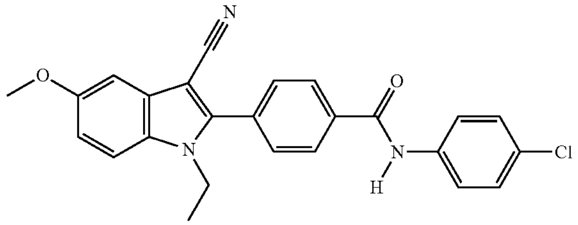
648
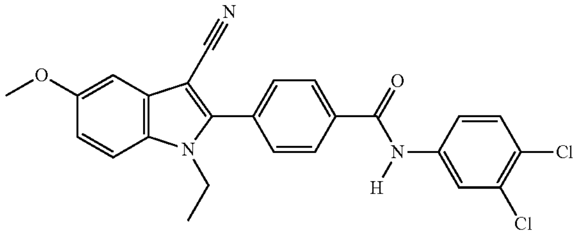
649
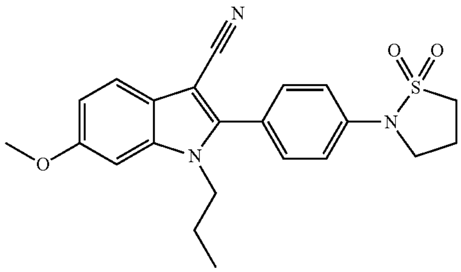
650
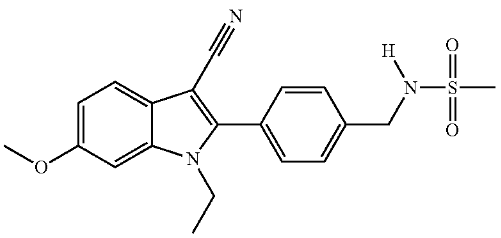
-continued
651
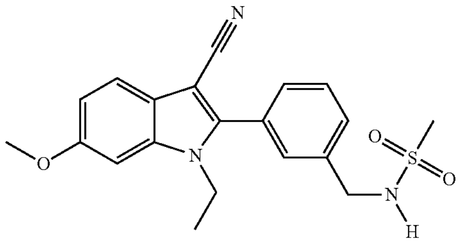
652
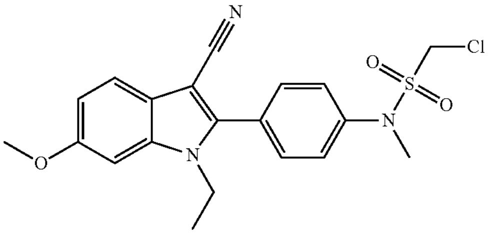
653
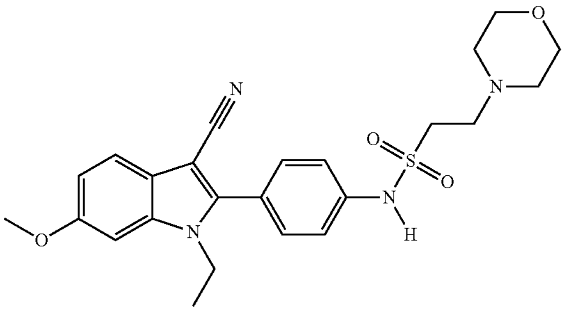
654
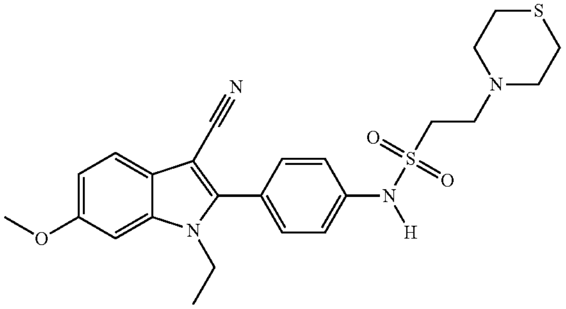
655
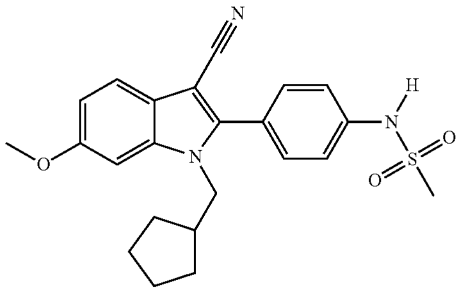

-continued
656
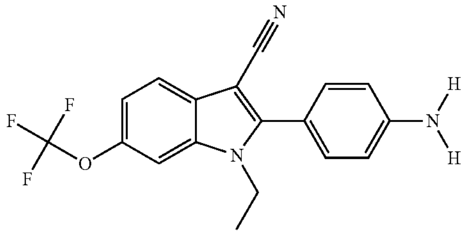
657
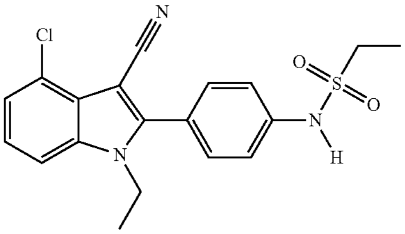
658
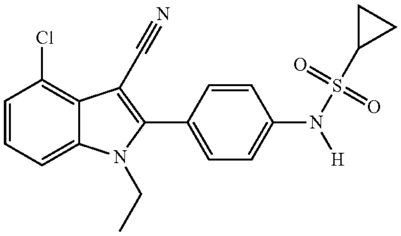
659
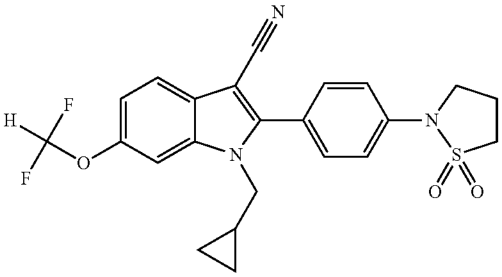
660
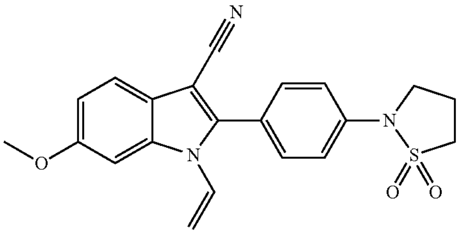
661
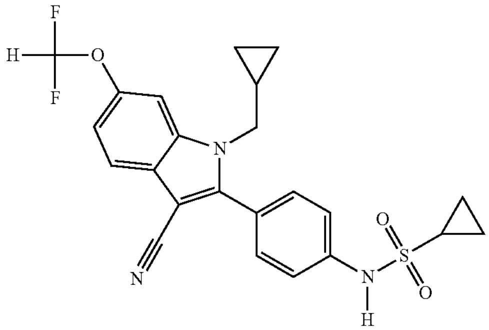
-continued
662
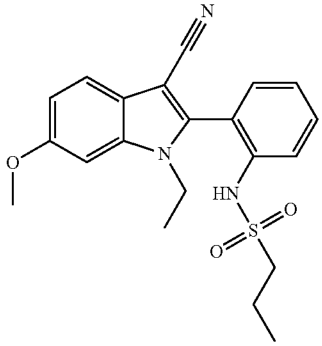
663
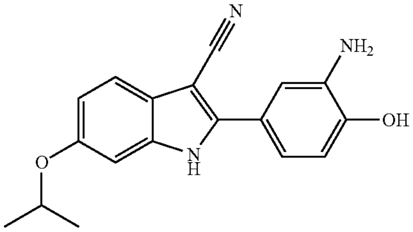
664
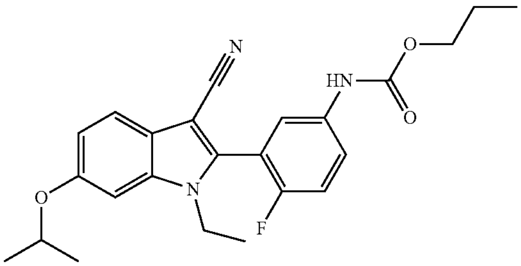
665
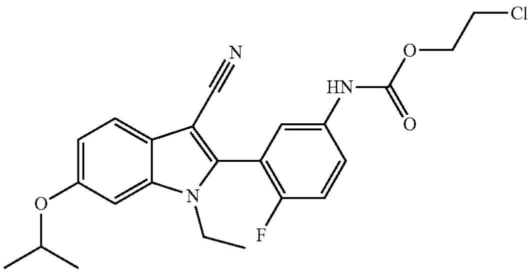
666
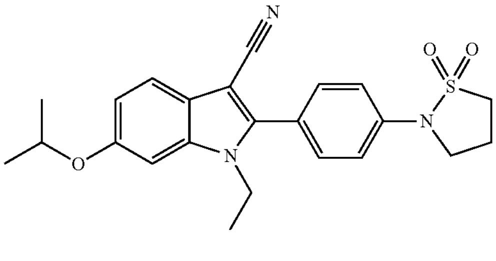

-continued
667
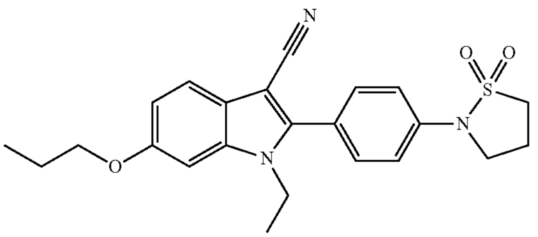
668
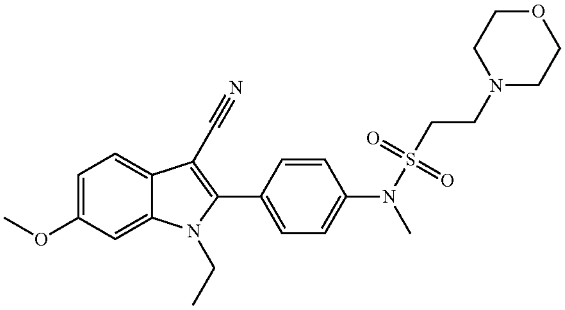
669
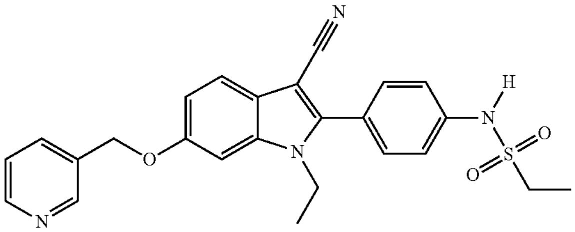
670
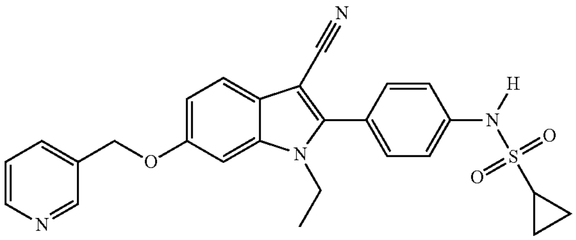
671
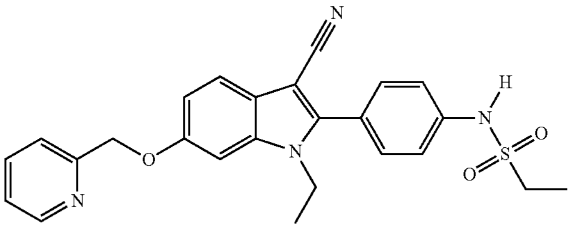
672
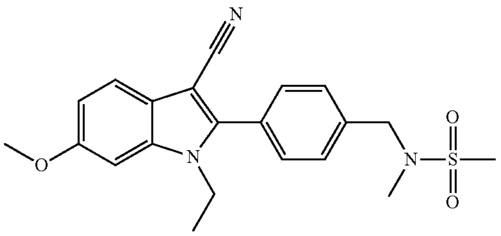
-continued
673
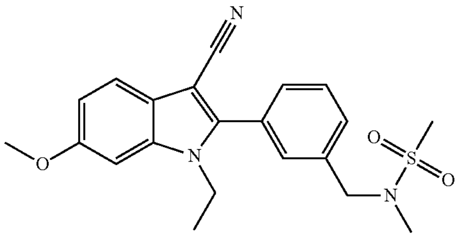
674
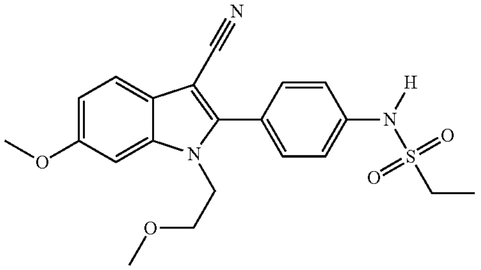
675
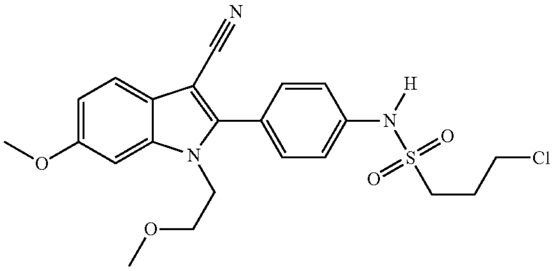
676
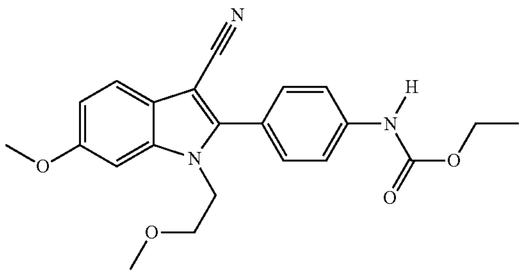
677
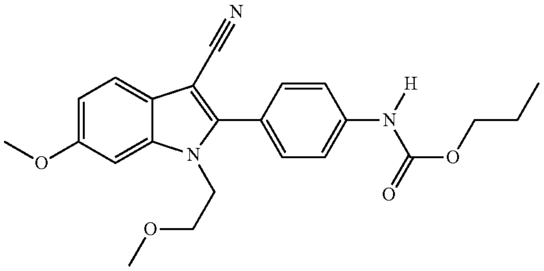

-continued
678
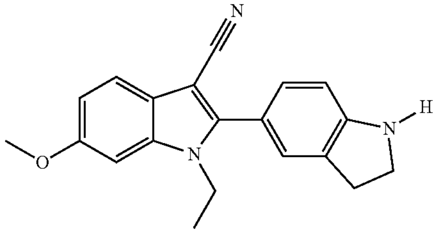
679
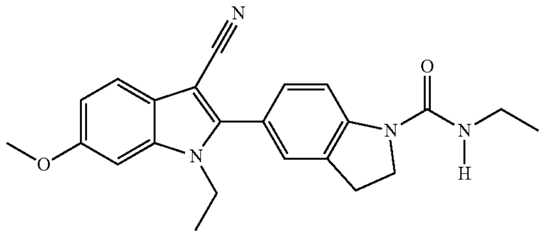
680
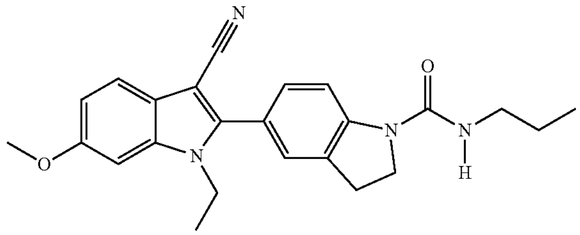
681
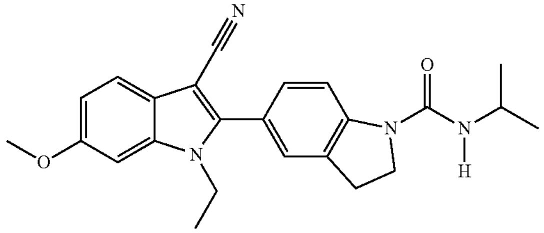
682
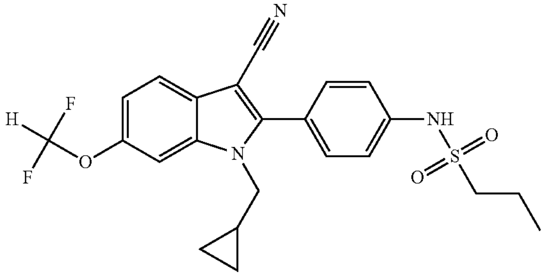
683
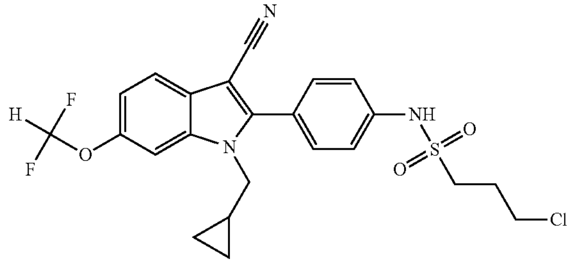
-continued
684
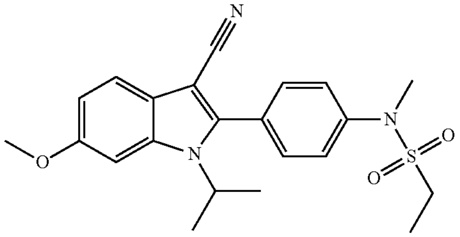
685
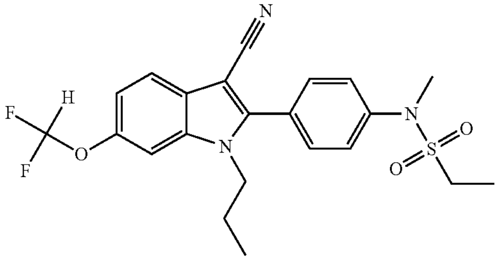
686
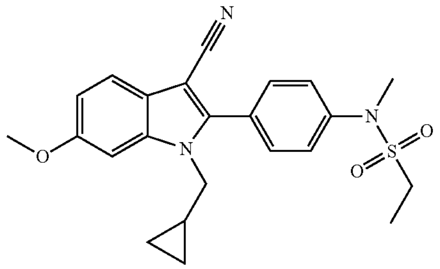
687
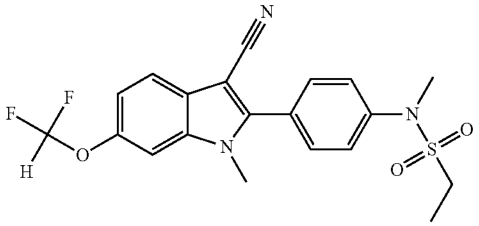
688
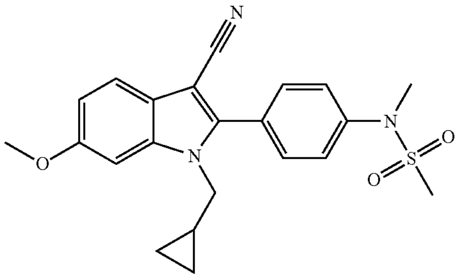
689
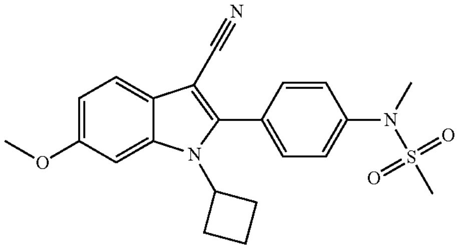

-continued
690
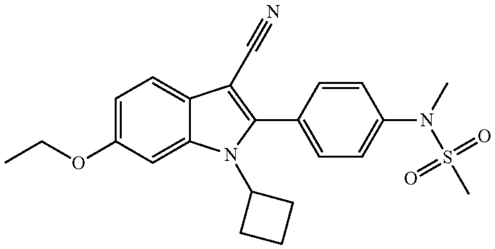
691
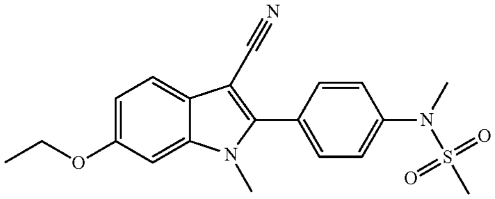
692
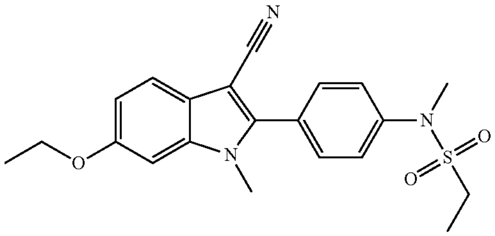
693
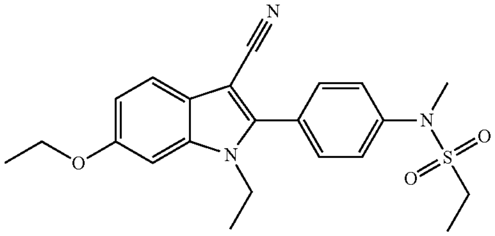
694
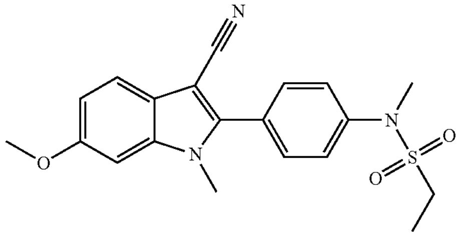
695
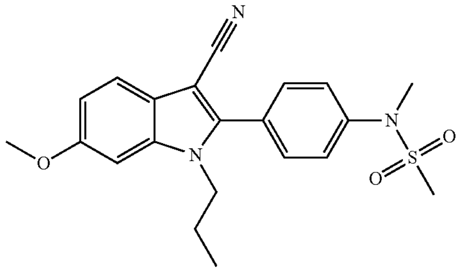
-continued
696
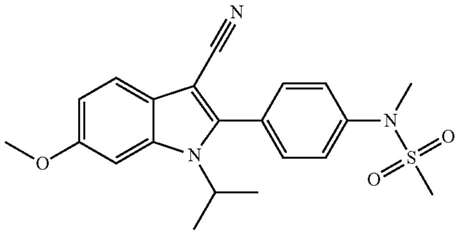
697
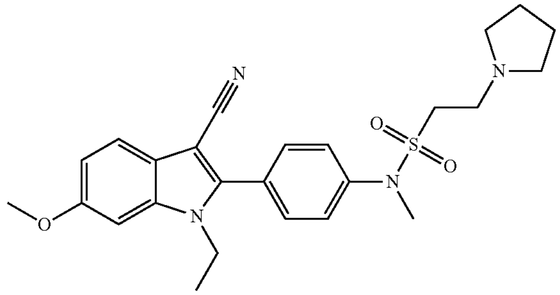
698
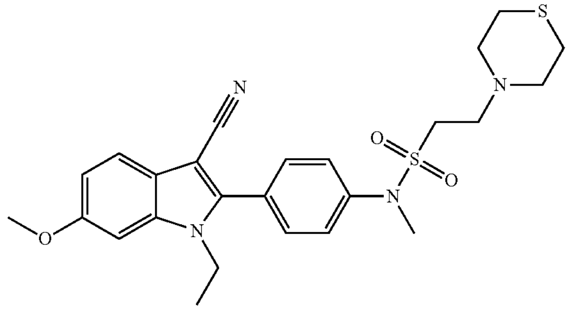
699
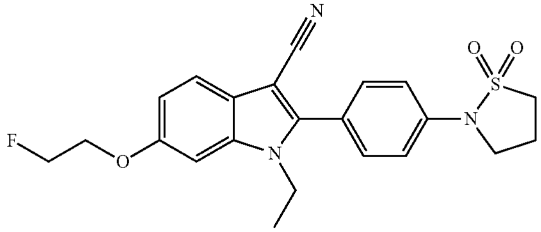
701
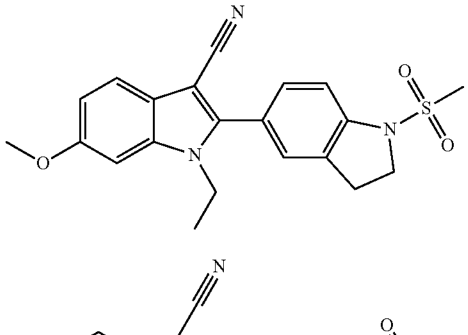
702
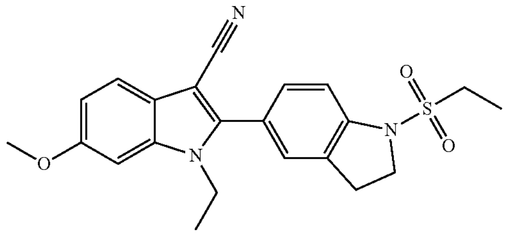

-continued
703
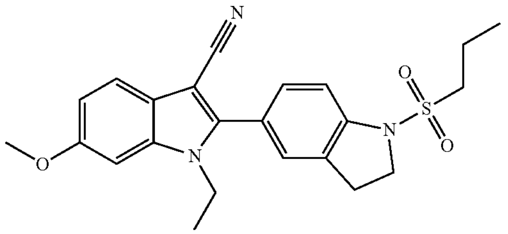
704
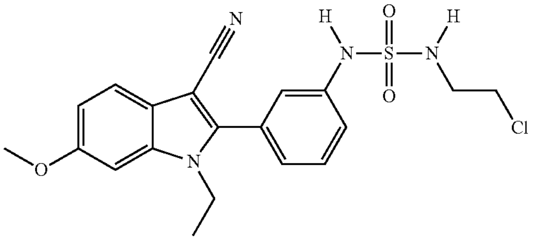
705
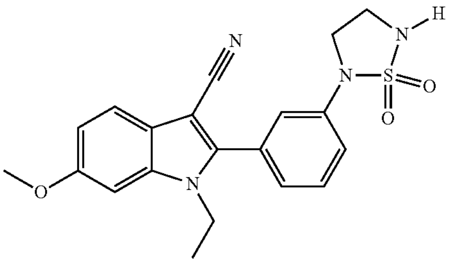
706
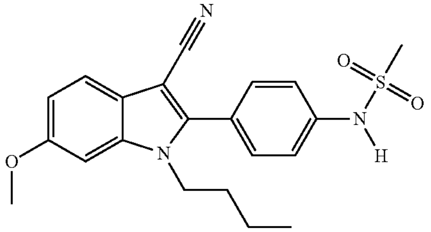
707
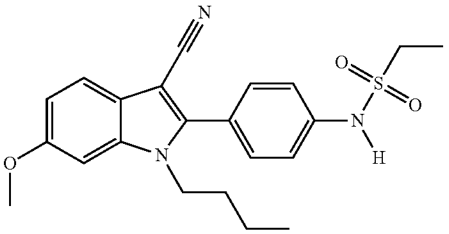
708
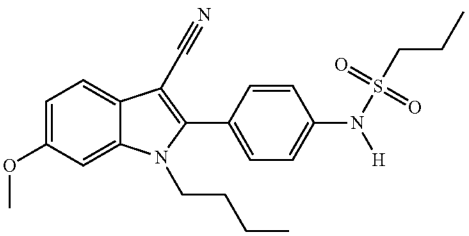
-continued
709
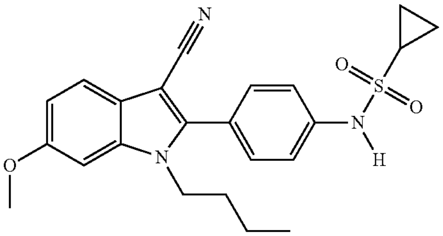
710
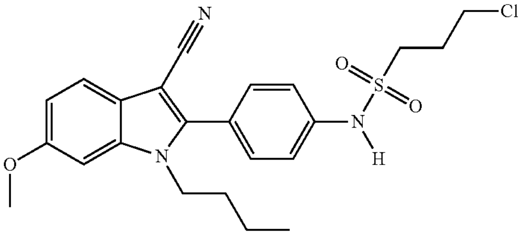
711
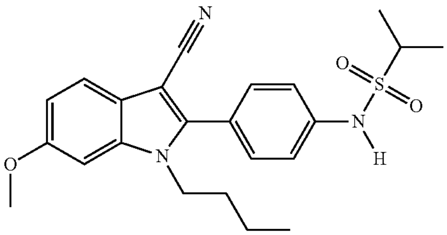
712
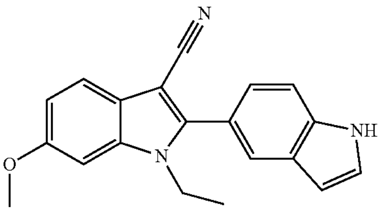
713
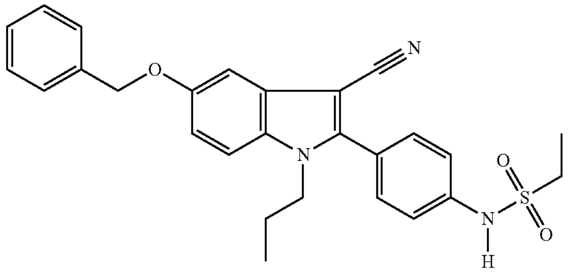
714
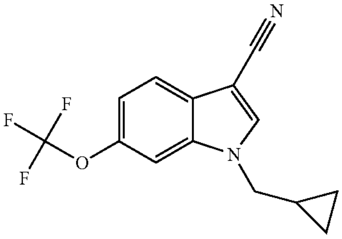

-continued
715
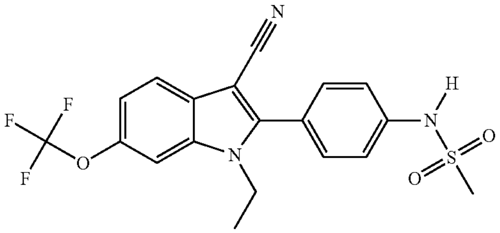
716
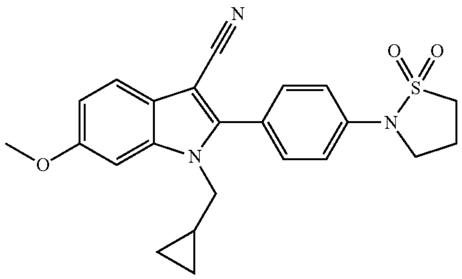
717
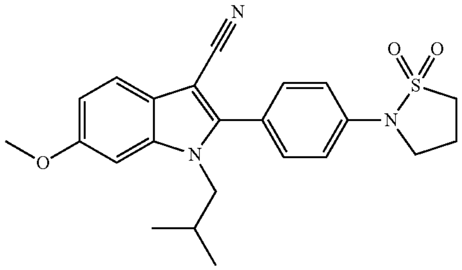
718
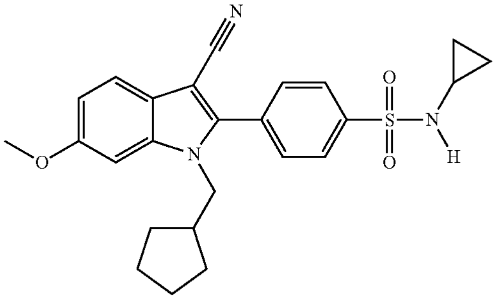
719
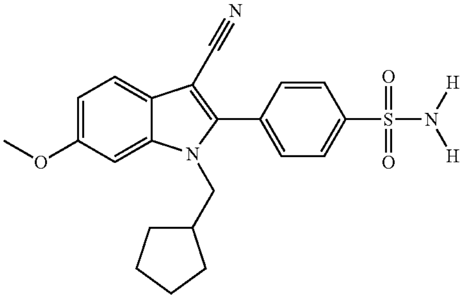
-continued
720
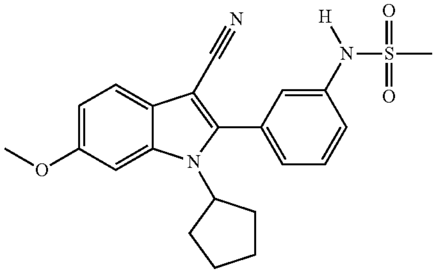
721
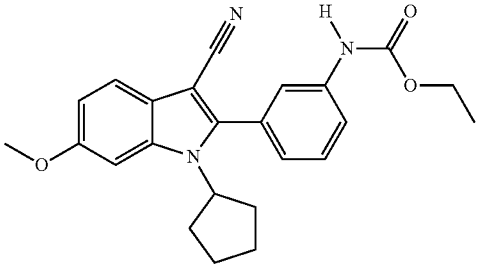
722
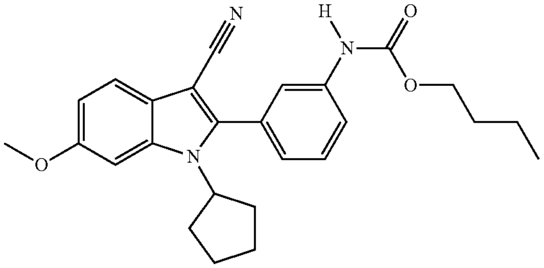
723
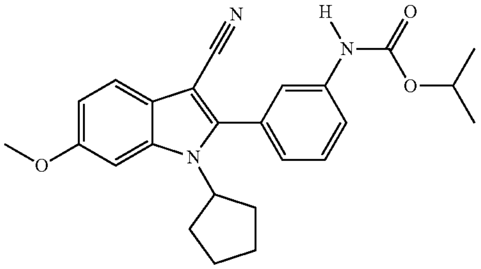
724
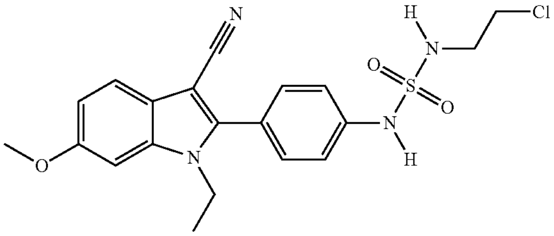
725
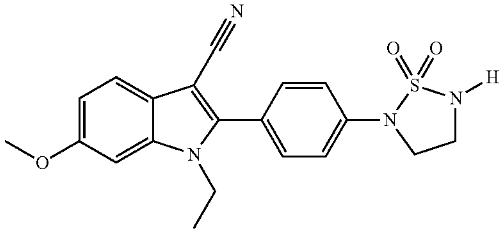

-continued
726
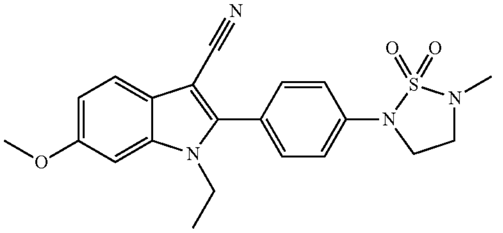
727
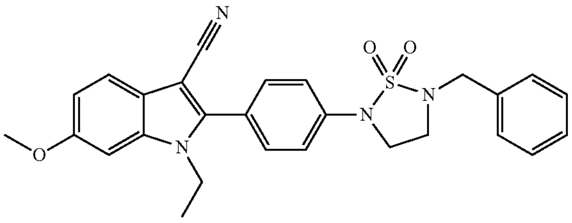
728
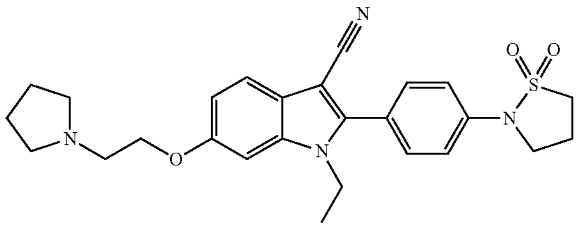
729
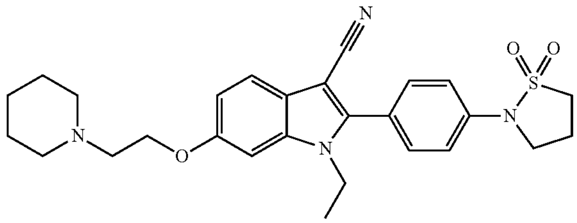
730
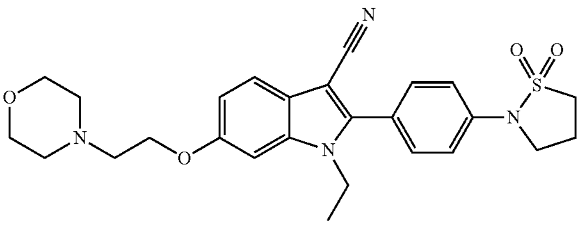
731
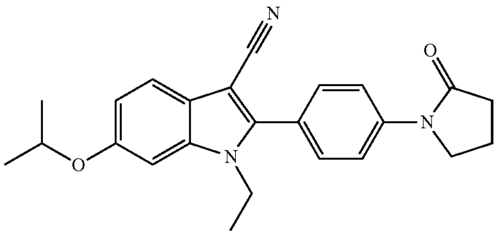
-continued
732
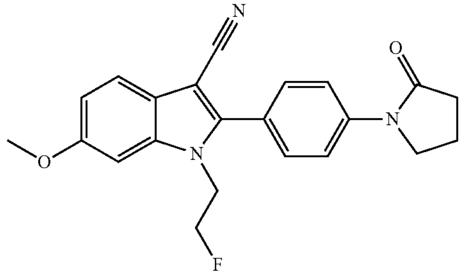
733
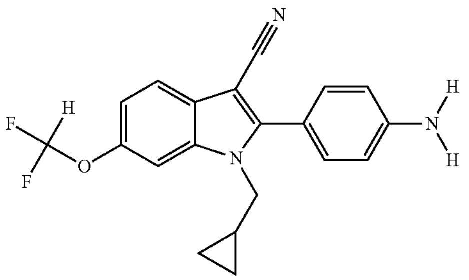
734
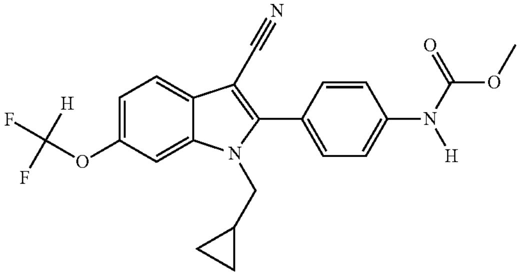
735
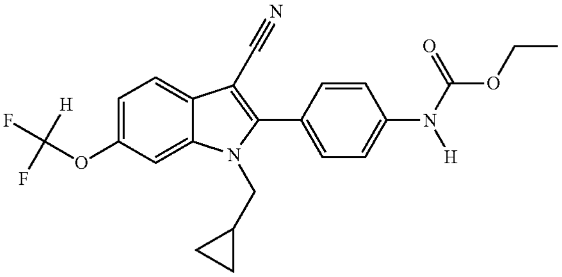
736
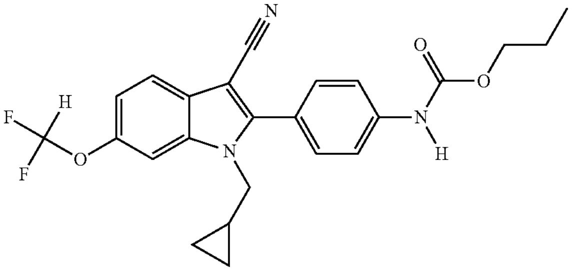

-continued
737
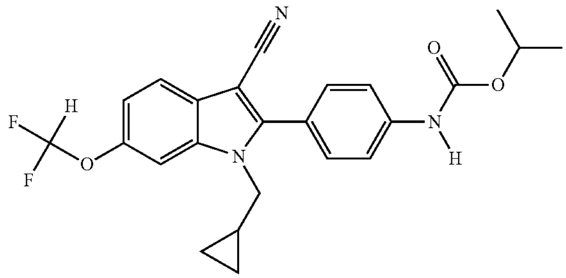
738
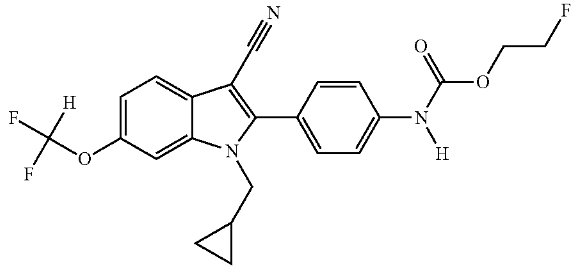
739
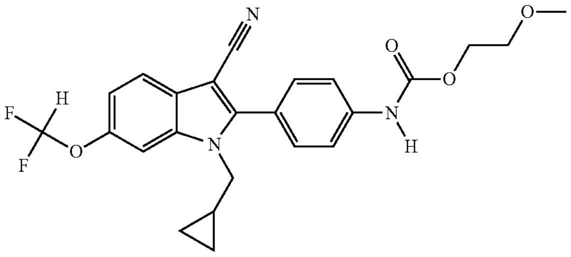
740
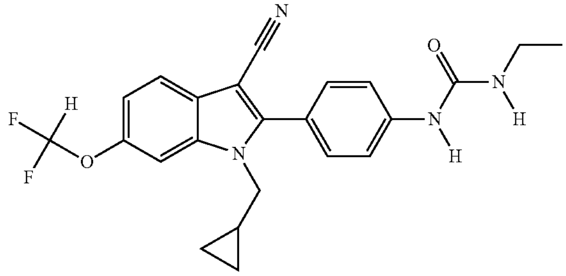
741
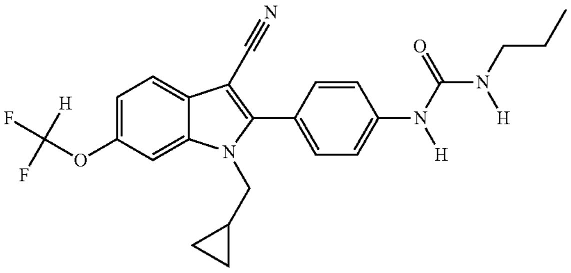
-continued
742
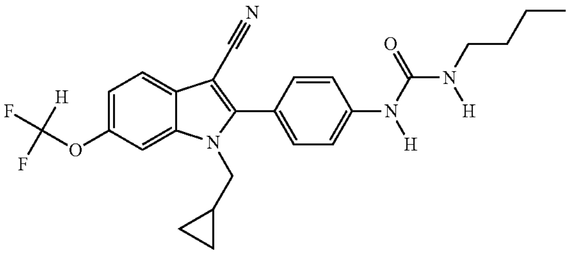
743
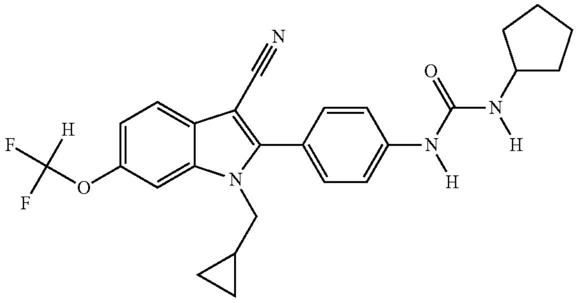
744
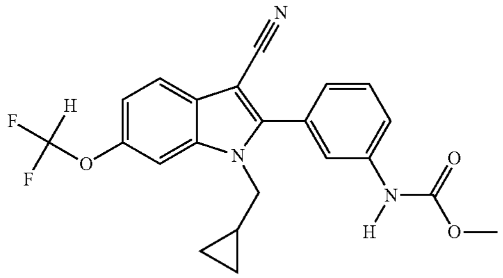
745
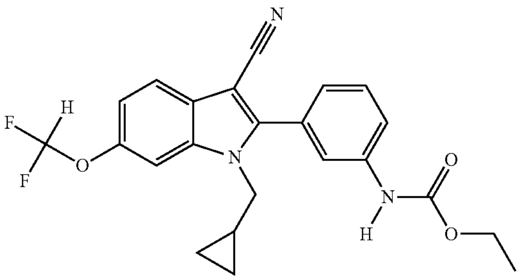
746
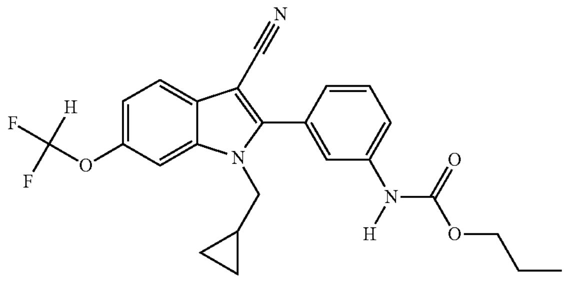

-continued
747
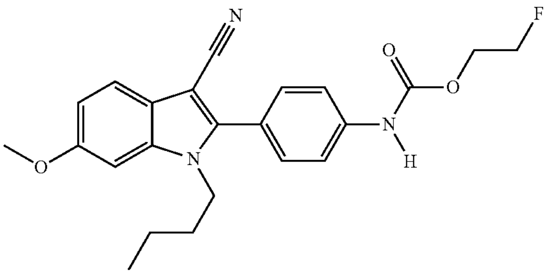
748
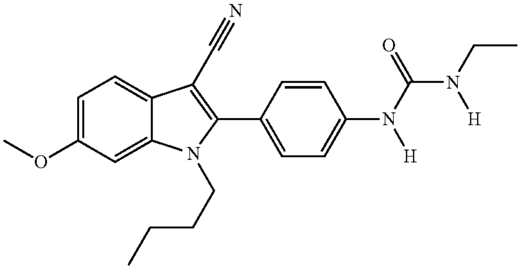
749
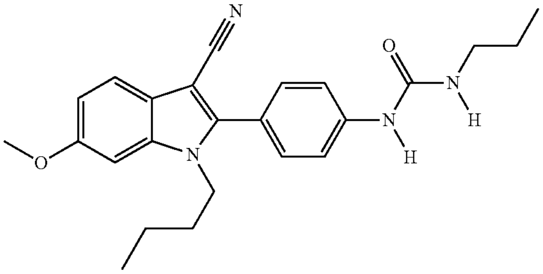
750
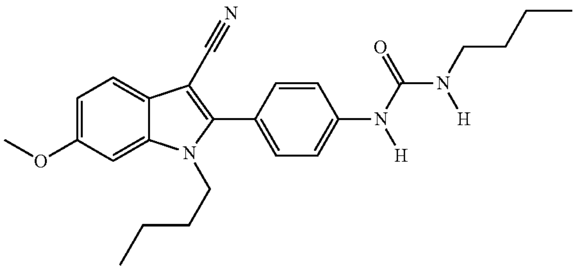
751
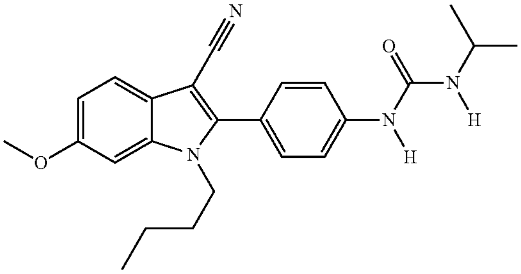
-continued
752
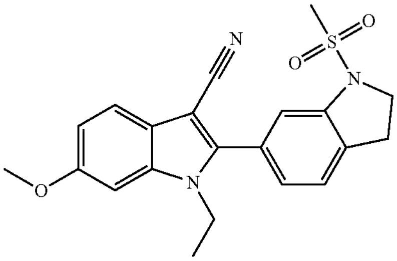
753
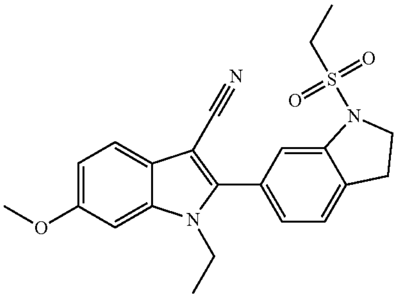
754
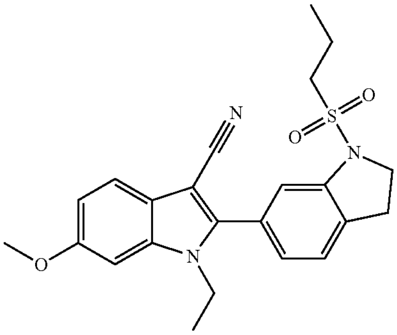
755
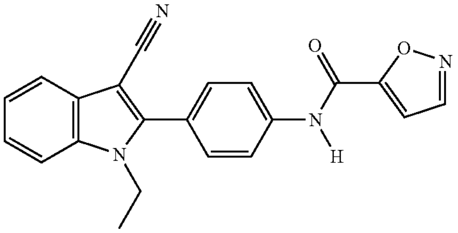
756
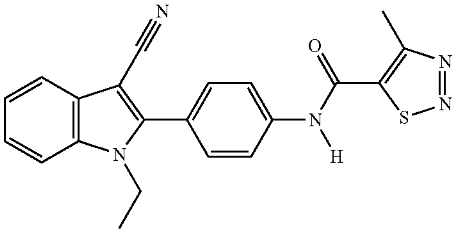
757
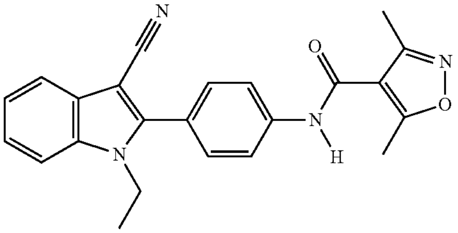

-continued
758
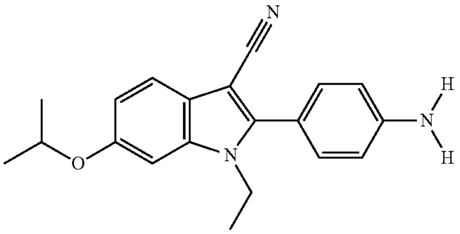
759
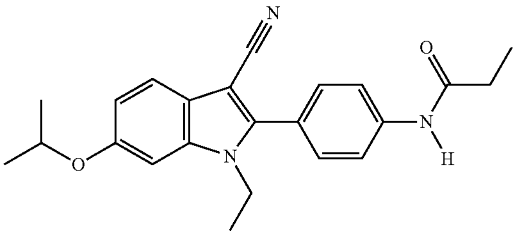
760
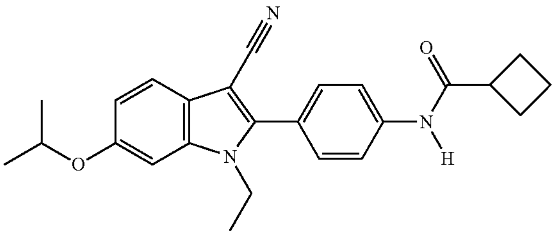
761
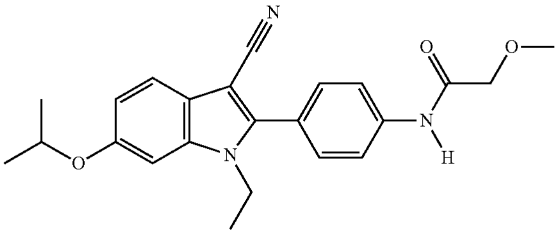
762
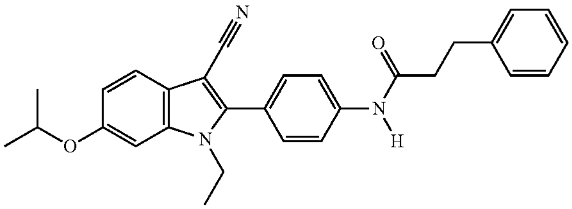
763
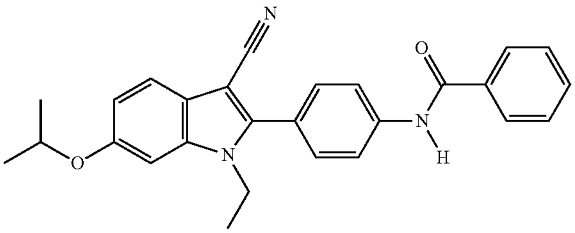
-continued
764
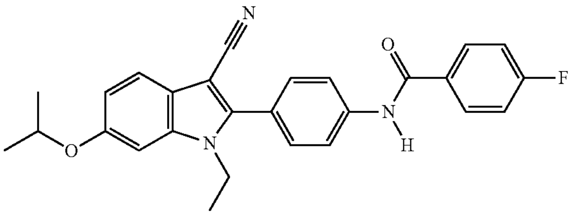
765
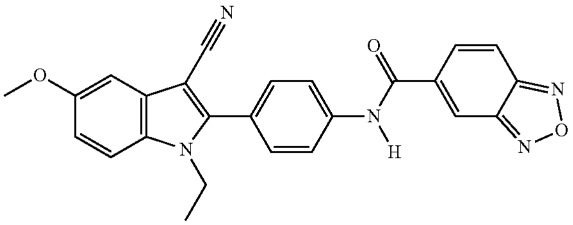
766
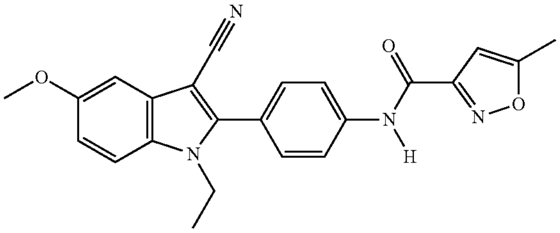
767
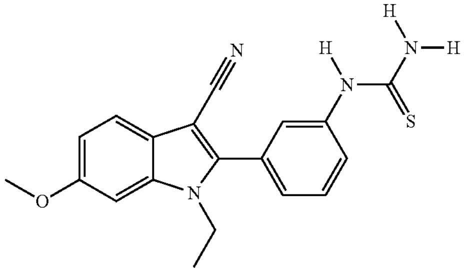
768
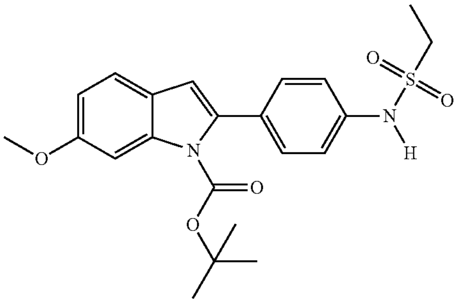
769
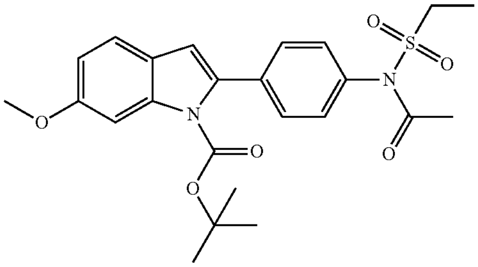

770
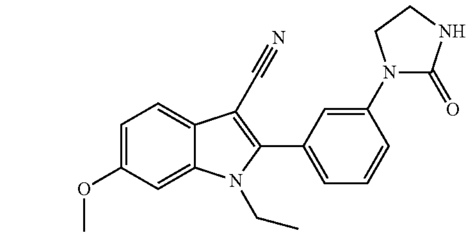
771
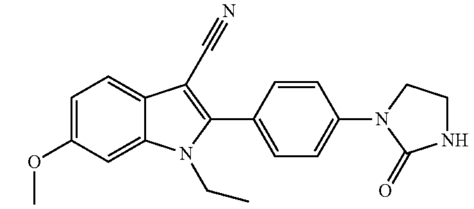
772
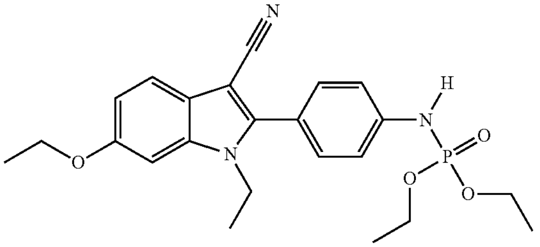
773
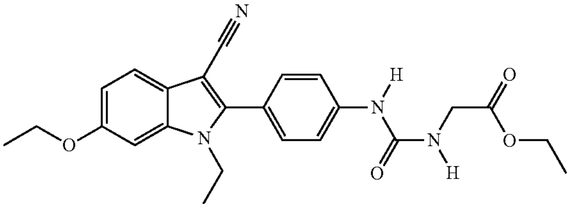
774
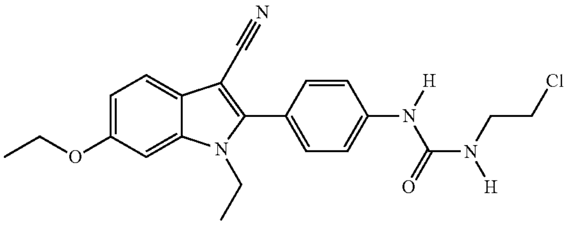
775
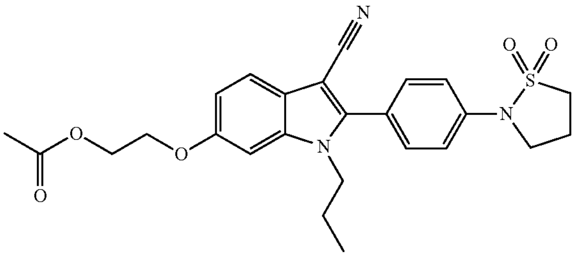
776
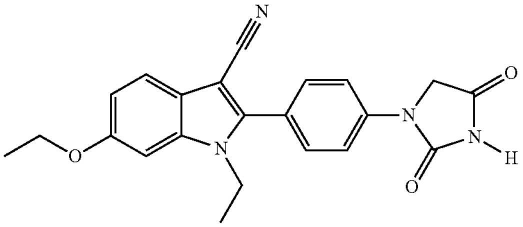
777
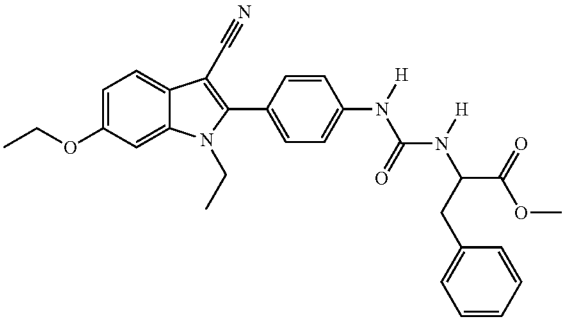
778
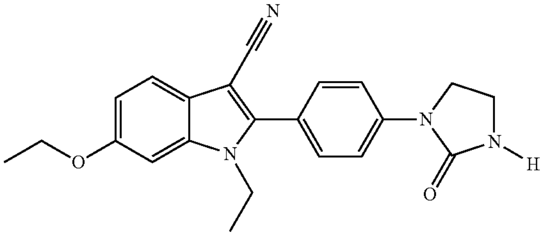
779
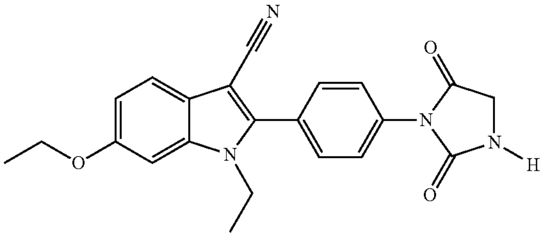
780
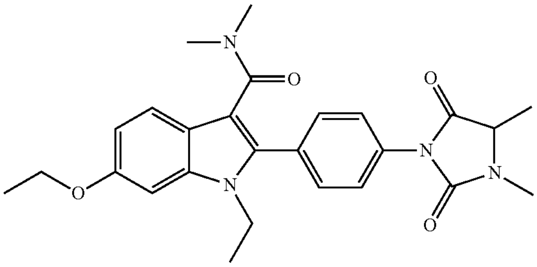

-continued
781
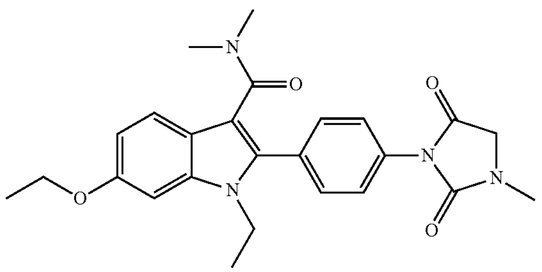
782
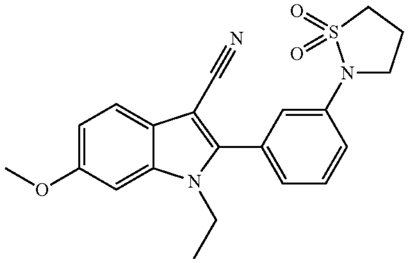
783
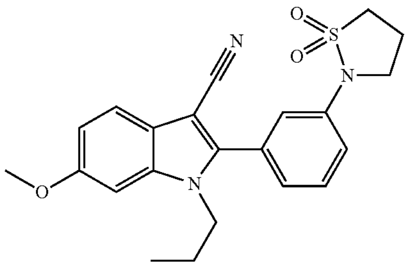
784
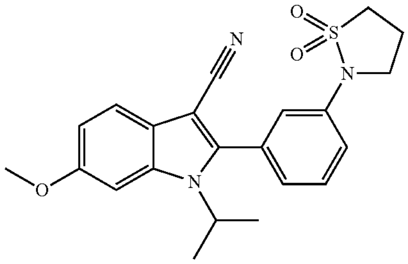
785
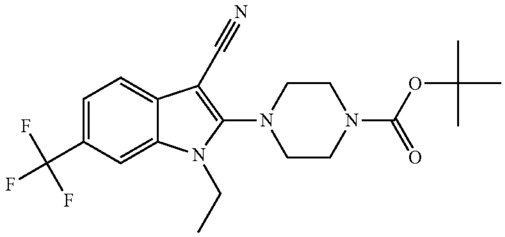
786
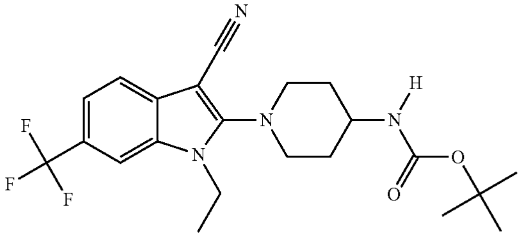
-continued
787
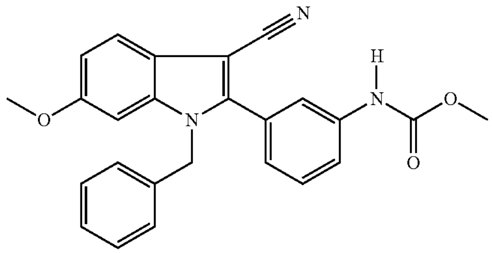
788
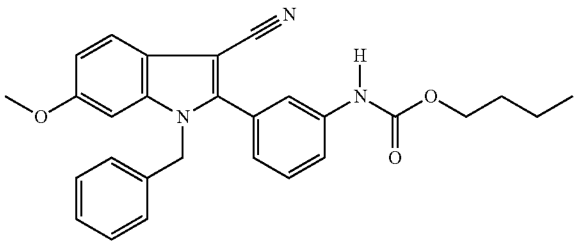
789
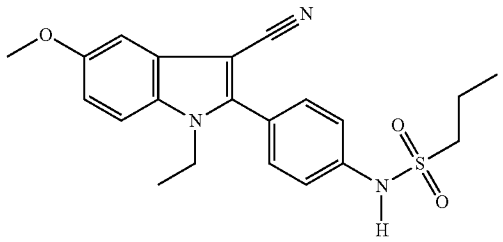
790
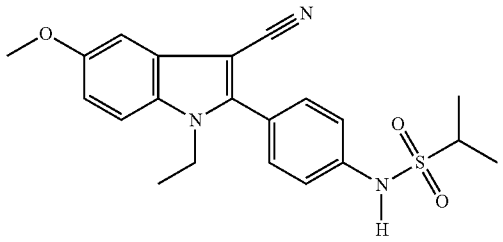
791
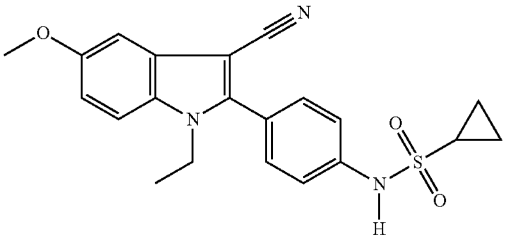
792
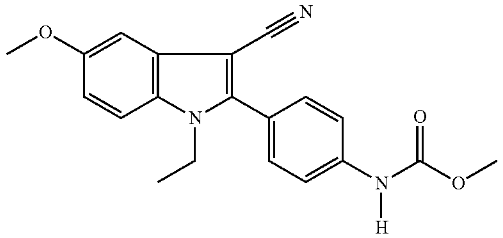

-continued
793
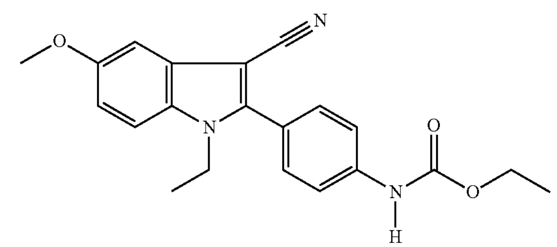
794
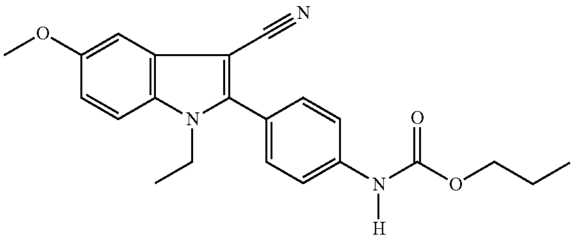
795
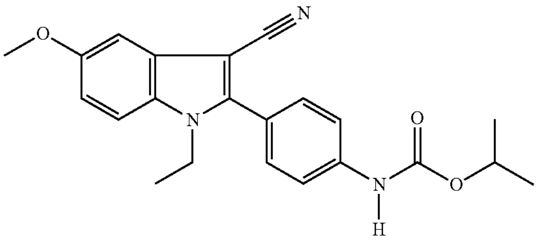
796
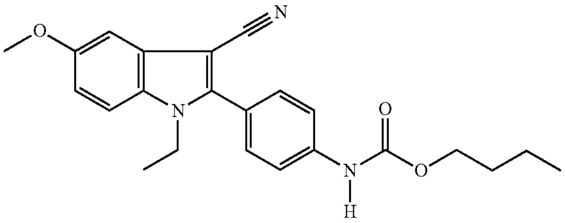
797
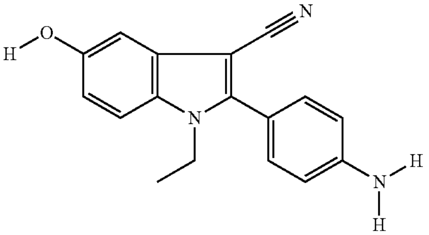
798
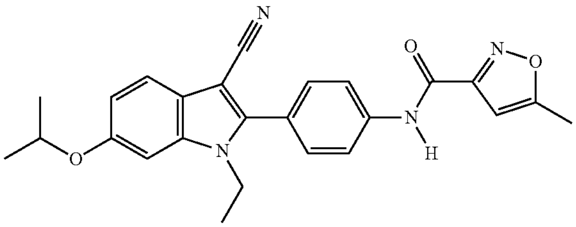
-continued
799
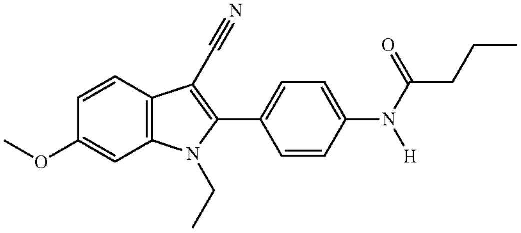
801
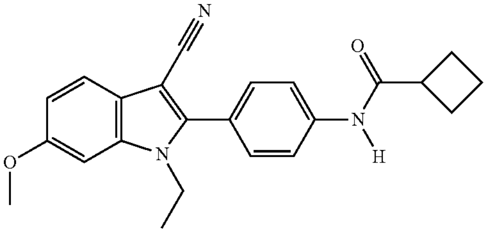
802
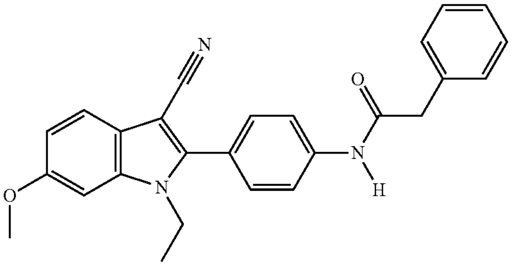
803
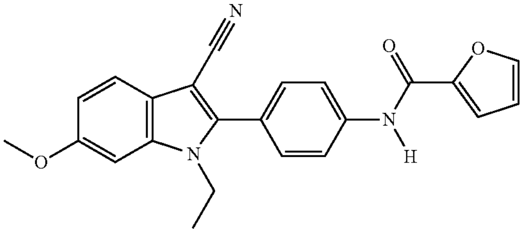
804
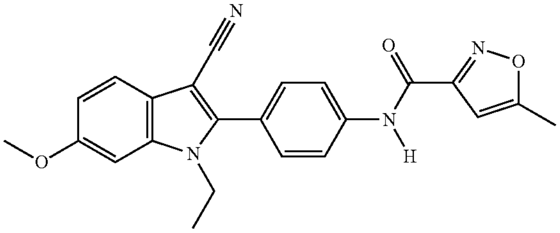
805
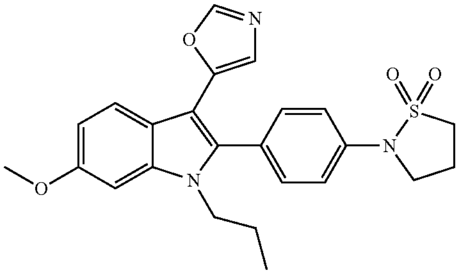

-continued
806
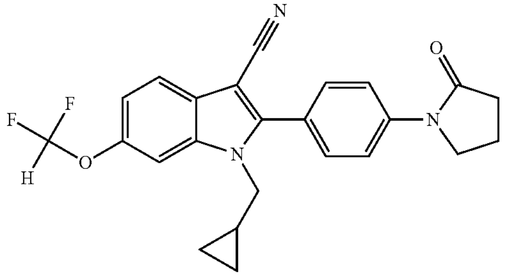
807
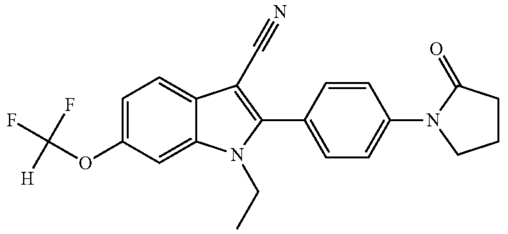
808
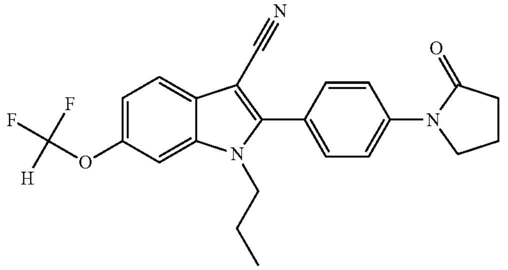
809
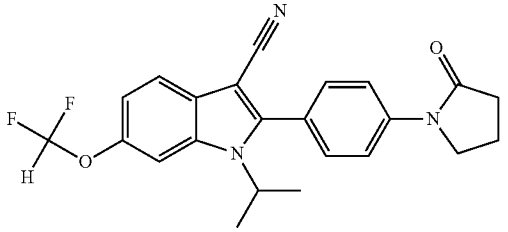
810
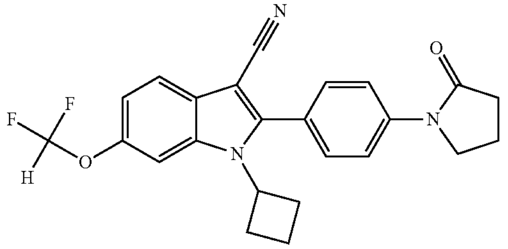
811
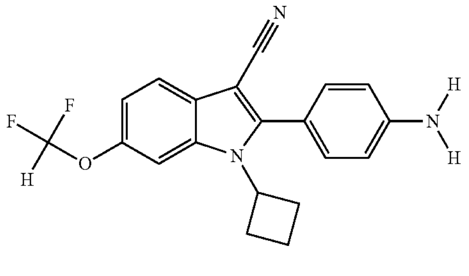
-continued
812
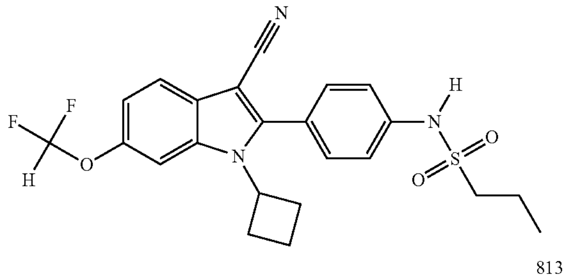
813
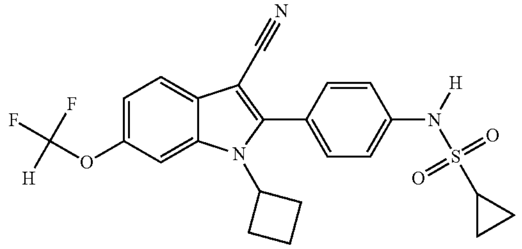
814
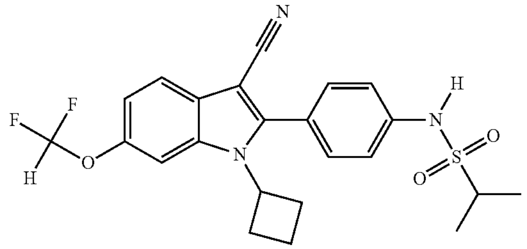
815
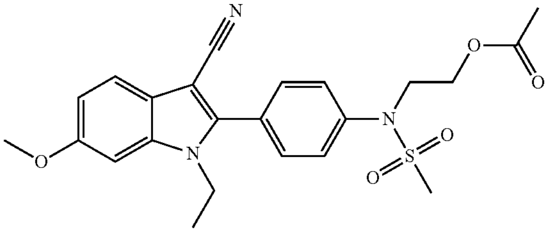
816
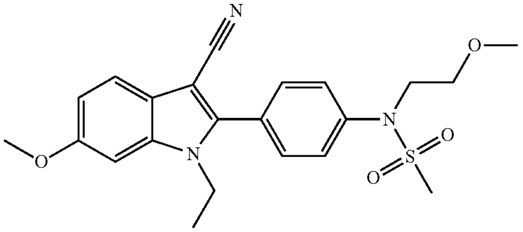
817
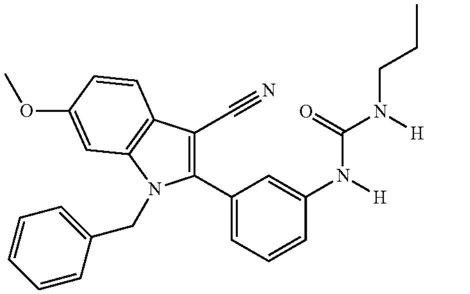

-continued
818
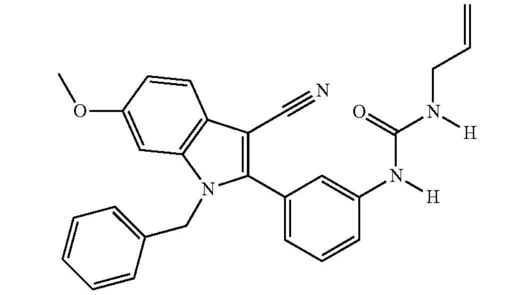
819
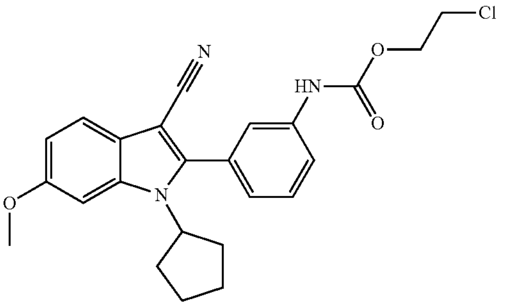
820
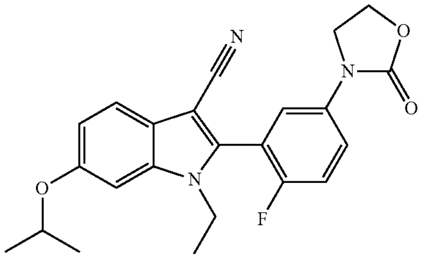
821
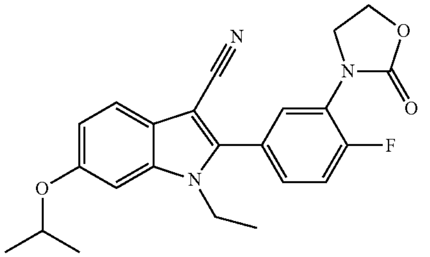
822
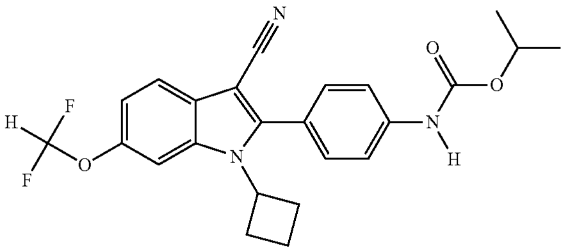
-continued
823
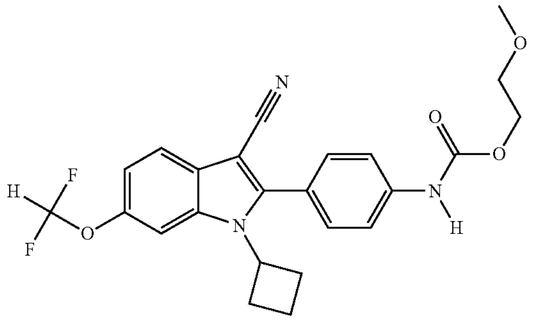
824
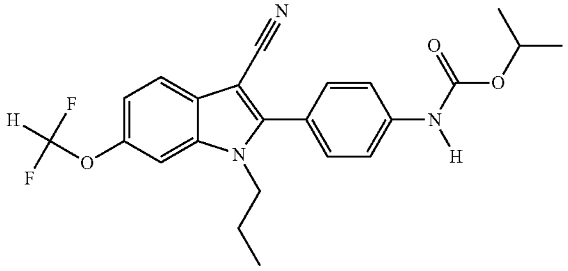
825
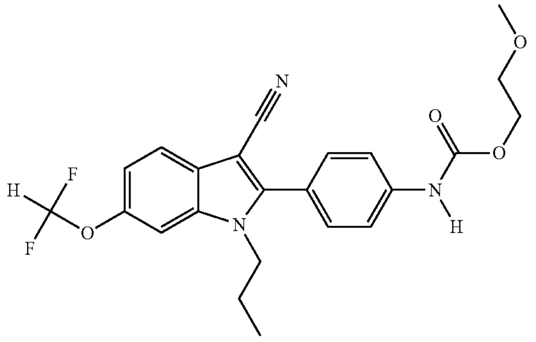
826
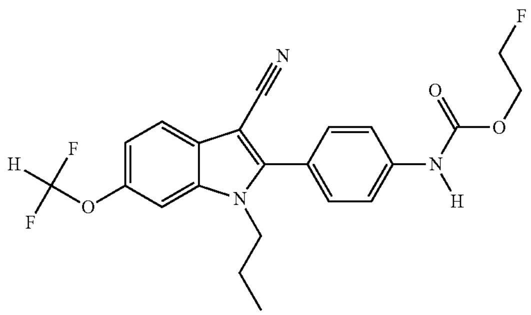
827
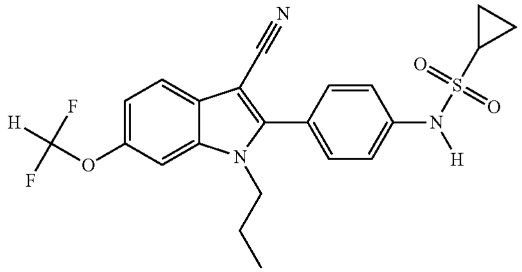

-continued
828
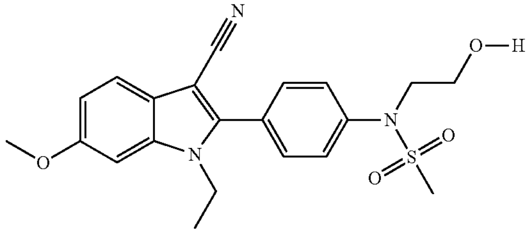
829
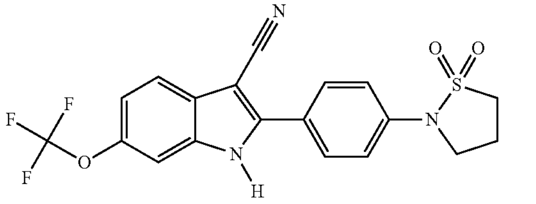
830
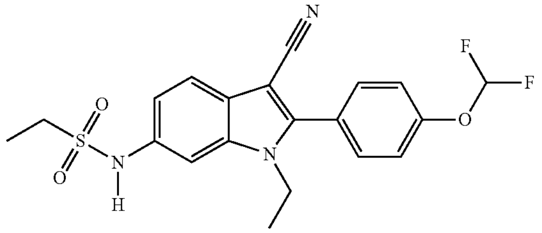
831
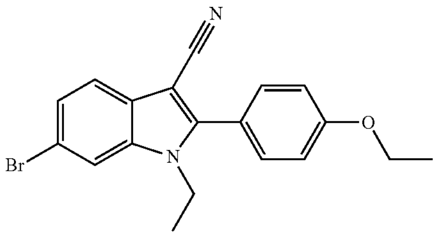
832
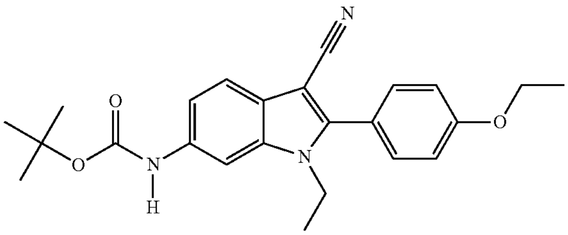
833
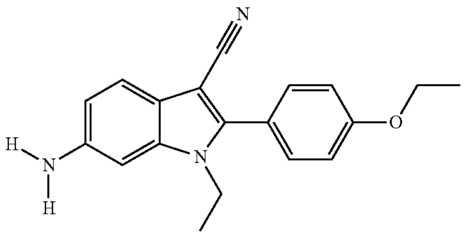
-continued
834
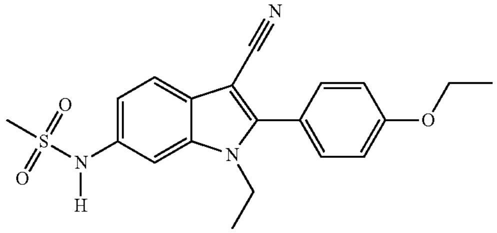
835
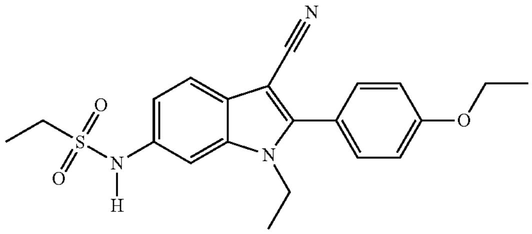
836
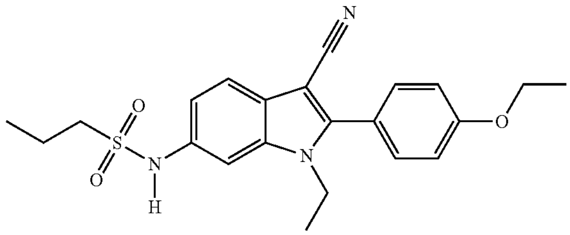
837
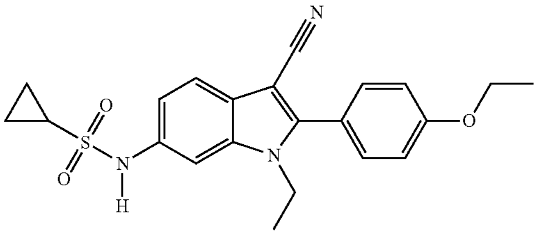
838
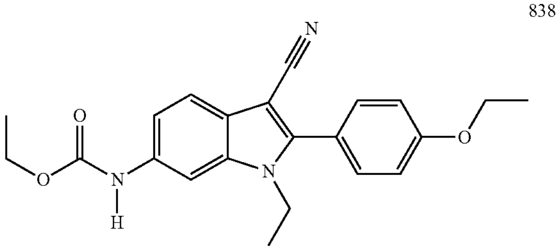
839
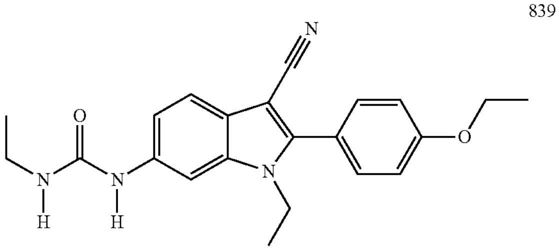

-continued
840
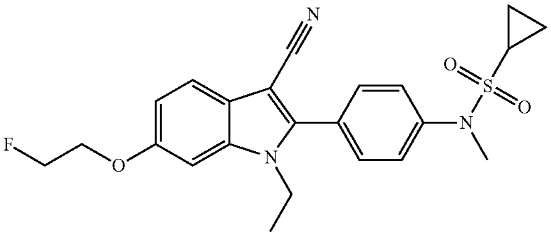
841
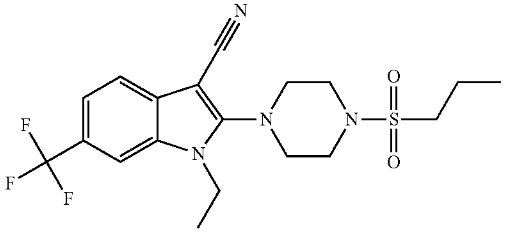
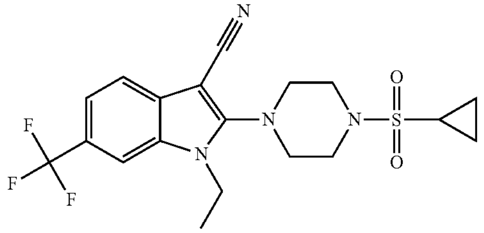
843
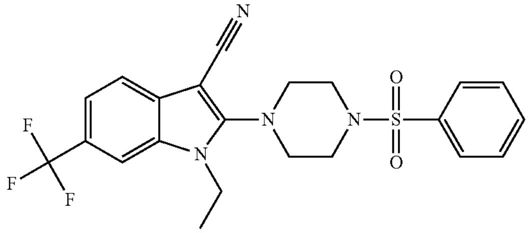
844
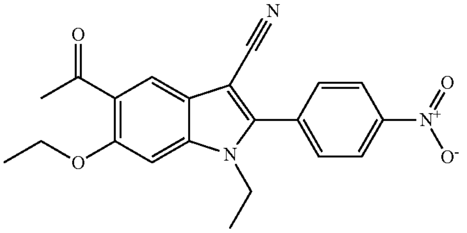
845
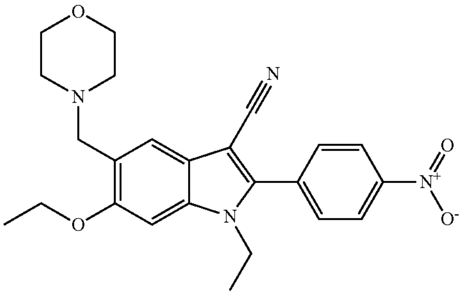
-continued
846
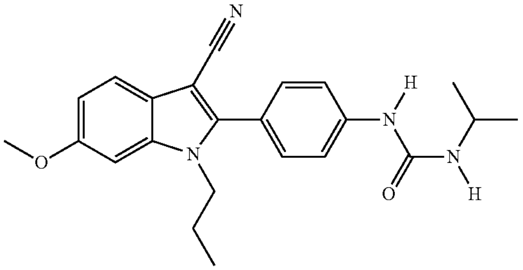
847
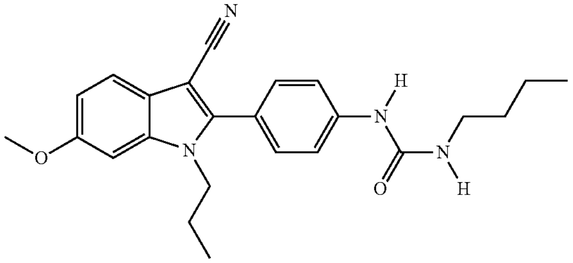
848
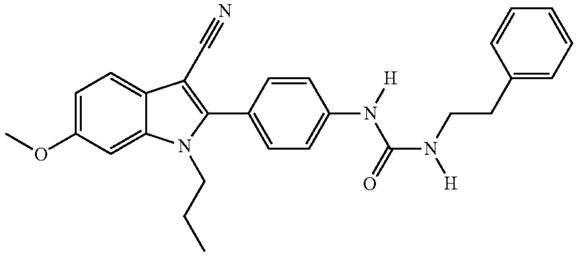
849
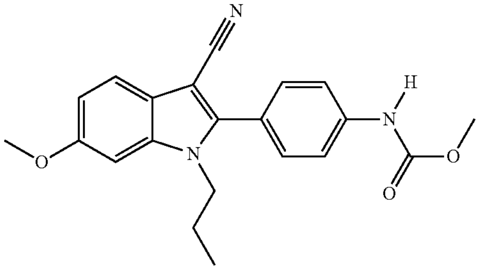
850
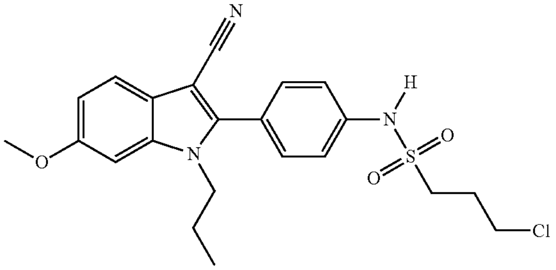

851
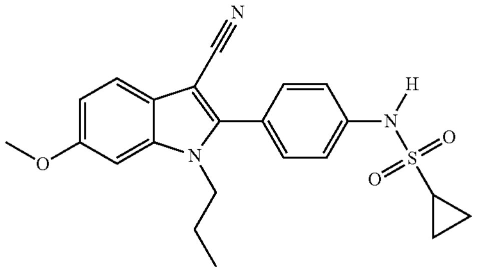
852
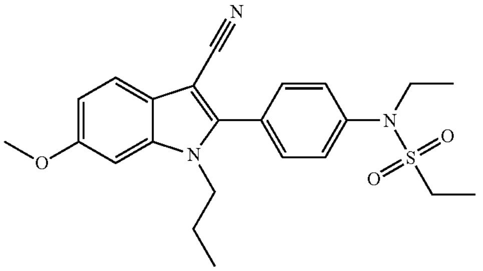
853
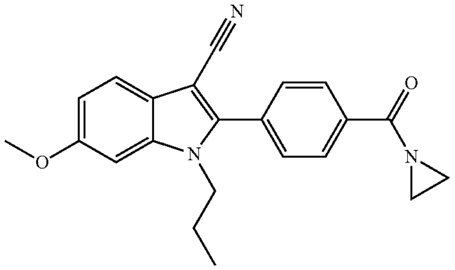
854
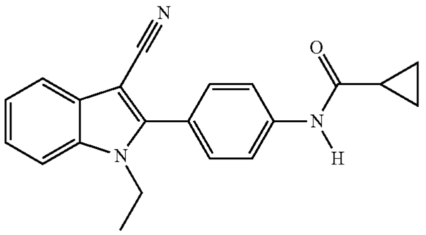
855
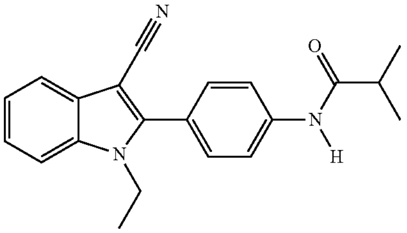
856
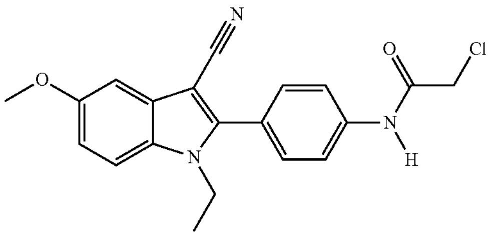
857
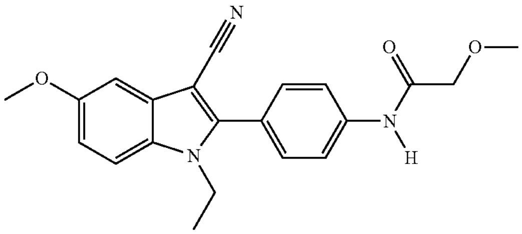
858
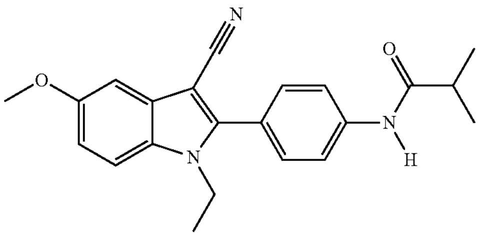
859
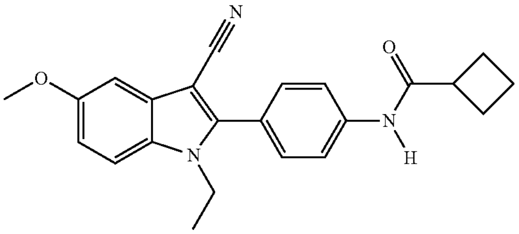
860
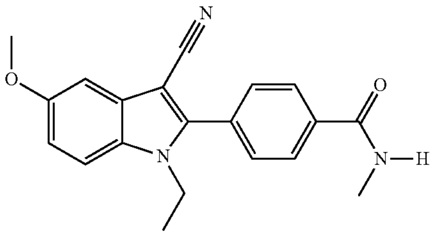
861
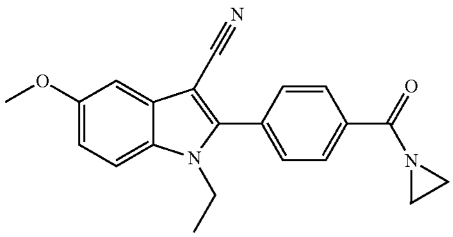
862
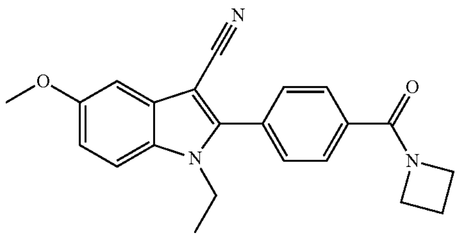

-continued
863
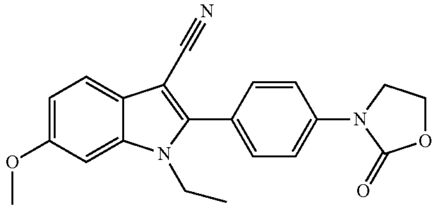
864
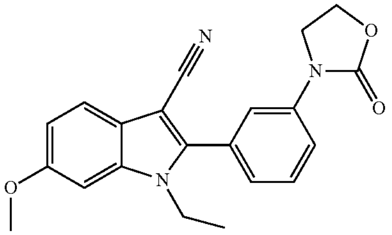
865
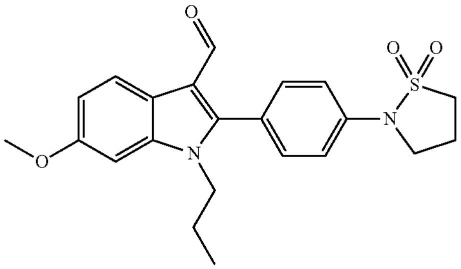
Embodiment 27
A compound selected from the group consisting of the following:
22
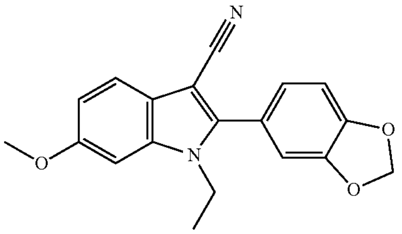
23
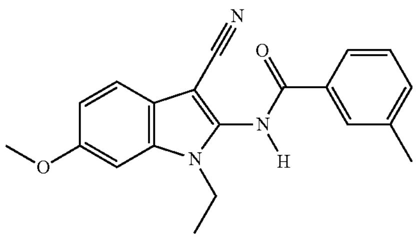
-continued
26
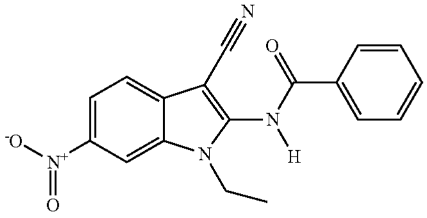
48
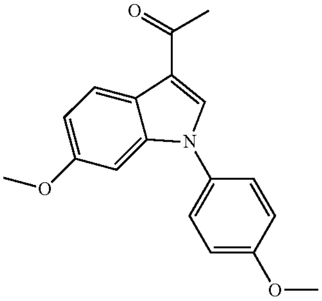
53
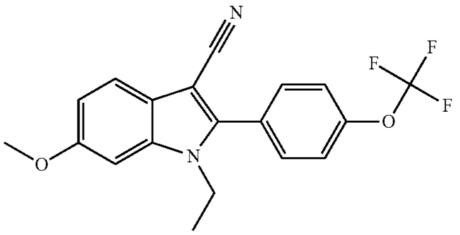
69
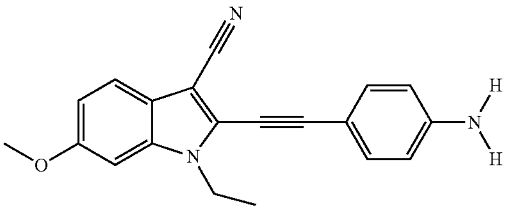
81
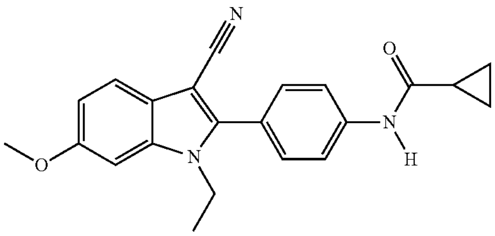
82
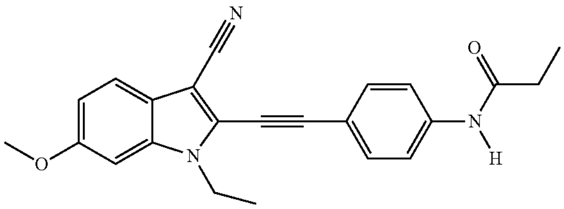

-continued
83
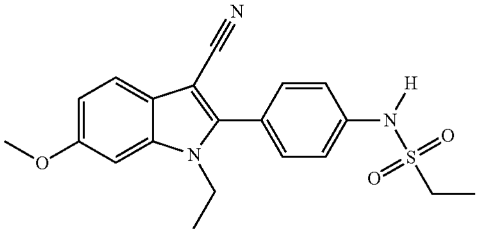
84
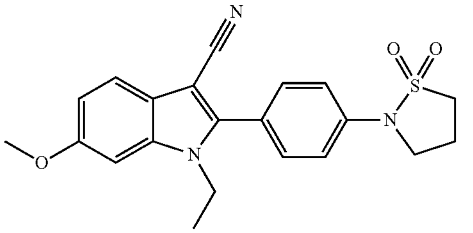
85
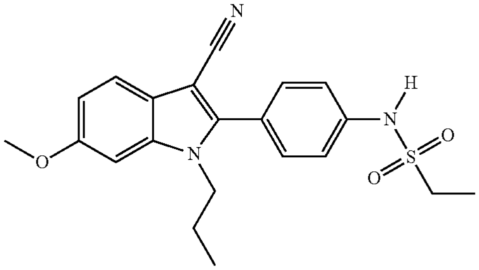
86
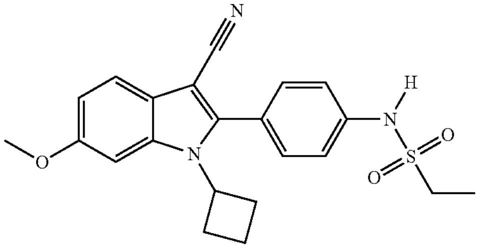
87
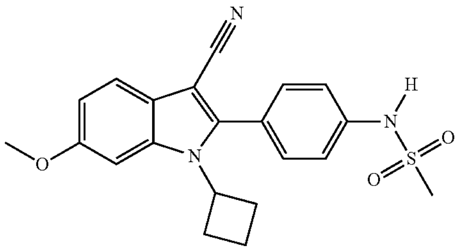
88
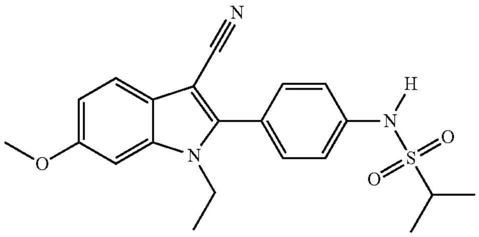
-continued
94
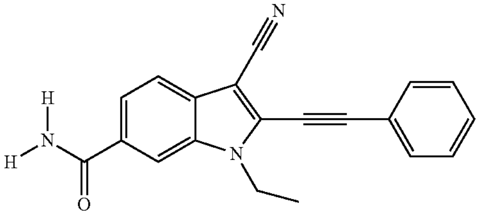
95
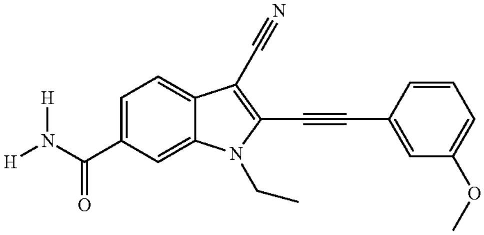
96
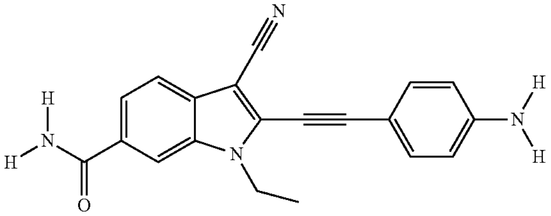
119
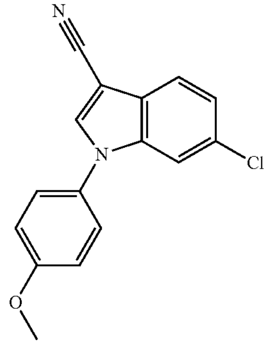
130
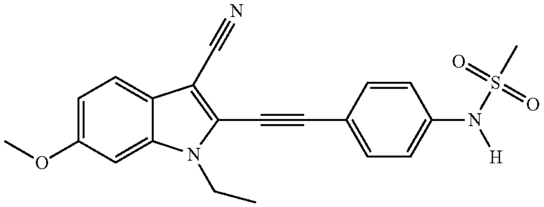
131
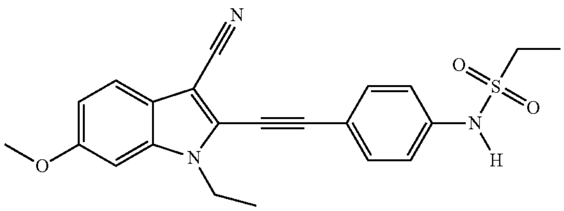

-continued
132
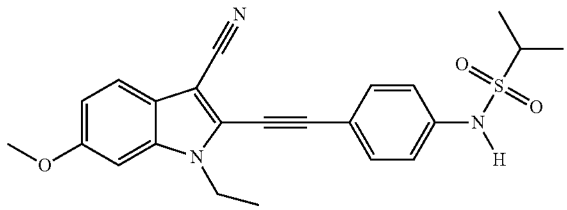
134
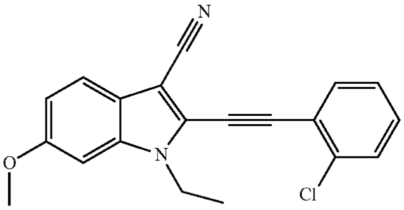
138
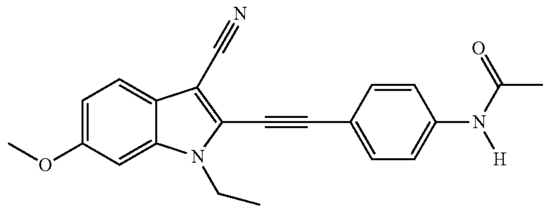
139
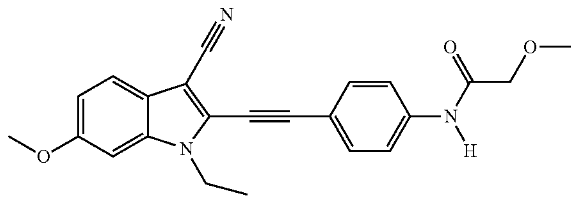
144
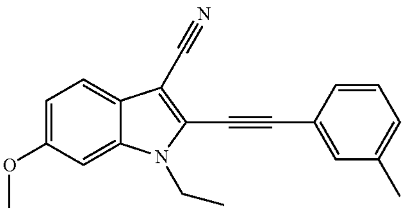
145
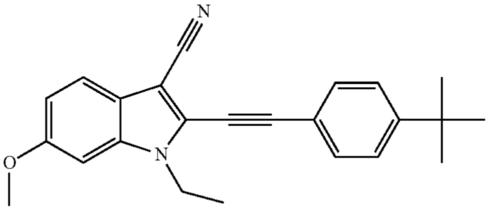
153
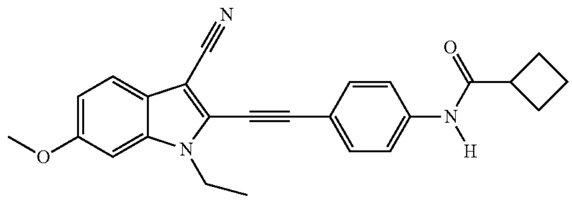
-continued
157
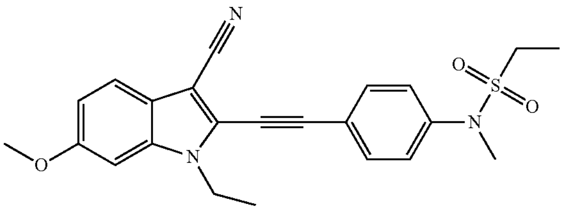
161
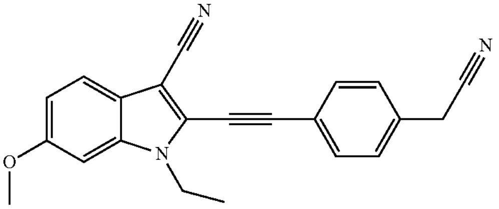
166
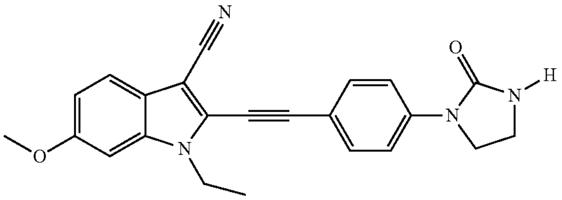
169
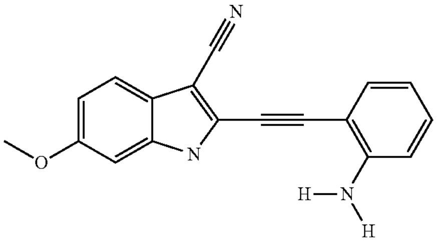
172
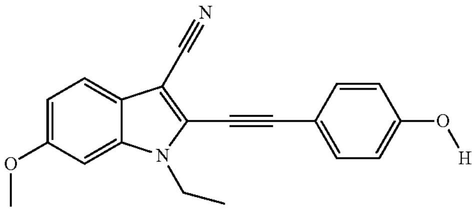
173
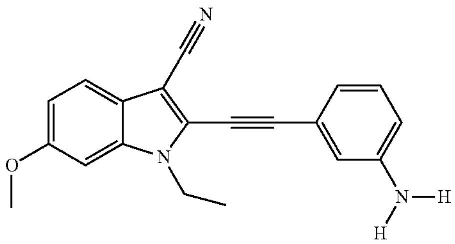
175
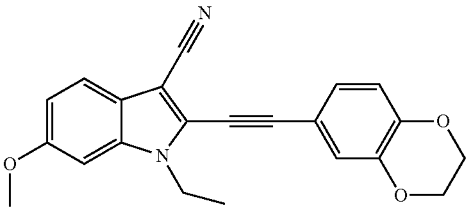

-continued
176
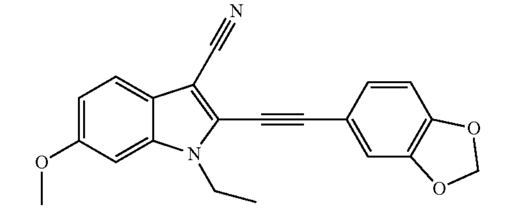
180
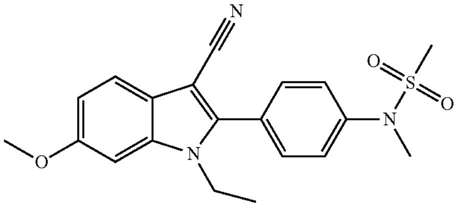
181
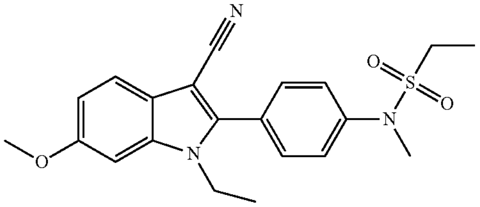
182
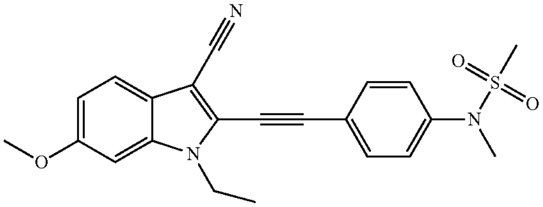
185
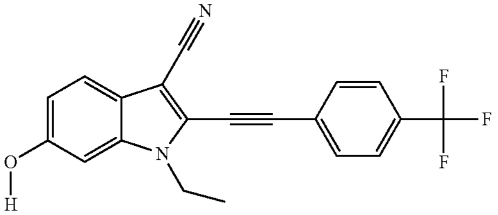
188
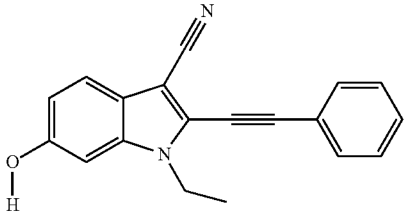
196
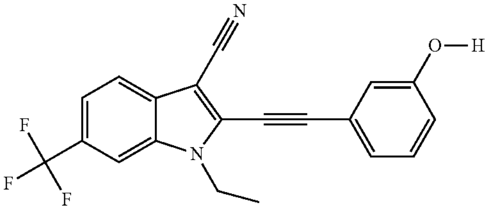
-continued
200
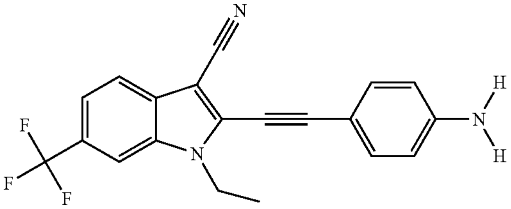
201
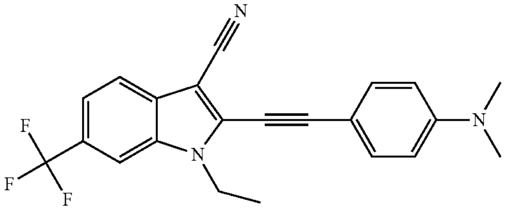
204
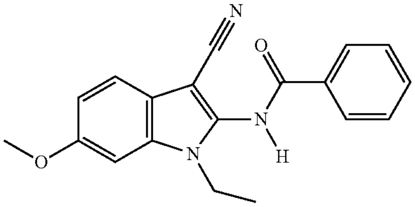
205
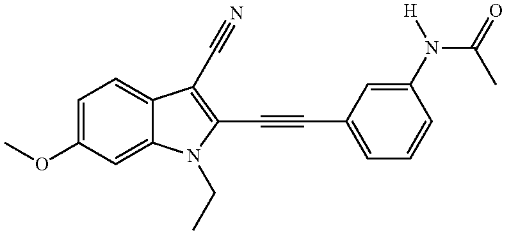
206
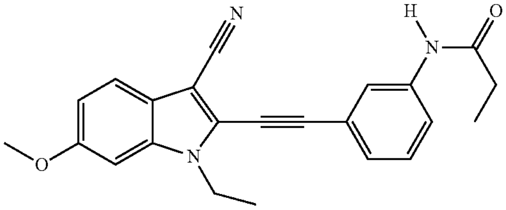
207
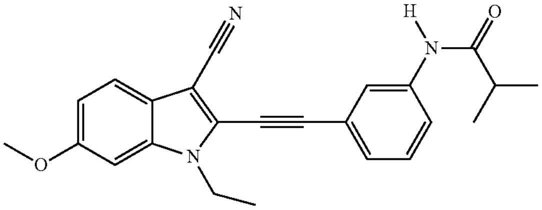
211
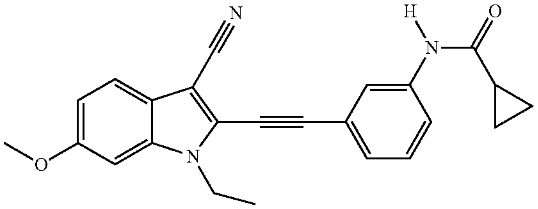

-continued
213
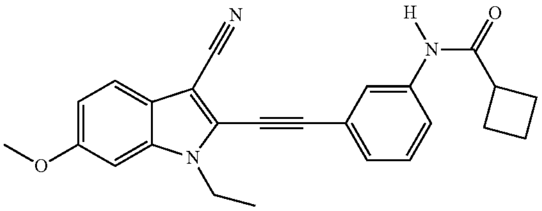
214
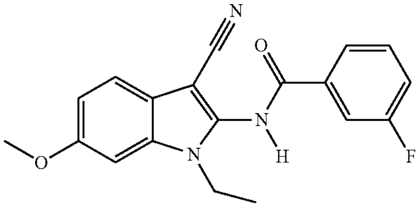
216
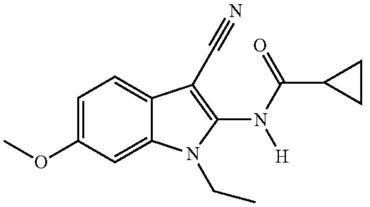
217
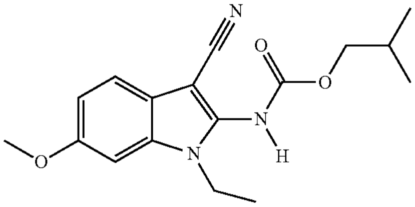
218
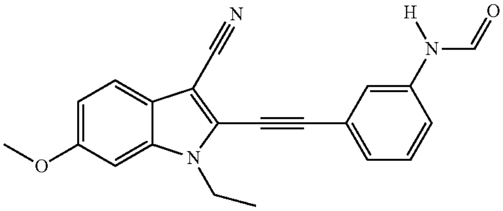
219
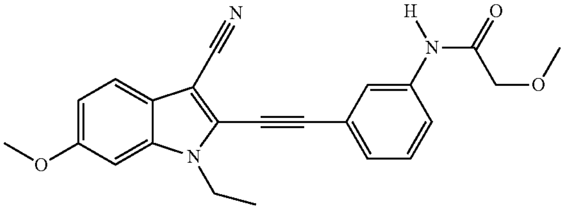
-continued
220
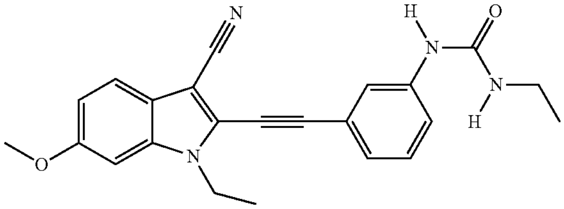
221
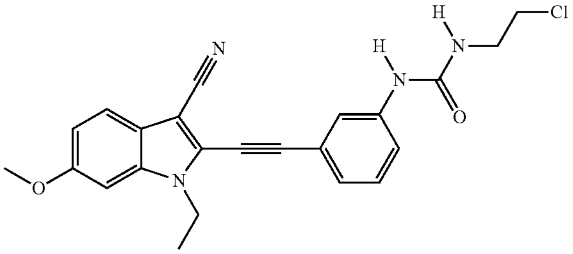
223
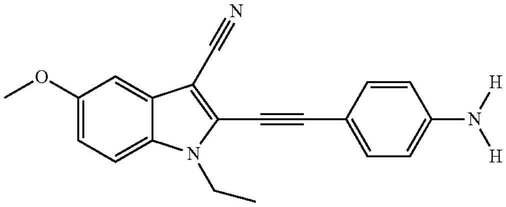
233
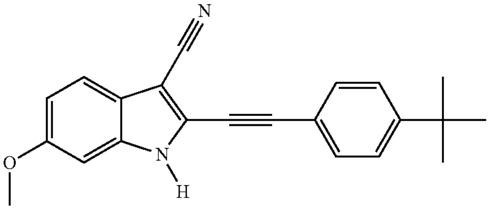
243
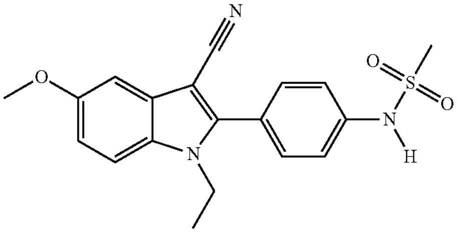
251
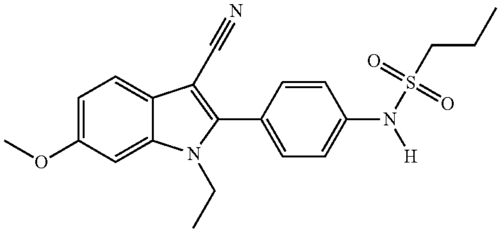

-continued
252
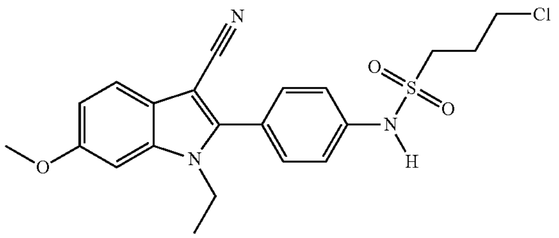
264
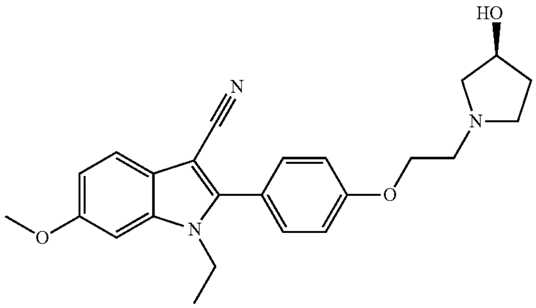
266
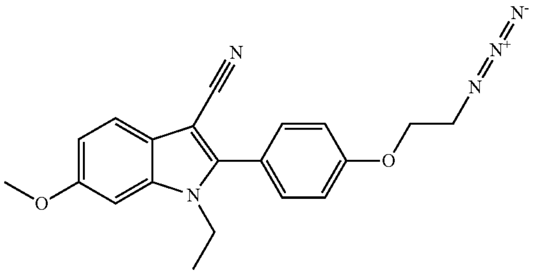
269
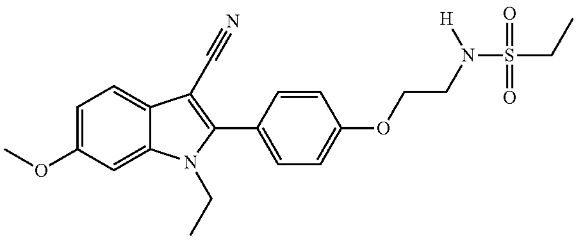
294
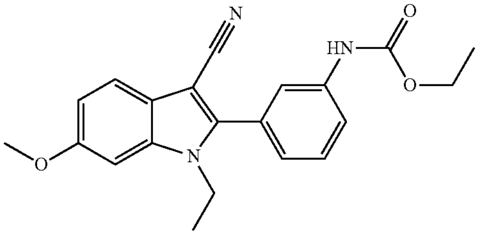
-continued
295
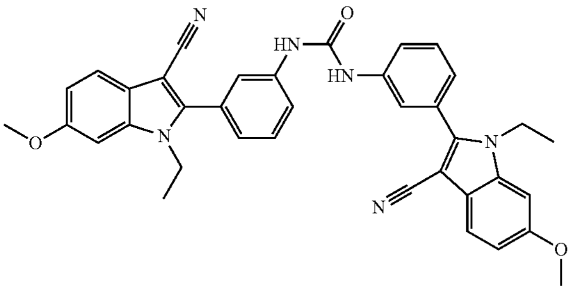
296
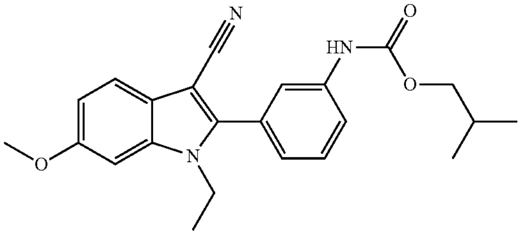
297
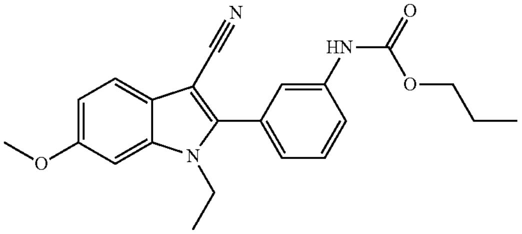
298
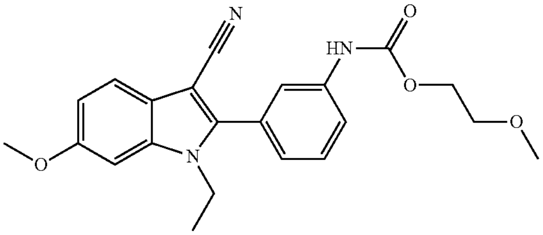
299
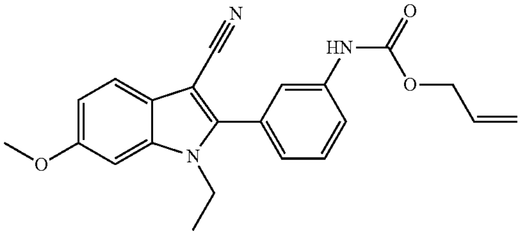
301
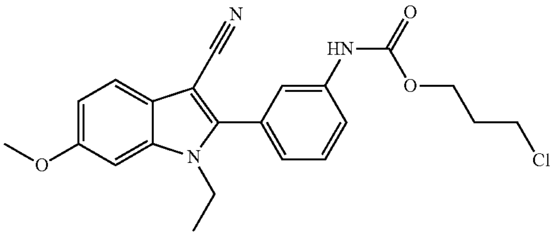

-continued
302
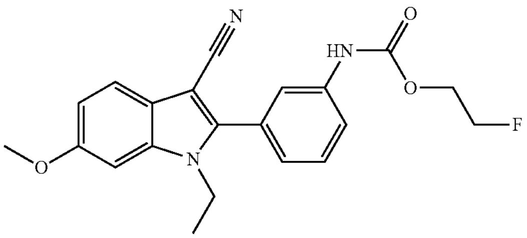
304
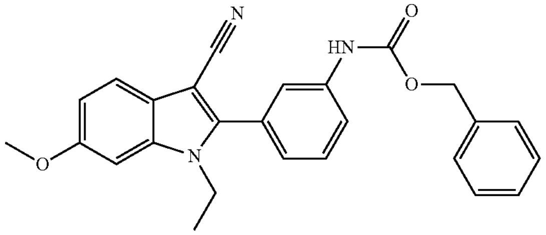
306
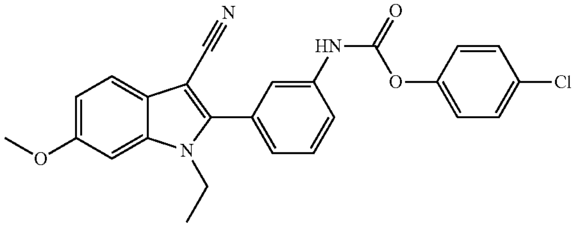
309
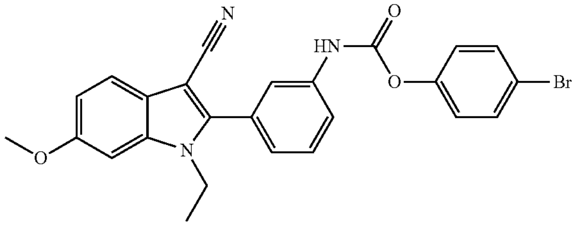
310
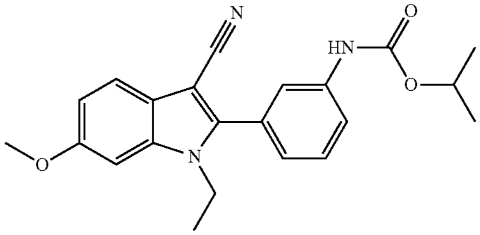
331
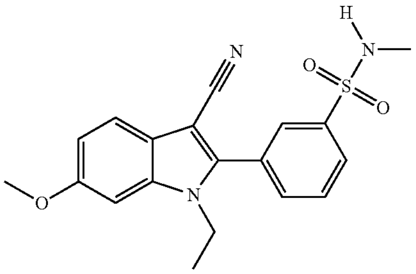
-continued
341
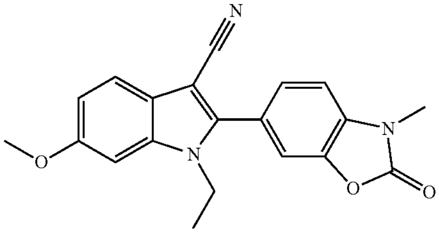
345
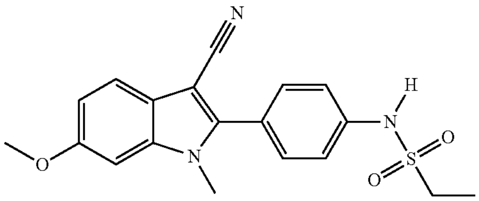
346
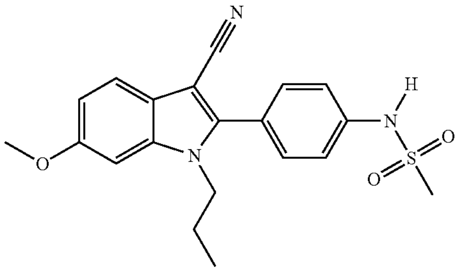
349
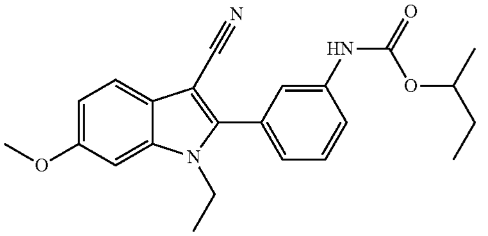
350
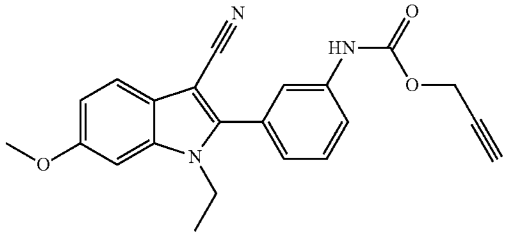
351
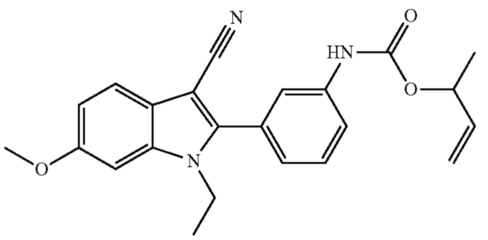

-continued
353
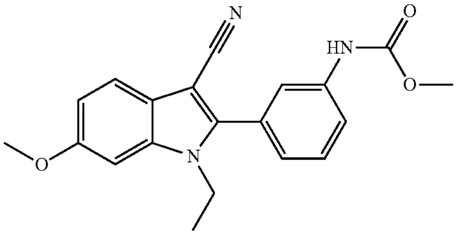
365
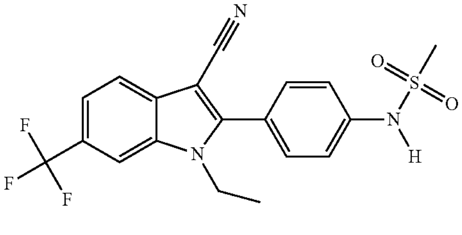
366
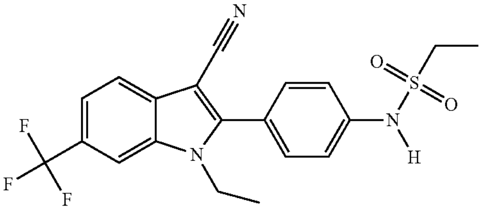
367
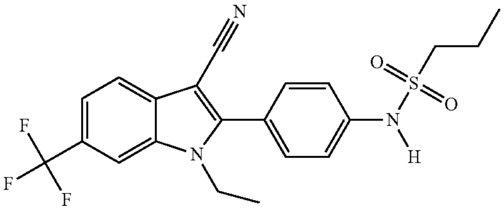
369
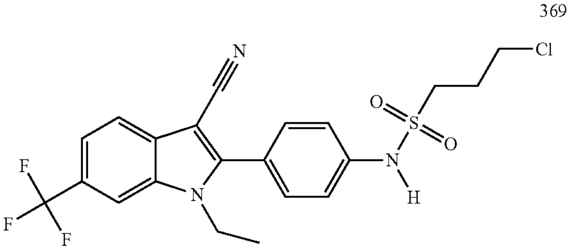
394
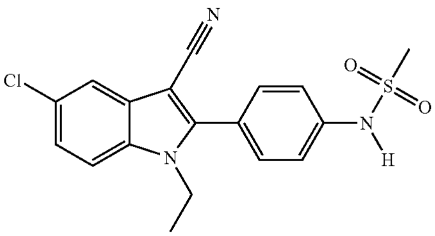
-continued
396
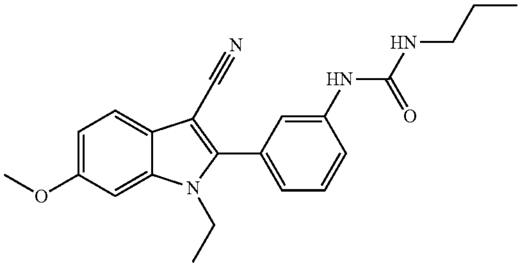
397
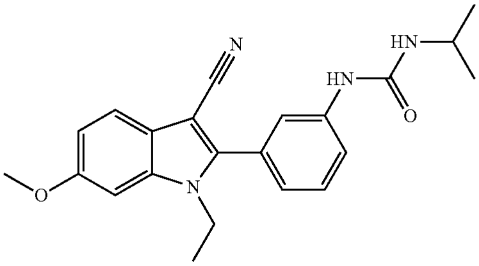
398
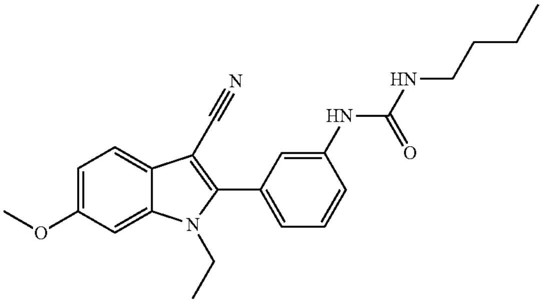
399
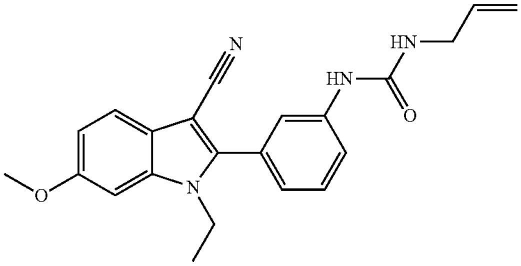
401
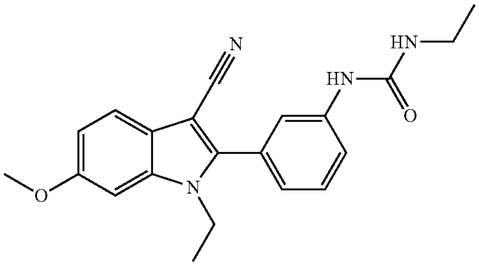

-continued
403
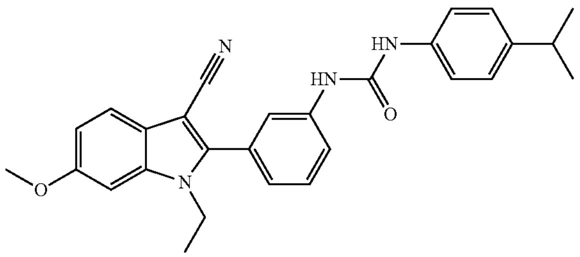
405
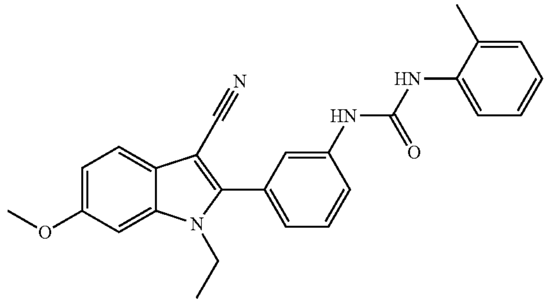
406
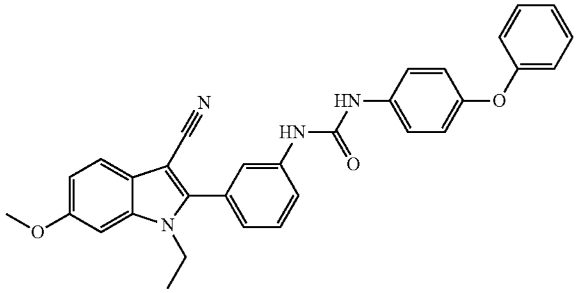
408
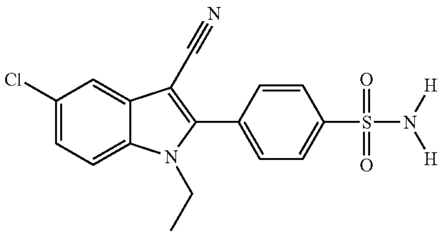
413
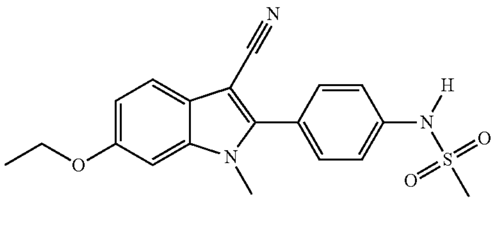
415
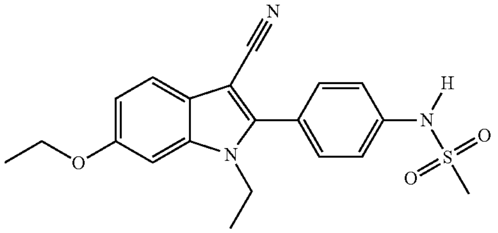
-continued
416
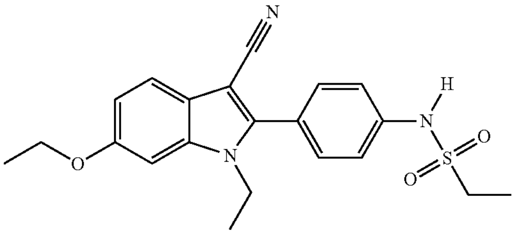
417
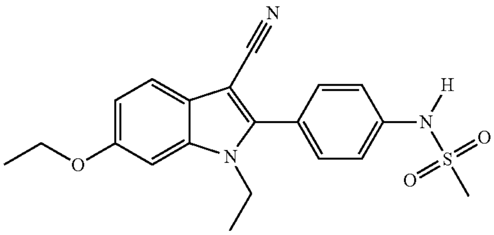
418
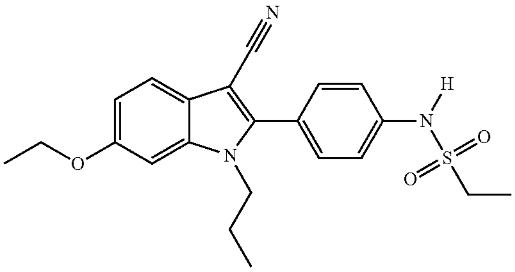
420
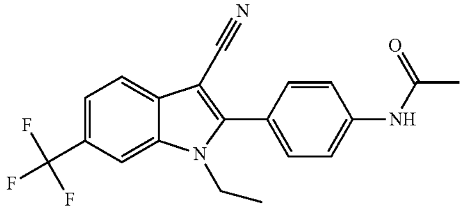
422
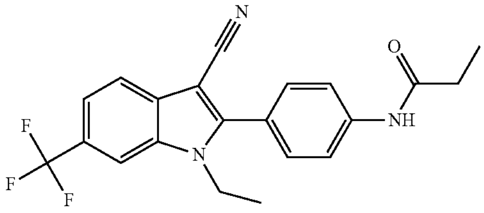
430
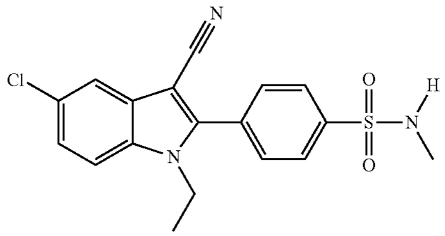

-continued
440
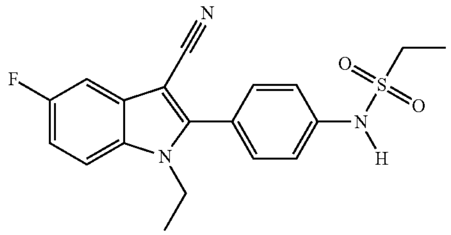
441
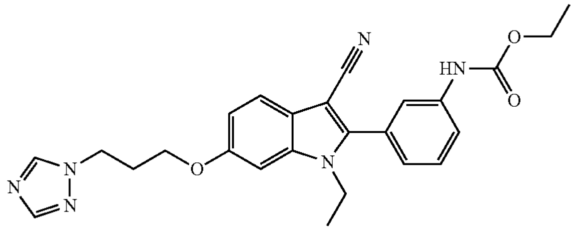
445
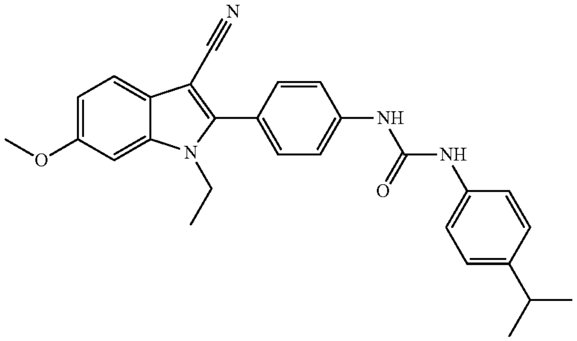
447
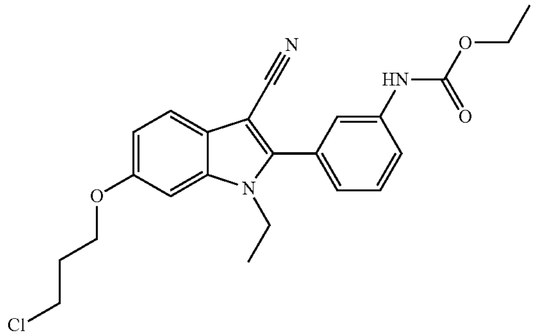
456
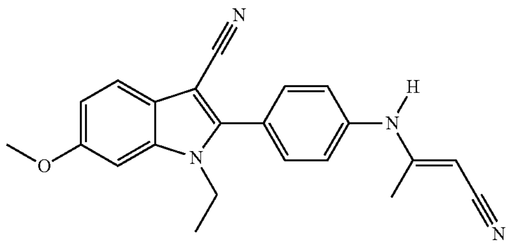
-continued
461
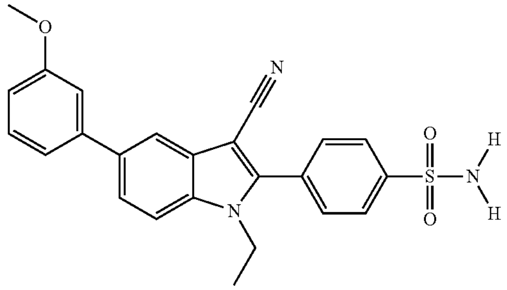
462
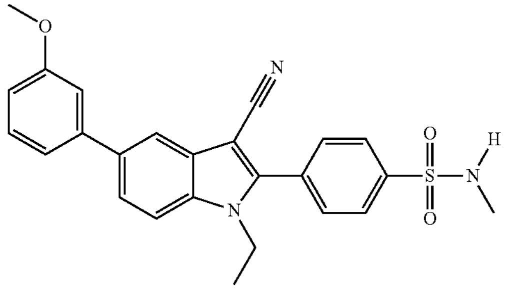
468
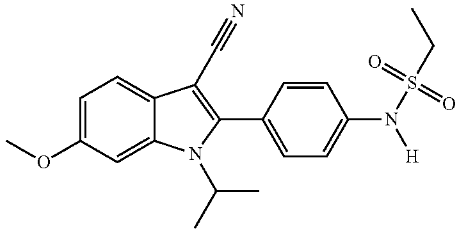
469
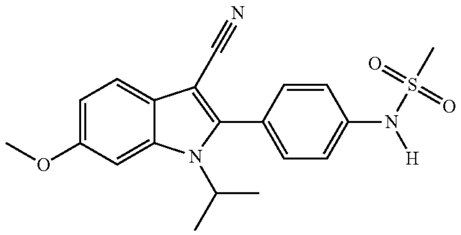
470
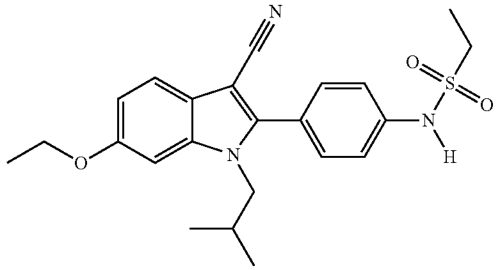
471
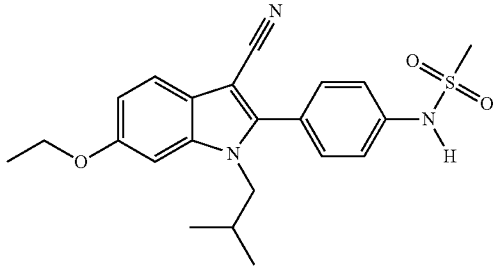

-continued
472
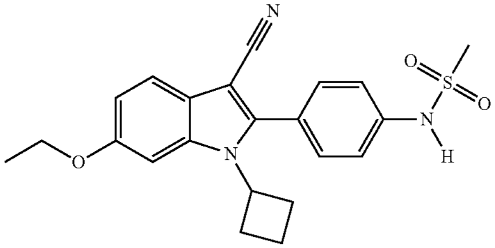
473
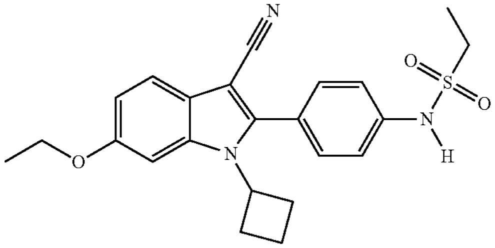
475
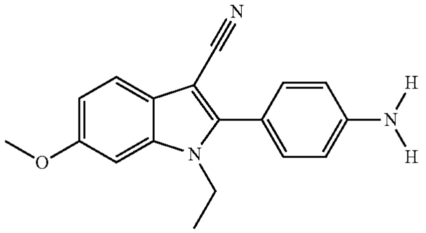
477
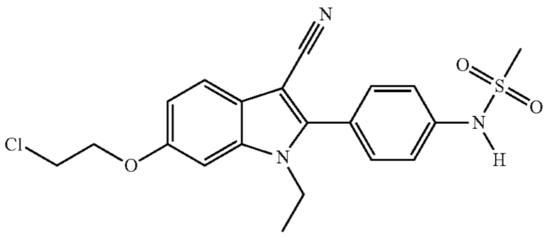
478
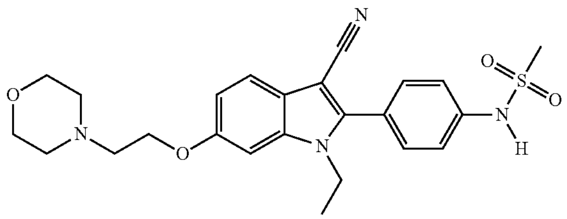
480
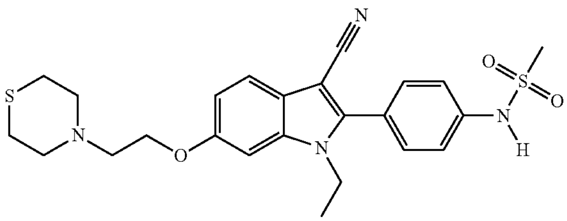
-continued
487
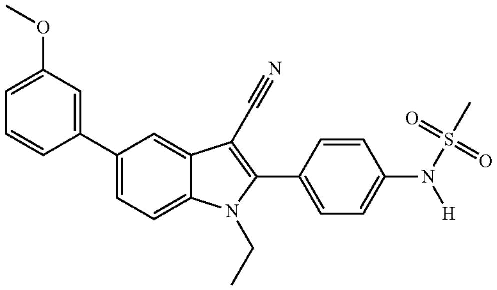
488
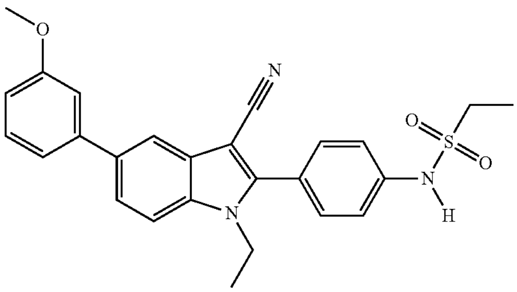
490
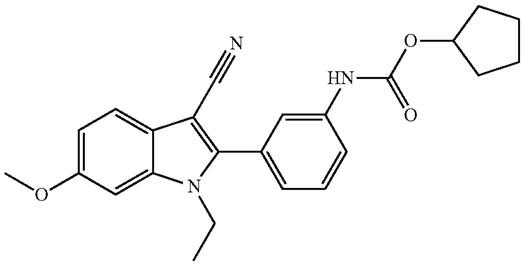
492
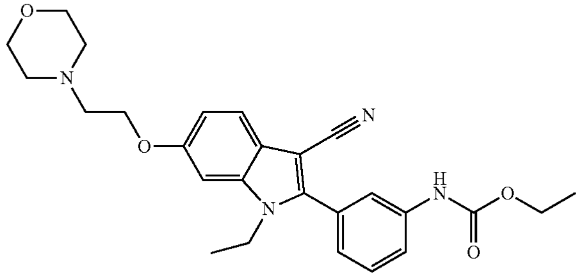
493
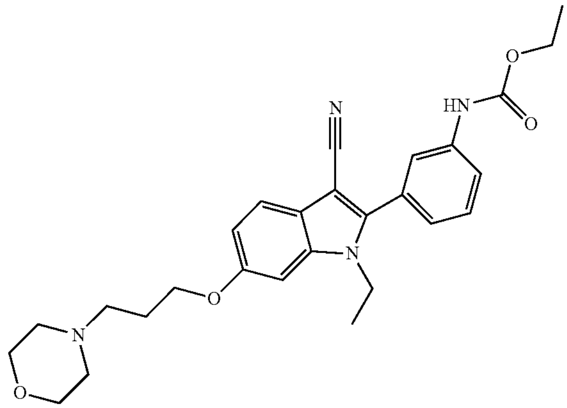

-continued
495
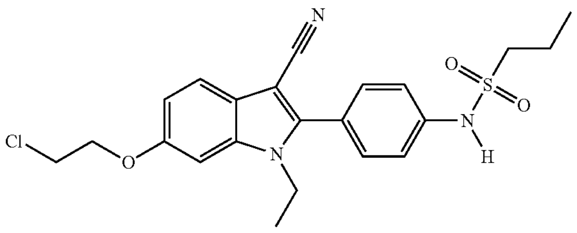
498
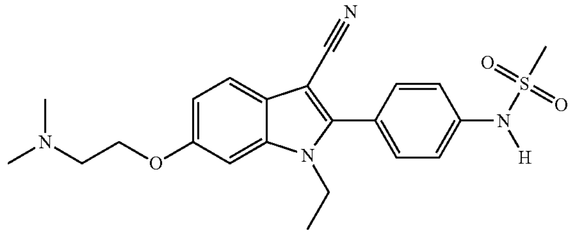
499
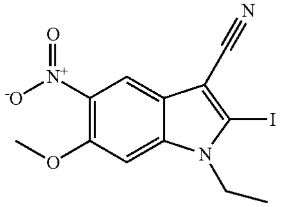
516
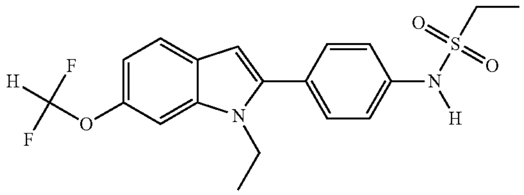
518
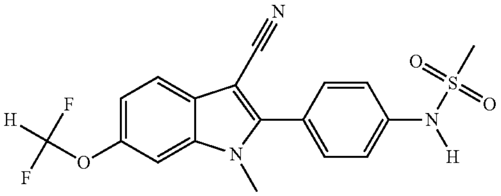
519
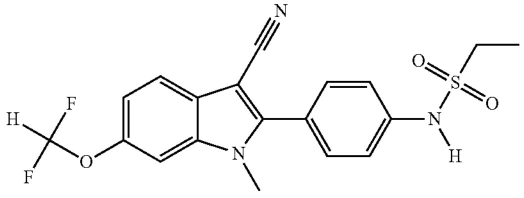
520
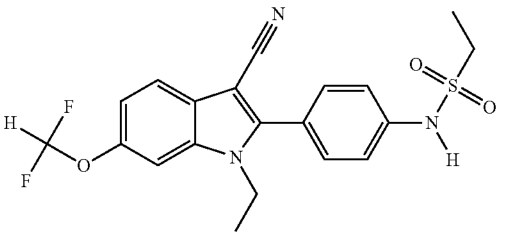
-continued
521
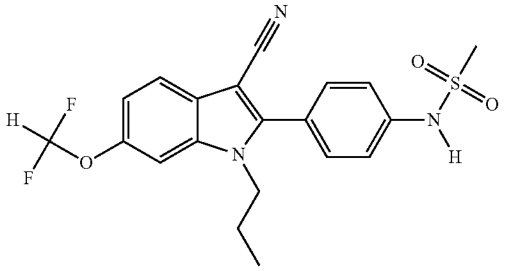
522
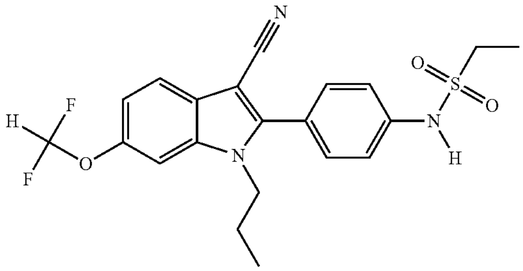
523
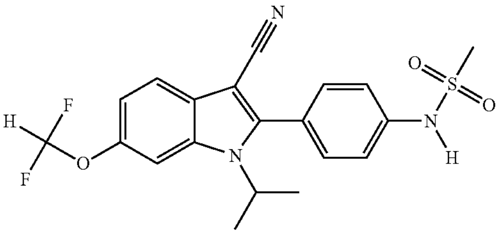
524
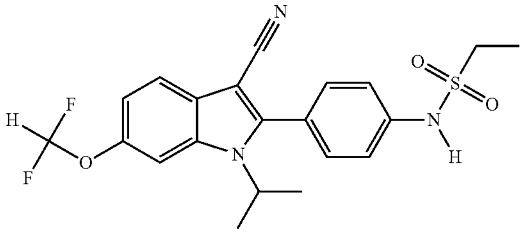
525
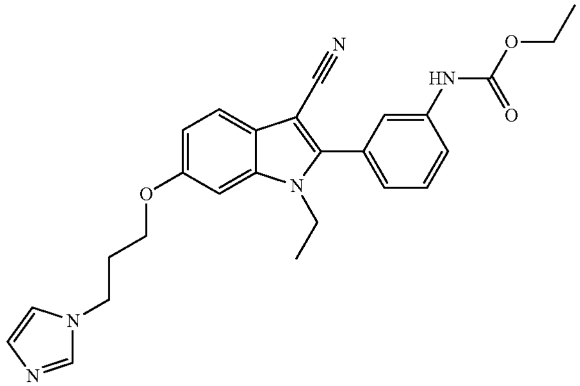

-continued
526
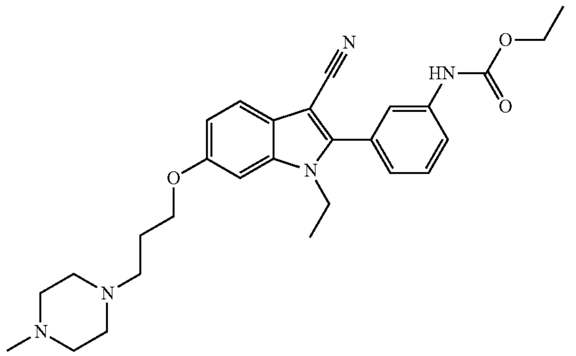
528
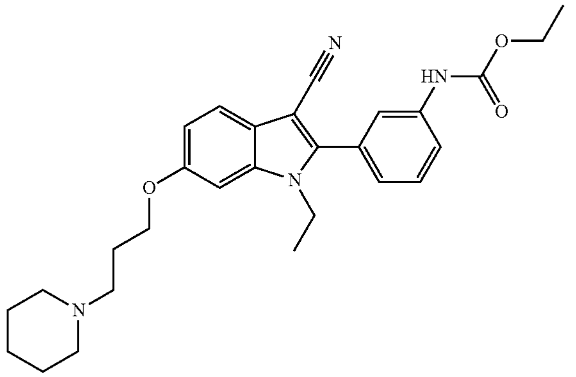
530
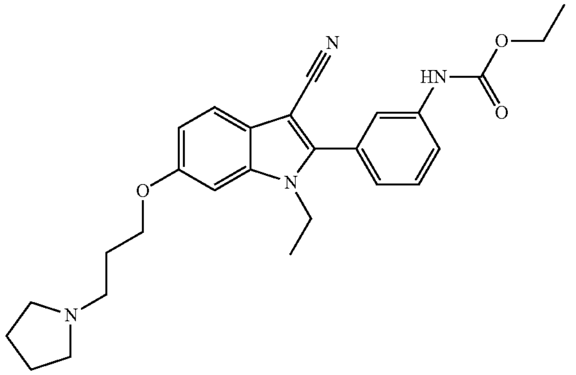
531
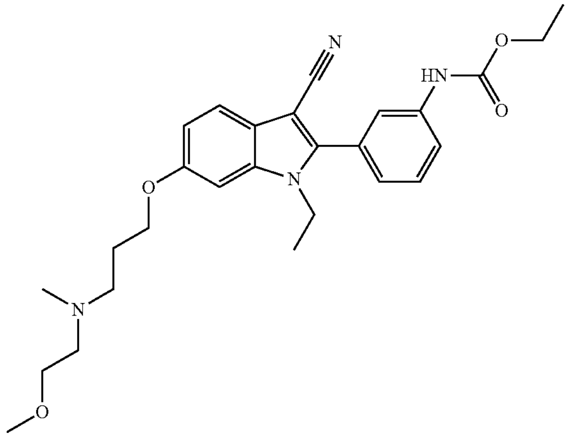
-continued
532
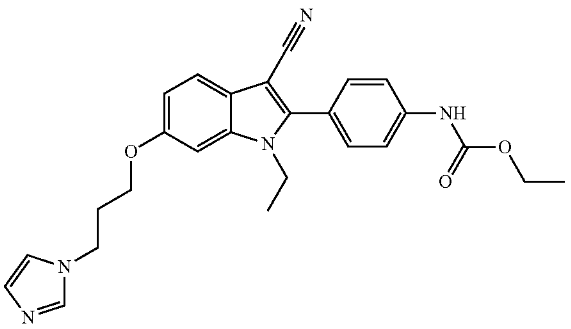
533
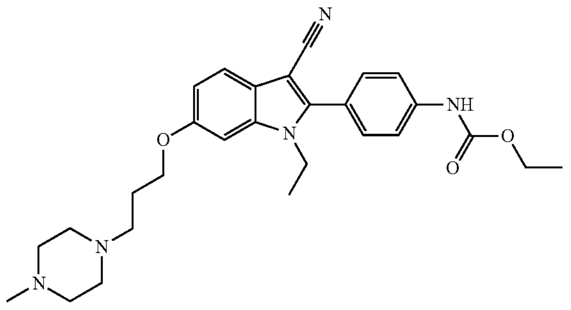
534
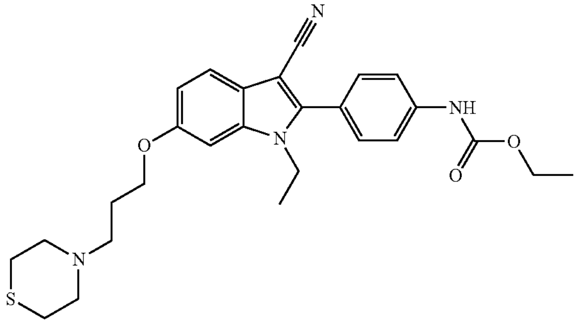
535
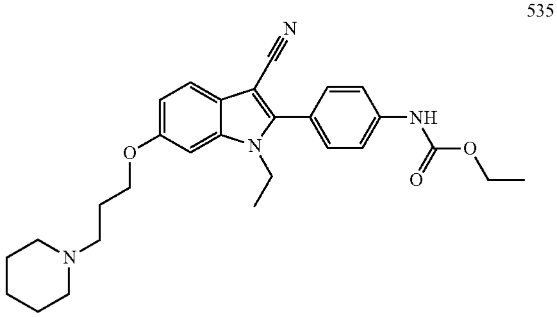
536
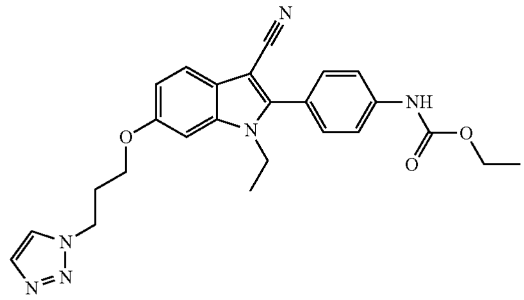

-continued
537
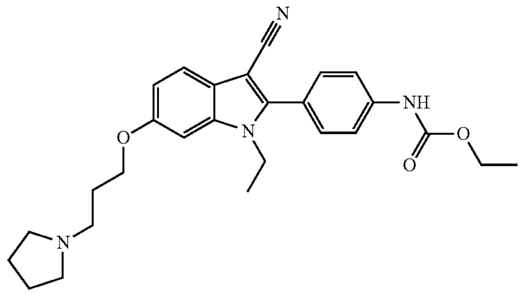
538
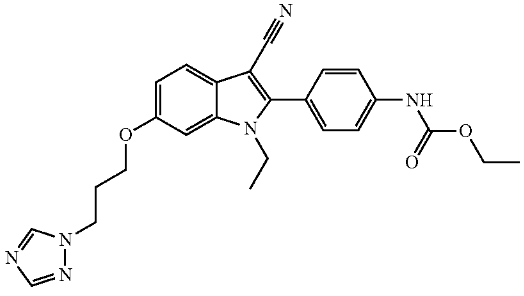
539
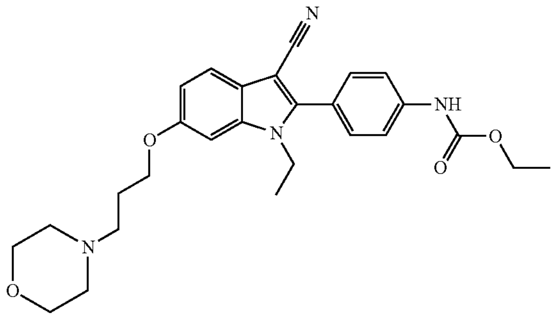
542
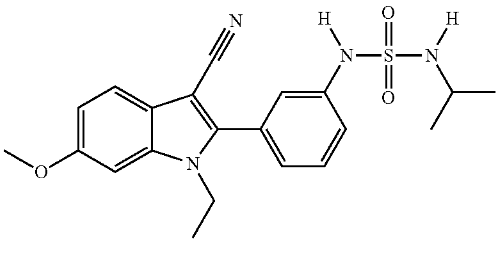
543
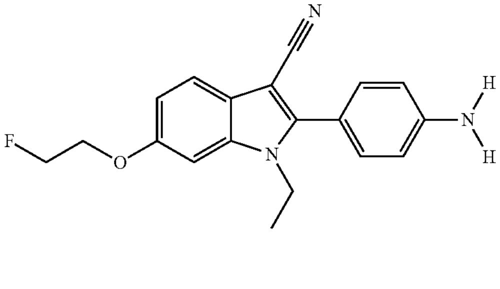
-continued
544
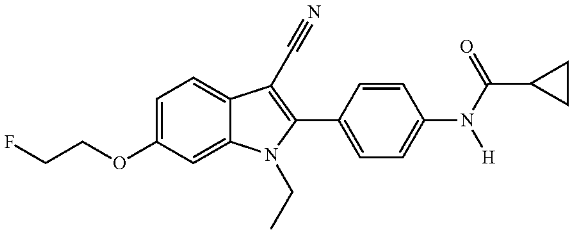
545
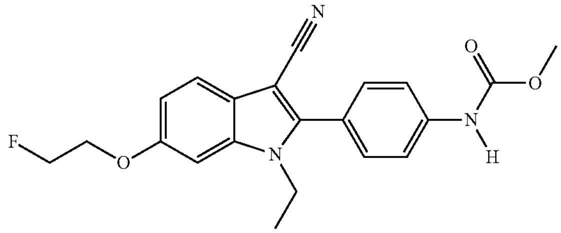
546
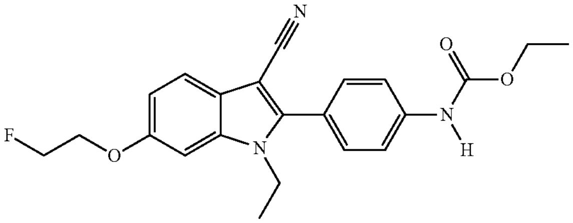
547
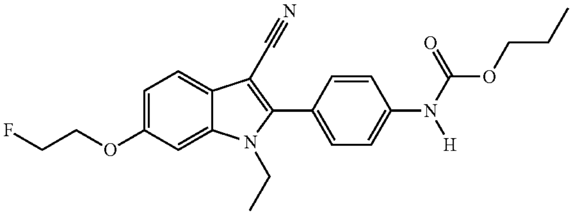
548
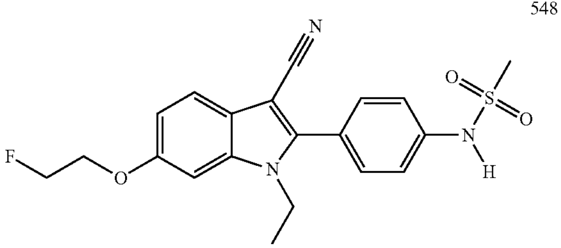
549
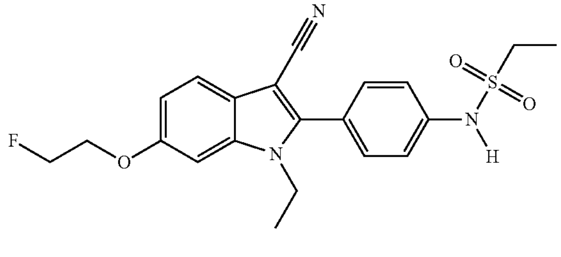

-continued
550
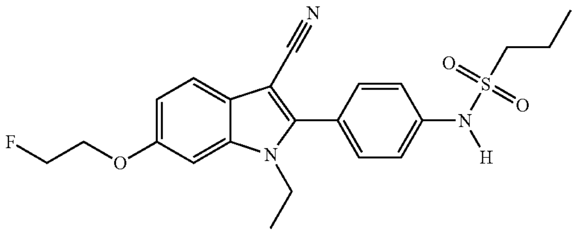
551
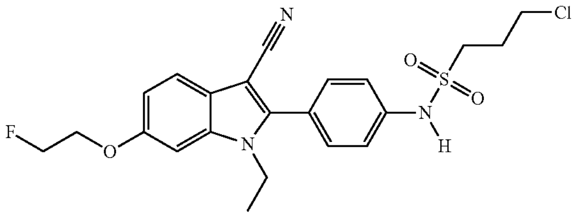
552
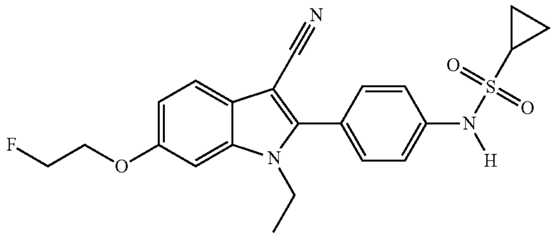
557
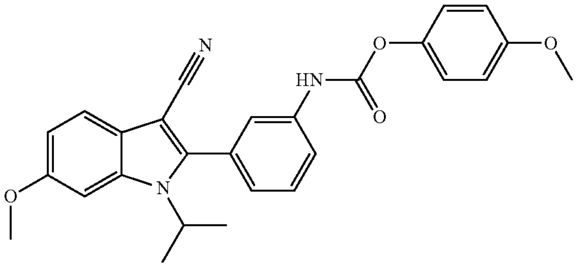
562
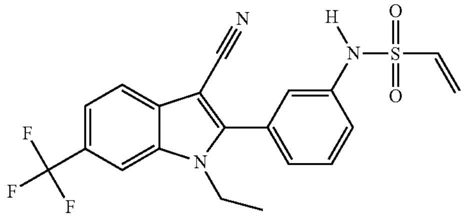
563
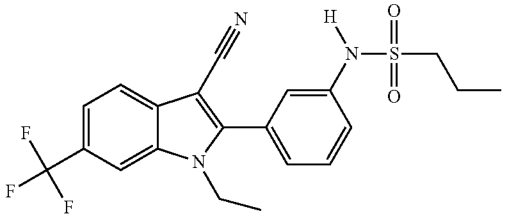
-continued
567
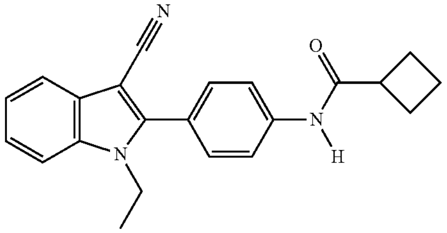
570
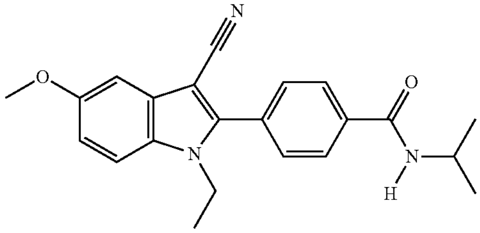
580
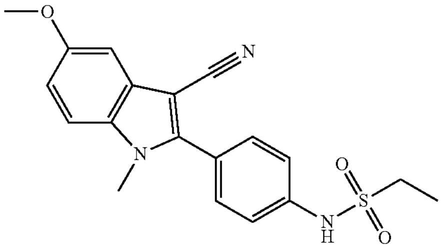
581
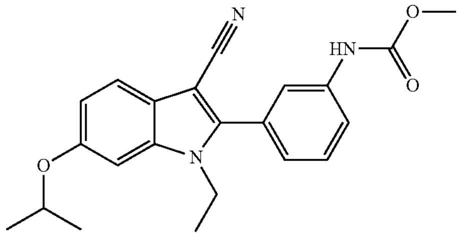
582
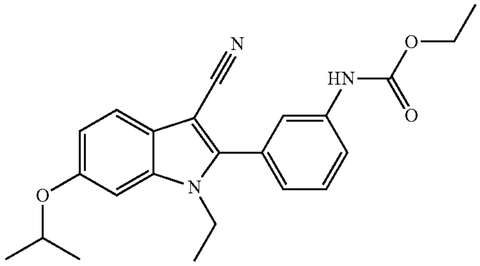
585
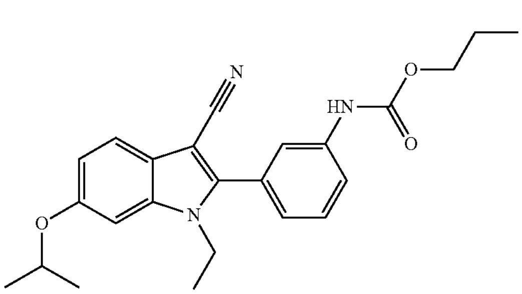

-continued
596
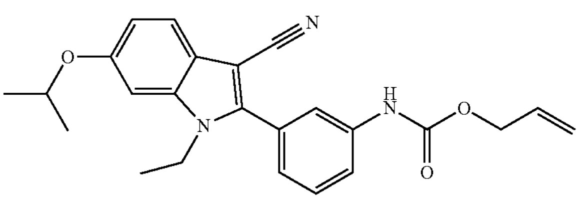
601
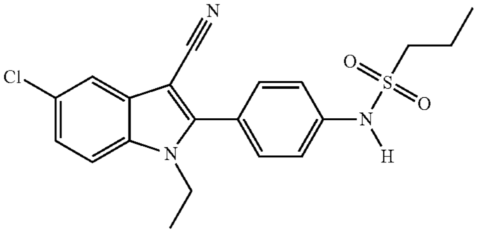
602
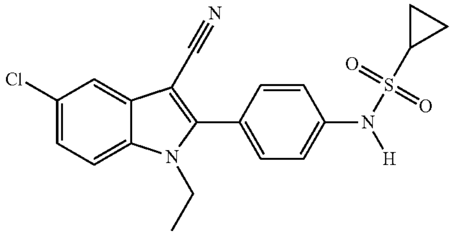
606
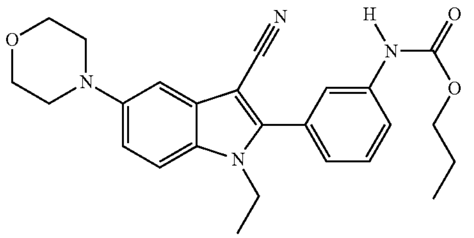
607
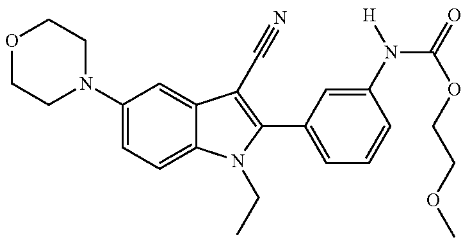
611
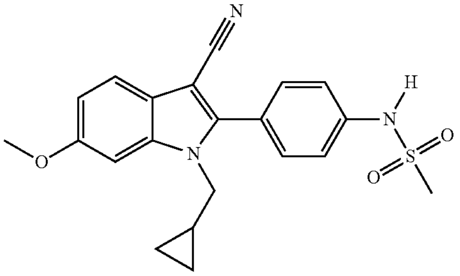
-continued
612
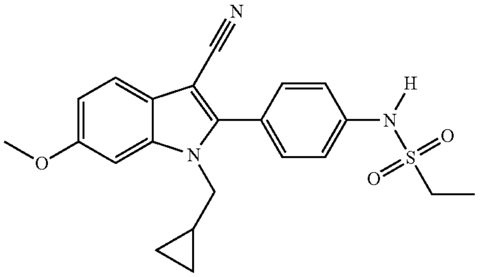
613
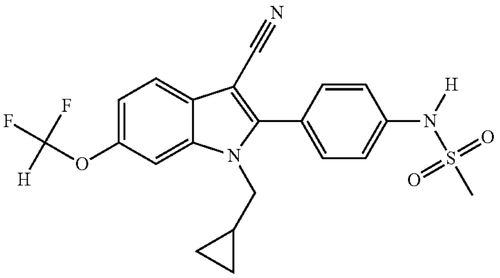
614
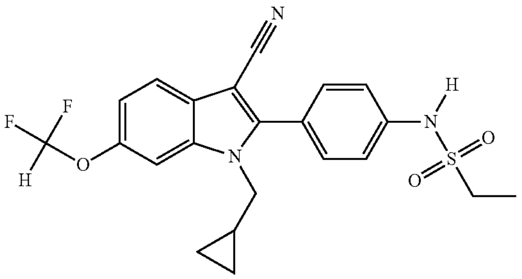
616
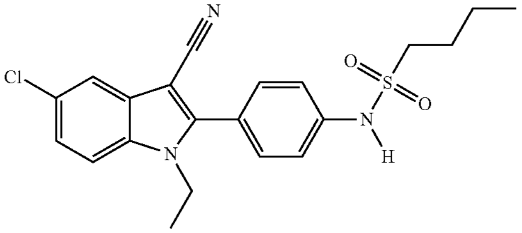
617
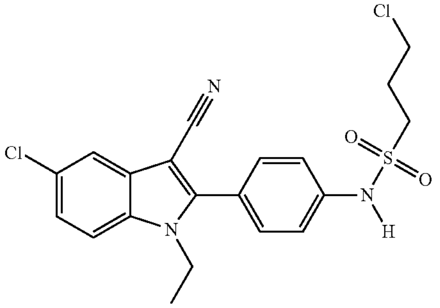

-continued
618
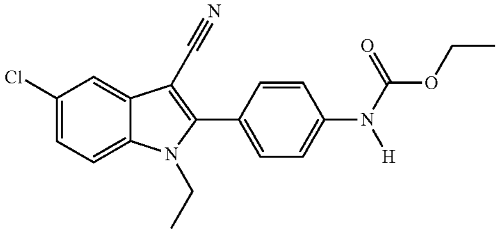
619
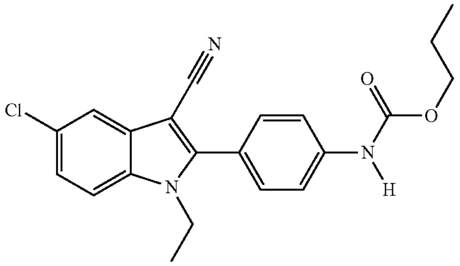
621
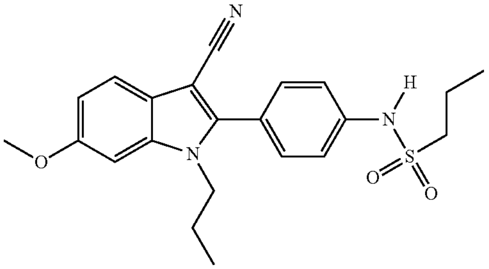
622
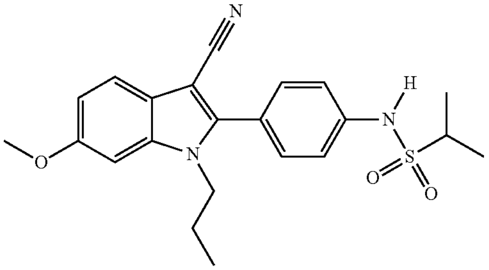
623
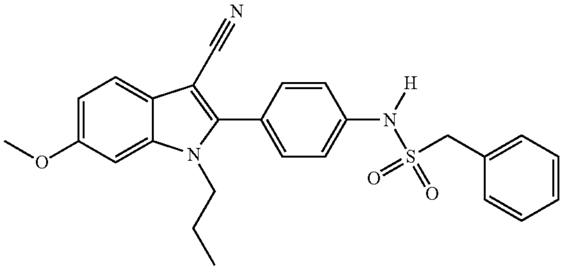
625
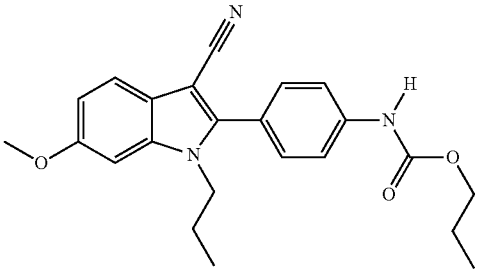
-continued
626
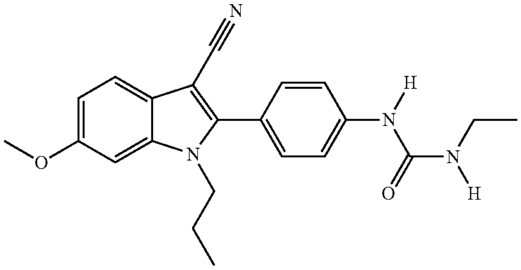
627
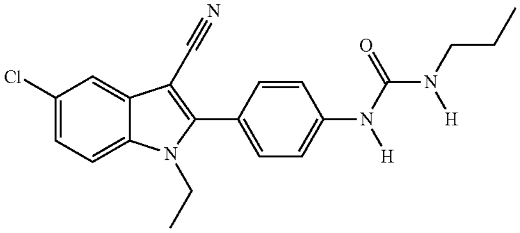
628
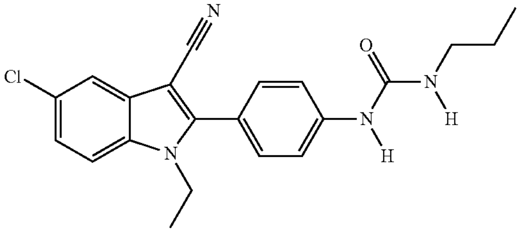
631
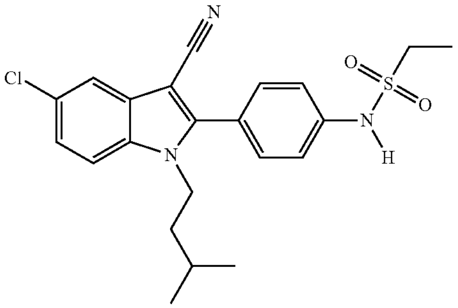
633
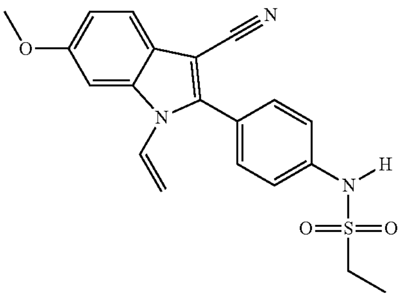

635
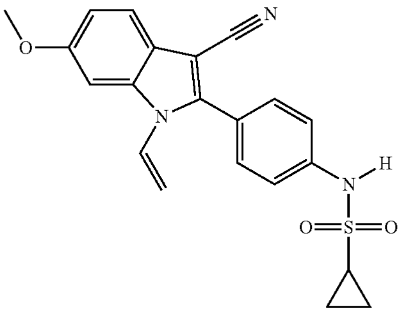
636
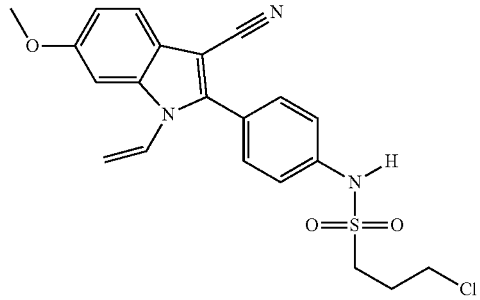
637
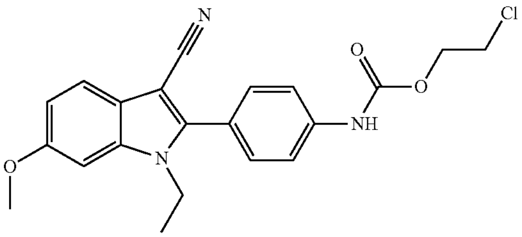
641
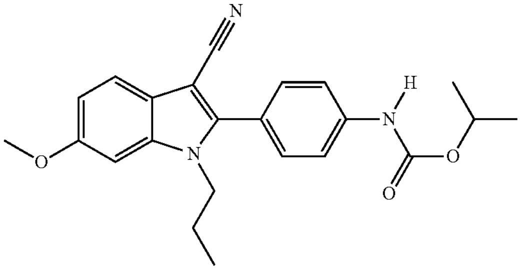
650
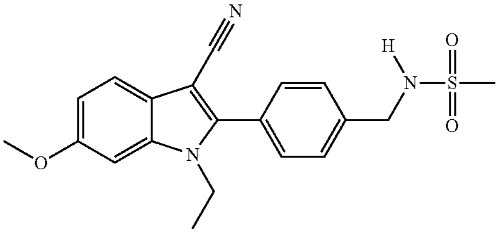
652
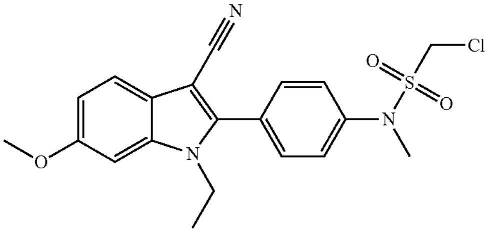
661
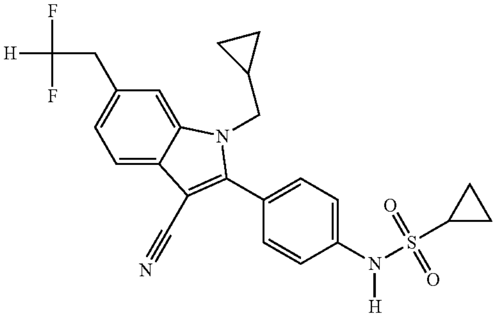
662
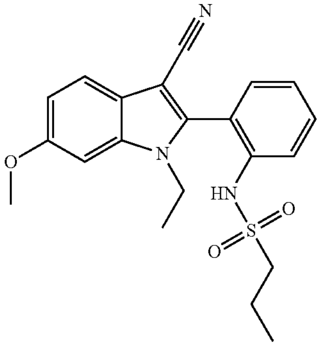
666
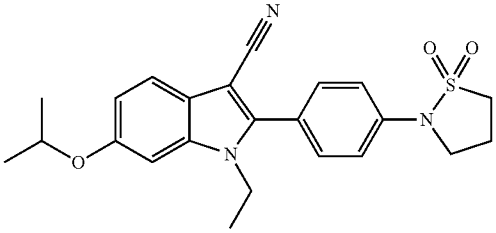
667
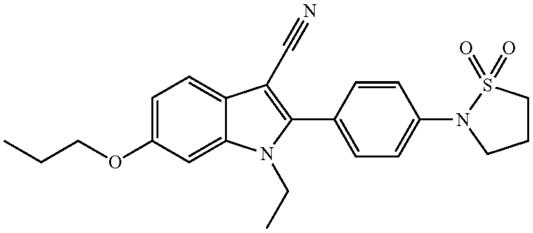
669
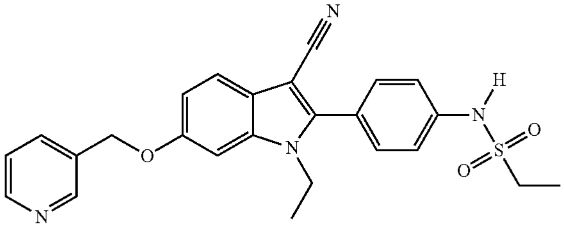

-continued
670
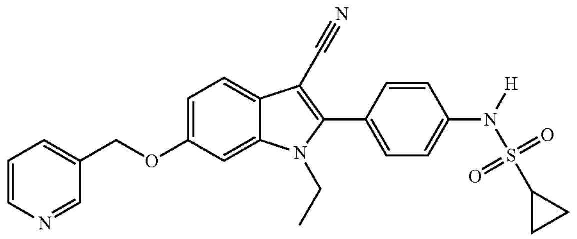
671
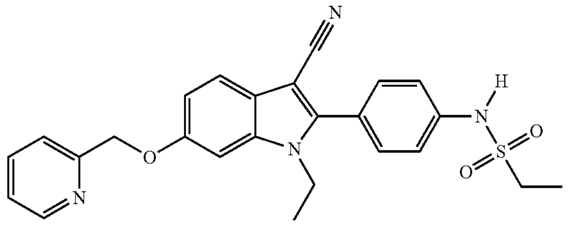
672
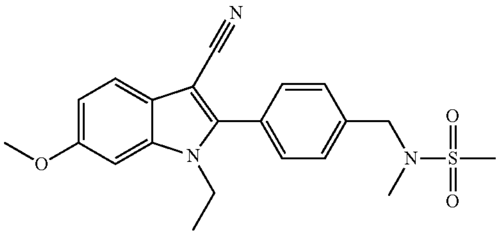
676
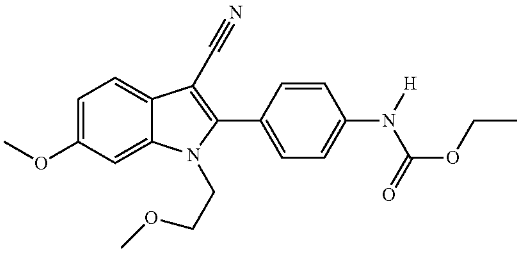
677
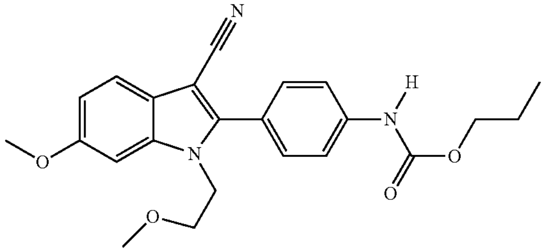
679
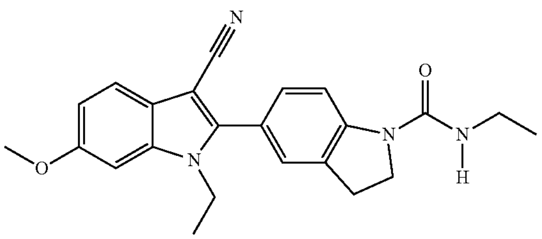
-continued
680
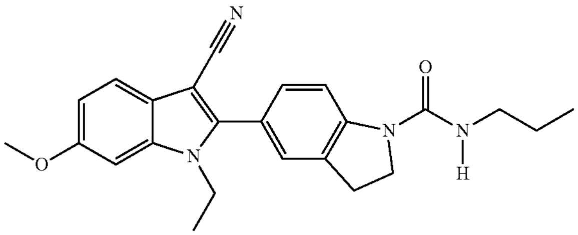
681
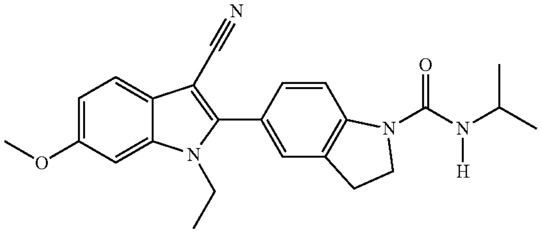
687
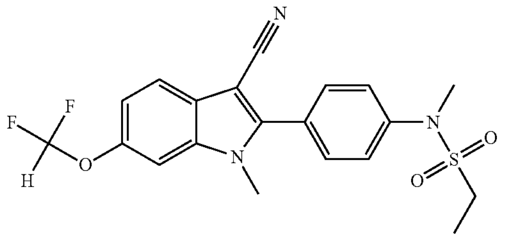
690
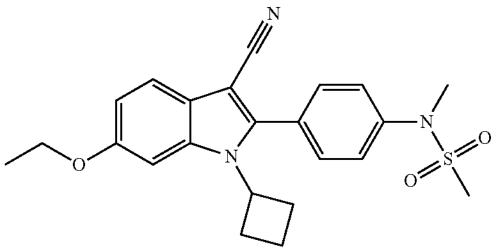
691
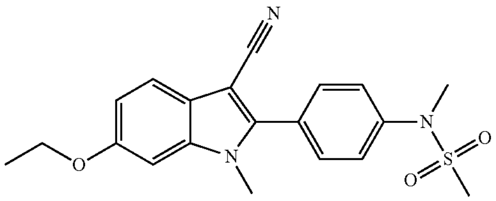
692
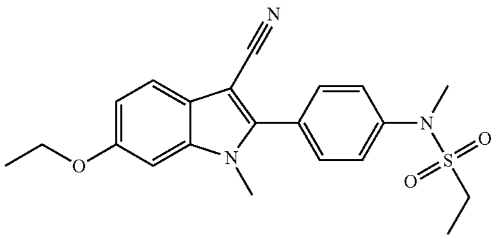

-continued
693
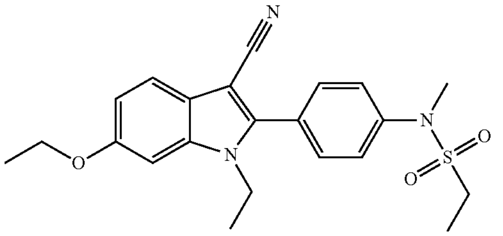
697
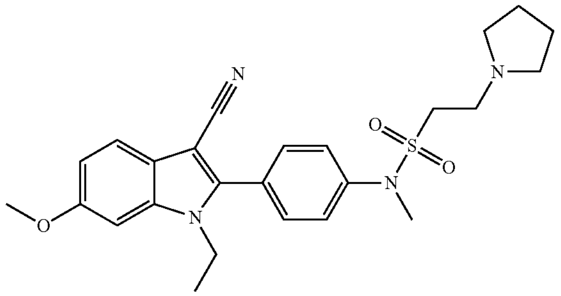
698
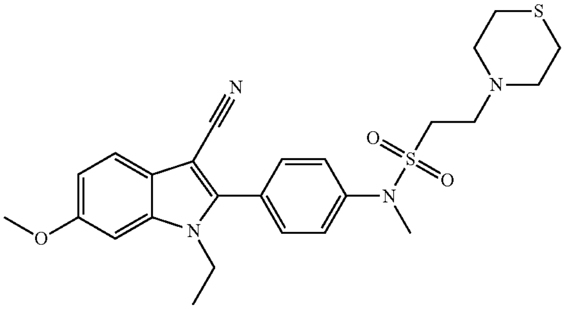
699
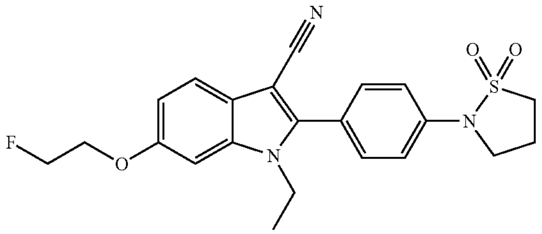
701
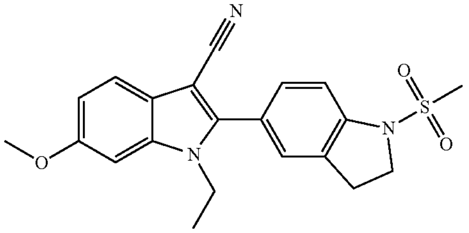
702
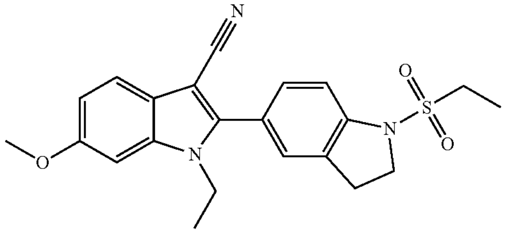
-continued
706
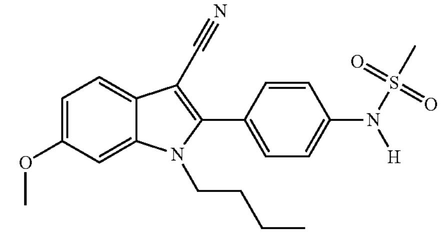
707
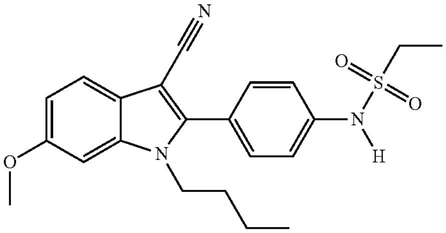
709
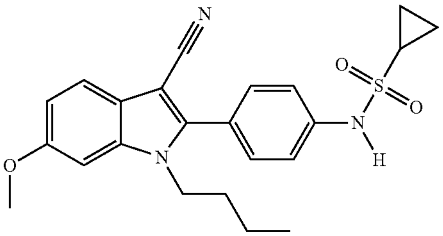
713
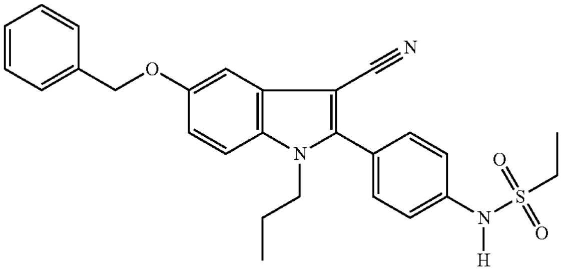
715
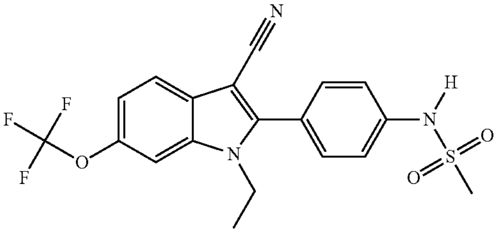
716
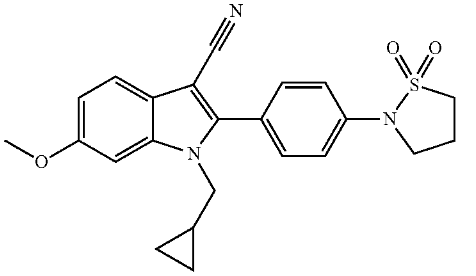

-continued
717
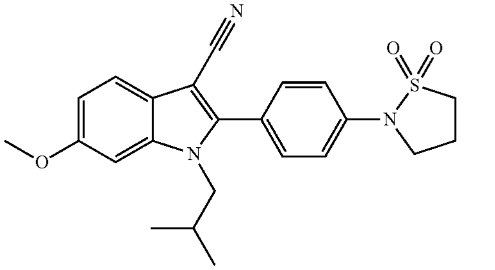
720
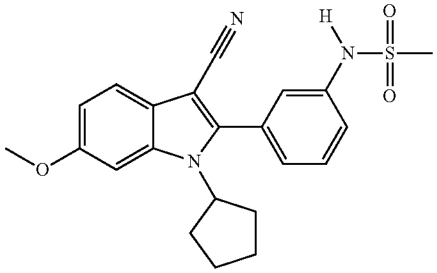
723
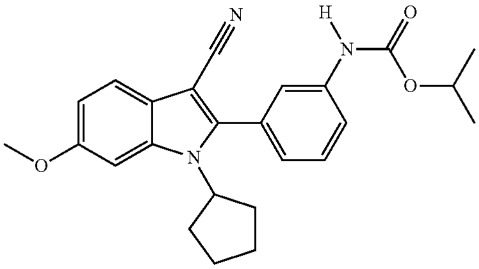
724
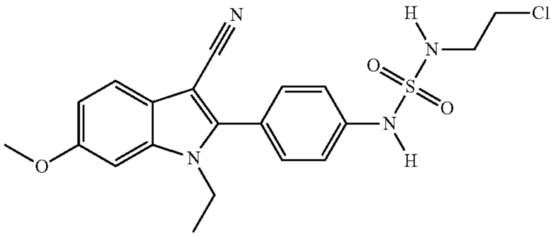
725
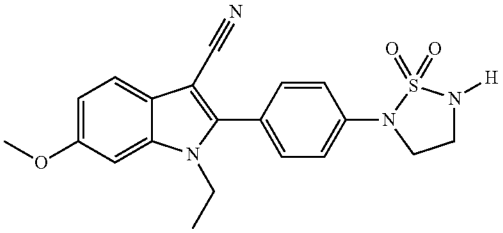
726
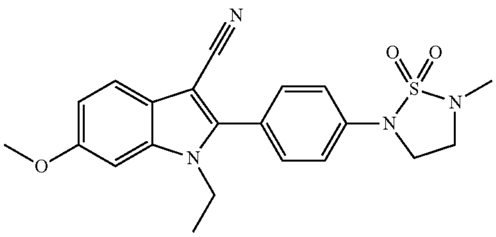
-continued
727
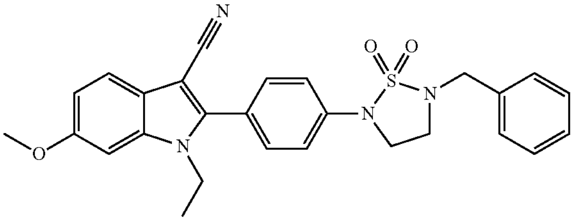
728
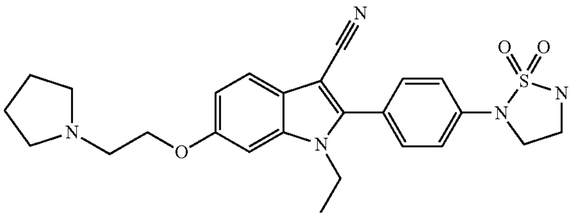
730
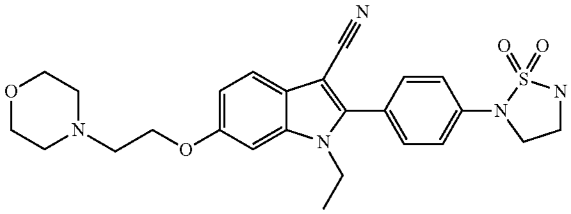
731
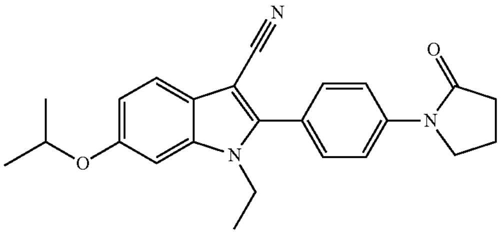
732
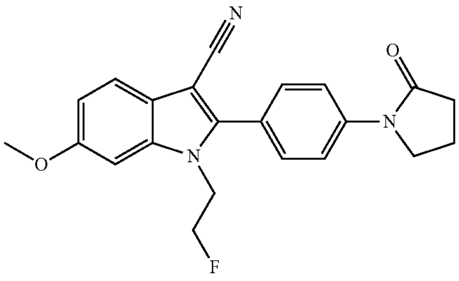
734
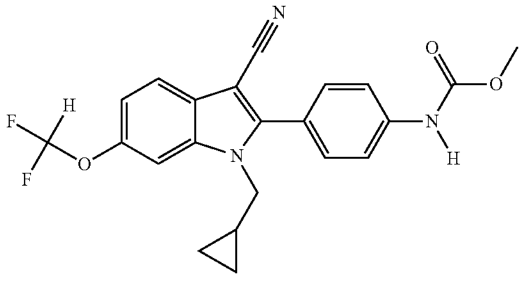

-continued
735
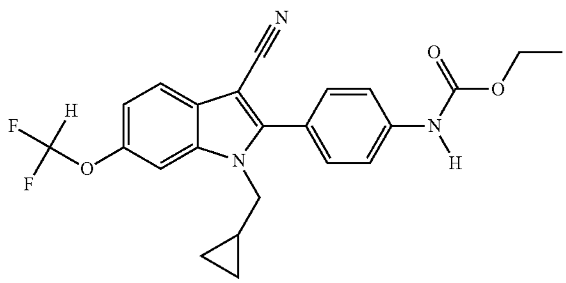
736
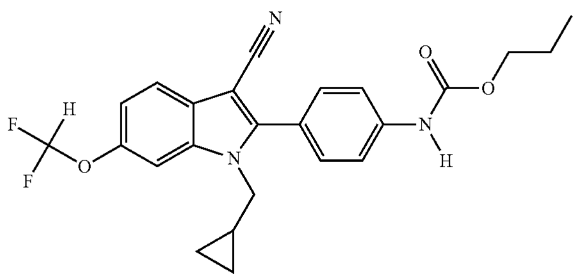
737
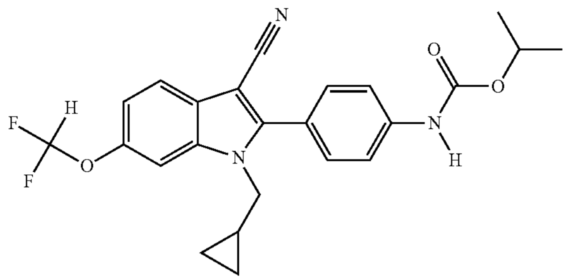
738
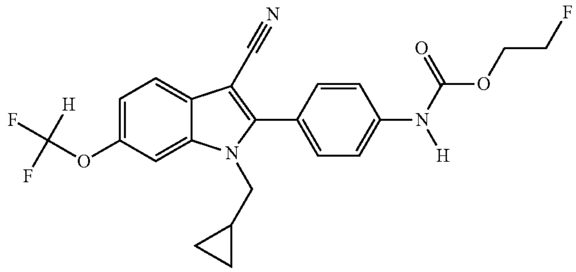
741
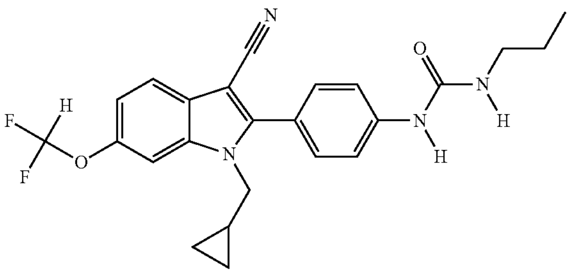
-continued
742
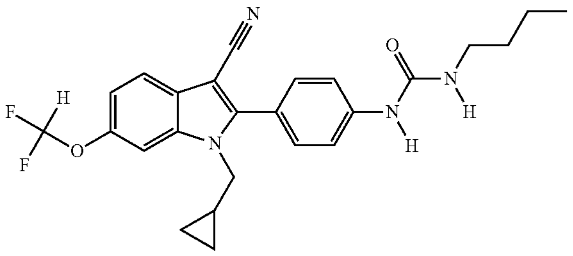
743
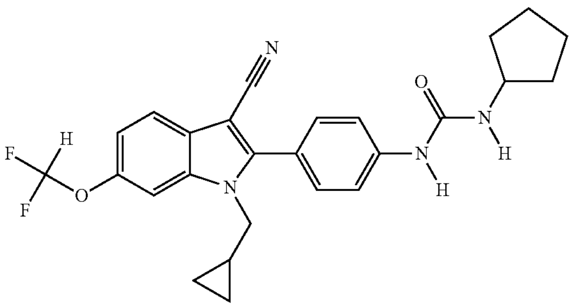
744
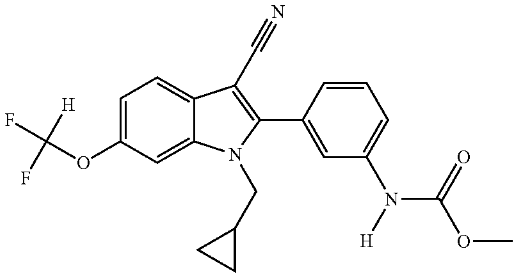
745
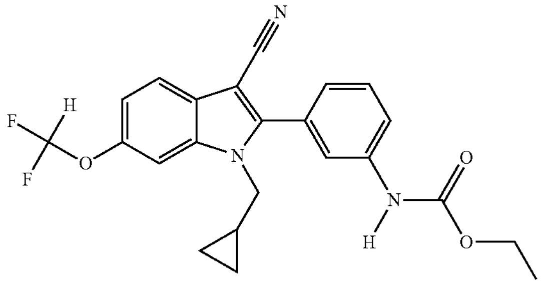
747
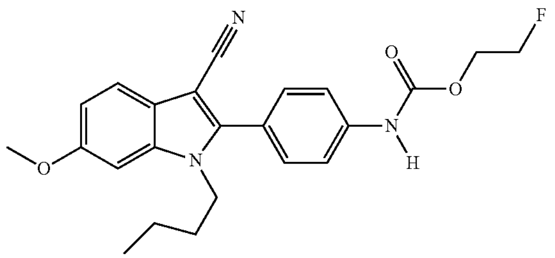

-continued
748
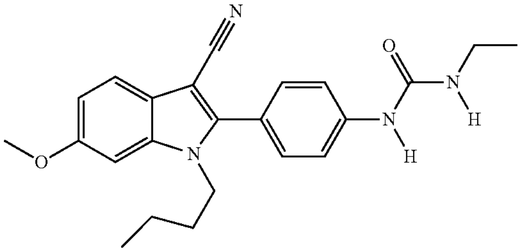
749
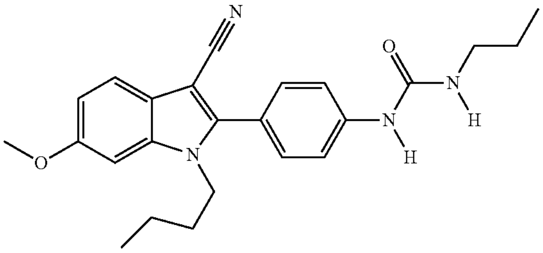
750
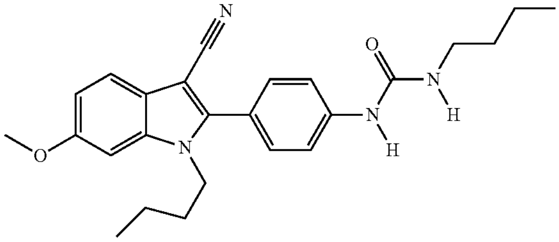
751
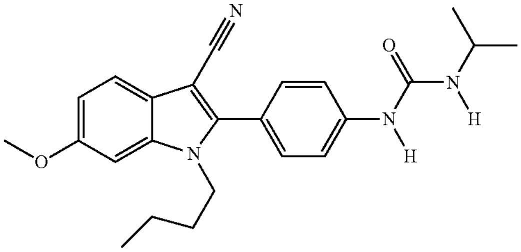
752
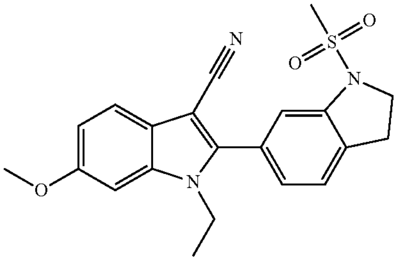
-continued
753
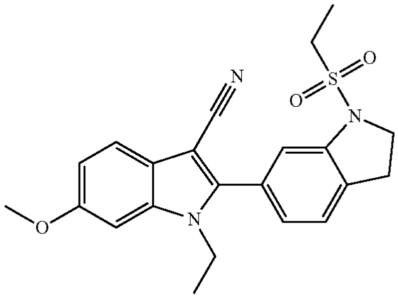
755
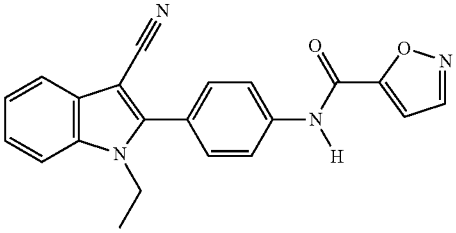
756
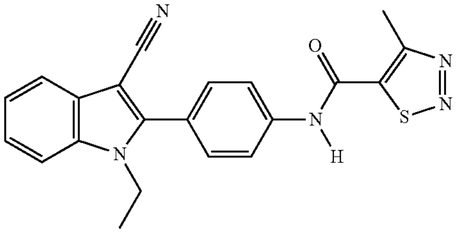
757
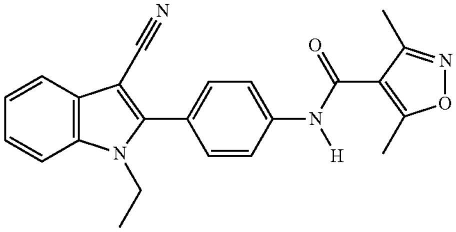
758
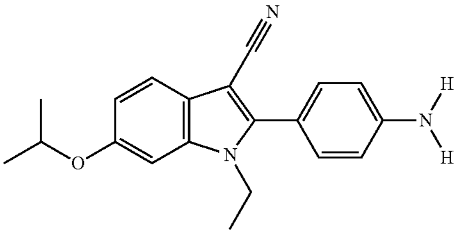
759
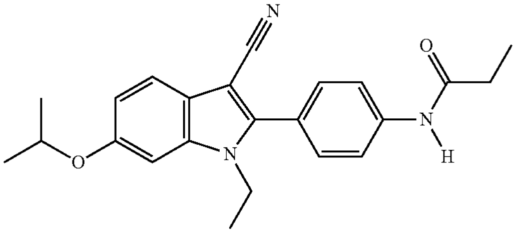

-continued
760
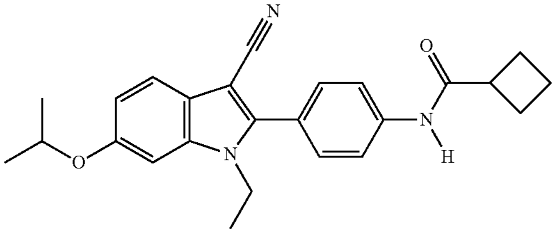
761
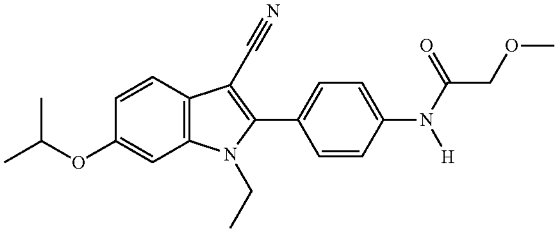
762
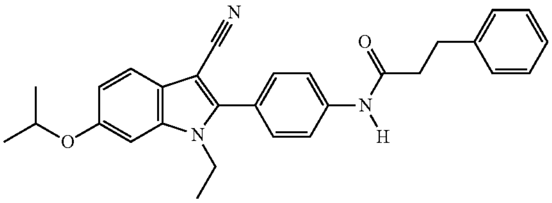
763
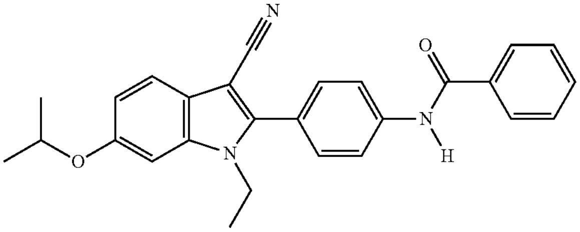
764
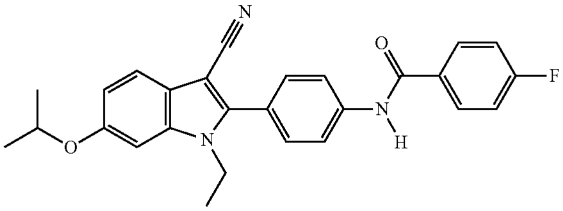
767
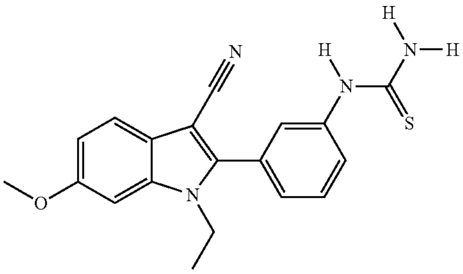
-continued
771
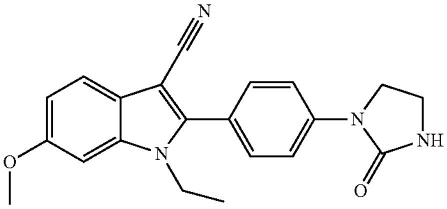
772
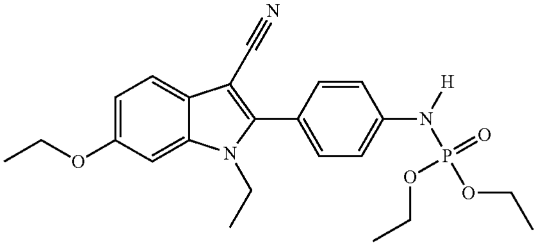
774
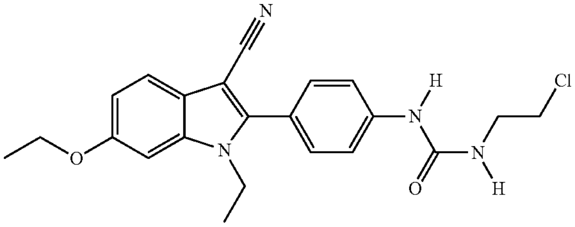
775
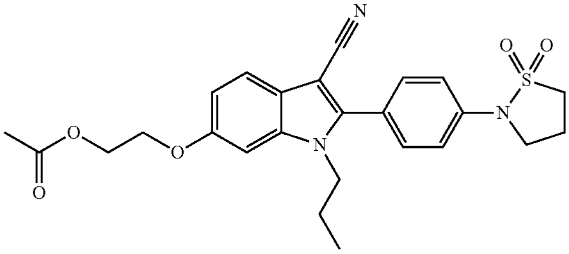
776
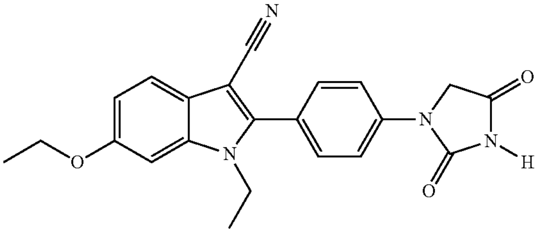
777
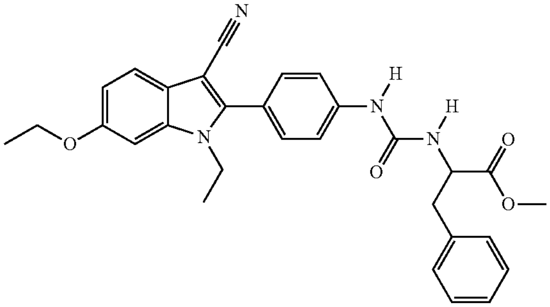

778
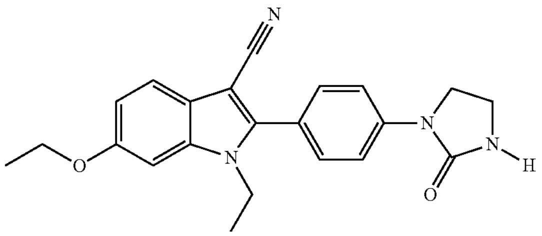
779
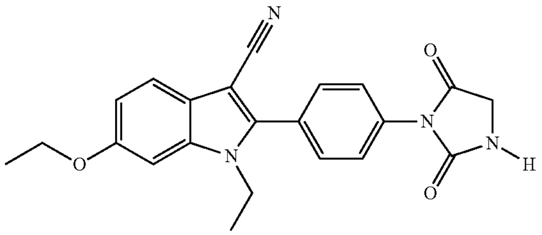
780
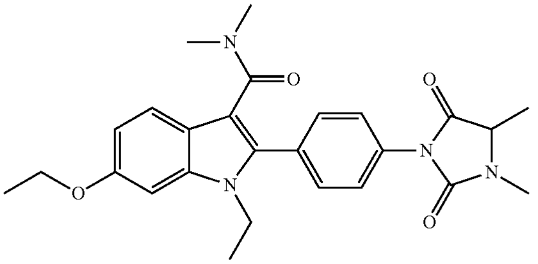
781
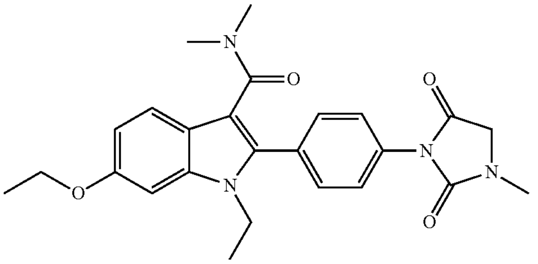
784
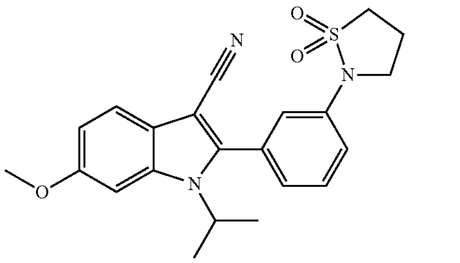
789
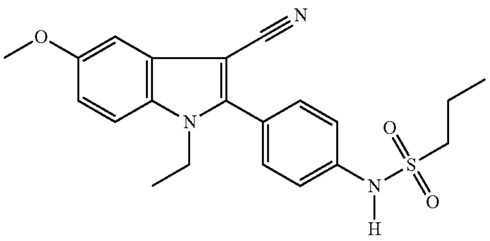
790
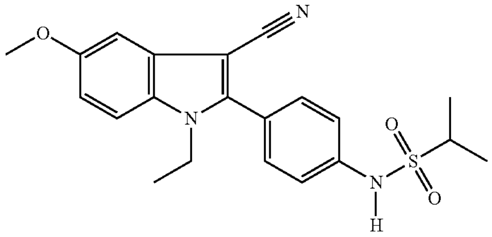
791
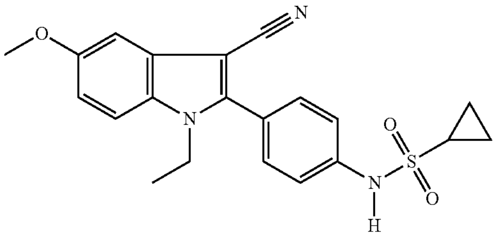
792
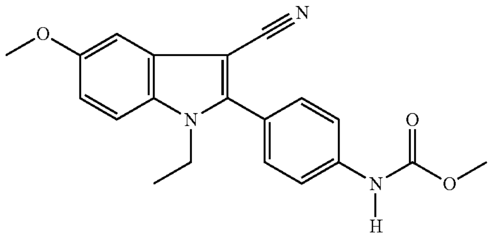
793
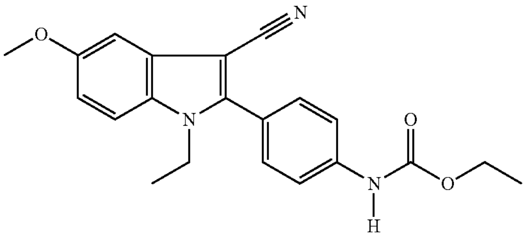
794
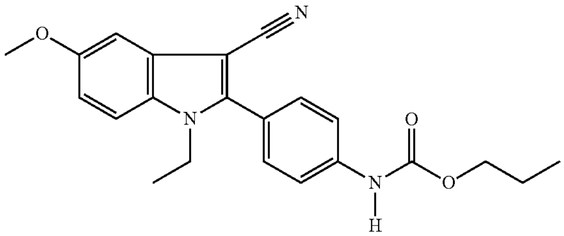
795
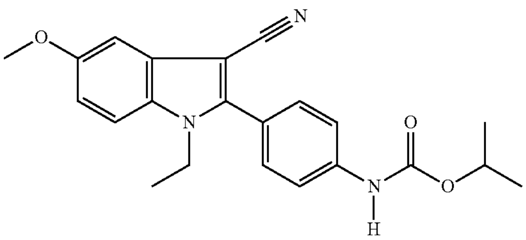

-continued
799
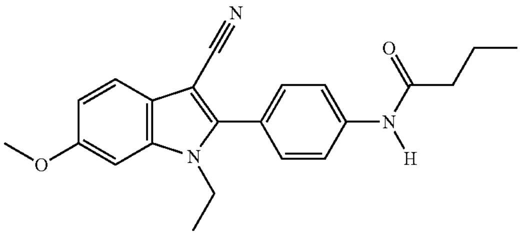
801
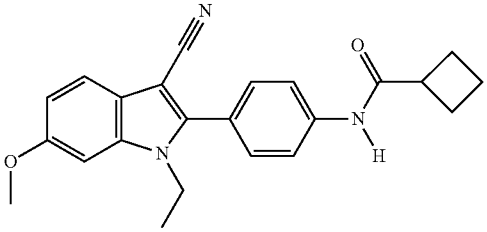
802
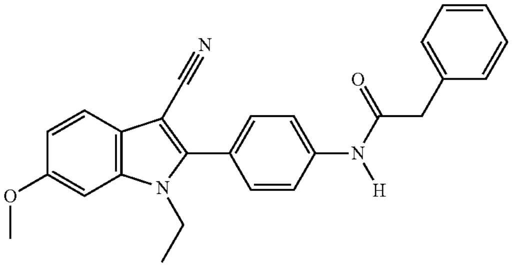
807
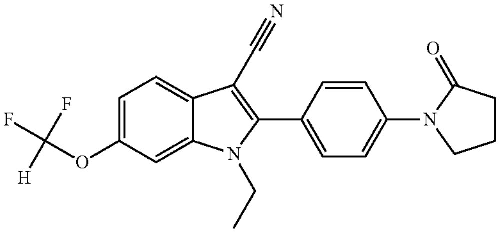
813
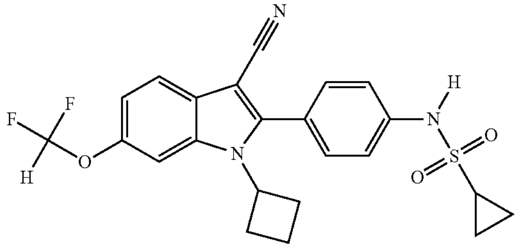
818
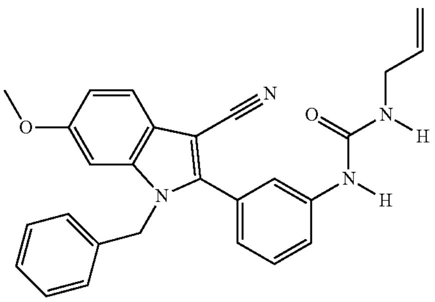
-continued
822
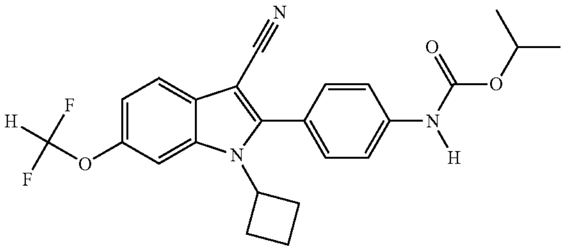
827
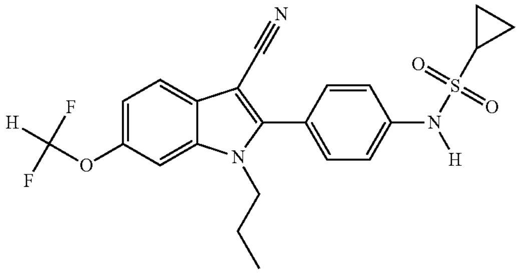
834
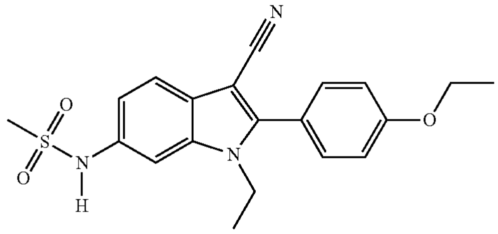
835
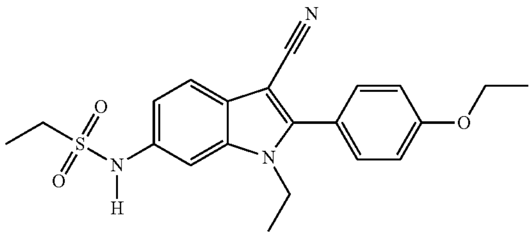
848
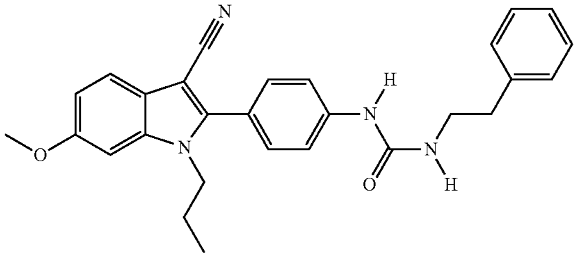

-continued
850
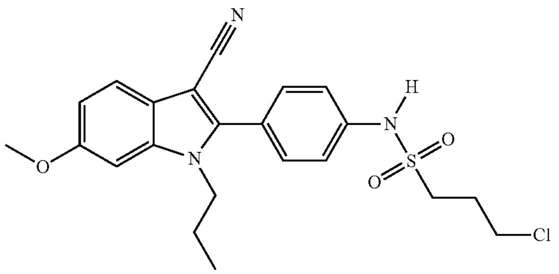
851
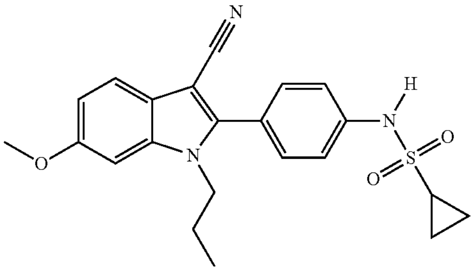
853
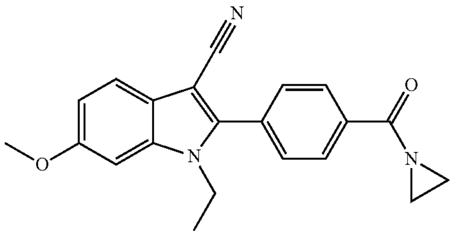
854
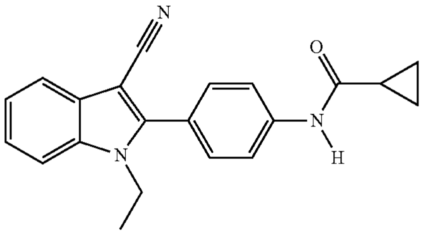
855
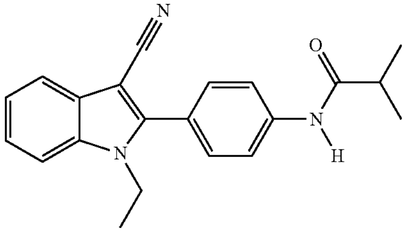
858
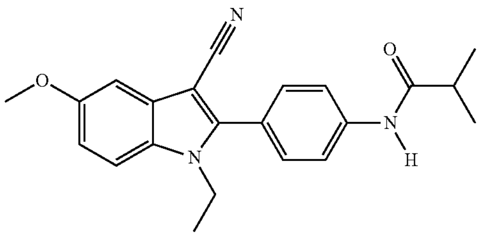
-continued
859
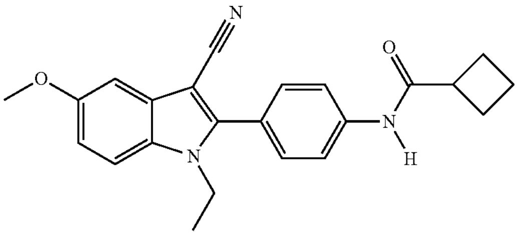
861
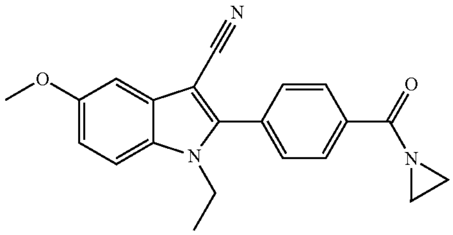
863
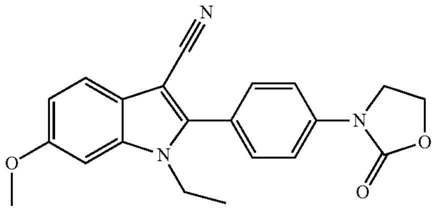
Embodiment 27
A compound selected from the group consisting of the following:
22
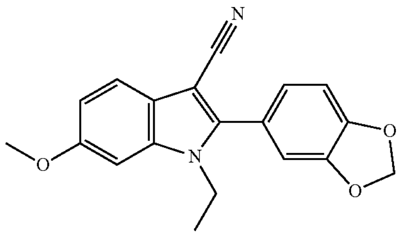
23
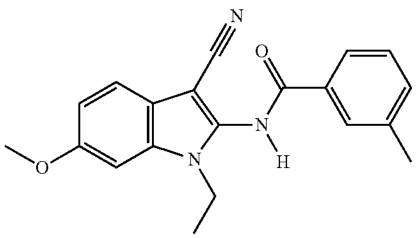

-continued
81
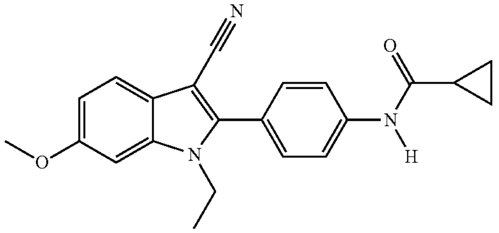
83
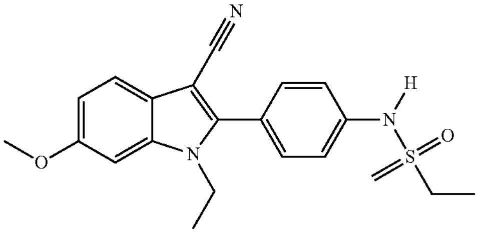
84
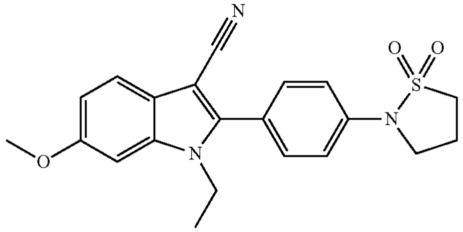
85
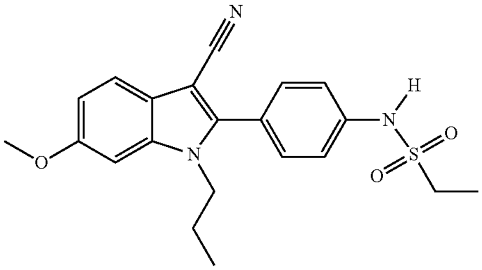
86
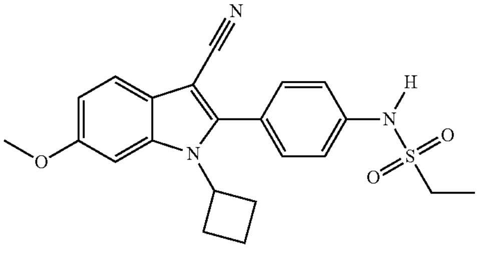
87
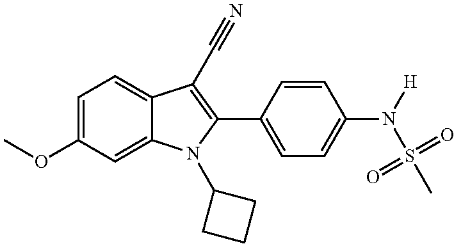
-continued
130
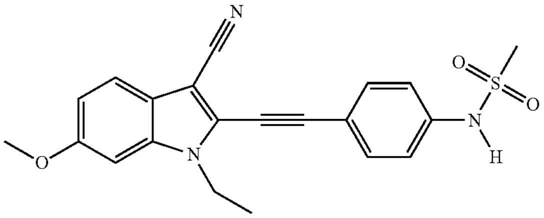
131
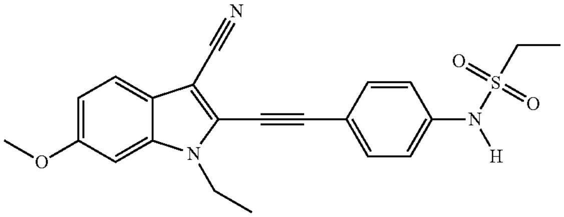
166
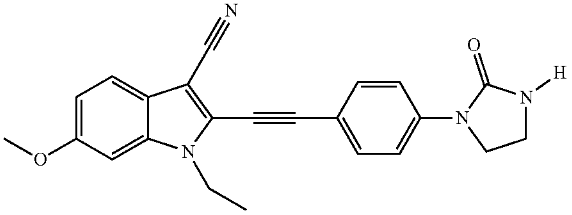
180
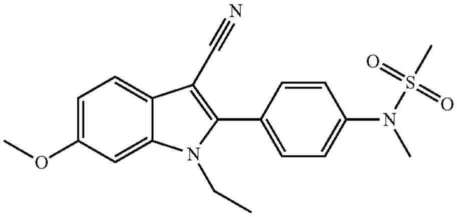
182
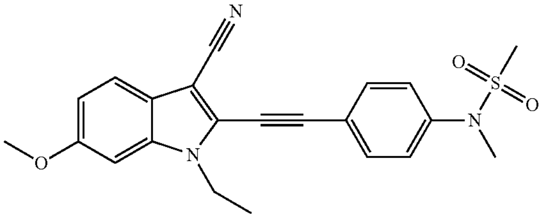
204
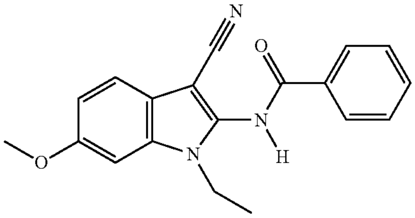

-continued
214
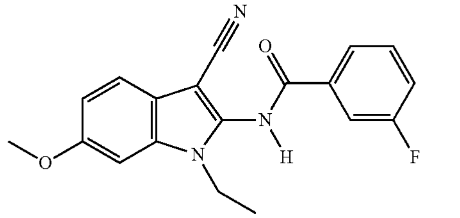
217
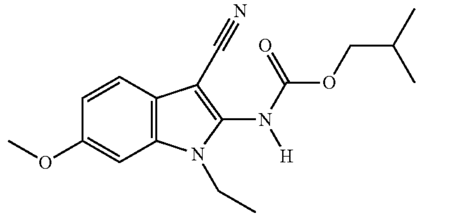
243
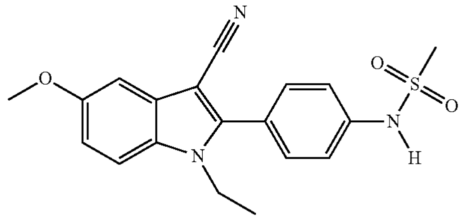
252
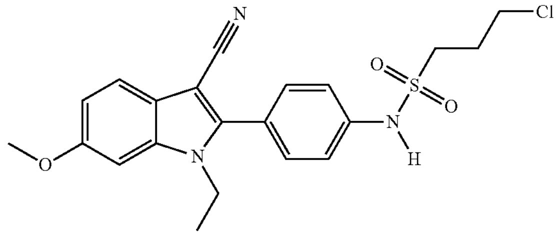
294
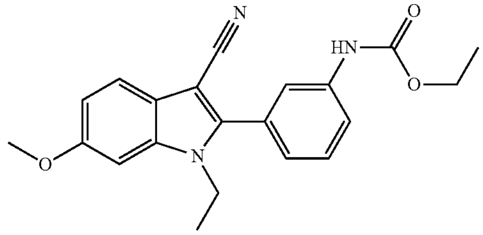
346
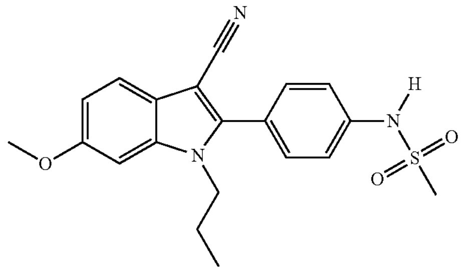
-continued
349
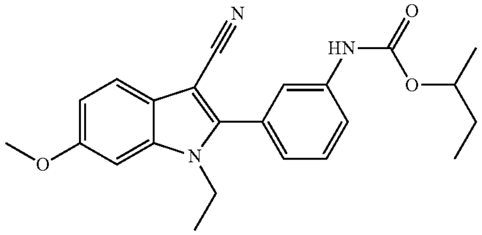
353
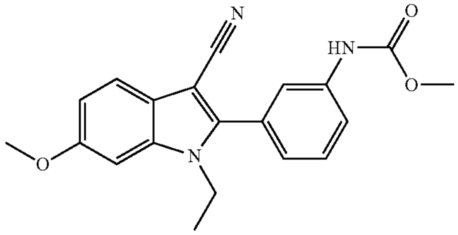
365
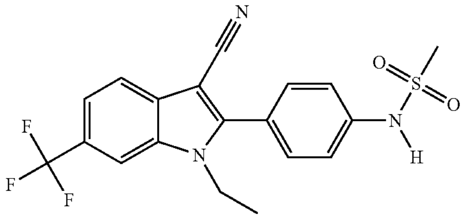
366
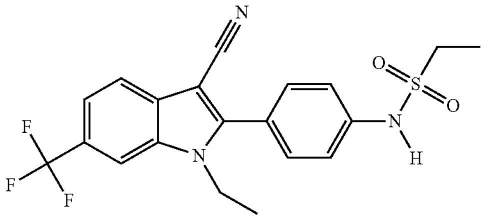
369
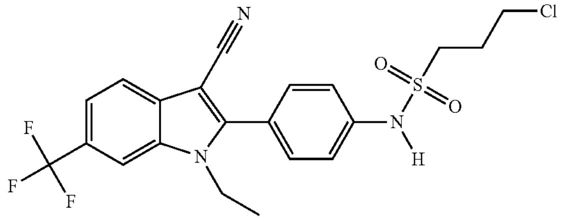
394
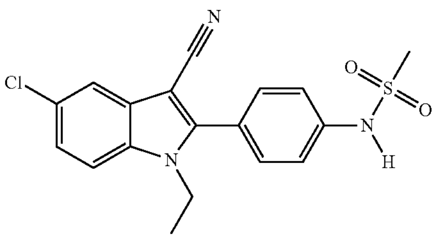

-continued
396
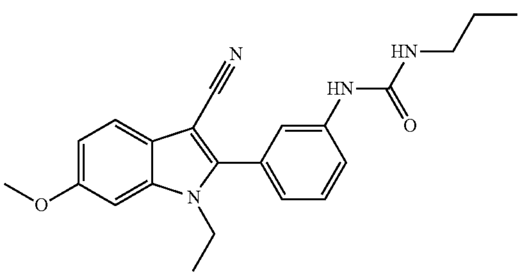
397
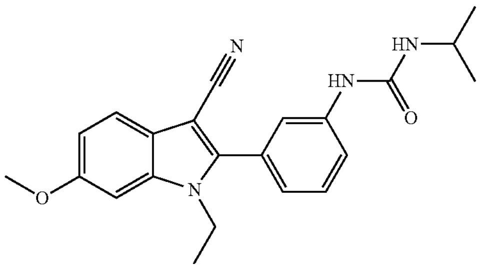
398
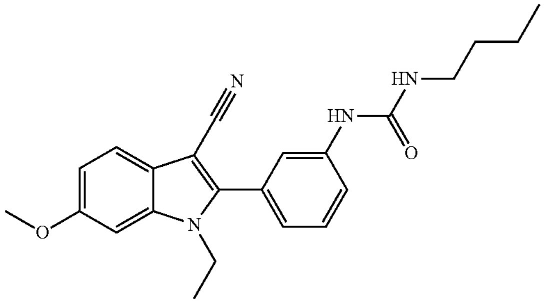
399
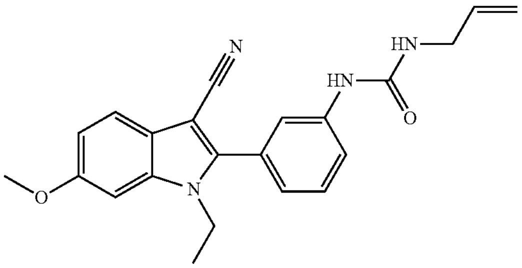
401
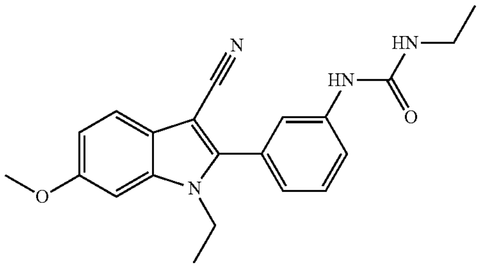
-continued
406
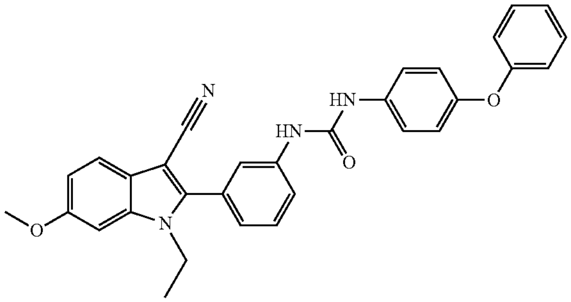
413
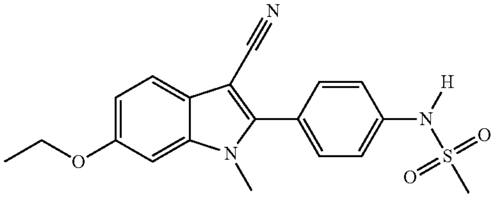
415
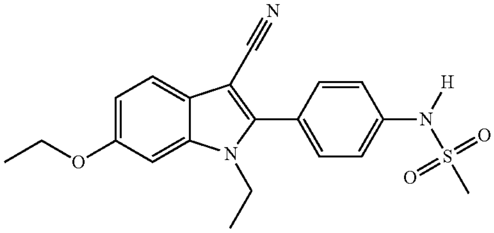
416
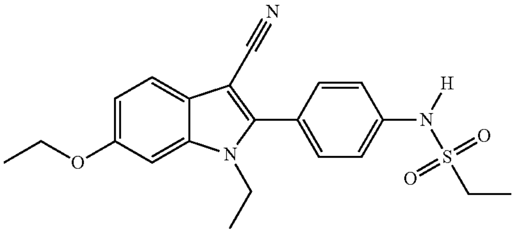
417
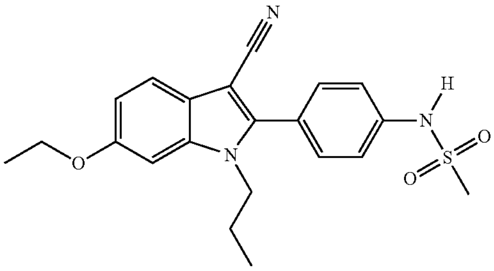
418
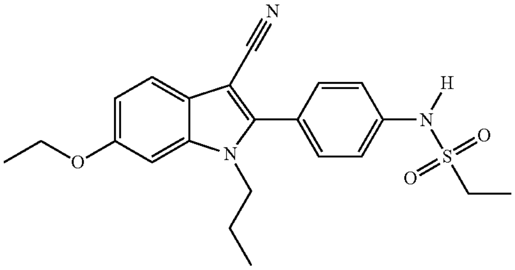

-continued
447
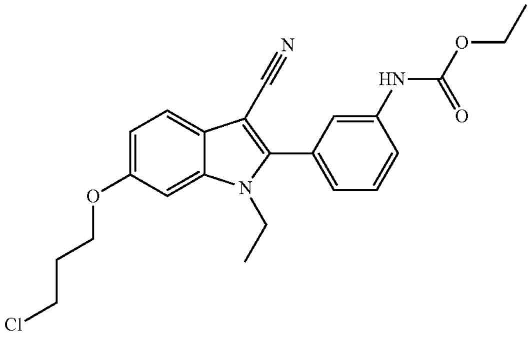
461
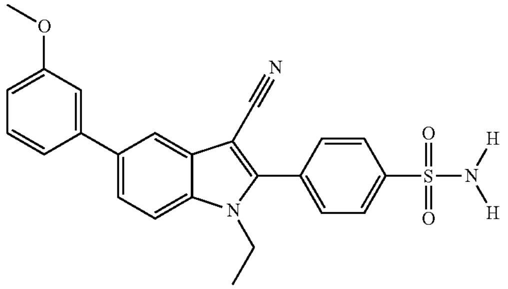
462
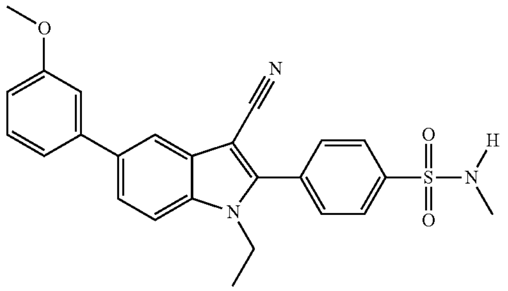
468
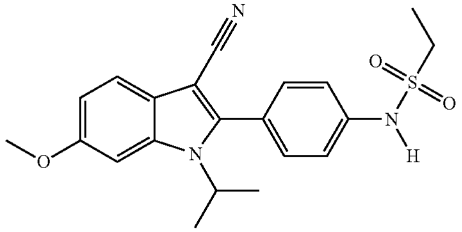
470
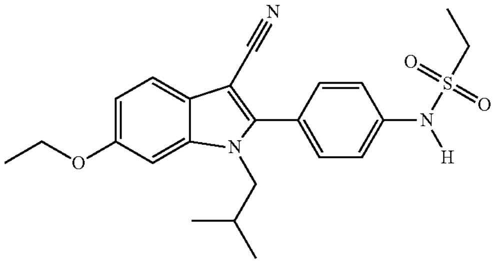
-continued
471
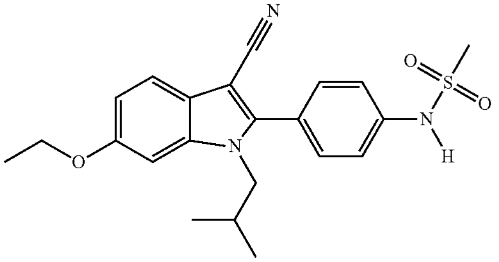
472
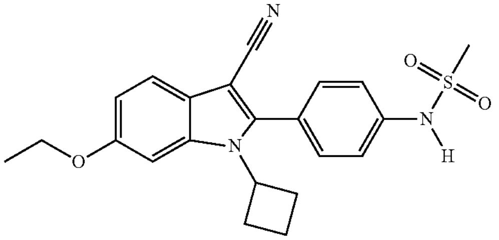
473
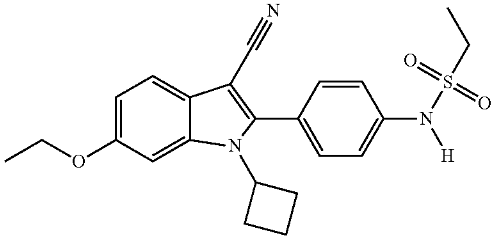
475
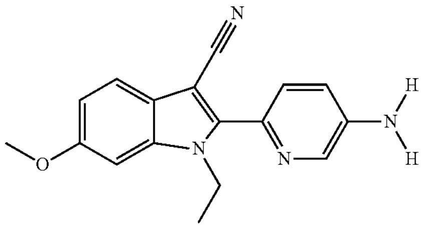
477
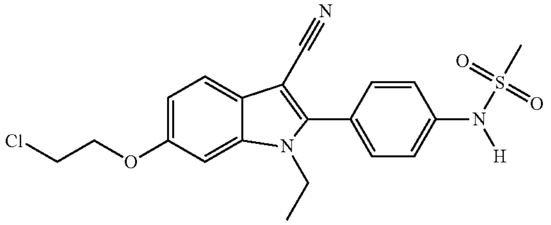
478
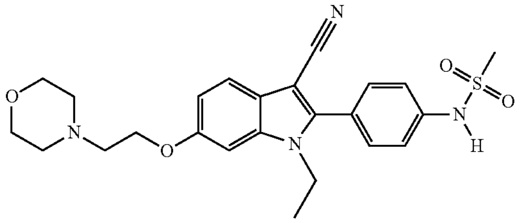

-continued
480
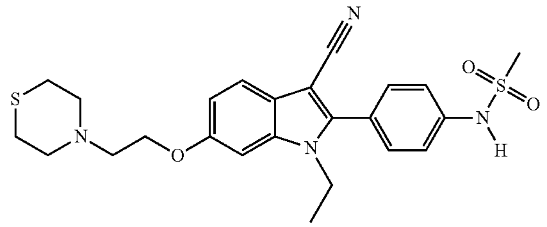
488
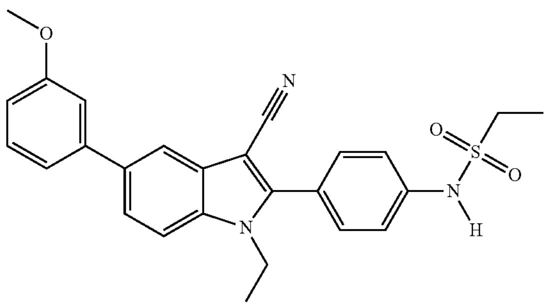
493
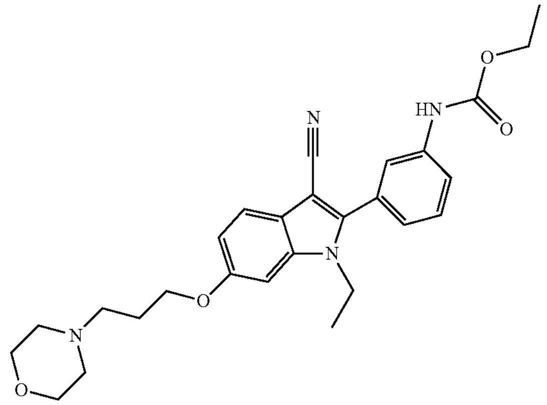
495
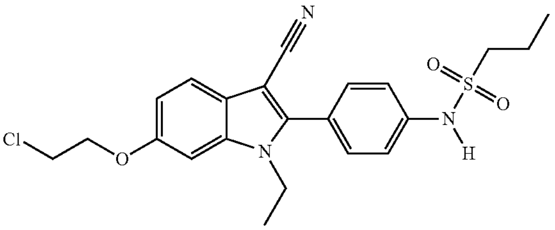
499
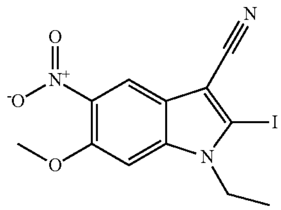
-continued
518
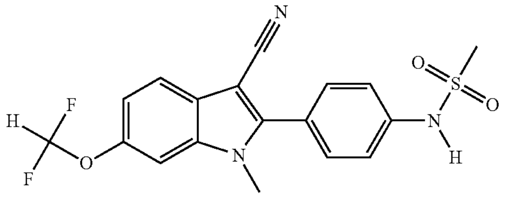
519
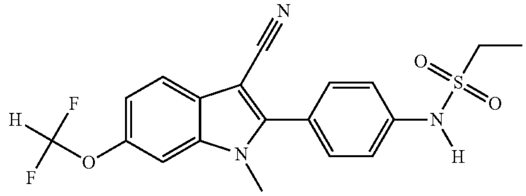
520
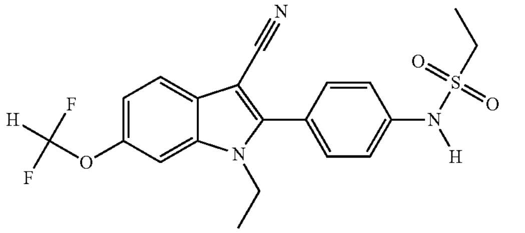
521
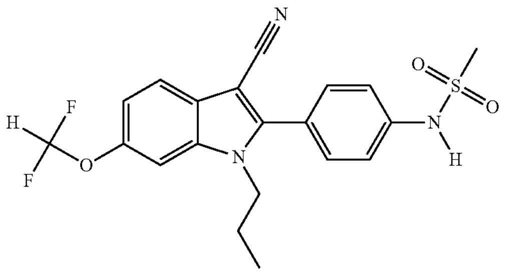
522
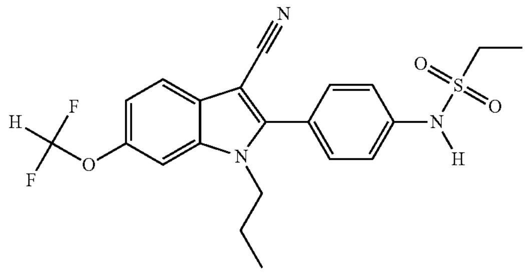
523
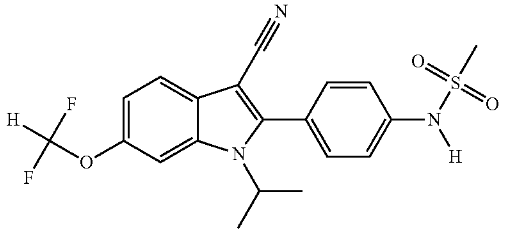

-continued
524
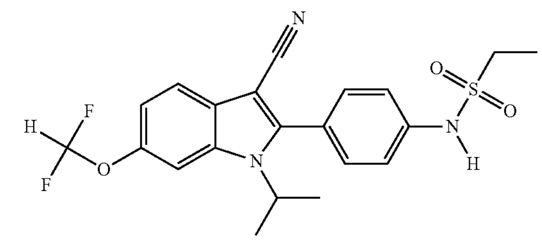
526
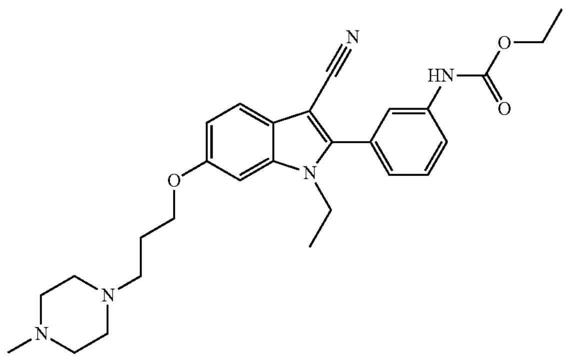
528
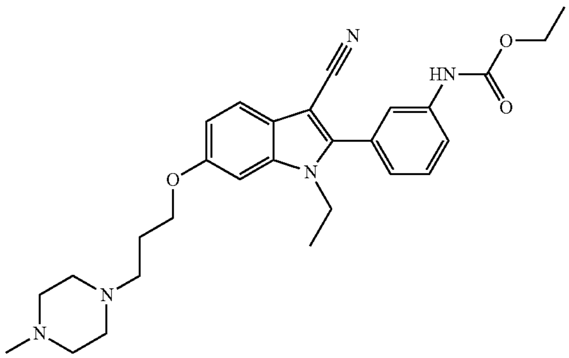
530
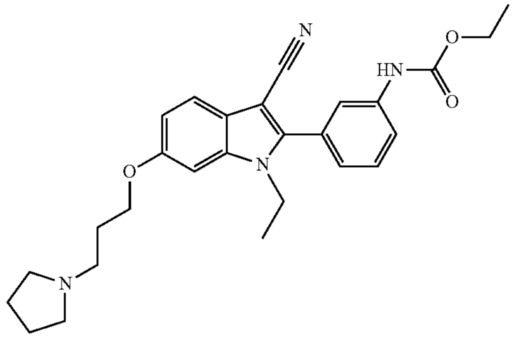
-continued
534
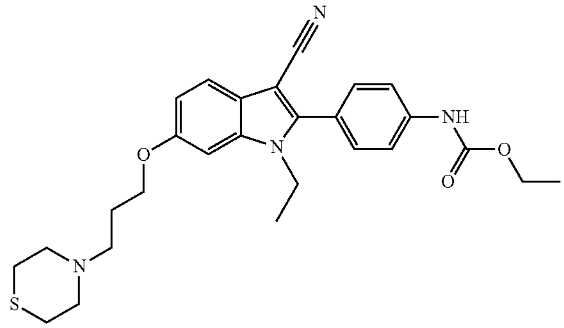
535
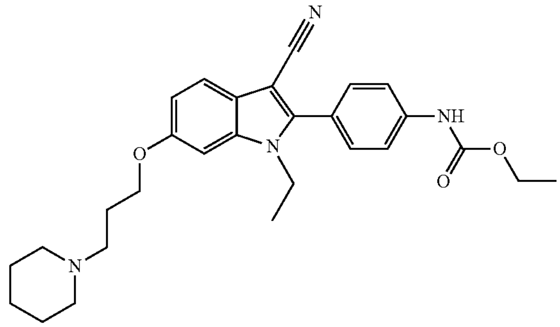
537
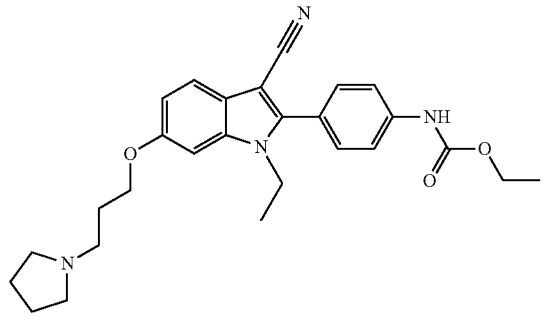
539
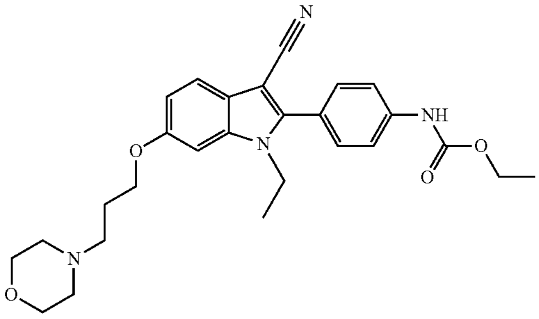
544
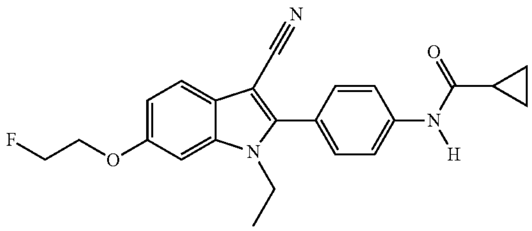

-continued
546
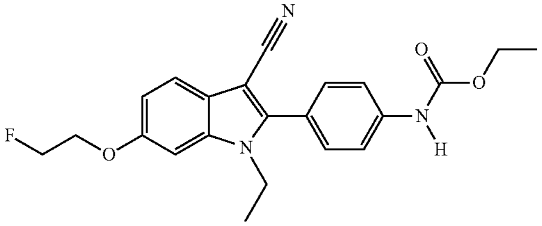
547
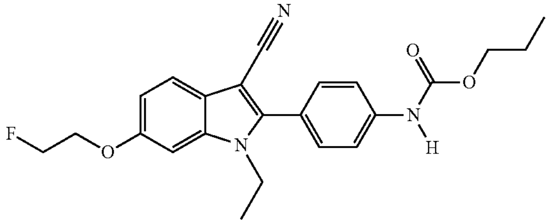
549
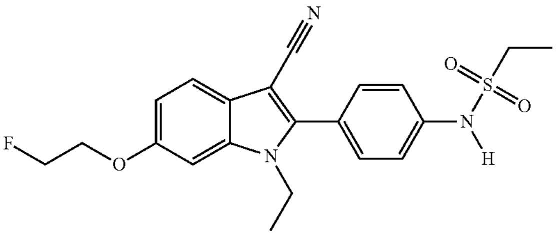
552
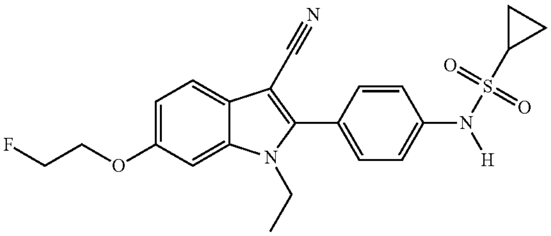
562
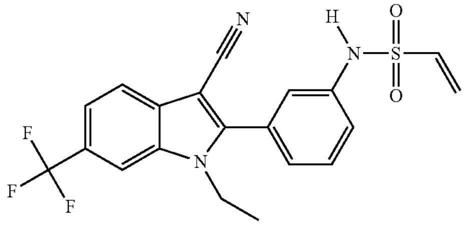
580
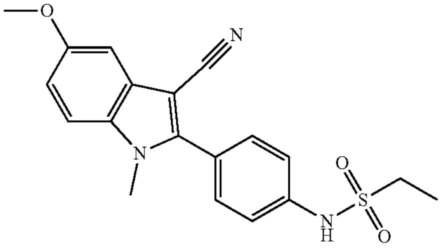
-continued
601
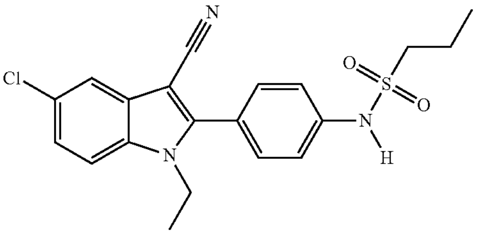
602
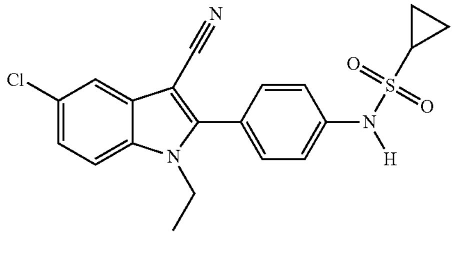
606
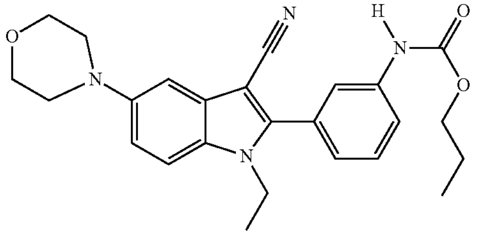
607
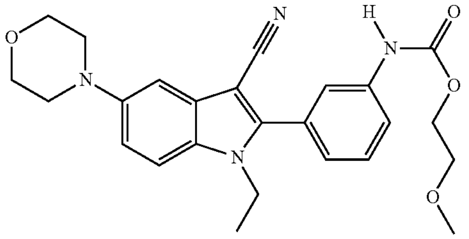
611
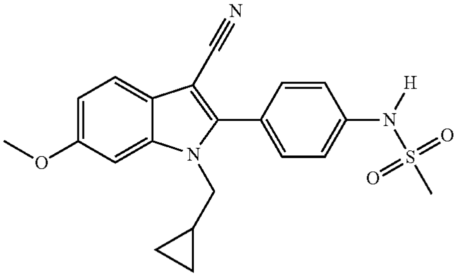
613
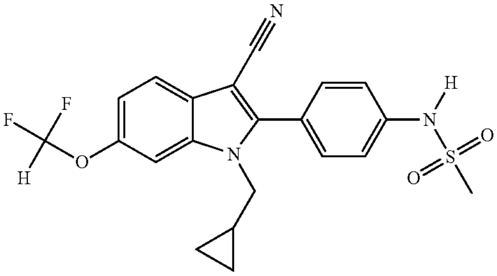

-continued
614
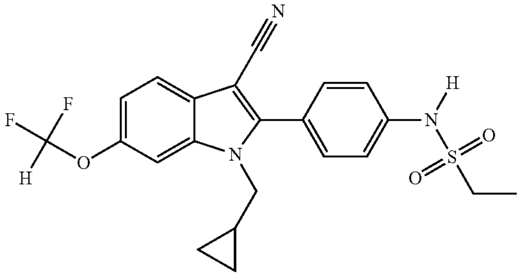
616
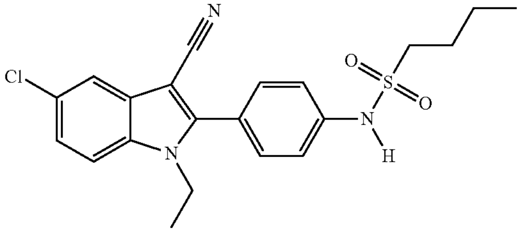
617
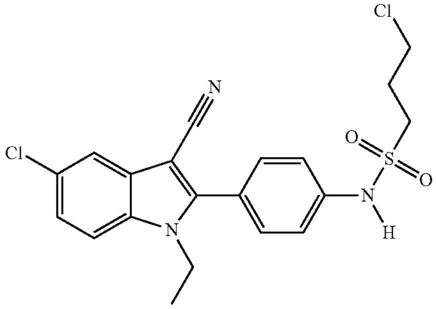
618
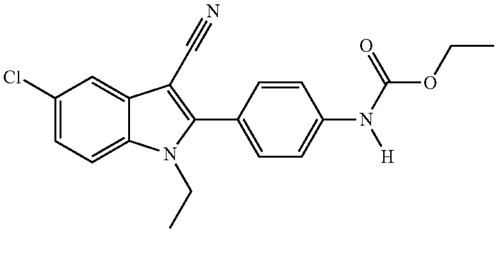
625
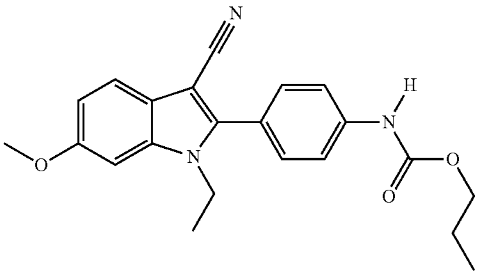
-continued
627
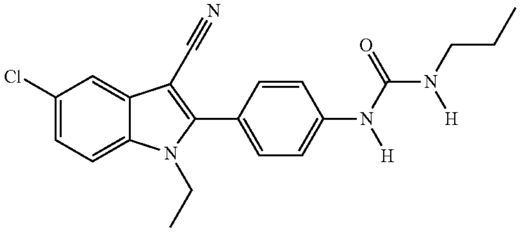
628
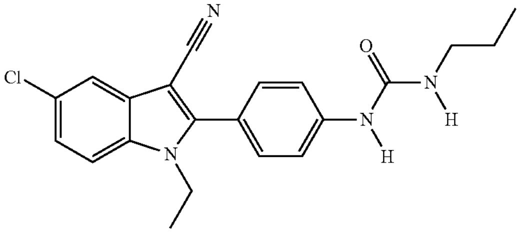
635
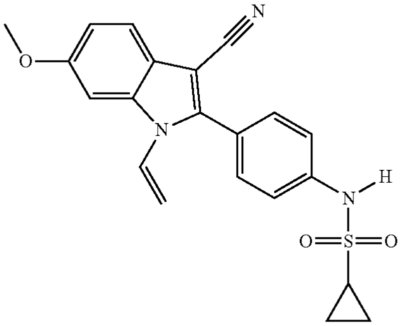
637
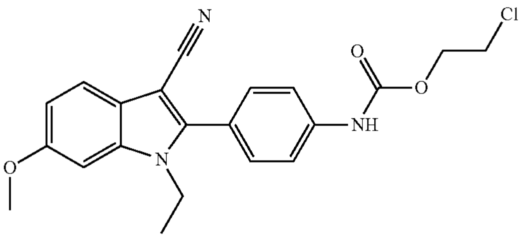
652
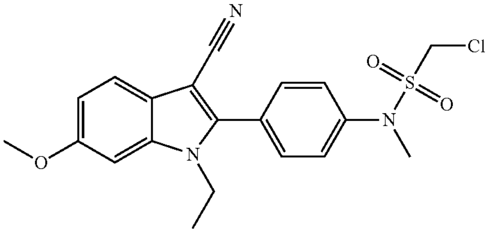

-continued
661
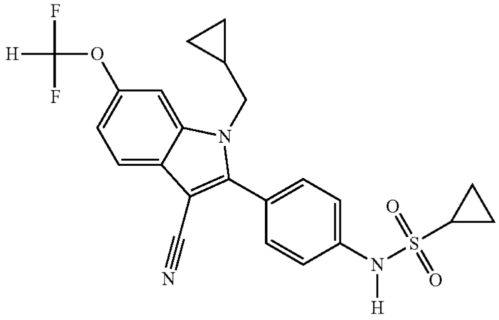
662
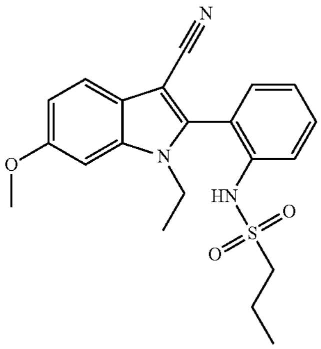
666
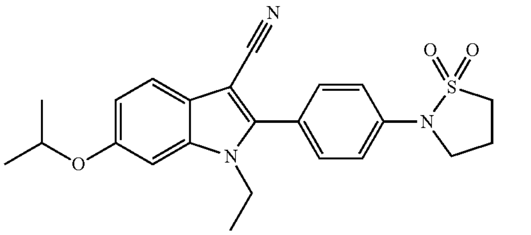
667
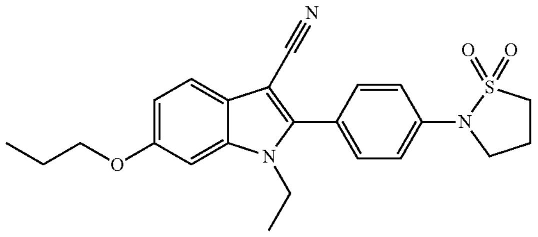
669
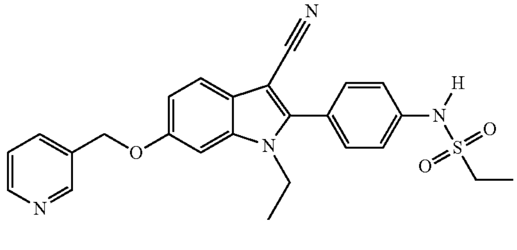
-continued
670
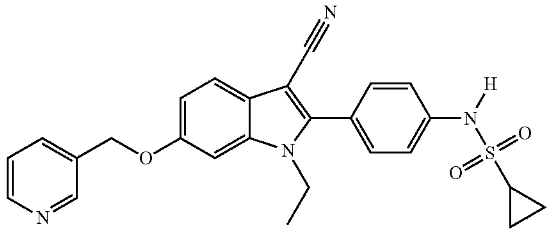
671
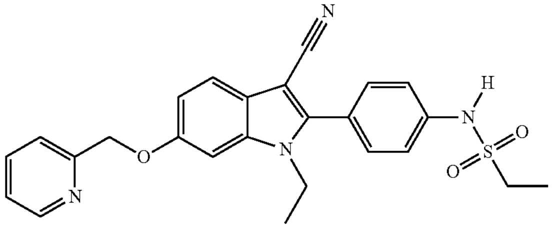
672
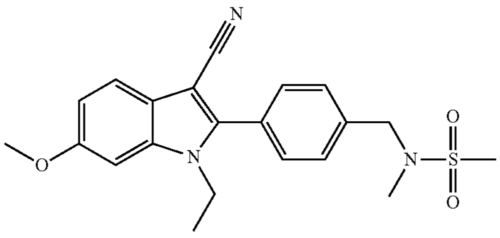
680
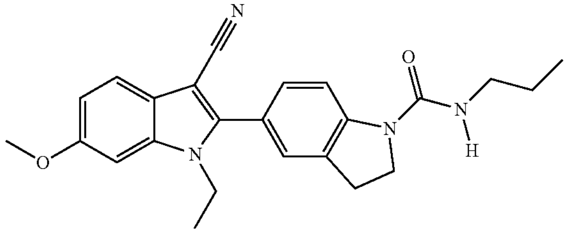
687
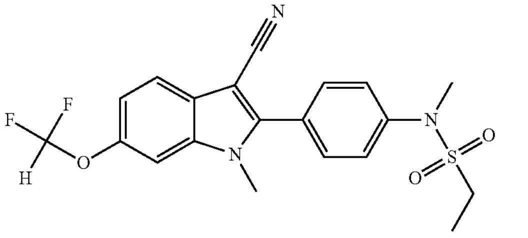
692
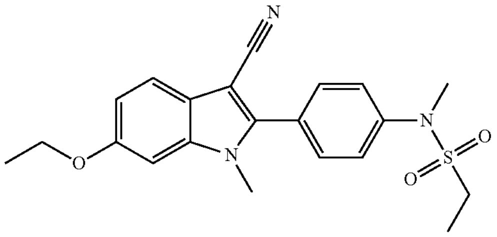

-continued
697
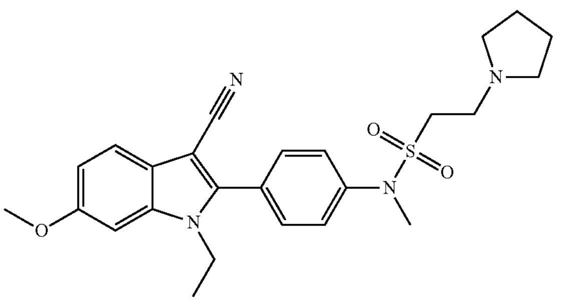
699
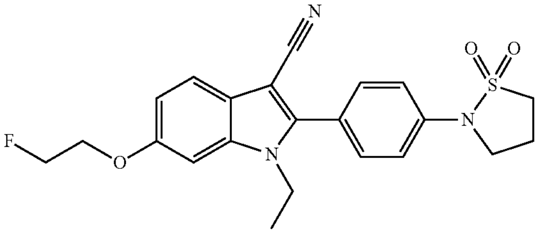
706
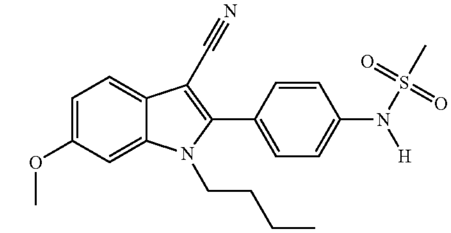
709
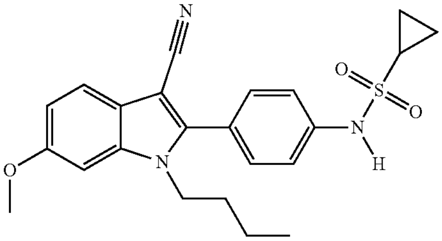
713
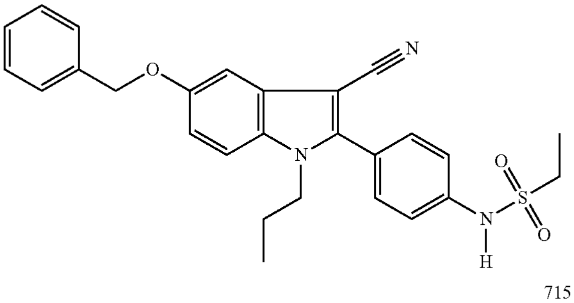
715
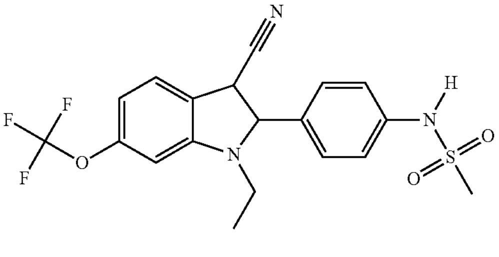
-continued
716
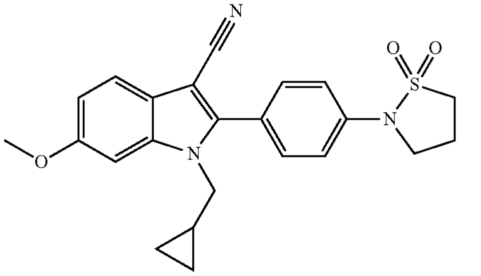
720
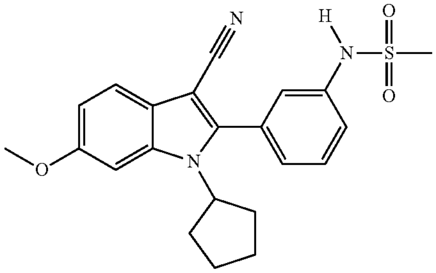
726
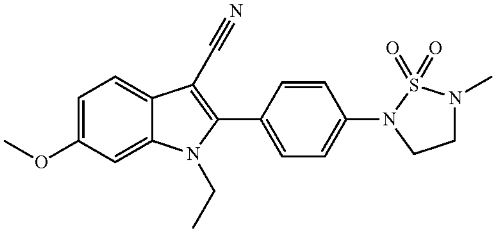
728
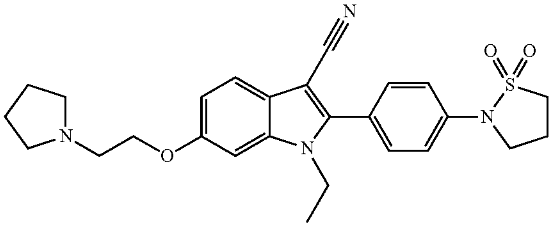
730
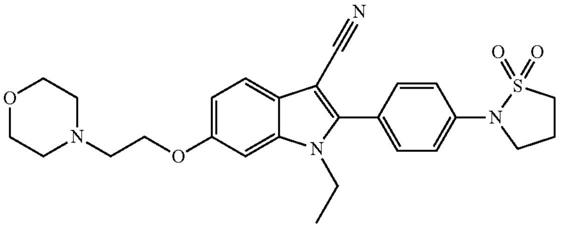
731
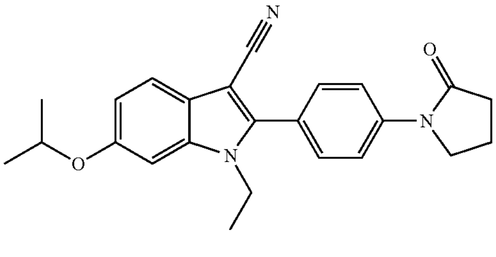

-continued
735
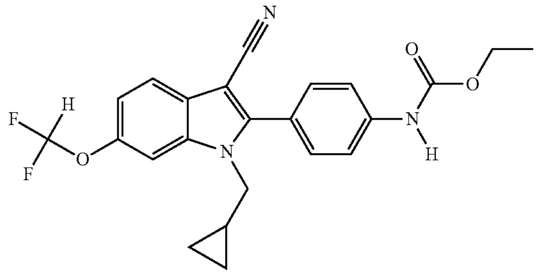
744
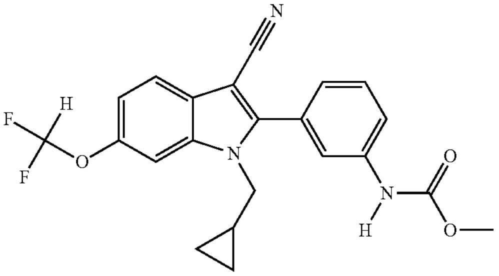
736
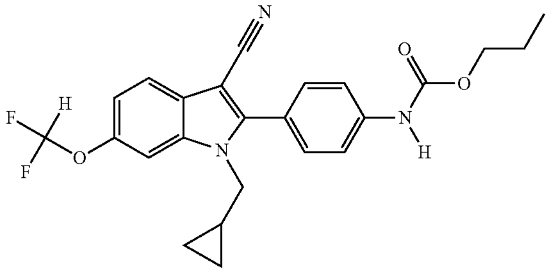
745
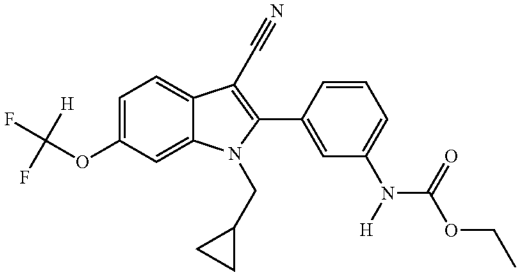
738
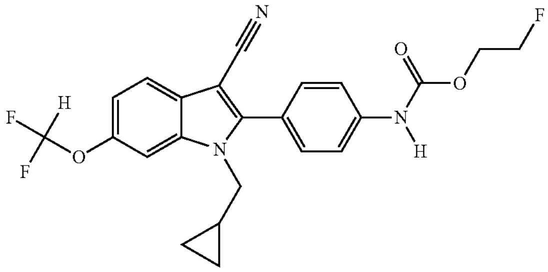
747
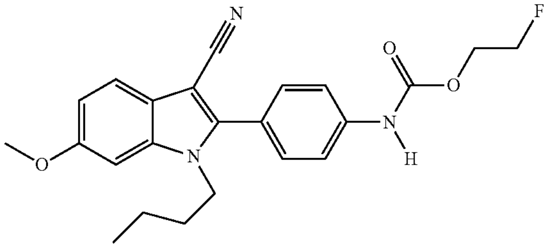
741
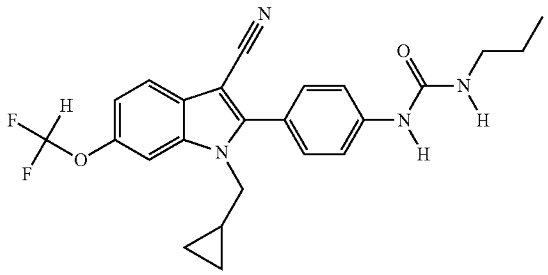
748
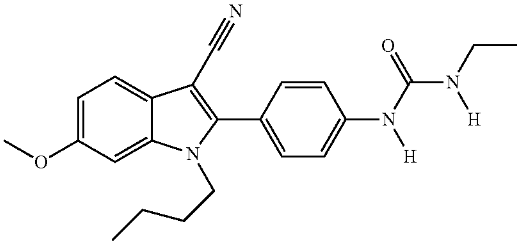
743
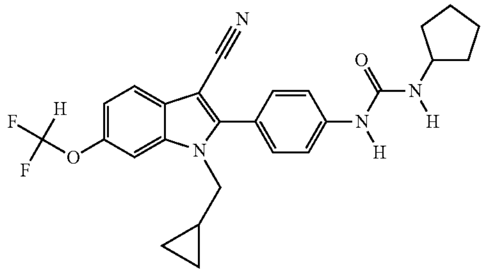
749
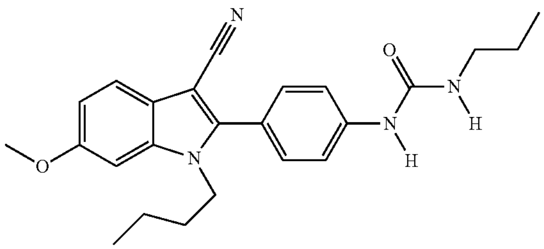

-continued
750
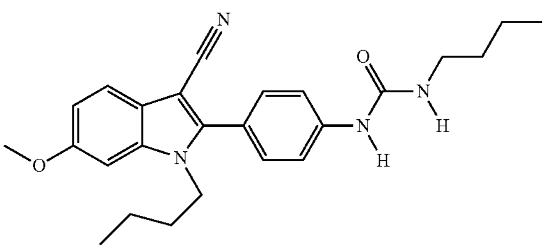
751
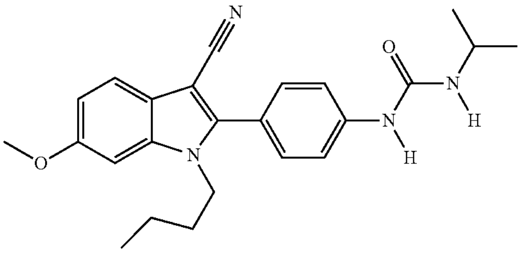
753
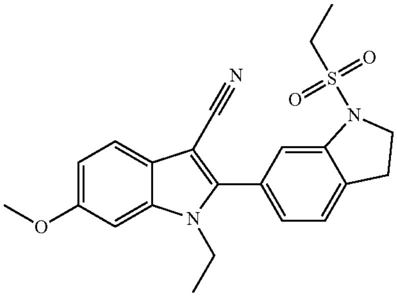
755
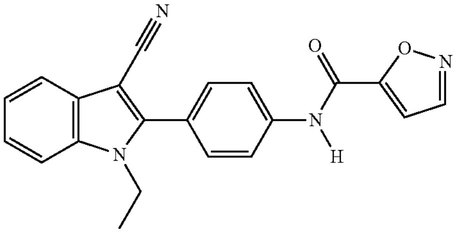
756
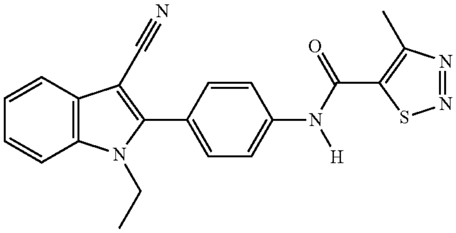
757
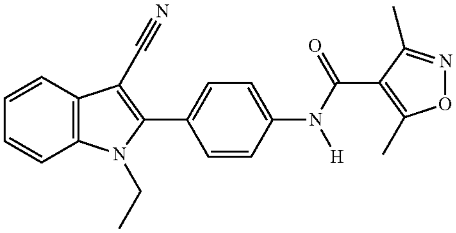
-continued
758
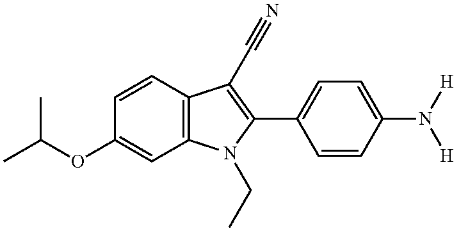
759
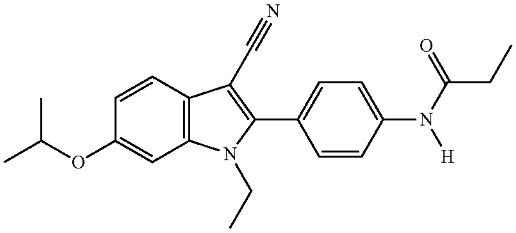
760
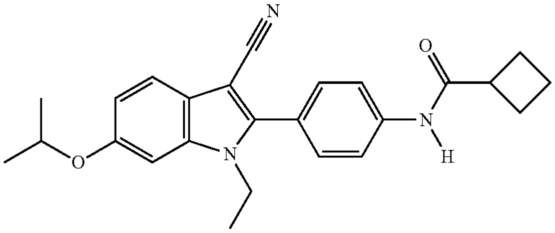
761
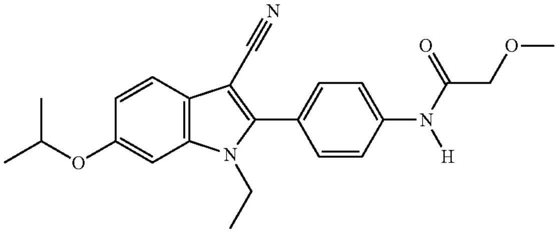
762
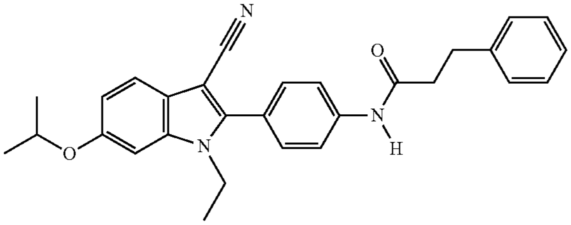
763
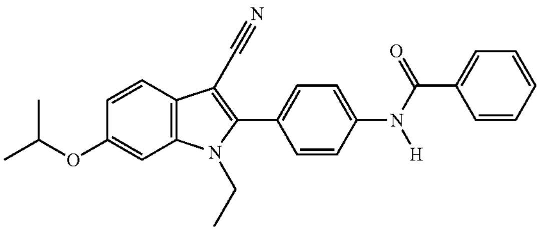

-continued
764
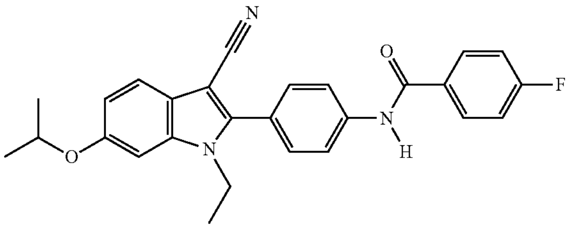
767
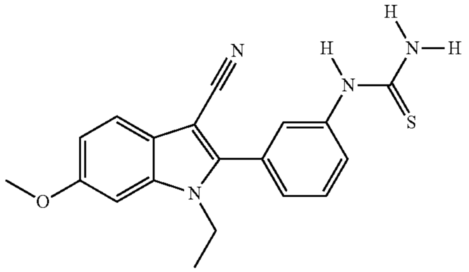
771
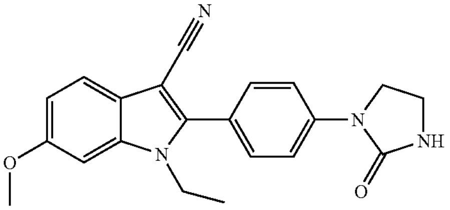
772
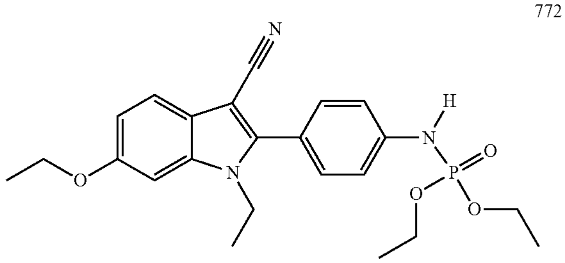
774
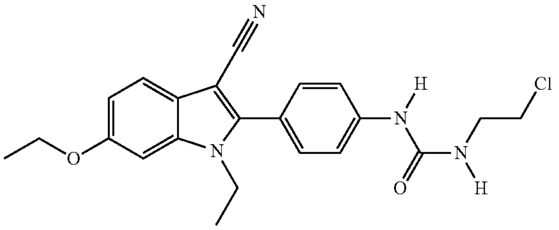
776
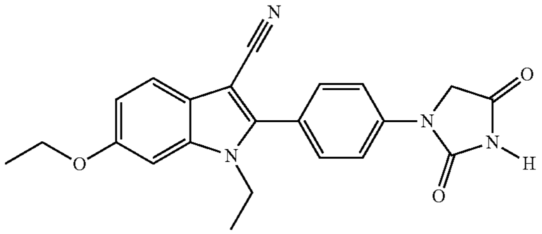
-continued
777
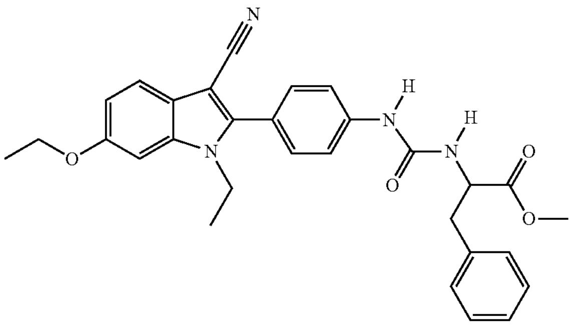
778
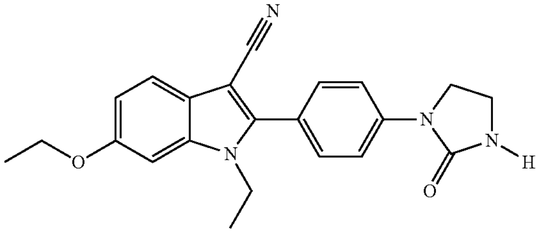
779
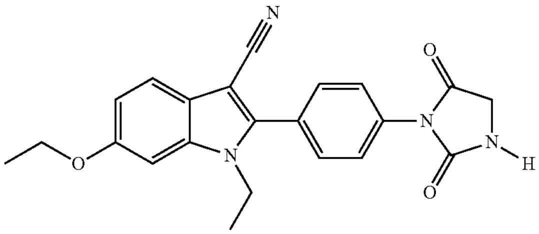
781
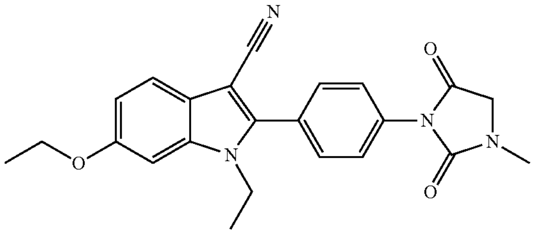
789
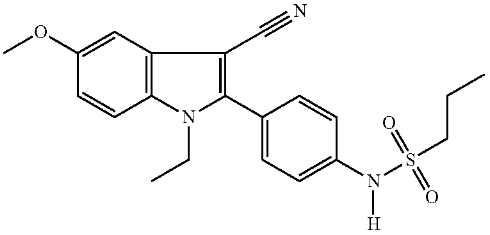
790
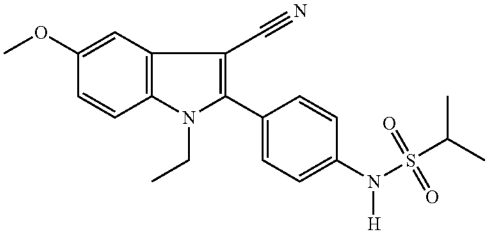

-continued
791
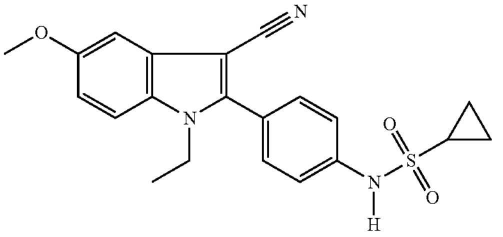
792
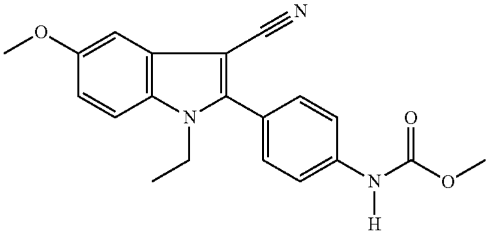
793
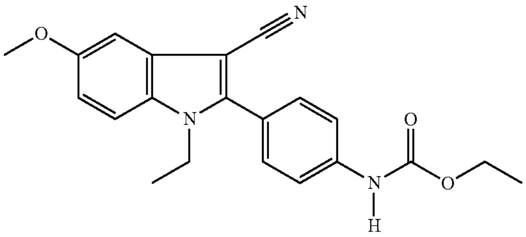
794
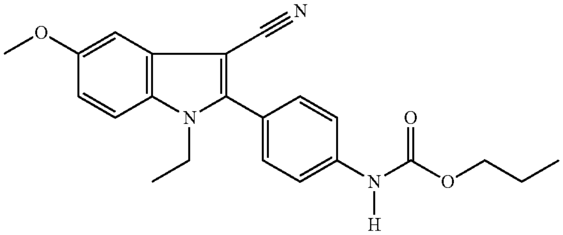
795
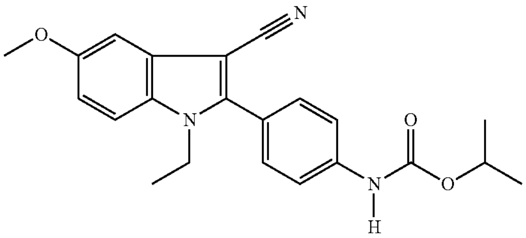
799
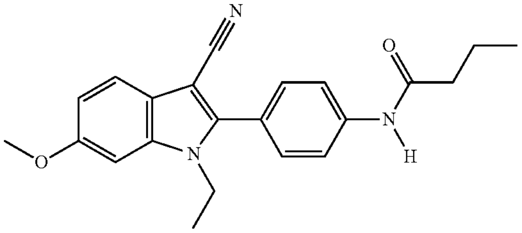
-continued
801
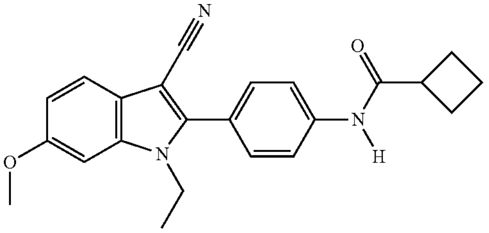
802
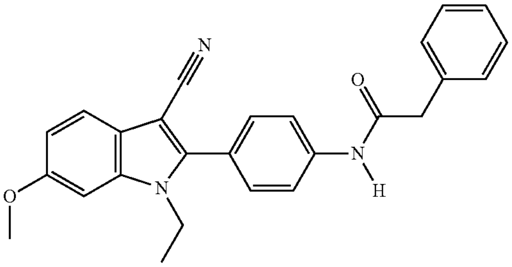
807
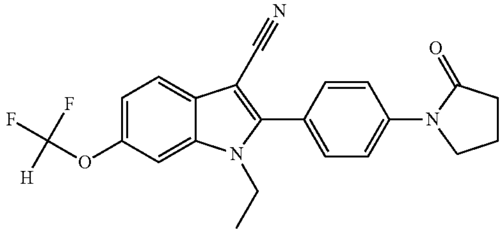
813
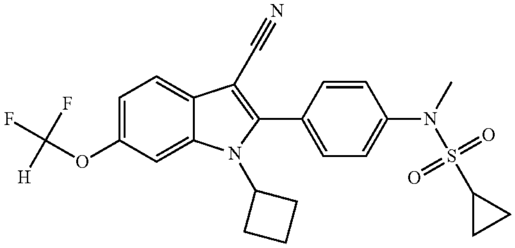
818
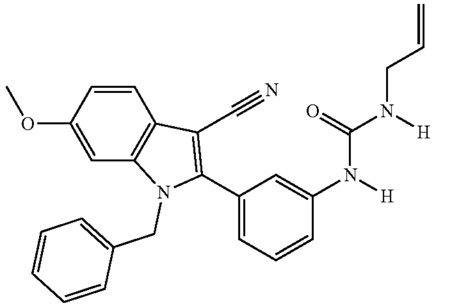
827
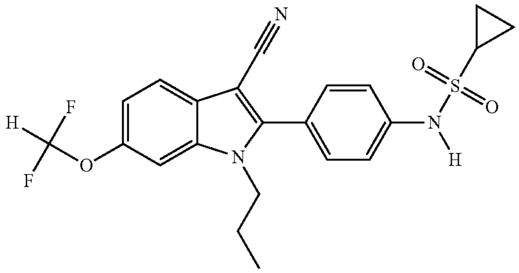

-continued

853

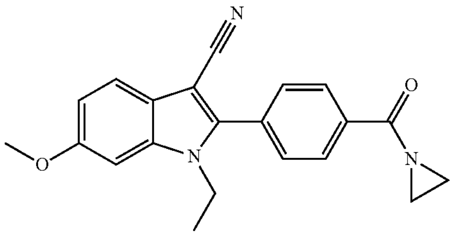

858

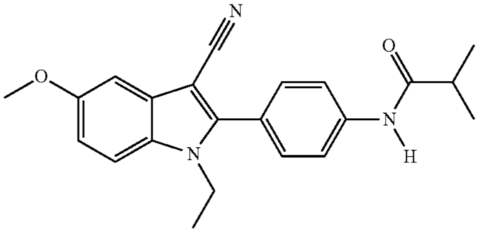

863

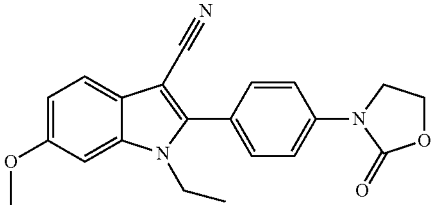

Embodiment 29

A pharmaceutical composition for affecting viral IRES activity in a subject infected with a virus, comprising one or more compound having the following formula:

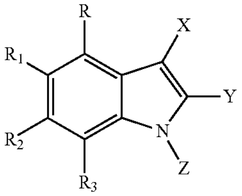

wherein:

X is:
- hydrogen;
- a nitro group;
- a cyano group;
- a —$COR_a$ group, where $R_a$ is:
  - a $C_1$ to $C_6$ alkyl,
  - a $C_6$ to $C_8$ aryl optionally substituted with an alkoxy or a halogen, or
  - a dialkyl-amino;
- a —$COOR_x$ group, where $R_x$ is a $C_1$ to $C_6$ alkyl;
- a formyl group;
- a $C_6$ to $C_8$ aryl optionally substituted with an alkoxy; or
- a 5 or 6-membered heteroaryl optionally substituted with:
  - a $C_1$ to $C_6$ alkyl,
  - a $C_6$ to $C_8$ aryl optionally substituted with an alkoxy or one or more halogens, or
  - a 5 to 6 membered heteroaryl;

Y is:
- a hydrogen;
- a haloalkyl;

- a halogen;
- an amino optionally substituted with one or more $C_1$ to $C_6$ alkyls;
- a benzofuran;
- a benzothiophene;
- a dibenzofuran;
- a dibenzothiophene;
- a benzothiazole;
- a naphthalene;
- an indole, optionally substituted on the nitrogen with a $C_1$ to $C_6$ alkyl;

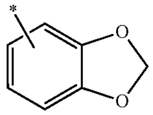 ; 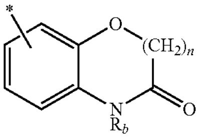 , where $R_b$ is a hydrogen or a $C_1$ to $C_6$ alkyl, and n is 0 or 1;

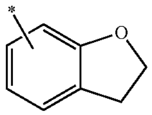 ; 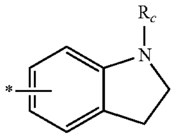 , where $R_c$ is a hydrogen, a —$CONHR_x$, where $R_x$ is as defined above, or an —$SO_2R_x$, where $R_x$ is as defined above; or

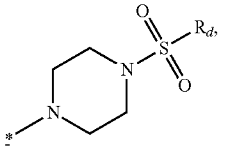

where $R_d$ is a $C_1$ to $C_6$ alkyl or a $C_6$ to $C_8$ aryl;
- a —$NHCOR_e$ group, where $R_e$ is:
  - a $C_1$ to $C_6$ alkyl;
  - a $C_6$ to $C_8$ aryl optionally substituted with:
    - a $C_1$ to $C_6$ alkyl,
    - an alkoxy,
    - a cyano group,
    - a nitro group, or
    - a halogen;
- a —$NHCOOR_x$ group, where $R_x$ is as defined above;
- a —$CH_2O$—$R_f$ group, where $R_f$ is a $C_6$ to $C_8$ aryl;
- a —$NR_gR_h$ group, where $R_g$ is a $C_1$ to $C_6$ alkyl or a hydrogen and $R_h$ is a $C_6$ to $C_8$ aryl optionally substituted with an alkoxy;
- a $C_1$ to $C_6$ alkyl;
- a 5 or 6 membered heteroaryl, optionally substituted with:
  - a $C_1$ to $C_6$ alkyl, optionally substituted with a $C_6$ to $C_8$ aryl,
  - a $C_6$ to $C_8$ aryl, optionally substituted with —$COOR_x$, where $R_x$ is as defined above, or
  - an amino group;

a 5 or 6 membered heterocycle optionally substituted with:
a —$COOR_x$ group, where $R_x$ is as defined above, or
a —$NHCOOR_x$ group, where $R_x$ is as defined above;
a $C_6$ to $C_8$ aryl, optionally substituted with one or more of the following:
an alkoxy, optionally substituted with:
an alkoxy,
a hydroxy,
one or more halogens,
a 5 or 6 membered heterocycle, optionally substituted with:
a $C_1$ to $C_6$ alkyl, or
a hydroxy,
an amino group optionally substituted with one or more $C_1$ to $C_6$ alkyls,
a —$NR_iSO_2R_x$ group, where $R_x$ is as defined above and $R_i$ is:
a hydrogen,
a $C_1$ to $C_6$ alkyl,
a —$COR_x$ group, where $R_x$ is as defined above,
a haloalkyl, or
a haloalkoxy,
a —$NR_jCOR_k$ group, where $R_k$ is:
a $C_1$ to $C_6$ alkyl,
a hydrogen, or
an amino optionally substituted with one or more $C_1$ to $C_6$ alkyls, and $R_j$ is:
a hydrogen,
a $C_1$ to $C_6$ alkyl,
a —$COR_x$ group, where $R_x$ is as defined above,
a haloalkyl, or
a haloalkoxy,
a —$N{=}N^+{=}N^-$ group, or
a —$COR_l$, where $R_l$ is a 5 or 6 membered heterocycle optionally substituted with a hydroxy,
an amino optionally substituted with one or more $C_1$ to $C_6$ alkyls,
a nitro group,
a $C_1$ to $C_6$ alkyl group, optionally substituted with:
a —$NHSO_2R_x$ group, where $R_x$ is as defined above, or
a —$NR_xSO_2R_x$ group, where $R_x$ is as defined above,
a haloalkoxy,
a halogen,
a hydroxy,
a —$COOR_x$ group, where $R_x$ is as defined above,
a —$COR_m$ group, where $R_m$ is:
an amino optionally substituted with one or more $C_1$ to $C_6$ alkyls, where the $C_1$ to $C_6$ alkyls are optionally substituted with:
a hydroxy
a 5 or 6 membered heterocycle,
an amino optionally substituted with one or more $C_1$ to $C_6$ alkyls,
an alkoxy,
a 3 to 7 membered heterocycle, optionally substituted with a $C_1$ to $C_6$ alkyl, optionally substituted with a dialkyl-amino,
a —$NHR_n$ group, where $R_n$ is:
a —$CH_2CONH_2$, or
a $C_6$ to $C_8$ aryl optionally substituted with:
an alkyl,
one or more halogens,
a nitro group, or
one or more alkoxys, a —$NR_oCOR_p$ group, where $R_p$ is:
a $C_1$ to $C_6$ alkyl optionally substituted with:
a halogen,
an alkoxy, or
a $C_6$ to $C_8$ aryl,
a 5 or 6 membered heterocycle,
a $C_6$ to $C_8$ aryl, optionally substituted with a halogen,
a 5 or 6 membered heteroaryl optionally substituted with one or more C, to $C_6$ alkyls,
a hydrogen,

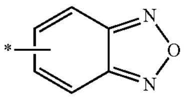
-
or
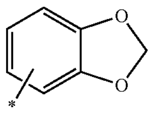
, and where $R_o$ is:
a hydrogen,
a $C_1$ to $C_6$ alkyl,
a —$COR_x$ group, where $R_x$ is as defined above,
a haloalkyl, or
a haloalkoxy,
a —$NR_qCONR_qR_r$ group, where $R_q$ is:
a hydrogen,
a $C_1$ to $C_6$ alkyl,
a haloalkyl,
a haloalkoxy, or
a —$COR_x$ group, where $R_x$ is as defined above,
and where $R_r$ is:
a $C_6$ to $C_8$ aryl optionally substituted with:

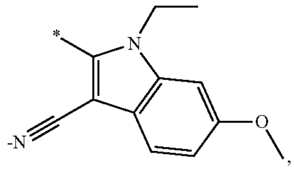
, a $C_1$ to $C_6$ alkyl,
a haloalkyl,
a —$OR_s$ group, where $R_s$ is a $C_6$ to $C_8$ aryl, or
a —$COOR_x$ group, where $R_x$ is as defined above,
a $C_1$ to $C_6$ alkyl optionally substituted with one or more of the following:
a halogen,
an alkylene,
a $C_6$ to $C_8$ aryl, or
a —$COOR_x$ group, where $R_x$ is as defined above,
a —$COOR_x$ group, where $R_x$ is as defined above,
a —$NR_tCOOR_u$ group, where $R_u$ is:
a $C_1$ to $C_{12}$ alkyl, optionally substituted with:
a $C_6$ to $C_8$ aryl optionally substituted with a $C_1$ to $C_6$ alkyl or an alkoxy,
an alkylene,
an alkoxy,
an alkyne,
a halogen, or
a 5 or 6 membered heterocycle,
a $C_6$ to $C_8$ aryl, optionally substituted with:
an alkoxy,
a halogen, or
a $C_1$ to $C_6$ alkyl, or
a 5 or 6 membered heterocycle, and $R_t$ is:
a hydrogen,
a $C_1$ to $C_6$ alkyl,
a —$COR_x$ group, where $R_x$ is as defined above,
a haloalkyl, or
a haloalkoxy,
a —$NR_vSO_2R_w$ group, where $R_v$ is:
a hydrogen,
a —$COR_x$, where $R_x$ is as defined above, or
a $C_1$ to $C_6$ alkyl, optionally substituted with:
a halogen,
a —$COR_x$ group, where $R_x$ is as defined above,
a —$OCOR_x$ group, where $R_x$ is as defined above,
a hydroxyl,
a hydroxyl, or
an alkoxy,
and where $R_w$ is:
a $C_1$ to $C_6$ alkyl optionally substituted with:
a halogen,
a haloalkyl,
a $C_6$ to $C_8$ aryl, or
a 5 or 6 membered heterocycle,
a $C_2$ to $C_6$ alkylene,
an alkyl- or dialkyl-amino optionally substituted with a halogen,
a 5 or 6 membered heterocycle, or
a 5 or 6 membered heteroaryl optionally substituted with:
a $C_1$ to $C_6$ alkyl,
a 5 or 6 membered heterocycle, or

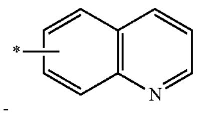

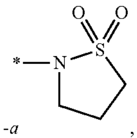
-a ,
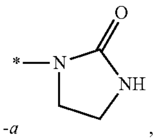
-a ,
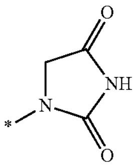
-a ,
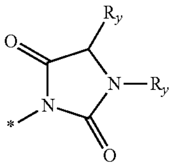
-a , optionally substituted with a $C_1$ to $C_6$ alkyl, where $R_y$ is a $C_1$ to $C_6$ alkyl or hydrogen,

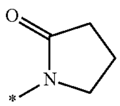
-a ,
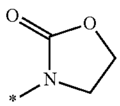
-a ,
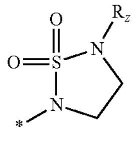
-a , where $R_z$ is hydrogen or a $C_1$ to $C_6$ alkyl, optionally substituted with a $C_6$ to $C_8$ aryl,
a —$SR_x$ group, where $R_x$ is as defined above,
a —$SO_2R_{aa}$ group, where $R_{aa}$ is:
a $C_1$ to $C_6$ alkyl,
an amino group,
an alkyl- or dialkyl-amino group optionally substituted with a hydroxy or a —$COOR_x$ group, where $R_x$ is as defined above,
a 5 or 6 membered heteroaryl,
a $C_6$ to $C_8$ aryl, or
a —$NHR_{bb}$ group, where $R_{bb}$ is:

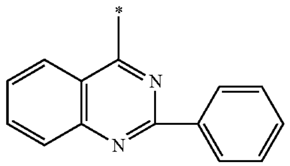
,
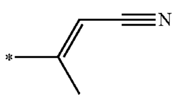
, a —C(=S)$NH_2$ group, or
a —$PO(OR_x)_2$, where $R_x$ is as defined above;

-a
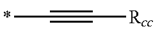

$R_{cc}$ group, where $R_{cc}$ is:
a naphthalene,
a 5 or 6 membered heteroaryl,

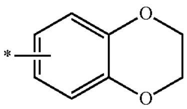
-a , a $C_6$ to $C_8$ aryl, optionally substituted with one or more of the following:
an alkoxy,
an hydroxy,
a halogen,
a $C_1$ to $C_6$ alkyl, optionally substituted with a cyano group,
an amino optionally substituted with one or more $C_1$ to $C_6$ alkyls,
a —$NHPOR_xR_x$, where $R_x$ is as defined above,
a —$NR_{ee}CONR_{ff}R_{ff}$ group, where $R_{ee}$ is a hydrogen or a $C_1$ to $C_6$ alkyl, optionally substituted with a halogen, and $R_{ff}$ is:
a hydrogen,
a haloalkyl,
a haloalkoxy,
a $C_1$ to $C_6$ alkyl, or
a —$COR_x$, where $R_x$ is as defined above,
a —$NR_{gg}COR_{hh}$ group, where $R_{hh}$ is:
a hydrogen,
a $C_1$ to $C_6$ alkyl optionally substituted with:
an alkoxy,
a halogen, or
an amino optionally substituted with one or more $C_1$ to $C_6$ alkyls, an amino optionally substituted with one or more $C_1$ to $C_6$ alkyls,
where the alkyls are optionally substituted with a halogen,
a 5 or 6 membered heterocycle,
a 5 or 6 membered heteroaryl,
and $R_{gg}$ is:
a hydrogen,
a $C_1$ to C 6 alkyl,
a haloalkyl,
a haloalkoxy, or
a —$COR_x$ group, where $R_x$ is as defined above,
a haloalkyl,
5 or 6 membered heterocycle groups,
an amino optionally substituted with one or more $C_1$ to $C_6$ alkyls,
a —$NR_{ii}SO_2R_x$ group, where $R_x$ is as defined above, and $R_{ii}$ is:
a hydrogen,
a $C_1$ to $C_6$ alkyl,
a haloalkyl,
a haloalkoxy,
a —$COR_x$ group, where $R_x$ is as defined above;

Z is:
a hydrogen;
a $C_1$ to $C_6$ alkyl optionally substituted with:
an alkoxy,
one or more halogens, or
a $C_6$ to $C_8$ aryl;
a $C_2$ to $C_6$ alkylene;
a $C_6$ to $C_8$ aryl optionally substituted with an alkoxy or one or more $C_1$ to $C_6$ alkyls;
a —$COOR_x$ group, where $R_x$ is as defined above; or

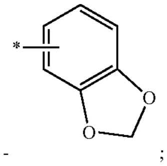
;

R is a hydrogen, a halogen or an alkoxy;

$R_1$ is:
a hydrogen;
a hydroxy;
a halogen;
a haloalkyl;
a nitro group;
a 5 or 6 membered heteroaryl;
a 5 or 6 membered heterocycle;
an alkoxy optionally substituted with:
one or more halogens,
a $C_6$ to $C_8$ aryl, or
a 5 or 6 membered heterocycle;
a $C_6$ to $C_8$ aryl optionally substituted with an alkoxy;
a —$COR_x$ group, where $R_x$ is as defined above;
a $C_1$ to $C_6$ alkyl optionally substituted with a dialkyl-amino or a 5 or 6 membered heterocycle; or
$R_1$ joins together with $R_2$ to form:

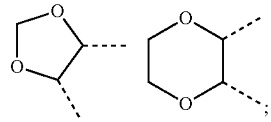
;

$R_2$ is:
a nitro group;
a hydrogen;
a halogen;
a hydroxy group;
a $C_1$ to $C_6$ alkyl group, optionally substituted with one or more halogens;
an amino group;
an alkoxy group optionally substituted with:
one or more halogens,
an —$OCOR_x$ group, where $R_x$ is as defined above,
a dialkyl-amino optionally substituted with an alkoxy,
a 5 or 6 membered heterocycle group optionally substituted with a $C_1$ to $C_6$ alkyl,
a 5 or 6 membered heteroaryl group, or
a $C_6$ to $C_8$ aryl group;
a —$COOR_x$ group, where $R_x$ is as defined above;
a haloalkyl;
an amide group optionally substituted with:
a hydroxy group, or
a $C_6$ to $C_8$ aryl;
a 5 or 6 membered heteroaryl;
a —$OCOR_x$ group, where $R_x$ is as defined above;
a —$NHCOR_{jj}$ group, where $R_{jj}$ is:
an alkoxy, or
an amino optionally substituted with one or more $C_1$ to $C_6$ alkyls;
a —$OR_{kk}$ group, where $R_{kk}$ is a 5 to 6 membered heteroaryl;
a —$NHSO_2R_x$ group, where $R_x$ is as defined above; or
$R_2$ joins together with $R_1$ to form:

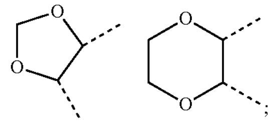
;

$R_3$ is:
a hydrogen; or
$CH_2OCOR_x$, and $R_x$ is as defined above;

or a pharmaceutically acceptable salt thereof, a pharmaceutically acceptable excipient, and optionally one or more compound known in the art to affect IRES activity.

Embodiment 30

The pharmaceutical composition of Embodiment 29, wherein said one or more compound known in the art to affect IRES activity affects IRES mediated translation of the single ORF encoding the polyprotein.

Embodiment 31

A method for affecting viral IRES activity in a subject infected with a virus, comprising administering to said subject one or more compound having the following formula:

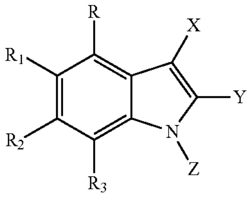

wherein:

X is:

hydrogen;

a nitro group;

a cyano group;

a —$COR_a$ group, where $R_a$ is:

a $C_1$ to $C_6$ alkyl, a $C_6$ to $C_8$ aryl optionally substituted with an alkoxy or a halogen, or a dialkyl-amino;

a —$COOR_x$ group, where $R_x$ is a $C_1$ to $C_6$ alkyl;

a formyl group;

a $C_6$ to $C_8$ aryl optionally substituted with an alkoxy; or a 5 or 6-membered heteroaryl optionally substituted with:

a $C_1$ to $C_6$ alkyl, a $C_6$ to $C_8$ aryl optionally substituted with an alkoxy or one or more halogens, or a 5 to 6 membered heteroaryl;

Y is:

a hydrogen;

a haloalkyl;

a halogen;

an amino optionally substituted with one or more $C_1$ to $C_6$ alkyls;

a benzofuran;

a benzothiophene;

a dibenzofuran;

a dibenzothiophene;

a benzothiazole;

a naphthalene;

an indole, optionally substituted on the nitrogen with a $C_1$ to $C_6$ alkyl;

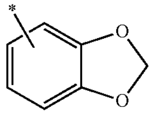 ; 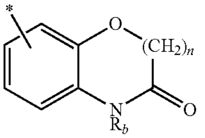 , where $R_b$ is a hydrogen or a $C_1$ to $C_6$ alkyl, and n is 0 or 1;

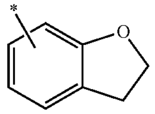 ;

where $R_c$ is a hydrogen, a —$CONHR_x$, where $R_x$ is as defined above, or an —$SO_2R_x$, where $R_x$ is as defined above; or

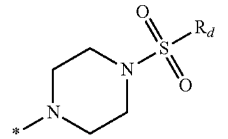 , where $R_d$ is a $C_1$ to $C_6$ alkyl or a $C_6$ to $C_8$ aryl;

a —$NHCOR_e$ group, where $R_e$ is:

a $C_1$ to $C_6$ alkyl;

a $C_6$ to $C_8$ aryl optionally substituted with:

a $C_1$ to $C_6$ alkyl, an alkoxy, a cyano group, a nitro group, or a halogen;

a —$NHCOOR_x$ group, where $R_x$ is as defined above;

a —$CH_2O$—$R_f$ group, where $R_f$ is a $C_6$ to $C_8$ aryl;

a —$NR_gR_h$ group, where $R_g$ is a $C_1$ to $C_6$ alkyl or a hydrogen and $R_h$ is a $C_6$ to $C_8$ aryl optionally substituted with an alkoxy;

a $C_1$ to $C_6$ alkyl;

a 5 or 6 membered heteroaryl, optionally substituted with:

a $C_1$ to $C_6$ alkyl, optionally substituted with a $C_6$ to $C_8$ aryl, a $C_6$ to $C_8$ aryl, optionally substituted with —$COOR_x$, where $R_x$ is as defined above, or an amino group;

a 5 or 6 membered heterocycle optionally substituted with:

a —$COOR_x$ group, where $R_x$ is as defined above, or a —$NHCOOR_x$ group, where $R_x$ is as defined above;

a $C_6$ to $C_8$ aryl, optionally substituted with one or more of the following:

an alkoxy, optionally substituted with:

an alkoxy, a hydroxy, one or more halogens, a 5 or 6 membered heterocycle, optionally substituted with:

a $C_1$ to $C_6$ alkyl, or a hydroxy, an amino group optionally substituted with one or more $C_1$ to $C_6$ alkyls, a —$NR_iSO_2R_x$ group, where $R_x$ is as defined above and $R_i$ is:

a hydrogen, a $C_1$ to $C_6$ alkyl, a —$COR_x$ group, where $R_x$ is as defined above, a haloalkyl, or a haloalkoxy, a —$NR_jCOR_k$ group, where $R_k$ is:

a $C_1$ to $C_6$ alkyl, a hydrogen, or an amino optionally substituted with one or more $C_1$ to $C_6$ alkyls, and $R_j$ is:

a hydrogen, a $C_1$ to $C_6$ alkyl, a —$COR_x$ group, where $R_x$ is as defined above, a haloalkyl, or a haloalkoxy, a —$N{=}N^+{=}N^-$ group, or a —$COR_l$, where $R_l$ is a 5 or 6 membered heterocycle optionally substituted with a hydroxy, an amino optionally substituted with one or more $C_1$ to $C_6$ alkyls,
a nitro group,
a $C_1$ to $C_6$ alkyl group, optionally substituted with:
a —$NHSO_2R_x$ group, where $R_x$ is as defined above, or
a —$NR_xSO_2R_x$ group, where $R_x$ is as defined above,
a haloalkoxy,
a halogen,
a hydroxy,
a —$COOR_x$ group, where $R_x$ is as defined above,
a —$COR_m$ group, where $R_m$ is:
an amino optionally substituted with one or more $C_1$ to $C_6$ alkyls, where the $C_1$ to $C_6$ alkyls are optionally substituted with:
a hydroxy
a 5 or 6 membered heterocycle,
an amino optionally substituted with one or more $C_1$ to $C_6$ alkyls,
an alkoxy,
a 3 to 7 membered heterocycle, optionally substituted with a $C_1$ to $C_6$ alkyl, optionally substituted with a dialkyl-amino,
a —$NHR_n$ group, where $R_n$ is:
a —$CH_2CONH_2$, or
a $C_6$ to $C_8$ aryl optionally substituted with:
an alkyl,
one or more halogens,
a nitro group, or
one or more alkoxys,
a —$NR_oCOR_p$ group, where $R_p$ is:
a $C_1$ to $C_6$ alkyl optionally substituted with:
a halogen,
an alkoxy, or
a $C_6$ to $C_8$ aryl,
a 5 or 6 membered heterocycle,
a $C_6$ to $C_8$ aryl, optionally substituted with a halogen,
a 5 or 6 membered heteroaryl optionally substituted with one or more $C_1$ to $C_6$ alkyls,
a hydrogen,

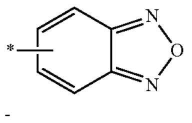

or

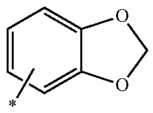

, or
and where $R_o$ is:
a hydrogen,
a $C_1$ to $C_6$ alkyl,
a —$COR_x$ group, where $R_x$ is as defined above,
a haloalkyl, or
a haloalkoxy,
a —$NR_qCONR_qR_r$ group, where $R_q$ is:
a hydrogen,
a $C_1$ to $C_6$ alkyl,
a haloalkyl,
a haloalkoxy, or
a —$COR_x$ group, where $R_x$ is as defined above,
and where $R_r$ is:
a $C_6$ to $C_8$ aryl optionally substituted with:

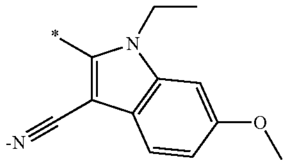

, a $C_1$ to $C_6$ alkyl,
a haloalkyl,
a —$OR_s$ group, where $R_s$ is a $C_6$ to $C_8$ aryl, or
a —$COOR_x$ group, where $R_x$ is as defined above,
a $C_1$ to $C_6$ alkyl optionally substituted with one or more of the following:
a halogen,
an alkylene,
a $C_6$ to $C_8$ aryl, or
a —$COOR_x$ group, where $R_x$ is as defined above,
a —$COOR_x$ group, where $R_x$ is as defined above,
a —$NR_tCOOR_u$ group, where $R_u$ is:
a $C_1$ to $C_{12}$ alkyl, optionally substituted with:
a $C_6$ to $C_8$ aryl optionally substituted with a $C_1$ to $C_6$ alkyl or an alkoxy,
an alkylene,
an alkoxy,
an alkyne,
a halogen, or
a 5 or 6 membered heterocycle,
a $C_6$ to $C_8$ aryl, optionally substituted with:
an alkoxy,
a halogen, or
a $C_1$ to $C_6$ alkyl, or
a 5 or 6 membered heterocycle,
and $R_t$ is:
a hydrogen,
a $C_1$ to $C_6$ alkyl,
a —$COR_x$ group, where $R_x$ is as defined above,
a haloalkyl, or
a haloalkoxy,
a —$NR_vSO_2R_w$ group, where $R_v$ is:
a hydrogen,
a —$COR_x$, where $R_x$ is as defined above, or
a $C_1$ to $C_6$ alkyl, optionally substituted with:
a halogen,
a —$COR_x$ group, where $R_x$ is as defined above,
a —$OCOR_x$ group, where $R_x$ is as defined above,
a hydroxyl,
a hydroxyl, or
an alkoxy,
and where $R_w$ is:
a $C_1$ to $C_6$ alkyl optionally substituted with:
a halogen,
a haloalkyl,
a $C_6$ to $C_8$ aryl, or
a 5 or 6 membered heterocycle,
a $C_2$ to $C_6$ alkylene,
an alkyl- or dialkyl-amino optionally substituted with a halogen,
a 5 or 6 membered heterocycle, or
a 5 or 6 membered heteroaryl optionally substituted with:
a $C_1$ to $C_6$ alkyl,
a 5 or 6 membered heterocycle, or

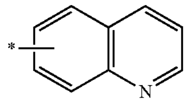

-

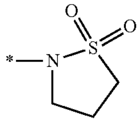

-a ,

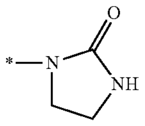

-a ,

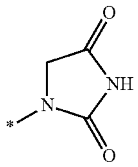

-a ,

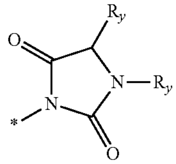

-a , optionally substituted with a $C_1$ to $C_6$ alkyl, where $R_y$ is a $C_1$ to $C_6$ alkyl or hydrogen,

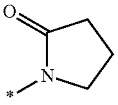

-a ,

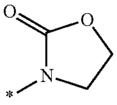

-a ,

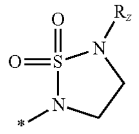

-a , where $R_z$ is hydrogen or a $C_1$ to $C_6$ alkyl, optionally substituted with a $C_6$ to $C_8$ aryl, a —$SR_x$ group, where $R_x$ is as defined above, a —$SO_2R_{aa}$ group, where $R_{aa}$ is:

a $C_1$ to $C_6$ alkyl, an amino group, an alkyl- or dialkyl-amino group optionally substituted with a hydroxy or a —$COOR_x$ group, where $R_x$ is as defined above, a 5 or 6 membered heteroaryl, a $C_6$ to $C_8$ aryl, or a —$NHR_{bb}$ group, where $R_{bb}$ is:

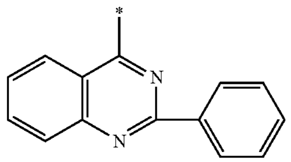

- ,

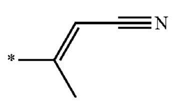

- , a —C(=S)$NH_2$ group, or a —$PO(OR_x)_2$, where $R_x$ is as defined above;

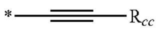

-a group, where $W_{cc}$ is:

a naphthalene, a 5 or 6 membered heteroaryl,

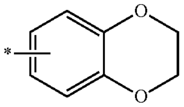

-a , a $C_6$ to $C_8$ aryl, optionally substituted with one or more of the following:

an alkoxy, an hydroxy, a halogen, a $C_1$ to $C_6$ alkyl, optionally substituted with a cyano group, an amino optionally substituted with one or more $C_1$ to $C_6$ alkyls, a —$NHPOR_xR_x$, where $R_x$ is as defined above, a —$NR_{ee}CONR_{ff}R_{ff}$ group, where $R_{ee}$ is a hydrogen or a $C_1$ to $C_6$ alkyl, optionally substituted with a halogen, and $R_{ff}$ is:

a hydrogen, a haloalkyl, a haloalkoxy, a $C_1$ to $C_6$ alkyl, or a —$COR_x$, where $R_x$ is as defined above, a —$NR_{gg}COR_{hh}$ group, where $R_{hh}$ is:

a hydrogen, a $C_1$ to $C_6$ alkyl optionally substituted with:

an alkoxy, a halogen, or an amino optionally substituted with one or more $C_1$ to $C_6$ alkyls, an amino optionally substituted with one or more $C_1$ to $C_6$ alkyls, where the alkyls are optionally substituted with a halogen, a 5 or 6 membered heterocycle, a 5 or 6 membered heteroaryl, and $R_{gg}$ is:

a hydrogen, a $C_1$ to $C_6$ alkyl, a haloalkyl, a haloalkoxy, or a —$COR_x$ group, where $R_x$ is as defined above, a haloalkyl, 5 or 6 membered heterocycle groups, an amino optionally substituted with one or more $C_1$ to $C_6$ alkyls, a —$NR_{ii}SO_2R_x$ group, where $R_x$ is as defined above, and $R_{ii}$ is:

a hydrogen, a $C_1$ to $C_6$ alkyl, a haloalkyl, a haloalkoxy, a —$COR_x$ group, where $R_x$ is as defined above;

Z is:

a hydrogen;

a $C_1$ to $C_6$ alkyl optionally substituted with:

an alkoxy, one or more halogens, or a $C_6$ to $C_8$ aryl;

a $C_2$ to $C_6$ alkylene;

a $C_6$ to $C_8$ aryl optionally substituted with an alkoxy or one or more $C_1$ to $C_6$ alkyls;

a —$COOR_x$ group, where $R_x$ is as defined above; or

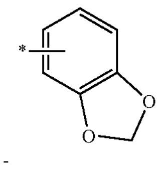

;

R is a hydrogen, a halogen or an alkoxy;

$R_1$ is:

a hydrogen;

a hydroxy;

a halogen;

a haloalkyl;

a nitro group;

a 5 or 6 membered heteroaryl;

a 5 or 6 membered heterocycle;

an alkoxy optionally substituted with:

one or more halogens, a $C_6$ to $C_8$ aryl, or a 5 or 6 membered heterocycle;

a $C_6$ to $C_8$ aryl optionally substituted with an alkoxy;

a —$COR_x$ group, where $R_x$ is as defined above;

a $C_1$ to $C_6$ alkyl optionally substituted with a dialkyl-amino or a 5 or 6 membered heterocycle; or $R_1$ joins together with $R_2$ to form:

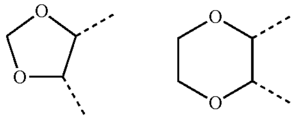

;

$R_2$ is:

a nitro group;

a hydrogen;

a halogen;

a hydroxy group;

a $C_1$ to $C_6$ alkyl group, optionally substituted with one or more halogens;

an amino group;

an alkoxy group optionally substituted with:

one or more halogens, an —$OCOR_x$ group, where $R_x$ is as defined above, a dialkyl-amino optionally substituted with an alkoxy, a 5 or 6 membered heterocycle group optionally substituted with a $C_1$ to $C_6$ alkyl, a 5 or 6 membered heteroaryl group, or a $C_6$ to $C_8$ aryl group;

a —$COOR_x$ group, where $R_x$ is as defined above;

a haloalkyl;

an amide group optionally substituted with:

a hydroxy group, or a $C_6$ to $C_8$ aryl;

a 5 or 6 membered heteroaryl;

a —$OCOR_x$ group, where $R_x$ is as defined above;

a —$NHCOR_{jj}$ group, where $R_{jj}$ is:

an alkoxy, or an amino optionally substituted with one or more $C_1$ to $C_6$ alkyls;

a —$OR_{kk}$ group, where $R_{kk}$ is a 5 to 6 membered heteroaryl;

a —$NHSO_2R_x$ group, where $R_x$ is as defined above; or $R_2$ joins together with $R_1$ to form:

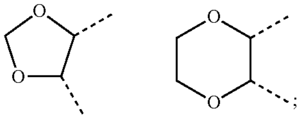

;

$R_3$ is:

a hydrogen; or $CH_2OCOR_x$, and $R_x$ is as defined above;

or a pharmaceutically acceptable salt thereof, and a pharmaceutically acceptable excipient and optionally one or more compound known in the art to affect IRES activity.

Embodiment 32

The method of Embodiment 31, wherein said compound known in the art to affect IRES activity affects IRES mediated translation of the single ORF encoding the polyprotein.

Embodiment 33

A pharmaceutical composition for affecting viral IRES activity in a subject infected with a virus, comprising one or more compound having the following formula, in an amount effective for affecting viral IRES activity:

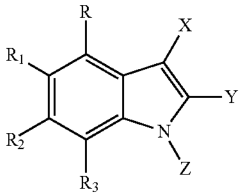

wherein:

X is:

hydrogen;

a nitro group;

a cyano group;

a —$COR_a$ group, where $R_a$ is:

a $C_1$ to $C_6$ alkyl, a $C_6$ to $C_8$ aryl optionally substituted with an alkoxy or a halogen, or a dialkyl-amino;

a —$COOR_x$ group, where $R_x$ is a $C_1$ to $C_6$ alkyl;

a formyl group;

a $C_6$ to $C_8$ aryl optionally substituted with an alkoxy; or a 5 or 6-membered heteroaryl optionally substituted with:

a $C_1$ to $C_6$ alkyl, a $C_6$ to $C_8$ aryl optionally substituted with an alkoxy or one or more halogens, or a 5 to 6 membered heteroaryl;

Y is:

a hydrogen;

a haloalkyl;

a halogen;

an amino optionally substituted with one or more $C_1$ to $C_6$ alkyls;

a benzofuran;

a benzothiophene;

a dibenzofuran;

a dibenzothiophene;
a benzothiazole;
a naphthalene;
an indole, optionally substituted on the nitrogen with a $C_1$ to $C_6$ alkyl;

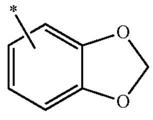
;
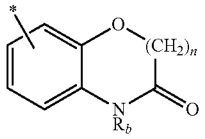
, where $R_b$ is a hydrogen or a $C_1$ to $C_6$ alkyl, and n is 0 or 1;

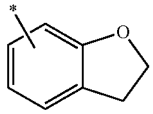
;
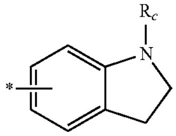
, where $R_c$ is a hydrogen, a —CONH$R_x$, where $R_x$ is as defined above, or an —$SO_2R_x$, where $R_x$ is as defined above; or

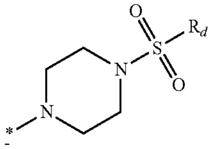
, where $R_d$ is a $C_1$ to $C_6$ alkyl or a $C_6$ to $C_8$ aryl;
a —NHCO$R_e$ group, where $R_e$ is:
a $C_1$ to $C_6$ alkyl;
a $C_6$ to $C_8$ aryl optionally substituted with:
a $C_1$ to $C_6$ alkyl,
an alkoxy,
a cyano group,
a nitro group, or
a halogen;
a —NHCOO$R_x$ group, where $R_x$ is as defined above;
a —$CH_2$O—$R_f$ group, where $R_f$ is a $C_6$ to $C_8$ aryl;
a —N$R_g R_h$ group, where $R_g$ is a $C_1$ to $C_6$ alkyl or a hydrogen and $R_h$ is a $C_6$ to $C_8$ aryl optionally substituted with an alkoxy;
a $C_1$ to $C_6$ alkyl;
a 5 or 6 membered heteroaryl, optionally substituted with:
a $C_1$ to $C_6$ alkyl, optionally substituted with a $C_6$ to $C_8$ aryl,
a $C_6$ to $C_8$ aryl, optionally substituted with —COO$R_x$, where $R_x$ is as defined above, or
an amino group;
a 5 or 6 membered heterocycle optionally substituted with:
a —COO$R_x$ group, where $R_x$ is as defined above, or
a —NHCOO$R_x$ group, where $R_x$ is as defined above;
a $C_6$ to $C_8$ aryl, optionally substituted with one or more of the following:
an alkoxy, optionally substituted with:
an alkoxy,
a hydroxy,
one or more halogens,
a 5 or 6 membered heterocycle, optionally substituted with:
a $C_1$ to $C_6$ alkyl, or
a hydroxy,
an amino group optionally substituted with one or more $C_1$ to $C_6$ alkyls,
a —N$R_i SO_2 R_x$ group, where $R_x$ is as defined above and $R_i$ is:
a hydrogen,
a $C_1$ to $C_6$ alkyl,
a —CO$R_x$ group, where $R_x$ is as defined above,
a haloalkyl, or
a haloalkoxy,
a —N$R_j$CO$R_k$ group, where $R_k$ is:
a $C_1$ to $C_6$ alkyl,
a hydrogen, or
an amino optionally substituted with one or more $C_1$ to $C_6$ alkyls,
and $R_j$ is:
a hydrogen,
a $C_1$ to $C_6$ alkyl,
a —CO$R_x$ group, where $R_x$ is as defined above,
a haloalkyl, or
a haloalkoxy,
a —N═$N^+$═$N^-$ group, or
a —CO$R_l$, where $R_l$ is a 5 or 6 membered heterocycle optionally substituted with a hydroxy,
an amino optionally substituted with one or more $C_1$ to $C_6$ alkyls,
a nitro group,
a $C_1$ to $C_6$ alkyl group, optionally substituted with:
a —NH$SO_2R_x$ group, where $R_x$ is as defined above, or
a —N$R_x SO_2 R_x$ group, where $R_x$ is as defined above,
a haloalkoxy,
a halogen,
a hydroxy,
a —COO$R_x$ group, where $R_x$ is as defined above,
a —CO$R_m$ group, where $R_m$ is:
an amino optionally substituted with one or more $C_1$ to $C_6$ alkyls, where the $C_1$ to $C_6$ alkyls are optionally substituted with:
a hydroxy
a 5 or 6 membered heterocycle,
an amino optionally substituted with one or more $C_1$ to $C_6$ alkyls,
an alkoxy,
a 3 to 7 membered heterocycle, optionally substituted with a $C_1$ to $C_6$ alkyl, optionally substituted with a dialkyl-amino,
a —NH$R_n$ group, where $R_n$ is:
a —$CH_2CONH_2$, or
a $C_6$ to $C_8$ aryl optionally substituted with:
an alkyl,
one or more halogens,
a nitro group, or
one or more alkoxys,
a —N$R_o$CO$R_p$ group, where $R_p$ is:
a $C_1$ to $C_6$ alkyl optionally substituted with:
a halogen,
an alkoxy, or
a $C_6$ to $C_8$ aryl,
a 5 or 6 membered heterocycle,
a $C_6$ to $C_8$ aryl, optionally substituted with a halogen,
a 5 or 6 membered heteroaryl optionally substituted with one or more $C_1$ to $C_6$ alkyls,
a hydrogen,

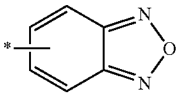

- or

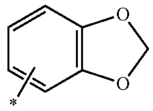

, and where $R_o$ is:

a hydrogen, a $C_1$ to $C_6$ alkyl, a —$COR_x$ group, where $R_x$ is as defined above, a haloalkyl, or a haloalkoxy, a —$NR_qCONR_qR_r$ group, where $R_q$ is:

a hydrogen, a $C_1$ to $C_6$ alkyl, a haloalkyl, a haloalkoxy, or a —$COR_x$ group, where $R_x$ is as defined above, and where $R_r$ is:

a $C_6$ to $C_8$ aryl optionally substituted with:

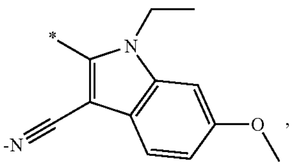

, a $C_1$ to $C_6$ alkyl, a haloalkyl, a —$OR_s$ group, where $R_s$ is a $C_6$ to $C_8$ aryl, or a —$COOR_x$ group, where $R_x$ is as defined above, a $C_1$ to $C_6$ alkyl optionally substituted with one or more of the following:

a halogen, an alkylene, a $C_6$ to $C_8$ aryl, or a —$COOR_x$ group, where $R_x$ is as defined above, a —$COOR_x$ group, where $R_x$ is as defined above, a —$NR_tCOOR_u$ group, where $R_u$ is:

a $C_1$ to $C_{12}$ alkyl, optionally substituted with:

a $C_6$ to $C_8$ aryl optionally substituted with a $C_1$ to $C_6$ alkyl or an alkoxy, an alkylene, an alkoxy, an alkyne, a halogen, or a 5 or 6 membered heterocycle, a $C_6$ to $C_8$ aryl, optionally substituted with:

an alkoxy, a halogen, or a $C_1$ to $C_6$ alkyl, or a 5 or 6 membered heterocycle, and $R_t$ is:

a hydrogen, a $C_1$ to $C_6$ alkyl, a —$COR_x$ group, where $R_x$ is as defined above, a haloalkyl, or a haloalkoxy, a —$NR_vSO_2R_w$ group, where $R_v$ is:

a hydrogen, a —$COR_x$, where $R_x$ is as defined above, or a $C_1$ to $C_6$ alkyl, optionally substituted with:

a halogen, a —$COR_x$ group, where $R_x$ is as defined above, a —$OCOR_x$ group, where $R_x$ is as defined above, a hydroxyl, a hydroxyl, or an alkoxy, and where $R_w$ is:

a $C_1$ to $C_6$ alkyl optionally substituted with:

a halogen, a haloalkyl, a $C_6$ to $C_8$ aryl, or a 5 or 6 membered heterocycle, a $C_2$ to $C_6$ alkylene, an alkyl- or dialkyl-amino optionally substituted with a halogen, a 5 or 6 membered heterocycle, or a 5 or 6 membered heteroaryl optionally substituted with:

a $C_1$ to $C_6$ alkyl, a 5 or 6 membered heterocycle, or

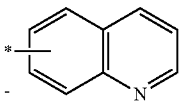

-

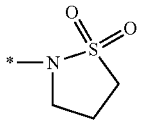

-a ,

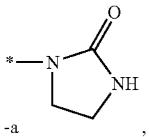

-a ,

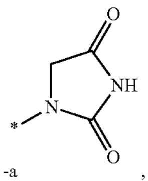

-a ,

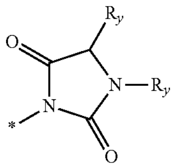

-a , optionally substituted with a $C_1$ to $C_6$ alkyl, where $R_y$ is a $C_1$ to $C_6$ alkyl or hydrogen,

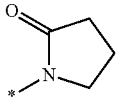

-a ,

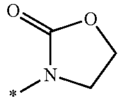

-a ,

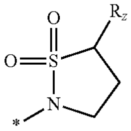

-a , where $R_z$ is hydrogen or a $C_1$ to $C_6$ alkyl, optionally substituted with a $C_6$ to $C_8$ aryl, a —$SR_x$ group, where $R_x$ is as defined above, a —$SO_2R_{aa}$ group, where $R_{aa}$ is:

a $C_1$ to $C_6$ alkyl, an amino group, an alkyl- or dialkyl-amino group optionally substituted with a hydroxy or a —$COOR_x$ group, where $R_x$ is as defined above, a 5 or 6 membered heteroaryl, a $C_6$ to $C_8$ aryl, or a —$NHR_{bb}$ group, where $R_{bb}$ is:

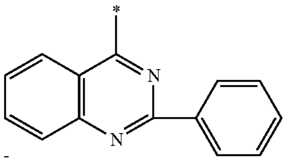,

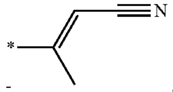, a $—C(=S)NH_2$ group, or a $—PO(OR_x)_2$, where $R_x$ is as defined above;

-a 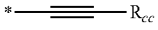

$R_{cc}$ group, where $R_{cc}$ is:

a naphthalene, a 5 or 6 membered heteroaryl,

-a 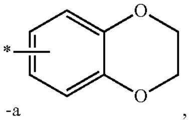, a $C_6$ to $C_8$ aryl, optionally substituted with one or more of the following:

an alkoxy, an hydroxy, a halogen, a $C_1$ to $C_6$ alkyl, optionally substituted with a cyano group, an amino optionally substituted with one or more $C_1$ to $C_6$ alkyls, a $—NHPOR_xR_x$, where $R_x$ is as defined above, a $—NR_{ee}CONR_{ff}R_{ff}$ group, where $R_{ee}$ is a hydrogen or a $C_1$ to $C_6$ alkyl, optionally substituted with a halogen, and $R_{ff}$ is:

a hydrogen, a haloalkyl, a haloalkoxy, a $C_1$ to $C_6$ alkyl, or a $—COR_x$, where $R_x$ is as defined above, a $—NR_{gg}COR_{hh}$ group, where $R_{hh}$ is:

a hydrogen, a $C_1$ to $C_6$ alkyl optionally substituted with:

an alkoxy, a halogen, or an amino optionally substituted with one or more $C_1$ to $C_6$ alkyls, an amino optionally substituted with one or more $C_1$ to $C_6$ alkyls, where the alkyls are optionally substituted with a halogen, a 5 or 6 membered heterocycle, a 5 or 6 membered heteroaryl, and $R_{gg}$ is:

a hydrogen, a $C_1$ to $C_6$ alkyl, a haloalkyl, a haloalkoxy, or a $—COR_x$ group, where $R_x$ is as defined above, a haloalkyl, 5 or 6 membered heterocycle groups, an amino optionally substituted with one or more $C_1$ to $C_6$ alkyls, a $—NR_{ii}SO_2R_x$ group, where $R_x$ is as defined above, and $R_{ii}$ is:

a hydrogen, a $C_1$ to $C_6$ alkyl, a haloalkyl, a haloalkoxy, a $—COR_x$ group, where $R_x$ is as defined above;

Z is:

a hydrogen;

a $C_1$ to $C_6$ alkyl optionally substituted with:

an alkoxy, one or more halogens, or a $C_6$ to $C_8$ aryl;

a $C_2$ to $C_6$ alkylene;

a $C_6$ to $C_8$ aryl optionally substituted with an alkoxy or one or more $C_1$ to $C_6$ alkyls;

a $—COOR_x$ group, where $R_x$ is as defined above; or

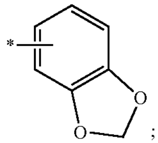;

R is a hydrogen, a halogen or an alkoxy;

$R_1$ is:

a hydrogen;

a hydroxy;

a halogen;

a haloalkyl;

a nitro group;

a 5 or 6 membered heteroaryl;

a 5 or 6 membered heterocycle;

an alkoxy optionally substituted with:

one or more halogens, a $C_6$ to $C_8$ aryl, or a 5 or 6 membered heterocycle;

a $C_6$ to $C_8$ aryl optionally substituted with an alkoxy;

a $—COR_x$ group, where $R_x$ is as defined above;

a $C_1$ to $C_6$ alkyl optionally substituted with a dialkyl-amino or a 5 or 6 membered heterocycle; or $R_1$ joins together with $R_2$ to form:

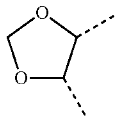 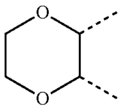;

$R_2$ is:

a nitro group;

a hydrogen;

a halogen;

a hydroxy group;

a $C_1$ to $C_6$ alkyl group, optionally substituted with one or more halogens;

an amino group;

an alkoxy group optionally substituted with:

one or more halogens, an $—OCOR_x$ group, where $R_x$ is as defined above, a dialkyl-amino optionally substituted with an alkoxy, a 5 or 6 membered heterocycle group optionally substituted with a $C_1$ to $C_6$ alkyl, a 5 or 6 membered heteroaryl group, or a $C_6$ to $C_8$ aryl group;

a —$COOR_x$ group, where $R_x$ is as defined above;

a haloalkyl;

an amide group optionally substituted with:

a hydroxy group, or a $C_6$ to $C_8$ aryl;

a 5 or 6 membered heteroaryl;

a —$OCOR_x$ group, where $R_x$ is as defined above;

a —$NHCOR_{jj}$ group, where $R_{jj}$ is:

an alkoxy, or an amino optionally substituted with one or more $C_1$ to $C_6$ alkyls;

a —$OR_{kk}$ group, where $R_{kk}$ is a 5 to 6 membered heteroaryl;

a —$NHSO_2R_x$ group, where $R_x$ is as defined above; or $R_2$ joins together with $R_1$ to form:

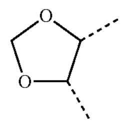 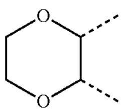 ;

$R_3$ is:

a hydrogen; or

—$CH_2OCOR_x$, and $R_x$ is as defined above;

or a pharmaceutically acceptable salt thereof and a pharmaceutically acceptable excipient.

DETAILED DESCRIPTION OF THE INVENTION

Figure 1:
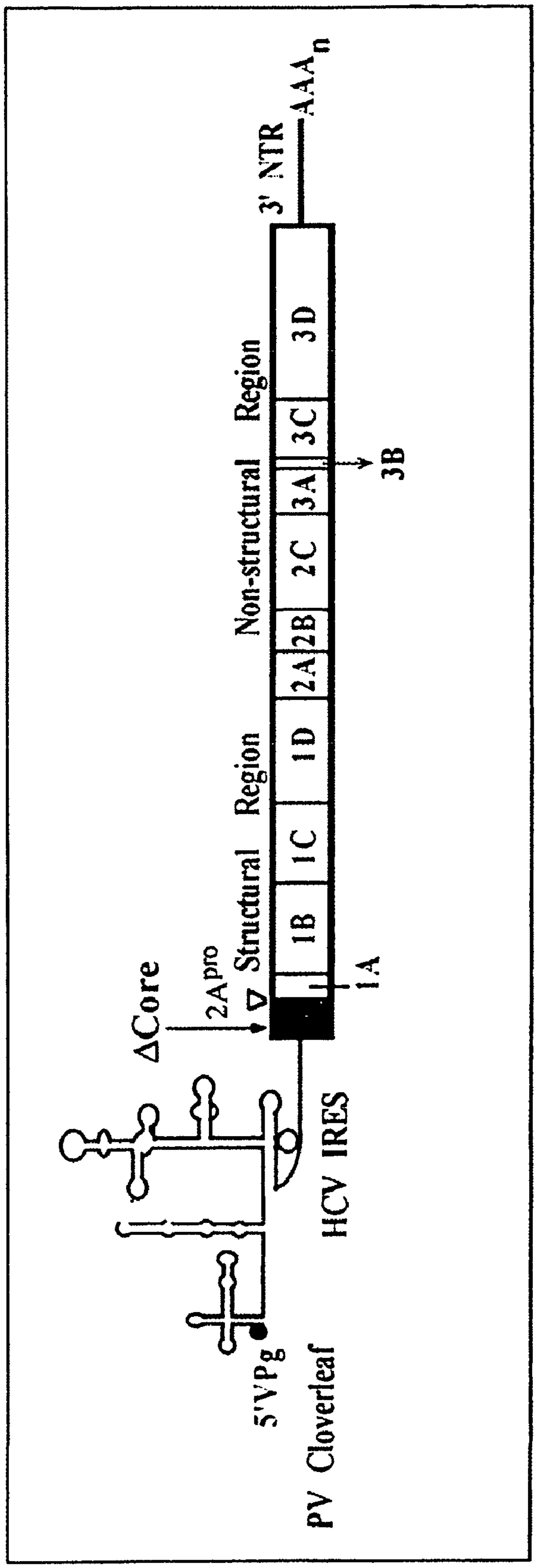
FIG. 1 illustrates the HCV-PV chimera construct. The cloverleaf-like RNA structure of PV, an essential cis-acting replication signal ending with the genome-linked protein VPg, is located at the 5' end of the genome. The solid (HCV) and open (PV) boxes depict open reading frames encoding viral polypeptides. The position of the HCV core fragment (the first 123 amino acids) gene is denoted by A Core. Overall, the HCV_specific sequence in the HCV-PV spans from nucleotides 18 to 710 (139).

In accordance with the present invention, compounds that modify HCV translation have been identified and methods of using these compounds for preventing or treating HCV infection are provided. Without being limited to one theory, it is believed that the compounds of the present invention inhibit IRES-mediated initiation and translation. The HCV IRES directs the translation of a single long ORF encoding a polyprotein that is posttranslationally processed into at least 10 mature viral proteins, including the structural proteins core (putative nucleocapsid), E1 and E2 and the nonstructural (NS) proteins NS2 to NS5B.

A. Compounds of the Invention

In one aspect of the invention, compounds of the invention are provided which are useful for preventing or treating HCV infection.

Preferred compounds of the present invention useful for preventing or treating HCV infection include those of Formula (I) as shown below.

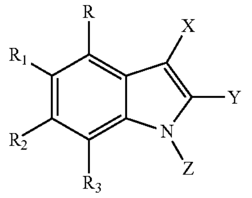

wherein:

X is:

hydrogen;

a nitro group;

a cyano group;

a —$COR_a$ group, where $R_a$ is:

a $C_1$ to $C_6$ alkyl, a $C_6$ to $C_8$ aryl optionally substituted with an alkoxy or a halogen, or a dialkyl-amino;

a —$COOR_x$ group, where $R_x$ is a $C_1$ to $C_6$ alkyl;

a formyl group;

a $C_6$ to $C_8$ aryl optionally substituted with an alkoxy; or a 5 or 6-membered heteroaryl optionally substituted with:

a $C_1$ to $C_6$ alkyl, a $C_6$ to $C_8$ aryl optionally substituted with an alkoxy or one or more halogens, or a 5 to 6 membered heteroaryl;

Y is:

a hydrogen;

a haloalkyl;

a halogen;

an amino optionally substituted with one or more $C_1$ to $C_6$ alkyls;

a benzofuran;

a benzothiophene;

a dibenzofuran;

a dibenzothiophene;

a benzothiazole;

a naphthalene;

an indole, optionally substituted on the nitrogen with a $C_1$ to $C_6$ alkyl;

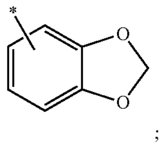 ; 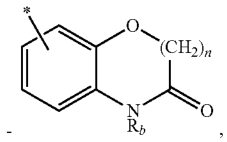 , where $R_b$ is a hydrogen or a $C_1$ to $C_6$ alkyl, and n is 0 or 1;

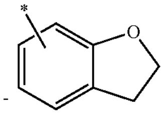 ; 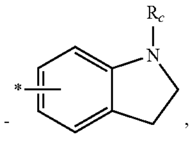 , where $R_c$ is a hydrogen, a —$CONHR_x$, where $R_x$ is as defined above, or an —$SO_2R_x$, where $R_x$ is as defined above; or

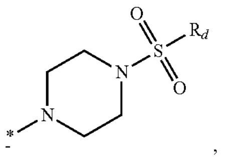

where $R_d$ is a $C_1$ to $C_6$ alkyl or a $C_6$ to $C_8$ aryl;

a —$NHCOR_e$ group, where $R_e$ is:

a $C_1$ to $C_6$ alkyl;

a $C_6$ to $C_8$ aryl optionally substituted with:

a $C_1$ to $C_6$ alkyl, an alkoxy, a cyano group, a nitro group, or a halogen;

a —$NHCOOR_x$ group, where $R_x$ is as defined above;

a —$CH_2O$—$R_f$ group, where $R_f$ is a $C_6$ to $C_8$ aryl;

a —$NR_gR_h$ group, where $R_g$ is a $C_1$ to $C_6$ alkyl or a hydrogen and $R_h$ is a $C_6$ to $C_8$ aryl optionally substituted with an alkoxy;

a $C_1$ to $C_6$ alkyl;

a 5 or 6 membered heteroaryl, optionally substituted with:

a $C_1$ to $C_6$ alkyl, optionally substituted with a $C_6$ to $C_8$ aryl, a $C_6$ to $C_8$ aryl, optionally substituted with —$COOR_x$, where $R_x$ is as defined above, or an amino group;

a 5 or 6 membered heterocycle optionally substituted with:

a —$COOR_x$ group, where $R_x$ is as defined above, or a —$NHCOOR_x$ group, where $R_x$ is as defined above;

a $C_6$ to $C_8$ aryl, optionally substituted with one or more of the following:

an alkoxy, optionally substituted with:

an alkoxy, a hydroxy, one or more halogens, a 5 or 6 membered heterocycle, optionally substituted with:

a $C_1$ to $C_6$ alkyl, or a hydroxy, an amino group optionally substituted with one or more $C_1$ to $C_6$ alkyls, a —$NR_iSO_2R_x$ group, where $R_x$ is as defined above and $R_i$ is:

a hydrogen, a $C_1$ to $C_6$ alkyl, a —$COR_x$ group, where $R_x$ is as defined above, a haloalkyl, or a haloalkoxy, a —$NR_jCOR_k$ group, where $R_k$ is:

a $C_1$ to $C_6$ alkyl, a hydrogen, or an amino optionally substituted with one or more $C_1$ to $C_6$ alkyls, and $R_j$ is:

a hydrogen, a $C_1$ to $C_6$ alkyl, a —$COR_x$ group, where $R_x$ is as defined above, a haloalkyl, or a haloalkoxy, a —$N{=}N^+{=}N^-$ group, or a —$COR_l$, where $R_l$ is a 5 or 6 membered heterocycle optionally substituted with a hydroxy, an amino optionally substituted with one or more $C_1$ to $C_6$ alkyls, a nitro group, a $C_1$ to $C_6$ alkyl group, optionally substituted with:

a —$NHSO_2R_x$ group, where $R_x$ is as defined above, or a —$NR_xSO_2R_x$ group, where $R_x$ is as defined above, a haloalkoxy, a halogen, a hydroxy, a —$COOR_x$ group, where $R_x$ is as defined above, a —$COR_m$ group, where $R_m$ is:

an amino optionally substituted with one or more $C_1$ to $C_6$ alkyls, where the $C_1$ to $C_6$ alkyls are optionally substituted with:

a hydroxy a 5 or 6 membered heterocycle, an amino optionally substituted with one or more $C_1$ to $C_6$ alkyls, an alkoxy, a 3 to 7 membered heterocycle, optionally substituted with a $C_1$ to $C_6$ alkyl, optionally substituted with a dialkyl-amino, a —$NHR_n$ group, where $R_n$ is:

a —$CH_2CONH_2$, or a $C_6$ to $C_8$ aryl optionally substituted with:

an alkyl, one or more halogens, a nitro group, or one or more alkoxys, a —$NR_oCOR_p$ group, where $R_p$ is:

a $C_1$ to $C_6$ alkyl optionally substituted with:

a halogen, an alkoxy, or a $C_6$ to $C_8$ aryl, a 5 or 6 membered heterocycle, a $C_6$ to $C_8$ aryl, optionally substituted with a halogen, a 5 or 6 membered heteroaryl optionally substituted with one or more $C_1$ to $C_6$ alkyls, a hydrogen,

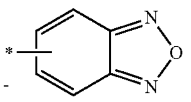
or
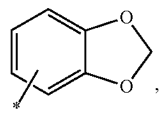
, and where $R_o$ is:

a hydrogen, a $C_1$ to $C_6$ alkyl, a —$COR_x$ group, where $R_x$ is as defined above, a haloalkyl, or a haloalkoxy, a —$NR_qCONR_qR_r$ group, where $R_q$ is:

a hydrogen, a $C_1$ to $C_6$ alkyl, a haloalkyl, a haloalkoxy, or a —$COR_x$ group, where $R_x$ is as defined above, and where $R_r$ is:

a $C_6$ to $C_8$ aryl optionally substituted with:

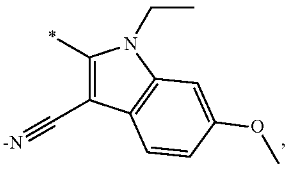

a $C_1$ to $C_6$ alkyl,
a haloalkyl,
a —$OR_s$ group, where $R_s$ is a $C_6$ to $C_8$ aryl, or
a —$COOR_x$ group, where $R_x$ is as defined above,
a $C_1$ to $C_6$ alkyl optionally substituted with one or more of the following:
a halogen,
an alkylene,
a $C_6$ to $C_8$ aryl, or
a —$COOR_x$ group, where $R_x$ is as defined above,
a —$COOR_x$ group, where $R_x$ is as defined above,
a —$NR_tCOOR_u$ group, where $R_u$ is:
a $C_1$ to $C_{12}$ alkyl, optionally substituted with:
a $C_6$ to $C_8$ aryl optionally substituted with a $C_1$ to $C_6$ alkyl or an alkoxy,
an alkylene,
an alkoxy,
an alkyne,
a halogen, or
a 5 or 6 membered heterocycle,
a $C_6$ to $C_8$ aryl, optionally substituted with:
an alkoxy,
a halogen, or
a $C_1$ to $C_6$ alkyl, or
a 5 or 6 membered heterocycle,
and $R_t$ is:
a hydrogen,
a $C_1$ to $C_6$ alkyl,
a —$COR_x$ group, where $R_x$ is as defined above,
a haloalkyl, or
a haloalkoxy,
a —$NR_vSO_2R_w$ group, where $R_v$ is:
a hydrogen,
a —$COR_x$, where $R_x$ is as defined above, or
a $C_1$ to $C_6$ alkyl, optionally substituted with:
a halogen,
a —$COR_x$ group, where $R_x$ is as defined above,
a —$OCOR_x$ group, where $R_x$ is as defined above,
a hydroxyl,
a hydroxyl, or
an alkoxy,
and where $R_w$ is:
a $C_1$ to $C_6$ alkyl optionally substituted with:
a halogen,
a haloalkyl,
a $C_6$ to $C_8$ aryl, or
a 5 or 6 membered heterocycle,
a $C_2$ to $C_6$ alkylene,
an alkyl- or dialkyl-amino optionally substituted with a halogen,
a 5 or 6 membered heterocycle, or
a 5 or 6 membered heteroaryl optionally substituted with:
a $C_1$ to $C_6$ alkyl,
a 5 or 6 membered heterocycle, or

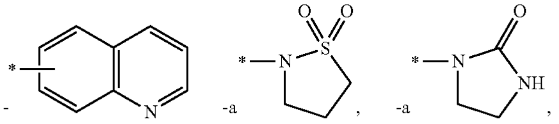

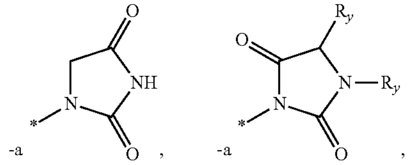

optionally substituted with a $C_1$ to $C_6$ alkyl, where $R_y$ is a $C_1$ to $C_6$ alkyl or hydrogen,

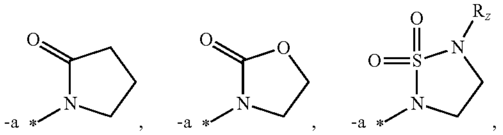

where $R_z$ is hydrogen or a $C_1$ to $C_6$ alkyl, optionally substituted with a $C_6$ to $C_8$ aryl,
a —$SR_x$ group, where $R_x$ is as defined above,
a —$SO_2R_{aa}$ group, where $R_{aa}$ is:
a $C_1$ to $C_6$ alkyl,
an amino group,
an alkyl- or dialkyl-amino group optionally substituted with a hydroxy or a —$COOR_x$ group, where $R_x$ is as defined above,
a 5 or 6 membered heteroaryl,
a $C_6$ to $C_8$ aryl, or
a —$NHR_{bb}$ group, where $R_{bb}$ is:

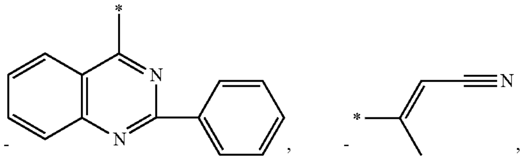

a —C(=S)$NH_2$ group, or
a —$PO(OR_x)_2$, where $R_x$ is as defined above;

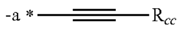

$R_{cc}$ group, where $R_{cc}$ is:
a naphthalene,
a 5 or 6 membered heteroaryl,

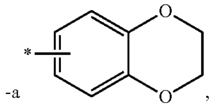

a $C_6$ to $C_8$ aryl, optionally substituted with one or more of the following:
an alkoxy,
an hydroxy, a halogen, a $C_1$ to $C_6$ alkyl, optionally substituted with a cyano group, an amino optionally substituted with one or more $C_1$ to $C_6$ alkyls, a —$NHPOR_xR_x$, where $R_x$ is as defined above, a —$NR_{ee}CONR_{ff}R_{ff}$ group, where $R_{ee}$ is a hydrogen or a $C_1$ to $C_6$ alkyl, optionally substituted with a halogen, and $R_{ff}$ is:

a hydrogen, a haloalkyl, a haloalkoxy, a $C_1$ to $C_6$ alkyl, or a —$COR_x$, where $R_x$ is as defined above, a —$NR_{gg}COR_{hh}$ group, where $R_{hh}$ is:

a hydrogen, a $C_1$ to $C_6$ alkyl optionally substituted with:

an alkoxy, a halogen, or an amino optionally substituted with one or more $C_1$ to $C_6$ alkyls, an amino optionally substituted with one or more $C_1$ to $C_6$ alkyls, where the alkyls are optionally substituted with a halogen, a 5 or 6 membered heterocycle, a 5 or 6 membered heteroaryl, and $R_{gg}$ is:

a hydrogen, a $C_1$ to $C_6$ alkyl, a haloalkyl, a haloalkoxy, or a —$COR_x$ group, where $R_x$ is as defined above, a haloalkyl, 5 or 6 membered heterocycle groups, an amino optionally substituted with one or more $C_1$ to $C_6$ alkyls, a —$NR_{ii}SO_2R_x$ group, where $R_x$ is as defined above, and $R_{ii}$ is:

a hydrogen, a $C_1$ to $C_6$ alkyl, a haloalkyl, a haloalkoxy, a —$COR_x$ group, where $R_x$ is as defined above;

Z is:

a hydrogen;

a $C_1$ to $C_6$ alkyl optionally substituted with:

an alkoxy, one or more halogens, or a $C_6$ to $C_8$ aryl;

a $C_2$ to $C_6$ alkylene;

a $C_6$ to $C_8$ aryl optionally substituted with an alkoxy or one or more $C_1$ to $C_6$ alkyls;

a —$COOR_x$ group, where $R_x$ is as defined above; or

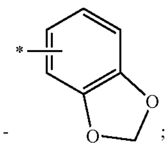

;

R is a hydrogen, a halogen or an alkoxy;

$R_1$ is:

a hydrogen;

a hydroxy;

a halogen;

a haloalkyl;

a nitro group;

a 5 or 6 membered heteroaryl;

a 5 or 6 membered heterocycle;

an alkoxy optionally substituted with:

one or more halogens, a $C_6$ to $C_8$ aryl, or a 5 or 6 membered heterocycle;

a $C_6$ to $C_8$ aryl optionally substituted with an alkoxy;

a —$COR_x$ group, where $R_x$ is as defined above;

a $C_1$ to $C_6$ alkyl optionally substituted with a dialkyl-amino or a 5 or 6 membered heterocycle; or $R_1$ joins together with $R_2$ to form:

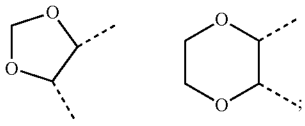

;

$R_2$ is:

a nitro group;

a hydrogen;

a halogen;

a hydroxy group;

a $C_1$ to $C_6$ alkyl group, optionally substituted with one or more halogens;

an amino group;

an alkoxy group optionally substituted with:

one or more halogens, an —$OCOR_x$ group, where $R_x$ is as defined above, a dialkyl-amino optionally substituted with an alkoxy, a 5 or 6 membered heterocycle group optionally substituted with a $C_1$ to $C_6$ alkyl, a 5 or 6 membered heteroaryl group, or a $C_6$ to $C_8$ aryl group;

a —$COOR_x$ group, where $R_x$ is as defined above;

a haloalkyl;

an amide group optionally substituted with:

a hydroxy group, or a $C_6$ to $C_8$ aryl;

a 5 or 6 membered heteroaryl;

a —$OCOR_x$ group, where $R_x$ is as defined above;

a —$NHCOR_{jj}$ group, where $R_{jj}$ is:

an alkoxy, or an amino optionally substituted with one or more $C_1$ to $C_6$ alkyls;

a —$OR_{kk}$ group, where $R_{kk}$ is a 5 to 6 membered heteroaryl;

a —$NHSO_2R_x$ group, where $R_x$ is as defined above; or $R_2$ joins together with $R_1$ to form:

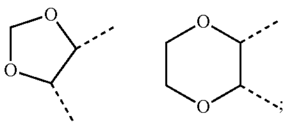

;

$R_3$ is:

a hydrogen; or $CH_2OCOR_x$, and $R_x$ is as defined above;

or a pharmaceutically acceptable salt thereof.

In another preferred embodiment, a compound or a composition of the present invention includes a compound of Formula I, wherein the compound of Formula I is not Compound 1

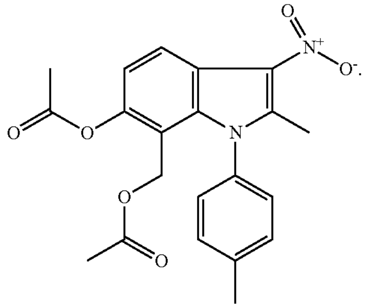

As used herein, the term “alkyl” generally refers to saturated hydrocarbyl radicals of straight or branched configuration, including methyl, ethyl, n-propyl, isopropyl, n-butyl, isobutyl, sec-butyl, tert-butyl, n-pentyl, n-hexyl, n-heptyl, octyl, n-octyl, and the like. In some embodiments, alkyl substituents may be $C_1$ to $C_{12}$, or $C_1$ to $C_8$ or $C_1$ to $C_6$ alkyl groups.

As used herein, “alkylene” generally refers to linear, branched or cyclic alkene radicals having one or more carbon-carbon double bonds, such as $C_2$ to $C_6$ alkylene groups including 3-propenyl.

As used herein, “aryl” refers to a carbocyclic aromatic ring structure. Included in the scope of aryl groups are aromatic rings having from five to twenty carbon atoms. Aryl ring structures include compounds having one or more ring structures, such as mono-, bi-, or tricyclic compounds. Examples of aryl groups that include phenyl, tolyl, anthracenyl, fluorenyl, indenyl, azulenyl, phenanthrenyl (i.e., phenanthrene), and napthyl (i.e., napthalene) ring structures. In certain embodiments, the aryl group may be optionally substituted.

As used herein, “heteroaryl” refers to cyclic aromatic ring structures in which one or more atoms in the ring, the heteroatom(s), is an element other than carbon. Heteroatoms are typically O, S or N atoms. Included within the scope of heteroaryl, and independently selectable, are O, N, and S heteroaryl ring structures. The ring structure may include compounds having one or more ring structures, such as mono-, bi-, or tricyclic compounds. In some embodiments, the heteroaryl groups may be selected from heteroaryl groups that contain two or more heteroatoms, three or more heteroatoms, or four or more heteroatoms. Heteroaryl ring structures may be selected from those that contain five or more atoms, six or more atoms, or eight or more atoms. Examples of heteroaryl ring structures include: acridine, benzimidazole, benzoxazole, benzodioxole, benzofuran, 1,3-diazine, 1,2-diazine, 1,2-diazole, 1,4-diazanaphthalene, furan, furazan, imidazole, indole, isoxazole, isoquinoline, isothiazole, oxazole, purine, pyridazine, pyrazole, pyridine, pyrazine, pyrimidine, pyrrole, quinoline, quinoxaline, thiazole, thiophene, 1,3,5-triazine, 1,2,4-triazine, 1,2,3-triazine, tetrazole and quinazoline.

As used herein, “heterocycle” refers to cyclic ring structures in which one or more atoms in the ring, the heteroatom(s), is an element other than carbon. Heteroatoms are typically O, S or N atoms. Included within the scope of heterocycle, and independently selectable, are O, N, and S heterocycle ring structures. The ring structure may include compounds having one or more ring structures, such as mono-, bi-, or tricyclic compounds. Example of heterocyclo groups include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl or tetrahydrothiopyranyl and the like. In certain embodiments, the heterocycle may optionally be substituted.

As used herein, “alkoxy” generally refers to a group with the structure —O—R, where R is an alkyl group as defined above.

For the purposes of this invention, halo substituents may be independently selected from the halogens such as fluorine, chlorine, bromine, iodine, and astatine. A haloalkyl is an alkyl group, as defined above, substituted with one or more halogens. A haloalkoxy is an alkoxy group, as defined above, substituted with one or more halogens.

For the purposes of this invention, where one or more functionalities encompassing X, Y, Z, R, $R_1$, $R_2$, and $R_3$, are incorporated into a molecule of Formula (I), each functionality appearing at any location within the disclosed compound may be independently selected, and as appropriate, independently substituted. Further, where a more generic substituent is set forth for any position in the molecules of the present invention, it is understood that the generic substituent may be replaced with more specific substituents, and the resulting molecules are within the scope of the molecules of the present invention.

By “substituted” or “optionally substituted” it is meant that the particular substituent may be substituted with a chemical group known to one of skill in the art to be appropriate for the referred-to substituent, unless a chemical group is specifically mentioned.

Exemplary X substituents include the following, where the * indicates the bond of attachment of the scaffold molecule.

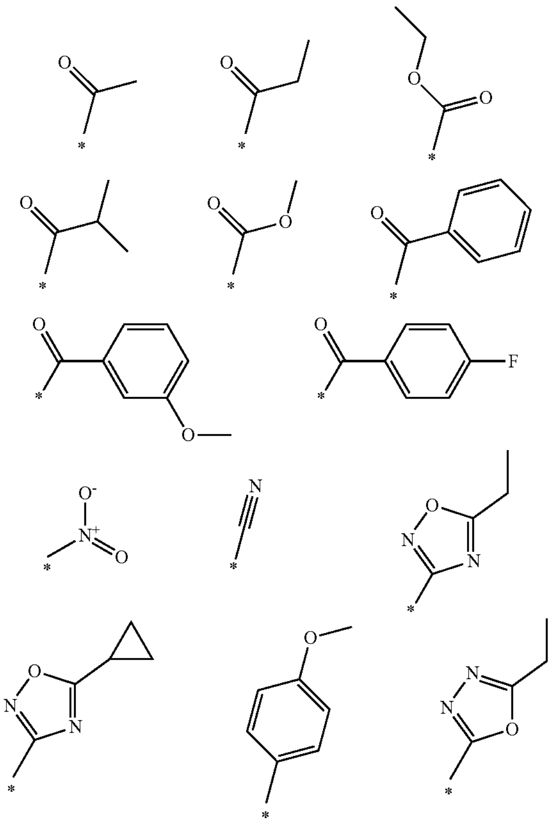

-continued

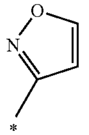 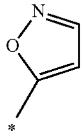 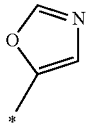

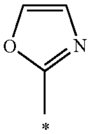 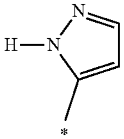 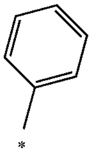

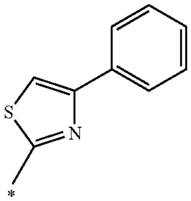 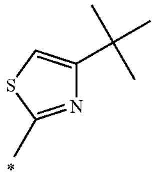

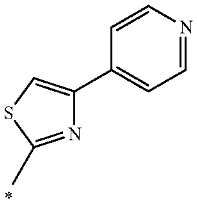 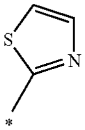

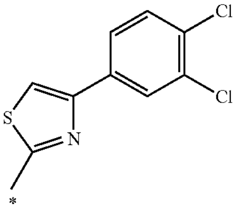 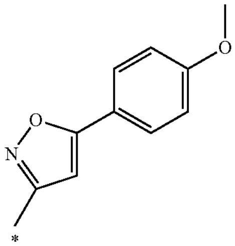

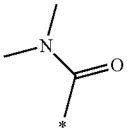  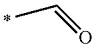

Preferred X substituents include —hydrogen; —a cyano group; and —a —$COR_a$ group, where $R_a$ is: —a $C_1$ to $C_6$ alkyl, or —a dialkyl-amino.

Preferred X substituents also include the following, where the * indicates the bond of attachment of the scaffold molecule.

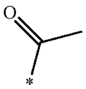  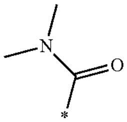

More preferred X substituents include the following, where the * indicates the bond of attachment of the scaffold molecule.

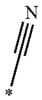 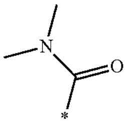

Exemplary Y substituents include the following, where the * indicates the bond of attachment of the scaffold molecule.

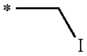 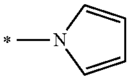

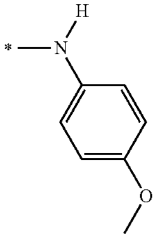 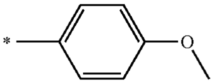

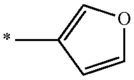 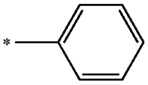

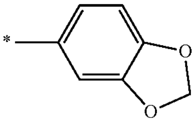 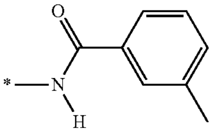

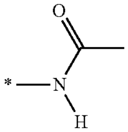 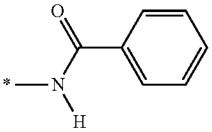

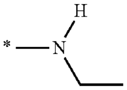 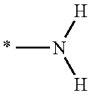

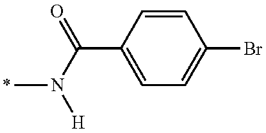

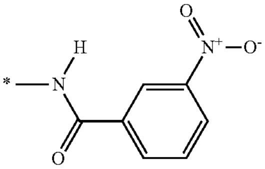

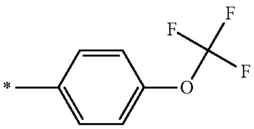

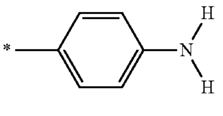 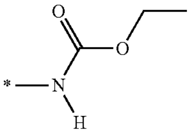

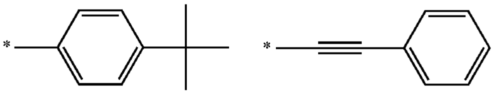

-continued
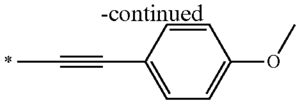
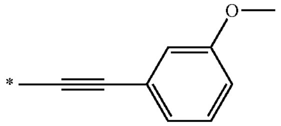
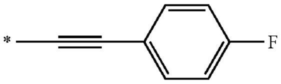
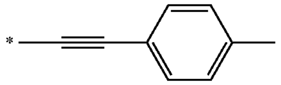
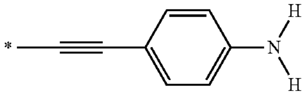
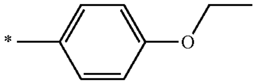
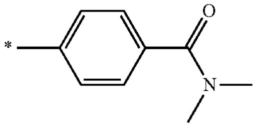
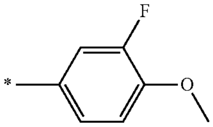
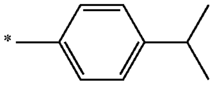
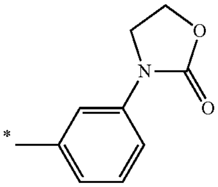
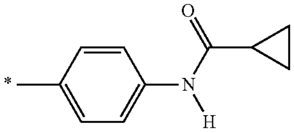
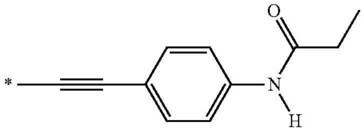
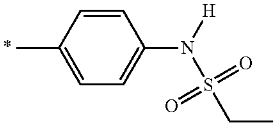
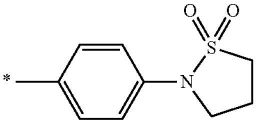
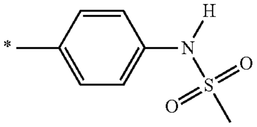
-continued
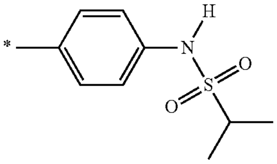
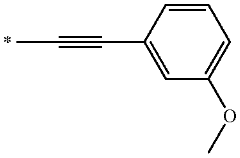
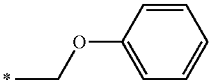
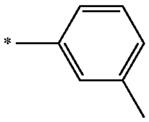
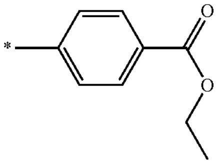
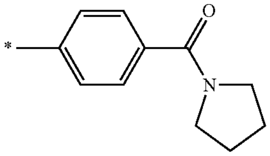
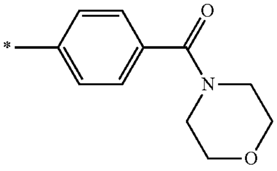
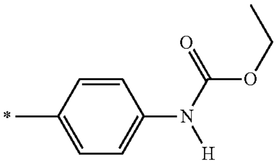
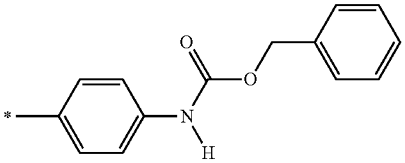
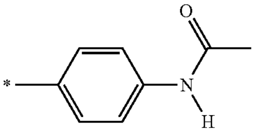
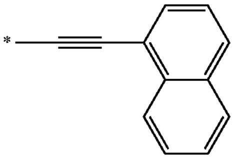
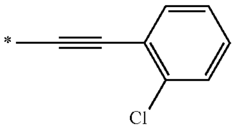
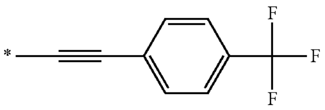
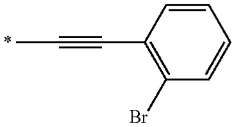

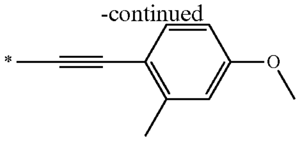
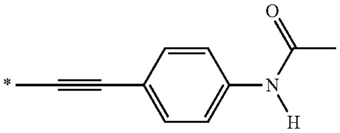
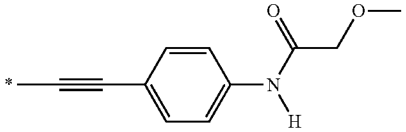
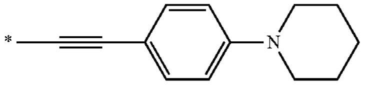
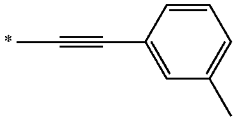
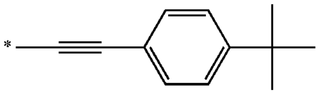
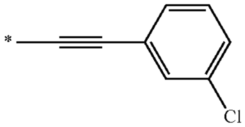
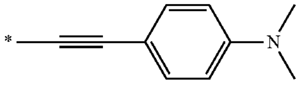
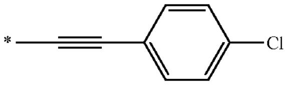
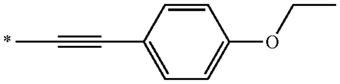
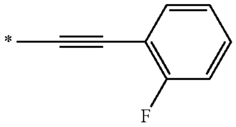
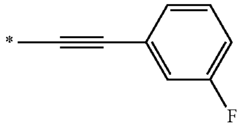
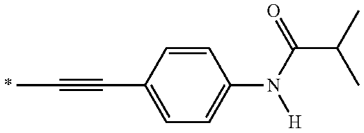
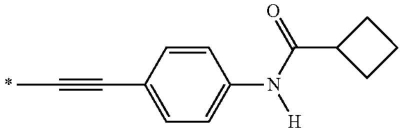
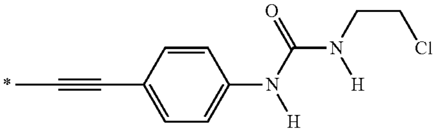
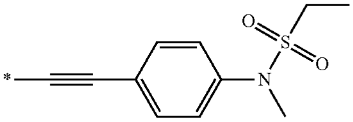
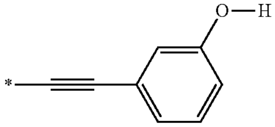
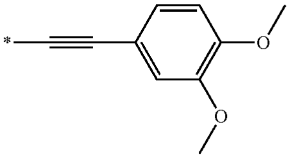
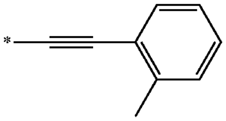
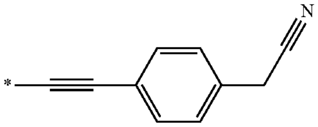
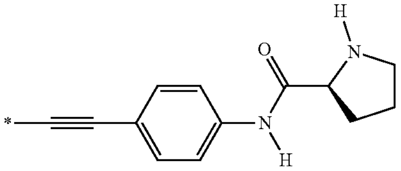
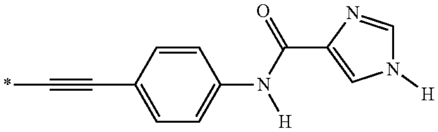
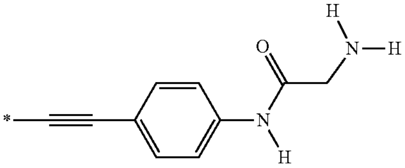
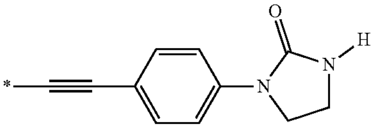
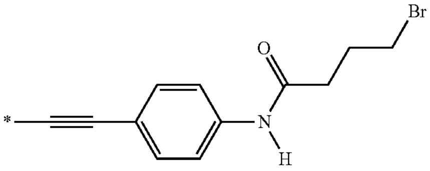
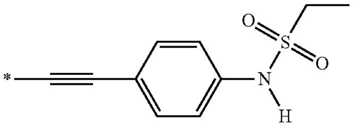
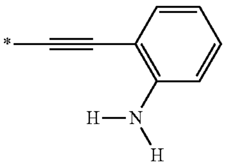

-continued
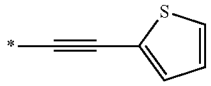
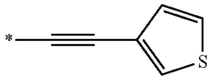
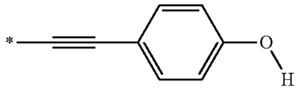
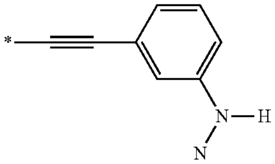
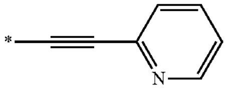
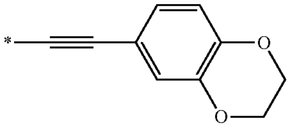
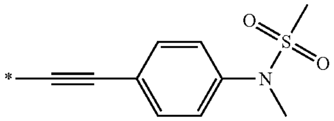
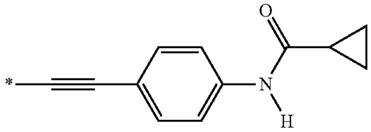
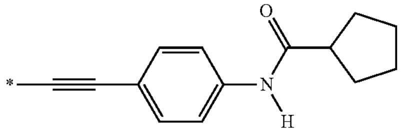
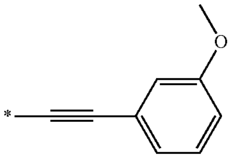
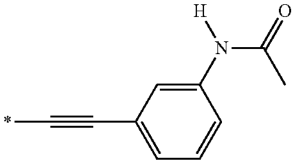
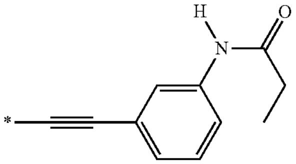
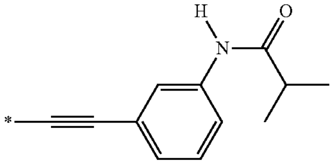
-continued
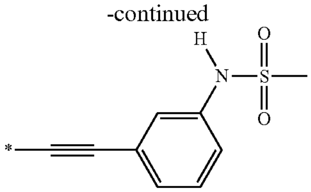
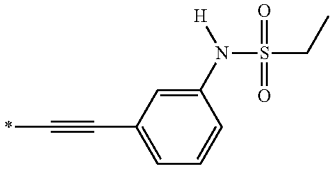
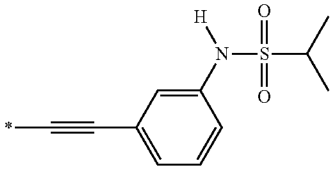
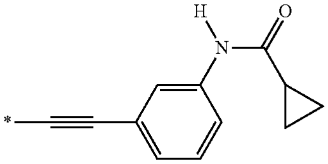
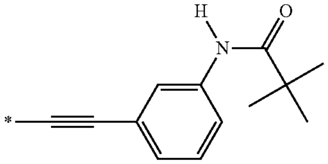
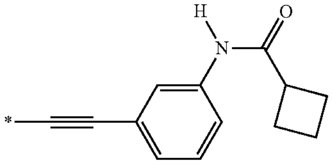
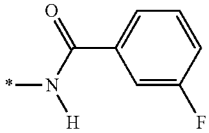
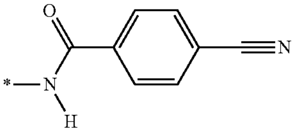
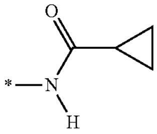
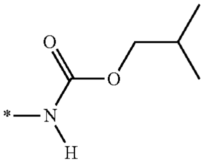
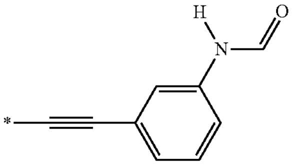

-continued
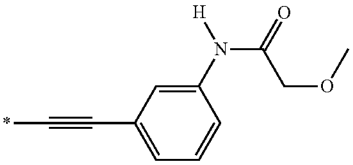
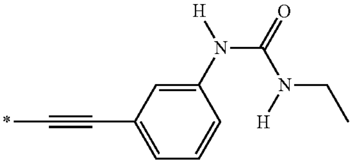
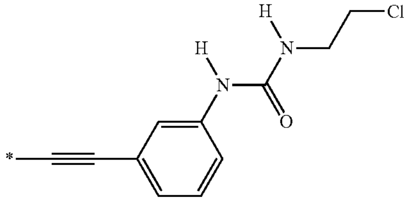
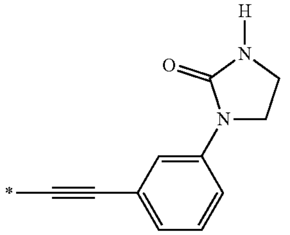
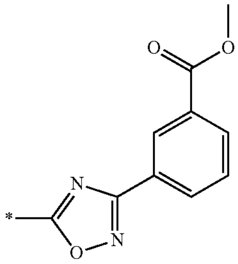
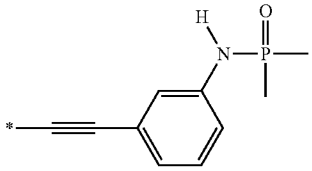
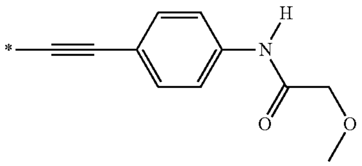
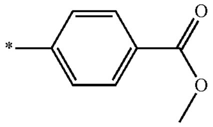
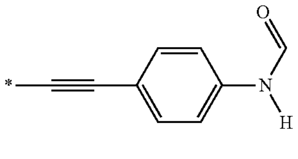
-continued
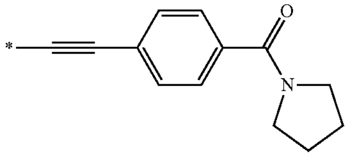
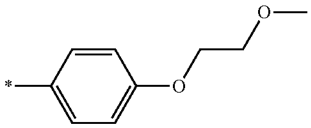
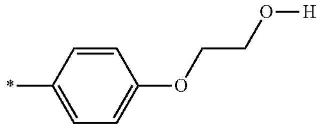
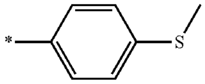
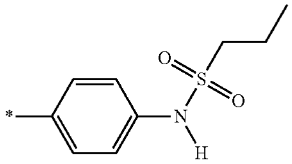
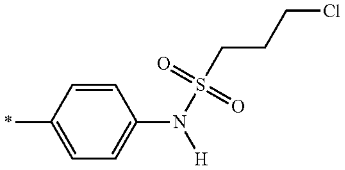
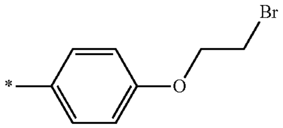
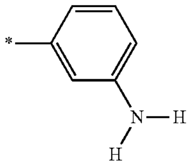
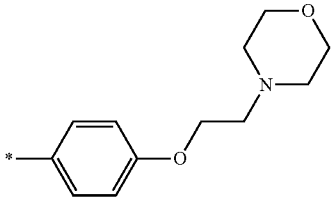
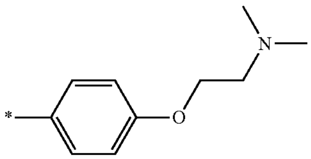
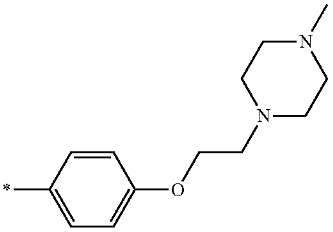

-continued
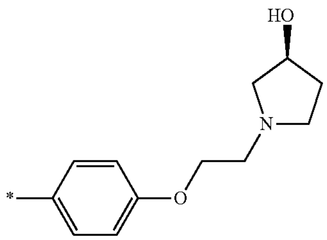
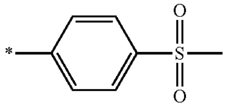
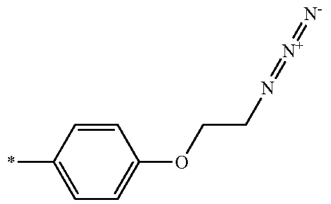
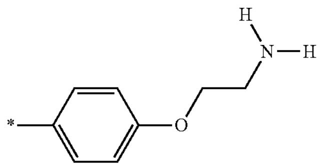
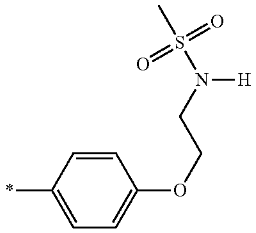
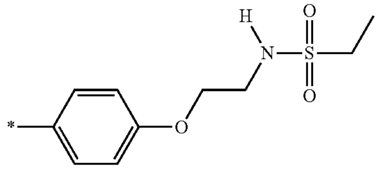
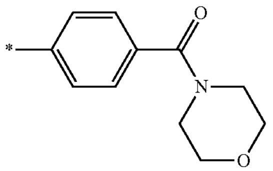
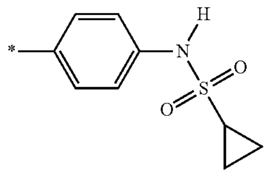
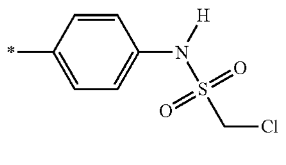
-continued
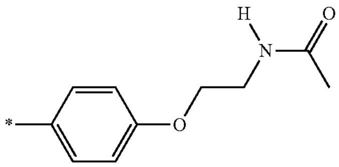
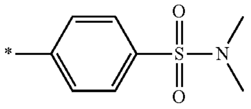
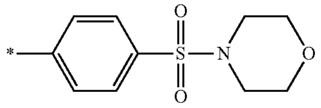
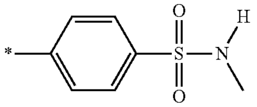
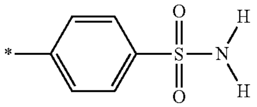
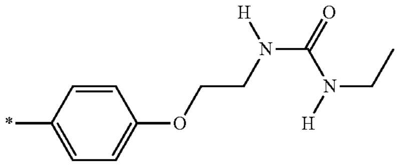
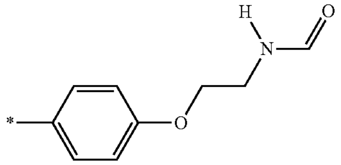
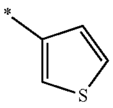
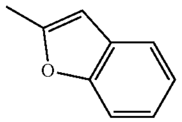
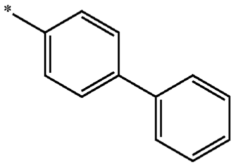
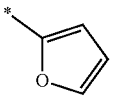
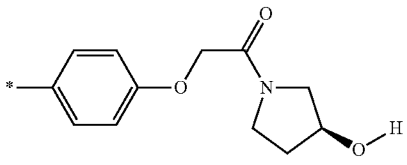
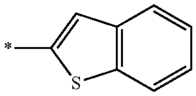

-continued
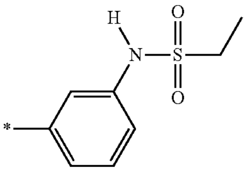
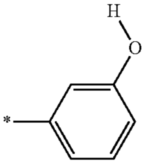
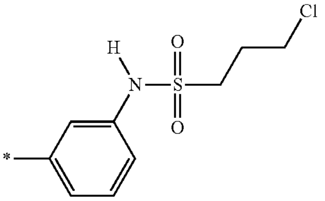
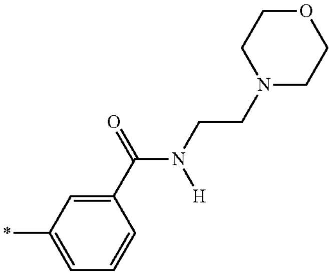
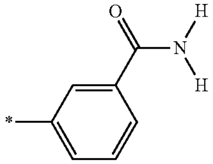
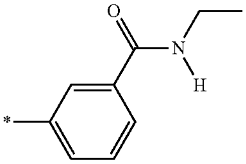
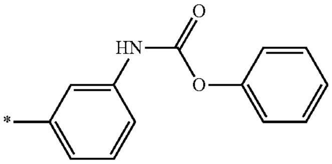
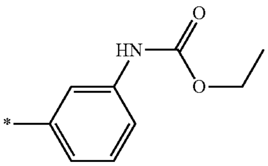
-continued
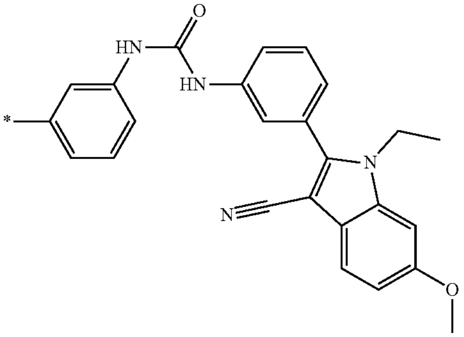
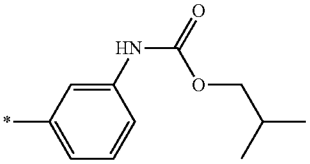
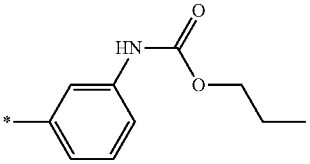
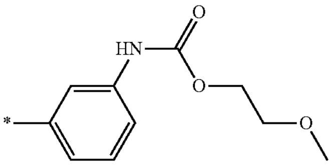
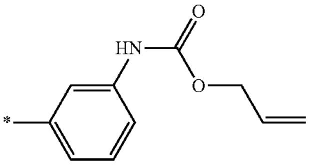
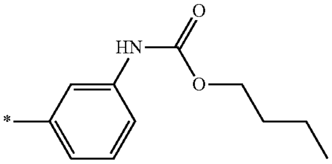
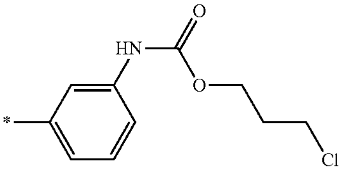
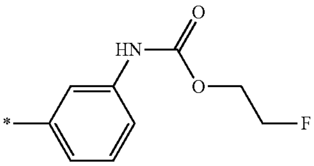
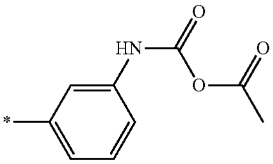

-continued
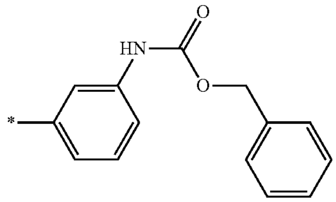
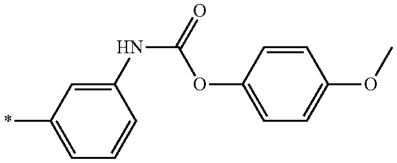
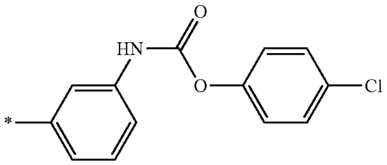
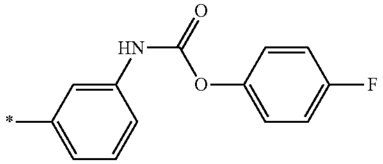
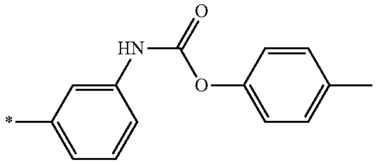
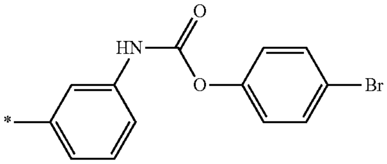
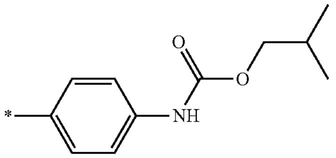
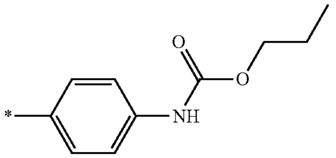
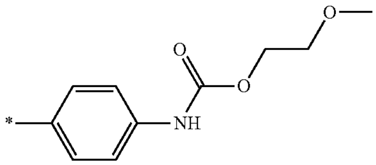
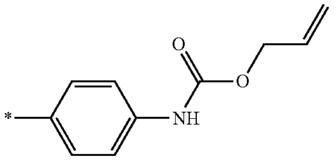
-continued
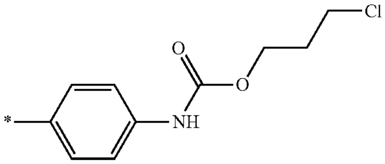
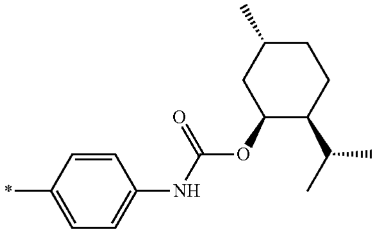
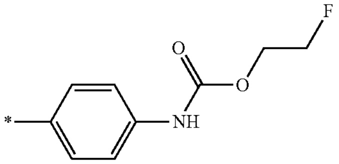
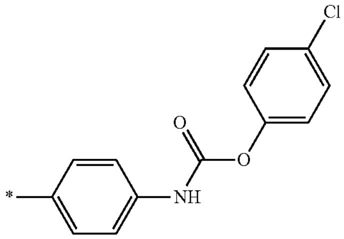
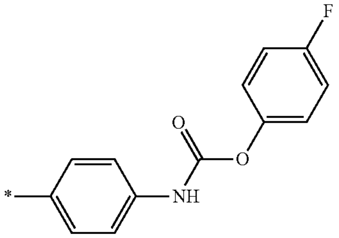
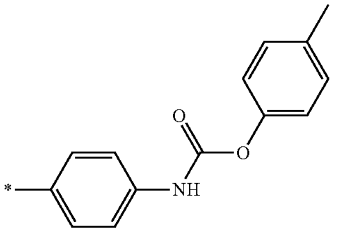
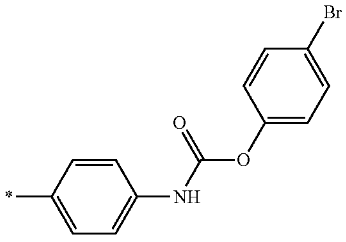
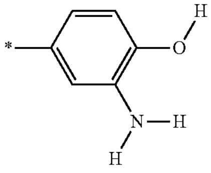

-continued
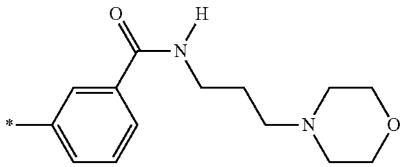
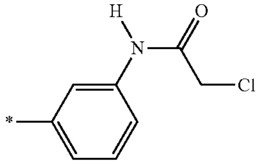
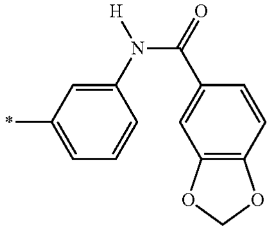
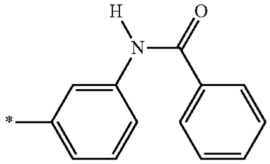
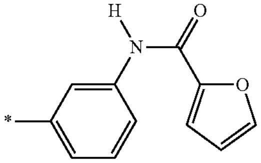
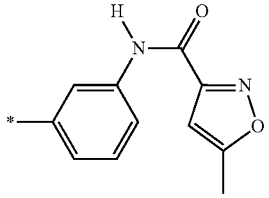
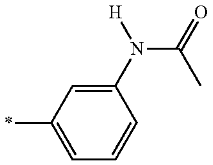
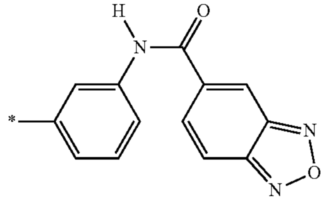
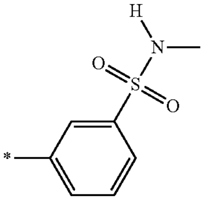
-continued
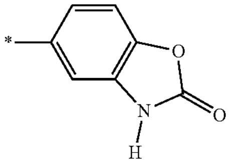
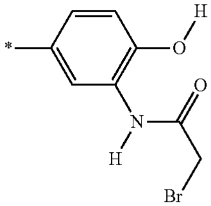
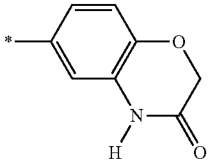
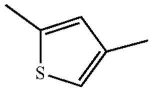
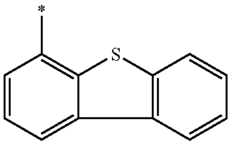
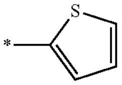
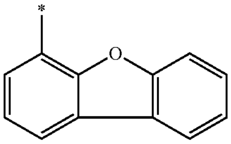
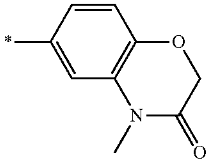
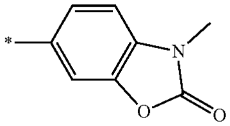
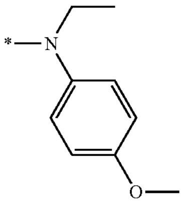
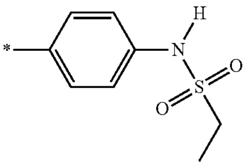

-continued
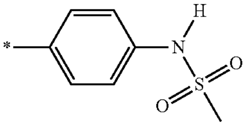
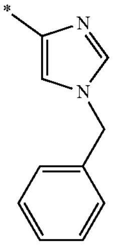
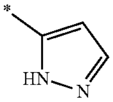
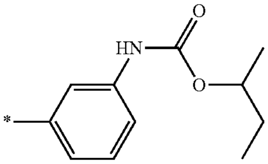
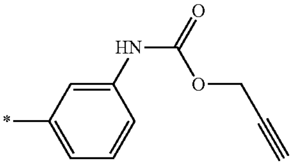
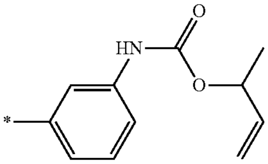
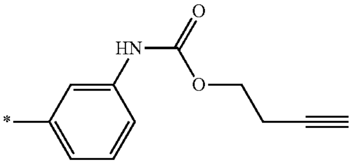
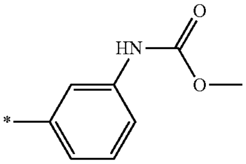
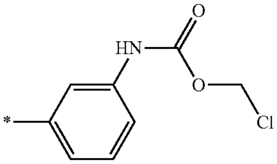
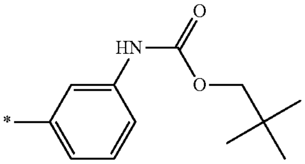
-continued
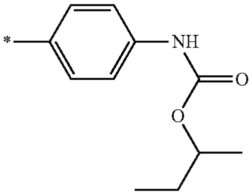
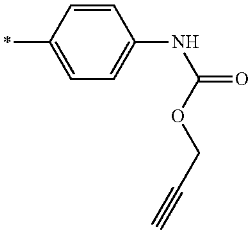
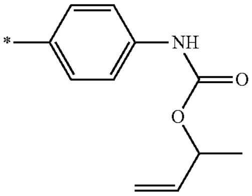
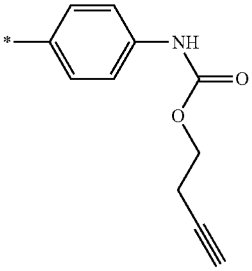
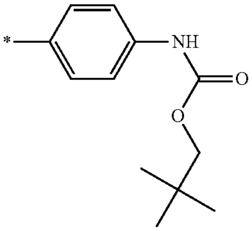
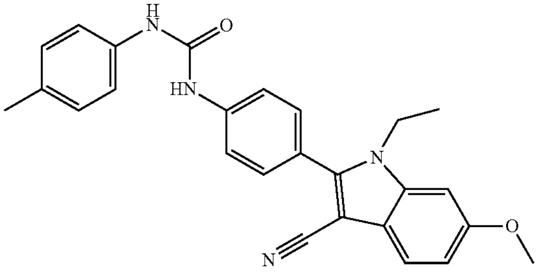
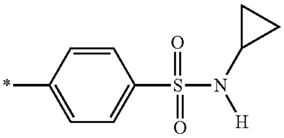
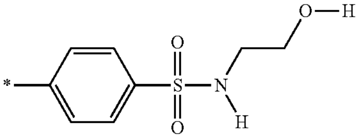

-continued
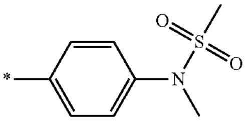
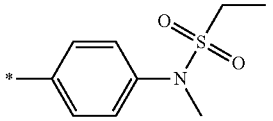
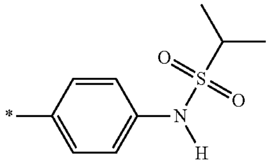
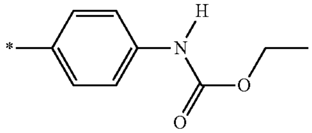
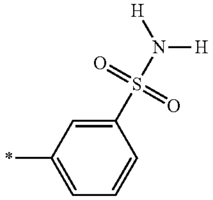
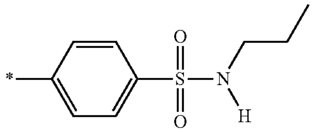
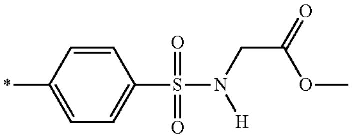
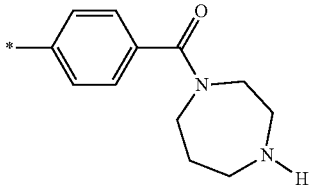
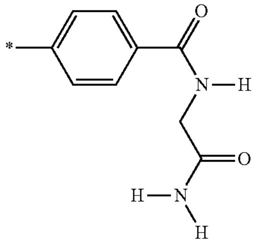
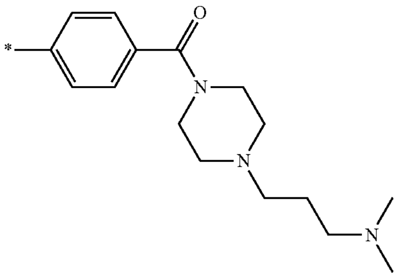
-continued
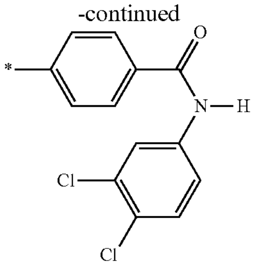
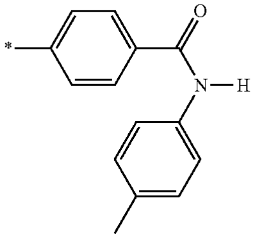
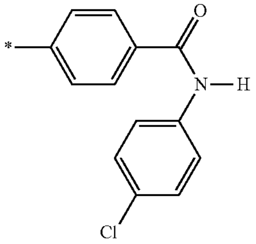
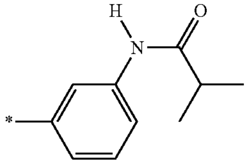
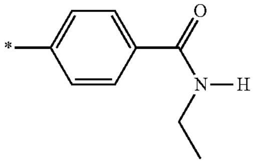
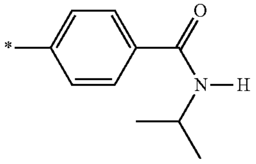
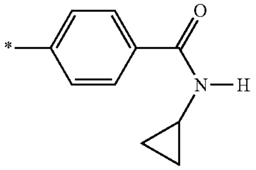
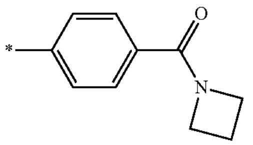
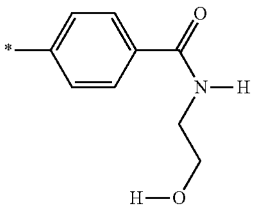

-continued
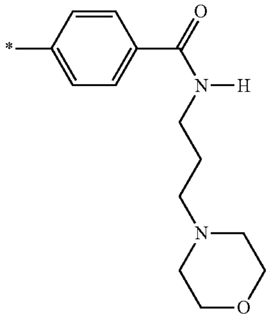
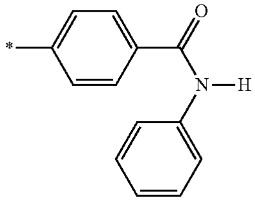
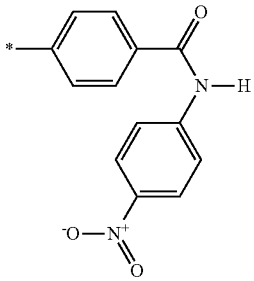
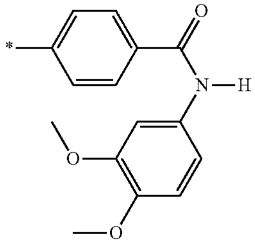
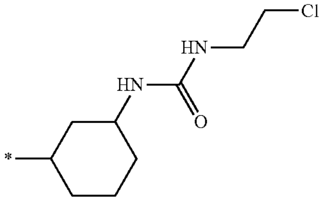
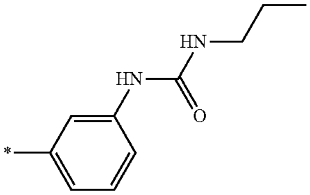
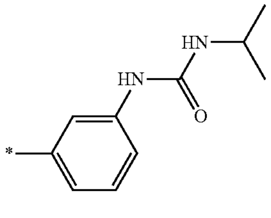
-continued
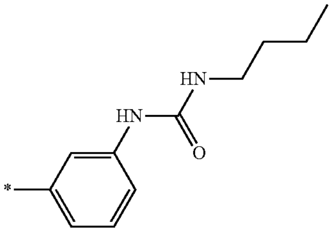
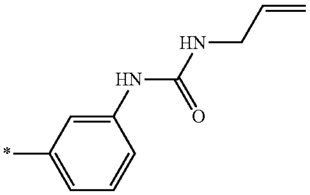
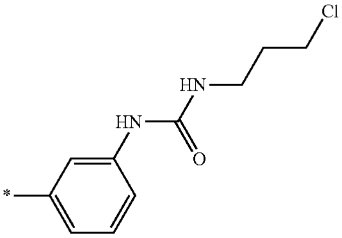
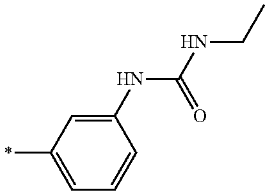
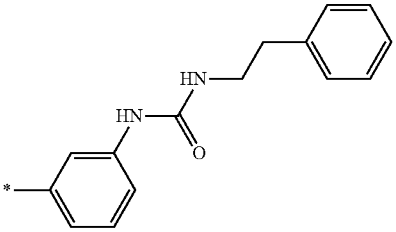
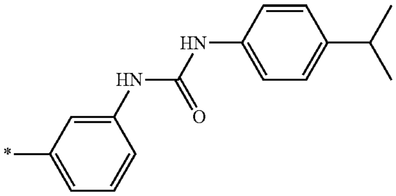
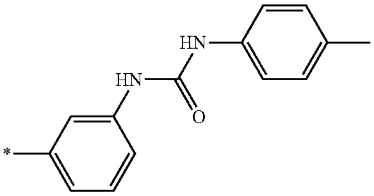
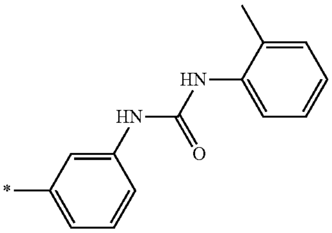

-continued
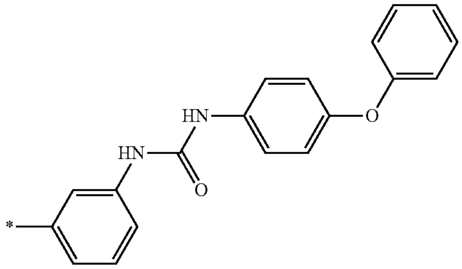
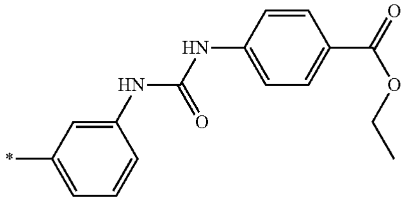
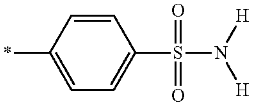
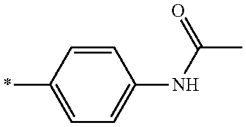
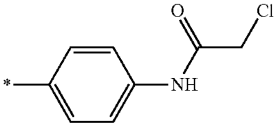
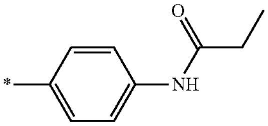
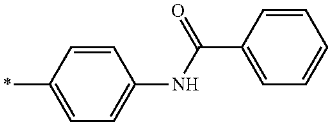
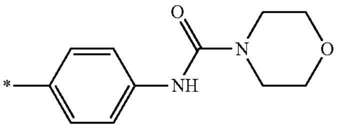
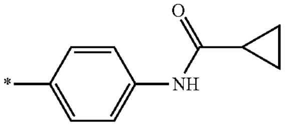
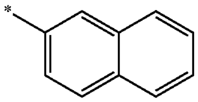
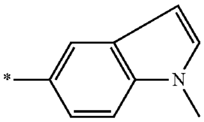
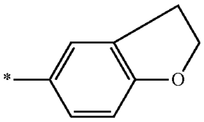
-continued
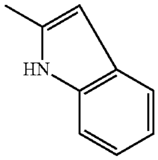
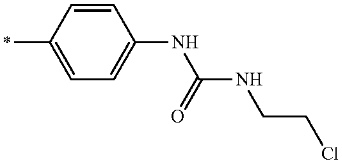
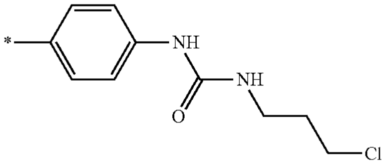
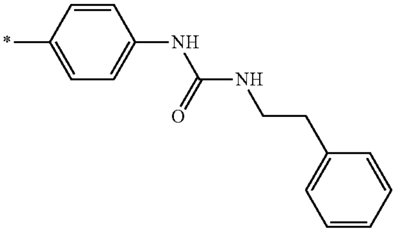
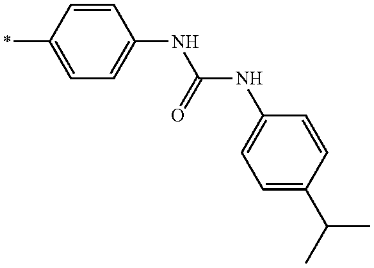
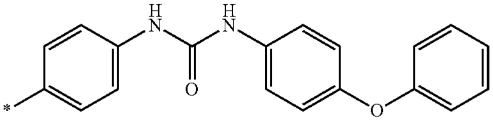
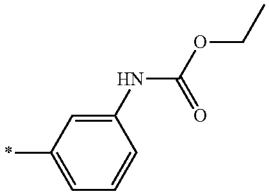
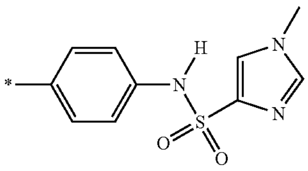
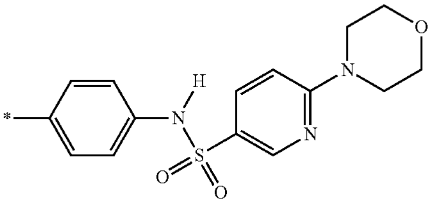

-continued
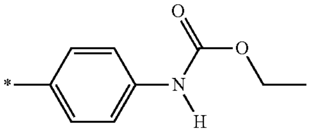
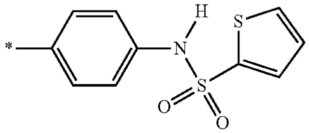
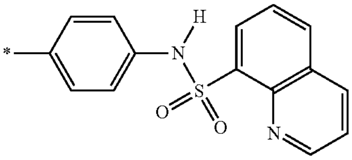
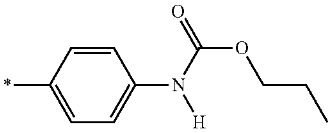
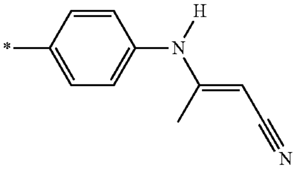
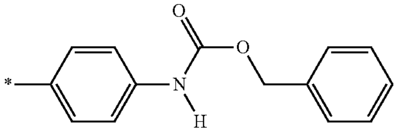
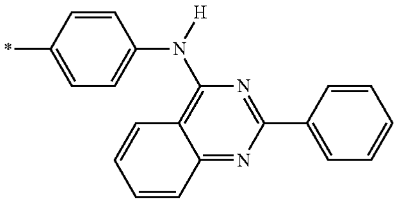
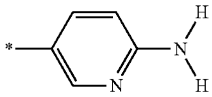
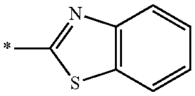
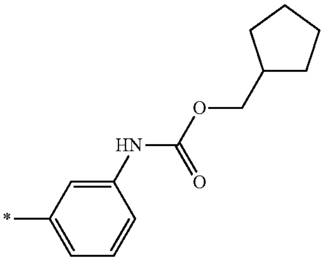
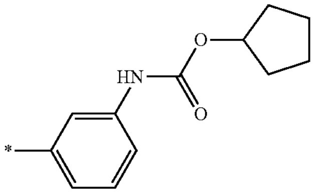
-continued
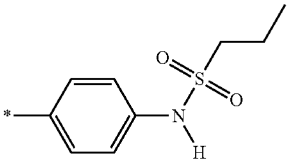
*—I
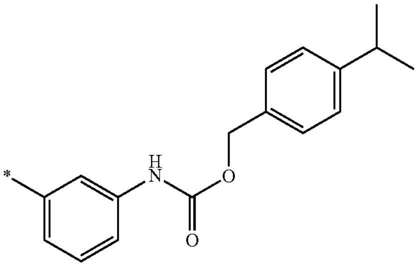
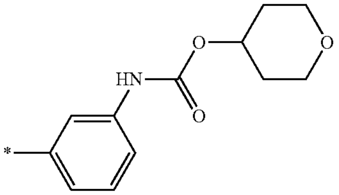
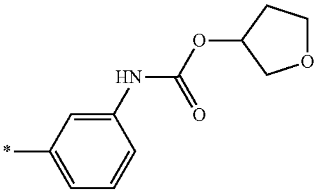
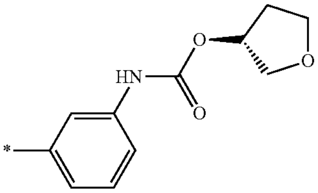
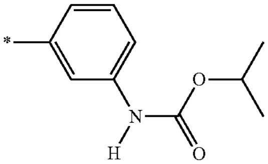
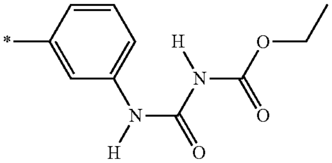
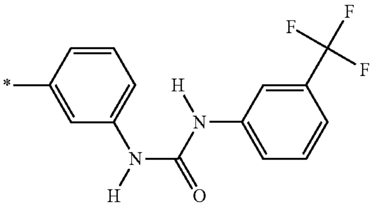
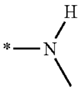

-continued
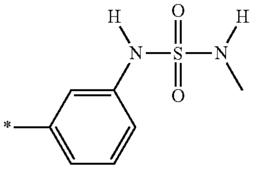
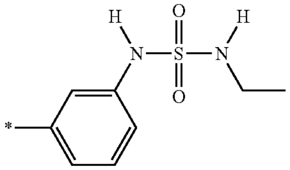
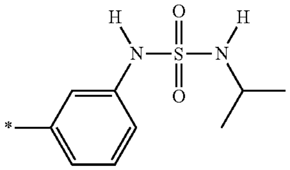
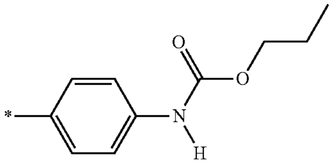
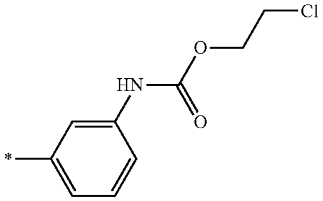
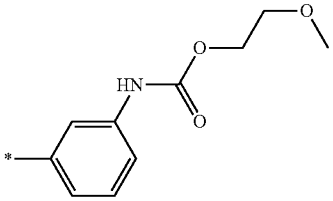
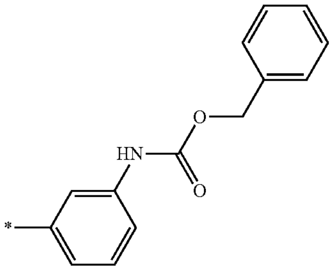
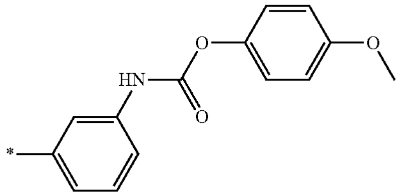
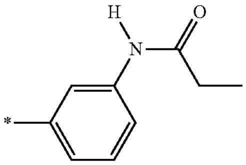
-continued
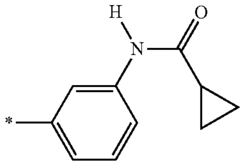
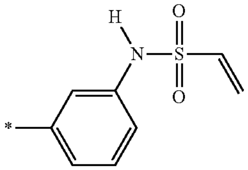
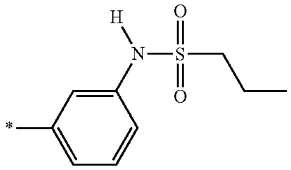
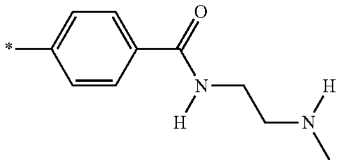
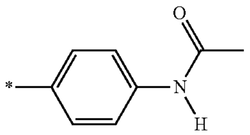
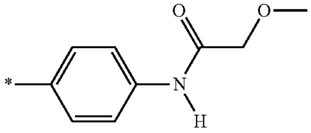
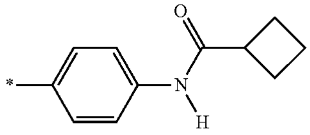
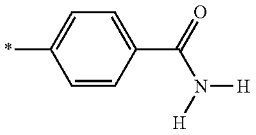
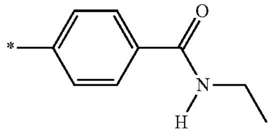
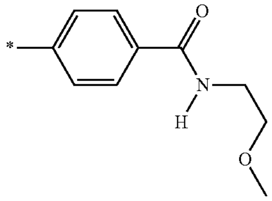
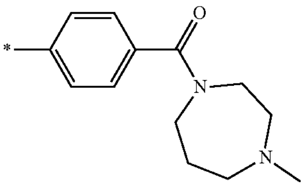

-continued
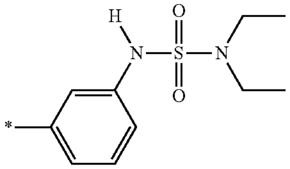
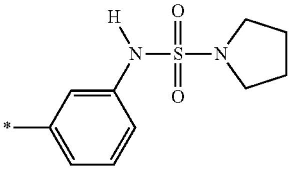
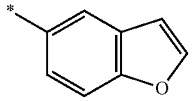
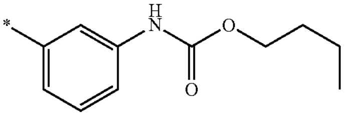
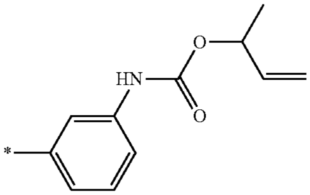
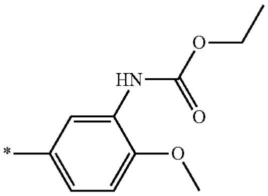
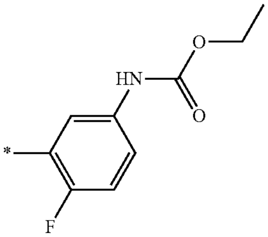
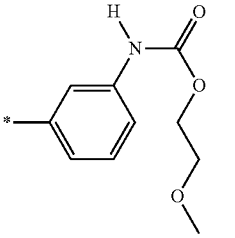
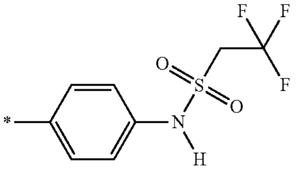
-continued
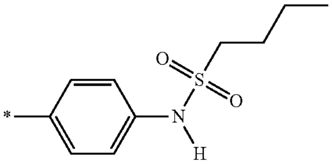
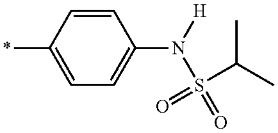
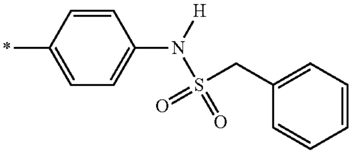
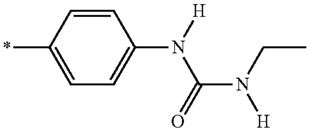
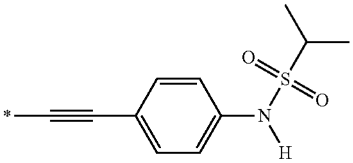
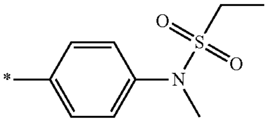
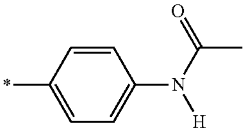
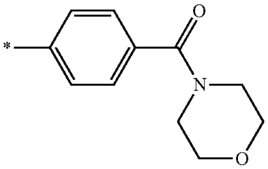
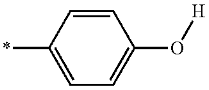
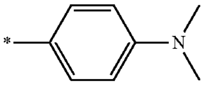
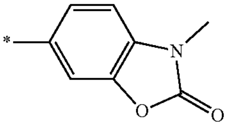
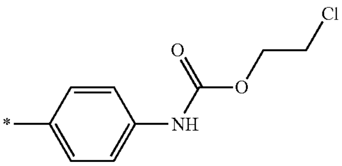

-continued
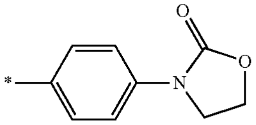
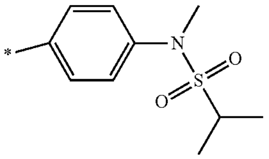
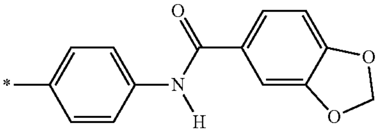
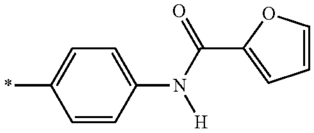
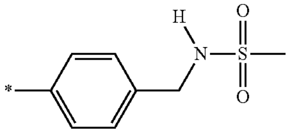
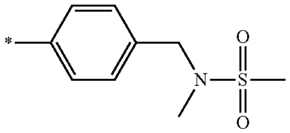
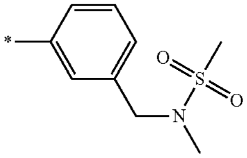
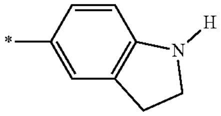
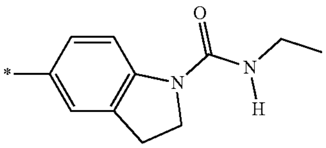
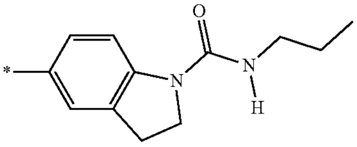
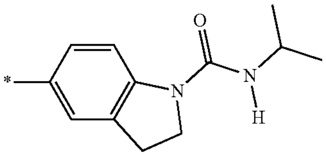
-continued
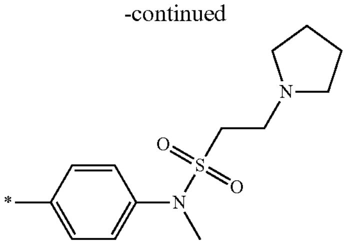
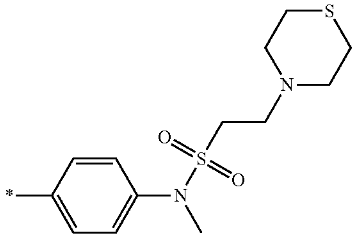
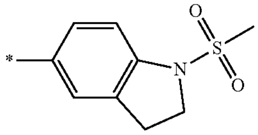
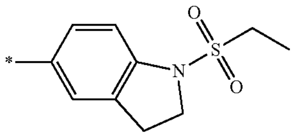
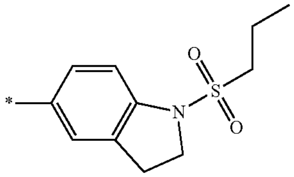
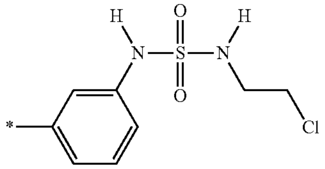
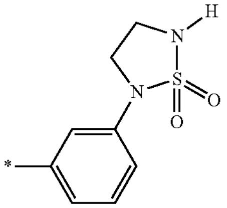
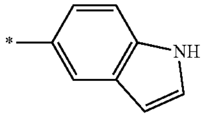
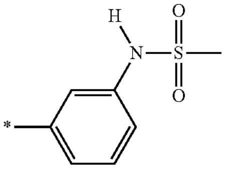
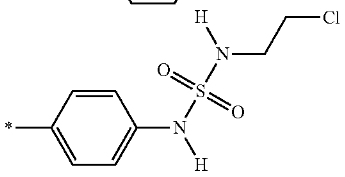

-continued
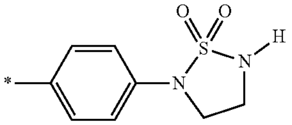
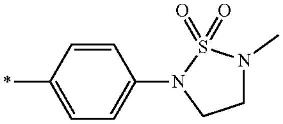
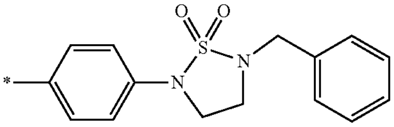
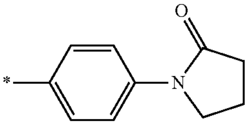
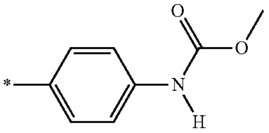
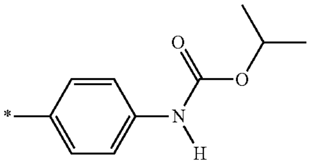
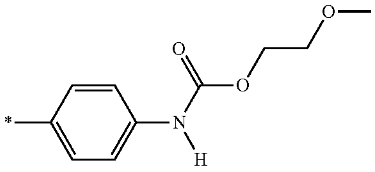
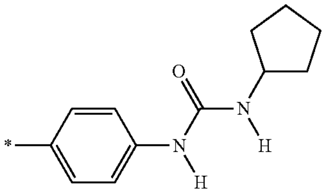
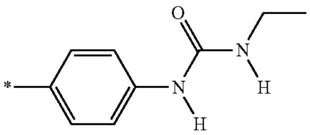
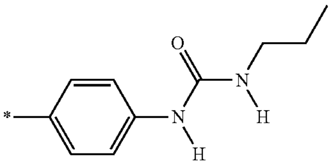
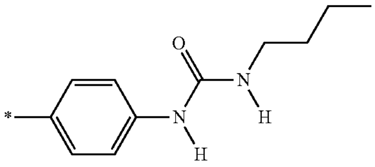
-continued
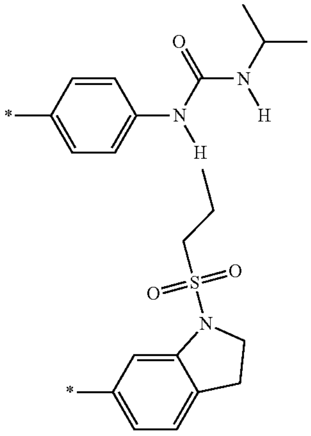
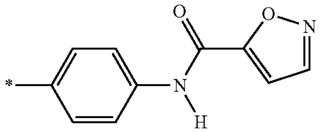
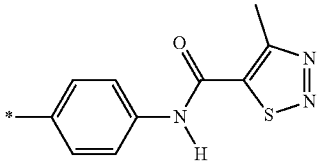
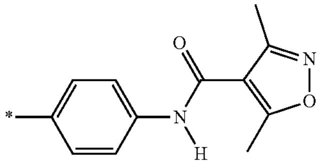
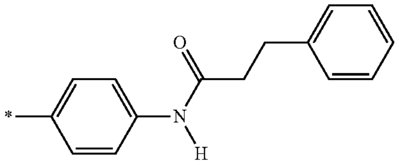
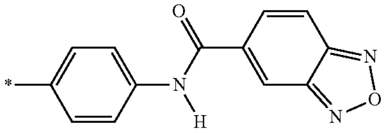
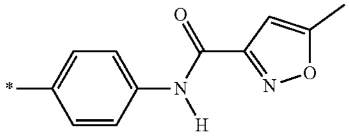
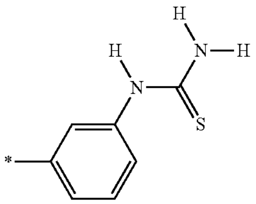
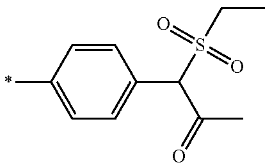

-continued
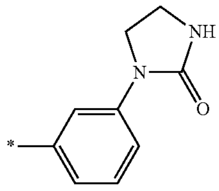
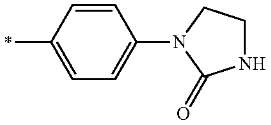
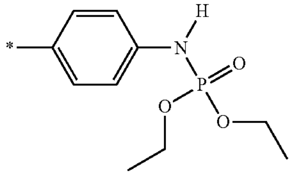
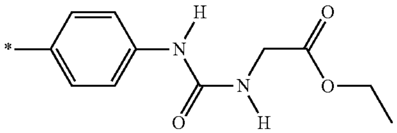
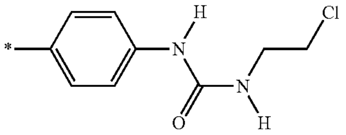
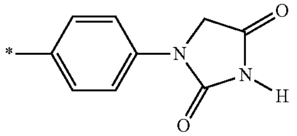
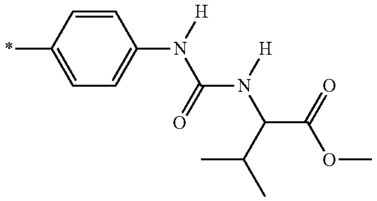
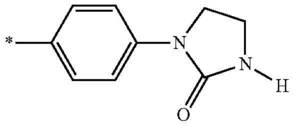
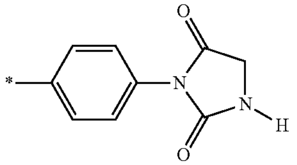
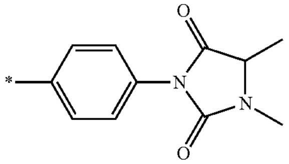
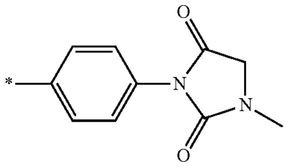
-continued
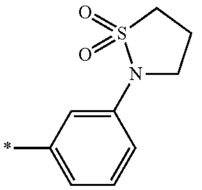
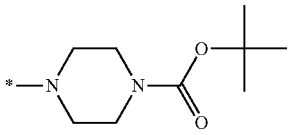
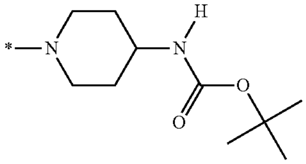
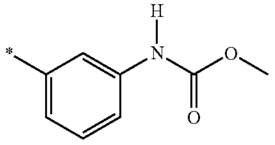
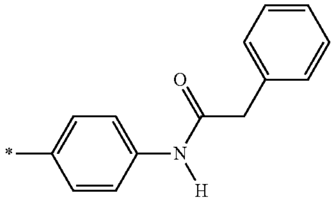
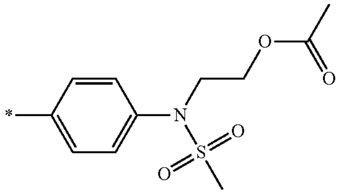
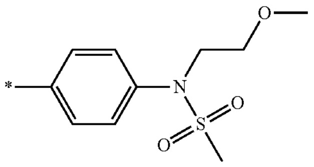
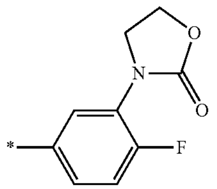
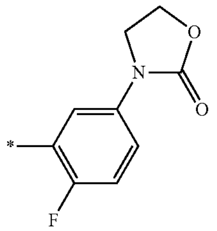

-continued
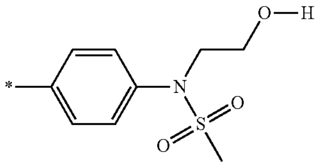
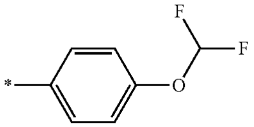
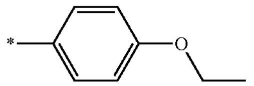
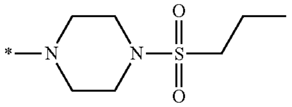
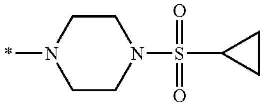
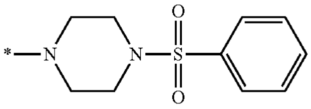
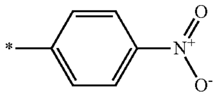
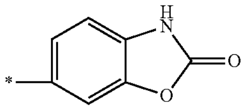
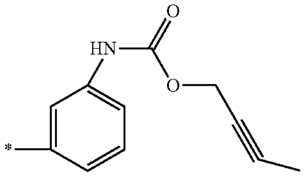
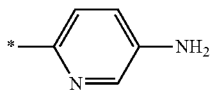
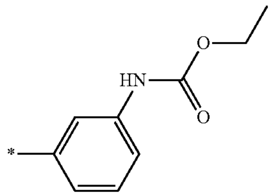
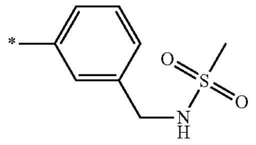
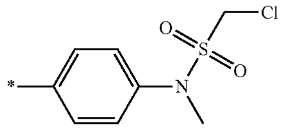
-continued
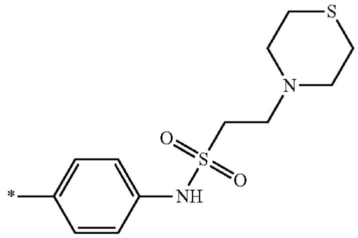
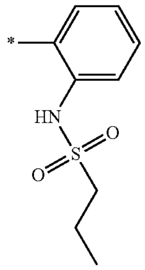
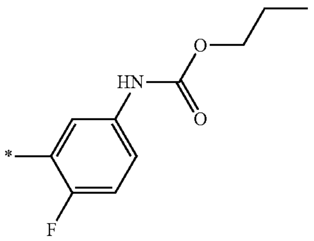
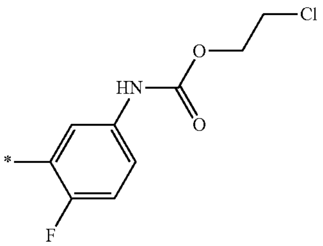
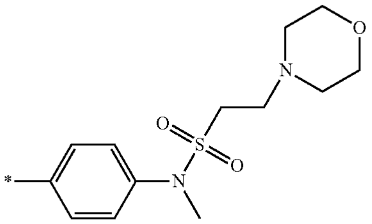
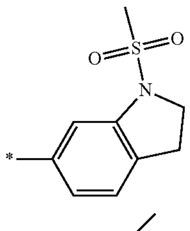
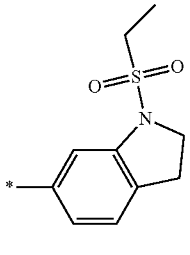

-continued
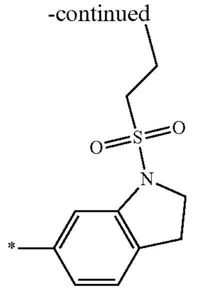
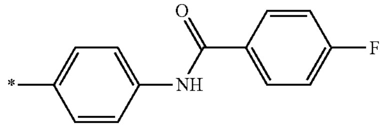
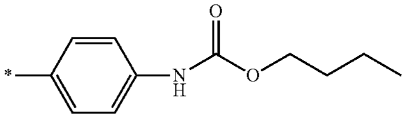
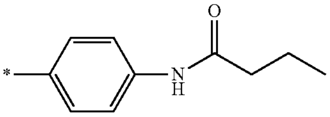
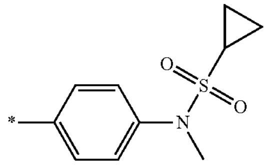
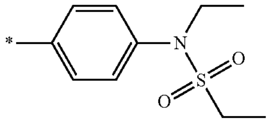
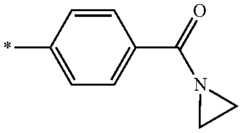
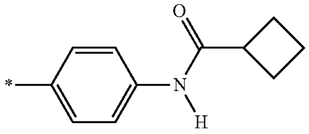
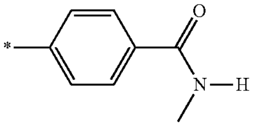
Preferred Y substituents include the following, where the * indicates the bond of attachment of the scaffold molecule.
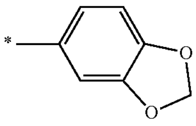
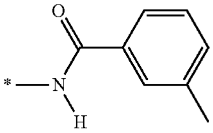
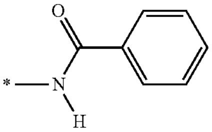
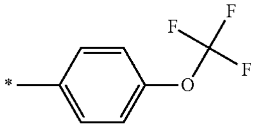
-continued
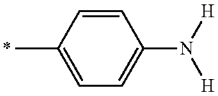
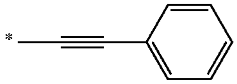
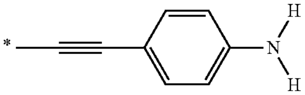
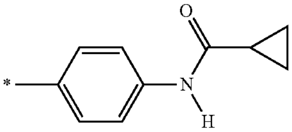
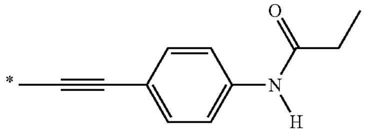
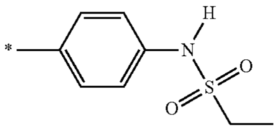
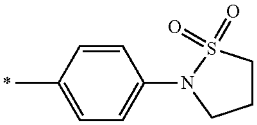
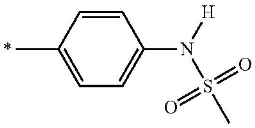
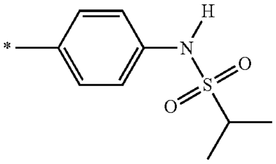
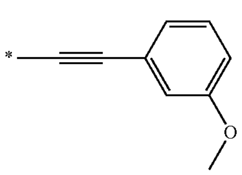
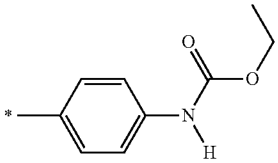
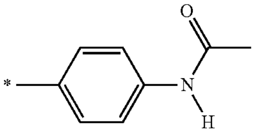
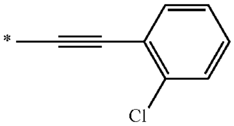
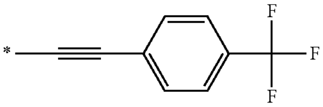
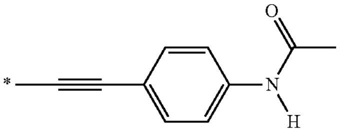
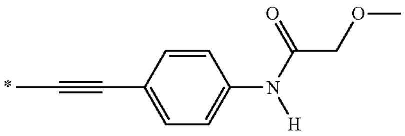
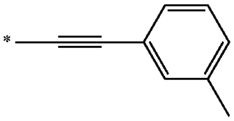
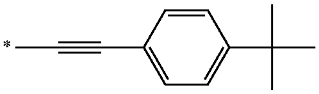
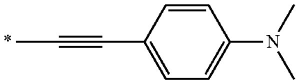

-continued
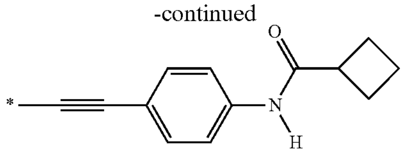
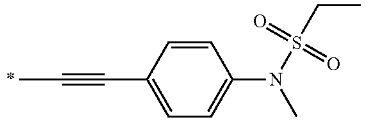
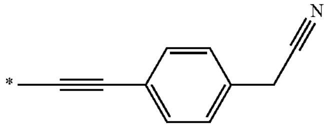
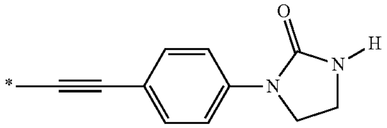
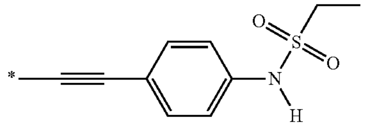
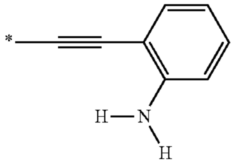
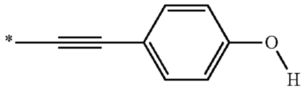
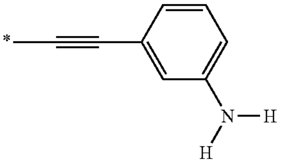
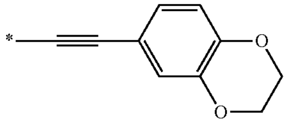
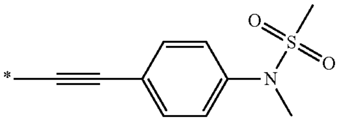
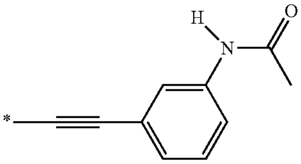
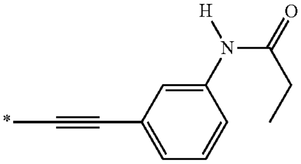
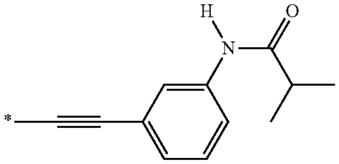
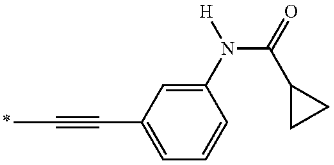
-continued
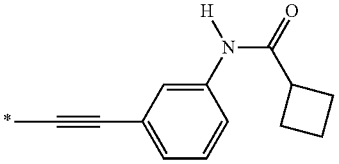
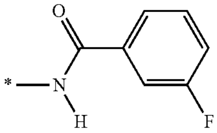
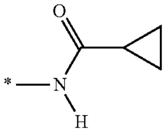
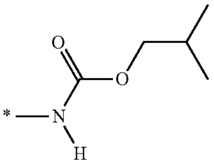
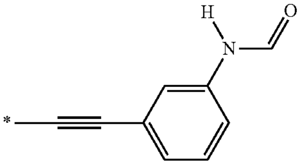
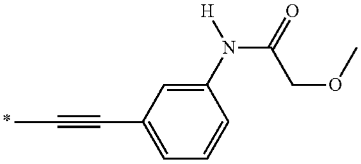
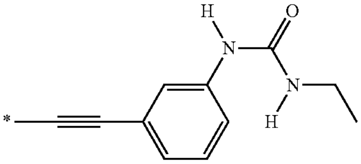
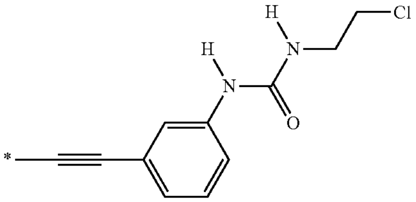
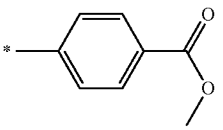
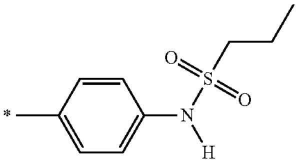
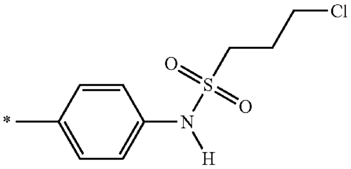
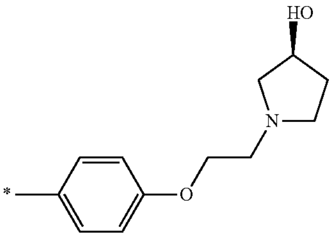

-continued
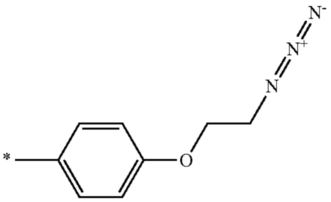
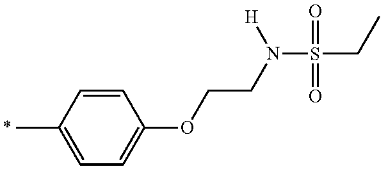
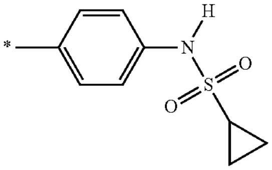
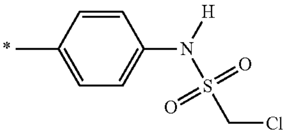
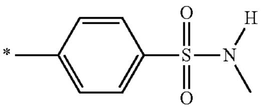
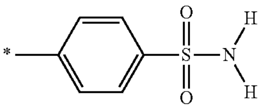
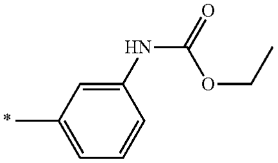
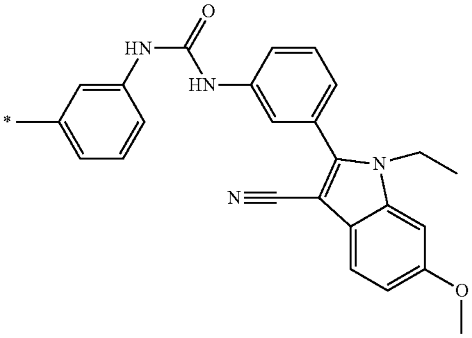
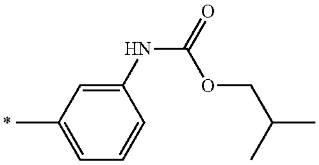
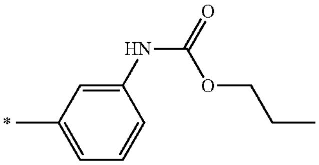
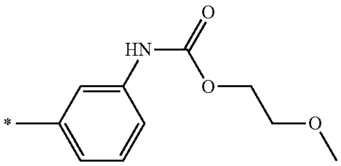
-continued
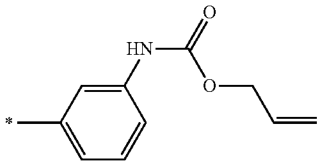
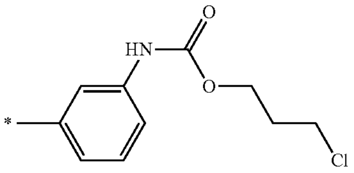
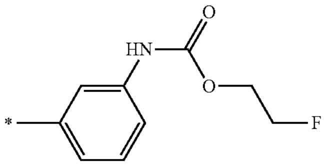
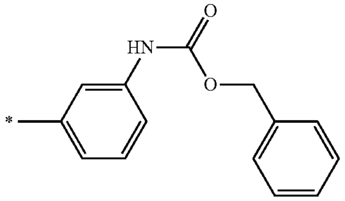
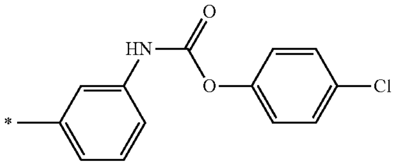
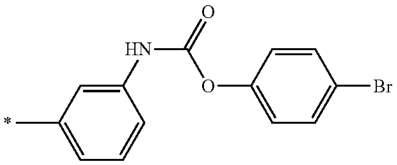
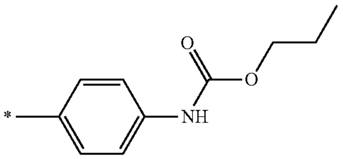
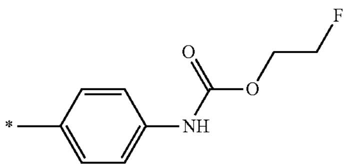
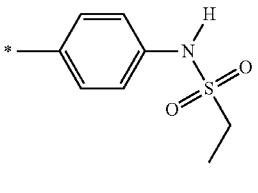
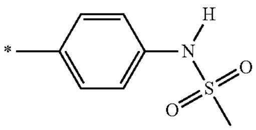
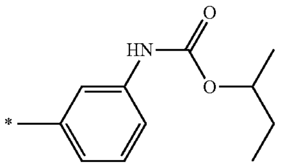

-continued
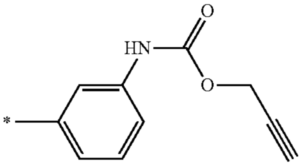
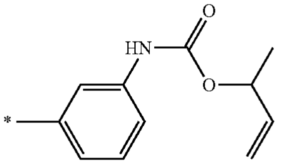
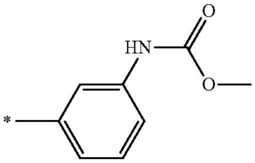
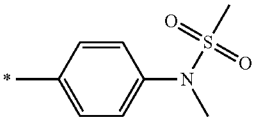
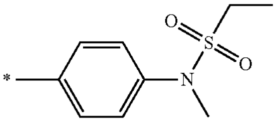
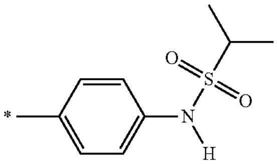
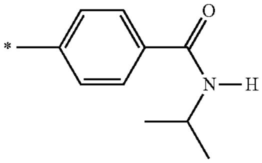
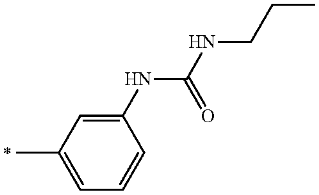
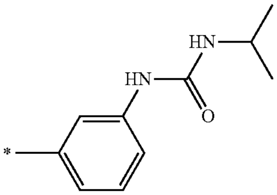
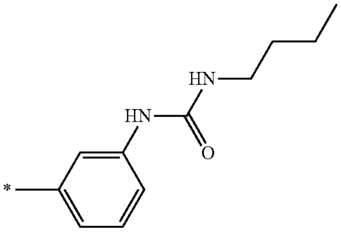
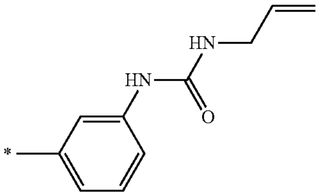
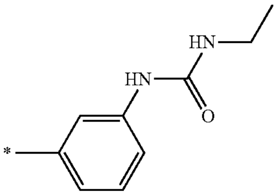
-continued
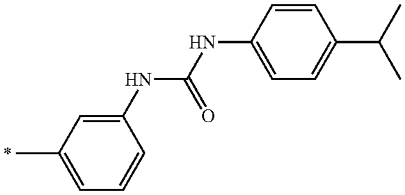
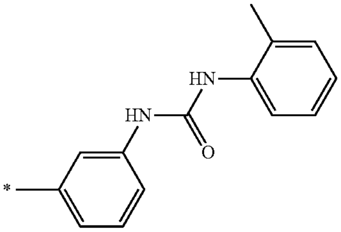
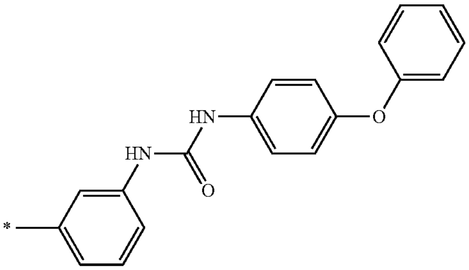
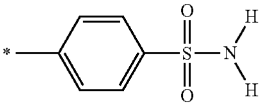
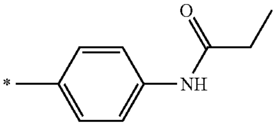
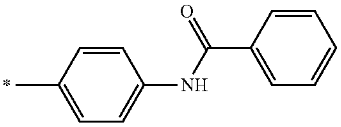
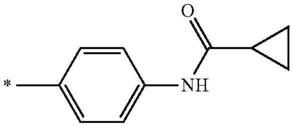
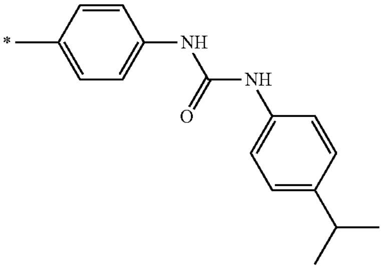
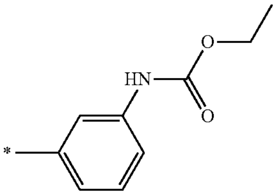
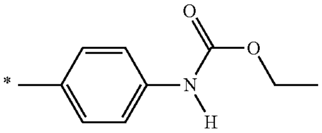

-continued
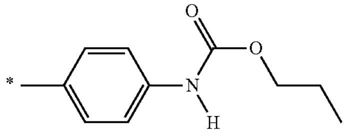
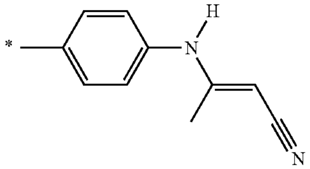
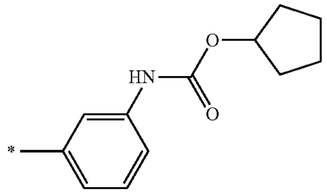
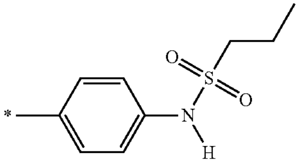
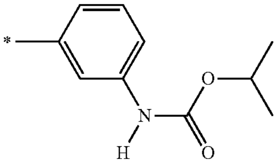
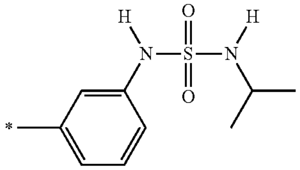
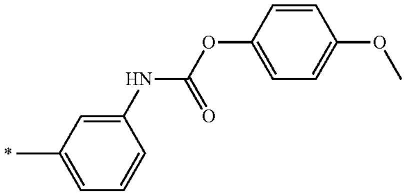
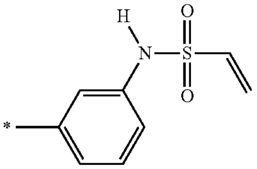
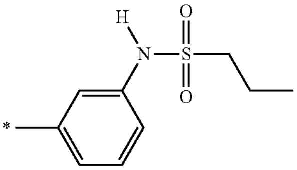
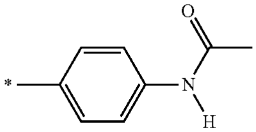
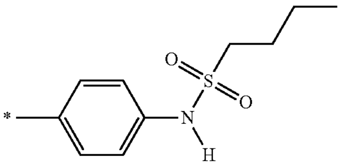
-continued
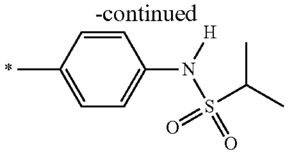
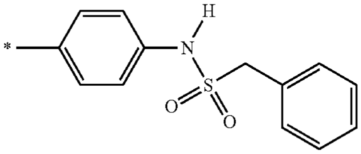
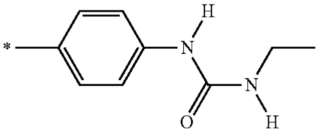
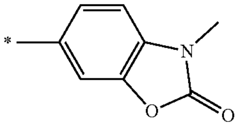
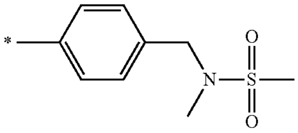
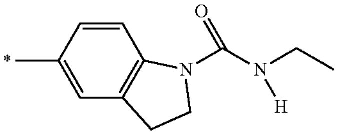
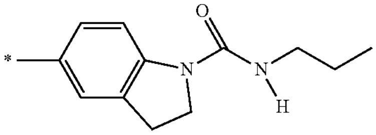
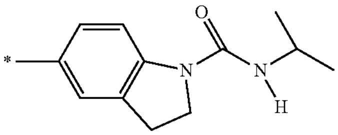
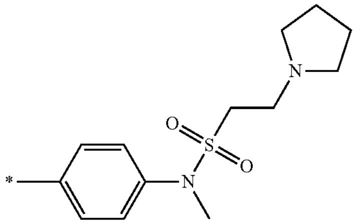
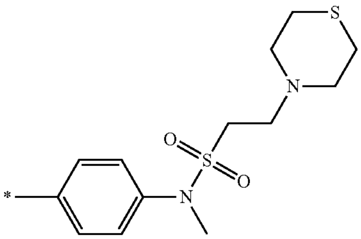
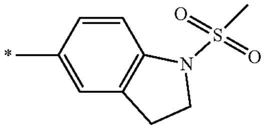
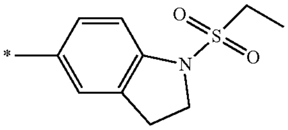
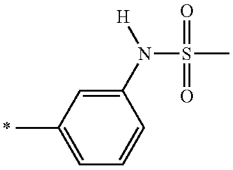

-continued
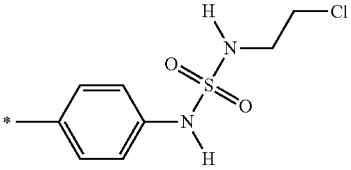
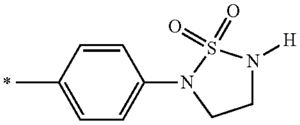
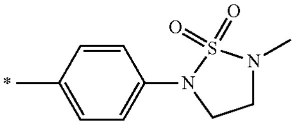
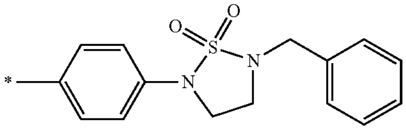
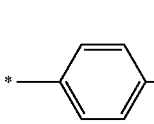
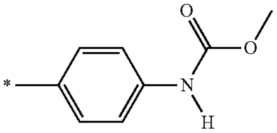
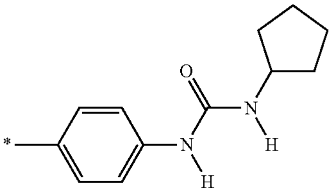
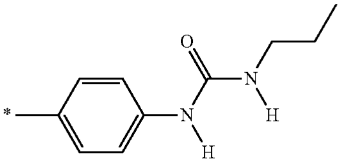
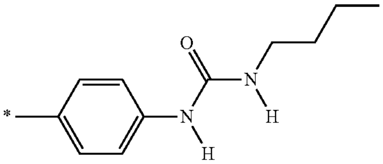
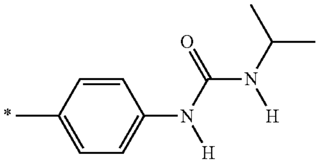
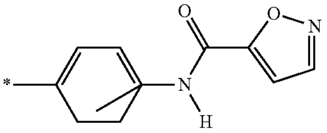
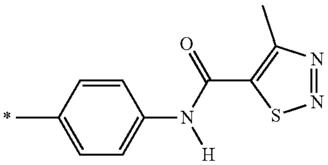
-continued
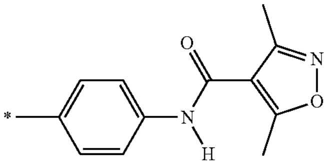
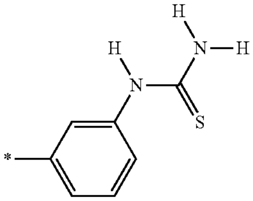
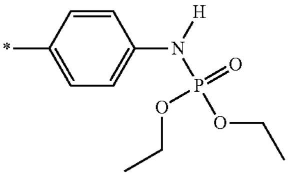
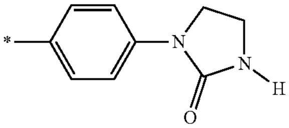
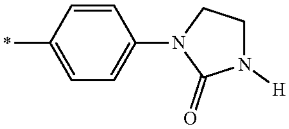
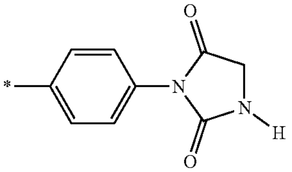
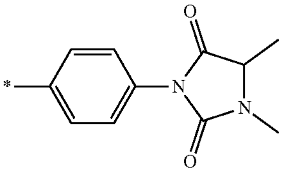
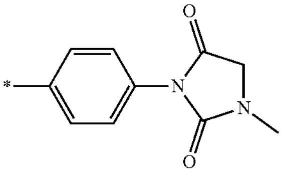
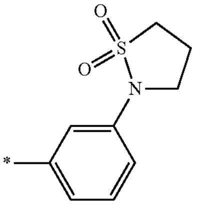
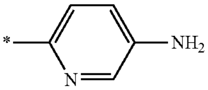
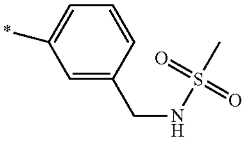
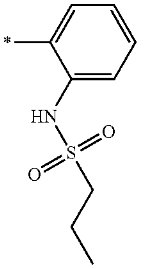
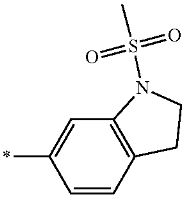
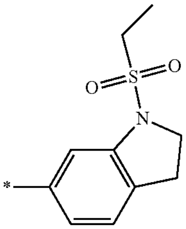
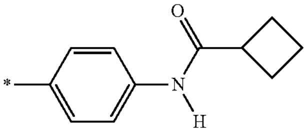
*—H
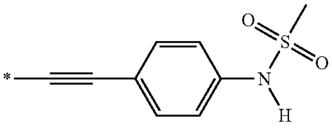

-continued
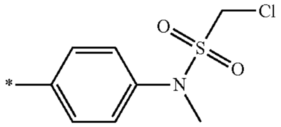
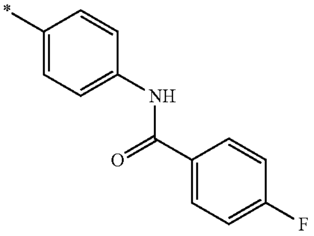
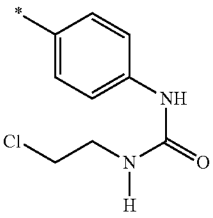
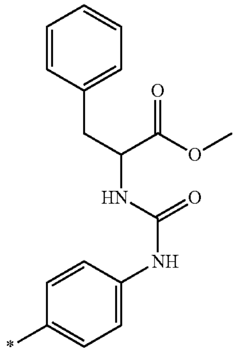
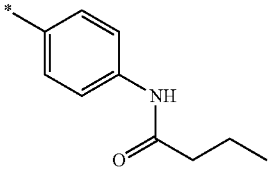
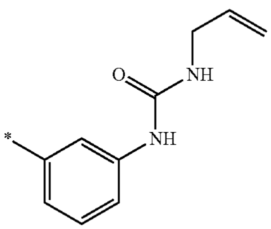
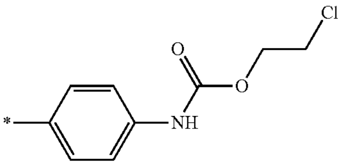
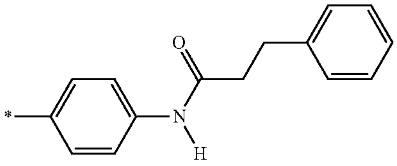
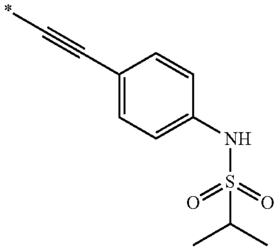
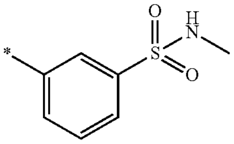
-continued
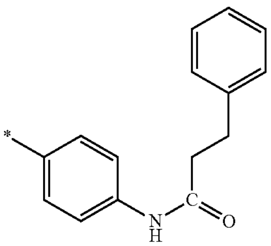
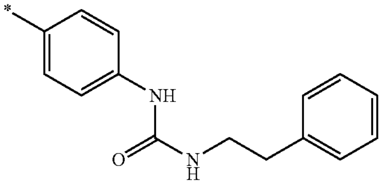
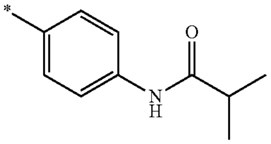
More preferred Y substituents include the following, where the * indicates the bond of attachment of the scaffold molecule.
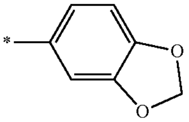
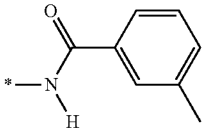
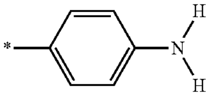
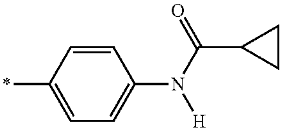
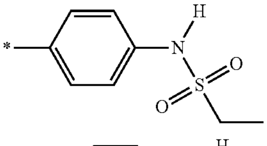
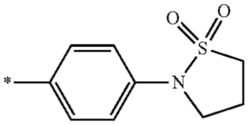
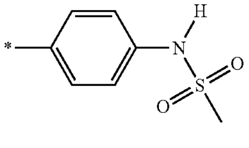
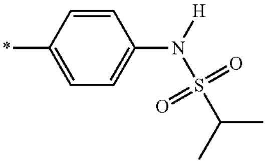
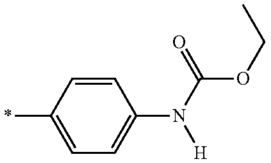
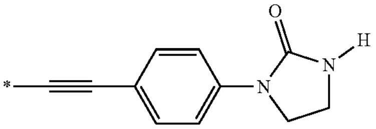

-continued
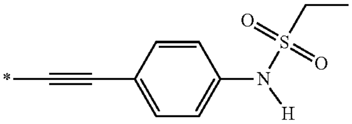
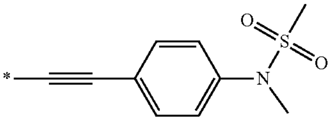
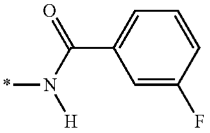
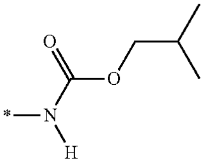
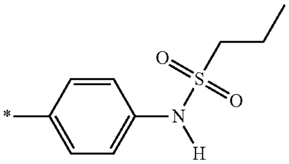
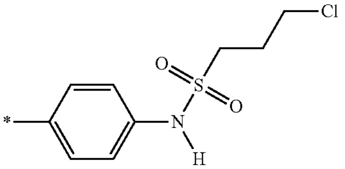
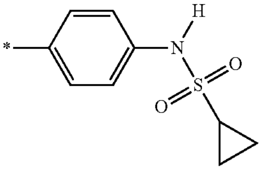
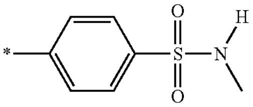
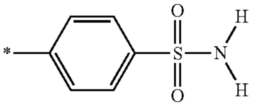
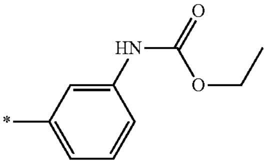
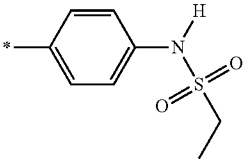
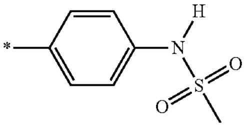
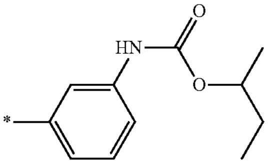
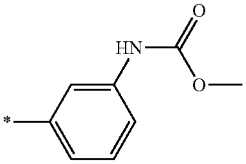
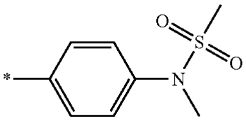
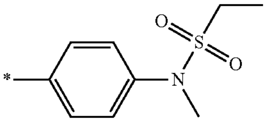
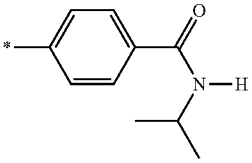
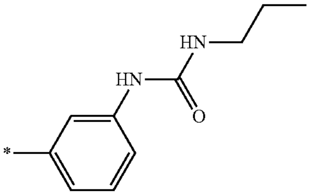
-continued
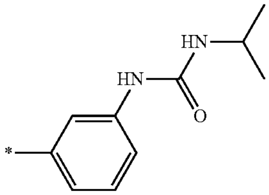
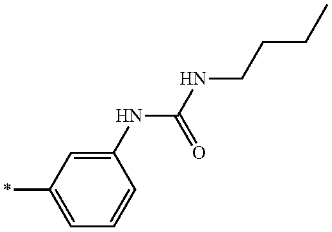
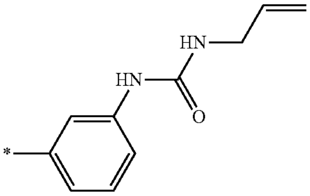
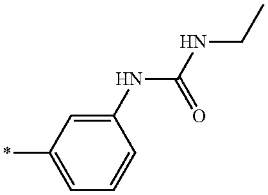
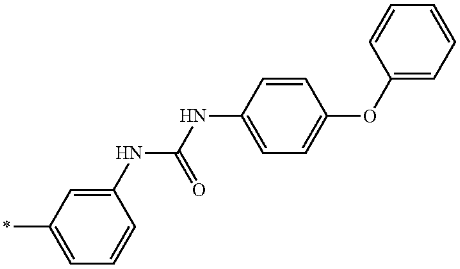
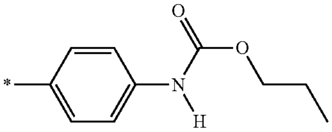
*—I
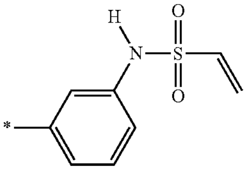
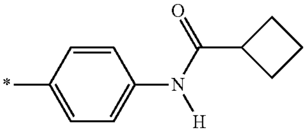
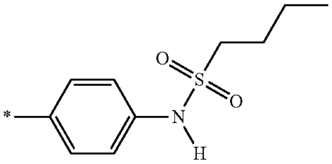
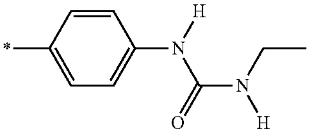

-continued
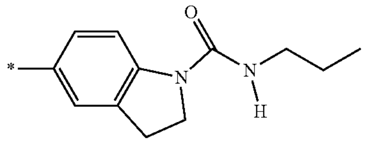
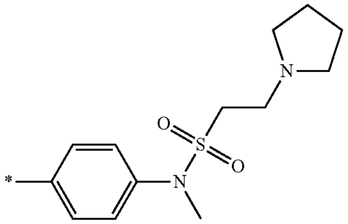
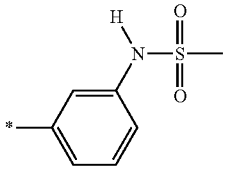
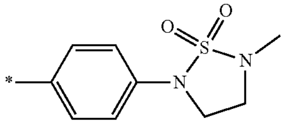
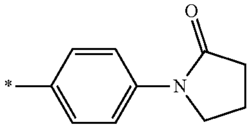
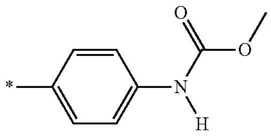
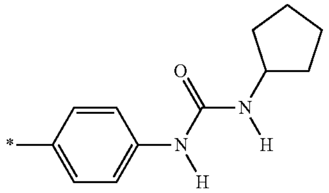
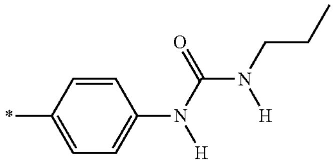
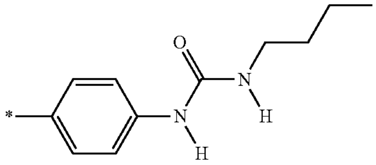
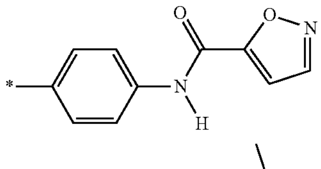
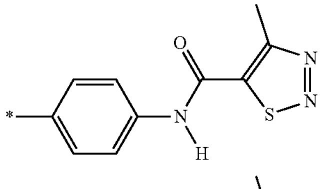
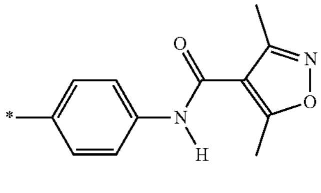
-continued
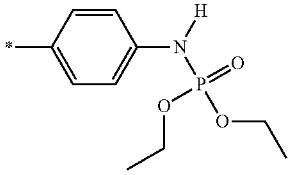
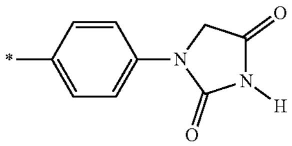
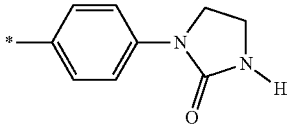
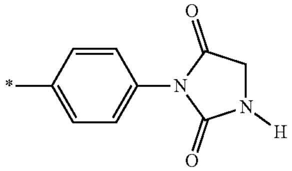
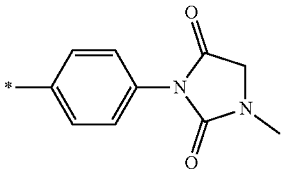
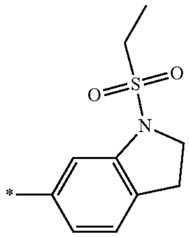
*—H
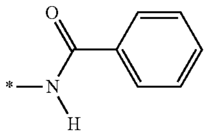
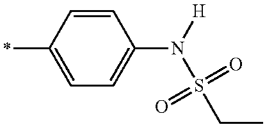
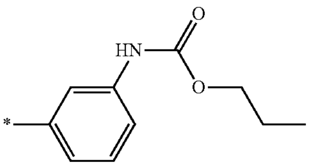
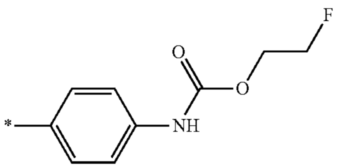
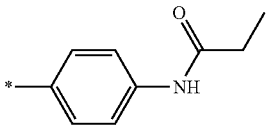
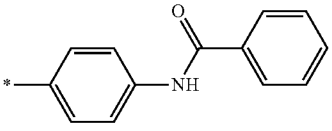
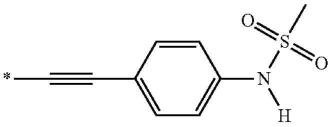

-continued
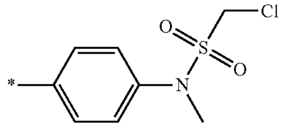
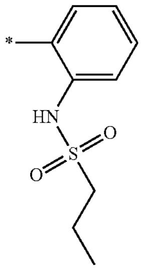
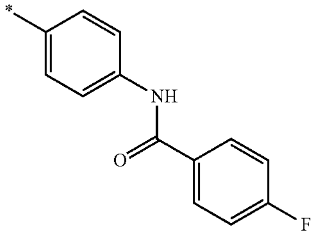
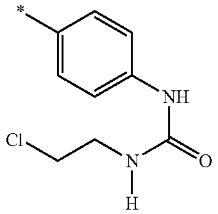
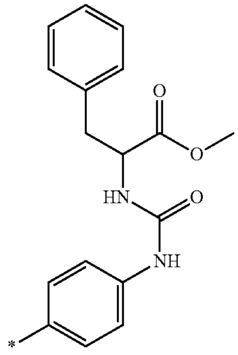
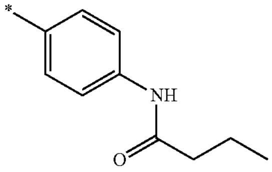
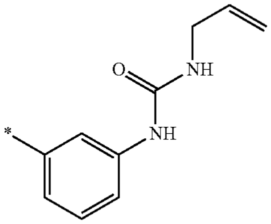
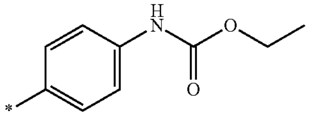
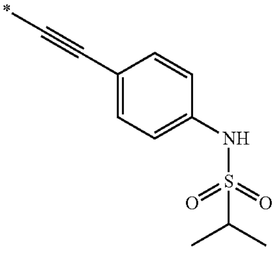
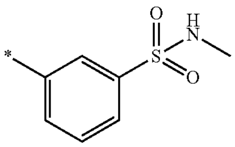
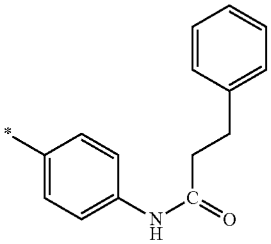
-continued
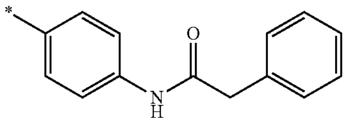
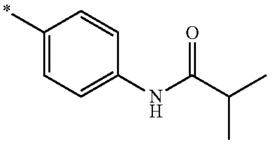
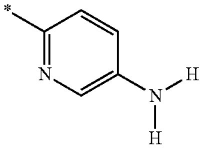
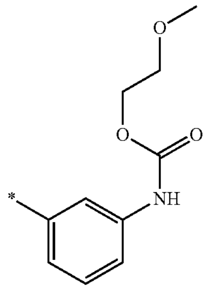
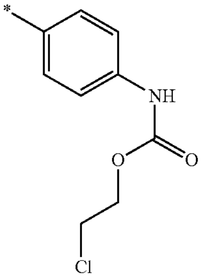
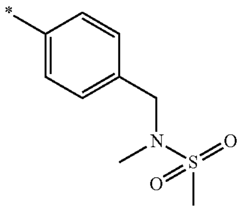
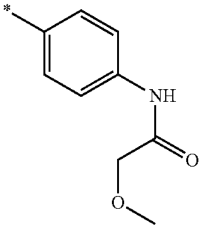
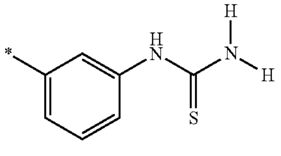
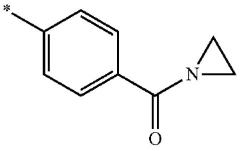
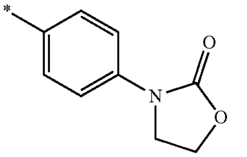
Exemplary Z substituents include the following, where the * indicates the bond of attachment of the scaffold molecule.
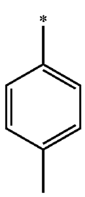
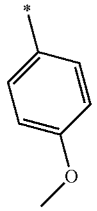
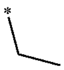
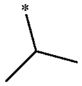
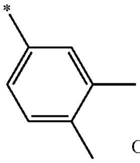
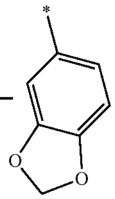
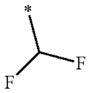
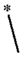
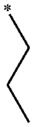

-continued

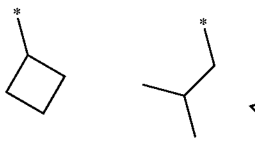

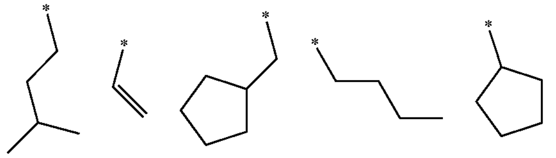

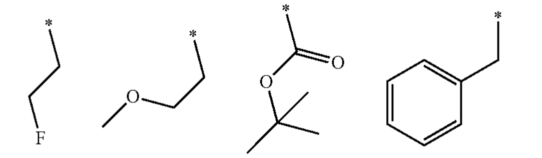

Preferred Z substituents include —a hydrogen; —a $C_1$ to $C_6$ alkyl optionally substituted with: —an alkoxy, —one or more halogens, or —a $C_6$ to $C_8$ aryl; —a $C_2$ to $C_6$ alkylene; and —a $C_6$ to $C_8$ aryl optionally substituted with an alkoxy.

Preferred Z substituents also include the following, where the * indicates the bond of attachment of the scaffold molecule.

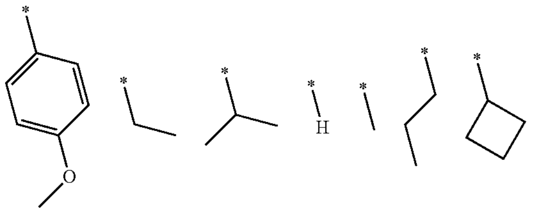

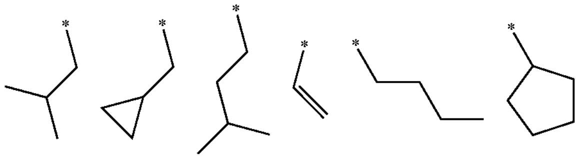

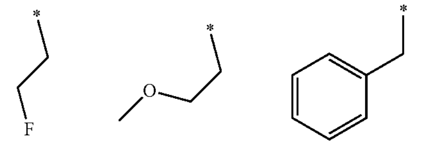

More preferred Z substituents include —a hydrogen; —a $C_1$ to $C_6$ alkyl optionally substituted with: —a $C_6$ to $C_8$ aryl; —a $C_2$ to $C_6$ alkylene; and —a $C_6$ to $C_8$ aryl optionally substituted with an alkoxy.

More preferred Z substituents include the following, where the * indicates the bond of attachment of the scaffold molecule.

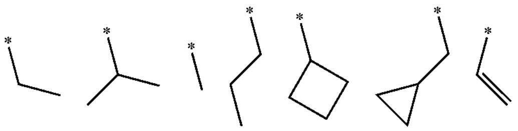

-continued

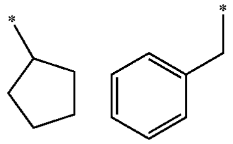

Exemplary R substituents include the following:

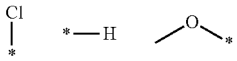

Preferred R substituents include the following:

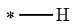

Exemplary $R_1$ substituents include the following:

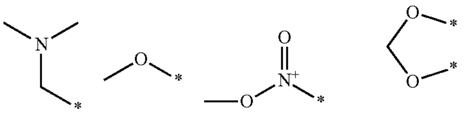

connects R1 and R2

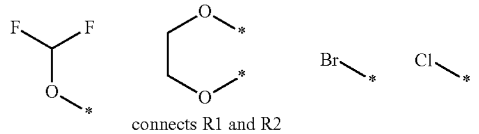

connects R1 and R2

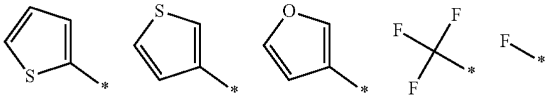

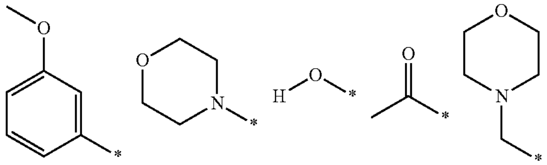

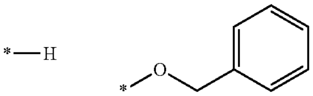

Preferred $R_1$ substituents include —a hydrogen; —a halogen; —a nitro group; —a 5 or 6 membered heterocycle; —an alkoxy optionally substituted with: —a $C_6$ to $C_8$ aryl; —a $C_6$ to $C_8$ aryl optionally substituted with an alkoxy.

Preferred $R_1$ substituents also include the following:

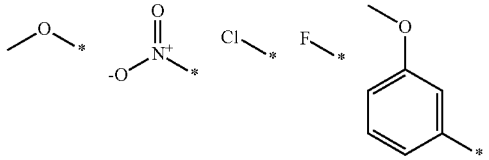

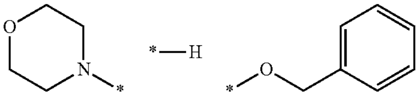

More preferred $R_1$ substituents include the following:
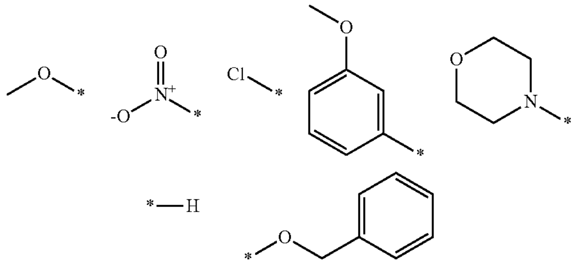
Exemplary $R_2$ substituents include the following:
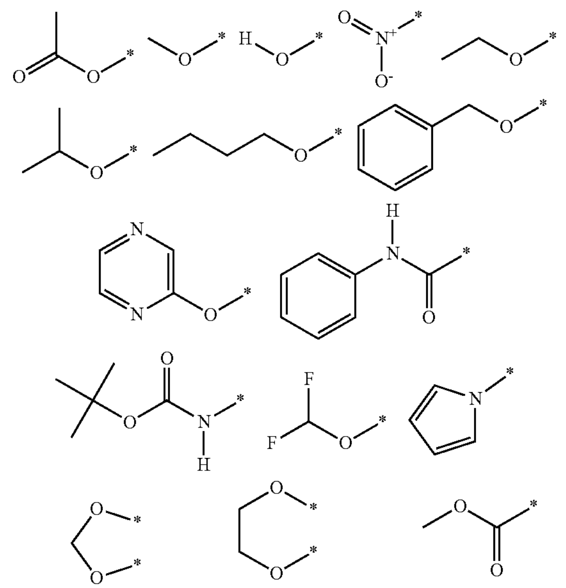
connects R1 and R2 connects R1 and R2
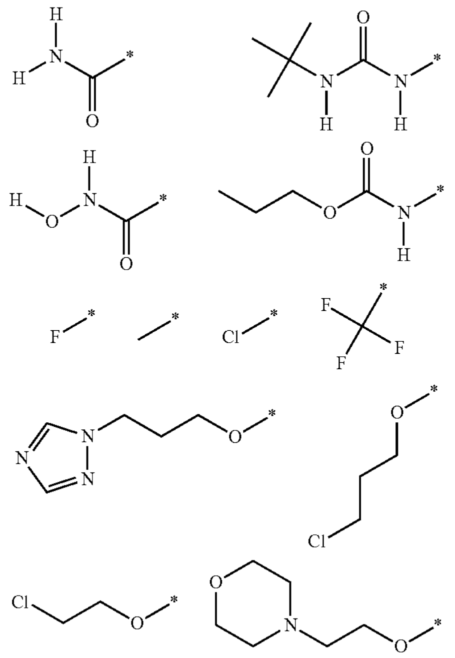
-continued
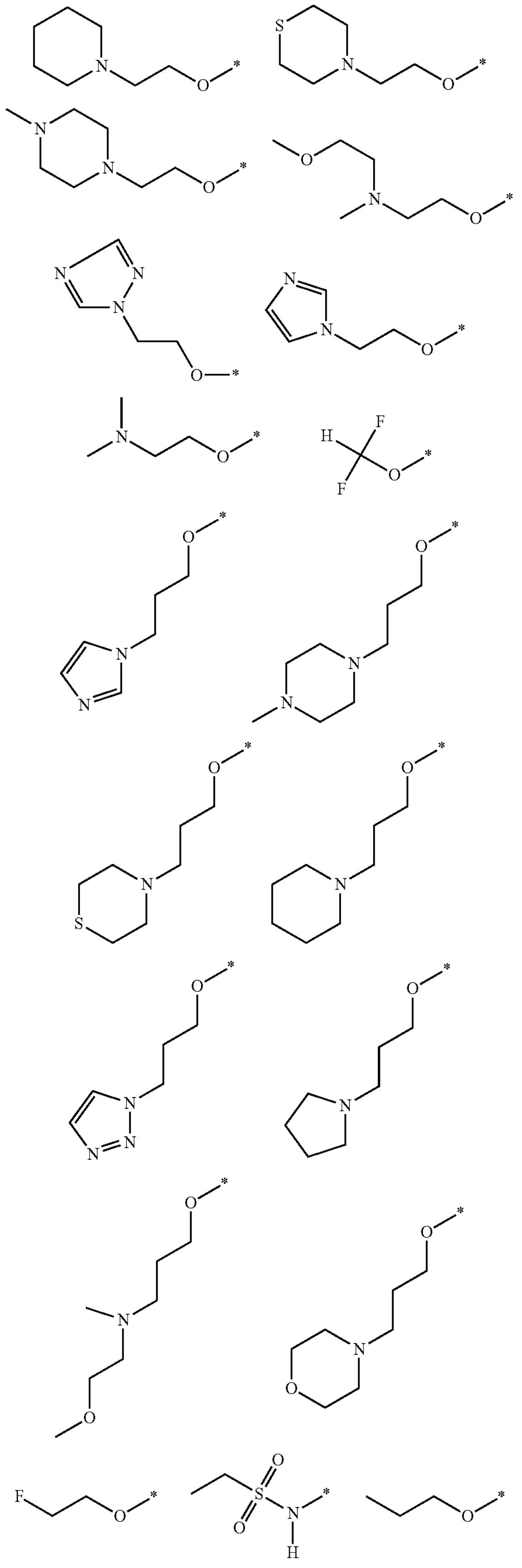

-continued

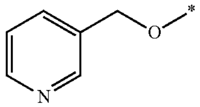

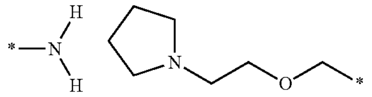

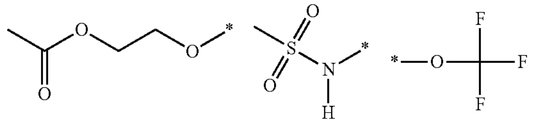

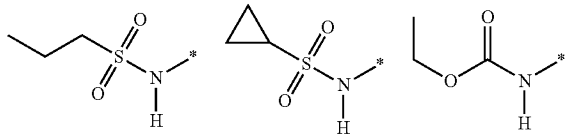

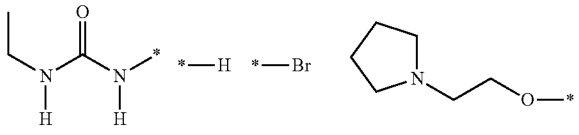

Preferred $R_2$ substituents include —a nitro group; —a hydrogen; —a halogen; _13 a hydroxy group; —a $C_1$ to $C_6$ alkyl group, optionally substituted with one or more halogens; an alkoxy group optionally substituted with: —one or more halogens, —an —$OCOR_x$ group, where $R_x$ is as defined above, —a dialkyl-amino optionally substituted with an alkoxy, —a 5 or 6 membered heterocycle group optionally substituted with a $C_1$ to $C_6$ alkyl, or —a 5 or 6 membered heteroaryl group; —an amide group; and —a —$NHSO_2R_x$ group, where $R_x$ is as defined above.

Preferred $R_2$ substituents also include the following:

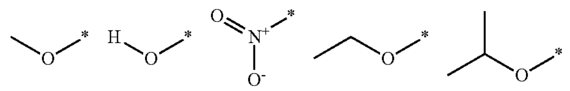

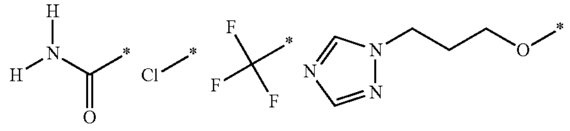

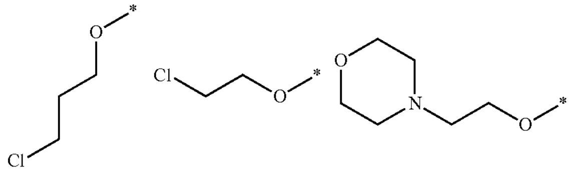

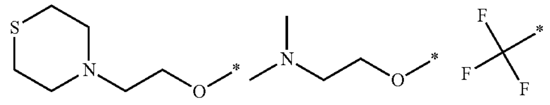

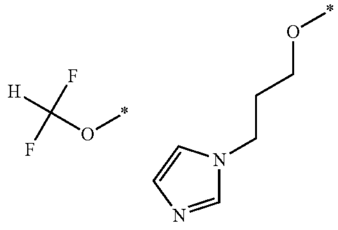

-continued

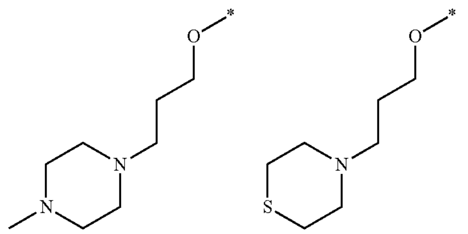

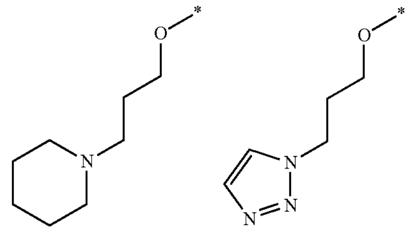

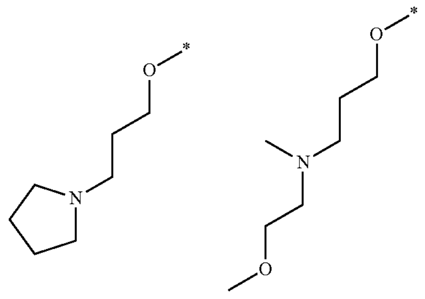

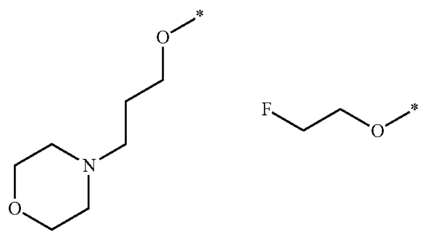

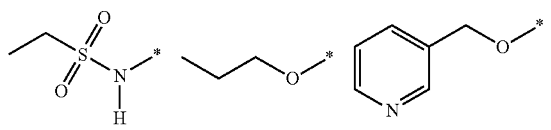

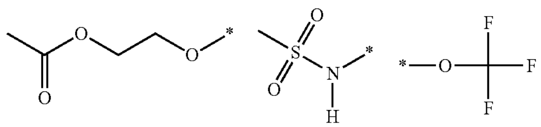

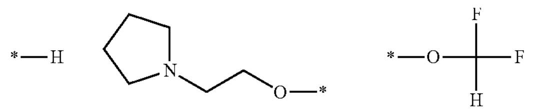

More preferred $R_2$ substituents include —a hydrogen; _—a $C_1$ to $C_6$ alkyl group, optionally substituted with one or more halogens; —an alkoxy group optionally substituted with: —one or more halogens, —a 5 or 6 membered heterocycle group optionally substituted with a $C_1$ to $C_6$ alkyl, or —a 5 or 6 membered heteroaryl group.

More preferred $R_2$ substituents also include the following:
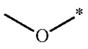
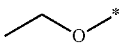
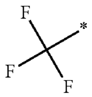
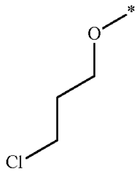
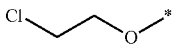
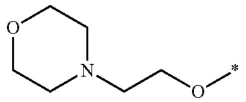
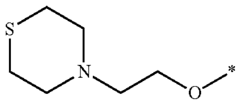
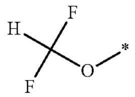
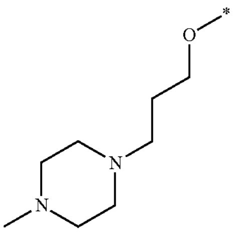
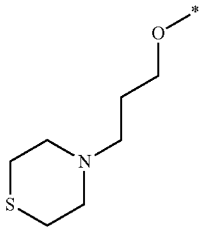
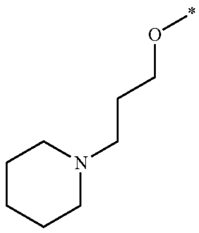
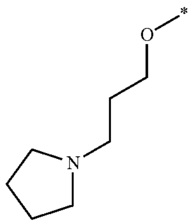
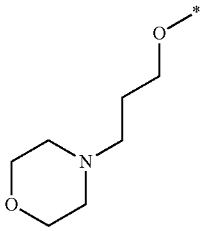
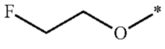
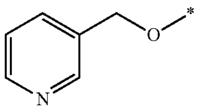
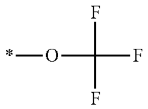
*—H
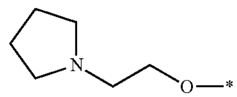
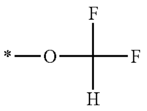
Exemplary $R_3$ substituents include the following:
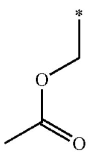
*—H
Preferred $R_3$ substituents include the following:
*—H
Compounds of the invention include the following:
1
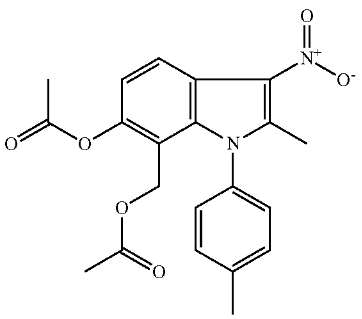
2
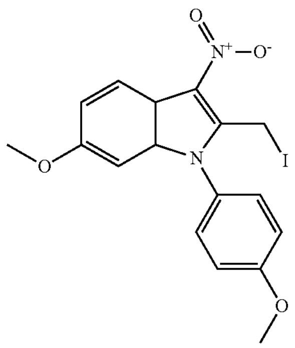
3
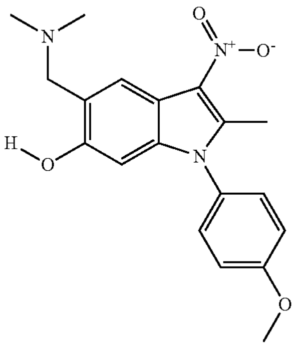
4
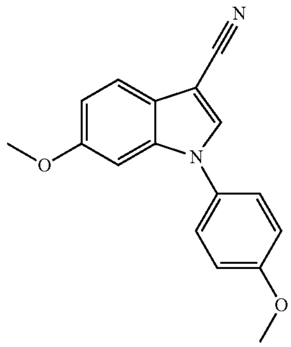

-continued
5
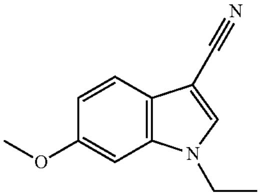
6
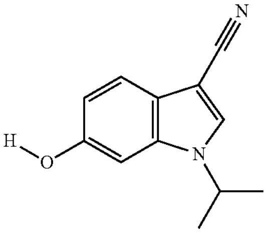
7
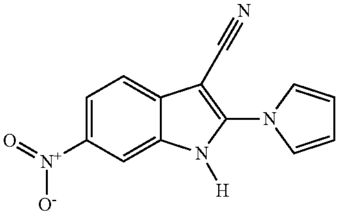
8
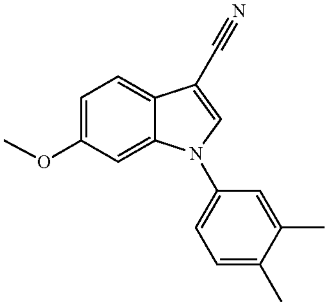
9
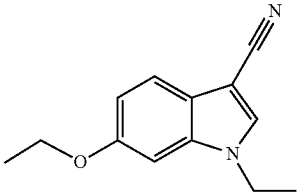
10
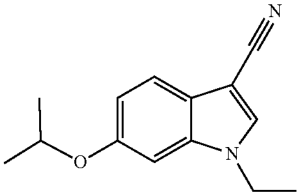
11
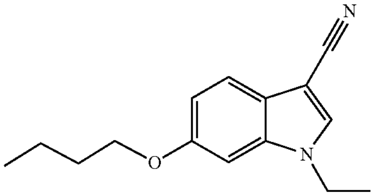
-continued
12
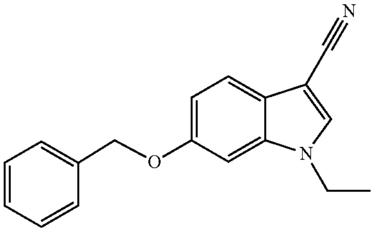
13
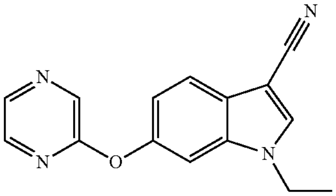
14
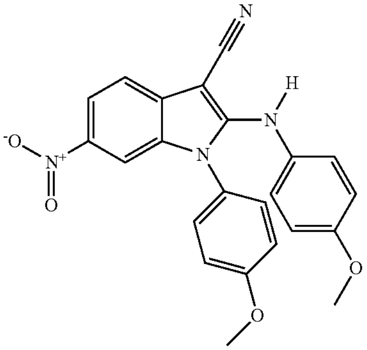
15
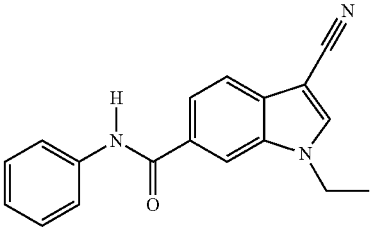
16
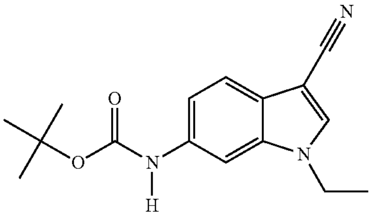
17
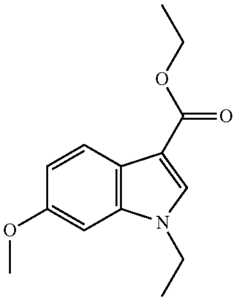

-continued
18
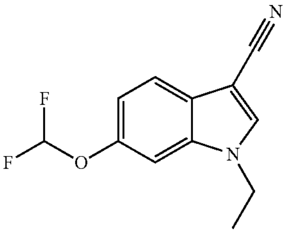
19
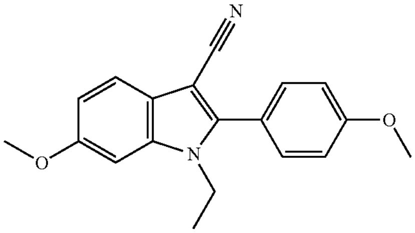
20
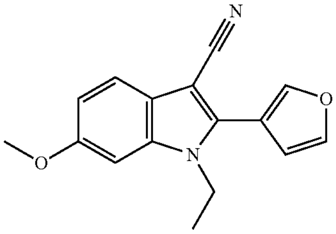
21
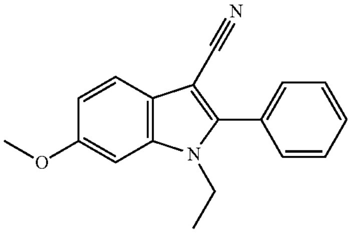
22
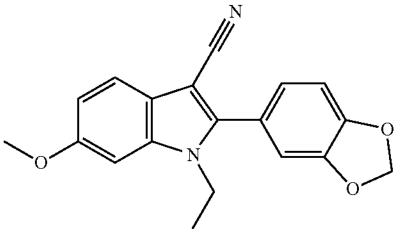
23
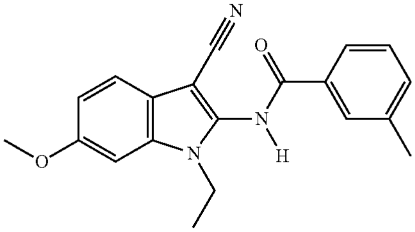
-continued
24
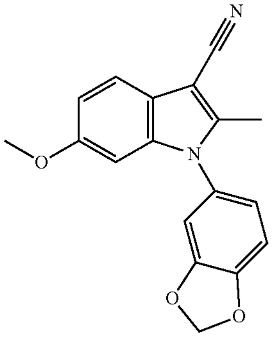
25
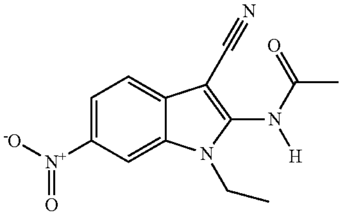
26
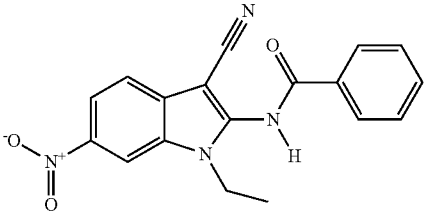
27
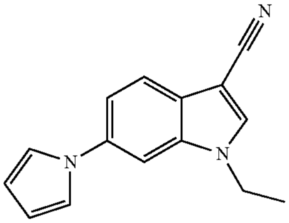
28
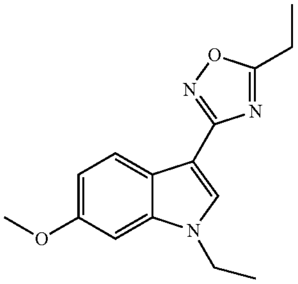
29
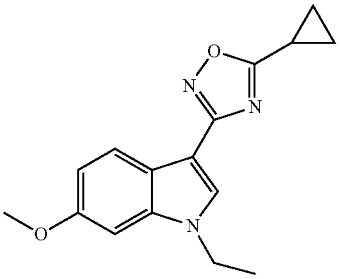

-continued
30
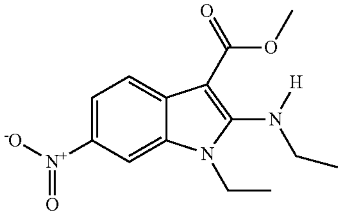
31
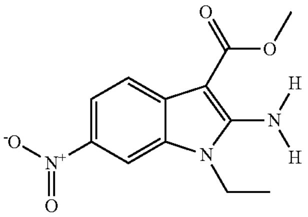
32
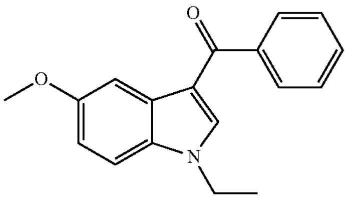
33
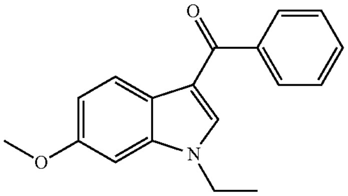
34
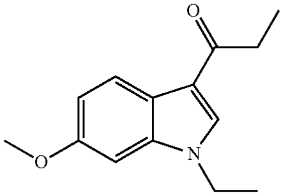
35
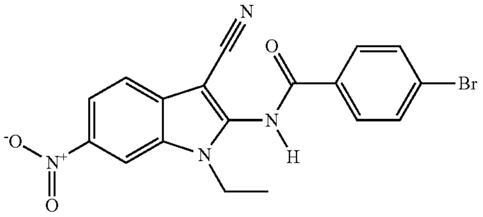
36
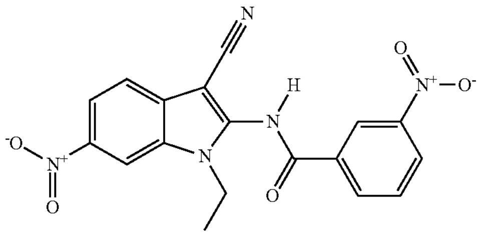
-continued
37
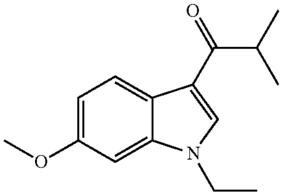
38
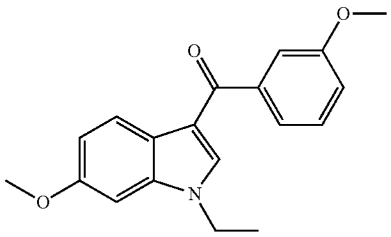
39
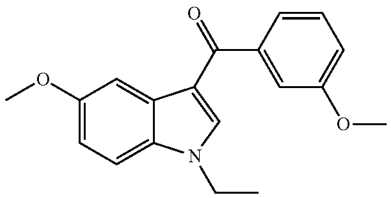
40
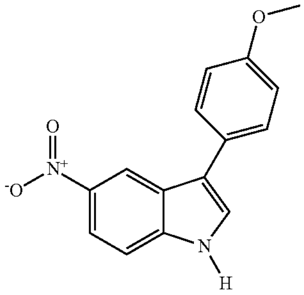
41
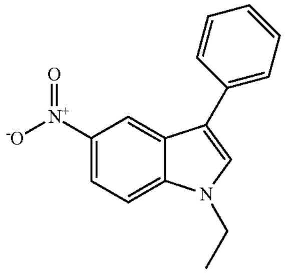
42
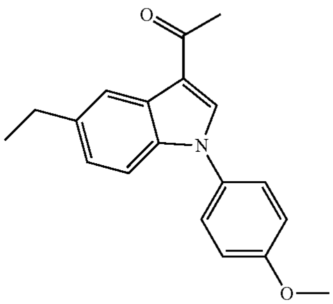

-continued
43
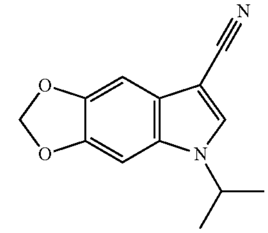
44
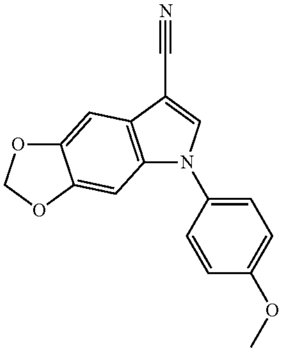
45
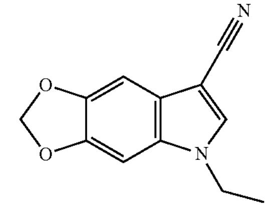
46
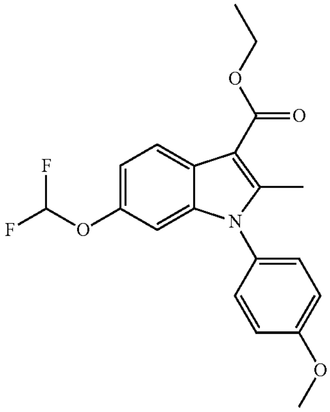
47
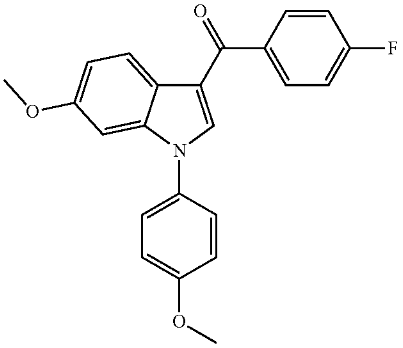
-continued
48
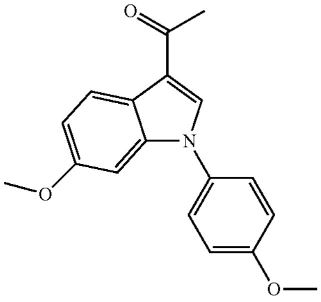
49
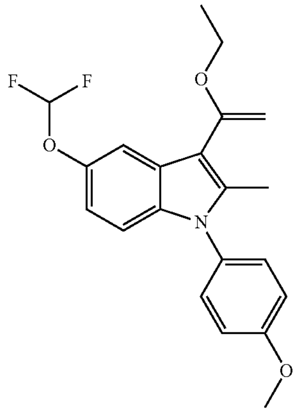
50
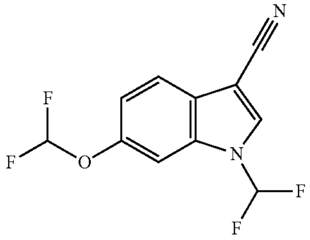
51
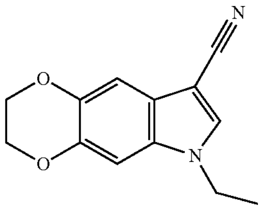
52
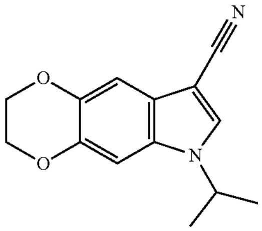

-continued
53
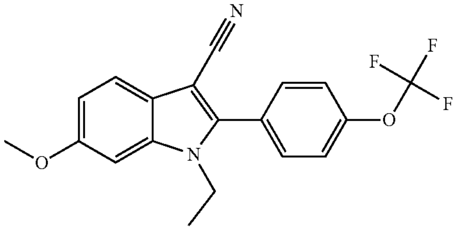
54
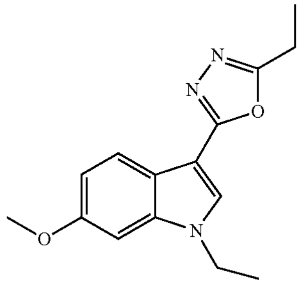
55
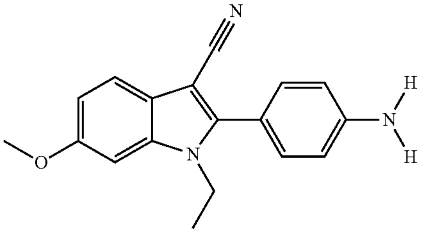
56
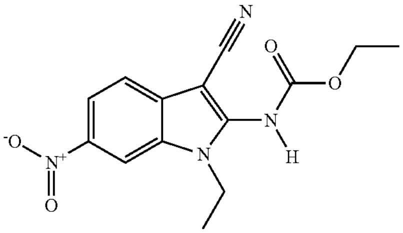
57
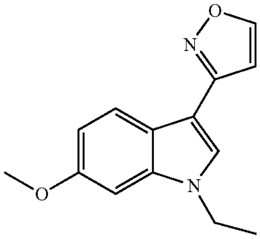
58
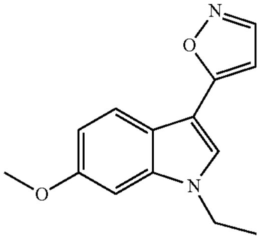
-continued
59
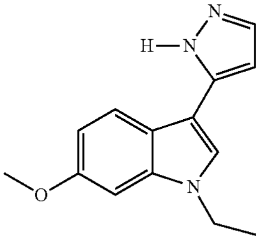
60
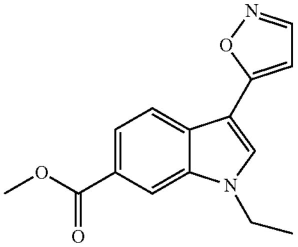
61
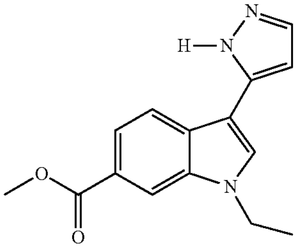
62
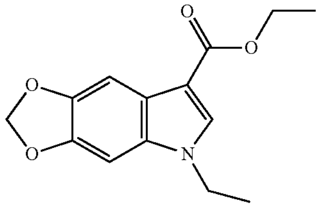
63
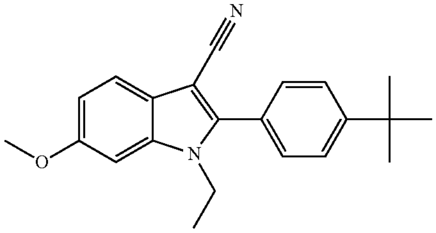
64
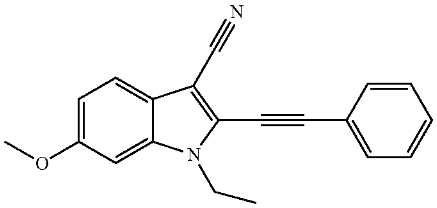
65
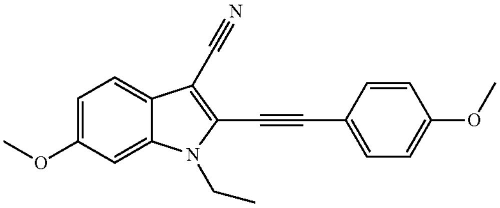

-continued
66
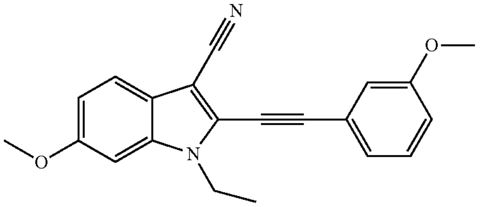
67
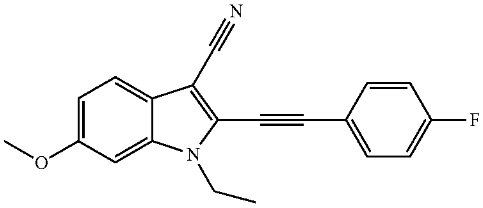
68
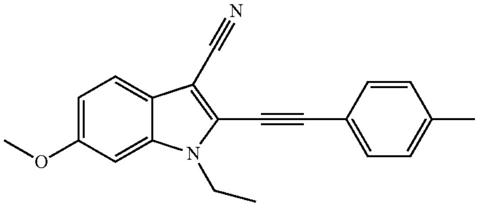
69
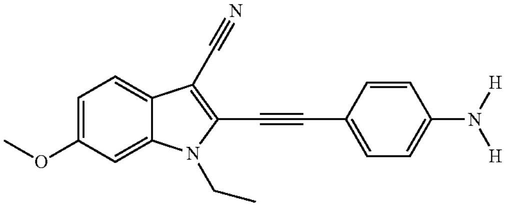
70
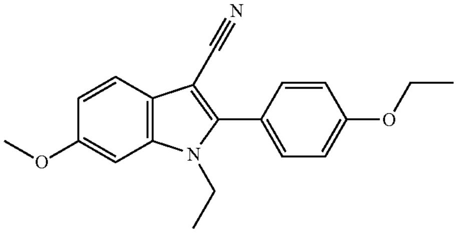
71
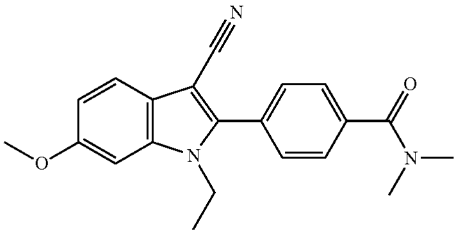
72
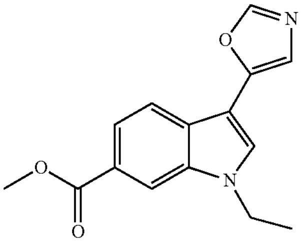
-continued
73
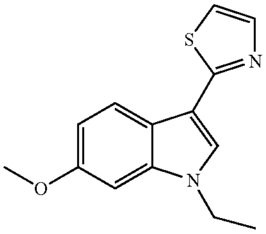
74
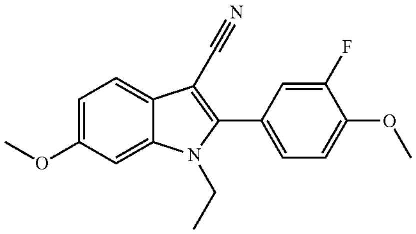
75
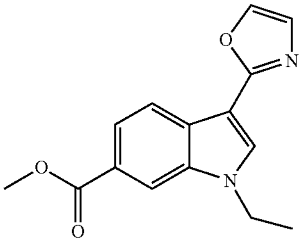
76
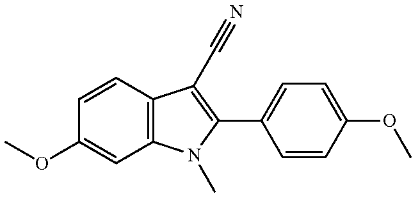
77
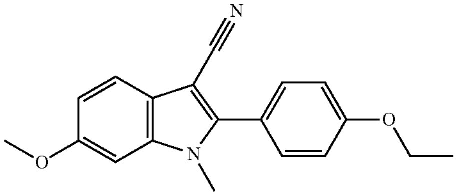
78
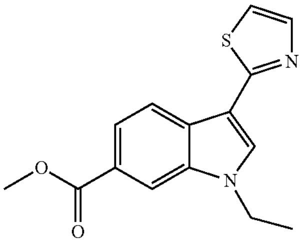
79
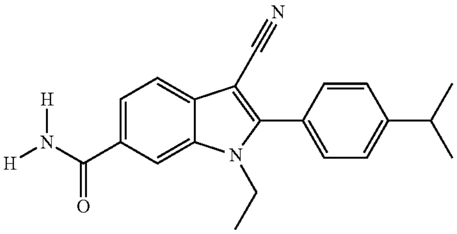

-continued
80
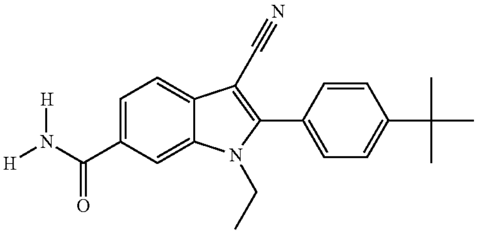
81
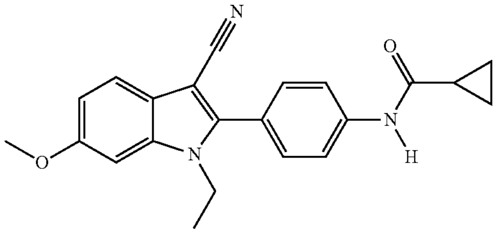
82
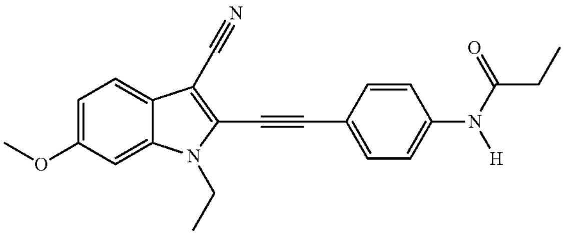
83
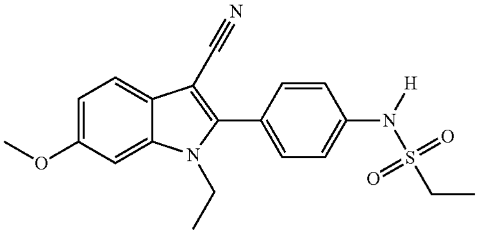
84
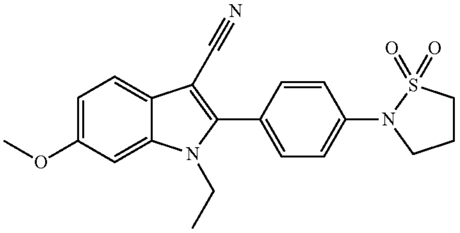
85
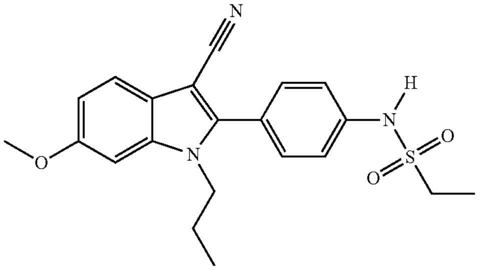
-continued
86
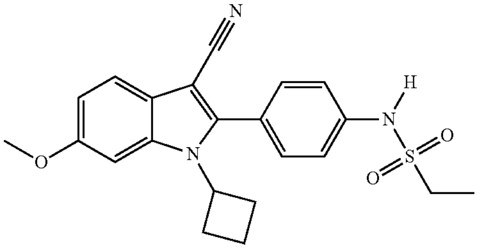
87
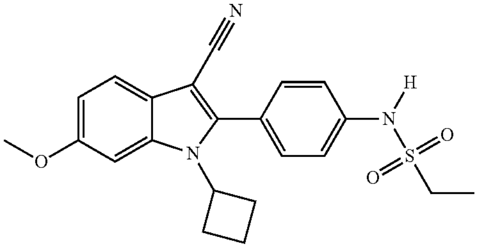
88
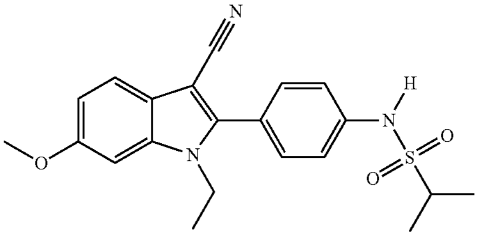
89
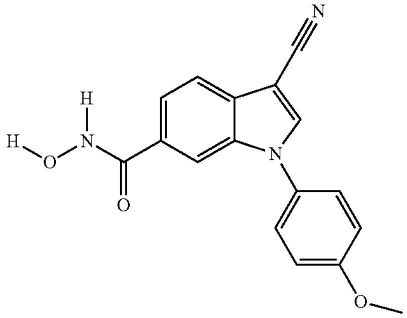
90
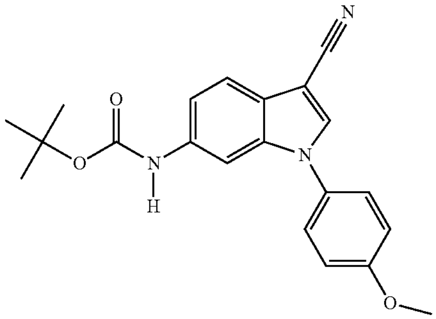
91
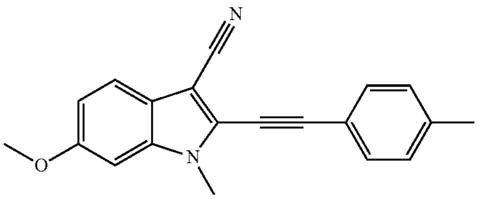

-continued
92
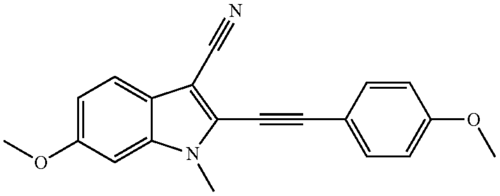
93
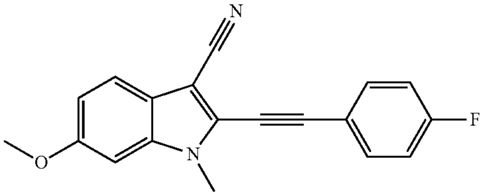
94
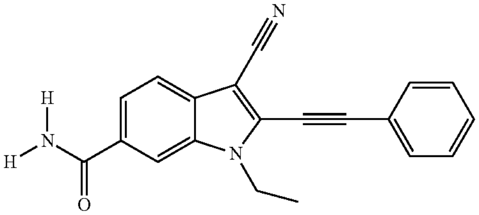
95
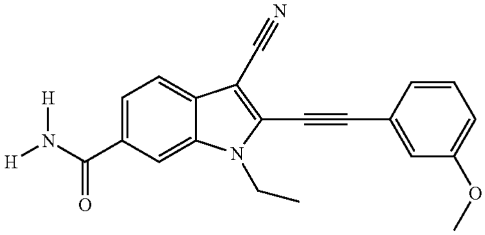
96
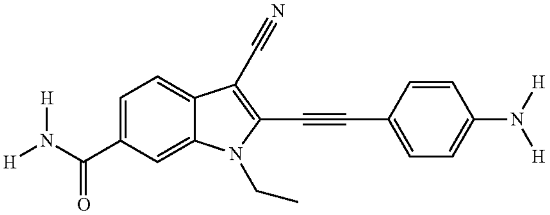
97
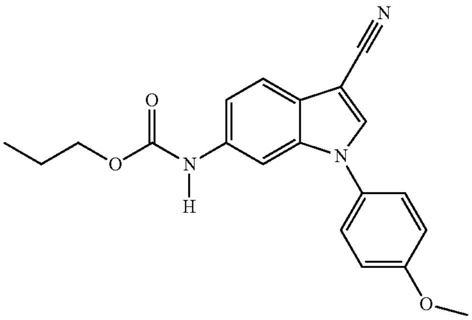
-continued
98
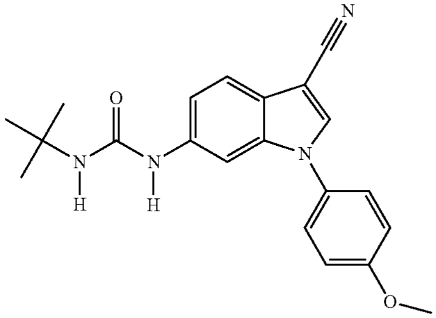
99
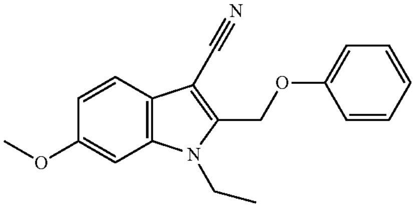
100
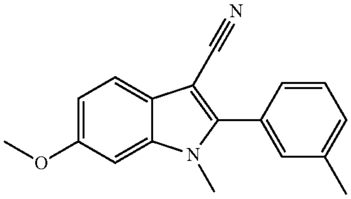
101
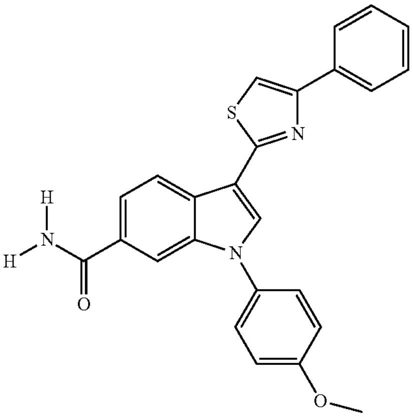
102
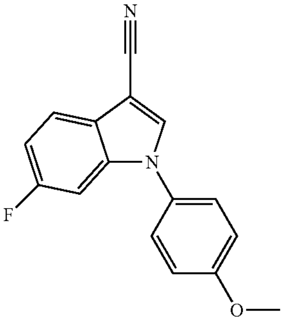

-continued
103
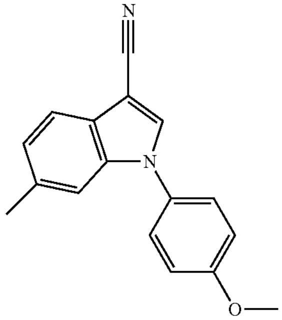
104
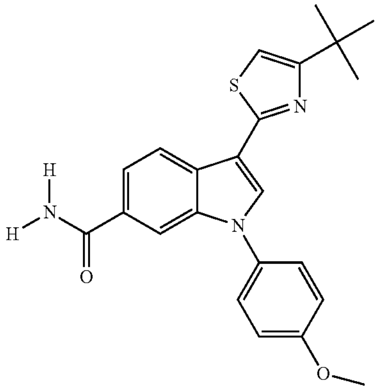
105
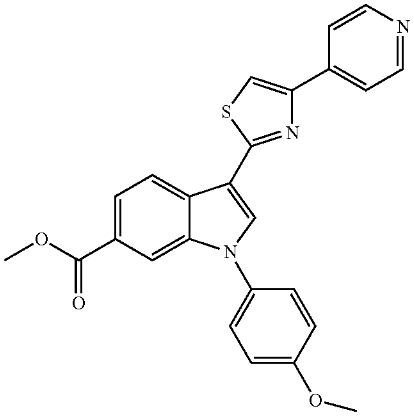
106
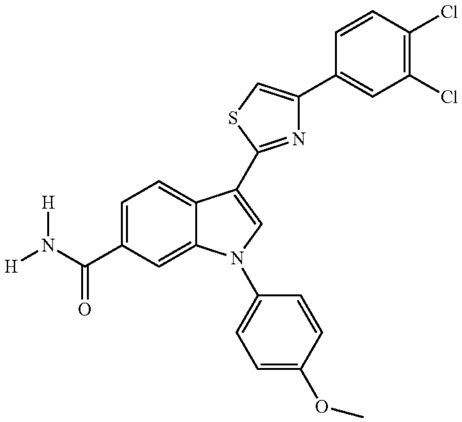
-continued
107
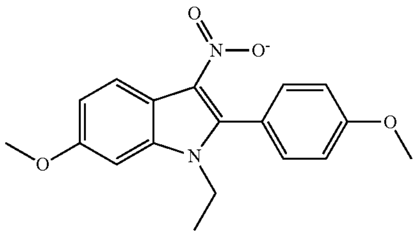
108
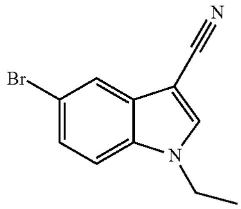
109
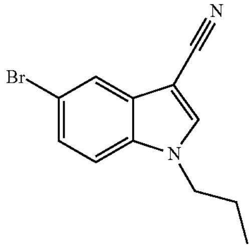
110
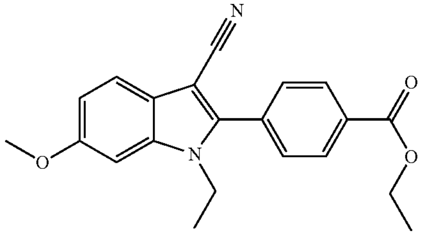
111
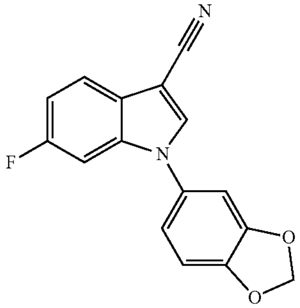
112
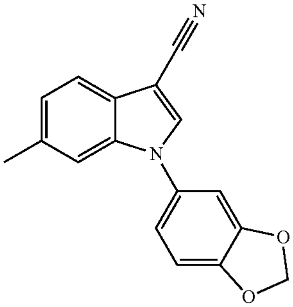

113
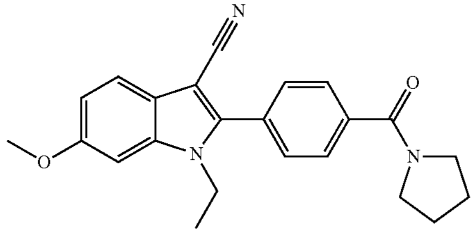
114
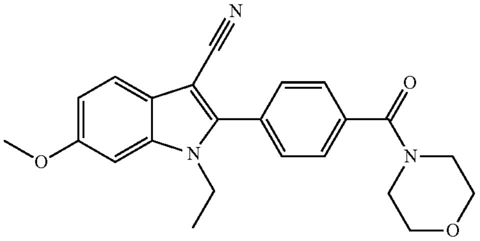
115
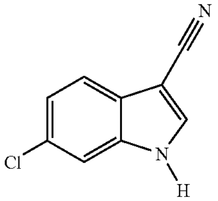
116
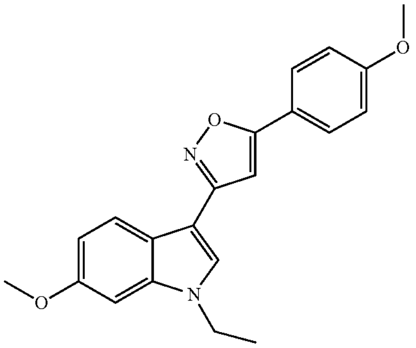
117
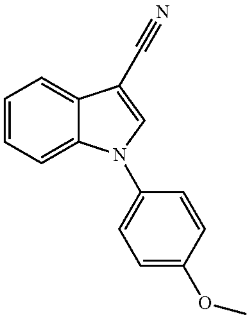
118
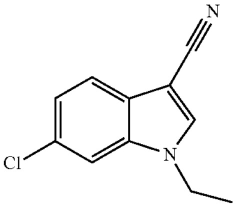
119
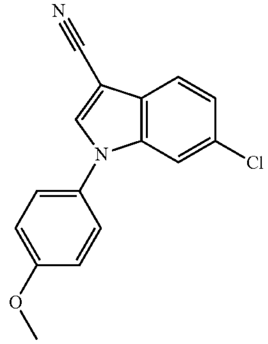
120
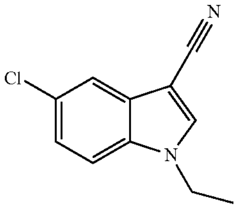
121
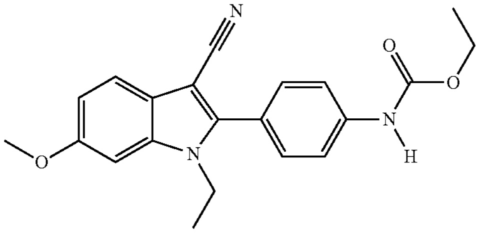
122
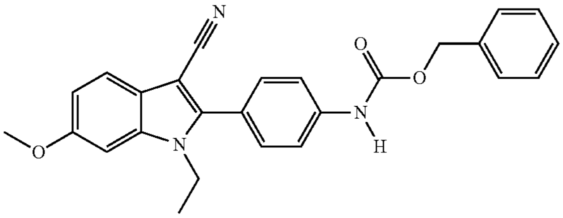
123
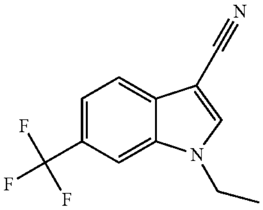
124
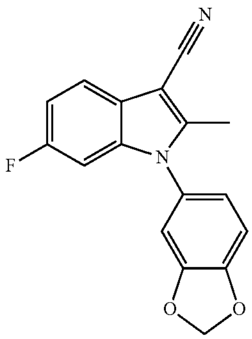

-continued
125
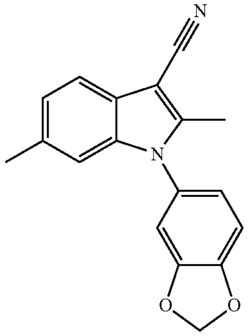
126
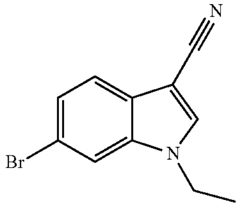
127
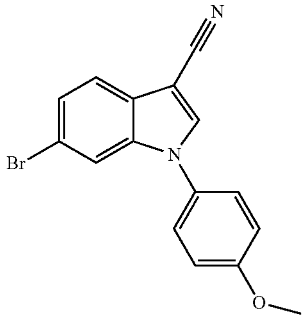
128
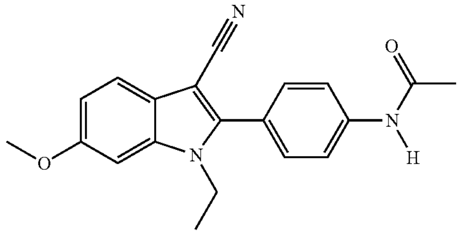
129
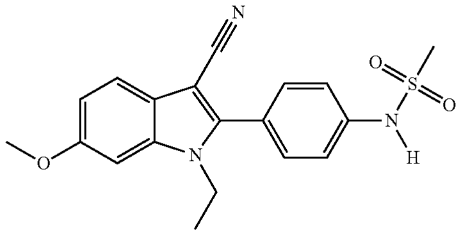
130
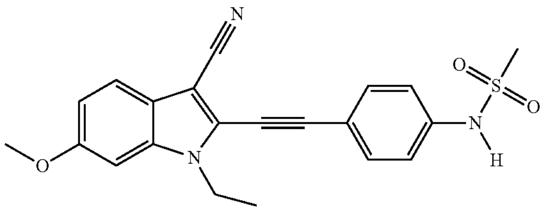
-continued
131
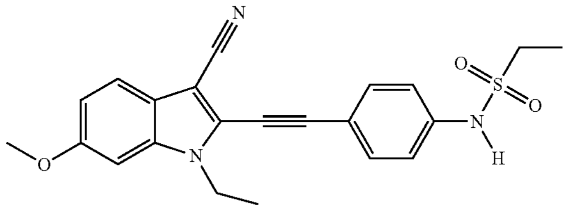
132
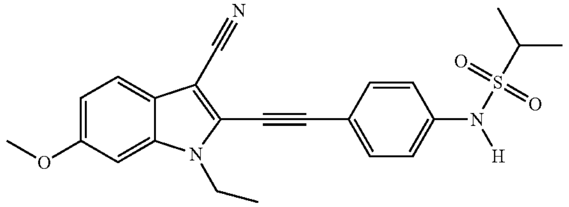
133
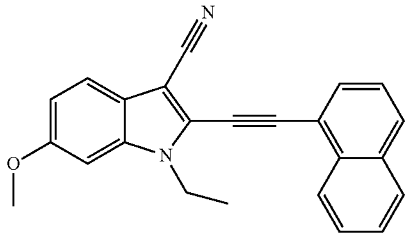
134
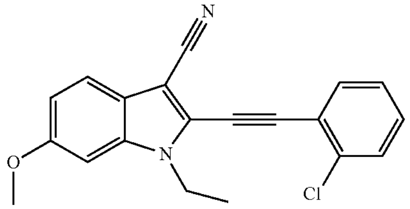
135
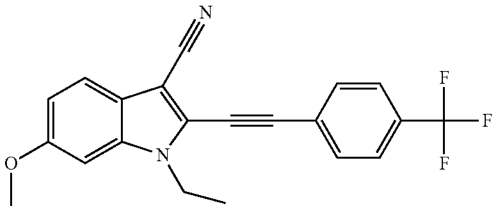
136
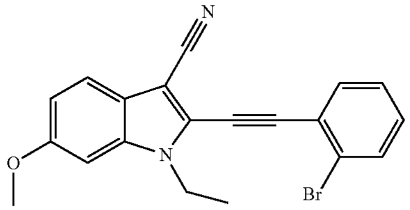
137
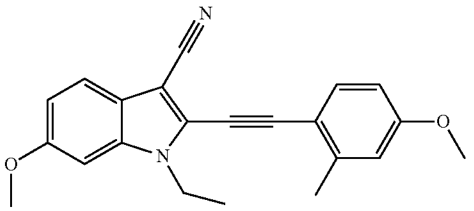

-continued
138
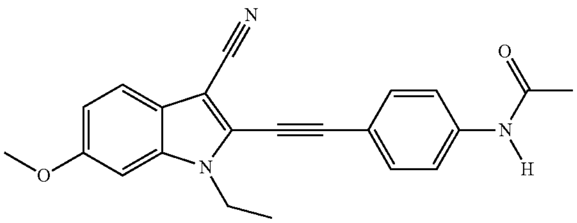
139
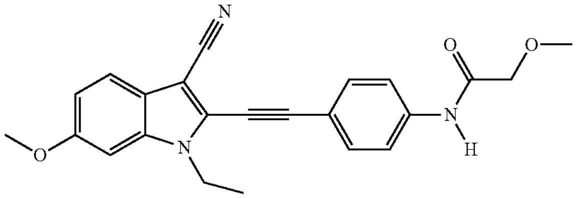
140
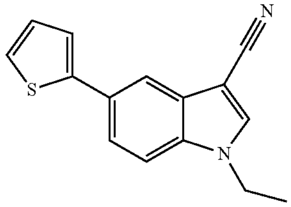
141
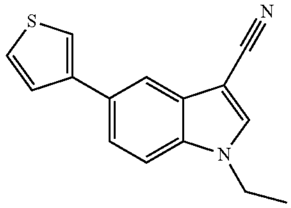
142
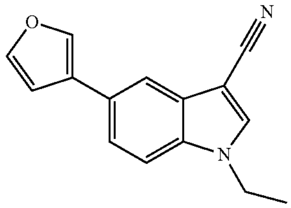
143
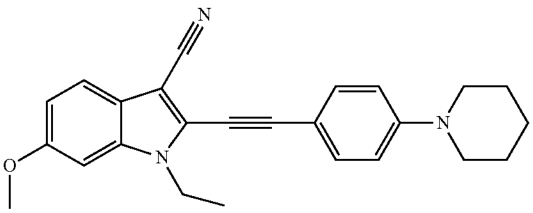
144
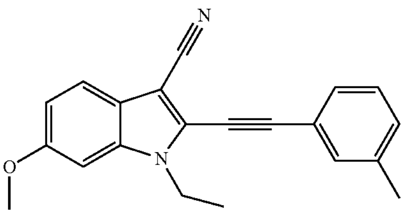
-continued
145
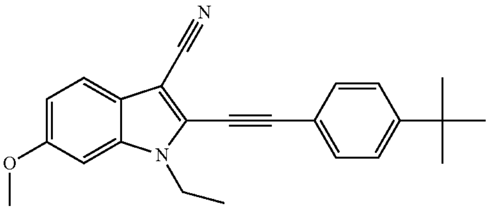
146
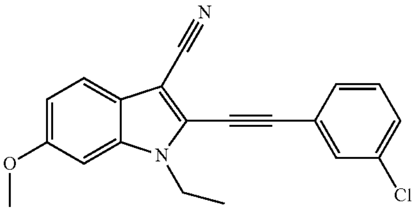
147
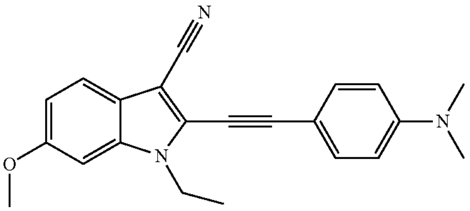
148
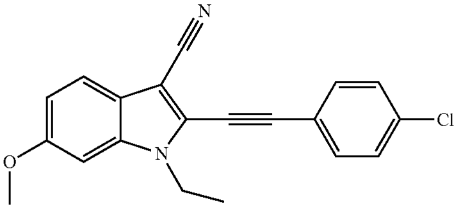
149
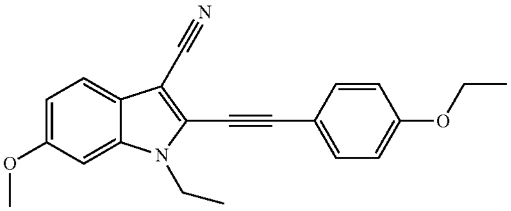
150
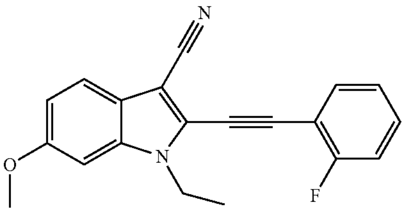
151
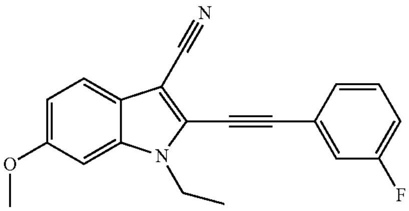

-continued
152
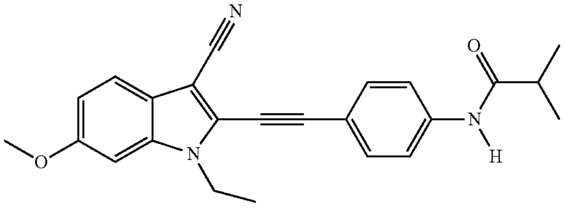
153
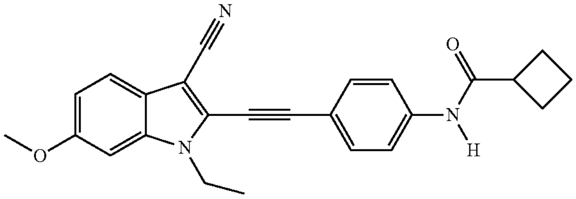
154
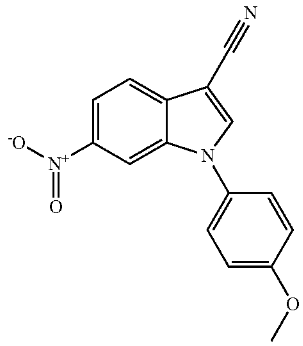
155
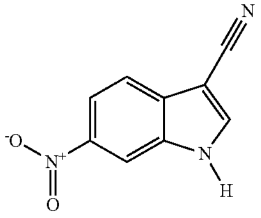
156
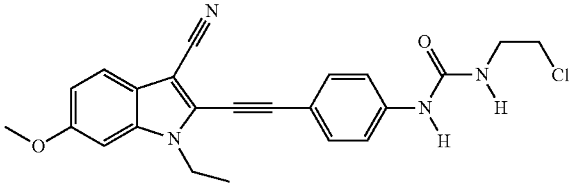
157
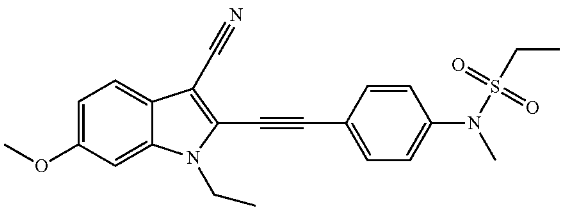
-continued
158
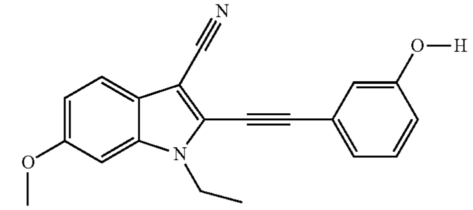
159
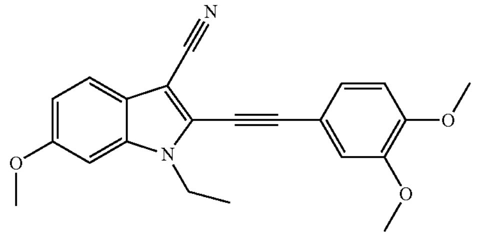
160
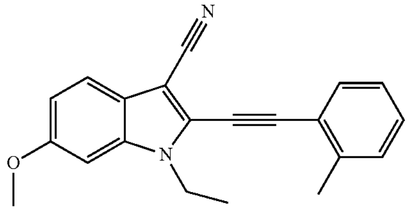
161
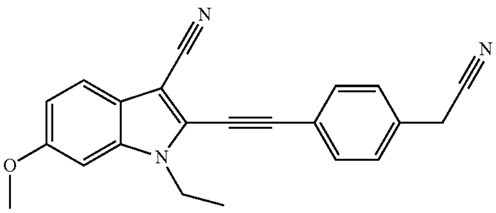
162
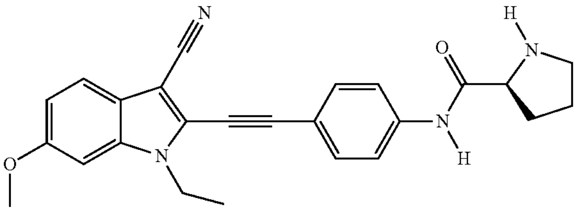
163
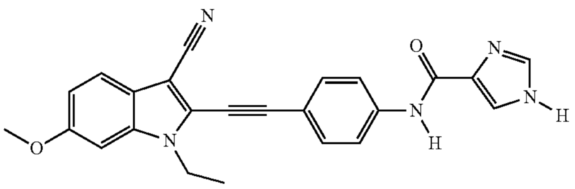
164
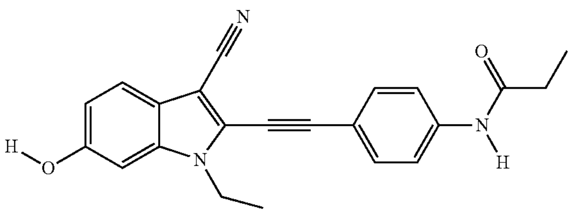

-continued
165
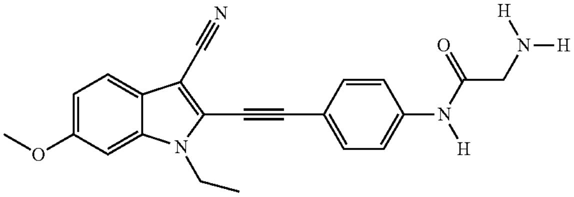
166
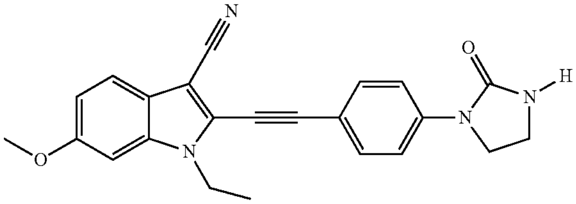
167
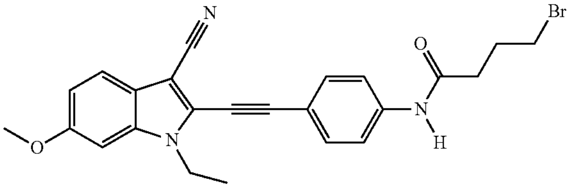
168
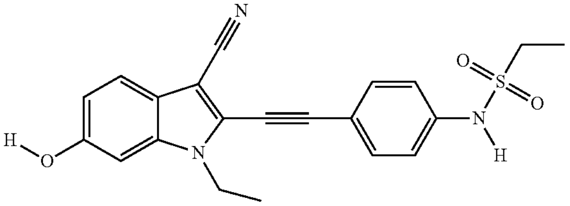
169
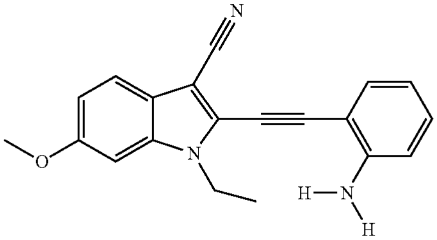
170
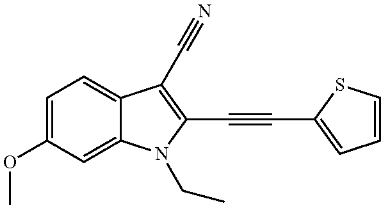
171
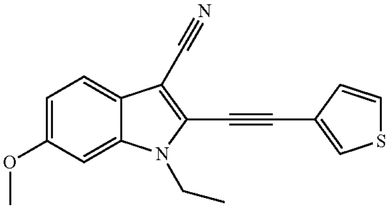
-continued
172
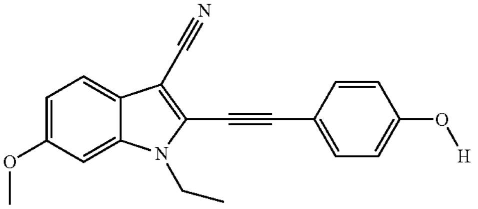
173
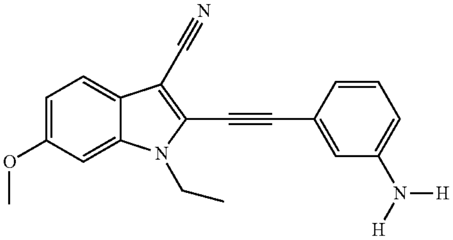
174
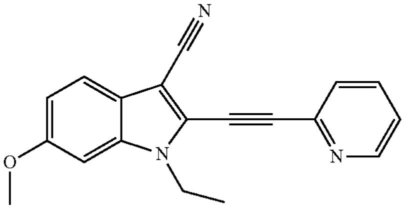
175
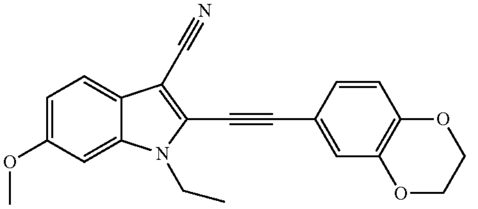
176
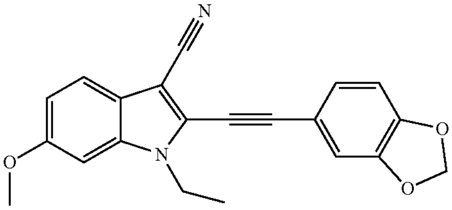
177
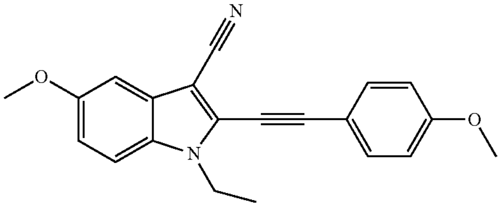
178
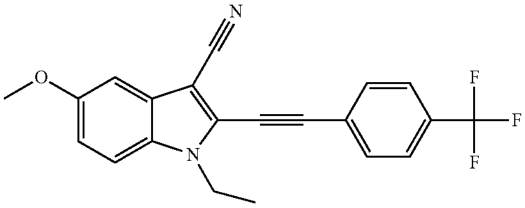

179
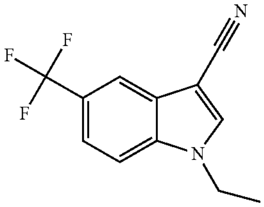
180
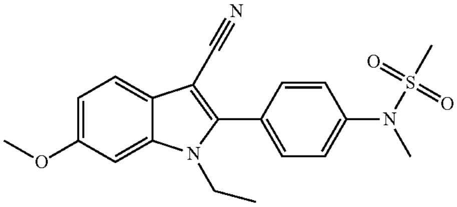
181
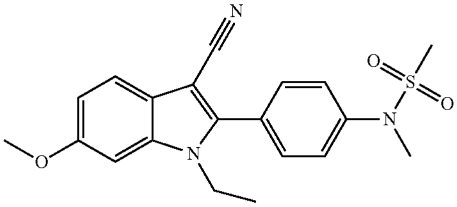
182
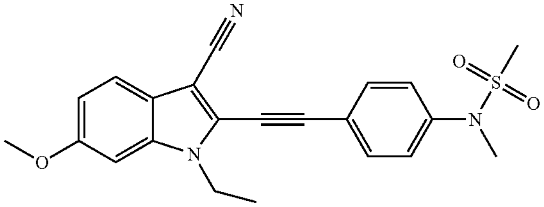
183
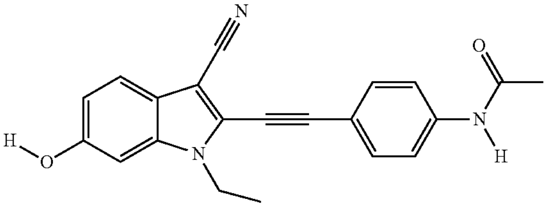
184
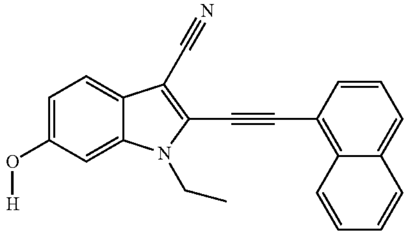
185
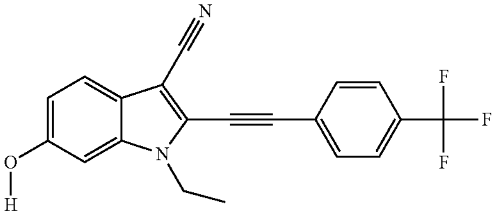
186
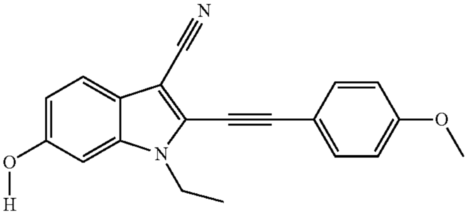
187
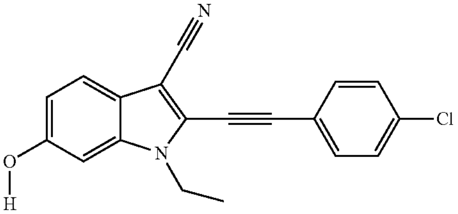
188
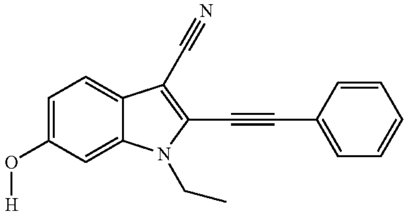
189
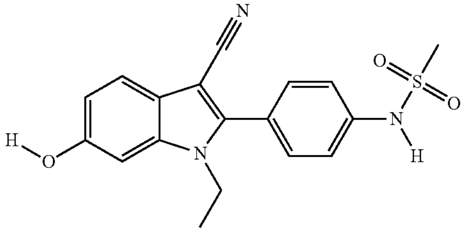
190
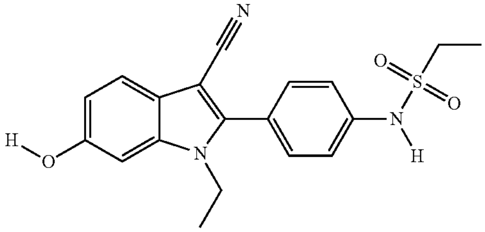
191
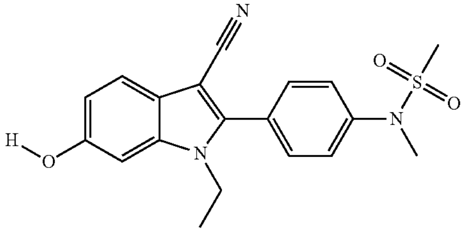
192
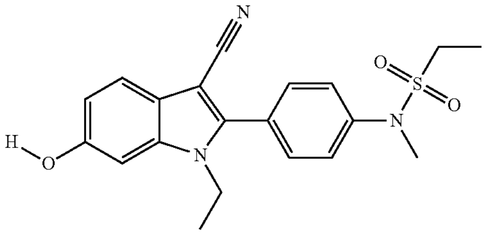

-continued
193
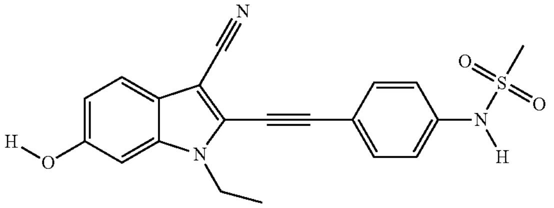
194
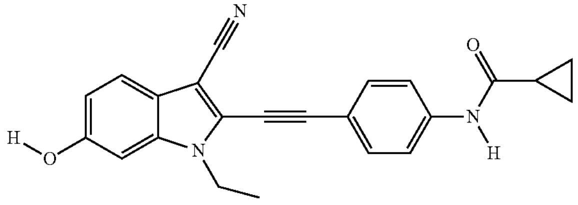
195
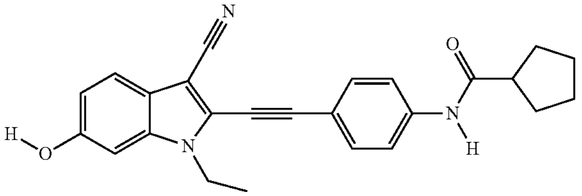
196
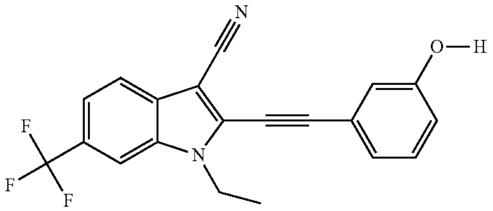
197
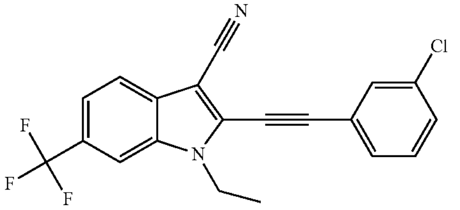
198
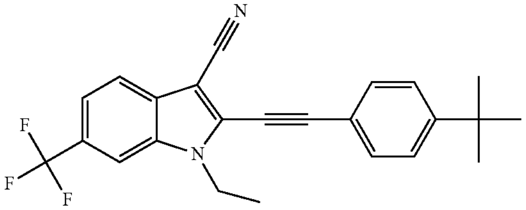
199
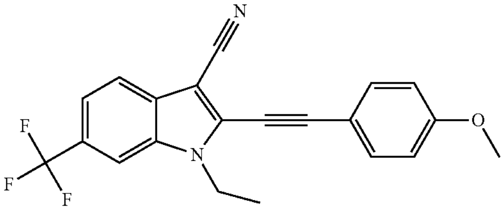
-continued
200
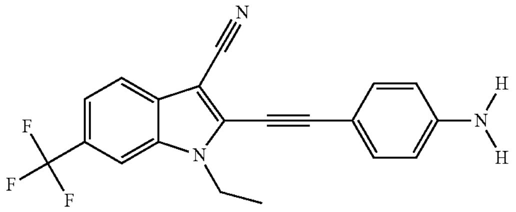
201
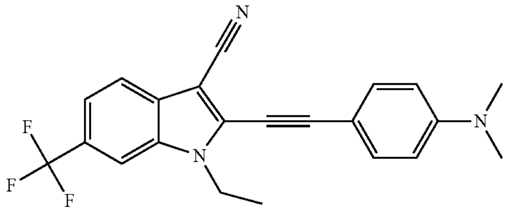
202
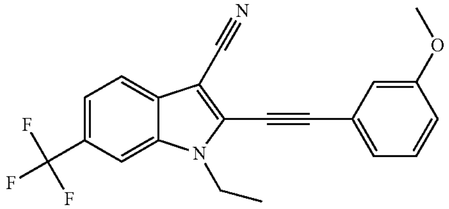
203
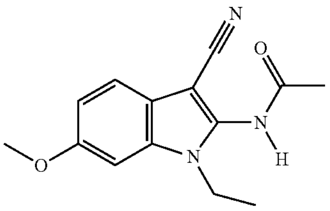
204
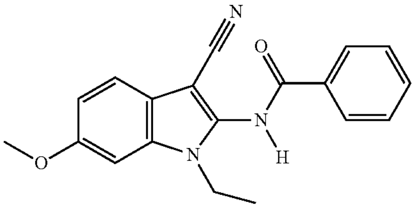
205
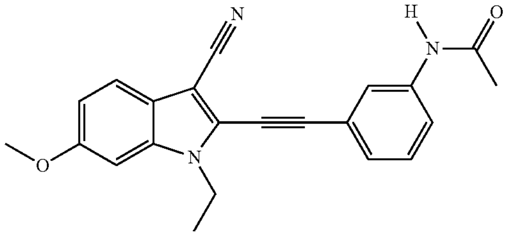
206
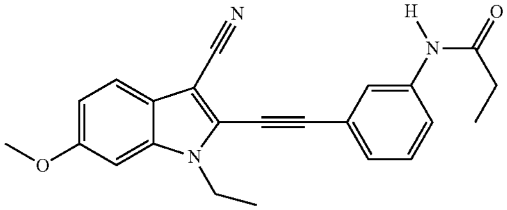

-continued
207
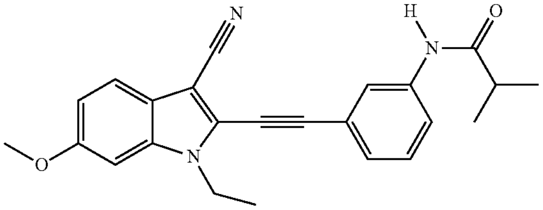
208
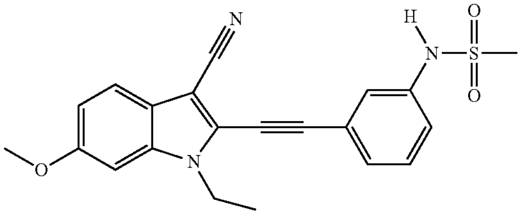
209
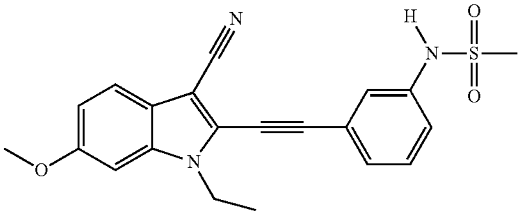
210
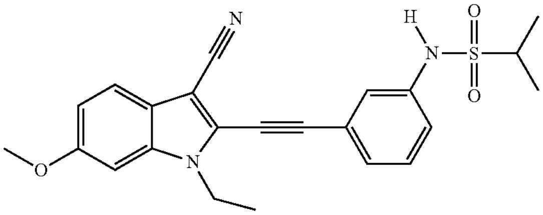
211
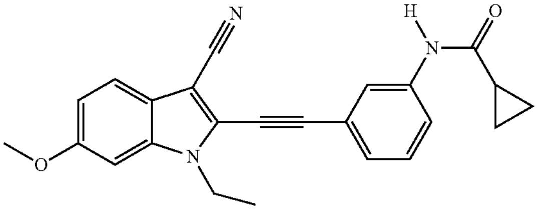
212
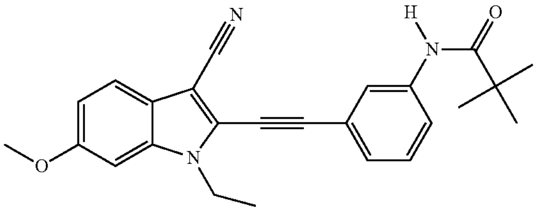
-continued
213
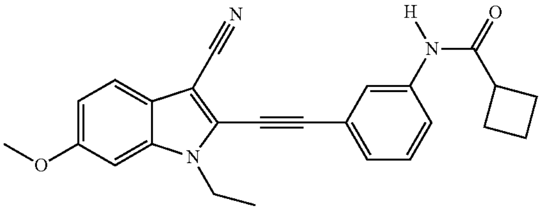
214
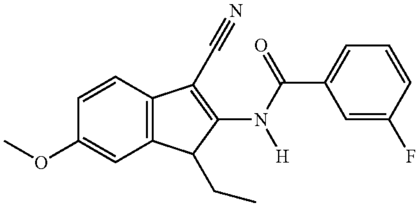
215
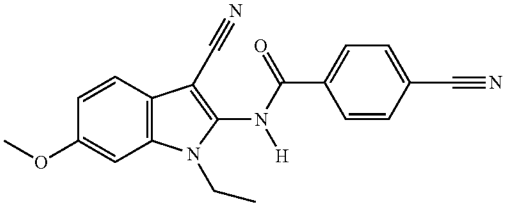
216
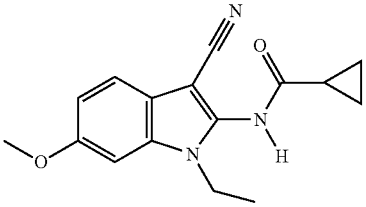
217
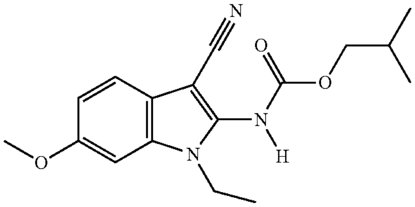
218
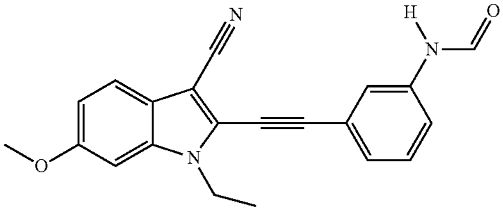
219
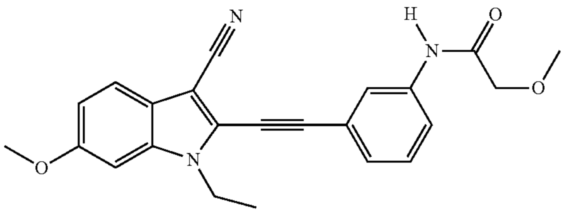

-continued
220
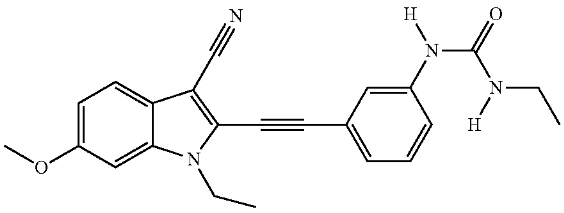
221
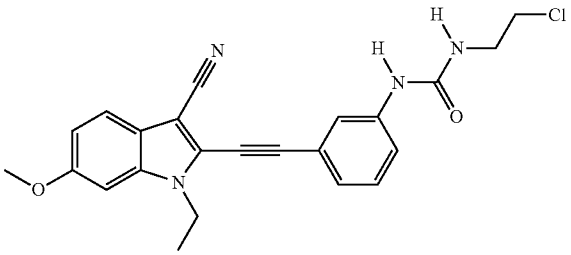
222
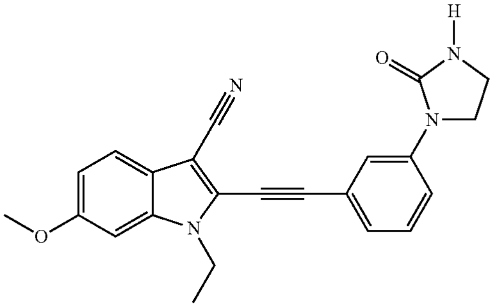
223
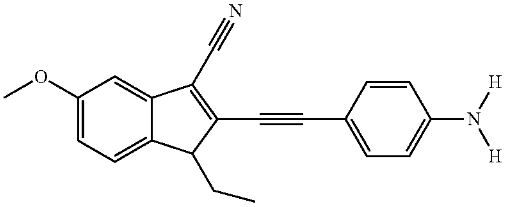
224
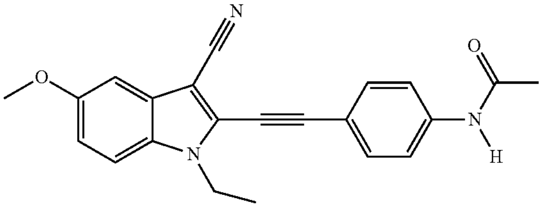
225
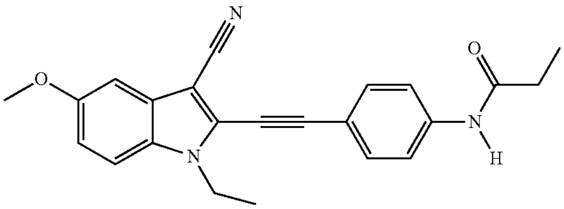
-continued
226
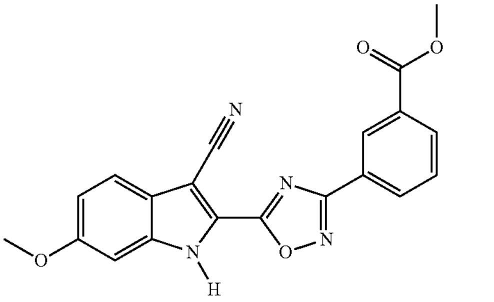
227
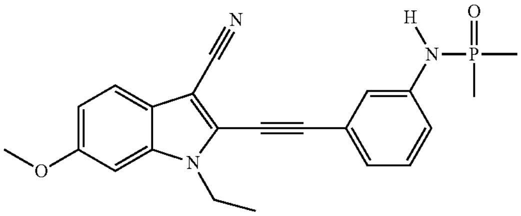
228
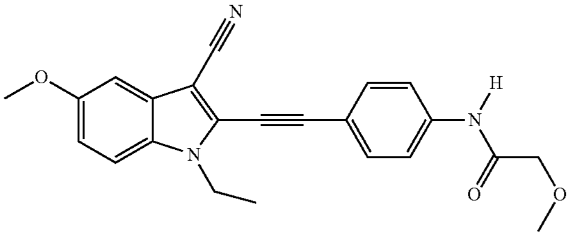
229
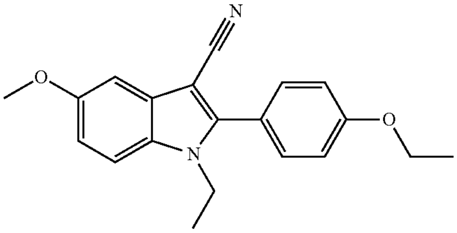
230
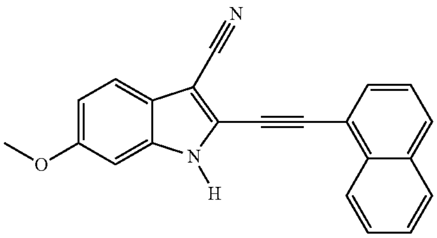
231
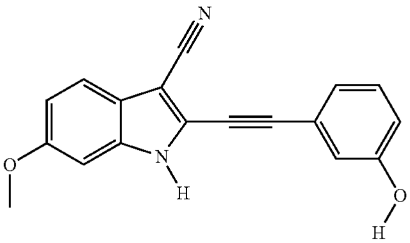

-continued
232
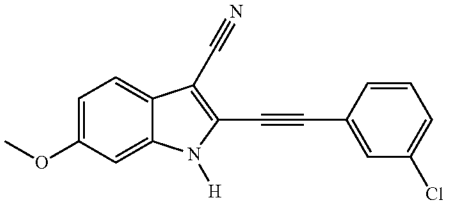
233
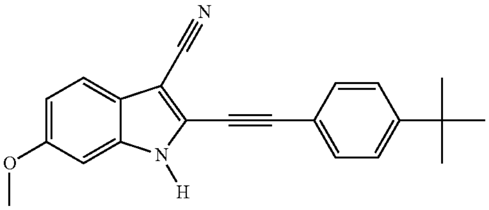
234
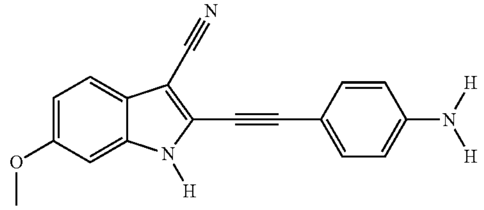
235
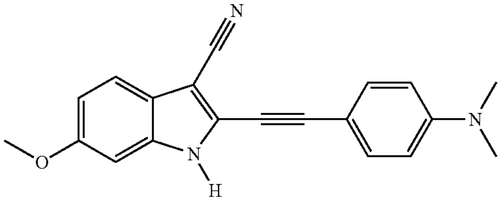
236
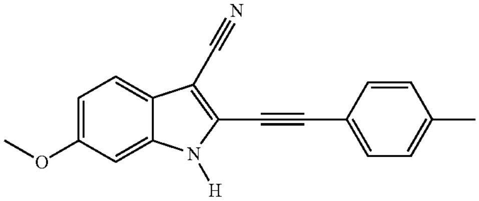
237
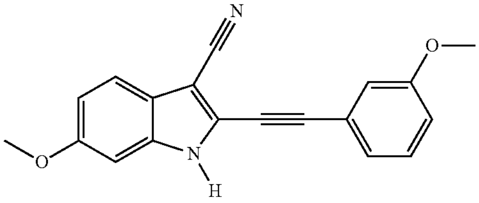
238
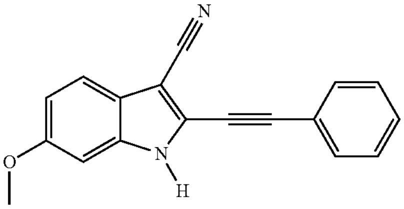
-continued
239
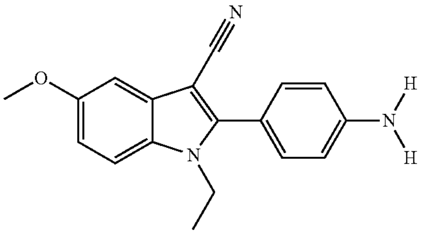
240
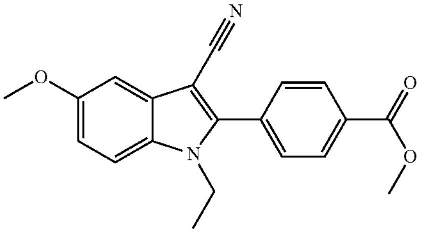
241
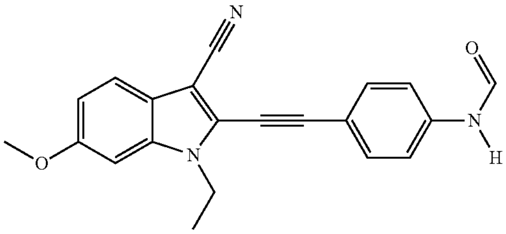
242
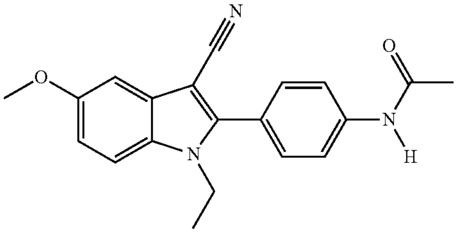
243
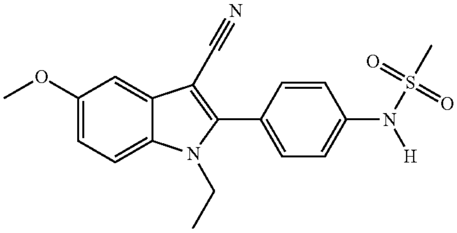
244
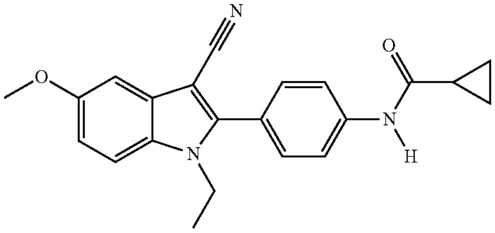

-continued
245
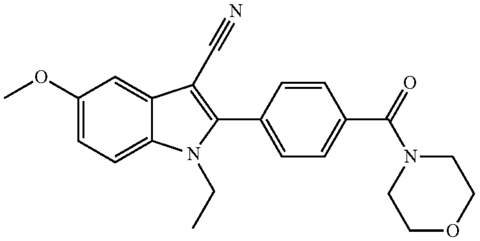
246
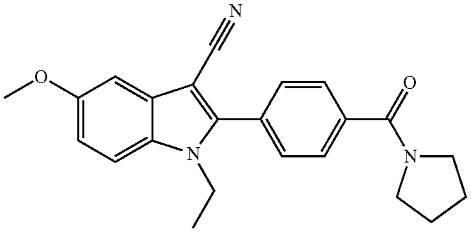
247
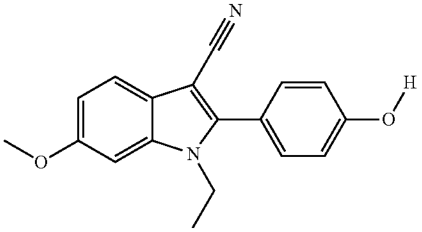
248
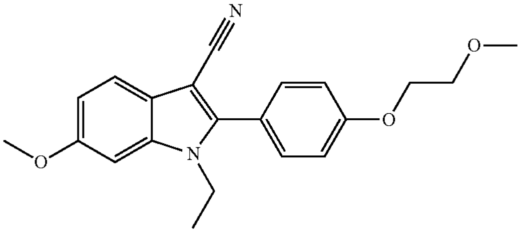
249
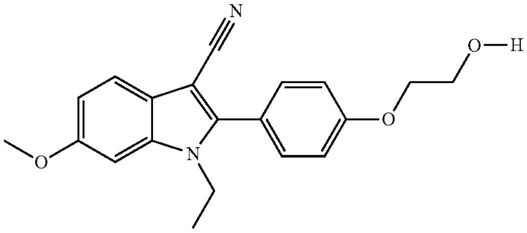
250
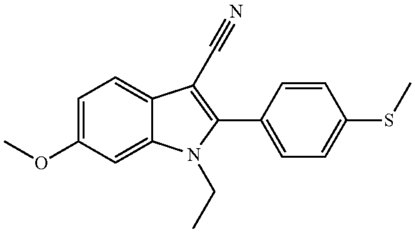
-continued
251
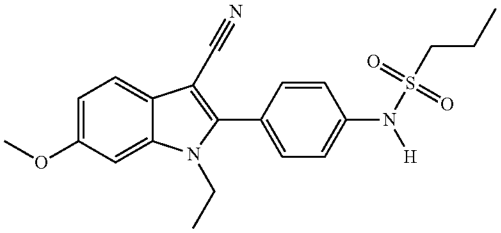
252
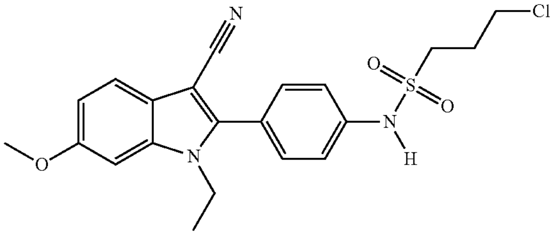
253
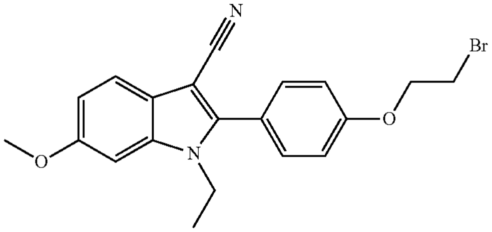
254
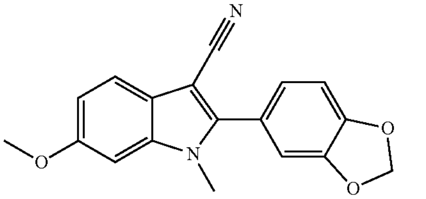
255
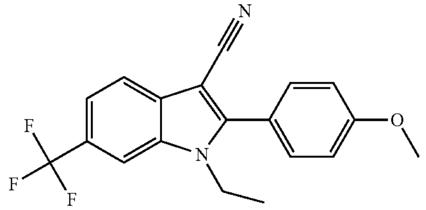
256
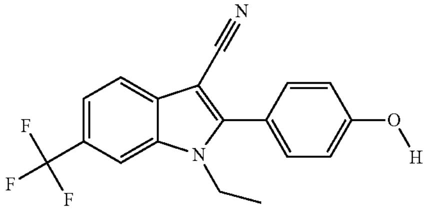
257
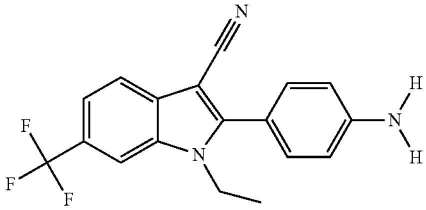

-continued
258
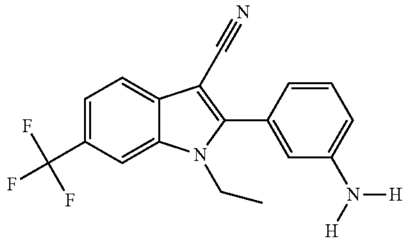
259
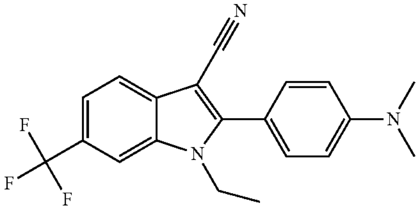
260
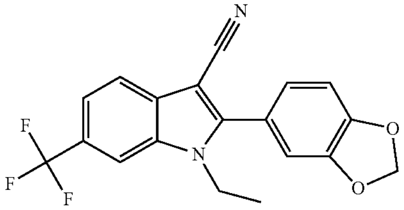
261
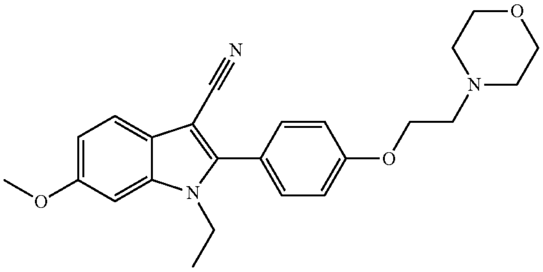
262
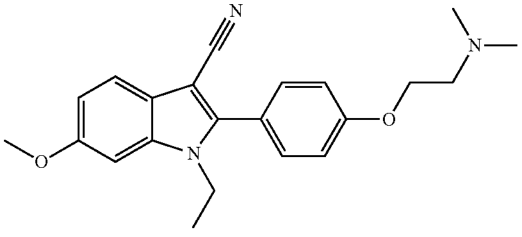
263
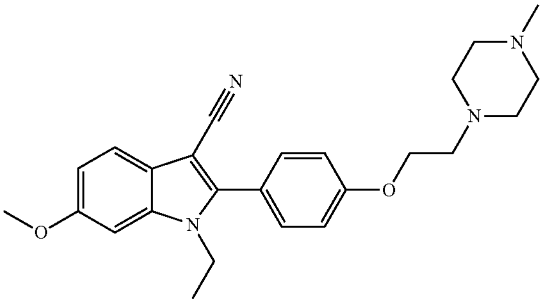
-continued
264
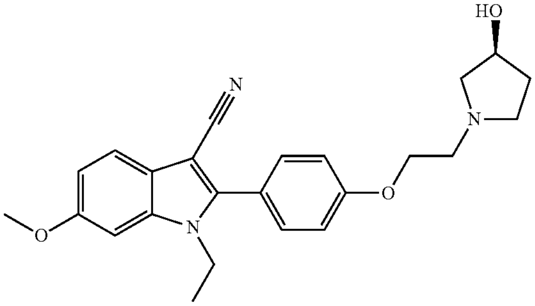
265
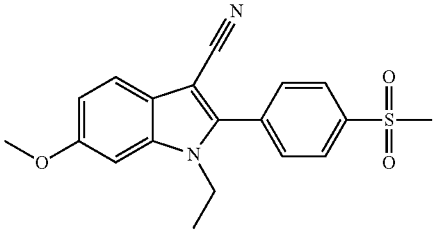
266
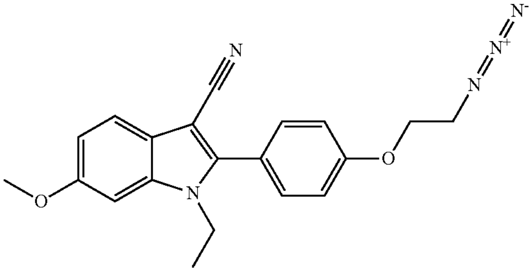
267
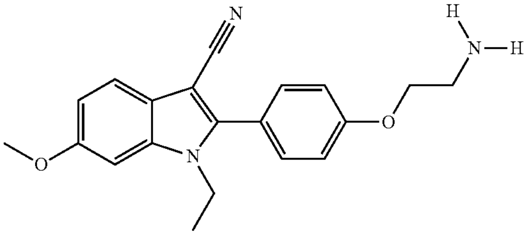
268
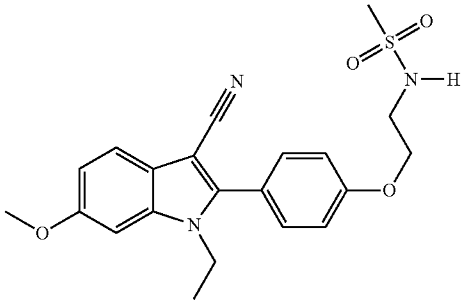
269
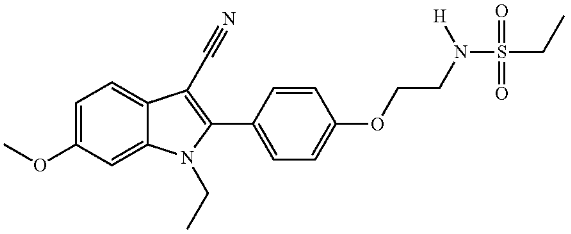

-continued
270
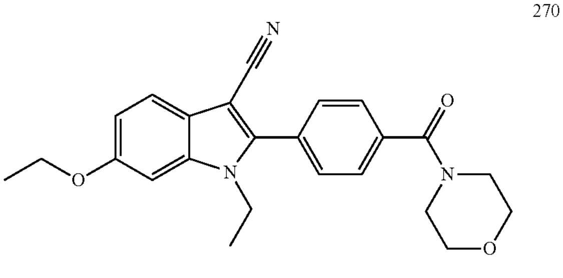
271
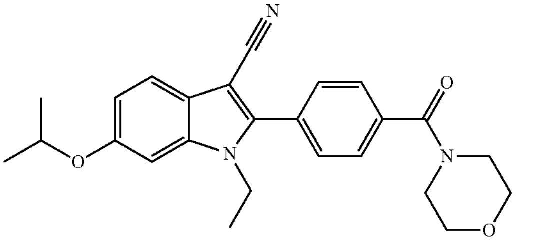
272
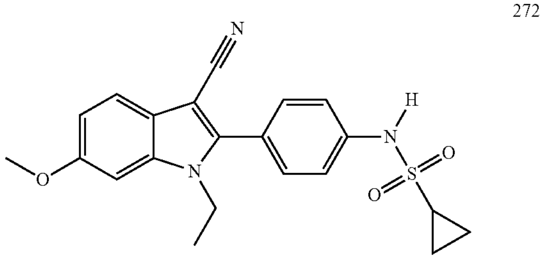
273
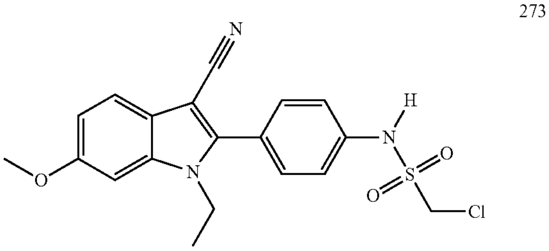
274
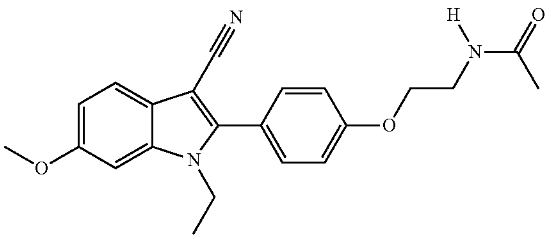
275
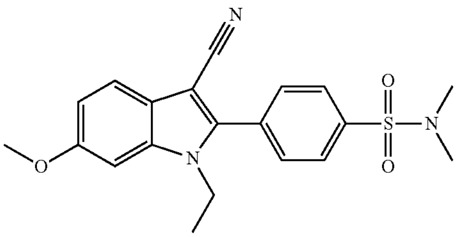
-continued
276
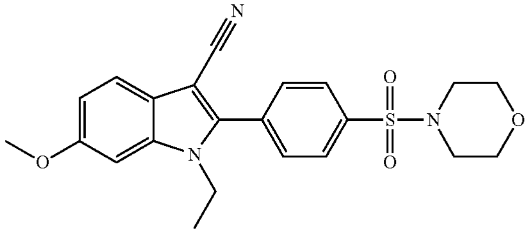
277
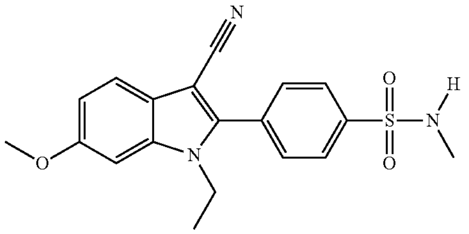
278
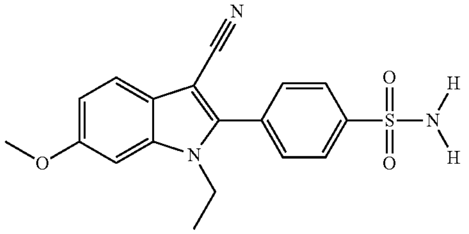
279
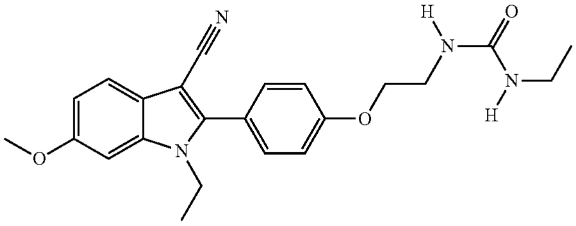
280
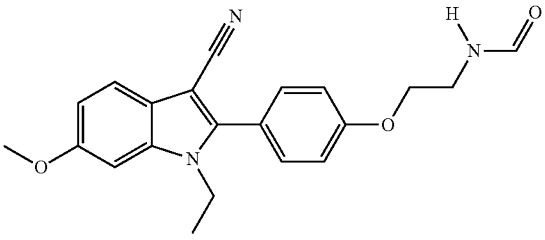
281
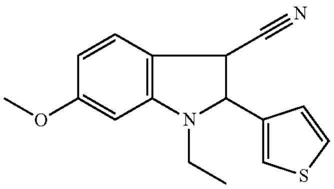

282
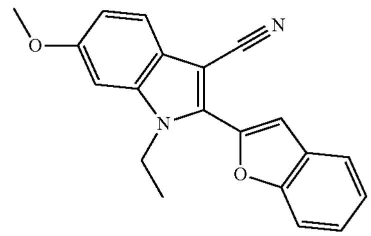
283
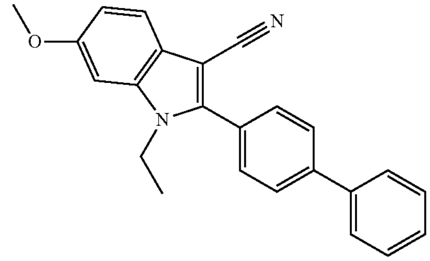
284
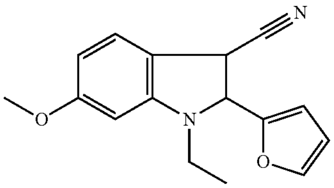
285
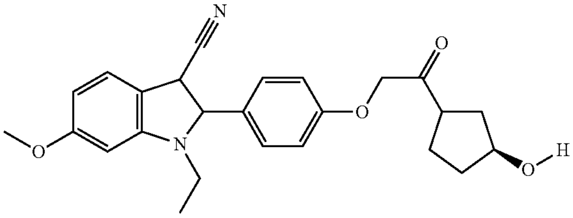
286
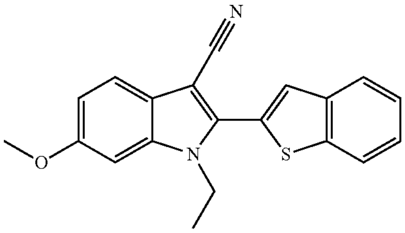
287
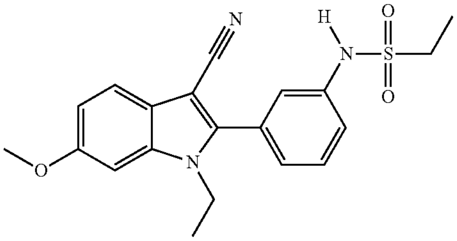
288
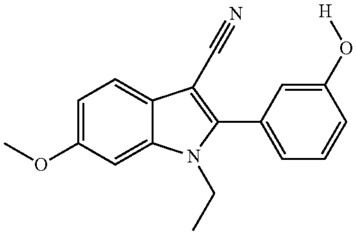
289
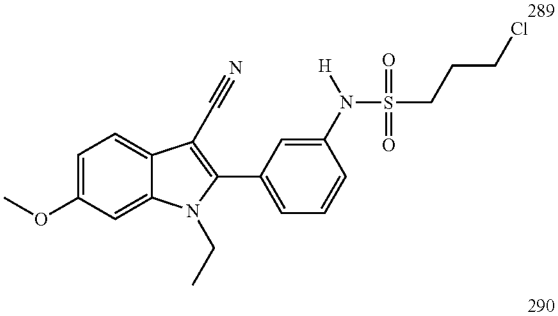
290
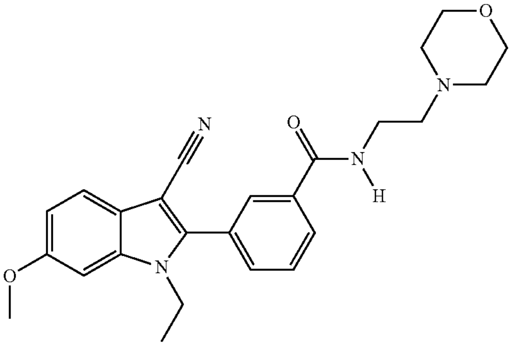
291
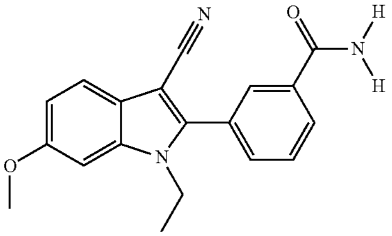
292
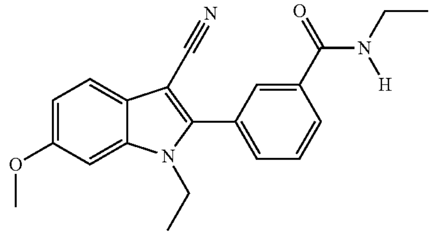
293
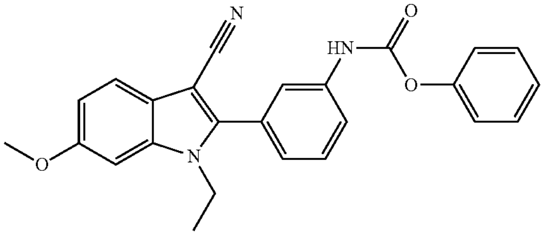

-continued
294
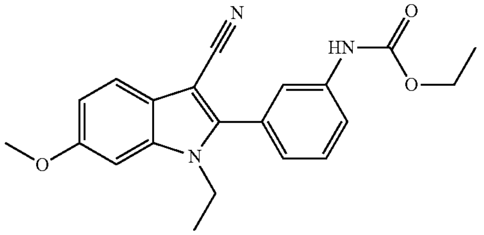
295
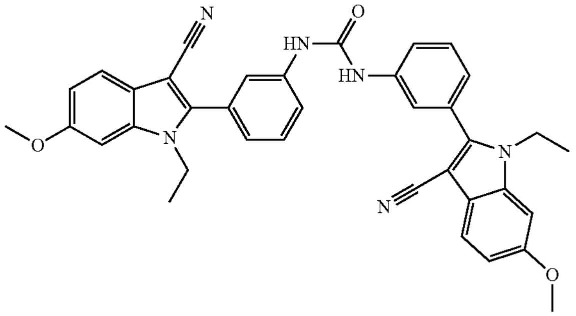
296
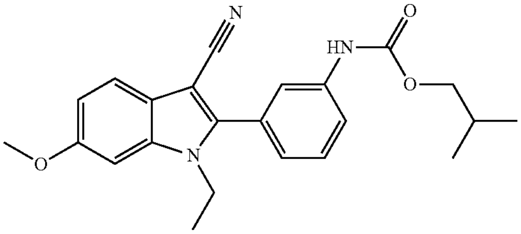
297
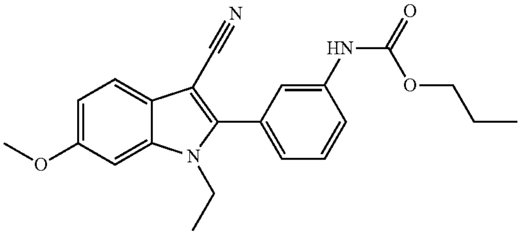
298
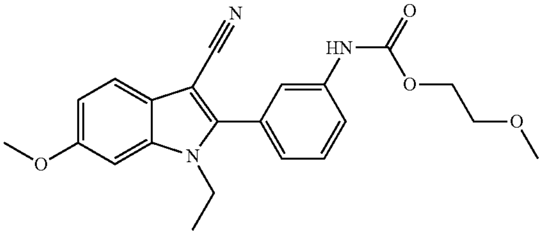
299
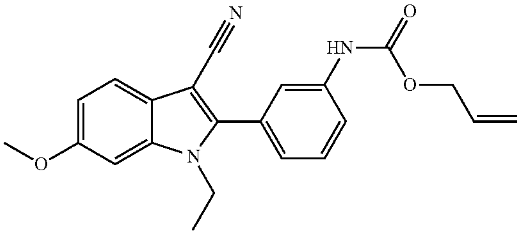
-continued
300
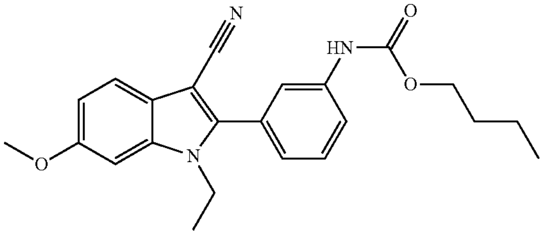
301
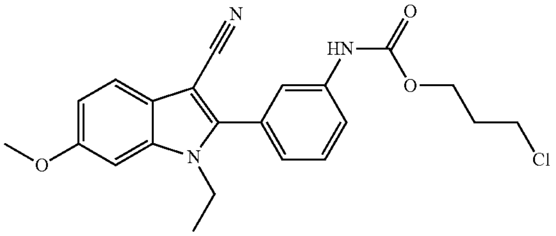
302
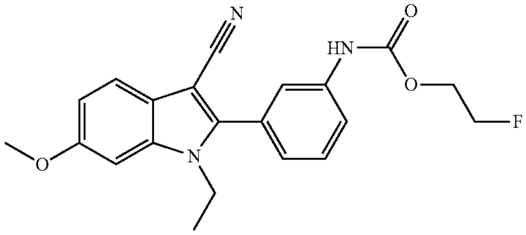
303
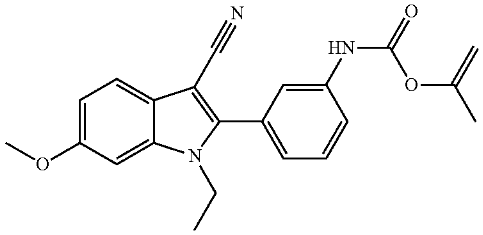
304
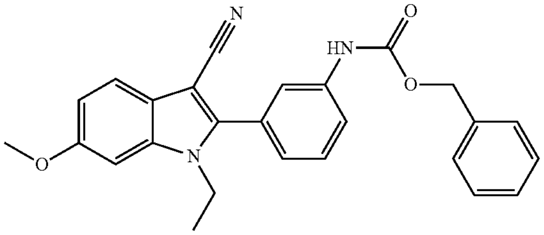
305
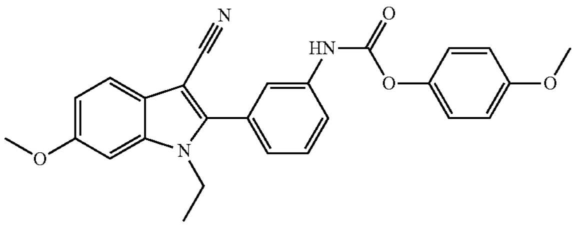

-continued
306
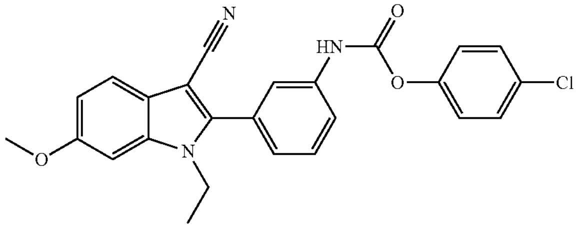
307
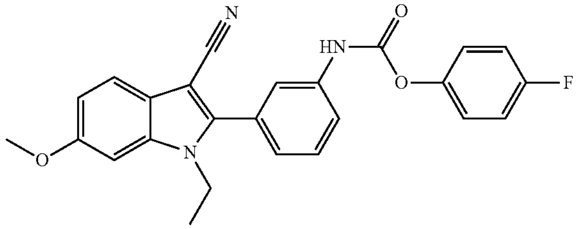
308
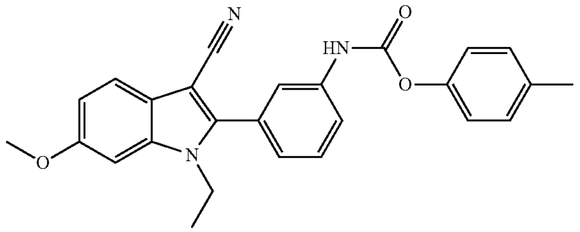
309
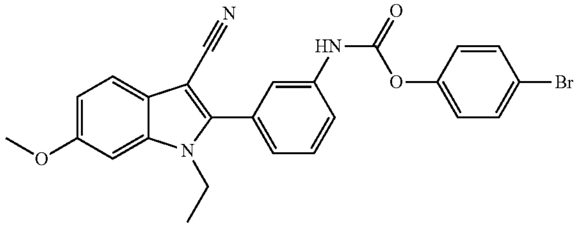
310
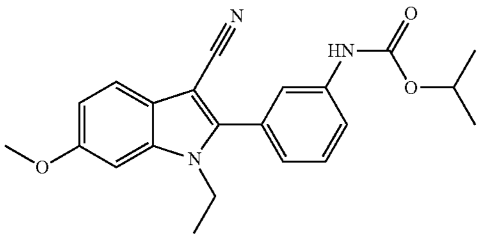
311
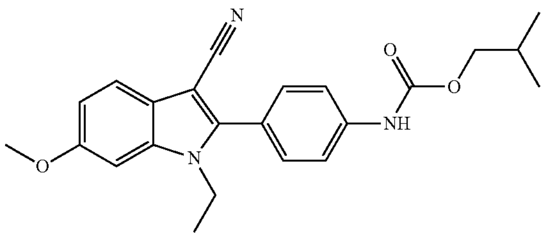
-continued
312
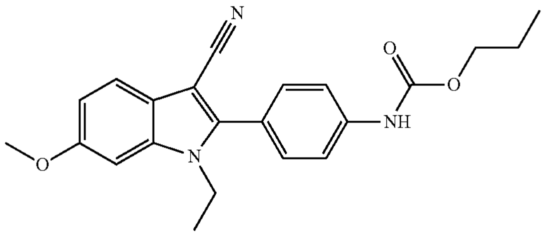
313
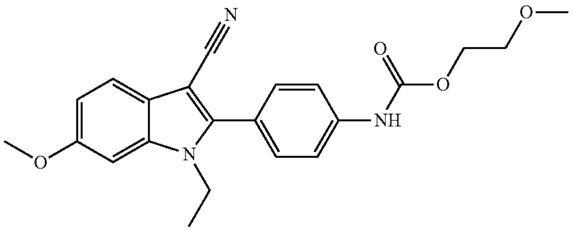
314
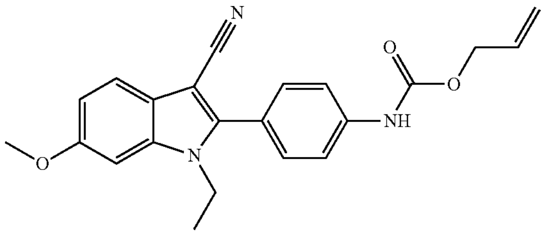
315
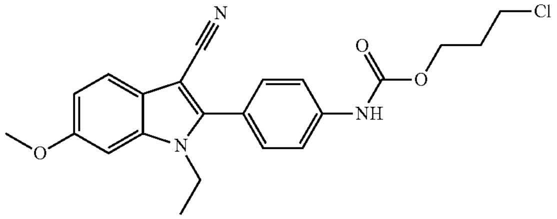
316
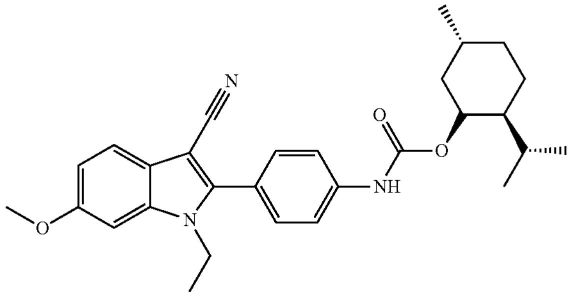
317
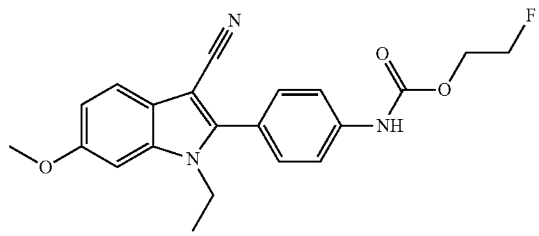

-continued
318
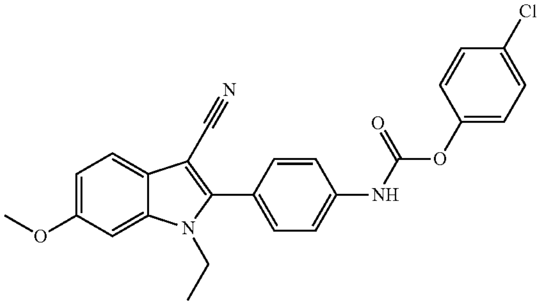
319
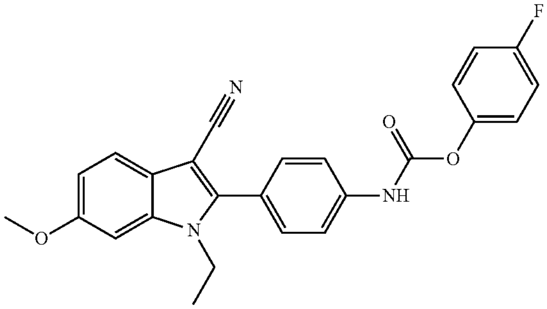
320
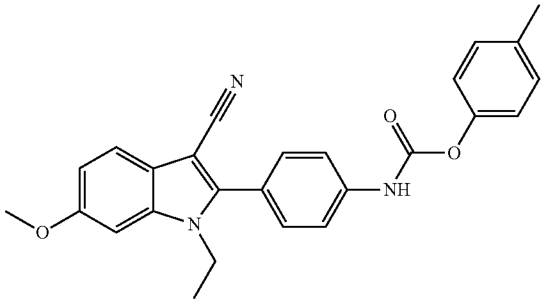
321
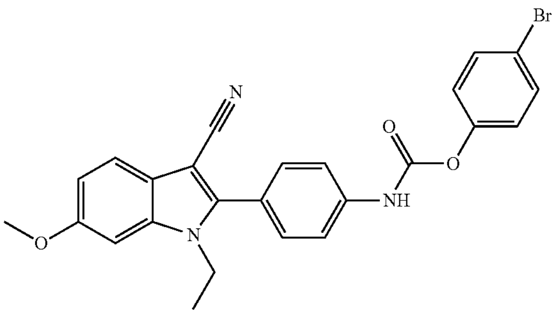
322
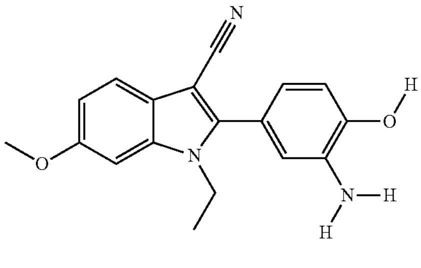
-continued
323
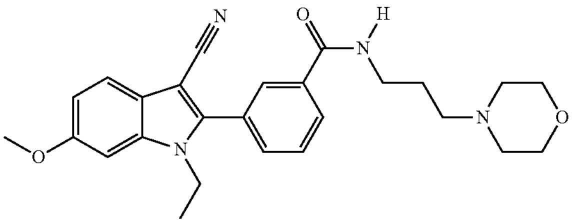
324
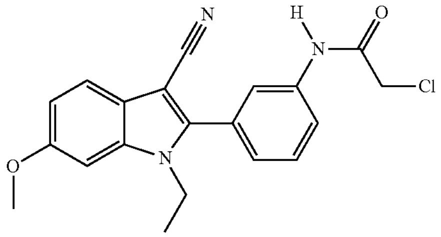
325
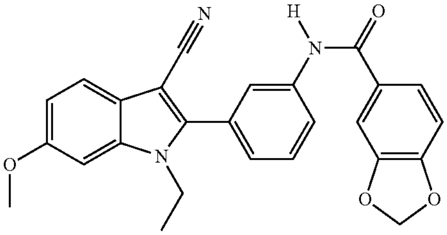
326
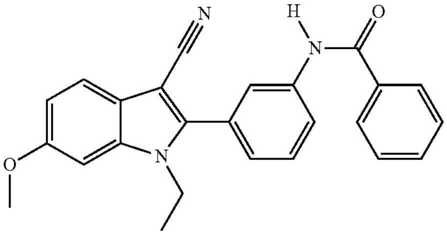
327
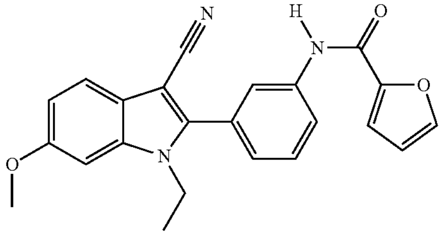
328
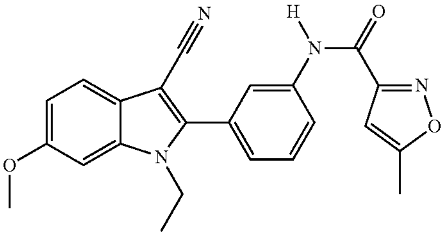

-continued
329
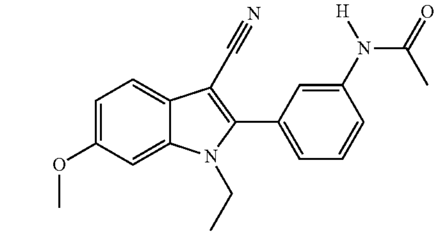
330
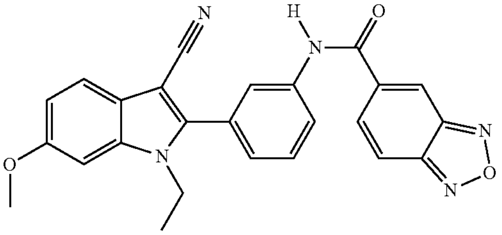
331
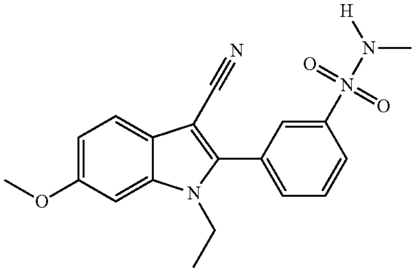
332
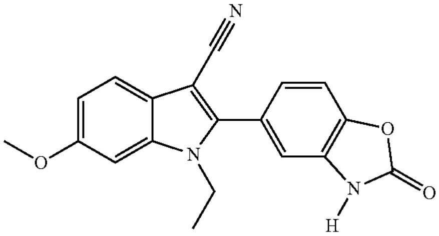
333
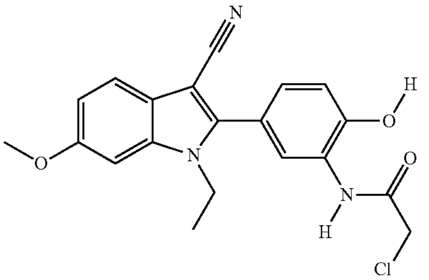
334
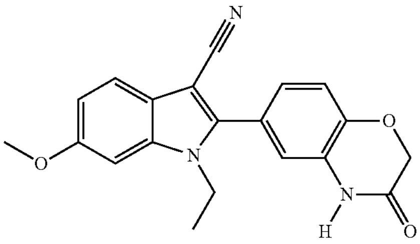
-continued
335
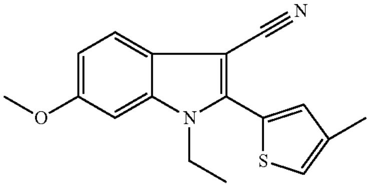
336
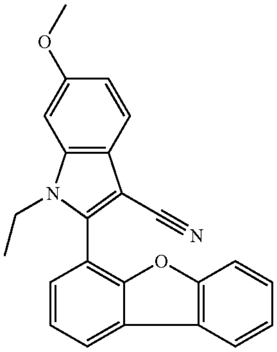
337
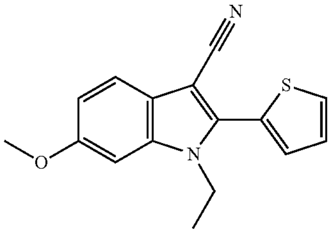
338
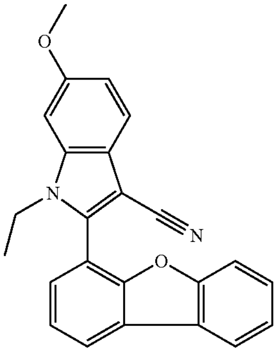
339
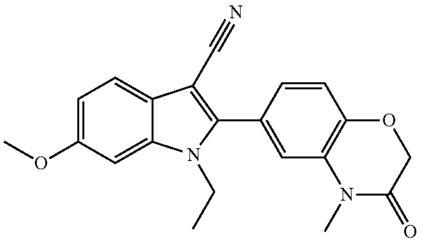
340
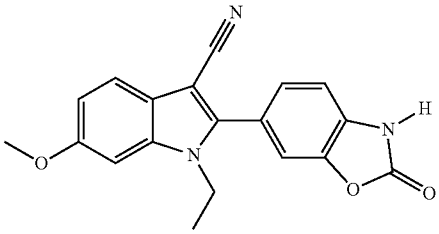

-continued
341
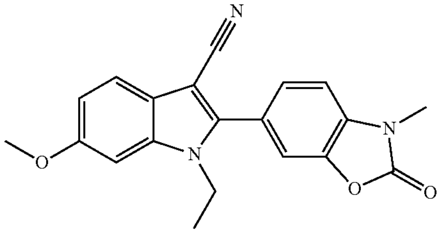
342
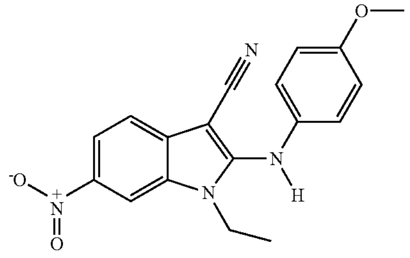
343
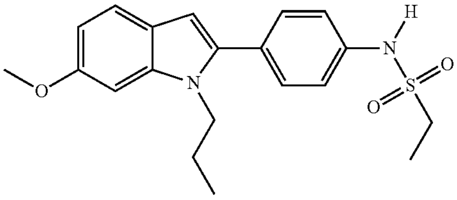
344
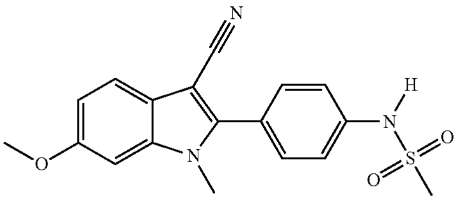
345
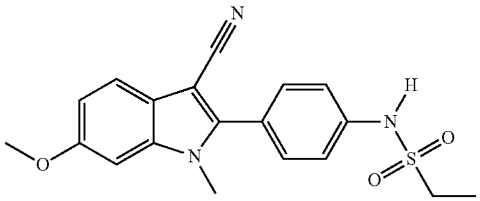
346
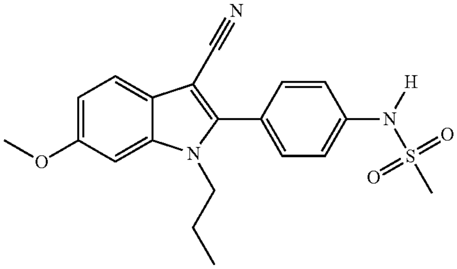
-continued
347
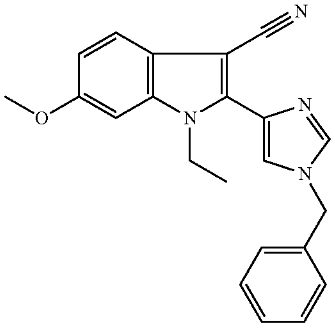
348
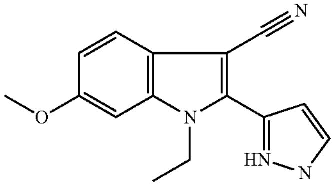
349
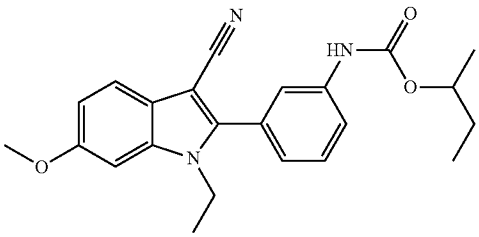
350
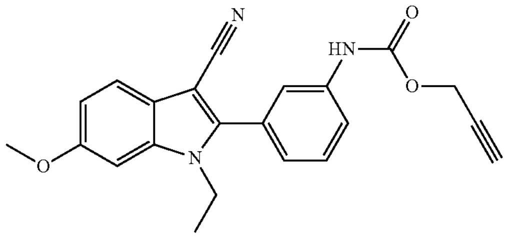
351
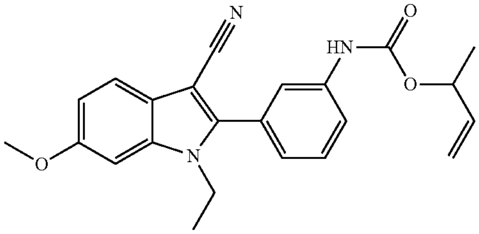
352
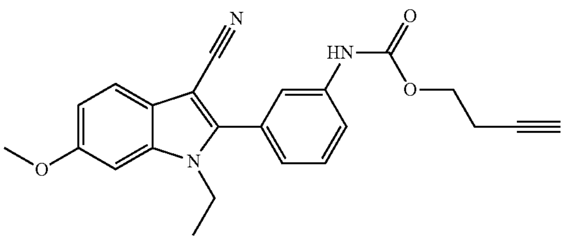

-continued
353
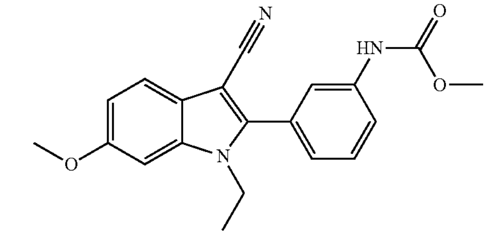
354
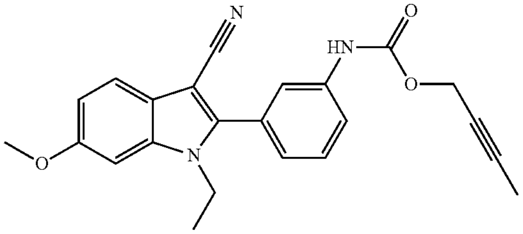
355
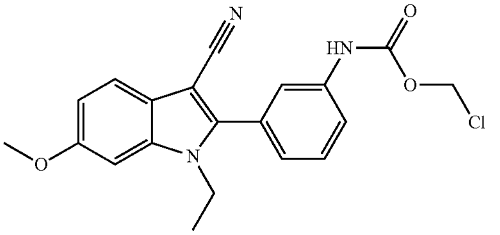
356
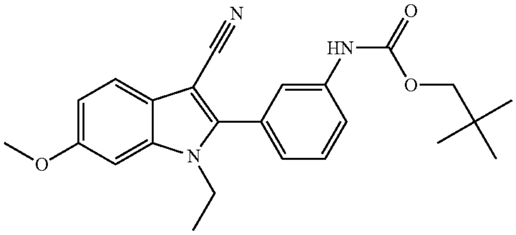
357
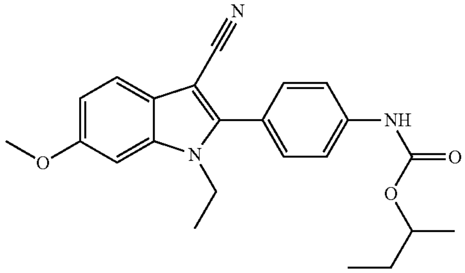
358
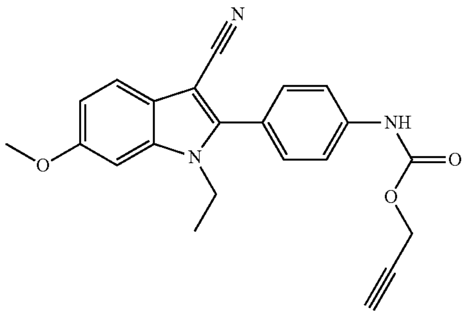
-continued
359
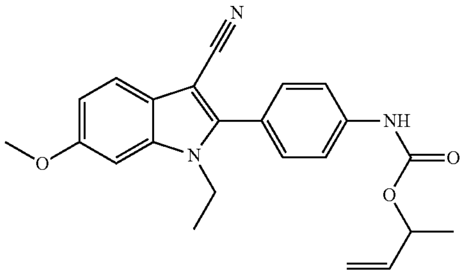
360
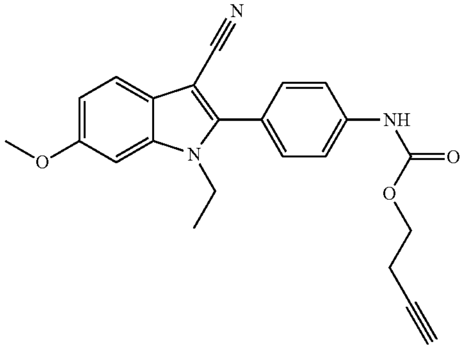
361
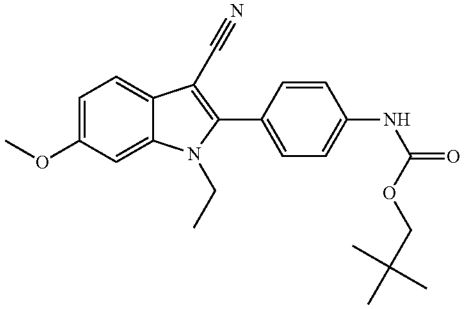
362
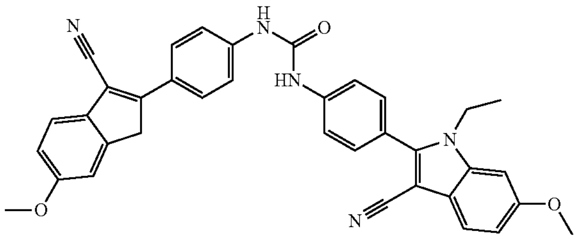
363
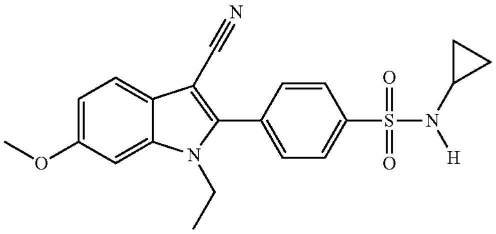

-continued
364
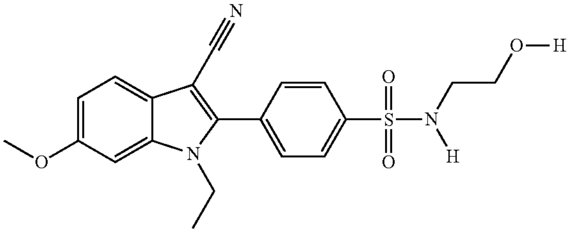
365
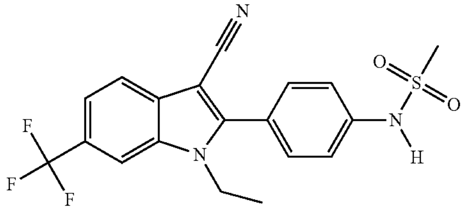
366
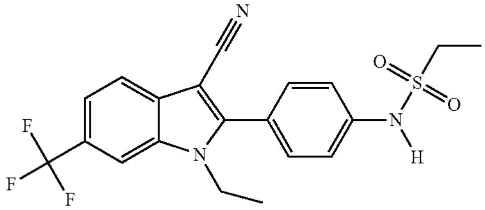
367
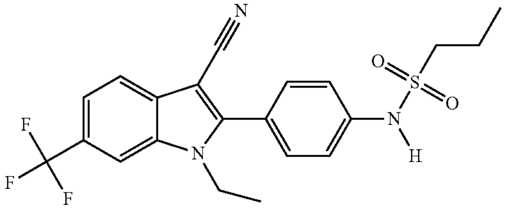
368
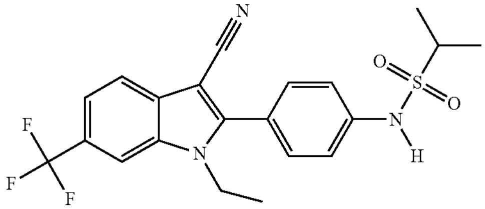
369
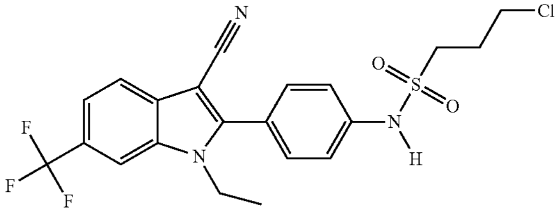
370
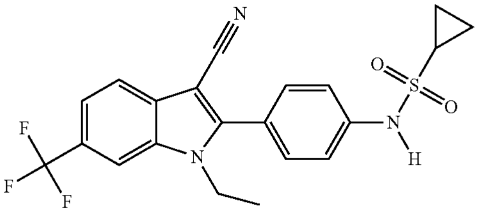
-continued
371
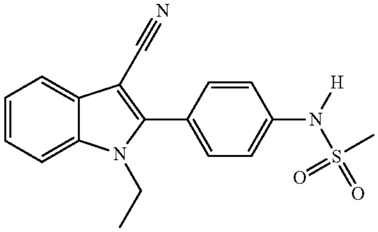
372
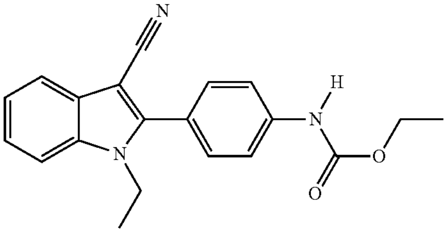
373
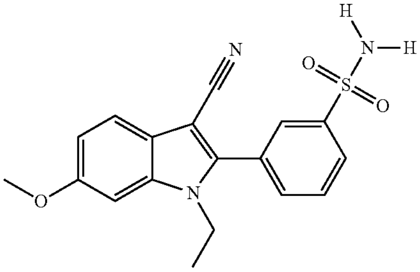
374
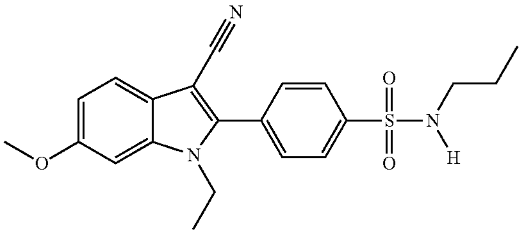
375
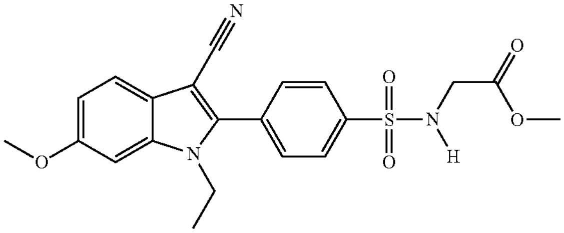
376
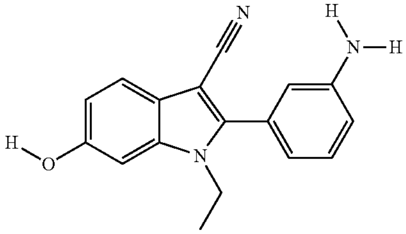

-continued
377
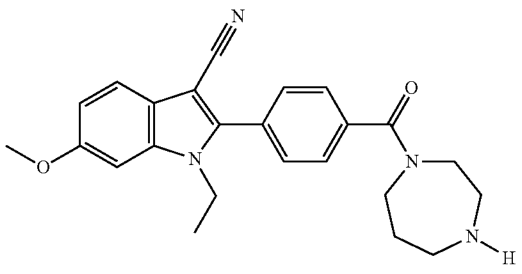
378
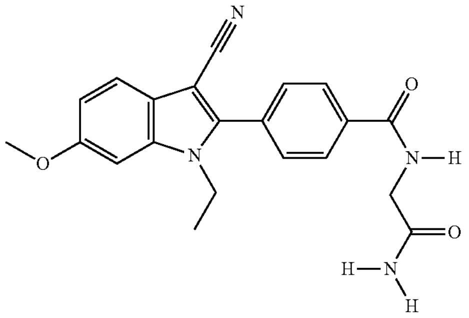
379
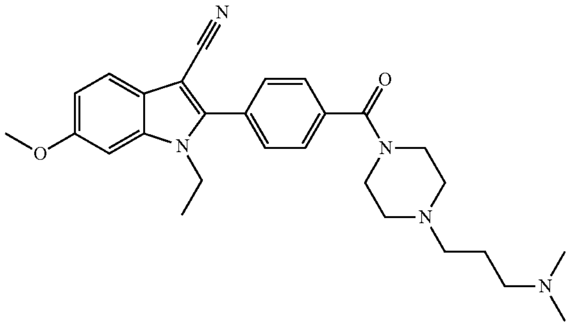
380
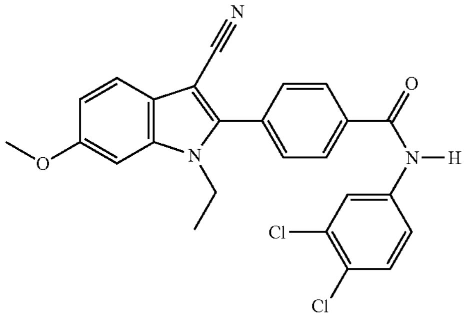
381
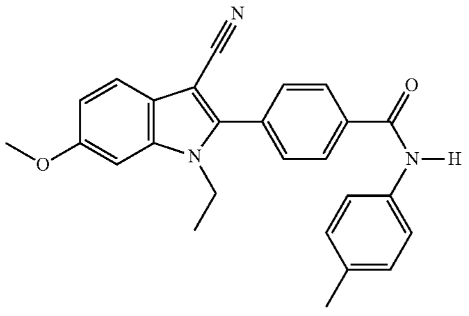
-continued
382
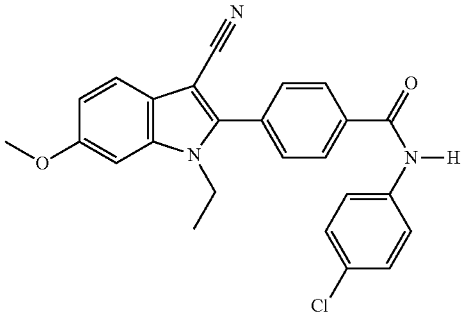
383
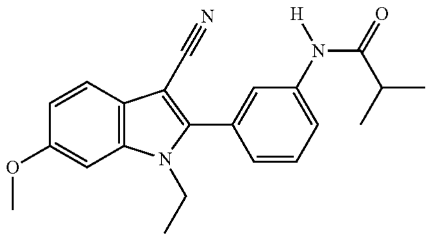
384
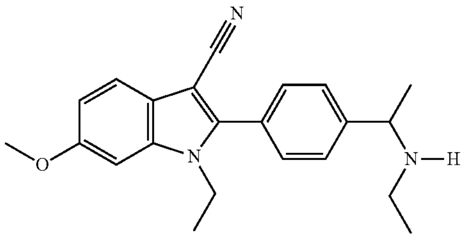
385
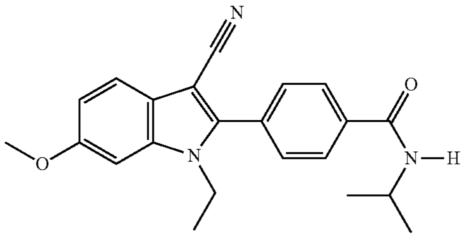
386
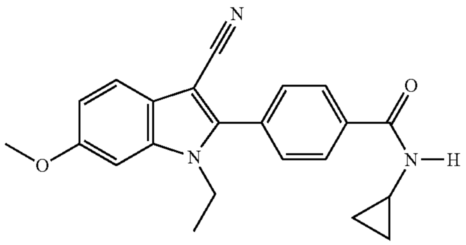
387
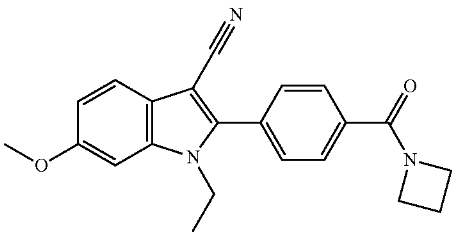

-continued
388
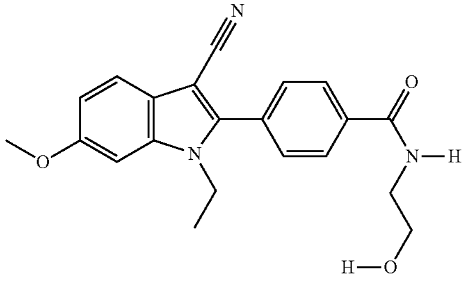
389
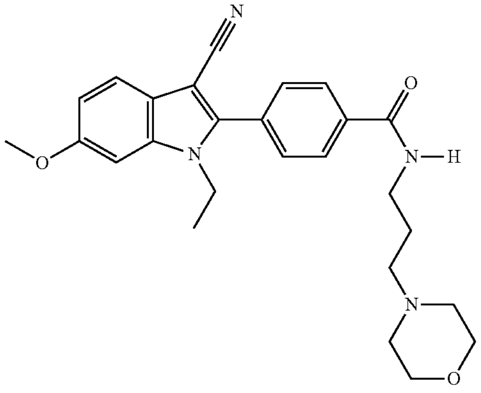
390
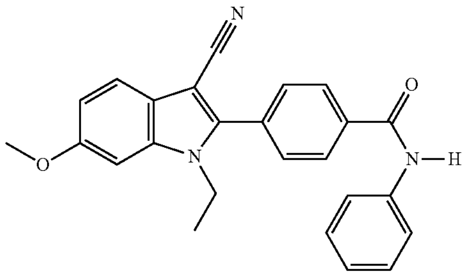
391
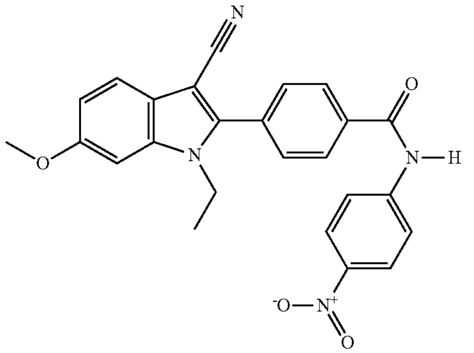
392
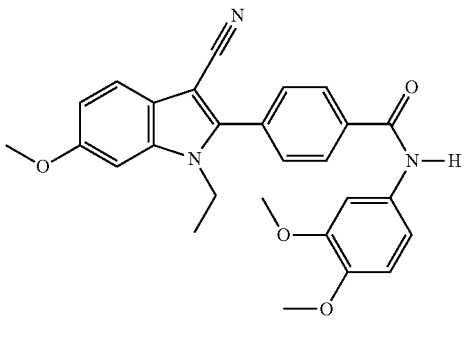
-continued
393
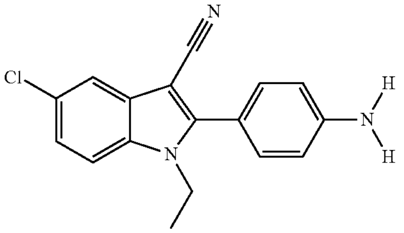
394
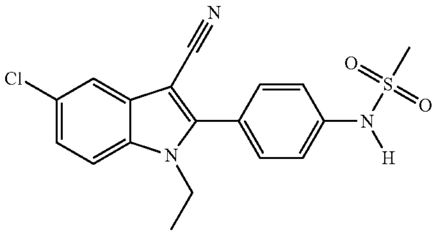
395
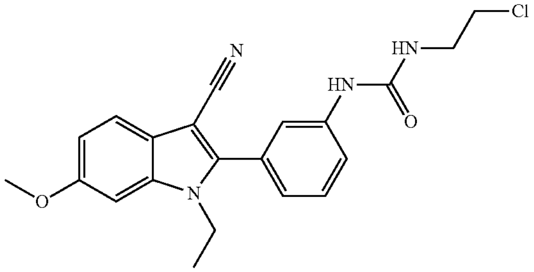
396
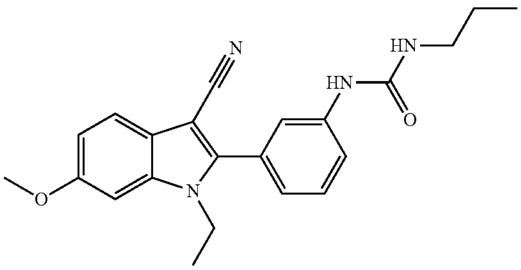
397
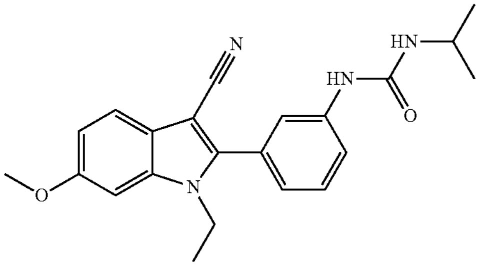
398
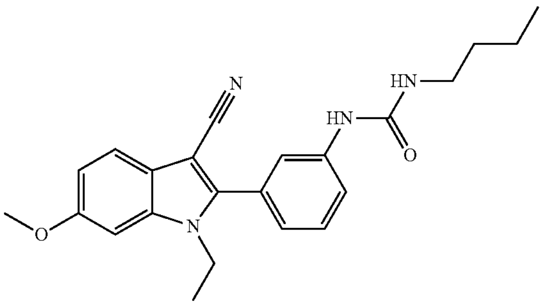

399
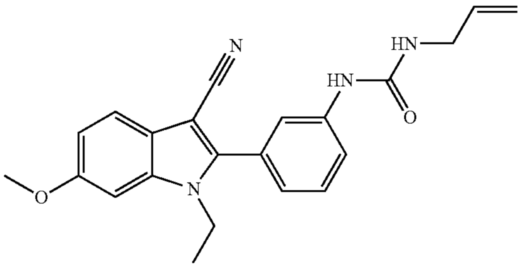
400
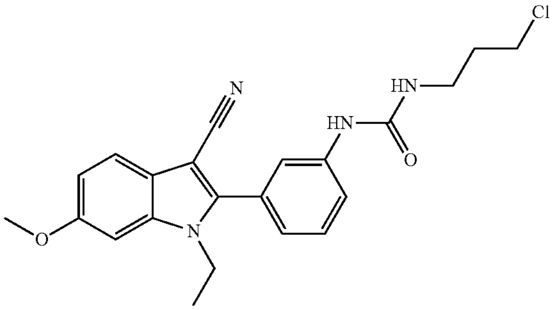
401
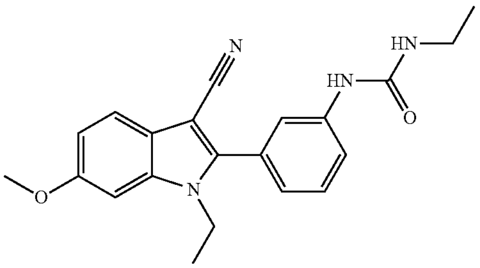
402
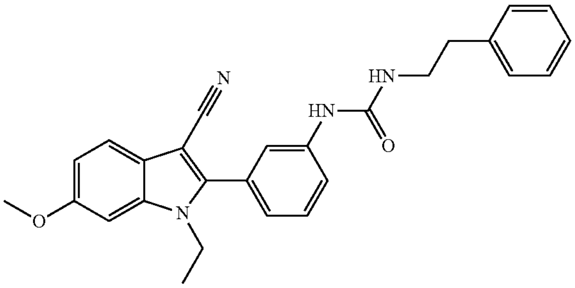
403
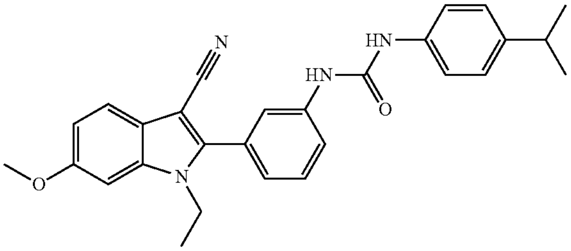
404
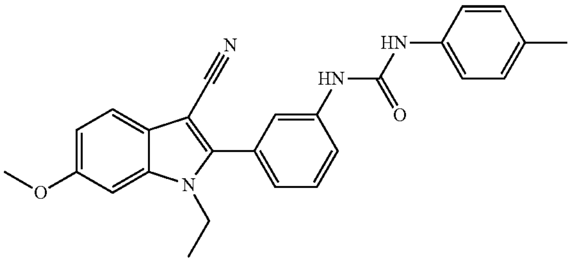
405
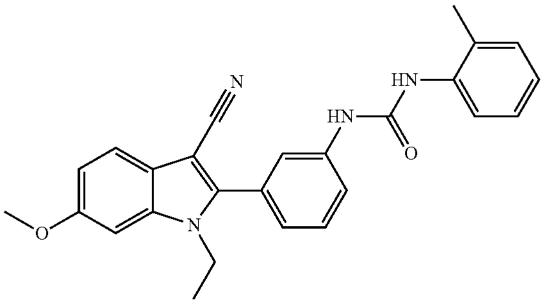
406
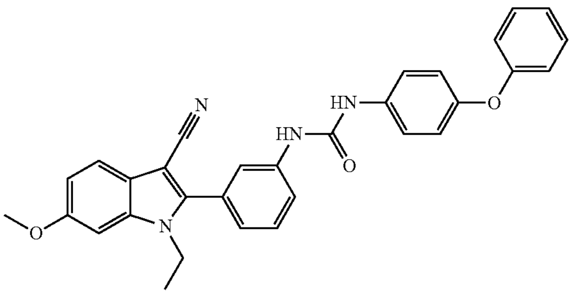
407
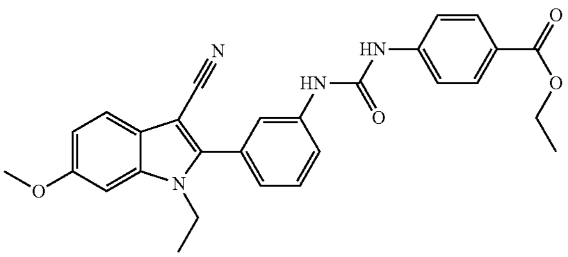
408
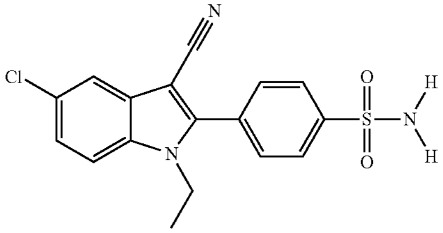

-continued
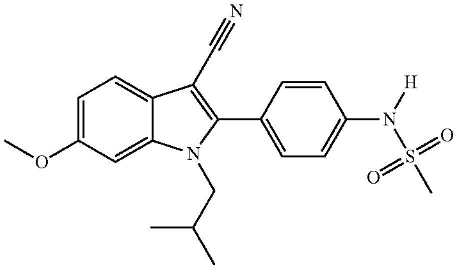
409
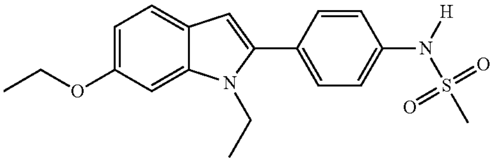
410
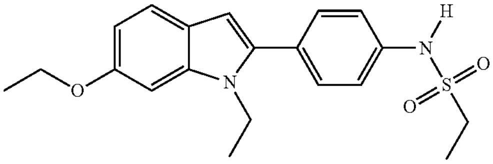
411
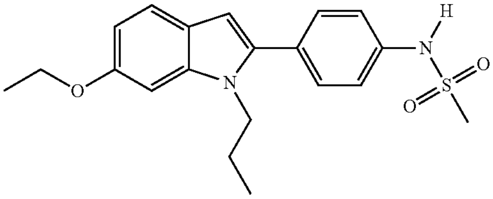
412
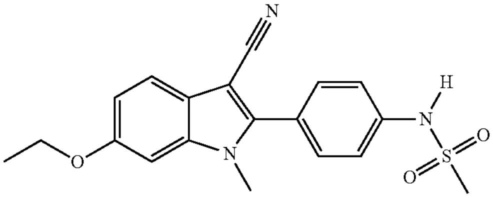
413
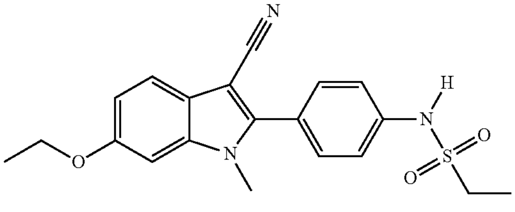
414
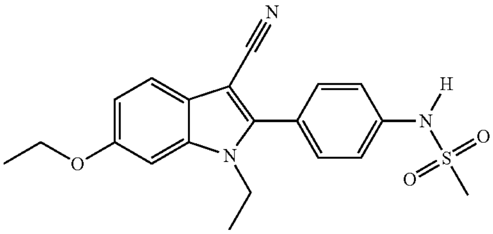
415
-continued
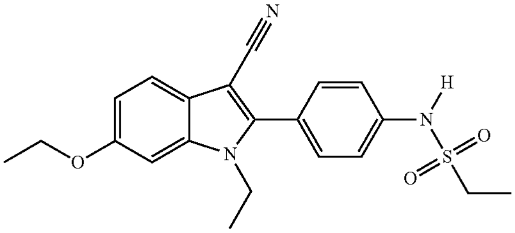
416
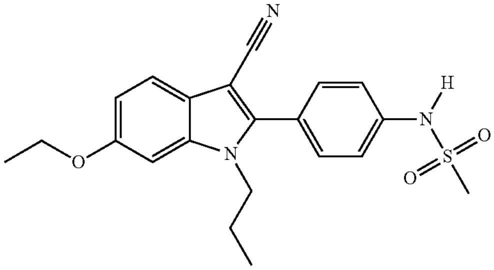
417
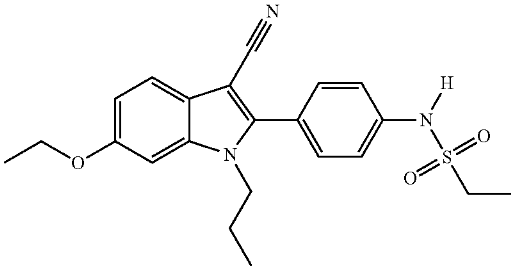
418
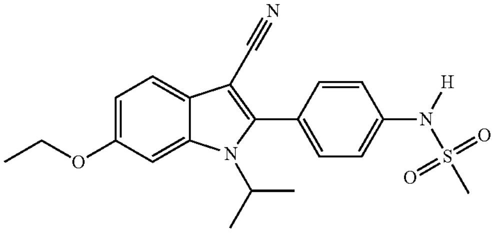
419
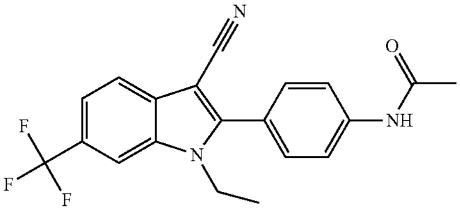
420
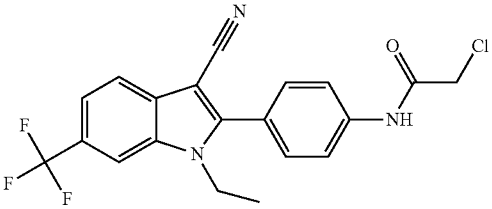
421

-continued
422
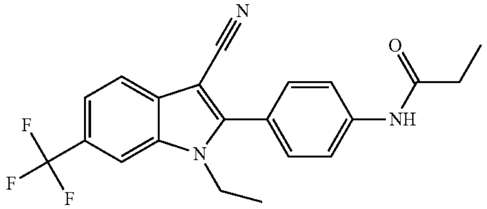
423
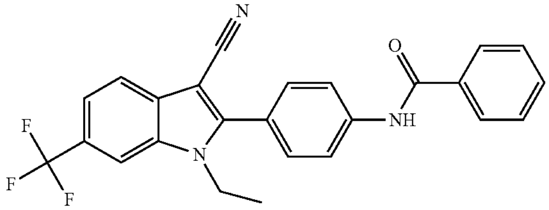
424
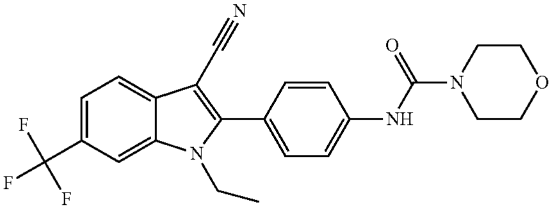
425
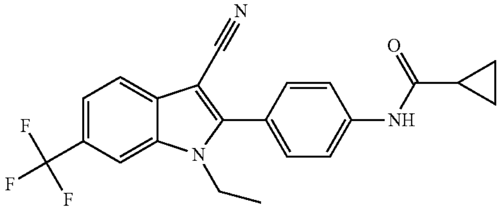
426
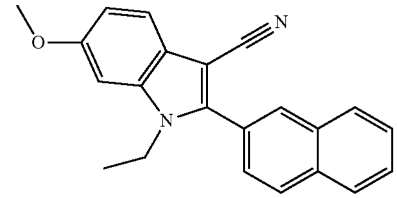
427
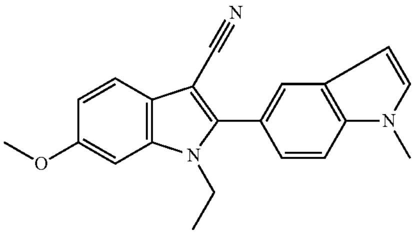
428
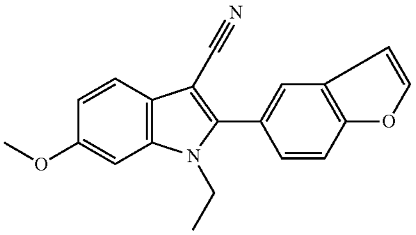
-continued
429
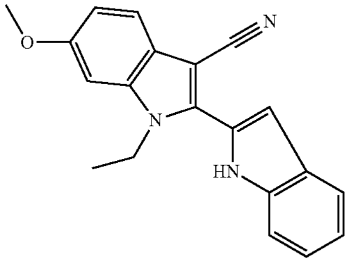
430
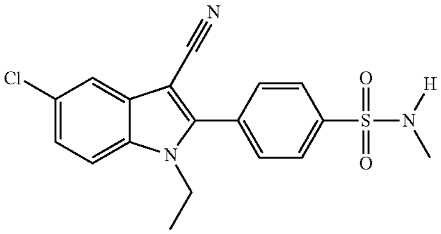
431
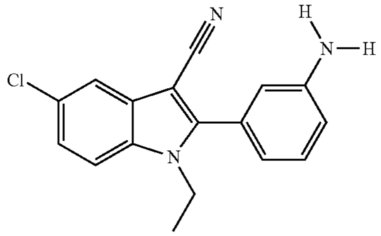
432
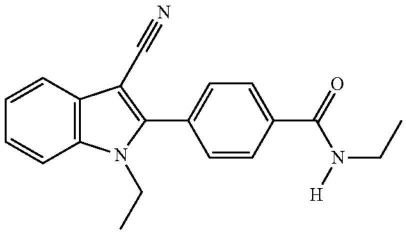
433
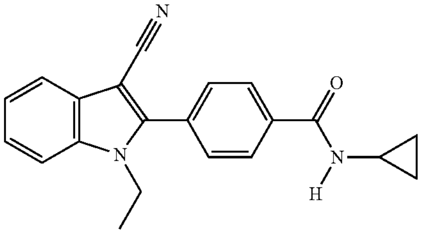
434
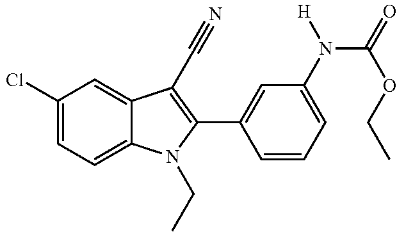

-continued
435
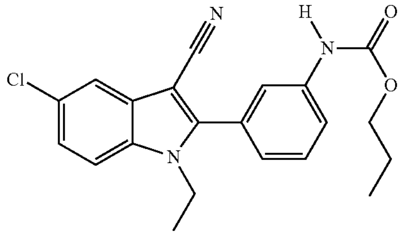
436
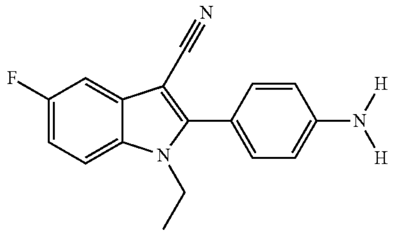
437
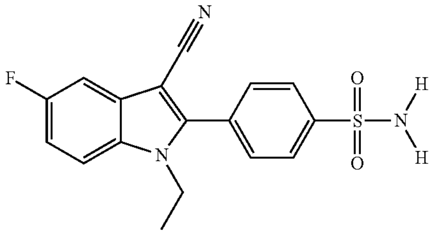
438
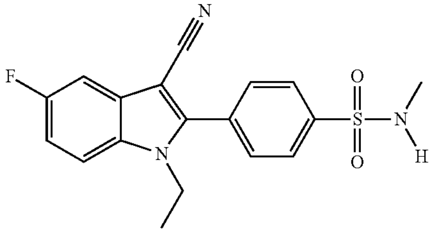
439
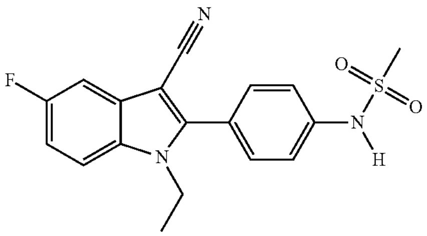
440
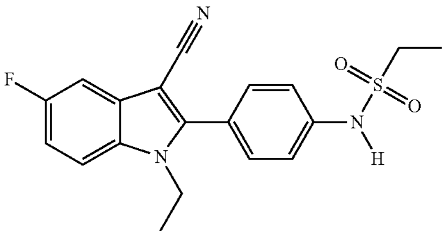
-continued
441
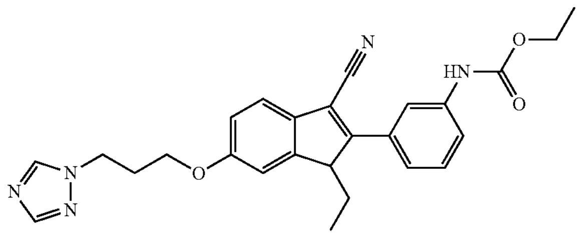
442
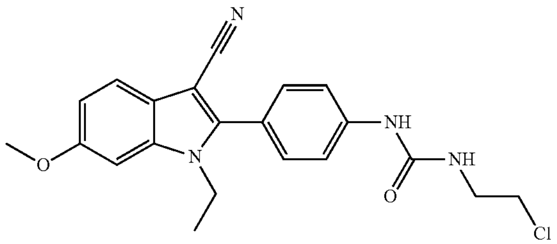
443
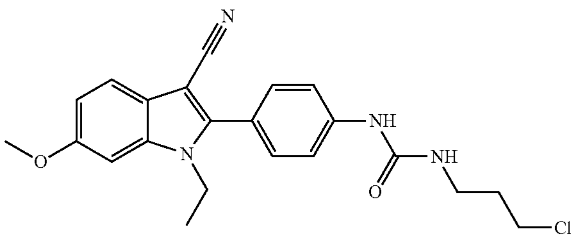
444
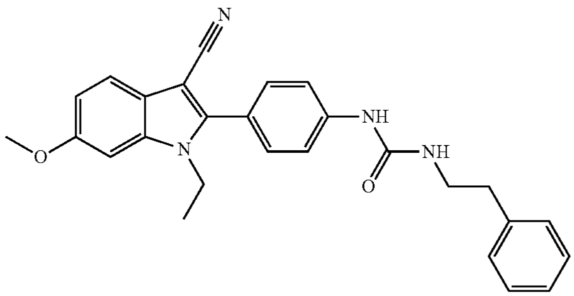
445
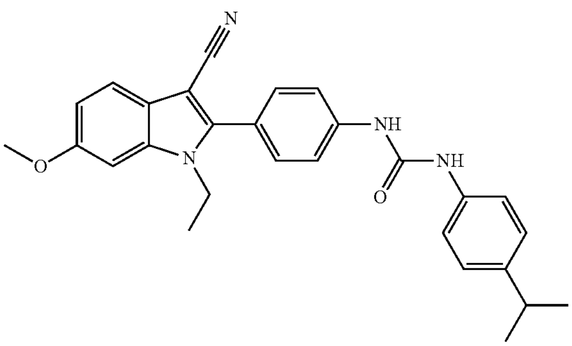

-continued
446
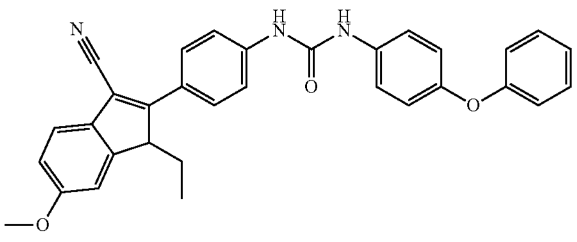
447
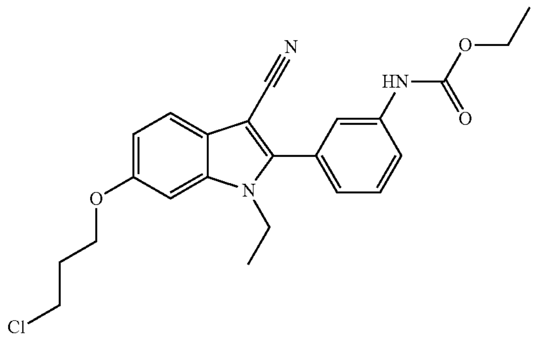
448
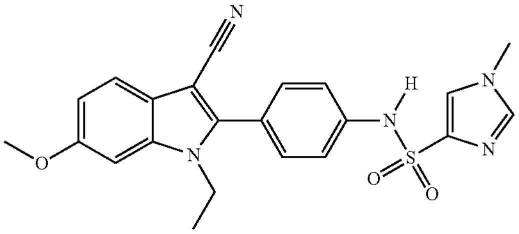
449
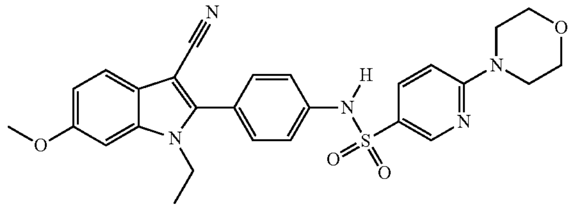
450
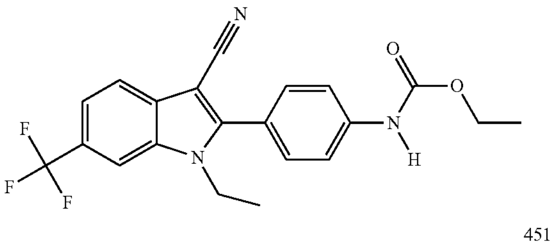
451
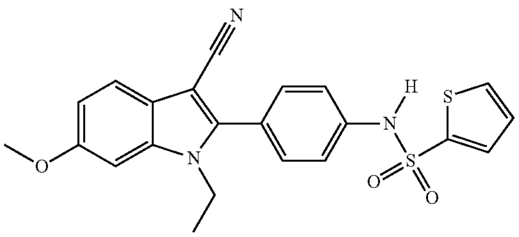
-continued
452
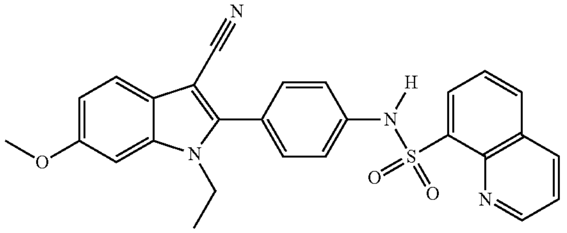
453
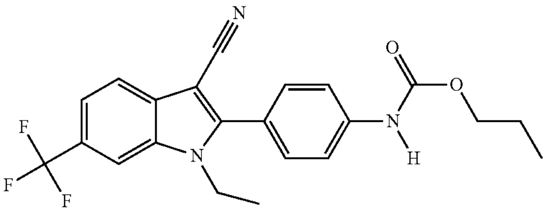
454
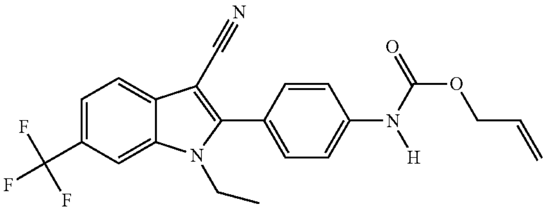
455
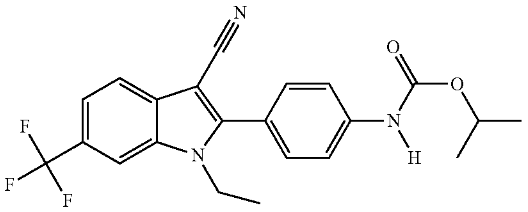
456
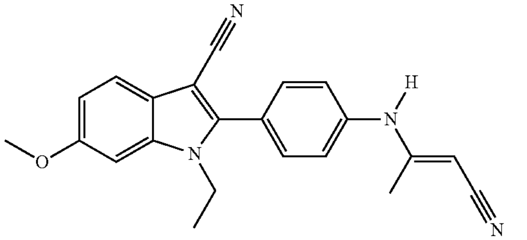
457
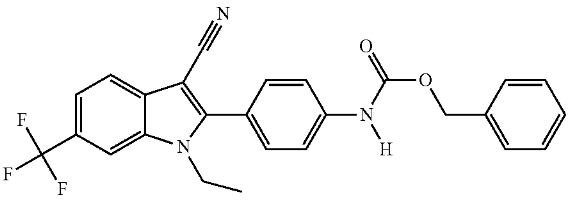

-continued
458
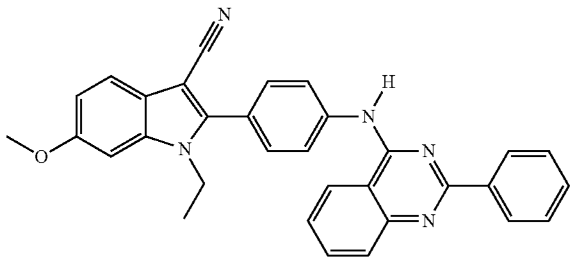
459
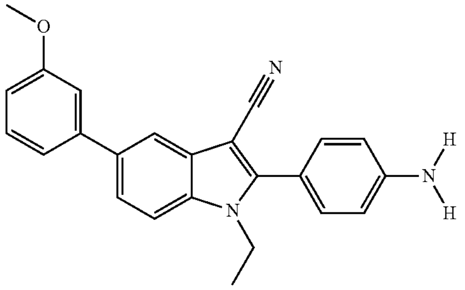
460
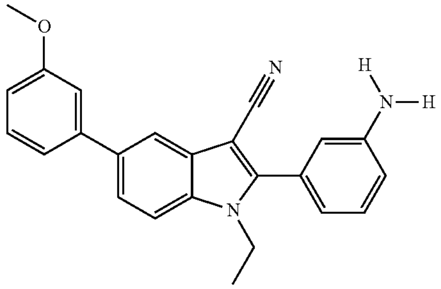
461
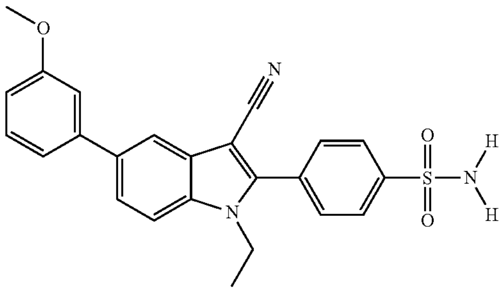
462
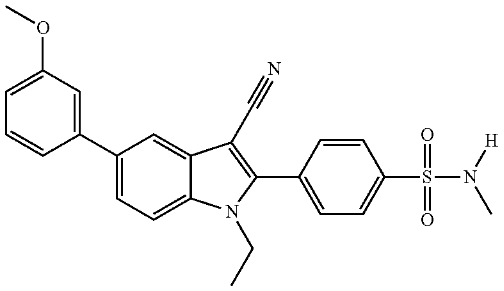
-continued
463
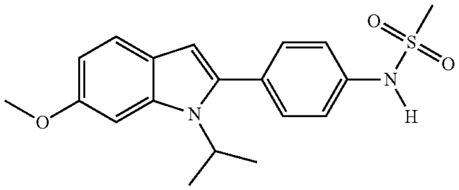
464
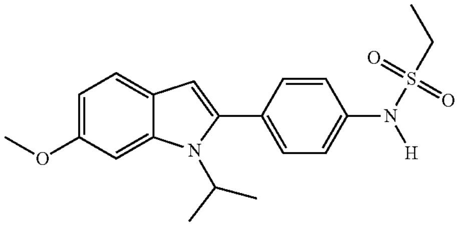
465
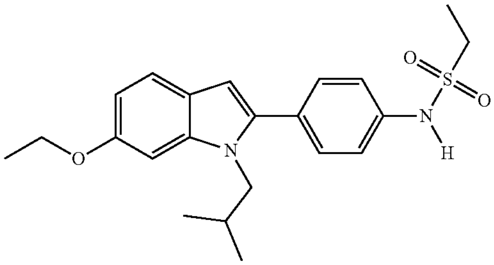
466
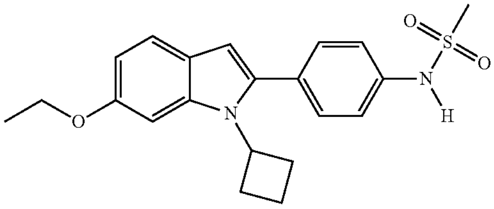
467
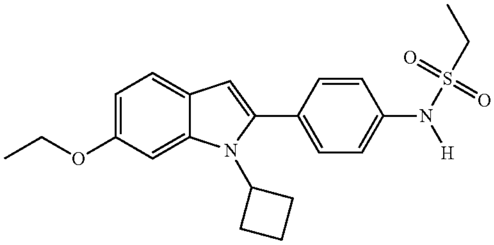
468
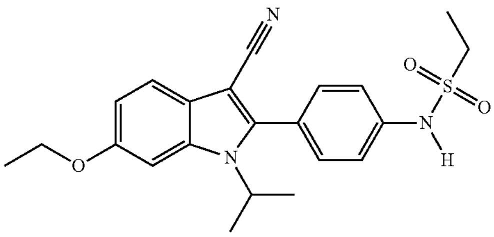

469
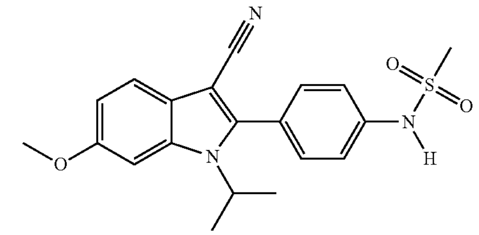
470
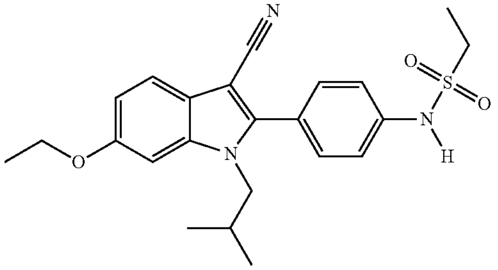
471
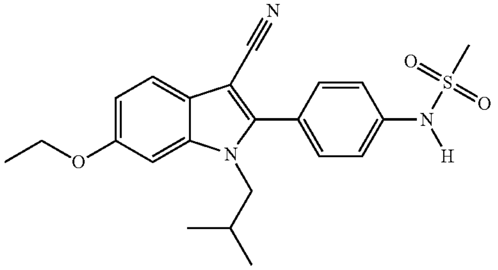
472
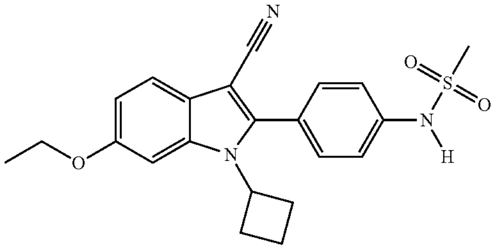
473
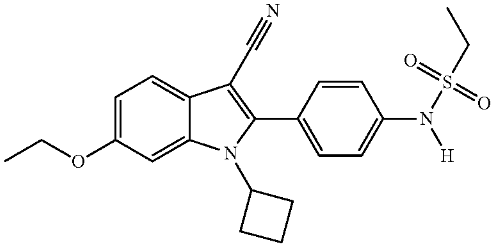
474
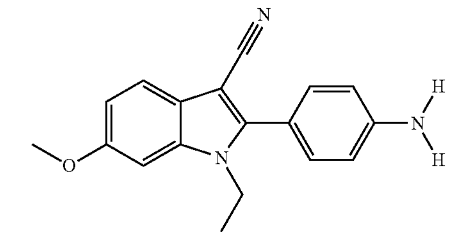
475
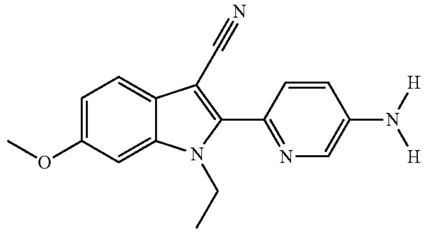
476
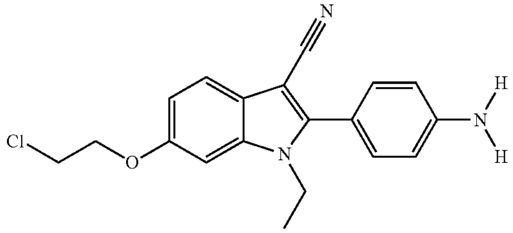
477
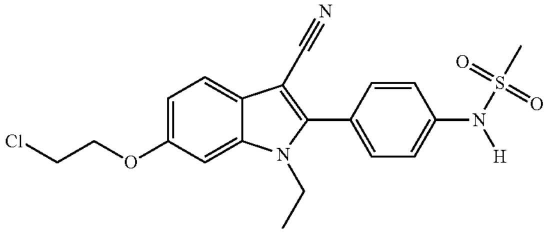
478
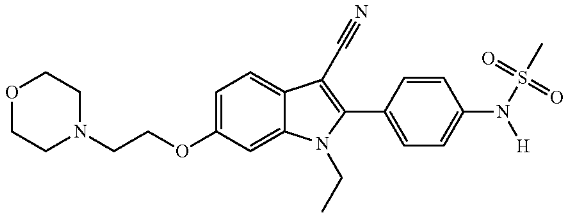
482
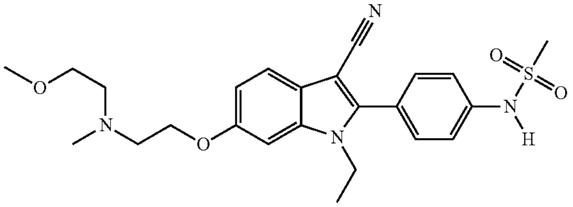
483
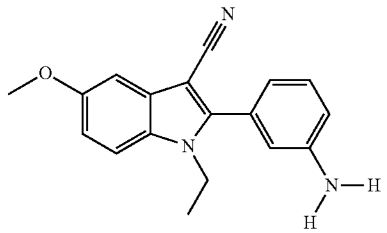

-continued
484
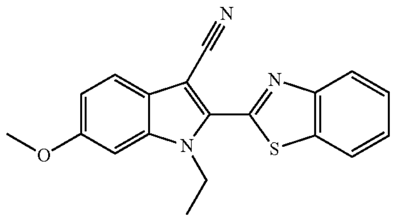
485
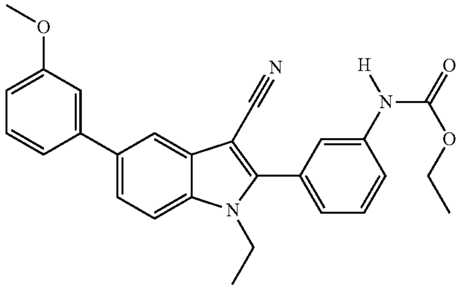
486
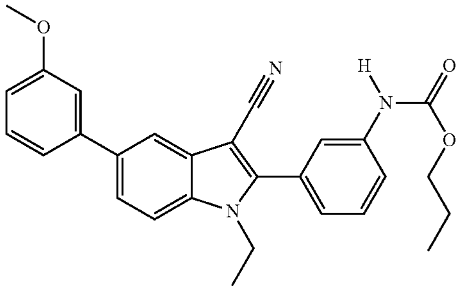
487
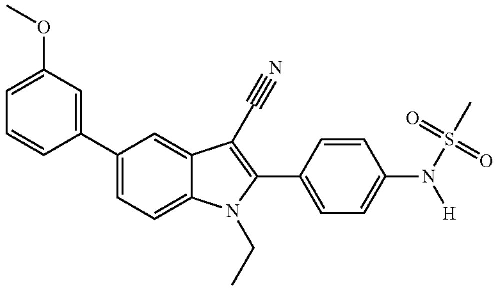
488
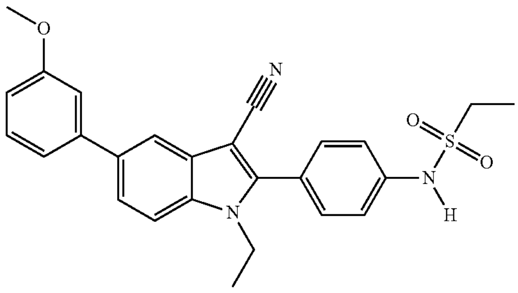
-continued
489
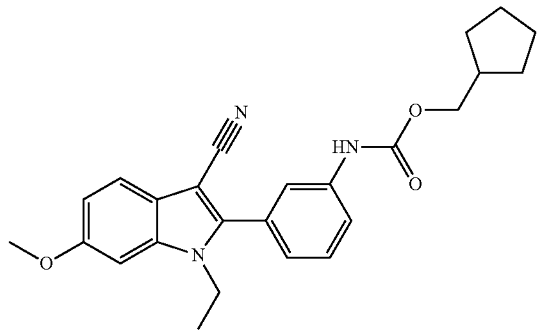
490
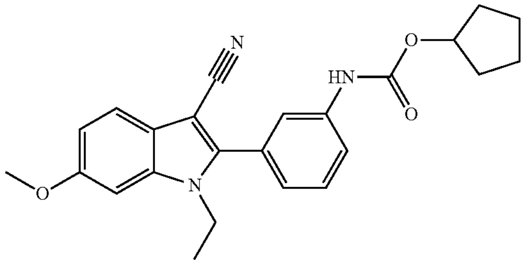
491
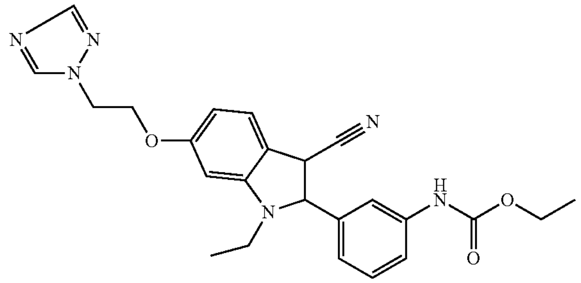
492
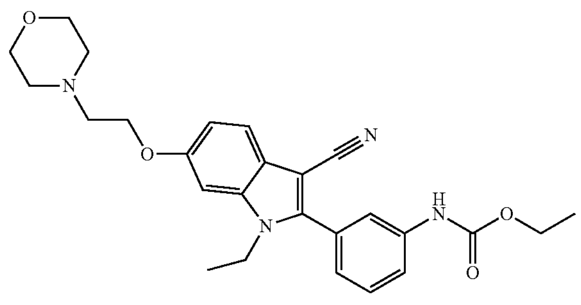

493
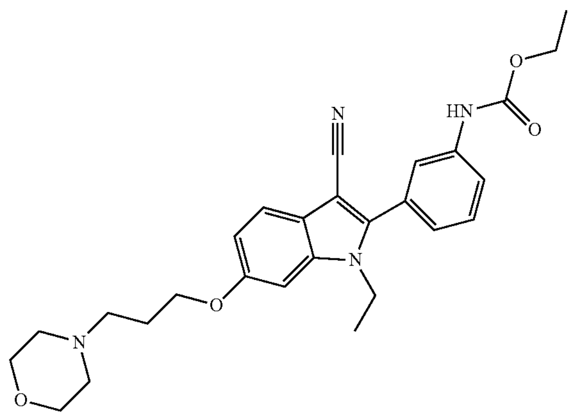
494
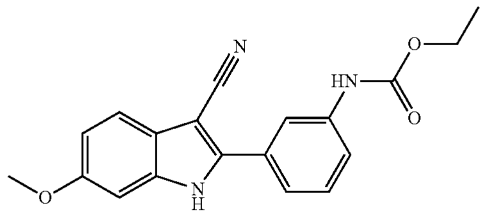
495
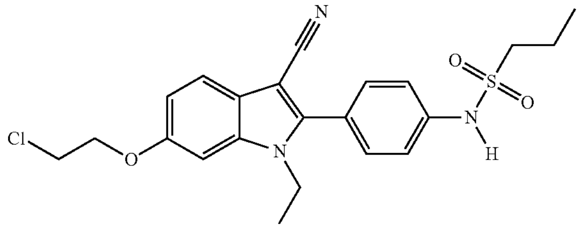
469
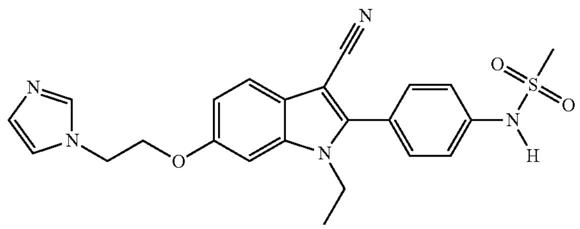
497
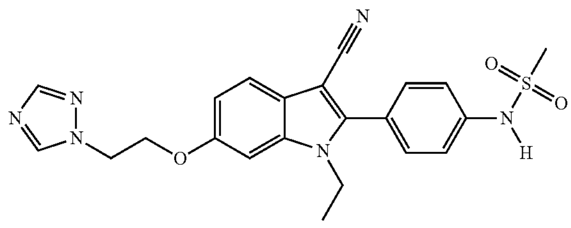
498
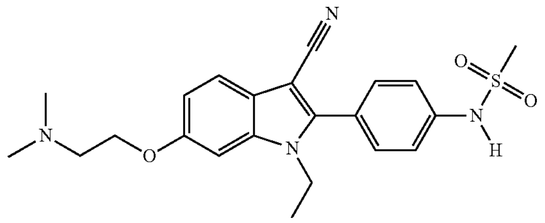
499
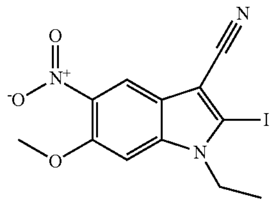
500
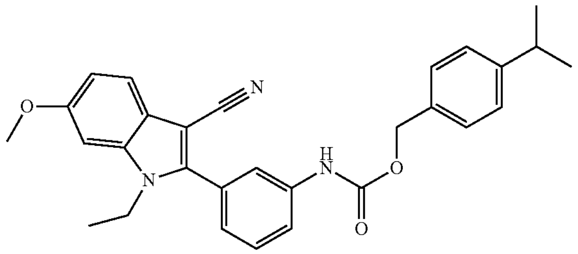
501
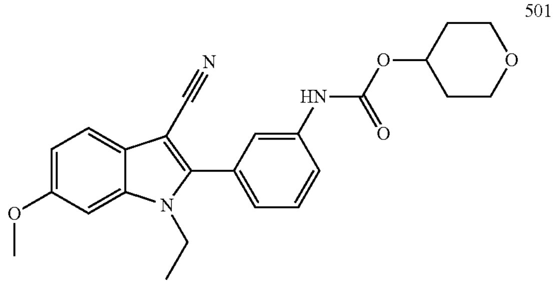
502
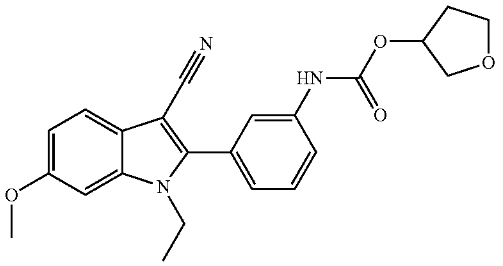
503
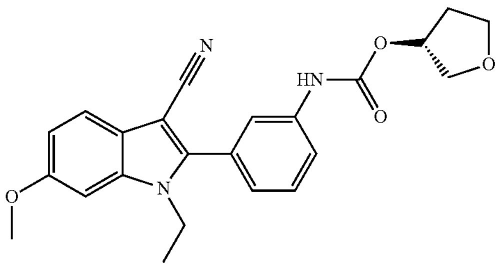

-continued
504
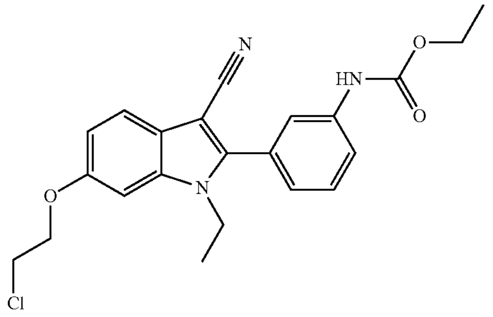
505
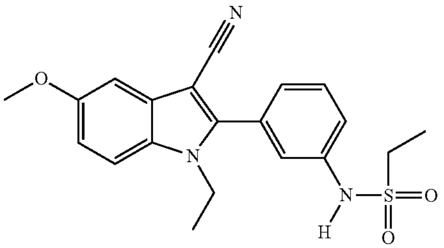
506
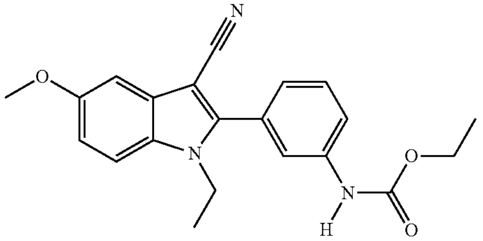
507
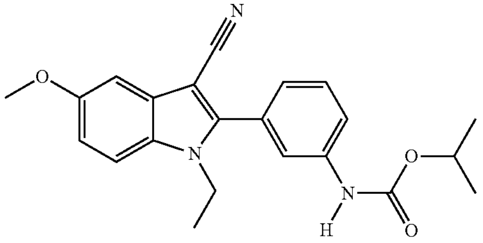
508
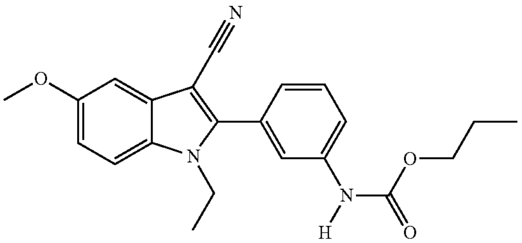
509
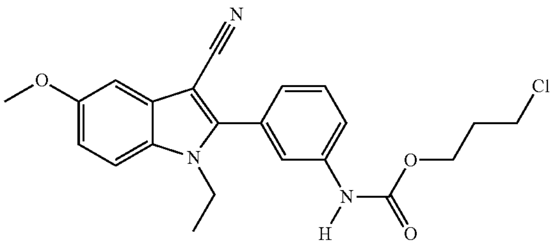
-continued
510
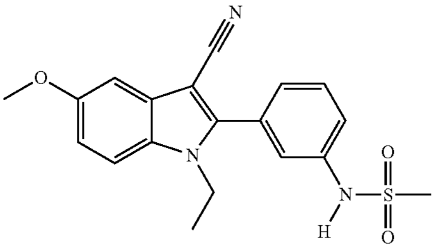
511
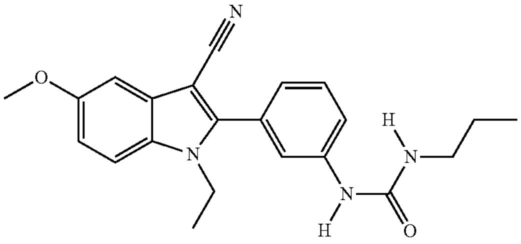
512
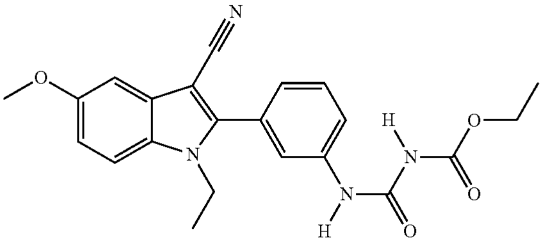
513
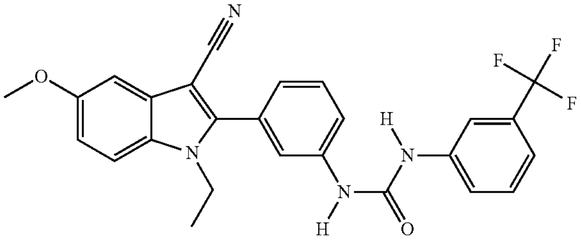
514
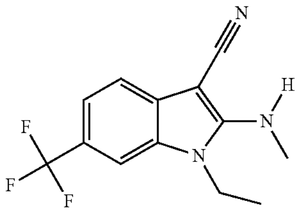
515
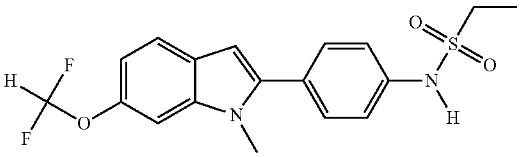

516
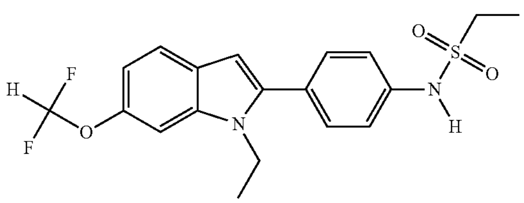
517
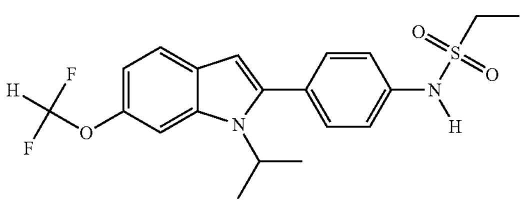
518
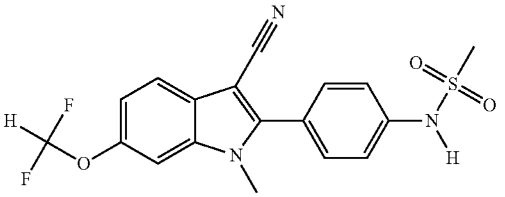
519
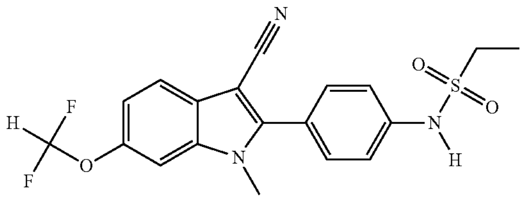
520
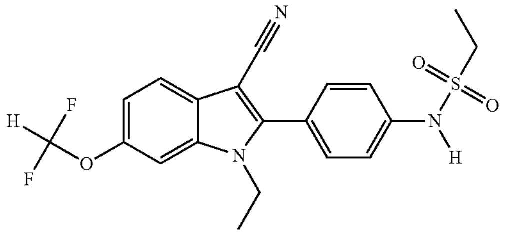
521
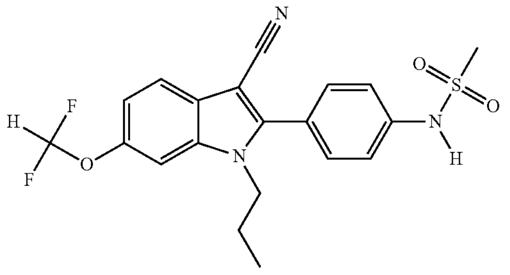
522
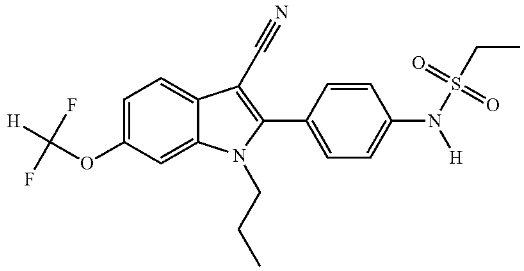
523
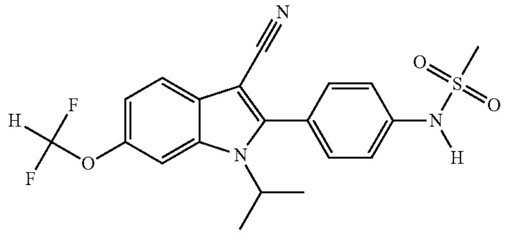
524
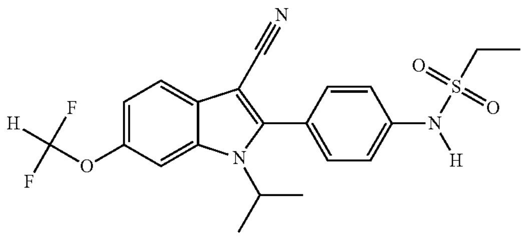
525
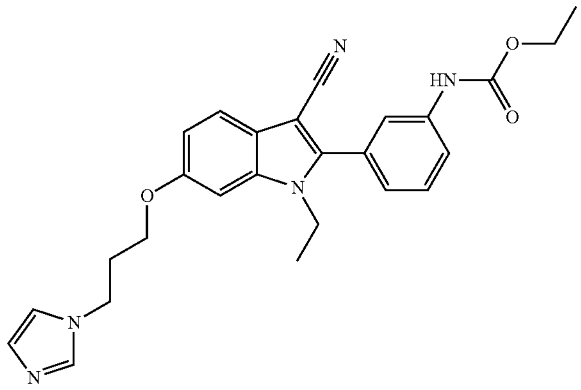
526
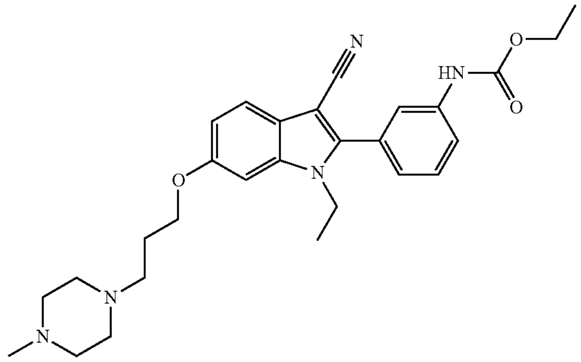

-continued
527
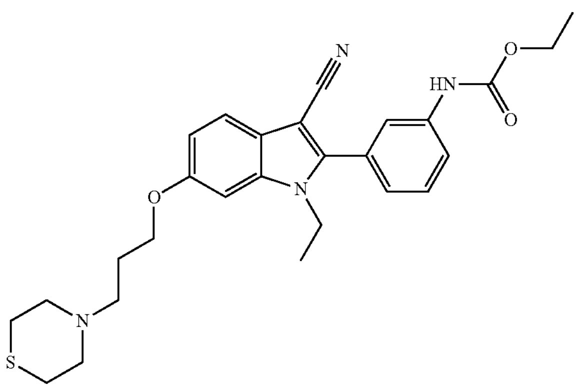
528
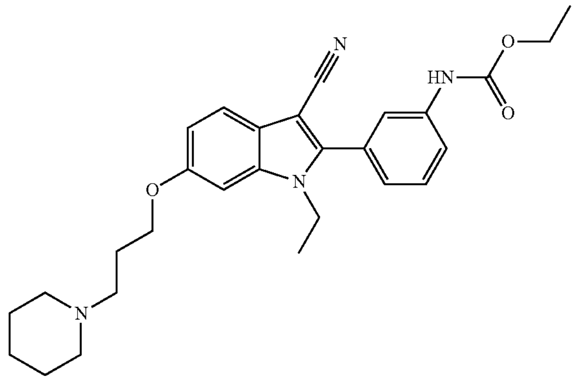
529
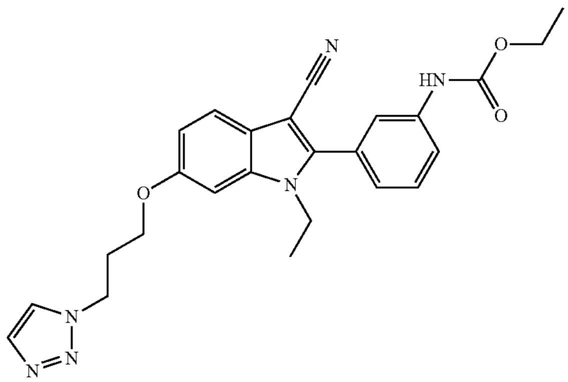
530
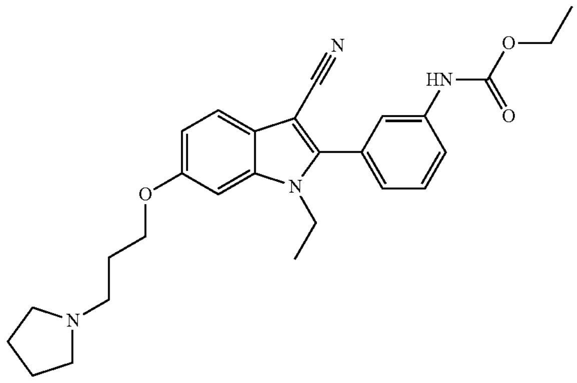
-continued
531
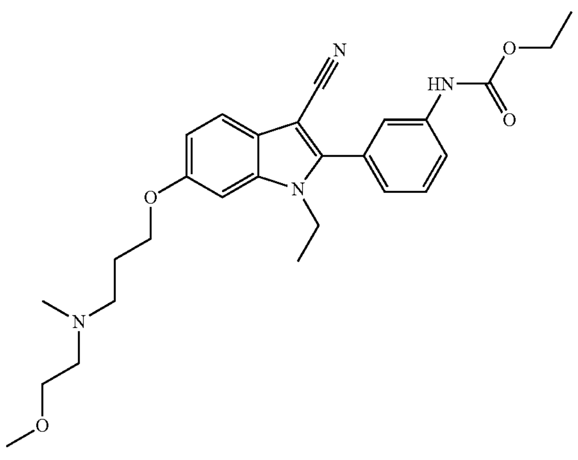
532
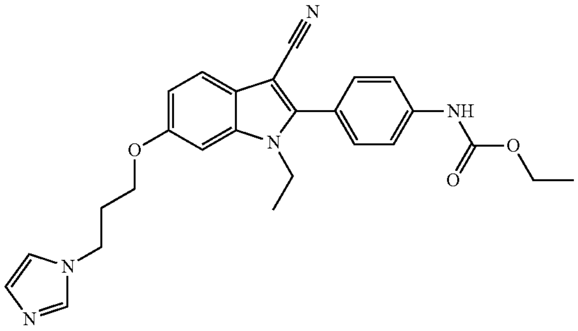
533
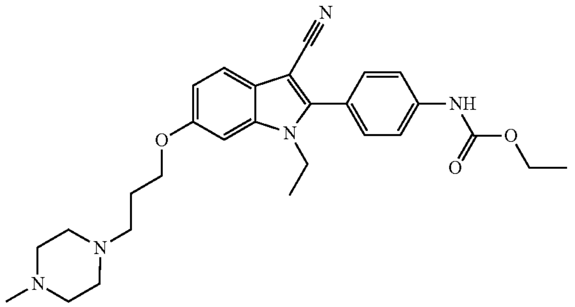
534
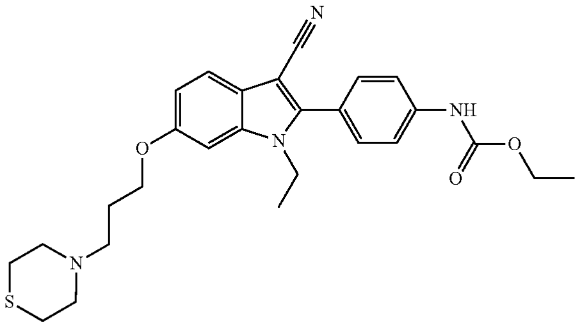

-continued
535
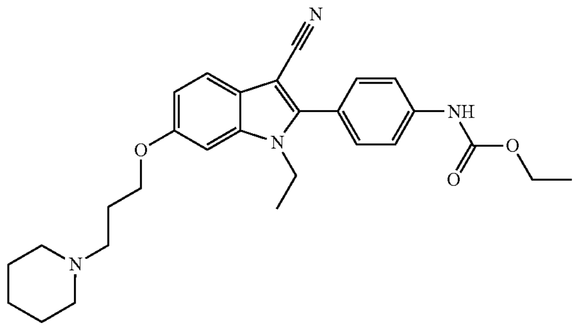
536
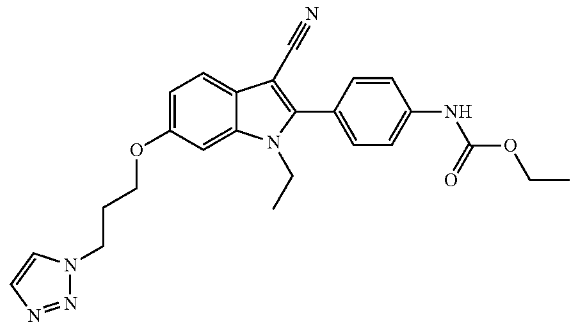
537
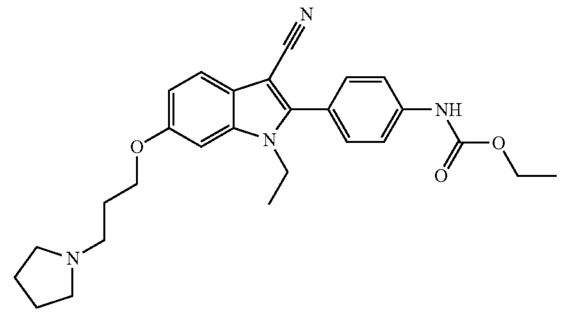
538
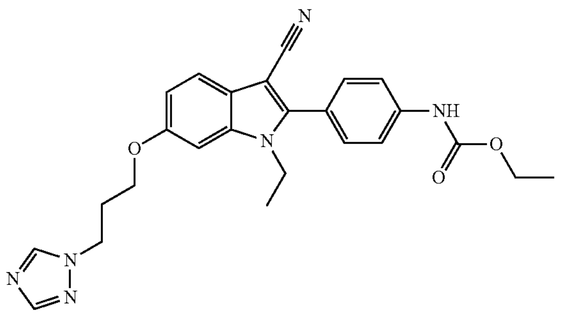
-continued
539
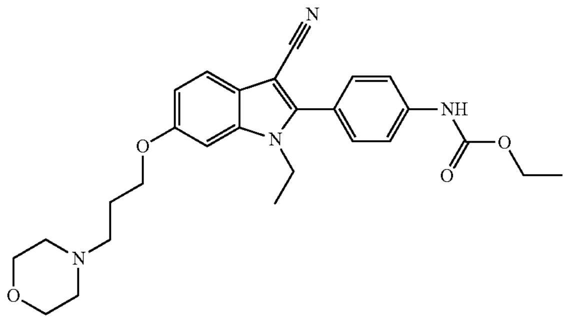
540
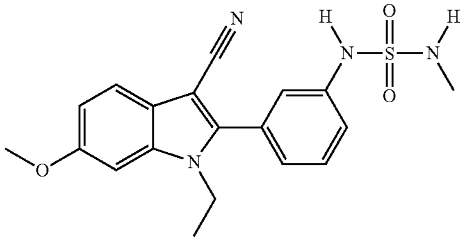
541
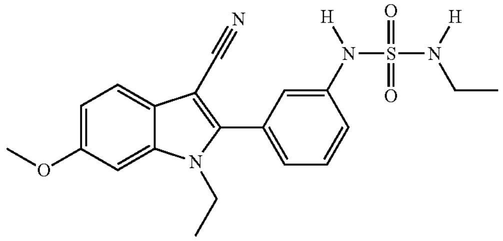
542
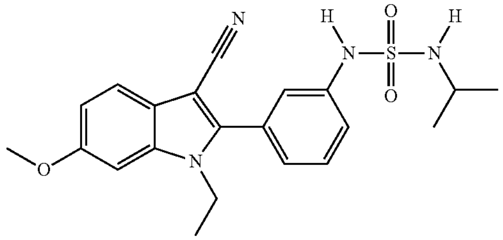
543
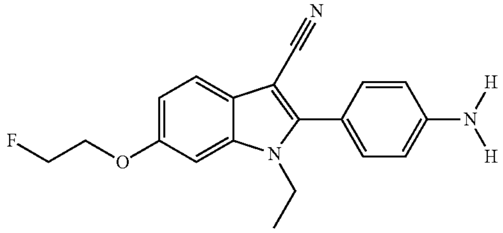
544
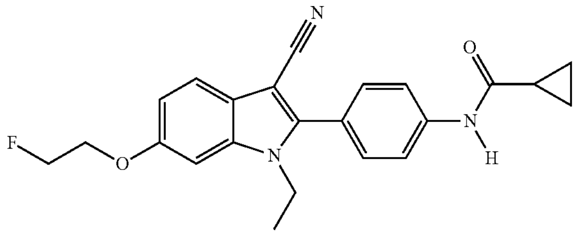

-continued
545
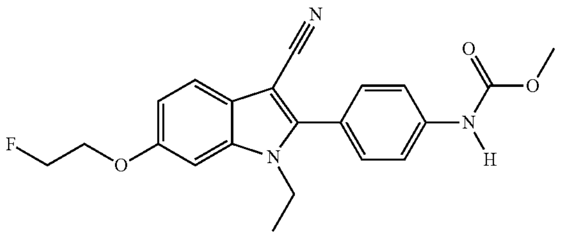
546
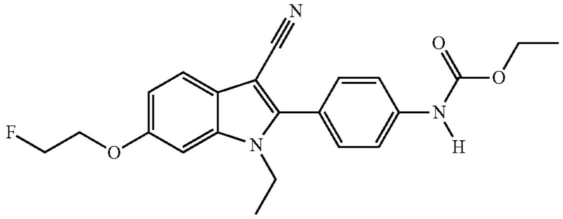
547
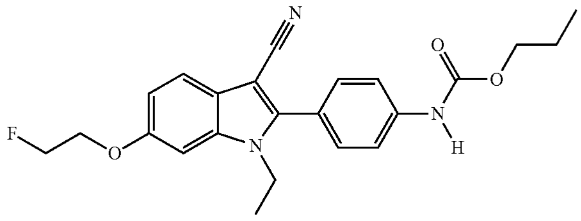
548
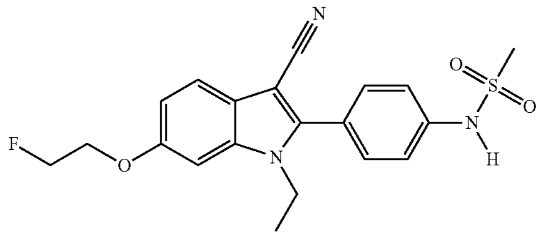
549
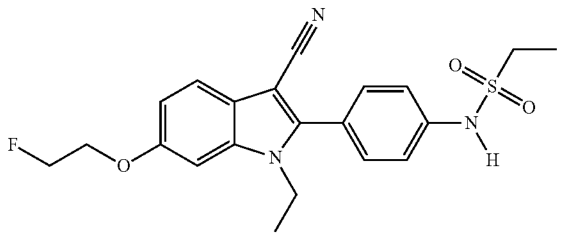
550
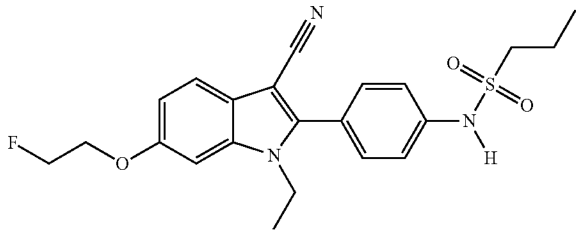
-continued
551
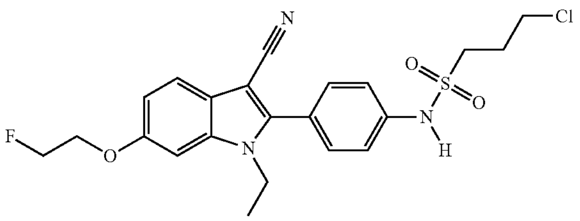
552
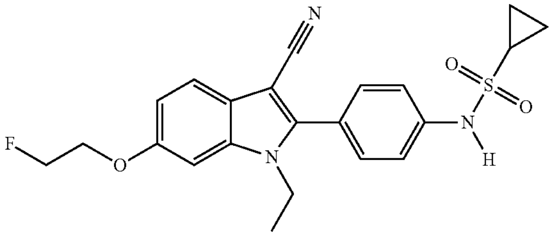
553
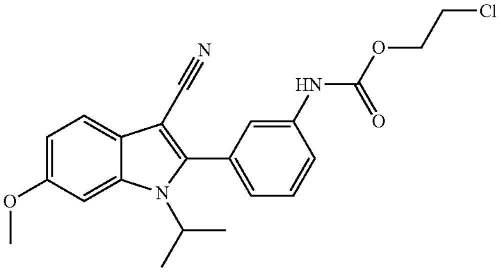
554
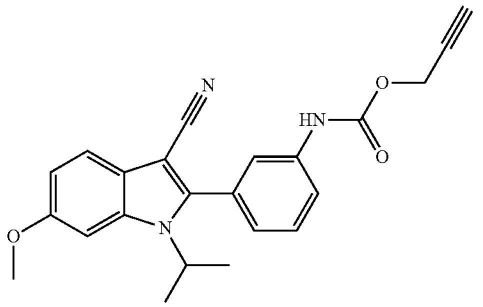
555
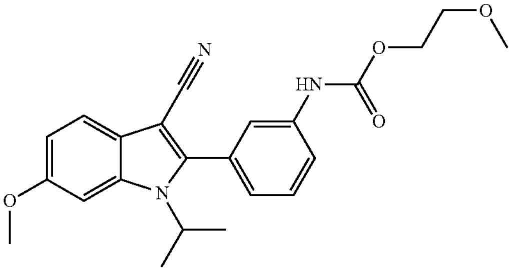

-continued
556
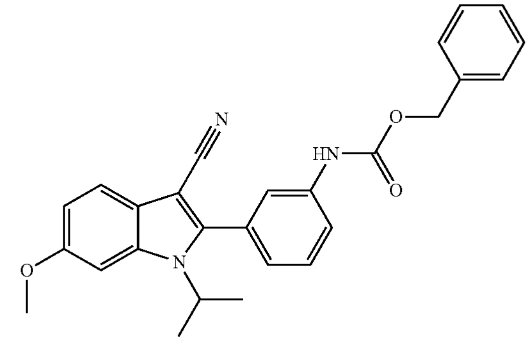
557
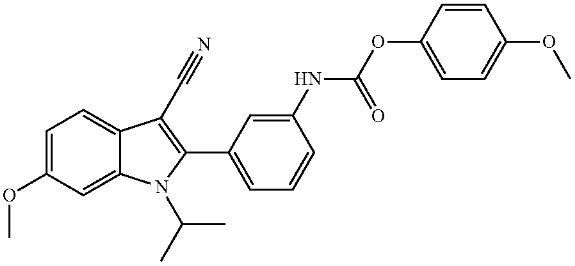
558
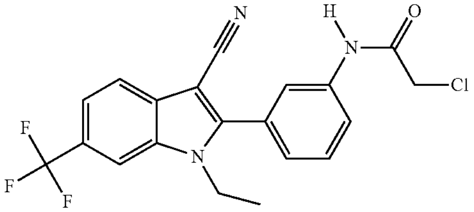
559
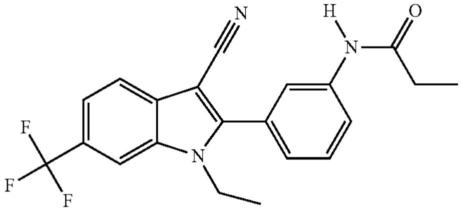
560
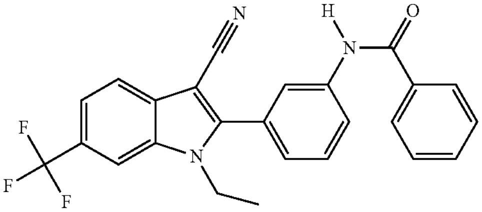
561
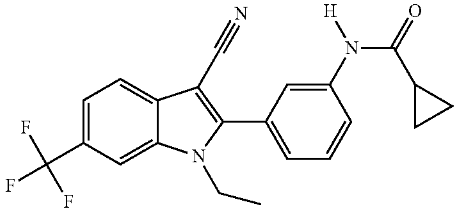
-continued
562
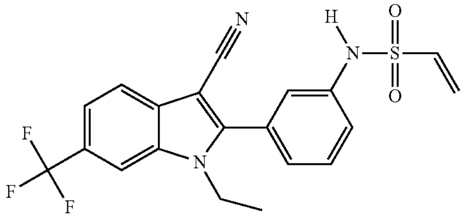
563
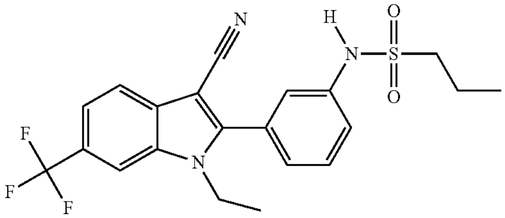
564
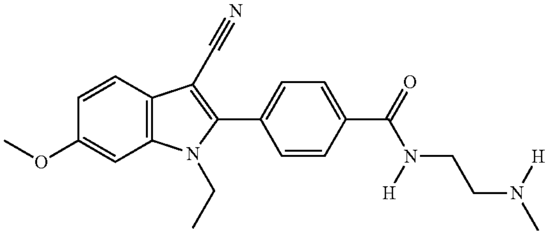
565
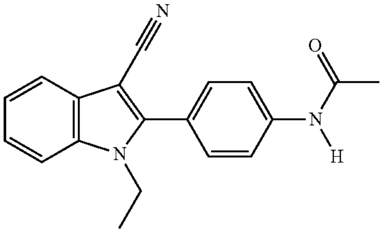
566
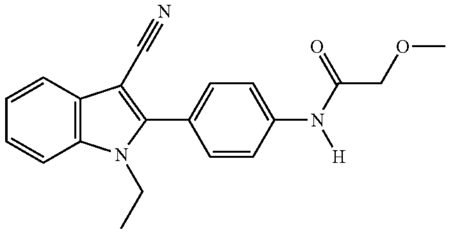
567
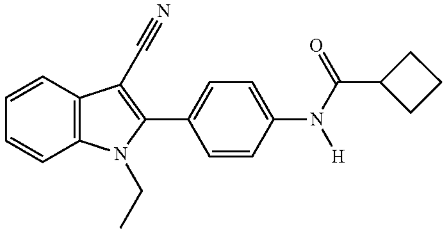

-continued
568
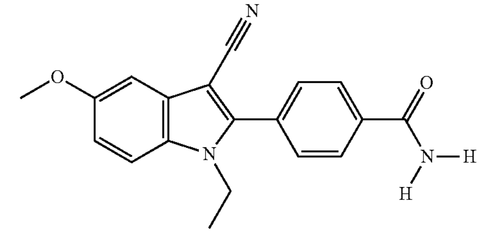
569
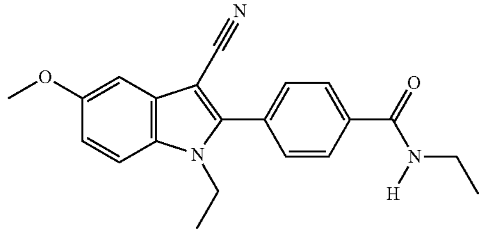
570
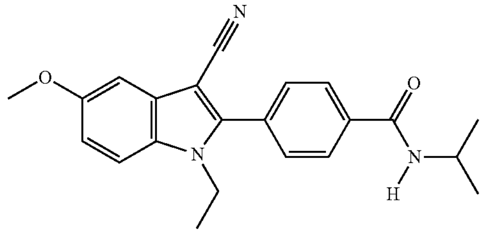
571
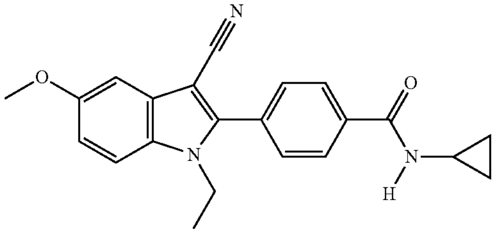
572
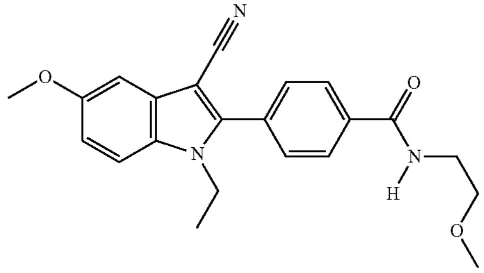
573
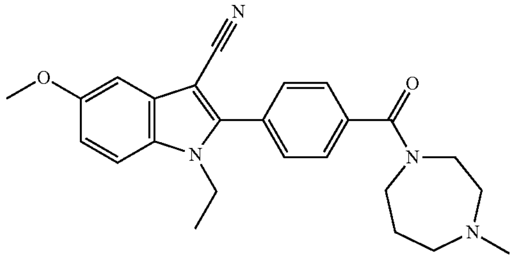
-continued
574
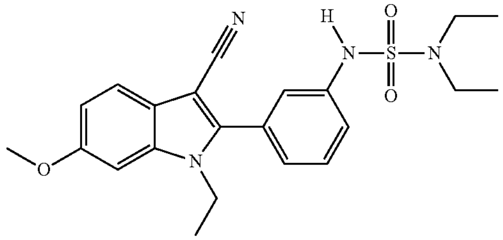
575
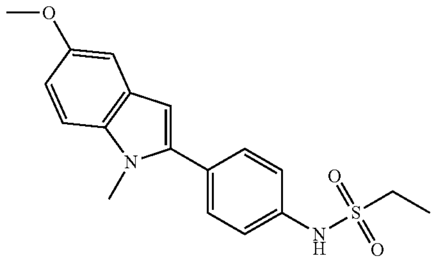
576
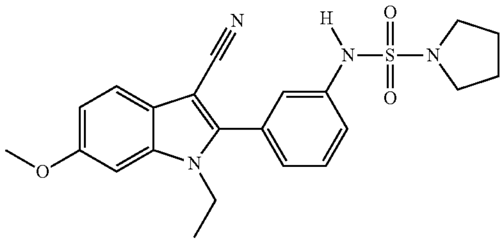
577
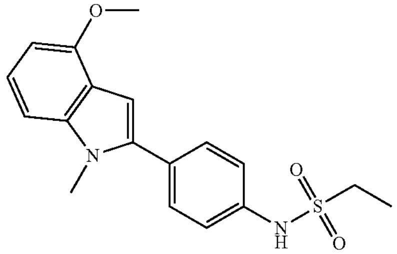
578
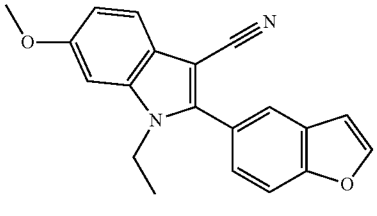
579
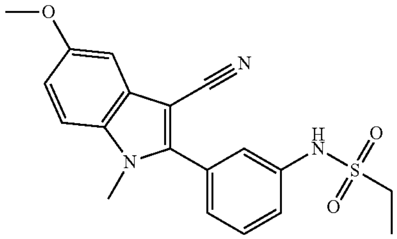

580
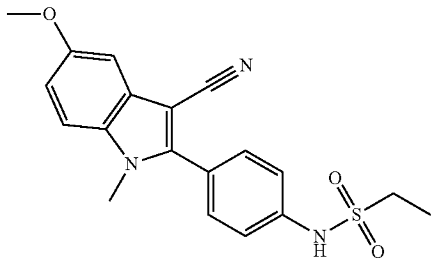
581
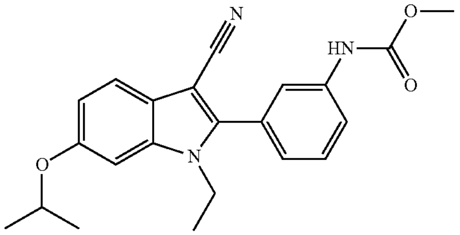
582
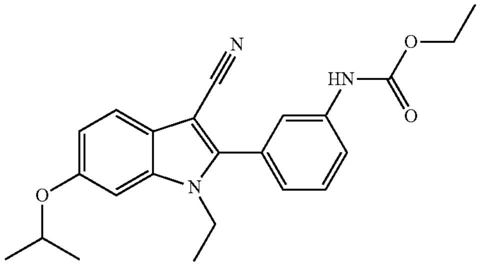
583
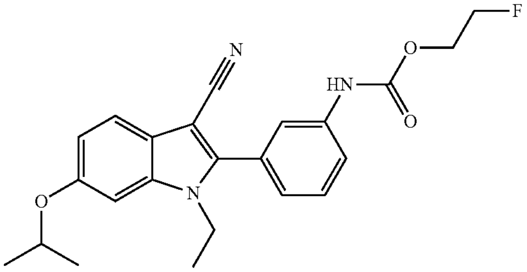
584
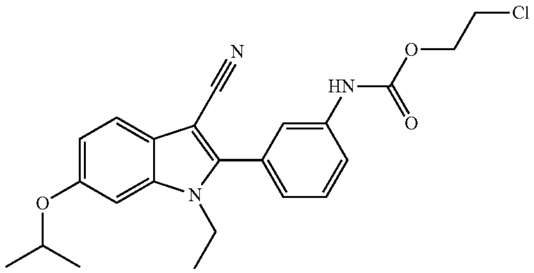
585
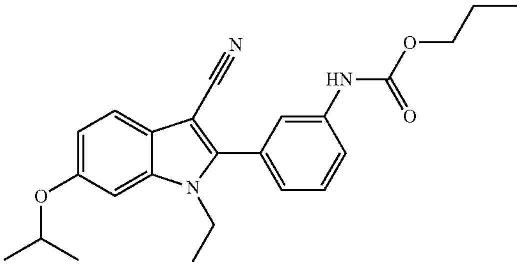
586
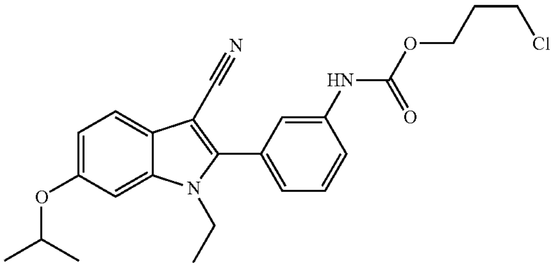
587
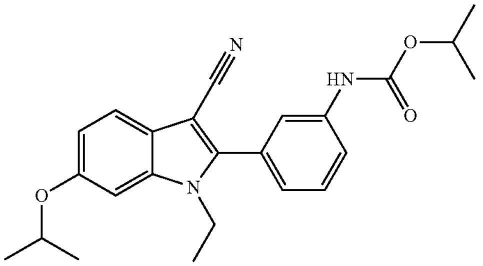
588
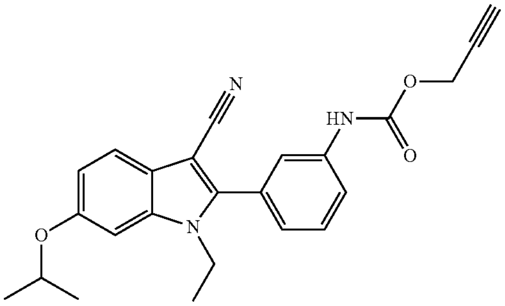
589
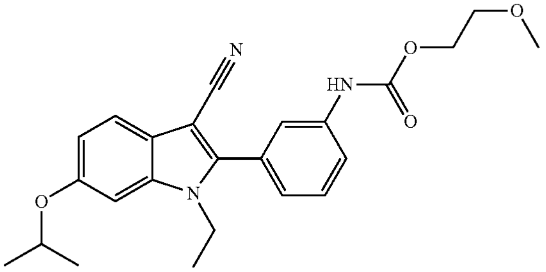

-continued
590
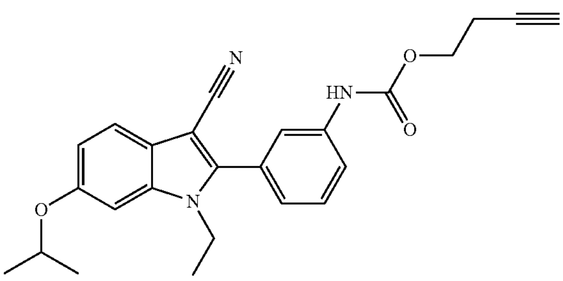
591
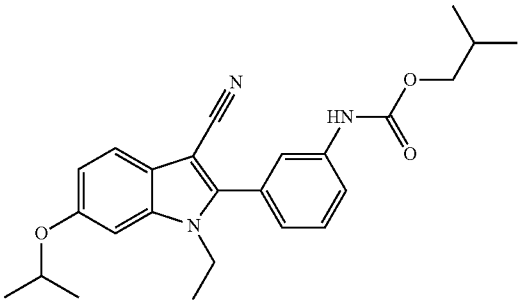
592
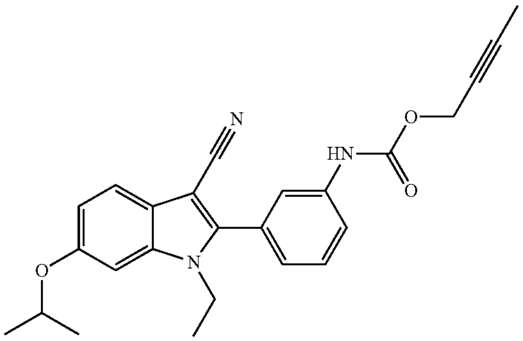
593
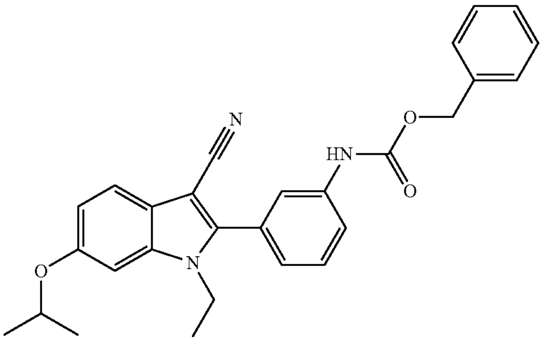
594
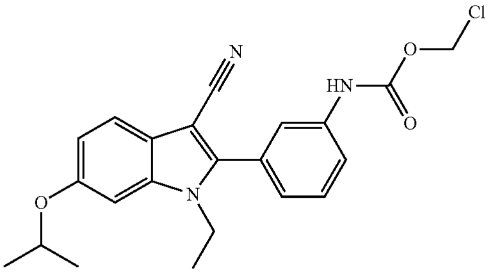
-continued
595
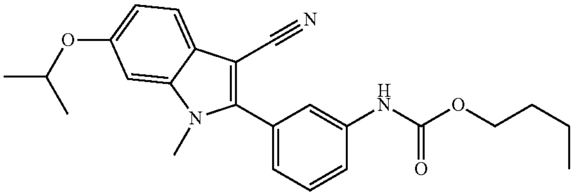
596
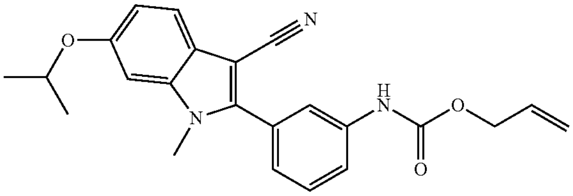
597
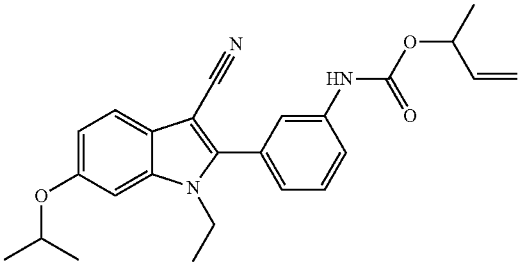
598
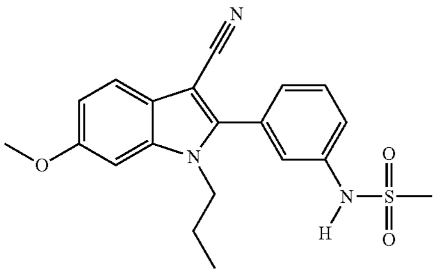
599
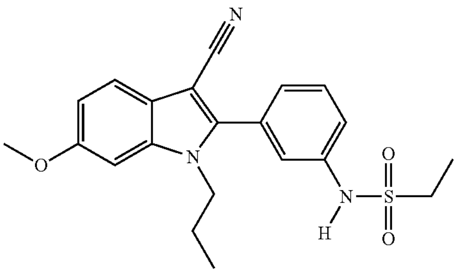
600
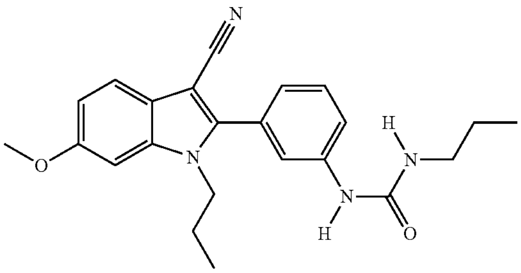

-continued
601
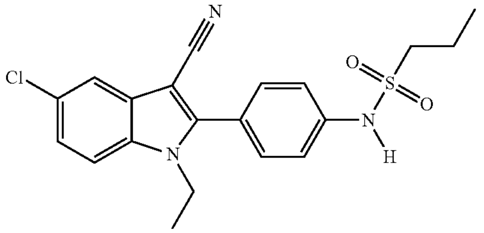
602
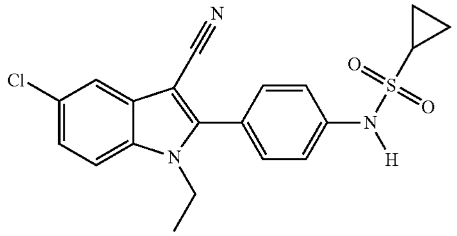
603
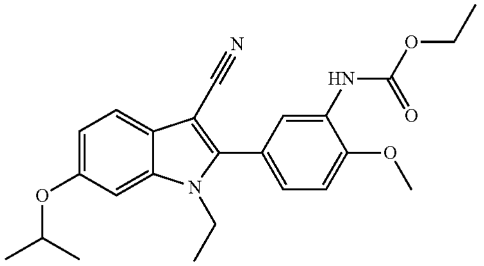
604
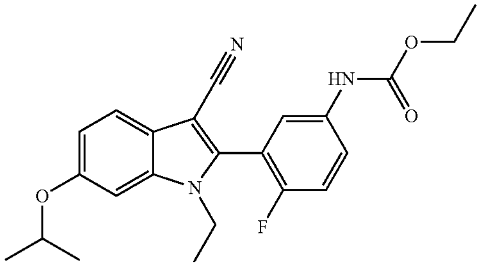
605
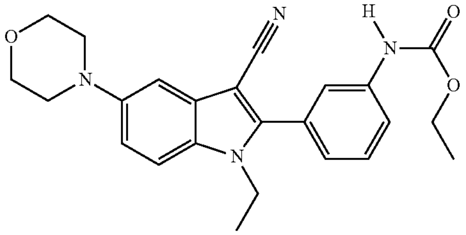
606
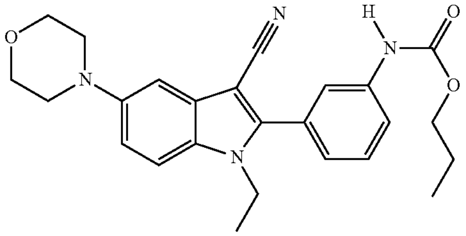
-continued
607
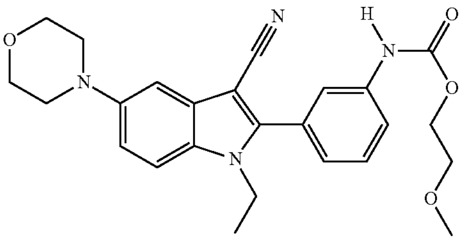
608
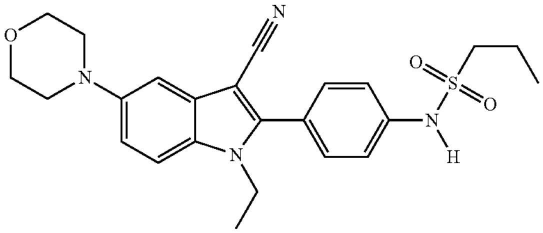
609
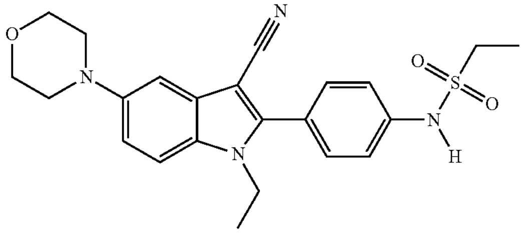
610
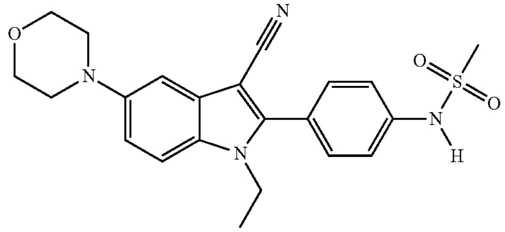
611
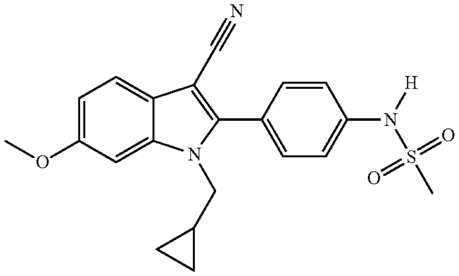
612
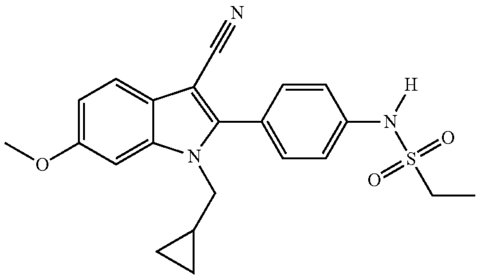

-continued
613
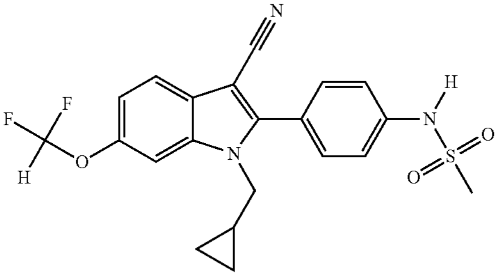
614
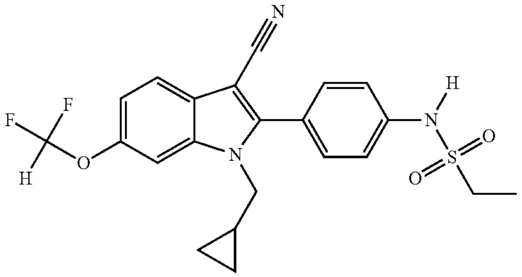
615
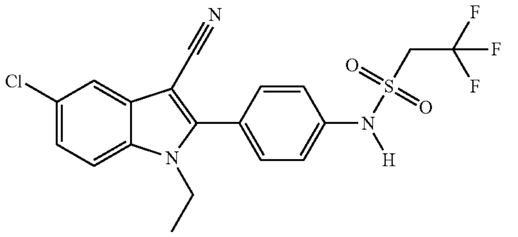
616
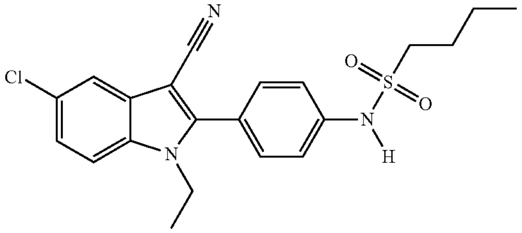
617
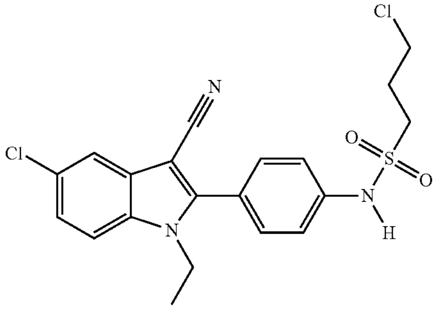
-continued
618
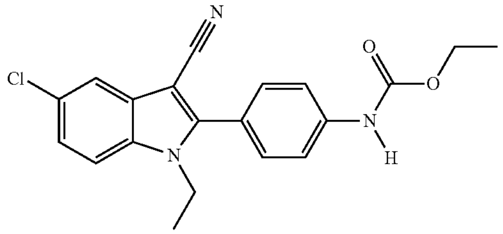
619
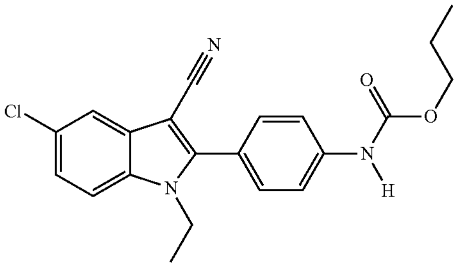
620
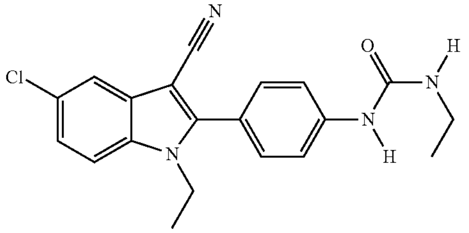
621
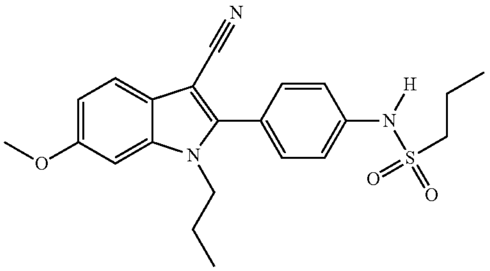
622
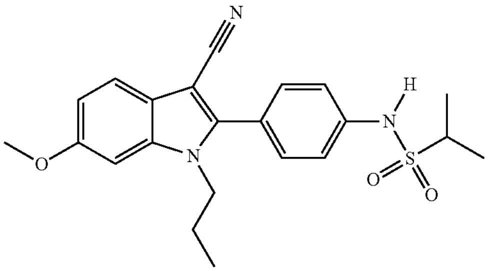
623
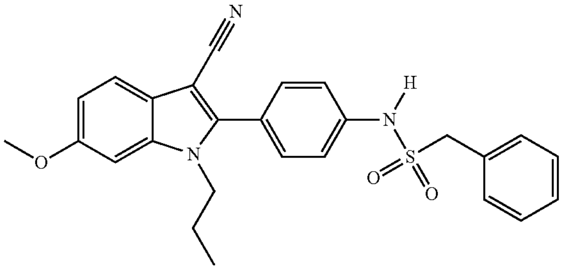

624
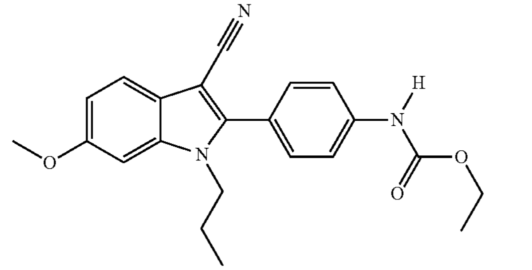
625
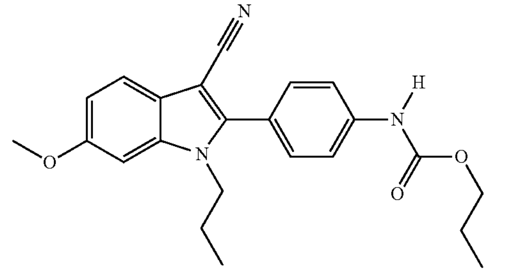
626
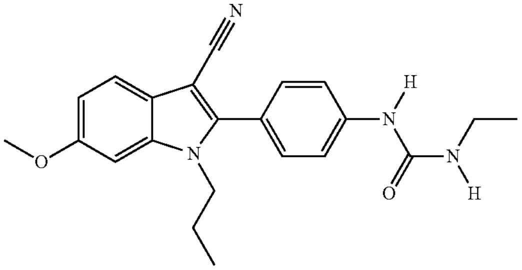
627
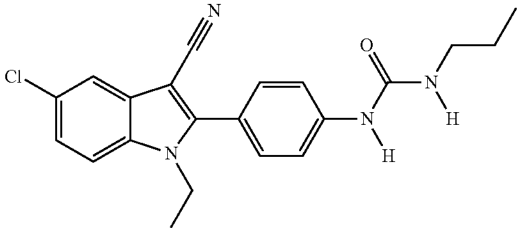
628
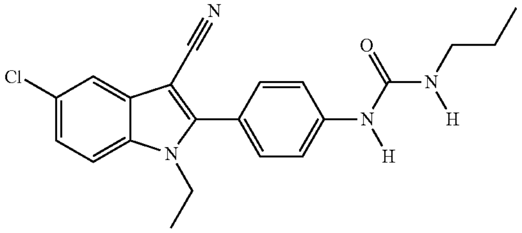
629
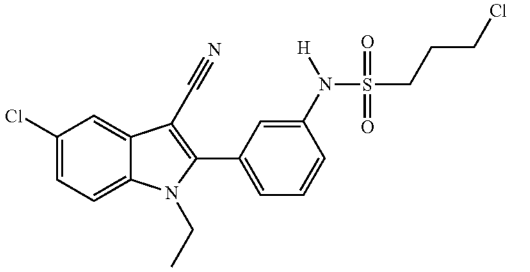
630
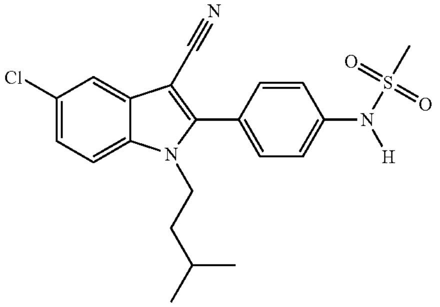
631
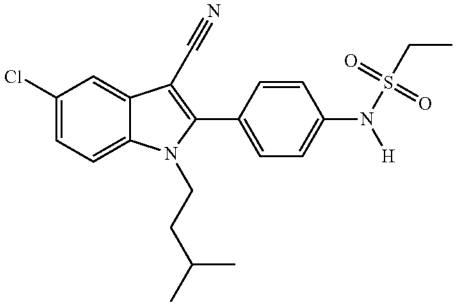
632
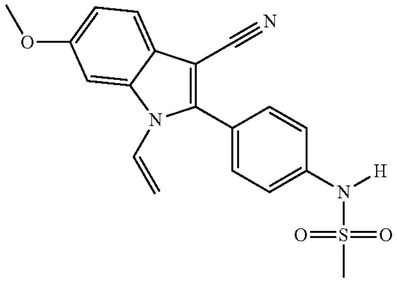
633
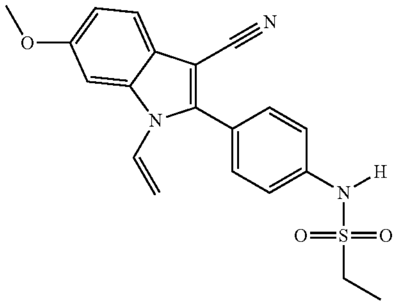
634
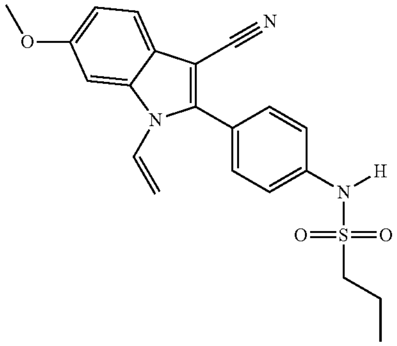

-continued
635
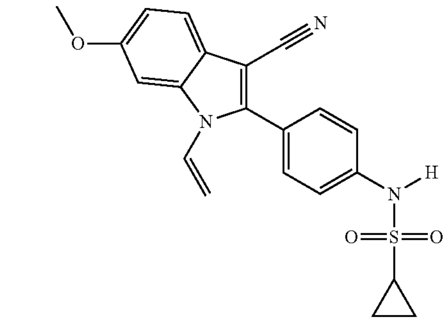
636
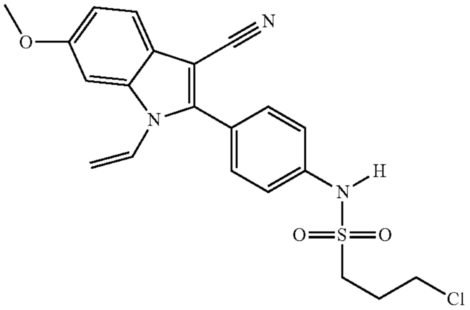
637
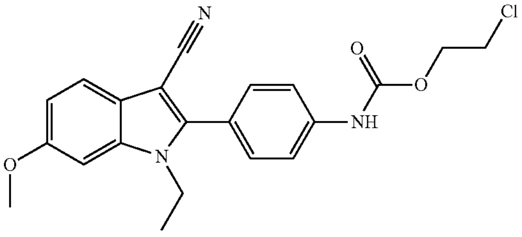
638
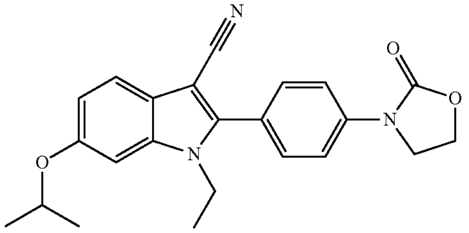
639
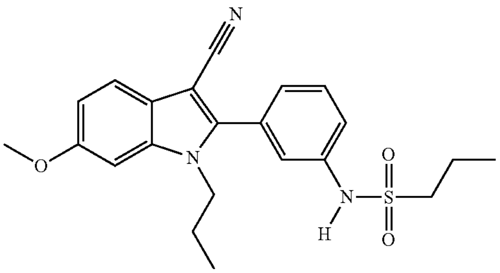
-continued
640
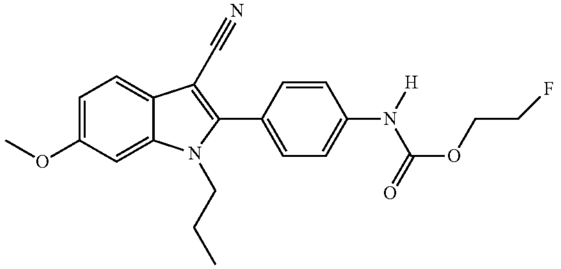
641
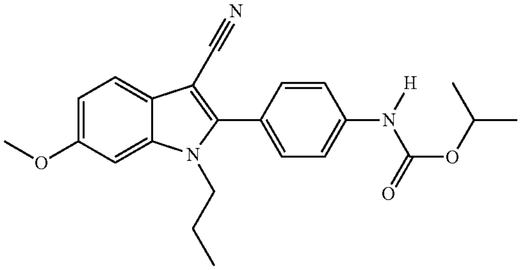
642
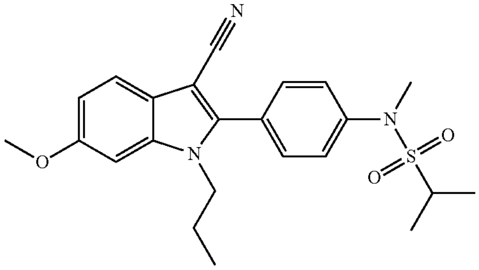
643
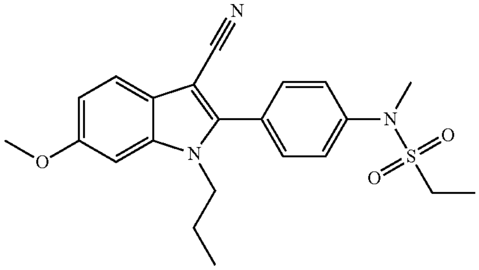
644
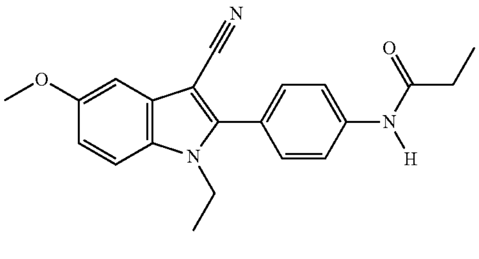

-continued
645
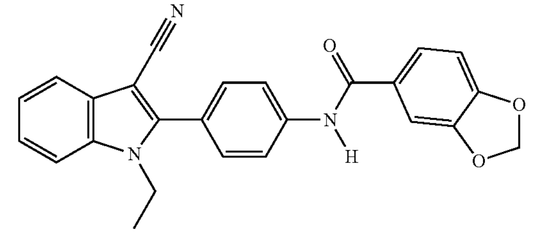
646
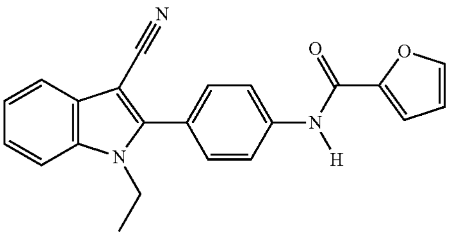
647
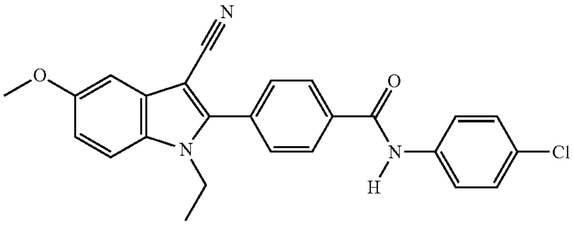
648
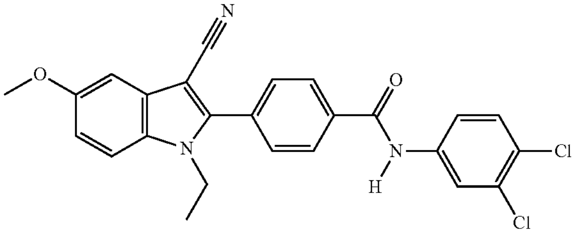
649
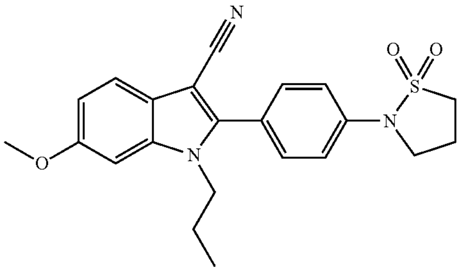
650
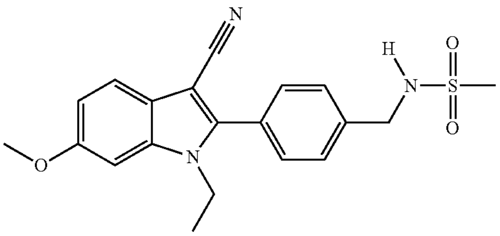
-continued
651
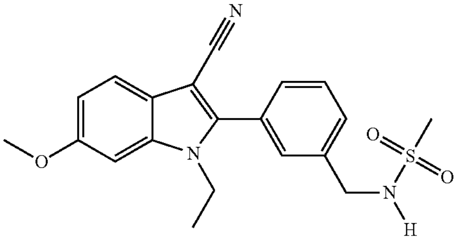
652
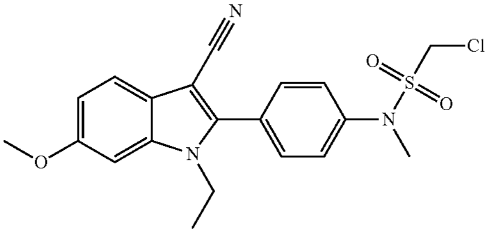
653
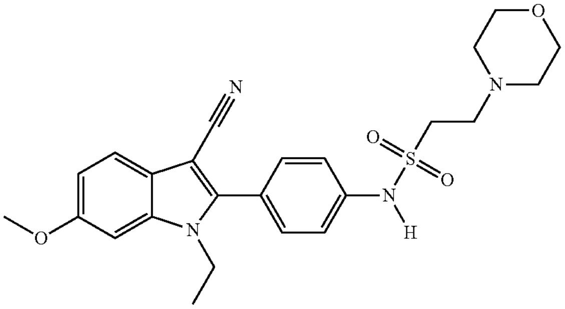
654
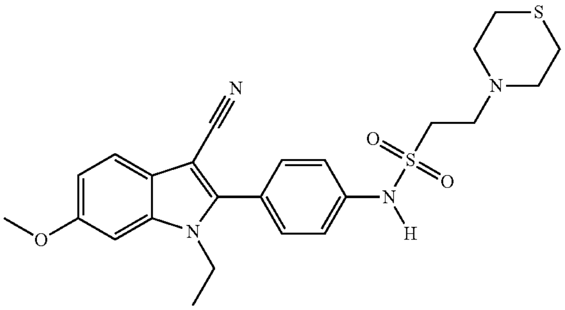
655
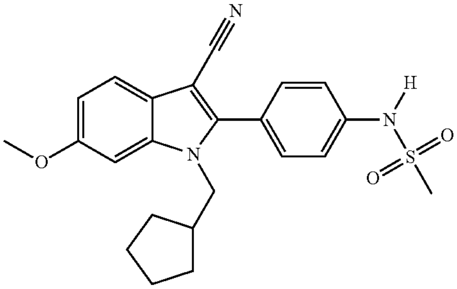

-continued
656
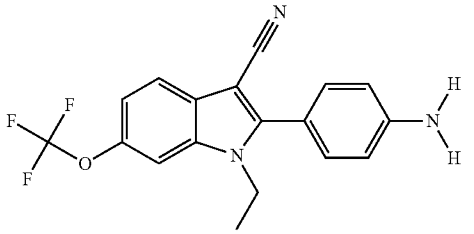
657
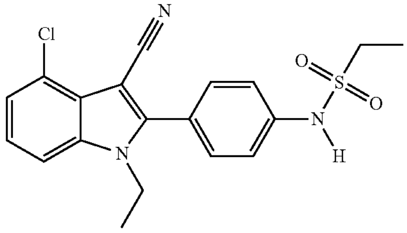
658
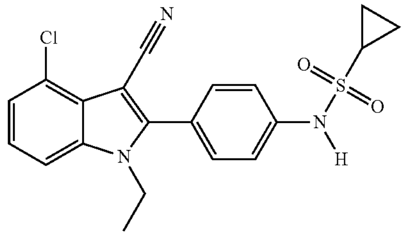
659
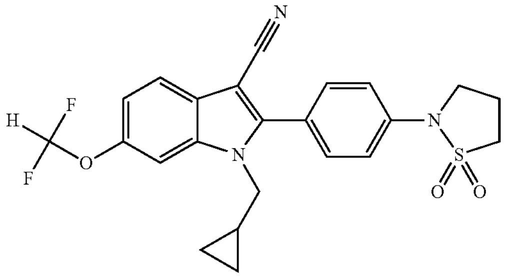
660
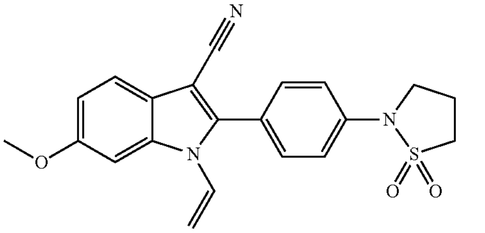
661
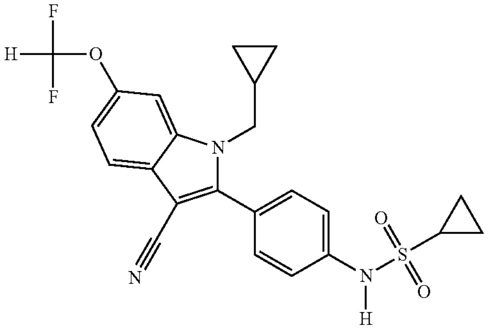
-continued
662
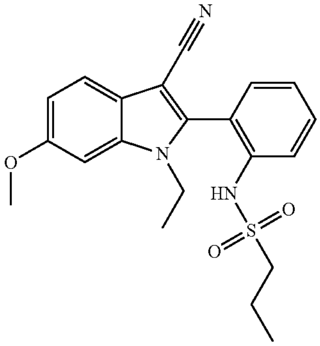
663
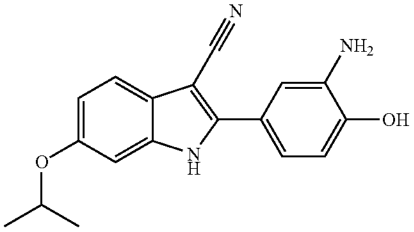
664
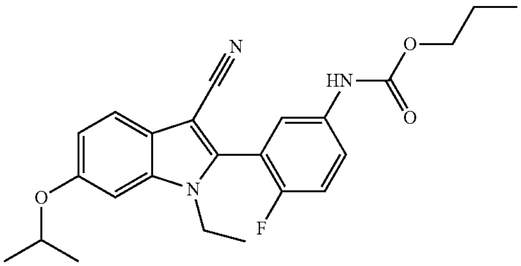
665
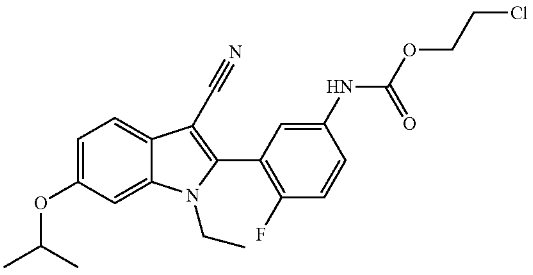
666
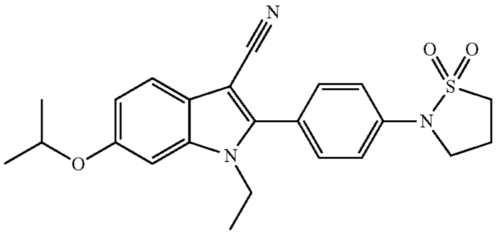

-continued
667
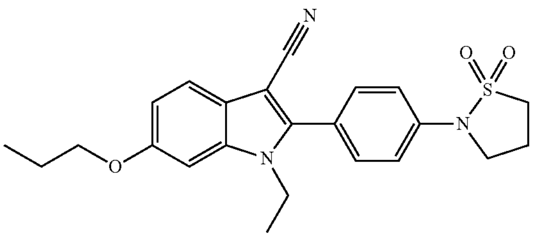
668
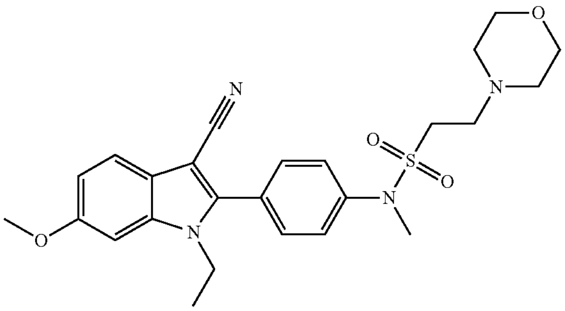
669
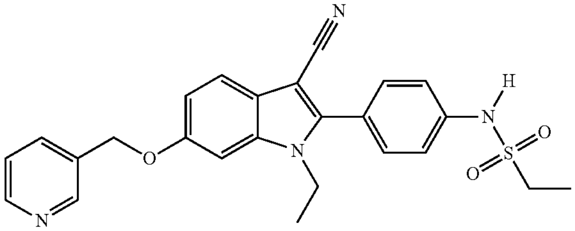
670
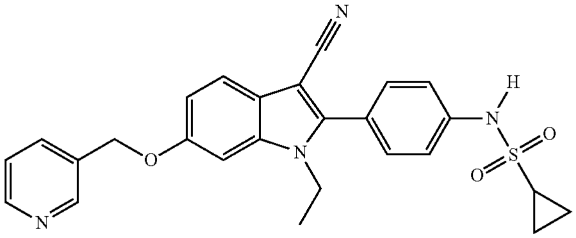
671
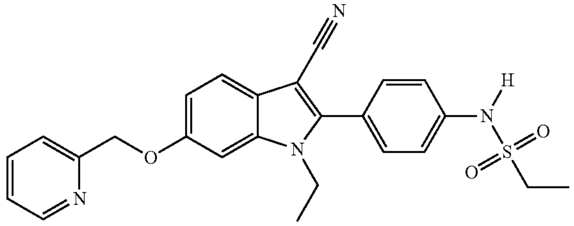
672
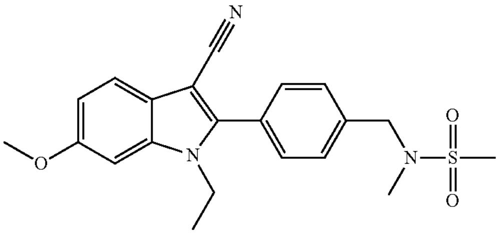
-continued
673
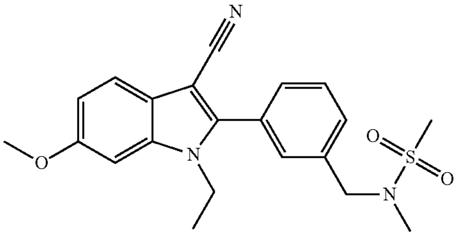
674
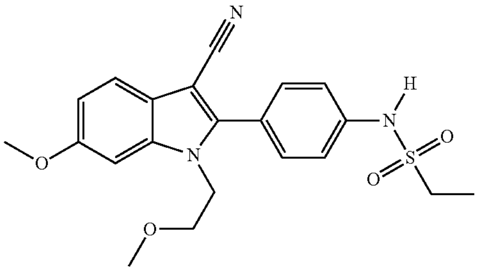
675
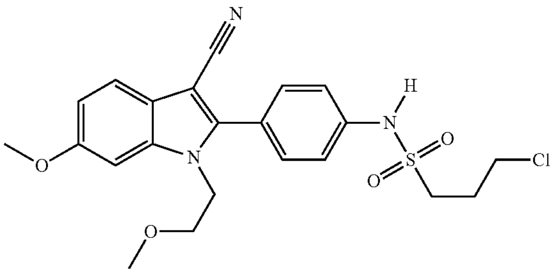
676
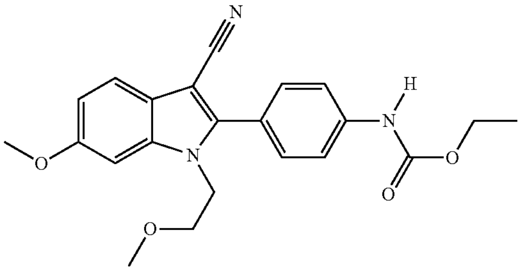
677
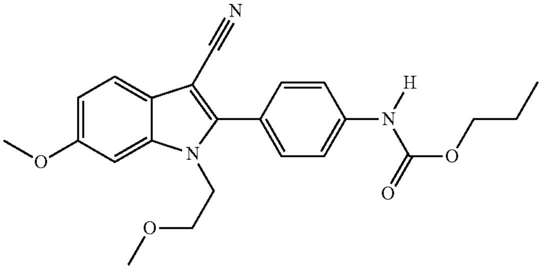

-continued
678
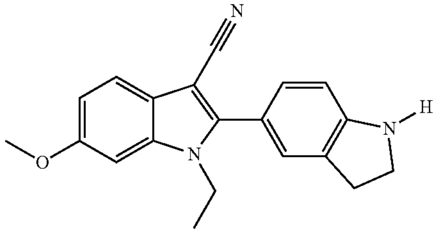
679
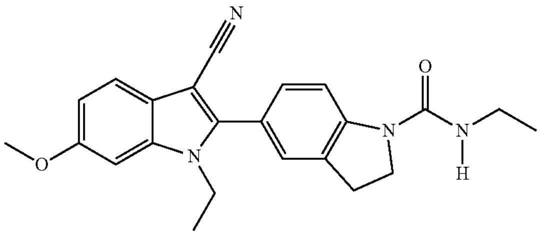
680
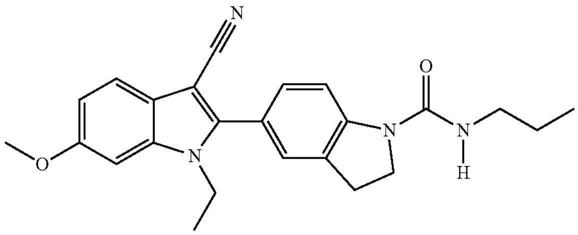
681
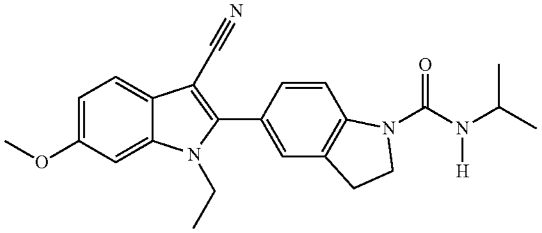
682
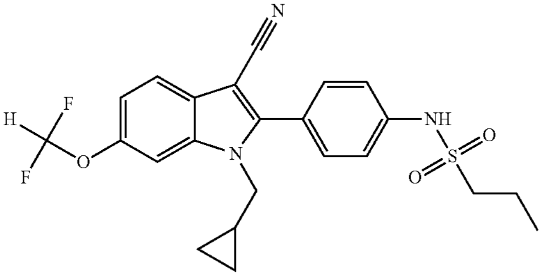
683
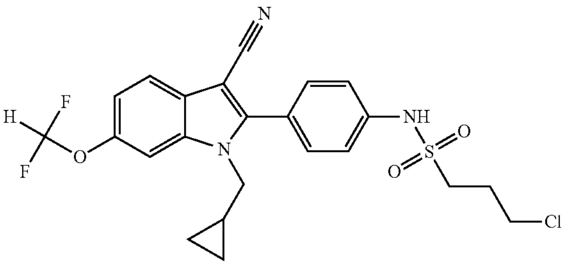
-continued
684
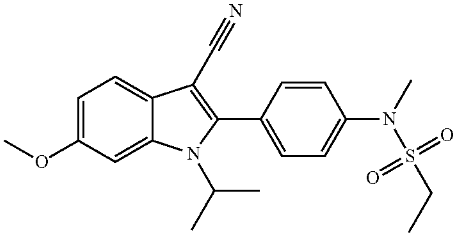
685
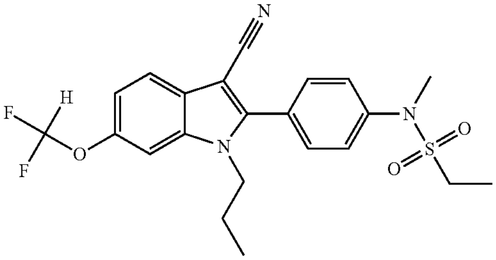
686
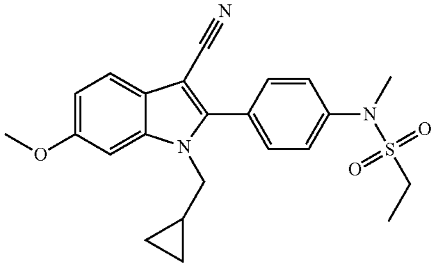
687
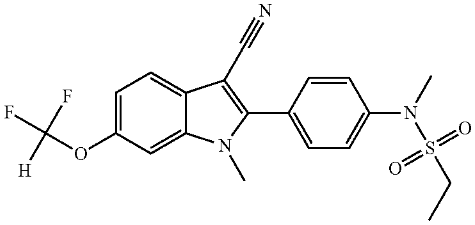
688
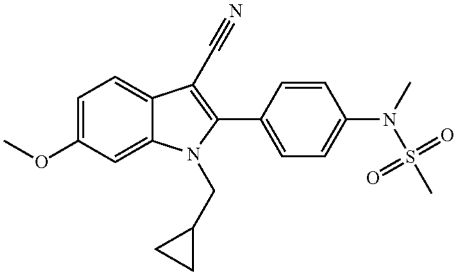
689
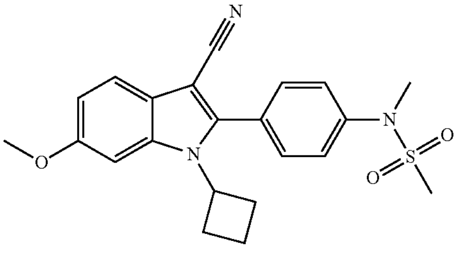

-continued
690
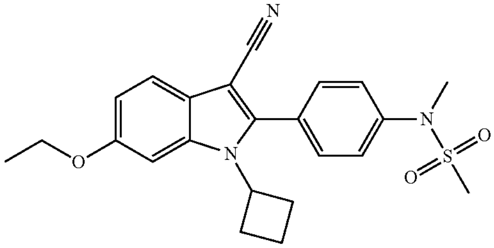
691
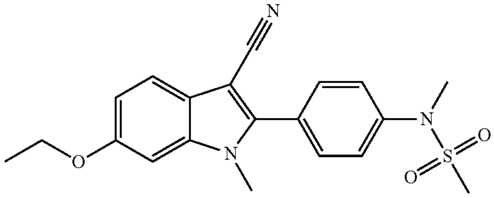
692
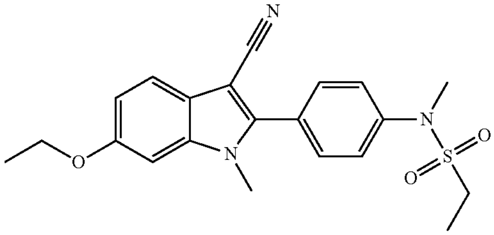
693
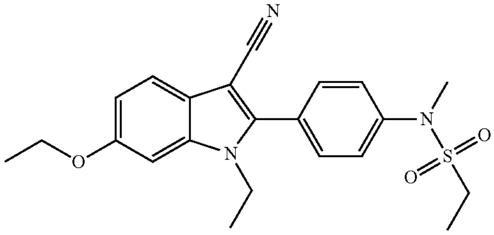
694
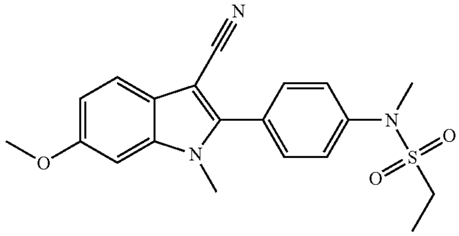
695
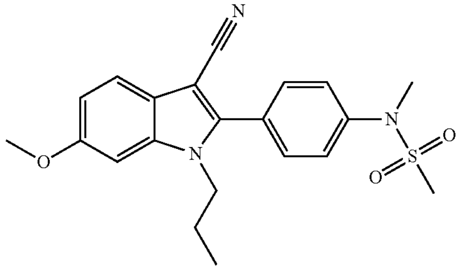
-continued
696
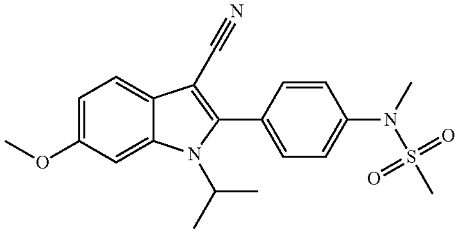
697
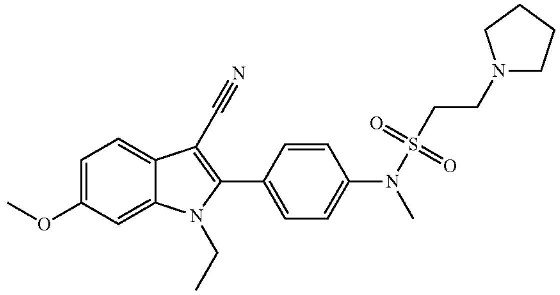
698
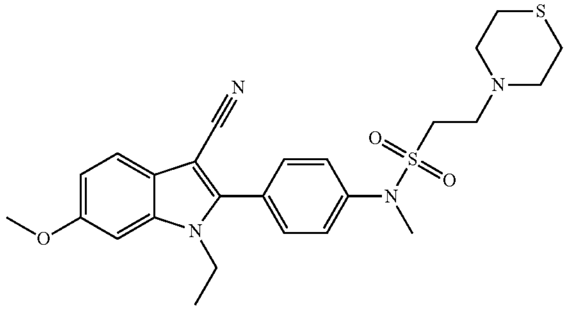
699
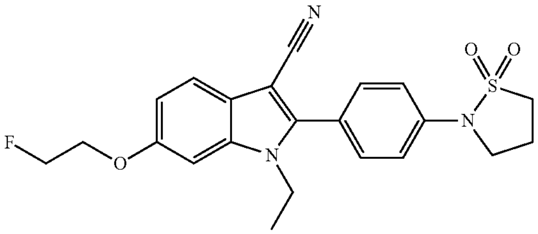
701
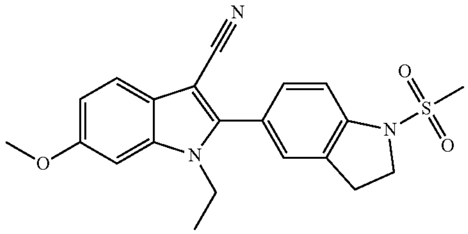
702
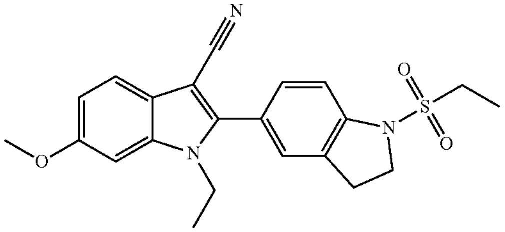

-continued
703
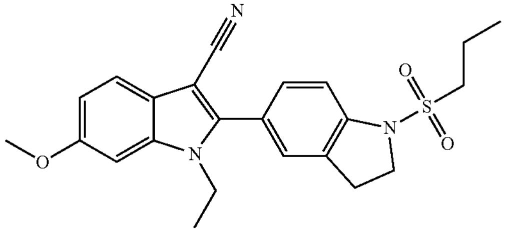
704
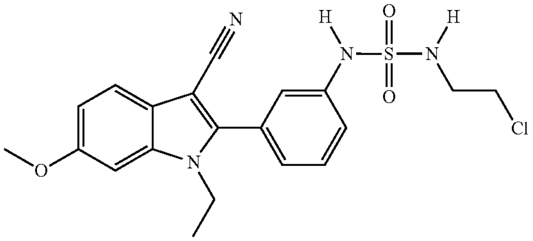
705
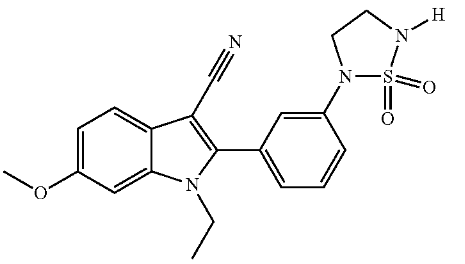
706
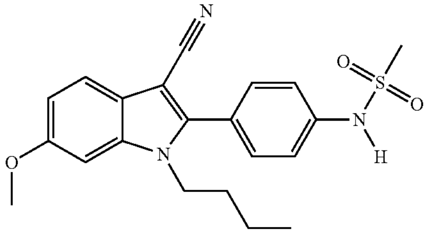
707
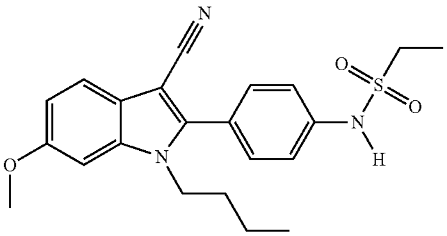
708
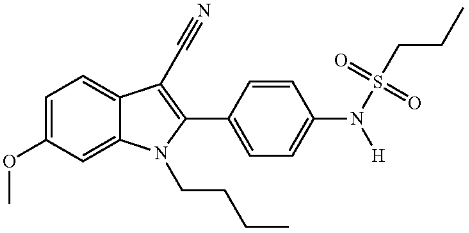
-continued
709
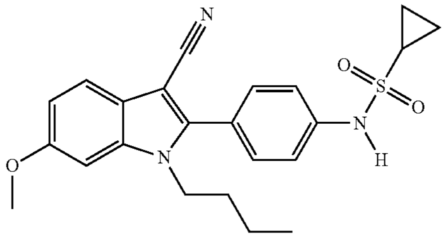
710
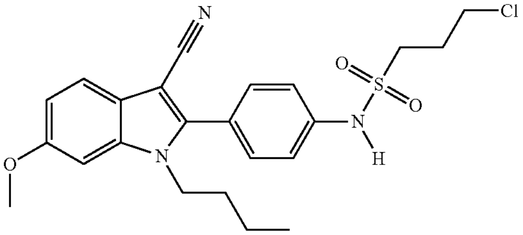
711
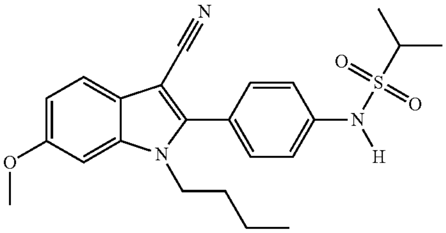
712
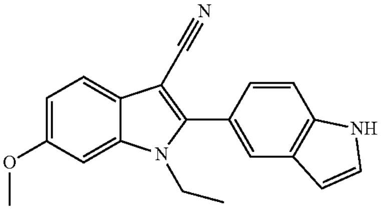
713
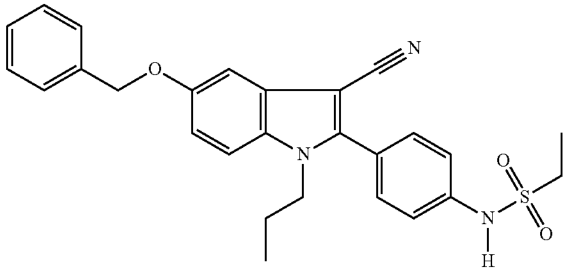
714
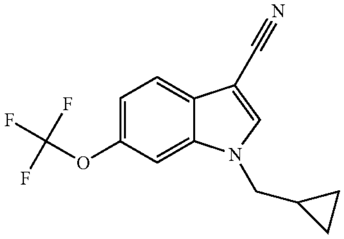

-continued
715
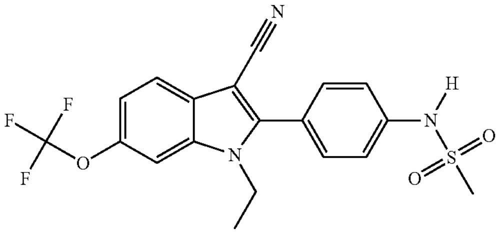
716
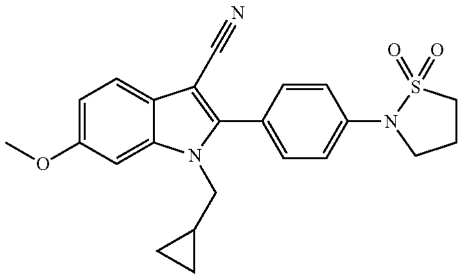
717
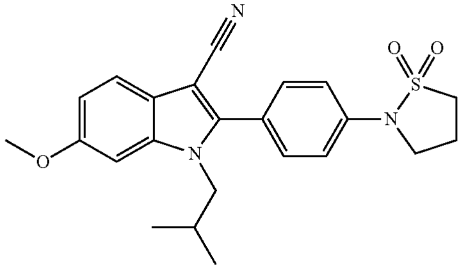
718
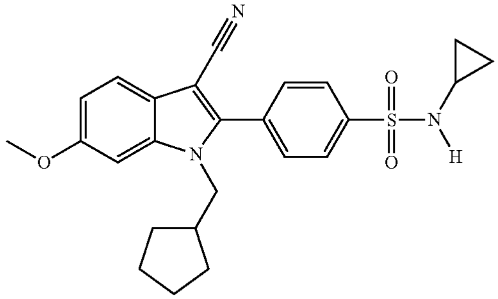
719
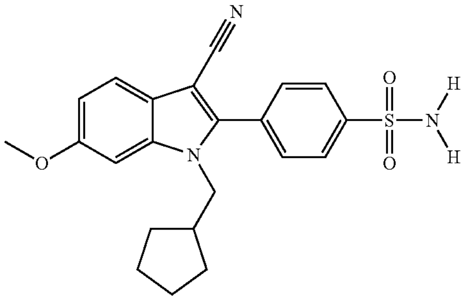
-continued
720
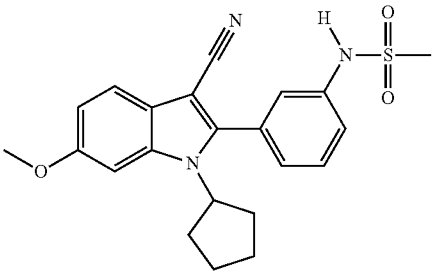
721
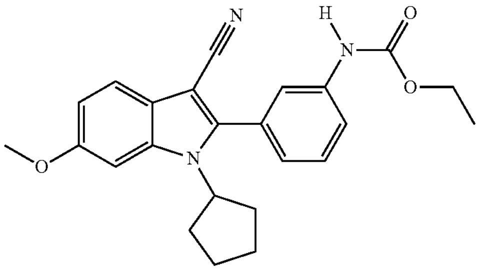
722
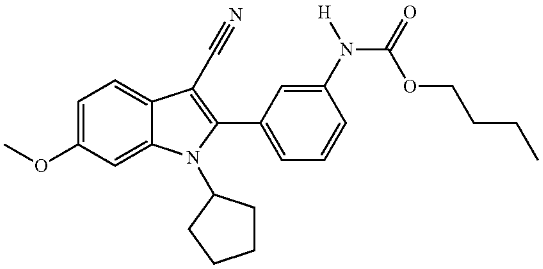
723
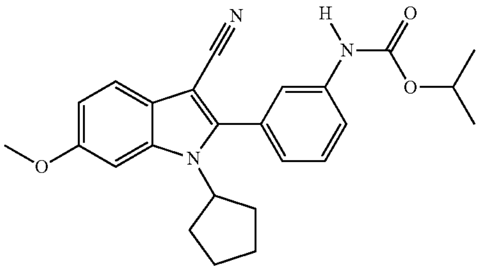
724
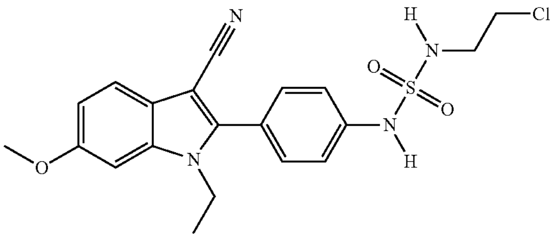
725
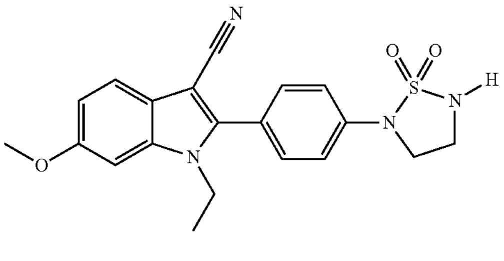

-continued
726
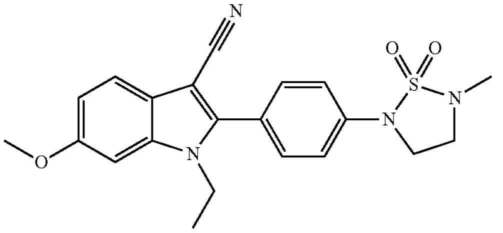
727
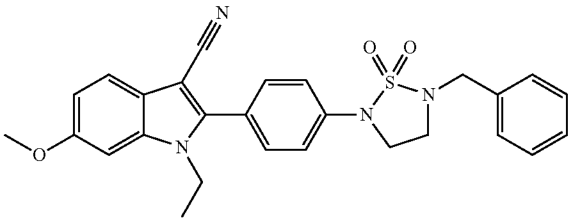
728
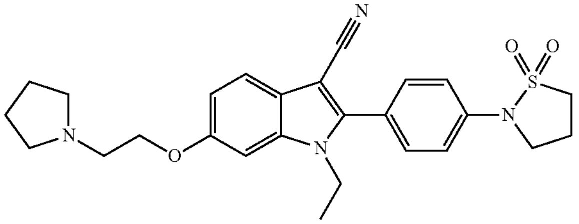
729
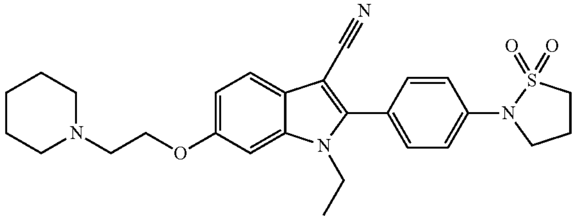
730
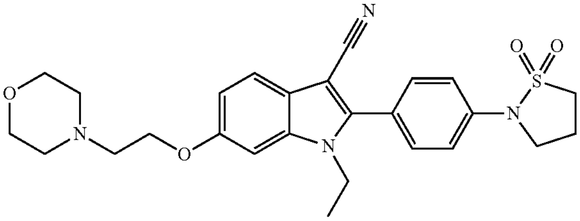
731
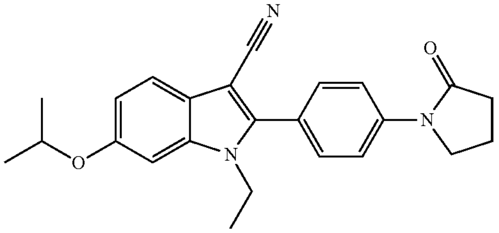
-continued
732
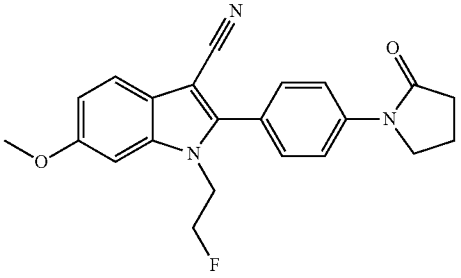
733
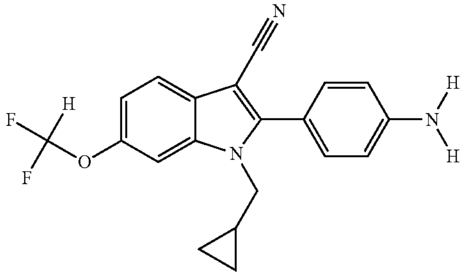
734
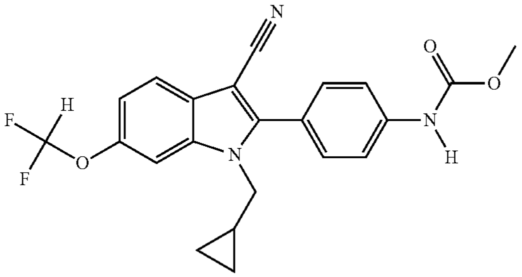
735
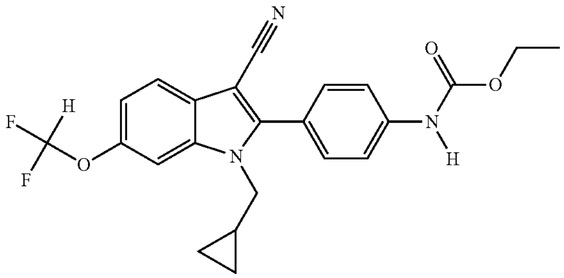
736
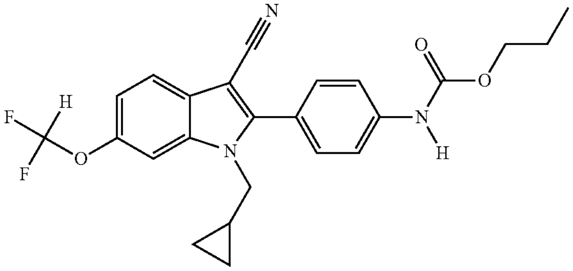

-continued
737
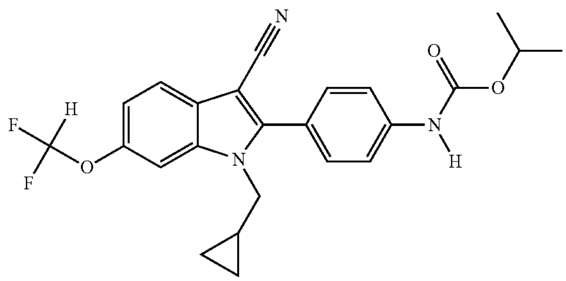
738
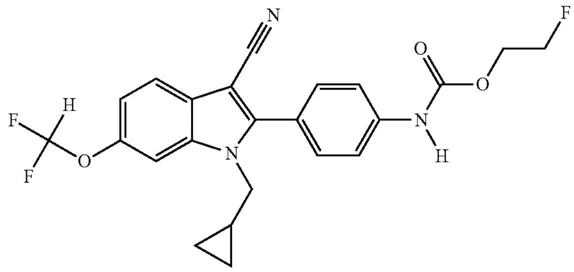
739
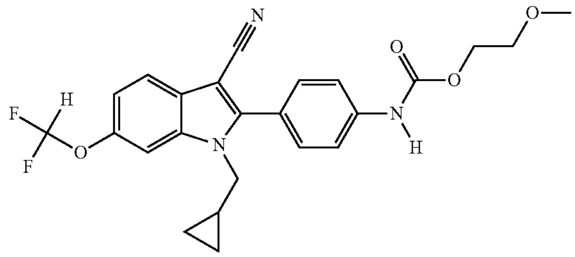
740
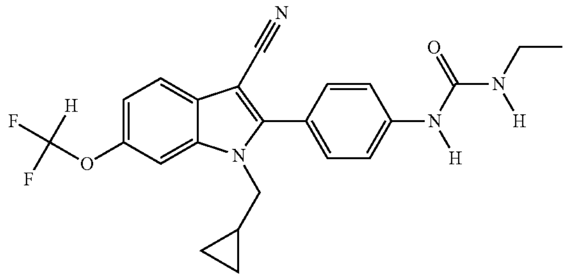
741
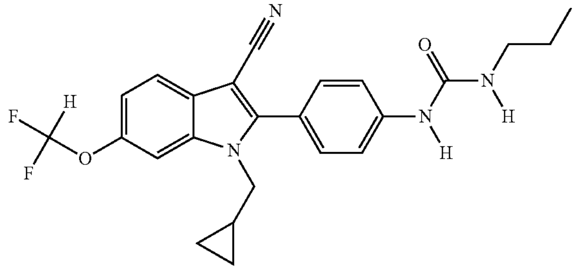
-continued
742
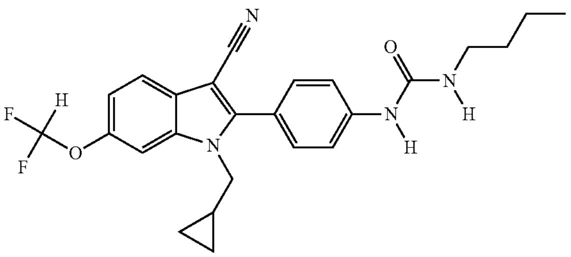
743
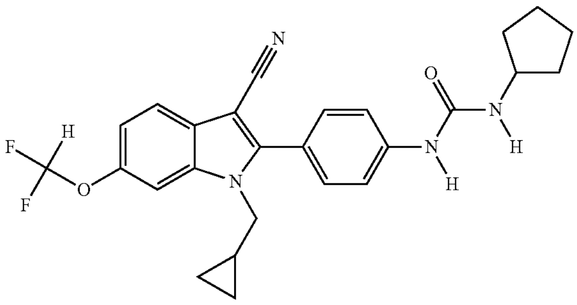
744
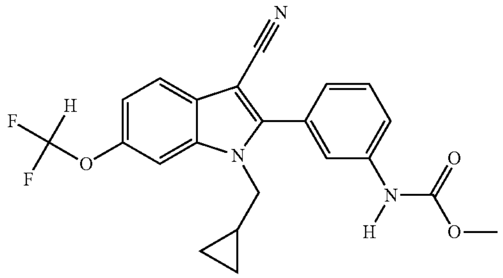
745
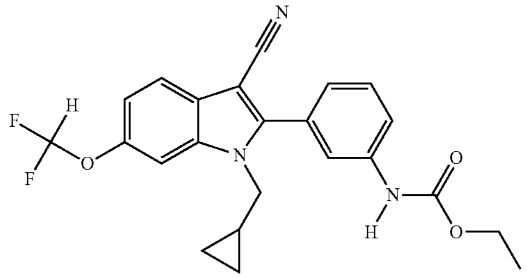
746
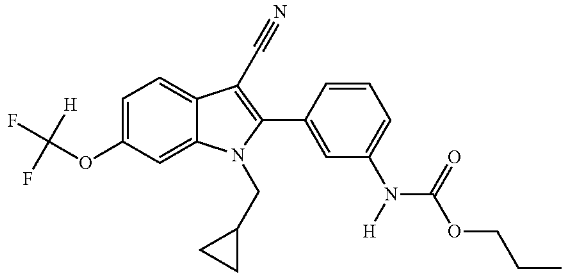

-continued
747
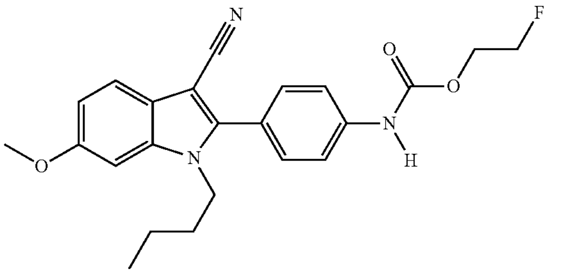
748
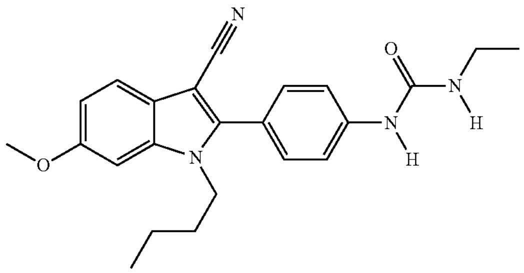
749
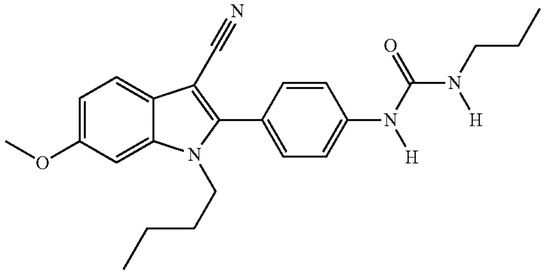
750
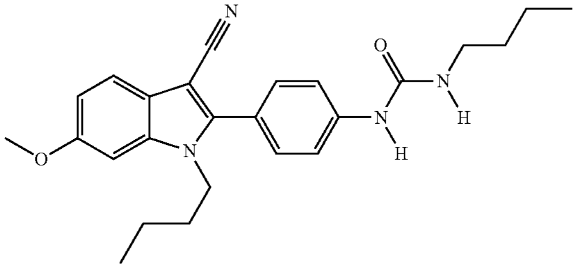
751
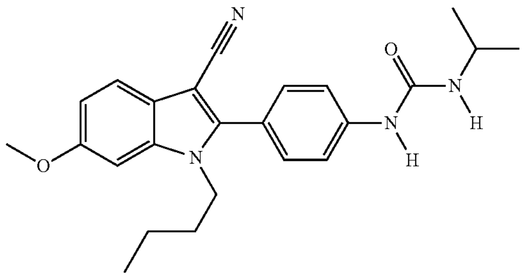
-continued
752
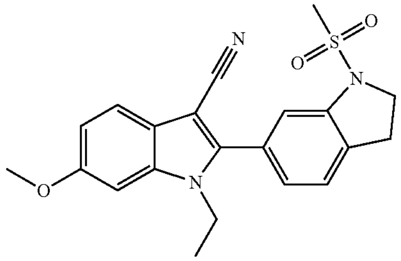
753
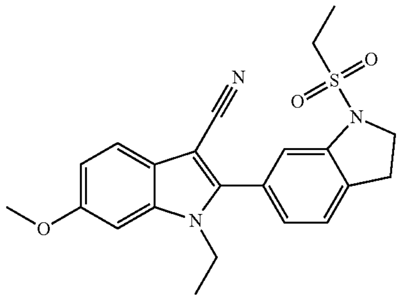
754
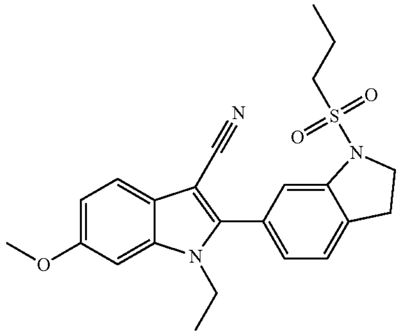
755
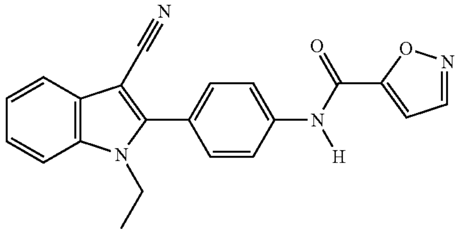
756
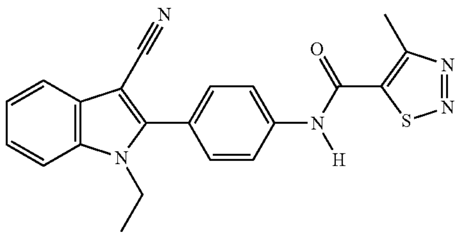
757
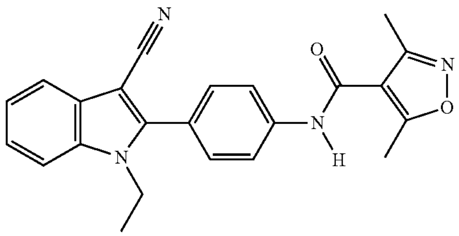

-continued
758
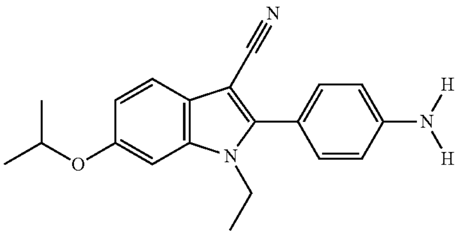
759
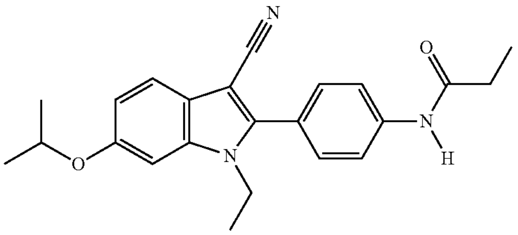
760
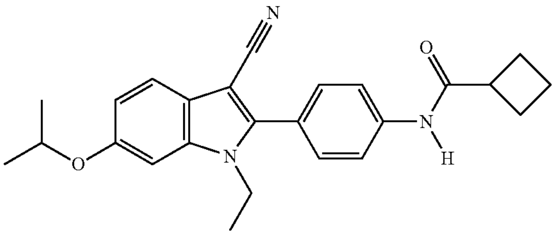
761
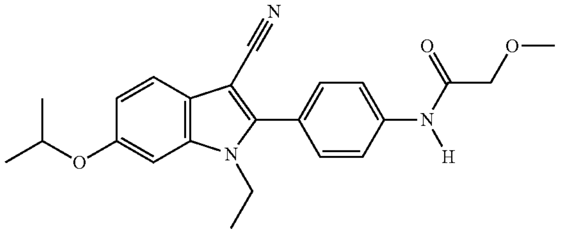
762
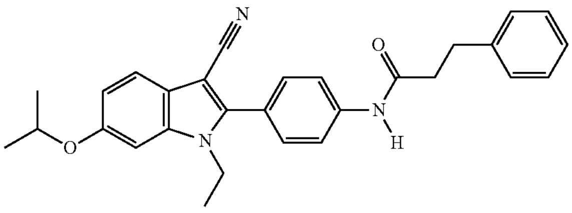
763
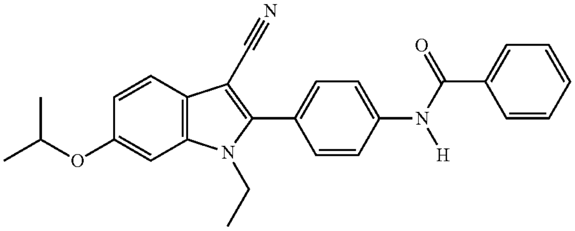
-continued
764
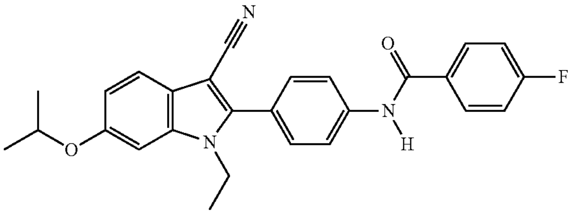
765
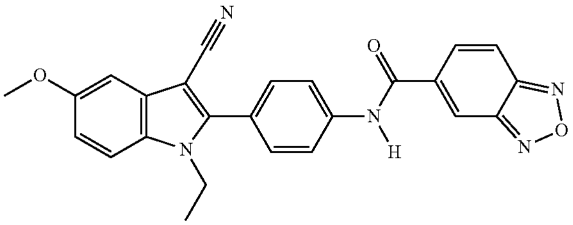
766
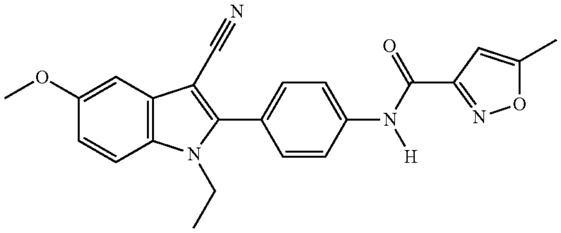
767
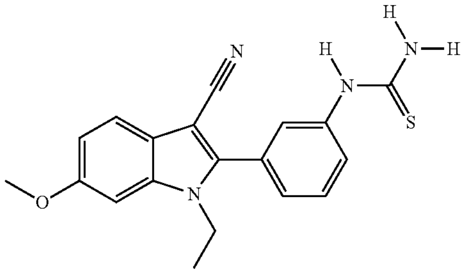
768
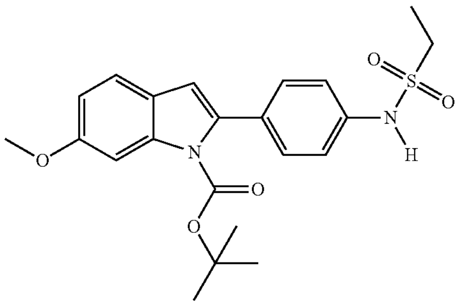
769
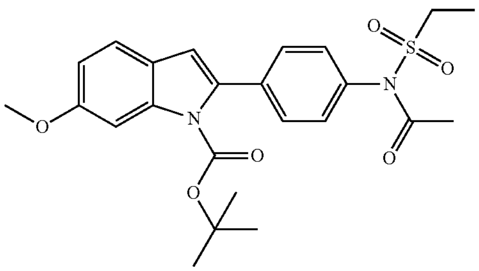

-continued
770
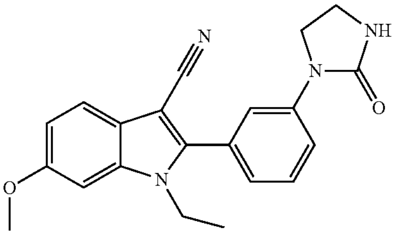
771
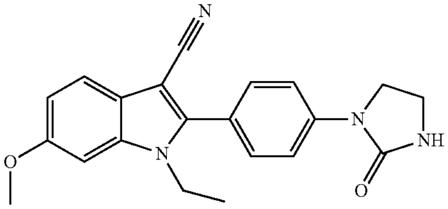
772
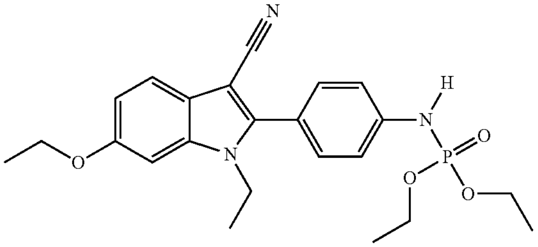
773
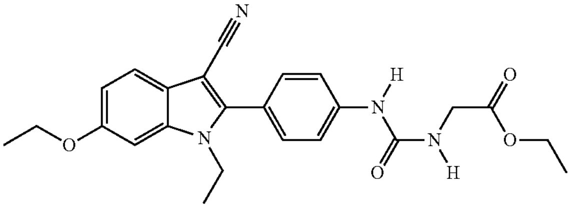
774
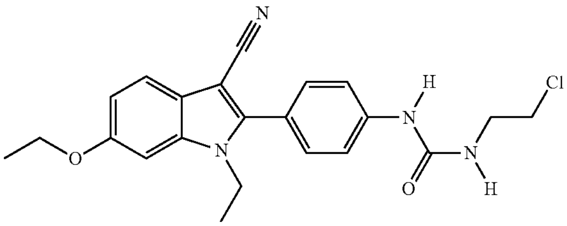
775
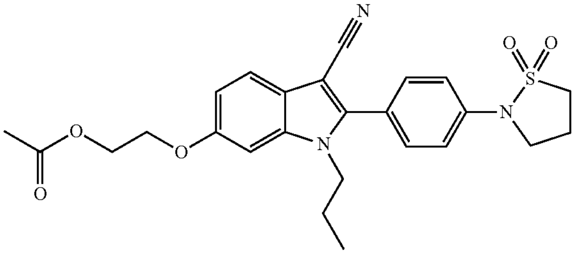
-continued
776
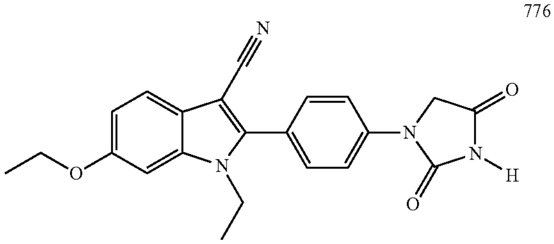
777
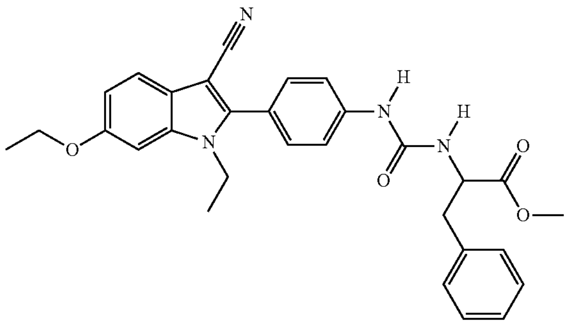
778
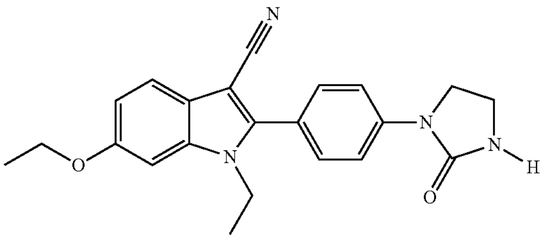
779
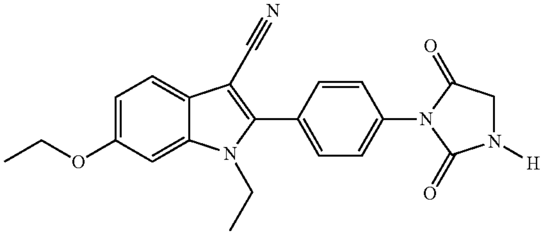
780
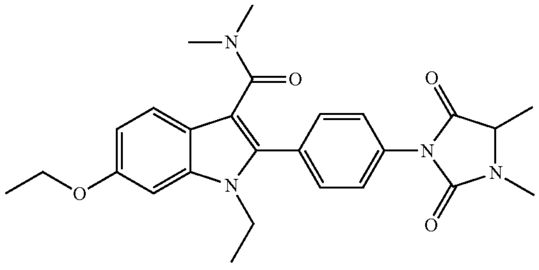

-continued
781
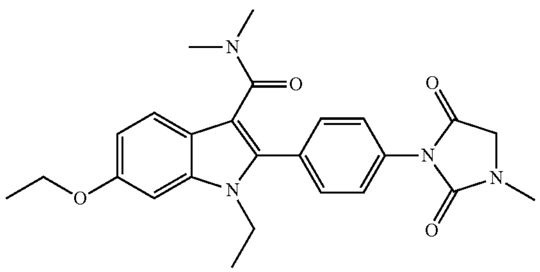
782
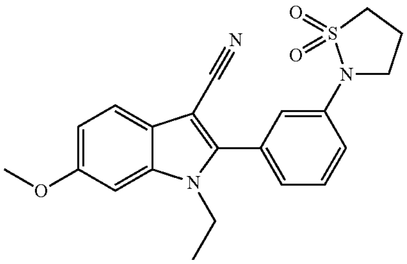
783
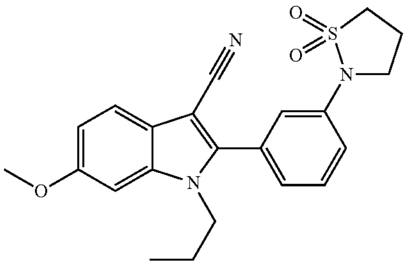
784
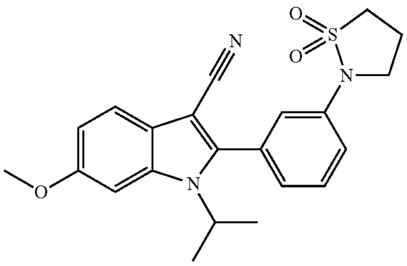
785
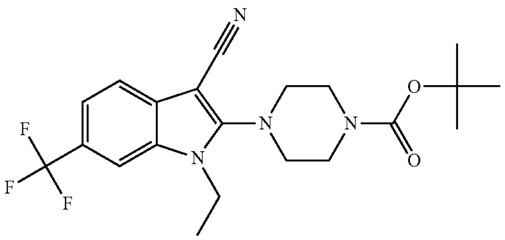
786
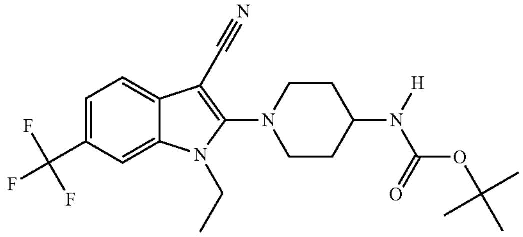
-continued
787
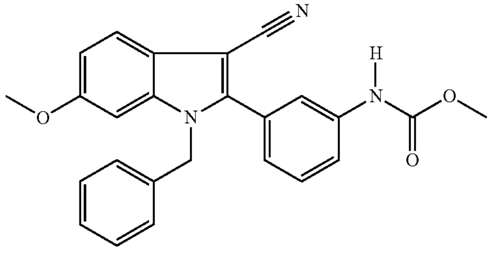
788
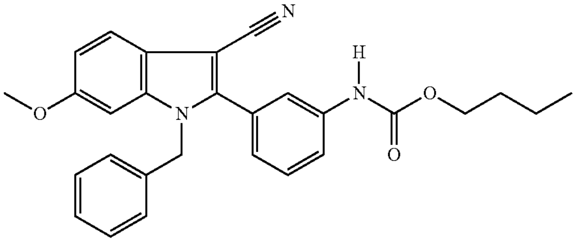
789
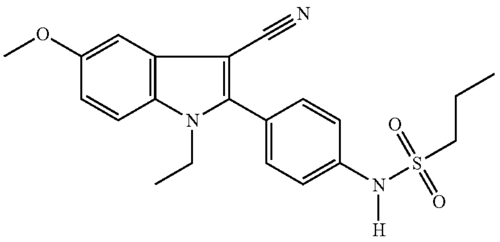
790
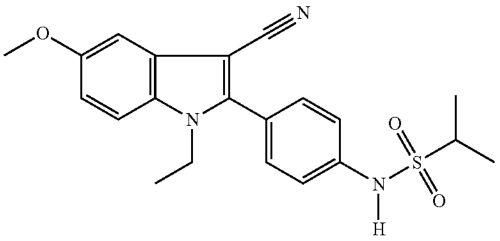
791
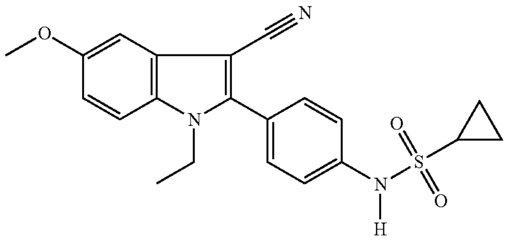
792
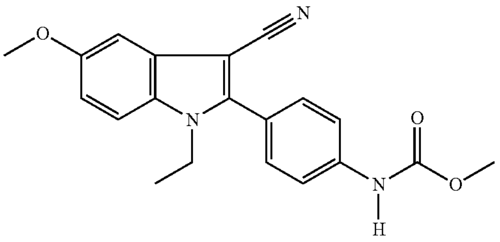

-continued
793
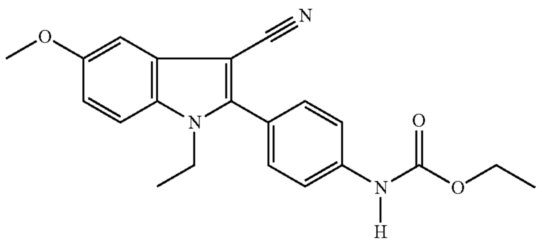
794
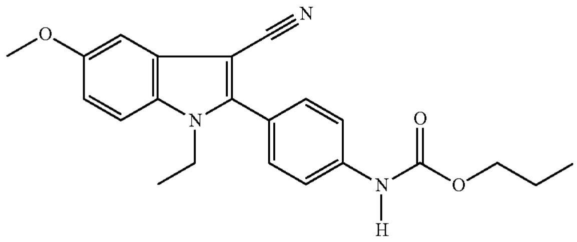
795
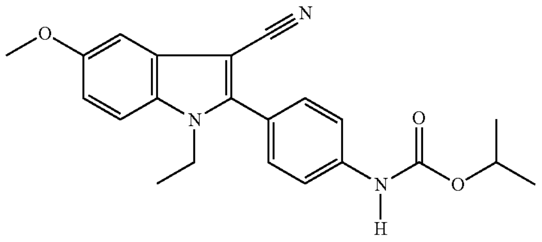
796
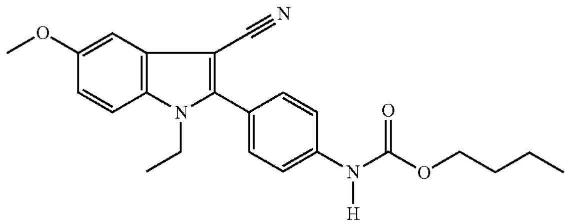
797
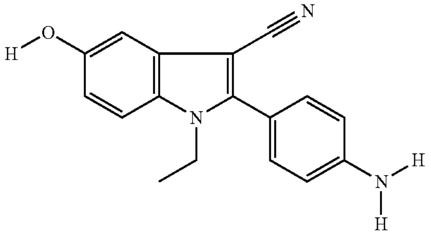
798
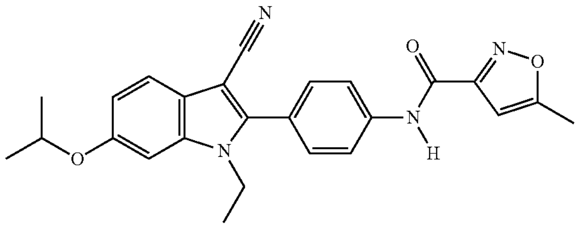
-continued
799
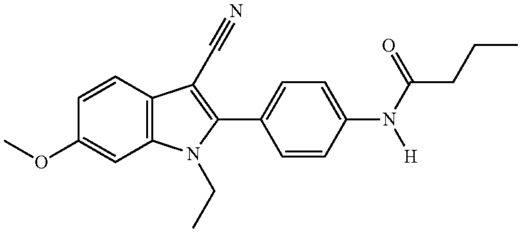
801
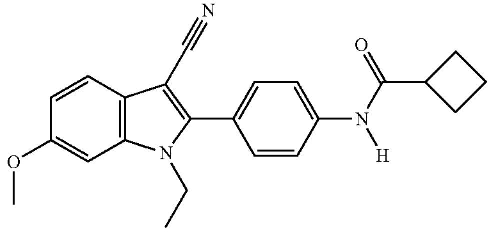
802
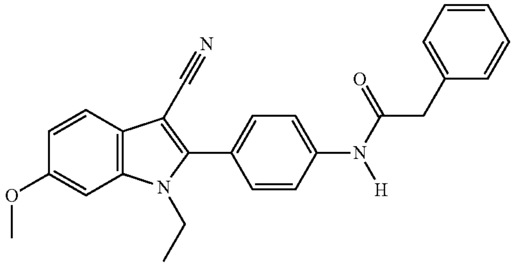
803
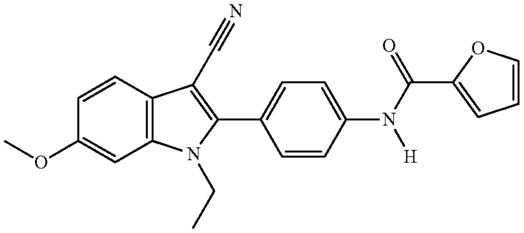
804
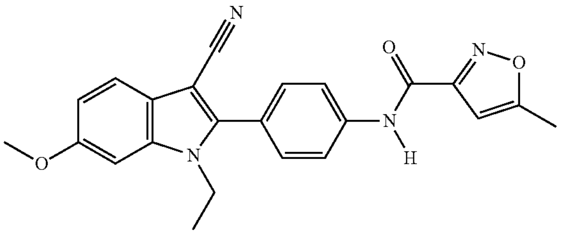
805
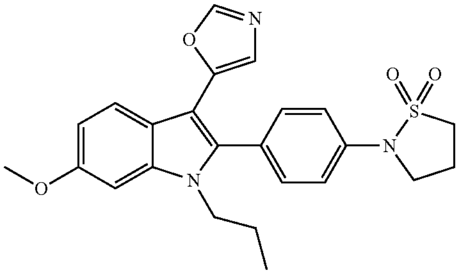

-continued
806
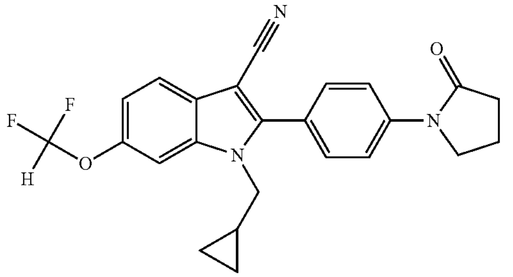
807
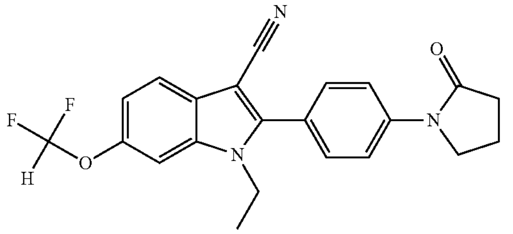
808
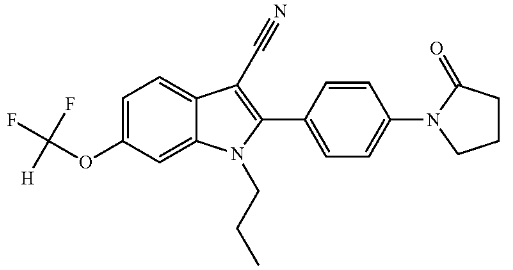
809
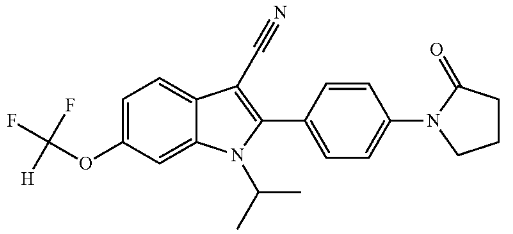
810
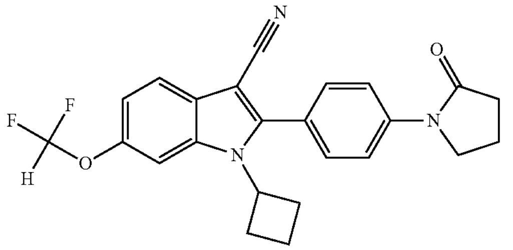
811
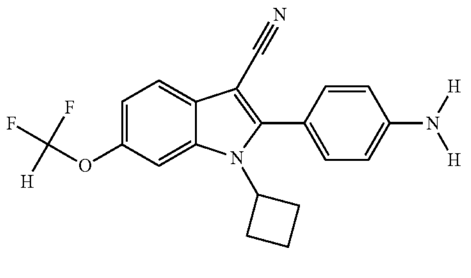
-continued
812
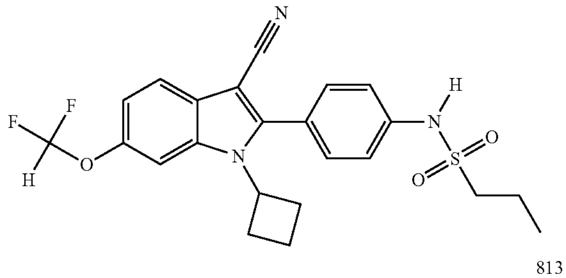
813
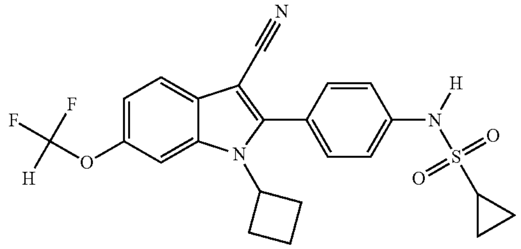
814
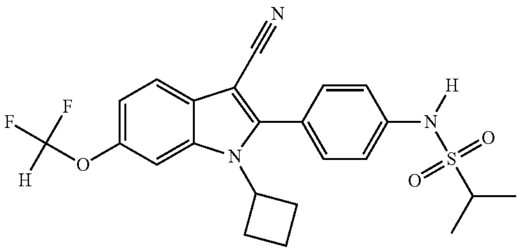
815
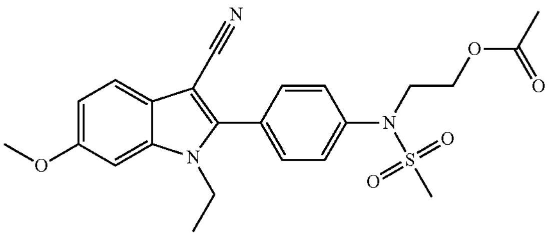
816
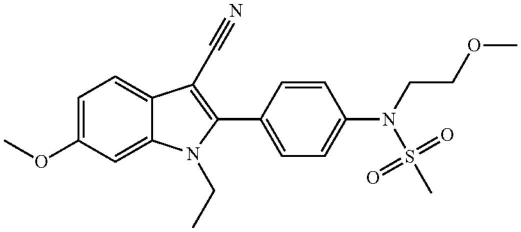
817
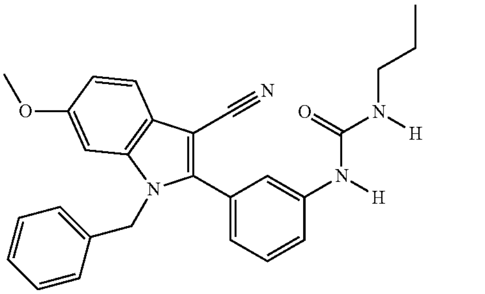

-continued
818
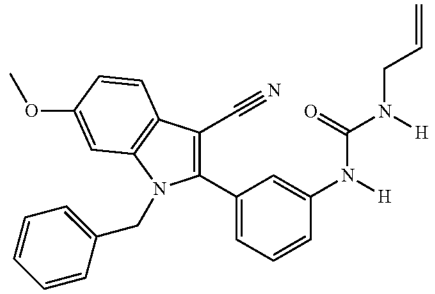
819
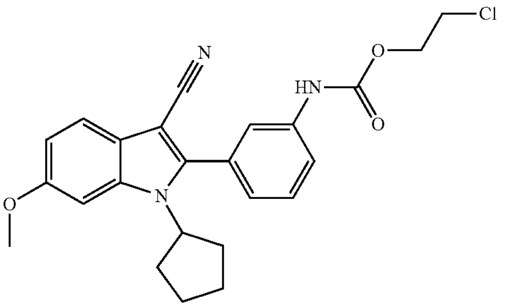
820
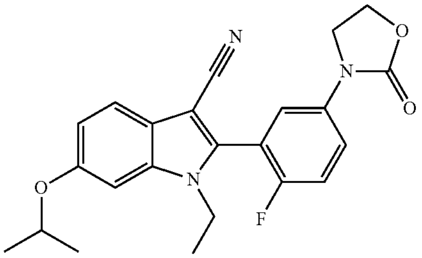
821
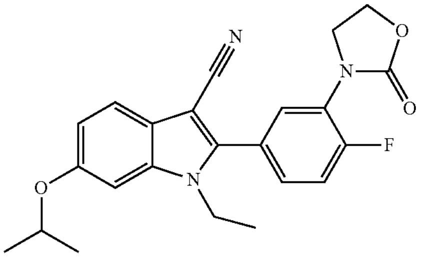
822
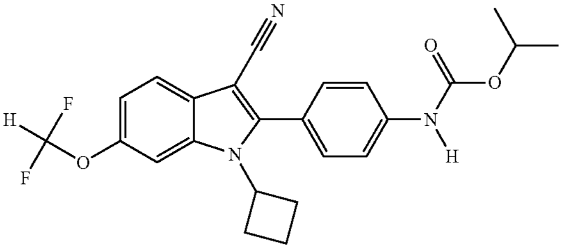
-continued
823
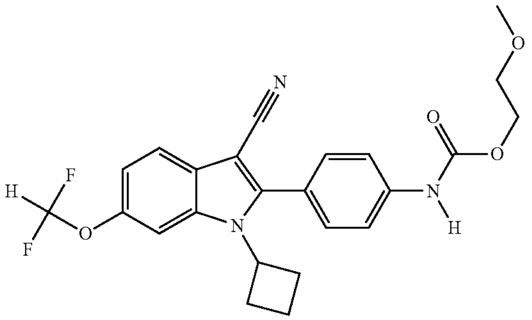
824
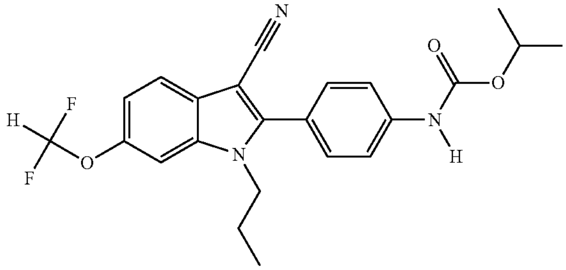
825
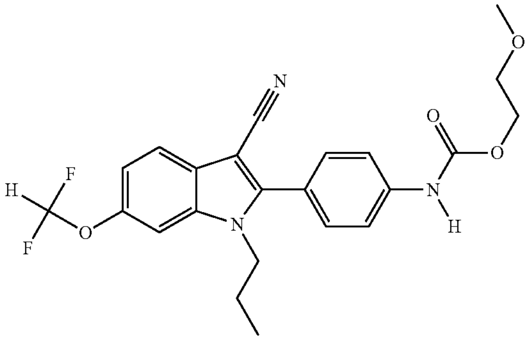
826
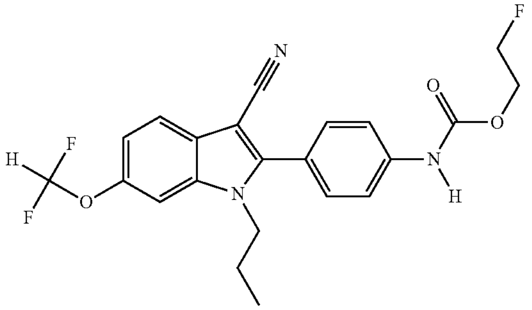
827
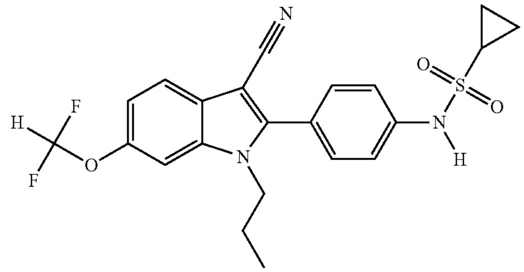

-continued
828
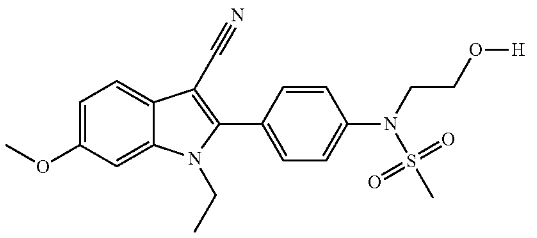
829
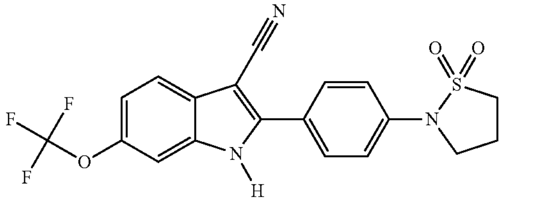
830
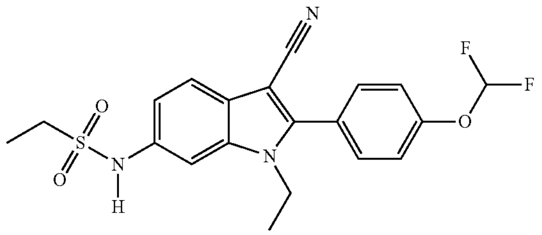
831
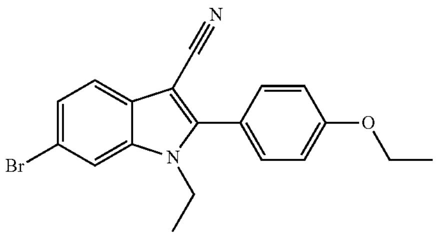
832
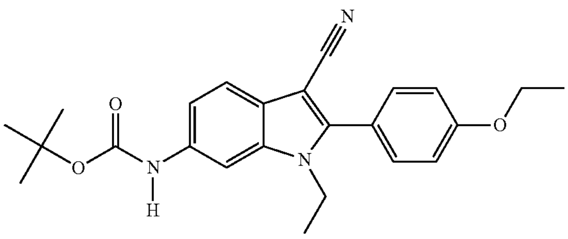
833
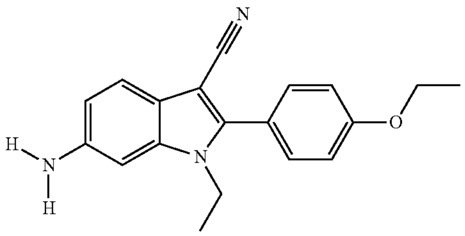
-continued
834
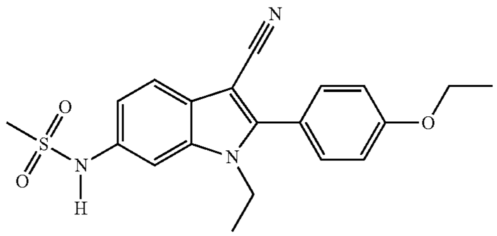
835
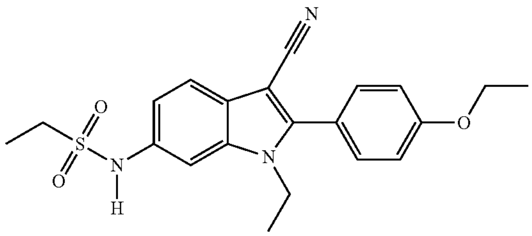
836
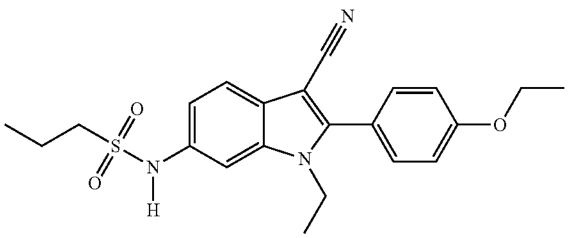
837
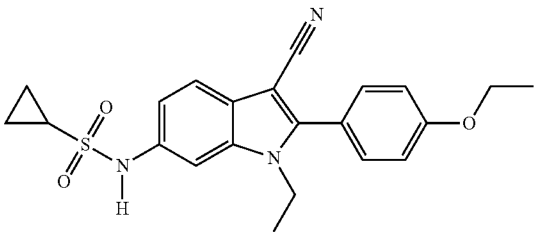
838
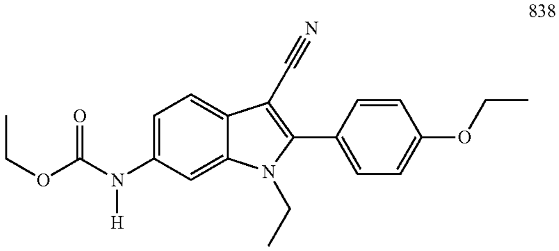
839
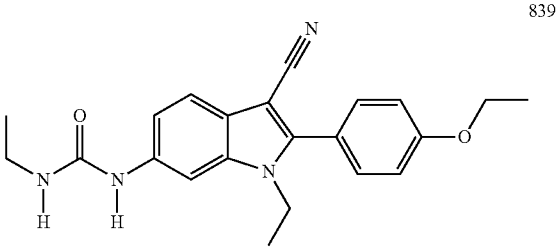

840
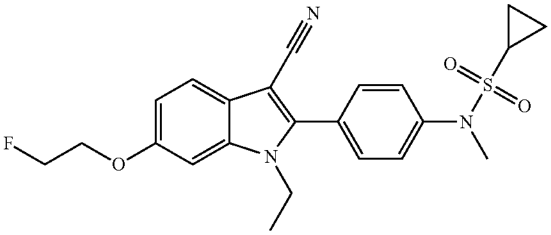
841
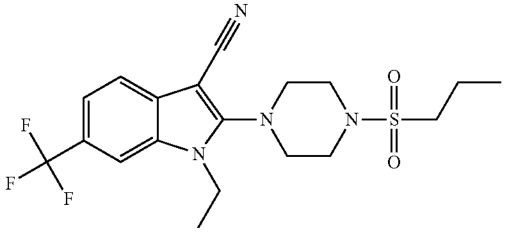
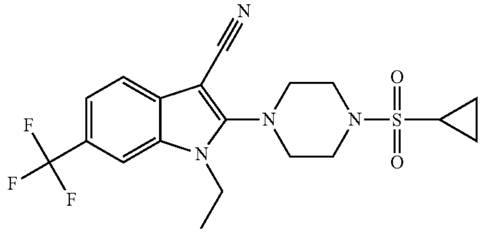
843
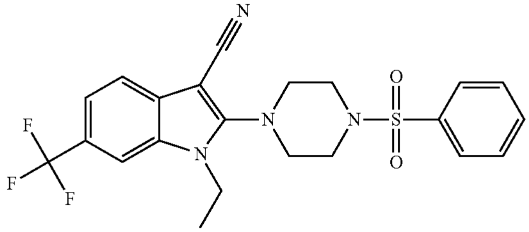
844
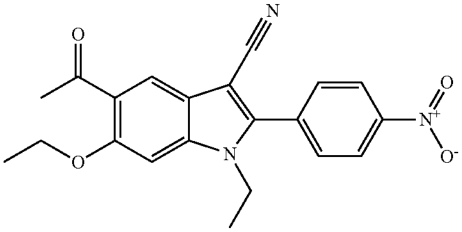
845
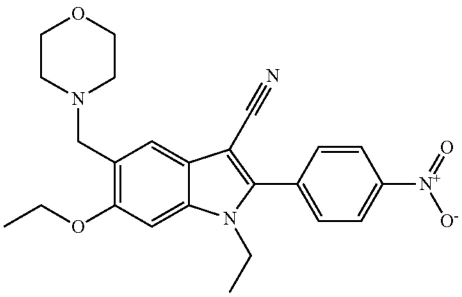
846
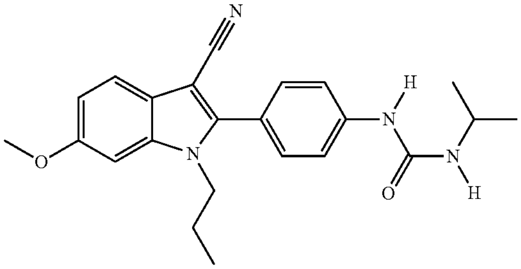
847
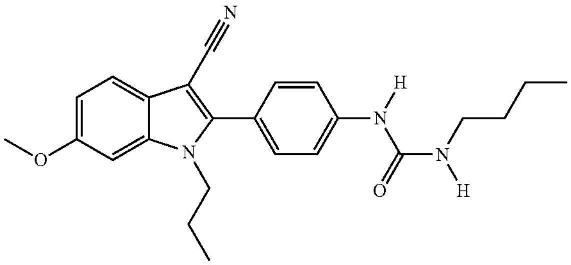
848
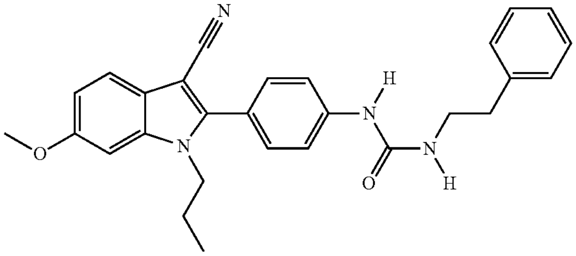
849
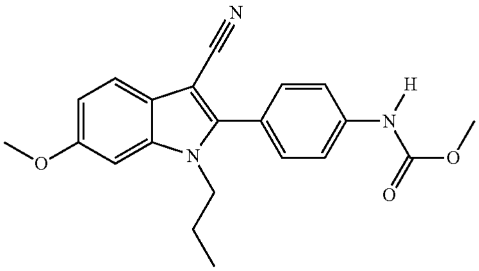
850
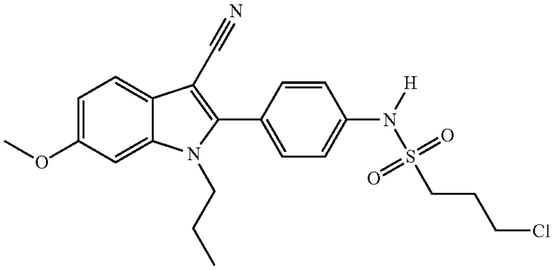

-continued
851
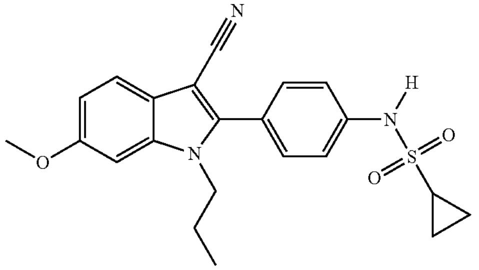
852
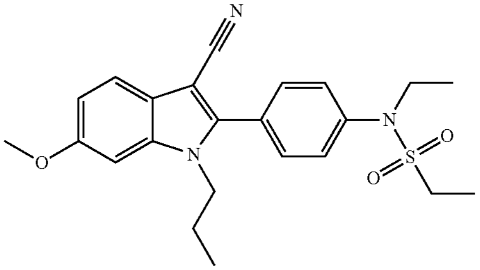
853
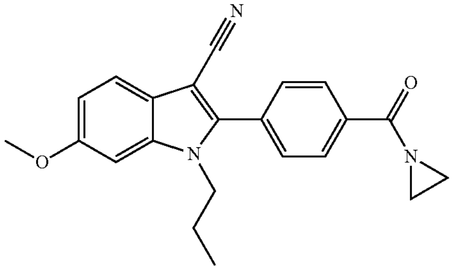
854
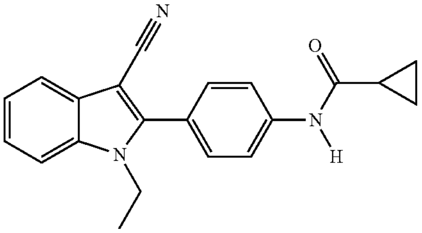
855
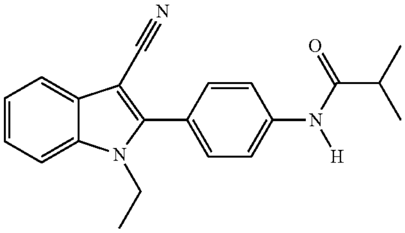
856
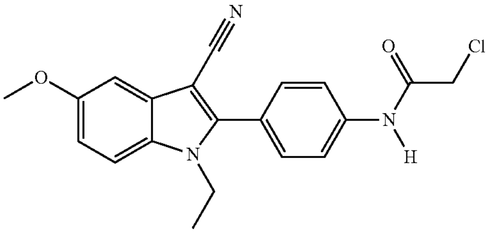
-continued
857
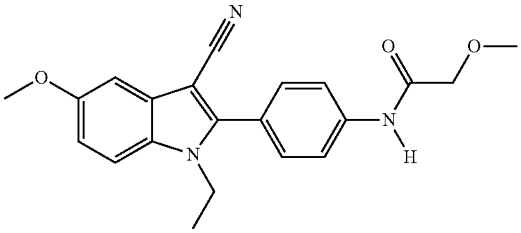
858
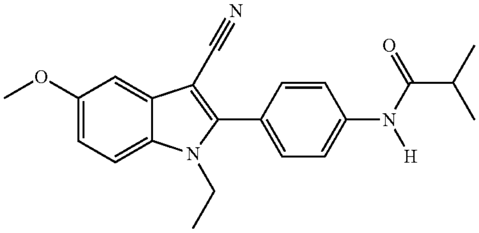
859
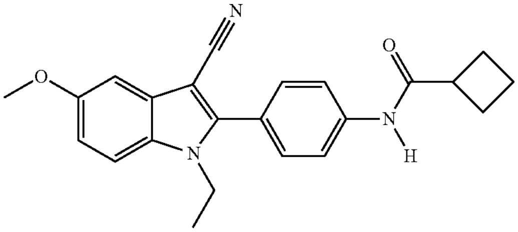
860
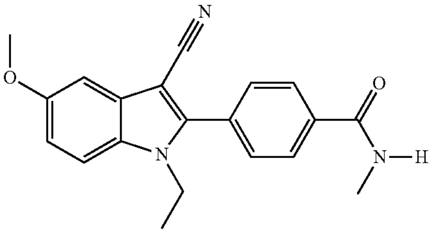
861
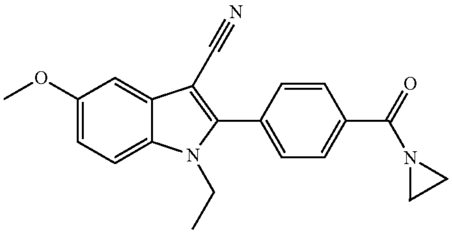
862
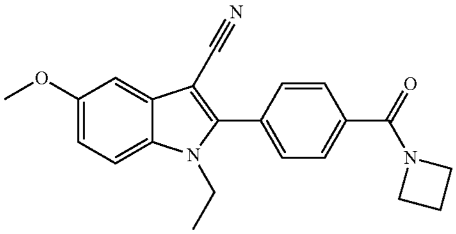

-continued
863
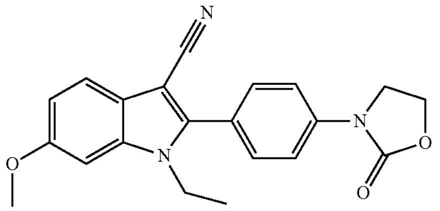
864
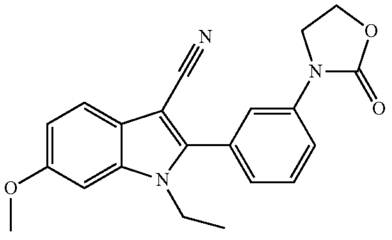
-continued
865
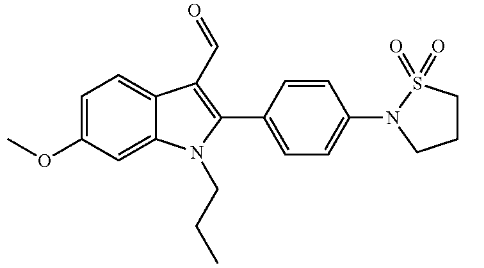
The above compounds were prepared using the schemes and examples set forth below. Other methods of producing these compounds are known to one of skill in the art.
Preferred compounds include the following compounds in Table A:
TABLE A
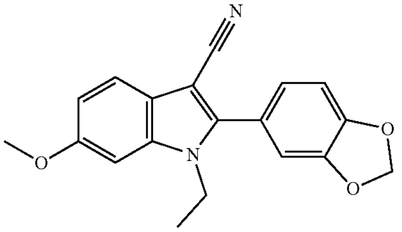
22
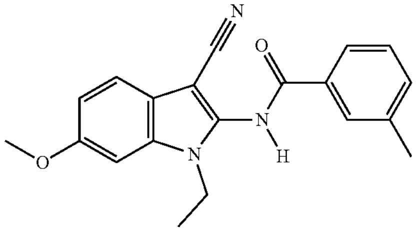
23
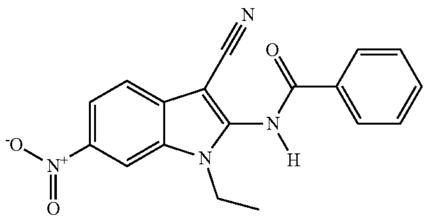
26

TABLE A-continued
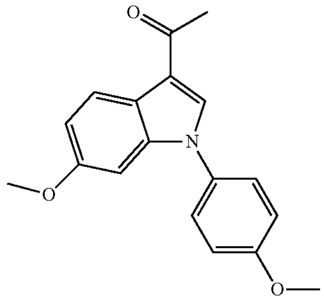
48
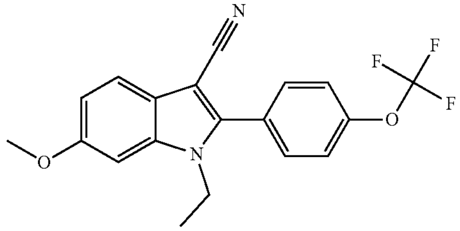
53
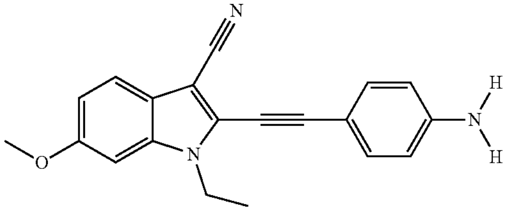
69
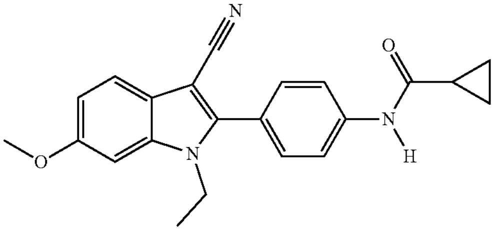
81
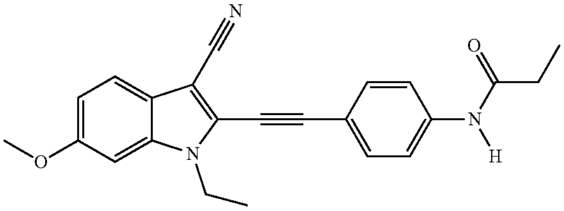
82

TABLE A-continued
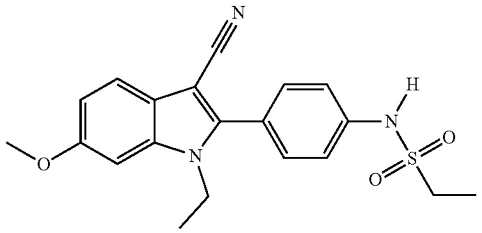
83
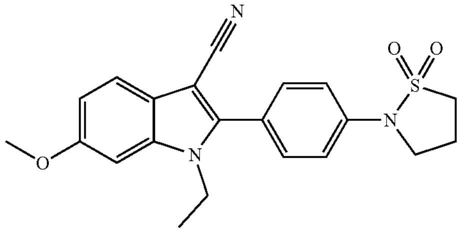
84
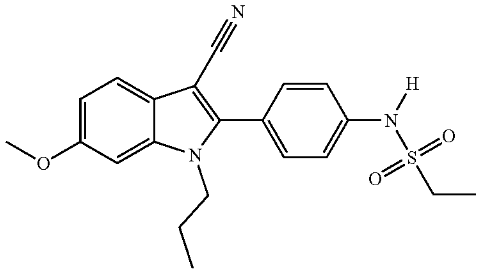
85
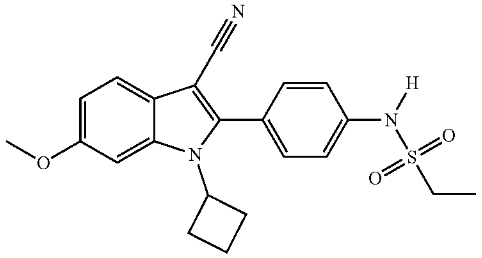
86
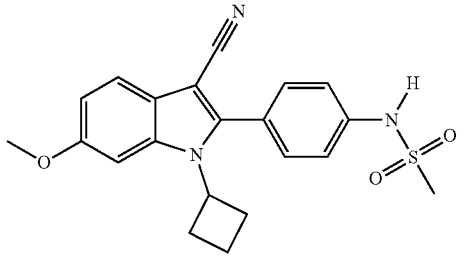
87

TABLE A-continued
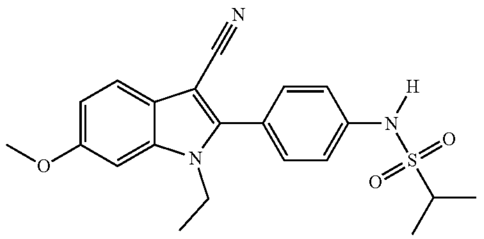
88
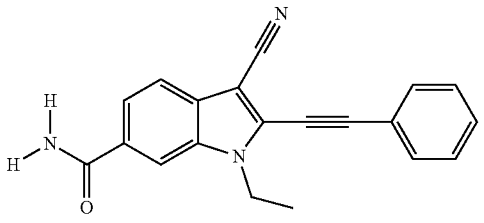
94
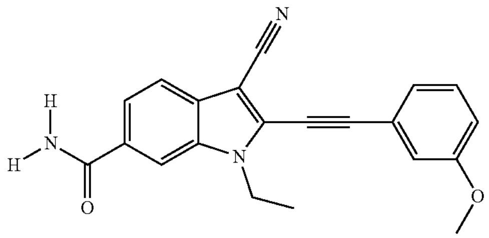
95
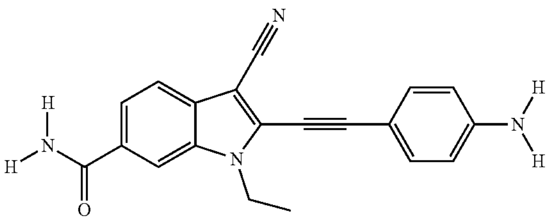
96
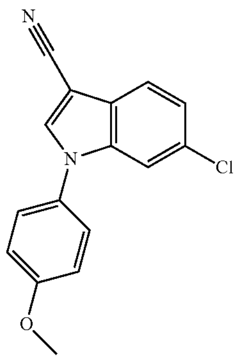
119

TABLE A-continued
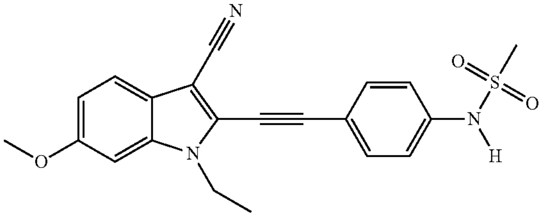
130
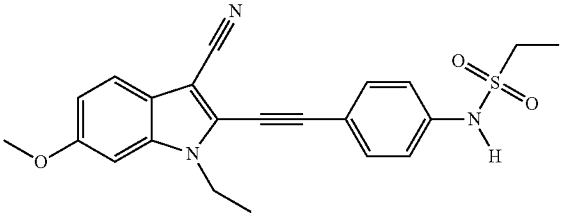
131
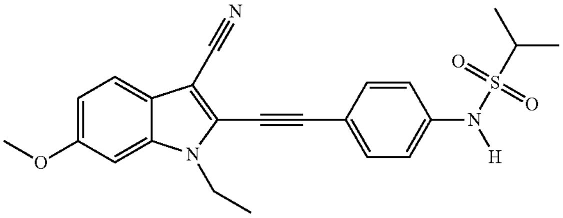
132
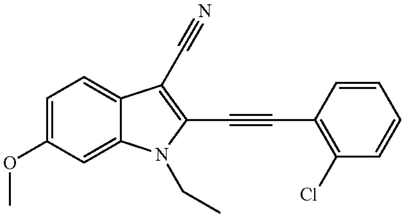
134
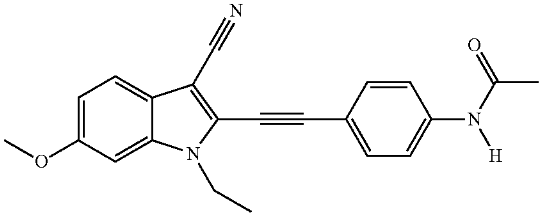
138
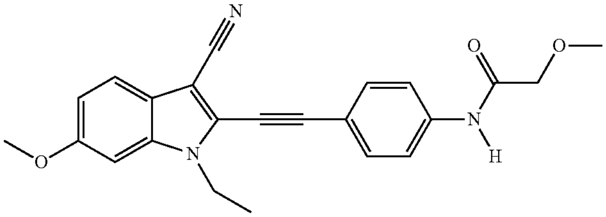
139

TABLE A-continued
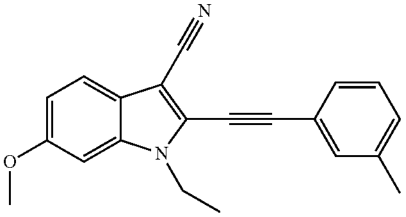
144
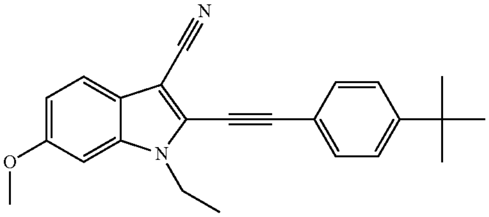
145
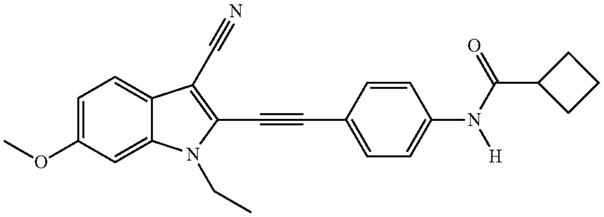
153
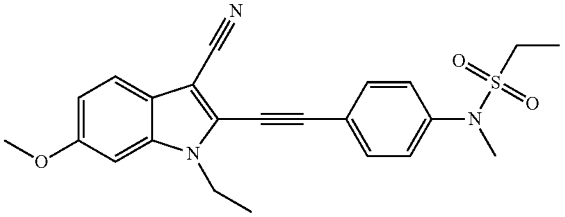
157
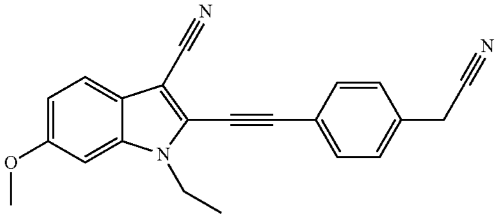
161
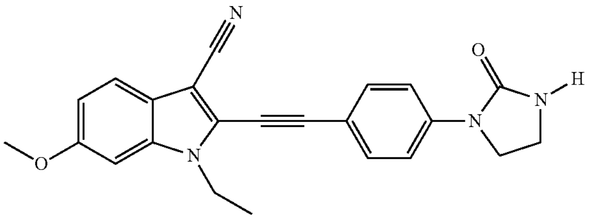
166

TABLE A-continued
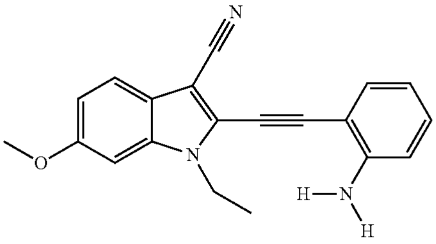
169
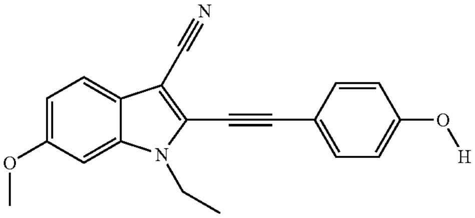
172
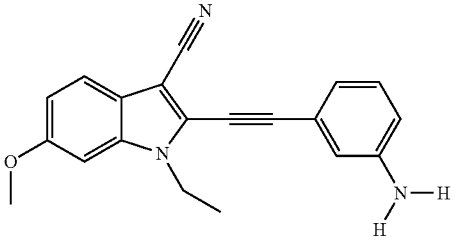
173
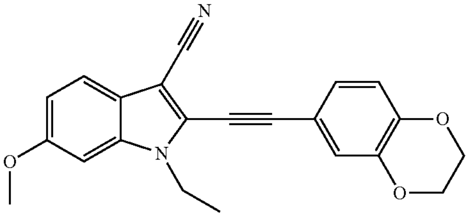
175
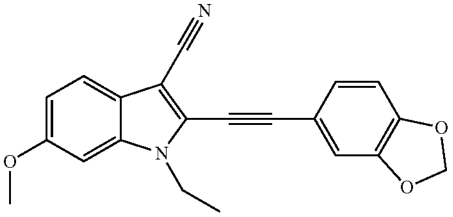
176

TABLE A-continued
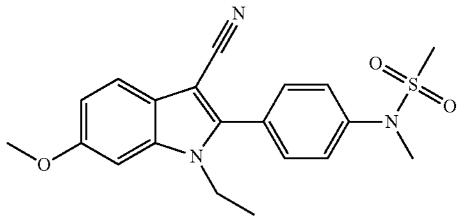
180
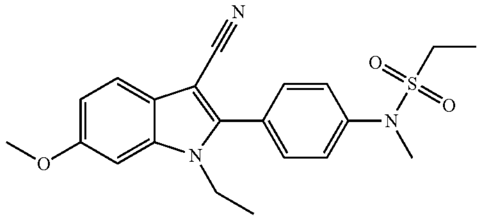
181
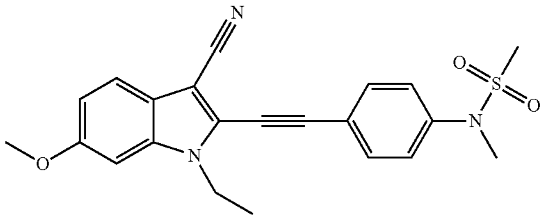
182
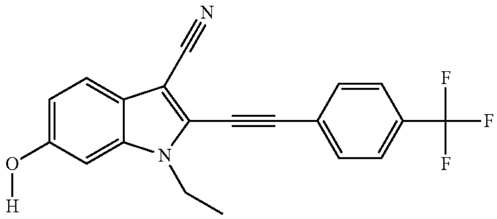
185
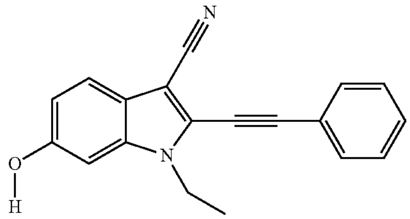
188
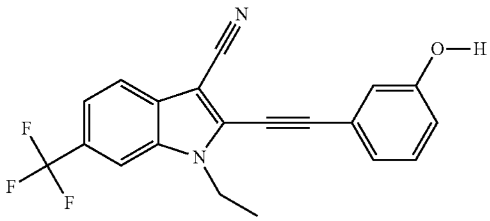
196

TABLE A-continued
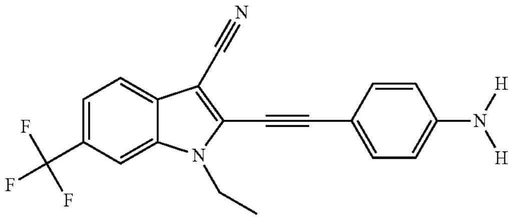
200
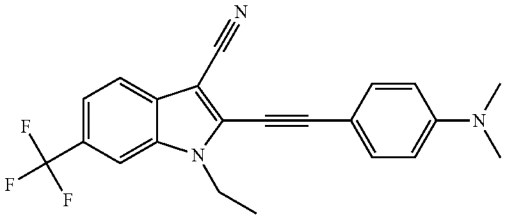
201
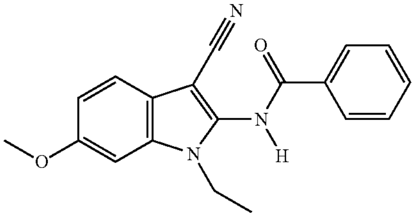
204
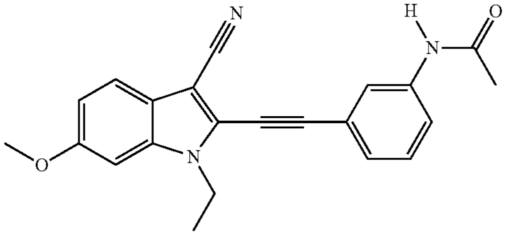
205
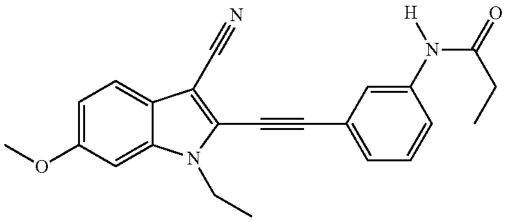
206
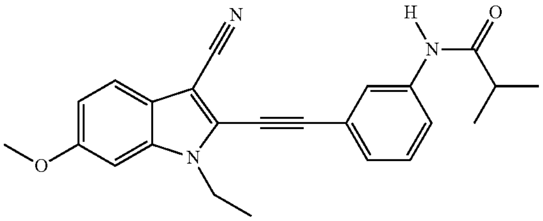
207

TABLE A-continued
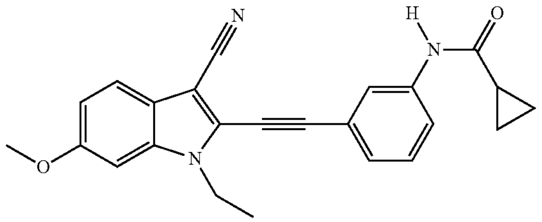
211
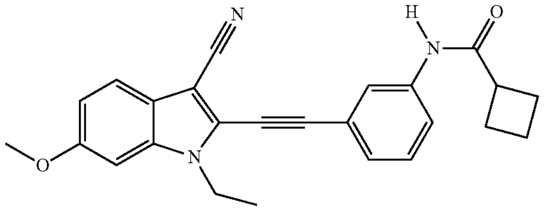
213
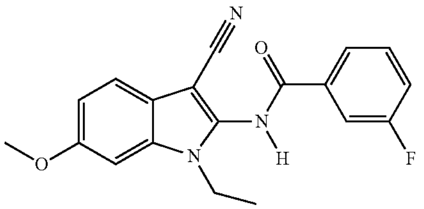
214
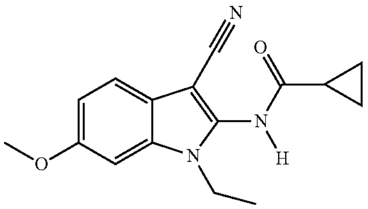
216
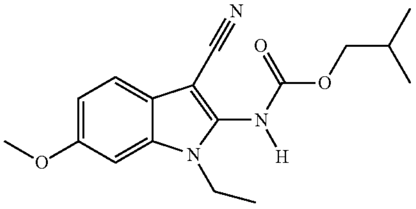
217
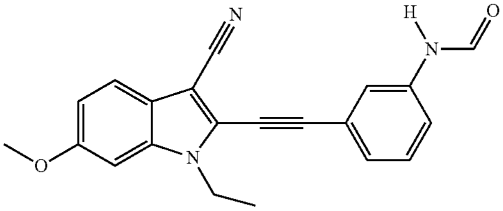
218

TABLE A-continued
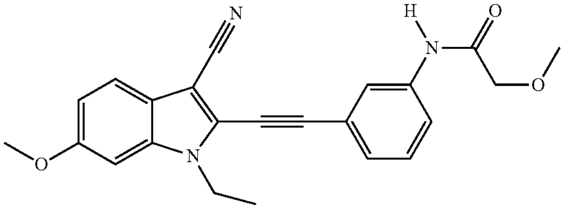
219
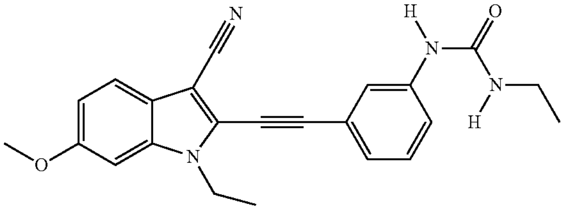
220
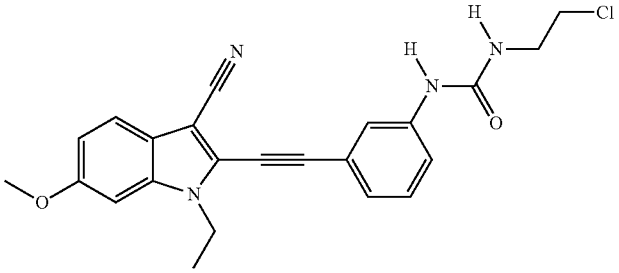
221
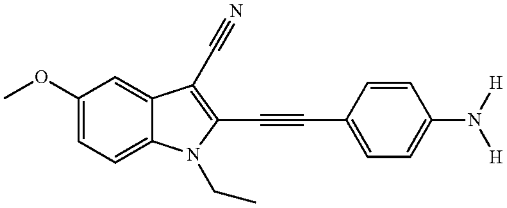
223
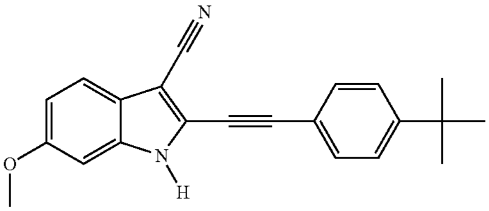
233
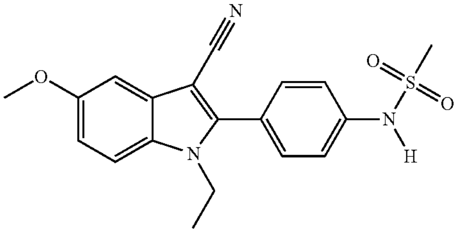
243

TABLE A-continued
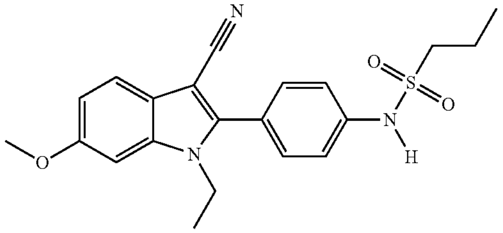
251
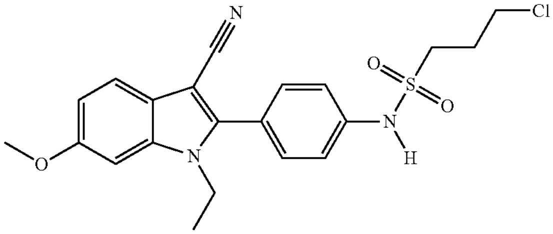
252
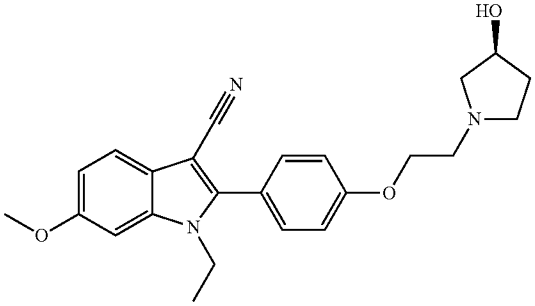
264
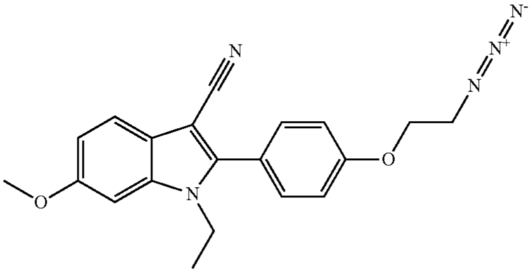
266
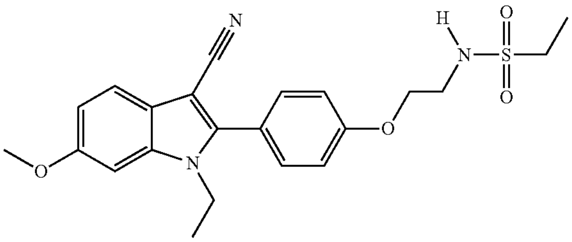
269

TABLE A-continued
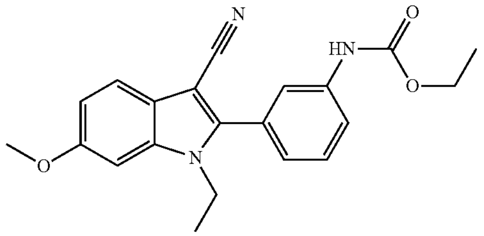
294
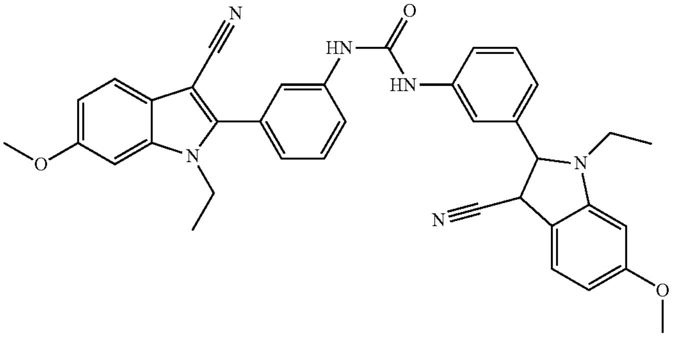
295
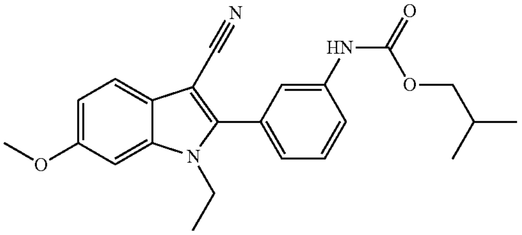
296
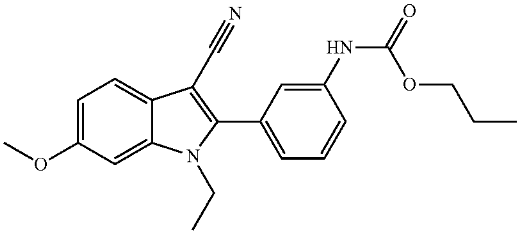
297
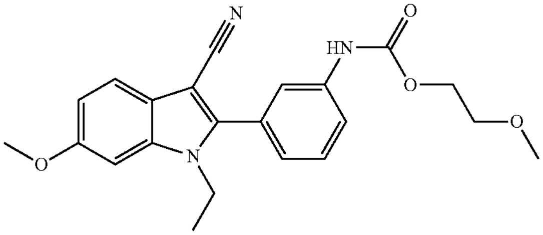
298

TABLE A-continued
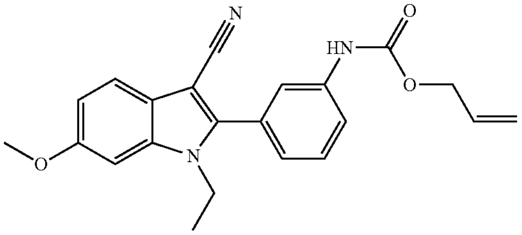
299
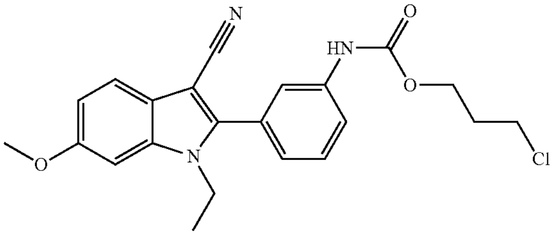
301
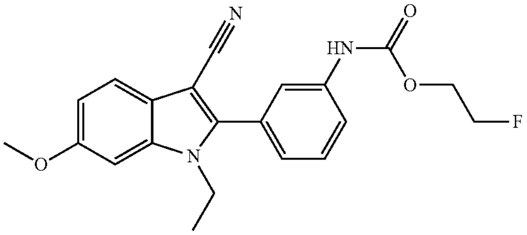
302
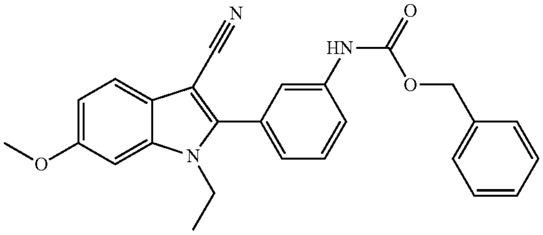
304
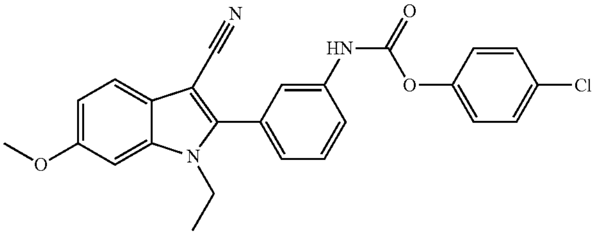
306

TABLE A-continued
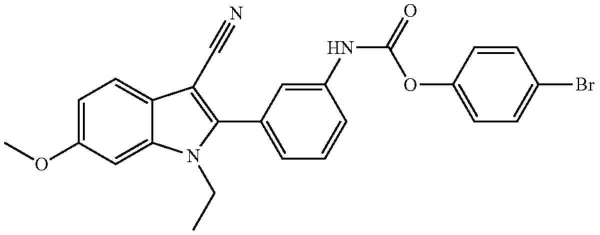
309
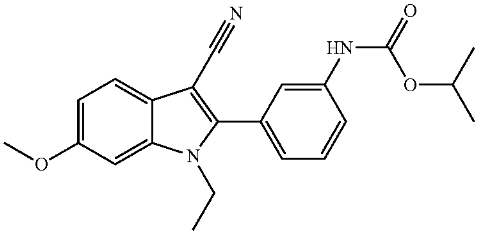
310
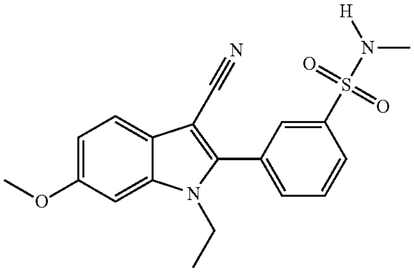
331
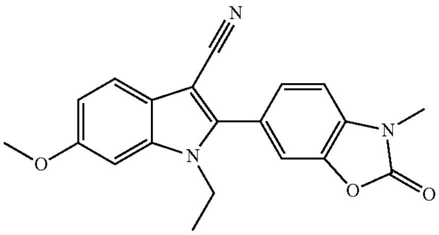
341
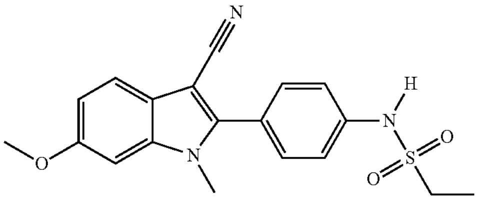
345

TABLE A-continued
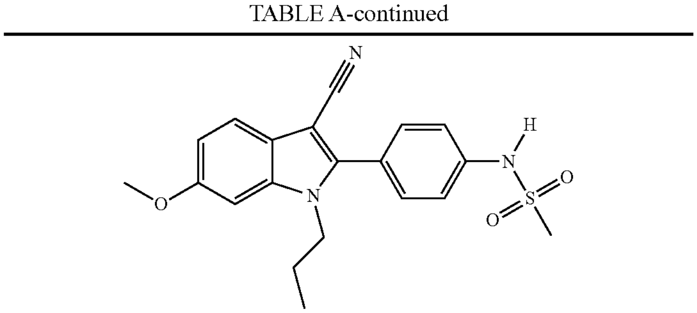
346
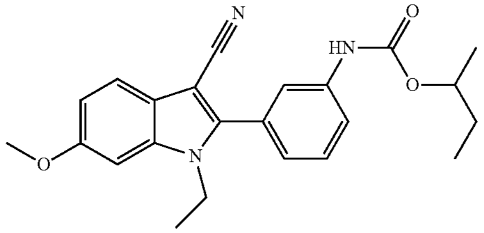
349
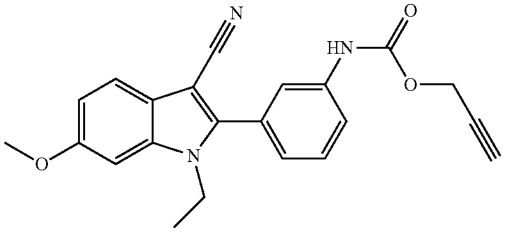
350
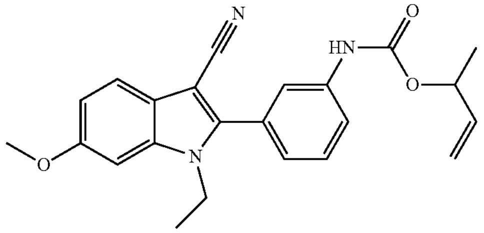
351
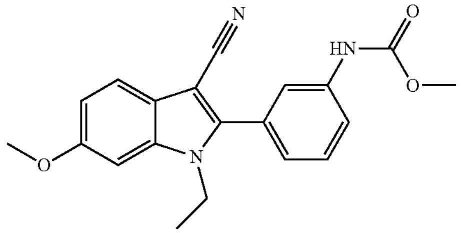
353

TABLE A-continued
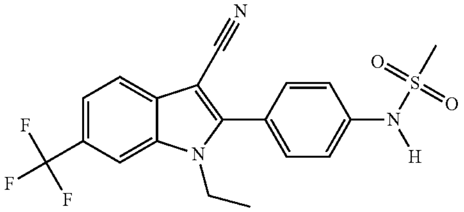
365
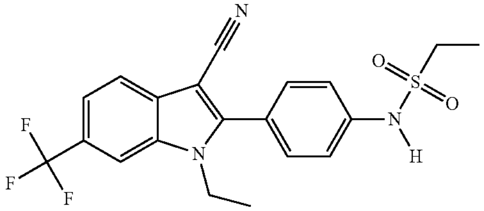
366
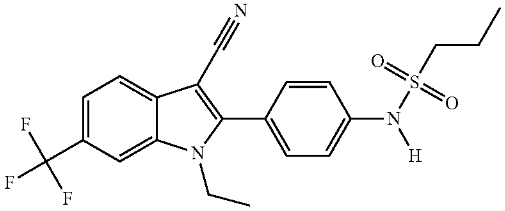
367
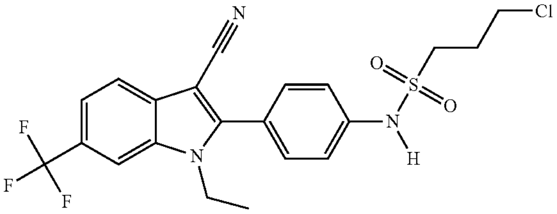
369
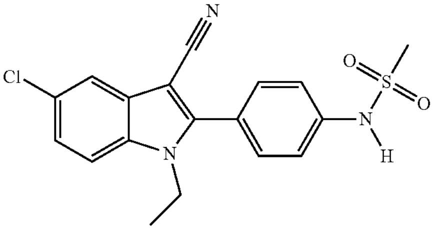
394

TABLE A-continued
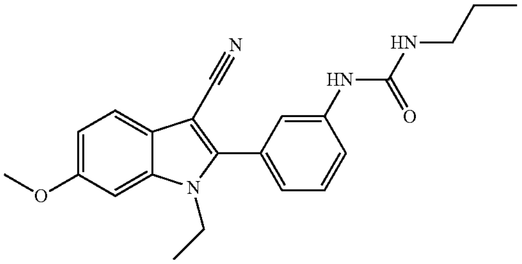
396
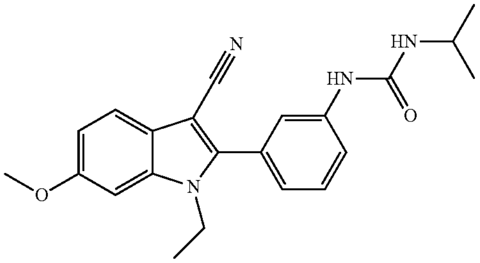
397
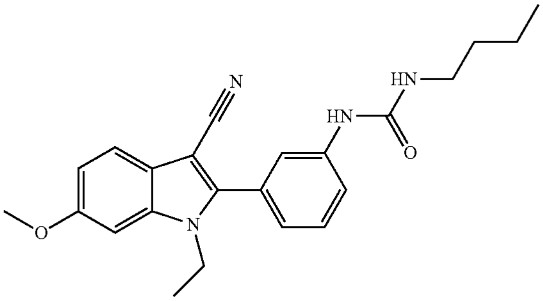
398
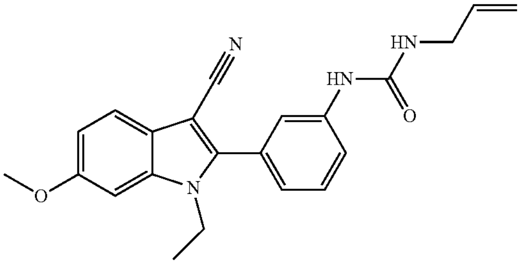
399
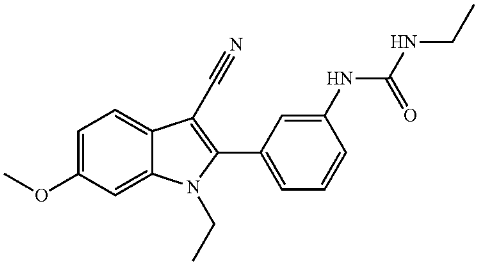
401

TABLE A-continued
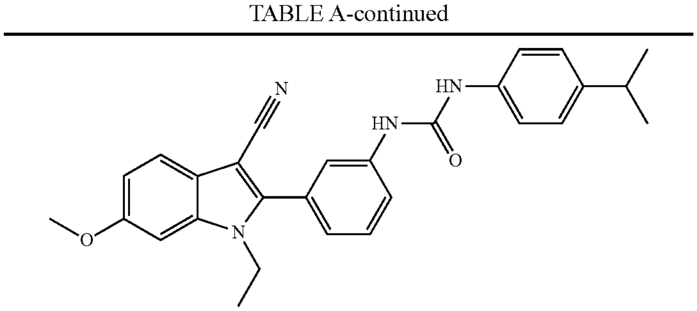
403
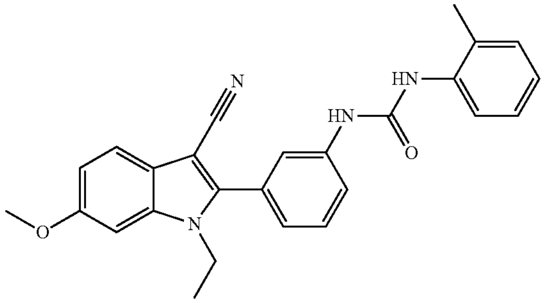
405
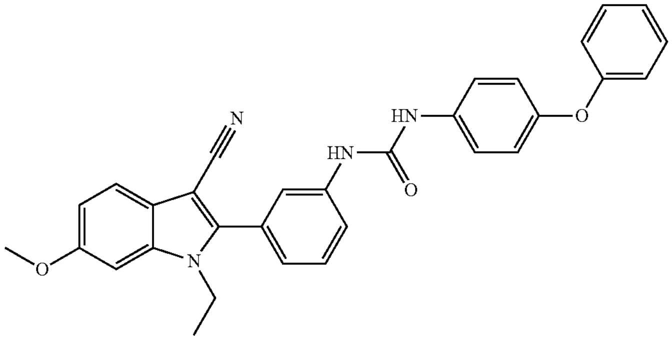
406
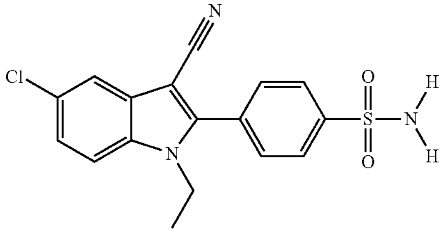
408
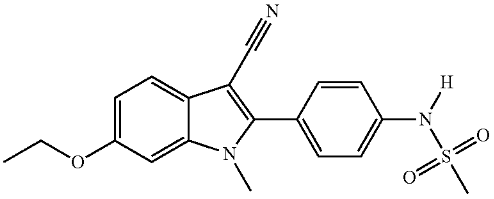
413

TABLE A-continued
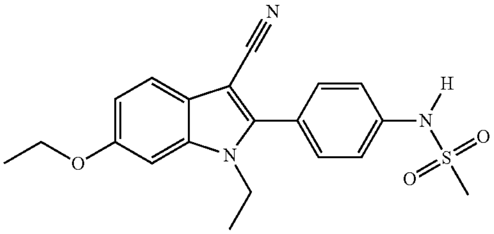
415
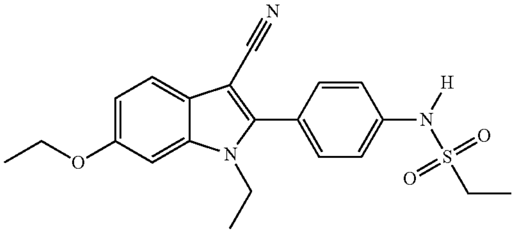
416
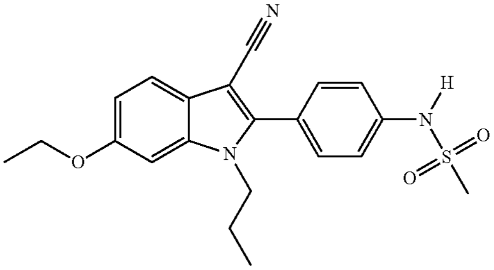
417
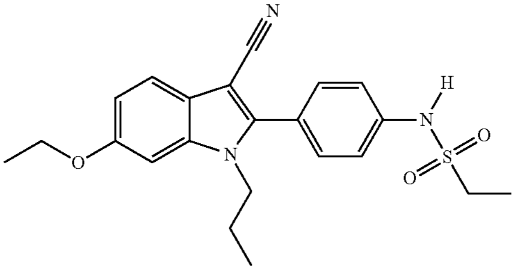
418
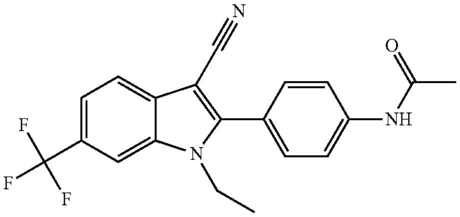
420

TABLE A-continued
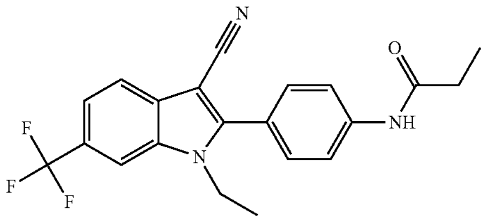
422
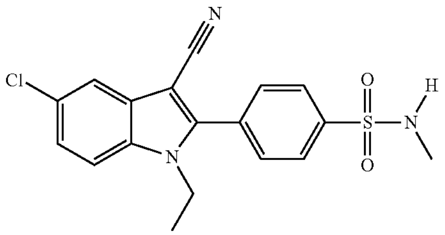
430
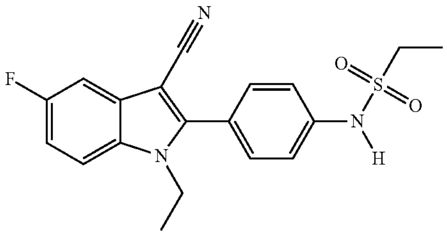
440
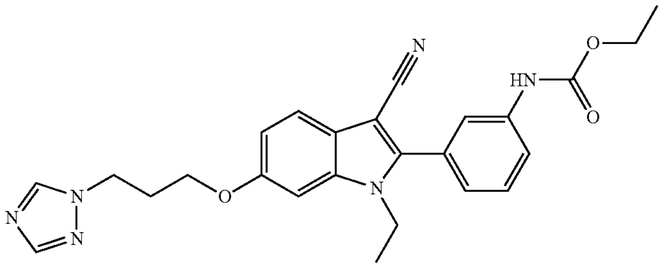
441
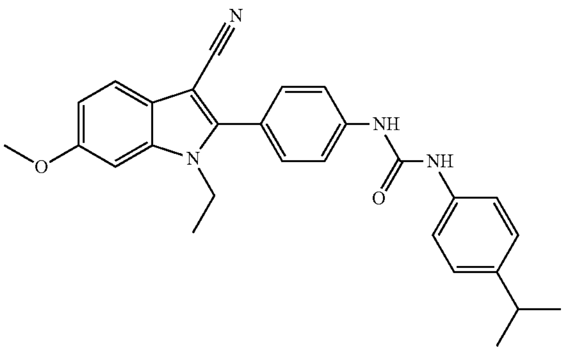
445

TABLE A-continued
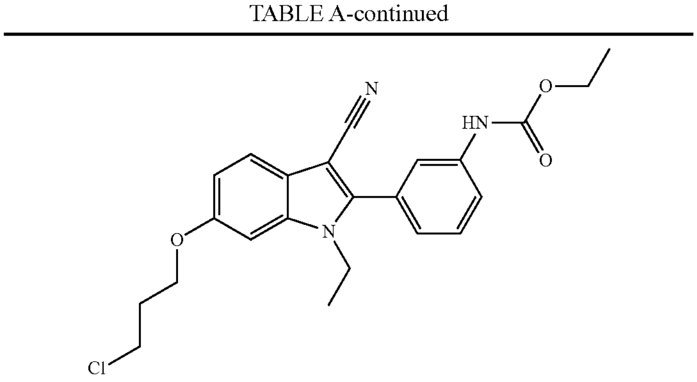
447
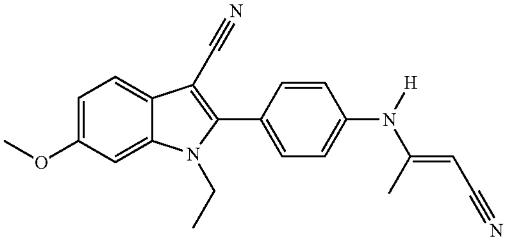
456
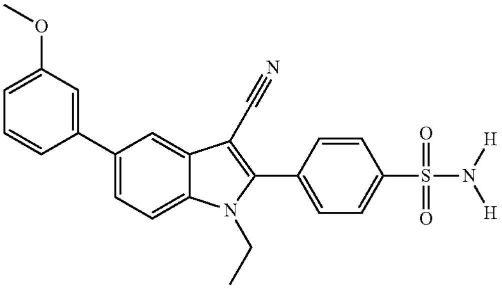
461
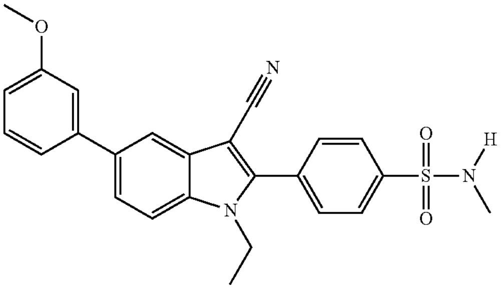
462
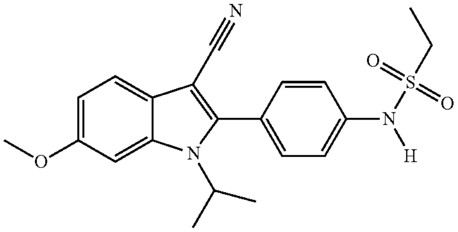
468

TABLE A-continued
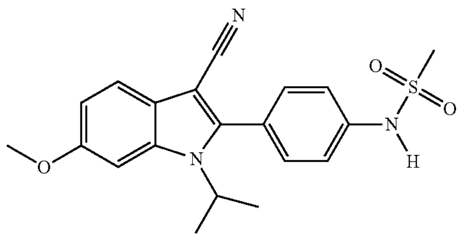
469
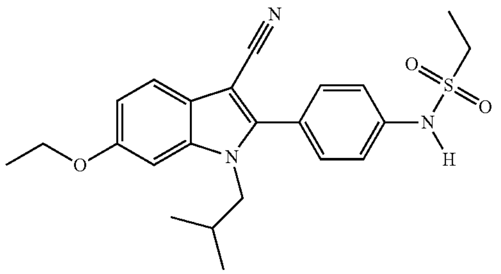
470
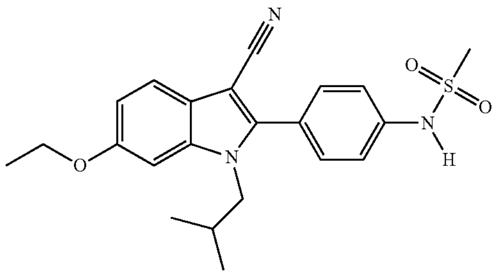
471
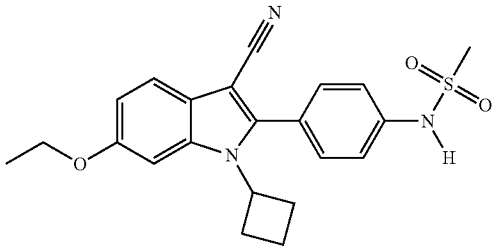
472
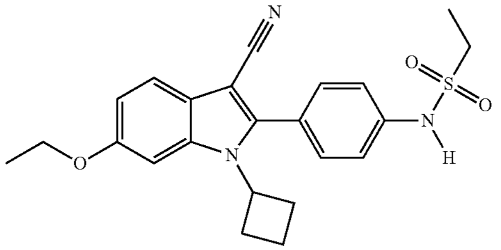
473

TABLE A-continued
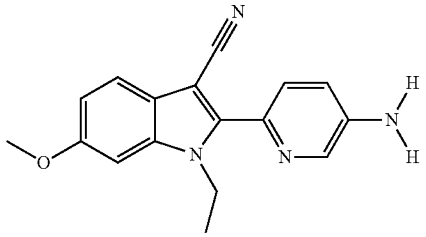
475
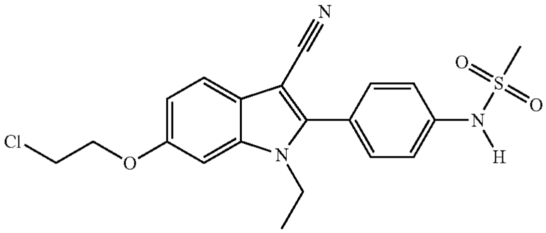
477
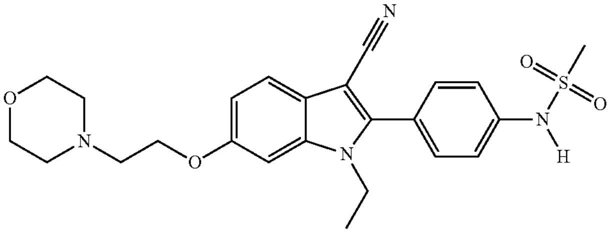
478
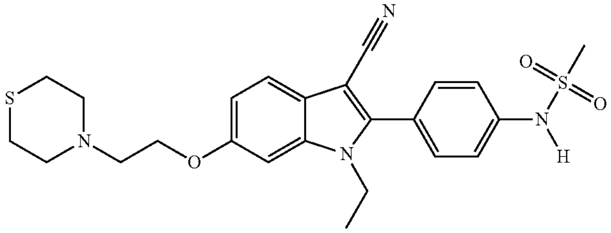
480
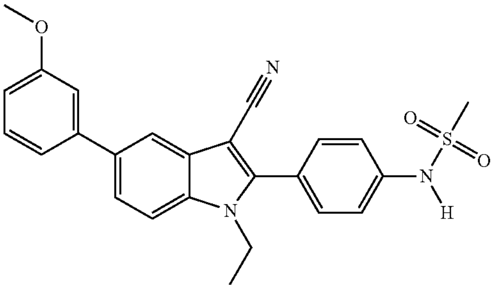
487

TABLE A-continued
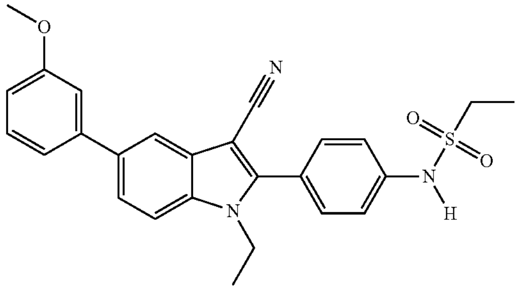
488
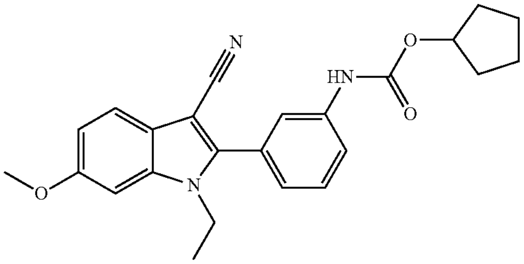
490
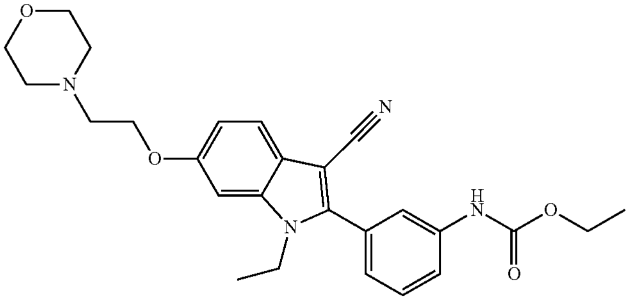
492
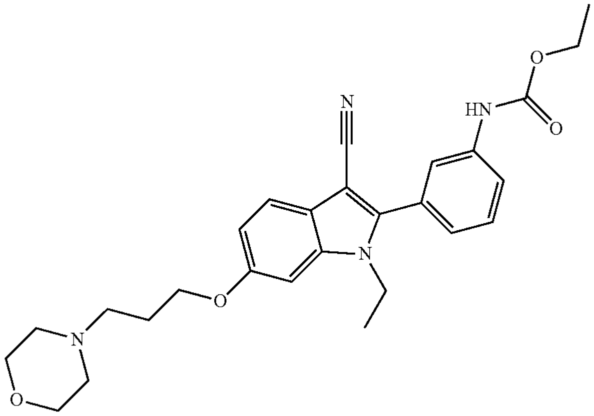
493

TABLE A-continued
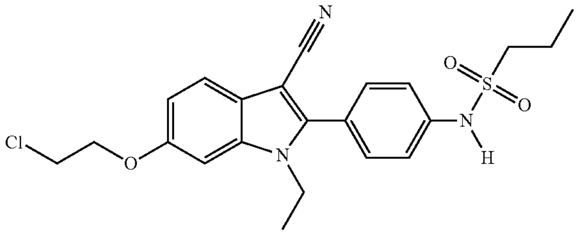
495
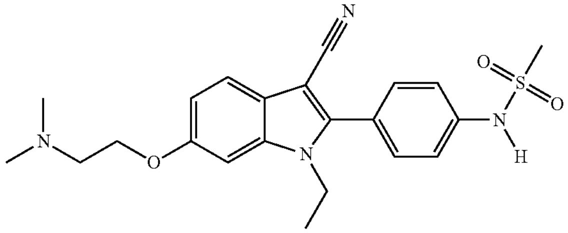
498
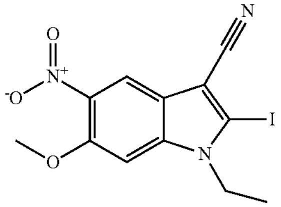
499
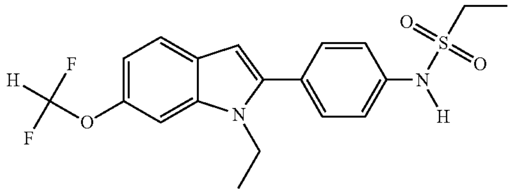
516
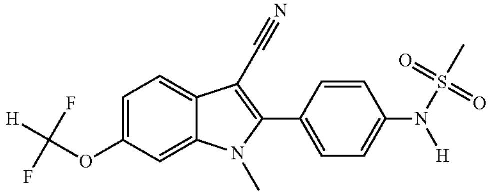
518
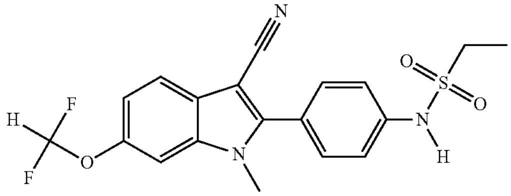
519

TABLE A-continued
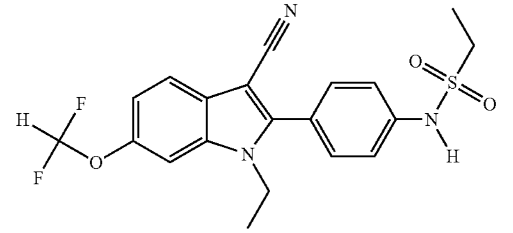
520
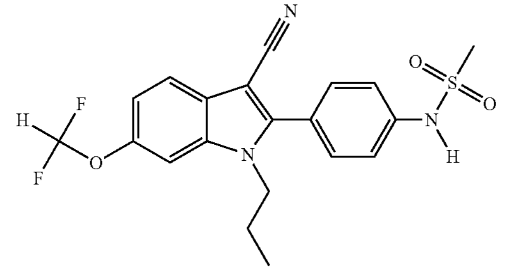
521
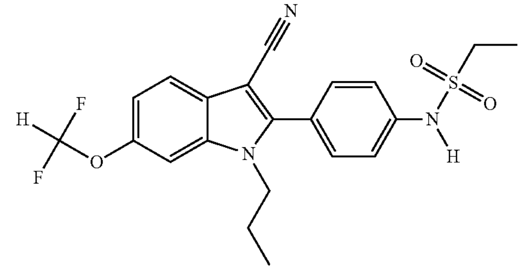
522
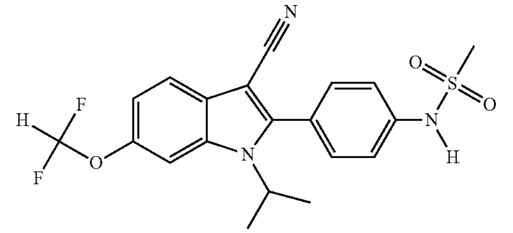
523
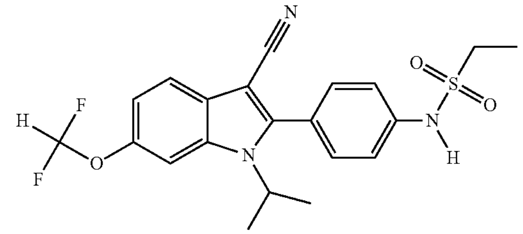
524

TABLE A-continued
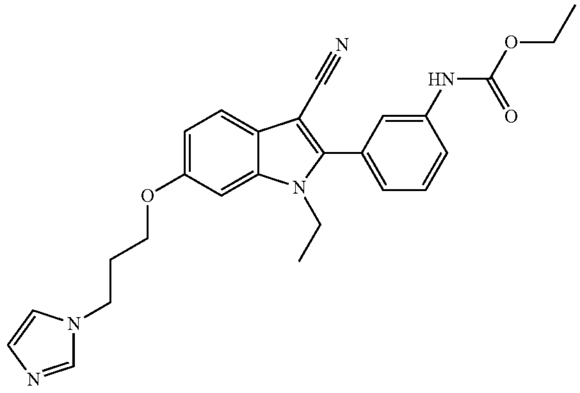
525
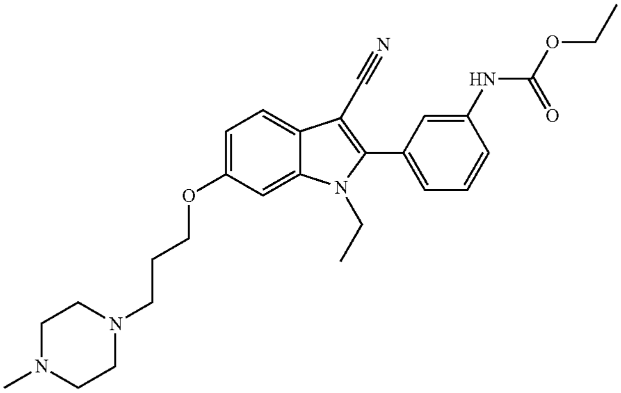
526
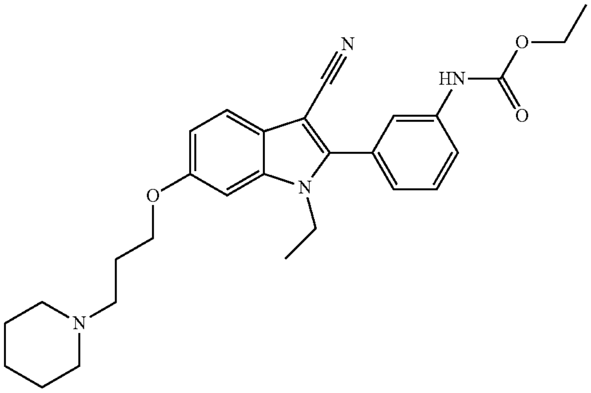
528

TABLE A-continued
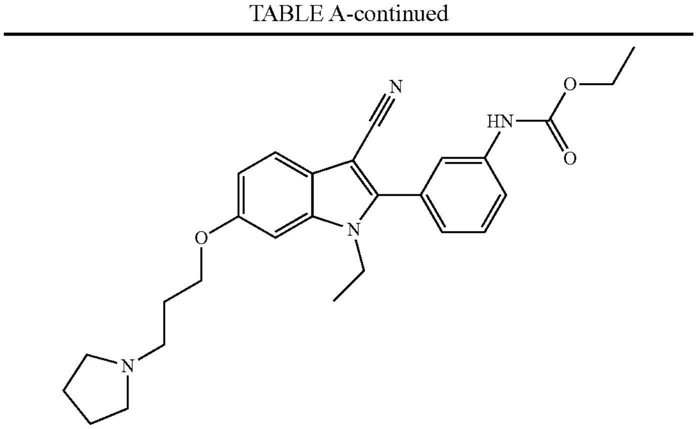
530
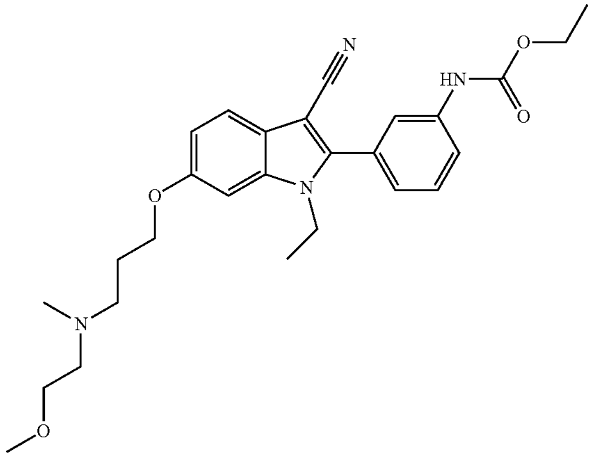
531
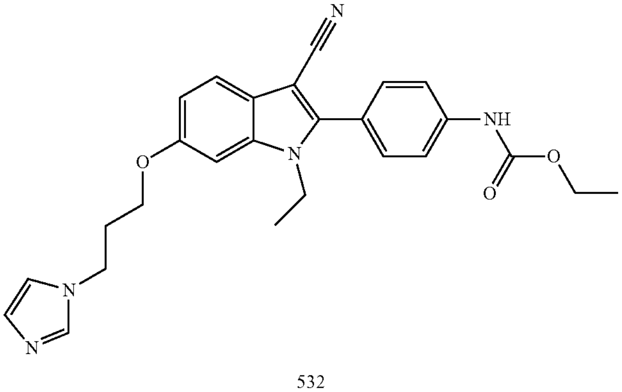
532

TABLE A-continued
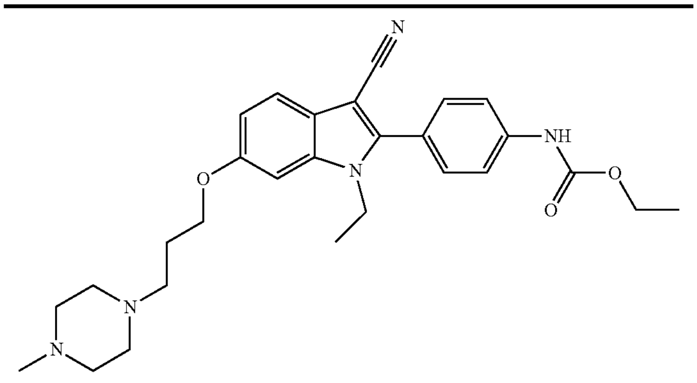
533
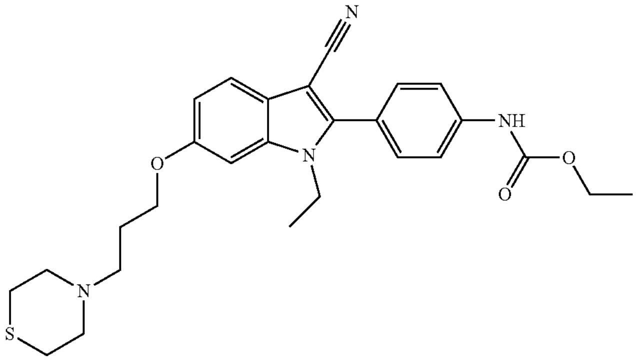
534
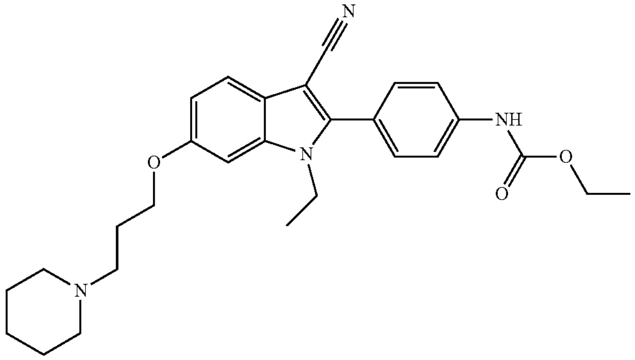
535
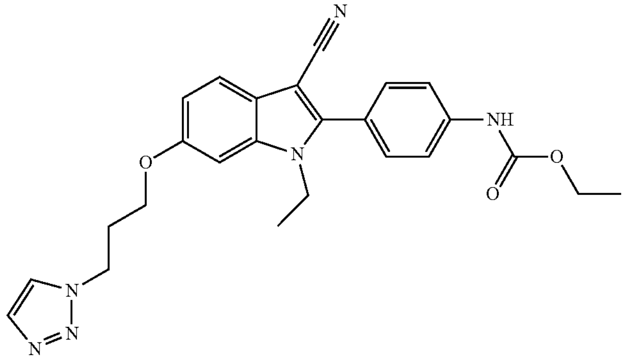
536

TABLE A-continued
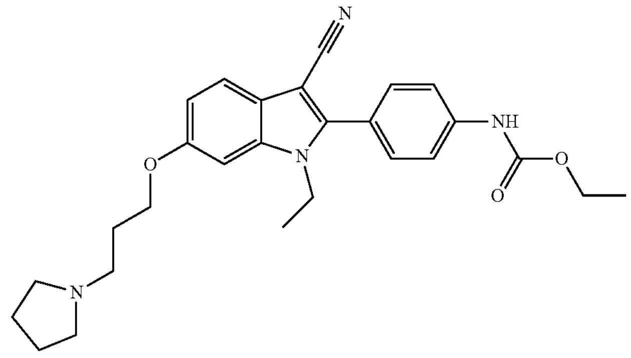
537
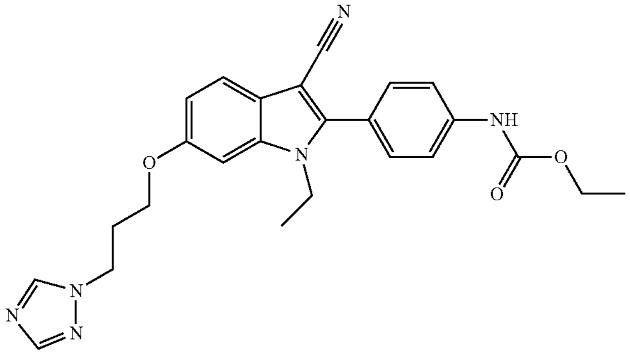
538
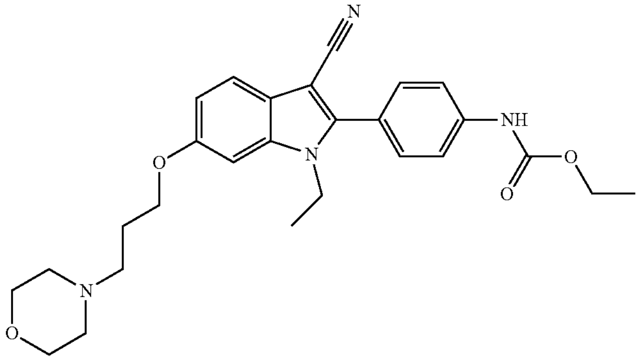
539
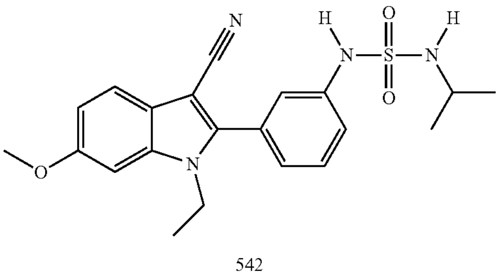
542

TABLE A-continued
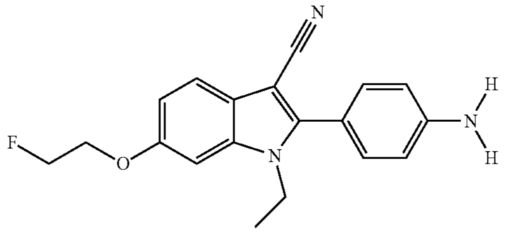
543
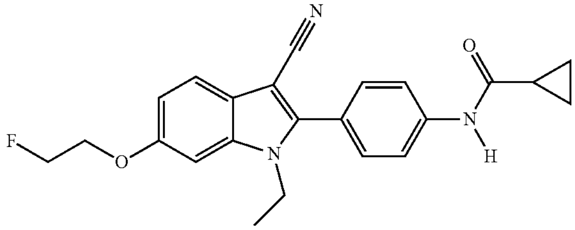
544
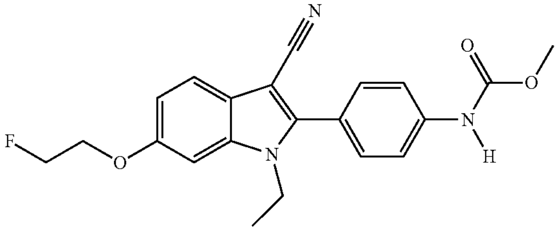
545
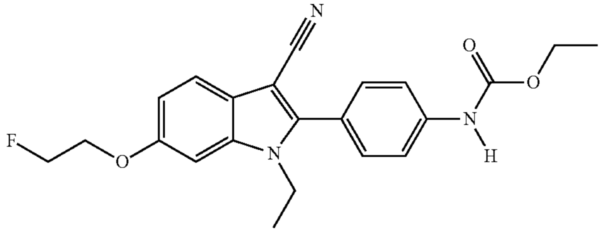
546
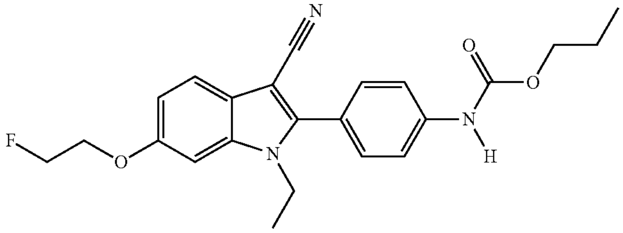
547

TABLE A-continued
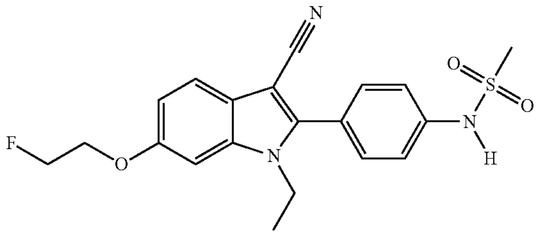
548
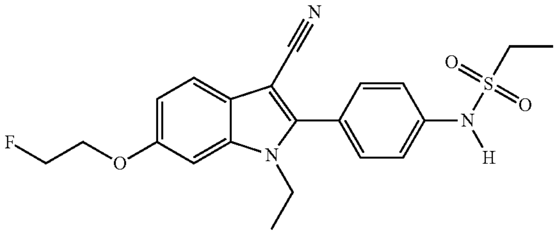
549
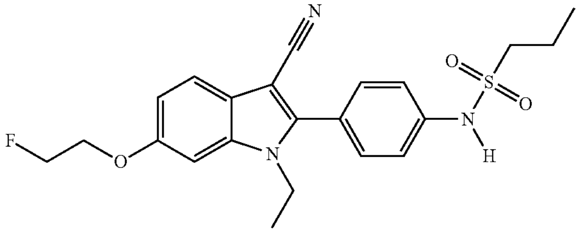
550
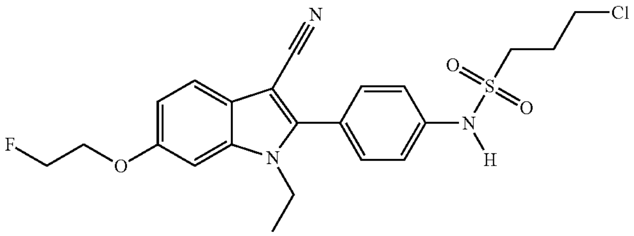
551
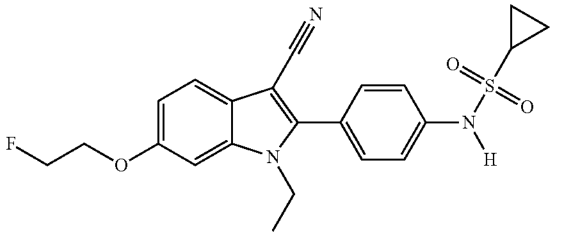
552

TABLE A-continued
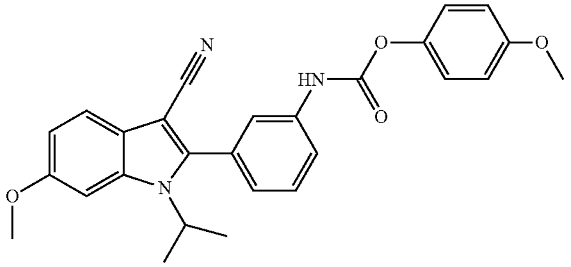
557
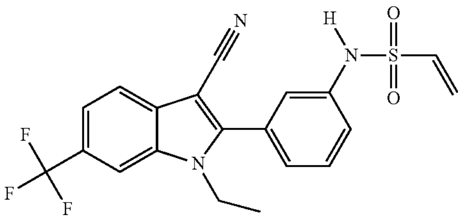
562
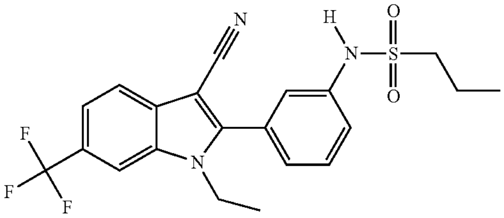
563
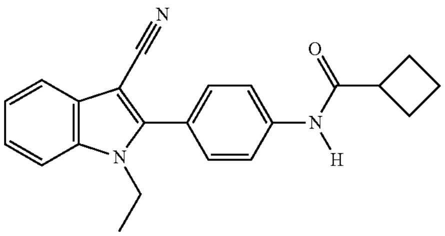
567
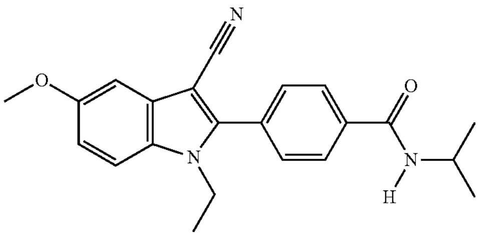
570

TABLE A-continued
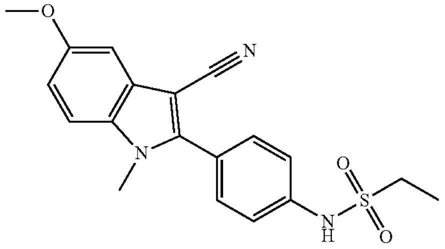
580
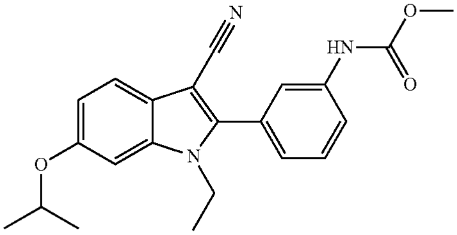
581
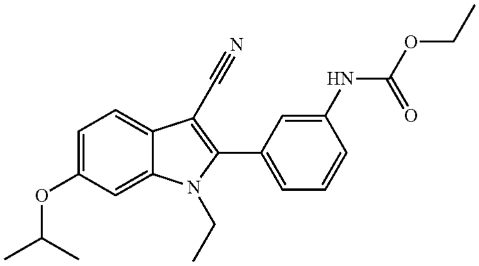
582
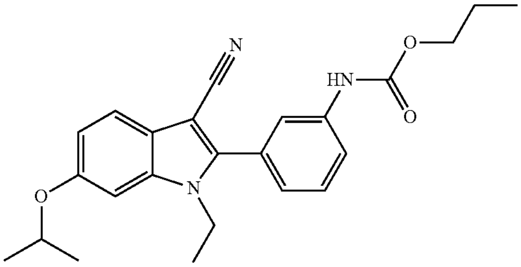
585
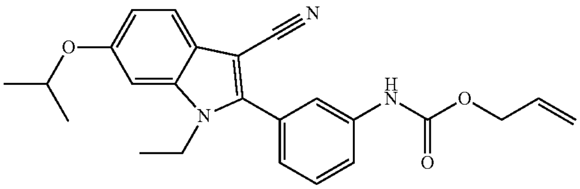
596

TABLE A-continued
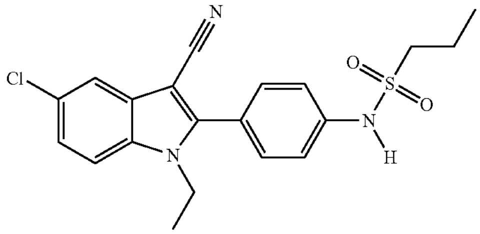
601
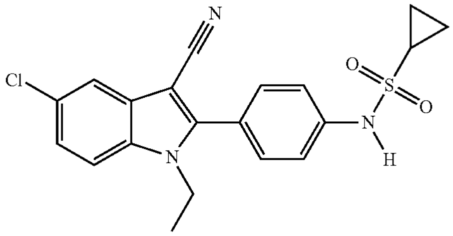
602
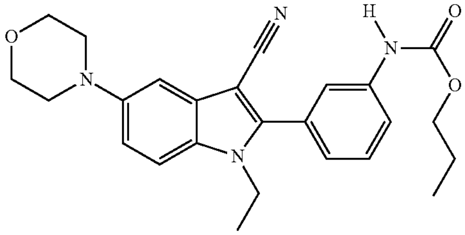
606
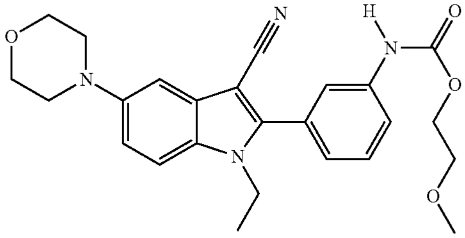
607
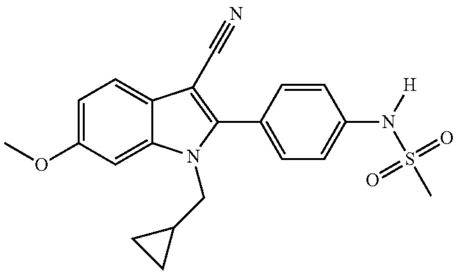
611

TABLE A-continued
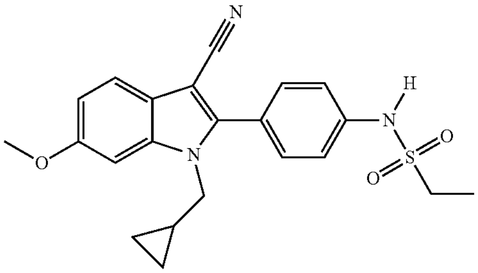
612
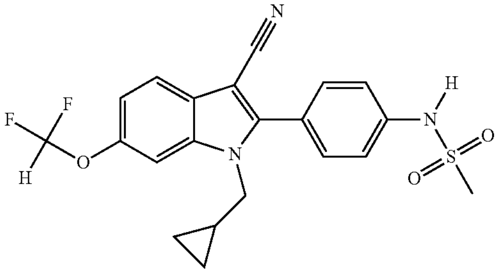
613
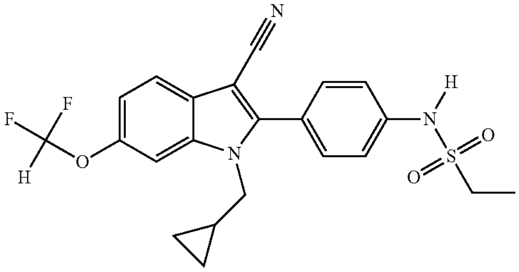
614
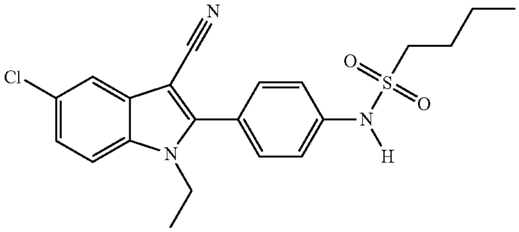
616
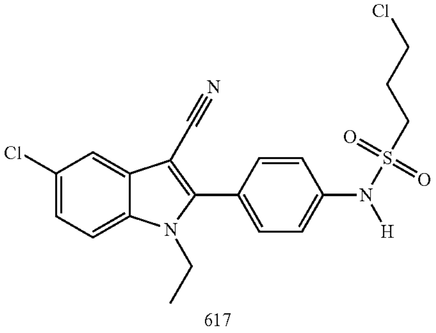
617

TABLE A-continued
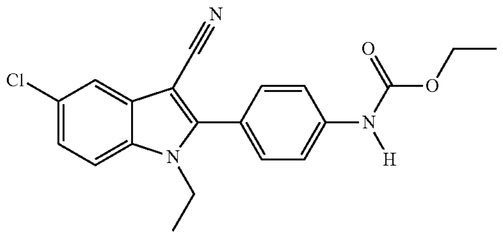
618
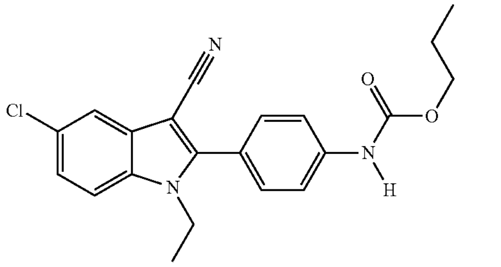
619
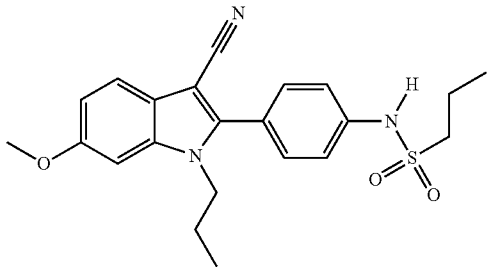
621
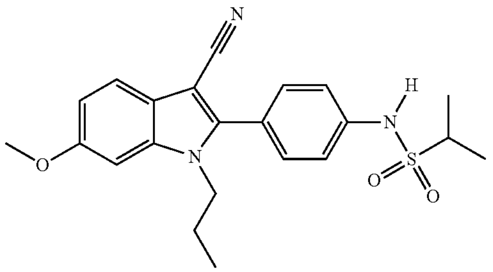
622
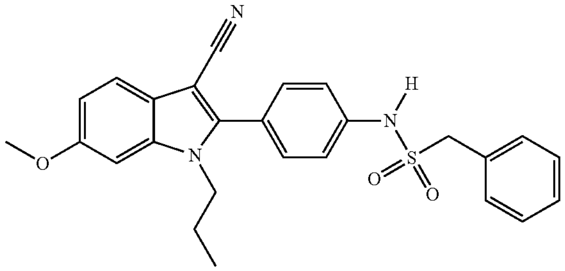
623

TABLE A-continued
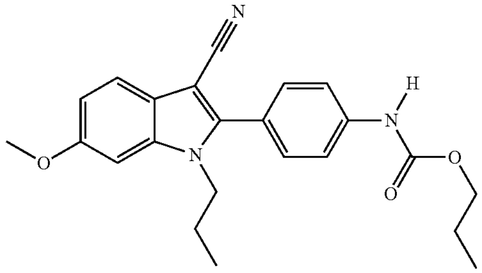
625
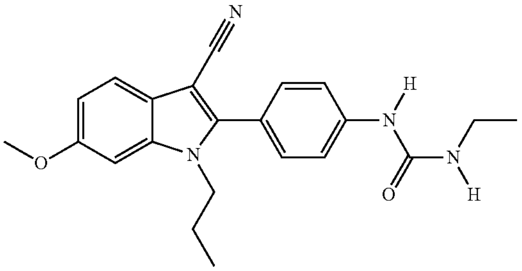
626
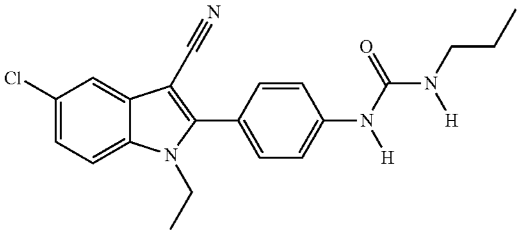
627
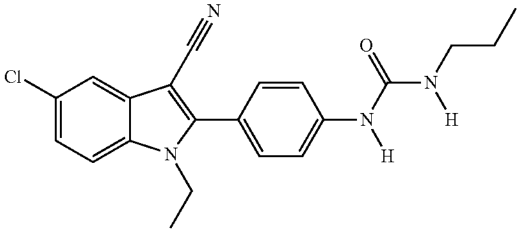
628
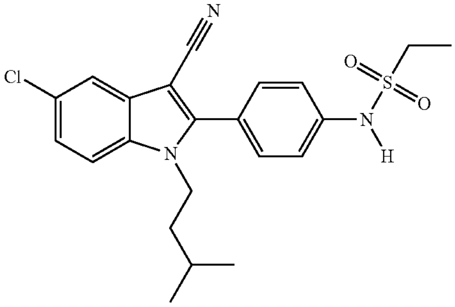
631

TABLE A-continued
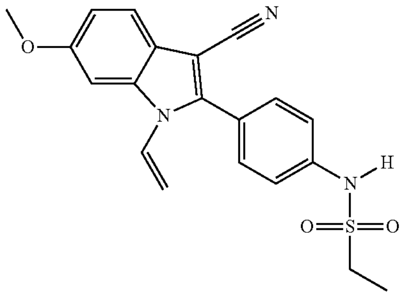
633
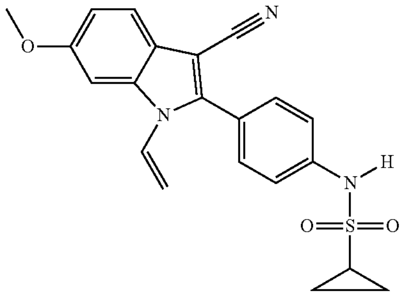
635
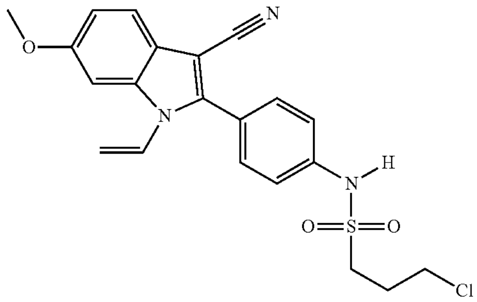
636
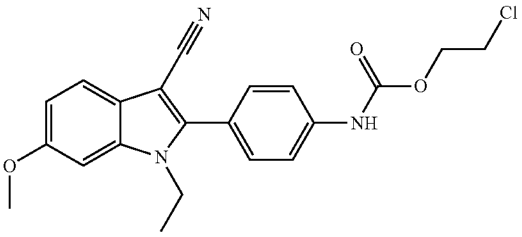
637
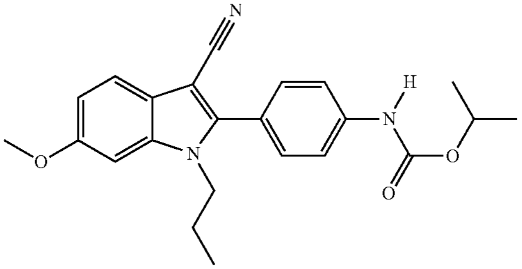
641

TABLE A-continued
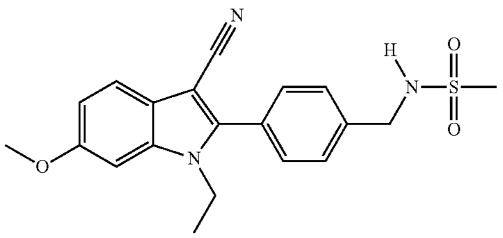
650
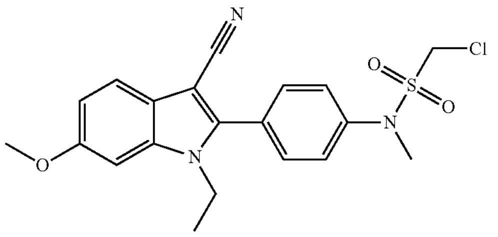
652
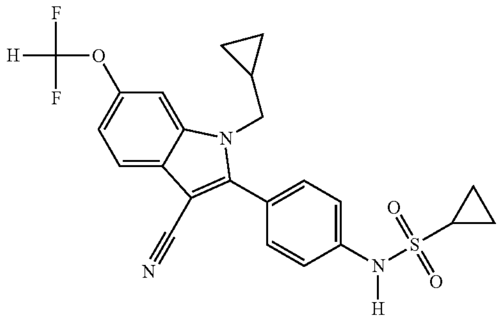
661
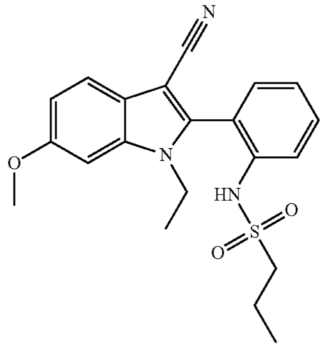
662
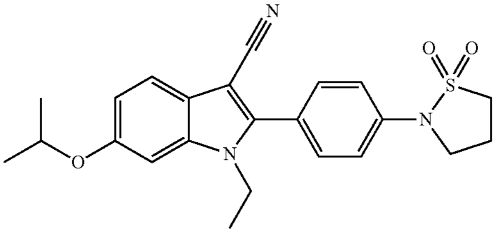
666

TABLE A-continued
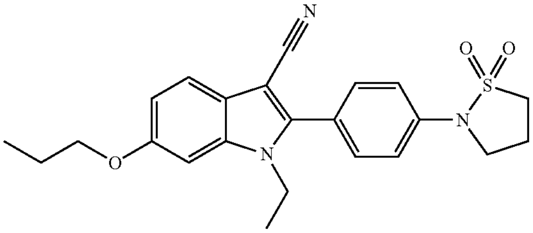
667
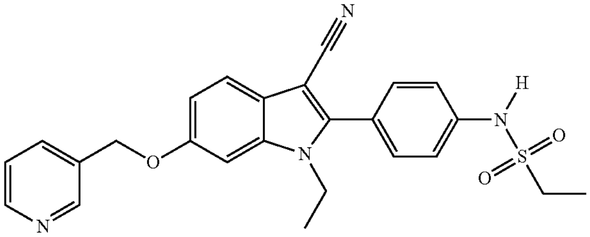
669
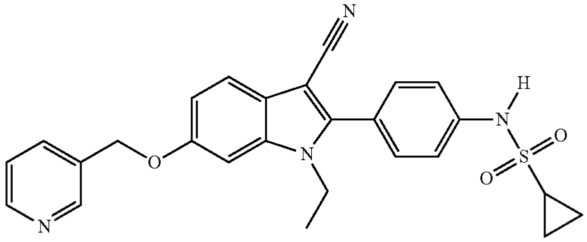
670
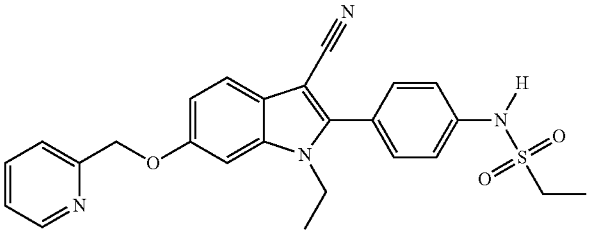
671
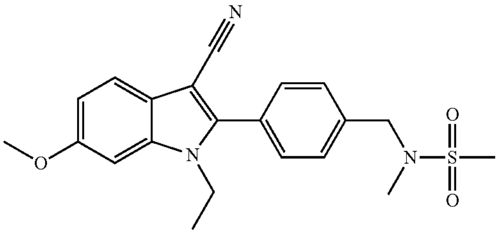
672
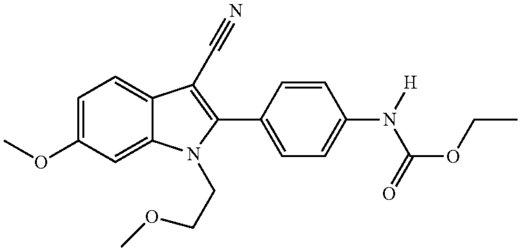
676

TABLE A-continued
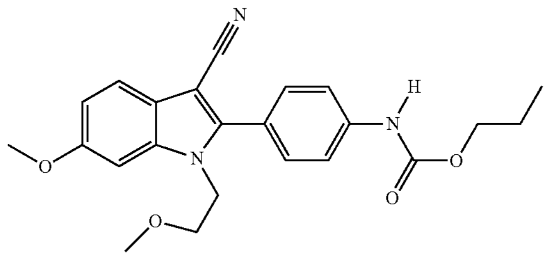
677
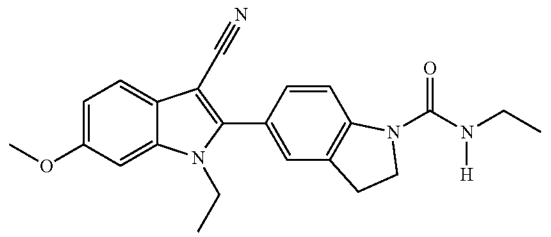
679
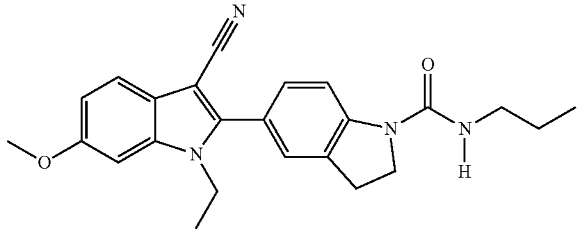
680
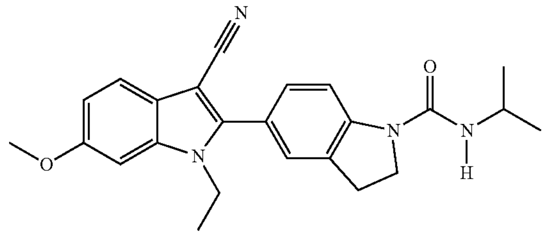
681
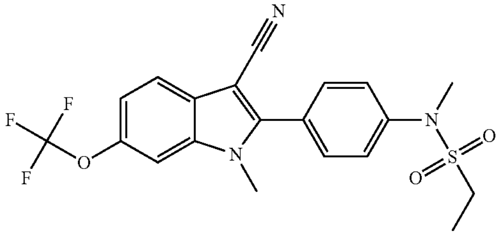
687

TABLE A-continued
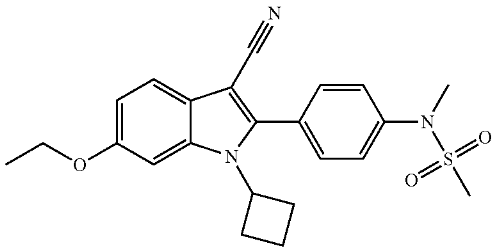
690
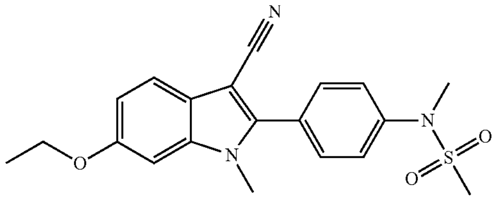
691
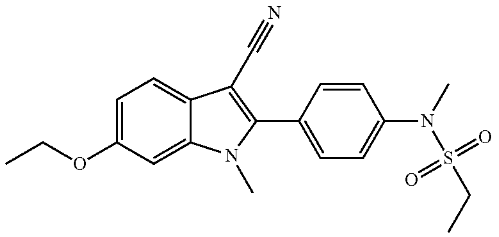
692
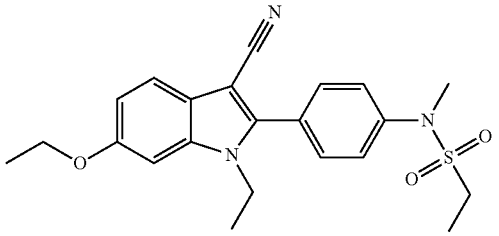
693
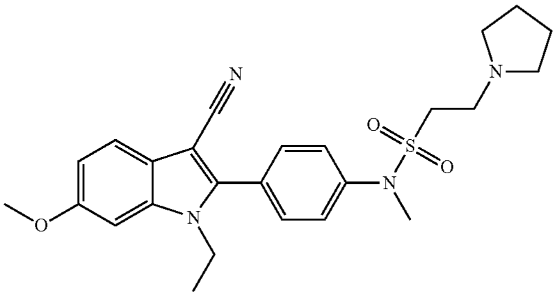
697

TABLE A-continued
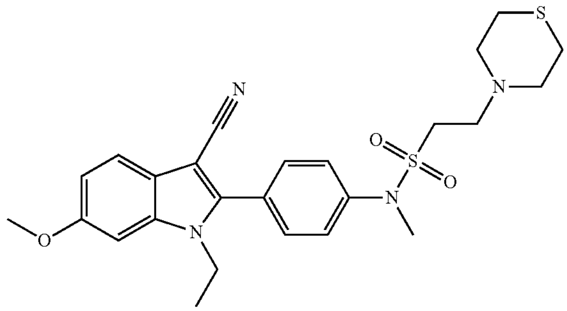
698
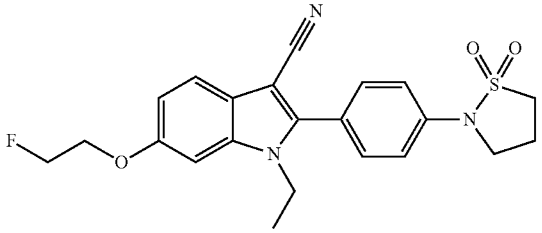
699
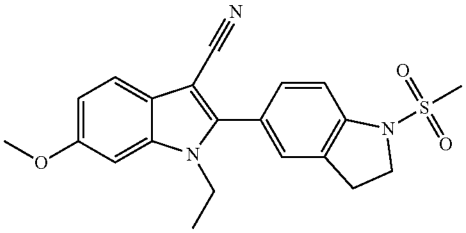
701
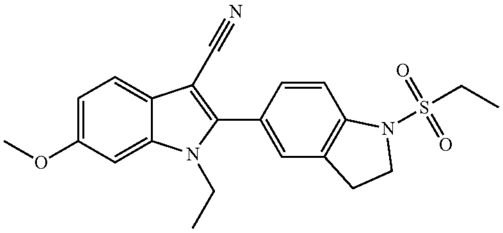
702
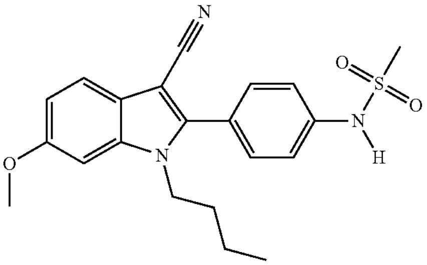
706

TABLE A-continued
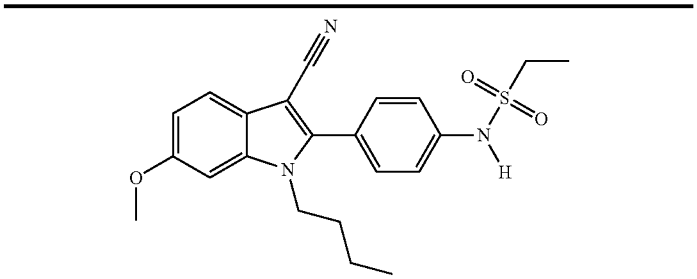
707
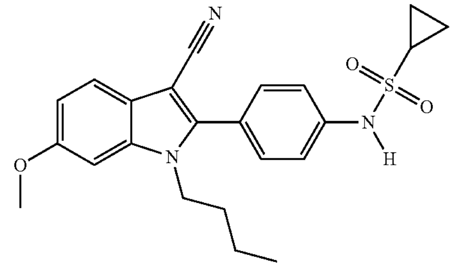
709
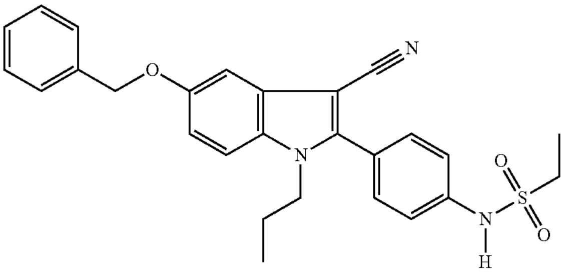
713
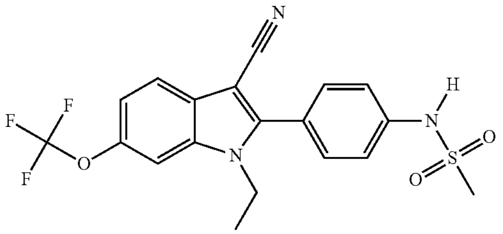
715
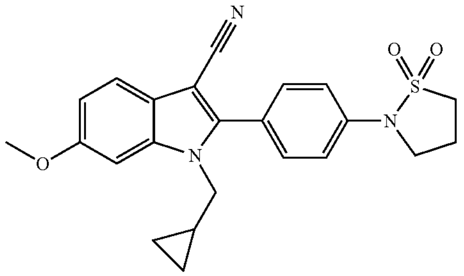
716

TABLE A-continued
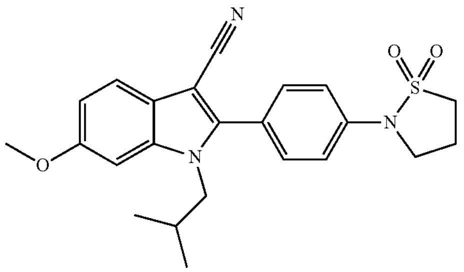
717
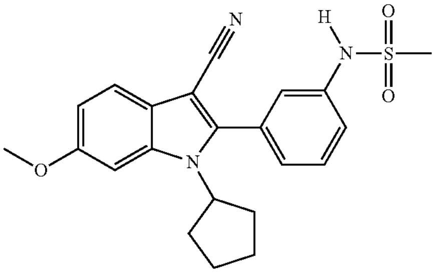
720
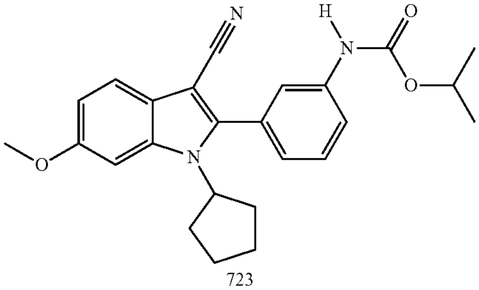
723
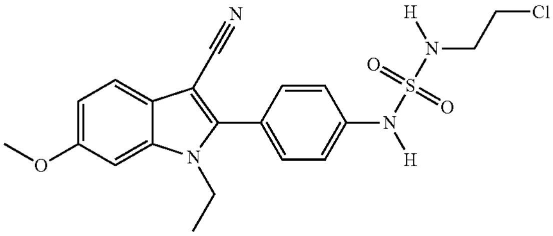
724
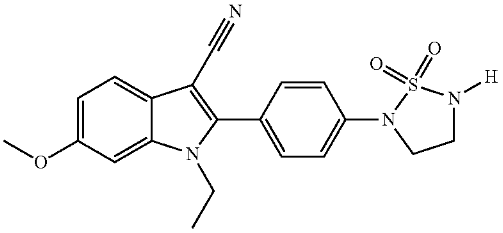
725

TABLE A-continued
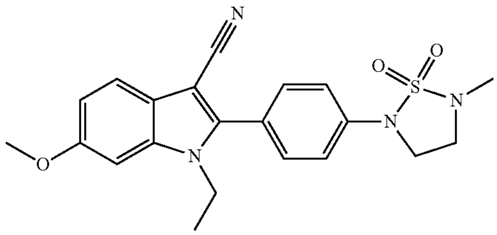
726
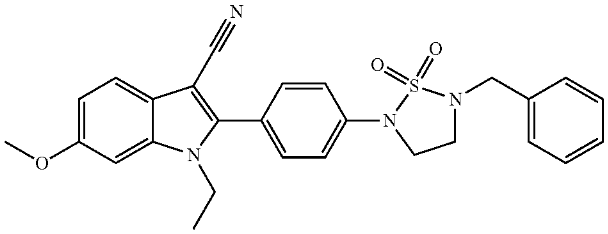
727
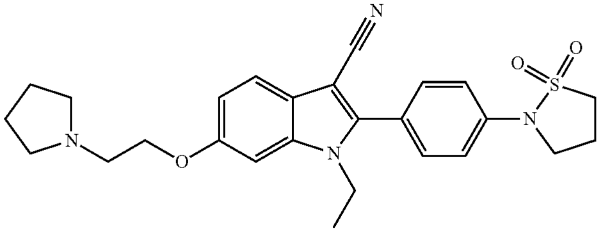
728
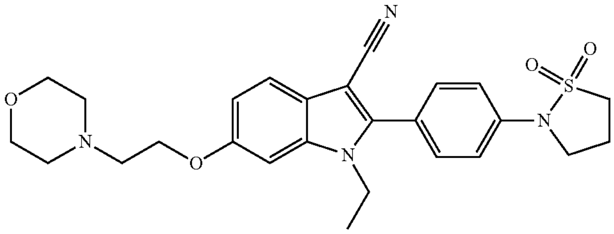
730
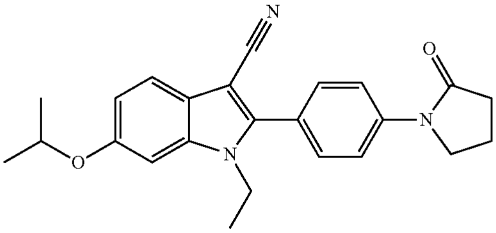
731

TABLE A-continued
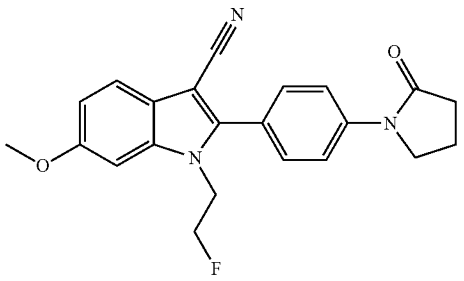
732
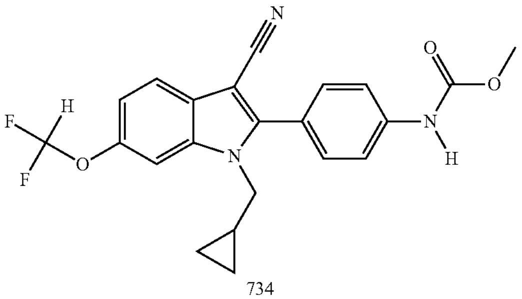
734
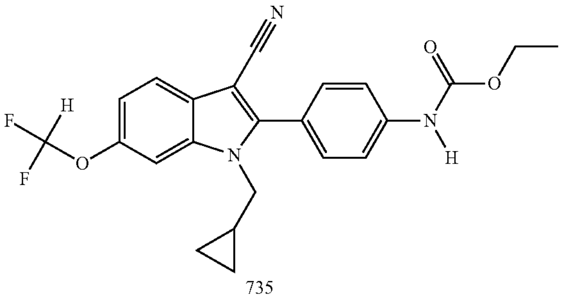
735
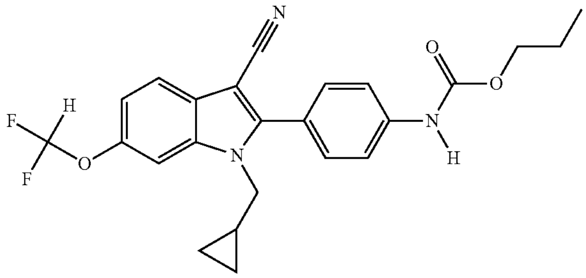
736
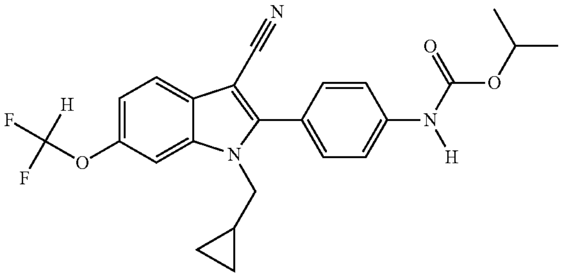
737

TABLE A-continued
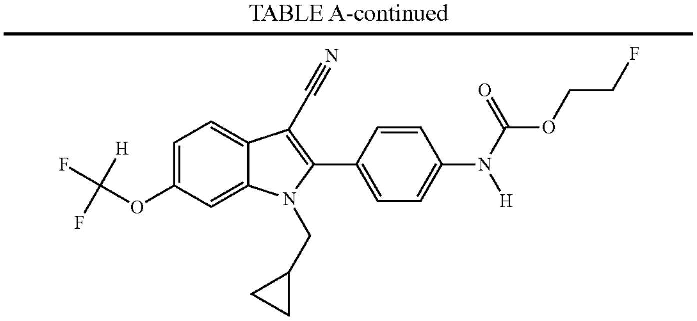
738
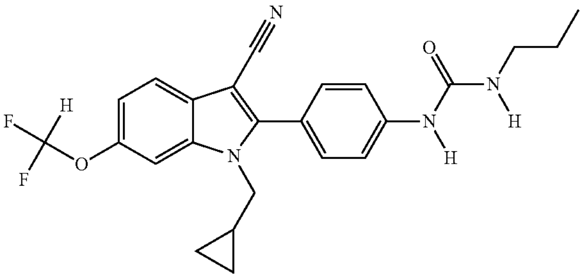
741
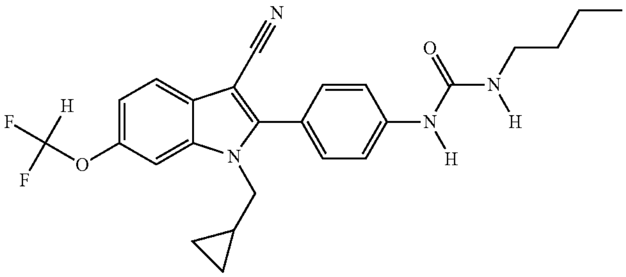
742
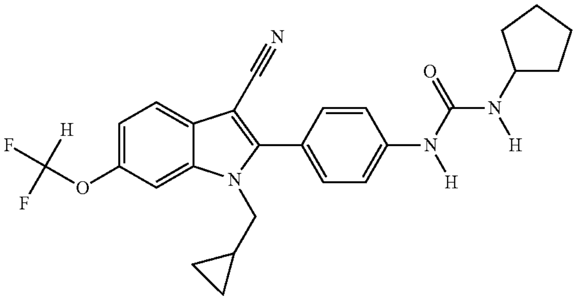
743
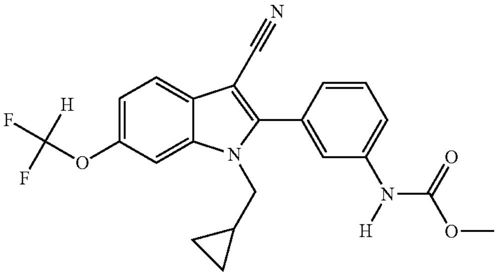
744

TABLE A-continued
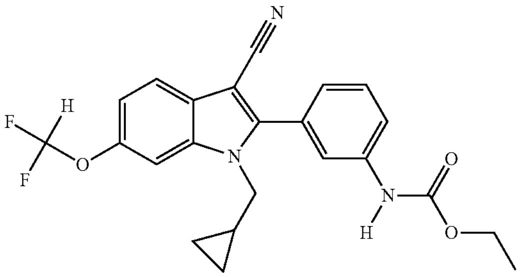
745
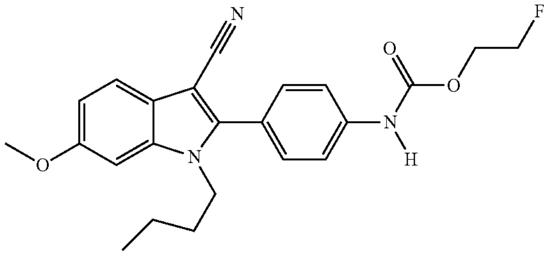
747
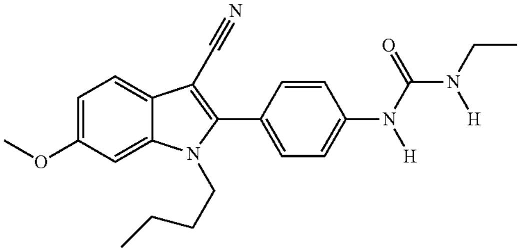
748
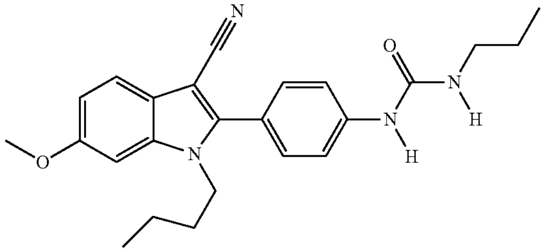
749
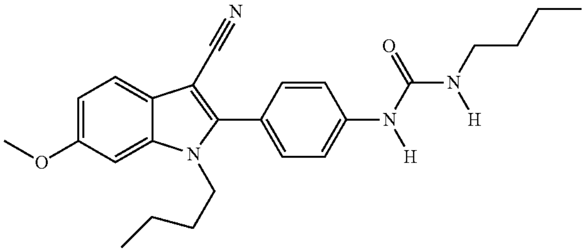
750

TABLE A-continued
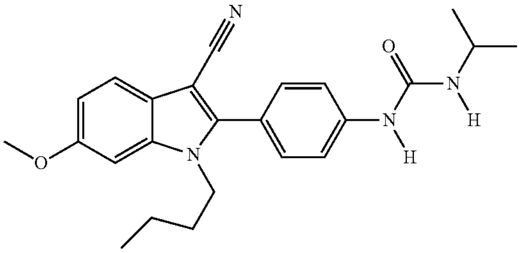
751
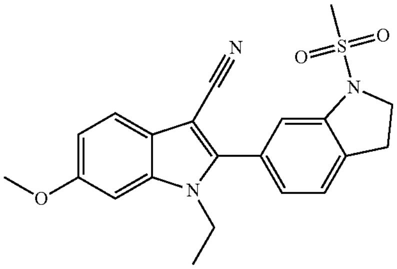
752
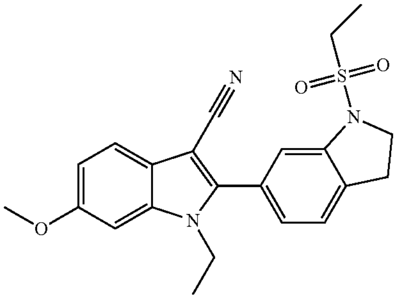
753
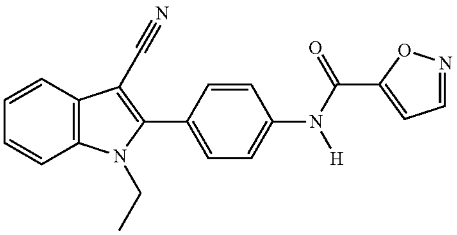
755
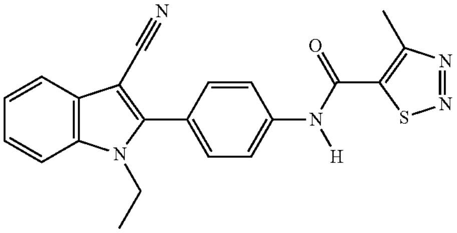
756

TABLE A-continued
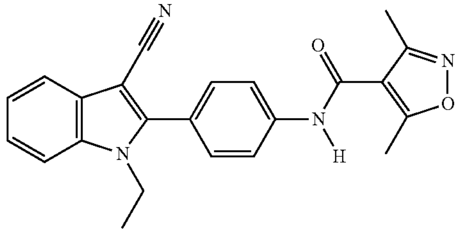
757
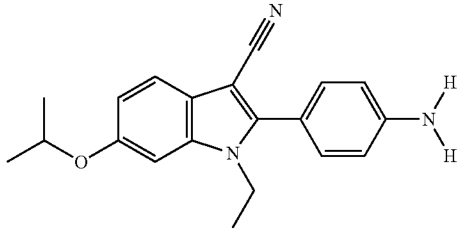
758
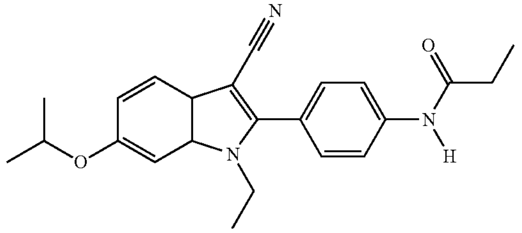
759
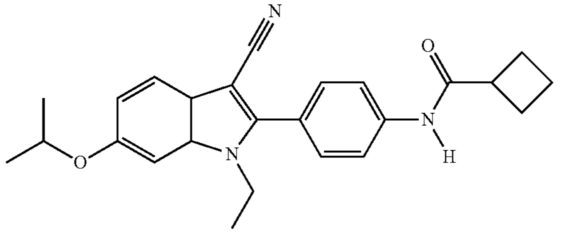
760
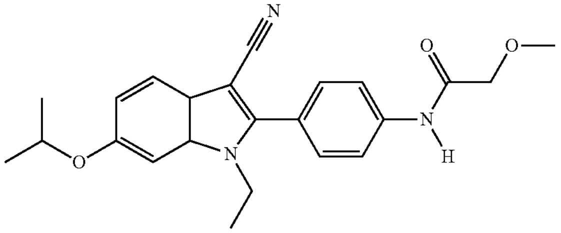
761
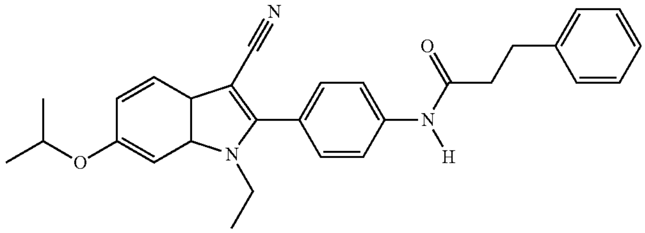
762

TABLE A-continued
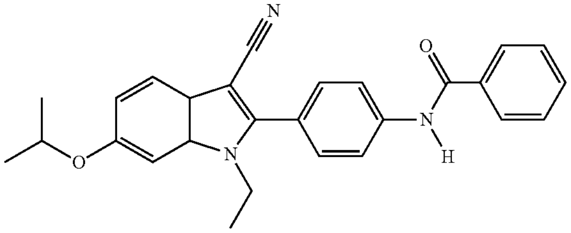
763
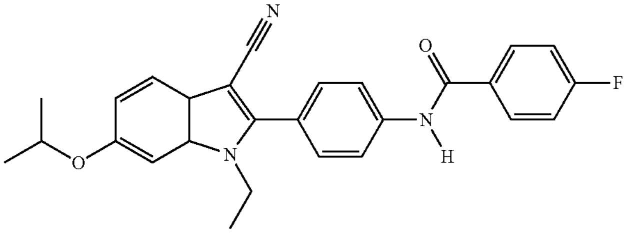
764
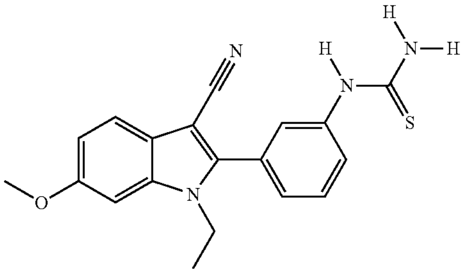
767
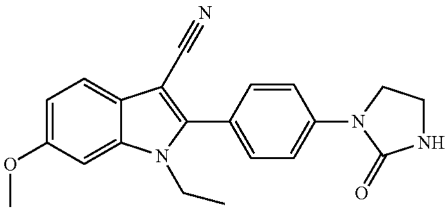
771
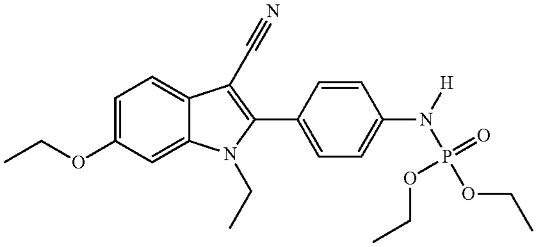
772

TABLE A-continued
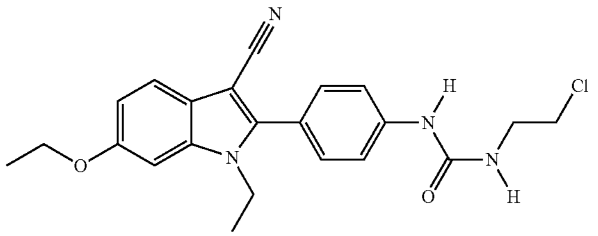
774
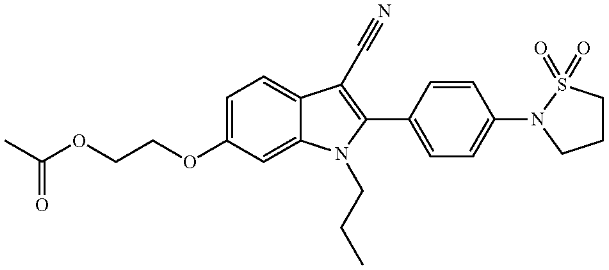
775
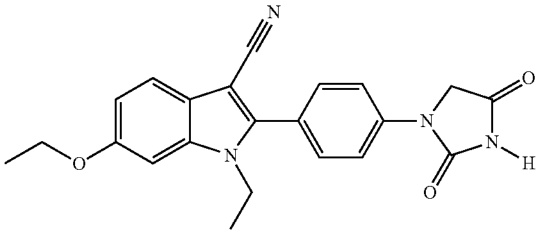
776
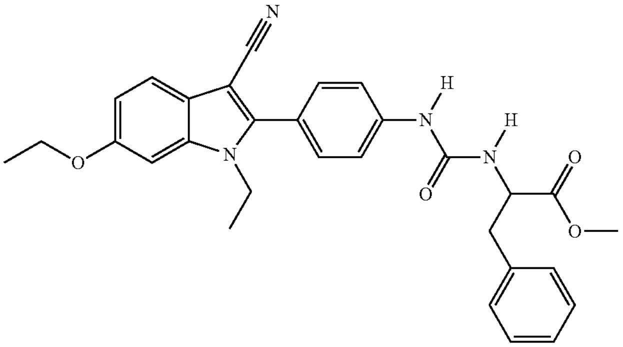
777
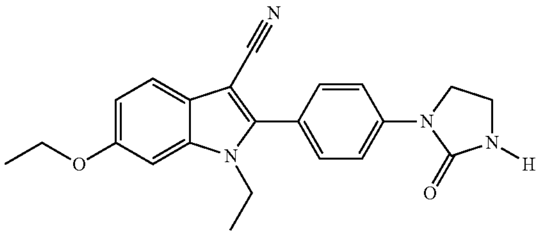
778

TABLE A-continued
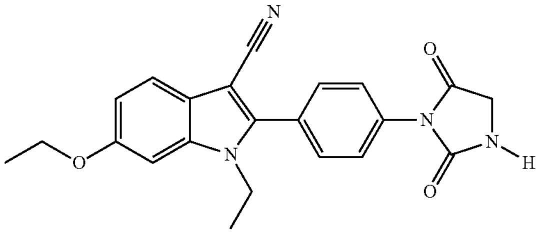
779
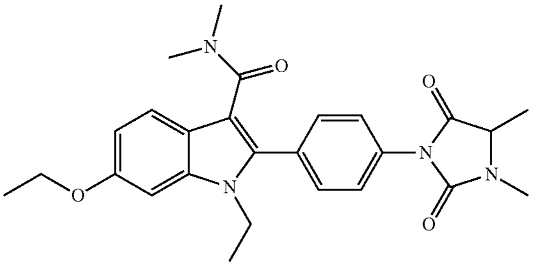
780
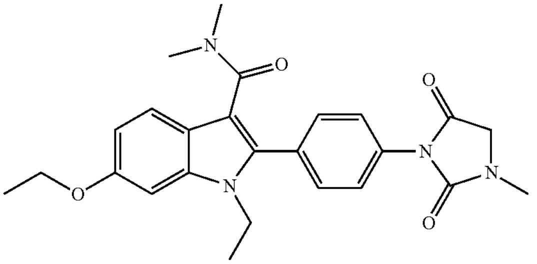
781
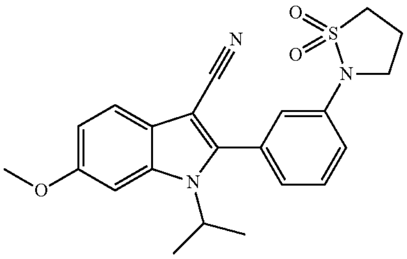
784
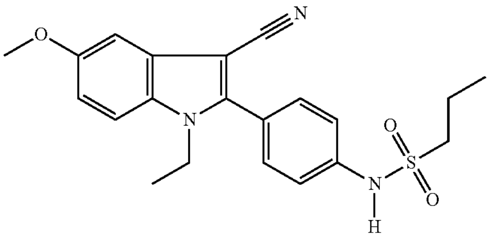
789

TABLE A-continued
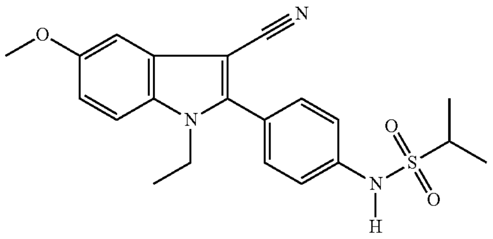
790
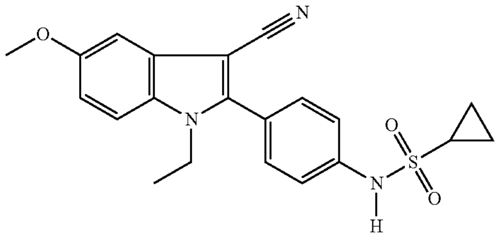
791
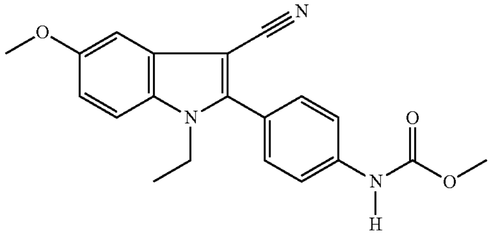
792
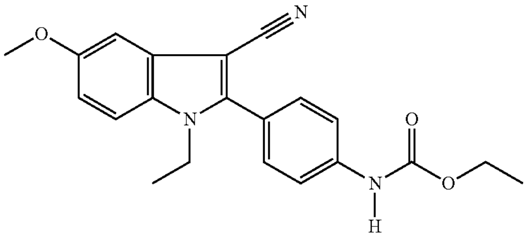
793
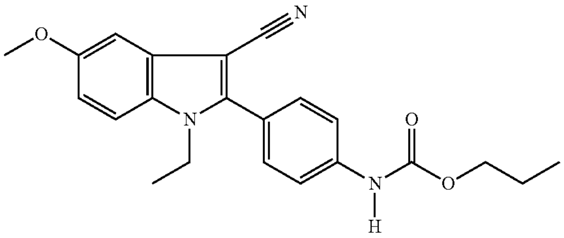
794

TABLE A-continued
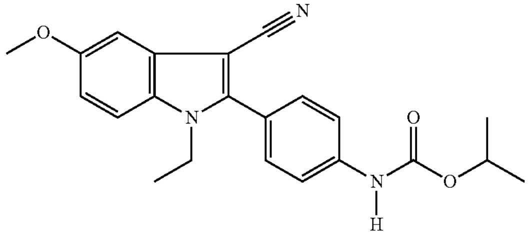
795
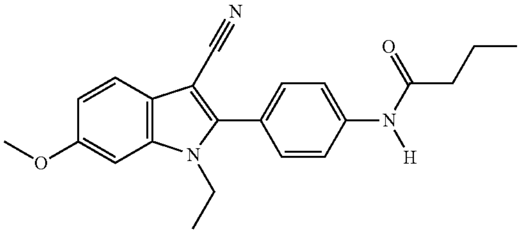
799
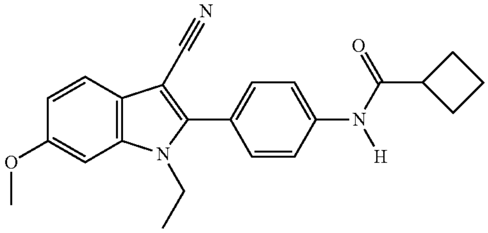
801
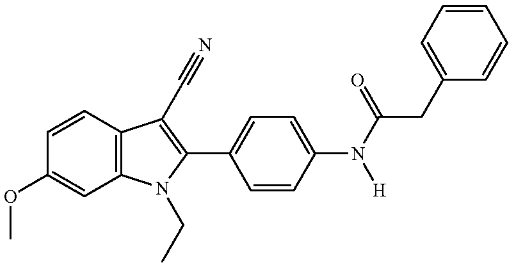
802
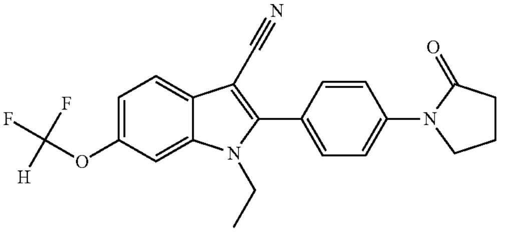
807

TABLE A-continued
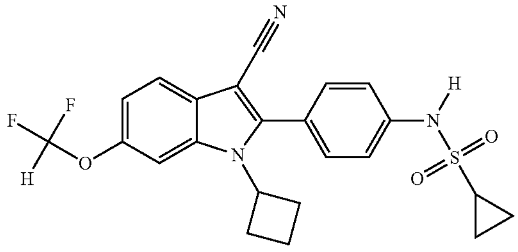
813
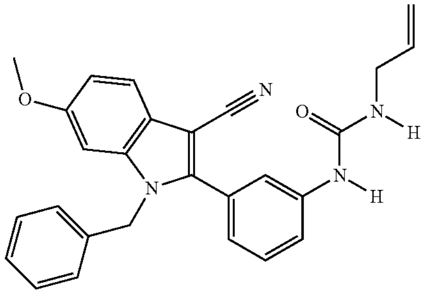
818
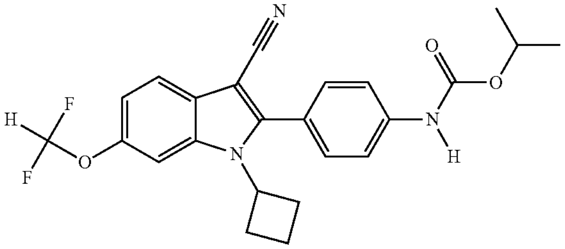
822
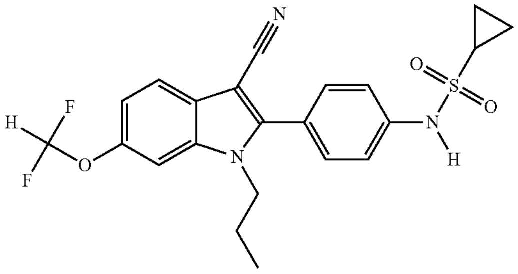
827
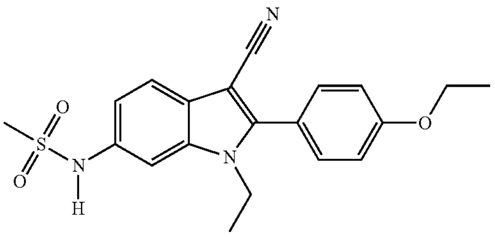
834

TABLE A-continued
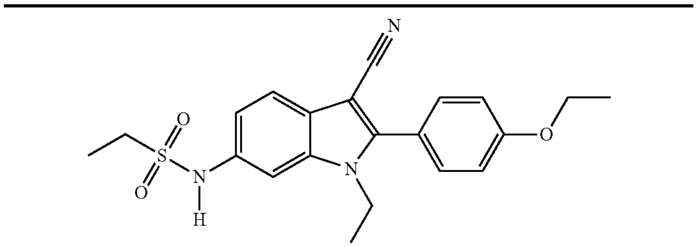
835
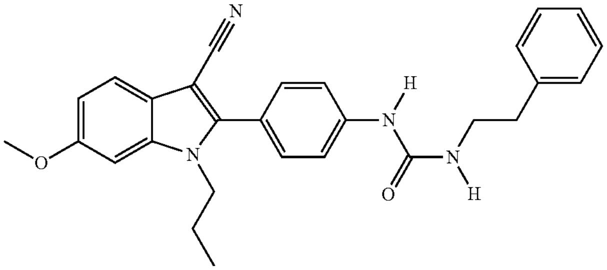
848
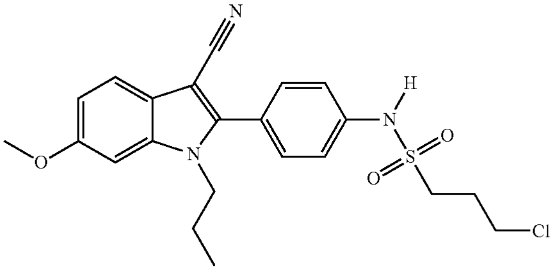
850
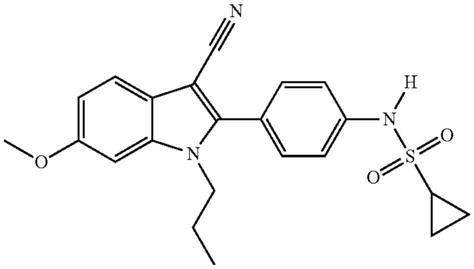
851
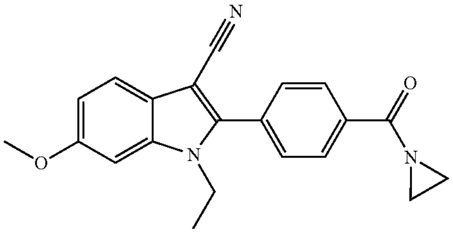
853

TABLE A-continued
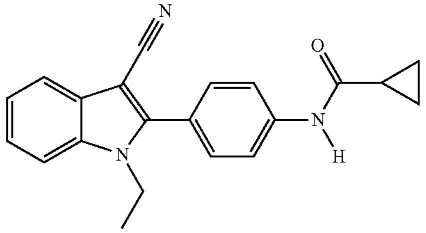
854
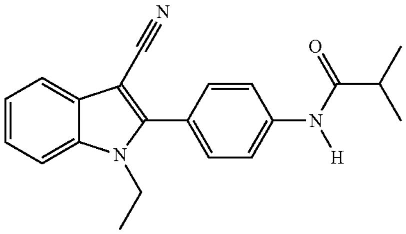
855
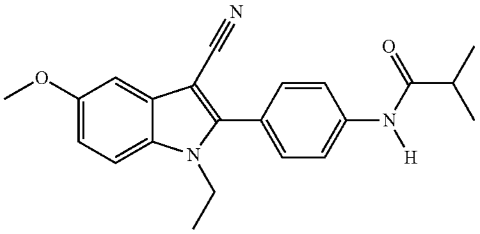
858
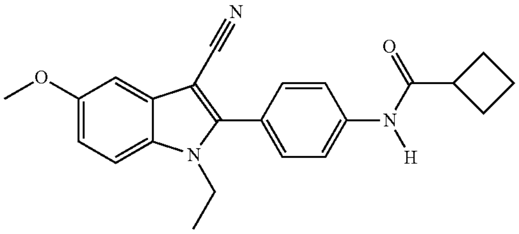
859
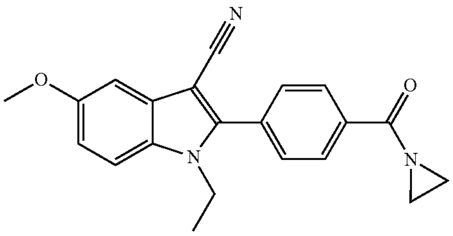
861

TABLE A-continued
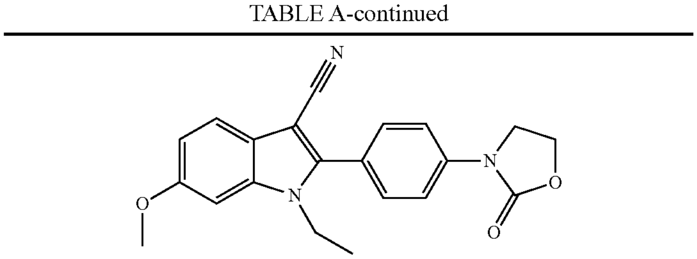
863
More preferred compounds include the following compounds in Table B:
TABLE B
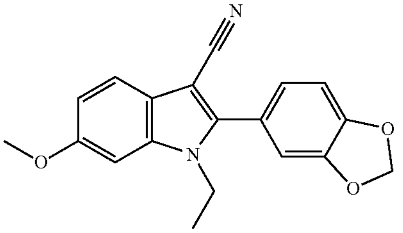
22
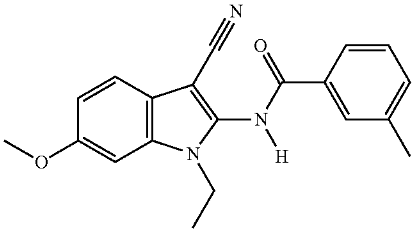
23
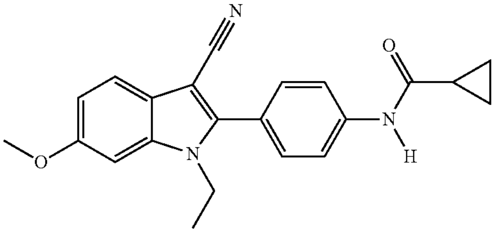
81
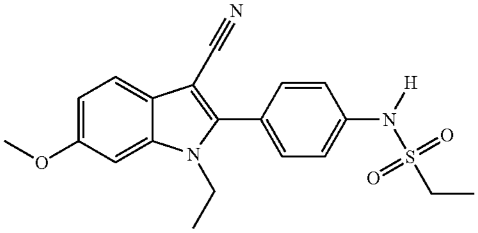
83

TABLE B-continued
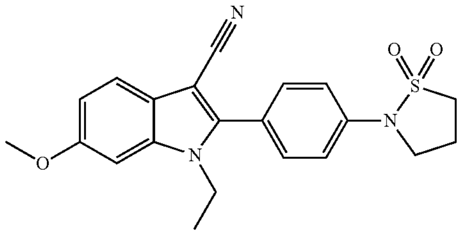
84
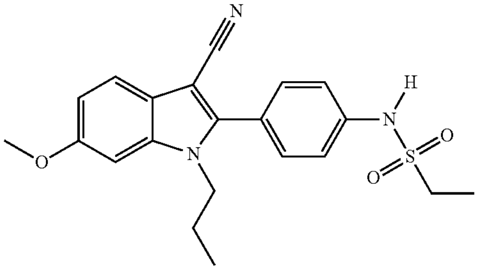
85
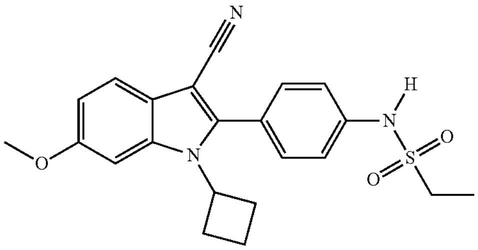
86
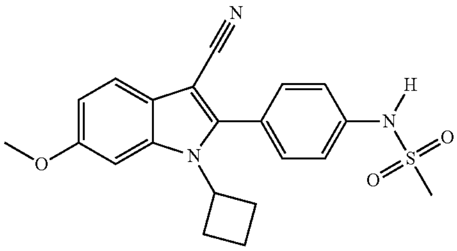
87
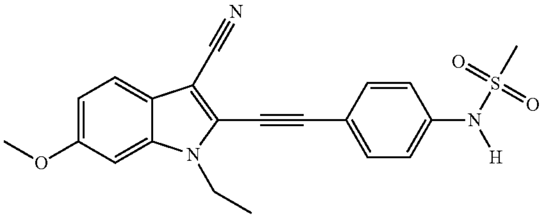
130

TABLE B-continued
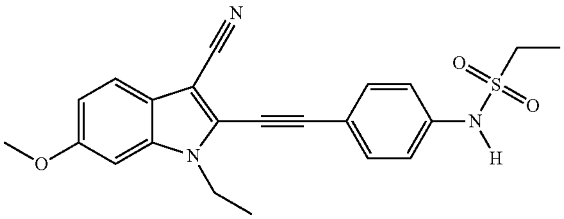
131
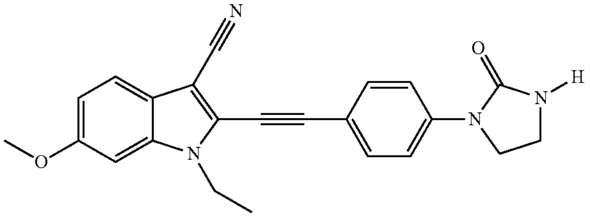
166
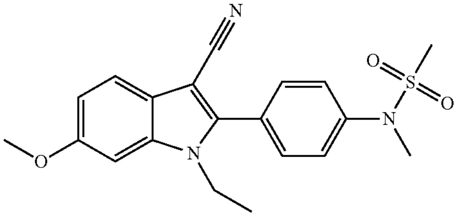
180
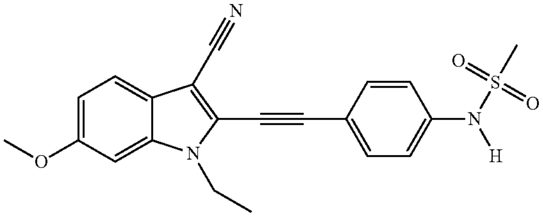
182
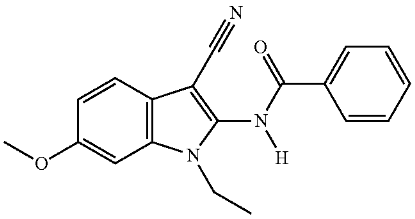
204

TABLE B-continued
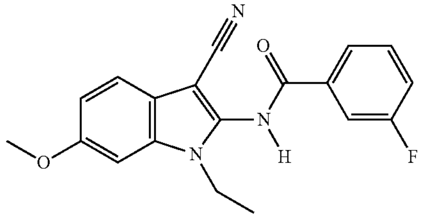
214
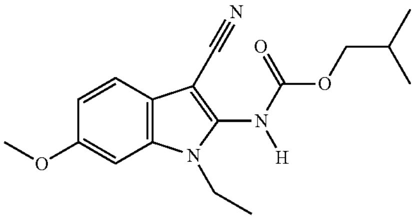
217
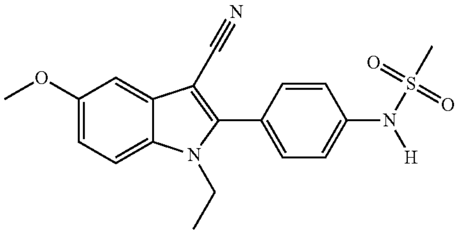
243
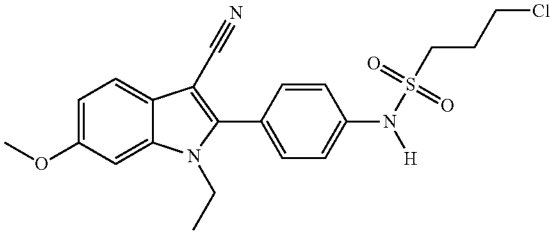
252
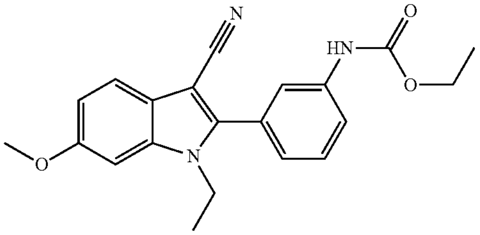
294

TABLE B-continued
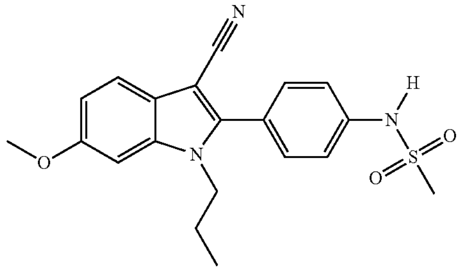
346
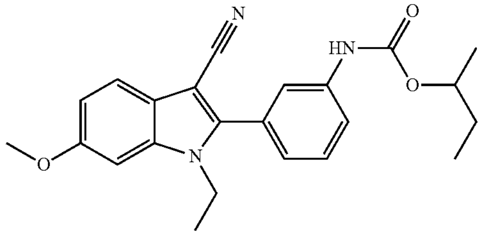
349
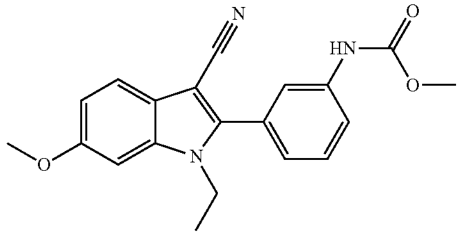
353
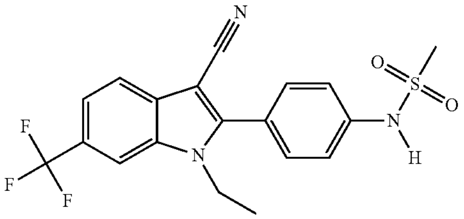
365
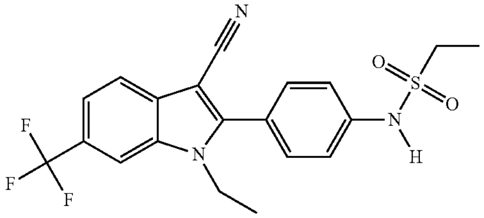
366

TABLE B-continued
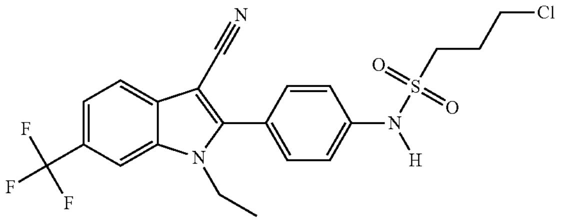
369
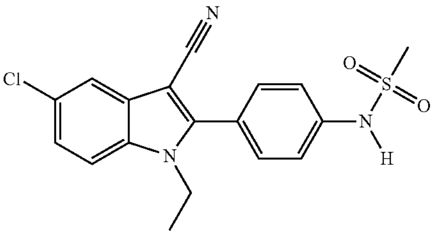
394
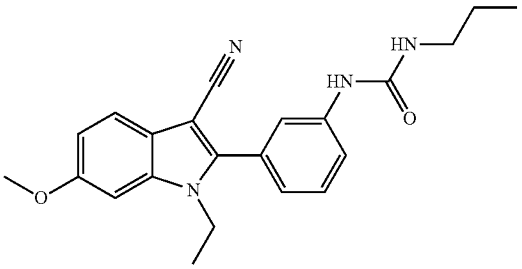
396
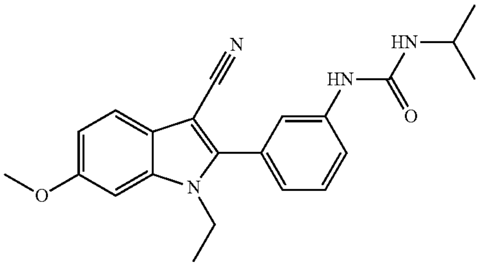
397
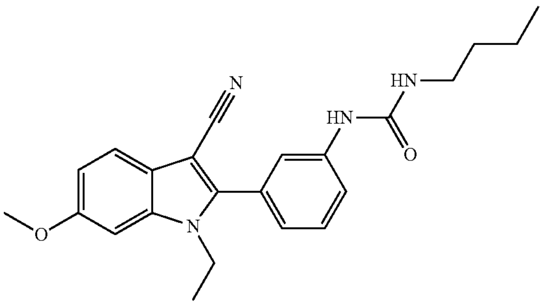
398

TABLE B-continued
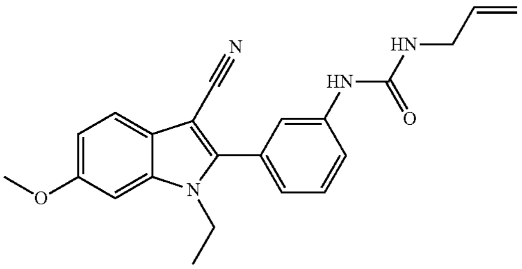
399
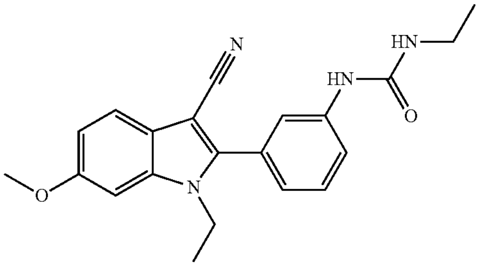
401
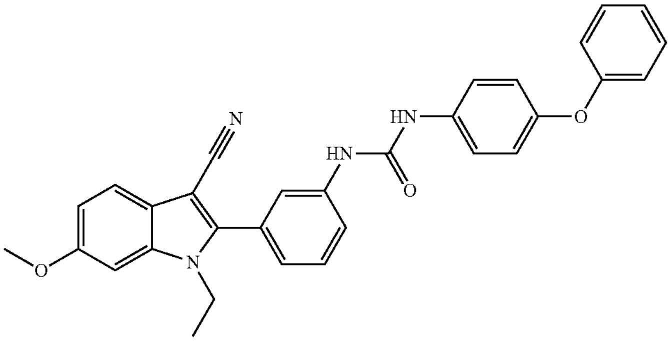
406
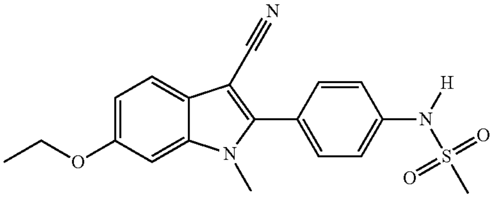
413
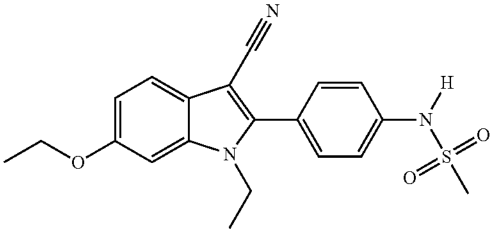
415

TABLE B-continued
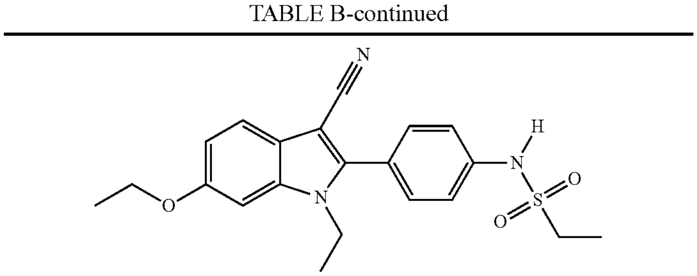
416
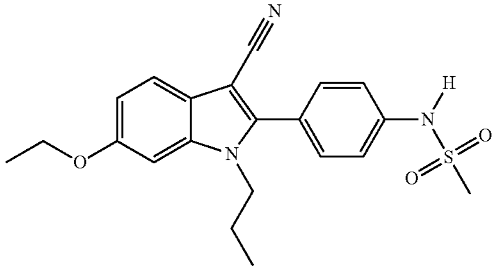
417
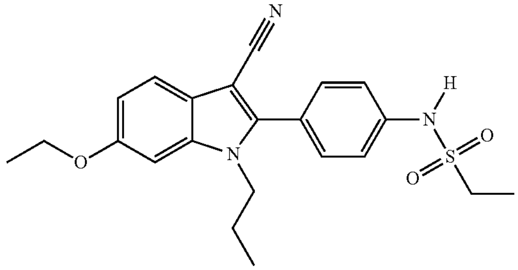
418
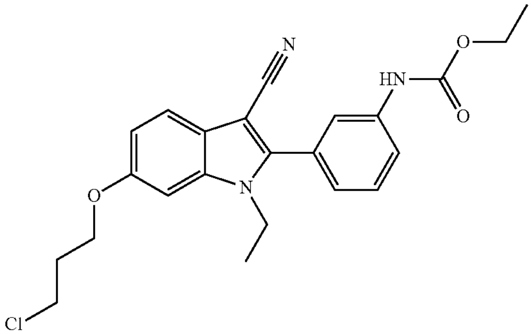
447
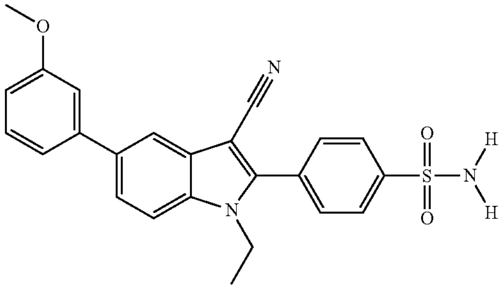
461

TABLE B-continued
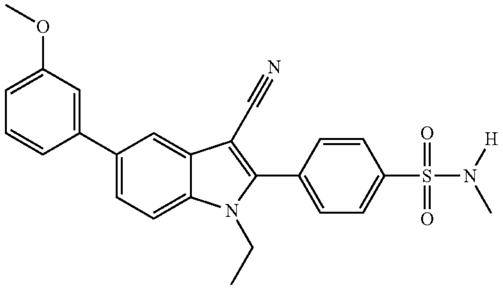
462
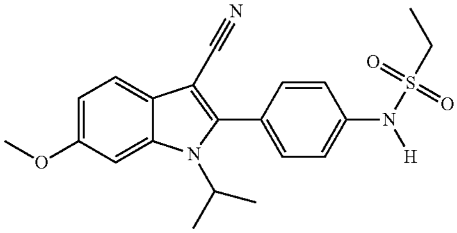
468
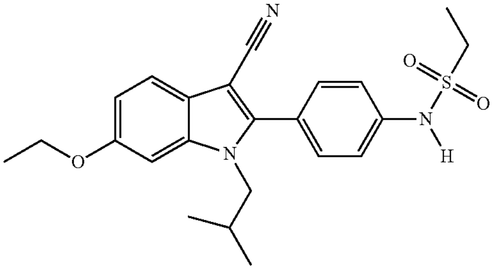
470
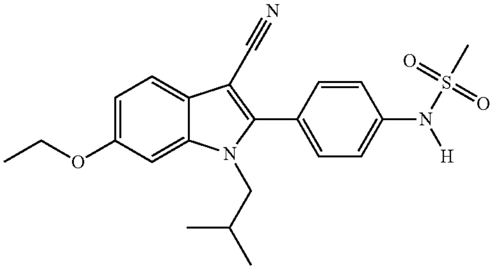
471
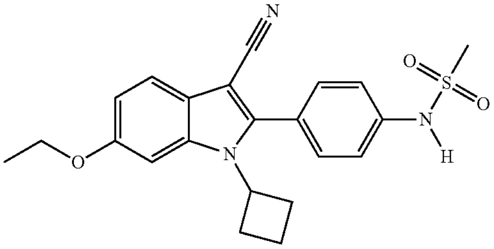
472

TABLE B-continued
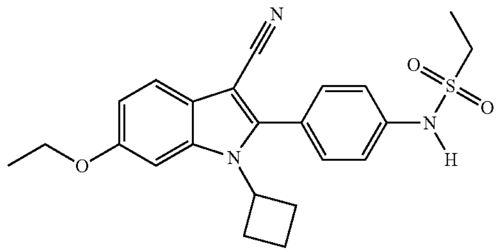
473
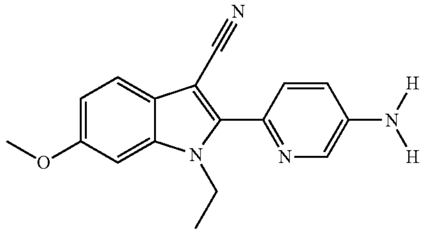
475
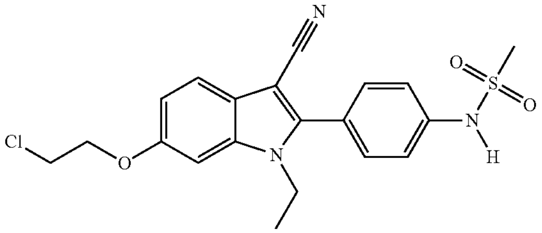
477
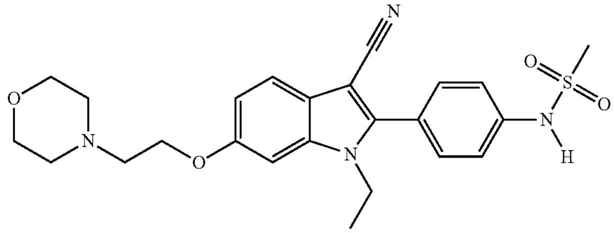
478
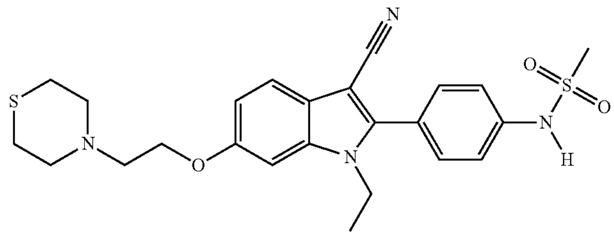
480

TABLE B-continued
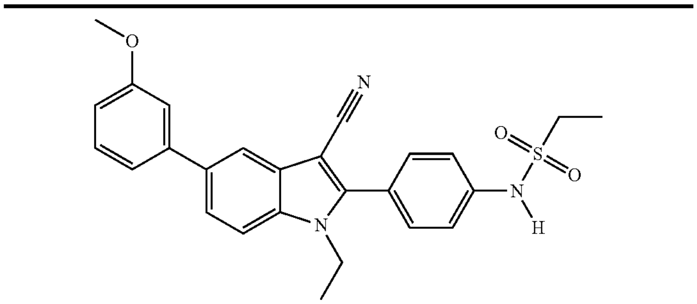
488
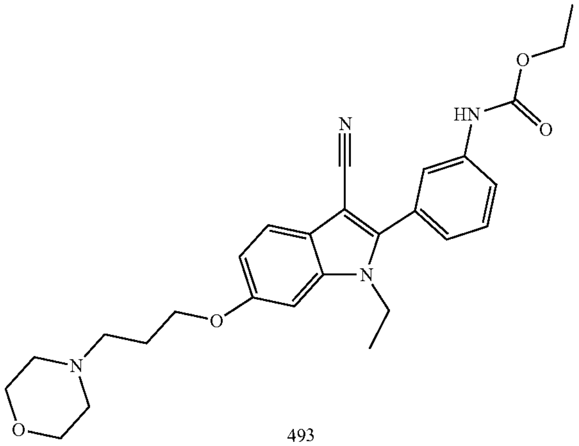
493
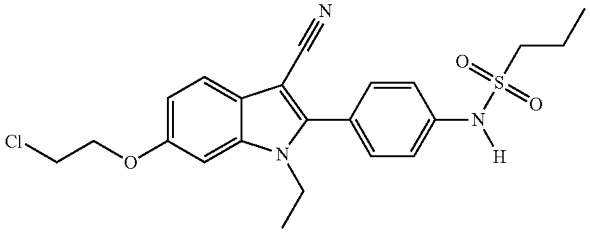
495
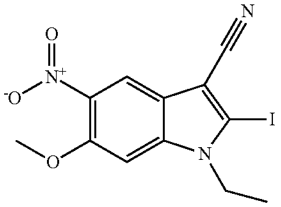
499
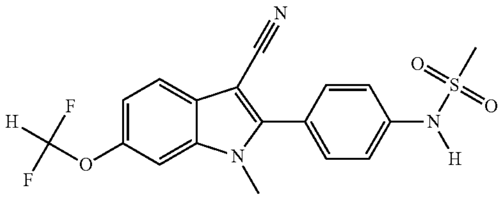
518

TABLE B-continued
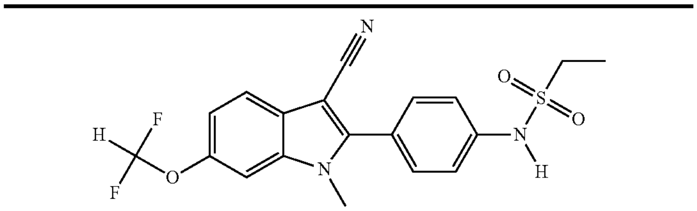
519
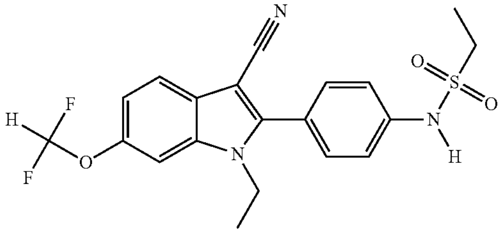
520
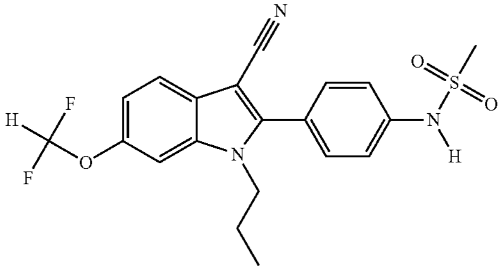
521
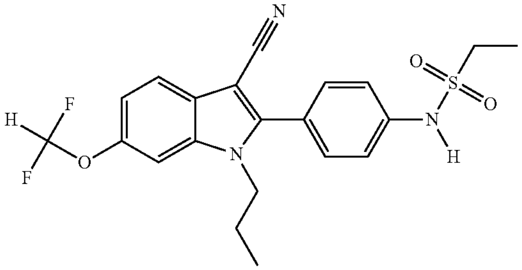
522
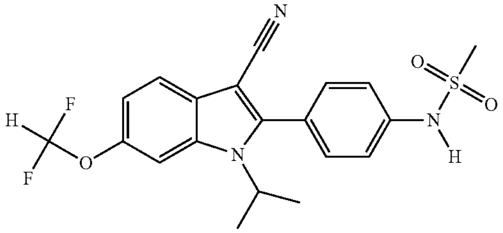
523

TABLE B-continued
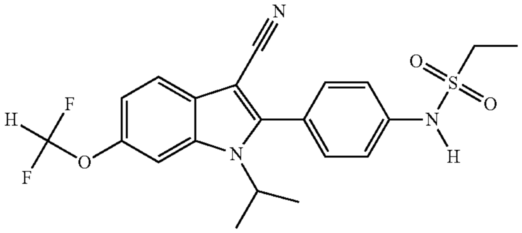
524
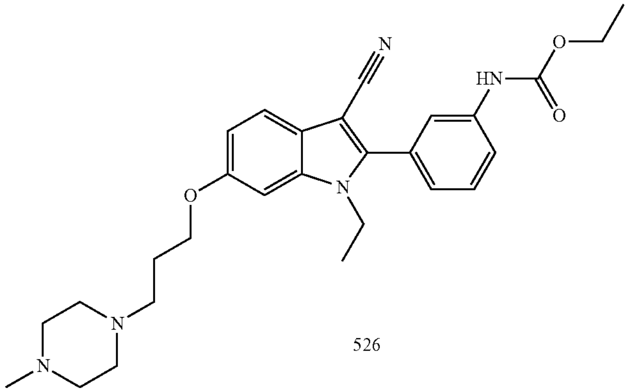
526
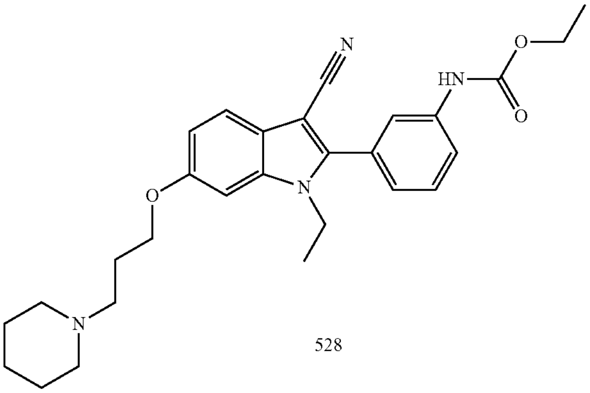
528
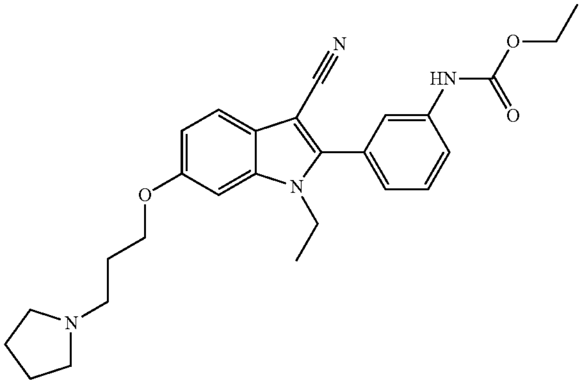
530

TABLE B-continued
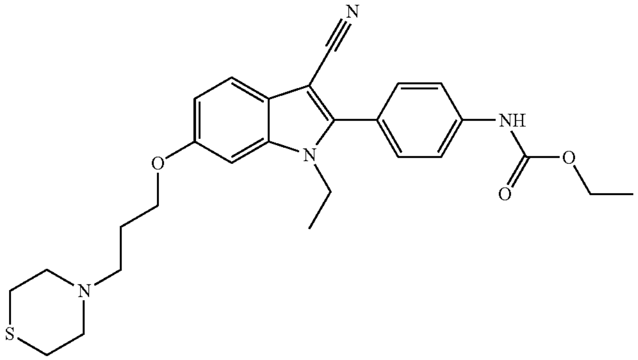
534
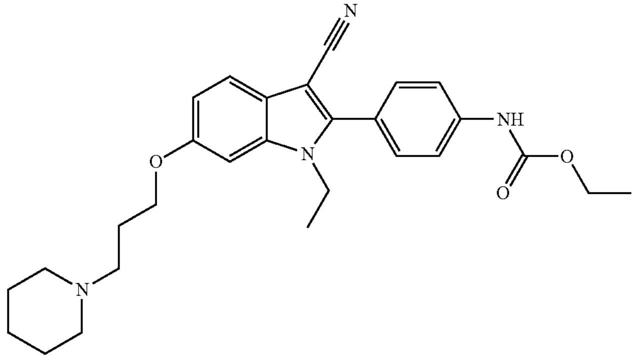
535
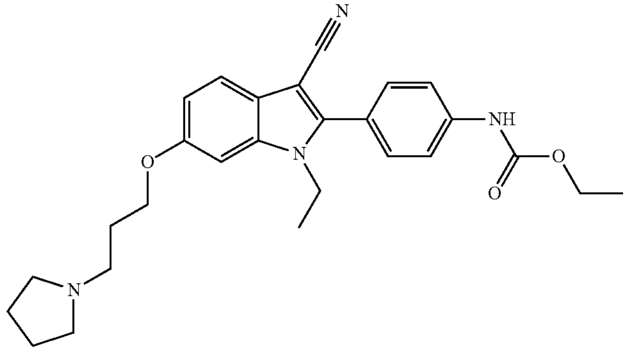
537

TABLE B-continued
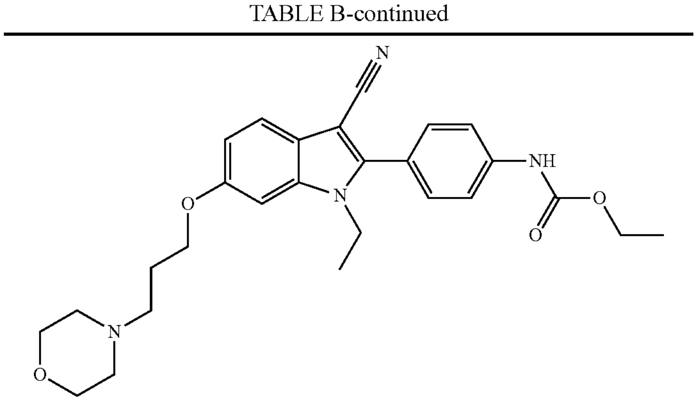
539
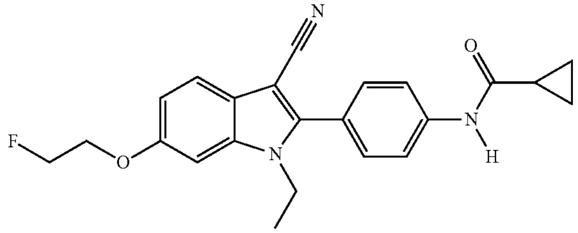
544
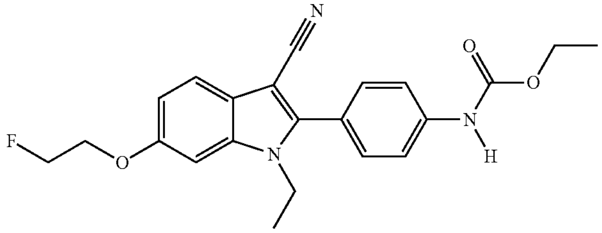
546
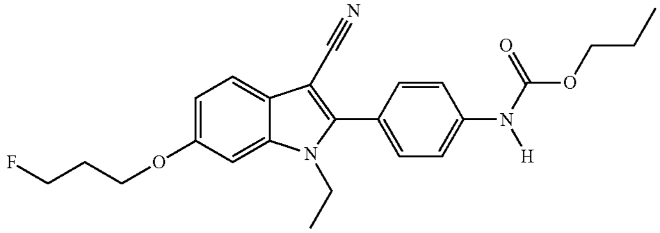
547
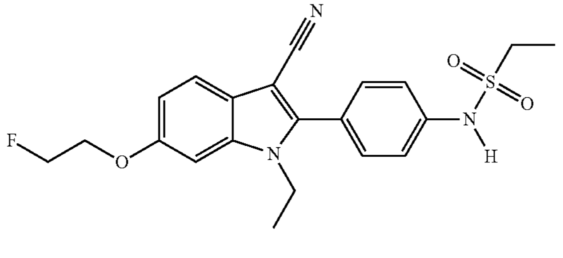
549

TABLE B-continued
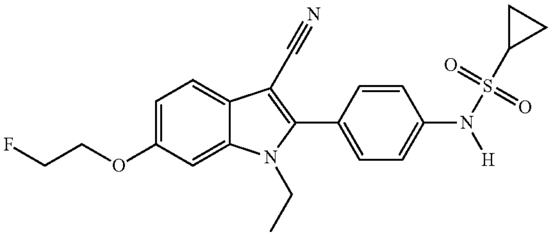
552
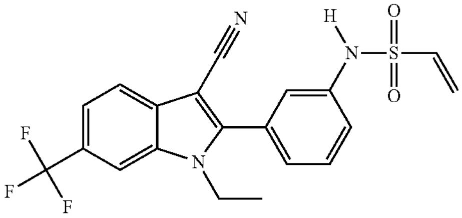
562
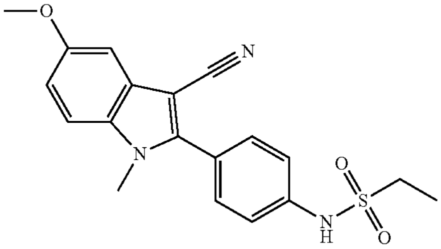
580
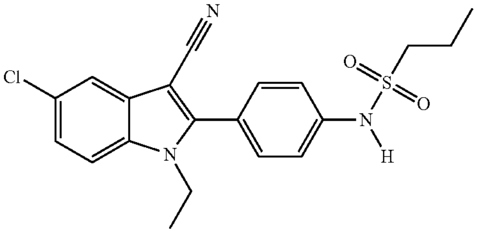
601
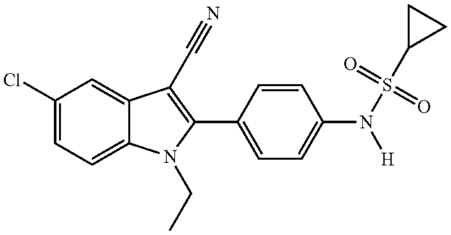
602

TABLE B-continued
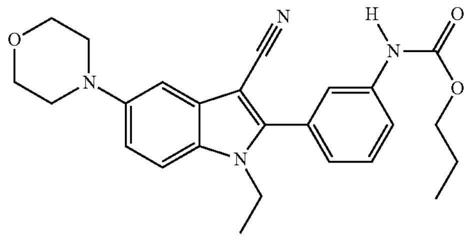
606
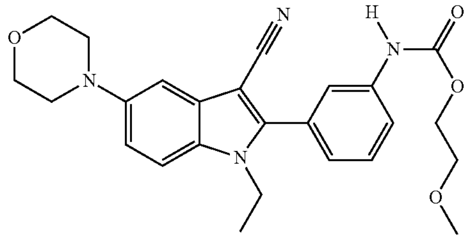
607
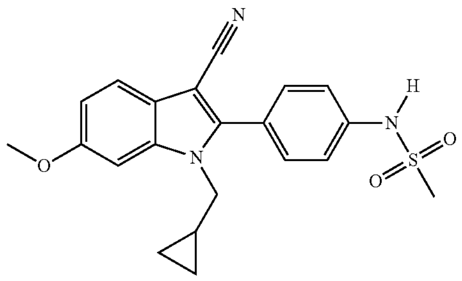
611
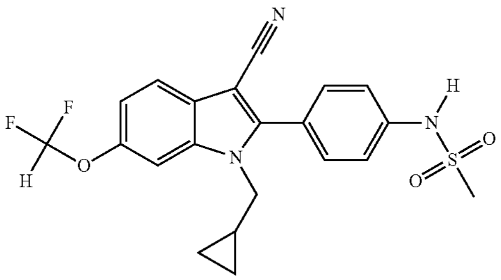
613
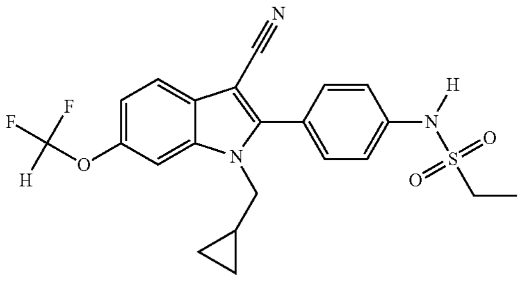
614

TABLE B-continued
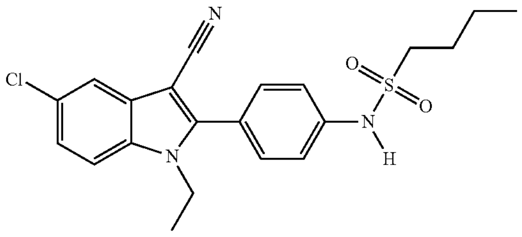
616
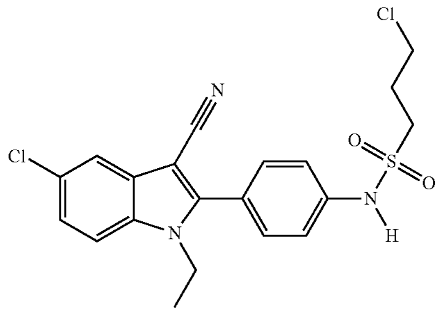
617
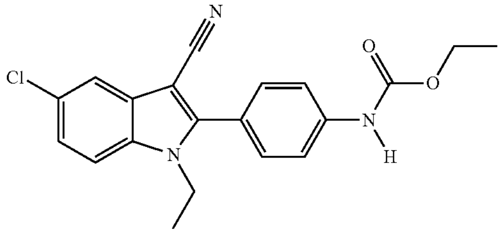
618
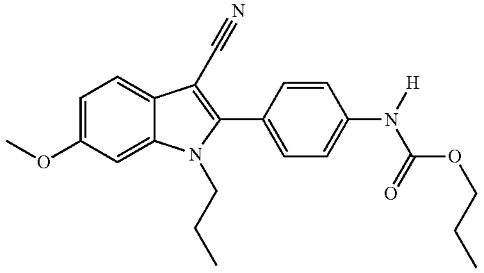
625
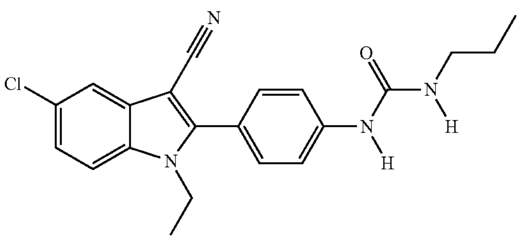
627

TABLE B-continued
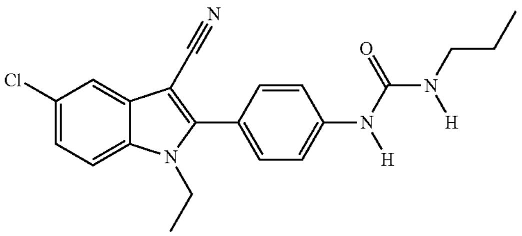
628
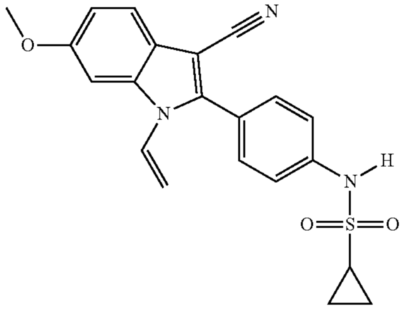
635
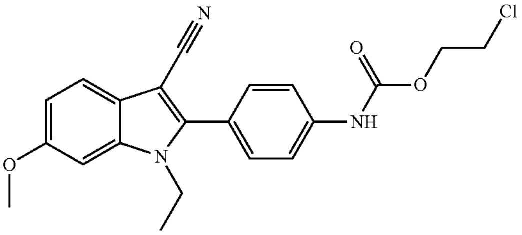
637
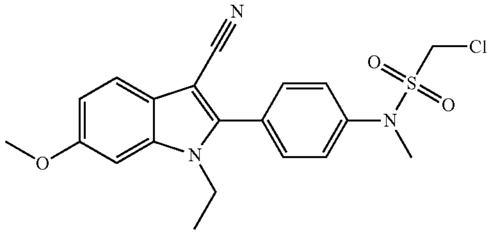
652
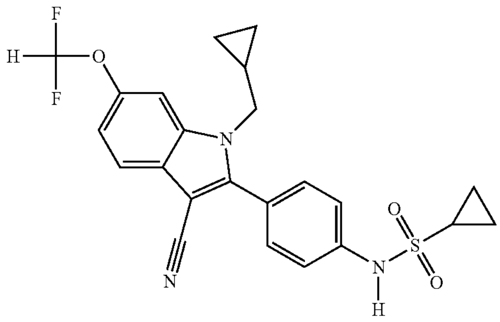
661

TABLE B-continued
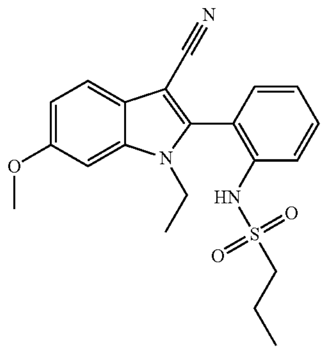
662
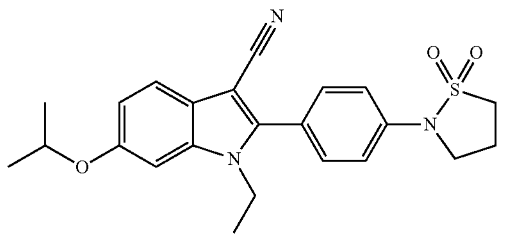
666
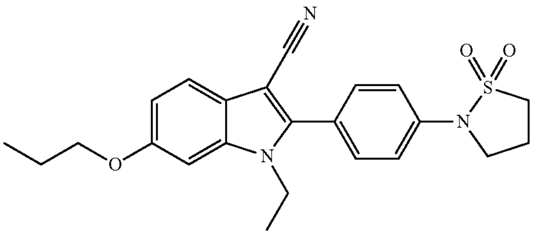
667
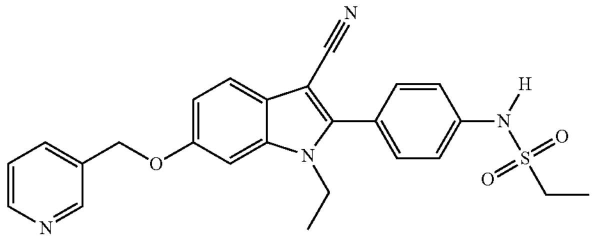
669
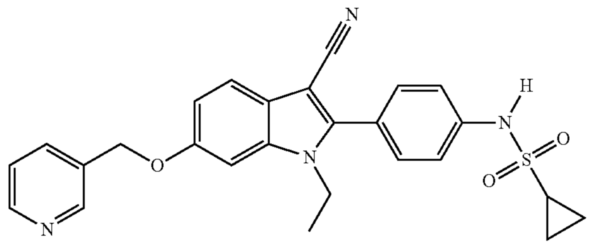
670

TABLE B-continued
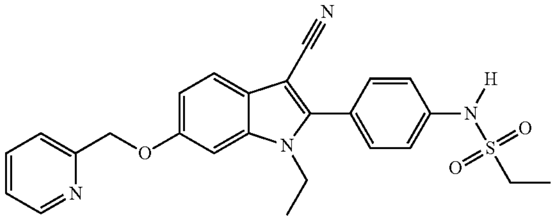
671
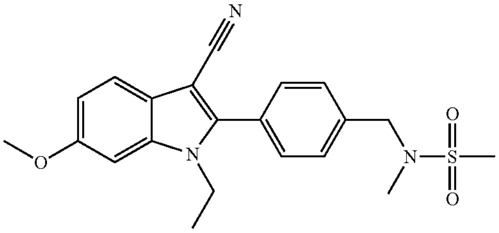
672
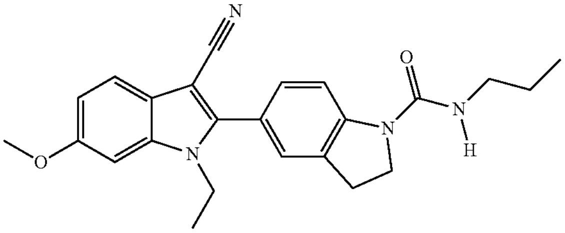
680
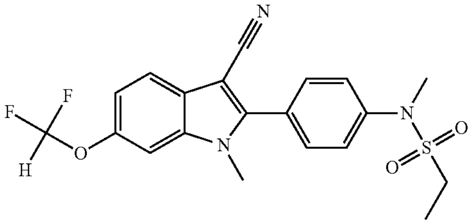
687
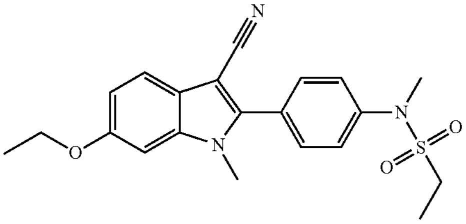
692

TABLE B-continued
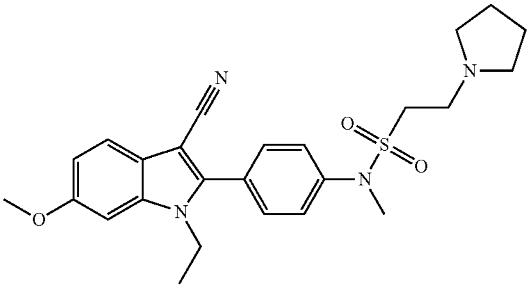
697
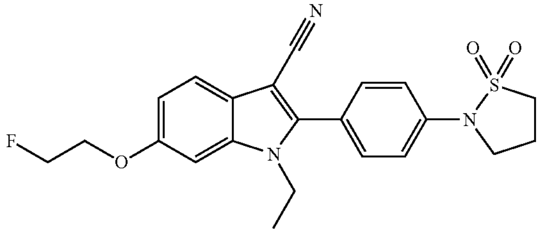
699
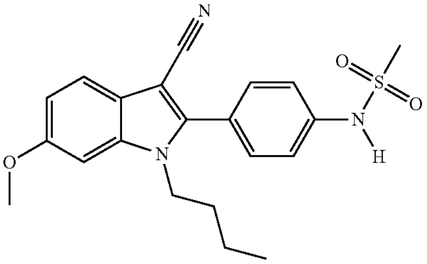
706
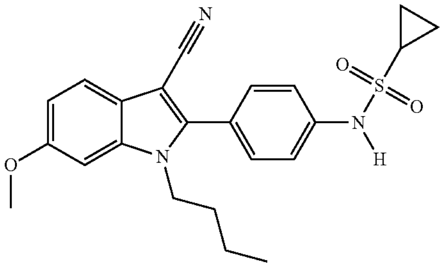
709
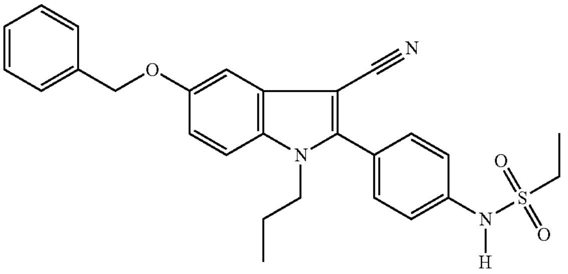
713

TABLE B-continued
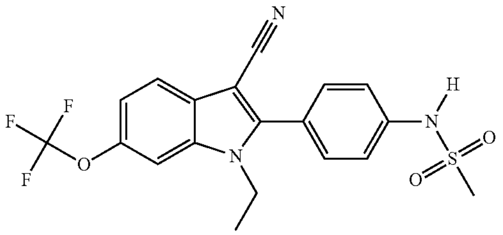
715
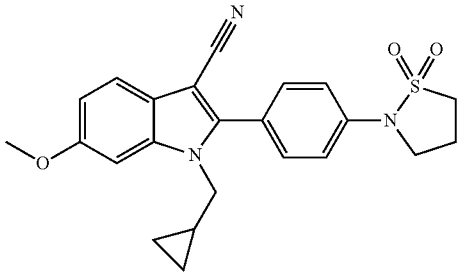
716
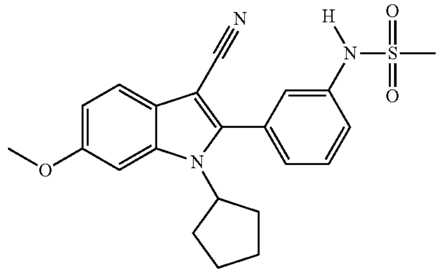
720
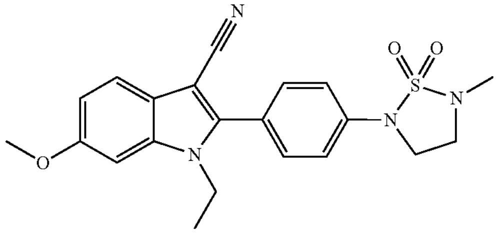
726
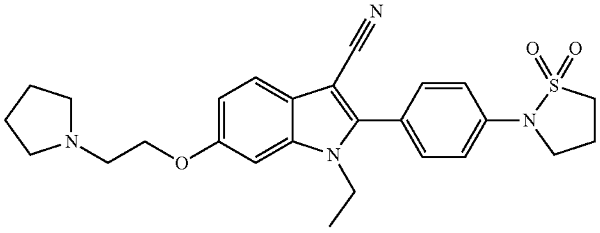
728

TABLE B-continued
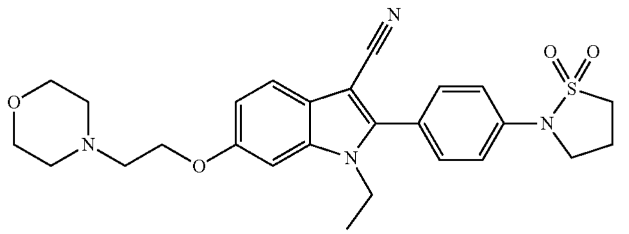
730
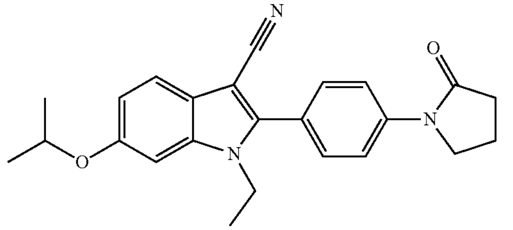
731
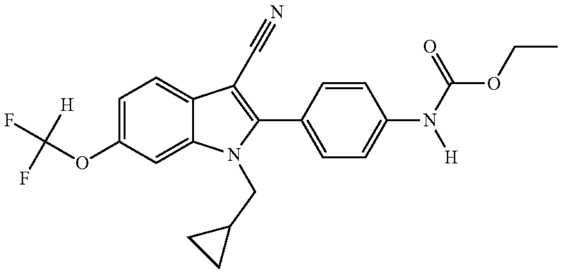
735
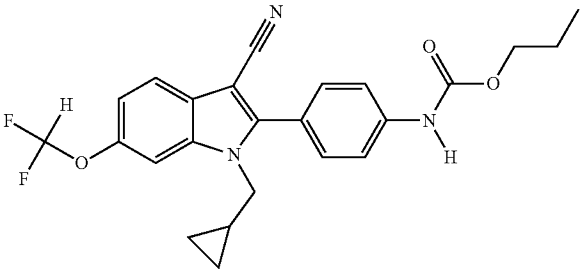
736
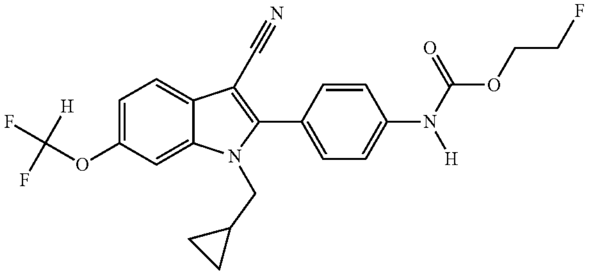
738

TABLE B-continued
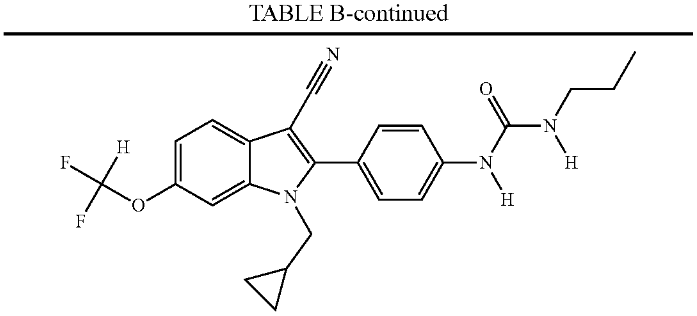
741
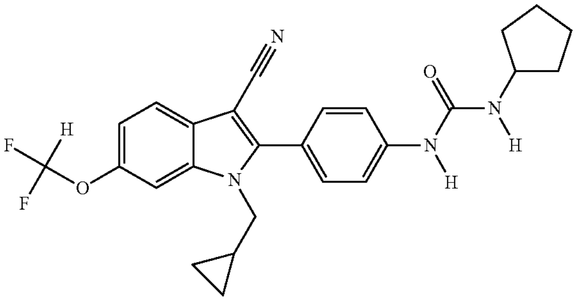
743
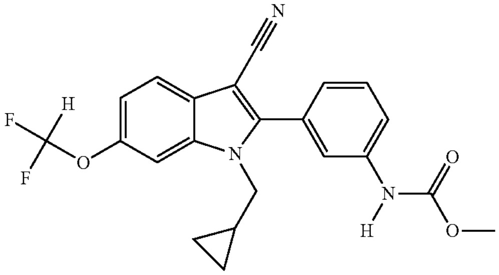
744
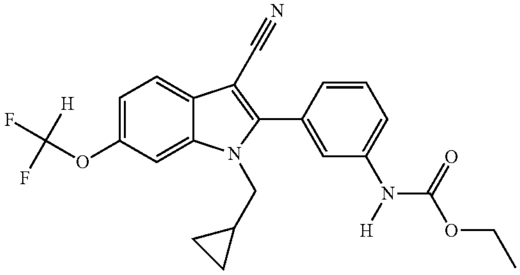
745
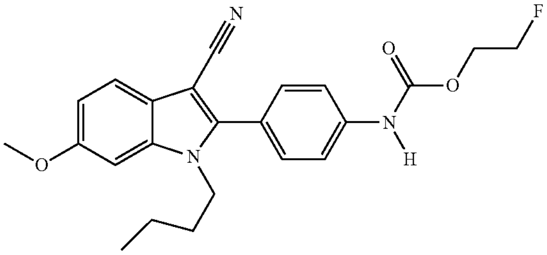
747

TABLE B-continued
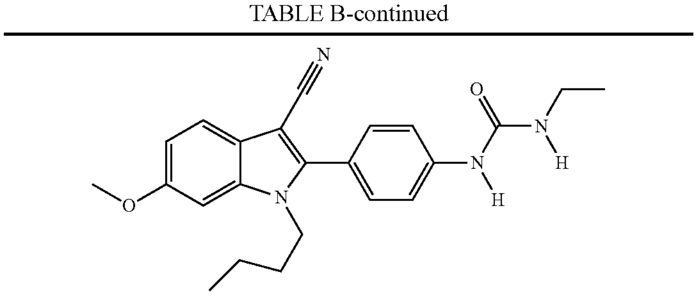
748
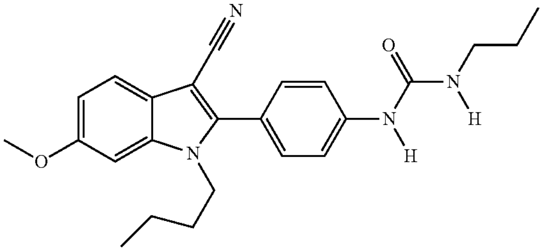
749
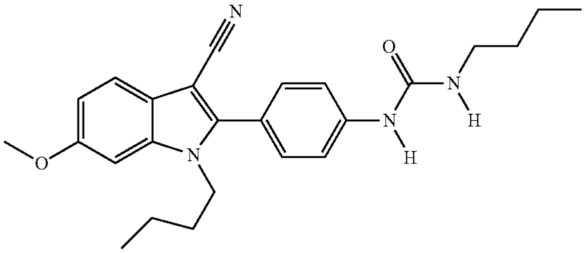
750
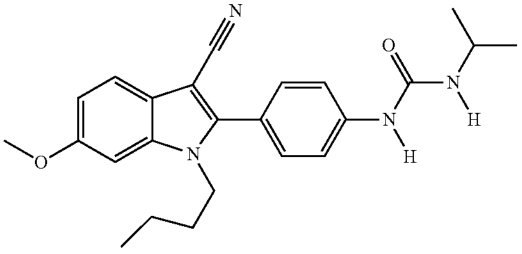
751
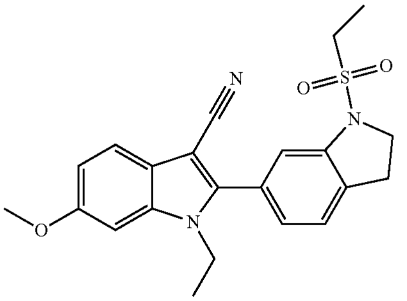
753

TABLE B-continued
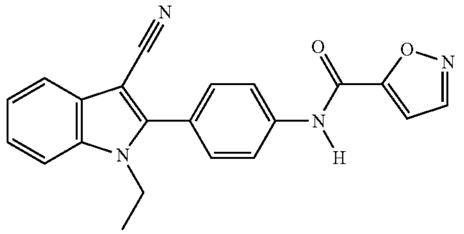
755
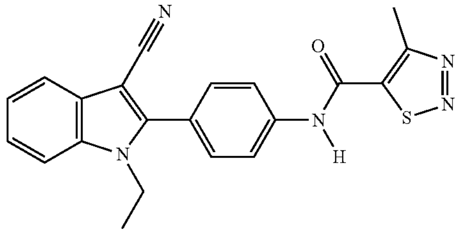
756
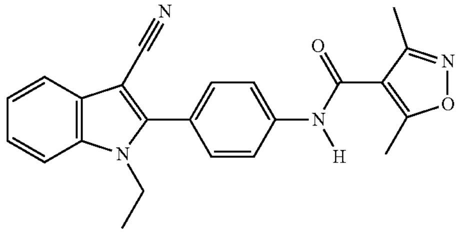
757
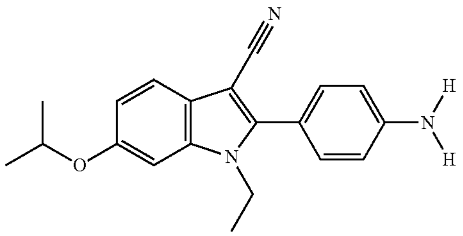
758
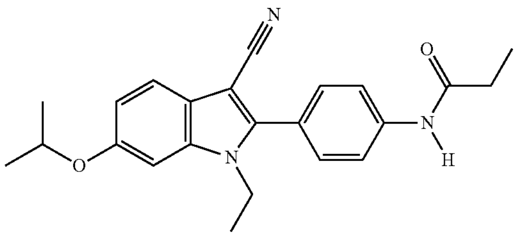
759

TABLE B-continued
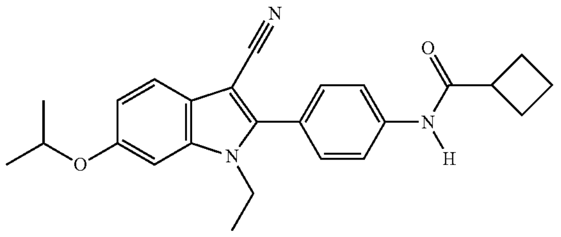
760
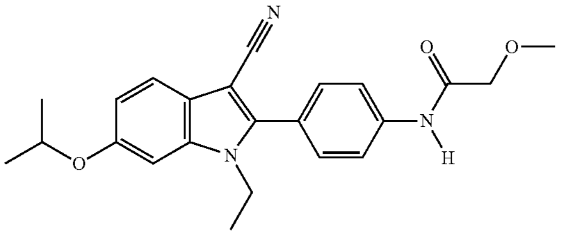
761
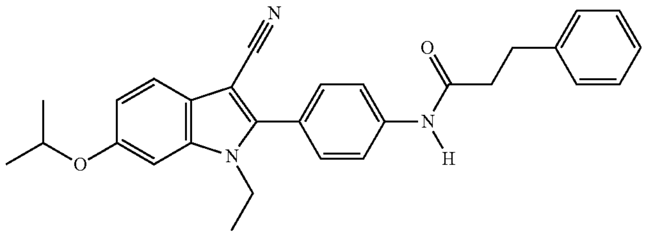
762
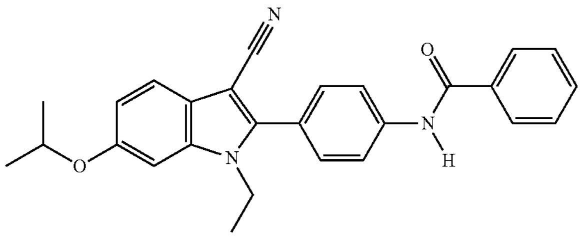
763
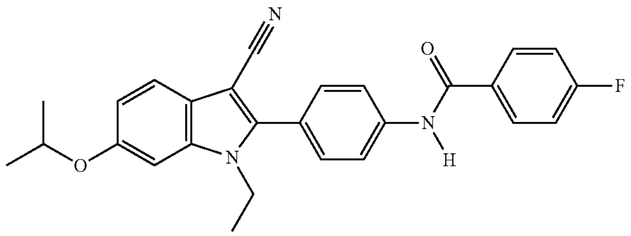
764

TABLE B-continued
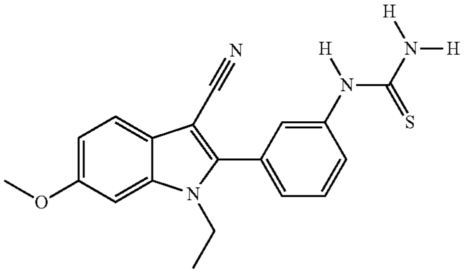
767
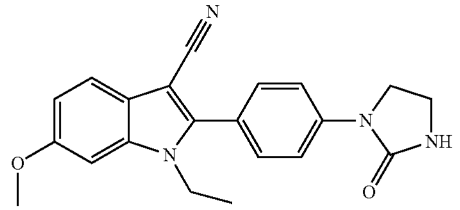
771
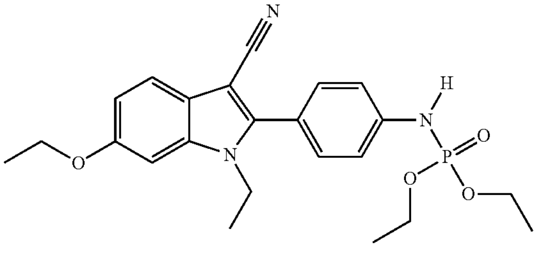
772
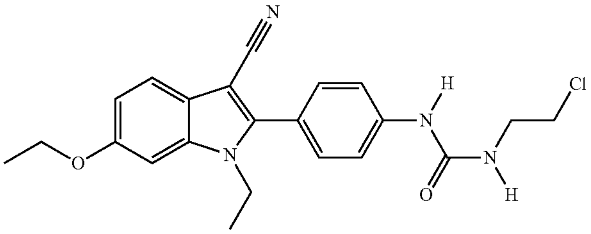
774
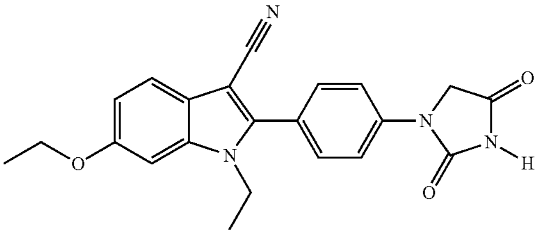
776

TABLE B-continued
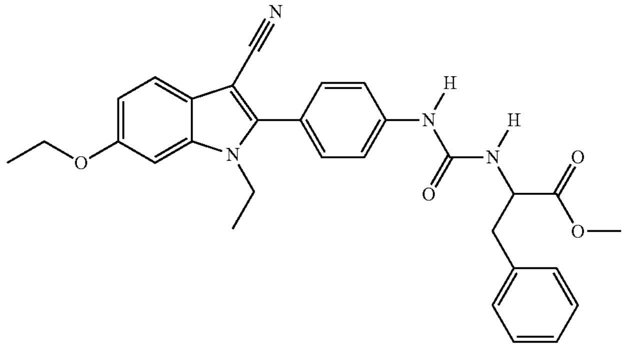
777
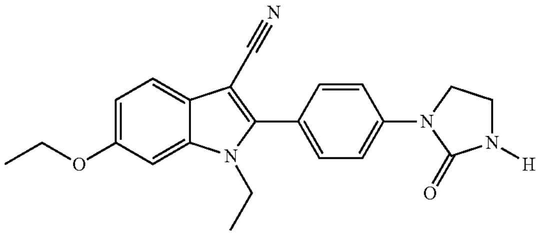
778
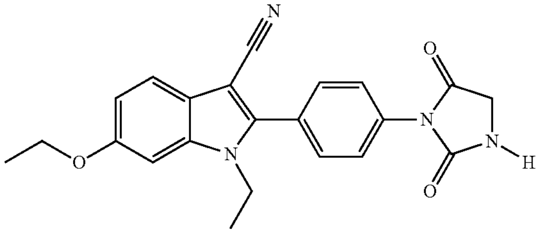
779
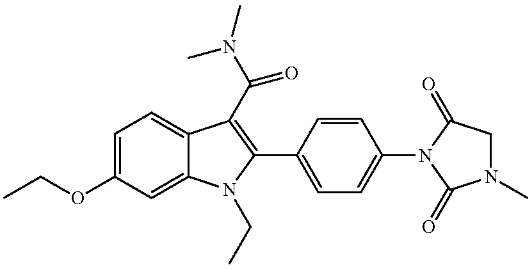
781

TABLE B-continued
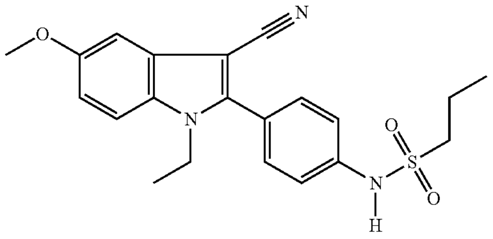
789
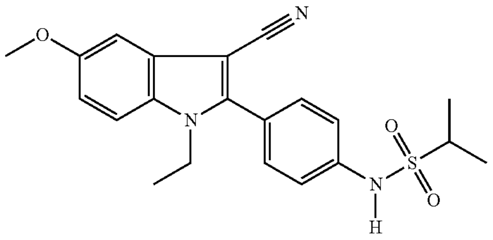
790
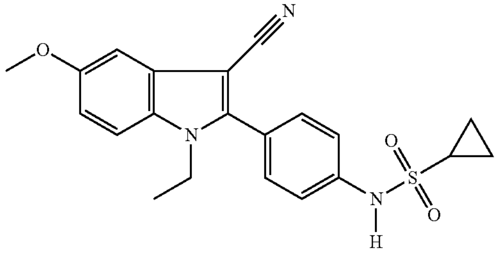
791
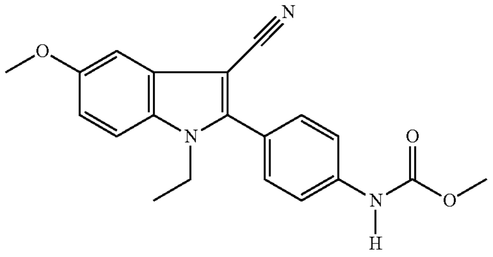
792
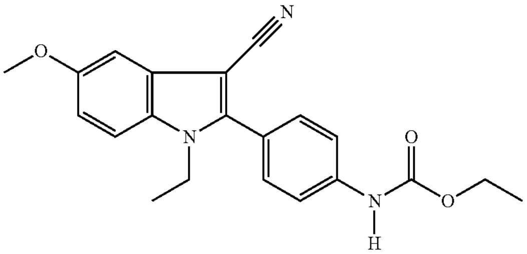
793

TABLE B-continued
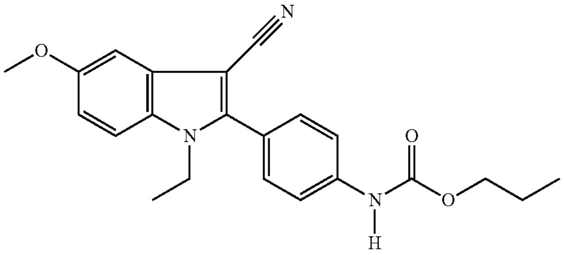
794
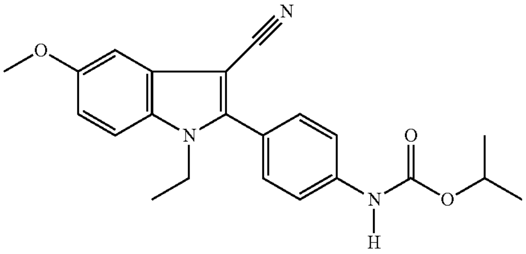
795
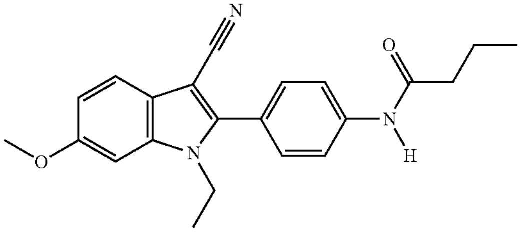
799
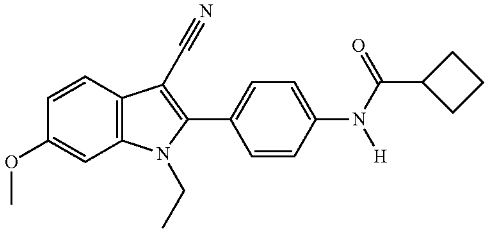
801
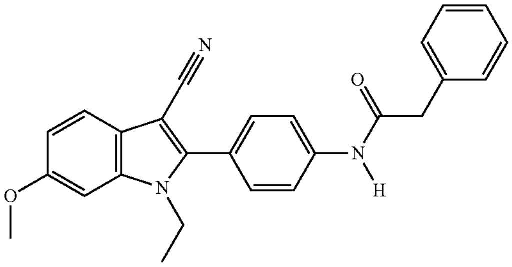
802

TABLE B-continued
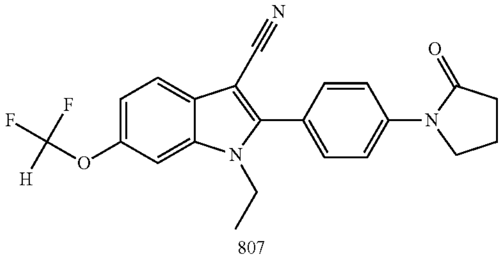
807
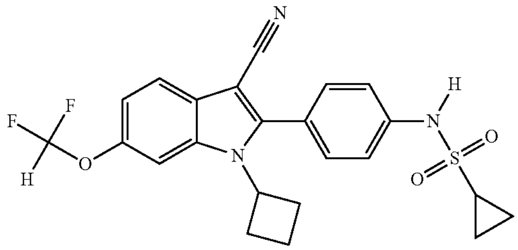
813
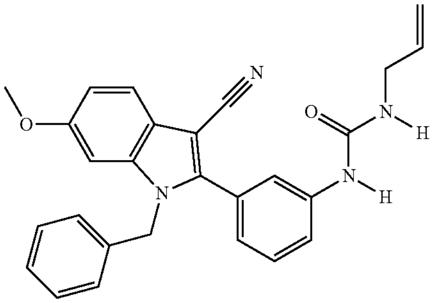
818
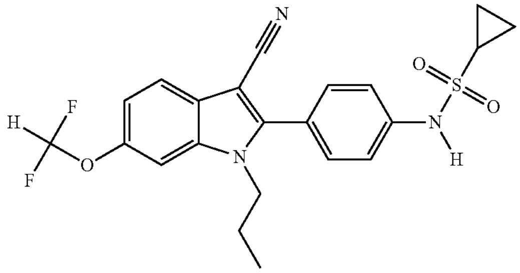
827
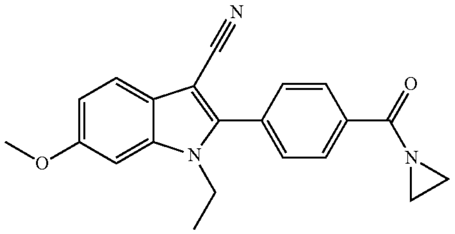
853

TABLE B-continued

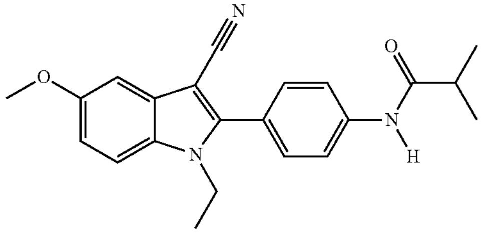

858

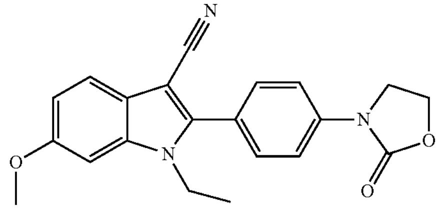

863

B. Preparation of Compounds of the Invention

Indole compounds of the present invention can be obtained via standard, well-known synthetic methodology. Many of the indole starting materials can be prepared the routes described below or by those skilled in the art.

Compounds of formula I, represented by structure II can be prepared by the methodology depicted in Scheme A below:

An α-nitroketone derivative A2 can be derived from treatment of the anion of nitromethane, obtained from the treatment of nitromethane with a base, such as, e.g., sodium or potassium t-butoxide or sodium hydride, with an activated carboxylic acid derivative, e.g., the acyl imidazolide A1. Reaction of the α-nitroketone A2 with amine derivative A3 can afford the nitro enamine A4 by mixing the components A3 and A4 and heating in a suitable solvent such as an alcohol or an aprotic solvent. Treatment of the nitro enamine A4 with quinone A5 in a polar protic solvent such as acetic acid at or near ambient temerature gives the compound of formula II.

I. Scheme A

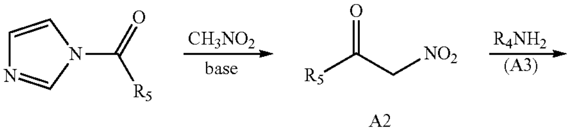

A1

A2

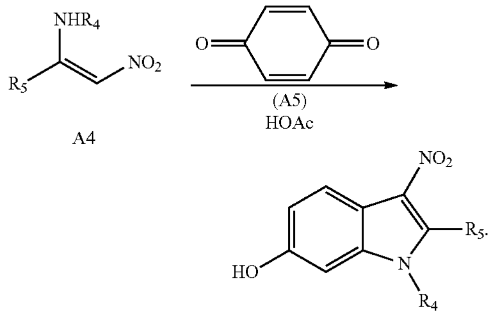

A4

II

Compounds of formula I, represented by structure III can be prepared as shown in Scheme B below:

Treatment of B1 with a reactive alkyl or aryl group containing a leaving group L in a suitable solvent, with or without heat in the presence of a base, such an inorganic base, e.g., sodium or potassium carbonate or an organic base, e.g., triethylamine, can afford the compound of structure III. Examples of leaving groups include but are not limited to halogens (e.g., chlorine, bromine or iodine) or alkyl or arylsulfonates.

II. Scheme B

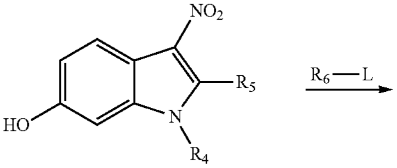

B1

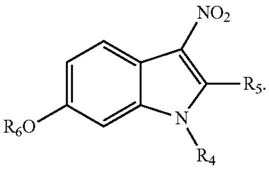

III

Compounds of formula I, represented by structure IV can be prepared as shown in Scheme C below:

Compounds of structure IV can be obtained by nitrating an indole of structure C1, to give the 3-nitroindole C2. The nitration can be carried out by treatment of C1 with a nitrating agent, such as nitric acid or sodium nitrite in a solvent such as acetic acid, acetic anhydride, sulfuric acid or in a mixed solvent system containing an organic solvent such as dichloromethane. The reaction can be carried out a temperature of −30° C. to +50° C. Treatment of C2 with a reactive functional group $R_9$ containing a suitable leaving group L (C3) can give compounds of structure IV. Reactive functional groups can consist of but are not limited to alkyl and aralkyl. L can represent a halide, particularly chloro, bromo or iodo or an alkylsulfonate. The reaction between C2 and C3 can be carried out in a suitable solvent in the presence of an inorganic base such as potassium carbonate or sodium hydride or an organic base such as a trialkylamine. Alternatively, the group $R_9$ can represent an aryl or heteroaryl group and L can represent a halide, particularly chloro, bromo or iodo. The reaction can be carried out in a polar or nonpolar solvent at a temperature from ambient to 200° C. in the presence of a copper catalyst, e.g., CuI, a base such as $Cs_2CO_3$ or $K_3PO_4$, and optionally an amine ligand such as 1,2-bis(methylamino) ethane or 1,2-cyclohexanediamine.

An alternative pathway is to convert C1 into C4 in similar fashion as described above and then carry out the nitration reaction to afford compounds of structure IV.

III. Scheme C

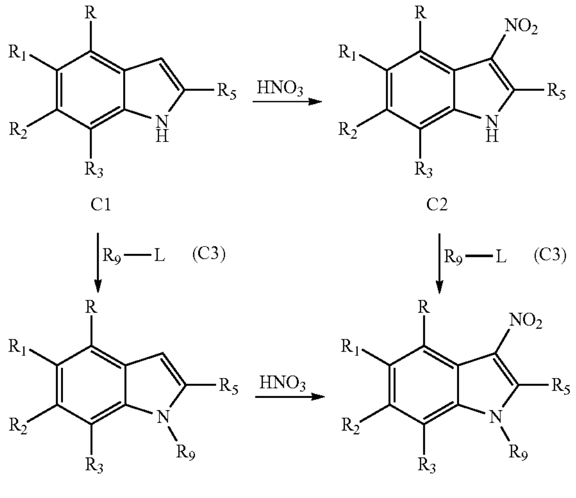

C1 C2 C4 IV

Compounds of formula I, represented by structure V can be prepared as shown in Scheme D.

Treatment of β-ketoesters of structure D1 with amines D2 gives the amino crotonate derivatives D3 by heating in a suitable solvent such as an alcohol or an aprotic solvent. Reaction between D3 and quinone D4 in a polar protic solvent, such as acetic acid gives compounds of structure V.

IV. Scheme D

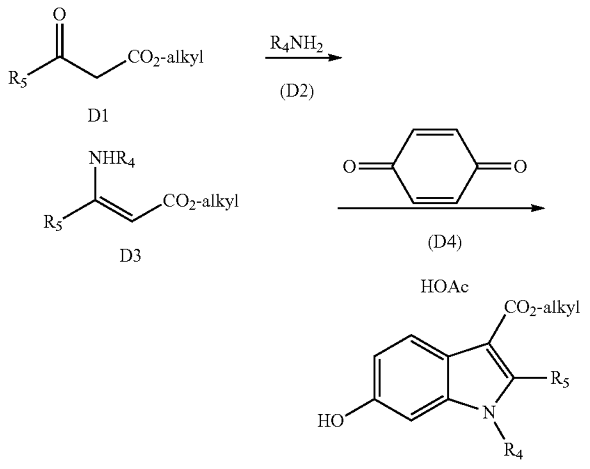

D1 D3 V

Compounds of the present invention, represented by structure VI compounds can be prepared by the chemistry described in scheme E below.

Indole-3-carboxylic esters E1 can be converted to indole-3-carboxylic acids E2 by treatment of compounds of structure E1 with, for example, either acid or base in aqueous or mixed aqueous-organic solvents at ambient or elevated temperature or by treatment with nucleophilic agents, for example, boron tribromide or trimethylsilyl iodide, in a suitable solvent. Compounds of type E2 can then be activated and treated with amines of type E3 to give compounds E4. Activation of the carboxylic acid can be carried out, for example, by any of the standard methods. For example, the acid E2 can be activated with coupling reagents such as EDCI or DCC with or without HOBt in the presence of the amine E3, or alternatively the acid can be activated as the acid chloride by treatment of the acid with, e.g., thionyl chloride or oxalyl chloride or as the acyl imidazolide, obtained by treatment of the acid with carbonyl diimidazole, followed by treatment of the amine E3. Compounds E4 can be converted to compounds of structure VI by treatment of E4 with a reactive functional group $R_9$ containing a suitable leaving group L (E5) as described previously. Alternatively, compounds of type E1 can be converted to compounds of structure E6 by treatment with E5. Indole-3-carboxylic esters E6 can then be converted to indole-3-carboxylic acids E7 by the methods described above. Conversion of E7 to compounds of structure VI can be carried out by the activation and reaction with an amine E3 as described above.

V. Scheme E

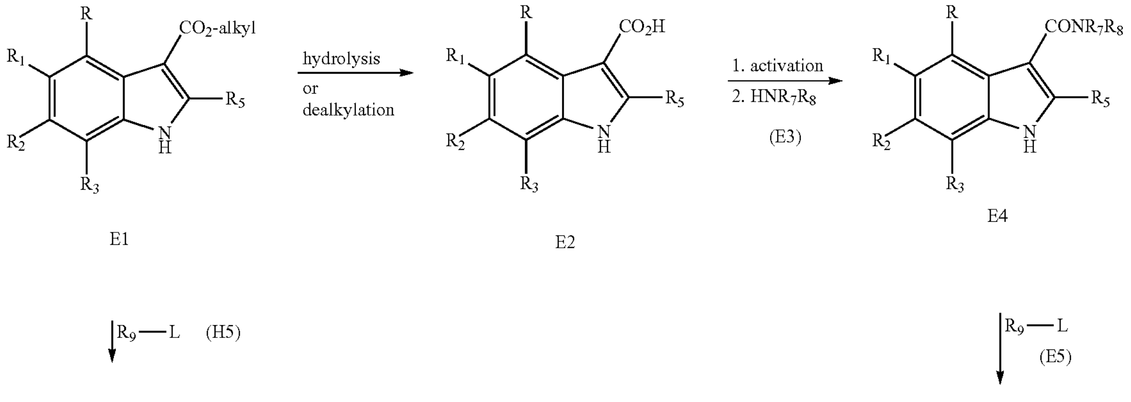

E1 E2 E4

-continued

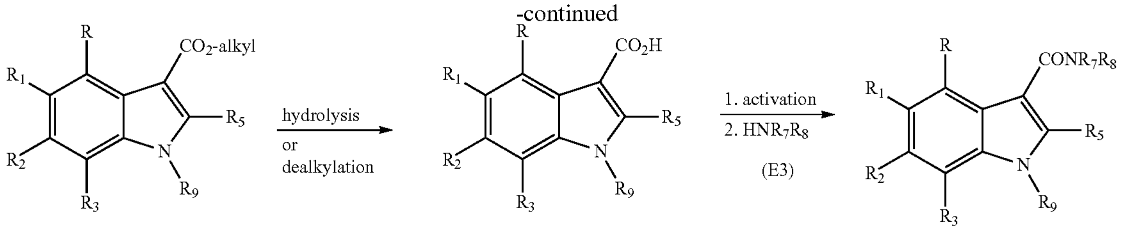

E6 E7 VI

Compounds of the present invention, represented by structure VII compounds can be prepared by the chemistry described in scheme F below.

Indoles F1 can be formylated with reagents such as phosphorous oxychloride in the presence of DMF to give the indole-3-carboxaldehydes F2. Conversion to compounds of structure VII can be accomplished by treatment of F2 with compounds F3 as described previously. Alternatively, compounds of type F1 can first be converted to F4 and then be formylated to compounds of structure VII.

VI. Scheme F

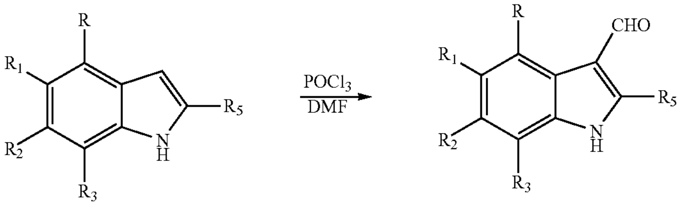

F1 F2

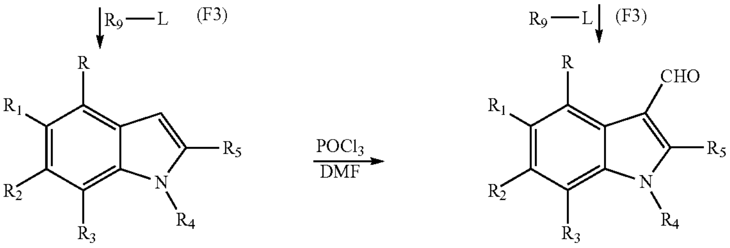

F4 VII

Compounds of formula G, represented by structure VIII can be prepared as shown in Scheme G.

Indole-3-carboxaldehydes of structure G1 can be converted to the indole-3-carboxylic acid derivatives by oxidation with reagents such as potassium permanganate under aqueous conditions.

VII. Scheme G

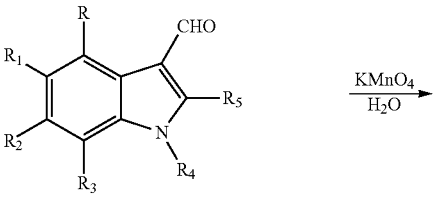

G1

-continued

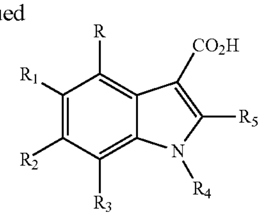

VIII

Compounds of formula H, represented by structure IX can be prepared as shown in Scheme H.

Indole-3-carboxaldehydes of structure H1 can be converted to the indole-3-carbonitrile derivatives H2 by a variety of methods. Treatment of H1 with a nitroalkane, e.g., nitropropane, in the presence of an amine source, e.g., ammonium hydrogen phosphate gives the indole-3-carbonitrile H2 derivative. An alternative pathway to compound H2 is via the intermediate H3. Conversion of H1 to the oxime derivative H3 can be followed by dehydration, e.g., treatment of the oxime with acetic anhydride and a base, or reaction of the oxime with thionyl chloride to give H2. The compound H2 can then be reacted with a reactive functional group $R_9$ containing a suitable leaving group L (H4) as described previously to afford compounds of structure IX.

Alternatively, H1 can be reacted with a reactive functional group $R_9$ containing a suitable leaving group L (H4) to give the intermediate H5 which can be reacted with a nitroalkane as above to give the indole-3-carbonitrile IX compound. Compound IX can also be obtained by conversion to the oxime H6 followed by a dehydration reaction as described above.

Compounds of the present invention, represented by structure X can also be prepared as described in scheme I below.

Indoles I1 can be cyanated with an appropriate cyanating agent, e.g., chlorosulfonyl isocyanate (I2) or a dialkyl phosphoryl isocyanate in a suitable solvent or solvent mixture, e.g. DMF, $CH_3CN$ or dioxane, to afford compounds of structure I3. The compound I3 can then be reacted with a reactive functional group $R_9$ containing a suitable leaving group L (I4) as described previously afford the compound X.

Alternatively, compound I1 can be reacted with a reactive functional group $R_9$ containing a suitable leaving group L to give compounds of structure 15 which can then be cyanated as above to give compounds of formula X.

VIII. Scheme H

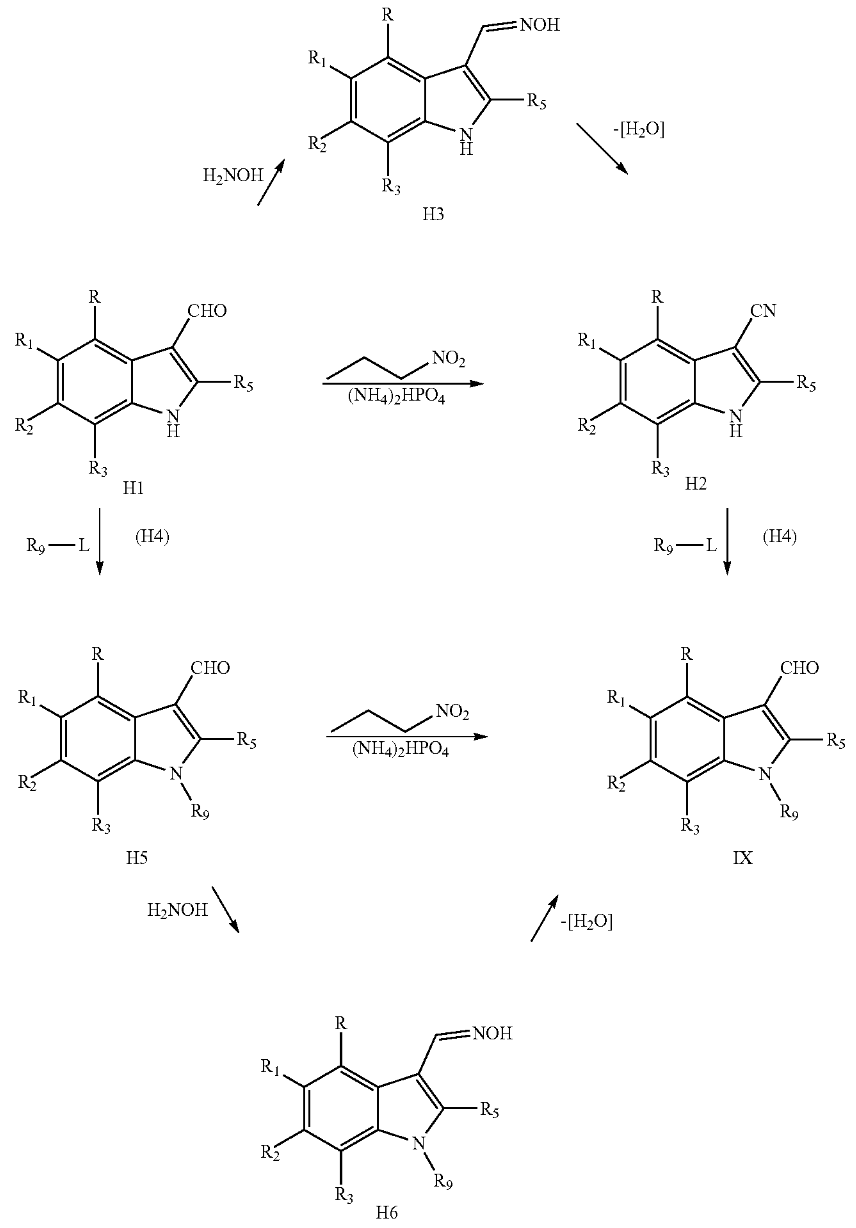

IX. Scheme I

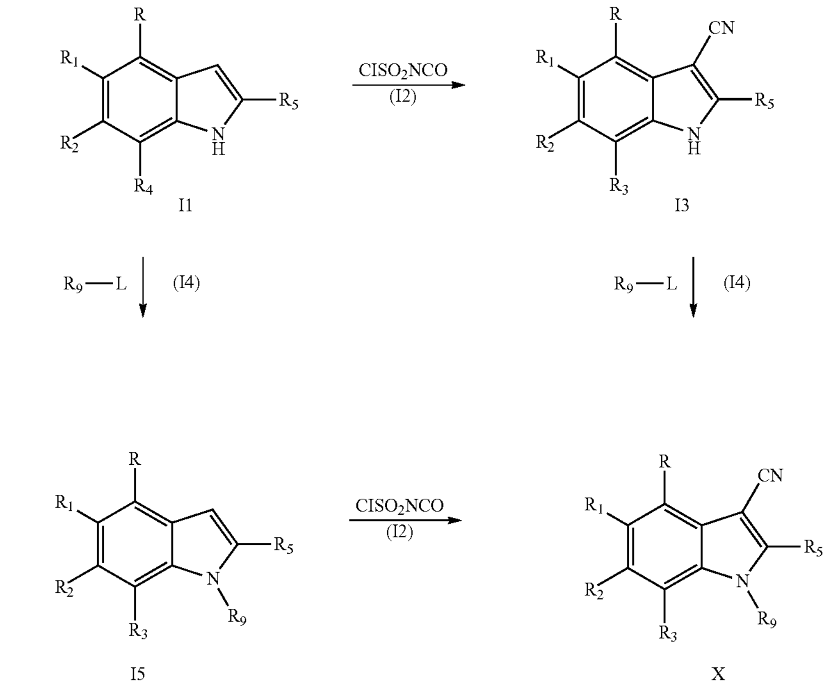

I1 I3 I5 X

Compounds of formula J, represented by structure XI can be prepared as shown in Scheme J.

Amino crotonates J1 can be reacted with amines J2 to give J3. Reaction of J3 with quinone in the presence of a polar, protic solvent, e.g., acetic acid, gives the compound of structure XI.

X. Scheme J

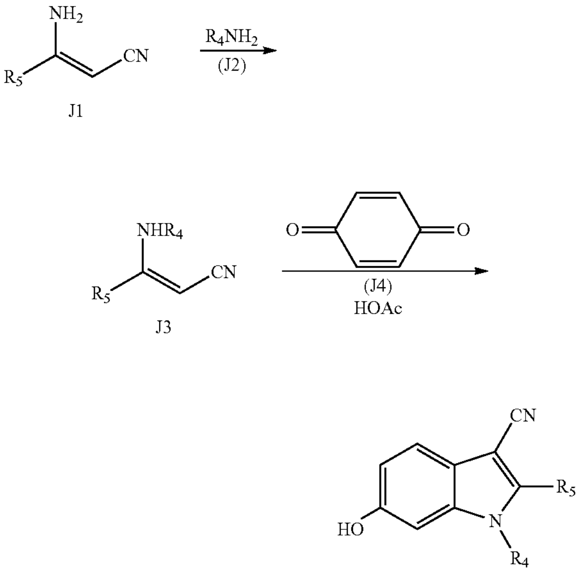

J1 J3 XI

Compounds of the present invention, represented by structure XII and XIII can be prepared as described in scheme K below.

Aldehydes of structure K1 can be reacted with an alkyl azidoacetate K2 by heating the components together in a suitable organic solvent, e.g., a protic or non-protic solvent, in the presence of an organic or inorganic base, to give the α-azidoacrylate K3. Heating K3 in the presence of a suitable non-reactive organic solvent, e.g., toluene or xylenes can give the 2-alkoxycarbonylindoles K4. Reduction of the ester functionality with a suitable reducing reagent, for example, lithium aluminum hydride, in a suitable solvent, e.g., ether or THF can give the intermediate K5. Reaction of K5 with a reactive functional group $R_9$ containing a suitable leaving group L (K6) as described in previously affords the compound K7. Cyanation of K7 with a cyanating agent, e.g., chlorosulfonyl isocyanate as described previously can give compound XII. Alternatively, cyanation of K5 with chlorosulfonyl isocyanate gives K8, which can be reacted with a reactive functional group $R_9$ containing a suitable leaving group L (K6) as described previously, affords, the compound XII.

An alternative use of intermediate K4 is exemplified below. Hydrolysis of the 2-alkoxycarbonyl group of the indole K4 either under acidic or basic conditions followed by decarboxylation can give the intermediate K9. Decarboxylation can be carried out thermally, i.e., heating in an appropriate solvent, e.g., toluene, xylenes, or quinoline. Alternatively, a source of copper can be added, for example, copper bronze, to facilitate decarboxylation. Reaction of K9 with a reactive functional group $R_9$ containing a suitable leaving group L (K6) as described above can afford the compounds K10. Cyanation of K10 with a cyanating agent, e.g., chlorosulfonyl isocyanate as described previously can give compound XIII. Alternatively, cyanation of K9 with chlorosulfonyl isocyanate gives K11, which can be reacted with a reactive functional group $R_9$ containing a suitable leaving group L (K6) as described in previously, affords the compound XIII.

XI. Scheme K

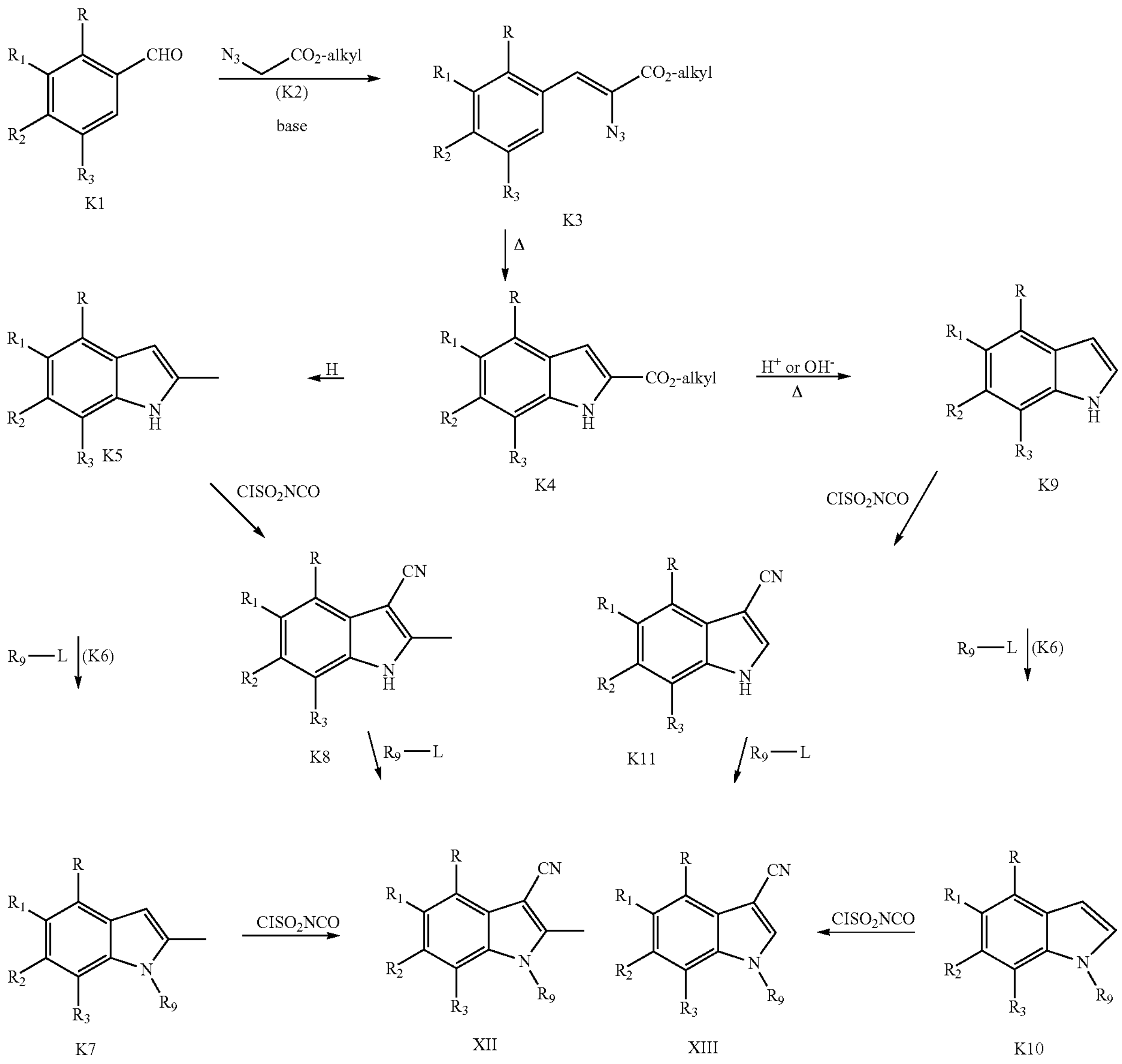

Compounds of formula L, represented by structure XIV can be prepared as shown in Scheme L.

Compounds of formula L1 can be halogenated on the 2-methyl group to give 2-bromomethyl or chloromethyl indoles L2. The halogenation reaction can be conducted with reagents, e.g., N-bromo- or chlorosuccinimide. The reaction can be conducted in a suitable solvent, such as chloroform, carbon tetrachloride, or THF and carried out in a range between ambient temperature and 80° C. Optionally, a radical initiator may be added, e.g., benzoyl peroxide or AIBN. The compound L2 can then be reacted with a nucleophile $R_5$—W (L3) to give compounds of structure XIV. The reaction can be conducted in a suitable solvent, e.g., THF, $CH_2Cl_2$ or DMF, within a temperature range of 0° C. to 120° C. A base, e.g., an inorganic base, such as potassium carbonate or an organic base, such as a trialkylamine can be used to remove the acid formed in the reaction. The group W can refer to an N, O or S atom.

XII. Scheme L

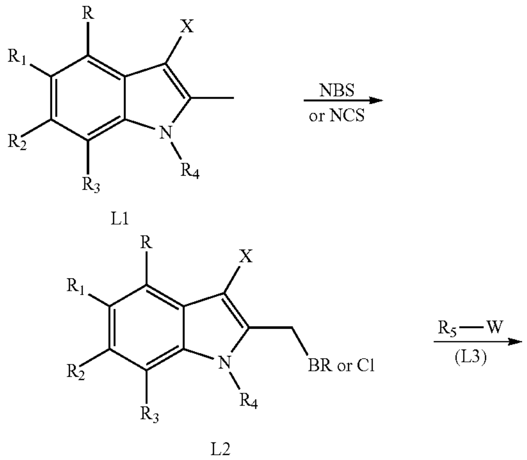

-continued

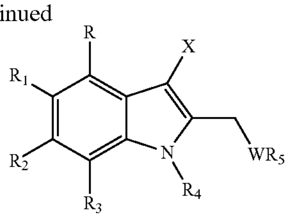

XIV

Compounds of the present invention, represented by structure XV can be prepared as described in scheme M below.

Anilines of structure M1 can be diazotized and the resulting diazonium salt can be reduced to give the phenyl hydrazine compound M2. Reaction between the hydrazine M2 and a ketone M3 under acidic conditions can give the indole compound M4. The conditions for the cyclization reaction can be carried out under typical conditions utilized by one skilled in the art, for example, acidic conditions, utilizing acids such as a Bronstead acid ,e.g., acetic acid, hydrochloric acid or polyphosphoric acid or a Lewis acid, e.g., zinc chloride. The reaction can be carried out in the presence of a co-solvent, e.g., $CH_2Cl_2$ or THF typically within a temperature range of 0° C. to 120° C. Reaction of M4 with a reactive functional group $R_9$ containing a suitable leaving group L (M5) as described previously, can afford compounds M6. Cyanation of the indole M6 with a cyanating agent such as chlorosulfonyl isocyanate can give the compound of structure XV.

Alternatively, the indole M4 can be cyanated to give compounds of structure M7. Reaction of M7 with a reactive functional group $R_9$ containing a suitable leaving group L (M5) as described above can give compounds of structure XV.

XIII. Scheme M

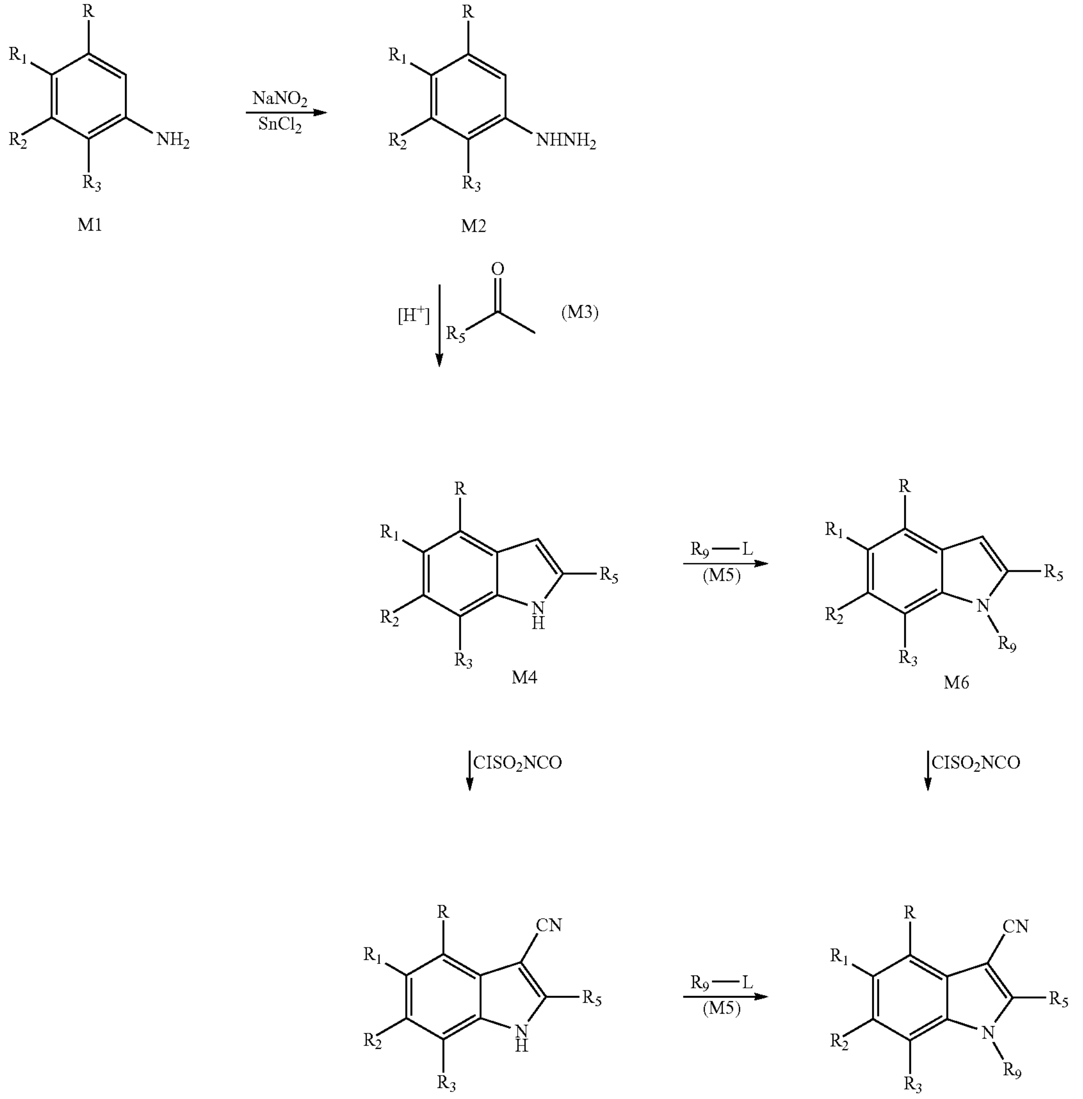

M1, M2, M4, M6, M7, XV

Compounds of formula I, represented by structure XVI can be prepared as shown in Scheme N.

XIV. Scheme N

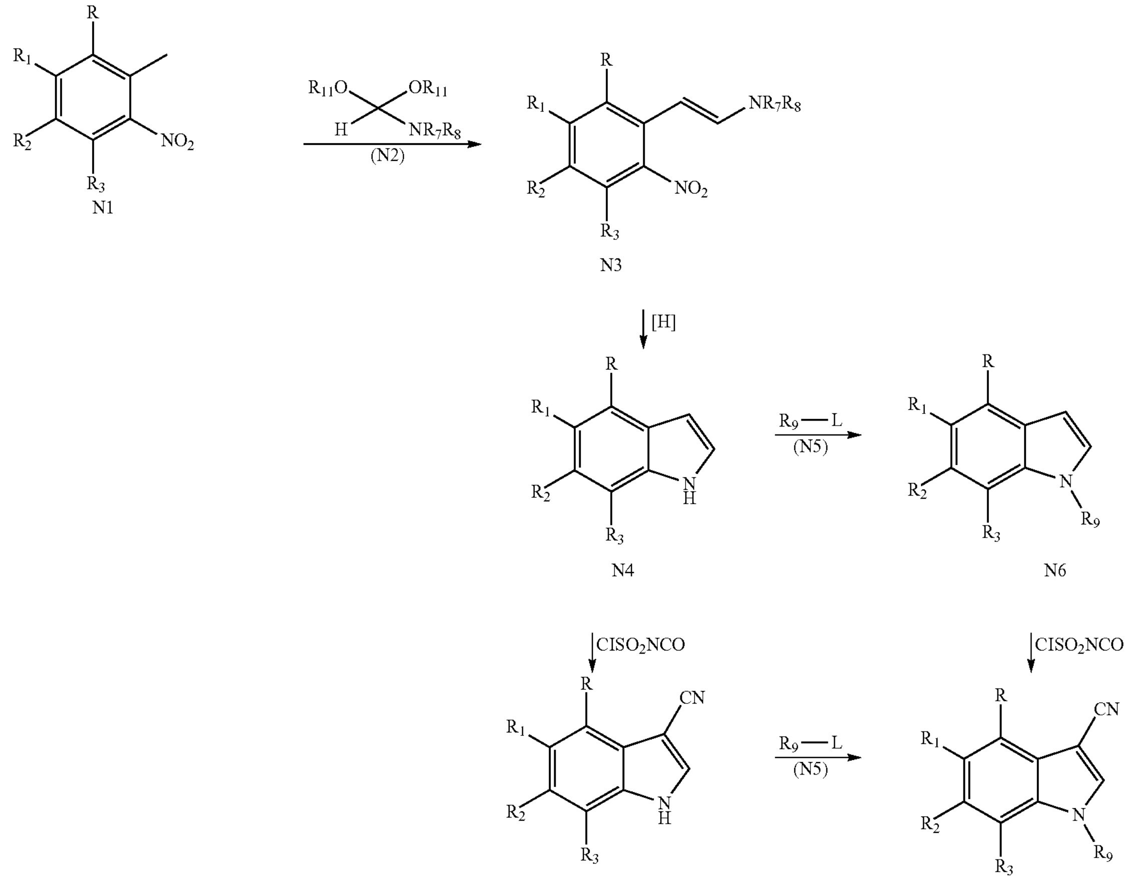

N1
N3
N4
N6
N7
XVI

Compounds of formula N1 can be reacted with a dialkylformamide dialkyl acetal, N2, e.g., dimethylformamide dimethyl acetal, optionally in the presence of a suitable solvent, e.g., DMF or dioxane, at a temperature range from ambient to 150° C. to give the compound of structure N3. Reduction of the nitro group of compounds of type N3 under standard conditions can give the indole compounds of structure N4. The reduction can be carried out via hydrogenation, using a sub-stoichiometric amount of a hydrogenation catalyst, e.g., platinum or palladium, in the presence of a hydrogen source in a protic or aprotic solvent. The reduction can be carried out in a temperature range of ambient to 80° C. Alternatively, the reduction can be carried out via chemical reduction, e.g., in the presence of stoichiometric amounts of Fe or Sn compounds in a suitable solvent at a temperature range of ambient to 100° C. The compound N4 can then be reacted with a reactive functional group $R_9$ containing a suitable leaving group L (N5) as described previously to afford compounds of structure N6. Cyanation of N6 with a cyanating agent such as chlorosulfonyl isocyanate in a suitable solvent can give the compounds of structure XVI.

Alternatively, compounds of structure N4 can be cyanated to give compounds of structure N7. Reaction with N7 with a reactive functional group $R_9$ containing a suitable leaving group L (N5) as described above can give compounds of structure XVI.

Compounds of formula I, represented by structure XVII can be prepared as shown in Scheme O.

Compounds of structure O1 can be converted to 2-iodo- or bromoindoles O2. Typically, a strong base, such as n-butyllithium or s-butyllithium or lithium diisopropylamide or lithium or potassium hexamethyldisilazide is employed, with formation of the 2-indolyl anion generated in a suitable unreactive solvent, e.g., ether or THF, or solvent mixtures containing them. The reaction is typically carried out in the range of −78° C. to ambient temperature. The 2-indolyl anion can then be quenched with an electrophilic source of halogen, including but not limited to iodine, bromine or N-bromosuccinimide to give compounds of structure O2. Reaction of 2-iodo- or bromoindoles O2 with a boronic acid (commonly referred to as a Suzuki reaction) or trialkyl stannane (commonly referred to as a Stille reaction) can give the compounds of structure XVII. The coupling reactions are carried out by methods known to those skilled in the art and include conducting the reaction in the presence of a catalyst, such as tetrakis (triphenylphosphine) palladium (0), bis (triphenylphosphine) palladium (II) dichloride or palladium acetate with added phosphine ligand. The reactions are carried out in a suitable solvent, e.g., DMF, toluene, dimethoxy ethane or dioxane at a temperature range of ambient to 150°

C. For the Suzuki reaction, a base is usually added. The base can be in aqueous solution, e.g., aqueous sodium carbonate or sodium bicarbonate, or the base can be employed under anhydrous conditions, e.g., cesium or potassium fluoride. For the Stille reaction a copper co-catalyst, e.g., copper iodide, can be added.

Alternatively, indoles O1 can be converted to the indole-2-boronic acid or indole-2-trialkylstannane derivatives O3 by reacting the 2-indolyl anion described above with a trialkylborate or chlorotrialkyl stannane derivative, respectively. Compounds of type O3 can be reacted with aryl and heteroaryl bromides and iodides under similar conditions to those described above to form compounds of structure XVII.

-continued

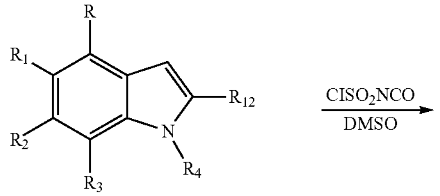

P3

XV. Scheme O

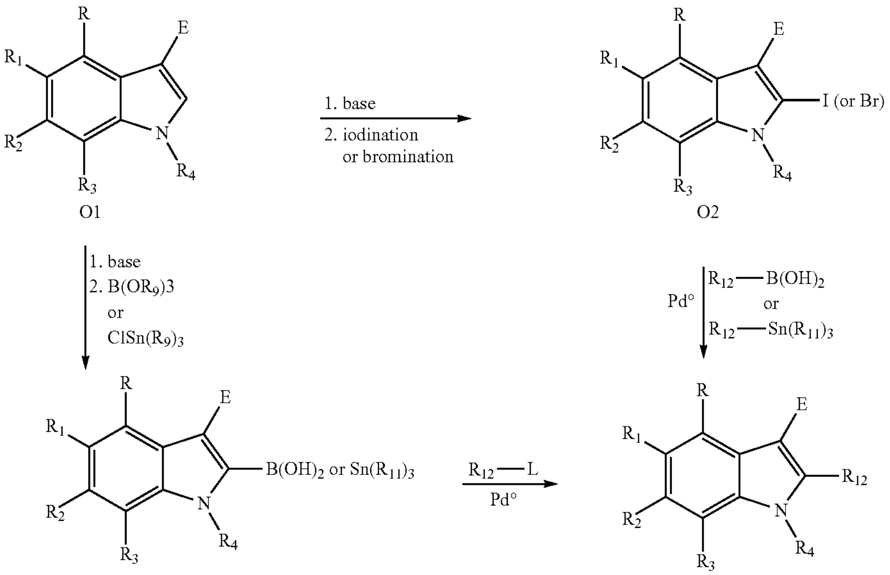

O1 O2 O3 XVII

Compounds of formula I, represented by structure XVIII can be prepared as shown in Scheme P.

Compounds of structure P1 can be converted to compounds P3 by treatment of P1 with an aryl or heteroaryl halide (P2) in the presence of organometallic catalysis. Such catalyst combinations can include palladium catalysts, e.g., palladium acetate and a source of copper, e.g., copper iodide. The reaction can be carried out in the presence of a base, e.g., cesium carbonate. The reaction can be carried out within a temperature range of ambient temperature to 150° C.

XVI. Scheme P

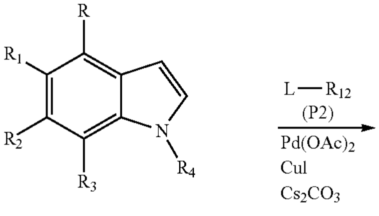

P1

-continued

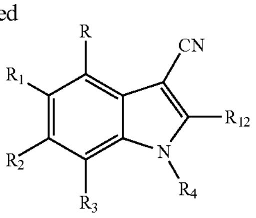

XVIII

Compounds of the present invention, represented by structure XIX can be prepared as described in scheme Q below.

Compounds of structure XIX can be prepared by protecting an indole compound of structure Q1 as e.g., the N-Boc derivative Q2. Alternatively, other protecting groups which can be utilized but not limited to include , e.g., benzyl, alkyl or aryl sulfonyl, or trialkyl silyl. Treatment of Q2 with a strong base, e.g., lithium diisopropyl amide in an aprotic solvent, e.g., THF followed by quenching with a trialkylborate derivative can give the indolyl-2-boronic acid Q3. Reaction with an aryl or heteroaryl halide Q4 in the presence of palladium catalysis, e.g., tetrakis (triphenylphosphine) palladium (0), bis (triphenylphosphine) palladium (II) dichloride or palladium acetate with added phosphine ligand, can give the compound Q5. Removal of the protecting group can give Q6. Reaction with Q6 with a reactive functional group $R_9$ containing a suitable leaving group L as described above can give compounds of structure Q7. Cyanation of compound Q7 can give the compounds of structure XIX.

XVII. Scheme Q

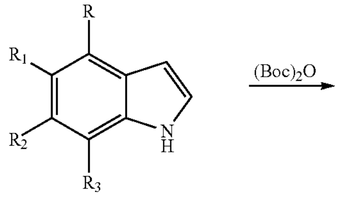

Q1

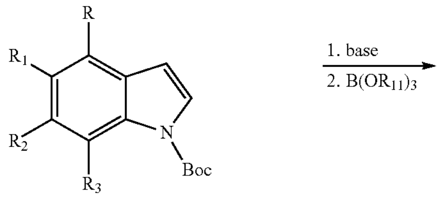

(Q2)

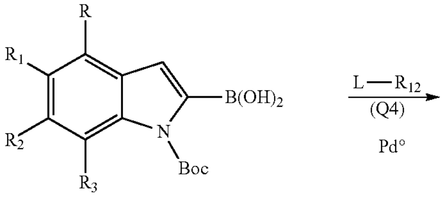

Q3

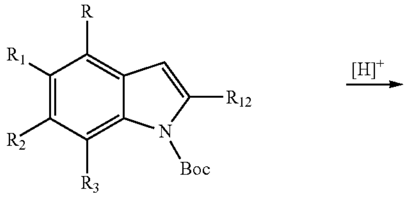

Q5

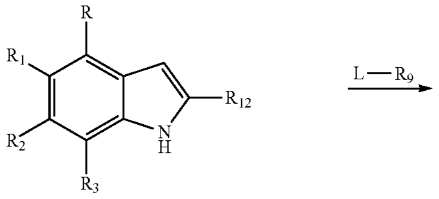

Q6

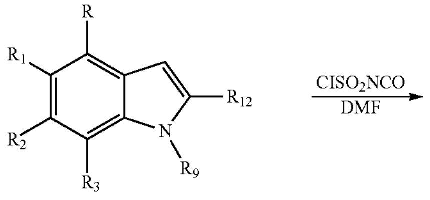

Q7

-continued

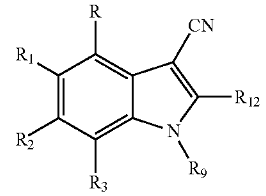

XIX

Compounds of formula I, represented by structure XX can be prepared as shown in Scheme R.

Compounds of structure R1 can be prepared by protecting an indole compound of structure R1 as e.g., the N-Boc derivative R2 as above. Compounds of structure R2 can be converted to 2-iodo- or bromoindoles R3. Typically, a strong base, such as n-butyllithium or s-butyllithium or lithium diisopropylamide or lithium or potassium hexamethyldisilazide is employed, with formation of the 2-indolyl anion generated in a suitable unreactive solvent, e.g., ether or THF, or solvent mixtures containing them. The reaction is typically carried out in the range of −78° C. to ambient temperature. The 2-indolyl anion can then be quenched with an electrophilic source of halogen, including but not limited to iodine, bromine or N-bromosuccinimide to give compounds of structure R3. After removal of the protecting group, compounds of R4 can be reacted with aryl or heteroaryl boronic acids or esters (R5) (commonly referred to as a Suzuki reaction) to give compounds of structure R6. The coupling reactions are carried out by methods known to those skilled in the art and include conducting the reaction in the presence of a catalyst, such as tetrakis (triphenylphosphine) palladium (0), bis (triphenylphosphine) palladium (II) dichloride or palladium acetate with added phosphine ligand. Reaction with R6 with a reactive functional group $R_9$ containing a suitable leaving group L as described above can give compounds of structure XX.

XVIII. Scheme R

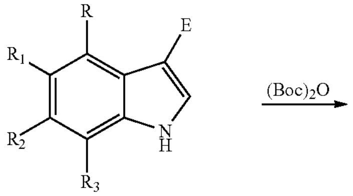

R1

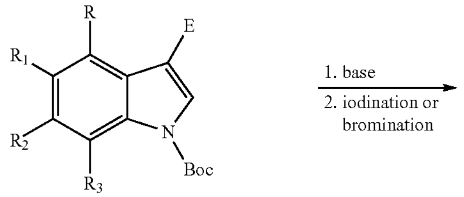

(R2)

-continued

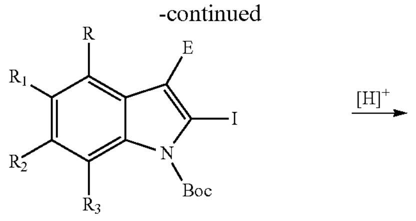

R3

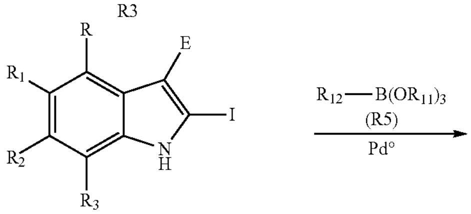

R4

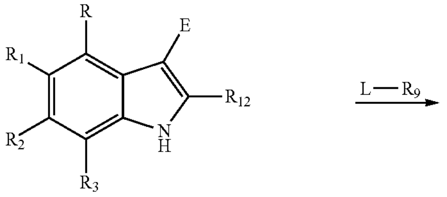

R6

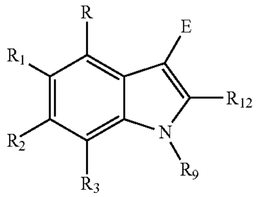

XX

Compounds of the present invention, represented by structure XXI can be prepared as described in scheme S below.

2-iodo- or bromoindoles of structure S1 can be reacted with alkenes in the presence of a palladium catalyst (commonly referred to as the Heck reaction) to give compounds of type XXI. The coupling reactions can be carried out by methods known to those skilled in the art. The choice of catalyst and solvents are similar to those described previously.

XIX. Scheme S

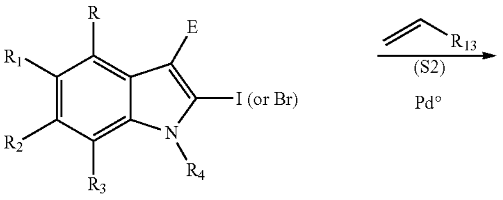

S1

-continued

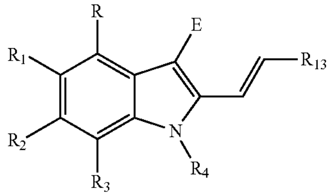

XXI

Compounds of formula I, represented by structure XXII can be prepared as shown in Scheme T.

2-Iodo- or 2-bromoindoles of structure T1 can be reacted with acetylenes in the presence of a palladium catalyst (commonly referred to as the Sonagashira reaction) to give compounds of type XXII. The coupling reactions can be carried out by methods known to those skilled in the art. A typical set of reaction conditions includes reacting the indoles of structure T1 with an acetylene compound T2 in the presence of a source of palladium, a copper co-catalyst and an amine source. The reaction is carried out in a suitably unreactive solvent and conducted within a temperature range from ambient to 150° C.

XX. Scheme T

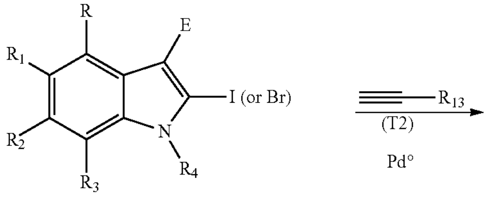

T1

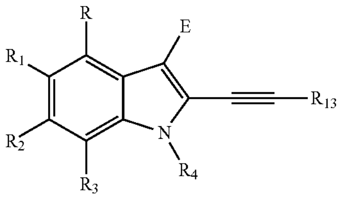

XXII

Compounds of formula I, represented by structure XXIII can be prepared as shown in Scheme U.

Compounds of structure XXIII can be obtained from the reduction of compounds XXI and XXII. Conditions for the reduction can include, but are not limited to catalytic reduction, e.g., hydrogenation over a source of platinum or palladium in a suitable solvent, e.g., $CH_2Cl_2$, ether, THF, methanol or solvent combinations.

XXI. Scheme U

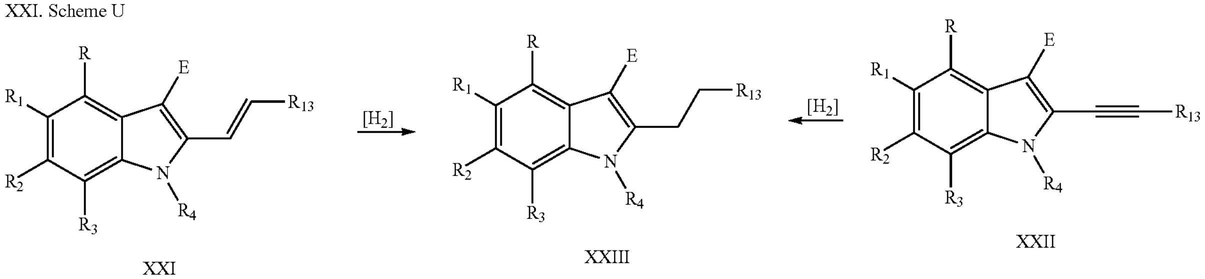

XXI

XXIII

XXII

Compounds of the present invention, represented by structure XXIV can be prepared as described in scheme V below.

Indoles of structure VI can be reacted with a suitable base, such as lithium diisopropylamide or potassium hexamethyldisilazide to generate the 2-indolyl anion in a suitable unreactive solvent, e.g., ether or THF, or solvent mixtures containing them. The reaction is typically carried out in the range of −78° C. to ambient temperature. The 2-indolyl anion can then be quenched with a source of zinc halide, e.g., zinc halide metal or soluitions containing them to give organozinc compounds of structure V2. Reaction of V2 with an arylhalide (V3) in the presence of a palladium catalyst (commonly referred to as the Negishi reaction) gives compounds of structure XXIV. Alternatively, 2-iodo or bromoindoles of structure V4, prepared from compounds V1 as described previously, can be reacted with organozinc compounds of structure V5 in the presence of a suitable palladium catalyst to give compounds of structure XXIV. The organozinc compound V5 can be derived from, e.g., an alkyl or alkenyl halide after treatment with activated zinc or an aryl or heteroaryl lithium or magnesium comound after treatment with zinc halide. Furthermore, the reactions of V2 or V4 can be carried out in the presence of a palladium source, e.g., as tetrakis (triphenylphosphine) palladium (0) or bis (triphenylphosphine) palladium (II) dichloride in a suitable solvent and at a temperature range from ambient to 150° C.

XXII. Scheme V

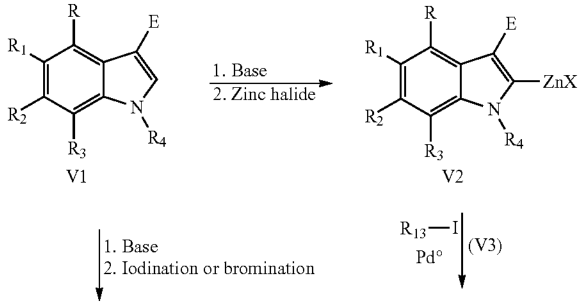

V1 V2

-continued

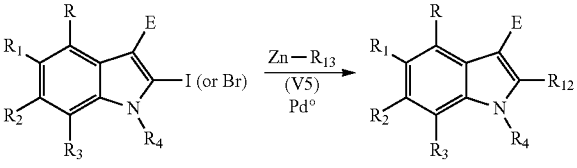

V4 XXIV

Compounds of formula I, represented by structure XXV-XXVIII can be prepared as shown in Scheme W.

2-Iodo- or bromoindoles of structure W1 can be reacted with acetylenes of structure W2 in the presence of a palladium catalyst (commonly referred to as the Sonagashira reaction) to give compounds of type XXV. The coupling reactions can be carried out by methods known to those skilled in the art. A typical set of reaction conditions includes reacting the indoles of structure W1 with an acetylene compound W2 in the presence of a source of palladium, an optional copper co-catalyst and an amine source. The reaction is carried out in a suitably unreactive solvent and conducted within a temperature range from ambient to 150° C. Reaction with XXV with a reactive functional group $R_9$ containing a suitable leaving group L as described above can give compounds of structure XXVI.

2-iodo- or bromoindoles of structure W1 can also be reacted with alkenes in the presence of a palladium catalyst (commonly referred to as the Heck reaction) to give compounds of type XXVII. The coupling reactions can be carried out by methods known to those skilled in the art. The choice of catalyst and solvents are similar to those described previously. Reaction with XXVII with a reactive functional group $R_9$ containing a suitable leaving group L as described above can give compounds of structure XXVIII.

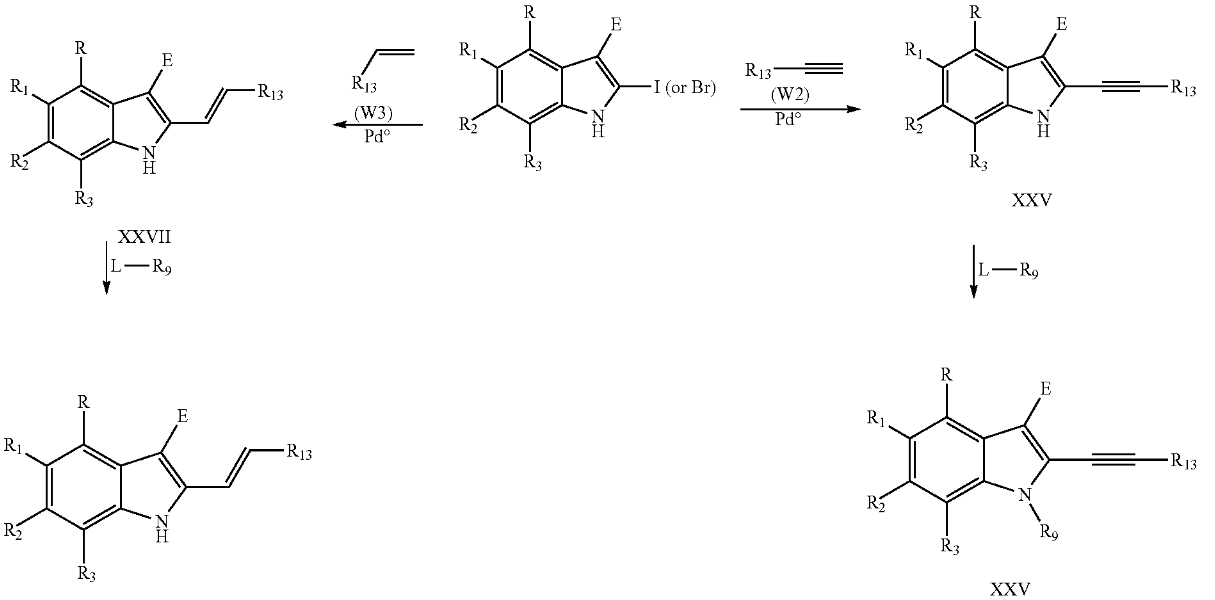

XXVII XXV XXVIII XXV

Compounds of formula I, represented by structure XXIX can be prepared as shown in Scheme X.

Indoles of structure X1 and be acylated with acyl halides of structure X2 to give compounds of structure XXIX. The reaction can be promoted with a Lewis acid. The choice of Lewis acid can be chosen from, but is not limited to aluminum chloride, ferric chloride, stannic chloride or diethyl aluminum. The reaction is typically carried out in a suitable non-reactive solvent including $CH_2Cl_2$, carbon disulfide or dichloroethane and is typically conducted within a temperature range of −20° C. to 80° C.

XXIV. Scheme X

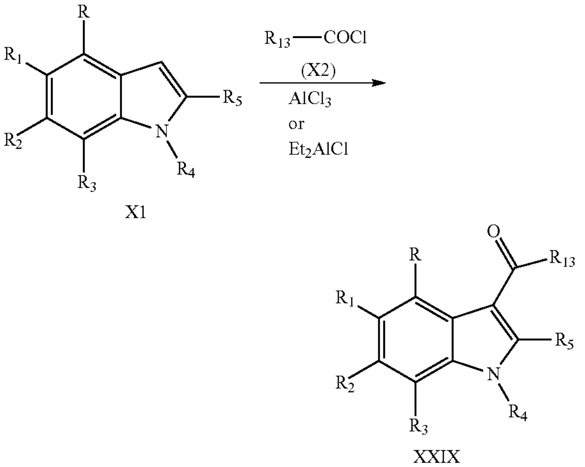

X1

XXIX

Compounds of formula I, represented by structure XXX can be prepared as shown in Scheme Y.

3-Cyanoindoles of structure Y1 can be converted to tetrazoles of structure Y2 by treatment with, e.g., sodium azide. Heating a mixture of Y2 and the reagent Y3 can give the 3-(1,2,4-oxadiazolyl)indole compound XXX. The reagent Y3 can be, e.g., an acyl halide or an acid derivative activated with a reagent such as dicyclohexyl carbodiimide or diisopropyl carbodiimide. The reaction can be carried out in a variety of solvents, including e.g., toluene, dioxane, pyridine and dichloroethane and can be carried out by heating Y2 and Y3 at a temperature range of 30° to 130° C.

XXV. Scheme Y

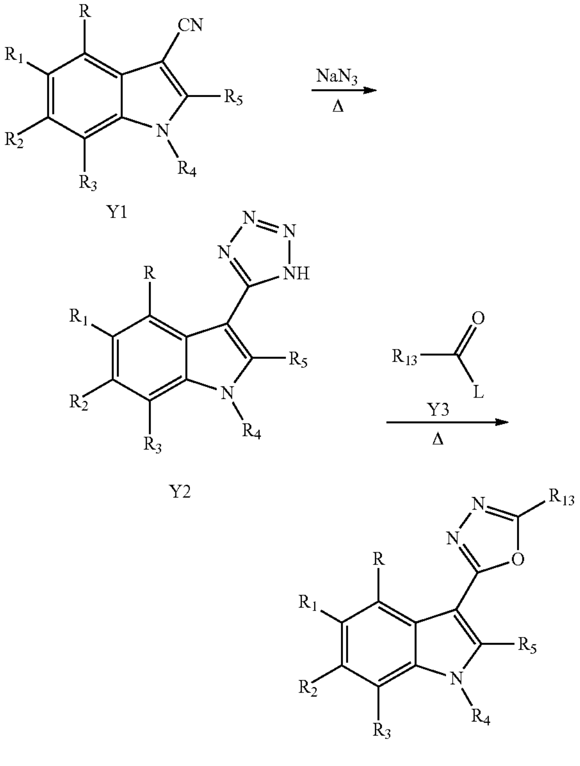

Y1

Y2

XXX

Compounds of formula I, represented by structure XXXI can be prepared as shown in Scheme Z.

3-Cyanoindoles of structure Z1 can be treated with hydroxylamine to give hydroxyamidine compounds of formula Z2. Reaction of hydroxyamidines of structure Z2 with compounds of structure Z3 can give O-acylhydroxyamidines Z4. Compounds Z3 can represent, for example, acyl halides or carboxylic acids activated with a reagent such as dicyclohexyl carbodiimide or diisopropyl carbodiimide. Heating compounds of structure Z4 in a non-reactive organic solvent, e.g., toluene, dichloroethane or dioxane in a temperature range of 30° C. to 150° C. can give compounds of structure XXXI.

XXVI. Scheme Z

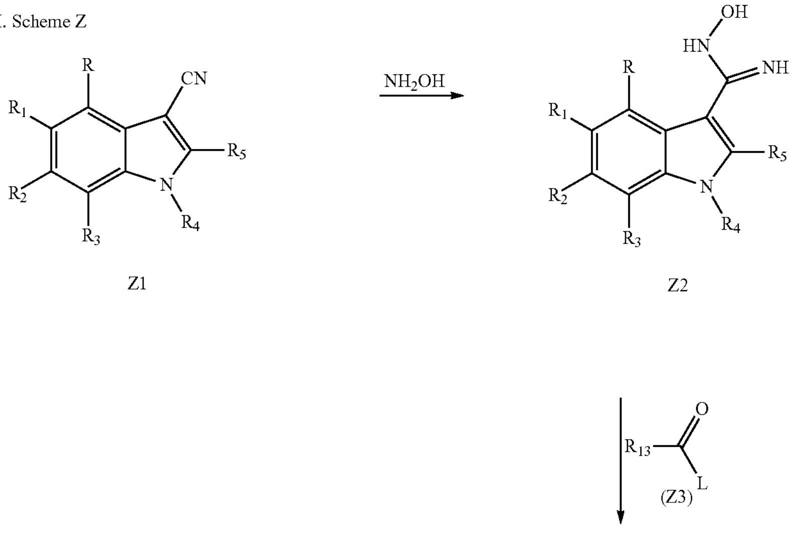

Z1

Z2

-continued

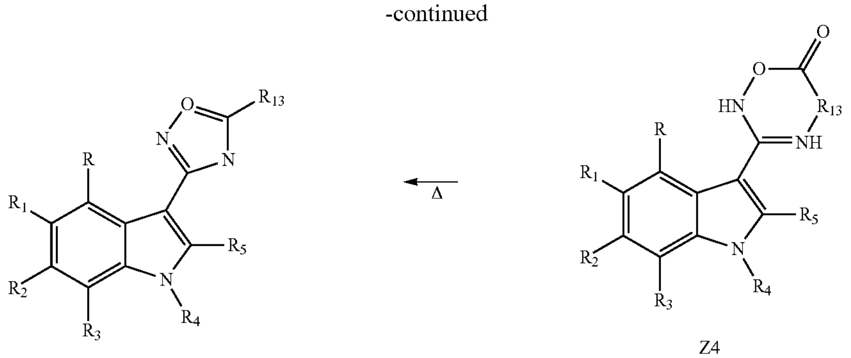

XXXI

Z4

Compounds of the present invention, represented by structure XXXII can be prepared as described in scheme AA below.

Ketoindoles of type AA1 can be converted to oximes of structure AA2 by heating the ketoindoles with hydroxylamine (free base or acid salt) in a suitable solvent. Bis-deprotonation of compounds of type AA2 with a strong organic base (e.g., n-butyllityium or sec-butyllithium or tert-butyllithium) followed by reaction with DMF can give compounds of formula XXXII.

XXVII. Scheme AA

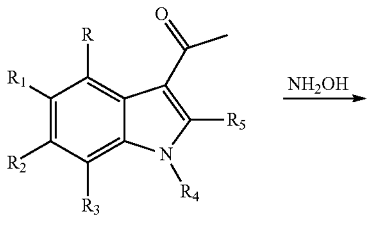

AA1

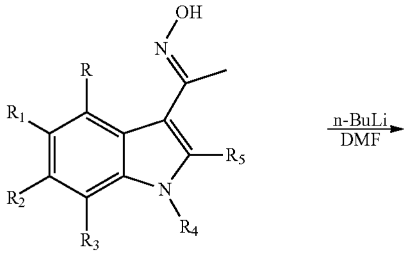

AA2

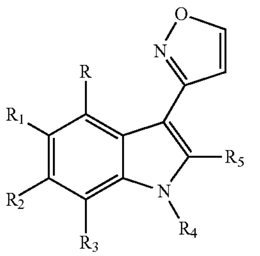

XXXII

Compounds of formula I, represented by structure XXXIII can be prepared as shown in Scheme AB.

3-Ketoindoles of structure AB1 can be homologated to vinylogous amides of structure AB3 by reaction with dialkyl amide dialkyl acetals AB2. The dialkyl amides can include e.g., lower alkyl amides such as formamide, acetamide and propionamide. Examples would include dimethlformamide dimethyl acetal and dimethyl acetamide dimethyl acetal. The reaction can be conducted by reacting AB1 and AB2 with or without additional solvent at a temperature from ambient to 150° C. Treatment of AB3 with hydroxylamine (free base or acid salt) in a suitable solvent can give compounds of structure XXXIII. The reaction is typically conducted within a temperature range from ambient to 120° C.

XXVIII. Scheme AB

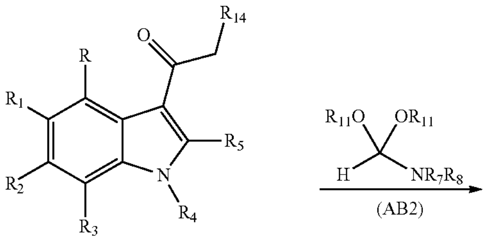

AB1

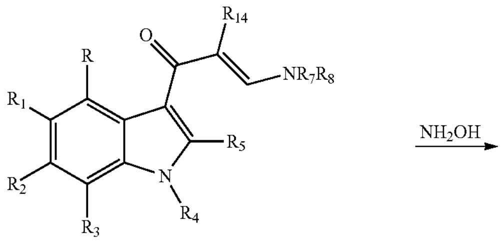

AB3

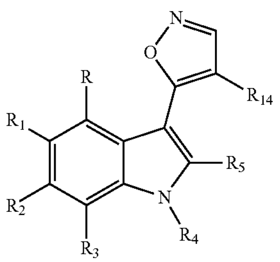

XXXIII

Compounds of formula I, represented by structure XXXIV can be prepared as shown in Scheme AC.

Vinylogous amides of structure AC1 (as prepared above) can be treated with hydrazines AC2 in a suitable organic solvent (DMF, alcohol or acetic acid) at temperatures ranging from ambient temperature to 150° C. to give compounds of structure XXXIV.

XXIX. Scheme AC

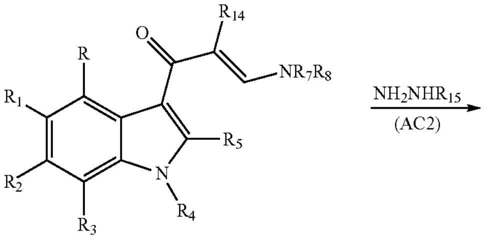

AC1

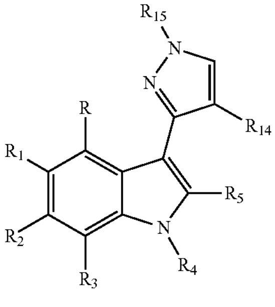

XXXIV

Compounds of the present invention, represented by structure XXXV can be prepared as described in scheme AD below.

Indole-3-carboxaldehydes of structure AD1 (as prepared in Scheme F) can be reacted with p-(toluenesulfonyl)methyl isocyanate (TOSMIC) in the presence of a base to give compounds of structure XXXV. Bases can include potassium carbonate or 1,8-diazabicyclo[5.4.0]undec-7-ene and the reaction can be carried out in a suitable organic solvent from ambient temperature to 150° C.

XXX. Scheme AD

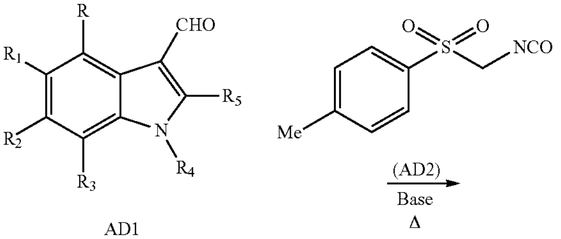

AD1

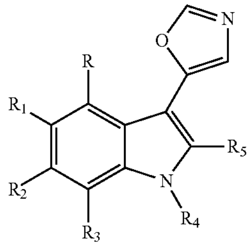

XXXV

Compounds of formula I, represented by structure XXXVI and XXXVII can be prepared as shown in Scheme AE.

3-Indolecarboxylic acids of structure AE1 (from Scheme E) can be converted to amides of structure AE2. Compounds of structure AE2 can be activated by any of the standard methods. For example, the acid AE1 can be activated with coupling reagents such as EDCI or DCC with or without HOBt in the presence of ammonia. Alternatively, the acid can be activated as the acid chloride or as the acyl imidazolide as described previously, followed by treatment of ammonia.

The indole-3-carboxamides of structure AE2 can be reacted with substituted aldehydes or ketones (AE3) containing a suitable leaving group L, in a suitable solvent at temperatures above ambient and up to 200° C. The reaction can be performed with or without added base to afford oxazoles of structure XXXVI.

The indole-3-carboxamides of structure AE2 can also be converted to thioamides of structure AE4 by treating the primary amides with Lawesson's reagent or phosphorous pentasulfide at or above ambient temperature in a suitable organic solvent. The resulting thioamides AE4 can be reacted with substituted aldehydes or ketones containing a suitable leaving group L (AE3), in a suitable solvent at temperatures above ambient and up to 150° C. The reaction can be performed with or without added base to afford thiazoles of structure XXXVII.

XXXI. Scheme AE

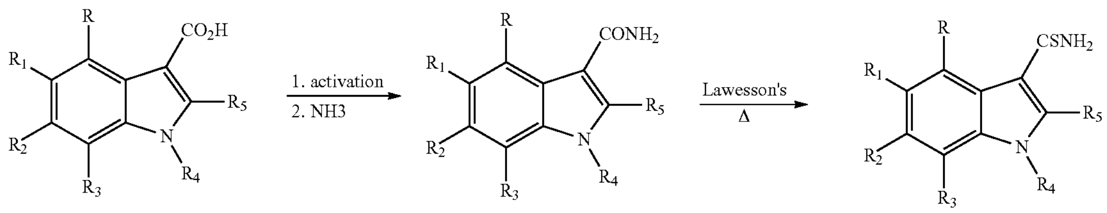

AE1 AE2 AE4

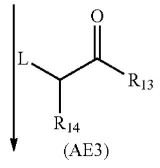

(AE3)

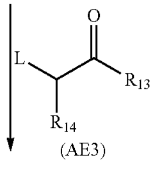

(AE3)

-continued

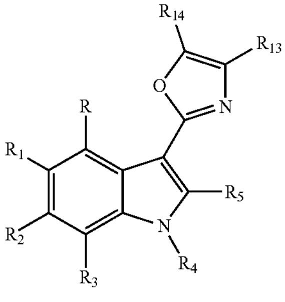

XXXVI

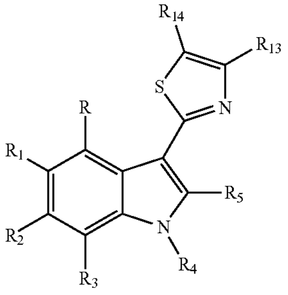

XXXVII

Compounds of the present invention, represented by structure XXXVIII and XXXIX can be prepared as described in scheme AF below.

3-Ketoindoles of structure AF1 can be halogenated (e.g., brominated) to give compounds of structure AF3. Suitable brominating agents can include but are not limited to phenyltrimethylammonium tribromide (AF2), N-bromosuccinimide or bromine and can be carried out in a variety of organic solvents.

Treatment of compounds AF3 with amides of type AF4 in a suitable solvent at temperatures above ambient and up to 200° C. with or without added base can give oxazoles of structure XXXVIII.

Treatment of compounds AF3 with thioamides of type AF5 in a suitable solvent at temperatures above ambient and up to 150° C. with or without added base can give thiazoles of structure XXXIX.

XXXII. Scheme AF

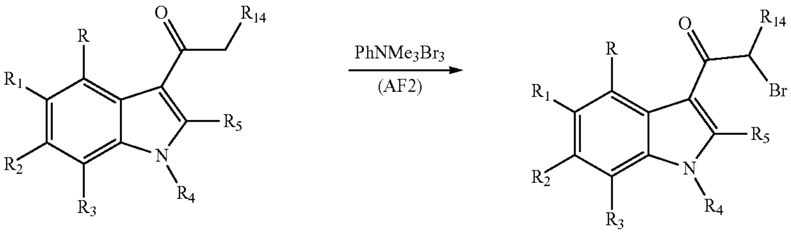

AF1

AF3

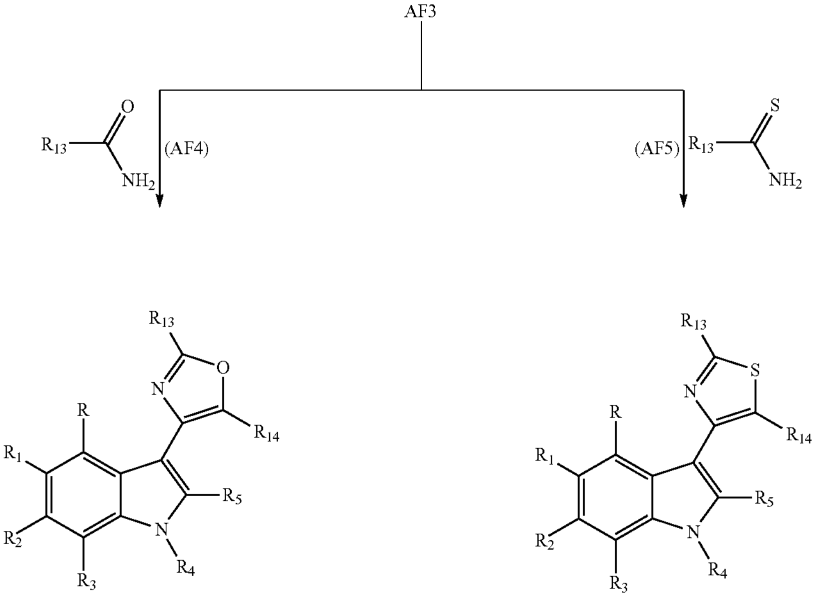

XXXVIII

XXXIX

Compounds of formula I, represented by structure XL can be prepared as shown in Scheme AG.

Indoles of structure AG1 can be brominated or iodinated to give compounds of structure AG2. Brominating agents may include but are notlimited to bromine or N-bromosuccinimide and iodinating reagents may include iodine monochloride or bis-trifluoroacetoxy iodobenzene. Reaction of 3-iodo- or bromoindoles AG2 with a boronic acid AG3 (commonly referred to as a Suzuki reaction) can give the compounds of structure XL. The coupling reactions are carried out by methods known to those skilled in the art and include conducting the reaction in the presence of a catalyst, such as tetrakis (triphenylphosphine) palladium (0), bis (triphenylphosphine) palladium (II) dichloride or palladium acetate with added phosphine ligand. The reactions are carried out in a suitable solvent, e.g., DMF, toluene, dimethoxy ethane or dioxane at a temperature range of ambient to 150° C. and typically in the presence of a base e.g., aqueous sodium carbonate or sodium bicarbonate, or the base can be employed under anhydrous conditions, e.g., cesium or potassium fluoride.

Alternatively, indole AG2 can be converted to the indole-3-boronic acid derivative AG5 by reacting the 3-haloindole AG2 with a strong organic base (alkyllithium or grignard reagent) and reacting the resultant anion with a trialkylborate reagent AG4. Compounds of type AG5 can be reacted with aryl and heteroaryl bromides and iodides under similar conditions to those described above to form compounds of structure XL.

catalyst and solvents are similar to those described in Scheme AG.

XXXIV. Scheme AH

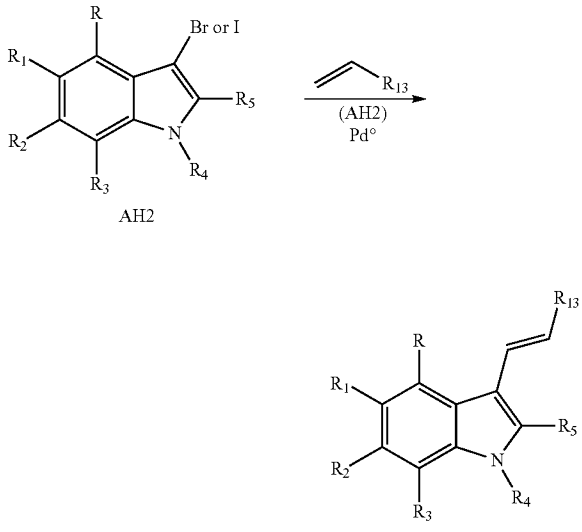

AH2

XLI

XXXIII. Scheme AG

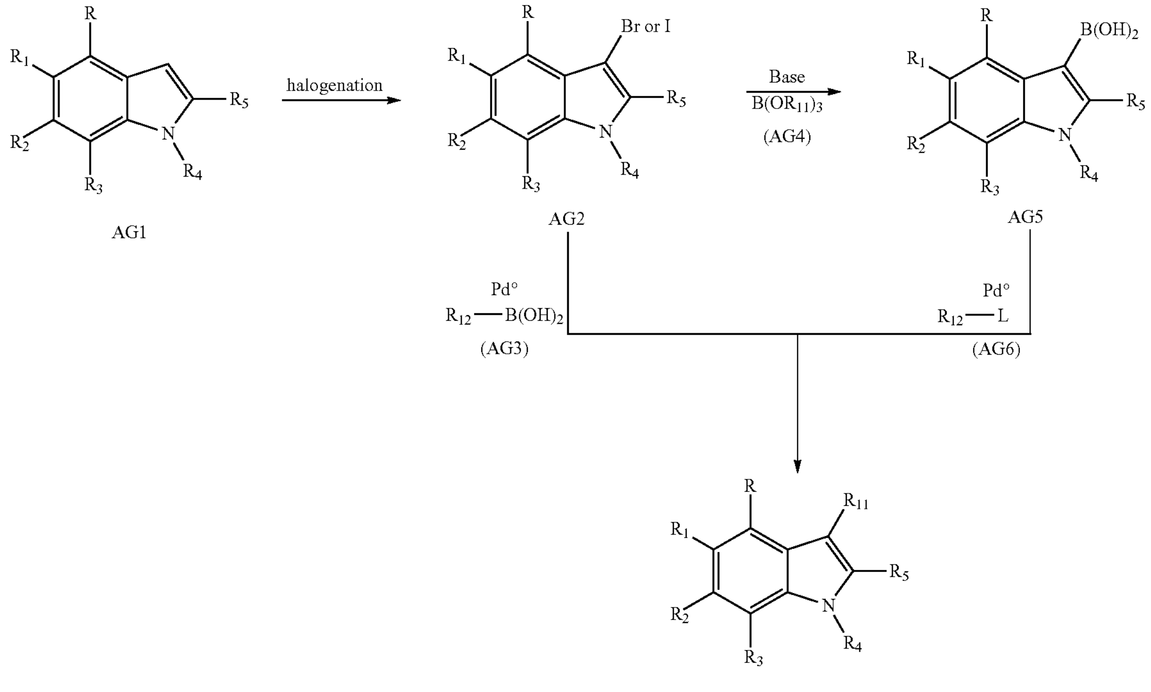

AG1

AG2

AG5

XL

Compounds of the present invention, represented by structure XLI can be prepared as described in scheme AH below.

3-iodo- or bromoindoles of structure AH1 can be reacted with alkenes AH2 in the presence of a palladium catalyst (commonly referred to as the Heck reaction) to give compounds of type XLI. The coupling reactions can be carried out by methods known to those skilled in the art. The choice of Compounds of formula I, represented by structure XLII can be prepared as shown in Scheme AI.

3-Iodo- or bromoindoles of structure AI1 can be reacted with acetylenes AI2 in the presence of a palladium catalyst (commonly referred to as the Sonagashira reaction) to give compounds of type XLII. The coupling reactions can be carried out by methods known to those skilled in the art. A typical set of reaction conditions includes reacting the indole of structure AI1 with an acetylene compound AI2 in the presence of a source of palladium, a copper co-catalyst and an amine source and carrying out the reaction at a temperature range of ambient to 150° C.

XXXV. Scheme AI

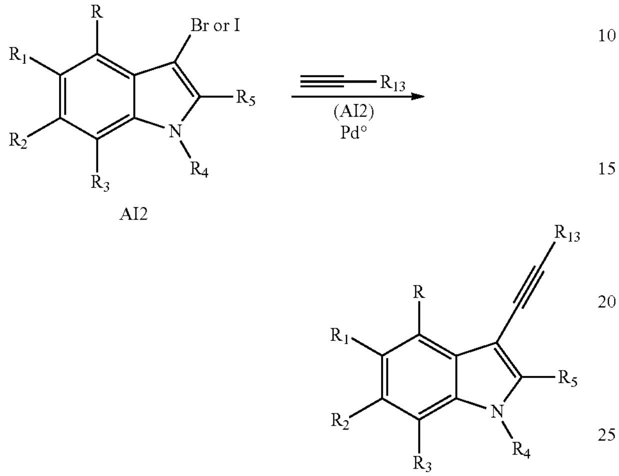

AI2

XLII

Compounds of the present invention, represented by structure XLIII and XLIV can be prepared as described in scheme AJ below.

Nitroanilines of structure AJ1 can be converted to indoles of structure XLIII by condensation and cyclization with nitriles of structure AJ2. The reaction can be carried out in a suitable organic solvent, e.g., DMF or dioxane. Treatment of compounds of structure XLIII with a base followed by reaction with a reactive functional group $R_9$ containing a suitable leaving group L can give the compounds of formula XLIV.

XXXVI. Scheme AJ

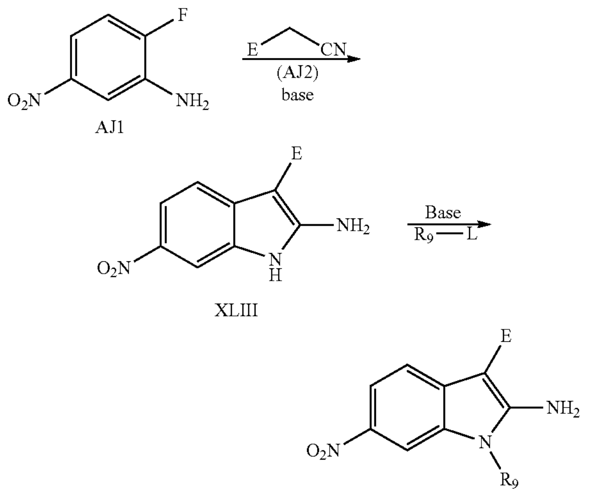

AJ1

XLIII

XLIV

Compounds of formula I, represented by structure XLV-XLVIII can be prepared as shown in Scheme AK.

2-aminoindoles of structure XLV can be alkylated with a reactive functional group $R_{15}$ containing a suitable leaving group L in the presence of a base, e.g., sodium hydride or potassium carbonate in a suitable organic solvent to give compounds of structure XLVI. A second alkylation utilizing a reactive functional group $R'_{15}$ containing a suitable leaving group L similarly can give compounds of structure XLVII.

Acylation of compounds of structure XLV with acyl chlorides of structure AK1 can give compounds of structure XLVIII. The reaction is typically carried out in the presence of an organic base, e.g., a trialkylamine or an inorganic base, e.g., potassium carbonate in a suitable organic solvent.

XXXVII. Scheme AK

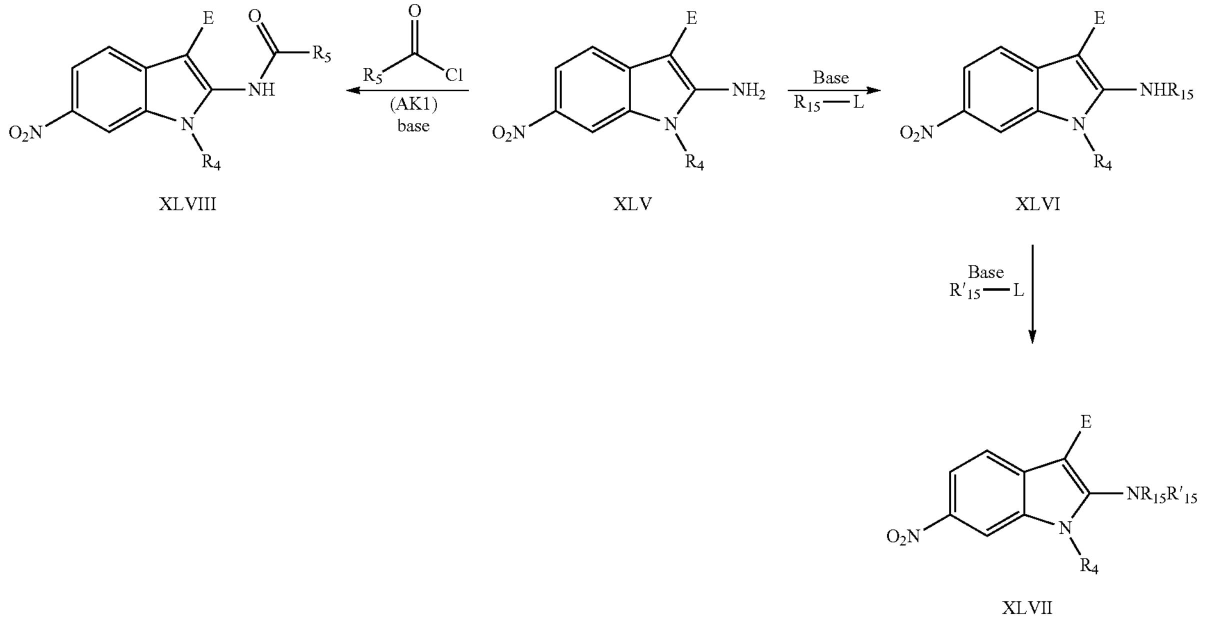

XLVIII

XLV

XLVI

XLVII

Compounds of the present invention, represented by structure XLIX can be prepared as described in scheme AL below.

Indole-3-carboxylic acids of structure AL1 can be activated to give compounds of structure AL2. Compounds of structure AL2 can represent, for example, acyl halides or carboxylic acids activated with a reagent such as dicyclohexyl carbodiimide or diisopropyl carbodiimide. Reaction of compounds of structure AL2 with hydroxyamidines of structure AL3 can give O-acylhydroxyamidines AL4. Hydroxyamidines may be obtained commercially or by treatment of nitrile compounds with hydroxylamine. Heating compounds of structure AL4 in a non-reactive organic solvent, e.g., toluene, dichloroethane or dioxane in a temperature range of 30° C. to 150° C. can give compounds of structure XLIX.

XXXVIII. Scheme AL

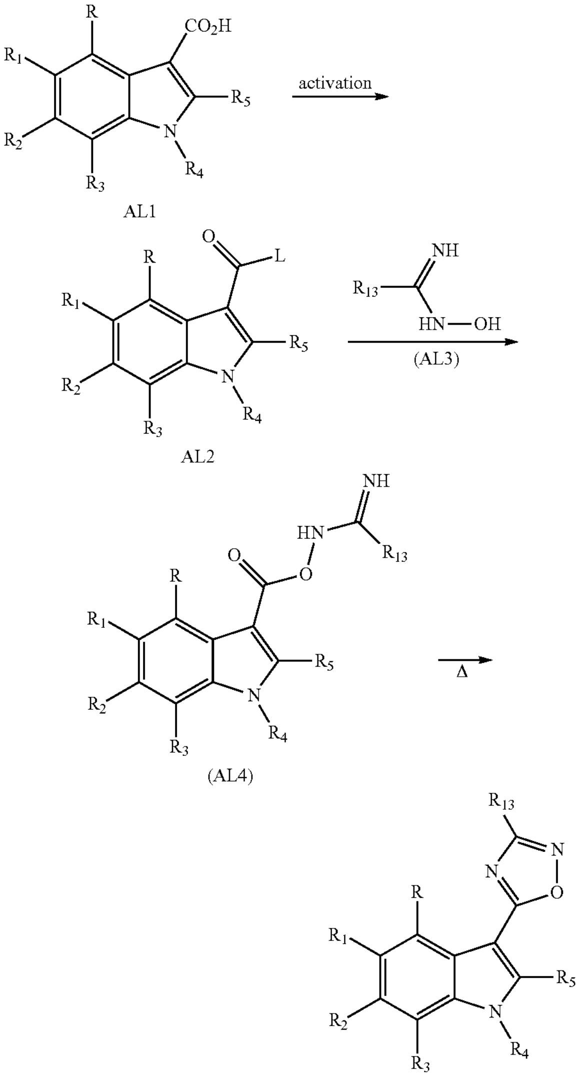

AL1
AL2
(AL4)
XLIX

C. Methods of the Invention

The methods of the invention generally comprise administering a therapeutically effective amount of one or more compound of the present invention to a subject in need of treatment for HCV infection. In a preferred embodiment, a therapeutically effective amount of a composition comprising a compound of Formula I as described herein is administered to a subject in need of treatment. In another preferred embodiment, in another preferred embodiment, a compound or a composition used in the methods of the present invention includes a compound of Formula I as described herein wherein the compound of Formula I is not Compound 1

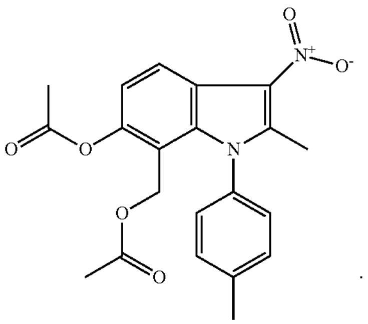

Compound 1.

The compound(s) of the present invention may be administered to the subject via any drug delivery route known in the art. Specific exemplary administration routes include oral, ocular, rectal, buccal, topical, nasal, ophthalmic, subcutaneous, intramuscular, intraveneous (bolus and infusion), intracerebral, transdermal, and pulmonary. Individuals infected with HCV can be treated with the compounds of the present invention to prevent or reduce further replication of HCV.

The term therapeutically effective amount, as used herein, refers to an amount of a compound of the present invention effective to inhibit HCV translation, thereby effectively treating or ameliorating the HCV infection. The effect of the compound can be determined by analyzing (1) the presence of HCV-RNA; (2) the presence of anti-HCV antibodies; (3) the level of serum alanine amino transferase (ALT) and aspartate aminotransferase (AST) (ALT and AST are elevated in patients chronically infected with HCV); and (4) hepatocellular damage. The precise effective amount for a subject will depend upon the subject's body weight, size and health. Therapeutically effective amounts for a given patient can be determined by routine experimentation that is within the skill and judgment of the clinician.

For any compound, the therapeutically effective amount can be estimated initially either in cell culture assays or in relevant animal models, such as marmosets and tarmarins. The animal model may also be used to determine the appropriate concentration range and route of administration. Such information can then be used to determine useful doses and routes for administration in humans. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred. The dosage contained in such compositions is preferably within a range of circulating concentrations that include an $ED_{50}$ with little or no toxicity. The dosage may vary within this range depending upon the dosage form employed, sensitivity of the patient, and the route of administration.

More specifically, the concentration-biological effect relationships observed with regard to the compound(s) of the present invention indicate an initial target plasma concentration ranging from approximately 0.1 μg/ml to approximately 100 μg/mL, preferably from approximately 1 μg/mL to approximately 50 μg/mL, more preferably from approximately 5 μg/mL to approximately 50 μg/mL, even more preferably from approximately 10 μg/mL to approximately 25 μg/mL. To achieve such plasma concentrations, the compounds of the invention may be administered at doses that vary from 0.1 μg to 100,000 mg, depending upon the route of administration. Guidance as to particular dosages and methods of delivery is provided in the literature and is generally available to practitioners in the art. In general the dose will be in the range of about 1 mg/day to about 10 g/day, or about 0.1 g to about 3 g/day, or about 0.3 g to about 3 g/day, or about 0.5 g to about 2 g/day, in single, divided, or continuous doses for a patient weighing between about 40 to about 100 kg (which dose may be adjusted for patients above or below this weight range, particularly children under 40 kg).

The exact dosage will be determined by the practitioner, in light of factors related to the subject that requires treatment. Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

D. Metabolites of the Compounds of the Invention

Also falling within the scope of the present invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammalian tissue or a mammal for a period of time sufficient to yield a metabolic product thereof. Such products typically are identified by preparing a radio-labeled (e.g. $C^{14}$ or $H^3$) compound of the invention, administering it in a detectable dose (e.g., greater than about 0.5 mg/kg) to a mammal such as rat, mouse, guinea pig, monkey, or to man, allowing sufficient time for metabolism to occur (typically about 30 seconds to 30 hours), and isolating its conversion products from urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds of the invention even if they possess no biological activity of their own.

E. Pharmaceutical Compositions of the Invention

While it is possible for the compounds of the present invention to be administered neat, it may be preferable to formulate the compounds as pharmaceutical compositions. As such, in yet another aspect of the invention, pharmaceutical compositions useful in the methods of the invention are provided. The pharmaceutical compositions of the invention may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5.0 to about pH 8.0.

More particularly, the pharmaceutical compositions of the invention comprise a therapeutically or prophylactically effective amount of one or more compound of the present invention, together with one or more pharmaceutically acceptable excipients. A therapeutically or prophylactically effective amount of a compound of the present invention includes a viral inhibitory amount of said compound or an amount effective for affecting viral IRES activity. By "viral inhibitory amount" it is meant an amount sufficient to inhibit viral replication or infectivity. By "an amount effective for affecting viral IRES activity" it is meant an amount sufficient to inhibit viral IRES mediated initiation and/or translation. Optionally, the pharmaceutical compositions of the invention may comprise a combination of compounds of the present invention, or may include a second active ingredient useful in the treatment of viral infections, such as anti-viral agents that include, but are not limited to: pegylated interferon, including by way of non-limiting example pegylated α-interferon; un-pegylated interferon, including by way of non-limiting example, un-pegylated α-interferon; ribavirin or prodrugs or derivatives thereof; a glucosidase inhibitor; protease inhibitors; polyermase inhibitors; p7 inhibitors; entry inhibitors, including fusion inhibitors such as Fuzeon (Trimeris); helicase inhibitors; a Toll-like receptor agonist, a caspase inhibitor, anti-fibrotics; drugs that target IMPDH (inosine monophosphate dehydrogenase inhibitors), such as Merimepadib™ (Vertex Pharmaceuticals Inc.); synthetic thymosin alpha 1 (ZADAXIN™, SciClone Pharmaceuticals Inc.); a glycosidase inhibitor; therapeutic viral vaccines, such as those produced by Chiron and Immunogenics; and immunomodulators, such as histamine.

Formulations of the present invention, e.g., for parenteral or oral administration, are most typically solids, liquid solutions, emulsions or suspensions, while inhaleable formulations for pulmonary administration are generally liquids or powders, with powder formulations being generally preferred. A preferred pharmaceutical composition of the invention may also be formulated as a lyophilized solid that is reconstituted with a physiologically compatible solvent prior to administration. Alternative pharmaceutical compositions of the invention may be formulated as syrups, creams, ointments, tablets, and the like.

The term "pharmaceutically acceptable excipient" refers to an excipient for administration of a pharmaceutical agent, such as the compounds of the present invention. The term refers to any pharmaceutical excipient that may be administered without undue toxicity. Pharmaceutically acceptable excipients are determined in part by the particular composition being administered, as well as by the particular method used to administer the composition. Accordingly, there exists a wide variety of suitable formulations of pharmaceutical compositions of the present invention (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions of the invention may be formulated in any form suitable for the intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions of the invention may be formulated as suspensions comprising a compound of the present invention in an admixture with at least one pharmaceutically acceptable excipient suitable for the manufacture of a suspension. In yet another embodiment, pharmaceutical compositions of the invention may be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions of the invention may be in the form of a sterile injectable preparation, such as a sterile injectable aqueous emulsion or oleaginous suspension. This emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol. The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or di-glycerides. In addition, fatty acids such as oleic acid may likewise be used in the preparation of injectables.

Generally, the compounds of the present invention useful in the methods of the present invention are substantially insoluble in water and are sparingly soluble in most pharmaceutically acceptable protic solvents and in vegetable oils. However, the compounds are generally soluble in medium-chain fatty acids (e.g., caprylic and capric acids) or triglycerides and have high solubility in propylene glycol esters of medium-chain fatty acids. Also contemplated in the invention are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In a preferred embodiment, the compounds of the present invention may be formulated for oral administration in a lipid-based formulation suitable for low solubility compounds. Lipid-based formulations can generally enhance the oral bioavailability of such compounds. As such, a preferred pharmaceutical composition of the invention comprises a therapeutically or prophylactically effective amount of a compound of the present invention, together with at least one pharmaceutically acceptable excipient selected from the group consisting of: medium chain fatty acids or propylene glycol esters thereof (e.g., propylene glycol esters of edible fatty acids such as caprylic and capric fatty acids) and pharmaceutically acceptable surfactants such as polyoxyl 40 hydrogenated castor oil.

In an alternative preferred embodiment, cyclodextrins may be added as aqueous solubility enhancers. Preferred cyclodextrins include hydroxypropyl, hydroxyethyl, glucosyl, maltosyl and maltotriosyl derivatives of α-, β-, and γ-cyclodextrin. A particularly preferred cyclodextrin solubility enhancer is hydroxypropyl-β-cyclodextrin (HPBC), which may be added to any of the above-described compositions to further improve the aqueous solubility characteristics of the compounds of the present invention. In one embodiment, the composition comprises 0.1% to 20% hydroxypropyl-β-cyclodextrin, more preferably 1% to 15% hydroxypropyl-β-cyclodextrin, and even more preferably from 2.5% to 10% hydroxypropyl-β-cyclodextrin. The amount of solubility enhancer employed will depend on the amount of the compound of the present invention in the composition.

F. Combination Therapy

It is also possible to combine any compound of the present invention with one or more other active ingredients useful in the treatment of HCV infection, including compounds, in a unitary dosage form, or in separate dosage forms intended for simultaneous or sequential administration to a patient in need of treatment. When administered sequentially, the combination may be administered in two or more administrations. In an alternative embodiment, it is possible to administer one or more compounds of the present invention and one or more additional active ingredients by different routes.

The skilled artisan will recognize that a variety of active ingredients may be administered in combination with the compounds of the present invention that may act to augment or synergistically enhance the viral inhibiting activity of the compounds of the invention. Such active ingredients include anti-HCV agents. Anti-HCV agents include agents that target the virus as well as agents that have an immunomodulatory effect. For example, anti-HCV agents include, but are not limited to, interferon, including, for example without limitation, IFN-α, ribavirin or prodrugs or derivatives thereof; a glucosidase inhibitor, protease inhibitors, polymerase inhibitors, helicase inhibitors, a Toll-like receptor agonist, a caspase inhibitor and a glycosidase inhibitor. Furthermore, the compounds of the invention may also be administered in combination with other compounds that affect IRES activity known to one of skill in the art.

According to the methods of the invention, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

To assist in understanding the present invention, the following Examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

The present invention is described in more detail with reference to the following non-limiting examples, which are offered to more fully illustrate the invention, but are not to be construed as limiting the scope thereof. The examples illustrate the preparation of certain compounds of the invention, and the testing of these compounds in vitro and/or in vivo. Those of skill in the art will understand that the techniques described in these examples represent techniques described by the inventors to function well in the practice of the invention, and as such constitute preferred modes for the practice thereof. However, it should be appreciated that those of skill in the art should in light of the present disclosure, appreciate that many changes can be made in the specific methods that are disclosed and still obtain a like or similar result without departing from the spirit and scope of the invention.

Example 1

Preparation of Compounds of the Invention

Example 1A

Preparation of 1-ethyl-6-methoxy-1H-indole-3-carbonitrile (compound 5)

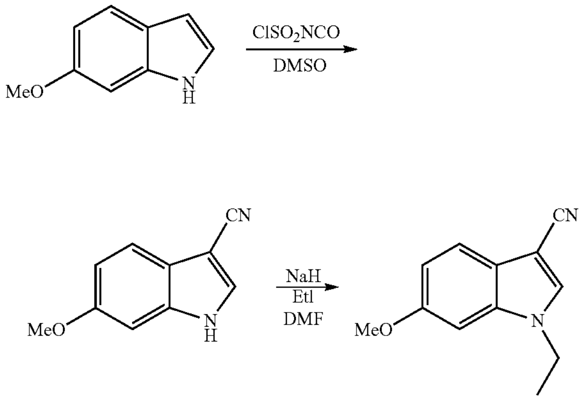

Step A: A solution of 6-methoxyindole (10.0 g, 68.0 mmol) in DMF (120 mL) was cooled to 0° C. and treated with chlorosulfonyl isocyanate (7.72 mL, 88.4 mmol). After the addition, the reaction mixture was stirred at this temperature for 1 h. The dark solution was poured into ice water (600 mL) and the light brown solid was collected by filtration, washed with additional $H_2O$ and dried to afford 9.9 g (85%) of 6-methoxy-1H-indole-3-carbonitrile as a light brown solid.

Step B: To a solution of 6-methoxy-1H-indole-3-carbonitrile (9.9 g, 57.6 mmol) in DMF (150 mL) was added NaH (60% dispersion in mineral oil, 3.45 g, 86.3 mmol). The reaction mixture was stirred for 15 min and then ethyl iodide (5.53 mL, 69.1 mmol) was added and the mixture was stirred at room temperature overnight. The reaction mixture was then diluted with $H_2O$ and extracted with EtOAc (2×). The organic phases were washed with $H_2O$ (3×) and saturated NaCl and then dried and concentrated to a semi-solid. The crude product was purified via column chromatography on silica gel (200 g) using $CH_2Cl_2$/hexanes (50-100%) as eluent to yield 6-methoxy-1-ethyl-1H-indole-3-carbonitrile as a tan solid.

Utilizing steps A and B above and substituting different indoles and alkyl halides gave the following compounds: Compounds 43, 45, 51, 52, 108, 109, 115, 118, 120, 123, 126, 179 and 714.

Example 1B

Preparation of 6-ethoxy-1-ethyl-1H-indole-3-carbonitrile (compound 9)

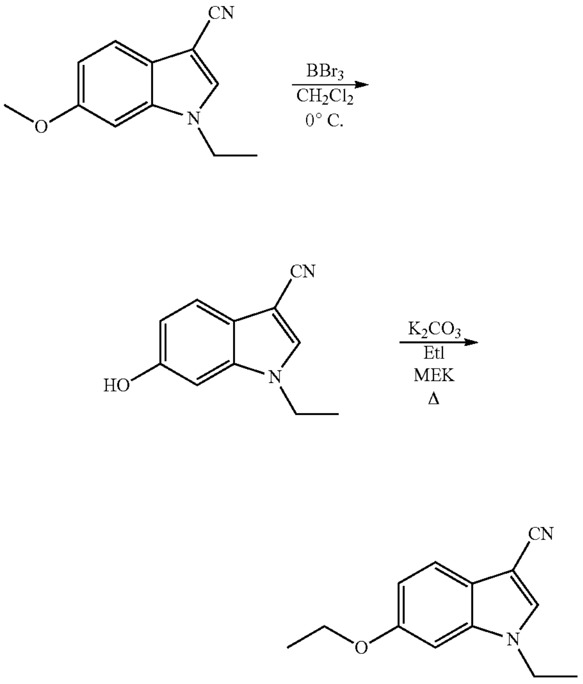

Step A: To a solution of 1-ethyl-6-methoxy-1H-indole-3-carbonitrile (2.85 g, 14.2 mmol), prepared by example 1A, step B, in $CH_2Cl_2$ (40 mL) was added a 1M solution of $BBr_3$ in $CH_2Cl_2$ (28.5 mL, 28.5 mmol) at 0° C. The mixture was allowed to warm to room temperature and kept for 2.5 h. The dark reaction mixture was then poured onto ice and sufficient 1M NaOH was added until the pH was 8-9. The product was extracted with $CH_2Cl_2$ (3×) and the combined organic phases were washed with saturated $NaHCO_3$ , $_{H2}O$ and saturated NaCl. After drying over $MgSO_4$, the solution was concentrated and the product was purified by chromatography ($EtOAc/CH_2Cl_2$, 0-10%) to afford 2.15 g (82%) of 6-hydoxy-1-ethyl-1H-indole-3-carbonitrile as a yellow solid.

Step B: To a solution 6-hydoxy-1-ethyl-1H-indole-3-carbonitrile (80 mg, 0.43 mmol) in 5 mL of methyl ethyl ketone was added anhydrous $K_2CO_3$ (71 mg, 0.52 mmol) and iodomethane (0.05 mL, 0.60 mmol). After stirring overnight at reflux, the reaction mixture was cooled, diluted with $H_2O$ and extracted with EtOAc (3×). The combined organic phases were dried and concentrated. Flash chromatography ($CH_2Cl_2$) gave 94 mg (100%) of 6-ethoxy-1-ethyl-1H-indole-3-carbonitrile as a white wax.

In similar fashion, following steps A and B, above, the following compounds were also prepared: compounds 6, 10, 11, 12 and 24

Example 1C

Preparation of 5-(4-methoxyphenyl)-5H-[1,3]dioxolo[4,5-f]indole-7-carbonitrile (compound 44)

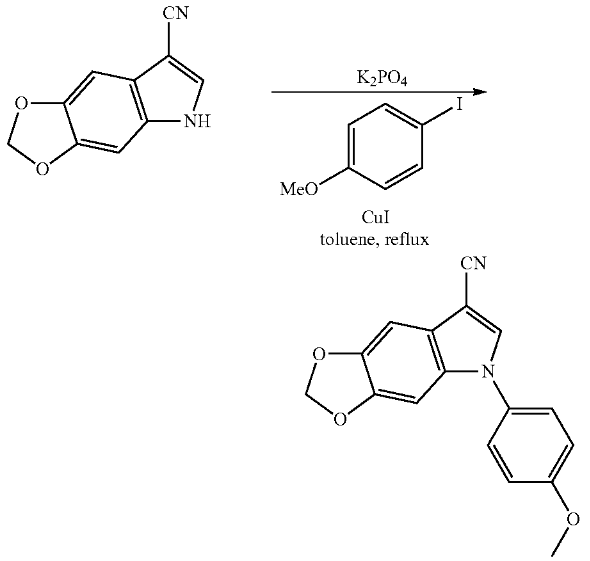

A mixture of p-iodoanisole (85 mg, 0.36 mmol), anhydrous $K_3PO_4$ (102 mg, 0.48 mmol), CuI (4.6 mg, 0.024 mmol) and N,N'-Dimethyl cyclohexane-1,2-diamine (14 mg, 0.096 mmol) was added to 5H-[1,3]dioxolo[4,5-f]indole-7-carbonitrile (45 mg, 0.24 mmol), prepared as described by the method of example 1A, step A, in anhydrous toluene (0.4 mL). After heating at reflux for 24 h, the solvent was evaporated under vacuum. The residue was dissolved with $CH_2Cl_2$ (5 mL) and the mixture was filtered. The filtrate was concentrated to afford crude product, which was purified by silica gel chromatography using EtOAc/petroleum ether (1:4) as eluent to yield 5-(4-methoxyphenyl)-5H-[1,3]dioxolo[4,5-f]indole-7-carbonitrile.

Utilizing the procedure above and substituting different aryl iodides gave the following compounds: compounds 4, 8, 102, 103, 111, 112, 117, 119, 124, 125, 127, 154.

Example 1D

Preparation of 1-ethyl-6-(pyrazin-2-yloxy)-1H-indole-3-carbonitrile (compound 13)

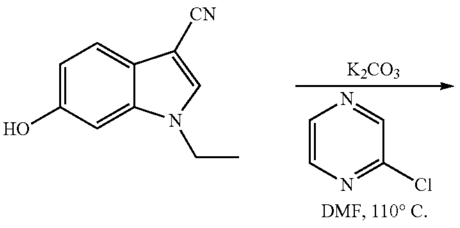

-continued

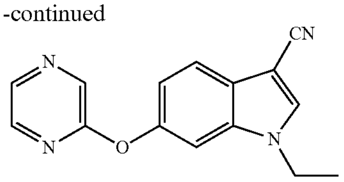

To a solution of 1-ethyl-6-hydroxy-1H-indole-3-carbonitrile (60 mg, 0.32 mmol) prepared as described in example 1A, step A, in DMF (5 mL) was added $K_2CO_3$ (55 mg, 0.40 mmol) and 2-chloropyridazine (45 mg, 0.40 mmol). The mixture was heated at 110° C. for 18 h. After cooling to room temperature, the reaction mixture was diluted with $H_2O$ and extracted with EtOAc (3×). The combined organic phases were washed with $H_2O$ and saturated NaCl, dried and concentrated. The product was isolated by chromatography (EtOAc/$CH_2Cl_2$, 1-3%) over silica gel to afford 76 mg (96%) of the title compound, 1-ethyl-6-(pyrazin-2-yloxy)-1H-indole-3-carbonitrile, as an off-white solid.

Example 1E

Preparation of 3-cyano-1-ethyl-1H-indole-6-carboxylic acid phenylamide (compound 15)

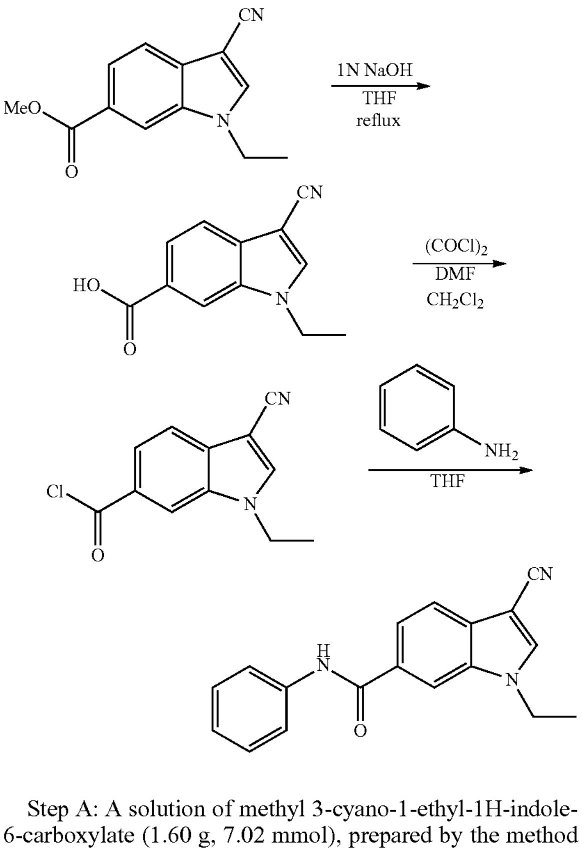

Step A: A solution of methyl 3-cyano-1-ethyl-1H-indole-6-carboxylate (1.60 g, 7.02 mmol), prepared by the method described in example 1A from methyl 1H-indole-6-carboxylate, in THF (35 mL) was treated with 1N NaOH (7.7 mL, 7.7 mmol) and heated at reflux for 2.5 h. After cooling to room temperature, most of the THF was removed and the solution was diluted with $H_2O$ and extracted with ether (2×). The ether extracts were discarded. The aqueous phase was then acidified with 6N HCl to pH 2 and then extracted with EtOAc (3×). The EtOAc layers were combined, washed with saturated NaCl and then dried and concentrated to afford 1.43 g (95%) of 3-cyano-1-ethyl-1H-indole-6-carboxylic acid as a white solid.

Step B: A suspension of 3-cyano-1-ethyl-1H-indole-6-carboxylic acid (0.42 g, 1.96 mmol) in $CH_2Cl_2$ (15 mL) was cooled to 0° C. The suspension was treated with DMF (2 drops) and then oxalyl chloride (0.34 mL, 3.92 mmol) was added via syringe during 2 minutes after which the ice bath was removed and the reaction mixture was allowed to warm to ambient temperature during 1.5 h during which time the reaction became a yellow solution. The solution was then concentrated in vacuo to afford 0.46 g (quantitative yield) of 3-cyano-1-ethyl-1H-indole-6-carbonyl chloride as a yellow solid.

Step C: A suspension of 3-cyano-1-ethyl-1H-indole-6-carbonyl chloride (70 mg, 0.30 mmol) in THF (5 mL) was cooled to 0° C. and treated with aniline (0.08 mL, 0.90 mmol). After the addition the reaction was warmed to ambient temperature and after stirring for an additional 16 hours, the reaction mixture was diluted with $H_2O$ and extracted with EtOAc (2×). The combined organic phases were washed with saturated NaCl and then dried and concentrated to afford the product. Chromatography (EtOAc/$CH_2Cl_2$, 2/98) over silica gel gave 44 mg (51%) of 3-cyano-1-ethyl-1H-indole-6-carboxylic acid phenylamide.

Utilizing essentially the procedure above gave the following compound: Compound 89.

Example 1F

Preparation of t-butyl (3-cyano-1-ethyl-1H-indol-6-yl)-carbamate (compound 16)

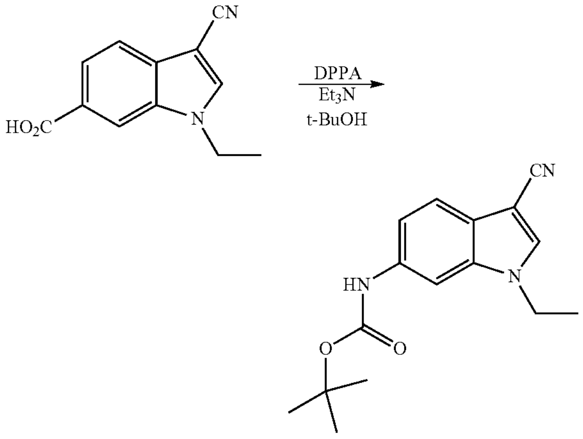

A solution of 3-cyano-1-ethyl-1H-indole-6-carboxylic acid (0.60 g, 2.80 mmol) from Example 1E, step A, in t-butanol (20 mL) was treated with $Et_3N$ (0.46 mL, 3.36 mmol) and diphenylphosphoryl azide (0.73 mL, 3.36 mmol) and then heated at reflux for 4 h. After cooling to room temperature, most of the t-butanol was removed in vacuo to give an oil, which was then dissolved in EtOAc. After washing with $H_2O$, the organic phase was back-extracted with EtOAc and the organic layers were combined and washed sequentially with additional $H_2O$, saturated $NaHCO_3$ and saturated NaCl. The organic phase was dried, concentrated and the resulting crude product was purified by chromatography over silica gel using $EtOAc/CH_2Cl_2$ (0-1%) to afford 0.52 g (65%) of t-butyl (3-cyano-1-ethyl-1H-indol-6-yl)-carbamate as a white solid.

The following compound was made in similar fashion: compound 90.

Example 1Ga

Preparation of 2-(4-aminophenyl)-1-ethyl-6-methoxy-1H-indole-3-carbonitrile via Suzuki route (compound 55)

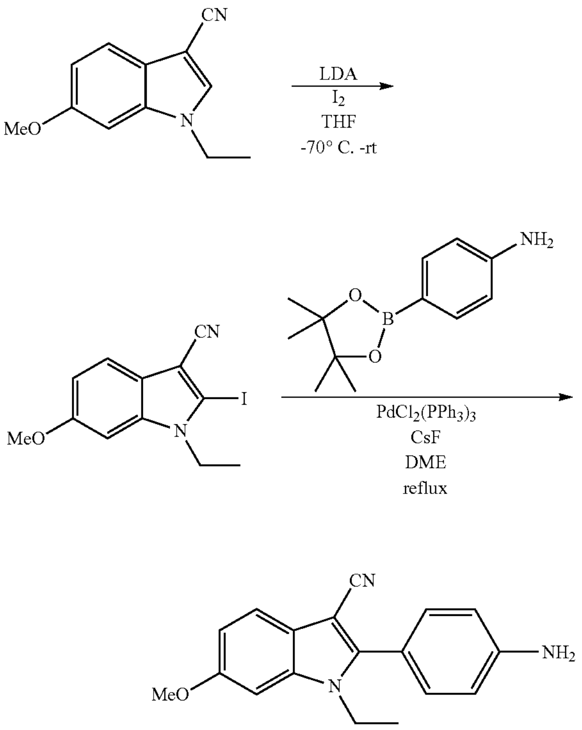

Step A: A 2M solution of lithium diisopropyl amide in THF/hexanes (Acros) (3.9 mL, 7.8 mmol) was diluted with THF (5 mL) in a flame-dried flask. After cooling the reaction to −30° C., a solution of 1-ethyl-6-methoxy-1H-indole-3-carbonitrile (1.30 g, 6.5 mmol) in THF (10 mL) was added dropwise during 10 min, maintaining the temperature at −30° C. After stirring for an additional 30 min at this temperature, a solution of iodine (2.31 g, 9.1 mmol) in THF (5 mL) was added during 10 min. After the addition, the reaction was warmed to ambient temperature during 1 h. The reaction was then diluted with ice-$H_2O$ and extracted with EtOAc (2×). The combined organic phases were washed with 1M sodium thiosulfate and saturated NaCl and then concentrated to a brown solid. Chromatography ($CH_2Cl_2$/hexanes, 1/1) over silica gel gave 1.31 g (62%) of 1-ethyl-2-iodo-6-methoxy-1H-indole-3-carbonitrile as an off-white solid.

Step B: A mixture of 1-ethyl-2-iodo-6-methoxy-1H-indole-3-carbonitrile (1.25 g, 3.83 mmol), 4-(4,4,5,5-tetramethyl)-1,3-2-dioxaboralanyl-2-yl-aniline (0.96 g, 4.90 mmol), CsF (1.46 g, 9.58 mmol) and $Pd(PPh_3)_2Cl_2$ (110 mg, 0.15 mmol) in DME (20 mL) was added to a flask and alternatively evacuated and flushed with $N_2$. The reaction was then heated at reflux for 24 h and then cooled to room temperature. The reaction mixture was diluted with $H_2O$ and extracted with EtOAc (2×). The combined organic phases were washed with $H_2O$ and saturated NaCl and then dried over $MgSO_4$ and concentrated. The crude reaction mix purified by flash chromatographt on silica gel using $EtOAc/CH_2Cl_2$ (5/95) as eluent to afford 765 mg (69%) of 2-(4-aminophenyl)-1-ethyl-6-methoxy-1H-indole-3-carbonitrile as a yellow solid.

Utilizing essentially the same procedure described above and substituting different boronic acids gave the following compounds: compounds 19, 20, 21, 22, 53, 63, 70, 71, 74, 76, 77, 79, 80, 100, 110, 229, 239, 240, 247, 250, 254, 255, 256, 257, 258, 259, 260, 281, 282, 283, 284, 286, 335, 336, 337, 338, 339, 347, 348, 426, 427, 428, 429, 476, 543, 578, 758.

Example 1Gb

Preparation of 2-(4-aminophenyl)-1-butyl-6-methoxy-1H-indole-3-carbonitrile via alternative Suzuki route

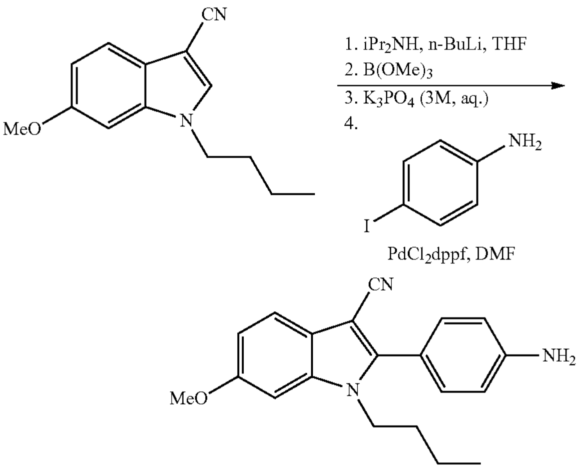

To a solution of $(i\text{-}Pr)_2NH$ (1.35 mL, 9.65 mmol) in THF (30 mL) cooled to −78° C. was added n-BuLi (3.7 mL, 2.5M in hexanes, 9.21 mmol) in one portion. The acetone/dry ice bath was exchanged for ice/water bath and the solution was stirred further for 40 min. The solution was cooled to −78° C. and solution of 1-butyl-6-methoxy-1H-indole-3-carbonitrile, prepared as in example 1A (2.0 g, 8.77 mmol) in THF (10 mL) was added dropwise. This solution was stirred for 15 min at −78° C., following by 20 min at −20° C. Trimethyl borate (1.0 mL, 8.77 mmol) was added, the reaction mixture was stirred for 15 min at −20° C. after which the cooling bath was removed and this solution was stirred further at room temperature for 1 h. A solution of $K_3PO_4$ was added (11.7 mL, 3M aqueous solution, 35.1 mmol) followed by a solution of 4-iodoaniline (2.5 g, 11.40 mmol) and $PdCl_2dppf$ catalyst (640 mg, 0.88 mmol) in DMF (40 mL, plus a 5 mL rinse). The reaction mixture was stirred overnight (ca. 18 h.) and then water (80 mL) was added and the product was extracted with EtOAc (3×50 mL). The combined organic fractions were dried over $MgSO_4$, filtered and concentrated under reduced pressure. The crude product was purified via flush chromatography on silica gel (5→60% EtOAc/Hexanes as eluant) to afford the desired 2-(4-aminophenyl)-1-butyl-6-methoxy-1H-indole-3-carbonitrile as a tan solid (2.4 g, 86% yield).

The following compounds were prepared in similar fashion utilizing other indole and aryl and hereroaryl bromides and iodides: Compounds 656, 659, 660, 661, 682, 683, 712, 731, 732, 733, 806, 807, 808, 809, 810, 811, 812, 813, 814, 827.

Example 1Gc

Preparation of 2-(4-aminophenyl)-6-methoxy-1-propyl-1H-indole-3-carbonitrile via Negishi route.

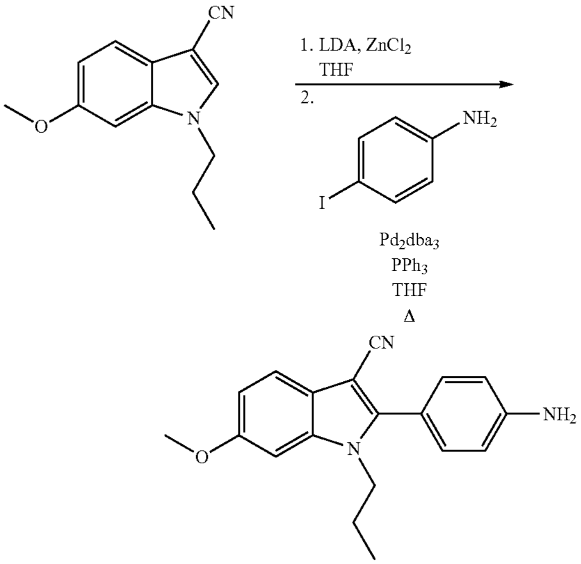

A nitrogen-purged flask fitted with a septum and a nitrogen needle was charged with dry THF (all additions performed by syringe) (20 mL). Diisopropylamine (Aldrich Sure-Seal, 2.00 mL, 14.3 mmol) was added, and the solution was cooled to 0° C. n-Butyllithium (8.50 mL of 1.6 M solution in hexane, 13.6 mmol) was added slowly. The flask was allowed to warm to room temperature briefly, and then was cooled to −78° C. A concentrated THF solution of 6-methoxy-1-propyl-1H-indole-3-carbonitrile (2.77 g, 12.9 mmol; prepared analogously to compound 5 of Example 1A) was added slowly, and the resulting solution was maintained at −78° C. for 30 min. The flask was then transferred to a water-ice bath and allowed to come to 0° C. for about 15 minutes. The solution was once again cooled to −78° C., and $ZnCl_2$ (0.5 M solution in THF, 27.0 mL, 13.5 mmol) was slowly added. A precipitate was observed at this point, which may have been the bis(indole) zinc compound, but the solution became homogeneous when the entire volume of zinc chloride solution was added. After about 10 minutes, the solution was allowed to come to room temperature, and a THF solution (5 mL) of 4-iodoaniline (3.47 g, 15.8 mmol) and triphenylphosphine (338 mg, 1.29 mmol) was added. The septum was removed, and solid $Pd_2(dba)_3$ (295 mg, 0.322 mmol) was added. A reflux condenser was fitted to the flask, and the solution was degassed by three successive cycles of vacuum pumping/$N_2$ purging. The solution was then heated to reflux overnight. After cooling to room temperature, the solution was poured into 4 volumes of water, and 4 volumes of ethyl acetate were added. The resulting mixture was vigorously stirred for 30 minutes, then filtered through celite (with ethyl acetate washing) to remove solid Zn-and Pd-containing material. The phases were separated, and the aqueous phase was extracted with more ethyl acetate. The organic phases were washed in sequence with saturated brine, combined, dried over anhydrous sodium sulfate, filtered and evaporated. A solid precipitate formed at this point, which was sufficiently pure product and was collected by trituration with ether and filtration. The remaining material was purified by column chromatography (eluting 1:2 ethyl acetate-hexane on silica gel 60). Total yield of the product, 2-(4-amino-phenyl)-6-methoxy-1-propyl-1H-indole-3-carbonitrile, was 2.75 g (8.99 mmol, 70%).

The following compounds were made using essentially the same procedure and substituting other aryl or heteroaryl iodides or bromides: Compounds 393, 408, 430, 431, 436, 437, 438, 459, 460, 461, 462, 483, 484, 632, 633, 634, 635, 636, 650, 651.

Example 1Gd

Preparation of 1-ethyl-2-(3-hydroxyphenyl)-6-methoxy-1H-indole-3-carbonitrile (Compound 288)

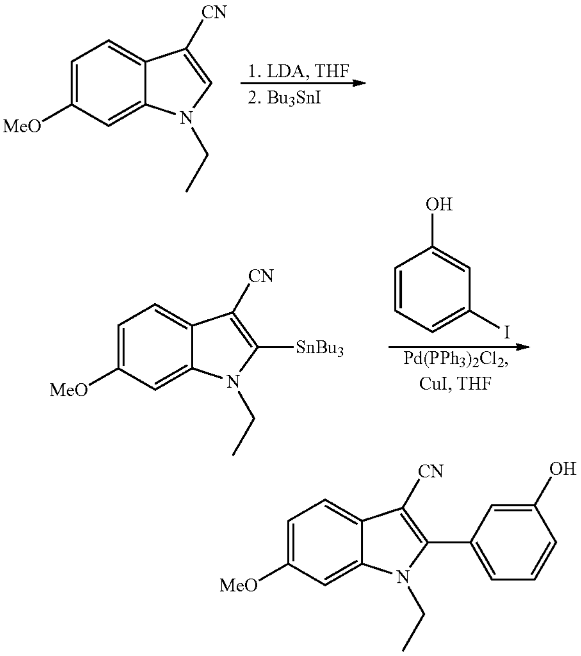

Step A: A solution of THF (60 mL) and diisopropylamine (5.5 mL, 39 mmol) was cooled to −78° C. n-Butyllithium (14.5 mL, 2.5M in hexanes, 36.2 mmol) was added dropwise over 5 minutes. The LDA mixture was stirred at −78° C. for 10 minutes, and then at 0° C. for 20 minutes. The solution was re-cooled to −78° C. 1-ethyl-6-methoxy-1H-indole-3-carbonitrile (5.0 g, 25 mmol), prepared as in example 1A, was taken up in THF (30 mL) and added dropwise to the LDA mixture over 15 minutes. The reaction was stirred at −78° C. for 10 minutes, and at 0° C. for 30 minutes. Once again, the reaction mixture was cooled to −78° C. Tributyltin iodide (10 mL, 35 mmol) was added dropwise. This was stirred at −78° C. for 15 minutes, and then at 0° C. for 30 minutes. The reaction mixture was absorbed onto silica gel and concentrated. Purification by chromatography ($CH_2Cl_2$) yielded 1-ethyl-6-methoxy-2-tributylstannanyl-1H-indole-3-carbonitrile (12.05 g, 98%).

Step B: 1-Ethyl-6-methoxy-2-tributylstannanyl-1H-indole-3-carbonitrile (1.0 g, 2.05 mmol), prepared in step A, was combined with 3-iodophenol (474 mg, 2.15 mmol), $Pd(PPh_3)_2Cl_2$ (67 mg, 0.102 mmol), CuI (75 mg, 0.39 mmol) and THF (4.0 mL). This mixture was heated at 65° C. overnight. The reaction mixture was diluted in EtOAc, and was filtered through celite. The filtrate was concentrated and the residue was purified by silica gel chromatography (4:1, $CH_2Cl_2$/EtOAc) to yield crude product. Ether trituration yielded 1-ethyl-2-(3-hydroxy-phenyl)-6-methoxy-1H-indole-3-carbonitrile (430 mg, 72%) as a yellow-white solid.

The following compounds were prepared similarly as above, using other commercially available iodides and bromides, or using iodides derived from a one step amidation of p-iodophenylsulfonyl chloride: Compounds 275, 276, 277, 278, 331, 363, 364, 373, 374, 375, 474, 475, 678.

Example 1Ge

Preparation of ethanesulfonic acid [4-(3-cyano-6-difluoromethoxy-1-ethyl-1H-indol-2-yl)-phenyl]-amide via Heck route (compound 519)

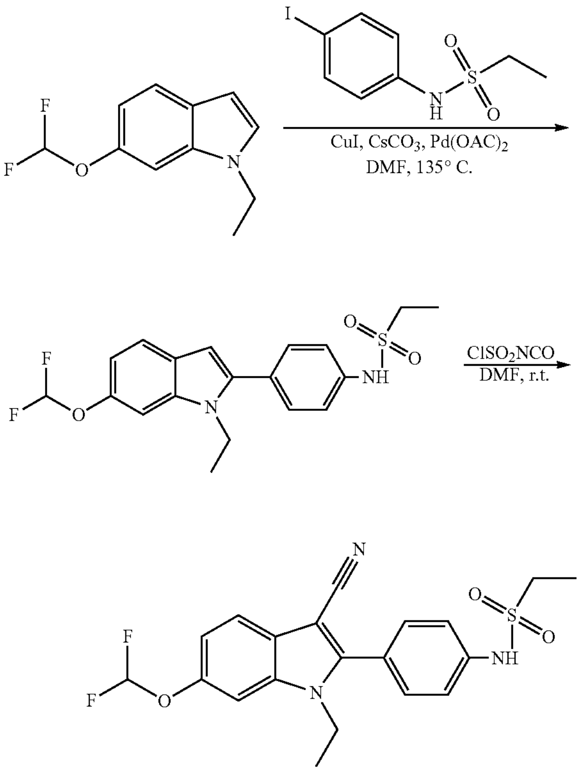

Step A: A solution of 6-difluoromethoxy-1-ethyl-1H-indole (402.8 mg, 2.04 mmol), ethanesulfonic acid (4-iodo-phenyl)-amide (712.1 mg, 2.29 mmol), cesium carbonate (733.2 mg, 3.82 mmol), triphenylphosphine (33.1 mg, 0.13 mmol) and palladium acetate (5.7 mg, 0.025 mmol) in DMA (5 ml) was heated to 135° C. for 48 h. The reaction mixture was diluted with water and extracted with EtOAc (2×10 mL). The combined organic phases were washed with brine, dried over $MgSO_4$, and then concentrated. The residue was purified via column chromatogrphy on silica gel (25 g) using EtOAc/Hexanes (10-20%) as eluent to afford 298.2 mg (37.1% yield) of ethanesulfonic acid [4-(6-difluoromethoxy-1-ethyl-1H-iodo-2-yl)-phenyl]-amide, compound 516, as a light brown solid.

Step B: Following the procedure 1A, step A, ethanesulfonic acid [4-(6-difluoromethoxy-1-ethyl-1H-iodo-2-yl)-phenyl]-amide was converted to ethanesulfonic acid [4-(3-cyano-6-difluoromethoxy-1-ethyl-1H-indol-2-yl)-phenyl]-amide, compound 519.

Following steps A and B above, the following compounds were prepared in similar fashion: Compounds 343, 344, 345, 346, 409, 410, 411, 412, 413, 414, 415, 416, 417, 418, 419, 463, 464, 465, 466, 467, 468, 469, 470, 471, 472, 473, 515, 517, 518, 520, 521, 522, 523, 524, 575, 577, 579, 580, 611, 612, 613, 614

Example 1H

Preparation of 1-ethyl-2-(4-fluorophenylethynyl)-6-methoxy-1H-indole-3-carbonitrile (compound 67)

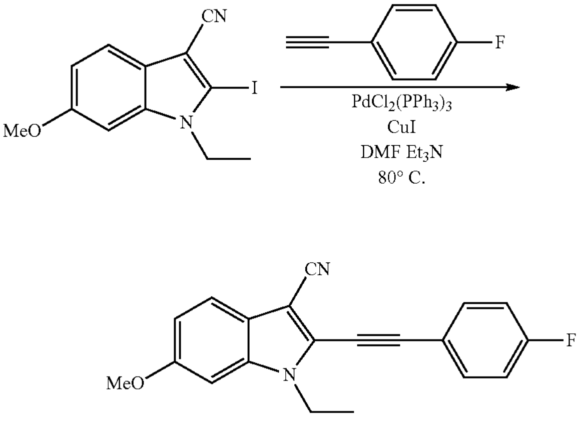

A mixture of 1-ethyl-2-iodo-6-methoxy-1H-indole-3-carbonitrile (150 mg, 0.46 mmol), prepared as described in example 1Ga, step A, 4-fluorophenylacetylene (80 mg, 0.0.69 mmol), bis(triphenylphosphine) palladium (II) dichloride (6 mg, 0.009 mmol) and CuI (4 mg, 0.018 mmol) was added to a sealable tube and alternatively evacuated and flushed with $N_2$. To the tube was then added DMF (4 mL) and $Et_3N$ (0.25 mL, 1.84 mmol) and the reaction was heated at 80° C. for 20 h and then cooled to room temperature. The reaction mixture was diluted with $H_2O$ and extracted with EtOAc (2×). The combined organic phases were washed with $H_2O$ (3×) and saturated NaCl and then dried over MgSO4 and concentrated. The crude reaction mix was absorbed on silica gel (0.6 g) and chromatographed over silica gel using EtOAc/hexanes (10-20%) as eluent to afford 120 mg (82%) of 1-ethyl-2-(4-fluorophenylethynyl)-6-methoxy-1H-indole-3-carbonitrile as a yellow solid.

Utilizing essentially the same procedure described above and substituting different acetylene derivatives gave the following compounds: compounds 64, 65, 66, 68, 69, 91, 92, 93, 94, 95, 96, 133, 134, 135, 136, 137, 143, 144, 145, 146, 147, 148, 149, 150, 151, 158, 159, 160, 161, 169, 170, 171, 172, 173, 174, 175, 176, 177, 178, 184, 185, 186, 187, 188, 196, 197, 198, 199, 200, 201, 202, 223, 230, 231, 232, 233, 234, 235, 236, 237, 238.

Example 1I

Preparation of 1-ethyl-3-(5-ethyl-[1,2,4]oxadiazol-3-yl)-6-methoxy-1H-indole (compound 28)

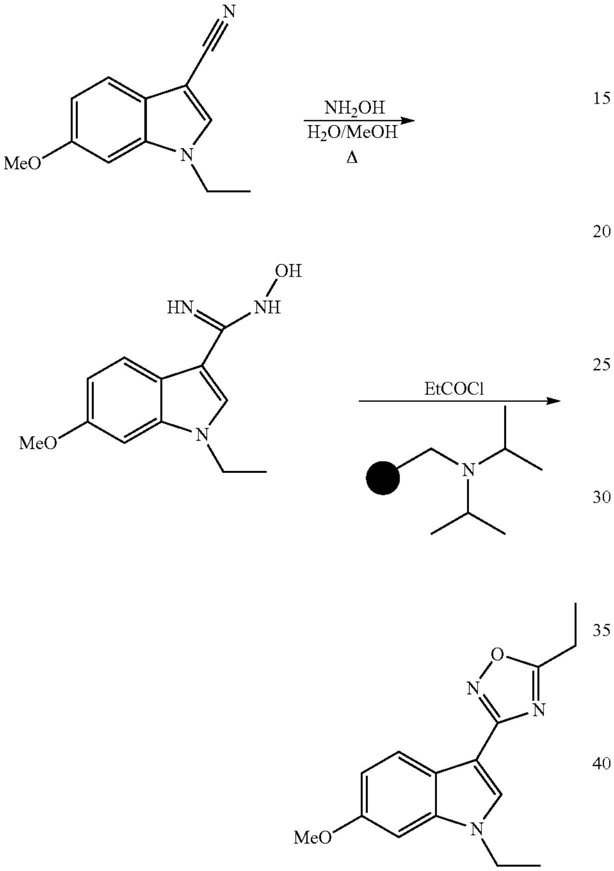

Step A: A solution of 1-ethyl-6-methoxy-1H-indole-3-carbonitrile (1.00 g, 5.00 mmol) in MeOH (10 mL) was treated with a 50% aqueous solution of hydroxylamine (0.38 mL, 6.25 mmol) and heated at reflux for 18 h. After cooling to room temperature, the heterogeneous mixture was filtered to afford 525 mg of desired product as a tan solid. The filtrate was concentrated to an oil, which was then dissolved in $CH_2Cl_2$ and chromatographed over silica gel using EtOAc/$CH_2Cl_2$ (15-50%) to afford an additional 295 mg of product as a tan solid. Total yield of 1-ethyl-N-hydroxy-6-methoxy-1H-indole-3-carboxamidine was 820 mg (70%).

Step B: The N-hydroxycarboxamidine above (50 mg, 0.21 mmol), polystyrene-diisopropylethylamine 165 mg, 3.90 mmol/g loading) and propionyl chloride (0.03 mL, 0.32 mmol) in $CH_2Cl_2$ (10 mL) were placed in a tube and rotated for 22 h at room temperature. After this time, trisamine resin (77 mg, 2.71 mmol/g loading) was then added and the tube rotated for an additional 30 min at room temperature. Solids were filtered and then the filtrate was concentrated and diluted with toluene (5 mL) and heated at 110° C. overnight. The crude reaction mixture was concentrated and purified by chromatography (EtOAc/$CH_2Cl_2$, 2/98) to afford 27 mg (46%) of 1-ethyl-3-(5-ethyl-[1,2,4]oxadiazol-3-yl)-6-methoxy-1H-indole as a white solid.

The following compound was prepared utilizing the above procedure with substitution of the appropriate acyl halide: compound 29.

Example 1J

Preparation of 1-ethyl-6-methoxy-3-(5-ethyl-[1,3,4]oxadiazol-2-yl)-1H-indole (compound 54)

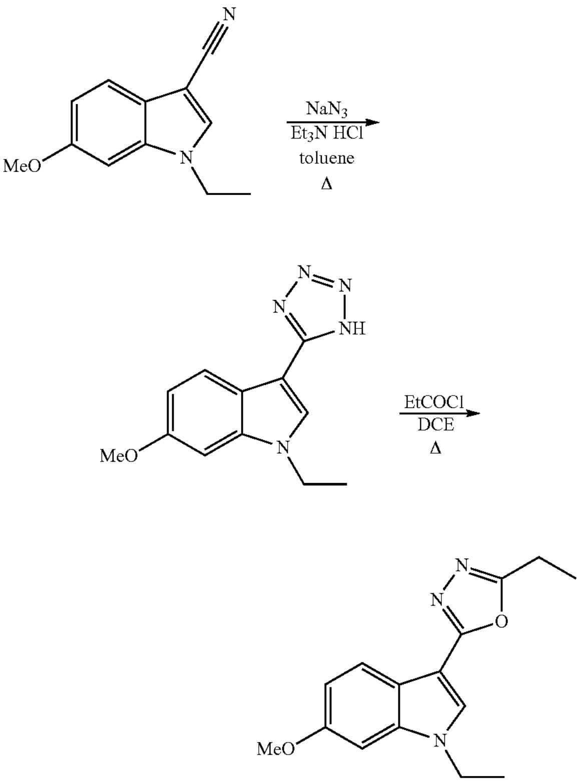

Step A: A mixture of 1-ethyl-6-methoxy-1H-indole-3-carbonitrile (1.00 g, 5.00 mmol) in toluene (30 mL) was treated with triethylamine hydrochloride (1.03 g, 7.50 mmol) and sodium azide (0.49 g, 7.50 mmol) and was heated at reflux for 16 h. After cooling to room temperature, the reaction mixture was diluted with saturated $NaHCO_3$ and extracted with EtOAc. The organic layer was then washed with additional $NaHCO_3$ (2×). The combined aqueous phases were acidified to pH 2 with 6N HCl. The resultant thick precipitate was extracted with hot EtOAc (3×) and the combined organic phases were washed with saturated NaCl and dried and concentrated to give 0.55 g (45%) of 1-ethyl-6-methoxy-3-(1H-tetrazol-5-yl)-1H-indole as a yellow solid.

Step B: A suspension of the tetrazole above (50 mg, 0.21 mmol) and propionyl chloride (0.03 mL, 0.31 mmol) in dichloroethane (5 mL) was heated at reflux for 21 h. After cooling the reaction mixture to room temperature, polystyrene trisamine resin (70 mg, 3.4 meq/g) was added and the reaction was rotated for 4 h at room temperature. After filtering off the resin, and removal of the solvent, the crude product was absorbed on silica gel and the product was isolated by silica gel chromatography (EtOAc/$CH_2Cl_2$, 5-10%) to afford 30 mg (53%) of 1-ethyl-6-methoxy-3-(5-ethyl-[1,3,4]oxadiazol-2-yl)-1H-indole as a tan solid.

Example 1K

Preparation of ethyl 5-difluoromethoxy-1-(4-methoxyphenyl)-2-methyl-1H-indole-3-carboxylate (compound 49)

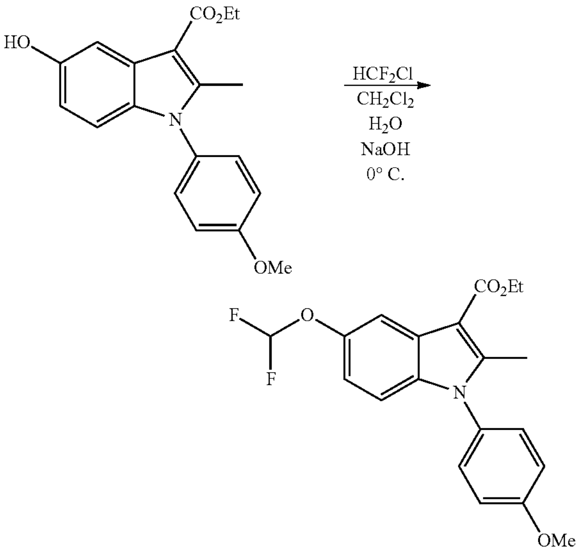

Freon-22 ($HCF_2Cl$) gas was bubbled into a solution of ethyl 5-hydroxy-1-(4-methoxyphenyl)-2-methyl-1H-indole-3-carboxylate (250 mg, 0.77 mmol) in $CH_2Cl_2$ (5 mL) at 0° C. containing a small amount of tetrabutylammonium bromide as a phase transfer catalyst. A 50% solution of NaOH was added dropwise at 0° C. After the addition, the mixture was stirred at 0° C. for 2 h. After the addition of $H_2O$, the organic phase was separated and washed with brine and dried over $Na_2SO_4$. The solvent was then concentrated and the residue was purified by column chromatography over silica gel using EtOAc/petroleum ether (1/2) as eluent to yield the desired product in 40% yield.

The following compounds were prepared utilizing the above procedure with substitution of the appropriate hydroxyindole: compounds 18, 46, and 50.

Example 1L

Preparation of 1-[5-methoxy-1-(4-methoxyphenyl)-1-H-indol-3-yl]-ethanone (compound 42)

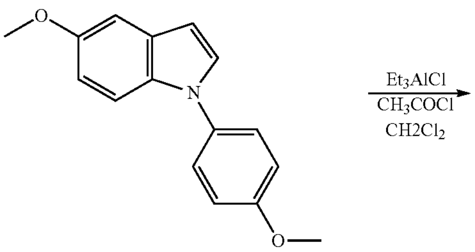

-continued

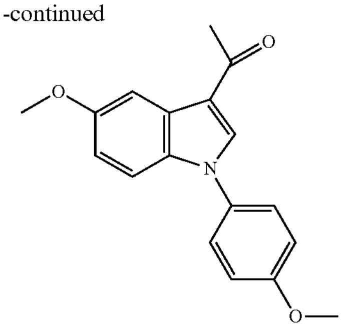

5-Methoxy-1-(4-methoxyphenyl)-1-H-indole (50 mg, 0.2 mmol), prepared by the method of example 1C, was dissolved in 1 mL of $CH_2Cl_2$ at 0° C. $Et_2AlCl$ (300 μL, 1M in hexanes, 0.3 mmol) was then added. After stirring at 0° C. for 30 min, a solution of acetyl chloride (22 μL, 0.3 mmol) in 1 mL of $CH_2Cl_2$ was added dropwise. This was stirred at 0° C. for a further 90 min. The reaction mixture was quenched with $H_2O$ and was extracted with $CH_2Cl_2$ and concentrated in vacuo. Purification by column chromatography on silica gel EtOAc/$CH_2Cl_2$ (5/95) yielded the title compound as a white solid (42 mg, 71%).

Utilizing essentially the same procedure described above and substituting different acyl chlorides, the following compounds were prepared: compounds 32, 33, 34, 37, 38, 39, 47, 48.

Example 1M

Preparation of 1-ethyl-3-isoxazol-3-yl-6-methoxy-1-H-indole (compound 57)

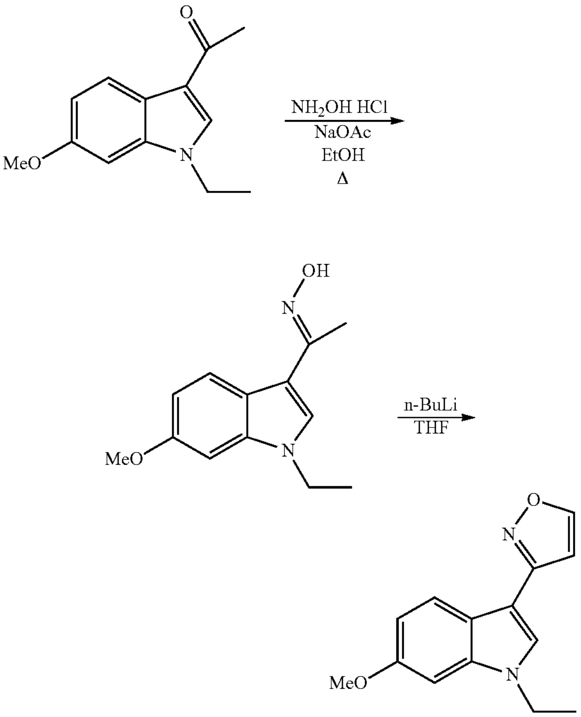

Step A: A mixture of 1-(1-ethyl-6-methoxy-1-H-indole-3-yl)ethanone (200 mg, 0.92 mmol), prepared from 1-ethyl-6-methoxy-1H-indole by the procedure described in example 1L, hydroxylamine hydrochloride (128 mg, 1.84 mmol), NaOAc (151 mg, 1.84 mmol) and EtOH (7 mL) was heated at 85° C. for 4 h. The reaction mixture was then partitioned between $H_2O$ and EtOAc. The organic phase was dried and concentrated in vacuo. Purification by column chromatography using EtOAc/$CH_2Cl_2$ (1/9) yielded 1-(1-ethyl-6-methoxy-1-H-indole-3-yl)ethanone oxime as a white solid (189 mg, 92%).

Step B: 1-(1-Ethyl-6-methoxy-1-H-indole-3-yl)ethanone oxime (100 mg, 0.43 mmol) was dissolved in THF (900 μL) at 0° C. n-BuLi (450 μL, 2.5 M in hexanes, 1.12 mol) was added dropwise, resulting in instant precipitation of solids. DMF (70 μL, 0.9 mol) in 260 μL of was then added dropwise. This was stirred at 0° C. for 1 h, then at room temperature for 1 h. The reaction mixture was pipetted into a mixture containing 1 mL of $H_2O$, 1 mL of THF, and 100 μL of concentrated $H_2\ _{SO4}$. This mixture was heated at 75° C. for 1 h and then was partitioned between $H_2O$ and EtOAc. The organic phase was dried and concentrated. Purification by column chromatography ($CH_2Cl_2$) yielded 1-ethyl-3-isoxazol-3-yl-6-methoxy-1-H-indole product as a white solid (13 mg, 12%).

Example 1N

Preparation of 1-ethyl-3-isoxazol-5-yl-6-methoxy-1H-indole (compound 58)

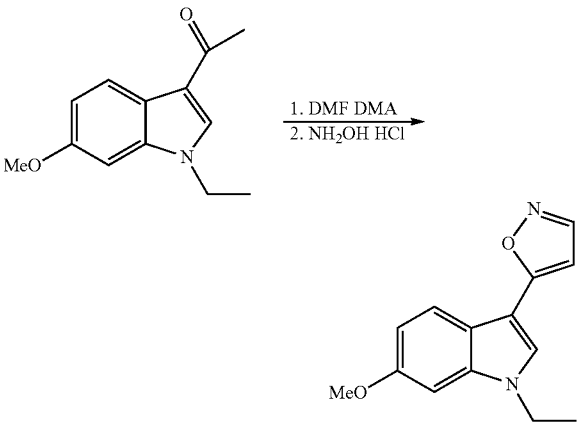

1-(1-Ethyl-6-methoxy-1H-indol-3-yl)ethanone (100 mg, 0.46 mmol), prepared from 1-ethyl-6-methoxy-1H-indole by the procedure described in example 1L, was heated with 1.5 mL of dimethylformamide dimethylacetal and 100 μL of pyrrolidine at 110° C. overnight. The dimethylformamide dimethylacetal was then concentrated in vacuo. The residue was redissolved in 1.25 mL of EtOH and 250 μL of $H_2O$, and was treated with hydroxylamine hydrochloride (66 mg, 0.95 mmol) and heated at 80° C. for 2 h. Partitioning between $H_2O$ and EtOAc and drying and concentration of the organic phase followed by purification by silica gel chromatography (EtOAc/$CH_2Cl_2$, 5/95) gave 1-ethyl-3-isoxazol-5-yl-6-methoxy-1H-indole as a white solid (72 mg, 66%).

Utilizing essentially the same procedure described above, the following compound was prepared: Compound 60.

Example 1O

Preparation of 1-ethyl-6-methoxy-3-(2H-pyrazol-3-yl)-1H-indole (compound 59)

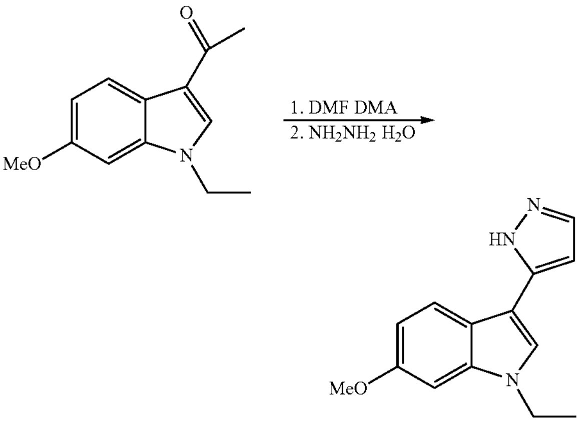

1-(1-Ethyl-6-methoxy-1H-indol-3-yl)-ethanone (100 mg, 0.46 mmol), prepared from 1-ethyl-6-methoxy-1H-indole by the procedure described in example 1L, was heated with 1.5 mL of dimethylformamide dimethyl acetal and 100 μL pyrrolidine at 110° C. overnight. The DMF dimethyl acetal was removed in vacuo. The residue was redissolved in 3 mL of acetic acid, hydrazine hydrate (70 μL, 1.38 mmol) was added, and the mixture was heated to 100° C. for 2 h. The acetic acid was removed in vacuo, and the residue was partitioned between EtOAc and saturated $NaHCO_3$. The organic phase was dried and concentrated and the product purified by silica gel chromatography (EtOAc/Hex, 1/1) to give 59 mg of 1-ethyl-6-methoxy-3-(2H-pyrazol-3-yl)-1H-indole (54%) as a colorless semisolid. Trituration in $Et_2O$ gave a white crystalline powder.

The following compound was prepared utilizing the above procedure: Compound 61.

Example 1P

Preparation of methyl 1-ethyl-3-oxazol-5-yl-1H-indole-6-carboxylate (compound 72)

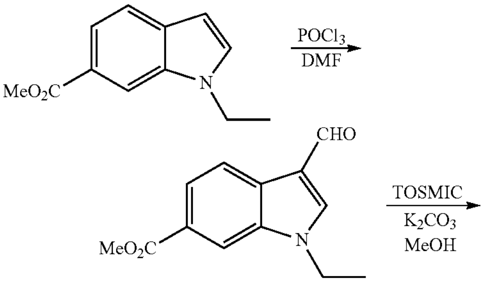

-continued

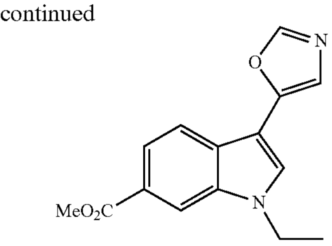

Step A: 1-Ethyl-1H-indole-6-carboxylic acid methyl ester (900 mg, 4.45 mmol) was dissolved in DMF (3.3 mL). This was added dropwise to an ice-cold solution of $POCl_3$ (430 μL, 4.5 mmol) in DMF (1.5 mL). The reaction mixture was stirred at room temperature for 90 minutes. The reaction mixture was then treated with 6N NaOH (3.5 ml). The mixture was then partitioned between $H_2O$ and ethyl acetate. Purification by silica gel chromatography (5-10% $EtOAc/CH_2Cl_2$) yielded 1-ethyl-3-formyl-1H-indole-6-carboxylic acid methyl ester (985 mg, 96%) as a white solid.

Step B: 1-Ethyl-3-formyl-1H-indole-6-carboxylic acid methyl ester (100 mg, 0.42 mmol), TOSMIC (100 mg, 0.52 mmol), $K_2CO_3$ (178 mg, 1.29 mmol), and MeOH (800 μL) were heated at 80° C. overnight. The reaction mixture was then partitioned between $H_2O$ and ether. After drying and concentrating the organic phase, the product was purified by silica gel chromatography ($EtOAc/CH_2Cl_2$, 10/90) to give methyl 1-ethyl-3-oxazol-5-yl-1H-indole-6-carboxylate (26 mg, 23%) as an off-white solid.

Example 1Q

Preparation of methyl 1-ethyl-3-oxazol-2-yl-1H-indole-6-carboxylate (compound 75)

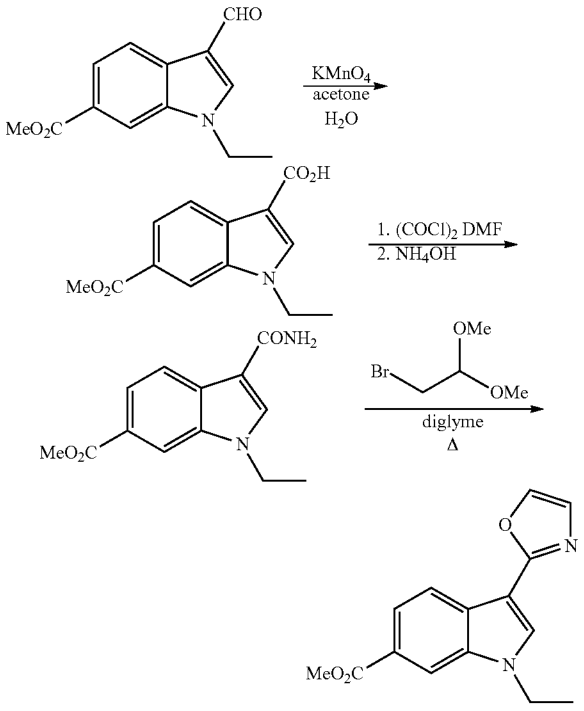

Step A: 1-Ethyl-3-formyl-1H-indole-6-carboxylic acid methyl ester (800 mg, 3.5 mmol), prepared as shown in example 1P, step A, was dissolved in acetone (98 mL). A solution of $KMnO_4$ (655 mg, 4.15 mmol) in $H_2O$ (31 mL) was added. The reaction mixture was stirred at room temperature for 90 minutes. Another addition of $KMnO_4$ (108 mg) in $H_2O$ (6 mL), followed by stirring for another 45 minutes was required to drive the reaction to completion. The reaction mixture was then quenched with 10% $H_2O_2$ (1.5 mL). The mixture was filtered through celite. The filtrate was stripped down under vacuum to roughly ⅓ of the volume. The residue was acidified with 6N HCl, and was extracted into ethyl acetate. The solids isolated from the ethyl acetate layer were triturated with acetone to yield 1-ethyl-1H-indole-3,6-dicarboxylic acid 6-methyl ester (696 mg, 79%) as a light orange solid.

Step B: 1-Ethyl-1H-indole-3,6-dicarboxylic acid 6-methyl ester (600 mg, 2.43 mmol) was suspended in a solution of $CH_2Cl_2$ (27 ml) and DMF (20 μL). Oxalyl chloride (470 μL, 5.38 mmol) was added, and the reaction mixture was stirred for 1 hour at room temperature. This mixture was then slowly poured into a rapidly stirring solution of concentrated $NH_4OH$ (10 mL). This was then partitioned in $H_2O$ and EtOAc. The residue from the ethyl acetate layer was triturated with acetone to yield 6-methoxycarbonyl-1-ethyl-1H-indole-3-carboxamide (511 mg, 85%) as a white solid.

Step C: A mixture of 150 mg (0.61 mmol) of 6-methoxy-carbonyl-1-ethyl-1H-indole-3-carboxamide in diglyme (3.6 mL), and bromoacetaldehyde dimethyl acetal (430 μL, 3.7 mmol) was heated at 125° C. for 2 h. The reaction mixture was cooled and partitioned in $H_2O$ and EtOAc. The organic phase was dried and concentrated and the product was purified by silica gel chromatography ($EtOAc/CH_2Cl_2$ 5-10%). The product containing fractions were combined and concentrated and the solid was triturated with hexanes to yield methyl 1-ethyl-3-oxazol-2-yl-1H-indole-6-carboxylate (75 mg, 46%) as a yellow solid.

Example 1R

Preparation of 1-ethyl-6-methoxy-3-thiazol-2-yl-1H-indole (compound 73)

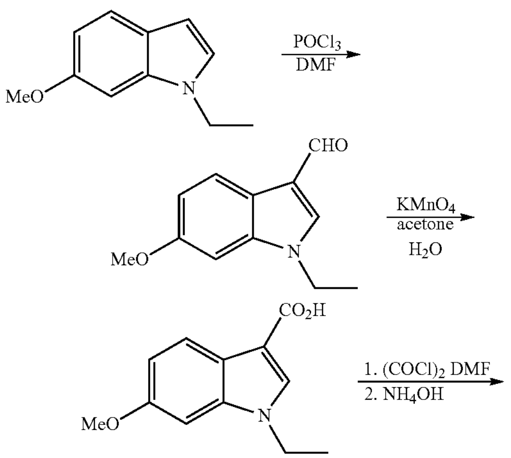

-continued

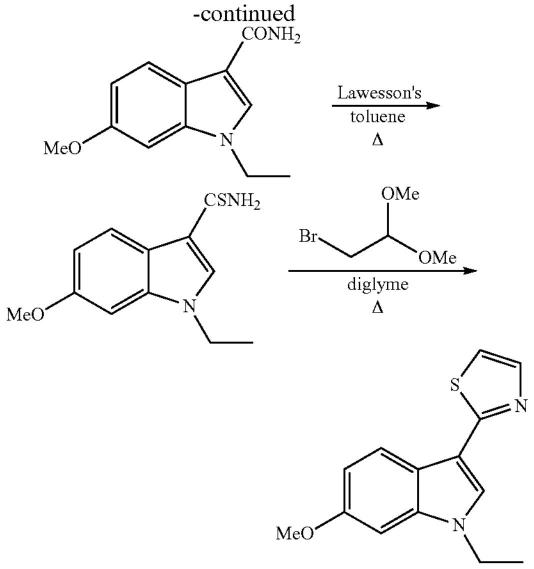

Step A: 1-Ethyl-6-methoxy-1H-indole (900 mg, 5.14 mmol) was dissolved in DMF (1.5 mL). This was added dropwise to an ice-cold solution of $POCl_3$ (500 μL, 5.2 mmol) in DMF (1.75 ml). After stirring at room temperature for 90 minutes, the reaction mixture was re-cooled in an ice bath and was slowly quenched with 6N NaOH (4 mL). The reaction mixture was partitioned between EtOAc and $H_2O$. Purification by silica gel chromatography ($EtOAc/CH_2Cl_2$, 5/95) yielded 1-ethyl-6-methoxy-1H-indole-3-carbaldehyde (849 mg, 81%) as a yellow solid.

Step B: 1-Ethyl-6-methoxy-1H-indole-3-carbaldehyde (600 mg, 2.95 mmol) was dissolved in acetone (85 mL). A solution of $KMnO_4$ (450 mg, 2.85 mmol) in $H_2O$ (28 mL) was added. This was stirred at room temperature for 5 hours. Another solution of $KMnO_4$ (450 mg, 2.85 mmol) in $H_2O$ (25 mL) was then added. After stirring for another hour at room temperature, the reaction was complete. The reaction mixture was quenched with 10% $H_2O_2$ (1.5 mL), and was then filtered through celite. The filtrate was stripped down under vacuum to roughly ⅓ of the volume. The residue was acidified with 6N HCl, and was extracted into ethyl acetate. Purification by silica gel column (hexanes/acetone/acetic acid, 70/30/1) yielded crude product. Trituration with ether yielded pure 1-ethyl-6-methoxy-1H-indole-3-carboxylic acid (365 mg, 56%) as a yellow solid.

Step C: 1-Ethyl-6-methoxy-1H-indole-3-carboxylic acid (250 mg, 1.14 mmol) was suspended in a solution of $CH_2Cl_2$ (12.5 mL) and DMF (10 μL). Oxalyl chloride (230 μL, 2.64 mmol) was added, and the reaction mixture was stirred for 1 hour at room temperature. This mixture was then slowly poured into a rapidly stirring solution of concentrated $NH_4OH$ (5 mL). This was then partitioned in $H_2O$ and EtOAc. The residue from the ethyl acetate layer was triturated with acetone to yield 1-ethyl-6-methoxy-1H-indole-3-carboxamide (134 mg, 54%) as a white solid.

Step D: 1-Ethyl-6-methoxy-1H-indole-3-carboxamide (120 mg, 0.55 mmol), Lawesson's reagent (240 mg, 0.6 mmol), and toluene (2 mL) were heated at 90° C. for 90 min. The reaction mixture was concentrated and purified by silica gel chromatography ($EtOAc/CH_2Cl_2$, 1/9) to yield 1-ethyl-6-methoxy-1H-indole-3-thiocarboxamide as a yellow solid (92 mg, 71%).

Step E: 1-Ethyl-6-methoxy-1H-indole-3-thiocarboxamide (83 mg, 0.36 mmol), glyme (3.6 mL) and bromoacetaldehyde dimethyl acetal (220 μL, 1.86 mmol) were heated at 80° C. for 16 h. More bromoacetaldehyde dimethyl acetal (250 μL was added. This was heated at 80° C. for 2 h. Addition of 250 μL more bromoacetaldehyde dimethyl acetal was followed by heating for another 2 hours. The reaction mixture was cooled to room temperature, absorbed onto silica and purified by silica gel chromatography (hexanes/EtOAc, 7/3) to afford 1-ethyl-6-methoxy-3-thiazol-2-yl-1H-indole as a brown oil (44 mg, 47%).

The following compounds were prepared following the procedure described above: Compounds 78, 101, 104, 105 and 106.

Example 1S

Preparation of 1-ethyl-6-methoxy-2-phenoxymethyl-1H-indole-3-carbonitrile (compound 99)

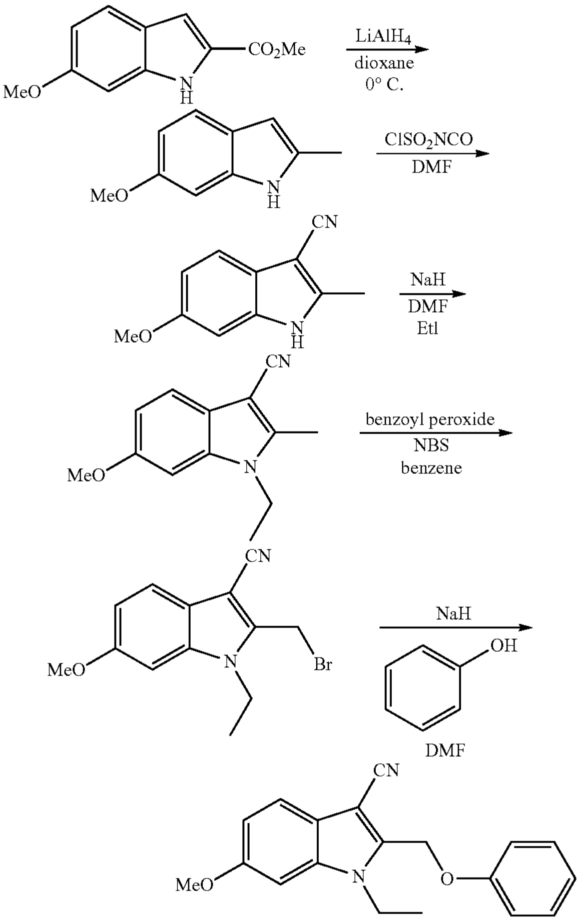

Step A: To a suspension of $LiAlH_4$ (7.6 g, 0.2 mol) in dioxane (100 mL) was added dropwise a solution of methyl 6-methoxy-1H-indole-2-carboxylate (8.2 g, 0.04 mol) in dioxane (50 mL) at 0° C. After the addition, the mixture was stirred at room temperature for 1 h and then heated at reflux for 5 h. After cooling to 0° C., the reaction was quenched by water (dropwise) and then 15% aqueous NaOH. After stirring at room temperature for 1 h, the mixture was filtered through Celite. The solid was washed with large amount of EtOAc. The solvent was washed with brine, dried over $Na_2SO_4$ and evaporated under vacuum. The residue was purified by flash column chromatography on silica gel using EtOAc/petroleum ether (1/5) as eluent to yield 61% of 6-methoxy-2-methyl-1H-indole.

Step B: To a solution of 6-methoxy-2-methyl-1H-indole (3.9 g, 24 mmol) in acetonitrile (200 mL) and DMF (20 mL) was added dropwise a solution of $ClSO_2NCO$ (4 mL, 1.3 eq.) in acetonitrile (31 mL) at 0° C. After the addition, the mixture was stirred at room temperature for 3 h. Then it was poured into ice water and saturated $NaHCO_3$ was added to it until it became basic. The aqueous phase was extracted with $CH_2Cl_2$ and then evaporated. The residue was purified with flash column chromatography on silica gel using EtOAc/petroleum ether (1/5) as eluent to yield 81% of 6-methoxy-2-methyl-1H-indole-3-carbonitrile.

Step C: To a suspension of NaH (0.6 g, 2 eq.) in DMF (7 mL) was added a solution of 6-methoxy-2-methyl-1H-indole-3-carbonitrile (1.3 g, 7.0 mmol) in DMF (8 mL) followed by ethyl iodide (1.2 mL, 2 eq.) at 0° C. After stirring for 1 h, the mixture was poured into ice water and the extracted with $CH_2Cl_2$. The organic layer was washed with brine and dried with $Na_2SO_4$. The solvent was evaporated under vacuum and purified with flash column chromatography on silica gel using EtOAc/petroleum ether (1/5) as eluent to yield 92% of 1-ethyl-6-methoxy-2-methyl-1H-indole-3-carbonitrile.

Step D: To a solution of 1-ethyl-6-methoxy-2-methyl-1H-indole-3-carbonitrile (1.38 g, 6.45 mmol) in benzene (130 mL) was added benzoyl peroxide (226 mg) and NBS (1.21 g, 1.05 eq.). Then the mixture was heated to reflux for 3 h. After cooling and filtering, the filtrate was concentrated under vacuum. The crude 2-bromomethyl-1-ethyl-6-methoxy-1H-indole-3-carbonitrile (1.6 g, 86%) was used without further purification.

Step E: To a solution of NaH (44 mg, 4 eq.) in DMF (0.5 mL) was added 2-bromomethyl-1-ethyl-6-methoxy-1H-indole-3-carbonitrile (80 mg, 0.274 mmol) and phenol (2 eq.). After stirring for 20 h, the mixture was poured into ice water and extracted with $CH_2Cl_2$. The organic layer was washed with brine and dried with $Na_2SO_4$. The solvent was evaporated under vacuum and purified with flash column chromatography on silica gel using EtOAc/petroleum ether (1/5) as eluent to yield 1-ethyl-6-methoxy-2-phenoxymethyl-1H-indole-3-carbonitrile, compound 99.

Example 1T

Preparation of 6-nitro-2-pyrrol-1-yl-1H-indole-3-carbonitrile (compound 7)

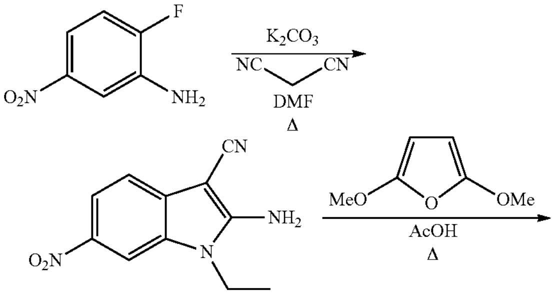

-continued

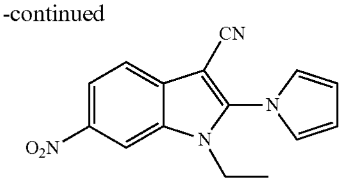

Step A: A solution of 2-fluoro-5-nitroaniline (11.7 g, 74.9 mmol) in dimethylformamide (120 mL) was treated with malononitrile (5.28 g, 80.0 mmol) and potassium carbonate (11.05 g, 80.0 mmol) (Modification of *Chem. Heterocyclic Cpd.* (*Engl. Trans.*, 9, 37 (2001). The resulting heterogeneous mixture was heated to gentle reflux for 3 h, then cooled and poured into water (500 mL). The resulting precipitate was collected by filtration and taken up into ethyl acetate (300 mL). This solution was dried over $Na_2SO_4$, filtered and partially evaporated to give a precipitate, which was collected by filtration. Further evaporation and filtration gave a second crop. The two crops were combined and dried under vacuum to give 2-amino-1-ethyl-6-nitro-1H-indole-3-carbonitrile (7.90 g, 52%) as an orange powder.

Step B: A solution of 2-amino-6-nitro-1H-indole-3-carbonitrile (362 mg, 1.79 mmol) in acetic acid (5 mL) was treated with 2,5-dimethoxytetrahydrofuran (0.30 mL, 2.27 mmol), and the solution was heated to reflux for 14 h. After cooling to ambient temperature, the solution was poured into water (100 mL), and solid sodium bicarbonate was added until $CO_2$ evolution ceased. The mixture was extracted with EtOAc (2×100 mL), and the extracts were washed with saturated brine, combined, dried over $MgSO_4$, filtered and concentrated. The residual material was separated by silica gel chromatography (EtOAc/hexanes, 1/4) to afford 6-nitro-2-pyrrol-1-yl-1H-indole-3-carbonitrile, compound 5, as a yellow solid (232 mg, 51%).

Example 1U

Preparation of N-(3-cyano-1-ethyl-6-nitro-1H-indol-2-yl)acetamide (compound 25)

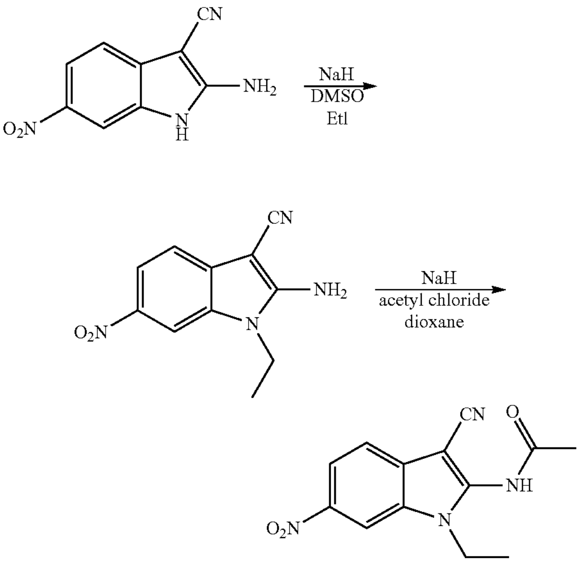

Step A: Sodium hydride (42 mg, 1.05 mmol, 60% w/w suspension in mineral oil) was washed with hexane and taken up in dimethylsulfoxide (1 mL). A solution of 2-amino-6-nitro-1H-indole-3-carbonitrile, prepared in procedure 1T) in dimethylsulfoxide (1 mL) was added by syringe, and the resulting mixture was stirred for 20 min. Then, iodoethane (77 μL, 0.96 mmol) was added by syringe, and the mixture was stirred for 14 h. The reaction was then poured into EtOAc (50 mL), and this solution was washed with water (3×50 mL) and saturated brine (40 mL). The aqueous phases were back-extracted with EtOAc, and the organic extracts were combined, dried over $Na_2SO_4$, filtered and evaporated. The residual material was separated by column chromatography over silica gel (EtOAc/hexanes, 1/1) to afford first a small amount of a dialkylated analog, then the desired compound, 2-amino-1-ethyl-6-nitro-1H-indole-3-carbonitrile (114 mg, 52%), and finally unreacted starting material. The desired product was isolated as an orange powder.

Step B: Sodium hydride (44 mg, 1.10 mmol, 60% w/w in mineral oil) was washed with hexanes and suspended in 1,4-dioxane (3 mL). A solution of 2-amino-1-ethyl-6-nitro-1H-indole-3-carbonitrile (120 mg, 0.521 mmol), prepared in step B, above, in dioxane (2 mL) was added, and the resulting mixture was allowed to stir for 30 min. Then, acetyl chloride (45 μL, 0.63 mmol) was added by syringe, and the solution was stirred for an additional 12 h. The reaction was partitioned between water and EtOAc (20 mL each), and the organic phase was washed with brine. The aqueous phases were back-extracted in sequence with ethyl acetate, and the organic extracts were combined, dried over $MgSO_4$, filtered and evaporated. The resulting solid was triturated with $Et_2O$, collected by filtration and dried under vacuum to afford N-(3-cyano-1-ethyl-6-nitro-1H-indol-2-yl)-acetamide (100 mg, 71%), compound 25, as an off-white powder.

Using this procedure and substituting the appropriate acid chlorides or chloroformates gave the following compounds: Compounds 23, 26, 35, 36, 203, 204, 214, 215, 216.

Example 1V

Preparation of N-ethyl-3-phenyl-5-nitroindole (compound 41)

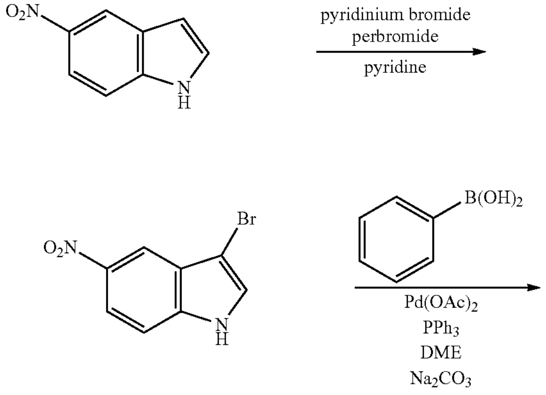

-continued

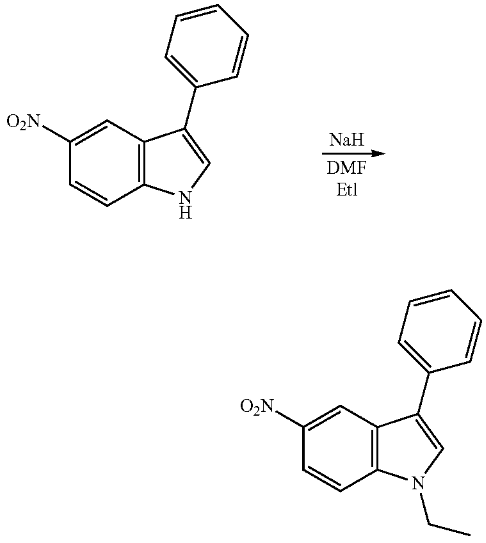

Step A: To a solution of 5-nitroindole (5.00 g, 30.8 mmol) in pyridine (200 mL) at −4° C. was added a solution of pyridinium bromide perbromide (10.99 g, 34.3 mmol) in pyridine (200 mL) dropwise under nitrogen with stirring. After complete addition, the reaction mixture was stirred for 5 min at 0° C. The reaction mixture was diluted in 0° C. water (200 mL) and extracted with 200 mL of $Et_2O$. The organic layer was washed with 6 M HCl (300 mL), 5% $NaHCO_3$ (300 mL), and brine (300 mL). The organic phase was dried over $MgSO_4$ and solvent was removed to give 3-bromo-5-nitroindole as a yellow powder, 80% pure with 20% 5-nitroindole (6.80 g, 74% yield).

Step B: A solution of 3-bromo-5-nitroindole from above (625 mg, 2.1 mmol), phenylboronic acid (381 mg, 3.13 mmol), triphenylphosphine (109.3 mg, 0.417 mmol) in dimethoxyethane (4.16 mL) was degassed. To this mixture 2N sodium carbonate (6.25 mL) was added, and reaction mixture was degassed again. To the reaction was added palladium (II) acetate (23.4 mg, 0.104 mmol), and the reaction was refluxed under dry nitrogen with stirring for 8 hours. The reaction mixture was then diluted with 1 M HCl (100 mL), and extracted with ethyl acetate (100 mL). The organic phase was washed with water (100 mL), and brine (100 mL). The organic phase was dried over $MgSO_4$ and concentrated in vacuo. The crude product was purified by chromatography over silica gel (EtOAc/hexanes, 10/90) to afford 3-phenyl-5-nitroindole as an orange powder (45 mg, 9% yield).

Step C: To a mixture of 60% NaH in mineral oil (8.7 mg, 0.630 mmol) and DMF (1.0 mL) was added dropwise a solution of 3-phenyl-5-nitroindole (40.0 mg, 2.1 mmol) in DMF (0.75 mL). The reaction mixture was stirred for 20 min at 0° C. under $N_2$. Ethyl iodide (14.8 μL, 0.185 mmol) was added dropwise and the reaction mixture was stirred for an additional 3 hours. The reaction mixture was diluted with water (250 mL), and extracted with EtOAc (30 mL). The organic phase was washed with water (250 mL) and was then dried over $MgSO_4$ and the solvent was removed in vacuo. The desired N-ethyl-3-phenyl-5-nitroindole was obtained as a yellow powder (40.0 mg, 89.5% yield).

In similar fashion the following compound was prepared: Compound 40

Example 1W

Preparation of [3-Cyano-1-(4-methoxyphenyl)-1H-indol-6-yl]-carbamic acid propyl ester (compound 97)

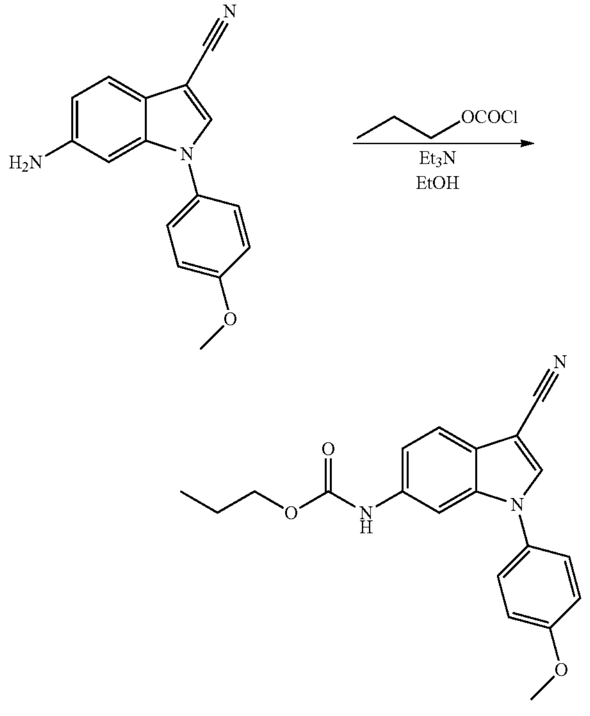

6-Amino-1-(4-methoxyphenyl)-1H-indole-3-carbonitrile (30 mg, 0.12 mmol), was suspended in EtOH (300 μL). Propyl chloroformate (168 μL, 1.5 mmol) was added, and this mixture was stirred at room temperature overnight. The addition of triethylamine (300 μL), followed by another hour of stirring at room temperature, completed the reaction. This reaction mixture was loaded directly onto a silica column, and was eluted with $CH_2Cl_2$. Another silica column (3/2, ether/hexanes) was needed to fully purify the product, [3-cyano-1-(4-methoxy-phenyl)-1H-indol-6-yl]-carbamic acid propyl ester (19 mg, 45%), as a white solid.

Example 1X

Preparation of N-[4-(3-cyano-1-ethyl-6-methoxy-1H-indol-2-ylethynyl)-phenyl]-methanesulfonamide (compound 130)

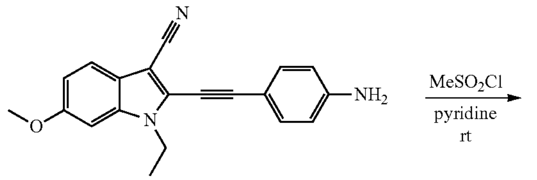

-continued

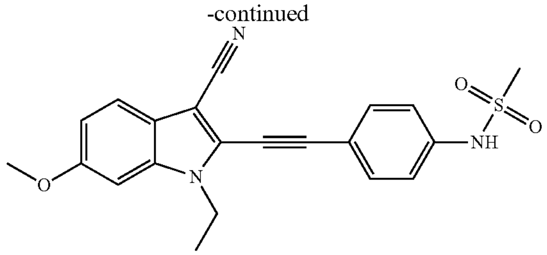

2-(4-Aminophenylethynyl)-1-ethyl-6-methoxy-1H-indole-3-carbonitrile (50 mg, 0.16 mmol), prepared as described by the method of Example 1H, was dissolved in pyridine (550 μL) at room temperature. Methanesulfonyl chloride (17 μL, 0.21 mmol) was added dropwise. This was stirred overnight at room temperature. The reaction mixture was then diluted in ethyl acetate and was washed with aqueous HCl, followed by brine. The organic layer was dried and concentrated. Purification by silica gel chromatography (9/1, $CH_2Cl_2$/EtOAc) yielded N-[4-(3-cyano-1-ethyl-6-methoxy-1H-indol-2-ylethynyl)-phenyl]-methanesulfonamide (58 mg, 92%) as an off-white solid.

The following compounds were made using the procedure shown above, by substituting the appropriate aminophenylethynyl indoles and sulfonyl chlorides: Compounds 131, 132, 208, 209, and 210.

Example 1Y

Preparation of N-[4-(3-Cyano-1-ethyl-6-methoxy-1H-indol-2-yl)-phenyl]-methanesulfonamide (compound 129)

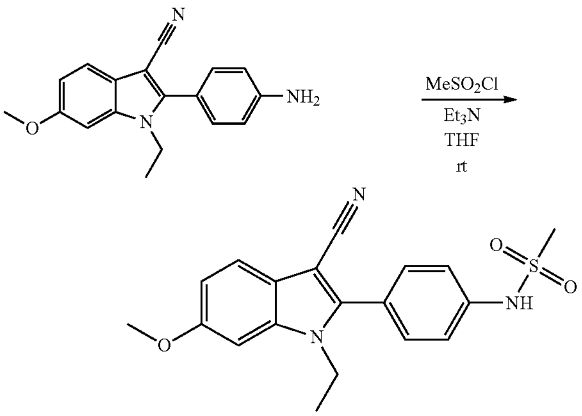

A solution of 2-(4-aminophenyl)-1-ethyl-6-methoxy-1H-indole-3-carbonitrile (70 mg, 0.24 mmol), prepared as described in Example 1Ga, step B in THF (3 mL) was cooled to 0° C. and treated with triethylamine (0.04 mL, 0.31 mmol) and methanesulfonylchloride (0.02 mL, 0.29 mmol) at stirred, warming to room temperature overnight. The reaction mixture was then diluted with $H_2O$ and extracted with ethyl acetate (3×). The organic phase was washed with $H_2O$ and saturated NaCl, dried and concentrated and purified by flash chromatography using EtOAc/hexanes (30-50%) to afford 60 mg (68%) of N-[4-(3-Cyano-1-ethyl-6-methoxy-1H-indol-2-yl)-phenyl]-methanesulfonamide as a tan solid.

Using essentially the same procedure as above and substituting the appropriate aminophenylindole and sulfonyl chloride or carrying out the reaction in pyridine as both base and solvent gave the following compounds: 83, 85, 86, 87, 88, 243, 251, 252, 272, 273, 287, 289, 365, 366, 367, 368, 369, 370, 371, 394, 439, 440, 448, 449, 451, 452, 477, 487, 488, 495, 505, 510, 548, 549, 550, 551, 552, 562, 563, 598, 599, 601, 602, 608, 609, 610, 615, 616, 617, 621, 622, 623, 629, 630, 631, 639, 655, 657, 658, 662, 669, 670, 671, 674, 675, 701, 702, 703, 706, 707, 708, 709, 710, 711, 713, 715, 720, 789, 790, 791, 850, 851.

Example 1Za

Preparation of N-[4-(3-cyano-1-ethyl-6-methoxy-1H-indol-2-ylethynyl)-phenyl]-acetamide (compound 138)

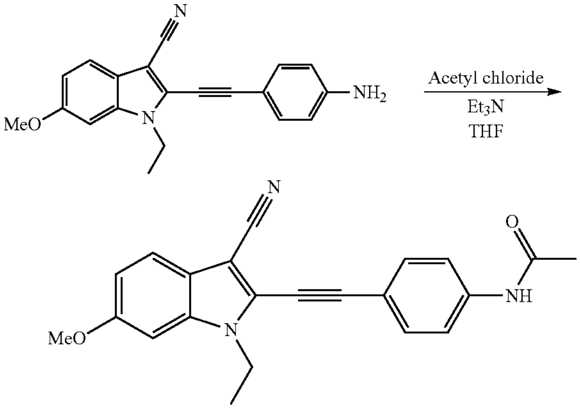

2-(4-Aminophenylethynyl)-1-ethyl-6-methoxy-1H-indole-3-carbonitrile (95 mg, 0.29 mmol), prepared as described in Example 1H, was dissolved in THF (1.4 mL). Triethylamine (84 μL, 0.6 mmol) was added, followed by dropwise addition of acetyl chloride (44 μL, 0.5 mmol). This was stirred at room temperature for 1 h. The reaction mixture was partitioned between $H_2O$ and EtOAc. The organic layer was dried and concentrated. Purification by silica chromatography (9/1, $CH_2Cl_2$/EtOAc) yielded N-[4-(3-cyano-1-ethyl-6-methoxy-1H-indol-2-ylethynyl)-phenyl]-acetamide (103 mg, 96%) as a yellow solid.

The following compounds were prepared by the procedure shown above, substituting the appropriate aminophenylethynyl indoles and acid chlorides: Compounds 82, 139, 152, 153, 162, 163, 165, 167, 205, 206, 207, 211, 212, 213, 219, 224, 225, 228.

Example 1Zb

Preparation of N-[4-(3-cyano-1-ethyl-6-methoxy-1H-indol-2-ylethynyl)-phenyl]-formamide (compound 241)

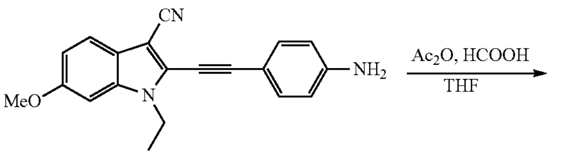

-continued

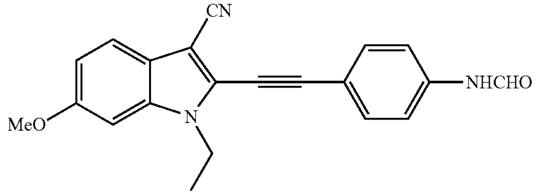

Acetic anhydride (2.5 mL) and 98% formic acid (1.0 mL) were heated at 65° C. for 1 hour. This was cooled to 0° C. 2-(4-Aminophenylethynyl)-1-ethyl-6-methoxy-1H-indole-3-carbonitrile (100 mg, 0.32 mmol), prepared as in example 1H, was taken up in THF (1.2 mL) and added to the formic acetic anhydride mixture. This was stirred at 0° C. for 30 minutes. The reaction mixture was then partitioned between $H_2O$ and EtOAc. The EtOAc layer was washed with saturated $NaHCO_3$, followed by saturated brine. The organic layer was dried and concentrated. Purification by silica gel chromatography (4/1, $CH_2Cl_2$/EtOAc) yielded of N-[4-(3-cyano-1-ethyl-6-methoxy-1H-indol-2-ylethynyl)-phenyl]-formamide (105 mg, 96%) as a yellow solid.

The following compound was prepared similarly as described above: Compound 218.

Example 1AA

Preparation of N-[4-(3-Cyano-1-ethyl-6-methoxy-1H-indol-2-yl)-phenyl]-acetamide (compound 128)

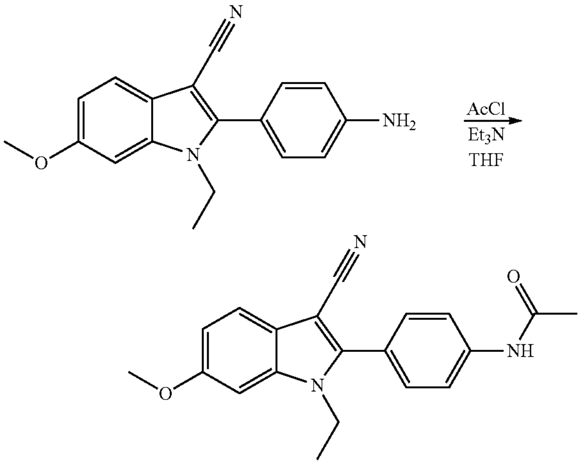

A solution of 2-(4-aminophenyl)-1-ethyl-6-methoxy-1H-indole-3-carbonitrile (70 mg, 0.24 mmol), prepared as described in example 1Ga, step B in THF (3 mL) was cooled to 0° C. and treated with triethylamine (0.04 mL, 0.31 mmol) and acetyl chloride (0.02 mL, 0.29 mmol) and stirred, warming to room temperature overnight. The reaction mixture was then diluted with $H_2O$ and extracted with ethyl acetate (3×). The organic phase was washed with $H_2O$ and saturated NaCl, dried and concentrated and purified by flash chromatography using EtOAc/hexanes (30-50%) to afford 57 mg (71%) of N-[4-(3-cyano-1-ethyl-6-methoxy-1H-indol-2-yl)-phenyl] acetamide as a tan solid.

Using essentially the same procedure as above and substituting appropriate aminophenyl indoles and the acid chlorides, the following compounds were prepared: Compounds 81, 242, 244, 324, 325, 326, 327, 328, 329, 330, 383, 420, 421, 422, 423, 424, 425, 544, 558, 559, 560, 561, 565, 566 567, 644, 645, 646, 755, 756, 757, 759, 760, 761, 762, 763, 764, 765, 766, 798, 799, 801, 802, 803, 804, 854, 855, 856, 857, 858, 859.

Example 1AB

Preparation of 1-[3-(3-cyano-1-ethyl-6-methoxy-1H-indol-2-ylethynyl)phenyl]-3-ethyl urea (compound 220)

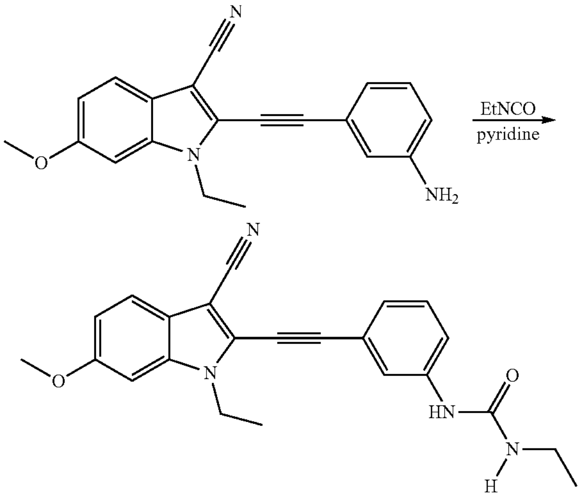

2-(3-Aminophenylethynyl)-1-ethyl-6-methoxy-1H-indole-3-carbonitrile (100 mg, 0.32 mmol), prepared as described in Example 1H, was dissolved in pyridine (670 μL). Ethyl isocyanate (62 μL, 0.75 mmol) was added. The reaction mixture was then heated at 100° C. for 2 h. The mixture was then diluted in EtOAc, and was washed with aqueous HCl, followed by brine. The organic layer was dried and concentrated. Purification by silica chromatography (4/1, $CH_2Cl_2$/EtOAc), followed by trituration with hexanes/acetone (1/1), yielded 1-[3-(3-cyano-1-ethyl-6-methoxy-1H-indol-2-yl-ethynyl)-phenyl]-3-ethyl urea (44 mg, 36%) as a white solid.

Example 1AC

Preparation of 1-(2-chloroethyl)-3-[4-(3-cyano-1-ethyl-6-methoxy-1H-indol-2-ylethynyl)-phenyl] urea (compound 156)

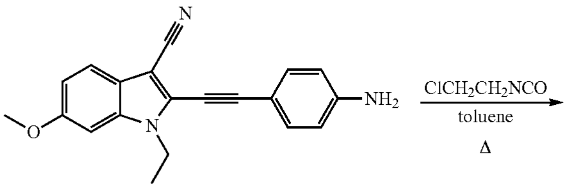

-continued

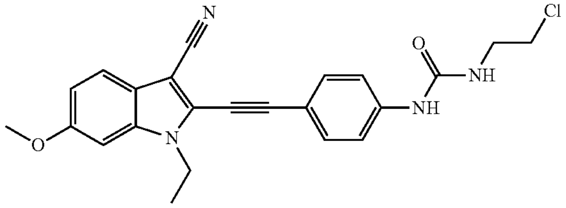

2-(4-Aminophenylethynyl)-1-ethyl-6-methoxy-1H-indole-3-carbonitrile (100 mg, 0.32 mmol), prepared as described in Example 1H, was suspended in toluene (600 μL). 2-Chloroethyl isocyanate (32 μL, 0.37 mmol) was added, and the mixture was heated at 100° C. for 5 h. The reaction mixture was then cooled, diluted in acetone, and absorbed onto silica. Purification by column chromatography (5-10% EtOAc in $CH_2Cl_2$) yielded 1-(2-chloro-ethyl)-3-[4-(3-cyano-1-ethyl-6-methoxy-1H-indol-2-ylethynyl)-phenyl] urea (73 mg, 54%) as a yellow solid.

The following compounds were prepared using the procedure above: Compound 221.

Example 1AD

Preparation of Ethanesulfonic acid [4-(3-cyano-1-ethyl-6-methoxy-1H-indol-2-ylethynyl)-phenyl]methyl amide (compound 157)

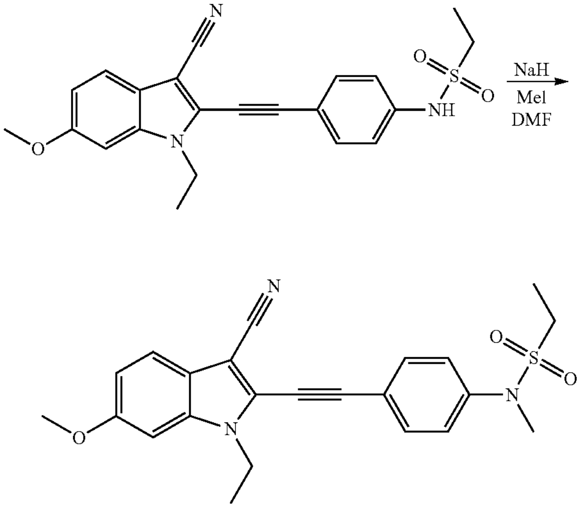

N-[4-(3-cyano-1-ethyl-6-methoxy-1H-indol-2-ylethynyl) phenyl] ethanesulfonamide (70 mg, 0.17 mmol), prepared as in example 1X, was combined with $K_2CO_3$ (49 mg, 0.35 mmol), and DMF (1.0 mL). Iodomethane (16 μL, 0.26 mmol) was added, and the mixture was stirred at room temperature for 1 hour. The reaction mixture was then diluted in EtOAc, and was washed with $H_2O$ and then brine. The organic layer was dried and concentrated. Purification by silica chromatography (95/5, $CH_2Cl_2$/EtOAc) yielded a light tan solid. Trituration gave ethanesulfonic acid [4-(3-cyano-1-ethyl-6-methoxy-1H-indol-2-ylethynyl)-phenyl]methyl amide (61 mg, 85%) as an orange-white solid.

The following compounds were prepared using the procedure above, substituting the appropriate sulfonamide: Compound 182, 652, 840.

Example 1AE

Preparation of 1-ethyl-5-methoxy-2-[4-(morpholine-4-carbonyl)-phenyl]-1H-indole-3-carbonitrile (compound 245)

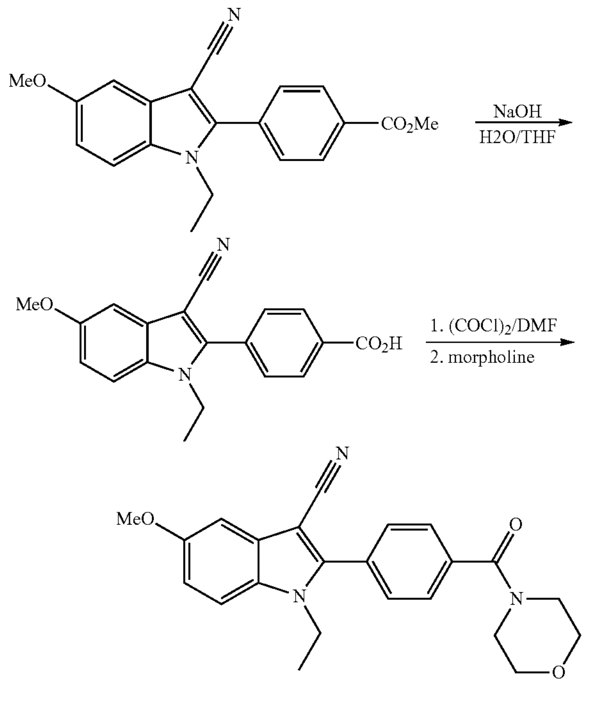

Step A: Methyl 4-(3-cyano-1-ethyl-5-methoxy-1H-indol-2-yl)-benzoate (350 mg, 1.05 mmol), prepared as described in Example 1Ga step B, was combined with NaOH (40 mg, 1 mmol), $H_2O$ (0.8 mL), and THF (3.4 mL) and was heated at 80° C. for 1 hour. The reaction mixture was diluted in $H_2O$ and was then ether-washed. The aqueous layer was acidified with aqueous HCl, and was extracted into EtOAc. The organic layer was dried and concentrated to yield 4-(3-cyano-1-ethyl-6-methoxy-1H-indol-2-yl)-benzoic acid (311 mg, 92%) as a pure white solid.

Step B: 4-(3-cyano-1-ethyl-6-methoxy-1H-indol-2-yl)-benzoic acid (50 mg, 0.16 mmol) was suspended in $CH_2Cl_2$ (2.2 mL) and catalytic DMF (2 μL). Oxalyl chloride (22 μL, 0.25 mmol) was added. The reaction mixture was stirred at room temperature for 1 hour, at which time full dissolution occurred. This reaction mixture was pipetted dropwise into a vigorously stirring solution of morpholine (1.0 mL) in $CH_2Cl_2$ (5 ml). After addition was complete, the reaction mixture was washed with aqueous HCl solution. The organic layer was dried and concentrated. Purification by silica column (1:1 $CH_2Cl_2$/EtOAc) yielded 1-ethyl-6-methoxy-2-[4-(morpholine-4-carbonyl)-phenyl]-1H-indole-3-carbonitrile (56 mg, 90%) as a white solid.

The following compounds were prepared similarly as described above: Compounds 113, 114, 246, 270, 271 290, 291, 292, 323, 377, 378, 379, 380, 381, 382, 384, 385, 386, 387, 388, 389, 390, 391, 392, 432, 433, 564, 568, 569, 570, 571, 572, 573, 647, 648, 853, 860, 861, 862.

Example 1AF

Preparation of cyclopropanecarboxylic acid [4-(3-cyano-1-ethyl-6-hydroxy-1H-indol-2-ylethynyl)-phenyl] amide (compound 194)

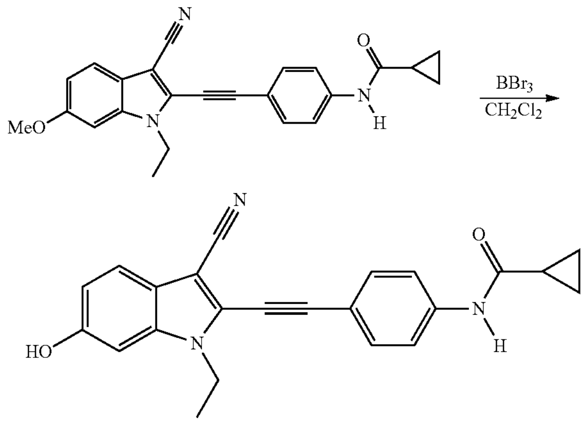

Cyclopropanecarboxylic acid [4-(3-cyano-1-ethyl-6-methoxy-1H-indol-2-ylethynyl)-phenyl]-amide (60 mg, 0.16 mmol), prepared as described in example 1Za, was stirred in $BBr_3$ (800 μL, 1M in $CH_2Cl_2$, 0.8 mmol) at room temperature for 1 hour. The reaction mixture was quenched with $H_2O$, and was extracted with $CH_2Cl_2$. The organic layer was dried and concentrated. Purification by silica chromatography (EtOAC) gave impure product. These crude product was triturated with 1/1 hexanes/acetone to yield cyclopropanecarboxylic acid [4-(3-cyano-1-ethyl-6-hydroxy-1H-indol-2-ylethynyl)-phenyl]-amide (32 mg, 54%) as an off-white solid.

The following compounds were prepared using the procedure above, substituting the appropriate sulfonamides (from example 1X) or amides (from Example 1Z): Compounds 164, 168, 183, 193, 195.

Example 1AG

Preparation of 1-ethyl-6-methoxy-2-[4-(2-oxo-imidazolidin-1-yl)-phenylethynyl]-1H-indole-3-carbonitrile (compound 166)

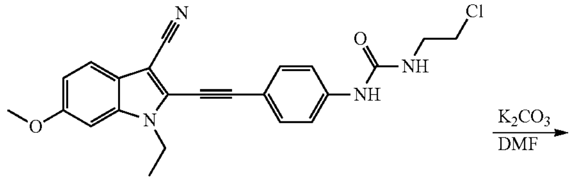

-continued

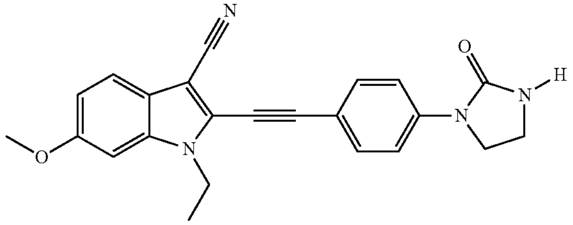

1-(2-Chloroethyl)-3-[4-(3-cyano-1-ethyl-6-methoxy-1H-indol-2-ylethynyl)-phenyl] urea (55 mg, 0.13 mmol), prepared as in Example 1AC, was combined with $K_2CO_3$ (50 mg, 0.36 mmol) and DMF (550 μL). This mixture was stirred at room temperature for 3 hours. The reaction mixture was diluted in EtOAc, and was washed with $H_2O$, and then with brine. The organic layer was dried and concentrated. Purification by silica chromatography (10-50%, EtOAc/$CH_2Cl_2$) yielded 1-ethyl-6-methoxy-2-[4-(2-oxo-imidazolidin-1-yl)-phenylethynyl]-1H-indole-3-carbonitrile (47 mg, 94%) as a white solid.

The following compounds were prepared using the above procedure, substituting the appropriate urea: Compound 222.

Example 1AH

Preparation of N-[4-(3-cyano-1-ethyl-6-methoxy-1H-indol-2-ylethynyl)-phenyl]-dimethylphosphinic amide (compound 227)

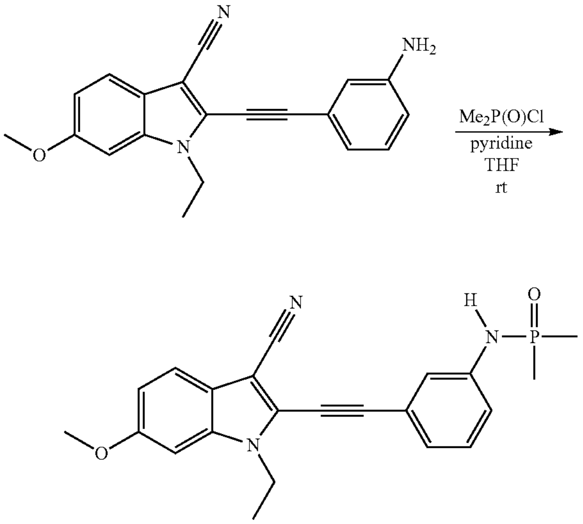

2-(3-Aminophenylethynyl)-1-ethyl-6-methoxy-1H-indole-3-carbonitrile (100 mg, 0.32 mmol), prepared as described in Example 1H, was dissolved in pyridine (300 μL) at 0° C. Dimethylphosphinic chloride (60 mg, 0.53 mmol) in THF (300 μL) was added. The reaction was stirred at room temperature for 2 hours. The reaction mixture was diluted in EtOAc, and was washed with aqueous HCl followed by brine. The organic layer was dried and concentrated. Purification by silica chromatography (acetone) yielded N-[4-(3-cyano-1-ethyl-6-methoxy-1H-indol-2-ylethynyl)-phenyl]-dimethylphosphinic amide (65 mg, 52%), compound 227, as a pure white solid. The silica column was then flushed with 9/1 $CH_2Cl_2$/MeOH to yield 9 mg of N-[4-(3-cyano-1-ethyl-6-methoxy-1H-indol-2-ylethynyl)-phenyl]-bis-(dimethylphosphinic) amide as a by-product.

Example 1AI

Preparation of 1-ethyl-6-methoxy-3-[5-(4-methoxyphenyl)-isoxazol-3-yl]-1H-indole (compound 116)

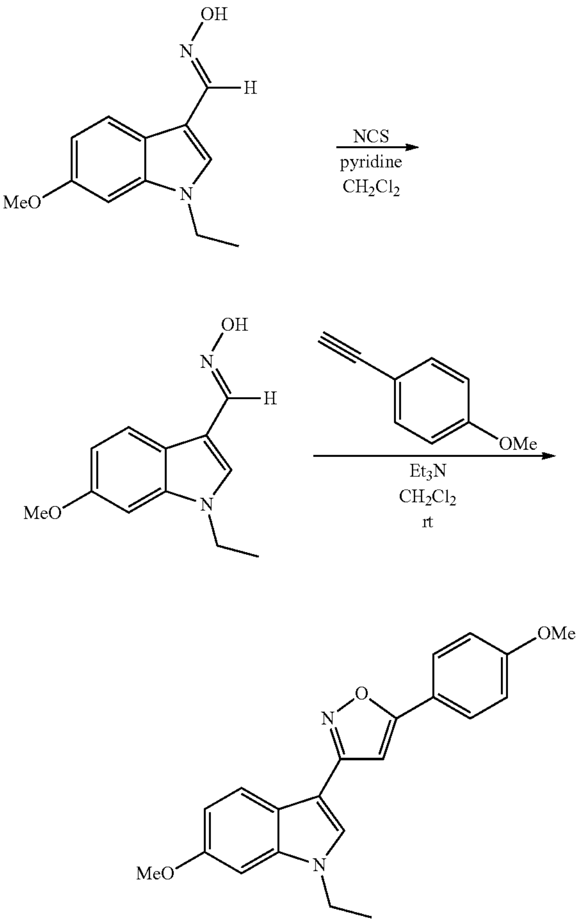

Step A: A mixture of 1-ethyl-6-methoxy-1H-indole-3-carbaldehyde oxime (0.20 g, 0.92 mmol), prepared from the aldehyde precursor in example 1R, in dichloroethane (3 mL) was treated with N-chlorosuccinimide (0.12 g, 0.92 mmol) and pyridine (0.04 mL, 0.46 mmol) and stirred at room temperature for 1 h. The reaction mixture was then poured into $H_2O$ and acidified with 1N HCl until the pH was 2. The mixture was extracted with EtOAc and the organic phases were washed with $H_2O$ and saturated NaCl and dried and concentrated to a mixture of chlorooximes, which were used in the next step without further purification.

Step B: The mixture of chlorooximes prepared above was dissolved in $CH_2Cl_2$ (5 mL) and to this was added 4-methoxyphenylacetylene (0.24 g, 1.84 mmol) and triethylamine (0.25 mL, 1.84 mmol) at 0° C. and the reaction was then stirred overnight warming to room temperature. The reaction was then diluted with $H_2O$ and extracted with EtOAc (3×). The organic phases were washed with $H_2O$ and saturated NaCl and dried and concentrated. Chromatography over silica gel (EtOAc/hexanes, 10-20%) gave 76 mg (24%) of 1-ethyl-6-methoxy-3-[5-(4-methoxy-phenyl)-isoxazol-3-yl]-1H-indole as a tan solid.

Example 1AJ

Preparation of [4-(3-cyano-1-ethyl-6-methoxy-1H-indol-2-yl)-phenyl]-carbamic acid ethyl ester (compound 121)

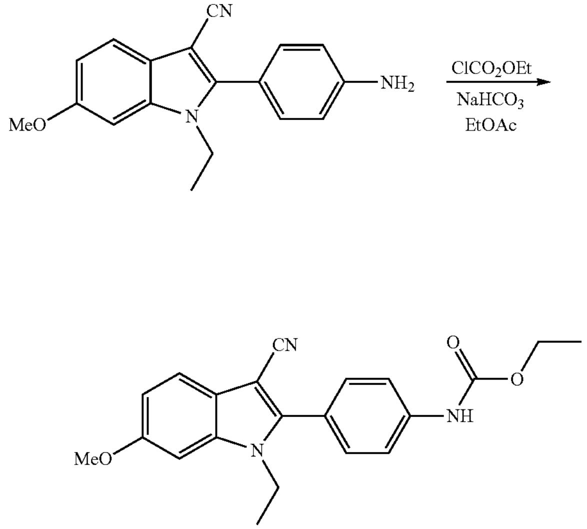

A biphasic mixture of 2-(4-amino-phenyl)-1-ethyl-6-methoxy-1H-indole-3-carbonitrile (70 mg, 0.24 mmol), prepared as described in example 1Ga step B, and ethyl chloroformate (0.03 mL, 0.29 mmol) in EtOAc (3 mL) and saturated $NaHCO_3$ (3 mL) was prepared at 0° C. and then allowed to warm to room temperature and stirred for 24 h. The reaction was then diluted with $H_2O$ and extracted with EtOAc (2×). The organic phases were washed with $H_2O$ and saturated NaCl and then dried and concentrated. Flash chromatography (EtOAc/hexanes 20-40%) gave 48 mg (55%) of [4-(3-cyano-1-ethyl-6-methoxy-1H-indol-2-yl)-phenyl]-carbamic acid ethyl ester as an off-white solid.

The following compound was prepared in similar fashion: Compound 122, 293, 294, 296, 297, 298, 299, 300, 301, 302, 303, 304, 305, 306, 307, 308, 309, 310, 311, 312, 313, 314, 315, 316, 317, 318, 319, 320, 321, 349, 350, 351, 352, 353, 354, 355, 356, 357, 358, 359, 360, 361, 372, 434, 435, 450, 453, 454, 455, 457, 485, 486, 489, 490, 500, 501, 502, 503, 506, 507, 508, 509, 545, 546, 547, 553, 554, 555, 556, 557, 581, 582, 583, 584, 585, 585, 586, 587, 588, 589, 590, 591, 592, 593, 594, 595, 596, 597, 603, 604, 605, 606, 607, 618, 619, 624, 625, 637, 640, 641, 664, 665, 676, 677, 721, 722, 723, 734, 735, 736, 737, 738, 739, 744, 745, 746, 747, 787, 788, 792, 793, 794, 795, 796, 797, 819, 822, 823, 824, 825, 826, 849.

Example 1AK

Preparation of 1-ethyl-5-thiophen-3-yl-1H-indole-3-carbonitrile (compound 141)

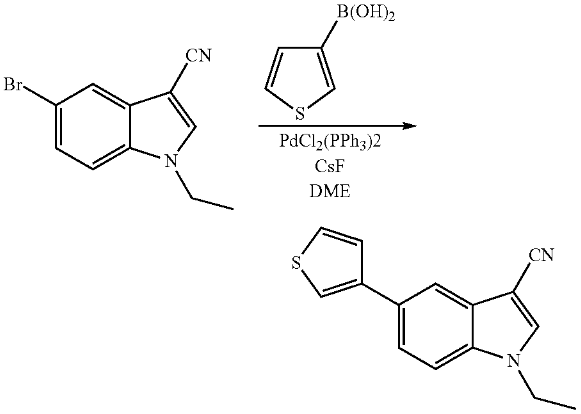

A tube was charged with a mixture of 5-bromo-1-ethyl-1H-indole-3-carbonitrile (100 mg, 0.40 mmol), thiophene-3-boronic acid (72 mg, 0.56 mmol), $PdCl_2(PPh_3)_2$ (11 mg, 0.016 mmol) and CsF (152 mg, 1 mmol) and then alternately evacuated and filled with nitrogen (3×) and diluted with dimethoxyethane (3 mL) and then heated to 90° C. for 19 h. After cooling, the crude reaction mixture was diluted with saturated $NaHCO_3$ and extracted with EtOAc (2×). The combined organic phases were washed with saturated NaCl and dried and concentrated. Flash chromatography over silica gel ($CH_2Cl_2$/hexanes, 40/60) gave 25 mg (25%) of 1-ethyl-5-thiophen-3-yl-1H-indole-3-carbonitrile as a white solid.

The following compounds were prepared in similar fashion: Compounds 140 and 142.

Example 1AL

Preparation of N-[4-(3-cyano-1-ethyl-6-methoxy-1H-indol-2-yl)-phenyl]-N-methyl methanesulfonamide (compound 180)

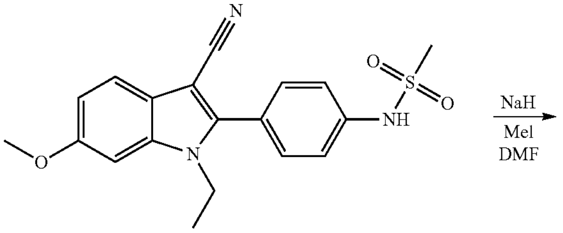

-continued

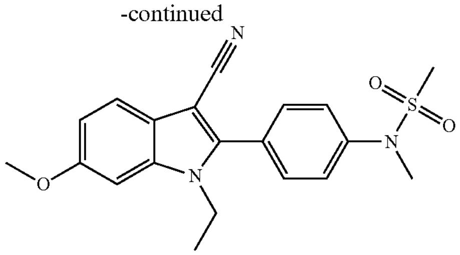

A solution of N-[4-(3-cyano-1-ethyl-6-methoxy-1H-indol-2-yl)-phenyl]methanesulfonamide (130 mg, 0.35 mmol), prepared as in Example 1Y, in DMF (10 mL) was treated with NaH (21 mg, 0.53 mmol), and stirred at room temperature for 10 min. Iodomethane (0.03 mL, 0.53 mmol) was added, and the mixture was stirred at room temperature for 18 h. The reaction mixture was then diluted with $H_2O$, and extracted with EtOAc (2×). The organic phases were washed with $H_2O$ and saturated NaCl and then dried and concentrated. Purification by flash chromatography over silica gel (EtOAc/$CH_2Cl_2$, 0-1%) gave 60 mg (45%) of N-[4-(3-cyano-1-ethyl-6-methoxy-1H-indol-2-yl)-phenyl]-N-methyl methanesulfonamide as a white solid.

In similar fashion the following compounds were prepared: Compounds 181, 642, 643, 672, 673, 816, 852.

Example 1AM

Preparation of N-[4-(3-cyano-1-ethyl-6-hydroxy-1H-indol-2-yl)-phenyl]-methanesulfonamide (compound 189)

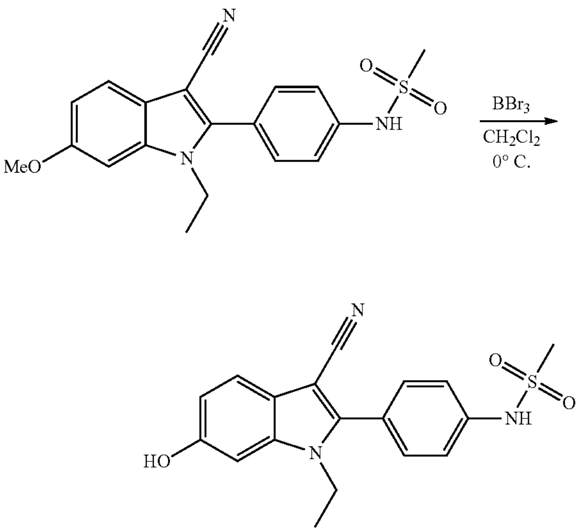

A solution of N-[4-(3-cyano-1-ethyl-6-methoxy-1H-indol-2-yl)-phenyl]methanesulfonamide (85 mg, 0.23 mmol) in $CH_2Cl_2$ (2 mL) was cooled to −5° C. A solution of boron tribromide (1.15 mL, 1.15 mmol, 1M solution in $CH_2Cl_2$) was added and the reaction mixture was allowed to warm to 110° C. over 4 h. The reaction mixture was poured into $H_2O$ and extracted with EtOAc (3×). The combined organic phases were washed with $H_2O$ and saturated NaCl and dried and concentrated. Chromatography over silica gel (EtOAc/$CH_2Cl_2$, 5-10%) gave 18 mg (22%) of N-[4-(3-cyano-1-ethyl-6-hydroxy-1H-indol-2-yl)-phenyl]methane sulfonamide as a tan solid.

The following compounds were made similarly: Compounds 190, 191, 192.

Example 1AN

Preparation of methyl 3-[5-(3-cyano-6-methoxy-1H-indol-2-yl)-[1,2,4]oxadiazol-3-yl]benzoate (compound 226)

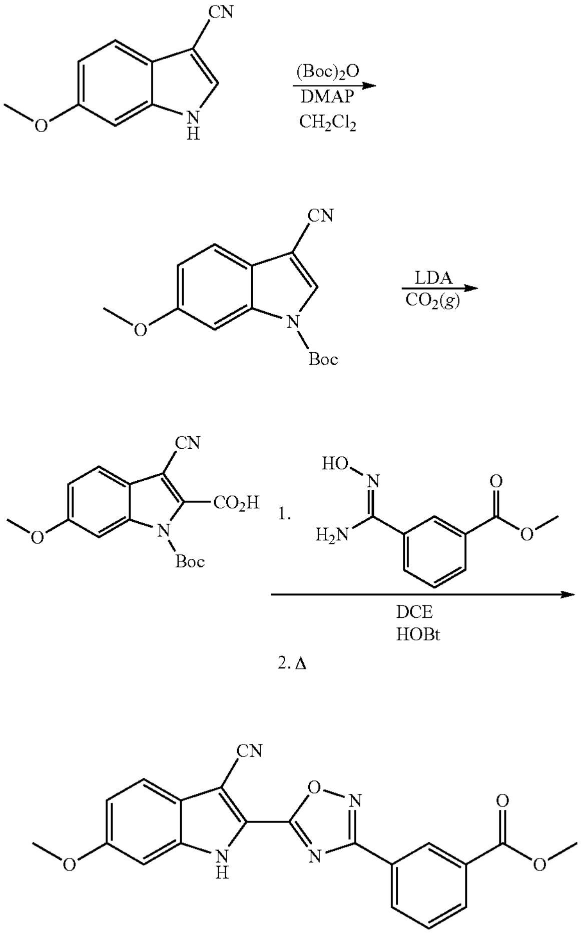

Step A: To a mixture of 6-methoxy-1H-indole-3-carbonitrile (5.88 g, 40 mmol), prepared as described in the previous examples, and $(Boc)_2O$ (9.59 g, 44.0 mmol) in DCM (50 mL) was added DMAP (0.10 g, 0.8 mmol). The mixture was stirred at room temperature for 48 h, then treated with water (30 mL) and dried over anhydrous $Na_2SO_4$. The crude product was chromatographed over silica gel (hexanes/EtOAc, 7/1) to furnish the desired intermediate, 3-cyano-6-methoxy-indole-1-carboxylic acid tert-butyl ester (8.48 g, 86%).

Step B: The above intermediate (2.72 g, 10.0 mmol) was dissolved in anhydrous THF (20 mL), and cooled at −78° C., followed by the addition of LDA (1.5 M monoTHF in cyclohexane, 10.0 mL, 15 mmol). After stirring for 45 min, $CO_2$ gas was introduced for 2 h. The mixture was then brought to room temperature and the solvent was removed in vacuo, and the residue was treated with water and acidified to pH=2 with 6 N HCl. The precipitate was collected and washed with water and dried to provide the acid intermediate, 3-cyano-6-methoxy-indole-1,2-dicarboxylic acid 1-tert-butyl ester (2.40 g, 73%).

Step C: To a solution of 3-cyano-6-methoxyindole-1,2-dicarboxylic acid 1-tert-butyl ester (474 mg, 1.5 mmol) prepared above, and HOBt (200 mg, 1.5 mmol) in DCE/DMF (10 mL/1 mL), was added DCC (310 mg, 1.5 mmol), followed by 3-(N-hydroxycarbamimidoyl)benzoic acid methyl ester (291 mg, 1.5 mmol). The mixture was stirred at room temperature for 2 h and filtered. The filtrate was collected and the solvent was replaced with chlorobenzene, followed by the heating at 150° C. for 48 h. After cooling to room temperature, the solvent was removed in vacuo and the residue was chromatographed (silica gel, $CH_2Cl_2$/EtOAc, 8/2) to furnish the intermediate, 3-cyano-6-methoxy-2-[3-(3-methoxycarbonylphenyl)-[1,2,4]oxadiazol-5-yl]-indole-1-carboxylic acid tert-butyl ester, which was treated with 50% TFA in DCM (10.0 mL) at room temperature for 1 h. After removal of the volatiles in vacuo, the residue was suspended in water and neutralized with $K_2CO_3$ to provide the desired product, methyl 3-[5-(3-cyano-6-methoxy-1H-indol-2-yl-)[1,2,4]oxadiazol-3-yl]benzoate, compound 226 (350 mg, 62%).

Example 1AO

Preparation of 1-ethyl-2-(4-methanesulfonylphenyl)-6-methoxy-1H-indole-3-carbonitrile (compound 265)

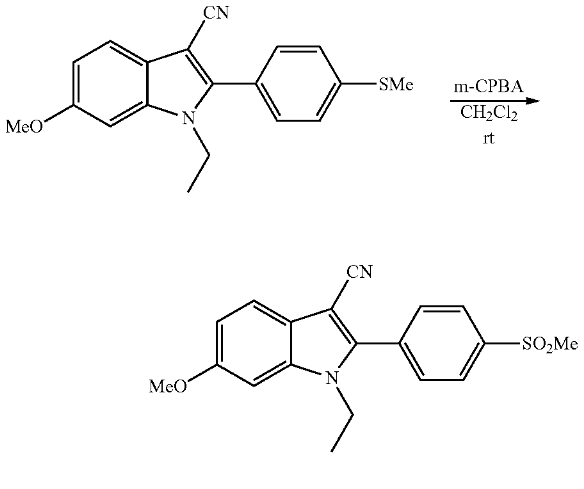

A solution of 1-ethyl-6-methoxy-2-(4-methylsulfanylphenyl)-1H-indole-3-carbonitrile (0.12 g, 0.37 mmol) in $CH_2Cl_2$ (5 mL) was treated with m-chloroperbenzoic acid (Aldrich, <77%, 0.26 g,) in one portion and the reaction was stirred for 10 h at room temperature. The reaction was then diluted with $H_2O$ and saturated $NaHCO_3$ and extracted twice with EtOAc. The organic phases were washed with $NaHCO_3$ (2×) and saturated NaCl and dried and concentrated to a dark semi-solid. The crude product was purified by flash chromatography (EtOAc/CH2C12, 0-3%) through a 5 gram silica cartridge topped with 1 gram of basic alumina to give 72 mg (55%) of 1-ethyl-6-methoxy-2-(4-methylsulfanylphenyl)-1H-indole-3-carbonitrile as an off-white solid.

Example 1AP

Preparation of N-{4-[3-cyano-1-ethyl-6-(2-morpholin-4-yl-ethoxy)-1H-indol-2-yl]-phenyl} methanesulfonamide (compound 478)

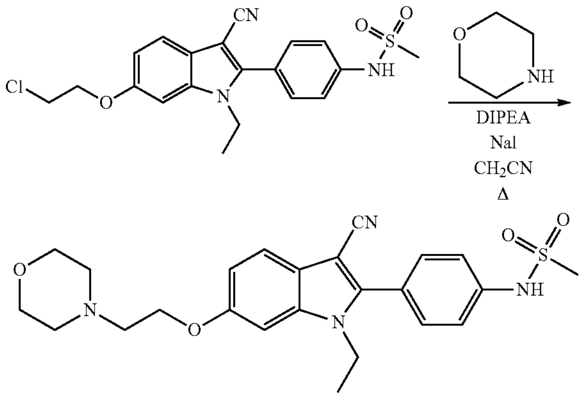

A solution of N-{4-[6-(2-chloroethoxy)-3-cyano-1-ethyl-1H-indol-2-yl]-phenyl} methanesulfonamide (90 mg, 0.21 mmol), morpholine (0.06 mL, 0.65 mmol), NaI (32 mg, 0.21 mmol) and diisopropyl ethylamine (0.06 mL, 0.32 mmol) in $CH_3CN$ (2 mL) was heated in a sealed tube at 100° C. for 25 h. The reaction mixture was cooled to room temperature, diluted with $H_2O$ and extracted with EtOAc (3×). The combined organic phases were washed with saturated NaCl, dried and concentrated. The crude solid was triturated with EtOAc and filtered to give 41 mg (41%) of N-{4-[3-cyano-1-ethyl-6-(2-morpholin-4-yl-ethoxy)-1H-indol-2-yl]-phenyl} methanesulfonamide as a tan solid.

The following compounds were made similarly: Compounds 479, 480, 481, 482, 496, 497 and 498.

Example 1AQ

Preparation of 2-morpholin-4-yl-ethanesulfonic acid [4-(3-cyano-1-ethyl-6-methoxy-1H-indol-2-yl)-phenyl] amide (compound 653)

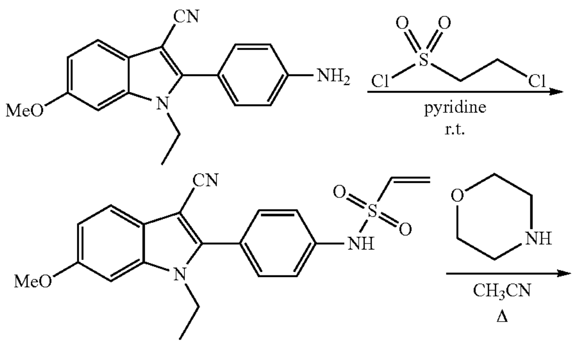

-continued

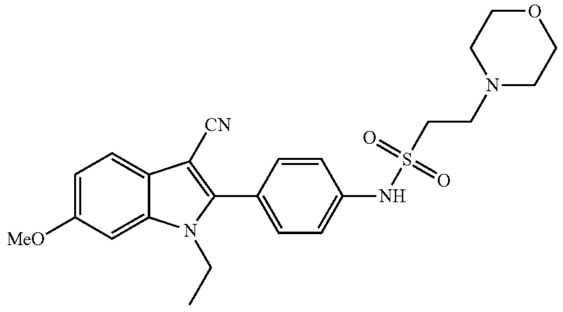

Step A: A solution of 2-(4-aminophenyl)-1-ethyl-6-methoxy-1H-indole-3-carbonitrile, prepared by example 1Ga step B, (0.82 mg, 2.82 mmol), in pyridine (10 mL) was treated dropwise with chloroethyl sulfonylchloride (0.38 mL, 3.66 mmol) at room temperature. After stirring for 4 h, the reaction mixture was quenched with ice-water and enough 6N HCl was added until the pH was lowered to 2. The suspension was extracted with hot EtOAc (3×). The organic phases were then washed sequentially with 1N HCl, $H_2O$ and saturated NaCl and dried and concentrated to give ethenesulfonic acid [4-(3-cyano-1-ethyl-6-methoxy-1H-indol-2-yl)-phenyl] amide as a pale orange solid which was used directly in the next step without further purification.

Step B: A suspension of ethenesulfonic acid [4-(3-cyano-1-ethyl-6-methoxy-1H-indol-2-yl)-phenyl] amide, prepared above, (70 mg, 0.18 mmol), morpholine (0.05 mL, 0.55 mmol) in $CH_3CN$ (1.5 mL) was heated at reflux for 1.5 h. After cooling to room temperature, the reaction was concentrated and the residue was purified by flash chromatography (acetone/EtOAc, 2/98) over silica gel to afford 89 mg (100%) of 2-morpholin-4-yl-ethanesulfonic acid [4-(3-cyano-1-ethyl-6-methoxy-1H-indol-2-yl)-phenyl] amide as a tan foam.

The following compound was made similarly: Compound 654.

Example 1AR

Preparation of 2-morpholin-4-yl-ethanesulfonic acid [4-(3-cyano-1-ethyl-6-methoxy-1H-indol-2-yl)-phenyl]methyl amide (compound 668)

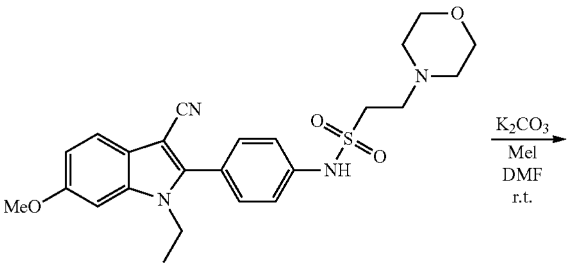

-continued

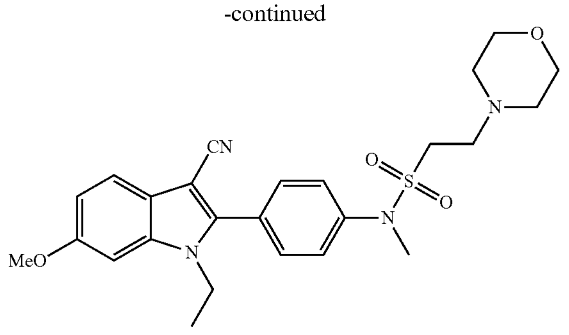

A solution of 2-morpholin-4-yl-ethanesulfonic acid [4-(3-cyano-1-ethyl-6-methoxy-1H-indol-2-yl)-phenyl] amide, prepared in example 1AQ (60 mg, 0.13 mmol) in DMF (3 mL) was treated with $K_2CO_3$ (35 mg, 0.26 mmol) and methyl iodide (0.02 mL, 0.26 mmol). After stirring at room temperature for 1.5 h, the reaction mixture was diluted with $H_2O$ and extracted with EtOAc (2×). The organic phases were then washed with $H_2O$ (3×) and saturated NaCl, and then dried and concentrated to afford a residue. Flash chromatography over silica gel (acetone/EtOAc, 0-2%) gave 31 mg (50%) of 2-morpholin-4-yl-ethanesulfonic acid [4-(3-cyano-1-ethyl-6-methoxy-1H-indol-2-yl)-phenyl]methyl amide as an off white solid.

The following compounds were made similarly: Compounds 684, 685, 686, 687, 688, 689, 690, 691, 692, 693, 694, 695, 696, 697, 698.

Example 1AS

Preparation of 2-[4-(1,1-dioxo-1$\lambda^6$-isothiazolidin-2-yl)phenyl]-1-ethyl-6-methoxy-1H-indole-3-carbonitrile (compound 84)

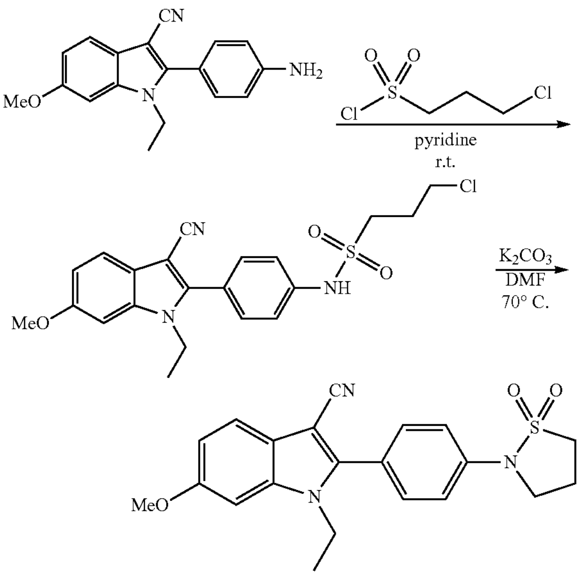

Step A: A solution of 2-(4-aminophenyl)-1-ethyl-6-methoxy-1H-indole-3-carbonitrile, prepared by example 1Ga step B, (2.78 g, 9.55 mmol) in pyridine (40 mL) was treated dropwise with 3-chloropropanesulfonyl chloride (1.45 mL, 11.9 mmol) and the reaction was stirred for 4 h at room temperature. The reaction was diluted with water and enough 6N HCl to lower the pH to 2. The reaction mixture was extracted with EtOAc (3×) and the combined organic layers were washed sequentially with 1N HCl, water and saturated NaCl and then dried and concentrated to give 3.9 g (95%), of 3-chloropropane-1-sulfonic acid [4-(3-cyano-1-ethyl-6-methoxy-1H-indol-2-yl)-phenyl] amide as a brown foam which was used directly in the next step.

Step B: A solution of 3-chloropropane-1-sulfonic acid [4-(3-cyano-1-ethyl-6-methoxy-1H-indol-2-yl)-phenyl] amide, prepared above (3.65 g, 2.33 mmol) in DMF (100 mL) was treated with $K_2CO_3$ and heated at 70° C. for 2 h. After cooling to room temperature, the reaction mixture was diluted with $H_2O$ and extracted 3x with hot EtOAc. The hot organic layers were washed with warm $H_2O$ (3×) and saturated NaCl and dried and concentrated to a solid. Trituration ($CH_2Cl_2$/hexanes) gave 2.27 g (68%) of 2-[4-(1,1-dioxo-1λ$^6$-isothiazolidin-2-yl)phenyl]-1-ethyl-6-methoxy-1H-indole-3-carbonitrile as a light brown solid.

The following compounds were made in similar fashion: Compound 649, 775.

Example 1AT

Preparation of 2-[4-(1,1-dioxo-1λ$^6$-isothiazolidin-2-yl)phenyl]-1-ethyl-6-methoxy-1H-indole-3-carbonitrile (compound 666)

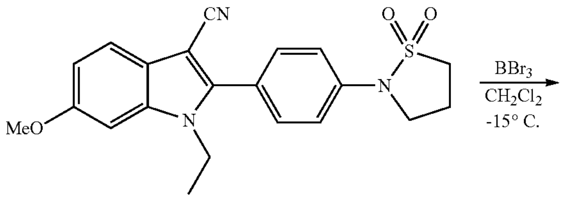

-continued

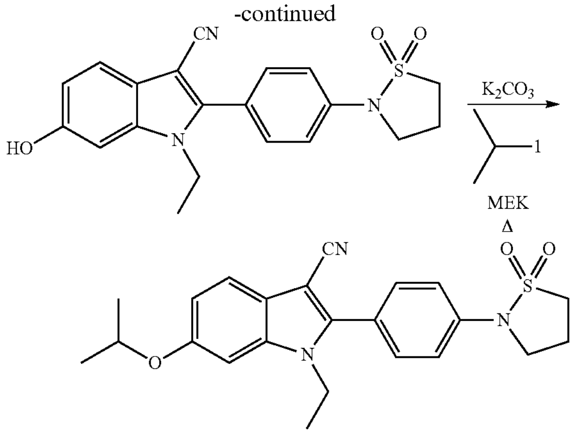

Step A: Following the procedure in example 1B step A, 2-[4-(1,1-dioxo-1λ$^6$-isothiazolidin-2-yl)phenyl]-1-ethyl-6-methoxy-1H-indole-3-carbonitrile was treated with 1M $BBr_3$ solution in $CH_2Cl_2$ at −15° C. for 1.5 h and then poured into ice-water and filtered and dried to afford 2-[4-(1,1-dioxo-1λ$^6$-isothiazolidin-2-yl)phenyl]-1-ethyl-6-hydroxy-1H-indole-3-carbonitrile in nearly quantitative yield.

Step B: Following the procedure in example 1B step B, 2-[4-(1,1-dioxo-1λ$^6$-isothiazolidin-2-yl)phenyl]-1-ethyl-6-hydroxy-1H-indole-3-carbonitrile, $K_2CO_3$, 2-iodopropane and methyl ethyl ketone were heated at reflux to give, after flash chromatography (EtOAc/$CH_2Cl_2$, 0-2%), 61% of 2-[4-(1,1-dioxo-1λ$^6$-isothiazolidin-2-yl)phenyl]-1-ethyl-6-isopropoxy-1H-indole-3-carbonitrile as an off-white solid.

The following compounds were made similarly: Compounds 667, 699

Example 1AU

Preparation of 2-[4-(1,1-dioxo-1λ$^6$-isothiazolidin-2-yl)-phenyl]-1-ethyl-6-(2-morpholin-4-yl-ethoxy)-1H-indole-3-carbonitrile (compound 729)

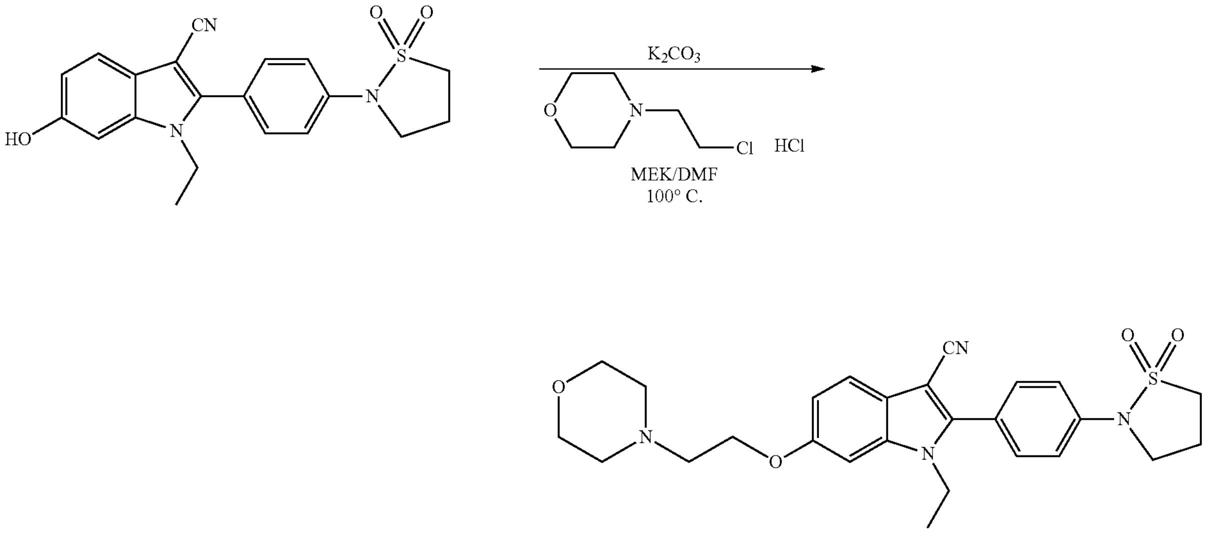

A mixture of 2-[4-(1,1-dioxo-1λ$^6$-isothiazolidin-2-yl)phenyl]-1-ethyl-6-hydroxy-1H-indole-3-carbonitrile, prepared in example 1AT above (70 mg, 0.25 mmol), $K_2CO_3$ (75 mg, 0.51 mmol), sodium iodide (27 mg, 0.18 mmol), 4-(2-chloroethyl) morpholine hydrochloride (42 mg, 0.25 mmol) in methyl ethyl ketone (3 mL) was heated in a sealed tube at 100° C. After 13 hours, DMF (3 mL) was added and the reaction was heated for an additional 6 h. After this time, an additional 42 mg of 4-(2-chloroethyl) morpholine hydrochloride and 135 mg of $K_2CO_3$ was added and the reaction was heated for an additional 6 h to complete the reaction. The reaction mixture was cooled to room temperature, diluted with water, and extracted with EtOAc (3×). The combined organic phases were washed with water (2×) and saturated NaCl and dried and concentrated. Pure 2-[4-(1,1-dioxo-1λ$^6$-isothiazolidin-2-yl)-phenyl]-1-ethyl-6-(2-morpholin-4-yl-ethoxy)-1H-indole-3-carbonitrile was obtained by flash chromatography ($MeOH/CH_2Cl_2$, 0-6%) to give 29 mg (34%) of a tan solid.

The following compounds were made similarly: Compounds 728 and 730.

Example 1AV

Preparation of 2-[4-(2,5-dioxo-imidazolidin-1-yl)-phenyl]-6-ethoxy-1-ethyl-1H-indole-3-carbonitrile (compound 779)

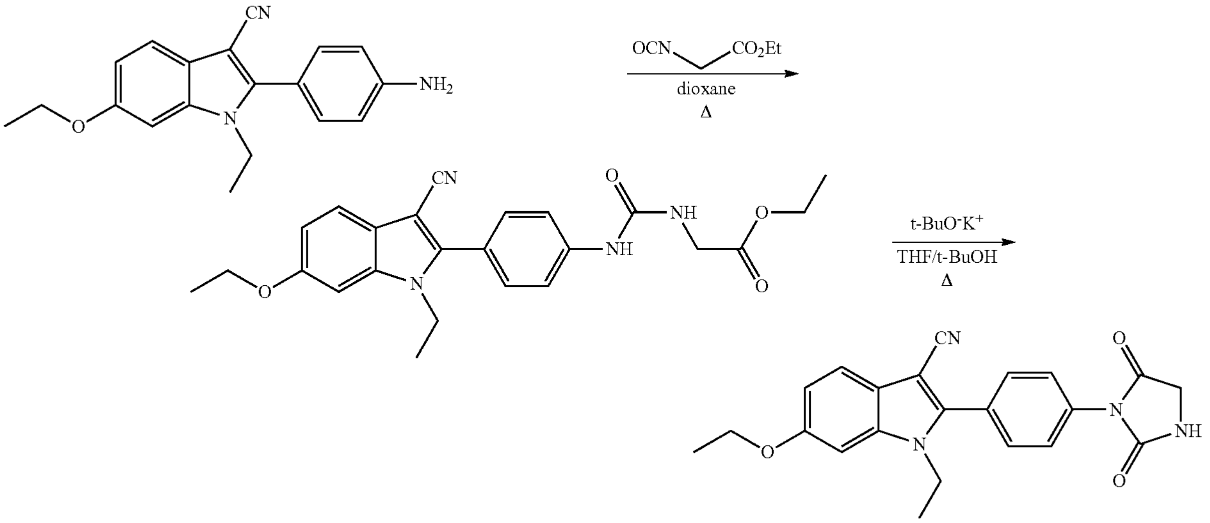

Step A: A solution of 2-(4-aminophenyl)-6-ethoxy-1-ethyl-1H-indole-3-carbonitrile (585 mg, 1.92 mmol) in 10 mL of 1,4-dioxane was treated with ethyl isocyanatoacetate (0.25 mL, 2.12 mmol), and the resulting solution was heated to reflux overnight. The solution was allowed to cool, and the solvent was removed by rotary evaporation. The residual material was triturated with ether, and the resulting precipitate was collected by filtration and dried under vacuum to afford compound 773 (587 mg, 1.35 mmol, 70%).

A similar procedure was used to prepare methyl 2-{3-[4-(3-cyano-6-ethoxy-1-ethyl-1H-indol-2-yl)-phenyl]-ureido}-3-phenyl-propionate (compound 777)

Step B: A solution of ethyl {3-[4-(3-cyano-6-ethoxy-1-ethyl-1H-indol-2-yl)-phenyl]-ureido}-acetate (compound 773, 101 mg, 0.232 mmol) in THF (10 mL) was treated with a solution of potassium tert-butoxide in tert-butanol (0.30 mL, 1.0 M, 0.30 mmol), and the resulting mixture was allowed to stir overnight. The reaction mixture was partitioned between water and ethyl acetate (50 mL each), and the organic phase was washed with saturated brine. The aqueous phases were extracted with more ethyl acetate, and the extracts were combined, dried over anhydrous magnesium sulfate, filtered and evaporated. The residual material was separated by column chromatography (eluting 2/1 ethyl acetate/hexane on silica gel 60) to afford 2-[4-(2,5-dioxo-imidazolidin-1-yl)-phenyl]-6-ethoxy-1-ethyl-1H-indole-3-carbonitrile, compound 779, which was purified further by trituration with ether, collection by filtration and drying under high vacuum (76 mg, 0.196 mmol, 84%).

Example 1AW

Preparation of 2-[4-(2,4-dioxo-imidazolidin-1-yl) phenyl]-6-ethoxy-1-ethyl-1H-indole-3-carbonitrile (compound 776)

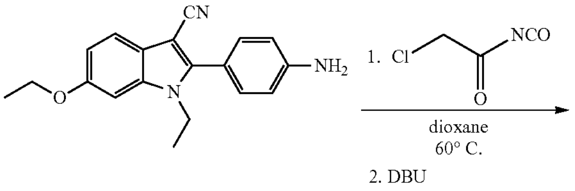

-continued

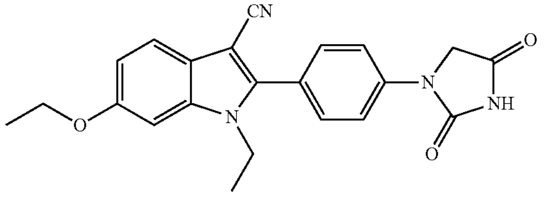

A solution of 2-(4-aminophenyl)-6-ethoxy-1-ethyl-1H-indole-3-carbonitrile (319 mg, 1.04 mmol) in 1,4-dioxane (3 mL) was treated with chloroacetyl isocyanate (0.10 mL, 1.17 mmol), and the resulting solution was warmed to 60° C. overnight. The solution was cooled, and DBU (0.20 mL, 1.31 mmol) was added. This mixture was stirred at ambient temperature overnight, and then was partitioned between water and ethyl acetate (50 mL each). The organic layer was washed with saturated brine, and then dried over anhydrous magnesium sulfate, filtered and evaporated. The residual material was triturated with ether, and the resulting solid was collected by filtration and dried under high vacuum to afford the title product (319 mg, 0.821 mmol, 79%).

Example 1AX

Preparation of N,N-Dimethyl-2-[4-(3,4-dimethyl-2,5-dioxo-imidazolidin-1-yl)-phenyl]-6-ethoxy-1-ethyl-1H-indole-3-carboxamide (compound 780) and N,N-Dimethyl-6-ethoxy-1-ethyl-2-[4-(3-methyl-2,5-dioxo-imidazolidin-1-yl)-phenyl]-1H-indole-3-carboxamide (compound 781)

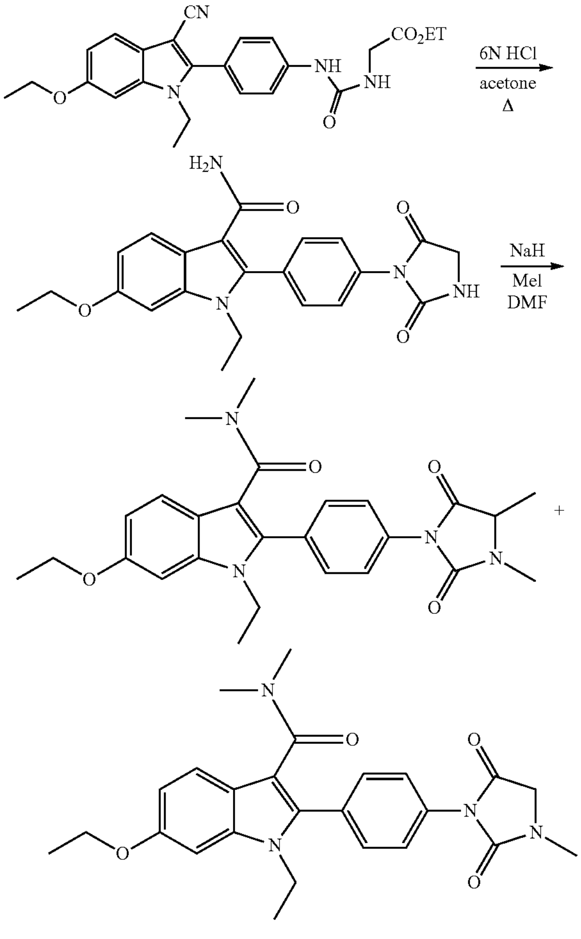

Step A. A solution of ethyl {3-[4-(3-cyano-6-ethoxy-1-ethyl-1H-indol-2-yl)-phenyl]-ureido} acetate (compound 773, 325 mg, 0.748 mmol), prepared in procedure 1AV, step A, in acetone (5 mL) was treated with HCl (3 mL, 6 N), and the resulting solution was heated to reflux overnight. The reaction mixture was cooled, and the resulting precipitate was collected by filtration, washed with ether and dried under high vacuum to afford the product, 6-ethoxy-1-ethyl-2-[4-(2,5-dioxo-imidazolidin-1-yl)-phenyl]-1H-indole-3-carboxamide (264 mg, 0.650 mmol, 87%).

Step B. Sodium hydride dispersion in mineral oil (75 mg) was washed with a small portion of hexane, and the hexane layer was decanted off. A solution of 6-ethoxy-1-ethyl-2-[4-(2,5-dioxo-imidazolidin-1-yl)-phenyl]-1H-indole-3-carboxamide (190 mg, 0.468 mmol) in dimethylformamide (2 mL) was added, and the mixture was stirred for 1 hour. Then, methyl iodide (0.10 mL, 1.61 mmol) was added by syringe. The resulting mixture was allowed to stir at ambient temperature overnight and then was poured into 50 mL of ethyl acetate. The organic phase was washed with water (3x50 mL) and saturated brine (20 mL), then dried over anhydrous magnesium sulfate, filtered and evaporated. The residual material was separated by column chromatogaphy (1/1 ethyl acetate/hexane, eluting on silica gel 60) to afford the title products, compounds 780 and 781.

Example 1AY

Preparation of N-[4-(3-cyano-1-ethyl-6-methoxy-1H-indol-2-yl)-phenyl]-N-(2-hydroxyethyl)-methanesulfonamide (compound 828)

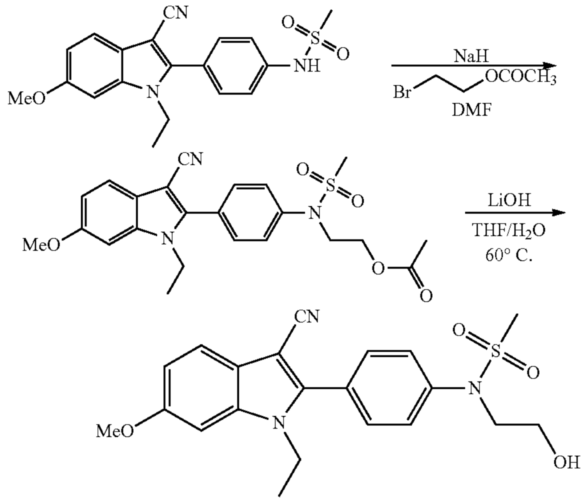

Step A: Sodium hydride dispersion in mineral oil (108 mg) was washed with a small portion of hexane, and the hexane layer was decanted off. A solution of N-[4-(3-cyano-1-ethyl-6-methoxy-1H-indol-2-yl)-phenyl]methanesulfonamide (compound 129, 500 mg, 1.35 mmol) in DMF (5 mL) was slowly added. After gas evolution was complete, 2-bromoethyl acetate (0.30 mL, 2.64 mmol) and sodium iodide (20 mg) were added. The mixture was stirred at ambient temperature overnight, and then was poured into 50 mL of ethyl acetate. This was washed with water (3x50 mL) and saturated brine (20 mL), then dried over anhydrous magnesium sulfate, filtered and evaporated. The residual material was separated by column chromatogaphy (1/1 ethyl acetate/hexane, eluting on silica gel 60) to afford compound 815 (364 mg, 0.799 mmol, 59%).

Step B: A mixture of N-(2-acetoxyethyl)-N-[4-(3-cyano-1-ethyl-6-methoxy-1H-indol-2-yl)-phenyl]methanesulfonamide (compound 815, 164 mg, 0.360 mmol) and lithium hydroxide hydrate (45 mg, 1.07 mmol) in 5 mL THF/1 mL water was warmed to 60° C. overnight. The mixture was cooled and poured into ethyl acetate (50 mL). This was washed with water (50 mL) and brine (20 mL), dried over anhydrous magnesium sulfate, filtered and evaporated to afford a solid. The solid was triturated with ether, collected by filtration and dried under high vacuum to afford N-[4-(3- cyano-1-ethyl-6-methoxy-1H-indol-2-yl)-phenyl]-N-(2-hydroxyethyl) methanesulfonamide, compound 828 (137 mg, 0.331 mmol, 92%).

Example 1AZ

Preparation of 1-ethyl-6-methoxy-2-[4-(2-methoxy-ethoxy)-phenyl]-1H-indole-3-carbonitrile (compound 248)

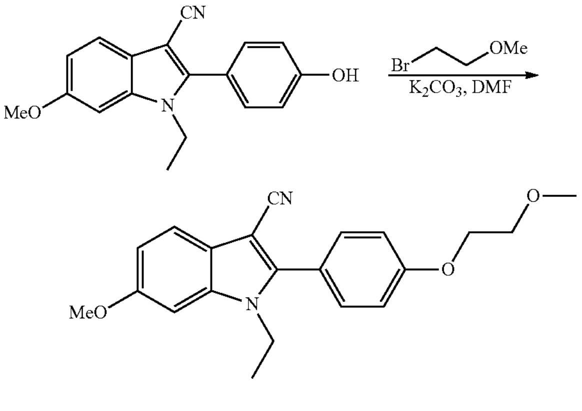

1-Ethyl-2-(4-hydroxy-phenyl)-6-methoxy-1H-indole-3-carbonitrile (40 mg, 0.14 mmol), prepared as in example 1Ga step B, was combined with $K_2CO_3$ (77 mg, 0.56 mmol), bromoethyl methyl ether (26 μL, 0.28 mmol), and DMF (450 μL). This was stirred at room temperature for 1 hour, and then at 75° C. for 3 hours. The reaction mixture was then partitioned between $H_2O$ and EtOAc. The organic layer was dried and concentrated. Purification by silica gel chromatography ($CH_2Cl_2$, 0-5% EtOAc) to yield 1-ethyl-6-methoxy-2-[4-(2-methoxyethoxy)-phenyl]-1H-indole-3-carbonitrile (44 mg, 90%) as a white solid.

The following compound was prepared similarly as above: Compound 249.

Example 1BA

Preparation of 1-ethyl-6-methoxy-2-[4-(2-morpholin-4-yl-ethoxy)-phenyl]-1H-indole-3-carbonitrile (compound 261)

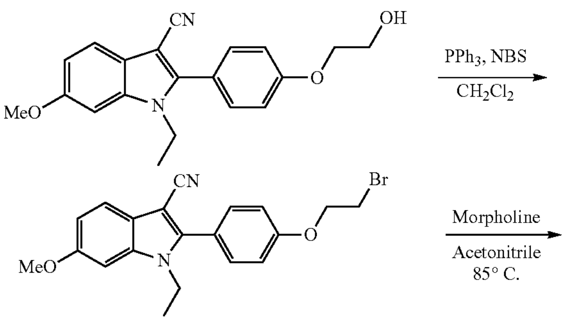

-continued

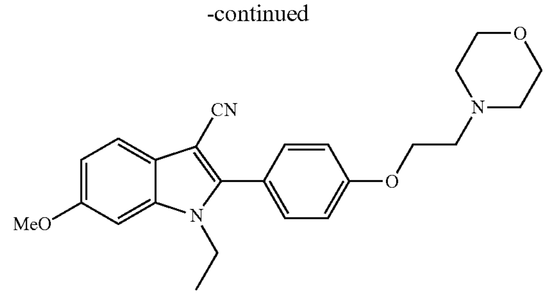

Step A: 1-Ethyl-6-methoxy-2-[4-(2-hydroxyethoxy)-phenyl]-1H-indole-3-carbonitrile (450 mg, 1.34 mmol), prepared as in example 1AZ, was combined with $PPh_3$ (878 mg, 3.35 mmol) in $CH_2Cl_2$ (32 mL) at 0° C. N-bromosuccinimide (600 mg, 3.37 mmol) was added in one portion. The reaction mixture was stirred at room temperature for 30 minutes. The reaction mixture was washed with aqueous $NaHCO_3$. The organic layer was dried and concentrated, and purified by silica gel chromatography ($CH_2Cl_2$) to yield 2-[4-(2-bromoethoxy)-phenyl]-1-ethyl-6-methoxy-1H-indole-3-carbonitrile (506 mg, 95%), compound 253 as a white solid.

Step B: 2-[4-(2-bromoethoxy)-phenyl]-1-ethyl-6-methoxy-1H-indole-3-carbonitrile (40 mg, 0.1 mmol), prepared as in step A above, was combined with morpholine (50 μL, 0.58 mmol) and acetonitrile (1.0 mL). This was heated at 85° C. for 2 h. The reaction mixture was then partitioned between $CH_2Cl_2$ and $H_2O$. The organic layer was dried and concentrated. Purification by silica gel chromatography (6/4, acetone/hexanes) yielded 1-ethyl-6-methoxy-2-[4-(2-morpholin-4-yl-ethoxy)-phenyl]-1H-indole-3-carbonitrile (39 mg, 96%) as a white solid.

The following compounds were prepared similarly as above, using different amines: Compounds 262, 263, 264.

Example 1BB

Preparation of N-{2-[4-(3-cyano-1-ethyl-6-methoxy-1H-indol-2-yl)-phenoxy]-ethyl} methanesulfonamide (compound 268)

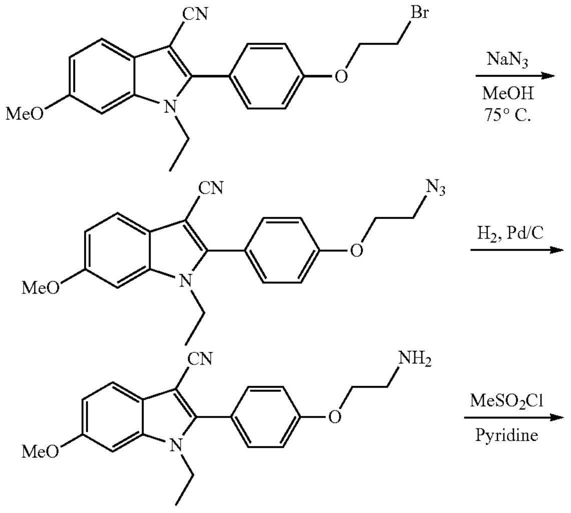

-continued

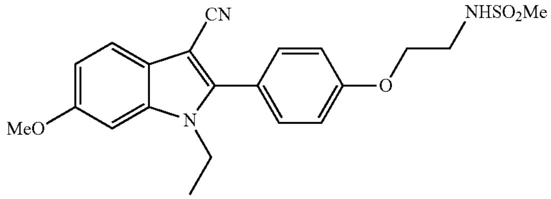

Step A: 2-[4-(2-Bromoethoxy)phenyl]-1-ethyl-6-methoxy-1H-indole-3-carbonitrile (258 mg, 0.65 mmol), prepared in example 1BA, step A, was combined with $NaN_3$ (144 mg, 2.2 mmol), and MeOH (3.2 mL). This was heated overnight at 75° C. The reaction mixture was then partitioned between $CH_2Cl_2$ and $H_2O$. The organic layer was dried and concentrated. Purification by silica gel chromatography ($CH_2Cl_2$) yielded 2-[4-(2-azidoethoxy)phenyl]-1-ethyl-6-methoxy-1H-indole-3-carbonitrile (187 mg, 80%), compound 266 as a white solid.

Step B: 2-[4-(2-Azidoethoxy)phenyl]-1-ethyl-6-methoxy-1H-indole-3-carbonitrile (410 mg, 1.14 mmol), prepared as in step A, above, was suspended in a solution of MeOH (20 mL) and concentrated HCl (500 μL). Pd/C (150 mg, 10%) was added, and this mixture was hydrogenated at 30 p.s.i. for 1 h. This was filtered and the filtrate was concentrated. The filtrate residue was partitioned between EtOAc and 0.5N NaOH. The organic layer was dried and concentrated. Purification by silica gel chromatography (10-30%, MeOH/$CH_2Cl_2$) yielded 2-[4-(2-aminoethoxy)phenyl]-1-ethyl-6-methoxy-1H-indole-3-carbonitrile (298 mg, 78%), compound 267, as a white solid.

Step C: 2-[4-(2-Aminoethoxy)phenyl]-1-ethyl-6-methoxy-1H-indole-3-carbonitrile (30 mg, 0.09 mmol), prepared in step B, above, was dissolved in pyridine (300 μL). Methanesulfonyl chloride (8 μL, 0.1 mmol) was added. This was stirred at room temperature for 45 minutes. More methansulfonyl chloride (4 μL, 0.05 mmol) was added. Stirring continued for another hour. The reaction mixture was partitioned between EtOAc and aqueous HCl. The organic layer was dried and concentrated. Purification by silica gel chromatography (1/1 $CH_2Cl_2$/EtOAc) yielded N-{2-[4-(3-cyano-1-ethyl-6-methoxy-1H-indol-2-yl)phenoxy]ethyl} methanesulfonamide, compound 268 (32 mg, 86%) as a white solid.

The following compound was prepared similarly as above: Compound 269.

Example 1BC

Preparation of N-{2-[4-(3-cyano-1-ethyl-6-methoxy-1H-indol-2-yl)-phenoxy]-ethyl} acetamide (compound 274)

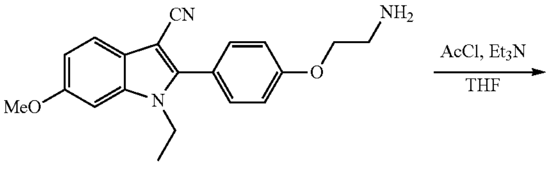

-continued

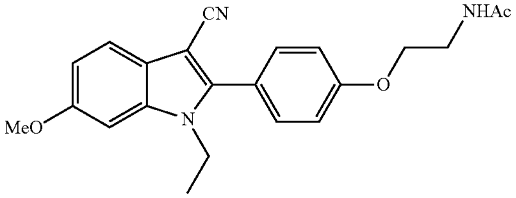

2-[4-(2-Aminoethoxy)phenyl]-1-ethyl-6-methoxy-1H-indole-3-carbonitrile (30 mg, 0.09 mmol), prepared as in example 1BB, step B, was dissolved in THF (400 μL), and $Et_3N$ (24 μL, 0.17 mmol). Acetyl chloride (10 μL, 0.14 mmol) was added, and the reaction mixture was stirred at room temperature for 2 h. The reaction mixture was partitioned between EtOAc and $H_2O$. The organic layer was dried and concentrated. Purification by silica gel chromatography (EtOAc) yielded N-{2-[4-(3-cyano-1-ethyl-6-methoxy-1H-indol-2-yl)phenoxy]ethyl} acetamide (33 mg, 97%) as a white solid.

Example 1BD

Preparation of 1-{2-[4-(3-cyano-1-ethyl-6-methoxy-1H-indol-2-yl)-phenoxy]ethyl}-3-ethyl-urea (Compound 279)

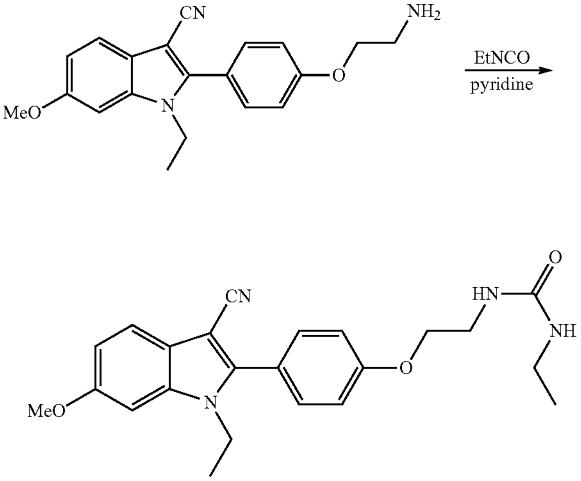

2-[4-(2-Aminoethoxy)phenyl]-1-ethyl-6-methoxy-1H-indole-3-carbonitrile (30 mg, 0.09 mmol), prepared as in example 1BB, was combined with ethyl isocyanate (18 μL, 0.21 mmol) and pyridine (300 μL). This mixture was stirred at room temperature for 90 minutes, and was then partitioned between EtOAc and aqueous HCl. The organic layer was dried and concentrated. Purification by silica gel chromatography (EtOAc) yielded 1-{2-[4-(3-cyano-1-ethyl-6-methoxy-1H-indol-2-yl)-phenoxy]-ethyl}-3-ethyl-urea (34 mg, 93%) as a white solid.

Example 1BE

Preparation of N-{2-[4-(3-cyano-1-ethyl-6-methoxy-1H-indol-2-yl)-phenoxy]ethyl}formamide (compound 280)

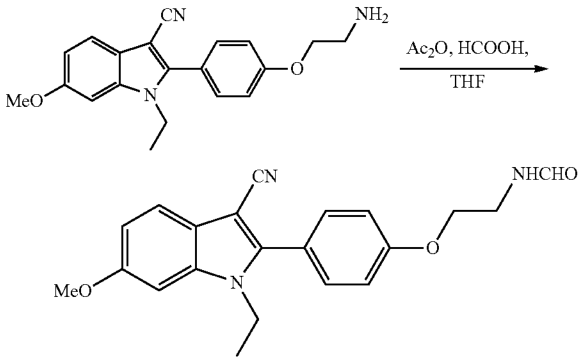

Acetic anhydride (700 μL) and 98% formic acid (280 μL) were heated at 65° C. for 1 h. This was cooled to 0° C. 2-[4-(2-Aminoethoxy)phenyl]-1-ethyl-6-methoxy-1H-indole-3-carbonitrile (30 mg, 0.09 mmol), prepared as in example 1BB, was taken up in THF (400 μL), and added to the mixed anhydride. This was stirred at 0° C. for 45 minutes. The mixture was then portioned between EtOAc and aqueous $NaHCO_3$. The organic layer was dried and concentrated. Purification by silica gel chromatography (4/1, $CH_2Cl_2$/acetone) yielded N-{2-[4-(3-cyano-1-ethyl-6-methoxy-1H-indol-2-yl)phenoxy]-ethyl} formamide (28 mg, 86%) as a white solid.

Example 1BF

Preparation of 1-ethyl-2-{4-[2-(3-hydroxypyrrolidin-1-yl)-2-oxo-ethoxy]phenyl}-6-methoxy-1H-indole-3-carbonitrile (compound 285)

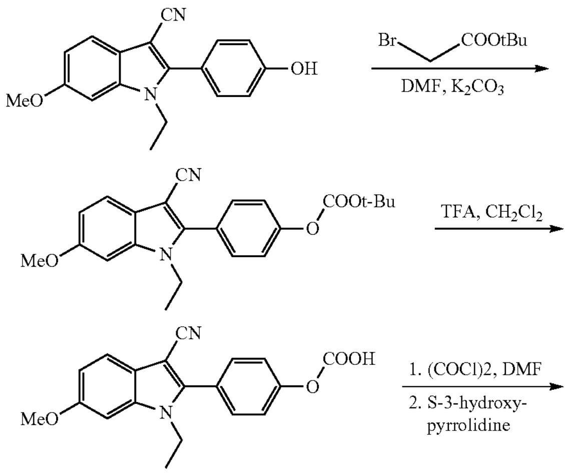

-continued

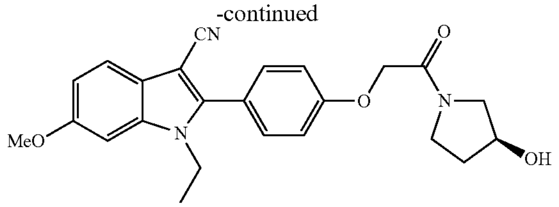

Step A: 1-Ethyl-2-(4-hydroxyphenyl)-6-methoxy-1H-indole-3-carbonitrile (559 mg, 1.91 mmol), was used to prepare [4-(3-cyano-1-ethyl-6-methoxy-1H-indol-2-yl)-phenoxy]-acetic acid tert-butyl ester (780 mg, 100%) utilizing essentially the same procedure as example 1AZ.

Step B: [4-(3-Cyano-1-ethyl-6-methoxy-1H-indol-2-yl)-phenoxy]-acetic acid tert-butyl ester (745 mg, 1.83 mmol) was stirred in 20% TFA in $CH_2Cl_2$ at room temperature for 3 hours. This was concentrated and the residue was partitioned between $H_2O$ and EtOAc. The organic layer was dried and concentrated. The residue was triturated with $CH_2Cl_2$ to yield [4-(3-cyano-1-ethyl-6-methoxy-1H-indol-2-yl)-phenoxy]-acetic acid (634 mg, 99%) as a white solid.

Step C: [4-(3-Cyano-1-ethyl-6-methoxy-1H-indol-2-yl)-phenoxy]-acetic acid (40 mg, 0.12 mmol) was suspended in $CH_2Cl_2$ (1.65 mmol) and DMF (2 μL). Oxalyl chloride (17 μL, 0.19 mmol) was added. This was stirred at room temperature for 30 minutes. The resulting solution was then pipetted into a stirring solution of S-3-hydroxypyrrolidine (150 μL) and $CH_2Cl_2$ (3.0 mL). The mixture was washed with aqueous HCl. The organic layer was dried and concentrated. Purification by silica gel chromatography (3/2 $CH_2Cl_2$/acetone) yielded 1-ethyl-2-{4-[2-(3-hydroxy-pyrrolidin-1-yl)-2-oxo-ethoxy]-phenyl}-6-methoxy-1H-indole-3-carbonitrile (40 mg, 79%), compound 285 as a white solid.

Example 1BG

Preparation of 1-ethyl-6-methoxy-2-(2-oxo-2,3-dihydro-benzooxazol-5-yl)-1H-indole-3-carbonitrile (Compound 332)

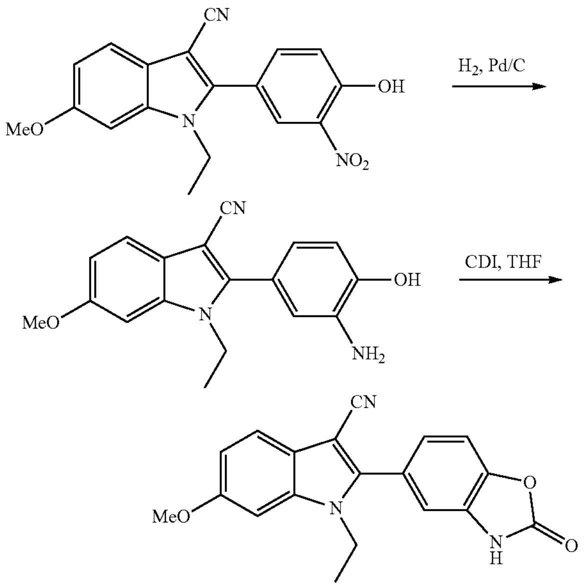

Step A: 1-Ethyl-2-(4-hydroxy-3-nitrophenyl)-6-methoxy-1H-indole-3-carbonitrile (369 mg, 1.1 mmol), prepared as in example 1Gd, was combined with EtOAc (20 mL) and Pd/C (150 mg, 10%). This mixture was hydrogenated at 30 p.s.i. for 1 h. This was filtered through celite. The filtrate was concentrated and triturated with ether to yield 2-(3-amino-4-hydroxyphenyl)-1-ethyl-6-methoxy-1H-indole-3-carbonitrile (307 mg, 91%), compound 322, as a white solid.

Step B: 2-(3-Amino-4-hydroxyphenyl)-1-ethyl-6-methoxy-1H-indole-3-carbonitrile (100 mg, 0.33 mmol), prepared as in step A, was combined with CDI (83 mg, 0.51 mmol), and THF (1.1 mL). This was heated at 65° C. for 1 hour. The reaction mixture was partitioned between EtOAc and aqueous HCl. The organic layer was dried and concentrated. Purification by silica gel chromatography (9/1, $CH_2Cl_2$/EtOAc) yielded 1-ethyl-6-methoxy-2-(2-oxo-2,3-dihydro-benzooxazol-5-yl)-1H-indole-3-carbonitrile (89 mg, 81%) as a white solid.

Example 1BH

Preparation of 1-ethyl-6-methoxy-2-(3-oxo-3,4-dihydro-2H-benzo [1,4]oxazin-6-yl)-1H-indole-3-carbonitrile (compound 334)

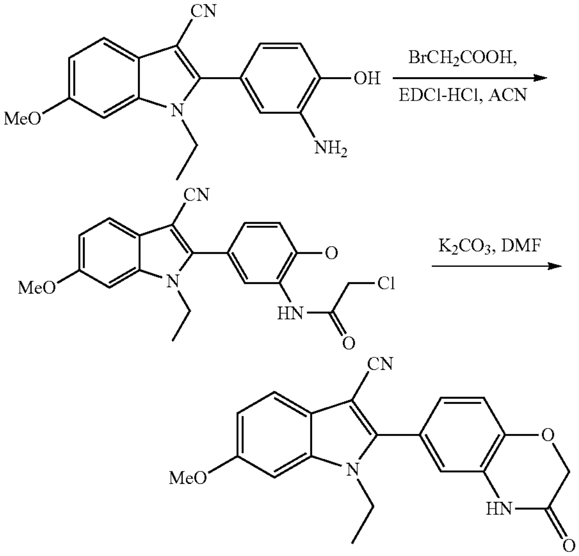

Step A: Bromoacetic acid (52 mg, 0.37 mmol) was combined with EDCI hydrochloride (62 mg, 0.4 mmol) and acetonitrile (900 µL) to form a homogeneous solution. 2-(3-Amino-4-hydroxyphenyl)-1-ethyl-6-methoxy-1H-indole-3-carbonitrile (100 mg, 0.33 mmol), prepared as in example 1BG, step B, was added to the solution. A thick paste soon formed. Another 1.1 mL of acetonitrile was added and the mixture was then stirred at room temperature for 2 hours. The reaction mixture was then partitioned between $H_2O$ and EtOAc. The organic layer was dried and concentrated. Purification by silica gel chromatography (4/1, $CH_2Cl_2$/EtOAc) yielded 2-chloro-N-[5-(3-cyano-1-ethyl-6-methoxy-1H-indol-2-yl)-2-hydroxyphenyl] acetamide (82 mg, 60%), compound 333, as a white solid.

Step B: 2-Chloro-N-[5-(3-cyano-1-ethyl-6-methoxy-1H-indol-2-yl)-2-hydroxy-phenyl] acetamide (57 mg, 0.13 mmol), prepared in step A, was combined with $K_2CO_3$ (55 mg, 0.4 mmol), and DMF (400 µL). This was heated at 80° C. for 1 hour. The reaction mixture was then partitioned between $H_2O$ and EtOAc. The organic layer was dried and concentrated. Purification by silica gel chromatography (9/1, $CH_2Cl_2$/EtOAc) yielded 1-ethyl-6-methoxy-2-(3-oxo-3,4-dihydro-2H-benzo[1,4]oxazin-6-yl)-1H-indole-3-carbonitrile (45 mg, 90%) as a white solid.

Example 1BI

Preparation of 1-ethyl-6-methoxy-2-(2-oxo-2,3-dihydro-benzooxazol-6-yl)-1H-indole-3-carbonitrile (Compound 340)

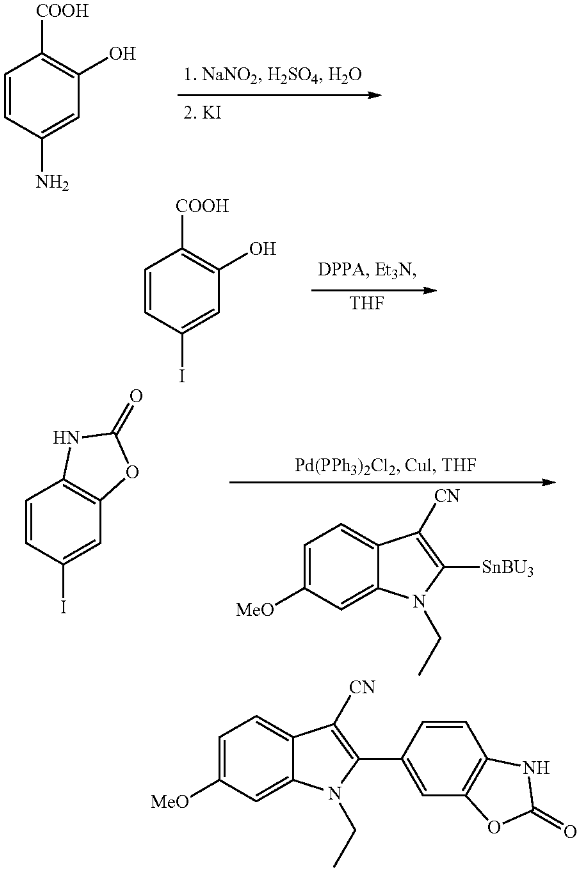

Step A: 4-Aminosalicylic acid (4.0 g, 26 mmol) was suspended in $H_2SO_4$ (26 mL, 2.7M) at −5° C. Sodium nitrite (1.8 g, 26.1 mmol) in $H_2O$ (6.5 mL) was cooled to ice bath temperature and was added dropwise to the aminosalicylic acid mixture over 5 minutes. The resulting suspension was stirred at −5° C. for 15 minutes. A solution of KI (6.8 g, 41 mmol) in $H_2SO_4$ (13 mL, 1M) was added dropwise to the diazonium salt, with considerable evolution of $N_2$. The reaction mixture was heated at 70° C. for 20 minutes. The reaction mixture was then partitioned between $H_2O$ and EtOAc. The organic layer was dried and concentrated. Purification by silica gel chromatography (7/3, hexanes/acetone, 1% acetic acid) yielded 4-iodosalicylic acid (5.33 g, 85-90% pure).

Step B: Crude 4-Iodosalicylic acid (1.0 g, 3.8 mmol) was dissolved in THF (28 mL) and $Et_3N$ (1.15 mL, 8.2 mmol). DPPA (1.7 mL, 7.8 mmol) was added. This was heated at 70°

C. overnight. The reaction mixture was then partitioned between $H_2O$ and EtOAc. The organic layer was dried and concentrated. Purification by silica gel chromatography (9/1, $CH_2Cl_2$/EtOAc) yielded 472 mg crude intermediate. Trituration with ether yielded 6-iodo-3H-benzooxazol-2-one (369 mg, 37%) as a white solid.

Step C: 6-Iodo-3H-benzooxazol-2-one (118 mg, 0.45 mmol) was used to prepare 1-ethyl-6-methoxy-2-(2-oxo-2,3-dihydro-benzooxazol-6-yl)-1H-indole-3-carbonitrile, compound 340 (75 mg, 55%), utilizing essentially the same procedure as in example 1Gd.

Example 1BJ

Preparation of 1-ethyl-6-methoxy-2-(4-methyl-3-oxo-3,4,-dihydro-2H-benzo[1,4]oxazin-6-yl)-1H-indole-3-carbonitrile (compound 339)

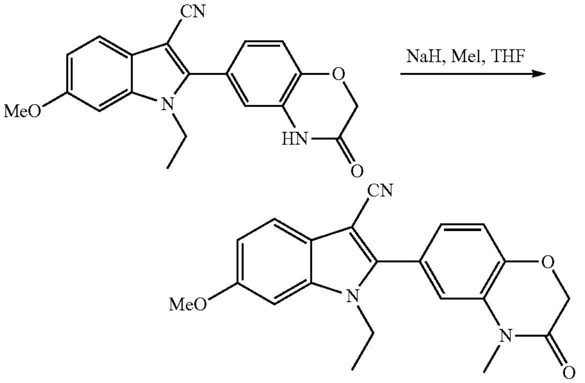

1-Ethyl-6-methoxy-2-(3-oxo-3,4-dihydro-2H-benzo [1,4] oxazin-6-yl)-1H-indole-3-carbonitrile (20 mg, 0.058 mmol), prepared as in example 1BH, was combined with NaH (14 mg, 60% suspension in oil, 0.35 mmol). THF (300 μL) was added. This was stirred at room temperature for 5 minutes. A solution of methyl iodide (4.4 μL) in THF (100 μL) was added. This was stirred at room temperature for 1 hour. The reaction mixture was partitioned between EtOAc and aqueous HCl. The organic layer was dried and concentrated. Purification by silica gel chromatography (9/1, $CH_2Cl_2$/EtOAc) yielded 1-ethyl-6-methoxy-2-(4-methyl-3-oxo-3,4,-dihydro-2H-benzo[1,4]oxazin-6-yl)-1H-indole-3-carbonitrile (16 mg, 76%) as a white solid.

The following compound was prepared similarly: Compound 341.

Example 1BK

Preparation of 1-ethyl-2-iodo-6-methoxy-5-nitro-1H-indole-3-carbonitrile (compound 499)

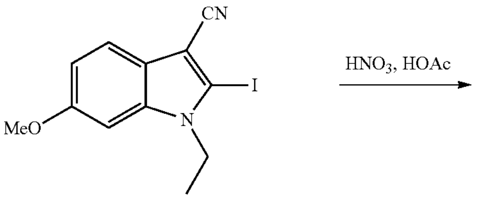

-continued

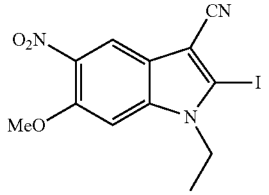

1-Ethyl-2-iodo-6-methoxy-1H-indole-3-carbonitrile (50 mg, 0.15 mmol), prepared as in example 1Ga, Step A, was suspended in acetic acid (620 μL) at 0° C. Nitric acid (4.25M in AcOH) was added. This was stirred at room temperature for 2 hours. The reaction mixture was then partitioned between $CH_2Cl_2$ and $H_2O$. The organic layer was washed with aqueous $NaHCO_3$, and then was dried and concentrated. Purification by silica gel chromatography (6/4, $CH_2Cl_2$/hexanes), followed by ether trituration, yielded 1-ethyl-2-iodo-6-methoxy-5-nitro-1H-indole-3-carbonitrile (16 mg, 29%) as a yellow solid.

Example 1BL

Preparation of 1'-ethanesulfonyl-1-ethyl-6-methoxy-2',3'-dihydro-1H,1H'-[2,6']biindolyl-3-carbonitrile (compound 753)

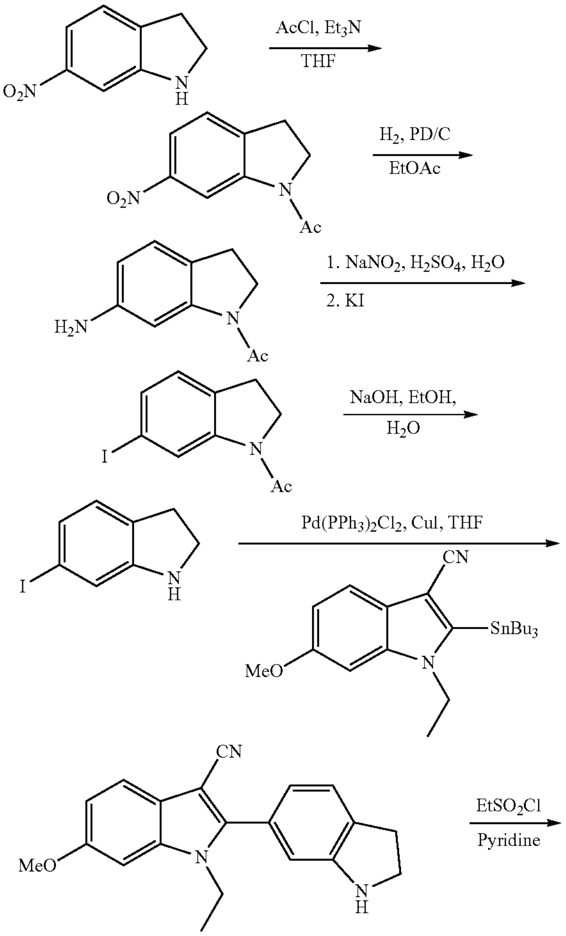

-continued

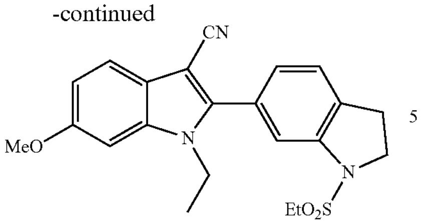

Step A: 6-Nitroindoline (3.0 g, 18.3 mmol) was dissolved in THF (45 mL) and $Et_3N$ (3.4 mL, 24.4 mmol) at 0° C. Acetyl chloride (1.5 mL, 21 mmol) was added dropwise. The mixture was stirred at room temperature for 30 minutes. The mixture was partitioned between EtOAc and aqueous HCl. The organic layer was dried and concentrated to yield 1-acetyl-6-nitroindoline (3.8 g, 100%) as a yellow solid.

Step B: 1-Acetyl-6-nitroindoline (3.8 g, 18.3 mmol) was suspended in EtOAc (200 mL). Pd/C (650 mg, 10%) was added, and the mixture was hydrogenated at 40-55 p.si.i. for 2 hours. The mixture was then filtered through celite. The filtrate was concentrated, and the residue was triturated with ether to yield 1-acetyl-6-aminoindoline (3.18 g, 99%) as an orange solid.

Step C: 1-Acetyl-6-aminoindoline (1.5 g, 8.5 mmol) was used to prepare 1-acetyl-6-iodoindoline (1.06 g, 43%), utilizing essentially the same procedure in example 1BI, Step A.

Step D: 1-Acetyl-6-iodoindoline (1.06 g, 3.7 mmol), NaOH (1.16 g, 29 mmol), EtOH (8 mL), and $H_2O$ (6 mL) were heated at 90° C. overnight. The reaction mixture was then partitioned between $H_2O$ and EtOAc. The organic layer was extracted into aqueous HCl. The aqueous layer was in turn basified with NaOH, and was extracted with EtOAc. The organic layer was dried and concentrated. Hexane trituration yielded 6-iodoindoline (577 mg, 64%) as a brown solid.

Step E: 1-Iodoindoline (600 mg, 2.45 mmol) was used to prepare 1-ethyl-6-methoxy-2',3'-dihydro-1H,1H'-[2,6']biindolyl-3-carbonitrile (535 mg, 67%), utilizing essentially the same procedure as in example 1Gd, Step B.

Step F: 1-Ethyl-6-methoxy-2',3'-dihydro-1H,1H'-[2,6']biindolyl-3-carbonitrile (30 mg, 0.095 mmol) was used to prepare 1'-Ethanesulfonyl-1-Ethyl-6-methoxy-2',3'-dihydro-1H,1H'-[2,6']biindolyl-3-carbonitrile (24 mg, 62%), utilizing the procedure in example 1Y.

The following compounds were prepared similarly as above: Compounds 752 and 754.

Example 1BM

Preparation of 5-acetyl-1-ethyl-6-methoxy-2-(4-nitro-phenyl)-1H-indole-3-carbonitrile (compound 844)

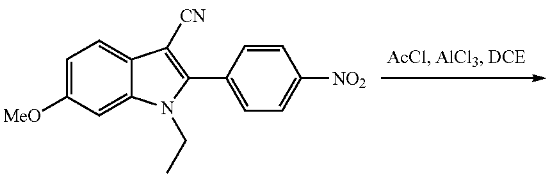

-continued

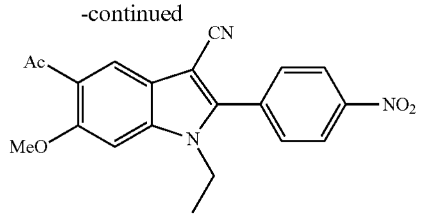

1-Ethyl-6-methoxy-2-(4-nitrophenyl)-1H-indole-3-carbonitrile (100 mg, 0.3 mmol), prepared by the method of example 1Gc was suspended in 1,2-dichloroethane (500 mL) at 0° C. Acetyl chloride (50 μL, 0.69 mmol) was added, followed by $AlCl_3$ (55 mg, 0.4 mmol) in one portion. This was stirred at 0° C. for 1 hour, at room temperature for 4 hours, and at 45° C. overnight. The reaction mixture was then partitioned between $CH_2Cl_2$ and $H_2O$. The organic layer was dried and concentrated. Purification by silica gel chromatography (195:5 $CH_2Cl_2$/EtOAc) yielded 5-acetyl-1-ethyl-6-methoxy-2-(4-nitro-phenyl)-1H-indole-3-carbonitrile (33 mg, 29%) as an orange solid.

Example 1BN

Preparation of 1-ethyl-6-methoxy-5-morpholin-4-ylmethyl-2-(4-nitro-phenyl)-1H-indole-3-carbonitrile (compound 845)

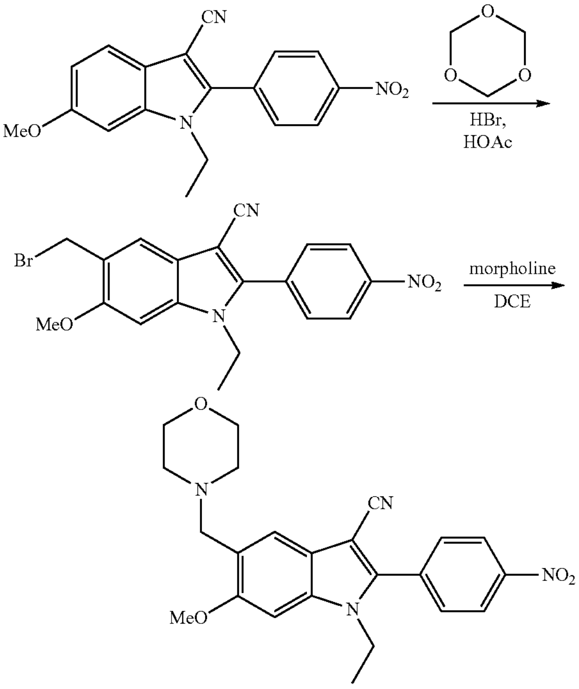

Step A: 1-Ethyl-6-methoxy-2-(4-nitrophenyl)-1H-indole-3-carbonitrile (100 mg, 0.3 mmol), prepared by the method of example 1Gc, was combined with 1,3,5-trioxane (64 mg, 0.71 mmol) and acetic acid (2.0 mL). 33% HBr in acetic acid (2.0 mL) was added. This was stirred at room temperature for 4 hours. The reaction mixture was then partitioned between $CH_2Cl_2$ and $H_2O$. The organic layer was washed with aqueous $NaHCO_3$, and was subsequently dried and concentrated. The crude material was carried through to the next step.

Step B: Crude 6-bromomethyl-1-ethyl-6-methoxy-2-(4-nitro-phenyl)-1H-indole-3-carbonitrile (0.3 mmol) was heated with morpholine (150 μL, 1.75 mmol) and DCE (1.0 mL) at 90° C. overnight. The reaction mixture was then partitioned between $H_2O$ and EtOAc. The organic layer was dried and concentrated. Purification by silica gel chromatography (50-100%, EtOAc/$CH_2Cl_2$), followed by trituration with 1/1 hexane/acetone yielded 1-ethyl-6-methoxy-5-morpholin-4-ylmethyl-2-(4-nitrophenyl)-1H-indole-3-carbonitrile (57 mg, 44% overall yield) as a yellow solid.

Example 1BO

2-[4-(1,1-dioxidoisothiazolidin-2-yl)phenyl]-1-cyclopropylmethyl-6-methoxy-1H-indole-3-carbonitrile (compound 716)

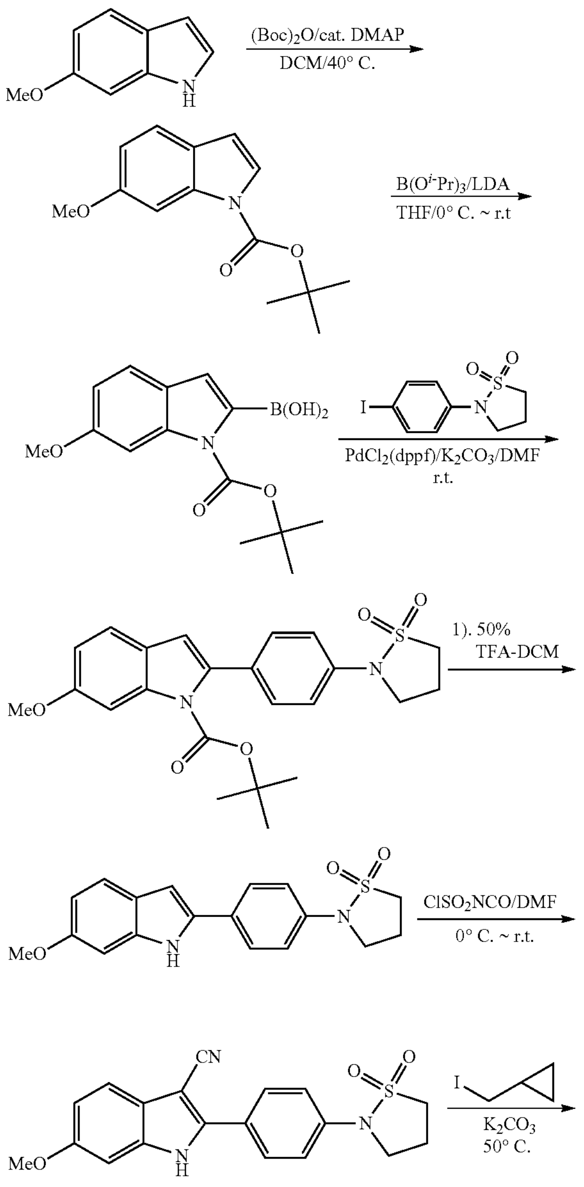

-continued

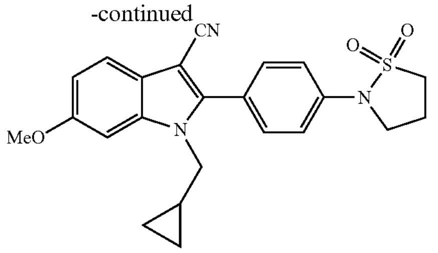

Step A: To a solution of 6-methoxyindole (5.88 g, 40.0 mmol) and di-tert-butyl dicarbonate (9.59 g, 44.0 mmol) in DCM (50 mL) was added, at 40° C. while stirring, DMAP (0.10 g). After stirring overnight, the mixture was washed sequentially with 0.1 N HCl, water and brine and dried over anhydrous $Na_2SO_4$. The solvent was evaporated and the residue was chromatographed (silica gel, EtOAc/hexanes, 1/7) to provide tert-butyl 6-methoxy-1H-indole-1-carboxylate (8.48 g, 86%).

Step B: The above Boc-indole (3.08 g, 12.5 mmol) and isopropylborate (4.83 mL, 21.9 mmol) were dissolved in anhydrous THF (20 mL) and the solution was cooled at 0° C. While stirring, LDA (12.5 mL, 1.5 M mono-THF complex in cyclohexane, 18.7 mmol) was added dropwise. The mixture was stirred at 0° C. for 15 min and then room temperature for 0.5 hr, followed by the addition of HCl (6 N, 3.0 mL, 18 mmol) in a ice-water bath. The organic solvent was removed in vacuo and the residue was suspended in $H_2O$ (100 mL) and acidified with HCl (6 N) to pH 4~5. The precipitate was collected via filtration and washed with water and hexanes and dried in air to provide 1-Boc-6-mehoxyindole-2-boronic acid (3.38 g, 93%).

Step C: To a solution of 4-iodoanilline (3.18 g, 14.5 mmol) in pyridine (15 mL) at 0° C., was added 3-chloropropanesulfonyl chloride (2.3 mL, 18.9 mmol). After the addition, the mixture was stirred for 2 hr at room temperature, and poured into ice-water (200 mL). The organic was separated and the aqueous layer was extracted with DCM (2×50 mL). The combined organics were washed with HCl (2 N, 2×15 mL), water (2×50 mL) and brine (20 mL) consecutively and dried over anhydrous $Na_2SO_4$. The solvent was then evaporated and the residue was chromatographed to furnish 3-chloro-N-(4-iodophenyl)propane-1-sulfonamide (4.68 g, 90%). The chlorosulfonamide obtained (3.47 g, 9.6 mmol) was then treated with $K_2CO_3$ (3.33 g, 24.1 mmol) in DMF (50 mL) at 50° C. for 2 hr. The mixture was poured into ice-water (300 mL) and the precipitate was collected and dried in air to provide essentially pure 2-(4-iodophenyl)isothiazolidine-1,1-dioxide (3.11 g, 100%).

Step D: To a mixture of 1-Boc-6-mehoxyindole-2-boronic acid prepared in step B above (0.36 g, 1.25 mmol), 2-(4-iodophenyl)isothiazolidine-1,1-dioxide (0.32 g, 1.0 mmol) and $PdCl_2$(dppf) (0.037 g, 0.05 mmol) in DMF (4.0 mL), was added aqueous $K_2CO_3$ solution (1.5 mL, 2.0 M, 3.0 mmol). The mixture was stirred at room temperature overnight and then poured into ice-water (100 mL). The precipitate was collected and washed with water and purified by flash column chromatography (silica gel, DCM/EtOAc, 9/1) to furnish 1-Boc-2-[4-(1,1-dioxidoisothiazolidin-2-yl)phenyl]-6-methoxy-1H-indole (0.43 g, 98%).

The following compound was made similarly: Compound 768

Step D: 1-Boc-2-[4-(1,1-dioxidoisothiazolidin-2-yl)phenyl]-6-methoxy-1H-indole (1.63 g, 3.7 mmol) was treated with TFA (25 mL) in DCM (25 mL) at room temperature for 4 hr. After the removal of the volatiles, the residue was carefully stirred with saturated $NaHCO_3$ for 0.5 hr. The precipitate was collected via filtration and washed with water thoroughly and dried to provide essentially pure 1-H-2-[4-(1,1-dioxidoisothiazolidin-2-yl)phenyl]-6-methoxyindole (1.17 g, 92%).

Step E: At 0° C., 1-H-2-[4-(1,1-dioxidoisothiazolidin-2-yl)phenyl]-6-methoxyindole (0.95 g, 2.8 mmol) was dissolved in DMF (10 mL) and treated with chlorosulfonyl isocyanate (0.36 mL, 4.2 mmol). The mixture was then stirred at room temperature overnight and poured into ice-water (150 mL) then stirred for 0.5 hr. The precipitate was collected via filtration and washed thoroughly with water and dried in air to furnish 1-H-2-[4-(1,1-dioxidoisothiazolidin-2-yl)phenyl]-6-methoxyindole-3-carbonitrile (0.89 g, 87%).

The following compound was prepared in the same fashion as described above: Compound 829

Step F: To a solution of 1-H-2-[4-(1,1-dioxidoisothiazolidin-2-yl)phenyl]-6-methoxyindole-3-carbonitrile (73 mg, 0.2 mmol) and $K_2CO_3$ (69 mg, 0.5 mmol) in DMF (3.0 mL) was added cyclopropylmethyl iodide (0.029 mL, 0.3 mmol). The mixture was stirred at 50° C. overnight and poured into ice-water (10 mL). The precipitate was collected via filtration, washed with water and purified by column chromatography to provide 2-[4-(1,1-dioxidoisothiazolidin-2-yl)phenyl]-6-methoxy-1-cyclopropylmethylindole-3-carbonitrile, compound 716 (73 mg, 87%).

The following compounds were prepared in the same fashion as described above: Compounds 717, 718, 719, 782, 783, 784.

Example 1BP

Preparation of 2-[4-(1,1'-dioxo-1λ$^6$-isothiazolidin-2-yl)-6-methoxy-3-oxazol-5-yl-1-propyl-1H-indole (compound 805)

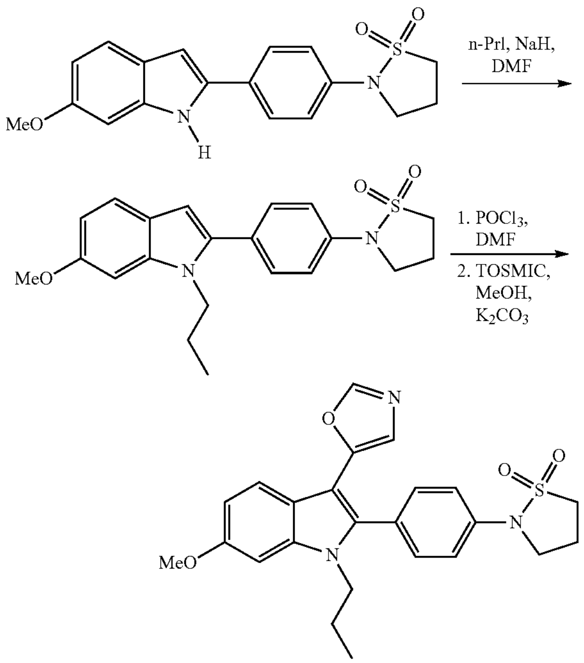

Step A: 2-[4-(1,1'-Dioxo-1λ$^6$-isothiazolidin-2-yl)-6-methoxy-indole (900 mg, 2.62 mmol), prepared in example 1BO, step D was used to prepare 2-[4-(1,1'-dioxo-1λ$^6$-isothiazolidin-2-yl)-6-methoxy-1-propyl-1H-indole (608 mg, 60%), utilizing essentially the same procedure as example 1A, Step B.

Step B: 2-[4-(1,1'-Dioxo-1λ$^6$-isothiazolidin-2-yl)-6-methoxy-1-propyl-1H-indole (50 mg, 0.13 mmol) was used to prepare 2-[4-(1,1'-dioxo-1λ$^6$-isothiazolidin-2-yl)-6-methoxy-3-oxazol-5-yl-1-propyl-1H-indole (9 mg, 15% overall yield) according to the protocol in example 1P.

Example BQ

Preparation of 2-[4-(cyclopropylsulfonyl)piperazin-1-yl]-1-ethyl-6-(trifluoromethyl)-1H-indole-3-carbonitrile (compound 842)

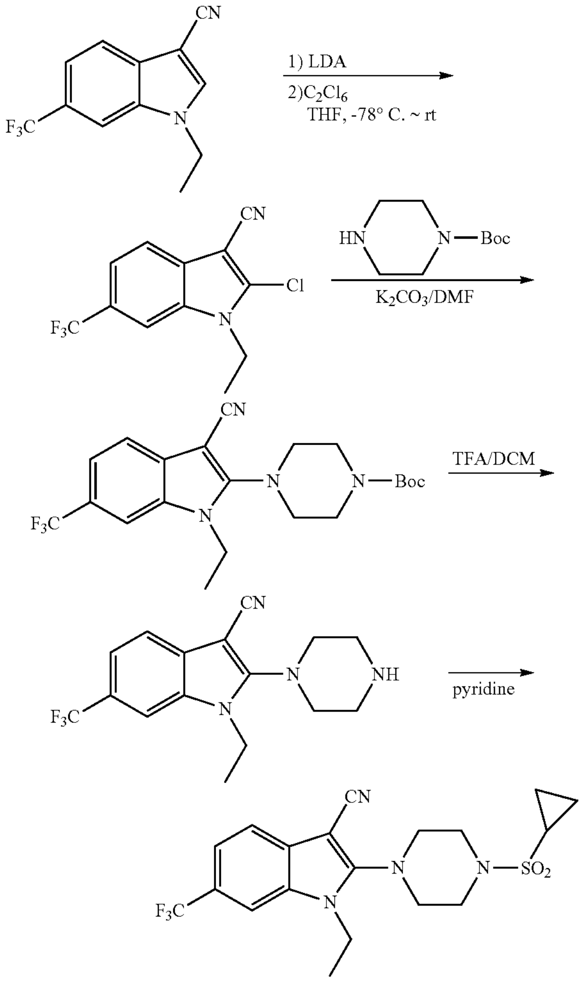

Step A: To a solution of 1-ethyl-6-trifluoromethylindole-3-carbonitrile (2.54 g, 10.0 mmol), prepared by the method of procedure 1A, in anhydrous THF (20.0 mL), at −78° C. was added LDA (8.3 mL, 1.5 M mono-THF in cyclohexane, 12.5 mmol) dropwise. The mixture was continued for 0.5 hr after the addition, followed by the addition of hexachloroethane and the mixture was then brought to room temperature slowly and stirred for 0.5 hr. The solvent was then evaporated and the residue was treated with water. The organics were extracted with dichloromethane, washed with water and brine and dried over anhydrous $Na_2SO_4$. The crude product obtained after the removal of the solvent was chromatographed (silica gel, dichloromethane/hexanes, 3 /2) to provide 2-chloro-1-ethyl-6-(trifluoromethyl)-1H-indole-3-carbonitrile (1.75 g, 64%).

Step B: The chloroindole obtained above (0.27 g, 1.0 mmol), $K_2CO_3$ (0.35 g, 2.5 mmol) and N-Boc-piperazine (0.28 g, 1.5 mmol) were stirred at 70° C. in DMF (5.0 mL) for 3 days and then poured into water (50 mL). The precipitate was collected via filtration and washed with water. Chromatography of this crude product (silica gel, dichloromethane/ethyl acetate, 9/1) provided 4-(3-cyano-1-ethyl-6-trifluoromethyl-1H-indol-2-yl)-piperazine-1-carboxylic acid tert-butyl ester, compound 785 (0.30 g, 71%).

The following compound was prepared in the same fashion as described above, by using other amines: Compounds 514, 785, 786.

Step C: 4-(3-cyano-1-ethyl-6-trifluoromethyl-1H-indol-2-yl)-piperazine-1-carboxylic acid tert-butyl ester (0.26 g, 6.1 mmol) was treated with TFA (5 mL) in dichloromethane (5 mL) for 1 hr at room temperature. After the removal of the volatiles, the residue was treated with saturated $NaHCO_3$ and the precipitate was collected via filtration, washed with water thoroughly and dried in air to furnish essentially pure 1-ethyl-2-piperazin-1-yl-6-(trifluoromethyl)-1H-indole-3-carbonitrile (0.20 g, 100%).

Step D: To a solution of 1-ethyl-2-piperazin-1-yl-6-(trifluoromethyl)-1H-indole-3-carbonitrile (32 mg, 0.1 mmol), pyridine (0.1 mL) in dichloromethaene (1.0 mL) was added cyclopropanesulfonyl chloride (28 mg, 0.2 mmol) and the mixture was stirred at room temperature overnight. This was then diluted with dichloromethane (5 mL), washed with HCl (2 N, 2x2 mL), water (2x5 mL) and brine (5 mL) and chromatographed over silica gel (dichloromethane/ethyl acetate, 9/1) to provide 2-[4-(cyclopropylsulfonyl)piperazin-1-yl]-1-ethyl-6-(trifluoromethyl)-1H-indole-3-carbonitrile, compound 842 (30 mg, 70%).

The following compounds were prepared in the same fashion as described above, using corresponding sulfonyl chlorides: Compounds 841, 843.

Example 1BR

Ethanesulfonic acid [3-cyano-2-(4-ethoxyphenyl)-1-ethyl-1H-indol-6-yl]-amide (compound 835)

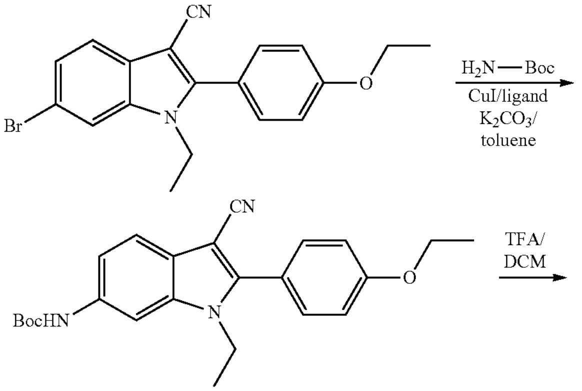

-continued

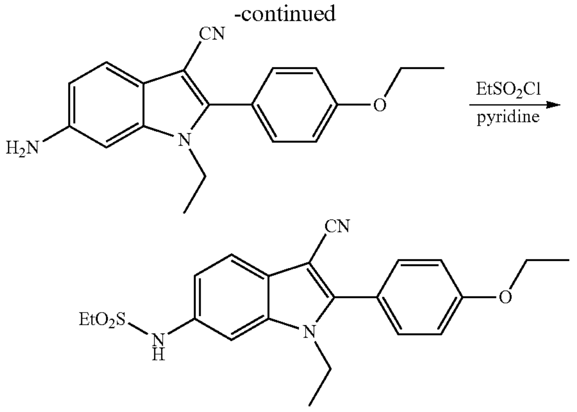

Step A: 6-Bromo-2-(4-ethoxyphenyl)-1-ethyl-1H-indole-3-carbonitrile (0.74 g, 2.0 mmol), compound 831, prepared from 6-bromoindole as described in example 1Gb, was mixed with $K_2CO_3$ (0.55 g, 4.0 mmol), CuI (0.02 g, 0.1 mmol), tert-butyl carbamate (0.35 g, 3.0 mmol), N,N'-dimethylcyclohexane-1,2-diamine ligand (0.028 g, 0.2 mmol) and anhydrous toluene (5.0 mL) in a sealed tube. The reaction system was flushed with nitrogen and then stirred at 110° C. overnight. After cooling, the solvent was replaced with dichloromethane and chromatographed (silica gel, dichloromethane) to provide [3-cyano-2-(4-ethoxy-phenyl)-1-ethyl-1H-indol-6-yl]-carbamic acid tert-butyl ester (0.68 g, 84%), compound 832.

Step B: Compound 832 prepared in step A above (0.63 g, 1.56 mmol) was treated with TFA/DCM (7.5 mL/7.5 mL) at room temperature for 2 hr, and the volatiles were removed in vacuum. The residue was treated with saturated $NaHCO_3$ and the precipitate was collected via filtration and washed thoroughly with water, dried in air to provide 6-amino-2-(4-ethoxyphenyl)-1-ethyl-1H-indole-3-carbonitrile (0.45 g, 96%), compound 833.

Step C: The above amine (31 mg, 0.1 mmol) was treated with ethanesulfonyl chloride (19 mg, 0.15 mmol) in pyridine (1.0 mL) at room temperature overnight to provide, after purification using column chromatography, ethanesulfonic acid [3-cyano-2-(4-ethoxy-phenyl)-1-ethyl-1H-indol-6-yl]-amide (83%), compound 835.

The following compound was prepared in the same fashion as described above: Compounds 830, 834, 836 and 837.

Example 1BS

Preparation of [3-cyano-2-(4-ethoxyphenyl)-1-ethyl-1H-indol-6-yl]-carbamic acid ethyl ester (compound 838)

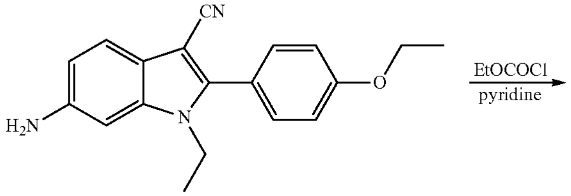

-continued

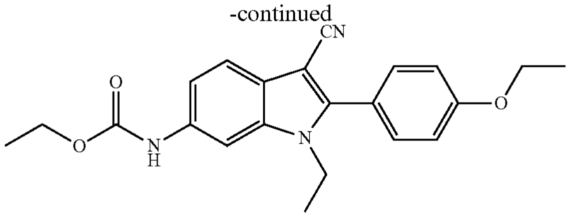

6-Amino-2-(4-ethoxyphenyl)-1-ethyl-1H-indole-3-carbonitrile (31 mg, 0.1 mmol), compound 833, prepared in example 1BR, step B was treated with ethyl chloroformate (16 mg, 0.15 mmol) in pyridine (1.0 mL) at room temperature overnight to furnish, after purification using column chromatography [3-cyano-2-(4-ethoxyphenyl)-1-ethyl-1H-indol-6-yl]-carbamic acid ethyl ester (30 mg, 79%).

Example 1BT

Preparation of 1-[3-cyano-2-(4-ethoxyphenyl)-1-ethyl-1H-indol-6-yl]-3-ethyl-urea (compound 839)

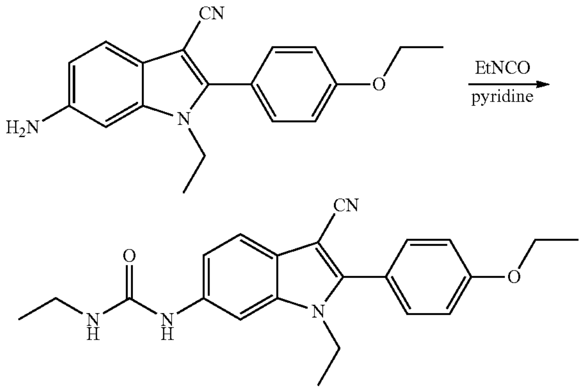

6-Amino-2-(4-ethoxyphenyl)-1-ethyl-1H-indole-3-carbonitrile (31 mg, 0.1 mmol) was treated with ethyl isocyanate (14 mg, 0.2 mmol) in dichloromethane (1.0 mL) at 40° C. overnight. The precipitate was collected via filtration, washed with dichloromethane an dried in air to furnish, 1-[3-cyano-2-(4-ethoxy-phenyl)-1-ethyl-1H-indol-6-yl]-3-ethyl-urea (36 mg, 95%).

Example 1BU

Preparation of 1-(2-chloroethyl)-3-[4-(3-cyano-1-ethyl-6-methoxy-1H-indol-2-yl)-phenyl]-urea (compound 442)

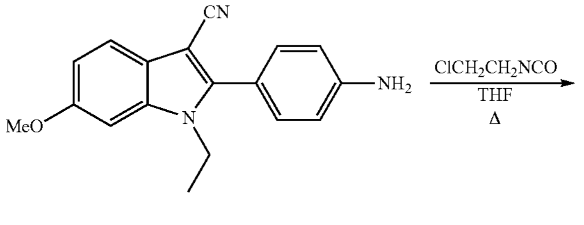

-continued

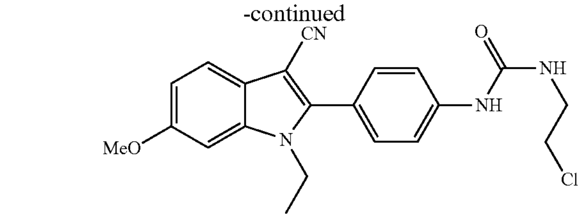

To solution of 2-(4-aminophenyl)-1-ethyl-6-methoxy-1H-indole-3-carbonitrile (50 mg, 0.172 mmole) in THF (2 mL) was added 2-chloroethyl isocyanate (22 uL, 0.258 mmole) at room temperature. After stirring overnight at reflux, the reaction mixture was concentrated in vacuo and the residue was diluted with ethyl acetate. The resulting semi-solid was triturated with hexane and the precipitate collected was collected by filtration and washed well with 50% ethyl acetate in hexane and dried in vacuo to afford (62 mg, 91%) of 1-(2-chloroethyl)-3-[4-(3-cyano-1-ethyl-6-methoxy-1H-indol-2-yl)-phenyl]-urea.

Utilizing essentially the same procedure, the following compounds were prepared: Compounds 295, 362, 395, 396, 397, 398, 399, 400, 401, 402, 403, 404, 405, 406, 407, 443, 444, 445, 446, 511, 512, 513, 600, 620, 626, 627, 628, 679, 680, 681, 740, 741, 742, 743, 748, 749, 750, 751, 774, 817, 818, 846, 847, 848.

Example 1BV

Preparation of 1-ethyl-6-methoxy-2-[4-(2-oxo-imidazolidin-1-yl)-phenyl]-1H-indole-3-carbonitrile (compound 771)

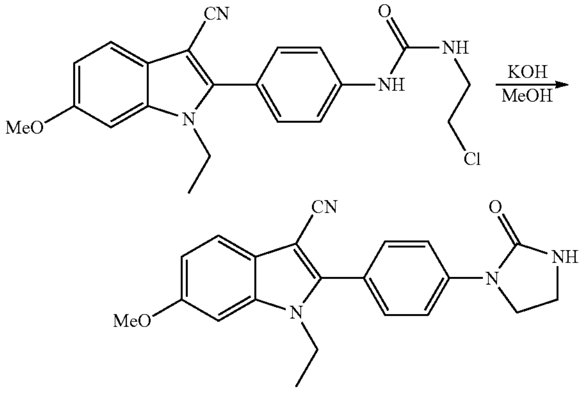

To a solution of 1-(2-chloroethyl)-3-[4-(3-cyano-1-ethyl-6-methoxy-1H-indol-2-yl)-phenyl]-urea (100 mg, 0.252 mmol) in MeOH (10 mL) was added aqueous 1M KOH (504 uL) and then stirred at 49° C. for 24 h. The solvents were removed under reduced pressure. The residue was diluted with ethyl acetate and then washed with water. The organic layer was dried over anhydrous $MgSO_4$, filtered and concentrated under reduced pressure. The residue was diluted with ethyl acetate and then triturated with hexane and the precipitate collected by filtration and washed well with 50% ethyl acetate in hexane and dried in vacuo to afford 1-ethyl-6-methoxy-2-[4-(2-oxo-imidazolidin-1-yl)-phenyl]-1H-indole-3-carbonitrile (56 mg, 62%).

Using essentially the same procedure, the following compounds were prepared: Compounds 770, 778

Example 1BW

Preparation of 1-ethyl-6-isopropoxy-2-[4-(2-oxo-oxazolidin-3-yl)-phenyl]-1H-indole-3-carbonitrile (compound 638)

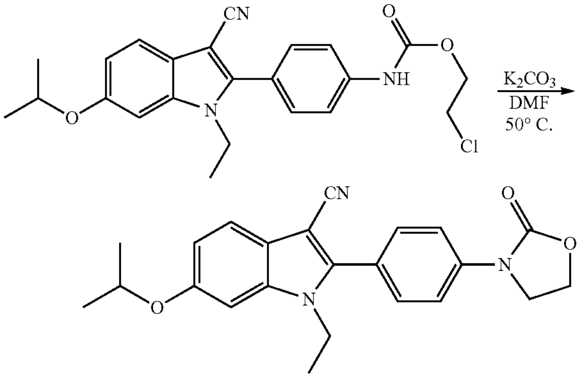

To a solution of [4-(3-cyano-1-ethyl-6-isopropoxy-1H-indol-2-yl)-phenyl]-carbamic acid 2-chloro-ethyl ester (30 mg, 0.07 mmol) in DMF (1 mL) was added aqueous $K_2CO_3$ (10 mg) and then stirred at 50° C. for 18 h. The reaction mixture was poured into cold water and the precipitate collected by filtration and washed with hexane and dried in vacuo to afford the title compound (21 mg, 81%).

The following compounds were made in similar fashion: Compounds 820, 821, 863, 864.

Example 1BX

Preparation of {3-[3-cyano-1-ethyl-6-(3-pyrrolidin-1-yl-propoxy)-1H-indol-2-yl]-phenyl}-carbamic acid ethyl ester (compound 530)

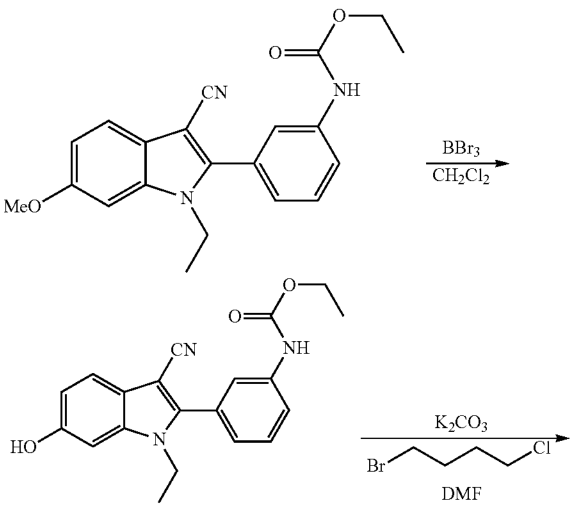

-continued

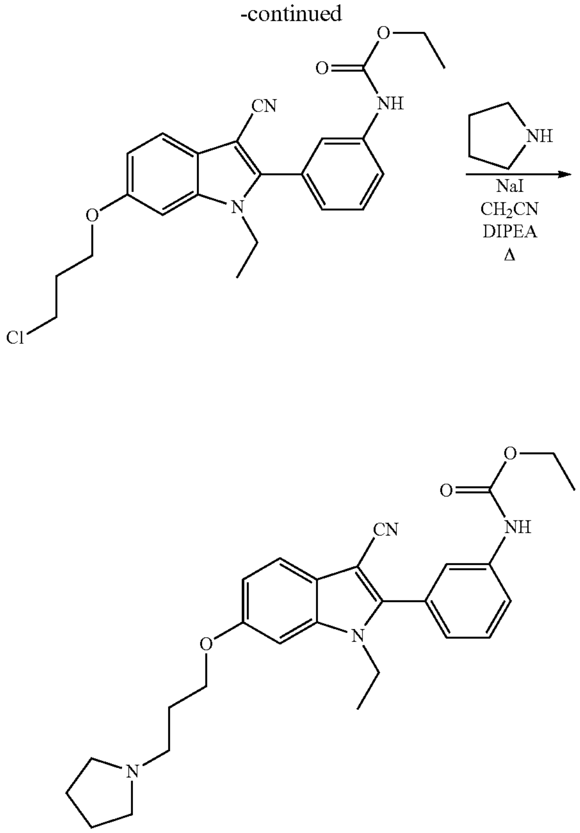

Step A: To a solution of [3-(3-cyano-1-ethyl-6-methoxy-1H-indol-2-yl)-phenyl]-carbamic acid ethyl ester (1.65 g, 4.37 mmole) in DCM (20 mL) was added 1M $BBr_3$ in DCM (13.12 mL) over a period of 20 min. The reaction mixture was stirred further 1 h at room temperature and then the solvents were removed under reduced pressure. The residue was dissolved in MeOH and then poured into cold water. The precipitate was collected by filtration and washed with hexane and dried in vacuo to afford [3-(3-cyano-1-ethyl-6-hydroxy-1H-indol-2-yl)-phenyl]-carbamic acid ethyl ester (1.5 g, 98%).

Step B: To a solution of [3-(3-cyano-1-ethyl-6-hydroxy-1H-indol-2-yl)-phenyl]-carbamic acid ethyl ester (1.2 g, 2.91 mmol) in DMF (10 mL) was added $K_2CO_3$ (538 mg, 3.9 mmole) and 3-bromo-1-chloroproane (383 uL, 3.9 mmole) and the reaction was stirred for overnight at 50° C. The reaction mixture was then poured into cold water and the precipitate was collected by filtration and washed with hexane and dried in vacuo to afford 1.1 g, 89% of the desired product.

Step C: To a solution of {3-[3-cyano-1-ethyl-6-(3-pyrrolidin-1-yl-propoxy)-1H-indol-2-yl]-phenyl}-carbamic acid ethyl ester (50 mg, 0.12 mmole) in $CH_3CN$ (2 mL) was added DIEA (31 uL, 0.18 mmol), sodium iodide (20 mg, 0.132 mmol) and pyrrolidine (30 uL, 0.36 mmole). The resulting mixture was stirred at reflux temperature for overnight. The solvent was evaporated and the residue was diluted with ethyl acetate and then triturated with hexane and the precipitate collected by filtration and washed well with 50% ethyl acetate in hexane and dried in vacuo to afford 1-ethyl-6-isopropoxy-2-[4-(2-oxo-oxazolidin-3-yl)-phenyl]-1H-indole-3-carbonitrile, compound 638 (46 mg, 85%).

The following compounds were made in similar fashion following steps A-C, above: Compounds 441, 447, 491, 492, 493, 504, 525, 526, 527, 528, 529, 531, 532, 533, 534, 535, 536, 537, 538, 539

Example 1BY

Preparation of [3-(3-cyano-1-ethyl-6-methoxy-1H-indol-2-yl)-phenyl]-thiourea (Compound 767)

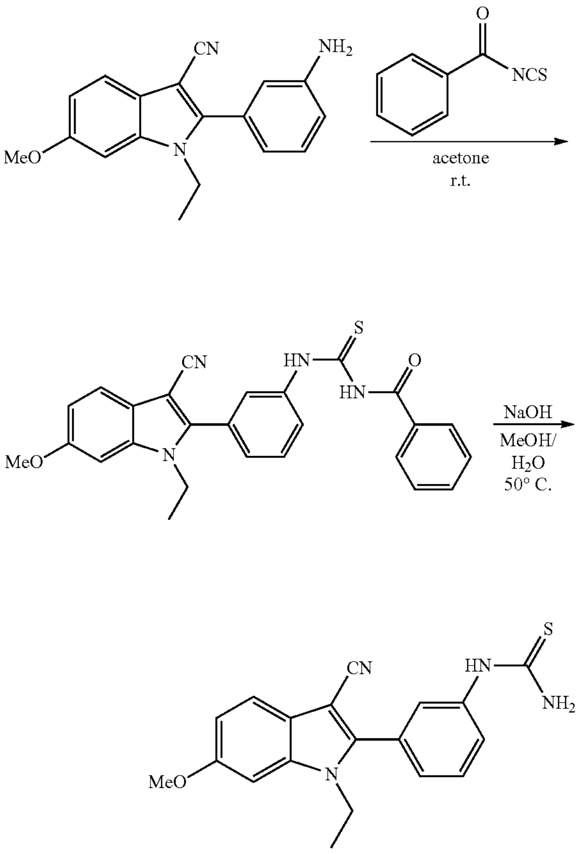

Step A: The starting material 2-(3-amino-phenyl)-1-ethyl-6-methoxy-1H-indole-3-carbonitrile (187 mg, 0.642 mmol) was dissolved in anhydrous acetone (3.0 mL). Benzoyl isothiocyanate (107 mg, 0.656 mmol) was added to the solution at room temperature and the mixture was stirred for 17 h during which time a precipitate had formed. The precipitate was filtered, washed with acetone and dried to give 264 mg of 1-benzoyl-3-[3-(3-cyano-1-ethyl-6-methoxy-1H-indol-2-yl)-phenyl]-thiourea (90% yield) as a light yellow solid.

Step B: A suspension of 1-benzoyl-3-[3-(3-cyano-1-ethyl-6-methoxy-1H-indol-2-yl)-phenyl]-thiourea (241 mg, 0.530 mmol) in methyl alcohol (2.0 ml) and water (0.5 mL) was stirred at room temperature as sodium hydroxide (31 mg, 0.78 mmol) was added. The reaction mixture was heated to 50° C. for 17 h. The reaction mixture was concentrated to remove methyl alcohol. Water was added to the mixture and the solid was filtered, washed with water and dried to give 179 mg of [3-(3-cyano-1-ethyl-6-methoxy-1H-indol-2-yl)-phenyl]-thiourea, compound 767 (96% yield) as a white solid.

Example 1BZ

Preparation of 1-ethyl-6-methoxy-2-[4-(2-phenylquinazolin-4-ylamino)-phenyl]-1H-indole-3-carbonitrile (Compound 458)

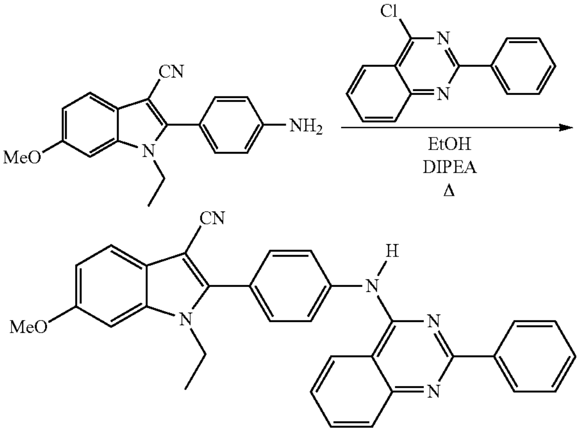

A solution of 2-(4-aminophenyl)-1-ethyl-6-methoxy-1H-indole-3-carbonitrile (100 mg, 0.343 mmol), 4-chloro-2-phenyl-quinazoline (83 mg, 0.34 mmol) and diisopropylethylamine (0.10 mL, 0.57 mmol) in absolute ethanol (3 mL) was heated to reflux overnight. The solution was cooled and evaporated, and the residue taken up in ethyl acetate (50 mL). This was washed with water and saturated brine (50 mL each), then dried over anhydrous sodium sulfate, filtered and evaporated. The resulting solid was triturated with ether, collected by filtration and dried under vacuum to afford 1-ethyl-6-methoxy-2-[4-(2-phenylquinazolin-4-ylamino)-phenyl]-1H-indole-3-carbonitrile (139 mg, 0.280 mmol, 82%).

Example 1CA

Preparation of diethyl [4-(3-cyano-6-ethoxy-1-ethyl-1H-indol-2-yl)-phenyl]-phosphoramidate (compound 772)

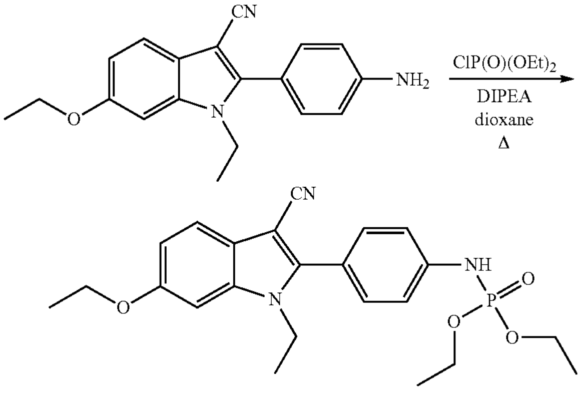

A solution of 2-(4-aminophenyl)-6-ethoxy-1-ethyl-1H-indole-3-carbonitrile (148 mg, 0.484 mmol), diethyl chlorophosphate (0.086 mL, 0.58 mmol) and diisopropylethylamine (0.10 mL, 0.57 mmol) in 1,4-dioxane (5 mL) was stirred at ambient temperature for 12 hours, then heated to 80° C. for an additional 24 hours. The solution was cooled and poured into 50 mL of ethyl acetate. This was washed with water and saturated brine (50 mL each), then dried over anhydrous magnesium sulfate, filtered and evaporated. The residual material was separated by flash chromatography (eluting 2/1 ethyl acetate/hexane on silica gel 60) to afford diethyl [4-(3-cyano-6-ethoxy-1-ethyl-1H-indol-2-yl)-phenyl]-phosphoramidate (108 mg, 0.245 mmol, 51%) as a white powder after evaporation.

Example 1CB

Preparation of 1-ethyl-6-methoxy-2-[4-(5-methyl-1,1-dioxo-1λ$^6$-[1,2,5]thiadiazolidin-2-yl)-phenyl]-1H-indole-3-carbonitrile (compound 726)

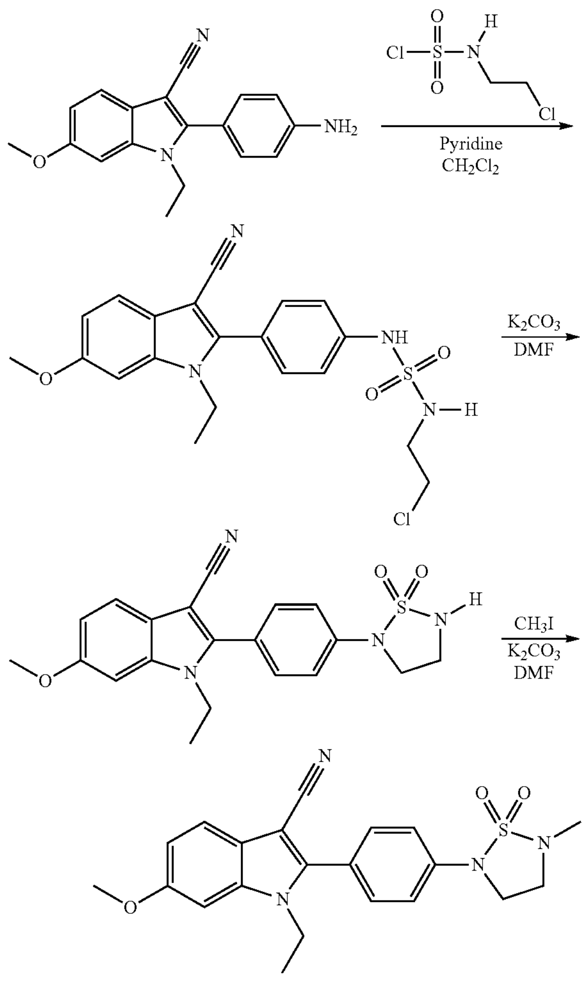

Step A: To a solution of 2-(4-aminophenyl)-1-ethyl-6-methoxy-1H-indole-3-carbonitrile (202 mg, 0.693 mmol) in pyridine (2.0 mL) was added the N-β-(chloroethylamino) sulfonyl chloride (222 mg, 1.39 mmol). The mixture was stirred at room temperature for 17 h then water (12.0 mL) was added and the mixture was extracted with ethyl acetate (3×2 mL). The extract was washed with 10% aqueous HCl (2×2 mL), water (2×2 mL), dried over $MgSO_4$, filtered and concentrated on a rotary evaporator. The crude product was purified by flash chromatography (0-5%, ethyl acetate/methylene chloride) to give 217 mg of N-(2-chloro-ethyl)-N'-[4-(3-cyano-1-ethyl-6-methoxy-1H-indol-2-yl)phenyl] sulfamide, compound 724, as a tan solid (75% yield).

In similar fashion the following compounds were prepared: Compounds 540, 541, 542, 574, 576, 704

Step B: To a solution of N-(2-chloro-ethyl)-N'-[4-(3-cyano-1-ethyl-6-methoxy-1H-indol-2-yl)phenyl] sulfamide (100 mg, 0.241 mmol) in anhydrous DMF (1.25 mL), was added potassium carbonate (71.0 mg, 0.514 mmol). The mixture was stirred at room temperature for 17 h, then diluted with water (7.5 mL). The reaction mixture was extracted with ethyl acetate (3×2 mL) and the extract was washed with water (2×2 mL), dried over $MgSO_4$ and concentrated to give 2-[4-(1,1-dioxo-1λ$^6$-[1,2,5]thiadiazolidin-2-yl)phenyl]-1-ethyl-6-methoxy-1H-indole-3-carbonitrile, compound 725, as a white solid (84 mg, 88% yield).

In similar fashion the following compound was prepared: Compound: 705

Step C: To a solution of 2-[4-(1,1-dioxo-1λ$^6$-[1,2,5]thiadiazolidin-2-yl)phenyl]-1-ethyl-6-methoxy-1H-indole-3-carbonitrile (34 mg, 0.086 mmol) in anhydrous DMF (1.0 mL) was added potassium carbonate (25 mg, 0.18 mmol) and iodomethane (20.4 mg, 0.144 mmol). The mixture was stirred at room temperature for 2 h. and then diluted with water (6.0 mL) to give a precipitate. The precipitate was filtered, washed with water and dried to give 1-ethyl-6-methoxy-2-[4-(5-methyl-1,1-dioxo-1λ$^6$-[1,2,5]thiadiazolidin-2-yl)-phenyl]-1H-indole-3-carbonitrile, compound 726, as a white solid (35 mg, 98% yield).

In similar fashion the following compound was prepared: Compound 727.

Example 2

Screening of Low Molecular Weight Compounds Using a Cell-Based HCV IRES Monocistronic Translation Assay Chemical libraries are screened using a cell-based monocistronic HCV IRES-regulated translation assay designed to closely mimic natural HCV mRNA translation and then compound analogs are made based on hits in the chemical libraries and screened as well. A DNA construct is prepared, termed pHCVIRESmono, in which HCV IRES sequences (HCV 2b, nucleotides 18-347) are inserted between a promoter and the firefly luciferase (Fluc) reporter gene. A stably transfected HepG 2 (hepatoblastoma) cell line (termed HepGmono-4) or a Huh7 cell line (termed Huhmono 7), or a Hela-cell line (termed Helamono), are established by transfection with the pHCVIRESmono DNA by selecting for resistance to hygromycin.

Example 3

Determination of Selectivity for HCV IRES-Regulated Translation Using the Cell-Based Cap-Dependent Translation Assays Since translation assays are used to screen HCV IRES inhibitors, the selected hits may specifically act on HCV IRES-driven translation or may modulate general protein synthesis in mammalian cells. The compounds that act on general translation will most likely have significant toxicity.

To address this possibility, various cell-based cap-dependent translation assays are established for the further evaluation of all selected compounds. Plasmid DNAs containing 130 nucleotides of vector sequence 5' to Fluc are constructed. This construct is referred to herein as pLuc. A stable cell line is established in cap-dependent translation assays using 293T cells (a human embryonic kidney cell line). HepGmono-4 and pLuc are treated with compound for 20 hours and activity is determined by quantifying the Fluc signal. A five-fold selectivity between the HCV IRES and cap-dependent translation is considered to be desirable. For example, using these cell-based cap-dependent translation assays, Applicants identified compounds that showed $IC_{50}$ values that were at least 5-fold greater in the cap-dependent translation assays than in the HCV IRES translation assay. FIG. 1 shows an example of a hit that was selective against HCV IRES-regulated translation over cap-dependent pLuc translation. Importantly, the compound had the same level of activity in an HCV IRES monocistronic 293T cell line as in HepGmono-4 (data not shown). It is thus unlikely that the selectivity of the compounds between HepGmono-4 (HepG 2) and the cap-dependent translations (293T) is due to the different cell types used.

Additionally, western blotting assays are used to further demonstrate that the compounds selectively inhibit HCV IRES-driven translation. Both HepGmono-4 and pLuc cells are treated with the compounds as described above, following treatment with the test compounds for 20 hours, cells are collected and lysed in Laminin buffer containing 0.5% SDS. Proteins are separated on a 10% SDS-PAGE, then transferred onto a nitrocellulose membrane, and blotted using antibodies against Fluc (RDI) and β-actin (Oncogene). For example, some of the compounds of the present invention were tested in this manner and as expected, the compounds that selectively inhibited HCV IRES-driven translation in assays using Fluc signal as an end point showed comparable reductions of the luciferase reporter protein levels in HepGmono-4 cells and were relatively inactive against pLuc in the Western blot (data not shown). Importantly, these compounds did not inhibit the expression of endogenous β-actin, the translation of which is cap-dependent in both cell lines. Consistently, compounds that did not show selectivity in the translation assays inhibited protein accumulation in both the HCV IRES and cap-dependent translation assays (data not shown). As expected, the general protein translation inhibitor puromycin also inhibited both the HCV IRES-driven and cap-dependent protein production (data not shown). Therefore, the Western blot results confirm that the compounds of the present invention selectively inhibit HCV IRES-driven translation.

Testing conditions for these cell lines are optimized and the effects of mRNA level on activity of the compounds are controlled by quantitating Fluc mRNA levels by RT real-time PCR. For example, some of the compounds of the present invention were tested in this manner, and no significant differences in Fluc mRNA levels were observed between the HepGmono-4, or the Helamono cells, or the Huhmono cells, and cap-dependent translation cell lines used (data not shown).

Example 4

Evaluation of the Selectivity for HCV IRES-Driven Translation Using Cellular IRES-Mediated Translation Assays A number of human mRNAs have been shown to harbor IRES elements (18, 19, 39, 44, 45, 91, 126, 130). Although the primary sequences and secondary structures of the HCV IRES are different from those of cellular IRESs, an important test for selectivity is to determine whether the selected compounds are active against cellular IRESs. The VEGF IRES has poor initiation activity in in vitro assays, but demonstrates substantial activity in cell-based translation assays (18, 45). For example, some of the compounds of the present invention were tested and all of the compounds that had good selectivity with respect to cap-dependent translation exhibited at least 5-fold higher $IC_{50}$ values against the VEGF IRES than against the HCV IRES (data not shown). These data indicate that the selected compounds have selectivity against viral IRES. In addition to having different structures, the VEGF IRES also have different interactions with non-canonical cellular translation factors. These differences may contribute to the selectivity of the HCV IRES inhibitors that we have identified.

Example 5

Evaluation of Cytotoxicity

Effects on cell proliferation are a critical issue for any drug discovery effort. Therefore, a cell proliferation/cytotoxicity assay is used to eliminate any compounds that affect mammalian cell growth. The effects of the selected hits on cell proliferation are tested in human cell lines 293 T and Huh7 (a human hepatoblastoma cell line). Cells are grown in Dulbecco's modified Eagle's medium supplemented with 10% fetal bovine serum, L-glutamine, penicillin, and streptomycin. Cells in log phase are treated with test compounds for three days, with 250 μM being the highest concentration of test compound used. The effect of the compounds on cell proliferation is assessed by using the CellTiter 96 AQueous One Solution Cell Proliferation Assay (Promega, Madison, Wis.). Compounds that have at least 5-fold higher $CC_{50}$ values relative to $IC_{50}$ values in HepGmono-4 are considered to have a sufficient window between activity and cytotoxicity and, hence, are selected for further evaluation. For example, some of the compounds of the present invention were tested in this manner, and importantly, all compounds that had good selectivity with respect to cap-dependent translation also demonstrated a greater than 5-fold ratio of $CC_{50}$ to $IC_{50}$ values.

Example 6

Evaluation of the Efficacy of the Compounds in the HCV Replicon System

The lack of reliable and readily accessible cell-culture and small animal models permissive for HCV replication has limited the development of new anti-HCV agents. Self-replicating subgenomic HCV systems, termed HCV replicons, have recently been described and have been widely used to assess the efficacy of anti-HCV inhibitors (8, 70, 104). Interferon (IFN) α and inhibitors of the HCV protease and polymerase have been reported to be active in the HCV replicon system (8, 17, 32, 68, 69, 117).

HCV replicons that include bicistronic and monocistronic systems are identified and assays for testing the HCV IRES inhibitors are established. In the bicistronic replicons, the HCV IRES directs the expression of the selective marker (Neo and/or a Fluc reporter), and the EMCV IRES mediates the expression of viral non-structural proteins. In the monocistronic replicon, the HCV IRES directly mediates viral protein synthesis. The HCV IRES inhibitors are analyzed in the bicistronic replicon by quantitating the Fluc reporter signal. Replicon-containing cells are cultured with the compounds of the invention for 2 days. Interferon (IFN) α is used as a positive control. For example, the compounds of the present invention were tested in this manner, and the experiments showed that compounds that selectively inhibited HCV IRES-mediated translation inhibited Fluc expression in the bicistronic replicon.

In the following table (Table 1),

* =Replicon or HCV-PV IC50>2μM

** =Replicon or HCV-PV IC50 between 0.5 μM and 2 μM

*** =Replicon or HCV-PV IC50<0.5 μM

Replicon IC50 values are determined by firefiy luciferase signal.

HCV-PV IC50 values are determined by viral RNA reduction.

TABLE 1

| Compound Number | Melting Point (° C.) | Mass Spec [M+H] | HCV-PV IC50 μM | Replicon IC5Os μM | NMR Data |
|---|---|---|---|---|---|
| 1 | | | | * | |
| 2 | | 311.1 | | * | |
| 3 | | 356.0 | | * | |
| 4 | | 279.2 | | * | |
| 5 | 64-66 | 201.3 | | * | |
| 6 | | 201.1 | | * | |
| 7 | 304-305 | 251.1 | | ** | $^1$H NMR (300 MHz, DMSO-$d_6$): δ 8.23 (1H, d, J=2.1 Hz), 8.08 (1H, dd, J=8.8, 2.1 Hz), 7.74 (1H, d, J=8.8 Hz), 7.55 (2H, t, J=2.2 Hz), 6.51 (2H, t, J=2.2 Hz). |
| 8 | | 277.3 | | ** | |
| 9 | 61-63 | 215.2 | | * | |
| 10 | 69-71 | 229.2 | | * | |
| 11 | 78-80 | 243.2 | | * | |
| 12 | 94-97 | 277.2 | | ** | |
| 13 | 161-164 | 265.3 | | * | |
| 14 | 206-207 | 415.2 | | * | $^1$H NMR (300 MHz, $CDCl_3$): δ 8.09 (1H, dd, J=8.8, 1.7 Hz), 7.75 (1H, d, J=1.7 Hz), 7.49 (1H, d, J=8.8 Hz),Hz 7.40 (2H, d, J=8.8 Hz), 7.22 (2H, d, J=8.8 Hz), 7.17 (2H, d, J=8.8 Hz), 6.93 (2H, d, J=8.8 Hz), 6.15 (1H, s), 3.93 (3H, s), 3.83 (3H, s). |
| 15 | 225-226 | 290.3 | | * | |
| 16 | 175-177 | 286.3 | | * | |
| 17 | | 248.1 | | * | |
| 18 | | 237.3 | | * | |
| 19 | | 307.4 | | * | |
| 20 | 159-160 | 267.2 | | * | |
| 21 | 125-125 | 277.3 | | * | |
| 22 | 146-149 | 321.1 | | ** | |
| 23 | 234-235 | 334.2 | | *** | |
| 24 | 123-124 | 307.1 | | ** | |
| 25 | 291-293 | 271.2 | | * | $^1$H NMR (300 MHz, DMSO-$d_6$): δ 10.81 (1H, s), 8.63 (1H, d, J=1.7 Hz), 8.10 (1H, dd, J=8.8, 1.7 Hz), 7.76 (1H, d, J=8.8 Hz), 4.35 (2H, q, J=7.0 Hz), 2.22 (3H, s), 1.26 (3H, t, J=7.0 Hz). |
| 26 | 287-288 | 335.3 | | ** | $^1$H NMR (300 MHz, $CDCl_3$): δ 10.83 (1H, s), 8.23 (1H, s), 8.00 (1H, d, J=8.8 Hz), 7.92 (2H, d, J=7.3 Hz), 7.60 (1H, d, J=8.5 Hz), 7.53-7.43 (1H, m), 7.41-7.30 (2H, m), 4.12 (2H, q, J=7.3 Hz), 1.31 (3H, t, J=7.3 Hz). |
| 27 | 138-140 | 236.3 | | ** | |
| 28 | 68-70 | 272.2 | | ** | |
| 29 | oil | 284.3 | | * | |
| 30 | 114-116 | 292.2 | | * | $^1$H NMR (300 MHz, DMSO-$d_6$): δ 8.19 (1H, d, J=2.3 Hz), 7.96 (1H, dd, J=8.8, 2.3 Hz), 7.69 (1H, d, J=8.8 Hz), 7.38 (1H, t, J=7 Hz), 4.32 (2H, q, J=7.0 Hz), 3.81 (3H, s), 3.61 (2H, pentet, J=7 Hz), 1.29 (3H, t, J=6.7 Hz), 1.24 (3H, t, J=7.0 Hz). |
| 31 | 189-190 | 264.1 | | * | $^1$H NMR (300 MHz, DMSO-$d_6$): δ 8.11 (1H, d, J=2.0 Hz), 7.94 (1H, dd, J=8.5, 2.0 Hz), 7.65 (1H, d, J=8.5 Hz), 7.54 (2H, br s), 4.21 (2H, q, J=7.0 Hz), 3.79 (3H, s), 1.20 (3H, t, J=7.0 Hz). |

TABLE 1-continued

| Compound Number | Melting Point (° C.) | Mass Spec [M+H] | HCV-PV IC50 μM | Replicon IC5Os μM | NMR Data |
|---|---|---|---|---|---|
| 32 | oil | 280.2 | | * | |
| 33 | 113-117 | 280.2 | | * | |
| 34 | 137-141 | 232.1 | | * | |
| 35 | 318-319 | 411.0, 413.0 [M-H] | | * | $^1$H NMR (300 MHz, DMSO-$d_6$): δ 11.29 (1H, s), 8.71 (1H, d, J=2.0 Hz), 8.13 (1H, dd, J=8.8, 2.0 Hz), 7.98 (2H, d, J=8.5 Hz), 7.84 (2H, d, J=8.5 Hz), 7.83 (1H, d, J=8.8 Hz), 4.41 (2H, q, J=7.0 Hz), 1.28 (3H, t, J=7.0 Hz). |
| 36 | 273-274 | 380.1 | | * | $^1$H NMR (300 MHz, DMSO-$d_6$): δ 11.58 (1H, s), 8.87 (1H, s), 8.72 (1H, s), 8.53 (1H, d, J=7.0 Hz), 8.47 (1H, d, J=7.0 Hz), 8.14 (1H, d, J=8.5 Hz), 7.91 (1H, t, J=8.2 Hz), 7.86 (1H, d, J=8.8 Hz), 4.45 (2H, q, J=7.0 Hz), 1.30 (3H, t, J=7.0 Hz). |
| 37 | 56-60 | 246.2 | | * | |
| 38 | 96-100 | 310.1 | | * | |
| 39 | 94-98 | 310.1 | | * | |
| 40 | 176-180 | 269.1 | | * | |
| 41 | 155-175 | 267.1 | | * | |
| 42 | 138-143 | 296.1 | | * | |
| 43 | | 229.2 | | * | |
| 44 | | 293.2 | | * | |
| 45 | 130-131 | 215.5 | | * | |
| 46 | | 376.2 | | * | |
| 47 | 140-145 | 376.2 | | * | |
| 48 | 138-142 | 296.3 | | ** | |
| 49 | 89-90 | 376.3 | | * | |
| 50 | 91-92 | 259.3 | | * | |
| 51 | 95-96 | 229.4 | | | |
| 52 | | 243.2 | | * | |
| 53 | 145-147 | 363.1 | | ** | |
| 54 | 99-101 | 272.3 | | * | |
| 55 | 183-185 | 292.2 | | * | |
| 56 | 223-224 | 301.2 | | ** | |
| 57 | 130-133 | 243.2 | | | |
| 58 | 76-79 | 243.2 | | * | |
| 59 | 81-85 | 242.2 | | * | |
| 60 | 133-136 | 271.2 | | * | |
| 61 | 153-158 | 270.2 | | * | |
| 62 | | 262.0 | | * | |
| 63 | 188-192 | 333.4 | | * | |
| 64 | 108-113 | 301.3 | | * | |
| 65 | 130-132 | 331.3 | | ** | |
| 66 | 119-122 | 331.3 | | * | |
| 67 | 132-136 | 319.3 | | ** | |
| 68 | 140-147 | 315.3 | | ** | |
| 69 | 163-166 | 316.3 | | ** | |
| 70 | 142-141 | 321.2 | | * | |
| 71 | 199.4 | 348.2 | | * | |
| 72 | 144-149 | 271.3 | | * | |
| 73 | oil | 259.2 | | * | |
| 74 | 179-182 | 325.3 | | * | |
| 75 | 118-123 | 271.3 | | * | |
| 76 | 118-120 | 293.3 | | * | |
| 77 | 117-118 | 307.3 | | * | |
| 78 | 110-114 | 287.2 | | * | |
| 79 | 257-260 | 332.4 | | * | |
| 80 | 292-294 | 356.5 | | ** | |
| 81 | 209-211 | 360.5 | *** | *** | |
| 82 | 223-228 | 372.5 | *** | ** | |
| 83 | 221-223 | 384.4 | *** | *** | |
| 84 | 232-237 | 396.4 | *** | *** | |
| 85 | 163-165 | 398.3 | *** | *** | |
| 86 | 158-160 | 410.3 | | *** | |
| 87 | 187-189 | 396.3 | *** | *** | |
| 88 | 209-213 | 398.4 | *** | ** | |
| 89 | 148-155 | 308.3 | | ** | |
| 90 | 80-95 | 364.4 | | * | |
| 91 | 160-161 | 301.2 | | | |
| 92 | 155-156 | 317.2 | | * | |
| 93 | 172.4-172.6 | 305.3 | | * | |
| 94 | 262-265 | 314.4 | | ** | |

TABLE 1-continued

| Compound Number | Melting Point (° C.) | Mass Spec [M+H] | HCV-PV IC50 μM | Replicon IC5Os μM | NMR Data |
|---|---|---|---|---|---|
| 95 | 248-251 | 344.4 | | ** | |
| 96 | 243-250 | 329.4 | | ** | |
| 97 | 164-167 | 350.4 | | * | |
| 98 | 180-185 | 363.2 | | * | |
| 99 | 123.4-123.8 | 307.0 | | * | |
| 100 | 128-129 | 277.2 | | * | |
| 101 | 204-209 | 426.6 | | ** | |
| 102 | 136.7-136.9 | 267.2 | | * | |
| 103 | 90-93 | 263.2 | | * | |
| 104 | 190-194 | 406.4 | | ** | |
| 105 | 204-206 | 442.4 | | * | |
| 106 | 230-243 | 494.4 | | * | |
| 107 | 157-158 | 327.1 | | * | |
| 108 | 94-96 | 249.2<br>251.2 | | * | |
| 109 | 54-56 | 263.2<br>265.2 | | * | |
| 110 | 128-130 | 349.3 | | ** | |
| 111 | 208.5 | 374.3 | | * | $^1$H NMR ($CDCl_3$, 400 MHz), δ = 7.75-7.72 (m, 2H), 7.13-7.10 (m, 2 H), 6.97-6.88 (m, 3H), 6.11 (s, 2H) |
| 112 | 173.1-173.5 | 277.3 | | ** | $^1$H NMR ($CDCl_3$, 400 MHz), δ = 7.67 (t, J=8.4 Hz, 2 H), 7.24 (d, J=14.8 Hz, 1H), 7.16 (d, J=8.0 Hz, 1 H), 6.96-6.90 (m, 3 H), 6.10 (s, 2 H), 2.46 (s, 3 H) |
| 113 | 193-194 | 374.3 | | * | |
| 114 | 207-298 | 390.3 | | * | |
| 115 | 175-177 | 177.1 | | * | |
| 116 | 116-118 | 349.4 | | * | |
| 117 | 120-123 | 249.3 | | * | |
| 118 | 62-65 | 205.2 | | ** | |
| 119 | 126-128 | 283.2 | | ** | |
| 120 | 69-71 | 205.5 | | * | |
| 121 | 167-169 | 364.5 | | ** | |
| 122 | 163-169 | 426.5 | | * | |
| 123 | 113-117 | 239.4 | | * | |
| 124 | 212.2-212.3 | 291.3 | | * | $CDCl_3$, 400 MHz, δ = 7.61 (dd, J=8.4 Hz and 4.4 Hz, 1 H), 7.04-6.96 (m, 2H), 6.77 (m, 3H), 6.12 (s, 2H), 2.42 (s, 3H) |
| 125 | 151.2-151.7 | 291.3 | | ** | $CDCl_3$, 400 MHz, δ = 7.57 (d, J=8.0 Hz, 1H), 7.09 (d, J=8.0 Hz, 1H), 6.97 (d, J=28.0 Hz, 1 H), 6.86 (s, 1 H), 6.79 (dd, J=11.2 Hz and 2.0 Hz, 2H), 6.12 (s, 2H), 2.42 (s, 3H), 2.40 (s, 3H) |
| 126 | 146-148 | 251.3 | | * | |
| 127 | 173-175 | 327.3 | | * | |
| 128 | 218-220 | 334.5 | | * | |
| 129 | 188-190 | 370.4 | | ** | |
| 130 | 227-233 | 394.5 | | *** | |
| 131 | 199-204 | 408.5 | | ** | |
| 132 | 209-212 | 422.5 | | ** | |
| 133 | 144-146 | 351.5 | | ** | |
| 134 | 155-157 | 335.4 | | ** | |
| 135 | 168-170 | 369.5 | | ** | |
| 136 | 159-161 | 381.4 | | ** | |
| 137 | 129-132 | 345.5 | | ** | |
| 138 | 235-239 | 358.5 | *** | ** | |
| 139 | 191-195 | 388.5 | *** | ** | |
| 140 | 83-96 | 253.3 | | * | |
| 141 | 145-146 | 253.4 | | * | |
| 142 | 103-105 | 237.4 | | * | |
| 143 | 168-171 | 384.5 | | * | |
| 144 | 97-100 | 315.4 | | ** | |
| 145 | 110-113 | 357.5 | | ** | |
| 146 | 169-172 | 335.3 | | ** | |
| 147 | 183-186 | 344.4 | | ** | |
| 148 | 155-157 | 335.4 | | ** | |
| 149 | 134-136 | 345.4 | | ** | |
| 150 | 141-143 | 319.4 | | ** | |
| 151 | 146-148 | 319.4 | | ** | |
| 152 | 207-211 | 386.5 | | * | |
| 153 | 225-228 | 398.5 | * | ** | |
| 154 | | 293.1 | | ** | DMSO, 400 MHz, δ = 8.13 (d, J=6.4 Hz, 1H), 8.01 (s, 2H), 7.84 (s, 1H), 7.54 |

TABLE 1-continued

| Compound Number | Melting Point (° C.) | Mass Spec [M+H] | HCV-PV IC50 μM | Replicon IC5Os μM | NMR Data |
|---|---|---|---|---|---|
| | | | | | (dd, J=12.4 Hz and 3.6 Hz, 1H), 7.15 (d, J=8.8 Hz, 2H), 3.83 (s, 3H) |
| 155 | | | | ** | $CDCl_3$, 300 MHz, δ = 9.31 (s, 1H), 8.32 (s, 1H), 8.19-8.17 (m, 1H), 7.75 (s, 1H), 2.70 (s, 3H) |
| 156 | 205-209 | 421.5 | | ** | |
| 157 | 149-153 | 422.5 | | ** | |
| 158 | 153-156 | 317.5 | | ** | |
| 159 | 147-150 | 361.3 | | ** | |
| 160 | 117-119 | 315.7 | | ** | |
| 161 | 174-176 | 340.3 | | ** | |
| 162 | 185-190 | 413.5 | | * | |
| 163 | 235-239 | 410.5 | | ** | |
| 164 | 273-280 | 358.5 | | ** | |
| 165 | 211-225 | 373.5 | | * | |
| 166 | 236-240 | 385.5 | | *** | |
| 167 | 196-200 | 464.5 | | ** | |
| 168 | 199-204 | 394.5 | | * | |
| 169 | 147-150 | 316.5 | | ** | |
| 170 | 148-151 | 307.4 | | ** | |
| 171 | 134-137 | 307.4 | | ** | |
| 172 | 221-223 | 317.4 | | ** | |
| 173 | 150-153 | 316.5 | | ** | |
| 174 | 139-142 | 302.4 | | ** | |
| 175 | 132-135 | 359.5 | | ** | |
| 176 | 162-164 | 343.5 | | ** | |
| 177 | 125-130 | 331.4 | | ** | |
| 178 | 119-123 | 369.4 | | * | |
| 179 | 79-80 | 239.4 | | ** | |
| 180 | 170-171 | 384.5 | ** | ** | |
| 181 | 177-178 | 398.5 | | ** | |
| 182 | 148-154 | 408.5 | | *** | |
| 183 | 276-284 | 344.5 | | ** | |
| 184 | 197-200 | 337.4 | | ** | |
| 185 | 157-160 | 355.4 | | ** | |
| 186 | 166-169 | 317.4 | | ** | |
| 187 | 187-191 | 321.4 | | ** | |
| 188 | 209-212 | 287.4 | | ** | |
| 189 | 252-253 | 356.4 | | * | |
| 190 | 234-236 | 370.4 | | ** | |
| 191 | 208-210 | 370.4 | ** | * | |
| 192 | 205-207 | 384.5 | | ** | |
| 193 | 228-232 | 378.5 [M-H] | | ** ** | |
| 194 | 278-284 | 370.4 | | ** | |
| 195 | 271-275 | 398.4 | | ** | |
| 196 | 187-189 | 354.3 | | ** | |
| 197 | 147-149 | 373.6 | | * | |
| 198 | 163-165 | 395.7 | | * | |
| 199 | 156-158 | 369.2 | *** | * | |
| 200 | 187-189 | 354.4 | | ** | |
| 201 | 147-150 | 381.2 | | ** | |
| 202 | 137-139 | 369.4 | | ** | |
| 203 | | 257.9 | | ** | DMSO, 300 MHz, δ = 10.34 (s, 1H), 7.42 (d, J=8.7 Hz, 1H), 7.14 (d, J=2.1 Hz, 1H), 6.87 (dd, J=8.7 Hz and 2.1 Hz, 1H), 4.08 (q, J=7.2 Hz, 2H), 3.80 3.80 (s, 3H), 2.12 (s, 3H), 1.21 (t, J=7.2 Hz,3H) |
| 204 | | 320.1 | | *** | DMSO, 300 MHz, δ = 10.81 (s, 1H), 8.02 (t, J=7.2 Hz, 2H), 7.67-7.47 (m, 4H), 7.21 (d, J=2.4 Hz, 1H), 6.90 (dd, J=8.4 Hz and 2.1 Hz, 1H), 4.12 (q, J=6.9 Hz, 2H), 3.83 (s, 3H), 1.24(t, J=27.5 Hz, 3H) |
| 205 | 181-184 | 358.4 | | ** | |
| 206 | 187-191. | 372.4 | | ** | |
| 207 | 179-183. | 386.4 | | ** | |
| 208 | 192-194. | 394.4 | | ** | |
| 209 | 180-183. | 408.4 | | ** | |
| 210 | 213-216 | 422.4 | | ** | |
| 211 | 186-191. | 384.4 | | ** | |
| 212 | 180-183 | 400.4 | | ** | |
| 213 | 165-168 | 398.4 | | ** | |
| 214 | 254.8-255.1 | 338.1 | | *** | $^1H$ NMR (DMSO, 300 MHz), δ = 7.88 (d, J=7.5 Hz, 1H), 7.82 (d, J=9.9 Hz, |

TABLE 1-continued

| Compound Number | Melting Point (° C.) | Mass Spec [M+H] | HCV-PV IC50 μM | Replicon IC5Os μM | NMR Data |
|---|---|---|---|---|---|
| | | | | | 1H), 7.64 (q, J=8.1 Hz, 1H), 7.21 (d, J=2.4 Hz, 1H), 7.56-7.48 (m, 2H), 7.21 (d, J=2.1 Hz, 1H), 6.91 (dd, J=8.7 Hz and 2.1 Hz, 1H), 4.12 (q, J=7.2 Hz, 2H), 4.13 (s, 3H), 1.23 (t, J=6.9 Hz, 3H) |
| 215 | 245-246 | 345.1 | | ** | $^1$H NMR (DMSO, 300 MHz), δ = 11.08 (s, 1H), 8.16 (d, J=8.4 Hz, 2H), 8.07 (d, J=7.8 Hz, 2H), 7.49 (d, J=8.4 Hz, 1H), 7.21 (d, J=2.1 Hz, 1H), 6.91 (dd, J=8.4 Hz and 1.8 Hz, 1H), 4.08 (q, J=2.1 Hz, 2H), 3.80 (s, 3H), 1.25 (t, J=7.2 Hz, 3H) |
| 216 | 261 | 283.9 | | ** | $^1$H NMR (DMSO, 300 MHz), δ = 10.58 (br, 1H), 7.42 (d, J=8.7 Hz, 1H), 7.15 (d, J=2.1 Hz, 1H), 6.86 (dd, J=8.7 Hz and 2.4 Hz, 1H), 4.08 (q, J=7.2 Hz, 2H), 3.80 (s, 3H), 2.04 (br, 1H), 1.21 (t, J=6.9 Hz, 3H), 0.89-0.84 (m, 5H) |
| 217 | 272-273 | 315.9 | | *** | $^1$H NMR (DMSO, 300 MHz), δ=9.94 (s, 1H), 7.43 (d, J=8.7 Hz, 1H), 7.15 (d, J=2.1 Hz, 1H), 6.87 (dd, J=8.7 Hz and 2.4 Hz, 1H), 4.12 (q, J=7.2 Hz, 2H), 3.91 (d, J=6.6 Hz, 2H), 3.80 (s, 3H), 1.89-1.92 (m, 1H), 1.21 (t, J=7.2 Hz, 3H), 0.89 (d, J=6.6 Hz, 6H) |
| 218 | 174-177 | 344.3 | | ** | |
| 219 | 145-149 | 388.4 | | ** | |
| 220 | 219-223 | 387.7 | | ** | |
| 221 | 195-200 | 421.3 | | ** | |
| 222 | 216-219 | 385.4 | | ** | |
| 223 | 210-216 | 316.4 | | ** | |
| 224 | 245-249 | 358.3 | | ** | |
| 225 | 231-236 | 372.3 | | ** | |
| 226 | 294-295 | 375.9 | | * | $^1$H NMR ($CDCl_3$, 300 MHz) δ (ppm), 3.72 (s, 3H), 3.80 (s, 3H), 6.75-6.91 (m, 2H), 7.42-7.56 (m, 2H), 8.04 (d, 1H), 8.23 (d, 1H), 8.67 (d, 1H). |
| 227 | 198-203 | 392.3 | | ** | |
| 228 | 195-198 | 388.3 | | * | |
| 229 | 142-147 | 321.3 | | * | |
| 230 | 218-220 | 323.4 | | * | |
| 231 | 201-203 | 289.3 | | * | |
| 232 | 190-193 | 307.3 | | * | |
| 233 | 232-234 | 329.4 | | ** | |
| 234 | 221-223 | 288.3 | | * | |
| 235 | 218-222 | 316.4 | | ** | |
| 236 | 145-147 | 287.3 | | * | |
| 237 | 146-148 | 303.3 | | * | |
| 238 | 189-191 | 273.3 | | * | |
| 239 | 212-218 | 292.3 | | * | |
| 240 | 164-167 | 335.3 | | * | |
| 241 | 184-188 | 344.3 | | * | |
| 242 | 242-248 | 334.3 | | * | |
| 243 | 194-198 | 370.3 | | *** | |
| 244 | 187-190 | 360.4 | | . | |
| 245 | 192-195 | 390.4 | | * | |
| 246 | 160-164 | 374.4 | | * | |
| 247 | 212-217 | 293.3 | | * | |
| 248 | 117-121 | 351.4 | | ** | |
| 249 | 132-136 | 337.4 | | ** | |
| 250 | 160-162 | 323.3 | | * | |
| 251 | 186-187 | 398.4 | *** | ** | |
| 252 | 176-177 | 432.4 | | ** | |
| 253 | 121-125 | 399.2 | | ** | |
| 254 | 153-154 | 307.21 | | * | |
| 255 | 149-151 | 435.5 | | ** | |
| 256 | 230-232 | 331.3 | | * | |
| 257 | 174-176. | 330.3 | | * | |
| 258 | 146-148 | 330.3 | | * | |
| 259 | foam | 358.3 | | * | |
| 260 | 109-111 | 359.3 | | * | |
| 261 | 138-143 | 406.4 | | ** | |
| 262 | 117-121 | 365.4 | | ** | |
| 263 | 121-127 | 419.4 | | ** | |
| 264 | glass | 406.5 | | ** | |
| 265 | 204-206 | 355.3 | | * | |

TABLE 1-continued

| Compound Number | Melting Point (° C.) | Mass Spec [M+H] | HCV-PV IC50 µM | Replicon IC5Os µM | NMR Data |
|---|---|---|---|---|---|
| 266 | 96-99 | 362.4 | | ** | |
| 267 | 106-112 | 336.4 | | | |
| 268 | 137-143 | 414.4 | | ** | |
| 269 | 153-158 | 428.4 | | ** | |
| 270 | 175-177 | 404.4 | | * | |
| 271 | 158-160 | 418.4 | | ** | |
| 272 | 173-176 | 396.4 | | ** | |
| 273 | 207-209 | 404.4 | | * | |
| 274 | 166-172 | 378.4 | | * | |
| 275 | 201-206 | 384.4 | | * | |
| 276 | 224-228 | 426.4 | | * | |
| 277 | 186-191 | 370.4 | | * | |
| 278 | 234-240 | 356.4 | | * | |
| 279 | 197-202 | 407.5 | | * | |
| 280 | 89-95 | 364.4 | | * | |
| 281 | 132-134 | 283.3 | | * | |
| 282 | 135-136 | 317.3 | | * | |
| 283 | 215-218 | 353.4 | | * | |
| 284 | 112-114 | 267.3 | | * | |
| 285 | 185-190 | 420.5 | | * | |
| 286 | 191-192 | 333.3 | | ** | $^1$H NMR (300 MHz, $CDCl_3$): δ 7.92-7.88 (2H, m), 7.67 (1H, s), 7.66 (1H, d, J=8.8 Hz), 7.46-7.42 (2H, m), 6.98 (1H, dd, J=8.8, 2.3 Hz), 6.88 (1H, d, J=2.3 Hz), 4.35 (2H, q, J=7.3 Hz), 3.92 (3H, s), 1.46 (3H, t, J=7.3 Hz). |
| 287 | 175-177 | 384.4 | | * | |
| 288 | 194-199 | 293.3 | | * | |
| 289 | 173-175 | 432.2 | | * | |
| 290 | | 433.1 | | * | $^1$H NMR ($CDCl_3$, 300MHz), δ7.97-7.92 (m, 2H), 7.70-7.62 (m, 3H), 7.10 (br, 1H), 6.98 (dd, J=8.7 Hz and 2.1 Hz, 1H), 6.88 (d, J=2.1Hz, 1H), 4.16 (q, J=7.5 Hz, 2H), 3.91 (s, 3H), 3.77 (t, J=4.2 Hz, 4H), 3.62 (q, J=5.4Hz, 2H), 2.68 (t, J=5.7 Hz, 2H), 2.59 (br, 4H), 1.36 (t, J=7.2 Hz, 3H) |
| 291 | | 319.9 | | * | $^1$H NMR ($CD_3OD$, 300MHz), δ 8.07 (d, J=7.2 Hz, 2H), 7.79-7.68 (m, 2H), 7.54 (d, J=8.7 Hz, 1H), 7.12 (d, J=2.1 Hz, 1H), 6.97 (dd, J=8.7 Hz and 2.1 Hz, 1H), 4.24 (q, J=7.5 Hz, 2H), 3.90 (s, 3H), 1.26 (t, J=7.2 Hz, 3H) |
| 292 | 176-177 | 348.0 | | * | $^1$H NMR ($CDCl_3$, 300 MHz), δ 7.93-7.88 (m, 2H), 7.69-7.60 (m, 3H), 6.98 (dd, J=8.7 Hz and 2.1 Hz, 1H), 6.88 (d, J=2.1 Hz, 1H), 6.17 (br, 1H), 4.15 (q, J=7.2 Hz, 2H), 3.91 (s, 3H), 3.53 (m, 2H), 1.35 (t, J=7.2 Hz, 3H), 1.28 (t, J=7.2 Hz, 3H) |
| 293 | | 412.5 | | * | |
| 294 | | 364.4 | | *** | |
| 295 | | 609.4 | | ** | |
| 296 | | 392.4 | | ** | |
| 297 | | 378.4 | | ** | |
| 298 | | 394.4 | | ** | |
| 299 | | 376.4 | | ** | |
| 300 | | 392.4 | | ** | |
| 301 | | 412.4 | | ** | |
| 302 | | 382.4 | | ** | |
| 303 | | 374.2 | | * | |
| 304 | | 426.4 | | ** | |
| 305 | | 442.4 | | * | |
| 306 | | 446.4 | | ** | |
| 307 | | 430.4 | | ** | |
| 308 | | 424.3 | | * | |
| 309 | | 490.3 | | ** | |
| 310 | | 378.4 | | ** | |
| 311 | | 392.1 | | * | |
| 312 | | 378.1 | | * | |
| 313 | | 394.1 | | * | |
| 314 | | 376.1 | | * | |
| 315 | | 412.0 | | * | |
| 316 | | 474.1 | | * | |
| 317 | | 382.1 | | * | |
| 318 | | 446.1 | | * | |

TABLE 1-continued

| Compound Number | Melting Point (° C.) | Mass Spec [M+H] | HCV-PV IC50 µM | Replicon IC5Os µM | NMR Data |
|---|---|---|---|---|---|
| 319 | | 430.1 | | * | |
| 320 | | 426.1 | | * | |
| 321 | | 490.9 | | * | |
| 322 | 223-230 | 308.4 | | * | |
| 323 | 102.9-103.4 | 447.2 | | * | $^1$H NMR ($CD_3OD$, 300 MHz), δ8.02-8.00 (m, 2H), 7.78-7.68 (m, 2H), 7.55 (d, J=8.4 Hz, 1H), 7.12 (s, 1H), 6.97 (dd, J=6.6 Hz and 1.5Hz, 1H), 4.24 (q, J=7.5Hz, 2H), 3.90 (s, 3H), 3.68 (t, J=4.2Hz, 4H), 3.52 (q, J=5.4Hz, 2H), 2.50 (t, J=6.9Hz, 6H), 1.86 (br, 2H), 1.28 (t, J=7.2Hz, 3H) |
| 324 | 165.3-165.7 | 368.1 | | * | (DMSO, 300 MHz), δ 10.56 (s, 1H), 7.85 (s, 1H), 7.73 (d, J=7.8 Hz, 1H), 7.54 (q, J=7.8 Hz, 2H), 7.31 (d, J=7.8 Hz, 1H), 7.23 (s, 1H), 6.92 (d, J=8.7 Hz, 1H), 4.27 (s, 2H), 4.18 ( q, J=7.5 Hz, 2H) , 3.83 (s, 3H) 1.20 (t, J=7.2 Hz, 3H) |
| 325 | | 462.1 | | * | (DMSO, 300 MHz), δ 10.30 (s, 1H), 8.02 (s, 1H), 7.91 (d, J=7.5 Hz, 1H), 7.58-7.54 (m, 4H), 7.51-7.49 (m, 2H), 7.04 (d, J=8.4 Hz, IH), 6.92 (dd, J=8.7 Hz and 1.8 Hz, 1H), 6.11 (s, 2H), 4.22 (q, J=7.5 Hz, 2H), 3.83 (s, 3H), 1.21 (t, J=6.9 Hz, 3H) |
| 326 | 137-138 | 396.1 | | * | |
| 327 | 154-155 | 386.1 | | * | (DMSO, 300 MHz), δ 10.45 (s, 1H), 8.02 (s, 1H), 7.95 (d, J=8.1 Hz, 2H), 7.55 (q, J=7.8 Hz, 2H), 7.33 (q, J=3.6 Hz, 2H), 7.25 (s, 1H), 6.95 (dd, J=3.6 and J=2.4 Hz, 1H), 6.70 (q, J=1.8 Hz, 1H), 4.22 ( q, J=7.5 Hz, 2H) , 3.84 (s, 3H), 1.22 (t, J=6.9 Hz, 3H) |
| 328 | 174-175 | 401.1 | | * | ($CDCl_3$, 300 MHz), δ 8.68 (s, 1H), 8.00 (s, 1H), 7.65 (m, 2H), 7.55 (t, J=8.4 Hz, 1H), 7.40 (d, J=7.2 Hz, 1H), 6.95 (dd, J=7.2 and 1.8 Hz, 1H), 6.90 (d, J=2.1, 1H), 6.54 (s, 1H), 4.20 ( q, J=7.2 Hz, 2H) , 3.92 (s, 3H), 2.53 (s, 3H), 1.39 (t, J=7.2Hz, 3H) |
| 329 | 175-176 | 334.0 | | * | ($CDCl_3$, 300 MHz), δ 7.79 (s, 1H), 7.64 (d, J=8.4 Hz, 1H), 7.58 (d, J=8.7 Hz, 1H), 7.49 (t, J=7.8 Hz, 1H), 7.38 (s, 1H), 7.30 (d, J=4.5 Hz, 1H), 6.99 (d, J=2.1 Hz, 1H), 6.92 (d, J=2.1 Hz, 1H) 4.19 (q, J=6.9 Hz, 2H), 3.91 (s, 3H), 2.22 (s, 3H), 1.39 (t, J=7.2 Hz, 3H) |
| 330 | 237-238 | 438.1 | | * | (DMSO, 300 MHz), δ 10.90 (s, 1H), 8.71 (s, 1H), 8.18 (d, J=9.9 Hz, IH), 8.06 (s, 1H), 7.97 (t, J=9.3 Hz, 2H), 7.63 (t, J=8.1 Hz, 1H), 7.53 (d, J=8.7, 1H), 7.39 (d, J=8.4 Hz, 1H), 7.27 (d, J=1.8 Hz, 1H), 6.94 (dd, J=8.7 Hz and 2.1 Hz, 1H), 4.23 ( q, J=6.6 Hz, 2H) , 3.84 (s, 3H), 1.23 (t, J=7.2 Hz, 3H) |
| 331 | 160-165. | 370.5 | | ** | |
| 332 | 239-145 | 334.5 | | * | |
| 333 | 237-240 | 384.5 | | ** | |
| 334 | 242-246 | 348.5 | | ** | |
| 335 | 87-88 | 297.5 | | ** | |
| 336 | 129-132 | 384.5 | | * | |
| 337 | 135-137 | 283.4 | | * | |
| 338 | 125-135 | 367.5 [M-H] | | * | |
| 339 | 215-219 | 362.5 | | ** | |
| 340 | 243-248 | 334.2 | | * | |
| 341 | 227-230 | 348.3 | | ** | |
| 342 | 258-261 | 337.3 | | * | $^1$H NMR (300 MHz, $CDCl_3$): δ 8.70 (1H, s), 7.79 (1H, d, J=1.8 Hz), 7.73 (1H, dd, J=8.5, 1.8 Hz), 7.07 (1H, d, J=8.5 Hz), 6.95 (2H, d, J=8.8 Hz), 6.65 (2H, d, J=8.8 Hz), 3.97 (2H, q, J=7.0 Hz), 3.54 (3H, s), 1.12 (3H, t, J=7.0 Hz). |
| 343 | 131-133 | 373.5 | | * | |

TABLE 1-continued

| Compound Number | Melting Point (° C.) | Mass Spec [M+H] | HCV-PV IC50 μM | Replicon IC5Os μM | NMR Data |
|---|---|---|---|---|---|
| 344 | 177-178 | 356.5 | | ** | |
| 345 | 191-192 | 370.5 | | ** | |
| 346 | 178-180 | 384.3 | | *** | |
| 347 | 146-148 | 357.3 | | * | |
| 348 | 126-128 | 267.2 | | * | |
| 349 | | 392.3 | | *** | |
| 350 | | 374.3 | | ** | |
| 351 | | 390.3 | | ** | |
| 352 | | 388.3 | | ** | |
| 353 | | 350.2 | | *** | |
| 354 | | 388.3 | | ** | |
| 355 | | 384.2 | | * | |
| 356 | | 404.3 [M-H] | | * | |
| 357 | | 392.3 | | * | |
| 358 | | 374.3 | | * | |
| 359 | | 390.3 | | * | |
| 360 | | 388.3 | | * | |
| 361 | | 404.3 | | * | |
| 362 | | 609.5 [M-H] | | ** | |
| 363 | 201-207 | 394.2 [M-H] | | ** | |
| 364 | 183-188 | 398.2 | | ** | |
| 365 | oil | 408.2 | | *** | |
| 366 | 223-225 | 420.2 | | *** | |
| 367 | 225-227 | 434.2 | | ** | |
| 368 | 168-170 | 434.2 | | ** | |
| 369 | 174-177 | 470.2 | | ** | |
| 370 | 159-164 | 432.2 | | * | |
| 371 | 168-170 | 340.2 | | * | $^1$H NMR (300 MHz, DMSO-$d_6$): δ 10.24 (1H, s), 7.75-7.60 (1H, m), 7.60 (2H, d, J=8.8 Hz), 7.45-7.25 (3H, m), 7.41 (2H, d, J=8.8 Hz), 4.21 (2H, q, J=7.0 Hz), 3.13 (3H, s), 1.22 (3H, t, J=7.0 Hz). |
| 372 | 211-212 | 334.3 | | ** | $^1$H NMR (300 MHz, DMSO-$d_6$): δ 9.98 (1H, s), 7.73-7.62 (2H, m), 7.69 (2H, d, J = 8.4 Hz), 7.54 (2H, d, J=8.4 Hz), 7.39-7.24 (2H, m), 4.26-4.12 (4H, m), 1.26 (3H, t, J=7.0 Hz), 1.20 (3H, t, J=7.3 Hz). |
| 373 | 222-228 | 354.2 [M-H] | | * | |
| 374 | 180-186 | 396.2 [M-H] | | * | |
| 375 | 161-166 | 425.6 [M-H] | | * | |
| 376 | | 278.4 | | * | |
| 377 | 153-156 | 403.1 | | * | $^1$H NMR (DMSO, 300 MHz), δ7.66-7.51 (m, 5H), 7.25 (d, J=2.1 Hz, 1H), 6.91 (dd, J=8.7 Hz and 2.4 Hz, 1H), 4.20 (q, J=7.5 Hz, 2H), 3.83 (s, 3H), 3.65-3.55 (m, 2H), 2.73-2.68 (m, 4H), 1.71-1.54 (m, 4H), 1.18 (t, J=7.2 Hz, 3H). |
| 378 | | 376.7 | | * | $^1$H NMR (DMSO, 300 MHz), δ 8.84 (t, J=1.8 Hz, 1H), 8.02 (d, J=8.1 Hz, 2H), 7.67 (d, J=7.8 Hz, 2H), 7.49 (d, J=8.7 Hz, 1H), 7.38 (s, 1H), 7.22 (s, 1H), 7.02 (s, 1H), 6.89 (d, J=7.2 Hz, 1H), 4.17 (q, J=6.9 Hz, 2H), 3.80-3.77 (m, 5H), 1.12 (t, J=7.2 Hz, 3H). |
| 379 | 228-232 | 472.2 | | ** | $^1$H NMR (DMSO, 300 MHz), δ7.72-7.67 (m, 2H), 7.78-7.68 (m, 2H), 7.55 (d, J=8.4 Hz, 1H), 7.12 (s, 1H), 6.97 (dd, J= 26.6 Hz and 1.5Hz, 1H), 4.20 (q. J=7.5 Hz, 2H), 3.83 (s, 3H), 3.06 (t, J=4.2 Hz, 6H), 2.76-2.69 (m, 6H), 2.50 (s, 6H), 1.96 (br, 2H), 1.18 (t, J=7.2 Hz, 3H). |
| 380 | | | | * | $^1$H NMR (DMSO, 300 MHz), δ 10.67 (s, 1H), 8.16 (d, J=2.4 Hz, 1H), 8.11 (d, J=4.5 Hz, 2H), 7.78 (d, J=8.4 Hz, 2H), 7.73 (d, J=2.4 Hz, 1H), 7.61 (d, J=9.0 Hz, 1H), 7.54 (d, J=9.0 Hz, 1H), |

TABLE 1-continued

| Compound Number | Melting Point (° C.) | Mass Spec [M+H] | HCV-PV IC50 μM | Replicon IC5Os μM | NMR Data |
|---|---|---|---|---|---|
| | | | | | 7.27 (s, 1H), 6.94 (d, J=8.7 Hz, 1H), 4.28-4.26 (m, 2H), 3.84 (s, 3H), 1.17 (t, J=7.2 Hz, 3H). |
| 381 | 216-220 | 410.1 | | * | $^1$H NMR (DMSO, 300 MHz), δ 10.34 (s, 1H), 8.10 (d, J=8.1 Hz, 2H), 7.75 (d, J=8.1 Hz, 2H), 7.65 (d, J=8.4 Hz, 2H), 7.53 (d, J=8.7 Hz, 1H), 7.26 (s, 1H), 7.14 (d, J=8.1 Hz, 2H), 6.94 (dd, J=8.7 Hz and 2.4 Hz, 1H), 4.21 (q, J=6.9 Hz, 2H), 3.83 (s, 3H), 2.25 (s, 3H), 1.17 (t, J=6.9 Hz, 3H). |
| 382 | 236-238 | | | ** | $^1$H NMR (DMSO, 300 MHz), δ 10.55 (s, 1H), 8.10 (d, J=7.8 Hz, 2H), 7.83-7.76 (m, 4H), 7.54 (d, J=8.4 Hz, 1H), 7.41 (d, J=8.1 Hz, 2H), 7.27 (s, 1H), 6.93 (dd, J=9.9 Hz and 1.2 Hz, 1H), 4.22 (q, J=6.9 Hz, 2H), 3.84 (s, 3H), 1.17 (t, J=7.2 Hz, 3H). |
| 383 | 161.2-162.2 | 362.1 | | * | $^1$H NMR ($CDCl_3$, 300MHz), δ 7.79 (s, 1H), 7.65-7.59 (m, 2H), 7.48 (t, J=7.8 Hz, 1H), 7.30 (t, J=11.4 Hz, 2H), 6.96 (dd, J=8.7 Hz and 2.1 Hz, 1H), 6.88 (d, J=2.1 Hz, 1H), 4.18 (q, J=7.2 Hz, 2H), 3.91 (s, 3H), 2.57-2.52 (m, 1H), 1.36 (t, J=7.2 Hz, 3H) 1.28-1.23 (m, 6H). |
| 384 | 199-201 | 348.0 | | * | $^1$H NMR ($CDCl_3$, 300 MHz), δ 7.93 (d, J=8.4 Hz, 2H), 7.67-7.61 (m, 3H), 6.98 (dd, J=8.7 Hz and 2.1 Hz, 1H), 6.88 (d, J=2.1 Hz, 1H), 6.14 (br, 1H), 4.14 (q, J=7.5 Hz, 2H), 3.93 (s, 3H), 3.57-3.53 (m, 2H), 1.36-1.26 (m, 6H). |
| 385 | 213-213.9 | 362.0 | | ** | $^1$H NMR (DMSO, 300 MHz), δ 8.37 (d, J=6.6 Hz, 1H), 7.98 (d, J=7.8 Hz, 2H), 7.65 (d, J=7.8 Hz, 2H), 7.50 (d, J=9.0 Hz, 1H), 7.23 (s, 1H), 6.90 (d, J=7.8 Hz, 1H), 4.19-4.16 (m, 2H), 4.08-4.06 (m, 1H), 3.80 (s, 3H), 1.14-1.12 (m, 9H). |
| 386 | 198-199 | 359.9 | | * | $^1$H NMR (DMSO, 300 MHz), δ 8.59 (d, J=4.2 Hz, 1H), 7.97 (d, J=8.1 Hz, 2H), 7.67 (d, J=8.1 Hz, 2H), 7.52 (d, J=8.7 Hz, 1H), 7.25 (d, J=2.1 Hz, 1H), 6.92 (dd, J=8.7 Hz and 2.1 Hz, 1H), 4.19 (q, J=7.2 Hz, 2H), 3.83 (s, 3H), 2.90-2.80 (m, 1H), 1.16 (t, J=7.2 Hz, 3H), 0.69 (q, J=4.8 Hz, 2H), 0.57 (q, J=3.3 Hz, 2H). |
| 387 | 189-189.5 | 360.1 | | * | $^1$H NMR (DMSO, 300 MHz), δ 7.81 (d, J=8.4 Hz, 2H), 7.67 (d, J=8.1 Hz, 2H), 7.53 (d, J=8.7 Hz, 1H), 7.25 (d, J=1.8 Hz, 1H), 6.93 (dd, J=8.7 Hz and 2.1 Hz, 1H), 4.35 (t, J=6.8 Hz, 2H), 4.18 (q, J=7.2 Hz, 2H), 4.06 (t, J=6.8 Hz, 2H), 3.83 (s, 3H), 2.24 (m, 2H), 1.16 (t, J=7.2 Hz, 3H). |
| 388 | 160.1-161.8 | 363.9 | | * | $^1$H NMR (DMSO, 300 MHz), δ 8.60 (t, J=2.1 Hz, 1H), 8.02 (d, J=8.4 Hz, 2H), 7.68 (d, J=8.1 Hz, 2H), 7.53 (d, J=9.0 Hz, 1H), 7.25 (s, 1H), 6.93 (dd, J=6.9 Hz and 1.8 Hz, 1H), 4.72 (t, J=5.4 Hz, 1H), 4.19 (q, J=7.2 Hz, 2H), 3.83 (s, 3H), 3.48 (q, J=6.0 Hz, 2H), 3.33 (m, 2H), 1.15 (t, J=7.2 Hz, 3H). |
| 389 | 130-132 | 447.1 | | * | $^1$H NMR ($CDCl_3$, 300 MHz), δ 8.36 (br, 1H), 8.12 (d, J=7.2 Hz, 2H), 7.67-7.59 (m, 3H), 6.97 (dd, J=9.3 Hz and 1.8 Hz, 1H), 6.89 (s, 1H), 4.18 (q, J=7.5 Hz, 2H), 3.98 (br, 2H), 3.84 (s, 3H), 3.67 (q, J=6.9Hz, 2H), 2.87 (br, 4H), 2.17 (s, 1H) 2.14 (br, 1H), 2.09 (s, 1H), 1.40 (t, J=10.5Hz, 3H), 1.31 (t, J=7.5 Hz, 3H). |
| 390 | 236-236.8 | 396.1 | | * | $^1$H NMR (DMSO, 300 MHz), δ 10.42 (s, 1H), 8.12 (d, J=8.4 Hz, 2H), 7.79-7.75 (m, 4H), 7.55 (d, J=8.7 Hz, 1H), |

TABLE 1-continued

| Compound Number | Melting Point (° C.) | Mass Spec [M+H] | HCV-PV IC50 μM | Replicon IC5Os μM | NMR Data |
|---|---|---|---|---|---|
| | | | | | 7.35 (t, J=10.6 Hz, 2H), 7.27 (d, J=2.1 Hz, 1H), 7.09 (t, J=10.6 Hz, 1H), 6.94 (dd, J=8.7Hz and 2.1 Hz, 1H), 4.23 (m, 2H), 3.84 (s, 3H), 1.18 (t, J=6.9 Hz, 3H). |
| 391 | 240-242 | | | ** | $^{1}$H NMR (DMSO, 300 MHz), δ 10.55 (s, 1H), 8.11 (d, J=8.1 Hz, 2H), 7.82 (m, 4H), 7.55 (d, J=8.7 Hz, 1H), 7.41 (d, J=9.0 Hz, 2H), 7.27 (d, J=1.8 Hz, 1H), 6.94 (dd, J=8.7 Hz and 2.1 Hz, 1H), 4.23 (q, J=7.1 Hz, 2H), 3.84 (s, 3H), 1.78 (t, J=7.1 Hz, 3H). |
| 392 | 243-246 | 456.1 | | * | $^{1}$H NMR (DMSO, 300 MHz), δ 10.27 (s, 1H), 8.11 (d, J=8.4 Hz, 2H), 7.76 (d, J=8.4 Hz, 2H), 7.54 (d, J=8.7 Hz, 1H), 7.48 (d, J=2.4 Hz, 1H), 7.33 (d, J=7.2 Hz, 1H), 7.29 (s, 1H), 6.96-6.91 (m, 2H), 4.25 (q, J=8.5 Hz, 2H), 3.84 (s, 3H), 3.73 (s, 3H), 3.72 (s, 3H), 1.18 (t, J=7.2 Hz, 3H). |
| 393 | 202-206 | 296.4 | | ** | |
| 394 | 192-195 | 372.3 | | *** | |
| | | [M-H] | | | |
| 395 | | 397.4 | | ** | |
| 396 | | 377.2 | *** | *** | |
| 397 | | 377.5 | *** | *** | |
| 398 | | 391.5 | | *** | |
| 399 | | 375.5 | | *** | |
| 400 | | 411.3 | | ** | |
| 401 | | 363.3 | *** | *** | |
| 402 | | 439.5 | | ** | |
| 403 | | 453.5 | | ** | |
| 404 | | 425.5 | | * | |
| 405 | | 425.5 | | ** | |
| 406 | | 503.5 | | *** | |
| 407 | | 483.5 | | ** | |
| 408 | 231-235 | 358.1 | | ** | |
| 409 | 163-164 | 398.3 | | ** | |
| 410 | 139-141 | 359.2 | | ** | |
| 411 | 148-149 | 373.3 | | ** | |
| 412 | 143-144 | 373.3 | | * | |
| 413 | 184-185 | 370.4 | | *** | |
| 414 | 156-157 | 384.4 | | ** | |
| 415 | 163-165 | 384.4 | | *** | |
| 416 | 173-175 | 398.4 | | *** | |
| 417 | 199-201 | 398.4 | | *** | |
| 418 | 183-184 | 412.4 | | *** | |
| 419 | 213-215 | 398.4 | | ** | |
| 420 | 241-243 | 372.5 | | ** | |
| 421 | 214-216 | 406.3 | | * | |
| 422 | 259-261 | 386.5 | | ** | |
| 423 | 291-294 | 434.4 | | * | |
| 424 | 150-153 | 443.5 | | * | |
| 425 | 273-275 | 398.4 | | ** | |
| 426 | 178-180 | 327.2 | | ** | |
| 427 | 199-202 | 330.3 | | ** | |
| 428 | 144-146 | 319.2 | | ** | |
| | | [M-H] | | * | |
| 429 | 200-206 | 314.3 | | ** | |
| 430 | 180-186 | 372.4 | | ** | |
| | | [M-H] | | * | |
| 431 | 167-173 | 296.4 | | * | |
| 432 | 160-162 | 318.1 | | * | (DMSO, 300 MHz), δ 8.64 (t, J=5.4 Hz, 1H), 8.02 (d, J=8.1 Hz, 2H), 7.80-7.65 (m, 4H), 7.40-7.28 (m, 2H), 4.21 (q, J=6.9 Hz, 2H), 3.29 (q, J=7.2 Hz, 2H), 1.20-1.08 (m, 6H). |
| 433 | 187-189 | 329.9 | | * | (DMSO, 300 MHz), δ 8.61 (d, J=3.6 Hz, 1H), 7.79 (d, J=8.1 Hz, 2H), 7.76-7.64 (m, 4H), 7.40-7.27 (m, 2H), 4.20 (q, J=7.2 Hz, 2H), 2.88-2.82 (m, 1H), 1.17 (t, J=7.2 Hz, 3H), 0.69 (q, J=7.2 Hz, 2H), 0.56 (q, J=7.8 Hz, 2H). |
| 434 | 170-175 | 368.4 | | * | |
| 435 | 112-117 | 382.5 | | * | |
| 436 | 196-202 | 280.5 | | * | |

TABLE 1-continued

| Compound Number | Melting Point (° C.) | Mass Spec [M+H] | HCV-PV IC50 µM | Replicon IC5Os µM | NMR Data |
|---|---|---|---|---|---|
| 437 | 220-227 | 342.3 [M-H] | | * | |
| 438 | 188-194 | 356.3 [M-H] | | * | |
| 439 | 181-186 | 358.4 | | ** | |
| 440 | 177-181 | 370.3 [M-H] | | ** | |
| 441 | | 459.5 | | ** | |
| 442 | | 397.5 | | * | |
| 443 | | 411.5 | | * | |
| 444 | | 439.5 | | * | |
| 445 | | 453.5 | | ** | |
| 446 | | 503.5 | | * | |
| 447 | | 426.5 | | *** | |
| 448 | 301-303 | 436.5 | | * | $^1$H NMR (300 MHz, DMSO-$d_6$): δ 10.65 (1H, s), 7.94 (1H, s), 7.76 (1H, s), 7.48 (1H, d, J=8.5 Hz), 7.45 (2H, d, J=8.5 Hz), 7.33(2H, d, J=8.5 Hz), 7.21 (1H, d, J=2.0 Hz), 6.90 (1H, dd, J=8.5, 2.0 Hz), (3H, s), 4.13 (2H, q, J=7.0 Hz), 3.82 (3H, s), 3.66 (3H, s), 1.15 (3H, t, J=7.0 Hz). |
| 449 | 242-243 | 518.5 | | * | $^1$H NMR (300 MHz, DMSO-$d_6$): δ 10.59 (1H, s), 8.49 (1H, d, J=2.3 Hz), 7.81 (1H, dd, J=9.1, 2.3 Hz), 7.52-7.44 (3H, m), 7.29 (2H, d, J=8.5 Hz), 7.21 (1H, d, J=2.3 Hz), 6.90 (2H, d, J=8.8 Hz), 4.12 (2H, q, J=7.0 Hz), 3.82 (3H, s), 3.63-3.55 (8H, m), 1.12 (3H, t, J=7.0 Hz). |
| 450 | 217-220 | 402.5 | | ** | |
| 451 | 179-182 | 438.4 | | * | $^1$H NMR (300 MHz, DMSO-$d_6$): δ 10.87 (1H, s), 7.94 (1H, dt, J=5.0, 1.0 Hz), 7.66 (1H, dt, J=3.5, 1.2 Hz), 7.55-7.48 (3H, m), 7.33 (2H, d, J=8.0 Hz), 7.22 (1H, d, J=1.8 Hz), 7.14 (1H, ddd, J=5.0, 3.8, 1.0 Hz), 6.90 (1H, dt, J=8.8, 1.0 Hz), 4.13 (2H, q, J=7.3 Hz), 3.83 (3H, s), 1.13 (3H, t, J = 7.3 Hz). |
| 452 | 299-301 | 483.4 | | * | $^1$H NMR (300 MHz, DMSO-$d_6$): δ 10.62 (1H, s), 9.12 (1H, dd, J=4.1, 1.7 Hz), 8.53-8.45 (2H, m), 8.29 (1H, d, J=8.5 Hz), 7.78-7.68 (2H, m), 7.44 (1H, d, J=8.8 Hz), 7.36 (2H, d, J=8.8 Hz), 7.27 (2H,d, J=8.8 Hz), 7.16 (1H, d, J=2.0 Hz), 6.87 (1H, dd, J=8.8, 2.0 Hz), 4.04 (2H, q, J=7.0 Hz), 3.80 (3H, s), 1.06 (3H, t, J=7.0 Hz). |
| 453 | 198-200 | 416.5 | | ** | |
| 454 | 180-182 | 412.4 | | * | $^1$H NMR (300 MHz, $CDCl_3$): δ7.44-7.11 (4.8H, m), 6.97 (1.2H, d, J=8.4 Hz), 6.78-6.69 (2H, m), 4.00-3.90 (2H, m), 3.713 (1.2H, s), 3.707 (1.8H, s), 2.93 (1H, v br), 2.12 (1.8H, s), 2.09 (1.2H, s), 1.17 (1.2H, t, J=7.3 Hz), 1.14 (1.8H, t, J=7.3 Hz). |
| 455 | 221-223 | 414.4 | | * | |
| 456 | 157-159 | 357.5 | | ** | |
| 457 | 156-158 | 464.5 | | ** | |
| 458 | 272-273 | 496.5 | | * | $^1$H NMR (300 MHz, DMSO-$d_6$): δ 10.10 (1H, s), 8.62 (1H, d, J=8.2 Hz), 8.49-8.45 (2H, m), 8.27 (2H, d, J=8.8 Hz), 7.90 (2H, d, J=3.8 Hz), 7.72 (2H, d, J=8.8 Hz), 7.70-7.62 (1H, m), 7.55-7.49 (4H, m), 7.26 (1H, d, J = 2.0 Hz), 6.94 (1H, dd, J=8.8, 2.0 Hz), 4.27 (2H, q, J=7.0 Hz), 3.85 (3H, s), 1.24 (3H, t, J=7.0 Hz). |
| 459 | 158-163 | 368.5 | | ** | |
| 460 | oil | 368.3 [M-H] | | ** | |
| 461 | 200-205 | 432.3 | | *** | |
| 462 | 135-140 | 444.2 [M-H] | | *** | |

TABLE 1-continued

| Compound Number | Melting Point (° C.) | Mass Spec [M+H] | HCV-PV IC50 µM | Replicon IC5Os µM | NMR Data |
|---|---|---|---|---|---|
| 463 | 178-179 | 359.5 | | * | |
| 464 | 164-166 | 401.5 | | * | |
| 465 | 99-100 | 401.5 | | * | |
| 466 | 164-166 | 385.5 | | ** | |
| 467 | 169-170 | 399.5 | | ** | |
| 468 | 201-202 | 398.5 | ** | *** | |
| 469 | 243-245 | 384.5 | | ** | |
| 470 | 178-180 | 426.5 | | *** | |
| 471 | 154-156 | 412.2 | | *** | |
| 472 | 215-217 | 410.5 | | *** | |
| 473 | 189-191 | 424.5 | | *** | |
| 474 | 218-222 | 293.5 | | * | |
| 475 | 178-181 | 293.5 | | *** | |
| 476 | 175-178 | 340.4 | | ** | |
| 477 | 194-195 | 418.4 | | *** | |
| 478 | 172-175 | 469.5 | | *** | |
| 479 | 190-192 | 467.5 | | * | |
| 480 | 207-208 | 485.4 | | *** | |
| 481 | 209-211 | 482.5 | | * | |
| 482 | 128-130 | 471.5 | | ** | |
| 483 | 149-150 | 292.2 | | * | $^1$H NMR (300 MHz, $CDCl_3$): δ 7.32-7.25 (2H, m), 7.19 (1H, d, J=2.4 Hz), 6.97 (1H, dd, J=8.9, 2.4 Hz), 6.92-6.80 (3H, m), 4.17 (2H, q, J=7.3 Hz), 3.89 (3H, s), 3.80 (2H, v br), 1.34 (3H, t, J=7.3 Hz). |
| 484 | 156-157 | 334.2 | | * | $^1$H NMR (300 MHz, $CDCl_3$): δ 8.16 (1H, d, J=8.5 Hz), 8.00 (1H, d, J=8.7 Hz), 7.68 (1H, d, J=8.8 Hz), 7.60-7.50 (2H, m), 7.25 (1H, obscurred), 7.10 (1H, d, J=8.8 Hz), 5.20 (2H, q, J=7.3 Hz), 4.02 (3H, s), 1.55 (3H, t, J=7.3 Hz). |
| 485 | 128-133 | 440.2 | | * | |
| 486 | 116-123 | 454.2 | | ** | |
| 487 | 175-179 | 446.2 | | ** | |
| 488 | 158-164 | 460.2 | | *** | |
| 489 | | 418.5 | | ** | |
| 490 | | 404.5 | | ** | |
| 491 | | 445.2 | | * | |
| 492 | | 463.2 | | ** | |
| 493 | | 477.2 | | *** | |
| 494 | | 336.2 | | * | |
| 495 | 126-128 | 444.3 | | ** | |
| 496 | 236-239 | | | ** | |
| 497 | 235-239 | | | * | |
| 498 | 192-194 | 427.5 | | ** | |
| 499 | 235-250 | | | *** | |
| 500 | | 468.2 | | * | |
| 501 | | 420.2 | | * | |
| 502 | | 406.2 | | * | |
| 503 | | 406.2 | | * | |
| 504 | | 412.2 | | * | |
| 505 | 164-166 | 384.2 | | * | $^1$H NMR (300 MHz, $CDCl_3$): δ 7.52 (1H, t, J=7.9 Hz), 7.47 (1H, t, J=1.9 Hz), 7.36-7.30 (3H, m), 7.18 (1H, d, J=2.3 Hz), 7.00 (1H, dd, J=8.9, 2.3 Hz), 6.91 (1H, br s), 4.18 (2H, q, J=7.3 Hz), 3.90 (3H, s), 3.25 (2H, q, J=7.3 Hz), 1.43 (3H, t, J=7.3 Hz), 1.38 (3H, t, J=7.3 Hz) |
| 506 | 156-157 | 364.2 | | * | $^1$H NMR (300 MHz, $CDCl_3$): δ 7.67 (1H, s), 7.48-7.44 (2H, m), 7.33 (1H, d, J=9.0 Hz), 7.26-7.23 (1H, m), 7.19 (1H, d, J=2.3 Hz), 6.98 (1H, dd, J=9.0, 2.3 Hz), 6.79 (1H, s), 4.24 (2H, q, J=7.3 Hz), 4.19 (2H, q, J=7.3 Hz), 1.36 (3H, t, J=7.3 Hz), 1.32 (3H, t, J=7.3 Hz). |
| 507 | 152-153 | 378.2 | | * | $^1$H NMR (300 MHz, $CDCl_3$): δ 7.66 (1H, s), 7.46 (2H, d, J=5.0 Hz), 7.33 (1H, d, J=9.0 Hz), 7.26-7.21 (1H, m), 7.19 (1H, d, J=2.3 Hz), 6.98 (1H, dd, J=9.0, 2.3 Hz), 6.72 (1H, s), 5.03 (1H, hp, H = 6.1 Hz), 4.19 (2H, q, J=7.3 Hz), 3.89 (3H, |

TABLE 1-continued

| Compound Number | Melting Point (° C.) | Mass Spec [M+H] | HCV-PV IC50 µM | Replicon IC5Os µM | NMR Data |
|---|---|---|---|---|---|
| | | | | | s), 1.36 (3H, t, J=7.3 Hz), 1.30 (6H, d, J=6.1 Hz). |
| 508 | glass | 378.2 | | * | $^{1}$H NMR (300 MHz, $CDCl_3$): δ 7.67 (1H, s), 7.48-7.45 (2H, m), 7.33 (1H, d, J=9.0 Hz), 7.27-7.23 (1H, m), 7.19 (1H, d, J=2.3 Hz), 6.98 (1H, dd, J=9.0, 2.3 Hz), 6.77 (1H, s), 4.19 (2H, q, J=7.0 Hz), 4.14 (2H, t, J=6.7 Hz), 3.89 (3H, s), 1.72 (2H, m, J=7.0 Hz), 1.37 (3H, t, J=7.0 Hz), 0.99 (3H, t, J=6.5 Hz). |
| 509 | 92-95 | 412.1 | | * | $^{1}$H NMR (300 MHz, $CDCl_3$): δ 7.67 (1H, s), 7.48-7.45 (2H, m), 7.33 (1H, d, J=8.8 Hz), 7.27-7.24 (1H, m), 7.19 (1H, d, J=2.3 Hz), 6.99 (1H, dd, J=8.8, 2.3 Hz), 6.83 (1H, s), 4.35 (2H, t, J=6.0 Hz), 4.19 (2H, q, J=7.3 Hz), 3.89 (3H, s), 3.66 (2H, t, J=6.5 Hz), 2.16 (2H, p, J=6.1 Hz), 1.37 (3H, t, J=7.3 Hz). |
| 510 | 210-211 | 368.3 | | ** | $^{1}$H NMR (300 MHz, 9:1 $CDCl_3$-DMSO-$d_6$): δ 9.64 (1H, s), 7.28-7.17 (3H, m), 7.14 (1H, d, J=9.0 Hz), 7.04 (1H, d, J=7.3 Hz), 6.91 (1H, d, J=2.0 Hz), 6.75 (1H, dd, J=9.0, 2.0 Hz), 3.95 (2H, q, J=7.3 Hz), 3.66 (3H, s), 2.81 (3H, s), 1.15 (3H, t, J=7.3 Hz). |
| 511 | 146-148 | 377.3 | | * | $^{1}$H NMR (300 MHz, $CDCl_3$): δ 7.34-7.27 (2H, m), 7.19 (1H, d, J=2.3 Hz), 6.97 (1H, dd, J=8.8, 2.3 Hz), 6.88-6.79 (3H, m), 4.17 (2H, q, J=7.0 Hz), 3.89 (3H, s), 3.87 (2H, v br), 1.34 (3H, t, J=7.0 Hz). |
| 512 | 67-69 | 407.2 | | * | $^{1}$H NMR (300 MHz, $CDCl_3$): δ 10.06 (1H, s), 7.86 (1H, s), 7.56-7.47 (2H, m), 7.36-7.30 (3H, m), 7.19 (1H, d, J=2.0 Hz), 7.00-6.96 (1H, m), 4.62 (1H, br), 4.27 (2H, q, J=7.0 Hz), 4.18 (2H, q, J=7.0 Hz), 3.89 (3H, s), 1.37 (3H, t, J=7.0 Hz), 1.33 (3H, t, J=7.0 Hz). |
| 513 | 210-211 | 479.2 | | * | $^{1}$H NMR (300 MHz, 9:1 $CDCl_3$-DMSO-$d_6$): δ 8.44 (2H, d, J=7.0 Hz), 7.61 (1H, s), 7.45 (1H, s), 7.36-7.13 (3H, m), 7.10 (2H, d, J=8.8 Hz), 6.93 (1H, d, J=7.6 Hz), 6.89 (1H, d, J=7.9 Hz), 6.85 (1H, d, J=2.3 Hz), 6.69 (1H, dd, J=8.8, 2.3 Hz), 3.94 (2H, q, J = 7.0 Hz), 3.60 (3H, s), 1.08 (3H, t, J=7.0 Hz). $^{19}$F NMR (300 MHz, 9:1 $CDCl_3$-DMSO-$d_6$): δ −63.02 (3F, s). |
| 514 | 248-250 | 268.2 | | * | |
| 515 | 137-139 | 381.1 | | ** | |
| 516 | 155-156 | 395.3 | | ** | . $^{1}$H NMR (300 MHz, $CDCl_3$): δ 7.57 (1H, d, J=8.5 Hz), 7.45 (2H, d, J=8.2 Hz), 7.31 (2H, d, J=8.2 Hz), 7.25 (1H, s), 6.95 (1H, dd, J=9.1, 1.7 Hz), 6.67 (1H, s), 6.54 (1H, t, J=74.8 Hz), 6.48 (1H, s), 4.15 (2H, q), 3.23 (2H, q), 1.45 (3H, t, J=7.5 Hz), 1.32 (3H, t, J=7.2 Hz). |
| 517 | 160-161 | 409.1 | | * | |
| 518 | 197-199 | 392.1 | | ** | |
| 519 | 174-175 | 406.1 | | *** | |
| 520 | 175-177 | 420.0 | | *** | $^{1}$H NMR (300 MHz, $CDCl_3$): δ 7.73 (1H, d, J=8.4 Hz), 7.52 (2H, d, J=8.2 Hz), 7.39 (2H, d, J=8.2 Hz), 7.25 (1H, s), 7.13 (1H, dd, J=7.5, 2.4 Hz), 6.96 (1H, s), 6.56 (1H, t, J=74.1 Hz), 4.16 (2H, q), 3.26 (2H, q), 1.46 (3H, t, J=7.5 Hz), 1.32 (3H, t, J=6.9 Hz). |
| 521 | 184-186 | [NH-] 418.1 | | *** | |

TABLE 1-continued

| Compound Number | Melting Point (° C.) | Mass Spec [M+H] | HCV-PV IC50 μM | Replicon IC5Os μM | NMR Data |
|---|---|---|---|---|---|
| 522 | 187-188 | [NH-] 432.1 | | *** | |
| 523 | 190-192 | [NH-] 418.1 | | *** | |
| 524 | 186-188 | 434.2 | | *** | |
| 525 | | 458.2 | | ** | |
| 526 | | 490.3 | | *** | |
| 527 | | 493.3 | | ** | |
| 528 | | 475.3 | | ** | |
| 529 | | 459.2 | | ** | |
| 530 | | 461.3 | | *** | |
| 531 | | 479.5 | | ** | |
| 532 | | 458.2 | | ** | |
| 533 | | 490.3 | | ** | |
| 534 | | 493.3 | | *** | |
| 535 | | 475.3 | | *** | |
| 536 | | 459.2 | | ** | |
| 537 | | 461.3 | | *** | |
| 538 | | 459.2 | | ** | |
| 539 | | 477.3 | | *** | |
| 540 | 182-183 | 385.2 | | ** | |
| 541 | 149-151 | 399.2 | | * | |
| 542 | 186-188 | 413.2 | | ** | |
| 543 | 197-200 | 324.2 | | ** | |
| 544 | 263-265 | 392.2 | *** | *** | |
| 545 | 203-205 | 382.2 | ** | ** | |
| 546 | 208-210 | 396.2 | | *** | |
| 547 | 180-182 | 410.2 | | *** | |
| 548 | 171-174 | 402.1 | | ** | |
| 549 | 150-153 | 416.1 | | *** | |
| 550 | 183-185 | 430.0 | | ** | |
| 551 | 187-190 | 462.3 | | ** | |
| 552 | 185-188 | 428.1 | | *** | |
| 553 | | 412.2 | | * | |
| 554 | | 388.2 | | * | |
| 555 | | 408.2 | | * | |
| 556 | | 440.2 | | * | |
| 557 | | 454.3 | | ** | |
| | | [M-H] | | | |
| 558 | 87-90 | 406.2 | | ** | |
| 559 | 92-94 | 386.2 | | * | |
| 560 | 207-210 | 434.2 | | * | |
| 561 | 182-185 | 398.2 | | * | |
| 562 | oil | 420.1 | | *** | |
| 563 | 210-212 | 436.1 | | ** | |
| 564 | 210-211 | 377.1 | | ** | $^{1}$H NMR (DMSO, 300 MHz), δ 8.61 (t, J=2.4 Hz, 1H), 8.35 (br, 2H), 8.04 (d, J=8.4 Hz, 2H), 7.73 (d, J=8.4 Hz, 2H), 7.52 (d, J=8.7 Hz, 2H), 7.26 (d, J=2.4 Hz, 1H), 6.94 (dd, J=8.7 Hz and 2.1 Hz, 1H), 4.20 (q, J=7.5 Hz, 2H), 3.83 (s, 3H), 3.55 (q, J=6.0 Hz, 2H), 3.09 (br, 2H), 2.60-2.53 (m, 3H), 1.15(t, J=7.2 Hz, 3H). |
| 565 | 228-229 | 304.2 | | * | $^{1}$H NMR (DMSO, 300 MHz), δ 10.23 (s, 1H), 7.79 (d, J=8.4 Hz, 2H), 7.69 (d, J=7.2 Hz, 1H), 7.62 (d, J=7.8 Hz, 1H), 17.54 (d, J=7.8 Hz, 2H), 7.38-7.22 (m, 2H), 4.20 (q, J=7.2 Hz, 2H), 2.07 (s, 3H), 1.19 (t, J=7.2 Hz, 3H). |
| 566 | | 334.1 | | * | $^{1}$H NMR ($CDCl_3$, 300 MHz), δ 8.42 (s, 1H), 7.80-7.76 (m, 3H), 7.54 (d, J=8.4 Hz, 2H), 7.44 (d, J=7.8 Hz, 1H), 7.36-7.26 (m, 2H), 4.20 (q, J=7.2 Hz, 2H), 4.07 (s, 2H), 3.55 (s, 3H), 1.36 (t, J=7.2 Hz, 3H). |
| 567 | 238.2-238.6 | 344.2 | | ** | $^{1}$H NMR ($CDCl_3$, 300 MHz), δ 7.78-7.73 (m, 2H), 7.60 (d, J=5.7 Hz, 2H), 7.51 (d, J=5.7 Hz, 1H), 7.38-7.28 (m, 2H), 4.20 (q, J=6.8 Hz, 2H), 3.26 (br, 1H), 2.43 (br, 2H), 2.27 (br, 2H), 2.06-1.90 (m, 2H), 1.36 (t, J=6.9 Hz, 3H). |
| 568 | 195-200 | 320.0 | | * | $^{1}$H NMR ($CDCl_3$, 400 MHz), δ 7.99 (d, J=8.4 Hz, 2H), 7.66 (d, J=7.6 Hz, 2H), 7.35 (d, J=9.2 Hz, 1H), 7.20 (s, 1H), 7.01 (d, J=9.0 Hz, 1H), 6.15 (br, 1H), |

TABLE 1-continued

| Compound Number | Melting Point (° C.) | Mass Spec [M+H] | HCV-PV IC50 μM | Replicon IC5Os μM | NMR Data |
|---|---|---|---|---|---|
| | | | | | 5.65 (br, 1H), 4.17 (q, J=6.8 Hz, 2H), 3.90 (s, 3H), 1.36 (t, J=7.6 Hz, 3H). |
| 569 | | 348.1 | | ** | $^1$H NMR ($CDCl_3$, 400 MHz), δ 7.93 (d, J=8.4 Hz, 2H), 7.62 (d, J=8.0 Hz, 2H), 7.34 (d, J=8.8 Hz, 1H), 7.19 (d, J=2.0 Hz, 1H), 7.01 (dd, J=8.8 Hz and J=2.4 Hz, 1H), 6.19 (br, 1H), 4.16 (q, J=7.2 Hz, 2H), 3.90 (s, 3H), 3.56-3.52 (m, 2H), 1.38-1.23 (m, 6H). |
| 570 | 220-222 | 362.1 | | ** | $^1$H NMR ($CDCl_3$, 300 MHz), δ 7.92 (d, J=8.1 Hz, 2H), 7.62 (d, J=8.1 Hz, 2H), 7.34 (d, J=9.0 Hz, 111), 7.19 (d, J=2.1 Hz, 1H), 7.00 (dd, J=9.0 Hz and 2.4 Hz, 1H), 6.02 (d, J=7.8 Hz, 1H), 4.35 (m, 1H), 4.16 (q, J=7.2 Hz, 2H), 3.90 (s, 3H), 1.36-1.26 (m, 9H). |
| 571 | | 360.0 | | ** | $^1$H NMR ($CDCl_3$, 400 MHz), δ 7.91 (d, J=8.0 Hz, 2H), 7.61 (d, J=8.0 Hz, 2H), 7.34 (d, J=8.8 Hz, 1H), 7.19 (d, J=2.0 Hz, 1H), 7.01 (dd, J=9.2 Hz and 2.4 Hz, 1H), 6.34 (s, 1H), 4.15 (q, J=7.2 Hz, 2H), 3.90 (s, 3H), 2.97-2.93 (m, 1H), 1.34 (t, J=7.2 Hz, 3H), 0.66 (q, J=7.2 Hz, 2H), 0.07 (t, J=2.1 Hz, 2H). |
| 572 | 168-171 | 378.0 | | ** | $^1$H NMR ($CDCl_3$, 300 MHz), δ 7.96 (d, J=8.4 Hz, 2H), 7.63 (d, J=8.4 Hz, 2H), 7.34 (d, J=8.7 Hz, 1H), 7.19 (d, J=2.1 Hz, IH), 7.02 (dd, J=8.4 Hz and 2.4 Hz, 1H), 6.60 (br, 1H), 4.16 (q, J=6.6 Hz, 2H), 3.90 (s, 3H), 3.68 (q, J=4.5 Hz, 2H), 3.59 (t, J=4.8 Hz, 2H), 3.41 (s, 3H), 1.35 (t, J=6.9 Hz, 3H). |
| 573 | | 417.2 | | * | $^1$H NMR ($CDCl_3$, 400 MHz), δ 7.59 (s, 4H), 7.34 (d, J=8.8 Hz, 1H), 7.20 (s, 1H), 7.01 (d, J=8.4 Hz, 1H), 4.15 (q, J=6.4 Hz, 2H), 3.90 (s, 3H), 3.90-3.79 (m, 2H), 3.60 (br, 1H), 3.54 (q, J=5.6 Hz, 1H), 2.78 (br, 1H), 2.69-2.67 (m, 1H), 2.61 (br, 2H), 2.41 (d, J=18.4 Hz, 3H), 2.04 (br, 1H), 1.92 (br, 1H), 1.34 (t, J=6.8 Hz, 3H). |
| 574 | 155-161 | 427.4 | | * | |
| 575 | 144-146 | 345.2 | | ** | |
| 576 | 141-142 | 425.4 | | * | |
| 577 | 171-173 | 345.4 | | ** | |
| 578 | 171-173 | 317.4 | | ** | |
| 579 | 178-179 | 368.5 [M-H] | | ** | |
| 580 | 198-200 | 370.4 | | *** | |
| 581 | | 378.5 | | ** | |
| 582 | | 392.5 | | ** | |
| 583 | | 410.4 | | ** | |
| 584 | | 426.4 | | * | |
| 585 | | 406.5 | | ** | |
| 586 | | 440.4 | | ** | |
| 587 | | 406.5 | | ** | |
| 588 | | 402.5 | | * | |
| 589 | | 422.5 | | ** | |
| 590 | | 446.5 | | ** | |
| 591 | | 420.5 | | * | |
| 592 | | 416.4 | | * | |
| 593 | | 454.5 | | * | |
| 594 | | 412.4 | | * | |
| 595 | | 420.5 | | * | |
| 596 | | 404.4 | | ** | |
| 597 | | 418.5 | | * | |
| 598 | 169-170 | 382.5 | | * | $^1$H NMR (300 MHz, $CDCl_3$): δ 7.64 (1H, d, J=8.8 Hz), 7.53 (1H, t, J=7.9 Hz), 7.46 (1H, t, J=1.9 Hz), 7.34-7.29 (2H, m), 6.97 (1H, dd, J=8.8, 2.3 Hz), 6.95 (1H, s), 6.86 (1H, d, J=2.3 Hz), 4.08 (2H, t, J=7.6 Hz), 3.91 (3H, s), 3.13 (3H, s), 1.75 (2H, hx, J=6.6 Hz), 0.80 (3H, t, J=7.3 Hz). |

TABLE 1-continued

| Compound Number | Melting Point (° C.) | Mass Spec [M+H] | HCV-PV IC50 μM | Replicon IC5Os μM | NMR Data |
|---|---|---|---|---|---|
| 599 | 163-164 | 398.4 | | * | $^1$H NMR (300 MHz, $CDCl_3$): δ 7.64 (1H, d, J=8.8 Hz), 7.51 (1H, dd, J=8.5, 7.3 Hz), 7.44 (1H, t, J=1.8 Hz), 7.30 (2H, dd, J=7.9, 2.0 Hz), 6.97 (1H, dd, J=8.8, 2.3 Hz), 6.86 (1H, d, J=2.3 Hz), 6.85 (1H, s), 4.08 (2H, t, J=7.6 Hz), 3.91 (3H, s), 3.25 (2H, q, J=7.3 Hz), 1.75 (2H, hx, J=7.6 Hz), 1.42 (3H, t, J=7.5 Hz), 0.80 (3H, t, J=7.4 Hz). |
| 600 | 144-145 | 391.5 | | * | $^1$H NMR (300 MHz, $CDCl_3$): δ 7.60 (1H, d, J=8.8 Hz), 7.57-7.54 (1H, m), 7.35-7.31 (2H, m), 7.13-7.09 (1H, m), 6.94 (1H, dd, J=8.8, 2.0 Hz), 6.84 (1H, d, J=2.0 Hz), 4.07 (2H, t, J=7.4 Hz), 3.89 (3H, s), 3.21 (2H, t, J=7.0 Hz), 1.68 (2H, hx, J=7.3 Hz), 1.53 (2H, hx, J=7.3 Hz), 0.91 (3H, t, J=7.3 Hz), 0.73 (3H, t, J=7.4 Hz). |
| 601 | 195-200 | 400.4 [M-H] | | *** | |
| 602 | 179-184 | 398.4 [M-H] | | *** | |
| 603 | | 422.4 | | * | |
| 604 | | 410.3 | | * | |
| 605 | 175-180 | 419.4 | | * | |
| 606 | 166-170 | 433.4 | | *** | |
| 607 | 189-194 | 449.5 | | *** | |
| 608 | 223-228 | 452.9 | | ** | |
| 609 | 230-234 | 439.4 | | ** | |
| 610 | 226-231 | 424.8 | | ** | |
| 611 | 126-128 | 396.4 | | ** | |
| 612 | 198-200 | 410.4 | | ** | |
| 613 | 198-200 | [NH-] 430.4 | | *** | |
| 614 | 176-177 | [NH-] 444.4 | | *** | |
| 615 | 220-225 | 440.3 [M-H] | | * | |
| 616 | 143-149 | 414.4 [M-H] | | *** | |
| 617 | 164-167 | 433.8 [M-H] | | *** | |
| 618 | 205-211 | 368.4 | | *** | |
| 619 | 201-206 | 382.3 | | ** | |
| 620 | 215-223 | 367.4 | | ** | |
| 621 | 187-188 | 412.4 | | ** | $^1$H NMR (300 MHz, $CDCl_3$): δ 7.64 (1H, d, J=8.8 Hz), 7.50 (2H, d, J=8.5 Hz), 7.36 (2H, d, J=8.5 Hz), 6.97 (1H, dd, J=8.8, 2.3 Hz), 6.86 (1H, d, J=2.3 Hz), 6.79 (1H, s), 4.05 (2H, t, J=7.6 Hz), 3.91 (3H, s), 3.23-3.17 (2H, m), 1.93 (2H, hx, J = 7.3 Hz), 1.73 (2H, hx, J=7.6 Hz), 1.09 (3H, t, J=7.4 Hz), 0.79 (3H, t, J=7.4 Hz). |
| 622 | 182-183 | 412.4 | | ** | $^1$H NMR (300 MHz, $CDCl_3$): δ 7.63 (1H, d, J=8.8 Hz), 7.48 (2H, d, J=8.5 Hz), 7.38 (2H, d, J=8.5 Hz), 6.96 (1H, dd, J=8.8, 2.3 Hz), 6.86 (1H, d, J=2.3 Hz), 6.83 (1H, s), 4.05 (2H, t, J=7.6 Hz), 3.90 (3H, s), 3.43 (1H, hp, J=6.6 Hz), 1.73 (2H, hx, J=7.6 Hz), 1.46 (6H, d, J= 6.6 Hz), 0.79 (3H, t, J = 7.5 Hz). |
| 623 | 217-218 | 460.4 | | ** | $^1$H NMR (300 MHz, $CDCl_3$): δ 7.65 (1H, d, J=8.8 Hz), 7.47 (2H, d, J=8.5 Hz), 7.40-7.28 (5H, m), 7.25 (2H, d, J=8.5 Hz), 6.97 (1H, dd, J=8.8, 2.3 Hz), 6.86 (1H, d, J=2.3 Hz), 6.55 (1H, s), 4.45 (2H, s), 4.05 (2H, t, J=7.6 Hz), 3.91 (3H, s), 1.74 (2H, hx, J=7.3 Hz), 0.80 (3H, t, J = 7.4 Hz). |

TABLE 1-continued

| Compound Number | Melting Point (° C.) | Mass Spec [M+H] | HCV-PV IC50 µM | Replicon IC5Os µM | NMR Data |
|---|---|---|---|---|---|
| 624 | 187-188 | 378.5 | | ** | $^1$H NMR (300 MHz, $CDCl_3$): δ 7.63 (1H, d, J=8.5 Hz), 7.57 (2H, d, J=8.8 Hz), 7.46 (2H, d, J=8.8 Hz), 6.95 (1H, dd, J=8.8, 2.3 Hz), 6.85 (1H, d, J=2.3 Hz), 6.79 (1H, s), 4.26 (2H, q, J=7.0 Hz), 4.05 (2H, t, J=7.5 Hz), 3.90 (3H, s), 1.72 (2H, hx, J=7.6 Hz), 1.34 (3H, t, J=7.0 Hz), 0.78 (3H, t, J=7.4 Hz). |
| 625 | 152-153 | 392.4 | | *** | $^1$H NMR (300 MHz, $CDCl_3$): δ 7.63 (1H, d, J=8.5 Hz), 7.57 (2H, d, J=8.5 Hz), 7.46 (2H, d, J=8.5 Hz), 6.95 (1H, dd, J=8.5, 2.3 Hz), 6.85 (1H, d, J=2.3 Hz), 6.77 (1H, s), 4.17 (2H, t, J=6.7 Hz), 4.05 (2H, t, J=7.4 Hz), 3.90 (3H, s), 1.73 (2H, hx, J=7.3 Hz), 1.00 (3H, t, J=7.4 Hz), 0.78 (3H, t, J=7.4 Hz). |
| 626 | 193-194 | 377.5 | | ** | $^1$H NMR (300 MHz, $CDCl_3$): δ 7.61 (1H, d, J=8.5 Hz), 7.52 (2H, d, J=8.8 Hz), 7.41 (2H, d, J=8.8 Hz), 7.30 (1H, br), 6.96 (1H, dd, J=8.8, 2.0 Hz), 6.86 (1H, d, J=2.0 Hz), 4.05 (2H, t, J=7.6 Hz), 3.90 (3H, s), 3.32 (2H, q, J=7.3 Hz), 1.71 (2H, hx, J=7.3 Hz), 1.19 (3H, t, J=7.3 Hz), 0.77 (3H, t, J=7.3 Hz). |
| 627 | 188-189 | 391.5 | | *** | $^1$H NMR (300 MHz, $CDCl_3$): δ 7.61 (1H, d, J=8.5 Hz), 7.52 (2H, d, J=8.8 Hz), 7.41 (2H, d, J=8.8 Hz), 7.34 (1H, br), 6.96 (1H, dd, J=8.5, 2.0 Hz), 6.86 (1H, d, J=2.0 Hz), 4.05 (2H, t, J=7.4 Hz), 3.90 (3H, s), 3.24 (2H, t, J=7.0 Hz), 1.72 (2H, hx, J=7.6 Hz), 1.57 (2H, hx, J=7.0 Hz), 0.95 (3H, t, J=7.3 Hz), 0.77 (3H, t, J=7.3 Hz). |
| 628 | 221-226 | 381.4 | | ** | |
| 629 | 204-210 | 436.3 | | * | |
| 630 | 205-210 | 416.3 | | ** | |
| 631 | 177-182 | 428.5 [M-H] | | ** | |
| 632 | 176-178 | 366.4 [M-H] | | ** | |
| 633 | 159-161 | 380.5 [M-H] | | ** | |
| 634 | 163-165 | 396.3 | | ** | |
| 635 | 200-201 | 392.5 [M-H] | | *** | |
| 636 | 97-89 | 428.4 [M-H] | | *** | |
| 637 | | 398.4 | | *** | |
| 638 | | 390.5 | | * | |
| 639 | 159-160 | 412.5 | | * | $^1$H NMR (300 MHz, $CDCl_3$): δ 7.63 (1H, d, J=8.8 Hz), 7.50 (1H, t, J=7.9 Hz), 7.44 (1H, t, J=1.8 Hz), 7.33-7.28 (2H, m), 7.18 (1H, s), 6.96 (1H, dd, J=8.8, 2.3 Hz), 6.86 (1H, d, J=2.3 Hz), 4.08 (2H, t, J=7.6 Hz), 3.90 (3H, s), 3.22-3.16 (2H, m), 1.90 (2H, hx, J=7.8 Hz), 1.74 (2H, hx, J=7.6 Hz), 1.05 (3H, t, J=7.4 Hz), 0.79 (3H, t, J=7.5 Hz). |
| 640 | 197-198 | 396.5 | | ** | $^1$H NMR (300 MHz, $CDCl_3$): δ 7.63 (1H, d, J=8.8 Hz), 7.58 (2H, d, J=8.8 Hz), 7.48 (2H, d, J=8.8 Hz), 6.95 (1H, dd, J=8.8, 2.0 Hz), 6.92 (1H, s), 6.85 (1H, d, J=2.0 Hz), 4.62 (2H, dt, J=74.3, 4.2 Hz), 4.50 (2H, dt, J=55.8, 4.2 Hz), 4.05 (2H, t, J=7.6 Hz), 3.90 (3H, s), 1.72 (2H, hx, J = 7.6 Hz), 0.78 (3H, t, J=7.4 Hz). $^{19}$F NMR (300 MHz, $CDCl_3$): δ 5.11 (1F, m). |
| 641 | 177-178 | 392.5 | | ** | $^1$H NMR (300 MHz, $CDCl_3$): δ 7.63 (1H, d, J=8.8 Hz), 7.57 (2H, d, |

TABLE 1-continued

| Compound Number | Melting Point (° C.) | Mass Spec [M+H] | HCV-PV IC50 μM | Replicon IC5Os μM | NMR Data |
|---|---|---|---|---|---|
| | | | | | J=8.5 Hz), 7.46 (2H, d, J=8.5 Hz), 6.95 (1H, dd, J=8.5, 2.0 Hz), 6.85 (1H, d, J=2.0 Hz), 6.72 (1H, s), 5.05 (1H, hp, J=7.1 Hz), 4.05 (2H, t, J = 7.6 Hz), 3.90 (3H, s), 1.72 (2H, hx, J=7.6 Hz), 1.33 (6H, d, J= 7.1 Hz), 0.78 (3H, t, J=7.4 Hz). |
| 642 | 152-153 | 426.5 | | | $^1$H NMR (300 MHz, $CDCl_3$): δ 7.66-7.57 (3H, m), 7.53 (2H, d, J=8.8 Hz), 6.97 (1H, dd, J=8.8, 2.0 Hz), 6.86 (1H, d, J = 2.0 Hz), 4.07 (2H, t, J=7.4 Hz), 3.91 (3H, s), 3.46 (3H,s), 3.40 (1H, hp, J = 7.0 Hz), 1.74 (2H, hx, J = 7.3 Hz), 1.40 (6H, d, J=7.0 Hz), 0.79 (3H, t, J =7.4 Hz). |
| 643 | 150-151 | 412.4 | | ** | $^1$H NMR (300 MHz, $CDCl_3$): δ 7.64 (1H, d, J=8.8 Hz), 7.58 (2H, d, J=9.0 Hz), 7.53 (2H, d, J = 9.0 Hz), 6.97 (1H, dd, J=8.8, 2.0 Hz), 6.86 (1H, d, J=2.0 Hz), 4.07 (2H, t, J=7.6 Hz), 3.91 (3H, s), 3.44 (3H, s), 3.12 (2H, q, J=7.6 Hz), 1.75 (2H, hx, J=7.6 Hz), 1.41 (3H, t, J=7.3 Hz), 0.79 (3H, t, J=7.5 Hz). |
| 644 | | 348.2 | | * | (DMSO, 300 MHz), δ 10.12 (s, 1H), 7.77 (d, J=8.4 Hz, 2H), 7.58 (d, J=8.7 Hz, 1H), 7.49 (d, J=8.7 Hz, 2H), 7.03 (s, IH), 6.92 (d, J=8.4 Hz, 1H), 4.13 (q, J=6.9 Hz, 2H), 3.77 (s, 3H), 2.31 (q, J=7.5 Hz, 2H), 1.16 (t, J=8.7 Hz, 3H), 1.06 (t, J=7.5 Hz, 3H). |
| 645 | 242-244 | 410.2 | | * | (DMSO, 300 MHz), δ 10.33 (s, 1H), 7.99 (d, J=8.4 Hz, 2H), 7.72 (d, J=7.8 Hz, 1H), 7.64-7.56 (m, 4H), 7.51 (d, J=1.8 Hz, 1H), 7.36-7.07 (m, 2H), 7.06 (d, J=8.1 Hz, IH), 6.12 (s, 2H), 4.22 (q, J=7.2 Hz, 2H), 1.21 (t, J=7.2 Hz, 3H). |
| 646 | | 356.2 | | ** | (DMSO, 300 MHz), δ10.47 (s, 1H), 8.01-7.96 (m, 3H), 7.72 (d, J=8.4 Hz, 1H), 7.65-7.59 (m, 3H), 7.38-7.29 (m, 3H), 6.71 (dd, J=3.9 Hz and J=1.8 Hz, 1H), 4.22 (q, J=6.9 Hz, 2H), 1.21 (t, J=7.2 Hz, 3H). |
| 647 | | 430.1 | | * | (DMSO, 300 MHz), δ 10.56 (s, 1H), 8.12 (d, J=8.4 Hz, 2H), 7.84-7.76 (m, 4H), 7.67 (d, J=9.0 Hz, IH), 7.41 (d, J=9.0 Hz, 2H), 7.11 (d, J=8.7 Hz, 1H), 6.98 (dd, J=8.7 Hz and 2.1 Hz, 1H), 4.22 (q, J=7.2 Hz, 2H), 3.82 (s, 3H), 1.18 (t, J=7.2 Hz, 3H). |
| 648 | | 464.0 | | ** | (DMSO, 300 MHz), δ 10.69 (s, 1H), 8.18-8.09 (m, 3H), 7.82-7.72 (m, 3H), 7.70-7.56 (m, 2H), 7.11 (d, J=2.1 Hz, 1H), 6.96 (dd, J=8.1 Hz and 2.4 Hz, IH), 4.22 (q, J=7.2 Hz, 2H), 3.82 (s, 3H), 1.19 (t, J=7.2 Hz, 3H). |
| 649 | 210-212 | 410.5 | | ** | $^1$H NMR (300 MHz, DMSO-$d_6$): δ 7.60 (2H, d, J=8.8 Hz), 7.50 (1H, d, J=8.8 Hz), 7.36 (2H, d, J=8.8 Hz), 7.25 (1H, d, J=2.1 Hz), 6.91 (1H, dd, J= 8.8, 2.1 Hz), 4.15 (2H, t, J=7.3 Hz), 3.833 (2H, t, J=6.4 Hz), 3.831 (3H, s), 3.57 (2H, t, J=7.3 Hz), 2.45-2.40 (2H, m), 1.54 (2H, hx, J = 7.3 Hz), 0.62 (3H, t, J=7.3 Hz). |
| 650 | 165-166 | 384.5 | | ** | $^1$H NMR (300 MHz, $CDCl_3$): δ 7.64 (1H, d, J=8.8 Hz), 7.54 (4H, s), 6.96 (1H, dd, J=8.8, 2.0 Hz), 6.87 (1H, d, J=2.0 Hz), 4.84 (1H, br t, J=6.1 Hz), 4.41 (2H, d, J=6.1 Hz), 4.13 (2H, q, J=7.3 Hz), 3.90 (3H, s), 2.97 (3H, s), 1.33 (3H, t, J=7.3 Hz). |

TABLE 1-continued

| Compound Number | Melting Point (° C.) | Mass Spec [M+H] | HCV-PV IC50 μM | Replicon IC5Os μM | NMR Data |
|---|---|---|---|---|---|
| 651 | 146-147 | 384.5 | | ** | $^1$H NMR (300 MHz, $CDCl_3$): δ 7.63 (1H, d, J=8.8 Hz), 7.56-7.45 (4H, m), 6.96 (1H, dd, J=8.8, 2.0 Hz), 6.87 (1H, d, J=2.0 Hz), 4.89 (1H, br t, J=5.9 Hz), 4.42 (2H, d, J=5.9 Hz), 4.13 (2H, t, J=7.0 Hz), 3.91 (3H, s), 2.94 (3H, s), 1.34 (3H, t, J=7.0 Hz). |
| 652 | 191-194 | 418.5 | | *** | |
| 653 | foam | 469.5 | | * | |
| 654 | 197-201 | 485.5 | | * | |
| 655 | 184-187 | 424.2 | | * | |
| 656 | 159-161 | 346.2 | | * | |
| 657 | 196-198 | 388.2 | | * | |
| 658 | 203-205 | 400.5 | | * | |
| 659 | 175-177 | 458.4 | | ** | |
| 660 | 215-217 | 394.5 | | ** | |
| 661 | 156-158 | 458.5 | | *** | |
| 662 | | 398.4 | | *** | |
| 663 | | 308.3 | | * | |
| 664 | | 424.4 | | * | |
| 665 | | 444.5 | | * | |
| 666 | 207-209 | 424.4 | | *** | |
| 667 | 242-244 | 424.4 | | *** | |
| 668 | 171-174 | 483.0 | | ** | |
| 669 | 213-215 | 461.5 | | *** | $^1$H NMR (300 MHz, 9:1 $CDCl_3$-DMSO-$d_6$): δ 9.73 (1H, s), 8.76 (1H, s), 8.54 (1H, d, J=5.2 Hz), 8.11 (1H, d, J=7.9 Hz), 7.58 (1H, dd, J=7.9, 5.2 Hz), 7.45 (1H, d, J=9.3 Hz), 7.28 (4H, s), 6.88-6.82 (2H, m), 5.15 (2H, s), 3.97 (2H, q, J=7.2 Hz), 2.99 (2H, q, J=7.3 Hz), 1.21 (3H, t, J=7.3 Hz), 1.15 (3H, t, J=7.2 Hz). |
| 670 | 231-233 | 473.4 | | *** | $^1$H NMR (300 MHz, 9:1 $CDCl_3$-DMSO-$d_6$): δ 9.59 (1H, s), 8.87 (1H, s), 8.60 (1H, d, J=5.2 Hz), 8.35 (1H, d, J=7.6 Hz), 7.80 (1H, dd, J=7.6, 5.2 Hz), 7.45 (1H, d, J=8.5 Hz), 7.32-7.23 (4H, m), 6.88 (1H, d, J=2.0 Hz), 6.83 (1H, dd, J=8.5, 2.0 Hz), 5.21 (2H, s), 3.97 (2H, q, J=7.3 Hz), 2.44-2.35 (1H, m), 1.14 (3H, t, J=7.3 Hz), 1.07-0.99 (2H, m), 0.84-0.78 (2H, m). |
| 671 | 221-222 | 461.4 | | *** | $^1$H NMR (300 MHz, 9:1 $CDCl_3$-DMSO-$d_6$): δ 9.72 (1H, s), 8.56 (1H, d, J=5.0 Hz), 8.13 (1H, br t, J=7 Hz), 7.87 (1H, d, J=7.6 Hz), 7.53-7.50 (1H, m), 7.41 (1H, d, J=8.5 Hz), 7.25 (4H, s), 7.01 (1H, d, J=2.0 Hz), 6.86 (1H, dd, J=8.5, 2.0 Hz), 5.50 (2H, s), 3.98 (2H, q, J=7.3 Hz), 2.97 (2H, q, J=7.3 Hz), 1.19 (3H, t, J=7.3 Hz), 1.11 (3H, t, J=7.3 Hz). |
| 672 | 165-166 | 415.5 | | *** | $^1$H NMR (300 MHz, $CDCl_3$): δ 7.65 (1H, d, J=8.8 Hz), 7.55 (4H, s), 6.97 (1H, dd, J=8.8, 2.3 Hz), 6.88 (1H, d, J=2.3 Hz), 4.41 (2H, s), 4.14 (2H, q, J=7.3 Hz), 3.91 (3H, s), 2.91 (3H, s), 2.86 (3H, s), 1.35 (3H, t, J=7.3 Hz). |
| 673 | 131-132 | 398.4 | | * | $^1$H NMR (300 MHz, $CDCl_3$): δ 7.65 (1H, d, J=8.8 Hz), 7.57-7.48 (4H, m), 6.97 (1H, dd, J=8.8, 2.0 Hz), 6.88 (1H, d, J=2.0 Hz), 4.42 (2H, s), 4.15 (2H, q, J=7.3 Hz), 3.91 (3H, s), 2.89 (3H, s), 2.87 (3H, s), 1.37 (3H, t, J=7.3 Hz). |
| 674 | 159-160 | 414.4 | | * | $^1$H NMR (300 MHz, 9:1 $CDCl_3$-DMSO-$d_6$): δ 9.67 (1H, s), 7.36 (1H, d, J=8.8 Hz), 7.31 (2H, d, J=8.8 Hz), 7.23 (2H, d, J=8.8 Hz), 6.76 (1H, d, J =2.0 Hz), 6.72 (1H, dd, |

TABLE 1-continued

| Compound Number | Melting Point (° C.) | Mass Spec [M+H] | HCV-PV IC50 µM | Replicon IC5Os µM | NMR Data |
|---|---|---|---|---|---|
| | | | | | J=8.8, 2.0 Hz), 4.05 (2H, t, J=5.6 Hz), 3.68 (3H, s), 3.44 (2H, t, J=5.6 Hz), 3.00 (3H, s), 2.95 (2H, q, J=7.3 Hz), 1.17 (3H, t, J=7.3 Hz). |
| 675 | | 460.4 | | ** | $^1$H NMR (300 MHz, 9:1 $CDCl_3$-DMSO-$d_6$): δ 9.83 (1H, s), 7.61-7.27 (5H, m), 6.82-6.78 (2H, m), 4.10 (2H, t, J=5.6 Hz), 3.74 (3H, s), 3.56-3.47 (4H, m), 3.16 (2H, t, J=7.3 Hz), 3.06 (3H, s), 2.21-2.01 (2H, m). |
| 676 | 174-175 | 394.4 | | ** | $^1$H NMR (300 MHz, 9:1 $CDCl_3$-DMSO-$d_6$): 5 8.77 (1H, s), 7.51 (2H, d, J=8.5 Hz), 7.41 (1H, d, J=8.5 Hz), 7.31 (2H, d, J=8.5 Hz), 6.80 (1H, d, J=2.0 Hz), 6.77 (1H, dd, J=8.5, 2.0 Hz), 4.12-4.04 (4H, m), 3.72 (3H, s), 3.46 (2H, t, J=5.6 Hz), 3.04 (3H, s), 1.18 (3H, t, J=7.2 Hz). |
| 677 | 133-134 | 408.4 | | ** | $^1$H NMR (300 MHz, $CDCl_3$): δ 7.64-7.51 (5H, m), 6.98-6.94 (2H, m), 6.78 (1H, s), 4.25 (2H, t, J=5.7 Hz), 4.17 (2H, t, J=6.7 Hz), 3.90 (3H, s), 3.63 (2H, t, J=5.7 Hz), 3.22 (3H, s), 1.73 (2H, hx, J=7.3 Hz), 1.00 (3H, t, J=7.4 Hz). |
| 678 | 184-188 | 318.3 | | * | |
| 679 | 212-220 | 389.5 | | ** | |
| 680 | 163-168 | 403.3 | | *** | |
| 681 | 192-197 | 403.3 | | ** | |
| 682 | 194-195 | 460.4 | | ** | |
| 683 | 157-159 | 494.2 | | ** | |
| 684 | 175-176 | 412.5 | | * | |
| 685 | 140-141 | 448.4 | | ** | |
| 686 | 173-174 | 424.5 | | ** | |
| 687 | 124-125 | 420.4 | | *** | |
| 688 | 178-179 | 410.4 | | ** | |
| 689 | 204-205 | 409.5 | | ** | |
| 690 | 192-193 | 423.9 | | ** | |
| 691 | 203-205 | 383.8 | ** | | |
| 692 | 175-176 | 397.8 | | ** | |
| 693 | 163-164 | 411.8 | | *** | |
| 694 | 135-136 | 383.8 | | ** | |
| 695 | 159-160 | 397.8 | | ** | |
| 696 | 194-196 | 397.8 | | ** | |
| 697 | foam | 467.0 | | *** | |
| 698 | foam | 499.5 | | ** | |
| 699 | 255-258 | 427.8 | | *** | |
| 701 | 188-194 | 395.8 | | ** | |
| 702 | 147-150 | 409.8 | | ** | |
| 703 | 160-165 | 424.5 | | ** | |
| 704 | 169-170 | 433.4 | | * | |
| 705 | 199-201 | 397.4 | | * | |
| 706 | 151-153 | 396.4 | | *** | |
| 707 | 159-161 | 412.5 | | ** | |
| 708 | 175-177 | 426.5 | | ** | |
| 709 | 166-168 | 424.4 | | *** | |
| 710 | oil | 458.5 | | * | |
| 711 | oil | 424.5 | | * | |
| 712 | 259-261 | 316.5 | | * | |
| 713 | 199-202 | 474.5 | | ** | |
| 714 | 52-53 | 281.4 | | ** | |
| 715 | 174-175 | 424.1 | | *** | |
| 716 | 204-205 | 422.4 | | ** | $^1$H NMR ($CDCl_3$, 300 MHz) δ (ppm) 0.04-0.12 (m, 2H), 0.41-0.50 (m, 2H), 0.98-1.13 (m, 1H), 2.54-2.67 (m, 2H), 3.45 (t, 2H), 3.87 (t, 3H), 3.91 (s, 2H), 3.99 (d, 2H), 6.93-6.99 (m, 2H), 7.36-7.43 (m, 2H), 7.49-7.56 (m, 2H), 7.61-7.66 (m, 1H). |
| 717 | 205-207 | 424.5 | | ** | |
| 718 | 195-196 | 450.2 | | ** | |
| 719 | 192-193 | 410.2 | | * | |
| 720 | 172-178 | 410.5 | | ** | |
| 721 | 158-160 | 404.6 | | ** | |
| 722 | 160-162 | 432.6 | | ** | |

TABLE 1-continued

| Compound Number | Melting Point (° C.) | Mass Spec [M+H] | HCV-PV IC50 µM | Replicon IC5Os µM | NMR Data |
|---|---|---|---|---|---|
| 723 | 175-180 | 418.6 | | ** | |
| 724 | 168-170 | 416.4 | | ** | |
| 725 | 215-216 | 397.5 | | ** | |
| 726 | 221-222 | 411.4 | ** | | |
| 727 | 217-218 | 487.5 | | ** | |
| 728 | 197-199 | 479.5 | | *** | |
| 729 | 213-217 | 493.6 | | * | |
| 730 | 210-214 | 495.2 | | *** | |
| 731 | 173-174 | 388.5 | | *** | |
| 732 | 219-221 | 378.2 | | ** | |
| 733 | 146-148 | 354.5 | | * | |
| 734 | 167-169 | 412.5 | | ** | |
| 735 | 123-125 | 426.5 | | *** | |
| 736 | 125-126 | [NH-] 438.5 | *** | | |
| 737 | 153-155 | [NH-] 438.5 | | ** | |
| 738 | 149-151 | [NH-] 442.4 | | *** | |
| 739 | oil | 456.5 | | * | |
| 740 | 203-205 | 424.9 | | ** | |
| 741 | 194-196 | 438.9 | | *** | |
| 742 | 171-173 | [NH-] 451.5 | | ** | |
| 743 | 129-129 | 465.5 | | *** | |
| 744 | 92-93 | 412.5 | | *** | |
| 745 | oil | 426.5 | | *** | |
| 746 | oil | 440.5 | | * | |
| 747 | 136-137 | 410.5 | | *** | |
| 748 | 186-188 | 391.6 | | *** | |
| 749 | 176-178 | 405.6 | | *** | |
| 750 | 173-174 | 419.6 | | *** | |
| 751 | 159-162 | 405.6 | | ** | |
| 752 | 198-202 | 396.5 | | ** | |
| 753 | 157-161 | 409.9 | | *** | |
| 754 | 146-150 | 424.5 | | ** | |
| 755 | | 357.2 | | *** | $^1$H NMR (DMSO, 300 MHz), δ11.02 (s, 1H), 8.83 (d, J=1.8 Hz, 1H), 8.01 (d, J=8.4 Hz, 2H), 7.71 (d, J=7.2 Hz, 1H), 7.66-7.63 (m, 3H), 7.39-7.26 (m, 3H), 4.22 (q, J=7.5 Hz, 2H), 1.20 (t, J=6.9 Hz, 3H). |
| 756 | | 388.0 | | *** | $^1$H NMR ($CDC1_3$, 300 MHz), δ 8.04 (s, 1H), 7.83 (d, J=8.4 Hz, 2H), 7.77 (d, J=7.5 Hz, 1H), 7.60 (d, J=8.7 Hz, 2H), 7.46 (d, J=7.2 Hz, 1H), 7.42-7.31 (m, 2H), 4.23 (t, J=7.8 Hz, 2H), 3.01 (s, 3H), 1.38 (t, J=7.2, 3H). |
| 757 | 218-225 | 358.2 | | *** | $^1$H NMR ($CDC1_3$, 300 MHz), δ7.79-7.76 (m, 3H), 7.58 (d, J=8.4 Hz, 2H), 7.46 (d, J=7.5 Hz, 2H), 7.39-7.32 (m, 2H), 4.23 (q, J=7.5 Hz, 2H), 2.71 (s, 3H), 2.54 (s, 3H), 1.38 (t, J=7.2 Hz, 3 H). |
| 758 | 149-153 | 320.2 | | *** | |
| 759 | | 376.2 | | *** | $^1$H NMR (DMSO, 300 MHz) δ 10.14 (s, 1H), 7.79 (d, J=8.4 Hz, 2H), 7.58-7.45 (m, 3H), 7.22 (d, J=1.5 Hz, 1H), 6.88 (dd, J=8.7 Hz and 1.8 Hz, 1H), 4.75-4.67 (m, 1H), 4.15 (q, J=6.9 Hz, 2H), 2.34 (q, J=7.6 Hz, 2H), 1.27 (d, J=6.0 Hz, 6H), 1.16-1.07 (m, 6H). |
| 760 | | 402.2 | | *** | (DMSO, 300 MHz) δ9.99 (s, 1H), 7.80 (d, J=8.7 Hz, 2H), 7.51-7.45 (m, 3H), 7.22 (s, 1H), 6.87 (dd, J=9.0 Hz and 1.8 Hz, 1H), 4.72-4.69 (m, 1H), 4.15 (q, J=6.6 Hz, 2H), 2.23-1.80 (m, 7H), 1.26 (d, J=6.0 Hz, 6H), 1.13 (t, J=7.2 Hz, 3H). |
| 761 | 169-173 | 392.1 | *** | | (DMSO, 300 MHz) δ10.06 (s, 1H), 7.90 (d, J=8.7 Hz, 2H), 7.54-7.46 (m, 3H), 7.22 (d, J=1.5 Hz, 1H), 6.88 (dd, J=8.4 Hz and 2.1 Hz, 1H), 4.75-4.66 (m, 1H), 4.15 (q, J=7.2 Hz, 2H), 4.03 (s, 2H), 3.37 (s, 3H), 1.26 (d, J=6.0 Hz, 6H), 1.16 (t, J=7.2 Hz, 3H). |

TABLE 1-continued

| Compound Number | Melting Point (° C.) | Mass Spec [M+H] | HCV-PV IC50 μM | Replicon IC5Os μM | NMR Data |
|---|---|---|---|---|---|
| 762 | 190-193 | 452.3 | | *** | (DMSO, 300 MHz) δ10.20 (s, 1H), 7.78 (d, J=8.7 Hz, 2H), 7.52-7.45 (m, 3H), 7.30-7.21 (m, 5H), 7.18-7.14 (m, 1H), 6.88 (dd, J=8.4 Hz and 2.1Hz, 1H), 4.73-4.69 (m, 1H), 4.15 (q, J=6.6 Hz, 2H), 2.91 (t, J-7.5 Hz, 2H), 2.65 (t, J=7.6 Hz, 2H), 1.27 (d, J=6.0 Hz, 6H), 1.14 (t, J=7.2 Hz, 3H). |
| 763 | 209.2-209.7 | 424.3 | | *** | (DMSO, 300 MHz) δ10.54 (s, 1H), 8.93-7.96 (m, 4H), 7.62-7.49 (m, 6H), 7.26 (d, J=1.8 Hz, 1H), 6.91 (dd, J=8.7 Hz and 2.1 Hz, 1H), 4.76-4.72 (m, 1H), 4.21 (q, J=7.2 Hz, 2H), 1.30 (d, J=6.0 Hz, 6H), 1.18 (t, J=6.9 Hz, 3H). |
| 764 | 213.5-231.7 | 442.2 | | *** | (DMSO, 300 MHz) δ10.52 (s, 1H), 8.06-7.96 (m, 4H), 7.58 (d, J=8.4 Hz, 2H), 7.49 (d, J=8.4 Hz, 1H), 7.37 (t, J=8.7 Hz, 2H), 7.24 (s, 1H), 6.89 (dd, J=9.0 Hz and 1.5 Hz, 1H), 4.72-4.66 (m, 1H), 4.18 (q, J=7.2 Hz, 2H), 1.27 (d, J=6.0 Hz, 6H), 1.16 (t, J=6.9 Hz, 3H). |
| 765 | 288.5-288.9 | 438.2 | | ** | (DMSO, 300 MHz) δ10.91 (s, 1H), 8.72 (s, 1H), 8.20 (d, J=9.3 Hz, 1H), 8.03-7.98 (m, 3H), 7.65-7.62 (d, J=9.0 Hz, 3H), 7.08 (d, J=2.4 Hz, 1H), 6.96 (dd, J=8.7 Hz and 2.4 Hz, 1H), 4.20 (q, J=6.8 Hz, 2H), 3.81 (s, 31-1), 1.19 (t, J=7.2 Hz, 3H). |
| 766 | 192.8-193.1 | 440.1 | | ** | (MeOD, 300 MHz) δ 7.98 (d, J=8.7 Hz, 2H), 7.60 (d, J=8.1 Hz, 2H), 7.50 (d, J=9.3 Hz, 1H), 7.11 (s, 1H), 6.99 (d, J=6.6 Hz, 1H), 6.60 (s, 1H), 4.24 (q, J=7.4 Hz, 2H), 3.87 (s, 3H), 2.54 (s, 3H), 1.30 (t, J=6.9 Hz, 3H). |
| 767 | 204-205 | 350.9 | | *** | |
| 768 | 170-175 | 429.4 | | * | |
| 769 | 118-123 | 473.5 | | * | |
| 770 | | 361.5 | | * | |
| 771 | | 361.5 | | *** | |
| 772 | 211-212 | 442.4 | | *** | $^1$H NMR (300 MHz, $CDCl_3$): δ 7.62 (1H, d, J=8.5 Hz), 7.42 (2H, d, J=8.5 Hz), 7.13 (2H, d, J=8.5 Hz), 6.95 (1H, dd, J=8.5, 1.8 Hz), 6.87 (1H, d, J=1.8 Hz), 5.67 (1H, d, J=8.8 Hz), 4.28-4.08 (8H, m), 1.47 (3H, t, J=6.9 Hz), 1.37 (6H, td, J=7.0, 0.6 Hz), 1.34 (3H, t, J=7.3 Hz). |
| 773 | 191-193 | 434.9 | | ** | $^1$H NMR (300 MHz, $CDCl_3$): δ 7.60 (1H, d, J=8.8 Hz), 7.52 (2H, d, J=8.8 Hz), 7.43 (2H, d, J=8.8 Hz), 6.94 (1H, dd, J=8.8, 2.2 Hz), 6.86 (1H, d, J=2.2 Hz), 4.24 (2H, q, J=7.0 Hz), 4.22-4.06 (6H, m), 1.47 (3H, t, J=7.0 Hz), 1.34-1.25 (6H, m). |
| 774 | 205-206 | 410.9 | | ** | $^1$H NMR (300 MHz, $CDCl_3$): δ 7.63 (1H, d, J=8.8 Hz), 7.53 (2H, d, J=9.0 Hz), 7.46 (2H, d, J=9.0 Hz), 6.98 (1H, br s), 6.96 (1H, dd, J=8.8, 2.0 Hz), 6.88 (1H, d, J=2.0 Hz), 4.17-4.09 (4H, m), 3.71-3.61 (4H, m), 1.48 (3H, t, J=7.0 Hz), 1.34 (3H, t, J=7.1 Hz). |
| 775 | | 482.1 | | ** | $^1$H NMR (300 MHz, $CDCl_3$): δ 7.64 (1H, d, J=8.5 Hz), 7.52 (2H, d, J=9.0 Hz), 7.40 (2H, d, J=9.0 Hz), 6.97 (1H, dd, J=8.5, 2.2 Hz), 6.90 (1H, d, J=2.2 Hz), 4.48 (2H, t, J=4.7 Hz), 4.26 (2H, t, J=4.7 Hz), 4.05 (2H, t, J=7.6 Hz), 3.87 (2H, t, J=6.6 Hz), 3.45 (2H, t, J=6.9 Hz), 2.61 (2H, p, J=7.3 Hz), 2.13 (3H, s), 1.72 (2H, hx, J=7.3 Hz), 0.79 (3H, t, J=7.4 Hz). |
| 776 | 257-258 | 389.5 | | *** | $^1$H NMR (300 MHz, DMSO-$d_6$): δ 11.32 (1H, s), 7.82 (2H, d, J=8.8 |

TABLE 1-continued

| Compound Number | Melting Point (° C.) | Mass Spec [M+H] | HCV-PV IC50 μM | Replicon IC5Os μM | NMR Data |
|---|---|---|---|---|---|
| | | | | | Hz), 7.61 (2H, d, J=8.8 Hz), 7.50 (1H, d, J=8.8 Hz), 7.24 (1H, d, J=1.8 Hz), 6.91 (1H, dd, J=8.8, 1.8 Hz), 4.52 (2H, s), 4.18 (2H, q, J=7.0 Hz), 4.11 (2H, q, J=7.0 Hz), 1.36 (3H, t, J=7.0 Hz), 1.16 (3H, t, J=7.0 Hz). |
| 777 | 124-127 | 511.6 | | *** | $^1$H NMR (300 MHz, $CDCl_3$): δ 7.58 (1H, d, J=8.8 Hz), 7.45 (2H, d, J=8.8 Hz), 7.39 (2H, d, J=8.8 Hz), 7.33 (1H, br s), 7.31-7.15 (5H, m), 6.94 (1H, dd, J=8.8, 2.2 Hz), 6.86 (1H, d, J=2.2 Hz), 4.84 (1H, t, J=6.0 Hz), 4.11 (2H, q, J=7.0 Hz), 4.08 (2H, q, J=7.3 Hz), 3.74 (3H, s), 3.18 (1H, dd, J=14.0, 5.6 Hz), 3.07 (1H, dd, J=14.0, 6.4 Hz), 1.47 (3H, t, J=7.0 Hz), 1.30 (3H, t, J=7.3 Hz). |
| 778 | 225-227 | 375.5 | | *** | $^1$H NMR (300 MHz, $CDCl_3$): δ 7.73 (2H, d, J=8.8 Hz), 7.62 (1H, d, J=8.8 Hz), 7.52 (2H, d, J=8.8 Hz), 6.95 (1H, dd, J=8.8, 2.0 Hz), 6.88 (1H, d, J=2.0 Hz), 4.13 (2H, q, J=7.0 Hz), 4.12 (2H, q, J=7.0 Hz), 4.04-3.99 (2H, m), 3.67-3.62 (2H, m), 1.47 (3H, t, J=7.0 Hz), 1.34 (3H, t, J=7.0 Hz). |
| 779 | 265-267 | 389.5 | | *** | $^1$H NMR (300 MHz, DMSO-$d_6$): δ 8.42 (1H, s), 7.72 (2H, d, J=8.8 Hz), 7.61 (2H, d, J=8.8 Hz), 7.53 (1H, d, J=8.5 Hz), 7.26 (1H, d, J=2.0 Hz), 6.93 (1H, dd, J=8.5, 2.0 Hz), 4.25-4.08 (6H, m), 1.36 (3H, t, J=7.0 Hz), 1.19 (3H, t, J=7.0 Hz). |
| 780 | 219-220 | 463.6 | | ** | $^1$H NMR (300 MHz, $CDCl_3$): δ 7.65 (1H, d, J=8.8 Hz), 7.58 (2H, d, J=8.8 Hz), 7.48 (2H, d, J=8.8 Hz), 6.97 (1H, dd, J=8.8, 2.0 Hz), 6.88 (1H, d, J=2.0 Hz), 4.18-4.08 (5H, m), 3.09 (3H, s), 3.00 (3H, s), 2.94 (3H, s), 1.53 (3H, d), 1.47 (3H, t, J=7.0 Hz), 1.34 (3H, t, J=7.0 Hz). |
| 781 | 207-208 | 449.8 | | *** | $^1$H NMR (300 MHz, $CDCl_3$): δ 7.64 (2H, d, J=8.8 Hz), 7.60 (4H, s), 6.97 (1H, d, J=8.8, 2.0 Hz), 6.88 (1H, d, J =2.0 Hz), 4.12 (2H, q, J=7.0 Hz), 4.11 (2H, q, J=7.0 Hz), 3.36 (3H, s), 3.23 (2H, s), 3.14 (3H, s), 2.88 (3H, s), 1.48 (3H, t, J=7.0 Hz), 1.33 (3H, t, J=7.0 Hz). |
| 782 | 188-190 | 396.5 | | ** | |
| 783 | 201-202 | 410.5 | | * | |
| 784 | 245-246 | 410.5 | | ** | |
| 785 | 151-153 | 423.5 | | ** | $^1$H NMR ($CDC1_3$, 300 MHz) δ (ppm) 1.38 (t, 3H), 3.30-3.37 (m, 4H), 3.51-3.58 (m, 4H), 4.06-4.18 (q, 2H), 7.45 (d, 1H), 7.54 (s, 1H), 7.66 (d, 1H). |
| 786 | 202-203 | 437.5 | | * | |
| 787 | 261-263 | 412.2 | | * | |
| 788 | 112-114 | 453.9 | | * | |
| 789 | 154-156 | 398.2 | | *** | |
| 790 | | 398.2 | | *** | |
| 791 | 149-152 | 396.5 | | *** | |
| 792 | 182-185 | 350.5 | | *** | |
| 793 | 154-155 | 364.5 | | *** | |
| 794 | 149-151 | 378.5 | | *** | |
| 795 | 183-185 | 378.5 | | *** | |
| 796 | 124-125 | 392.6 | | ** | |
| 797 | 209-212 | 277.9 | | ** | |
| 798 | 193.4-193.7 | 429.2 | | * | ($CD_3CN$, 400 MHz) δ9.19 (s, 1H), 7.95 (d, J=7.6 Hz, 2H), 7.61 (d, J=8.0 Hz, 2H), 7.56 (d, J=8.8 Hz, 1H), 7.10 (s, 1H), 6.92 (dd, J=8.8 Hz and 0.8 Hz, 1H), 6.56 (s, 1H), 4.74-4.64 (m, 1H), 4.18 |

TABLE 1-continued

| Compound Number | Melting Point (° C.) | Mass Spec [M+H] | HCV-PV IC50 μM | Replicon IC5Os μM | NMR Data |
|---|---|---|---|---|---|
| | | | | | (q, J=7.2 Hz, 2H), 2.51 (s, 3H), 1.27 (d, J=6.0 Hz, 6H), 1.27 (t, J=7.2 Hz, 3H). |
| 799 | | 362.2 | | *** | $^{1}$H NMR (DMSO, 300 MHz), δ 10.14 (s, 1H), 7.79 (d, J=8.4 Hz, 2H), 7.52-7.50 (m, 3H), 7.22 (s, 1H), 6.91 (d, J=8.7 Hz, 1H), 4.17 (q, J=7.5 Hz, 2H), 3.82 (s, 3H), 2.24 (t, J=7.2 Hz, 2H), 1.60 (q, J=7.2 Hz, 2H), 1.23 (t, J=7.2 Hz, 3H), 0.90 (t, J=7.2 Hz, 3H). |
| 801 | 199-219 | 374.2 | | *** | $^{1}$H NMR ($CDCl_3$, 300 Hz), 7.72 (d, J=8.4 Hz, 2H), 7.63 (d, J=8.7 Hz, 1H), 7.50 (d, J=8.7 Hz, 2H), 7.22 (s, 1H), 6.91 (dd, J=6.6 Hz and 2.1 Hz, 1H), 6.87 (d, J=2.1 Hz, 1H), 4.14 (q, J=7.2 Hz, 2H), 3.90 (s, 3H), 3.24-3.18 (m, 1H), 2.46-2.25 (m, 4H), 2.06-1.97 (m, 2H), 1.33 (t, J=8.1 Hz, 3H). |
| 802 | 196-198 | 410.2 | | ** | $^{1}$H NMR (DMSO, 300 Hz), δ 10.45 (s, 1 H), 7.80 (d, J=8.4 Hz, 2 H), 7.54-7.48 (m, 3 H), 7.33-7.21 (m, 6H), 6.92 (dd, J=6.6 Hz and 2.1 Hz, 1 H) 4.17 (q, J=6.6 Hz, 2H), 3.82 (s, 3 H), 3.67 (s, 2H), 1.15(t, J=7.2 Hz, 3 H). |
| 803 | 216-217 | 386.1 | | * | $^{1}$H NMR (DMSO, 300 Hz), δ 10.90 (s, 1H), 8.71 (s, 1H), 8.19 (d, J=9.3 Hz, 1H), 8.02-7.98 (m, 3H), 7.63 (d, J=8.7 Hz, 2H), 7.51 (d, J=8.7 Hz, 1H), 7.24 (d, J=2.1 Hz, 1H), 6.92 (dd, J=6.6 Hz and 2.1 Hz, 1H), 4.20 (q, J=6.6 Hz, 2H), 3.83 (s, 3H), 1.16 (t, J=6.6 Hz, 3H). |
| 804 | 214-216 | 401.2 | | * | $^{1}$H NMR (DMSO, 300 Hz), δ 10.92 (s, 1H), 8.00 (d, J=8.7 Hz, 2H), 7.59 (d, J=8.7 Hz, 2H), 7.51 (d, J=8.7 Hz, 1H), 7.23 (d, J=2.1 Hz, 1H), 6.92 (dd, J=6.6 Hz and 2.1 Hz, IH), 6.69 (s, 1H), 4.19 (q, J=6.6 Hz, 2H), 3.83 (s, 3H), 2.49 (s, 3H), 1.17 (t, J=7.2 Hz, 3H). |
| 805 | 217-222 | 452.5 | | * | |
| 806 | 157-159 | 422.5 | | ** | |
| 807 | 171-172 | 396.5 | | *** | |
| 808 | 195-197 | 410.5 | | ** | |
| 809 | 167-168 | 410.5 | | ** | |
| 810 | 209-211 | 422.5 | | ** | |
| 811 | 166-168 | 354.5 | | * | |
| 812 | 206-208 | 460.4 | | ** | |
| 813 | 176-177 | 458.4 | | *** | |
| 814 | 164-165 | [NH-] 458.5 | | * | |
| 815 | 153-154 | 473.5 | | * | $^{1}$H NMR (300 MHz, $CDCl_3$): δ 7.65 (1H, d, J=8.8 Hz), 7.61 (2H, d, J=8.8 Hz), 7.56 (2H, d, J=8.8 Hz), 6.98 (1H, dd, J=8.8, 2.3 Hz), 6.89 (1H, d, J=2.3 Hz), 4.24 (2H, t, J=5.4 Hz), 4.17 (2H, q, J=7.3 Hz), 4.02 (2H, q, J=5.4 Hz), 3.91 (3H, s), 3.00 (3H, s), 2.01 (3H, s), 1.38 (3H, t, J=7.3 Hz). |
| 816 | 186-187 | 445.5 | | ** | $^{1}$H NMR (300 MHz, $CDCl_3$): δ 7.66 (1H, d, J=8.5 Hz), 7.60 (2H, d, J=8.8 Hz), 7.55 (2H, d, J=8.8 Hz), 6.98 (1H, dd, J=8.5, 2.0 Hz), 6.89 (1H, d, J=2.0 Hz), 4.16 (2H, q, J=7.3 Hz), 3.93 (2H, t, J=6.0 Hz), 3.91 (3H, s), 3.53 (2H, t, J=6.0 Hz), 3.38 (3H, s), 3.07 (3H, s), 1.38 (3H, t, J=7.3 Hz). |
| 817 | 188-190 | 439.2 | | * | |
| 818 | 158-159 | 437.0 | | *** | |
| 819 | | 438.9 | | * | |
| 820 | | 408.4 | | ** | |
| 821 | | 408.4 | | * | |
| 822 | 144-145 | 439.9 | | ** | |
| 823 | 93-94 | 456.2 | | * | |
| 824 | 169-170 | 428.2 | | * | |
| 825 | 109-110 | 444.2 | | * | |

TABLE 1-continued

| Compound Number | Melting Point (° C.) | Mass Spec [M+H] | HCV-PV IC50 μM | Replicon IC5Os μM | NMR Data |
|---|---|---|---|---|---|
| 826 | 160-161 | 432.1 | | ** | |
| 827 | 189-191 | 446.1 | | *** | |
| 828 | 198-200 | 431.2 | | ** | $^1$H NMR (300 MHz, $CDCl_3$): δ 7.65 (1H, d, J=8.8 Hz), 7.62 (2H, d, J=8.8 Hz), 7.57 (2H, d, J=8.8 Hz), 6.98 (1H, dd, J=8.8, 2.0 Hz), 6.89 (1H, d, J=2.0 Hz), 4.17 (2H, q, J=7.2 Hz), 3.93 (2H, t, J=5.3 Hz), 3.91 (3H, s), 3.77 (2H, t, J=5.3 Hz), 3.06 (3H, s), 1.38 (3H, t, J=7.2 Hz). |
| 829 | 271-275 | 422.1 | | ** | |
| 830 | 178-179 | 420.1 | | ** | |
| 831 | 140-141 | 371.0 | | * | |
| 832 | 206-207 | 406.3 | | ** | $^1$H NMR ($CDC1_3$, 300 MHz) δ (ppm) 1.34 (t, 3H), 1.47 (t, 3H), 1.55 (s, 9H), 4.04-4.25 (m, 4H), 6.62 (s, 1H), 6.86-6.92 (m, 1H), 7.02-7.08 (m, 2H), 7.43-7.49 (m, 2H), 7.62 (d, 1H), 7.95 (d, 1H). |
| 833 | 183-185 | 306.3 | | ** | $^1$H NMR ($CDC1_3$, 300 MHz) δ (ppm) 1.21 (t, 3H), 1.37 (t, 3H), 3.84-4.09 (m, 6H), 6.54-6.71 (m, 2H), 6.85-7.01 (m, 2H), 7.23-7.45 (m, 3H). |
| 834 | 179-180 | 384.2 | | ** | |
| 835 | 178-179 | 398.2 | | ** | $^1$H NMR ($CDCl_3$, 300 MHz) δ (ppm), 1.32-1.52 (m, 9H), 3.06-3.17 (q, 2H), 4.07-4.24 (m 4H), 6.55 (s, 1H), 6.99-7.10 (m, 3H), 7.42-7.50 (m, 2H), 7.52-7.53 (m, 1H), 7.69 (d, 1H). |
| 836 | 167-169 | 412.2 | | * | |
| 837 | 144-145 | 410.2 | | * | |
| 838 | 193-194 | 378.1 | | ** | $^1$H NMR ($CDCl_3$, 300 MHz) δ (ppm), 1.31-1.39 (m, 6H), 1.48 (t, 3H), 4.07-4.31 (m, 6H), 6.73 (s, 1H), 6.88-6.95 (m, 1H), 7.01-7.08 (m, 2H), 7.42-7.53 (m, 2H), 7.63 (d, 1H), 7.99 (s, 1H). |
| 839 | 249-250 | 377.3 | | * | $^1$H NMR ($CDCl_3$, 300 MHz) δ (ppm), 1.13 (t, 3H), 1.32 (t, 3H), 1.43 (t, 3H), 3.20-3.32 (m, 2H), 4.13-4.26 (m, 4H), 5.77 (t, 1H), 7.06-7.18 (m, 3H), 7.48 (d, 1H), 7.52-7.59 (m, 2H), 8.02 (s, 1H), 8.18 (d, 1H). |
| 840 | 182-183 | 442.5 | | * | |
| 841 | 140-141 | 429.2 | | * | |
| 842 | 170-171 | 427.2 | | * | $^1$H NMR ($CDCl_3$, 300 MHz) δ (ppm) 1.04-1.13 (m, 2H), 1.20-1.28 (m, 2H), 1.44 (t, 3H), 2.30-2.43 (m, 1H) 3.44-3.61 (m, 8H), 4.10-4.23 (q, 2H), 7.49 (d, 1H), 7.56 (s, 1H), 7.72 (d, 1H). |
| 843 | 143-146 | 463.1 | | * | |
| 844 | 220-227 | 378.1 | | * | |
| 845 | 210-215 | 435.0 | | * | |
| 846 | 201-202 | 391.5 | | ** | |
| 847 | 166-167 | 405.5 | | ** | |
| 848 | 193-194 | 453.5 | | ** | |
| 849 | 159-161 | 364.5 | | ** | |
| 850 | 179-180 | 446.4 | | ** | |
| 851 | 186-187 | 410.4 | | ** | |
| 852 | 171-172 | 426.4 | | ** | |
| 853 | 159-161 | 346.2 | | *** | |
| 854 | | 330.2 | | ** | |
| 855 | | 332.1 | | ** | |
| 856 | 202-202 | 368.1 | | * | |
| 857 | 192-192 | 364.2 | | ** | |
| 858 | | 362.2 | | *** | |
| 859 | 191-192 | 374.2 | | ** | |
| 860 | 242-244 | 334.1 | | ** | |
| 861 | | 346.2 | | ** | |
| 862 | | 360.1 | | * | |
| 863 | | 362.5 | | ** | |
| 864 | | 362.5 | | ** | |
| 865 | 187-192 | 412.9 | | * | |

Example 7

Evaluation of the Activity of Compounds Using an HCV-Poliovirus Chimera

In an HCV-poliovirus (HCV-PV) chimera, the PV 5' UTR is replaced by the HCV 5' UTR and partial (the first 123 amino acids) core coding sequences (nucleotides 18 to 710 of HCV 1b) as shown in FIG. 1 (140). As a consequence, the expression of poliovirus proteins is proteins is under regulation of the HCV IRES. Poliovirus is a picornavirus in which protein translation initiation is mediated by an IRES element located in the 5' UTR. At the 5' end of the HCV-PV chimeric genome, there is the cloverleaf-like RNA structure of PV, an essential cis-acting replication signal ending with the genome-linked protein VPg. Replication kinetics of the HCV-PV chimera matches that of the parental poliovirus (Mahoney) and can result in cytopathic effects (CPE) in cell culture. Heptazyme, a ribozyme that targets the HCV IRES, was shown to be active against the chimeric virus in cell culture (76, 77).

To evaluate compounds for activity against the chimeric virus, HeLa cells are seeded and incubated at 37° C. under 5% $CO_2$ for 24 hours. The cells are then infected with HCV-PV at a multiplicity of infection (MOI) at 0.1 for 30 min and then treated with compound for 1 day (treatment time will be optimized). The activity of compounds is determined by a change in cytopathic effect, plaque assay, and/or viral RNA production (see e.g., Table 1).

Example 8

Evaluation of the Activity of Compounds Against a Wild-Type Poliovirus (WT-PV) and the Poliovirus IRES Translation Assay (WT-PV Mono Luc)

A DNA construct is prepared, termed pPVIRESmono, in which PV IRES sequences are inserted (nucleotide number 1-742) between a promoter and the firefly luciferase (Fluc) reporter gene. A stably transfected 293 T cell line, is established by transfection with the pPVIRESmono DNA by selecting for resistance to hygromycin. As previously described, cells are treated with compounds for 20 hours, and activity is determined by quantifying the Fluc signal. Additionally, to evaluate compounds activity against wild-type poliovirus, Hela cells are seeded and incubated at 37° C. under 5% $CO_2$ for 24 hours. Cells are then infected with wild-type poliovirus at a MOI at 0.1 for 30 minutes, and then treated with compound for one day. The activity of compounds is determined by changes in cytopathic effect, plaque assay, and RT-PCR using poliovirus IRES primers and probes (see e.g., Table 2).

Furthermore, if compounds are active against the poliovirus and other virus IRESs, then the compounds are useful for treating viral infection by any virus containing an IRES.

TABLE 2

| Compound No. | WT-PV CPE (100 μM) * | WT-PV CPE (10 μM)* | WT-PV CPE (1 μM)* | WTPV mono luc $IC_{50}$ (μM) |
|---|---|---|---|---|
| 4 | 3 | 2 | 1 | 0.8 |
| 5 | 3 | 2 | 1 | 9 |
| 9 | 3 | 2 | 2 | >100 |
| 10 | 3 | 2 | 2 | >100 |
| 19 | 3 | 2 | 1 | 15 |
| 24 | 3 | 2 | 2 | 1.5 |

Example 9

In Vitro Translation Assay

In vitro translation assays can be used to distinguish between the compounds that act on HCV IRES RNA or cellular translation factors. In exemplary assays, the mRNA that will direct translation is a transcribed runoff product from the T7 RNA polymerase promoter of the pHCVIRESmono plasmid DNA generated with Ambion RNA MegaTranscript kit (Ambion, Inc., Austin, Tex.). In vitro translation is performed using HeLa cell lysates using methods known to one of skill in the art. Preliminary results indicate that one or more of the compounds of the present invention has significantly higher activity against HCV IRES regulated translation after preincubating the compound with the HCV IRES RNA transcripts than after preincubating with HeLa cell lysate for 30 min at 37° C. or without preincubation (data not shown). This suggests that this compound may interact with the HCV IRES RNA in the in vitro translation assay. To demonstrate whether the compounds selectively act on the HCV IRES, pLuc is used together with cellular IRES mRNA transcripts as controls for in vitro translation.

All publications and patent applications cited herein are incorporated by reference to the same extent as if each individual publication or patent application was specifically and individually indicated to be incorporated by reference.

Although certain embodiments have been described in detail above, those having ordinary skill in the art will clearly understand that many modifications are possible in the embodiments without departing from the teachings thereof. All such modifications are intended to be encompassed within the claims of the invention.

REFERENCES

1. Ali, N., G. J. Pruijn, D. J. Kenan, J. D. Keene, and A. Siddiqui. 2000. Human La antigen is required for the hepatitis C virus internal ribosome entry site-mediated translation. J Biol Chem 275:27531-27540.
2. Ali, N. and A. Siddiqui. 1995. Interaction of polypyrimidine tract-binding protein with the 5' noncoding region of the hepatitis C virus RNA genome and its functional requirement in internal initiation of translation. J Virol 69:6367-6375.
3. Ali, N. and A. Siddiqui. 1997. The La antigen binds 5' noncoding region of the hepatitis C virus RNA in the context of the initiator AUG codon and stimulates internal ribosome entry site-mediated translation. Proc Natl Acad Sci USA 94:2249-2254.
4. Anwar, A. N. Ali, R. Tanveer, and A. Siddiqui. 2000. Demonstration of functional requirement of polypyrimidine tract-binding protein by SELEX RNA during hepatitis C virus internal ribosome entry site-mediated translation initiation. J Biol Chem 275:34231-34235.
5. Beales, L. P., D. J. Rowlands, and A. Holzenburg. 2001. The internal ribosome entry site (IRES) of hepatitis C virus visualized by electron microscopy. RNA 7:661-670.
6. Belsham, G. J. and J. K. Brangwyn. 1990. A region of the 5' noncoding region of foot-and-mouth disease virus RNA directs efficient internal initiation of protein synthesis within cells: involvement with the role of L protease in translational control. J Virol 64:5389-5395.
7. Belsham, G. J. and R. J. Jackson. 2000. Translation initiation on picornavirus RNA., p. 869-900. Cold Spring Harbor Laboratory Press, New York.

8. Blight, K. J., A. A. Kolykhalov, and C. M. Rice. 2000. Efficient initiation of HCV RNA replication in cell culture. Science 290:1972-1974.

9. Blight, K. J., J. A. McKeating, and C. M. Rice. 2002. Highly permissive cell lines for subgenomic and genomic hepatitis C virus RNA replication. J Virol 76:13001-13014.

10. Borvjagin, G., T. Pestova, and I. Shatsky. 1994. Pyrimidine tract binding protein strongly stimulates in vitro encephalomyocarditis virus RNA translation at the level of the preinitiation complex formation. FEBS Lett 351:291-302.

11. Brown, E. A., H. Zhang, L. H. Ping, and S. M. Lemon. 1992. Secondary structure of the 5' nontranslated regions of hepatitis C virus and pestivirus genomic RNAs. Nucleic Acids Res 20:5041-5045.

12. Buck C B, Shen X, Egan M A, Pierson T C, Walker C M, and Siliciano R F. 2001. The human immunodeficiency virus type 1 gag gene encodes an internal ribosome entry site. J Virol 75:181-191.

13. Bukh, J., R. H. Purcell, and R. H. Miller. 1992. Sequence analysis of the 5' noncoding region of hepatitis C virus. Proc Natl Acad Sci USA 89:4942-4946.

14. Bukh, J., R. H. Purcell, and R. H. Miller. 1994. Sequence analysis of the core gene of 14 hepatitis C virus genotypes. Proc Natl Acad Sci USA 91:8239-8243.

15. Buratti, E., S. Tisminetzky, M. Zotti, and F. E. Baralle. 1998. Functional analysis of the interaction between HCV 5'UTR and putative subunits of eukaryotic translation initiation factor eIF3. Nucleic Acids Res 26:3179-3187.

16. Chappell, S. A., J. P. LeQuesne, F. E. Paulin, M. L. deSchoolmeester, M. Stoneley, R. L. Soutar, S. H. Ralston, M. H. Helfrich, and A. E. Willis. 2000. A mutation in the c-myc-IRES leads to enhanced internal ribosome entry in multiple myeloma: a novel mechanism of oncogene deregulation. Oncogene 19:4437-4440.

17. Chung, R. T., W. He, A. Saquib, A. M. Contreras, R. J. Xavier, A. Chawla, T. C. Wang, and E. V. Schmidt. Hepatitis C virus replication is directly inhibited by IFN-alpha in a full-length binary expression system. 2001. Proc Natl Acad Sci USA 98:9847-9852.

18. Coldwell, M. J., S. A. Mitchell, M. Stoneley, M. MacFarlane, and A. E. Willis. 2000. Initiation of Apaf-1 translation by internal ribosome entry. Oncogene 19:899-905.

19. Creancier, L., D. Morello, P. Mercier, and A. C. Prats. 2000. Fibroblast growth factor 2 internal ribosome entry site (IRES) activity ex vivo and in transgenic mice reveals a stringent tissue-specific regulation. J Cell Biol 150:275-281.

20. Das, S., M. Ott, A. Yamane, A. Venkatesan, S. Gupta, and A. Dasgupta. 1998. Inhibition of internal entry site (IRES)-mediated translation by a small yeast RNA: a novel strategy to block hepatitis C virus protein synthesis. Front Biosci 3:D1241-D 1252.

21. Dever, T. E. 2002. Gene-specific regulation by general translation factors. Cell 108 :545-556.

22. Dumas, E., C. Staedel, M. Colombat, S. Reigadas, S. Chabas, T. Astier-Gin, A. Cahour, S. Litvak, and M. Ventura. 2003. A promoter activity is present in the DNA sequence corresponding to the hepatitis C virus 5' UTR. Nucleic Acids Res 31:1275-1281.

23. Fukushi, S., K. Katayama, C. Kurihara, N. Ishiyama, F. B. Hoshino, T. Ando, and A. Oya. 1994. Complete 5' noncoding region is necessary for the efficient internal initiation of hepatitis C virus RNA. Biochem Biophys. Res Commun. 199:425-432.

24. Fukushi, S., C. Kurihara, N. Ishiyama, F. B. Hoshino, A. Oya, and K. Katayama. 1997. The sequence element of the internal ribosome entry site and a 25-kilodalton cellular protein contribute to efficient internal initiation of translation of hepatitis C virus RNA. J Virol 71:1662-1666.

25. Fukushi, S., M. Okada, T. Kageyama, F. B. Hoshino, and K. Katayama. 1999. Specific interaction of a 25-kilodalton cellular protein, a 40S ribosomal subunit protein, with the internal ribosome entry site of hepatitis C virus genome. Virus Genes 19:153-161.

26. Fukushi, S., M. Okada, J. Stahl, T. Kageyama, F. B. Hoshino, and K. Katayama. 2001. Ribosomal protein S5 interacts with the internal ribosomal entry site of hepatitis C virus. J Biol Chem 276:20824-20826.

27. Funkhouser, A. W., D. E. Schultz, S. M. Lemon, R. H. Purcell, and S. U. Emerson. 1999. Hepatitis A virus translation is rate-limiting for virus replication in MRC-5 cells. Virology 254:268-278.

28. Glass, M. J., X. Y. Jia, and D. F. Summers. 1993 Identification of the hepatitis A virus internal ribosome entry site: in vivo and in vitro analysis of bicistronic RNAs containing the HAV 5' noncoding region. Virology. 193:842-852.

29. Gordon S. C., B. R. Bacon, I. M. Jacobson, M. I. Shiffman, N. H. Afdhal, J. G. McHutchison, T. J. Kwoh, and F. A. Dorr. 2002. A Phase II, 12-week study of ISIS 14803, an antisense inhibitor of HCV for the treatment of chronic hepatitis C. AASLD Abst. 795. Hepatology 36:362A.

30. Gosert, R., K. H. Chang, R. Rijnbrand, M. Yi, D. V. Sangar, and S. M. Lemon. 2000. Transient expression of cellular polypyrimidine-tract binding protein stimulates cap-independent translation directed by both picornaviral and flaviviral internal ribosome entry sites In vivo. Mol Cell Biol 20:1583-1595.

31. Gray, N, and M. Wickens. 1998. Control of translation initiation in animals. Annu Rev Cell Dev Biol 14:399-458.

31a. Griffith, A., and D. M. Coen. 2005. An unusual internal ribosome entry site in the herpes simplex virus thymidine kinase gene. Proc Natl Acad Sci USA. 102:9667-72.

32. Guo, J. T., V. V. Bichko, and C. Seeger. 2001. Effect of alpha interferon on the hepatitis C virus replicon. J Virol 75:8516-8523.

33. Hahm, B., Y. K. Kim, J. H. Kim, T. Y. Kim, and S. K. Jang. 1998. Heterogeneous nuclear ribonucleoprotein L interacts with the 3' border of the internal ribosomal entry site of hepatitis C virus. J Virol 72:8782-8788.

34. Haller, A. A., S. R. Stewart, and B. L. Semler. 1996. Attenuation stem-loop lesions in the 5' noncoding region of poliovirus RNA: neuronal cell-specific translation defects. J Virol 70:1467-1474.

35. Hellen, C. U. and T. V. Pestova. 1999. Translation of hepatitis C virus RNA. J Viral Hepat 6:79-87.

36. Hellen, C. U., G. W. Witherell, M. Schmid, S. H. Shin, T. V. Pestova, A. Gil, and E. Wimmer. 1993. A cytoplasmic 57-kDa protein that is required for translation of picornavirus RNA by internal ribosomal entry is identical to the nuclear pyrimidine tract-binding protein. Proc Natl Acad Sci USA 90:4672-7646

37. Hendrix, M., E. S. Priestley, G. F. Joyce, and C. H. Wong. 1997. Direct observation of aminoglycoside-RNA interactions by surface plasmon resonance. Journal of the American Chemical Society 119:3641-8.

38. Holcik, M. and R. G. Korneluk. 2000. Functional characterization of the X-linked inhibitor of apoptosis (XIAP) internal ribosome entry site element: role of La autoantigen in XIAP translation. Mol Cell Biol 20:4648-4657.

39. Holcik, M., C. Lefebvre, C. Yeh, T. Chow, and R. G. Korneluk. 1999. A new internal-ribosome-entry-site motif potentiates XIAP-mediated cytoprotection. Nat Cell Biol 1: 190-192.

40. Honda, M., M. R. Beard, L. H. Ping, and S. M. Lemon. 1999. A phylogenetically conserved stem-loop structure at the 5' border of the internal ribosome entry site of hepatitis C virus is required for cap-independent viral translation. J Virol 1165-1174.
41. Honda, M., E. A. Brown, and S. M. Lemon. 1996. Stability of a stem-loop involving the initiator AUG controls the efficiency of internal initiation of translation on hepatitis C virus RNA. RNA 2:955-968.
42. Honda, M., L. H. Ping, R. C. Rijnbrand, E. Amphlett, B. Clarke, D. Rowlands, and S. M. Lemon. 1996. Structural requirements for initiation of translation by internal ribosome entry within genome-length hepatitis C virus RNA. Virology 222:31-42.
43. Honda, M., R. Rijnbrand, G. Abell, D. Kim, and S. M. Lemon. 1999. Natural variation in translational activities of the 5' nontranslated RNAs of hepatitis C virus genotypes 1a and 1b: evidence for a long-range RNA-RNA interaction outside of the internal ribosomal entry site. J Virol 73:4941-4951.
44. Huez, I., S. Bornes, D. Bresson, L. Creancier, and H. Prats. 2001. New vascular endothelial growth factor isoform generated by internal ribosome entry site-driven CUG translation initiation. Mol Endocrinol. 15:2197-2210.
45. Huez, I., L. Creancier, S. Audigier, M. C. Gensac, A. C. Prats, and H. Prats. 1998. Two independent internal ribosome entry sites are involved in translation initiation of vascular endothelial growth factor mRNA. Mol Cell Biol 18:6178-6190
46. Ikeda, M., M. Yi, K. Li, and S. M. Lemon. 2002. Selectable subgenomic and genome-length dicistronic RNAs derived from an infectious molecular clone of the HCV-N strain of hepatitis C virus replicate efficiently in cultured Huh7 cells. J Virol 76:2997-3006.
47. Irvine, J. D., L. Takahashi, K. Lockhart, J. Cheong, J. W. Tolan, H. E. Selick, and J. R. Grove. 1999. MDCK (Madin-Darby canine kidney) cells: A tool for membrane permeability screening. J Pharm Sci 88:28-33.
48. Isoyama, T., N. Kamoshita, K. Yasui, A. Iwai, K. Shiroki, H. Toyoda, A. Yamada, Y. Takasaki, and A. Nomoto. 1999. Lower concentration of La protein required for internal ribosome entry on hepatitis C virus RNA than on poliovirus RNA. J Gen Virol 80 (Pt 9):2319-2327.
49. Ito, T. and M. M. Lai. 1999. An internal polypyrimidine-tract-binding protein-binding site in the hepatitis C virus RNA attenuates translation, which is relieved by the 3'-untranslated sequence. Virology 254:288-296.
50. Jang, S. K., H. G. Krausslich, M. J. Nicklin, G. M. Duke, A. C. Palmenberg, and E. Wimmer. 1988. A segment of the 5' nontranslated region of encephalomyocarditis virus RNA directs internal entry of ribosomes during in vitro translation. J Virol 62:2636-2643.
51. Jubin, R., N. E. Vantuno, J. S. Kieft, M. G. Murray, J. A. Doudna, J. Y. Lau, and B. M. Baroudy. 2000. Hepatitis C virus internal ribosome entry site (IRES) stem loop IIId contains a phylogenetically conserved GGG triplet essential for translation and IRES folding. J Virol 74:10430-10437.
52. Kalliampakou, K. I., L. Psaridi-Linardaki, and P. Mavromara. 2002. Mutational analysis of the apical region of domain II of the HCV IRES. FEBS Lett 511:79-84.
53. Kaminski, A., S. L. Hunt, J. G. Patton, and R. J. Jackson. 1995. Direct evidence that polypyrimidine tract binding protein (PTB) is essential for internal initiation of translation of encephalomyocarditis virus RNA.RNA 1:924-938
54. Kamoshita, N., K. Tsukiyama-Kohara, M. Kohara, and A. Nomoto. 1997. Genetic analysis of internal ribosomal entry site on hepatitis C virus RNA: implication for involvement of the highly ordered structure and cell type-specific transacting factors. Virology 233:9-18.
55. Kieft, J. S., K. Zhou, R. Jubin, M. G. Murray, J. Y. Lau, and J. A. Doudna. 1999. The hepatitis C virus internal ribosome entry site adopts an ion-dependent tertiary fold. J Mol Biol 292:513-529.
56. Kieft, J. S., K. Zhou, R. Jubin, M. G. Murray, J. Y. Lau, and J. A. Doudna. 2001. Mechanism of ribosome recruitment by hepatitis C IRES RNA. RNA 7:194-206.
57. Klinck, R., E. Westhof, S. Walker, M. Afshar, A. Collier, and F. Aboul-Ela. 2000. A potential RNA drug target in the hepatitis C virus internal ribosomal entry site. RNA 6:1423-1431.
58. Kolupaeva V G, Pestova T V, and Hellen C U T. 2000. An enzymatic foot-printing analysis of the interaction of 40S ribosomal subunits with the internal ribosomal entry site of hepatitis C virus. J Virol 74:6242-6250.
59. Kolupaeva, V. G., C. U. Hellen, and I. N. Shatsky. 1996. Structural analysis of the interaction of the pyrimidine tract-binding protein with the internal ribosomal entry site of encephalomyocarditis virus and foot-and-mouth disease virus RNAs. RNA 2:1199-1212.
60. Kolupaeva, V. G., T. V. Pestova, C. U. Hellen, and I. N. Shatsky. 1998. Translation eukaryotic initiation factor 4G recognizes a specific structural element within the internal ribosome entry site of encephalomyocarditis virus RNA. J Biol Chem 273:18599-18604.
61. Kozak, M. 1999. Initiation of translation in prokaryotes and eukaryotes. Gene 234:187-208.
62. Kruger, M., C. Beger, P. J. Welch, J. R. Barber, M. P. Manns, and F. Wong-Staal. 2001. Involvement of proteasome alpha-subunit PSMA7 in hepatitis C virus internal ribosome entry site-mediated translation. Mol Cell Biol 21: 8357-8364
63. La Monica, N. and V. R. Racaniello. 1989. Differences in replication of attenuated and neurovirulent polioviruses in human neuroblastoma cell line SH-SY5Y. J Virol 63:2357-2360.
64. Le, S. Y., N. Sonenberg, and J. V. Maizel, Jr. 1995. Unusual folding regions and ribosome landing pad within hepatitis C virus and pestivirus RNAs. Gene 154:137-143.
65. Lerat, H., Y. K. Shimizu, and S. M. Lemon. 2000. Cell type-specific enhancement of hepatitis C virus internal ribosome entry site-directed translation due to 5' nontranslated region substitutions selected during passage of virus in lymphoblastoid cells. J Virol 74:7024-7031.
66. L, K., T. M. Davis, C. Bailly, A. Kumar, D. W. Boykin, and W. D. Wilson. 2001. A heterocyclic inhibitor of the REV-RRE complex binds to RRE as a dimer. Biochemistry 40:1150-8.
67. Lipinski, J. 2000. J. Pharm. Tox. Meth. 44:235-249.
68. Llinas-Brunet M. 2002. NS3 serine protease inhibitors as potential antiviral agents for the treatment of hepatitis C virus infections. The 3rd internatl antiviral & vaccine discovery and development summit. March 13-14. Princeton, N.J.
69. Lohmann, V., F. Korner, A. Dobierzewska, and R. Bartenschlager. 2001. Mutations in hepatitis C virus RNAs conferring cell culture adaptation. J Virol 75:1437-1449.
70. Lohmann, V., F. Korner, J. Koch, U. Herian, L. Theilmann, and R. Bartenschlager. 1999. Replication of subgenomic hepatitis C virus RNAs in a hepatoma cell line. Science 285:110-113.

71. Lopez, d. Q., E. Lafuente, and E. Martinez-Salas. 2001. IRES interaction with translation initiation factors: functional characterization of novel RNA contacts with eIF3, eIF4B, and eIF4GII. RNA 7:1213-1226.
72. Lopez, d. Q. and E. Martinez-Salas. 2000. Interaction of the eIF4G initiation factor with the aphthovirus IRES is essential for internal translation initiation in vivo. RNA 6:1380-1392.
73. Lu, H. H. and E. Wimmer. 1996. Poliovirus chimeras replicating under the translational control of genetic elements of hepatitis C virus reveal unusual properties of the internal ribosomal entry site of hepatitis C virus. Proc Natl Acad Sci USA 93:1412-7.
74. Lukavsky, P. J., G. A. Otto, A. M. Lancaster, P. Sarnow, and J. D. Puglisi. 2000. Structures of two RNA domains essential for hepatitis C virus internal ribosome entry site function. Nat Struct Bio 7:1105-1110.
75. Lyons, A. J., J. R. Lytle, J. Gomez, and H. D. Robertson. Hepatitis C virus internal ribosome entry site RNA contains a tertiary structural element in a functional domain of stem-loop II. Nucleic Acids Res 29:2535-2546.
76. Macejak, D. G., K. L. Jensen, S. F. Jamison, K. Domenico, E. C. Roberts, N. Chaudhary, I. von_Carlowitz, L. Bellon, M. J. Tong, A. Conrad, P. A. Pavco, and L. M. Blatt. 2000. Inhibition of hepatitis C virus (HCV)-RNA-dependent translation and replication of a chimeric HCV poliovirus using synthetic stabilized ribozymes. Hepatology (Baltimore, Md.) 31:769-76.
77. Macejak, D. G., K. L. Jensen, P. A. Pavco, K. M. Phipps, B. A. Heinz, J. M. Colacino, and L. M. Blatt. 2001. Enhanced antiviral effect in cell culture of type 1 interferon and ribozymes targeting HCV RNA. J Viral Hepatitis 8:400-405.
78. Macejak, D. G. and P. Sarnow. 1991. Internal initiation of translation mediated by the 5' leader of a cellular mRNA. Nature 353:90-94.
79. Major M E, Rehermann B, and Feinstone. 2001. Hepatitis C viruses., p. 2535-2541. In D. Knipe and P. Howley (eds.), Fields Virology. Lippincott Williams and Wilkins, Philadelphia, Pa.
80. Manns M P, McHutchison J G, Gordon S C, Rustgi V K, Shiffman M, Reindollar R, Goodman Z D, Koury K, Ling M, and Albrecht J K. 2003. Peginterferon alfa-2b plus ribavirin compared with interferon alfa-2b plus ribavirin for initial treatment of chronic hepatitis C: a randomised trial. Lancet 358:958-965.
81. Martinez-Salas, E., R. Ramos, E. Lafuente, and d. Q. Lopez. 2001. Functional interactions in internal translation initiation directed by viral and cellular IRES elements. J Gen Virol 82:973-984.
82. Mazur, S., F. A. Tanious, D. Ding, A. Kumar, D. W. Boykin, I. J. Simpson, S. Neidle, and W. D. Wilson. 2000. A thermodynamic and structural analysis of DNA minor-groove complex formation. Journal of Molecular Biology 300:321-37.
83. McHutchison J G and Poynard T. 1999. Combination therapy with interferon plus ribavirin for the initial treatment of chronic hepatitis C. Semin. Liver Dis. 19 Suppl 1:57-65.
84. McHutchison, J. G., T. Poynard, R. Esteban-Mur, G. L. Davis, Z. D. Goodman, J. Harvey, M. H. Ling, J. J. Garaud, J. K. Albrecht, K. Patel, J. L. Dienstag, and T. Morgan. 2002. Hepatic HCV RNA before and after treatment with interferon alone or combined with ribavirin. Hepatology 35:688-693.
85. Meerovitch, K., J. Pelletier, and N. Sonenberg. 1989. A cellular protein that binds to the 5'-noncoding region of poliovirus RNA: implications for internal translation initiation. Genes Dev 3:1026-1034.
86. Meerovitch, K., Y. V. Svitkin, H. S. Lee, F. Lejbkowicz, D. J. Kenan, E. K. Chan, V. I. Agol, J. D. Keene, and N. Sonenberg. 1993. La autoantigen enhances and corrects aberrant translation of poliovirus RNA in reticulocyte lysate. J Virol 67: 3798-3807.
87. Mercer, D. F., D. E. Schiller, J. F. Elliott, D. N. Douglas, C. Hao, A. Rinfret, W. R. Addison, K. P. Fischer, T. A. Churchill, J. R. Lakey, D. L. Tyrrell, and N. M. Kneteman. 2001. Hepatitis C virus replication in mice with chimeric human livers. Nature Medicine 7:927-33.
88. Michel, Y. M., A. M. Borman, S. Paulous, and K. M. Kean. 2001. Eukaryotic initiation factor 4G-poly(A) binding protein interaction is required for poly(A) tail-mediated stimulation of picornavirus internal ribosome entry segment-driven translation but not for X-mediated stimulation of hepatitis C virus translation. Mol Cell Biol 21: 4097-4109.
89. Mitchell, S. A., E. C. Brown, M. J. Coldwell, R. J. Jackson, and A. E. Willis. 2001. Protein factor requirements of the Apaf-1 internal ribosome entry segment: roles of polypyrimidine tract binding protein and upstream of N-ras. Mol Cell Biol 21:3364-3374.
90. Moriguchi, e. al. 1992. Chem Pharm Bull 40:127-130.
91. Nanbru, C., I. Lafon, S. Audigier, M. C. Gensac, S. Vagner, G. Huez, and A. C. Prats. 2003. Alternative translation of the proto-oncogene c-myc by an internal ribosome entry site. J Biol Chem 272:32061-32066.
92. Niepmann, M., A. Petersen, K. Meyer, and E. Beck. 1997. Functional involvement of polypyrimidine tract-binding protein in translation initiation complexes with the internal ribosome entry site of foot-and-mouth disease virus. J Virol 71:8330-8339.
93. Odreman-Macchioli, F., F. E. Baralle, and E. Buratti. 2001. Mutational analysis of the different bulge regions of hepatitis C virus domain II and their influence on internal ribosome entry site translational ability. J Biol Chem 276: 41648-41655.
94. Odreman-Macchioli, F. E., S. G. Tisminetzky, M. Zotti, F. E. Baralle, and E. Buratti. 2000. Influence of correct secondary and tertiary RNA folding on the binding of cellular factors to the HCV IRES. Nucleic Acids Res 28:875-885.
95. Ohlmann, T., M. Lopez-Lastra, and J. L. Darlix. 2000. An internal ribosome entry segment promotes translation of the simian immunodeficiency virus genomic RNA. J Biol Chem 275:11899-11906.
96. Pain V M. 1996. Initiation of protein synthesis in eukaryotic cells. Eur J Biochem 236:747-771.
97. Pelletier, J. and N. Sonenberg . 1988. Internal initiation of translation of eukaryotic mRNA directed by a sequence derived from poliovirus RNA. Nature 334:320-325.
98. Pelletier, J. and N. Sonenberg . 1989. Internal binding of eucaryotic ribosomes on poliovirus RNA: translation in HeLa cell extracts. J Virol 63:441-444.
99. Pestova, T. V., S. I. Borukhov, and C. U. Hellen. 1998. Eukaryotic ribosomes require initiation factors 1 and 1A to locate initiation codons. Nature 394:854-859.
100. Pestova, T. V., I. N. Shatsky, S. P. Fletcher, R. J. Jackson, and C. U. Hellen. 1998. A prokaryotic-like mode of cytoplasmic eukaryotic ribosome binding to the initiation codon during internal translation initiation of hepatitis C and classical swine fever virus RNAs. Genes Dev 12: 67-83.
101. Pestova, T. V., I. N. Shatsky, and C. U. Hellen. 1996. Functional dissection of eukaryotic initiation factor 4F: the 4A subunit and the central domain of the 4G subunit are sufficient to mediate internal entry of 43S preinitiation complexes. Mol Cell Biol 16:6870-6878.

102. Peytou, V., R. Condom, N. Patino, R. Guedj, A. M. Aubertin, N. Gelus, C. Bailly, R. Terreux, and D. Cabrol_ Bass. 1999. Synthesis and antiviral activity of ethidium-arginine conjugates directed against the TAR RNA of HIV-1. Journal of Medicinal Chemistry 42:4042-53.

103. Pietschmann, T., V. Lohmann, A. Kaul, N. Krieger, G. Rinck, G. Rutter, D. Strand, and R. Bartenschlager. 2002. Persistent and transient replication of full-length hepatitis C virus genomes in cell culture. J Virol 76:4008-4021.

104. Pietschmann, T., V. Lohmann, G. Rutter, K. Kurpanek, and R. Bartenschlager. 2001. Characterization of cell lines carrying self-replicating hepatitis C virus RNAs. J Virol 75:1252-1264.

105. Poole, T. L., C. Wang, R. A. Popp, L. N. Potgieter, A. Siddiqui, and M. S. Collett. 1995. Pestivirus translation initiation occurs by internal ribosome entry. Virology 206: 750-754.

106. Pringle, C. 1999. Virus taxonomy—1999. The universal system of virus taxonomy, updated to include the new proposals ratified by the International Committee on Taxonomy of Viruses during 1998. Arch Virol 144:421-429.

107. Psaridi, L., U. Georgopoulou, A. Varaklioti, and P. Mavromara. 1999. Mutational analysis of a conserved tetraloop in the 5' untranslated region of hepatitis C virus identifies a novel RNA element essential for the internal ribosome entry site function. FEBS Lett 453:49-53.

108. Reynolds, J. E., A. Kaminski, A. R. Carroll, B. E. Clarke, D. J. Rowlands, and R. J. Jackson. 1996. Internal initiation of translation of hepatitis C virus RNA: the ribosome entry site is at the authentic initiation codon. RNA 2:867-878.

109. Reynolds, J. E., A. Kaminski, H. J. Kettinen, K. Grace, B. E. Clarke, A. R. Carroll, D. J. Rowlands, and R. J. Jackson. 1995. Unique features of internal initiation of hepatitis C virus RNA translation. EMBO J. 14: 6010-6020.

110. Rijnbrand R, Bredenbeek P; van der Straaten T, Whetter L, Inchauspe G, Lemon S, and Spaan W. 1995. Almost the entire 5' non-translated region of hepatitis C virus is required for cap-independent translation. FEBS Lett 365: 115-119.

111. Rijnbrand R C and Lemon S M. 2000. Internal ribosome entry site-mediated translation in hepatitis C virus replication. Curr Top. Microbiol Immunol. 242:85-116.

112. Rijnbrand, R., P. J. Bredenbeek, P. C. Haasnoot, J. S. Kieft, W. J. Spaan, and S. M. Lemon. 2001. The influence of downstream protein-coding sequence on internal ribosome entry on hepatitis C virus and other flavivirus RNAs. RNA 7:585-597.

113. Rijnbrand, R. C., T. E. Abbink, P. C. Haasnoot, W. J. Spaan, and P. J. Bredenbeek. 1996. The influence of AUG codons in the hepatitis C virus 5' nontranslated region on translation and mapping of the translation initiation window. Virology 226 :47-56.

114. Sachs, A. B., P. Sarnow, and M. W. Hentze. 1997. Starting at the beginning, middle, and end: translation initiation in eukaryotes. Cell 89:831-838.

115. Saito I, Miyamura T, Ohbayashi A, Harada H, Katayama T, Kikuchi S, Watanabe Y, Koi S, Onji M, Ohta Y, Choo Q, Houghton M, and Kuo G. 2003. Hepatitis C virus infection is associated with the development of hepatocellular carcinoma. Proc Natl Acad Sci U.S.A 87:6547-6549.

116. Schultz, D. E., M. Honda, L. E. Whetter, K. L. McKnight, and S. M. Lemon. 1996. Mutations within the 5' nontranslated RNA of cell culture-adapted hepatitis A virus which enhance cap-independent translation in cultured African green monkey kidney cells. J Virol 70:1041-1049.

117. Shimazaki, T., M. Honda, S. Kaneko, and K. Kobayashi. 2002. Inhibition of internal ribosomal entry site-directed translation of HCV by recombinant IFN-alpha correlates with a reduced La protein. Hepatology 35:199-208.

118. Simmonds, P. 2003. Variability of hepatitis C virus. Hepatology 21:570-583.

119. Sinha, R., P. Yang, S. Kodali, Y. Xiong, R. M. Kim, P. R. Griffin, H. R. Onishi, J. Kohler, L. L. Silver, and K. Chapman. 2001. Direct interaction of a vancomycin derivative with bacterial enzymes involved in cell wall biosynthesis. Chem Biol 8:1095-1106.

120. Sizova, D. V., V. G. Kolupaeva, T. V. Pestova, I. N. Shatsky, and C. U. Hellen. 1998. Specific interaction of eukaryotic translation initiation factor 3 with the 5' non-translated regions of hepatitis C virus and classical swine fever virus RNAs. J Virol 72:4775-4782.

121. Smith. 1994. Eur J Drug Metab Pharm 3:193-199.

122. Smith, D. B., J. Mellor, L. M. Jarvis, F. Davidson, J. Kolberg, M. Urdea, P. L. Yap, and P. Simmonds. 1995. Variation of the hepatitis C virus 5' non-coding region: implications for secondary structure, virus detection and typing. The International HCV Collaborative Study Group. J Gen Virol 76 (Pt 7):1749-1761.

123. Sonenberg N, Mathews M B, and Hershey J W B. 2000. Translational control of gene expression. Cold Spring Harbor. Cold Spring Harbor Laboratory Press, New York.

124. Spahn, C. M., J. S. Kieft, R. A. Grassucci, P. A. Penczek, K. Zhou, J. A. Doudna, and J. Frank. 2001. Hepatitis C virus IRES RNA-induced changes in the conformation of the 40s ribosomal subunit. Science 291:1959-1962.

125. Spatzenegger, M. and W. Jaeger. 1995. Clinical importance of hepatic cytochrome P450 in drug metabolism. Drug Metab Rev 27:397-417.

126. Subkhankulova, T., S. A. Mitchell, and A. E. Willis. 2001. Internal ribosome entry segment-mediated initiation of c-Myc protein synthesis following genotoxic stress. Biochem J 359:183-192.

127. Tang, S., A. J. Collier, and R. M. Elliott. 1999. Alterations to both the primary and predicted secondary structure of stem-loop IIIc of the hepatitis C virus 1b 5' untranslated region (5'UTR) lead to mutants severely defective in translation which cannot be complemented in trans by the wild-type 5'UTR sequence. J Virol 73:2359-2364.

128. Thiel, V. and S. G. Siddell. 1994. Internal ribosome entry in the coding region of murine hepatitis virus mRNA 5. J Gen Virol. 75 (Pt 11):3041-3046.

129. Tsukiyama-Kohara, K., N. Iizuka, M. Kohara, and A. Nomoto. 1992. Internal ribosome entry site within hepatitis C virus RNA. J Virol 66:1476-1483.

130. Vagner, S., M. C. Gensac, A. Maret, F. Bayard, F. Amalric, H. Prats, and A. C. Prats. 1995. Alternative translation of human fibroblast growth factor 2 mRNA occurs by internal entry of ribosomes. Mol Cell Biol 15:35-44.

131. Varaklioti A, Georgopoulou U, Kakkanas A, Psaridi L, Serwe M, Caselmann W H, and Mavromara P. 1998. Mutational analysis of two unstructured domains of the 5, untranslated region of HCV RNA. Biochem Biophys. Res Commun. 253:678-685.

132. Wang, C., S. Y. Le, N. Ali, and A. Siddiqui. 1995. An RNA pseudoknot is an essential structural element of the internal ribosome entry site located within the hepatitis C virus 5' noncoding region. RNA 1:526-537.

133. Wang, C., P. Sarnow, and A. Siddiqui. 1993. Translation of human hepatitis C virus RNA in cultured cells is mediated by an internal ribosome-binding mechanism. J Virol 67:3338-3344.

134. Wang, C., P. Sarnow, and A. Siddiqui. 1994. A conserved helical element is essential for internal initiation of translation of hepatitis C virus RNA. J Virol 68:7301-7307.

135. Wang, S. M., S. C. Fears, L. Zhang, J. J. Chen, and J. D. Rowley. 2000. Screening poly(dA/dT)-cDNAs for gene identification. Proceedings of the National Academy of Sciences of the United States of America 97:4162-7.

136. Wang, T. H., R. C. Rijnbrand, and S. M. Lemon. 2000. Core protein-coding sequence, but not core protein, modulates the efficiency of cap-independent translation directed by the internal ribosome entry site of hepatitis C virus. J Virol 74:11347-11358.

137. Wimmer, E., C. U. Hellen, and X. Cao. 1993. Genetics of poliovirus. Annu Rev Genet 27:353-436.

138. Wong, J. B., T. Poynard, M. H. Ling, J. K. Albrecht, and S. G. Pauker. 2000. Cost-effectiveness of 24 or 48 weeks of interferon alpha-2b alone or with ribavirin as initial treatment of chronic hepatitis C. International Hepatitis Interventional Therapy Group. Am. J. Gastroenterol. 95:1524-1530.

139. Zhao, W. D. and E. Wimmer. 2001. Genetic analysis of a poliovirus/hepatitis C virus chimera: new structure for domain II of the internal ribosomal entry site of hepatitis C virus. J Virol 75:3719-3730.

140. Zhao, W. D., E. Wimmer, and F. C. Lahser. 1999. Poliovirus/Hepatitis C virus (internal ribosomal entry site-core) chimeric viruses: improved growth properties through modification of a proteolytic cleavage site and requirement for core RNA sequences but not for core-related polypeptides. Journal of Virology 73:1546-54.

What is claimed is:

1. A compound of Formula (I):

(I)

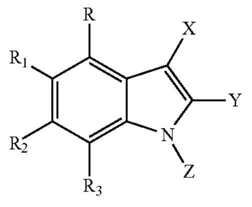

wherein:

X is:

-cyano;

Y is:

-aryl substituted with one or more of the following:

—$C_1$ to $C_6$ alkoxy, substituted with:

—$C_1$ to $C_6$ alkoxy,

-hydroxy,

-one or more halogen substituents,

-5 or 6 membered heterocycle, optionally substituted with:

—$C_1$ to $C_6$ alkyl, or

-hydroxy,

-amino optionally substituted with one or more $C_1$ to $C_6$ alkyl substituents, —$NR_iSO_2R_x$, where $R_x$ is $C_1$ to $C_6$ alkyl and $R_i$ is:

-hydrogen,

—$C_1$ to $C_6$ alkyl,

—$COR_x$, where $R_x$ is as defined above,

—$C_1$ to $C_6$ haloalkyl, or

—$C_1$ to $C_6$ haloalkoxy,

—$NR_jCOR_k$, where $R_k$ is:

—$C_1$ to $C_6$ alkyl,

-hydrogen, or

-amino optionally substituted with one or more $C_1$ to $C_6$ alkyl substituents, and $R_j$ is:

-hydrogen,

—$C_1$ to $C_6$ alkyl,

—$COR_x$, where $R_x$ is as defined above,

—$C_1$ to $C_6$ haloalkyl, or

—$C_1$ to $C_6$ haloalkoxy,

—$N{=}N^+{=}N^-$, or

—$COR_1$, where $R_1$ is 5 or 6 membered heterocycle optionally substituted with hydroxy, -amino optionally substituted with one or more $C_1$ to $C_6$ alkyl substituents, —$C_1$ to $C_6$ alkyl substituted with:

—$NHSO_2R_x$, where $R_x$ is as defined above, or

—$NR_xSO_2R_x$, where $R_x$, is as defined above,

—$C_1$ to $C_6$ haloalkoxy,

-hydroxy,

—$COOR_x$, where $R_x$ is as defined above,

—$COR_m$, where $R_m$ is:

-amino optionally substituted with:

(i) -cyclopropyl, cyclobutyl, cyclopentyl, or cyclohexyl, or (ii) one or more $C_1$ to $C_6$ alkyl substituents, where the $C_1$ to $C_6$ alkyl substituents are optionally substituted with:

-hydroxy

-5 or 6 membered heterocycle,

-amino optionally substituted with one or more $C_1$ to $C_6$ alkyl substituents, —$C_1$ to $C_6$ alkoxy, -3 to 7 membered heterocycle, optionally substituted with $C_1$ to $C_6$ alkyl, optionally substituted with di-$C_1$ to $C_6$ alkyl-amino, —$NHR_n$, where $R_n$ is:

—$CH_2CONH_2$, or

-aryl optionally substituted with:

—$C_1$ to $C_6$ alkyl,

-one or more halogen substituents,

-nitro, or

-one or more $C_1$ to $C_6$ alkoxy substituents,

—$NR_o$,$COR_p$, where $R_p$ is:

—$C_1$ to $C_6$ alkyl optionally substituted with:

-halogen,

—$C_1$ to $C_6$ alkoxy, or

-aryl,

-cyclopropyl,

-cyclobutyl,

-cyclopentyl,

-cyclohexyl,

-5 or 6 membered heterocycle,

-aryl, optionally substituted with halogen,

-5 or 6 membered heteroaryl optionally substituted with one or more $C_1$ to $C_6$ alkyl substituents, -hydrogen,

- 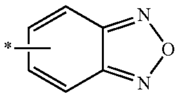 or 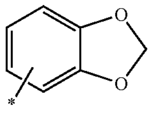, and where $R_o$ is:
-hydrogen,
—$C_1$ to $C_6$ alkyl,
—$COR_x$, where $R_x$ is as defined above,
—$C_1$ to $C_6$ haloalkyl, or
—$C_1$ to $C_6$ haloalkoxy,
—$NR_qCONR_qR_r$, where $R_q$ is:
-hydrogen,
—$C_1$ to $C_6$ alkyl,
—$C_1$ to $C_6$ haloalkyl,
—$C_1$ to $C_6$ haloalkoxy, or
—$COR_x$, where $R_x$ is as defined above,
and where $R_r$ is:
-aryl optionally substituted with:

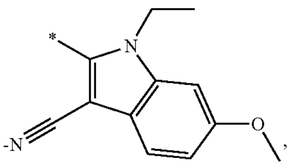,

—$C_1$ to $C_6$ alkyl,
—$C_1$ to $C_6$ haloalkyl,
—$OR_s$, where $R_s$ is aryl, or
—$COOR_x$, where $R_x$ is as defined above,
—$C_1$ to $C_6$ alkyl optionally substituted with one or more of the following:
-halogen,
—$C_2$ to $C_6$ alkenyl,
-aryl, or
—COOR, where $R_x$ is as defined above,
—$COOR_x$, where $R_x$ is as defined above,
-cyclopropyl, cyclobutyl, cyclopentyl, or cyclohexyl,
—$NR_tCOOR_u$, where $R_u$ is:
—$C_1$ to $C_{12}$ alkyl, optionally substituted with:
-aryl optionally substituted with $C_1$ to $C_6$ alkyl or $C_1$ to $C_6$ alkoxy,
—$C_2$ to $C_6$ alkenyl,
—$C_1$ to $C_6$ alkoxy,
—$C_2$ to $C_6$ alkynyl,
-halogen,
-5 or 6 membered heterocycle,
-cyclopropyl,
-cyclobutyl,
-cyclopentyl, or
-cyclohexyl,
-aryl, optionally substituted with:
—$C_1$ to $C_6$ alkoxy,
-halogen, or
—$C_1$ to $C_6$ alkyl,
-5 or 6 membered heterocycle,
-cyclopropyl, cyclobutyl, cyclopentyl, or cyclohexyl, wherein cyclopropyl, cyclobutyl, cyclopentyl or cyclohexyl are optionally substituted with one or more $C_1$ to $C_6$ alkyl substituents, and $R_t$ is:
-hydrogen,
—$C_1$ to $C_6$ alkyl,
—$COR_x$, where $R_x$ is as defined above,
—$C_1$ to $C_6$ haloalkyl, or
—$C_1$ to $C_6$ haloalkoxy,
—$NR_vSO_2R_w$, where $R_v$ is:
-hydrogen,
—$COR_x$, where $R_x$, is as defined above, or
—$C_1$ to $C_6$ alkyl, optionally substituted with:
-halogen,
—$COR_x$, where $R_x$ is as defined above,
—$OCOR_x$, where $R_x$ is as defined above,
-hydroxyl, or
—$C_1$ to $C_6$ alkoxy,
and where $R_w$ is:
—$C_1$ to $C_6$ alkyl optionally substituted with:
-halogen,
—$C_1$ to $C_6$ haloalkyl,
-aryl, or
-5 or 6 membered heterocycle,
-cyclopropyl,
-cyclobutyl,
-cyclopentyl,
-cyclohexyl,
—$C_2$ to $C_6$ alkenyl,
—$C_1$ to $C_6$ alkyl- or di-$C_1$ to $C_6$ alkyl-amino optionally substituted with halogen,
-5 or 6 membered heterocycle, or
-5 or 6 membered heteroaryl optionally substituted with:
—$C_1$ to $C_6$ alkyl,
-5 or 6 membered heterocycle, or

- 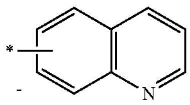 - 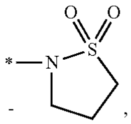, - 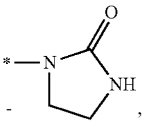,

- 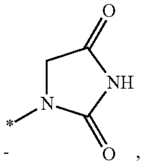, - 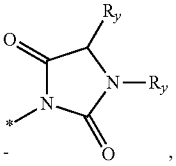, optionally substituted with $C_1$ to $C_6$ alkyl, where $R_y$ is $C_1$ to $C_6$ alkyl or hydrogen,

- 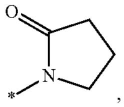, - 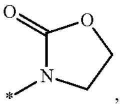, - 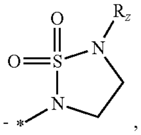, where $R_x$, is hydrogen or $C_1$ to $C_6$ alkyl, optionally substituted with aryl,
—$SR_x$, where $R_x$ is as defined above,
—$SO_2R_{aa}$, where $R_{aa}$ is:
—$C_1$ to $C_6$ alkyl,
-amino,
—$C_1$ to $C_6$ alkyl- or di-$C_1$ to $C_6$ alkyl-amino optionally substituted with hydroxy
or —$COOR_x$, where $R_x$ is as defined above,
-5 or 6 membered heteroaryl, -cyclopropylamino, cyclobutylamino, cyclopentylamino, or cyclohexylamino, -aryl, or —$NHR_{bb}$, where $R_{bb}$ is:

- 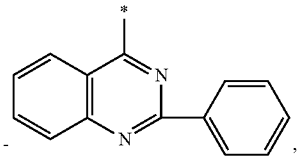 ,

- 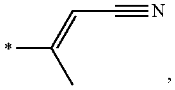 ,

—$C(=S)NH_2$, or

—$PO(OR_x)_2$, where $R_x$ is as defined above;

Z is:

-hydrogen;

—$C_1$ to $C_6$ alkyl optionally substituted with:

—$C_1$ to $C_6$ alkoxy,

-one or more halogen substituents, or

-aryl;

—$C_2$ to $C_6$ alkenyl;

-aryl optionally substituted with $C_1$ to $C_6$ alkoxy or one or more $C_1$ to $C_6$ alkyl substituents;

—$COOR_x$, where $R_x$ is as defined above;

- 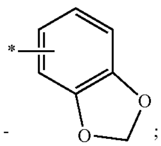 ;

-cyclopropyl;

-cyclobutyl;

-cyclopentyl;

-cyclohexyl;

-cyclopropylmethyl;

-cyclobutylmethyl; or

-cyclopentylmethyl;

R is hydrogen, halogen or $C_1$ to $C_6$ alkoxy;

$R_1$ is:

-hydrogen;

-hydroxy;

-halogen;

—$C_1$ to $C_6$ haloalkyl;

-nitro;

-5 or 6 membered heteroaryl;

-5 or 6 membered heterocycle;

—$C_1$ to $C_6$ alkoxy optionally substituted with:

-one or more halogen substituents,

-aryl, or

-5 or 6 membered heterocycle;

-aryl optionally substituted with $C_1$ to $C_6$ alkoxy;

—$COR_x$, where $R_x$ is as defined above;

—$C_1$ to $C_6$ alkyl optionally substituted with di-$C_1$ to $C_6$ alkyl-amino or 5 or 6 membered heterocycle;

-cyclopropyl;

-cyclobutyl;

-cyclopentyl; or -cyclohexyl;

and wherein when $R_2$ is unsubstituted methoxy, then $R_1$ is hydrogen;

$R_2$ is:

-nitro;

-hydrogen;

-halogen;

-hydroxy;

—$C_1$ to $C_6$ alkyl, optionally substituted with one or more halogen substituents;

-cyclopropyl;

-cyclobutyl;

-cyclopentyl;

-cyclohexyl;

-amino;

—$C_1$ to $C_6$ alkoxy optionally substituted with:

-one or more halogen substituents,

—$OCOR_x$, where $R_x$ is as defined above,

-di-$C_1$ to $C_6$ alkyl-amino optionally substituted with $C_1$ to $C_6$ alkoxy, -5 or 6 membered heterocycle optionally substituted with $C_1$ to $C_6$ alkyl, -5 or 6 membered heteroaryl, or -aryl;

—$COOR_x$, where $R_x$ is as defined above;

—$C_1$ to $C_6$ haloalkyl;

-amide optionally substituted with:

-hydroxy, or

-aryl;

-5 or 6 membered heteroaryl;

—$OCOR_x$, where $R_x$ is as defined above;

—$NHCOR_{jj}$, where $R_{jj}$ is:

—$C_1$ to $C_6$ alkoxy, or

-amino optionally substituted with one or more $C_1$ to $C_6$ alkyl substituents;

—$OR_{kk}$, where $R_{kk}$ is 5 to 6 membered heteroaryl;

—$NHSO_2R_x$, where $R_x$ is as defined above;

—$NHSO_2$cyclopropyl;

—$NHSO_2$cyclobutyl;

—$NHSO_2$cyclopentyl; or

—$NHSO_2$cyclohexyl;

and wherein when $R_1$ is unsubstituted methoxy, then $R_2$ is hydrogen; and $R_3$ is:

-hydrogen; or

—$CH_2OCOR_x$, where $R_x$ is as defined above;

or a pharmaceutically acceptable salt thereof.

2. A compound of Formula (I):

(I)

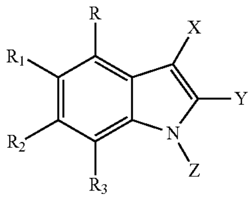

wherein:

X is:

-cyano;

Y is:

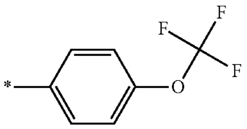

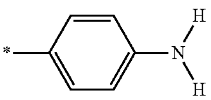

-continued
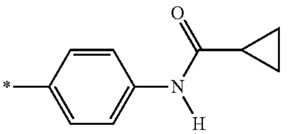
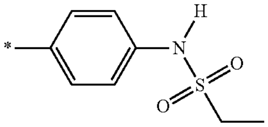
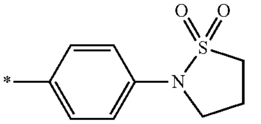
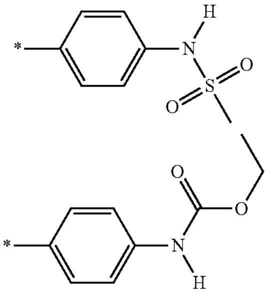
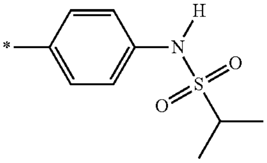
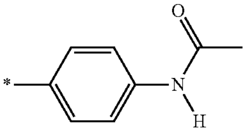
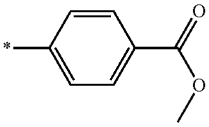
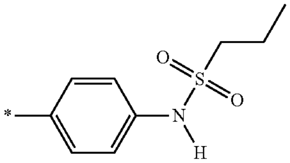
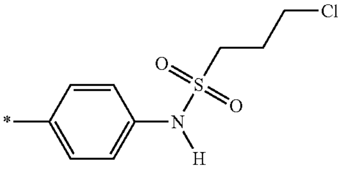
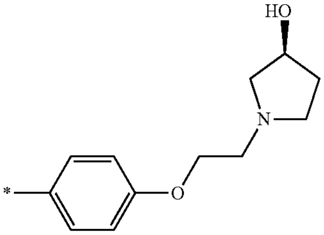
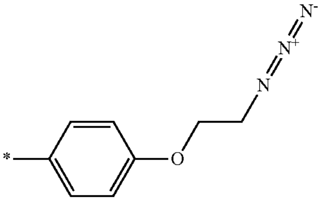
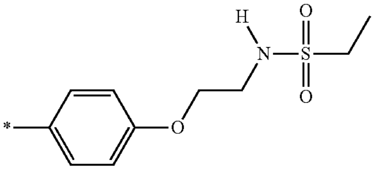
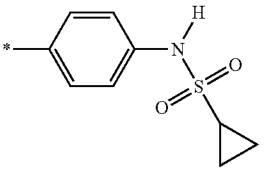
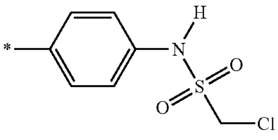
-continued
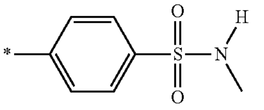
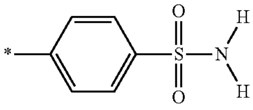
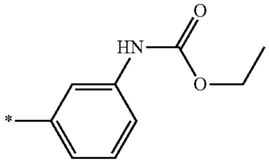
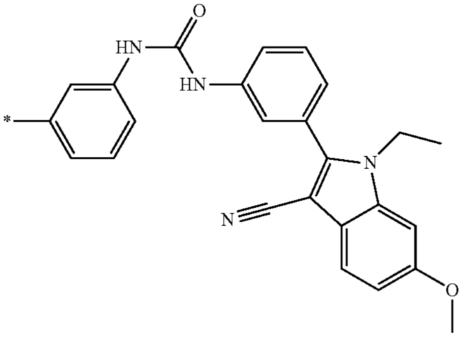
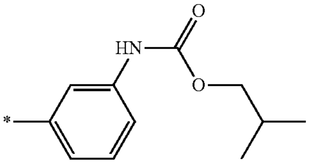
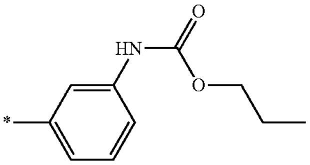
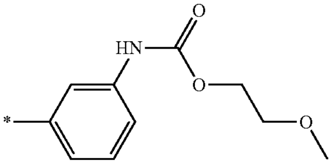
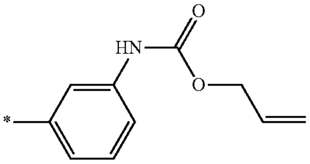
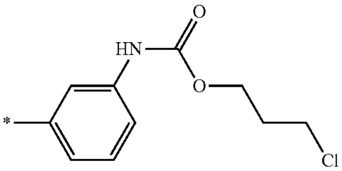
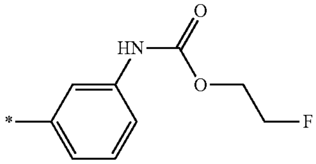

-continued
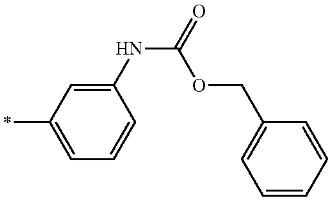
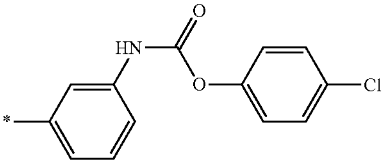
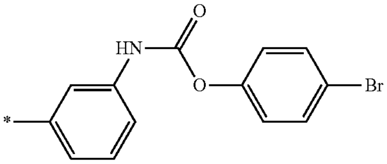
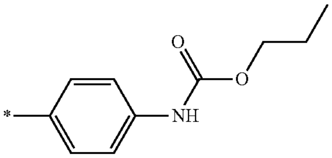
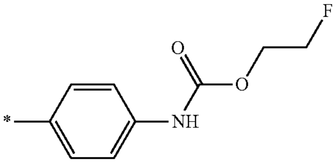
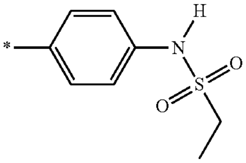
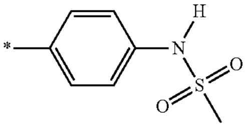
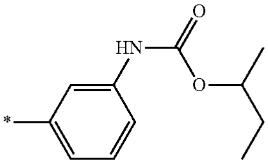
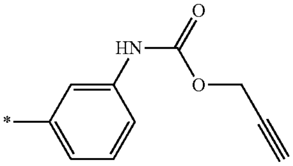
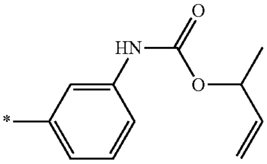
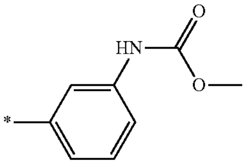
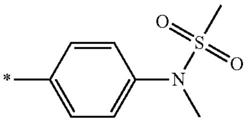
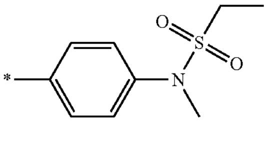
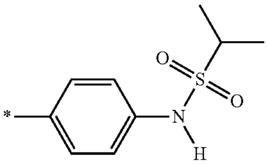
-continued
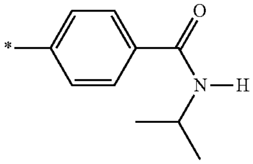
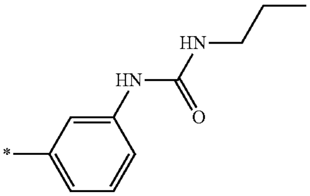
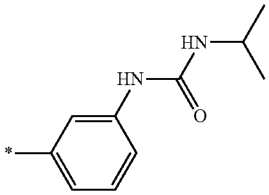
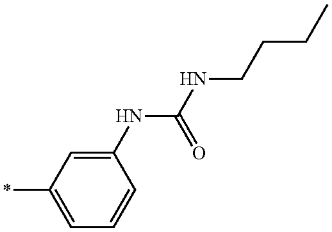
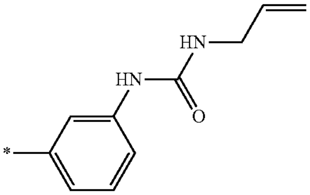
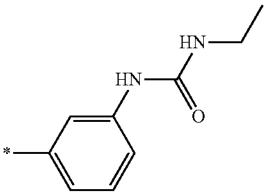
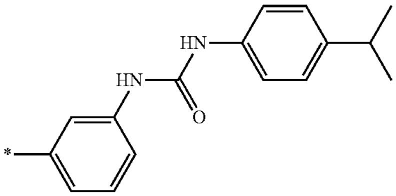
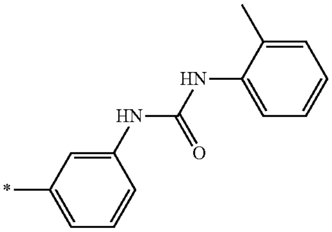
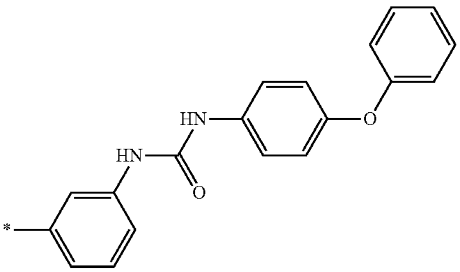
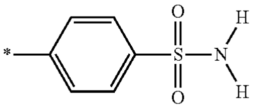
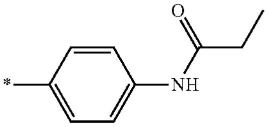

-continued
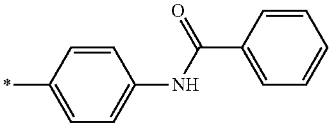
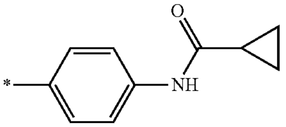
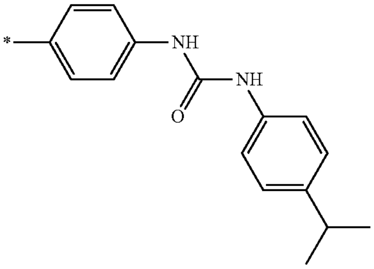
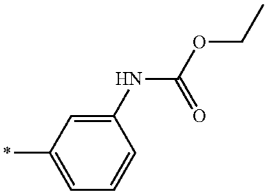
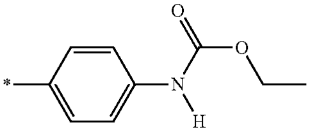
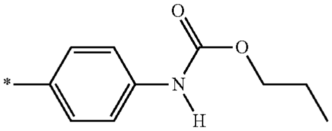
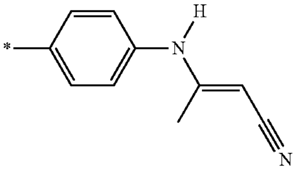
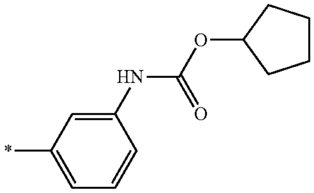
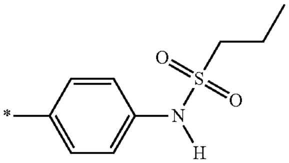
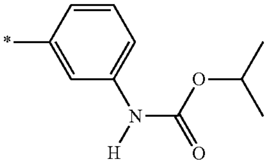
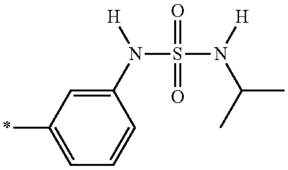
-continued
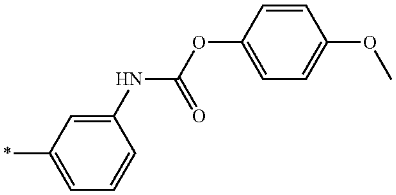
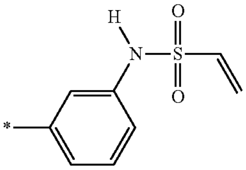
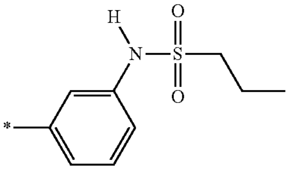
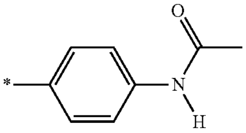
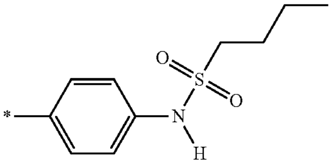
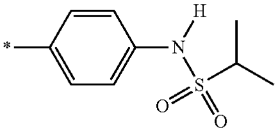
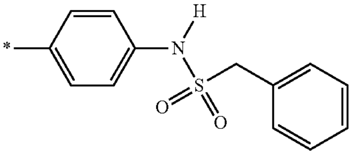
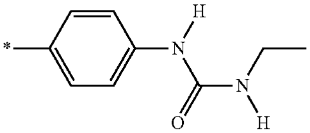
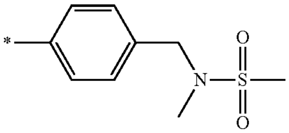
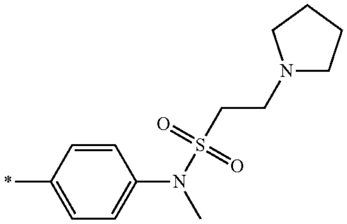
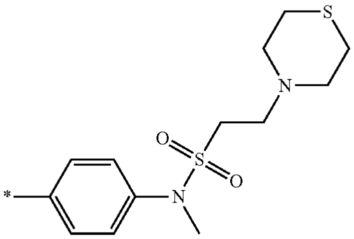

-continued
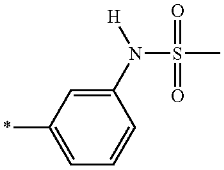
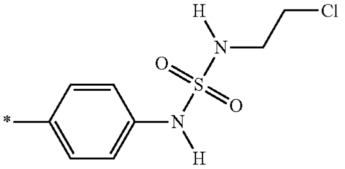
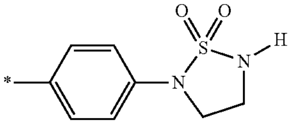
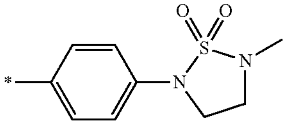
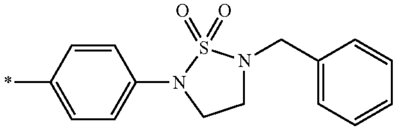
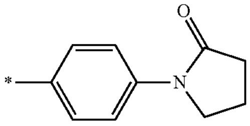
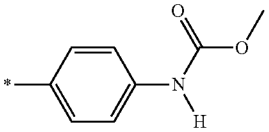
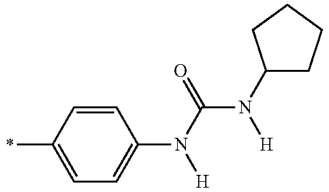
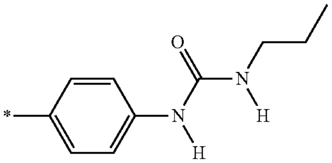
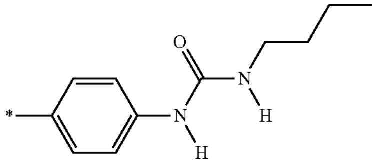
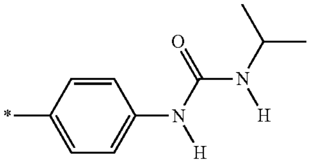
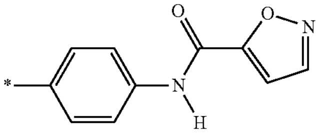
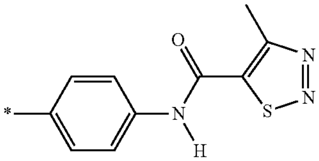
-continued
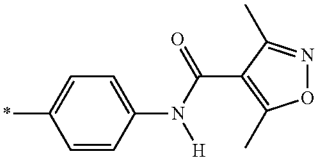
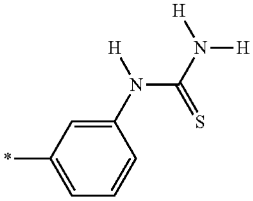
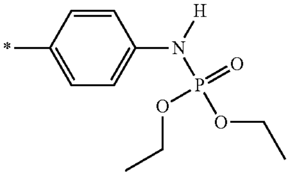
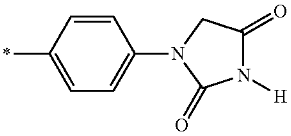
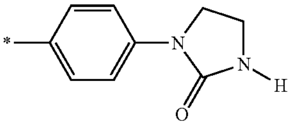
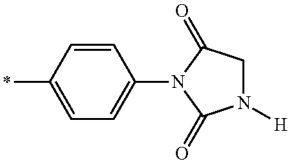
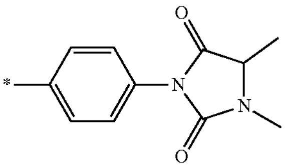
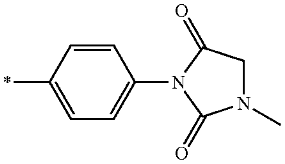
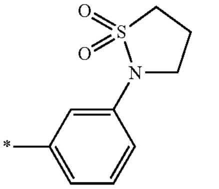
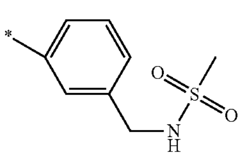
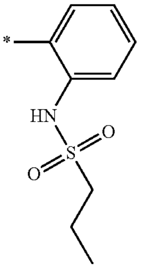
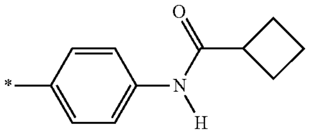
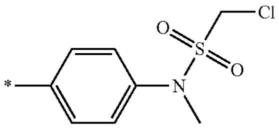

-continued

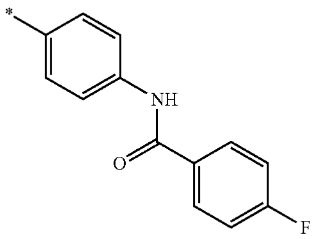

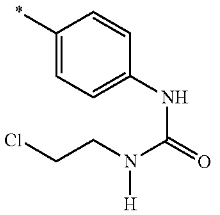

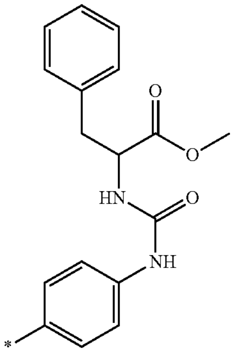

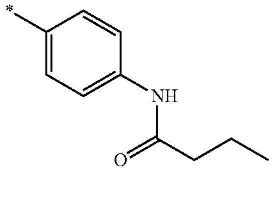

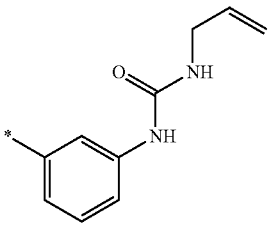

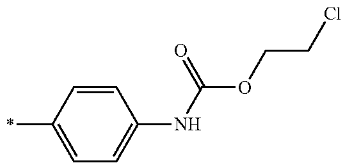

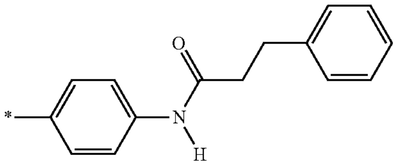

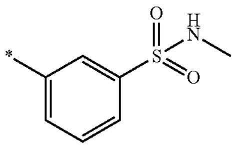

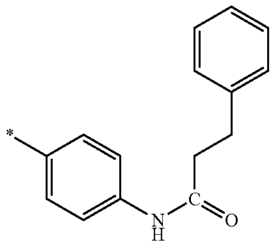

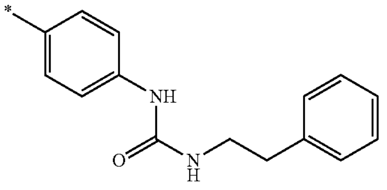

or

-continued

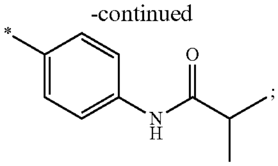

;

Z is:

-hydrogen;

—$C_1$ to $C_6$ alkyl optionally substituted with:

—$C_1$ to $C_6$ alkoxy,

-one or more halogen substituents, or

-aryl;

—$C_2$ to $C_6$ alkenyl;

-aryl optionally substituted with $C_1$ to $C_6$ alkoxy or one or more $C_1$ to $C_6$ alkyl substituents;

—$COOR_x$, where $R_x$ is as defined above;

- 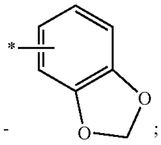 ;

-cyclopropyl;

-cyclobutyl;

-cyclopentyl;

-cyclohexyl;

-cyclopropylmethyl;

-cyclobutylmethyl; or

-cyclopentylmethyl;

R is hydrogen, halogen or $C_1$ to $C_6$ alkoxy;

$R_1$ is:

-hydrogen;

-hydroxy;

-halogen;

—$C_1$ to $C_6$ haloalkyl;

-nitro;

-5 or 6 membered heteroaryl;

-5 or 6 membered heterocycle;

—$C_1$ to $C_6$ alkoxy optionally substituted with:

-one or more halogen substituents,

-aryl, or

-5 or 6 membered heterocycle;

-aryl optionally substituted with $C_1$ to $C_6$ alkoxy;

—$COR_x$, where $R_x$ is as defined above;

—$C_1$ to $C_6$ alkyl optionally substituted with di-$C_1$ to $C_6$ alkyl-amino or 5 or 6 membered heterocycle;

-cyclopropyl;

-cyclobutyl;

-cyclopentyl; or

-cyclohexyl;

$R_2$ is:

-nitro;

-hydrogen;

-halogen;

-hydroxy;

—$C_1$ to $C_6$ alkyl, optionally substituted with one or more halogen substituents;

-cyclopropyl;

-cyclobutyl;

-cyclopentyl;

-cyclohexyl;

-amino;

—$C_1$ to $C_6$ alkoxy optionally substituted with:

-one or more halogen substituents,

—$OCOR_x$, where $R_x$ is as defined above,

-di-$C_1$ to $C_6$ alkyl-amino optionally substituted with $C_1$ to $C_6$ alkoxy, -5 or 6 membered heterocycle optionally substituted with $C_1$ to $C_6$ alkyl, -5 or 6 membered heteroaryl, or -aryl;

—$COOR_x$, where $R_x$ is as defined above;

—$C_1$ to $C_6$ haloalkyl;

-amide optionally substituted with:

-hydroxy, or

-aryl;

-5 or 6 membered heteroaryl;

—$OCOR_x$, where $R_x$ is as defined above;

—$NHCOR_{jj}$, where $R_{jj}$ is:

—$C_1$ to $C_6$ alkoxy, or

-amino optionally substituted with one or more $C_1$ to $C_6$ alkyl substituents;

—$OR_{kk}$, where $R_{kk}$ is 5 to 6 membered heteroaryl;

—$NHSO_2R_x$, where $R_x$ is as defined above;

—$NHSO_2$cyclopropyl;

—$NHSO_2$cyclobutyl;

—$NHSO_2$cyclopentyl; or

—$NHSO_2$cyclohexyl; and $R_3$ is:

-hydrogen; or

—$CH_2OCOR_x$, where $R_x$ is as defined above;

or a pharmaceutically acceptable salt thereof.

3. The compound of claim 1, wherein Z is selected from the group consisting of -cyclopropyl; -cyclobutyl; -cyclopentyl; -cyclohexyl; -cyclopropylmethyl;

-cyclobutylmethyl; -cyclopentylmethyl; -hydrogen; —$C_1$ to $C_6$ alkyl optionally substituted with:

—$C_1$ to $C_6$ alkoxy, -one or more halogen substituents, or -aryl; —$C_2$ to $C_6$ alkenyl; and -aryl optionally substituted with $C_1$ to $C_6$ alkoxy.

4. The compound of claim 1, wherein R is hydrogen.

5. The compound of claim 1, wherein $R_1$ is selected from the group consisting of -cyclopropyl; -cyclobutyl; -cyclopentyl; -cyclohexyl; -hydrogen; -halogen; -nitro; -5 or 6 membered heterocycle; —$C_1$ to $C_6$ alkoxy optionally substituted with: -aryl; -aryl optionally substituted with $C_1$ to $C_6$ alkoxy.

6. The compound of claim 1, wherein $R_2$ is selected from the group consisting of -nitro; -hydrogen; -halogen; -hydroxy; —$C_1$ to $C_6$ alkyl, optionally substituted with one or more halogen substituents; -cyclopropyl; -cyclobutyl; -cyclopentyl; -cyclohexyl; —$C_1$ to $C_6$ alkoxy optionally substituted with: -one or more halogen substituents, —$OCOR_x$, where $R_x$ is as defined above, -di-$C_1$ to $C_6$ alkyl-amino optionally substituted with $C_1$ to $C_6$ alkoxy, -5 or 6 membered heterocycle optionally substituted with $C_1$ to $C_6$ alkyl, or -5 or 6 membered heteroaryl; -amide; —$NHSO_2R_x$, where $R_x$ is as defined above; —$NHSO_2$cyclopropyl; —$NHSO_2$cyclobutyl; —$NHSO_2$cyclopentyl; or —$NHSO_2$cyclohexyl.

7. The compound of claim 1, wherein $R_3$ is hydrogen.

8. A compound selected from the group consisting of:

19

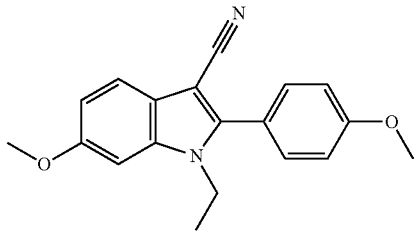

21

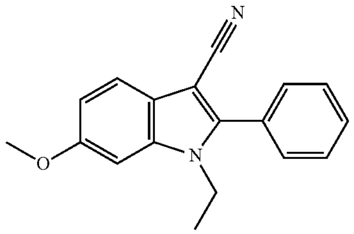

53

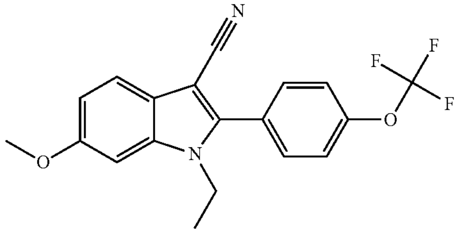

55

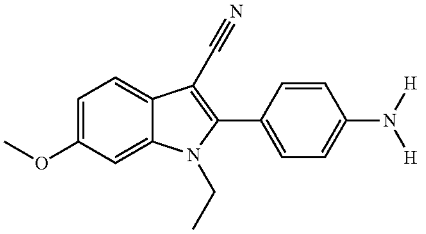

63

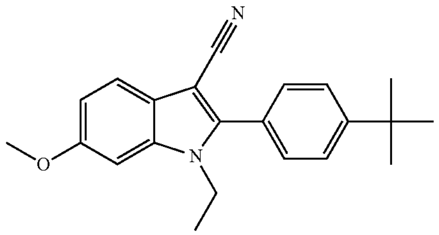

70

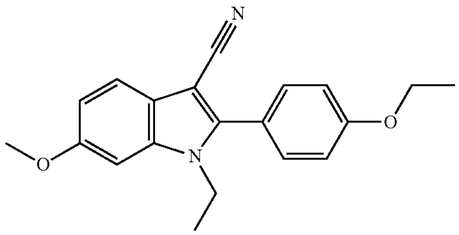

-continued
71
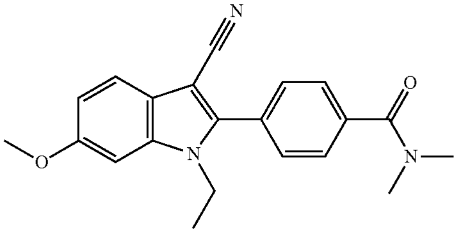
74
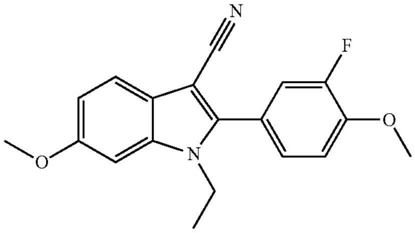
76
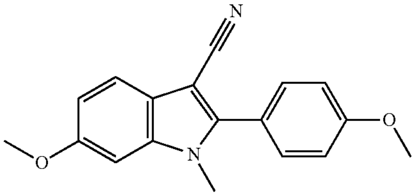
77
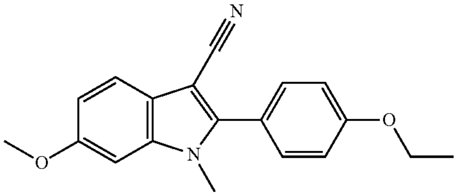
79
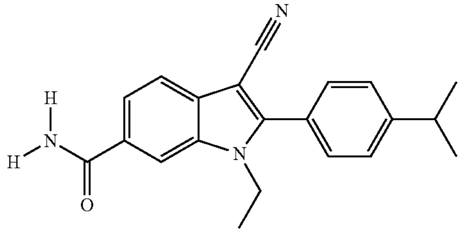
80
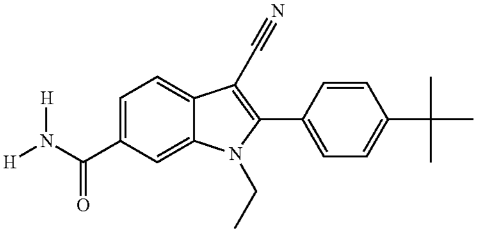
81
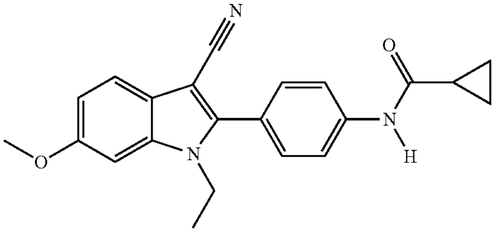
-continued
83
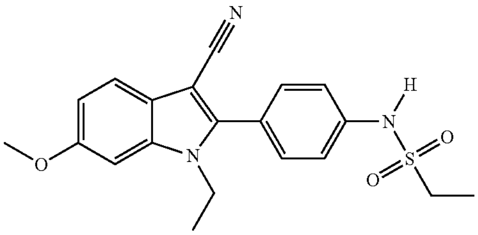
84
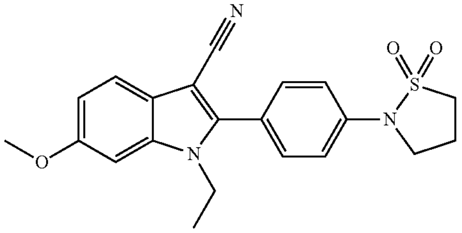
85
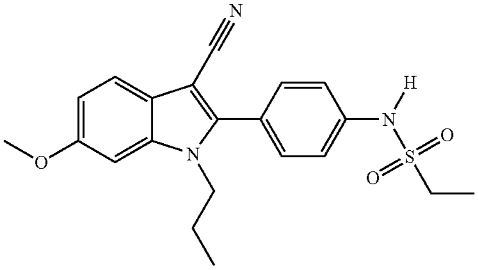
86
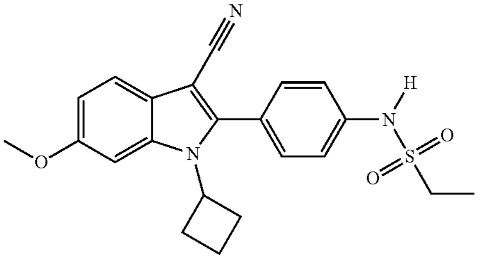
87
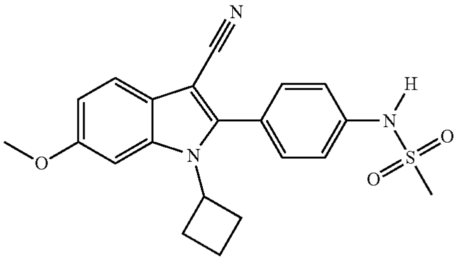
88
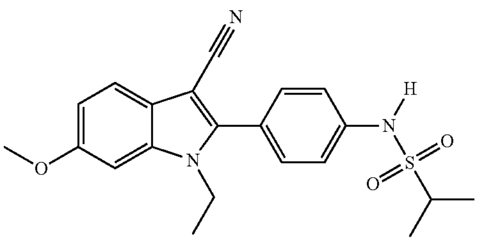

-continued
100
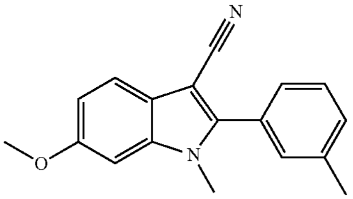
110
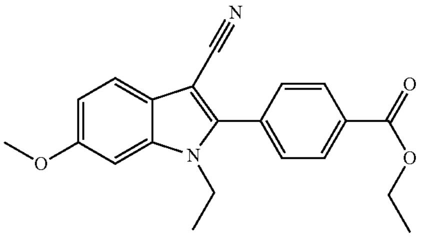
113
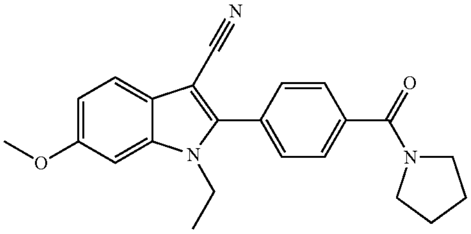
114
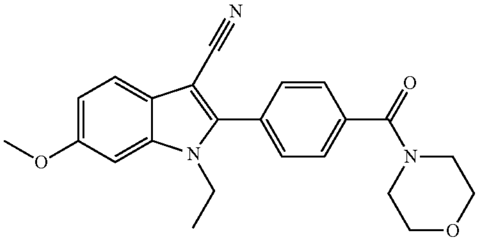
121
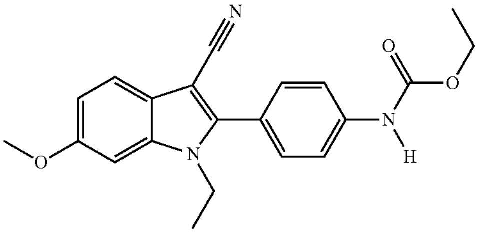
122
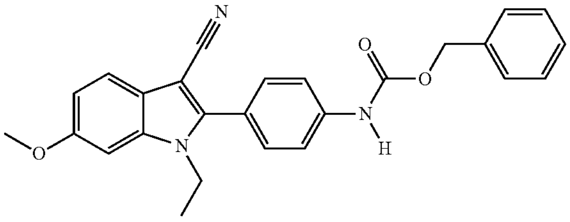
-continued
123
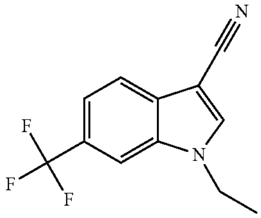
128
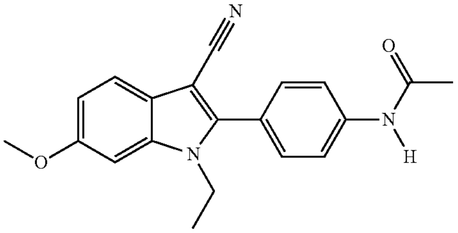
129
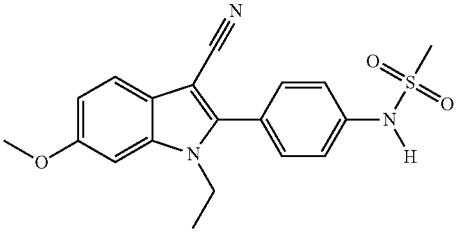
180
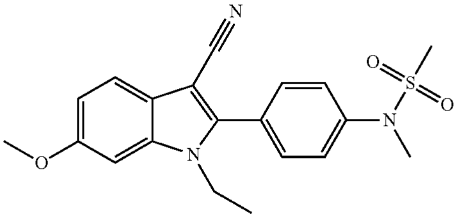
181
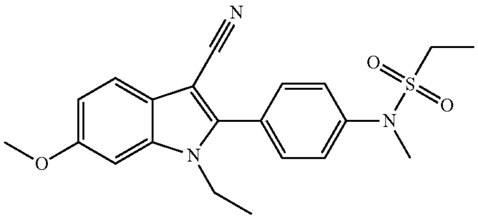
189
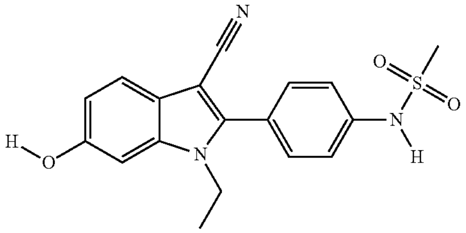
190
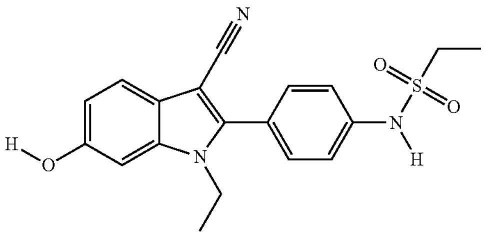

-continued
191
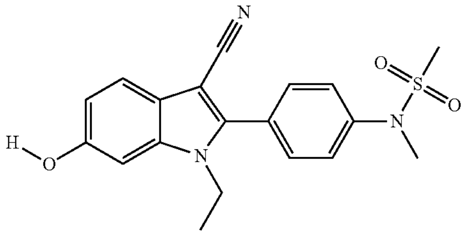
192
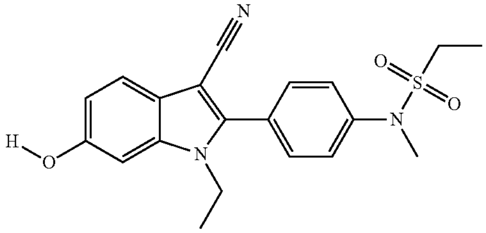
229
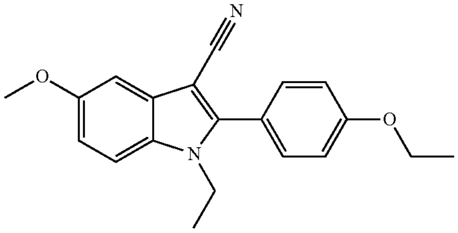
239
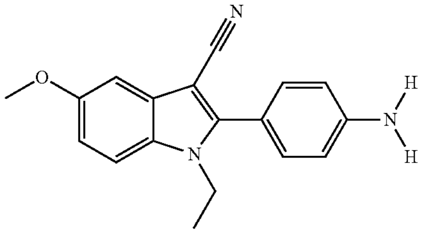
240
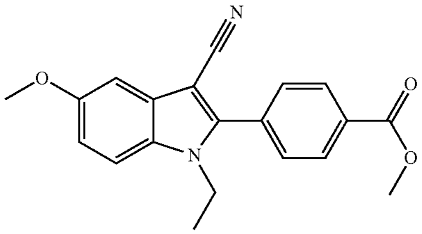
242
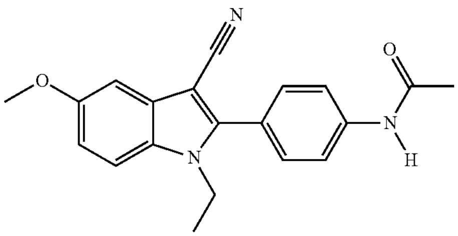
-continued
243
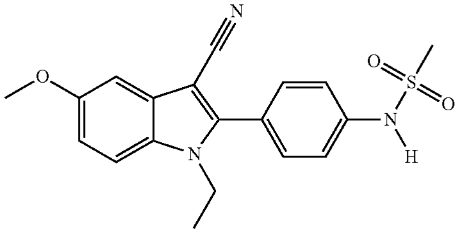
244
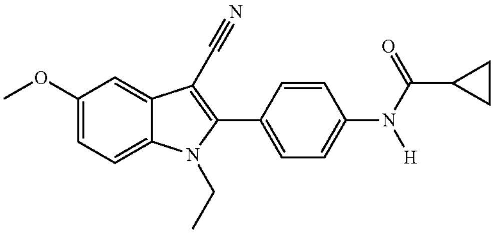
245
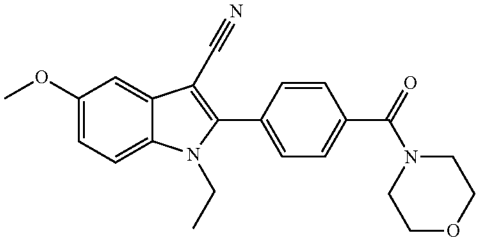
246
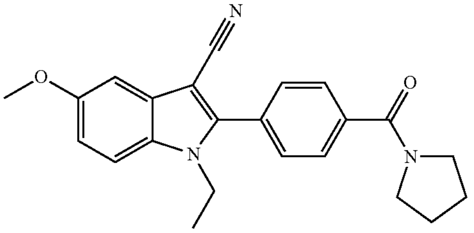
247
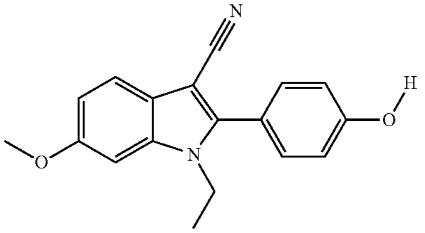
248
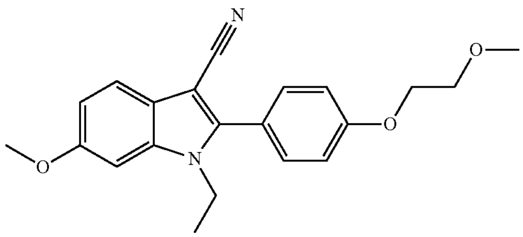

-continued
249
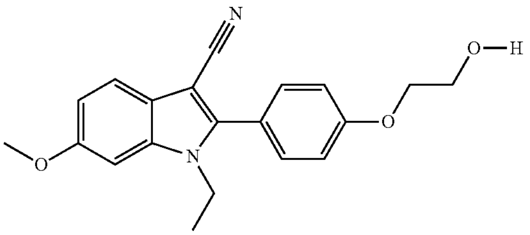
250
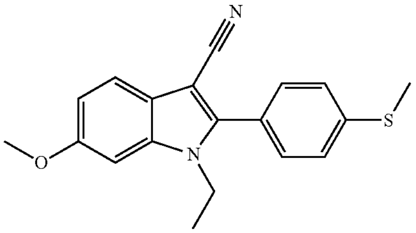
251
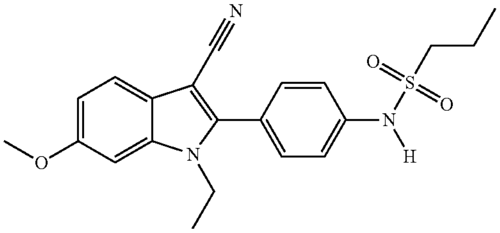
252
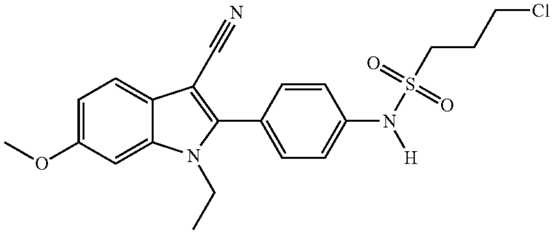
253
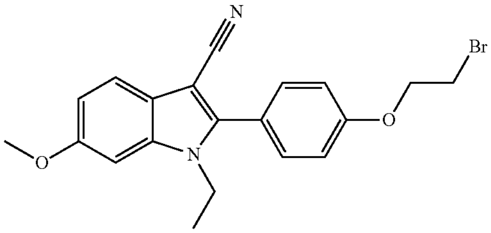
255
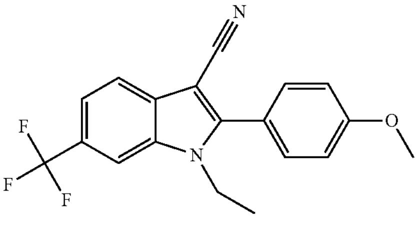
-continued
256
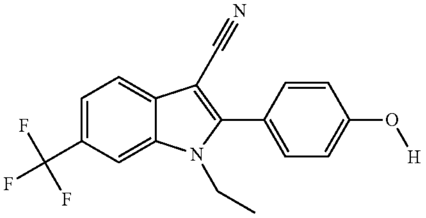
257
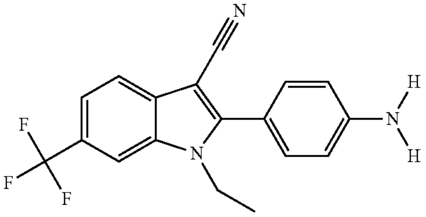
258
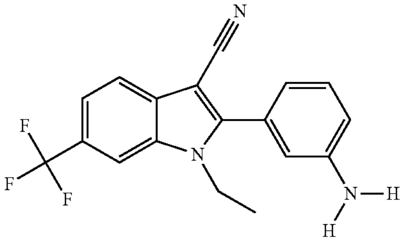
259
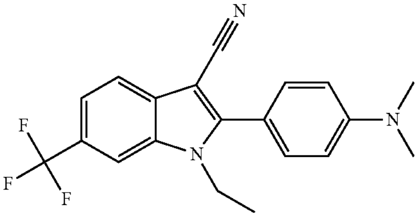
261
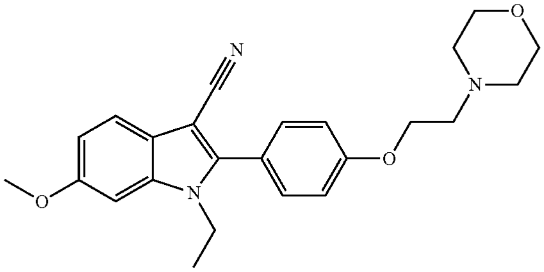
262
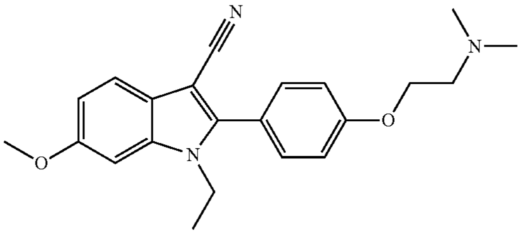

-continued
263
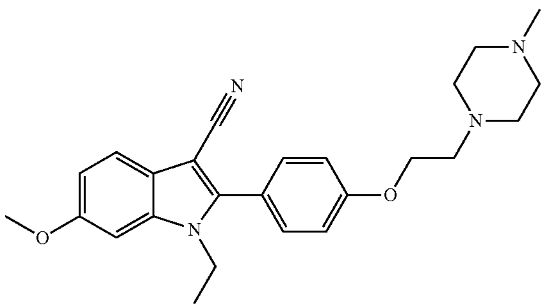
264
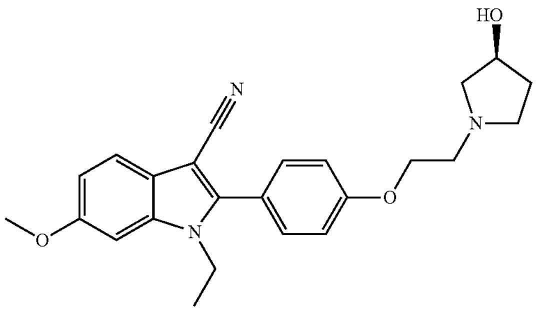
265
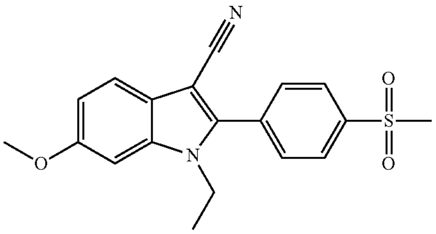
266
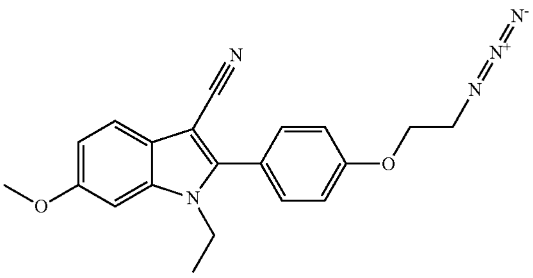
267
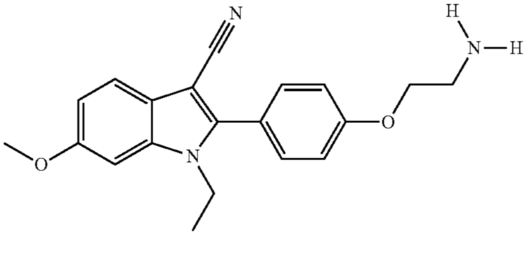
-continued
268
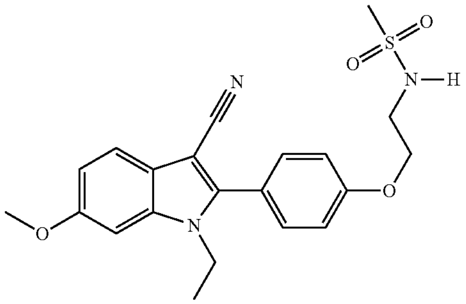
269
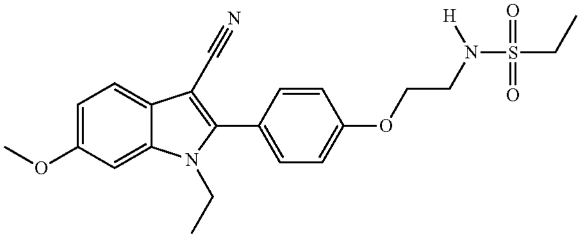
270
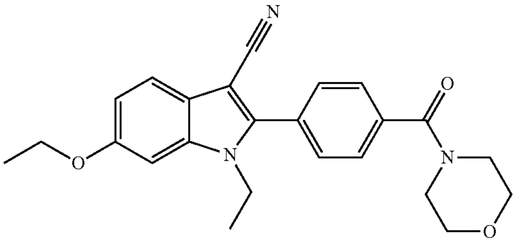
271
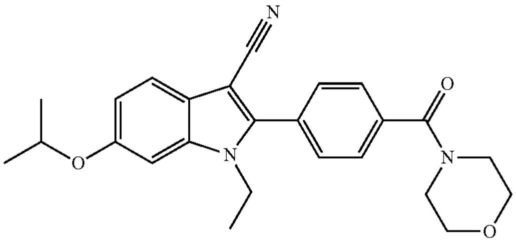
272
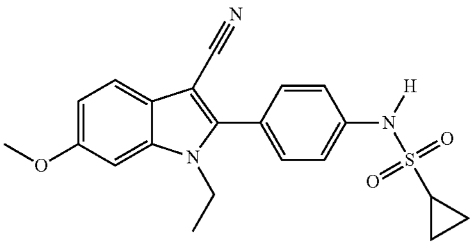
273
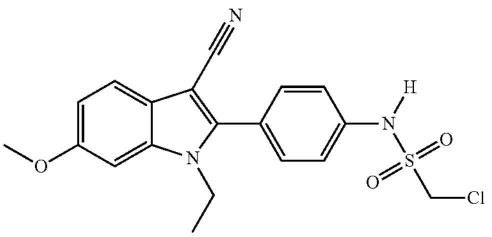

-continued
274
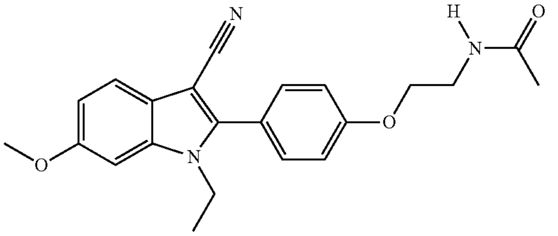
275
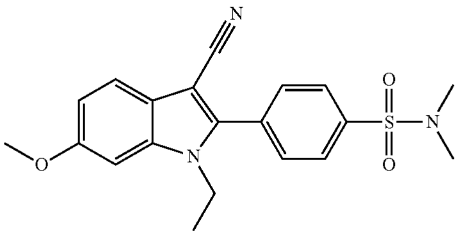
276
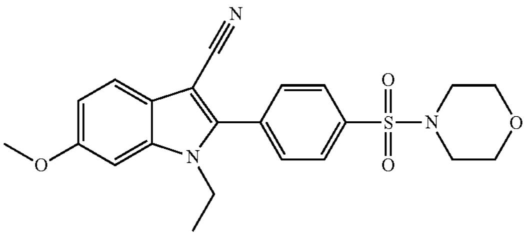
277
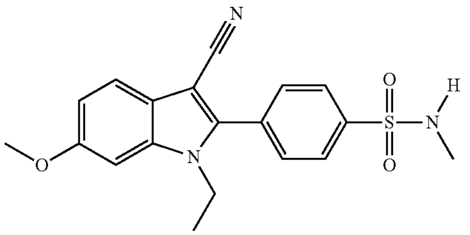
278
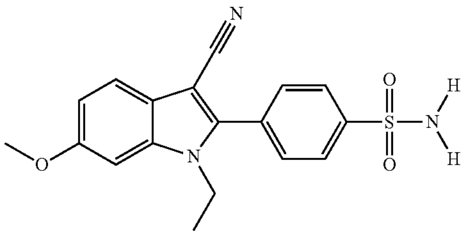
279
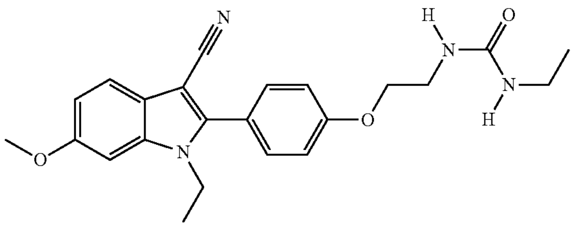
-continued
280
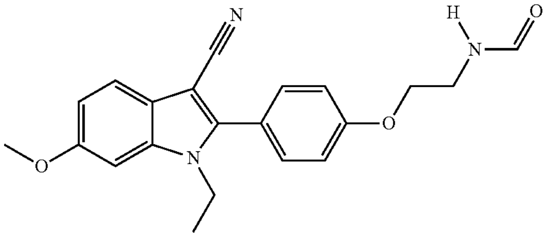
283
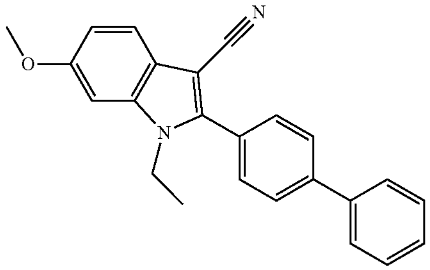
285
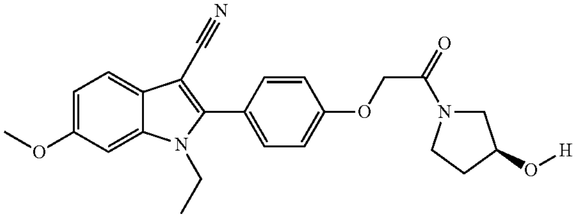
287
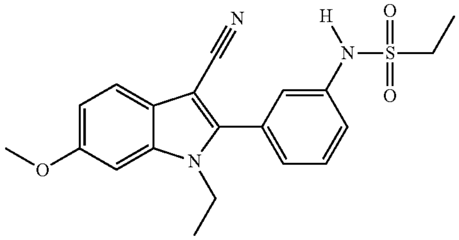
288
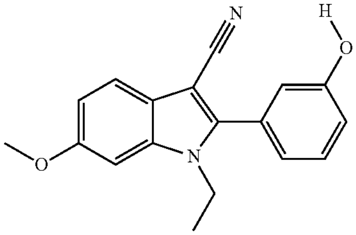
289
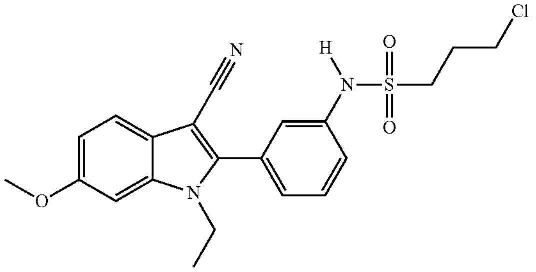

-continued
290
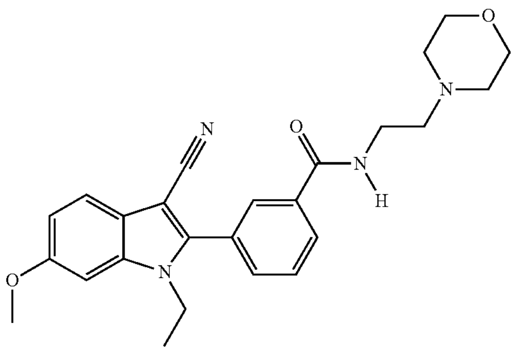
291
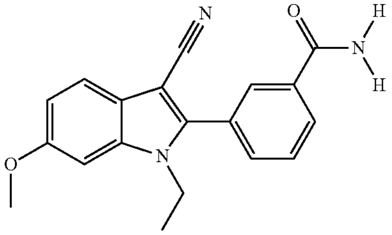
292
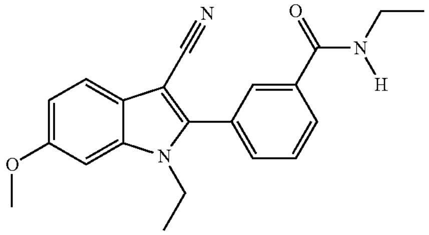
293
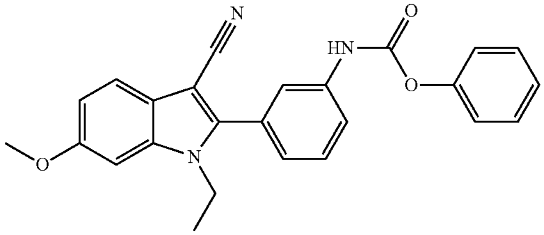
294
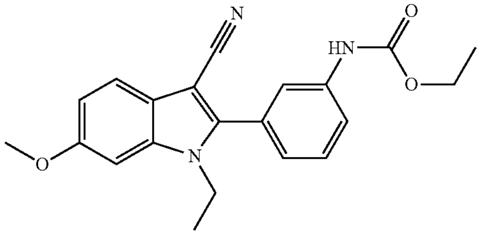
-continued
295
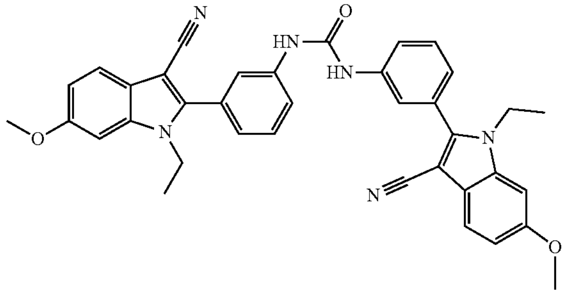
296
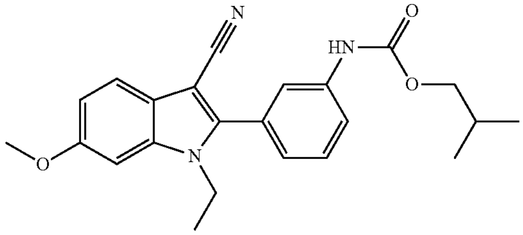
297
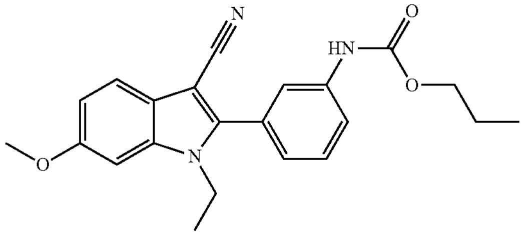
298
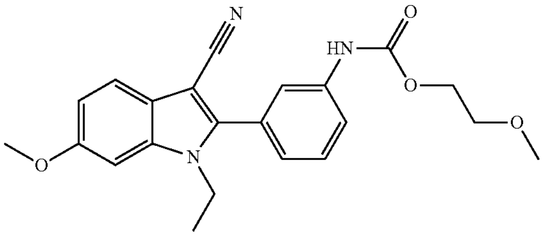
299
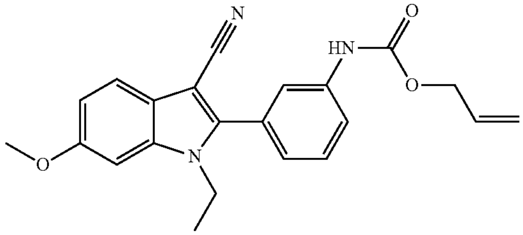
300
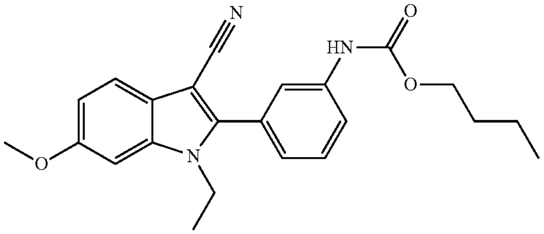

-continued
301
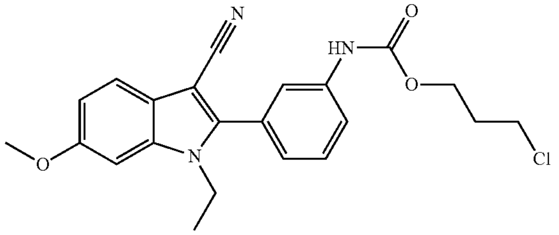
302
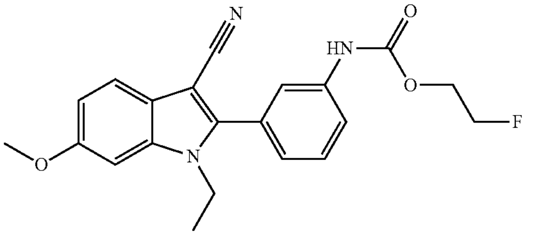
303
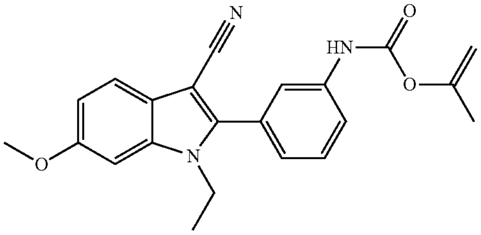
304
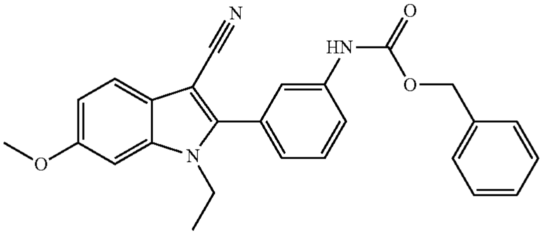
305
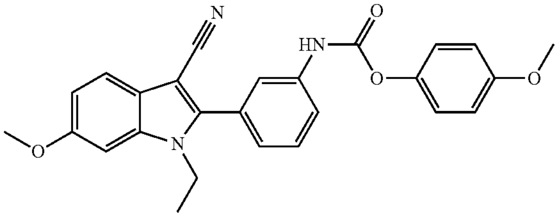
306
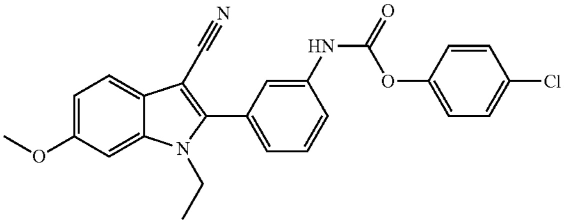
-continued
307
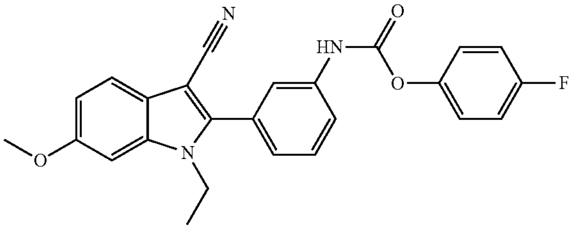
308
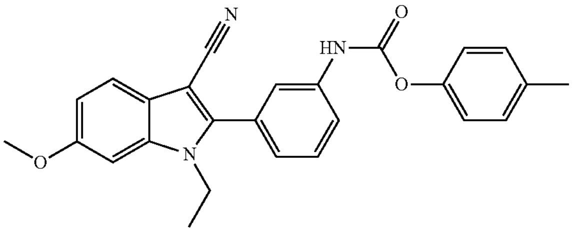
309
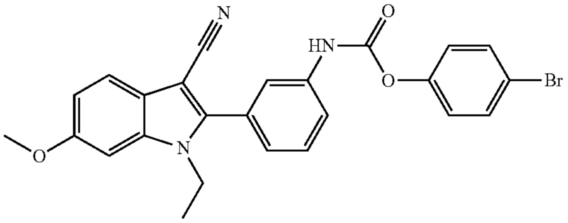
310
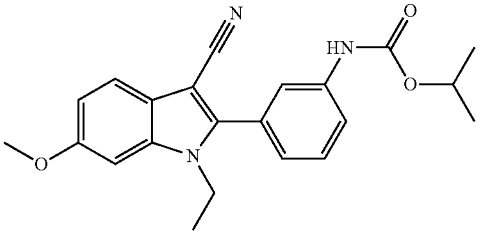
311
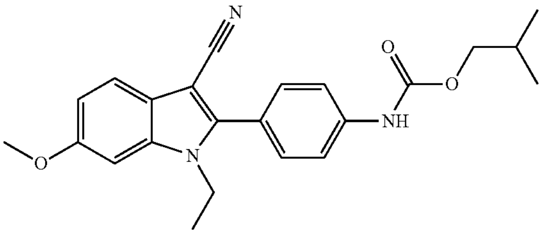
312
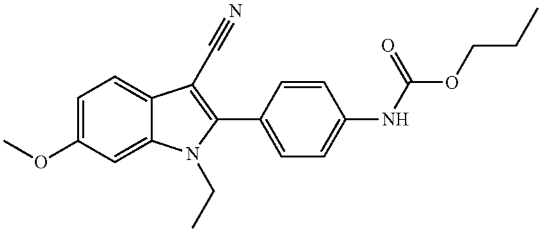

313
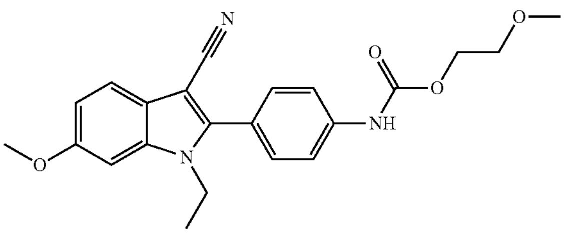
314
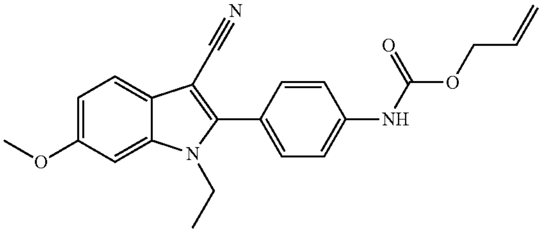
315
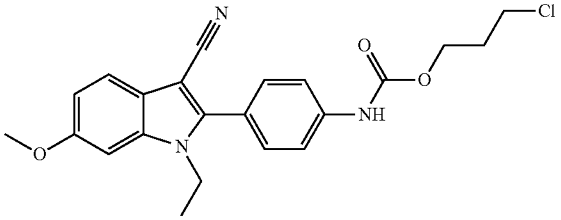
316
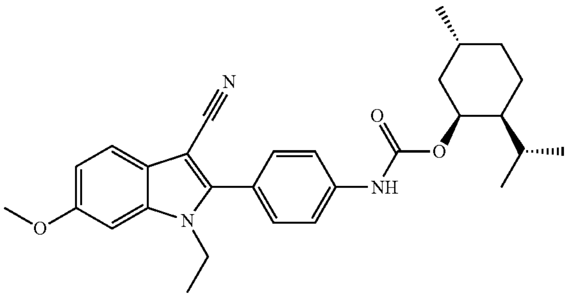
317
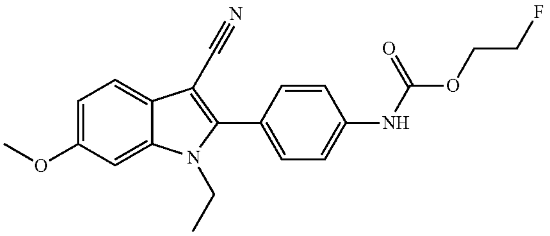
318
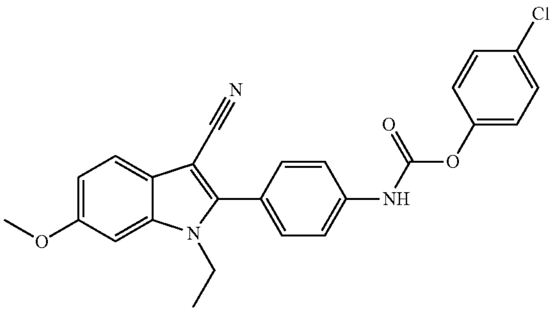
319
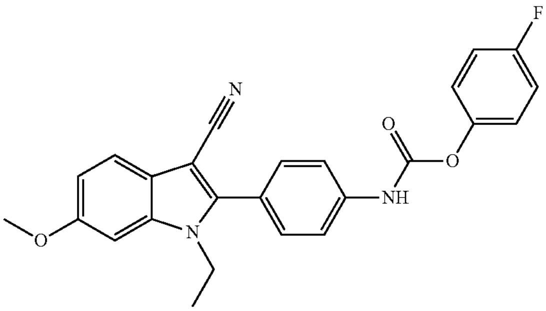
320
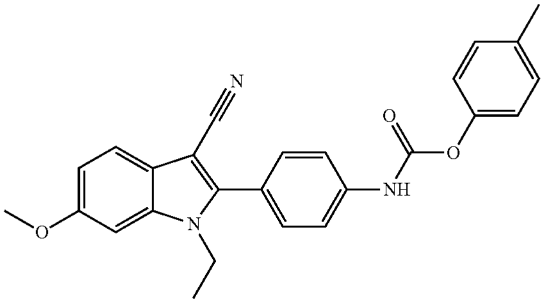
321
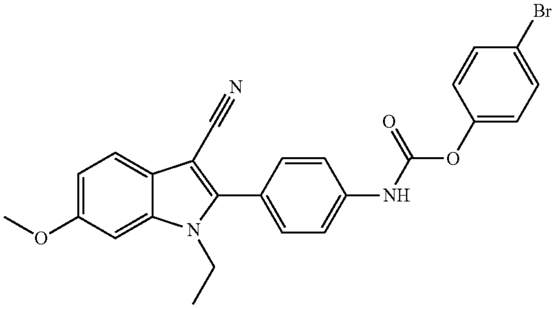
322
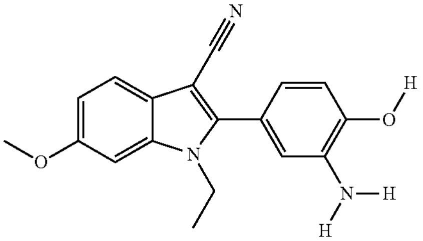

-continued
323
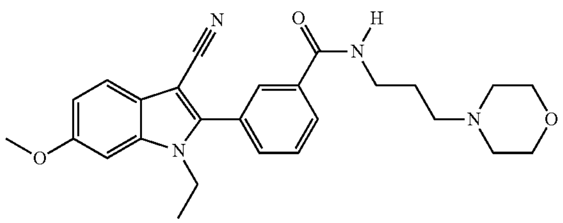
324
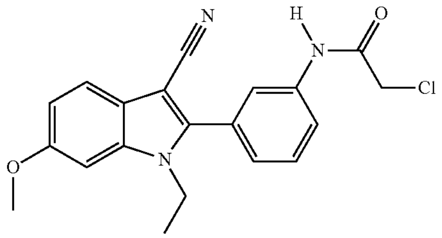
325
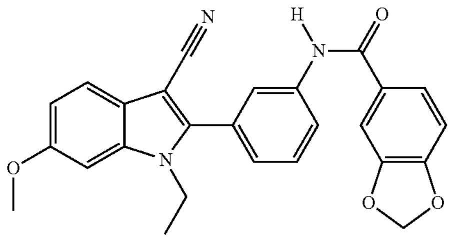
326
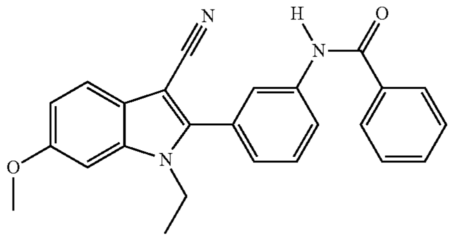
327
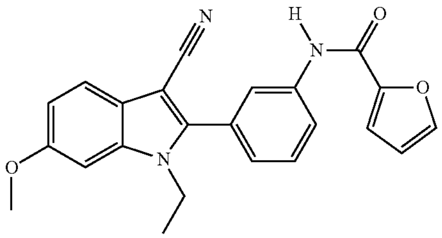
328
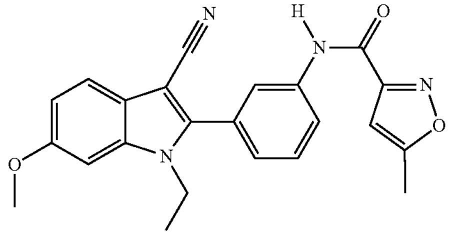
-continued
329
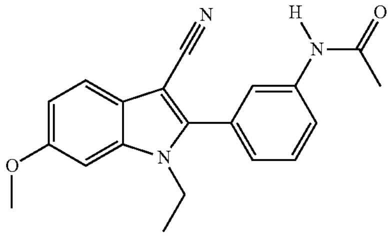
330
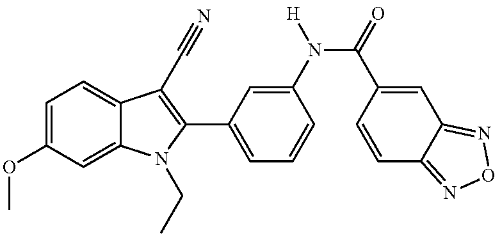
331
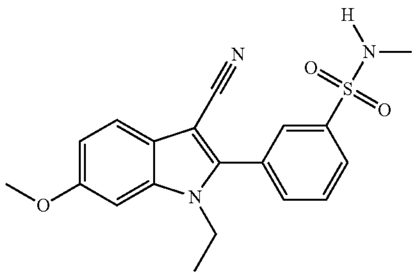
333
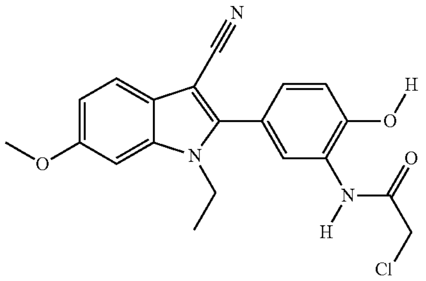
344
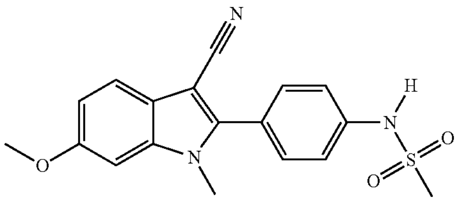
345
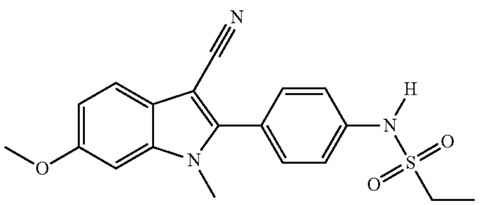

-continued
346
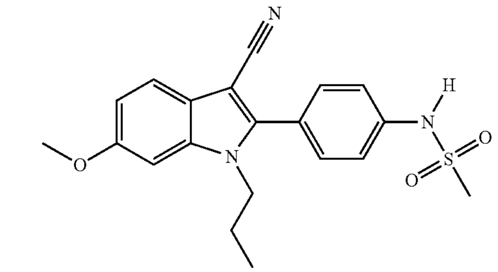
349
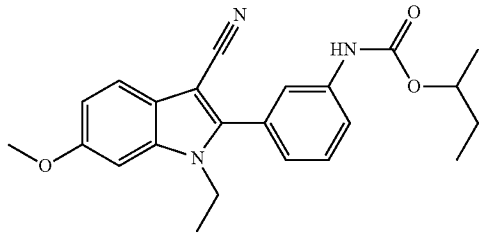
350
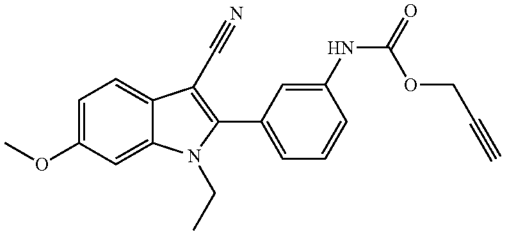
351
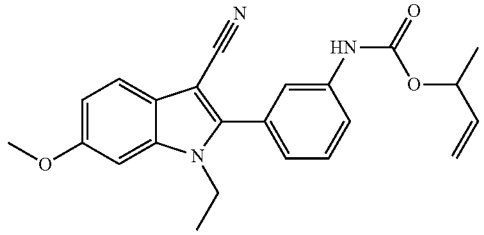
352
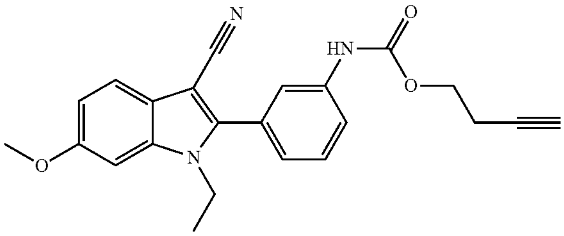
353
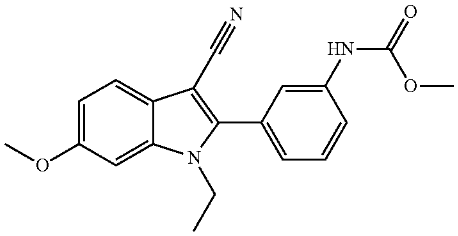
-continued
354
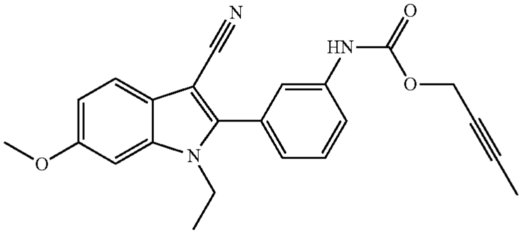
355
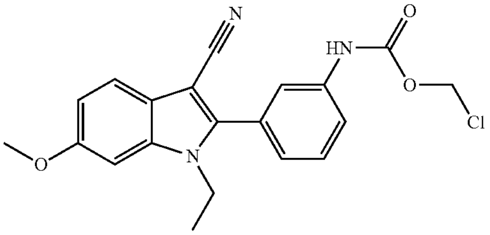
356
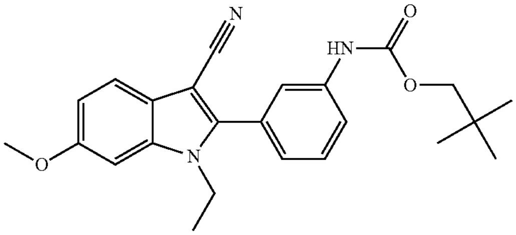
357
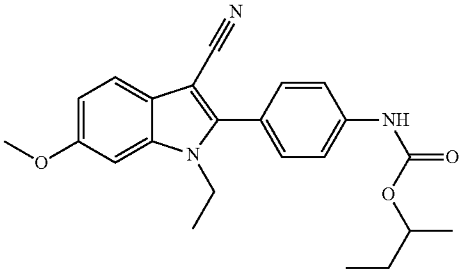
358
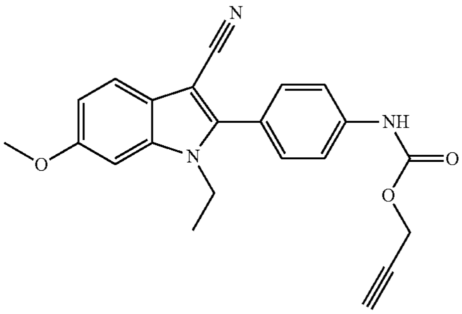
359
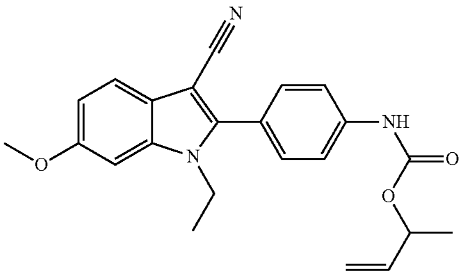

360
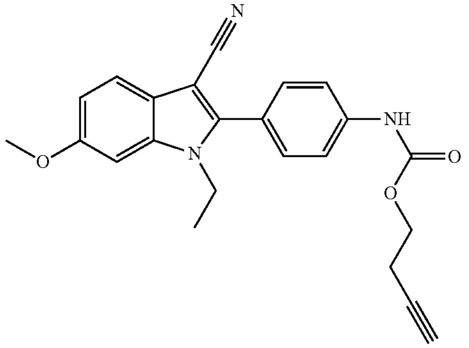
361
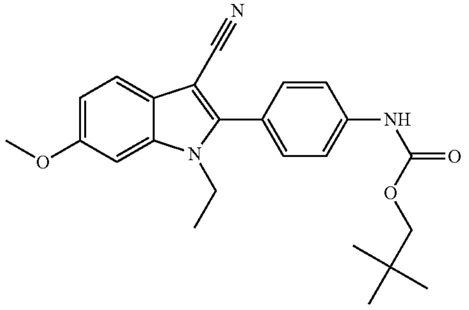
364
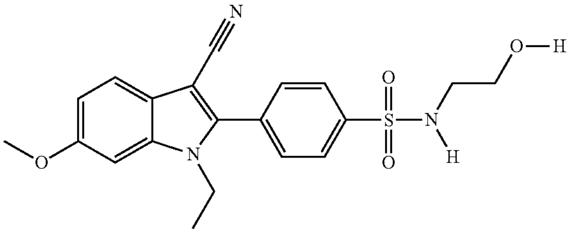
362
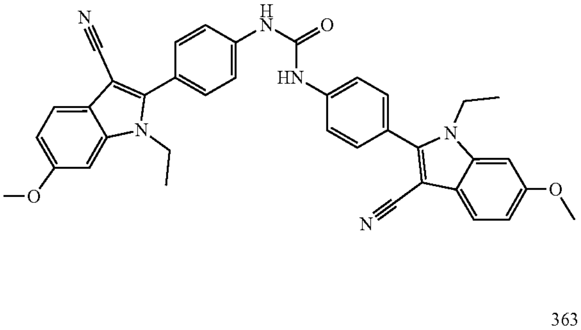
363
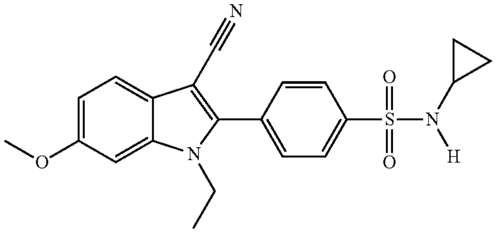
365
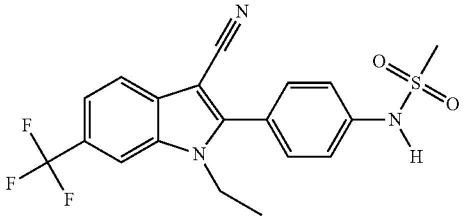
366
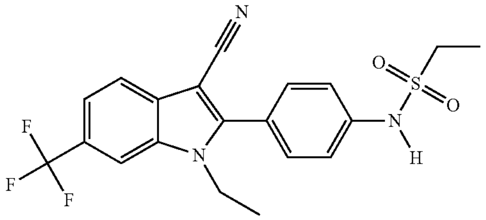
367
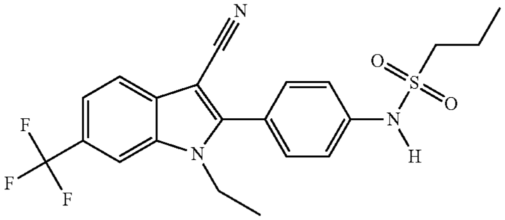
368
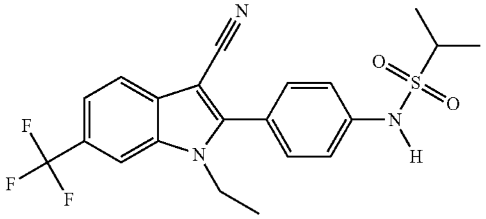
369
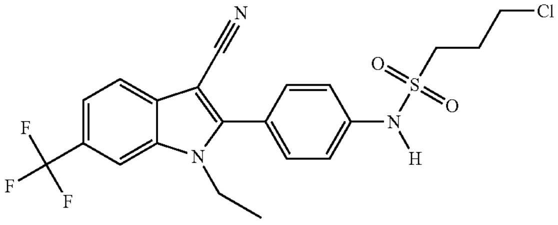
370
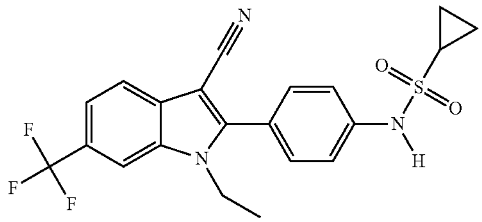
371
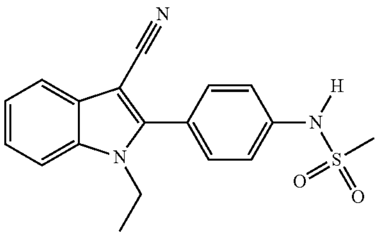

-continued
372
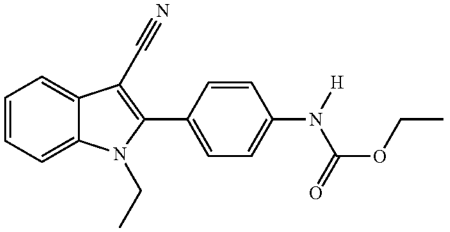
373
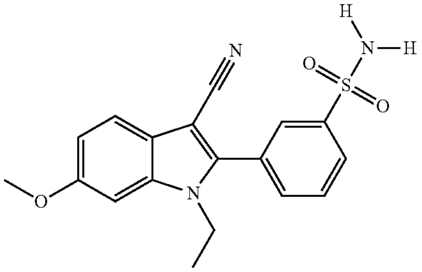
374
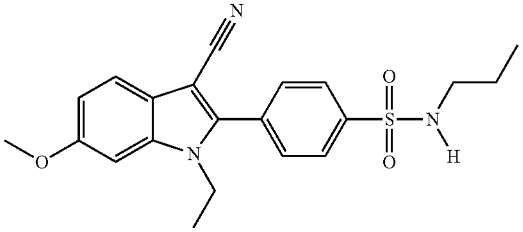
375
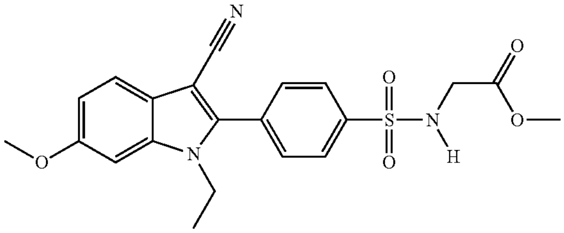
376
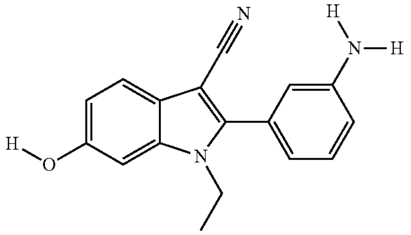
377
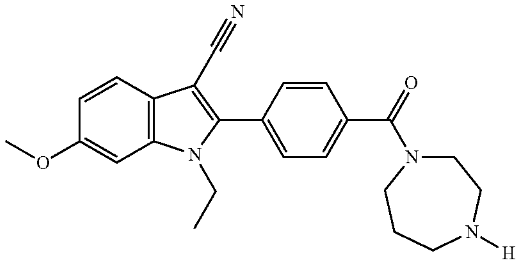
-continued
378
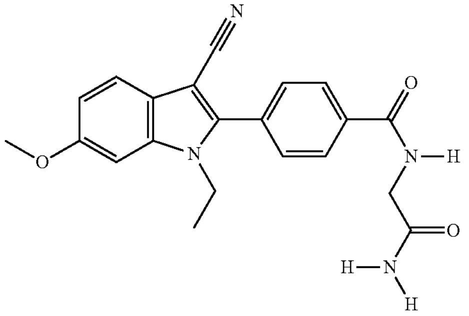
379
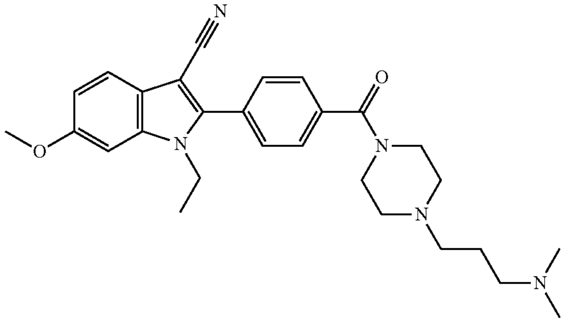
380
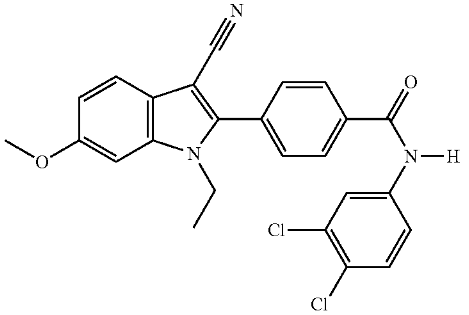
381
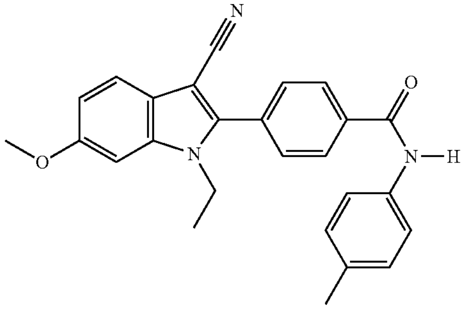
382
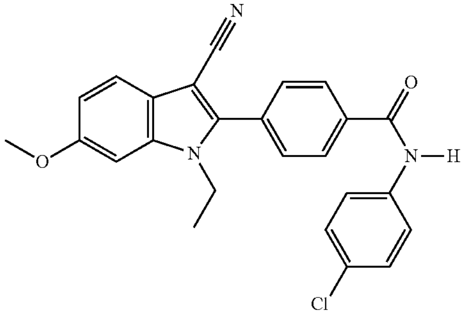

-continued
383
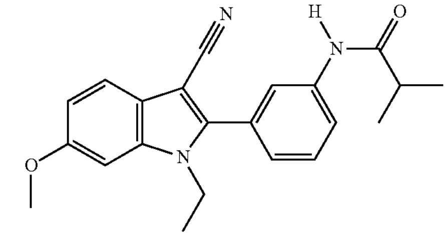
384
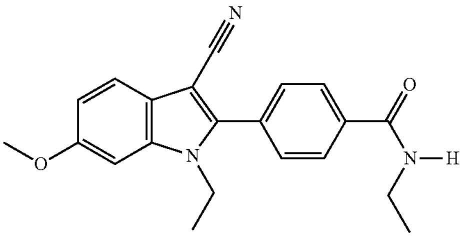
385
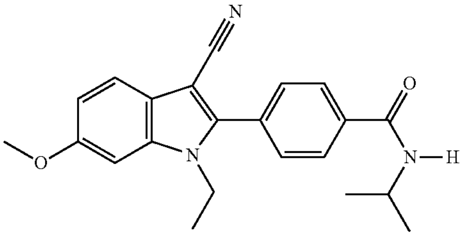
386
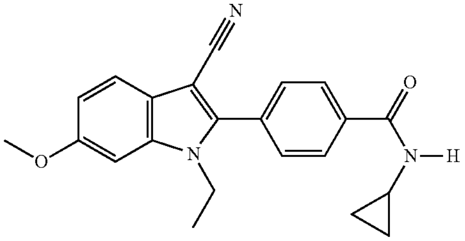
387
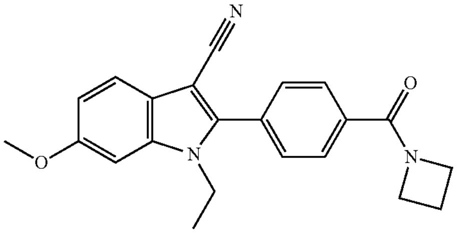
388
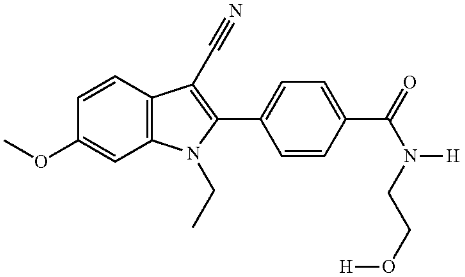
-continued
389
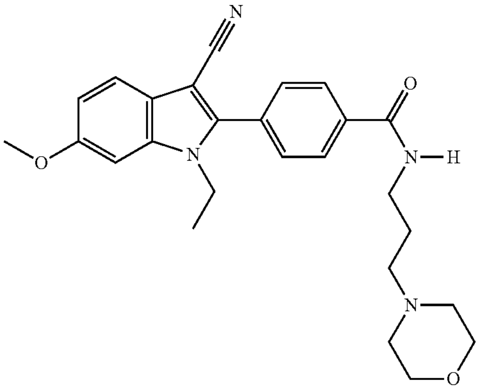
390
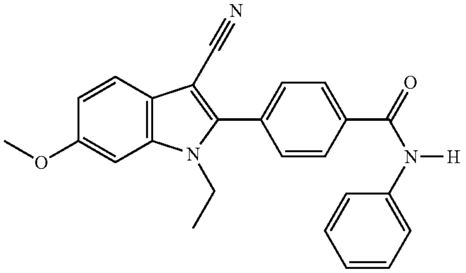
391
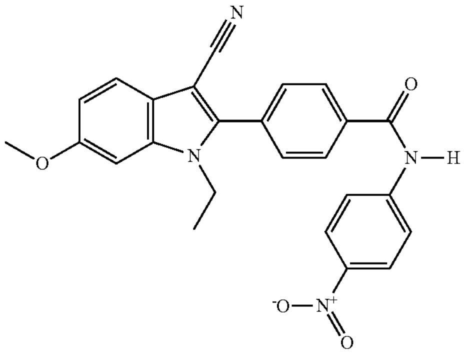
392
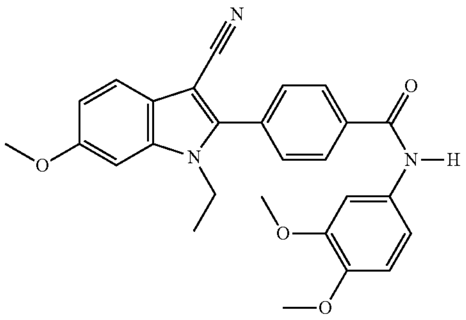
393
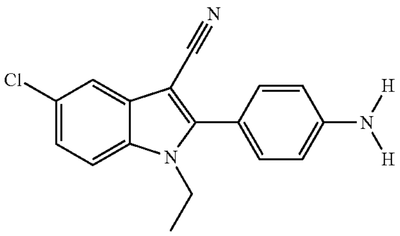

-continued
394
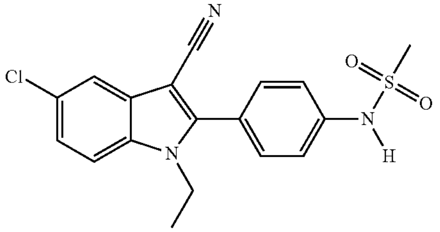
395
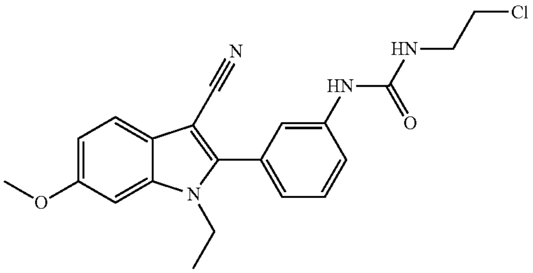
396
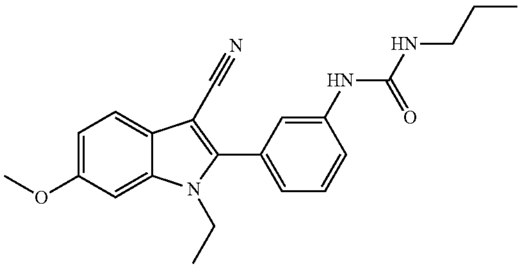
397
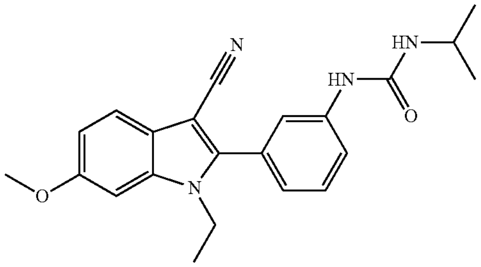
398
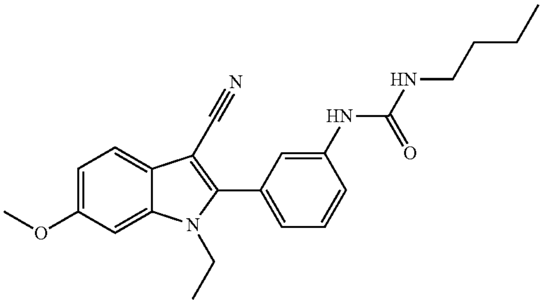
-continued
399
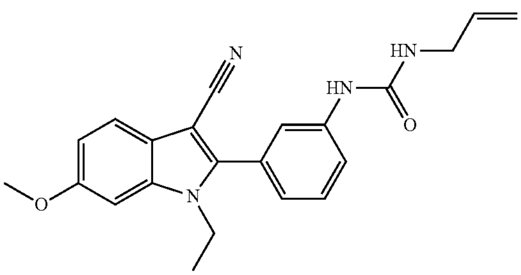
400
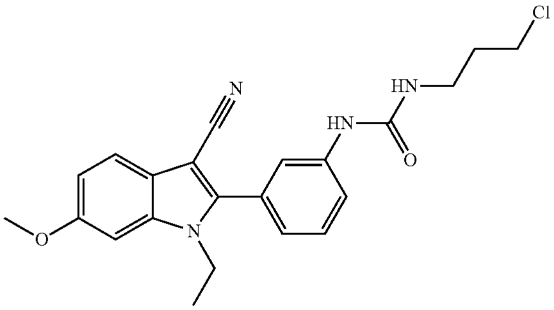
401
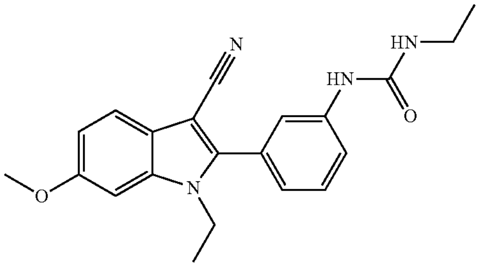
402
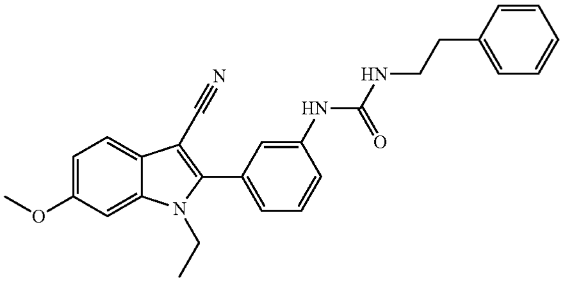
403
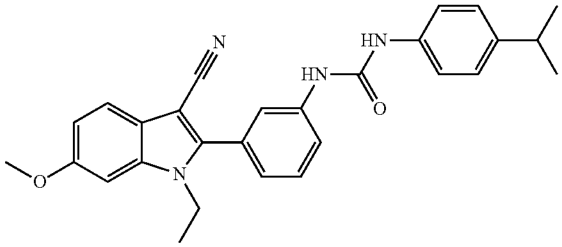

-continued
404
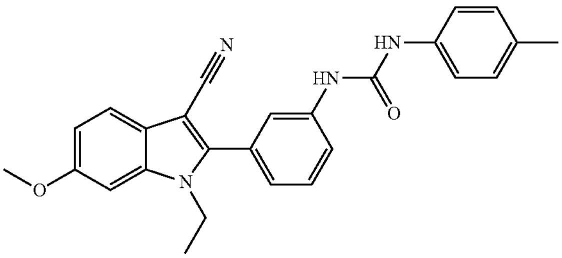
405
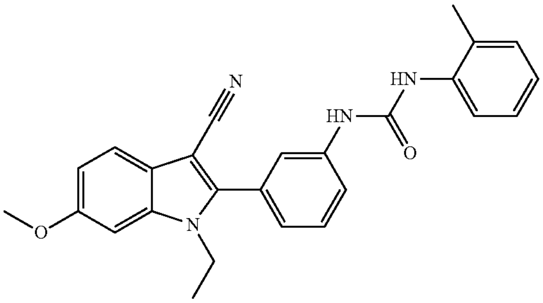
406
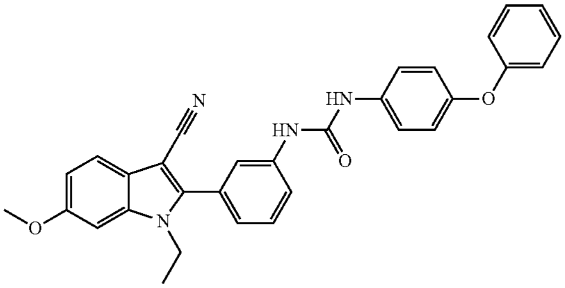
407
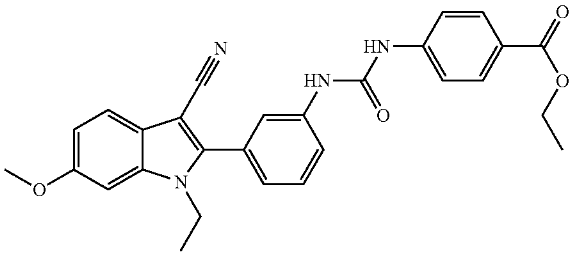
408
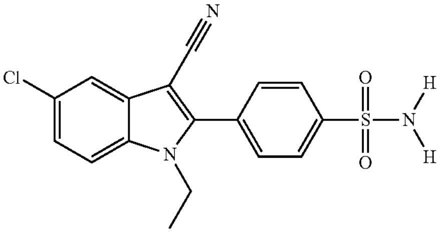
-continued
409
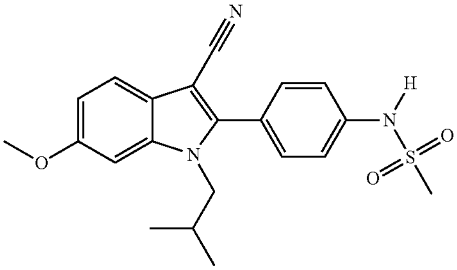
413
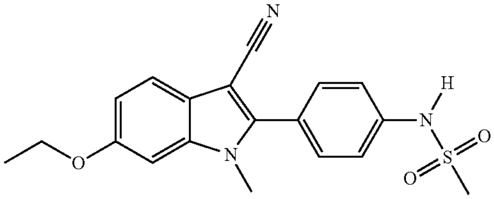
414
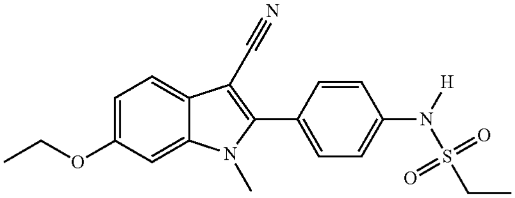
415
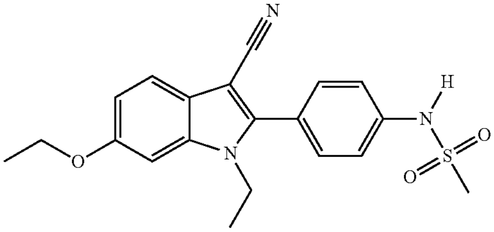
416
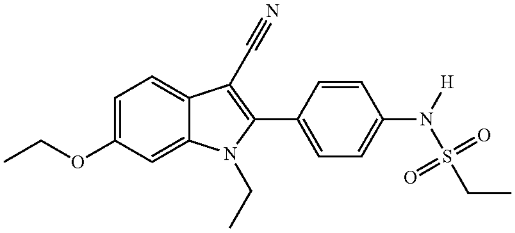
417
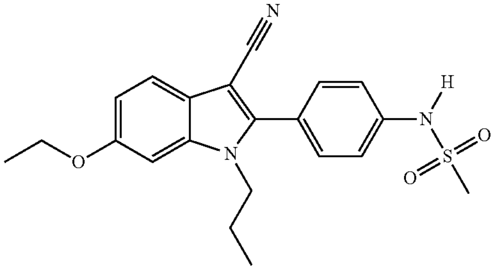

-continued
418
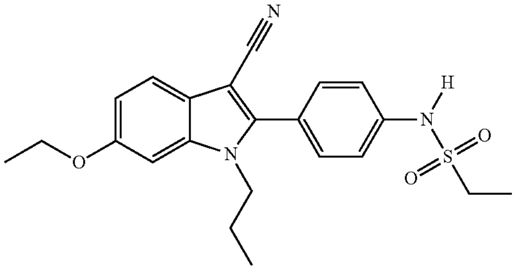
419
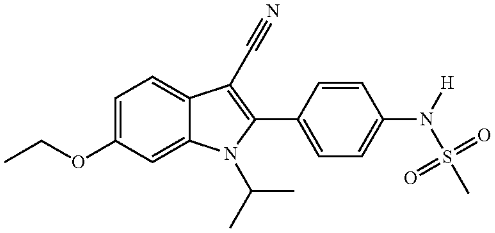
420
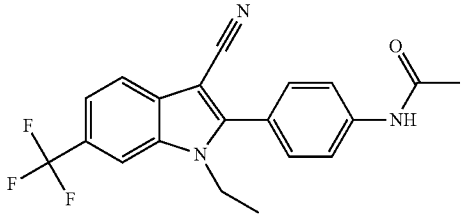
421
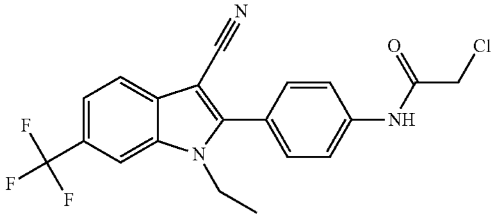
422
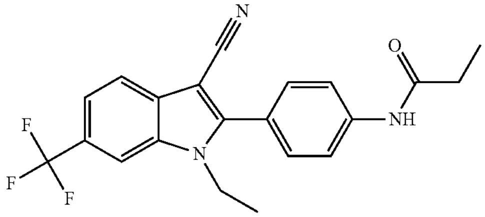
423
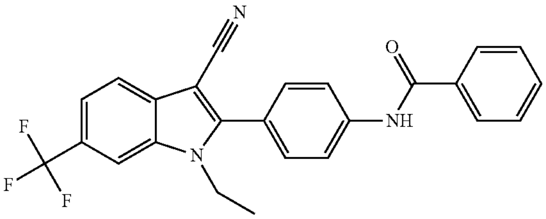
-continued
424
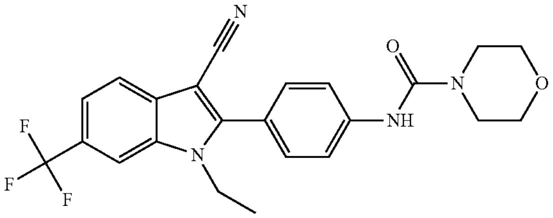
425
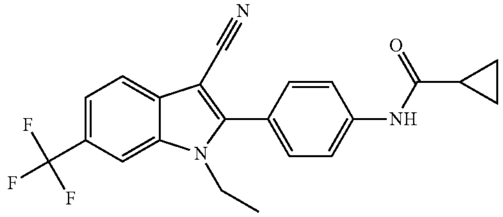
430
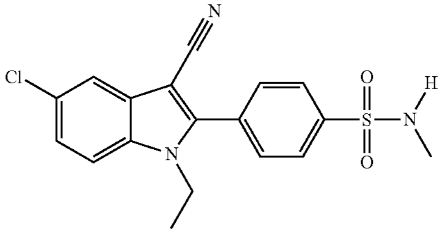
431
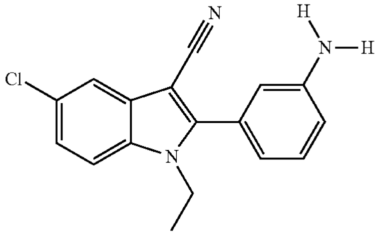
432
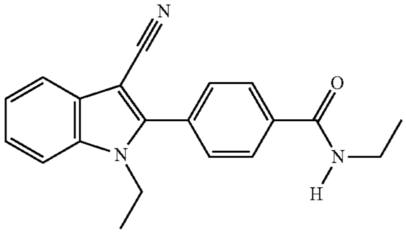
433
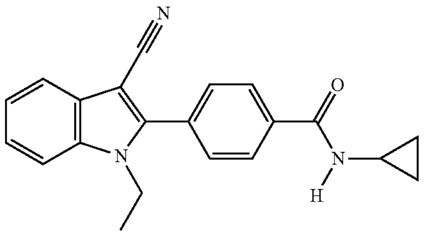

-continued
434
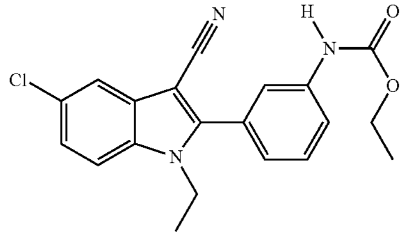
435
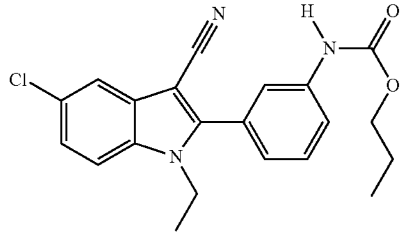
436
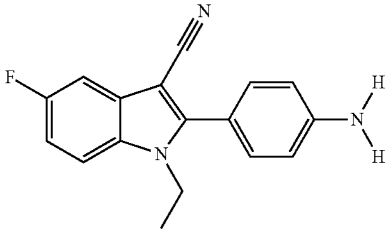
437
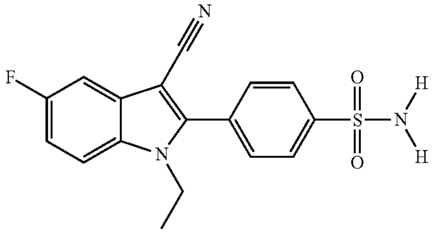
438
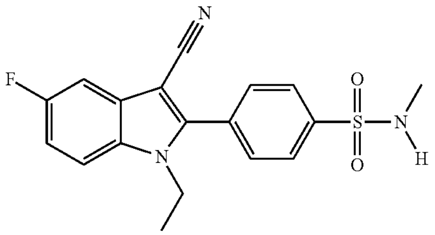
439
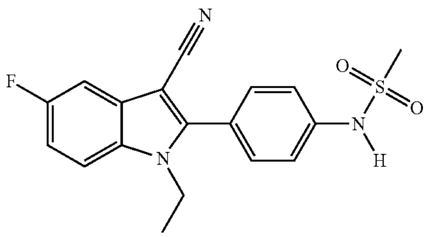
-continued
440
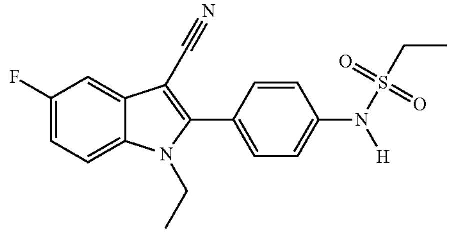
441
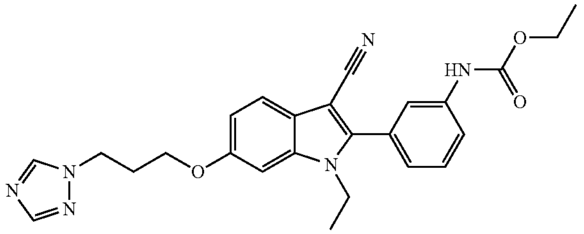
442
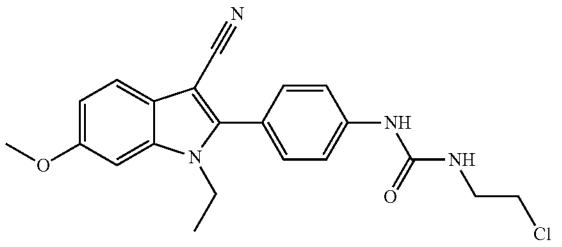
443
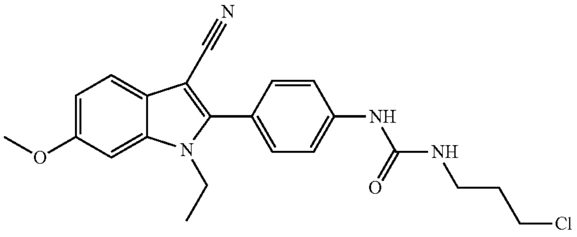
444
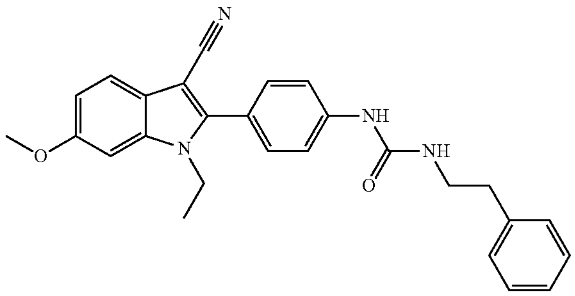

-continued
445
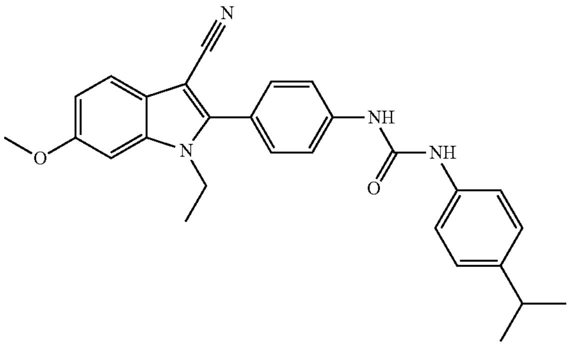
446
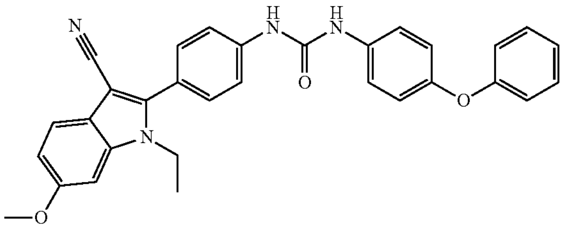
447
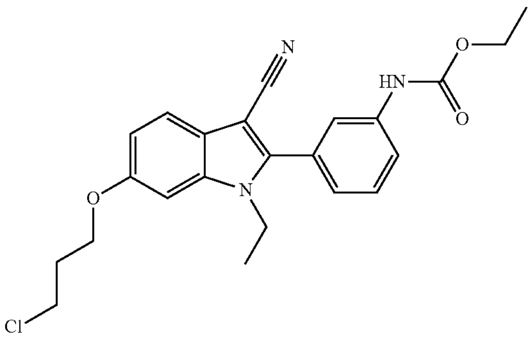
448
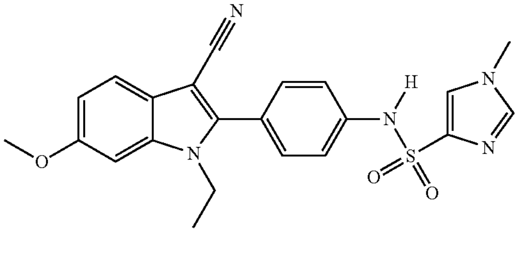
449
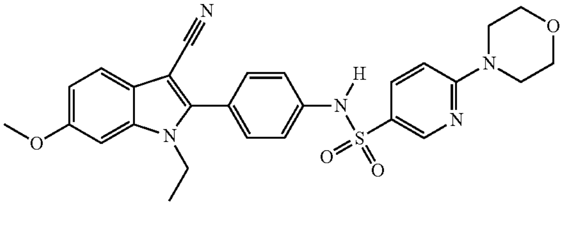
-continued
450
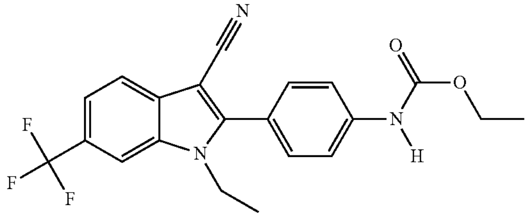
451
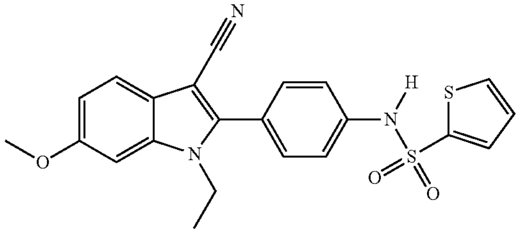
452
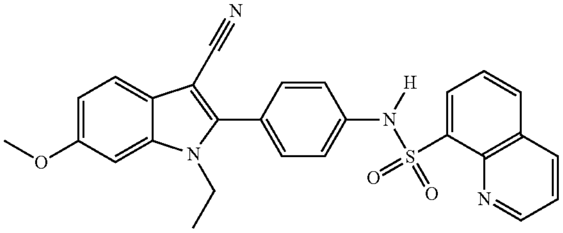
453
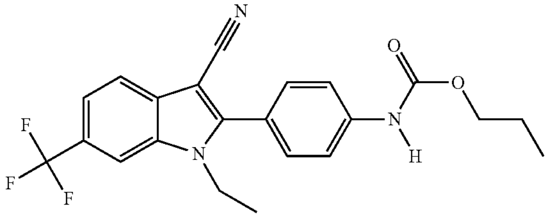
454
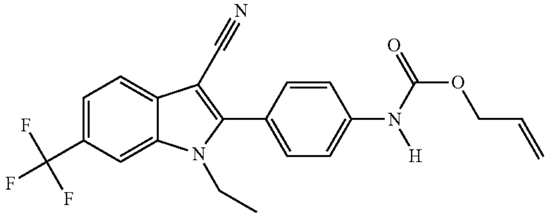
455
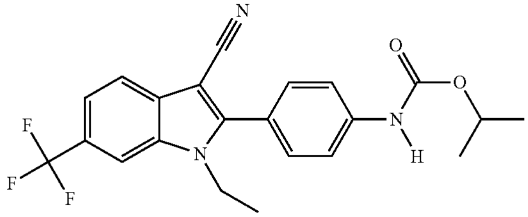

-continued
456
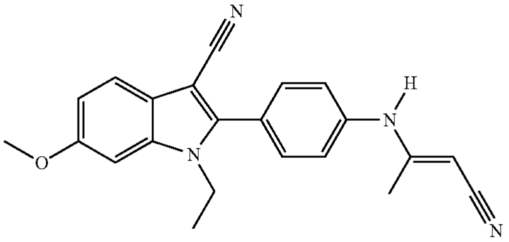
457
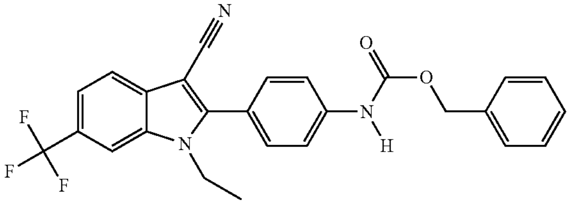
458
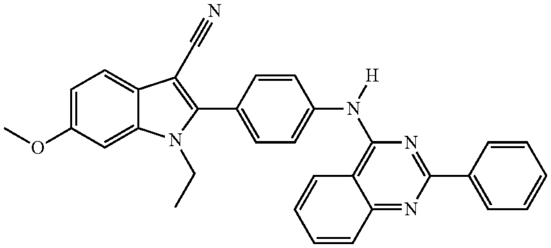
459
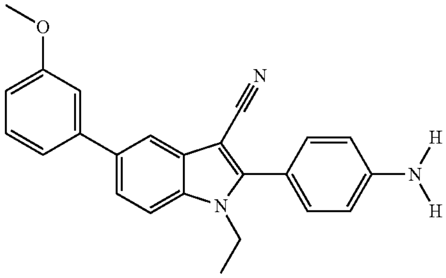
460
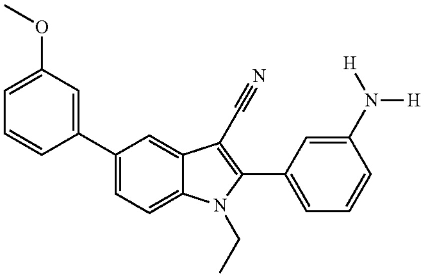
461
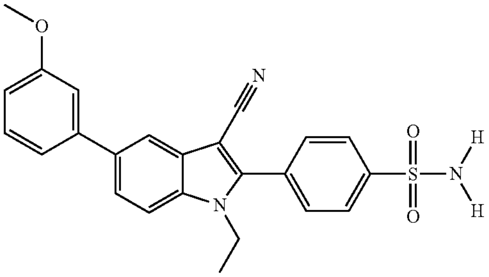
-continued
462
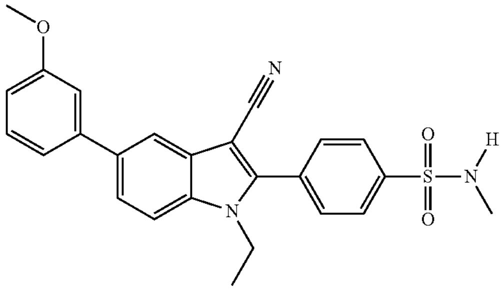
468
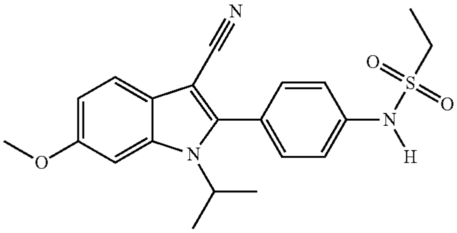
469
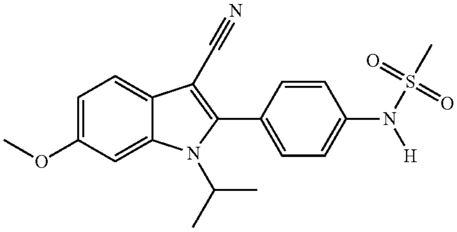
470
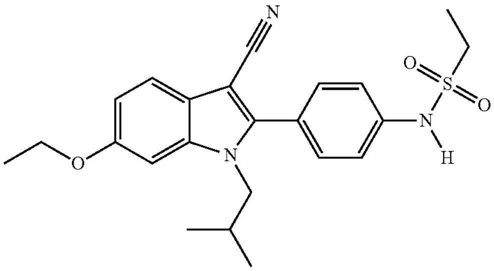
471
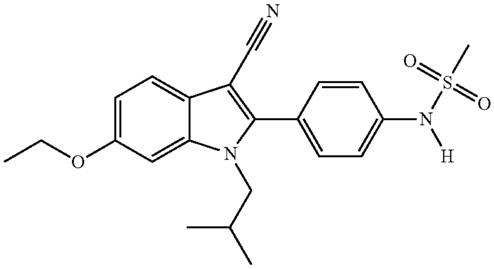
472
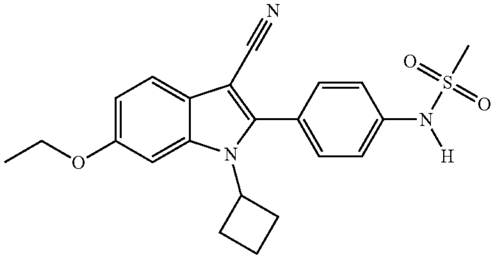

-continued
473
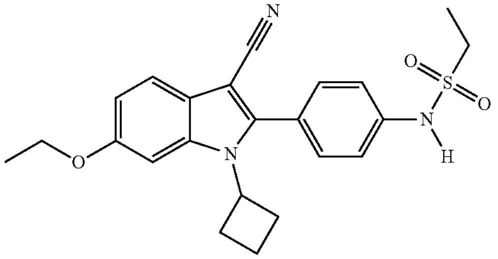
476
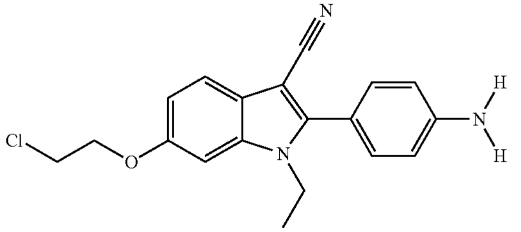
477
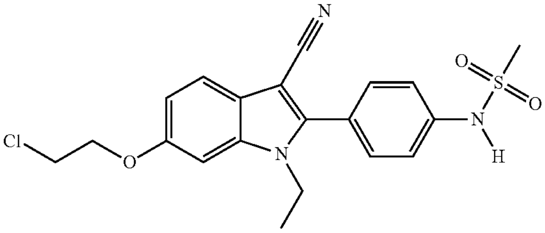
478
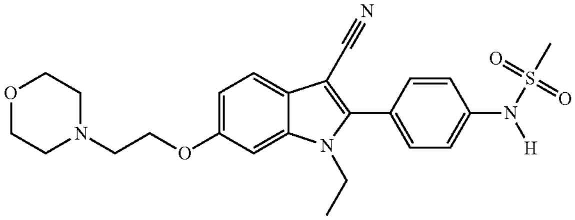
479
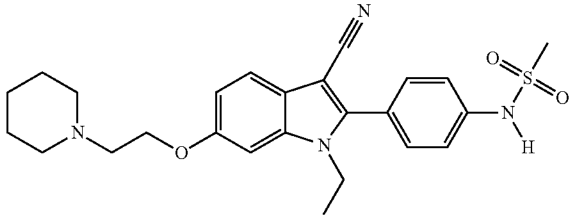
480
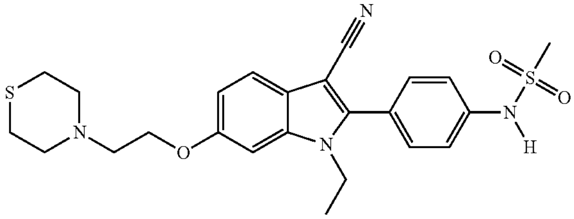
-continued
481
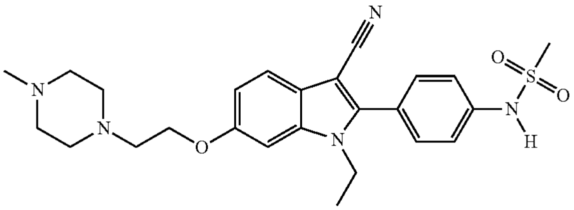
482
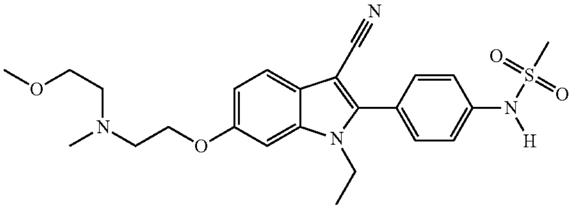
483
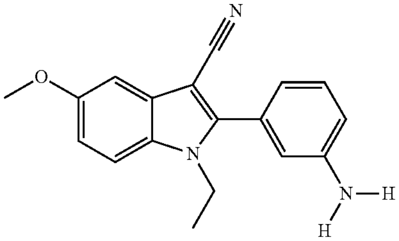
485
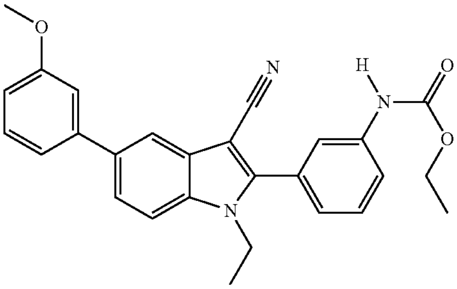
486
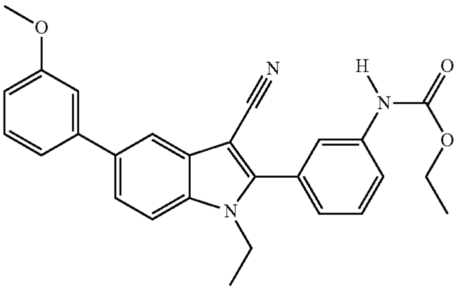
487
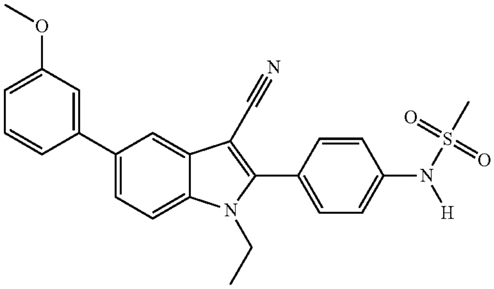

-continued
488
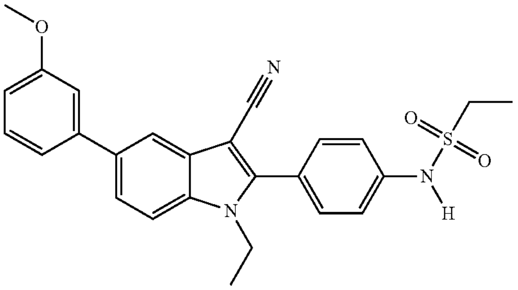
489
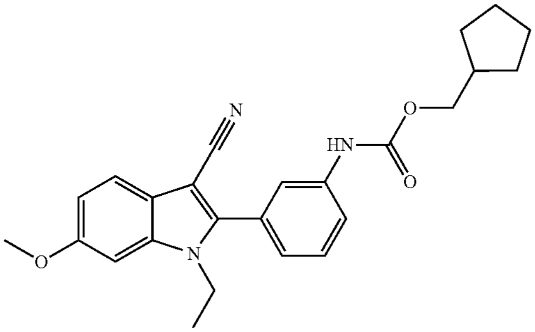
490
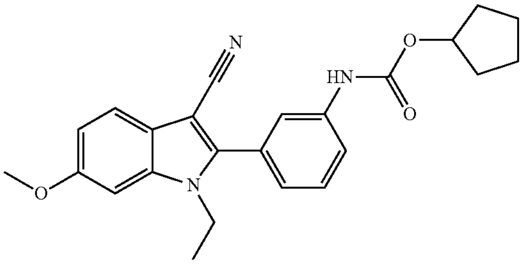
491
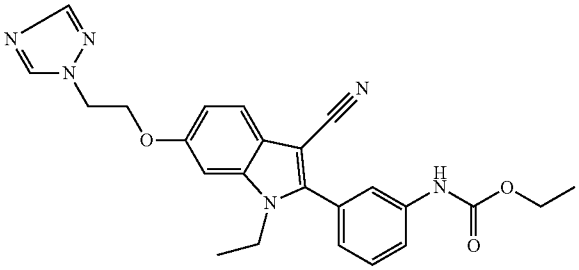
492
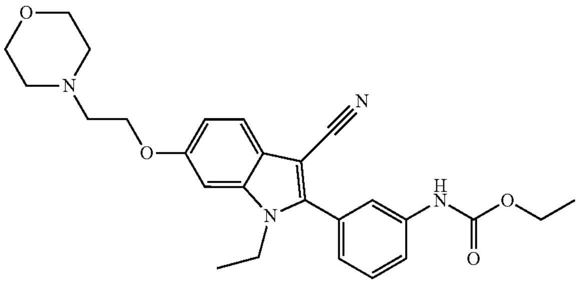
-continued
493
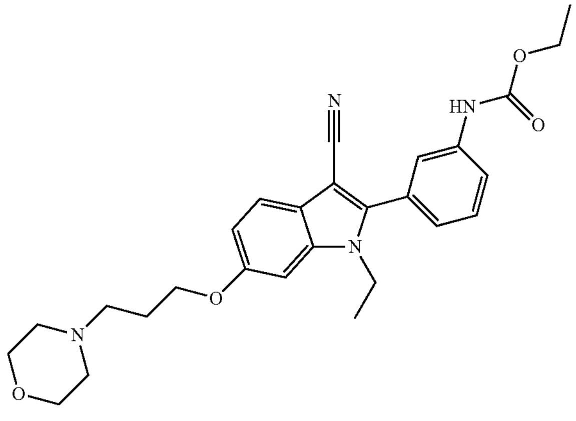
494
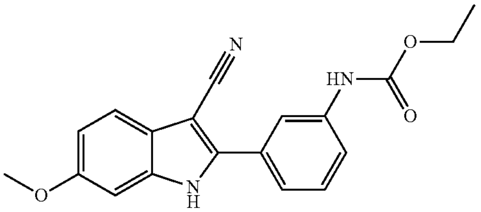
495
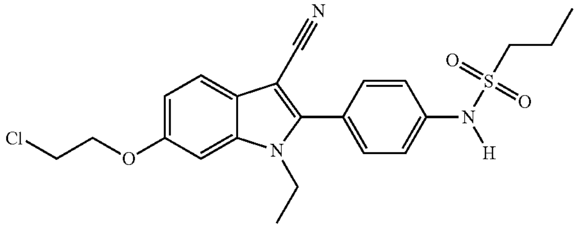
496
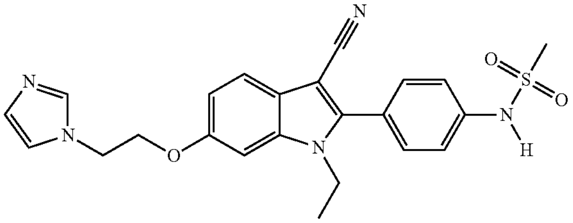
497
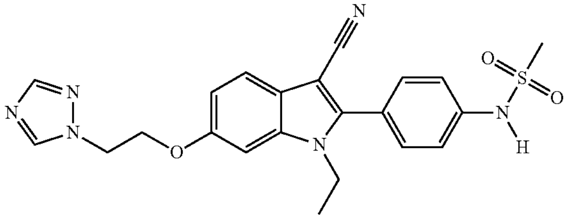

-continued
498
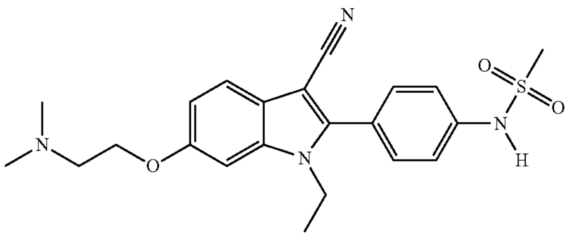
500
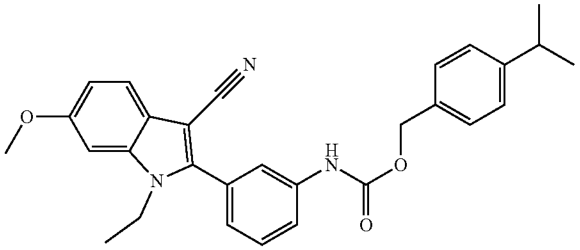
501
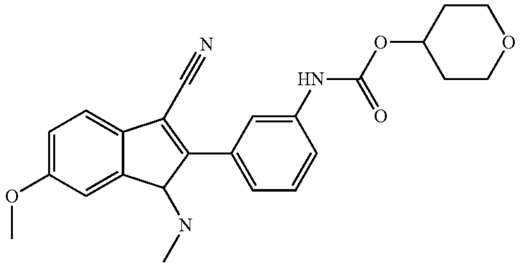
502
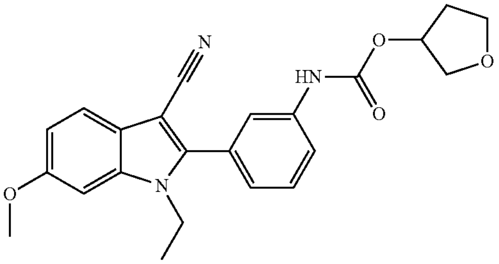
503
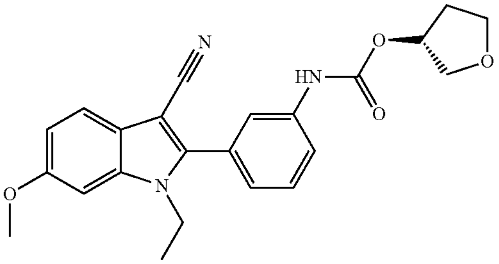
-continued
504
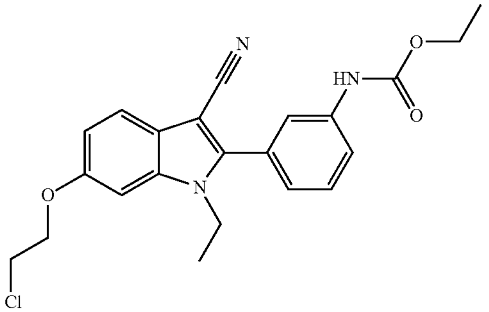
505
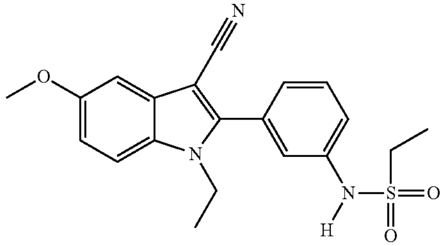
506
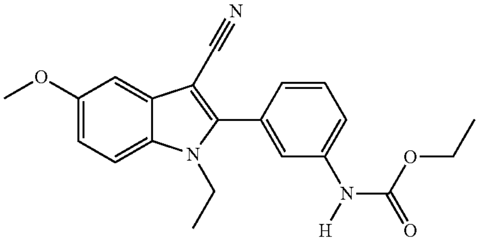
507
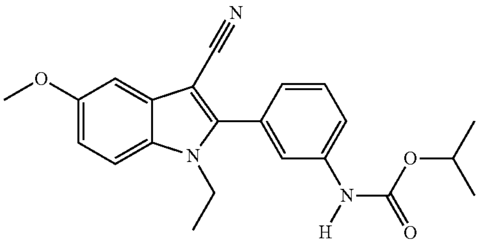
508
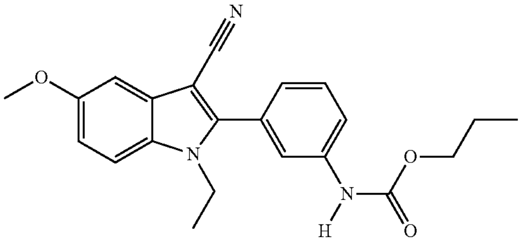
509
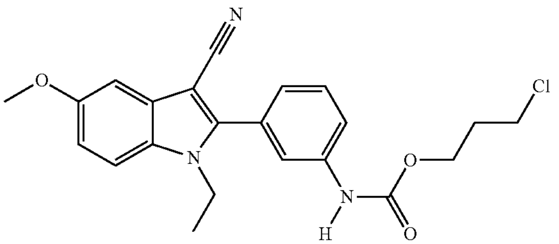

-continued
510
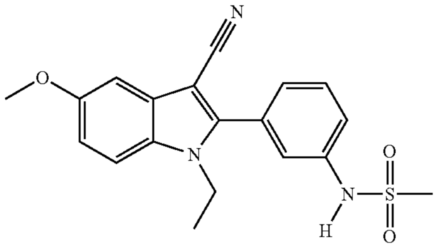
511
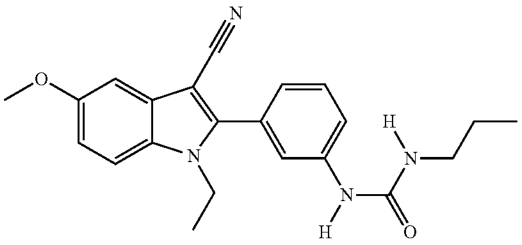
512
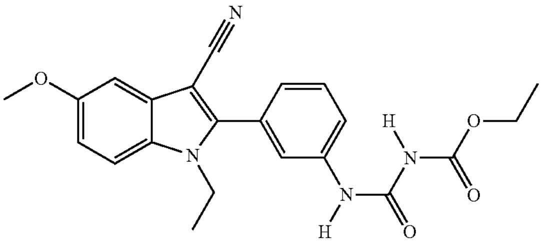
513
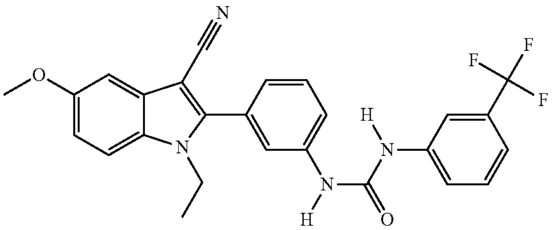
518
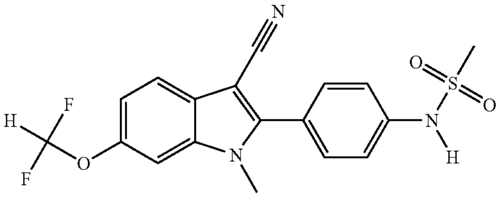
519
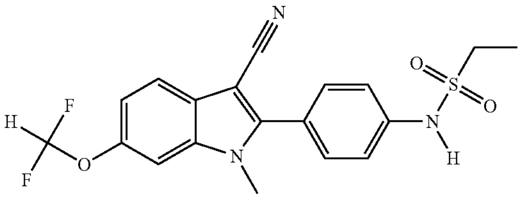
-continued
520
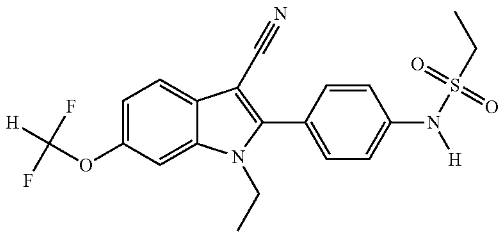
521
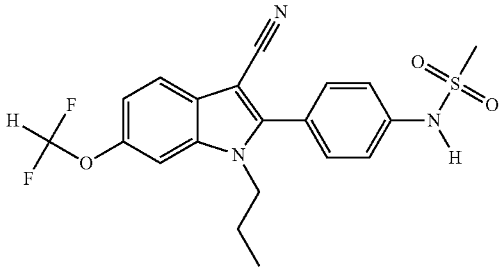
522
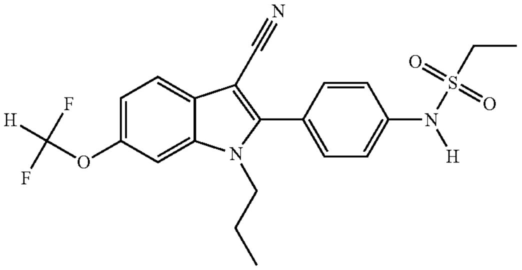
523
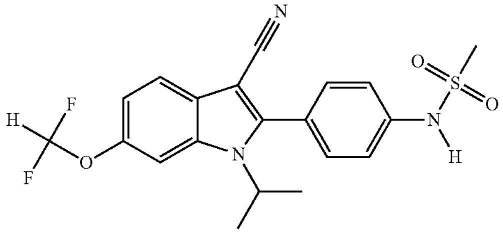
524
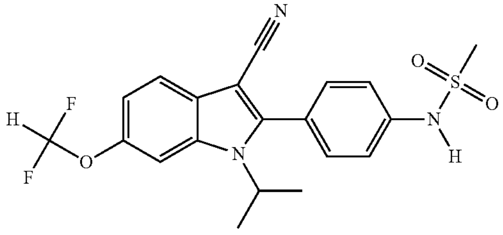

-continued
525
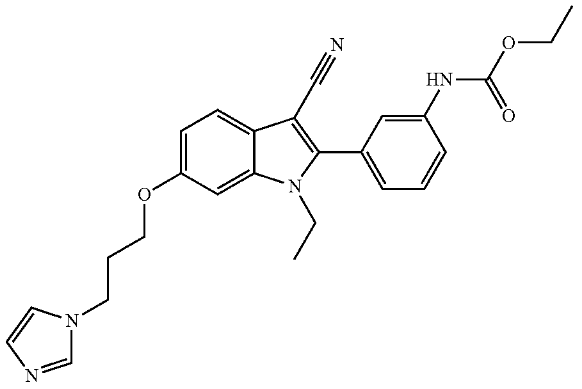
526
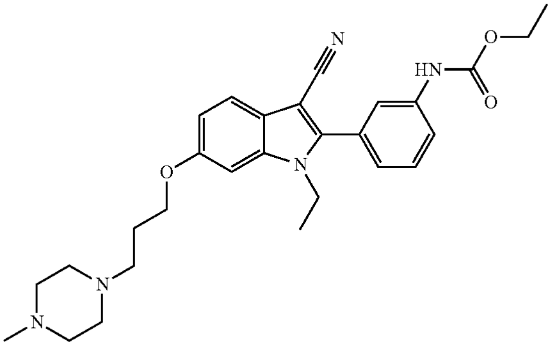
527
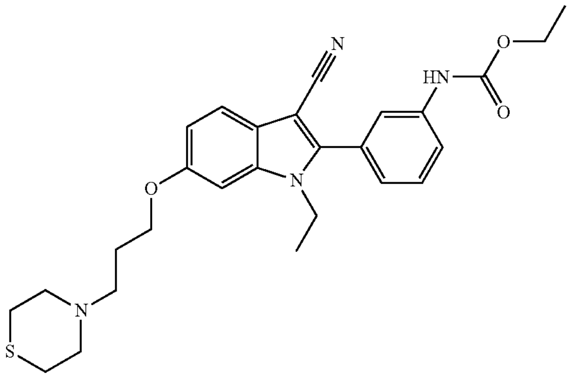
528
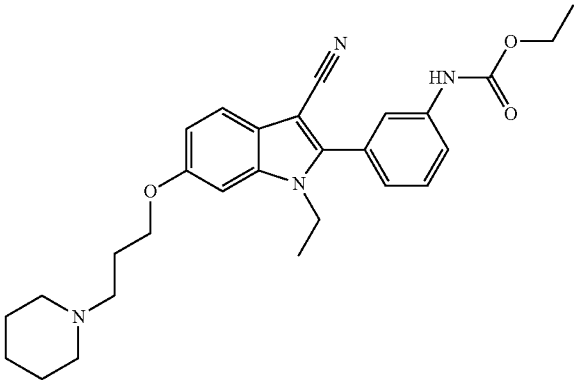
-continued
529
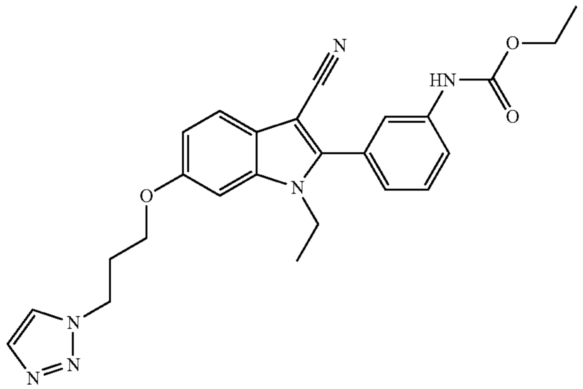
530
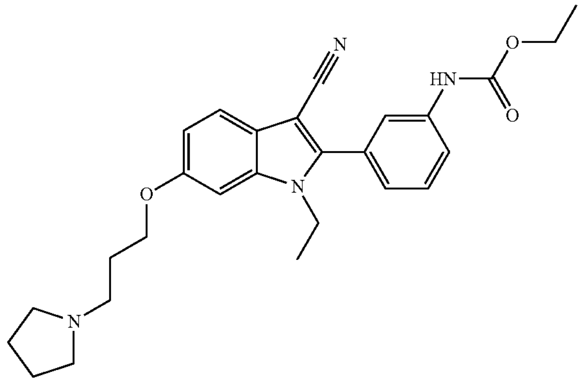
531
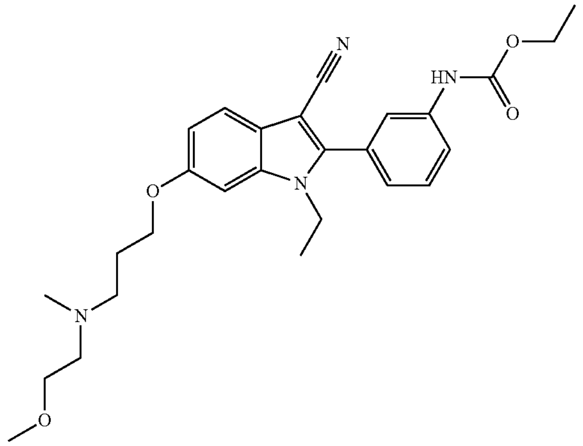
532
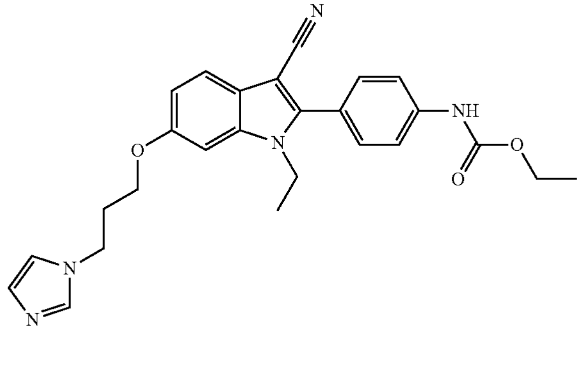

-continued
533
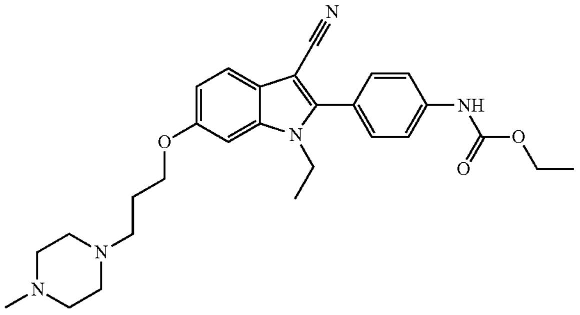
534
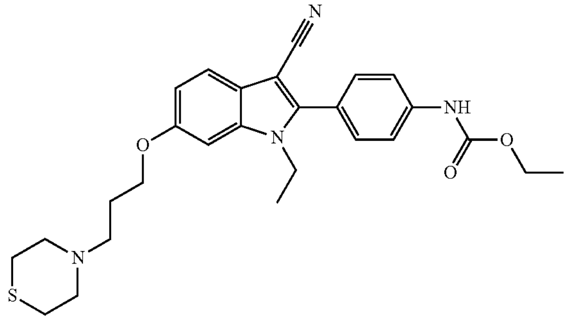
535
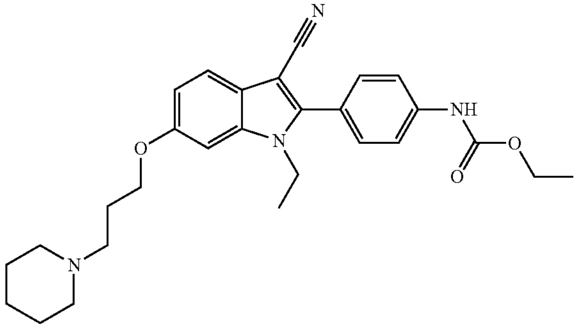
536
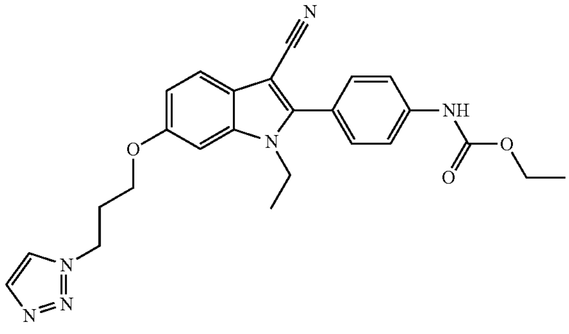
-continued
537
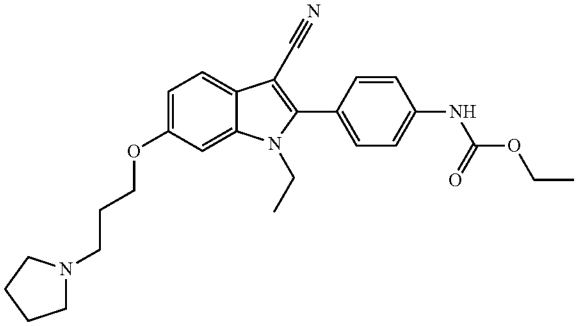
538
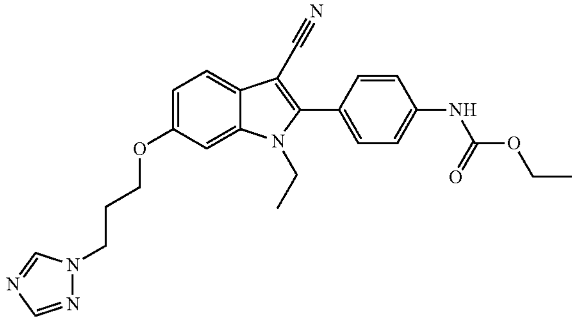
539
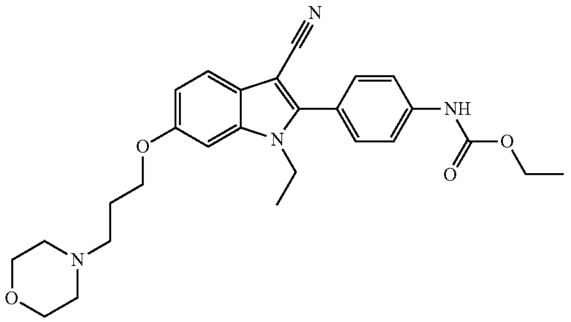
540
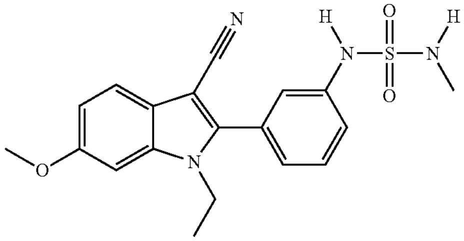
541
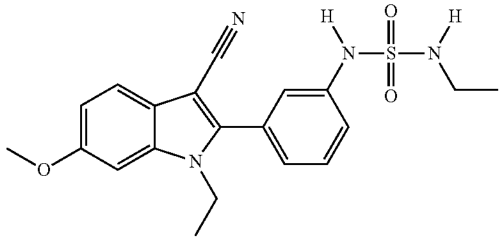

-continued
542
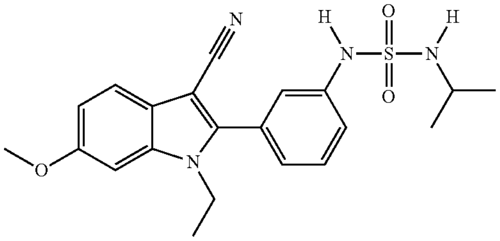
543
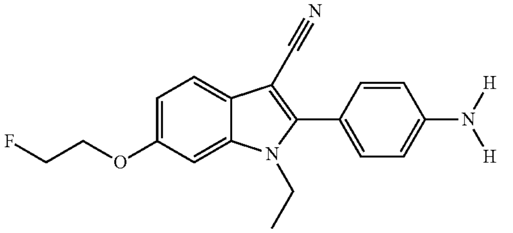
544
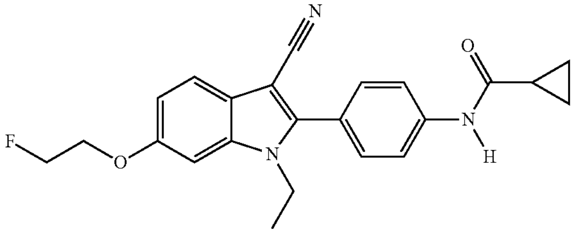
545
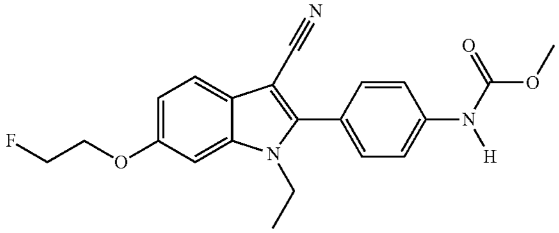
546
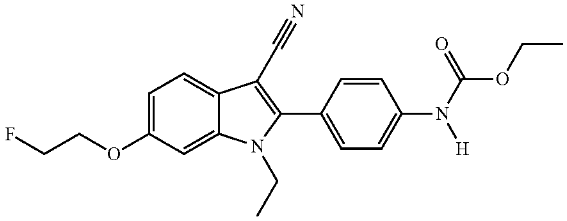
547
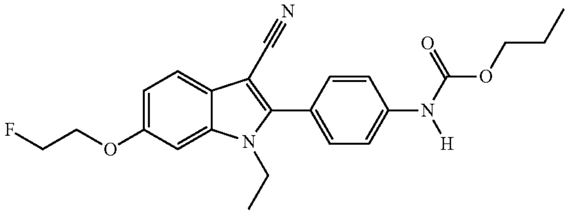
-continued
548
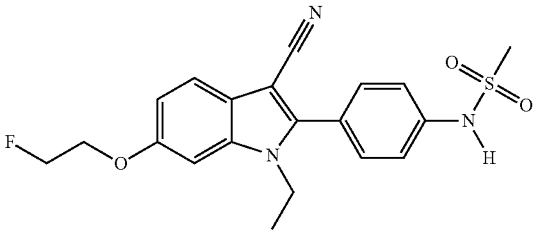
549
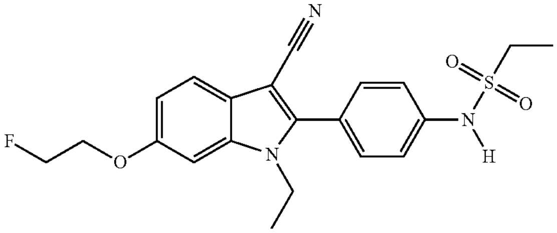
550
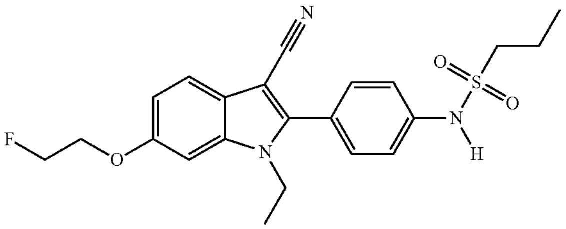
551
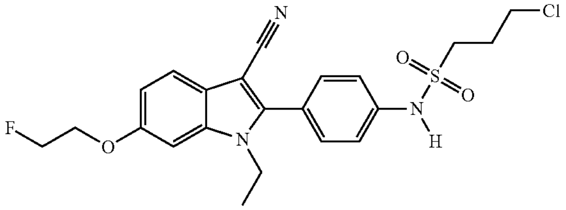
552
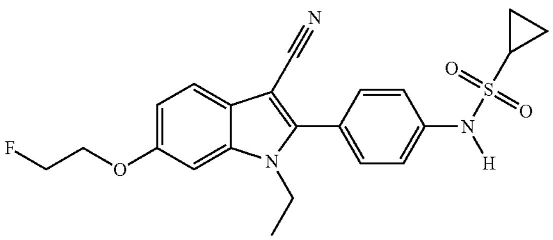
553
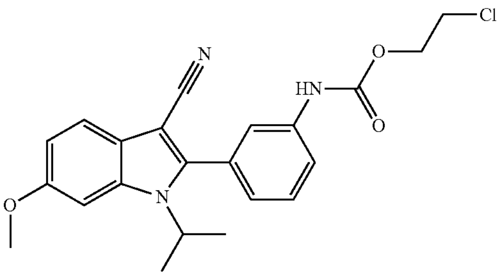

-continued
554
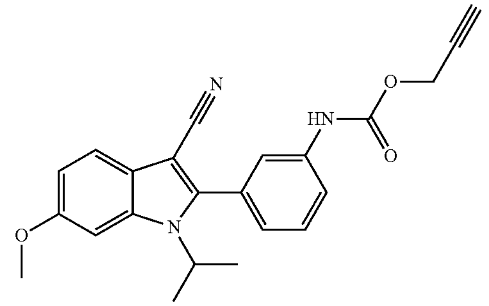
555
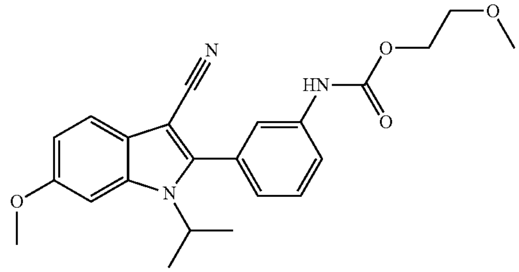
556
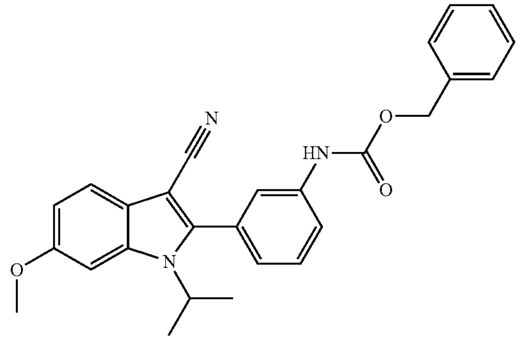
557
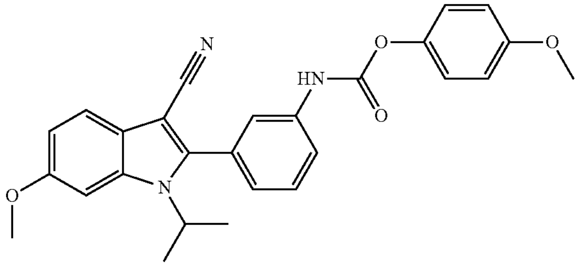
558
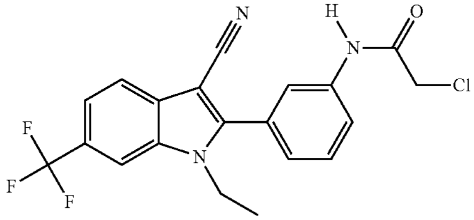
-continued
559
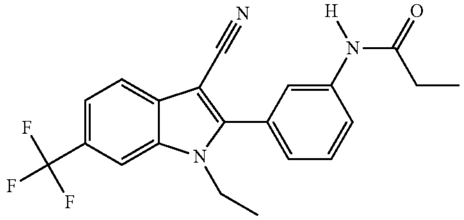
560
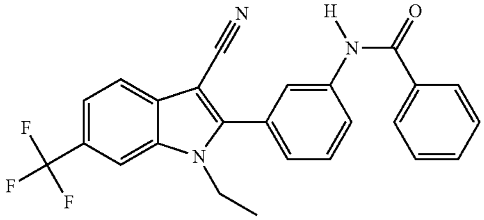
561
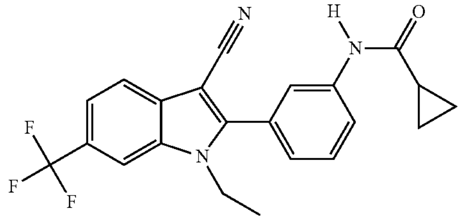
562
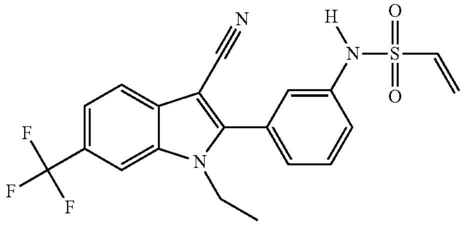
563
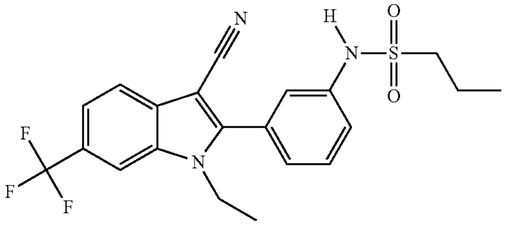
564
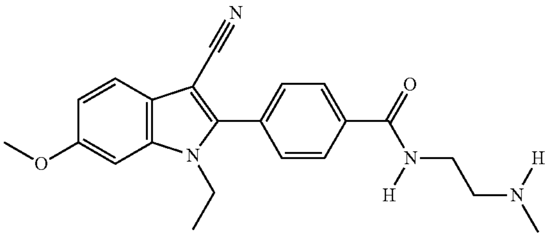

-continued
565
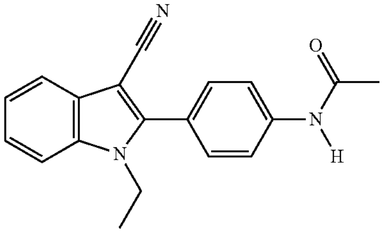
566
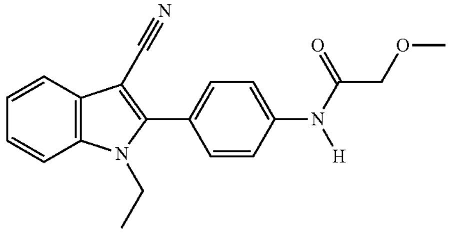
567
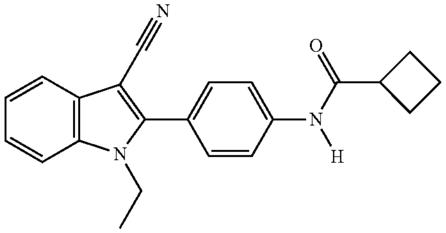
568
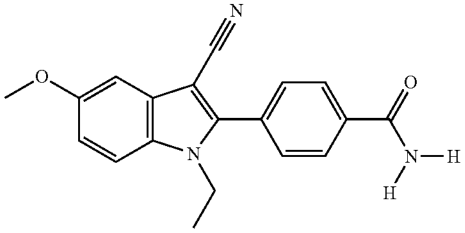
569
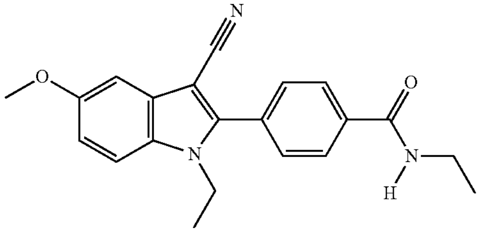
570
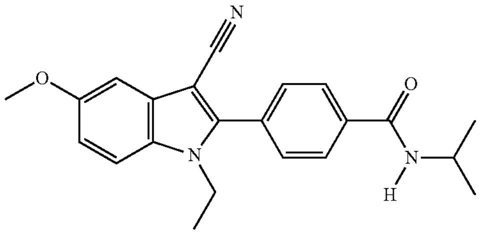
-continued
571
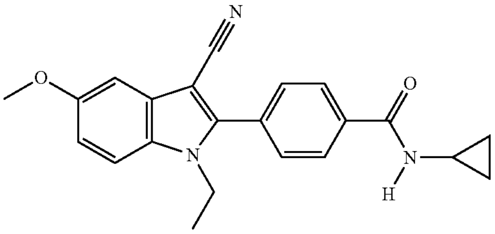
572
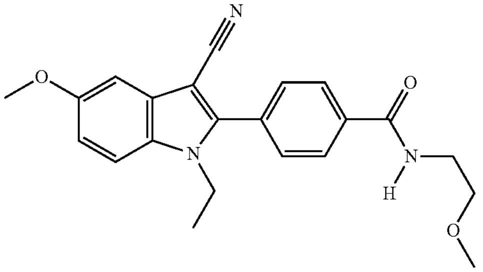
573
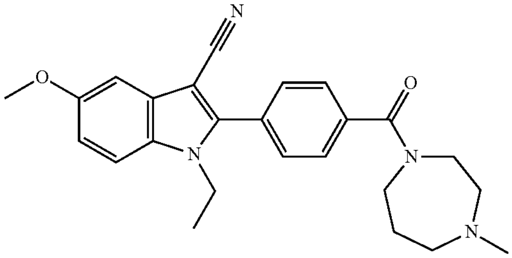
574
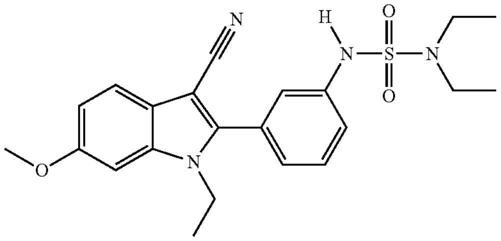
576
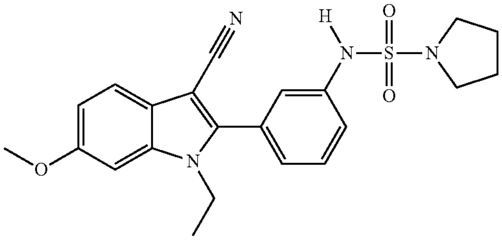
579
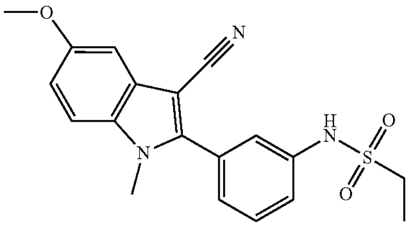

-continued
580
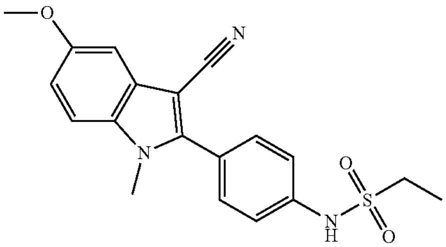
581
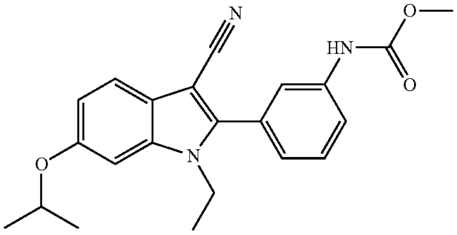
582
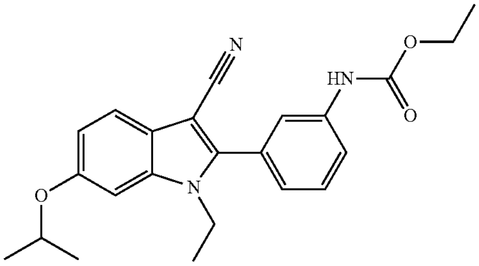
583
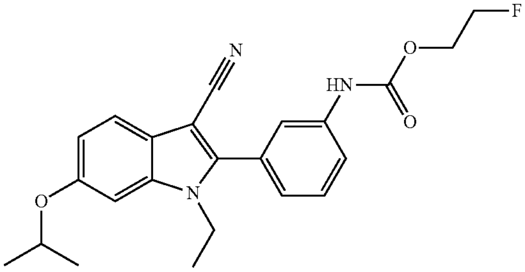
584
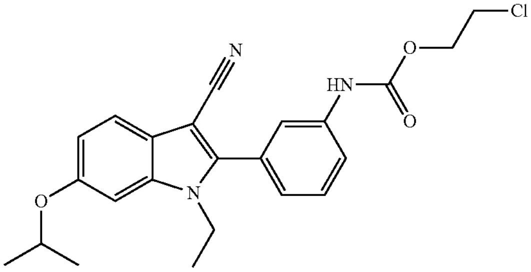
-continued
585
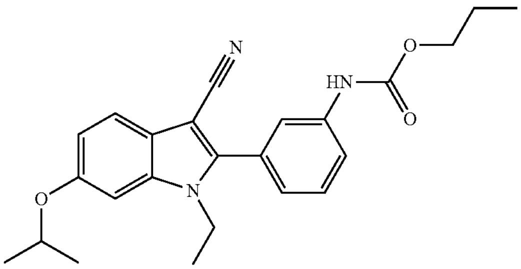
586
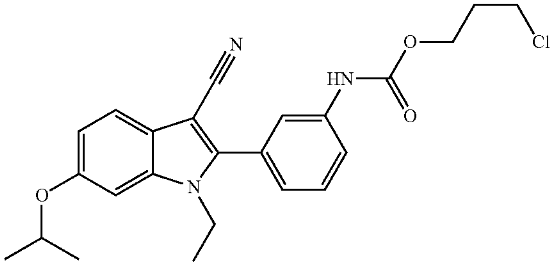
587
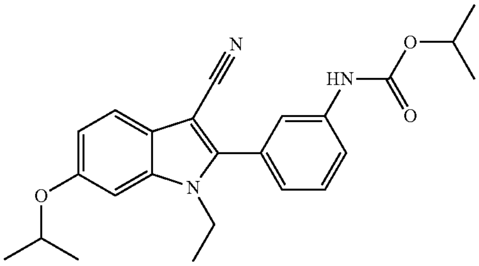
588
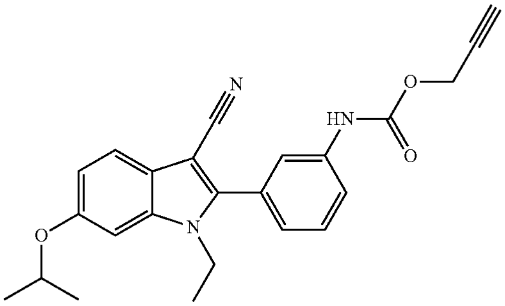
589
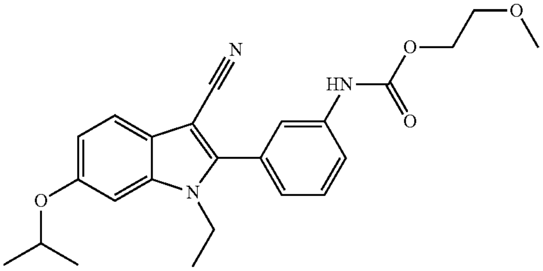

-continued
590
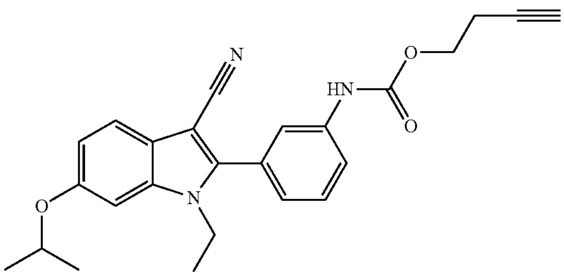
591
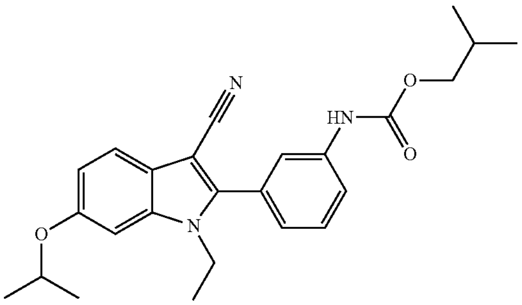
592
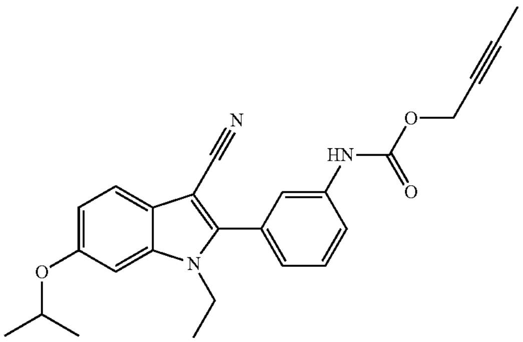
593
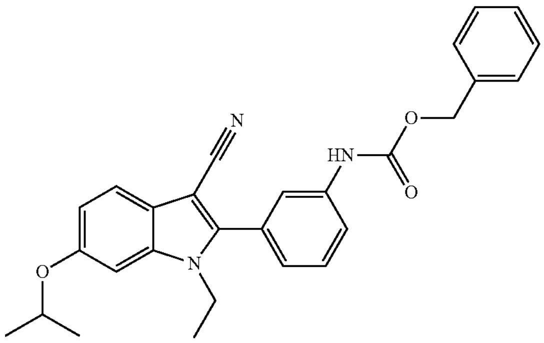
594
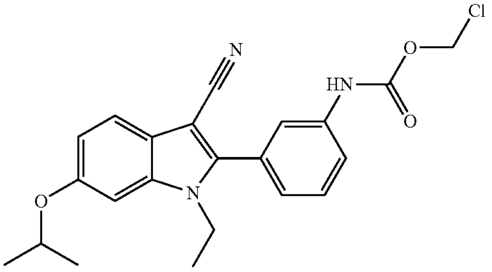
-continued
595
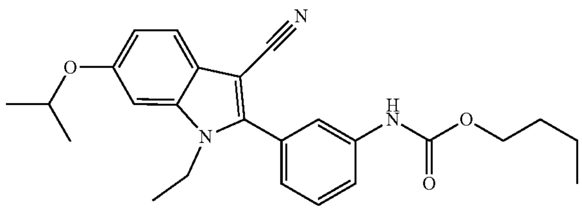
596
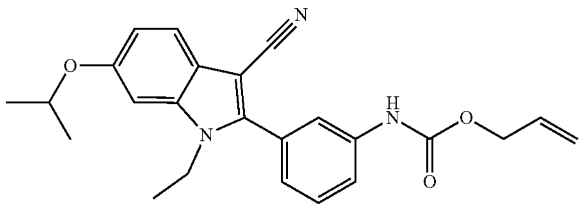
597
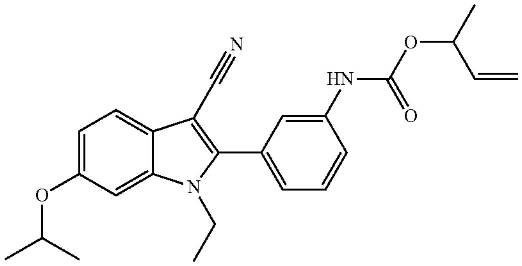
598
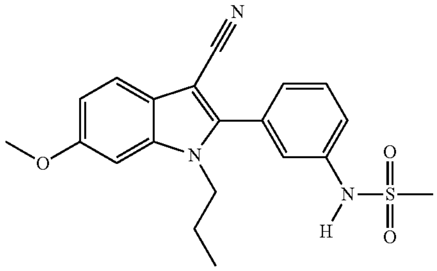
599
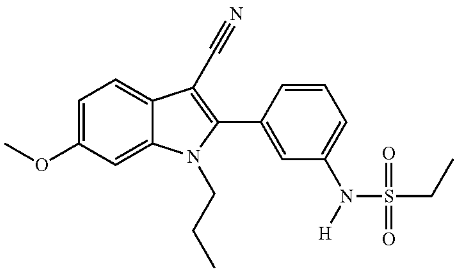
600
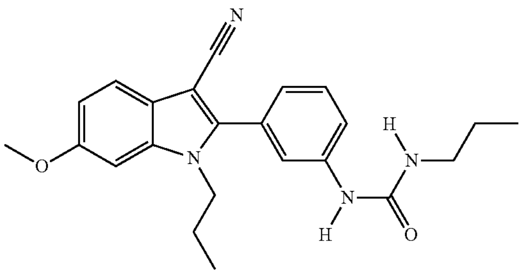

-continued
601
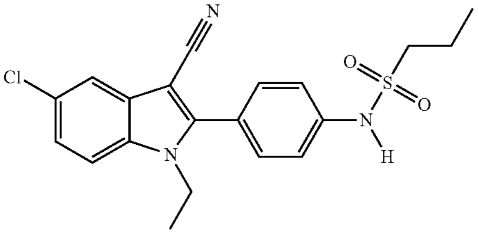
602
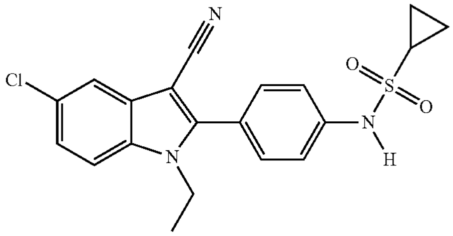
603
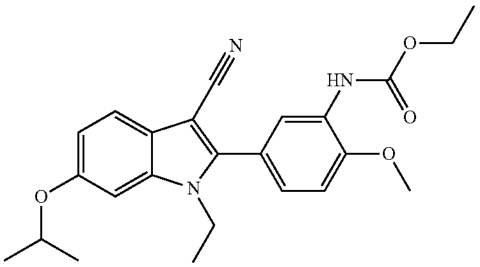
604
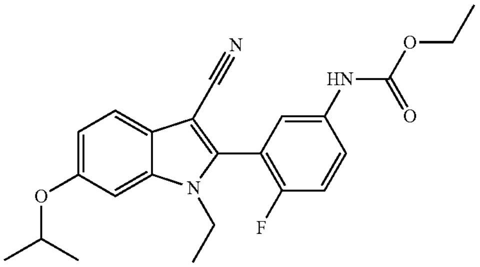
605
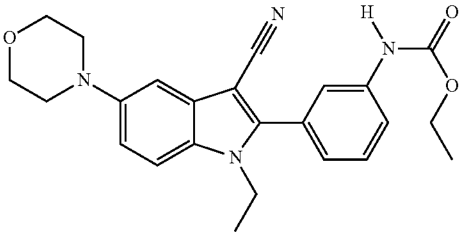
606
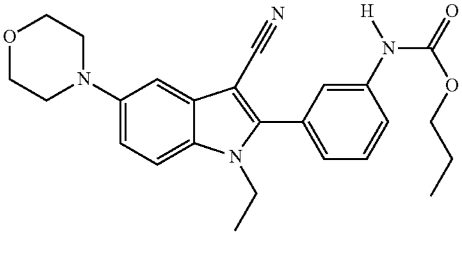
-continued
607
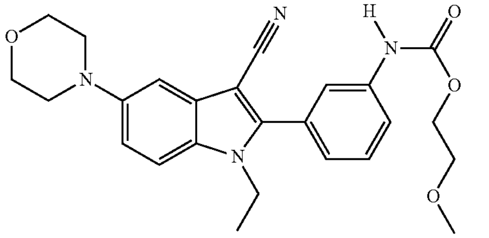
608
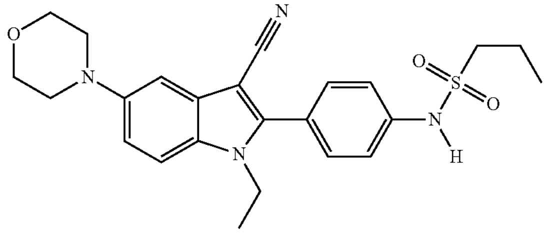
609
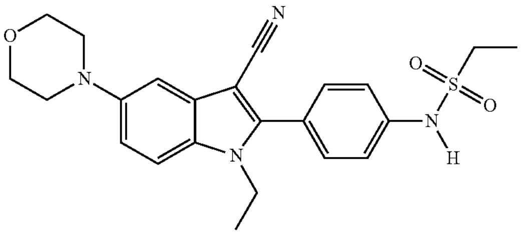
610
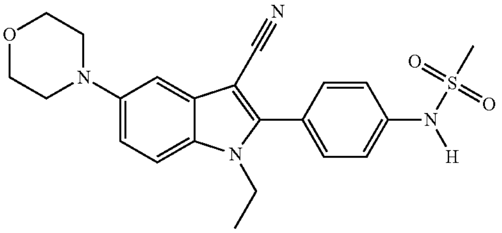
611
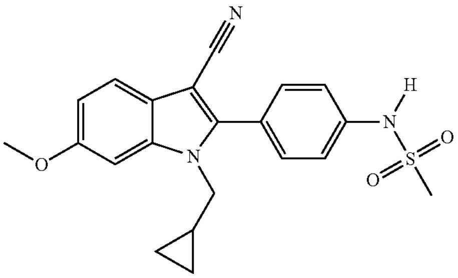
612
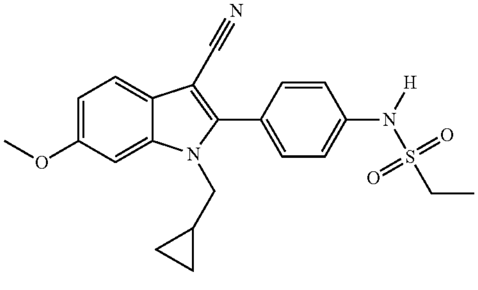

-continued
613
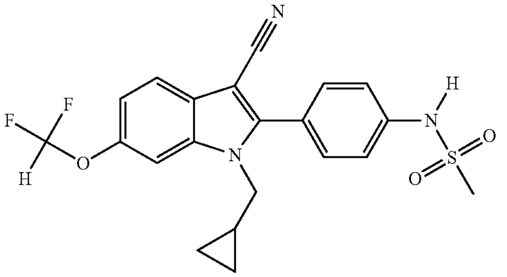
614
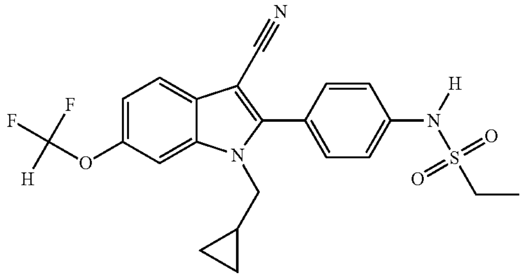
615
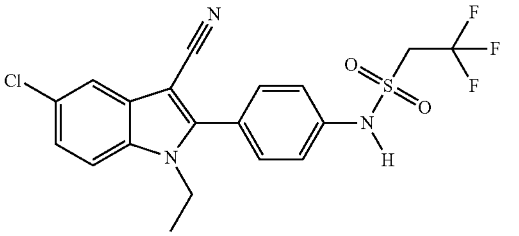
616
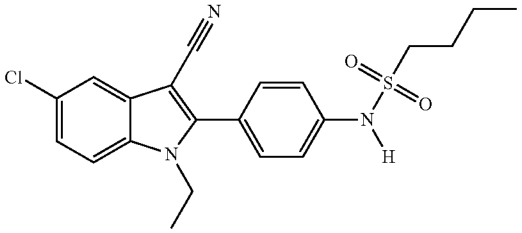
617
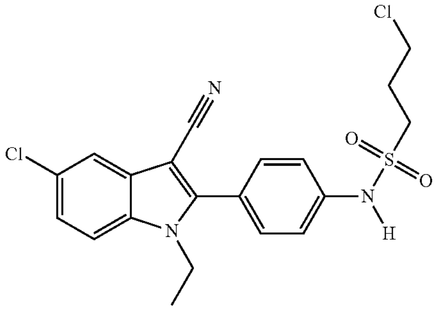
618
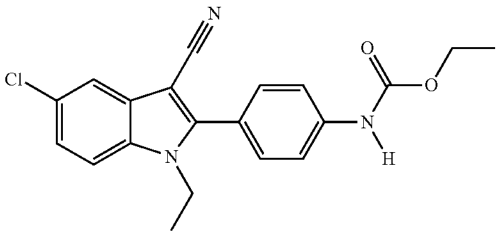
-continued
619
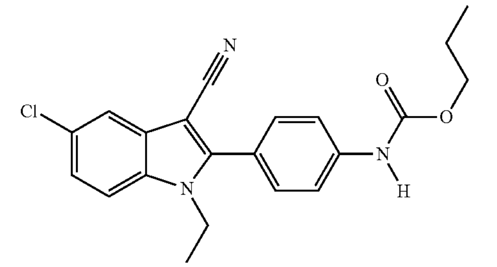
620
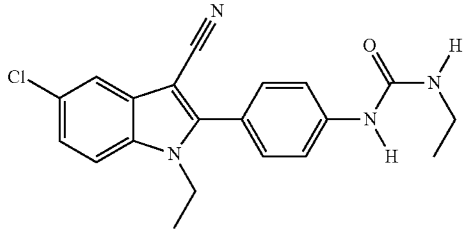
621
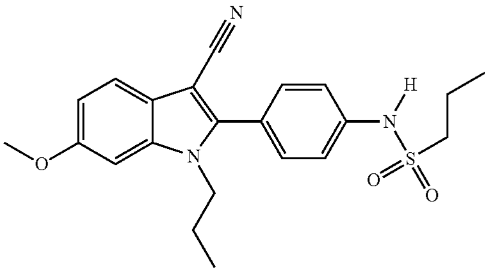
622
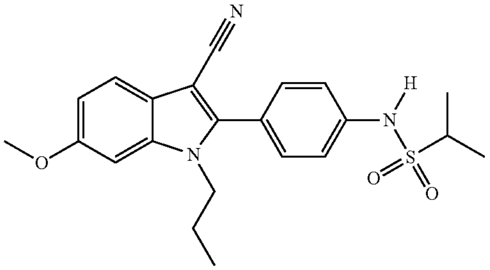
623
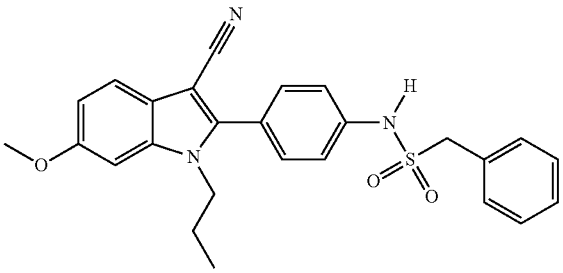
624
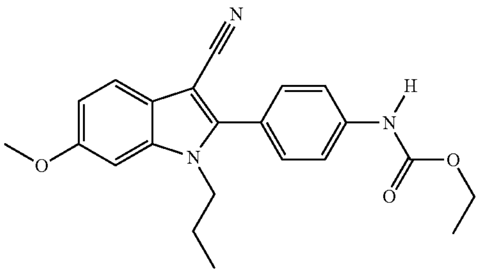

-continued
625
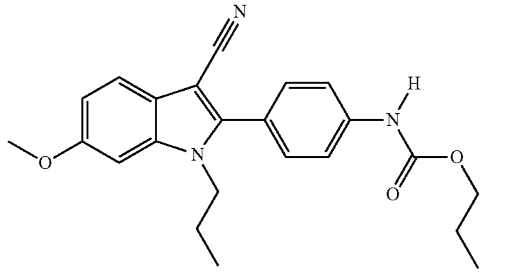
626
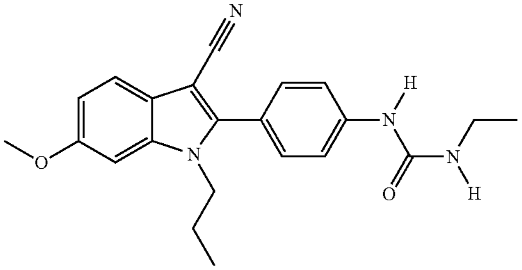
627
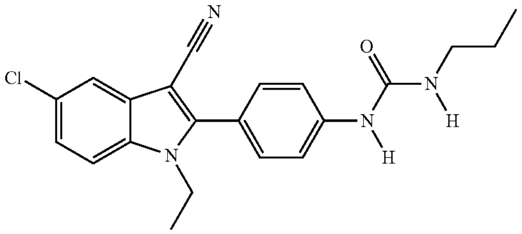
628
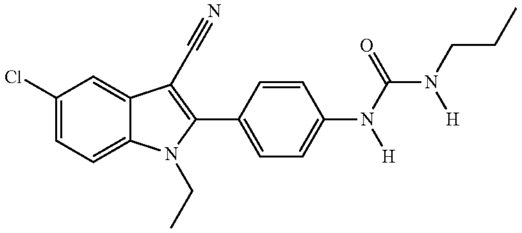
629
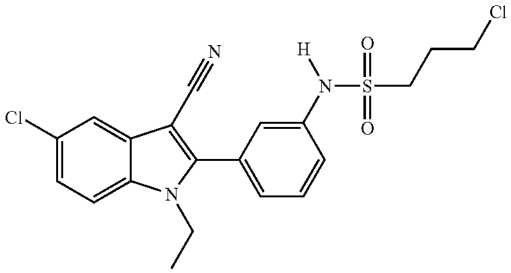
-continued
630
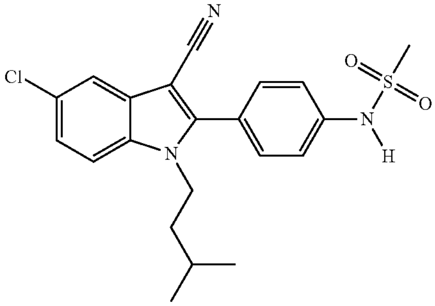
631
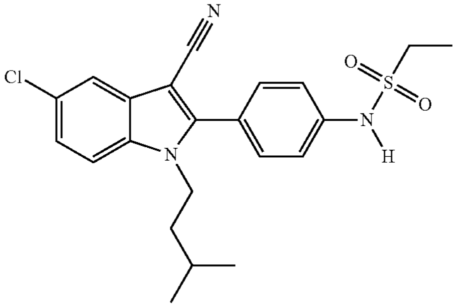
632
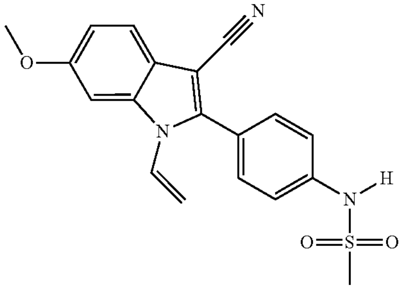
633
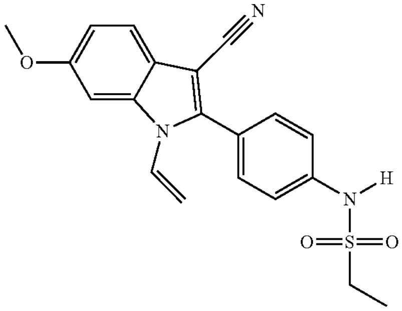
634
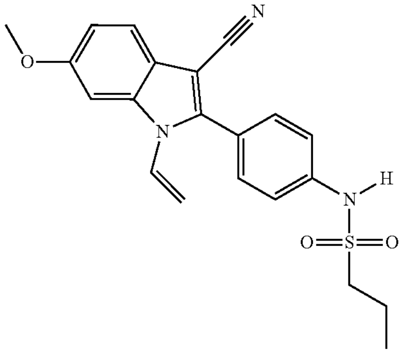

-continued
635
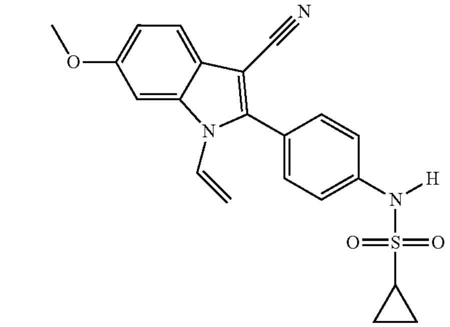
636
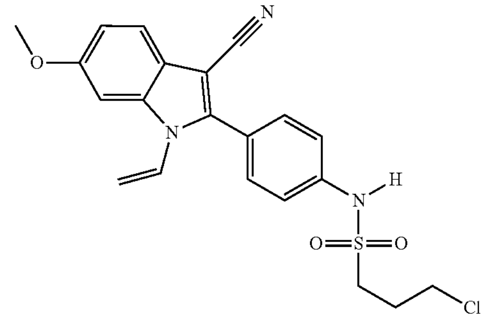
637
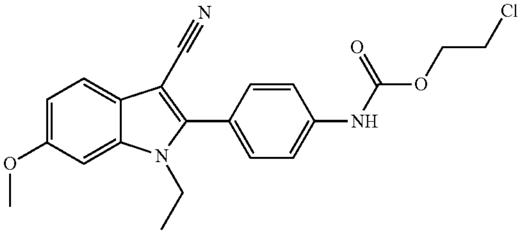
638
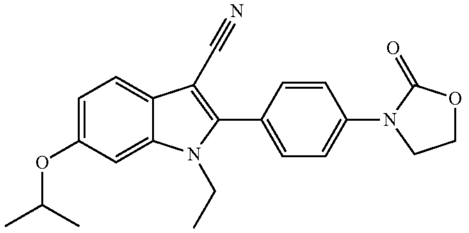
639
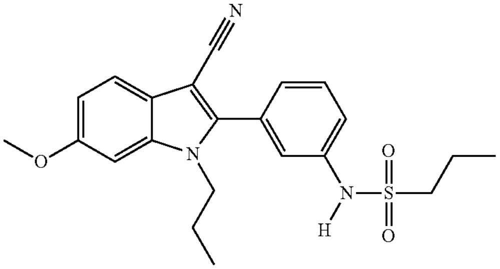
-continued
640
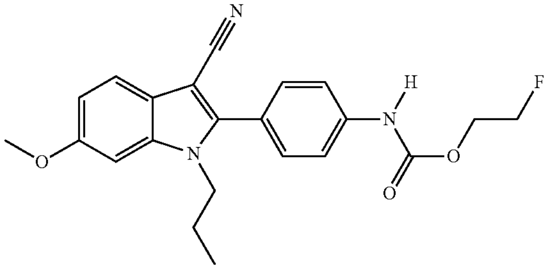
641
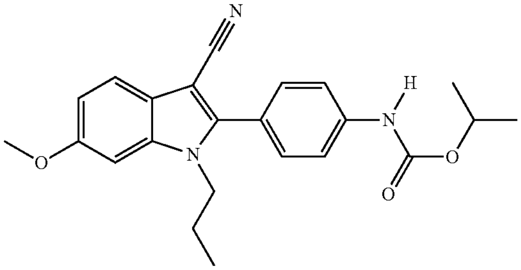
642
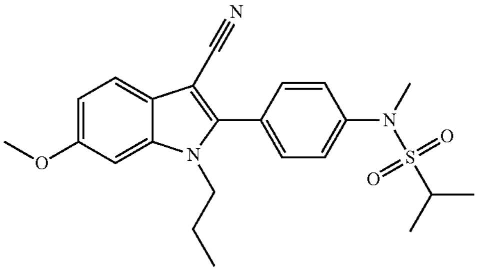
643
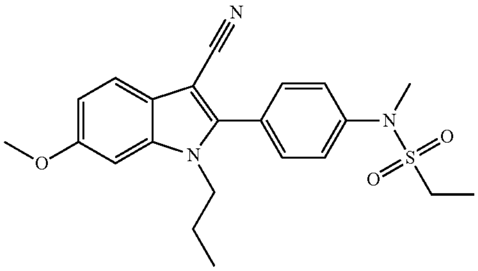
644
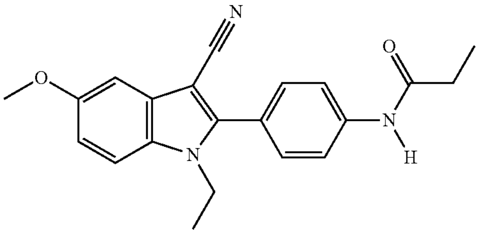
645
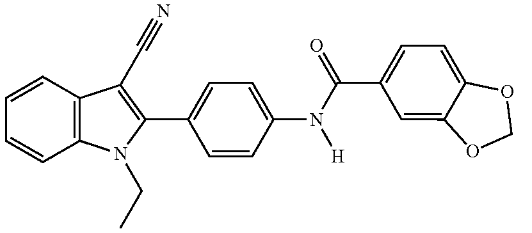

-continued
646
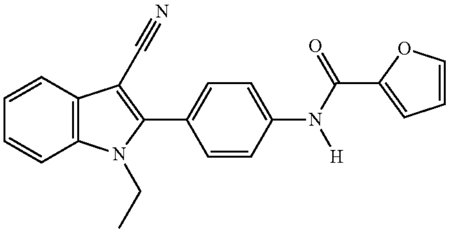
647
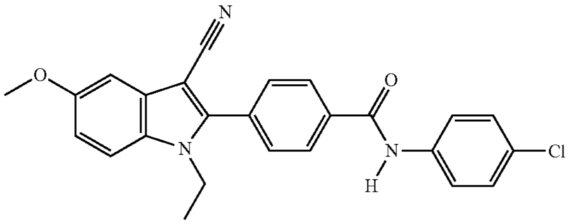
648
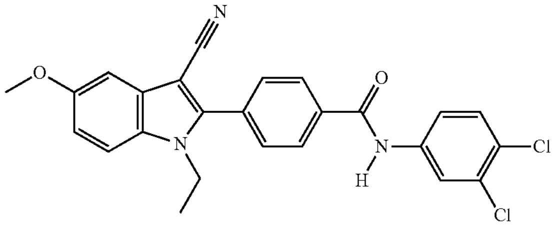
649
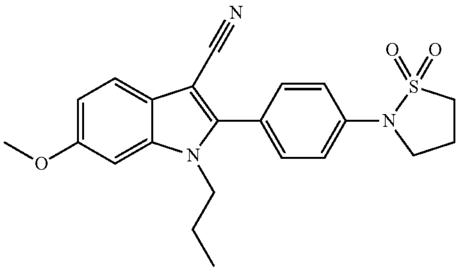
650
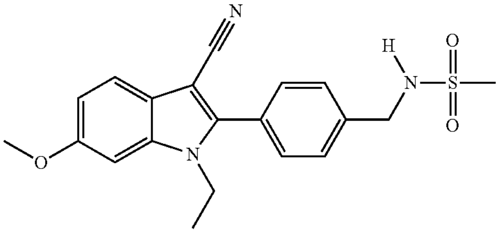
651
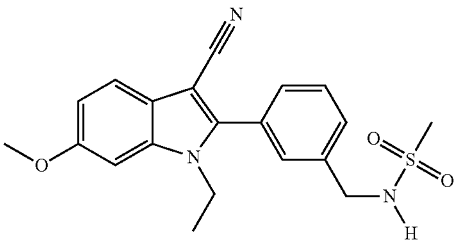
-continued
652
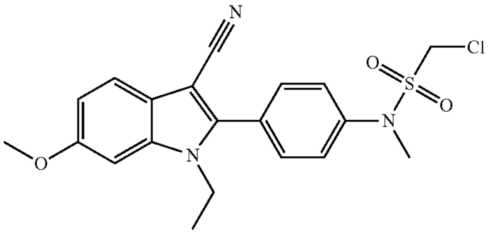
653
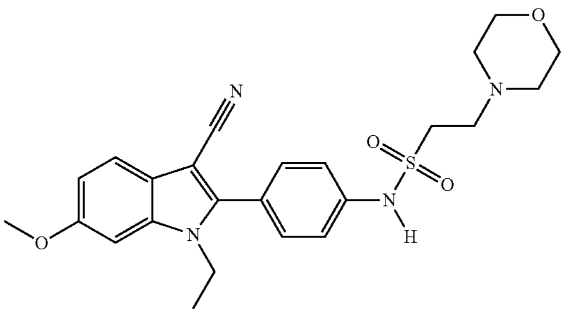
654
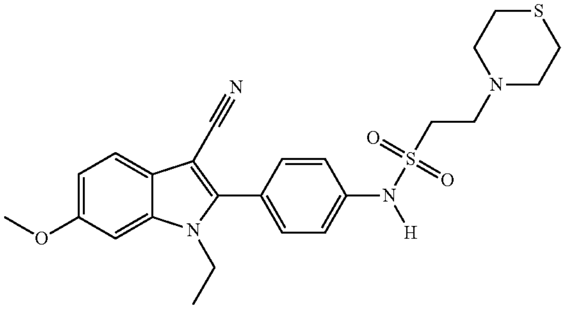
655
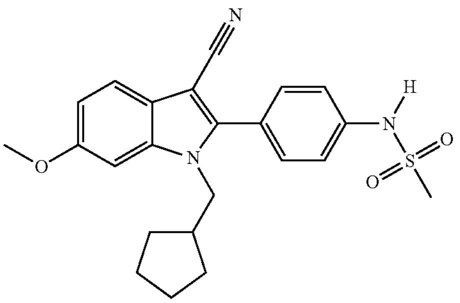
656
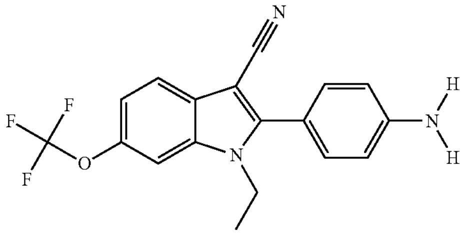

-continued
657
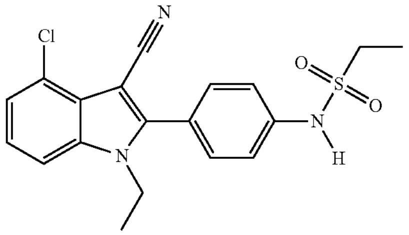
658
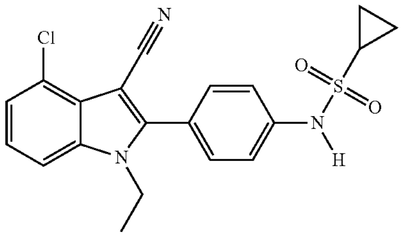
659
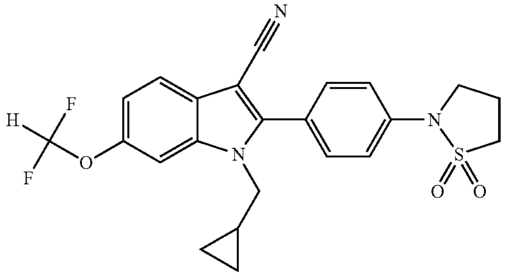
660
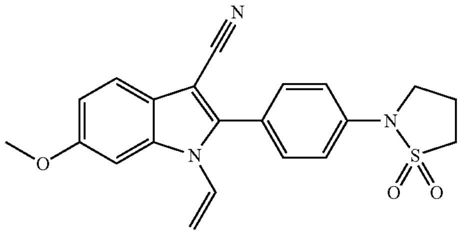
661
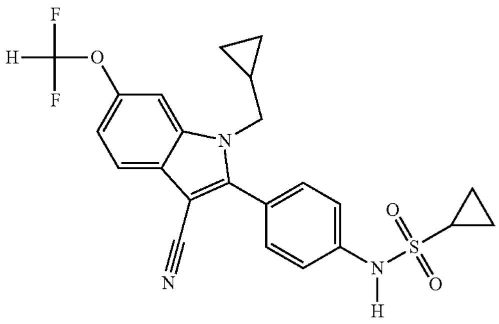
-continued
662
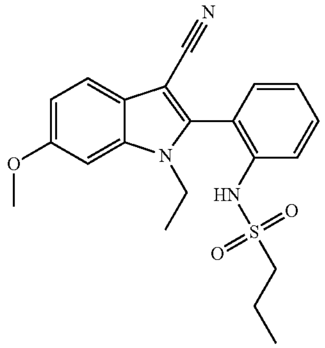
663
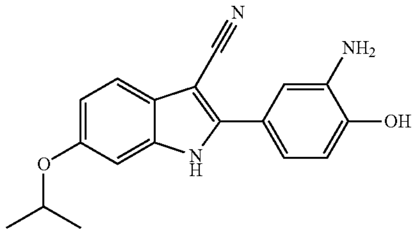
664
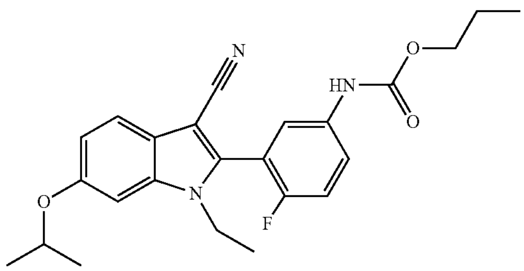
665
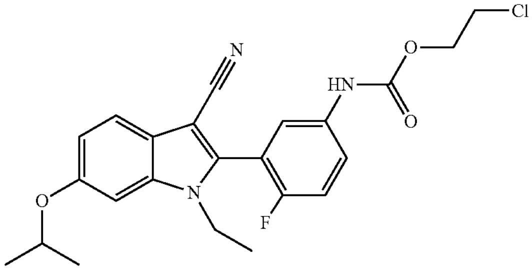
666
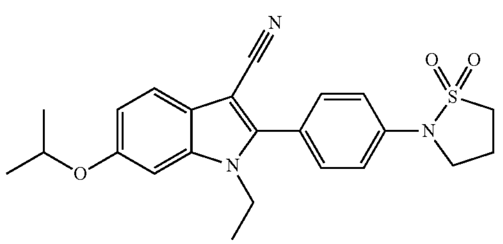

-continued
667
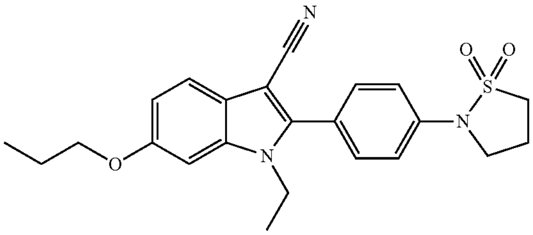
668
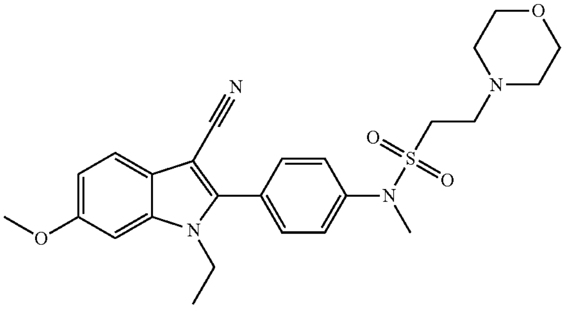
669
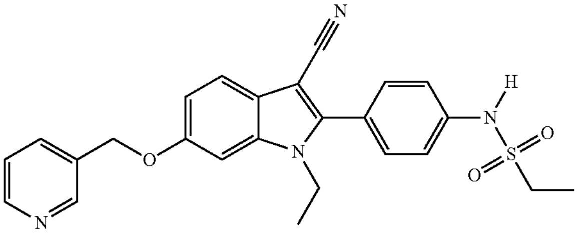
670
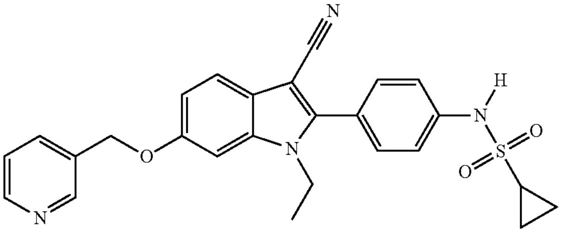
671
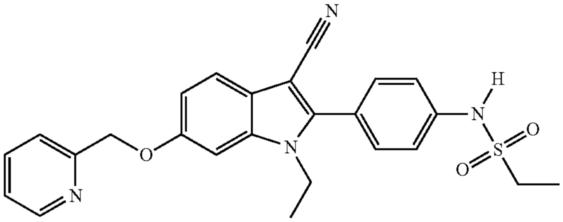
672
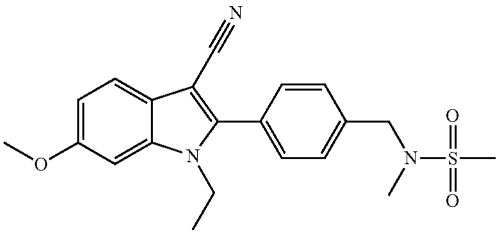
-continued
673
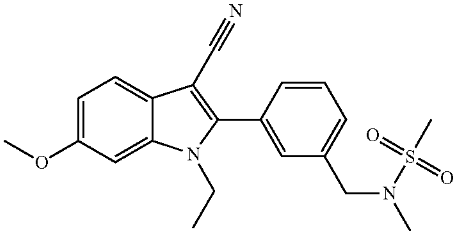
674
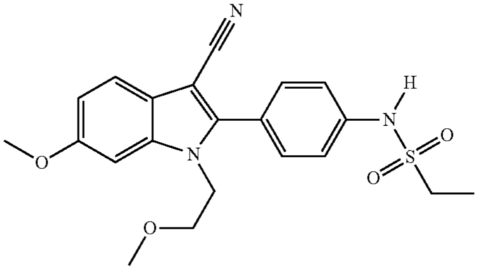
675
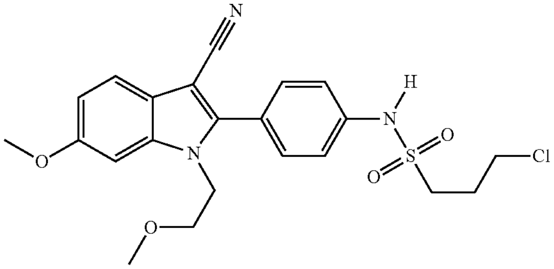
676
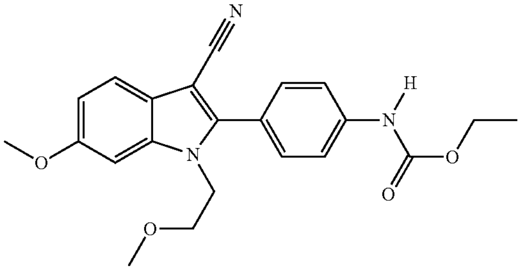
677
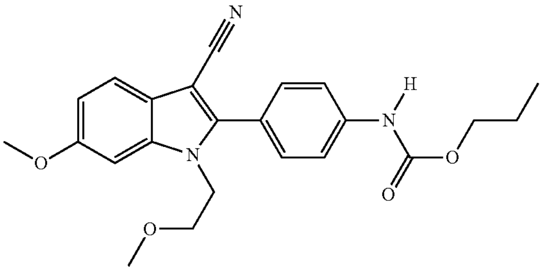

-continued
682
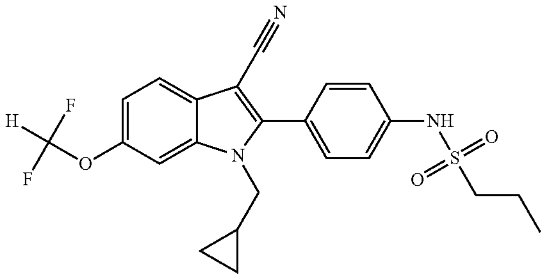
683
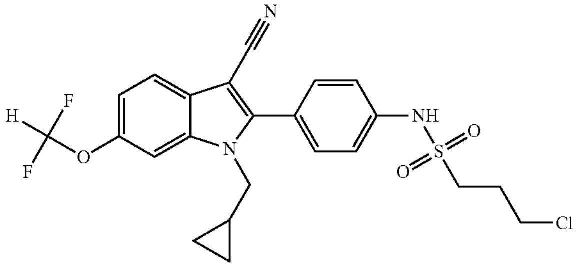
684
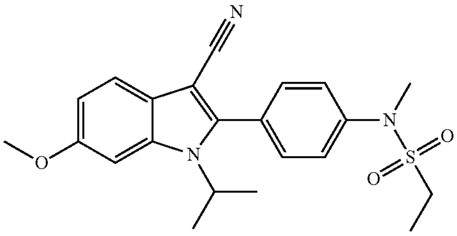
685
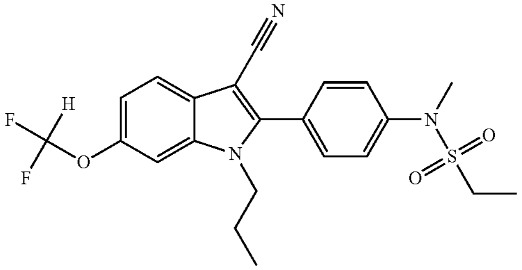
686
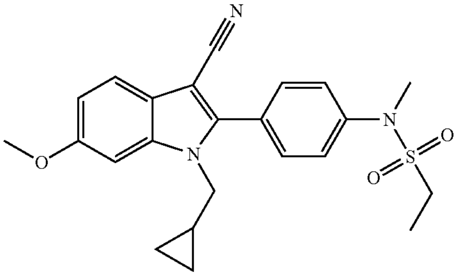
687
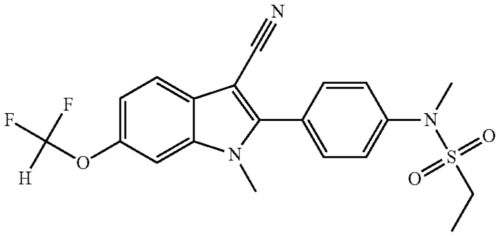
-continued
688
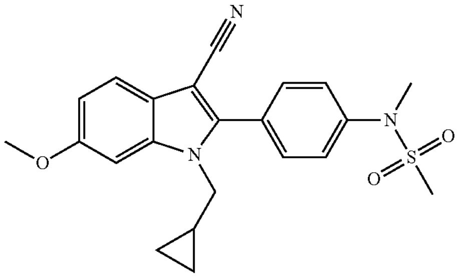
689
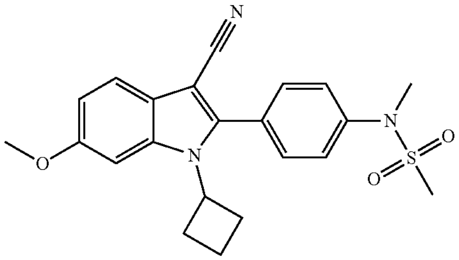
690
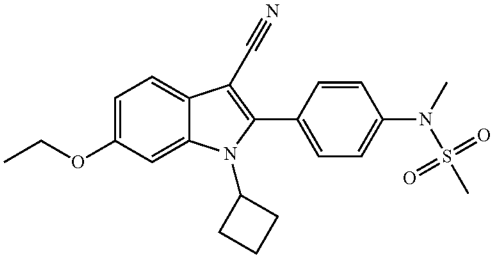
691
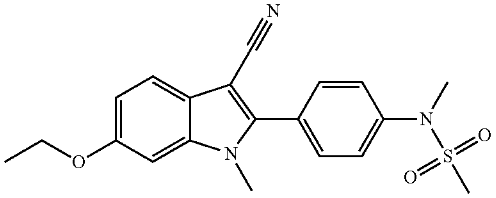
692
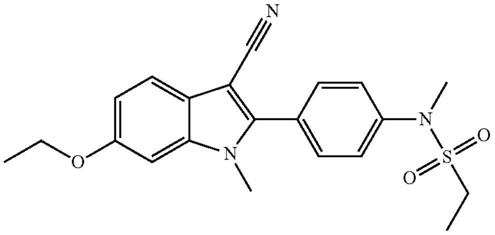
693
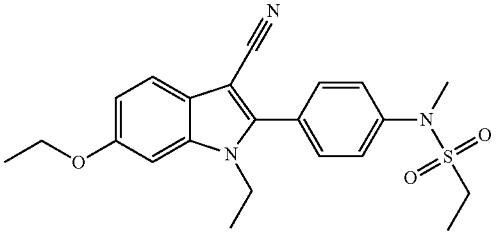

-continued
694
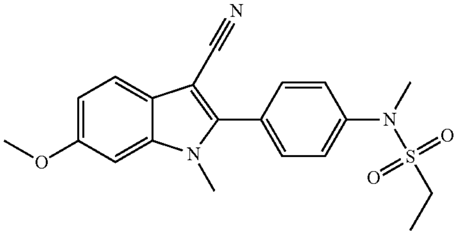
695
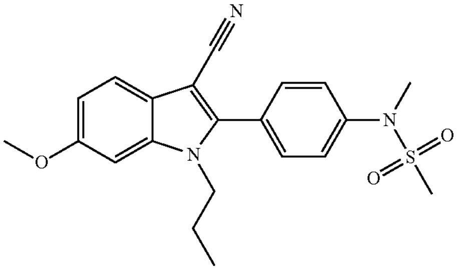
696
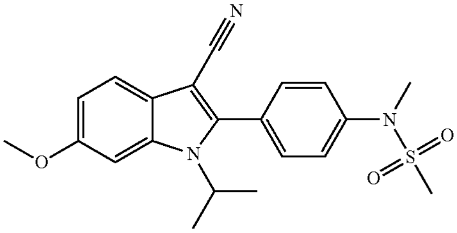
697
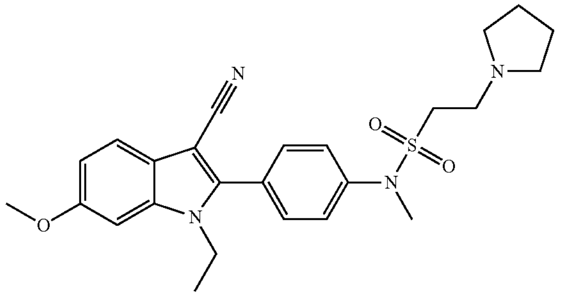
698
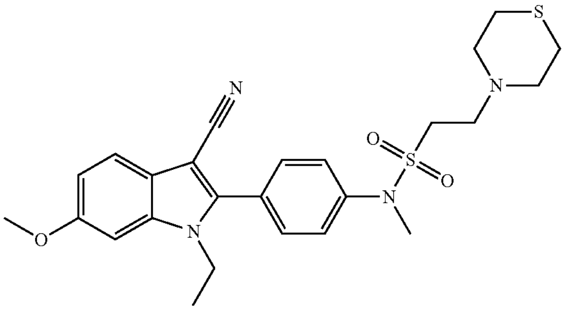
-continued
699
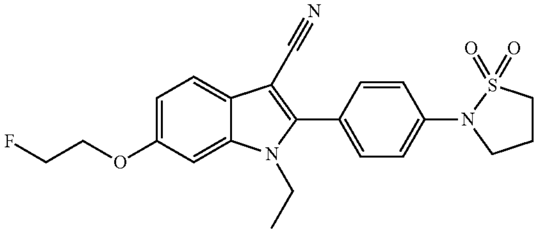
704
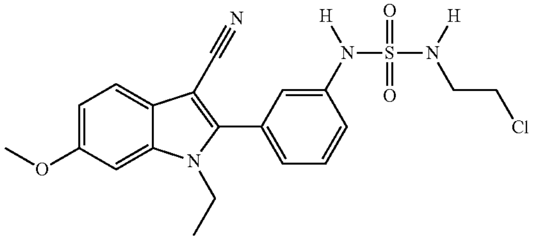
705
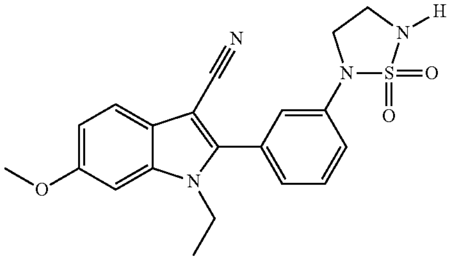
706
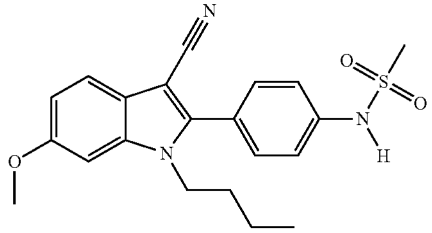
707
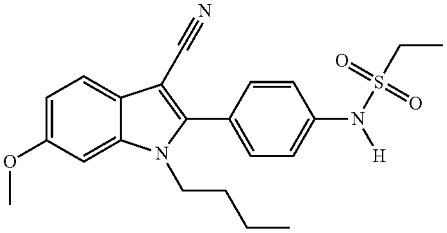
708
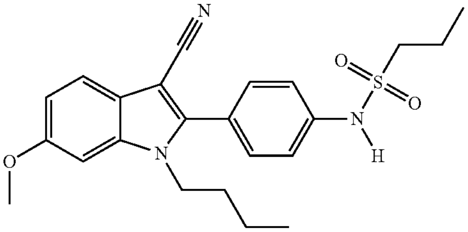

-continued
709
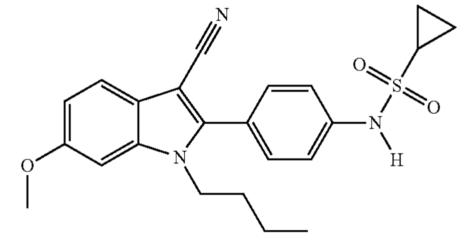
710
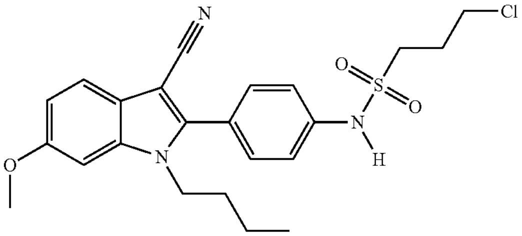
711
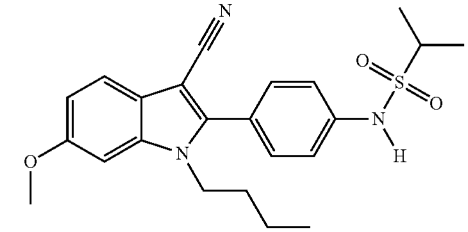
713
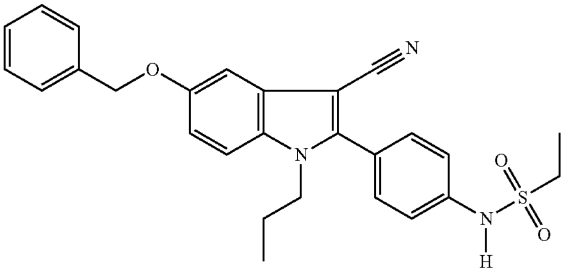
715
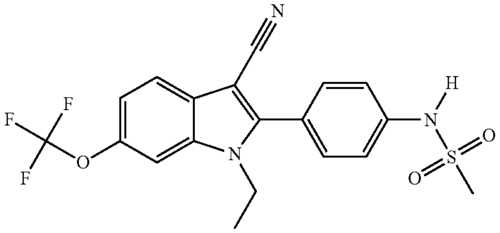
716
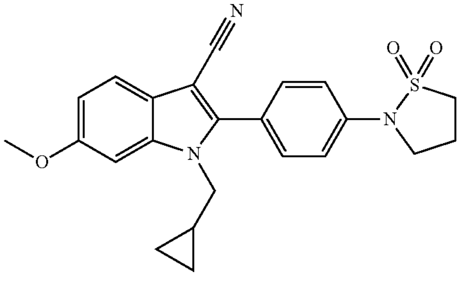
-continued
717
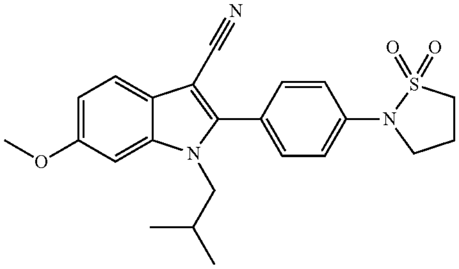
718
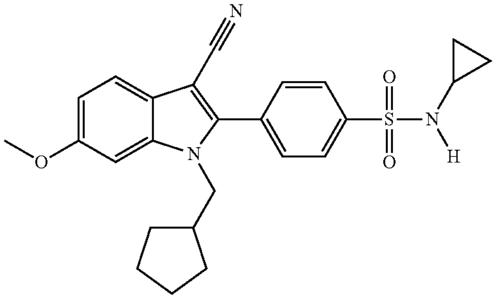
719
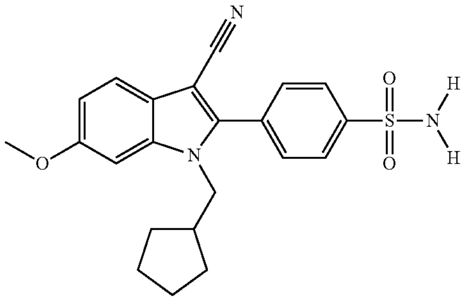
720
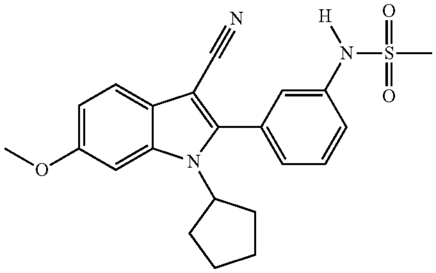
721
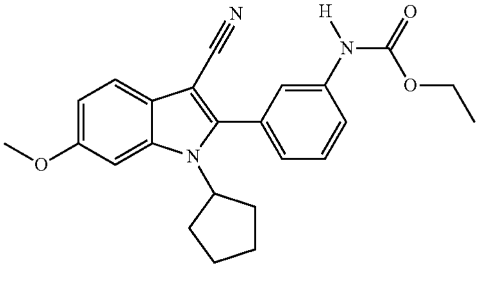

722
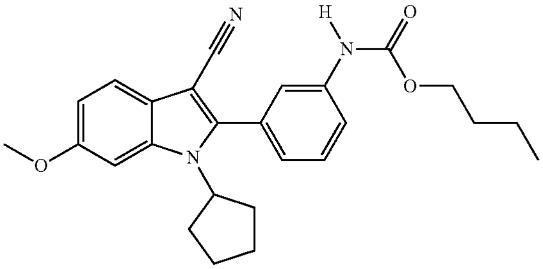
723
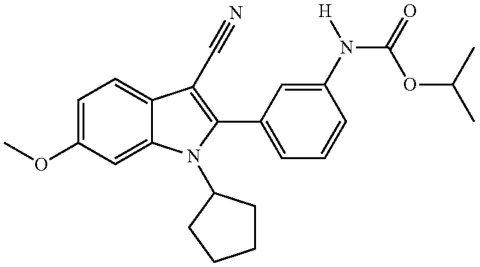
724
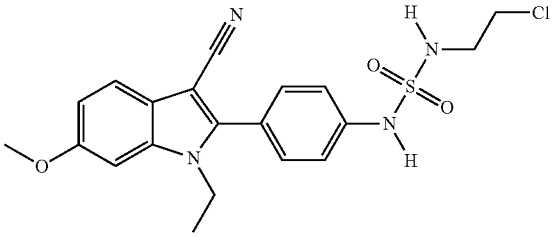
725
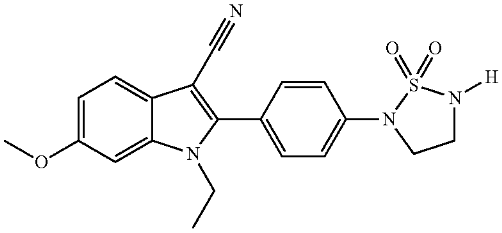
726
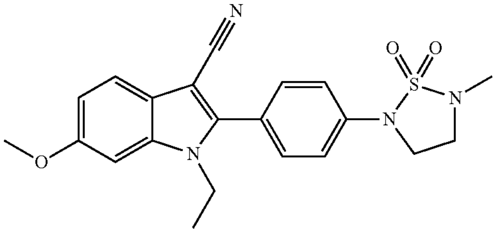
727
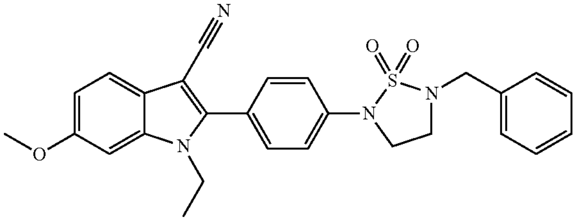
728
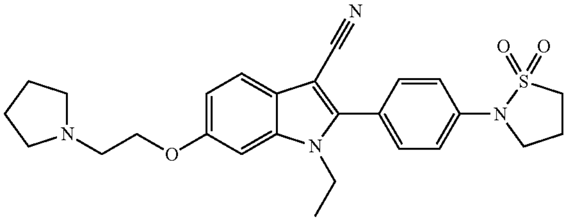
729
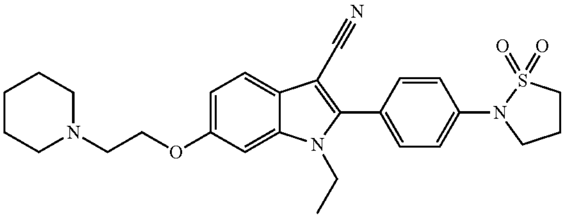
730
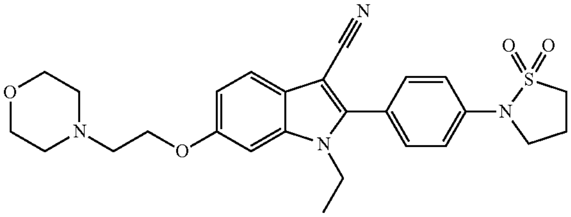
731
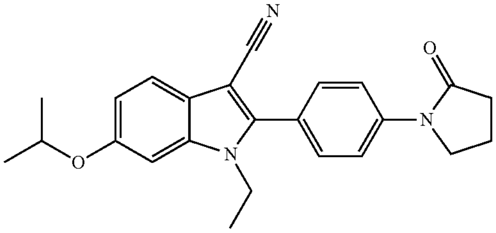
732
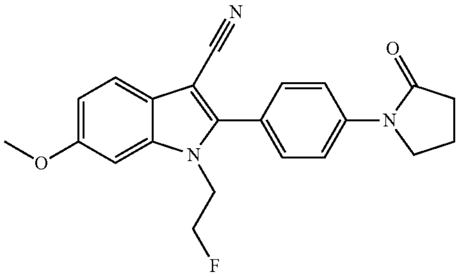
733
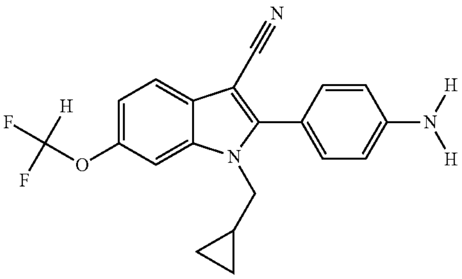

-continued
734
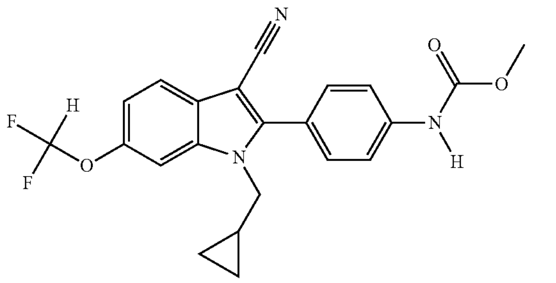
735
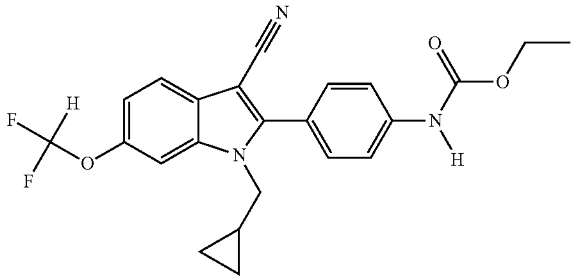
736
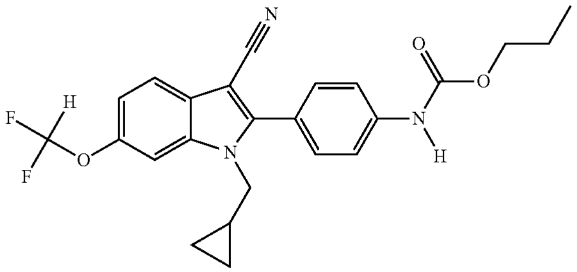
737
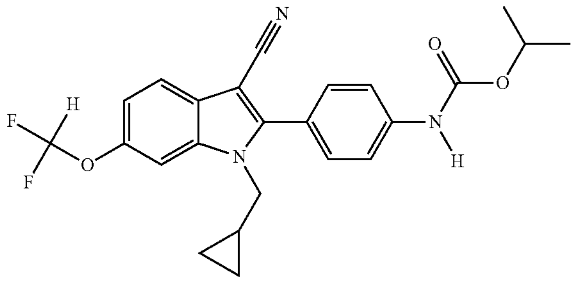
738
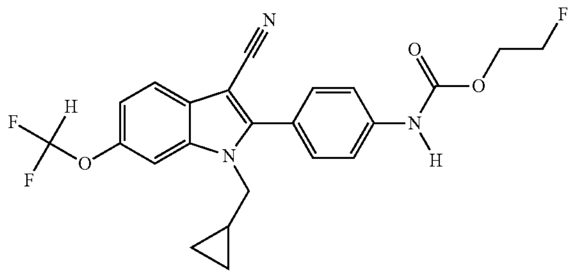
-continued
739
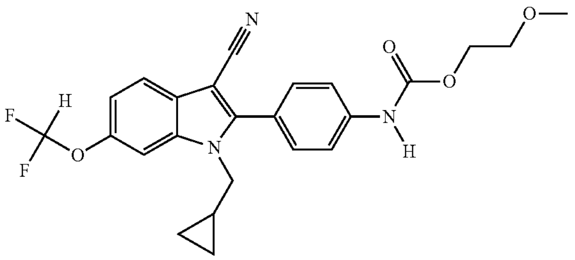
740
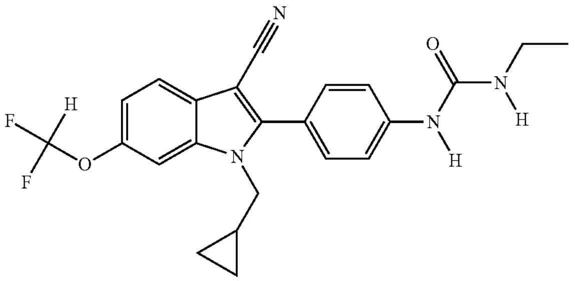
741
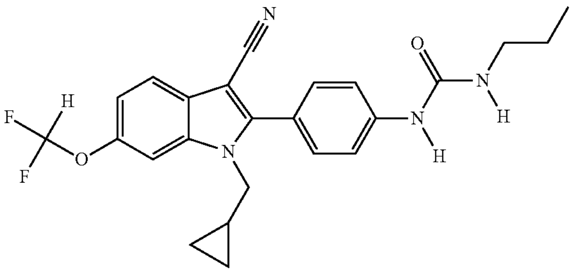
742
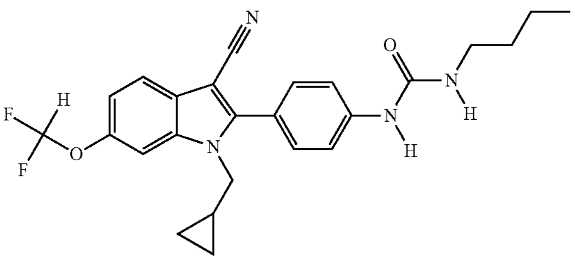
743
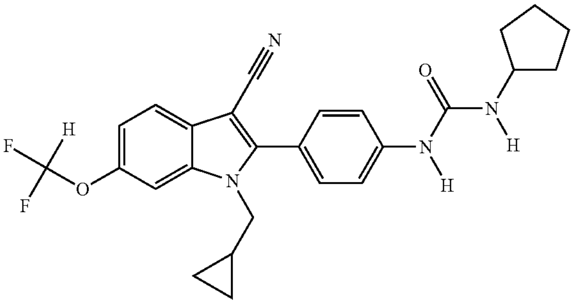

-continued
744
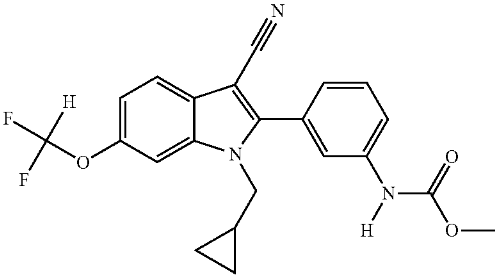
745
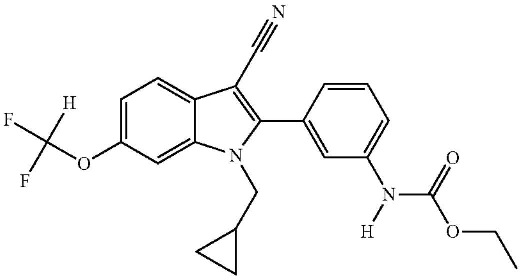
746
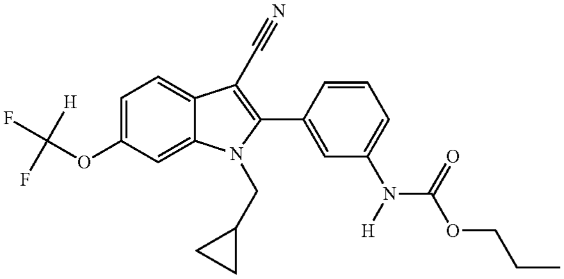
747
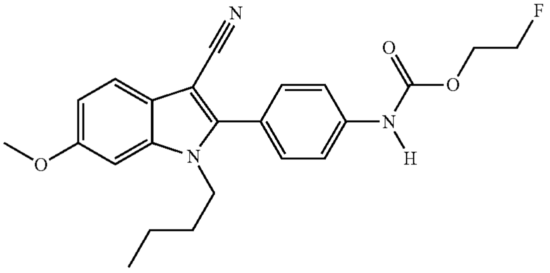
748
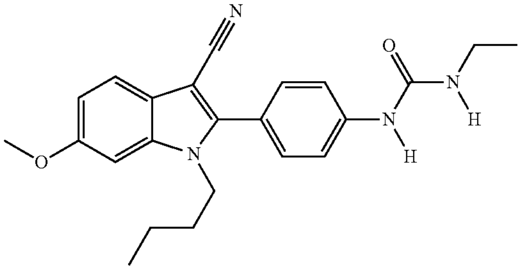
-continued
749
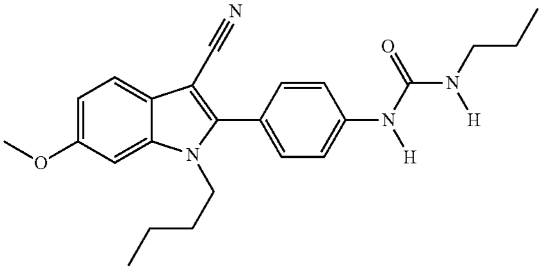
750
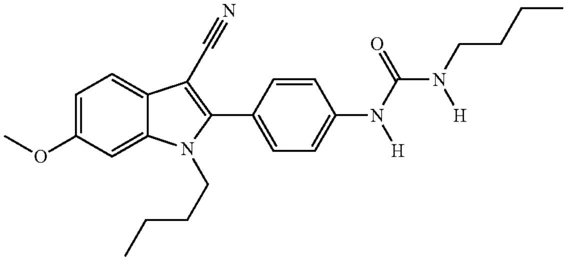
751
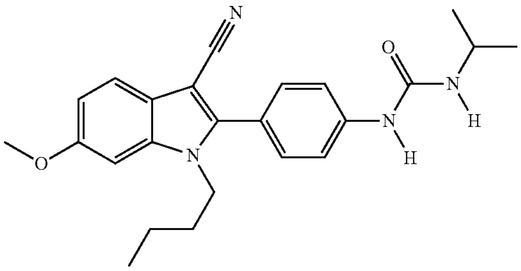
755
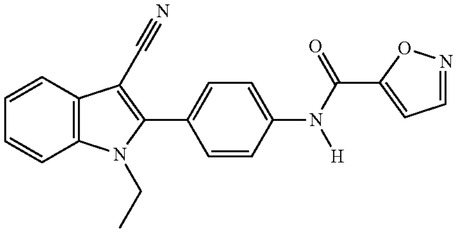
756
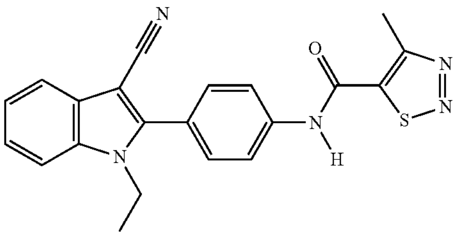
757
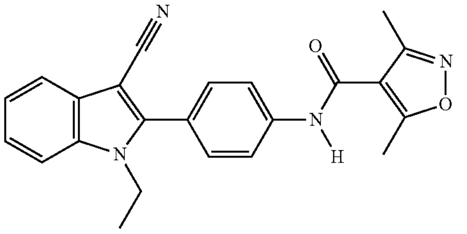

758
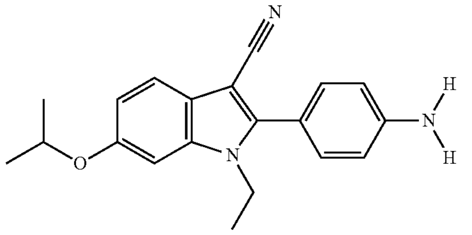
759
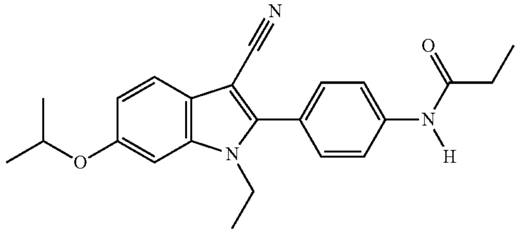
760
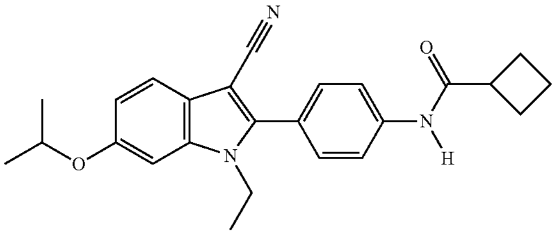
761
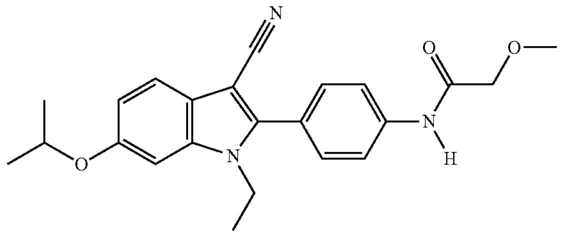
762
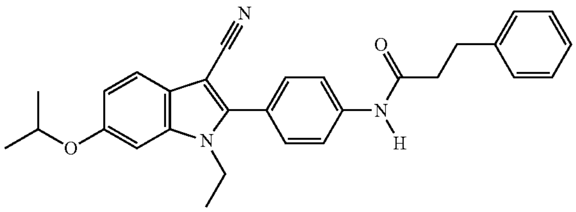
763
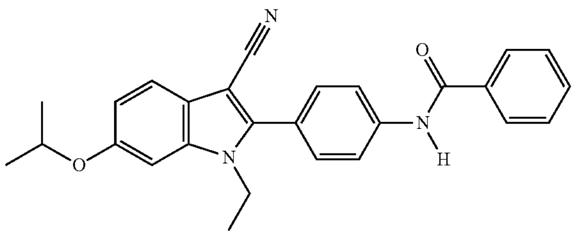
764
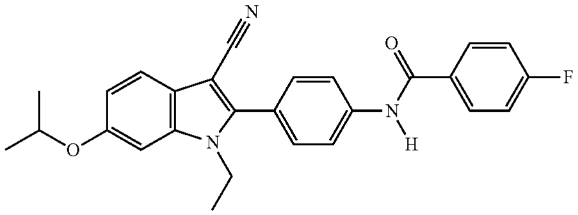
765
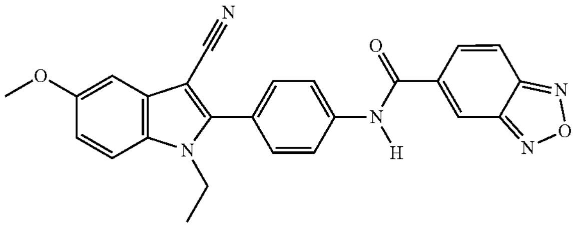
766
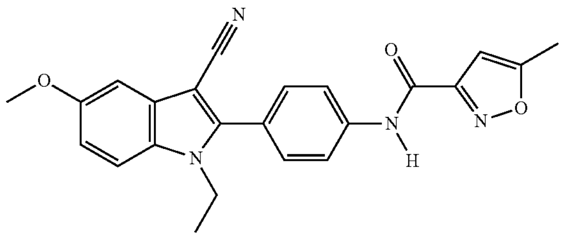
767
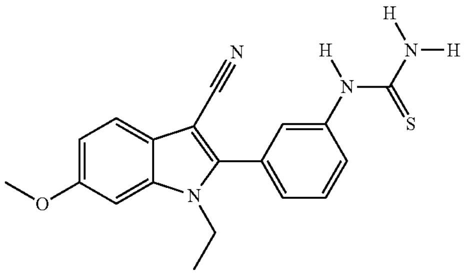
770
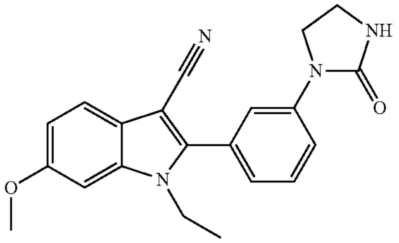
771
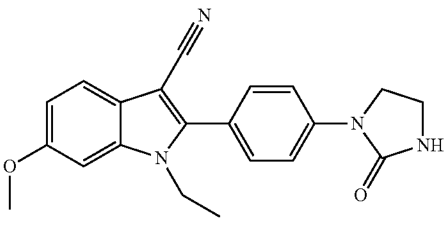

-continued
772
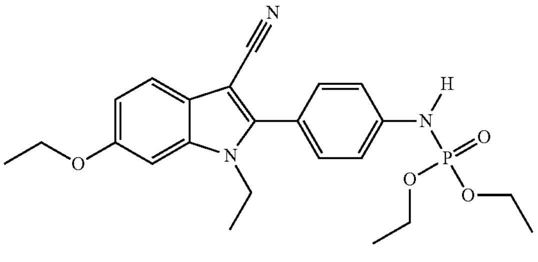
773
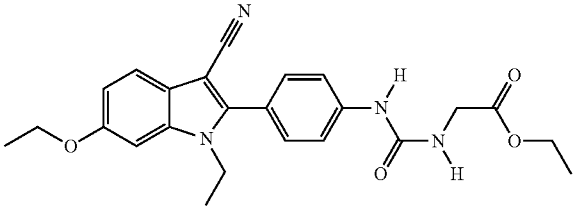
774
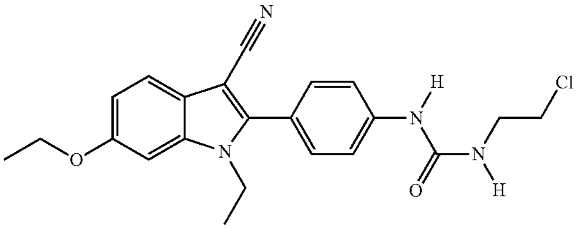
775
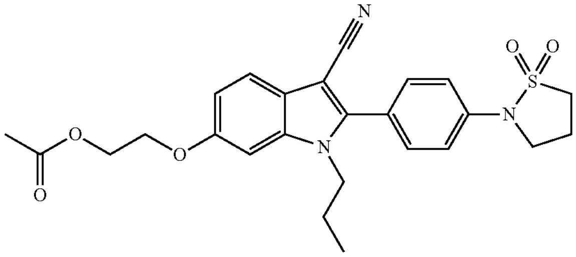
776
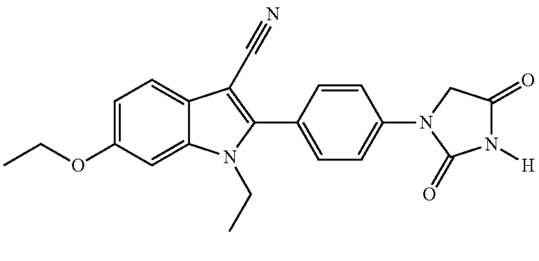
-continued
777
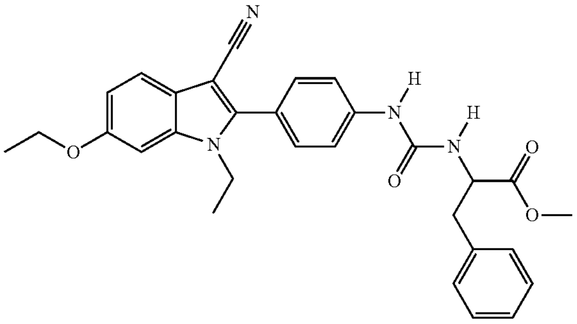
778
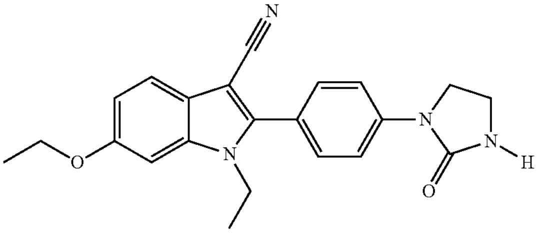
779
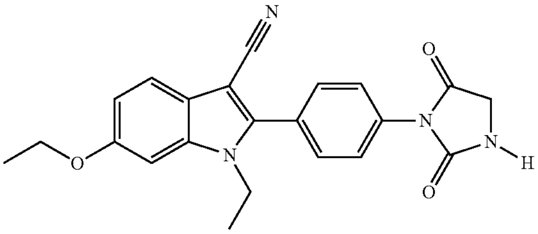
782
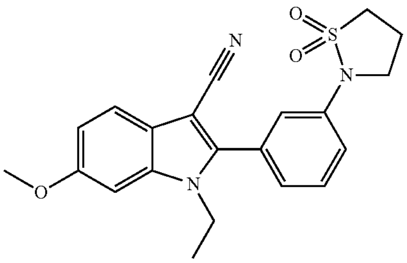
783
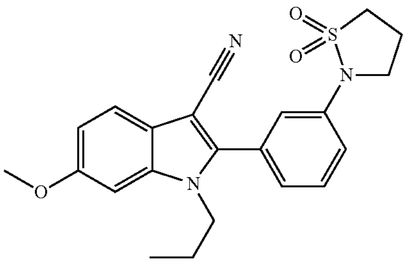

-continued
784
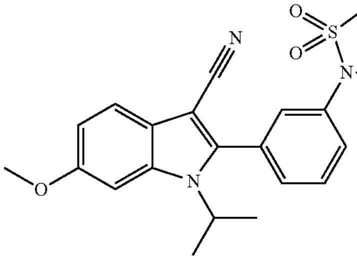
787
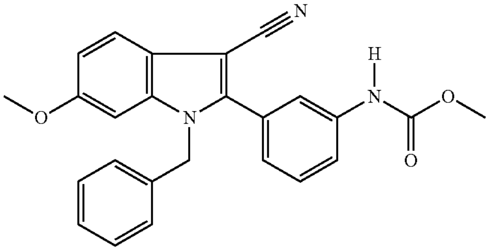
788
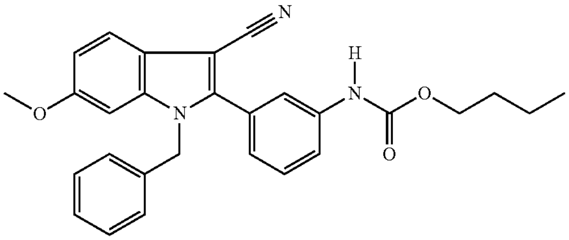
789
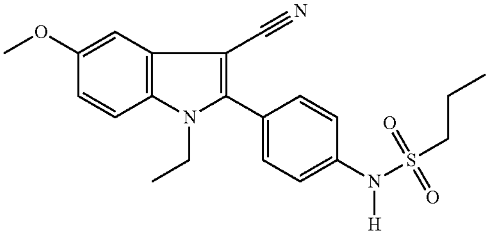
790
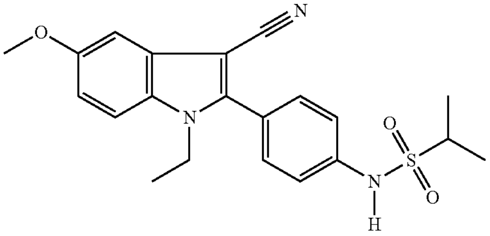
791
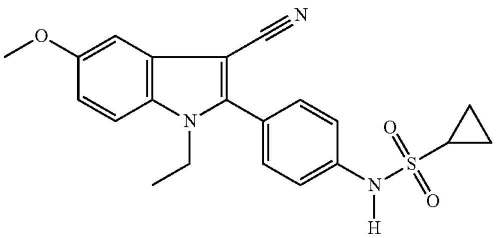
-continued
792
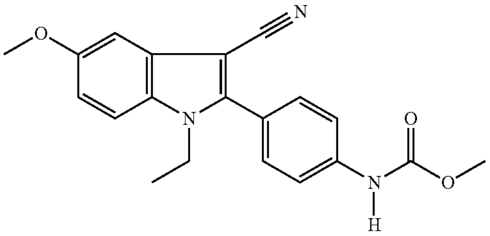
793
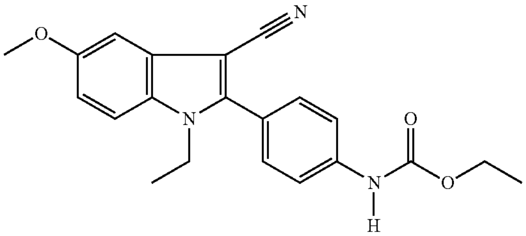
794
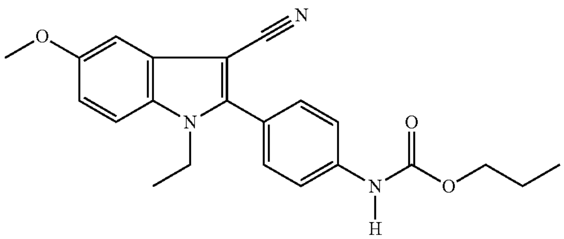
795
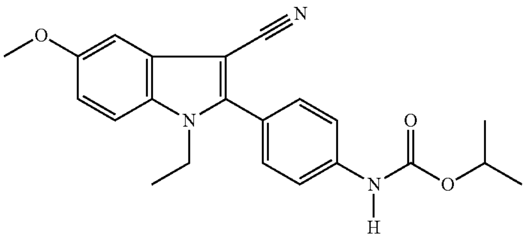
796
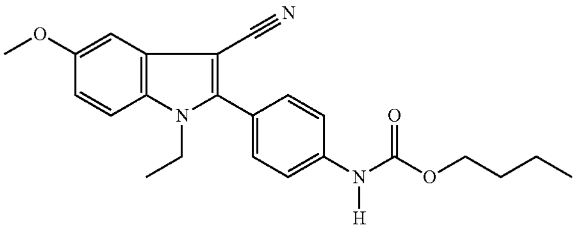
797
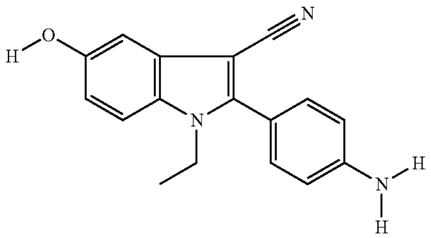

-continued
798
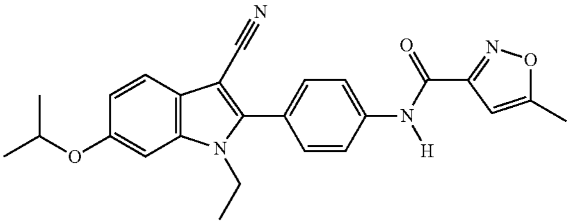
799
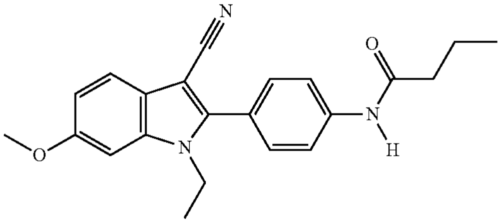
801
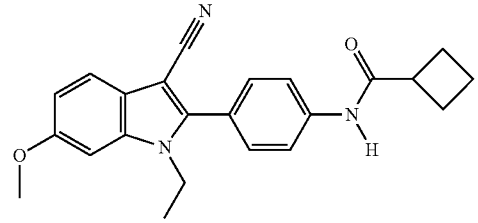
802
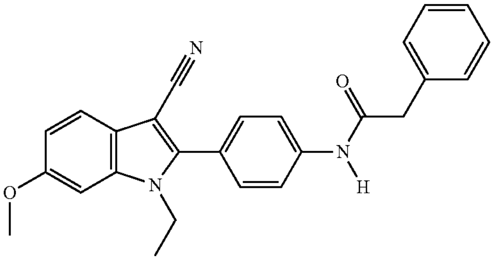
803
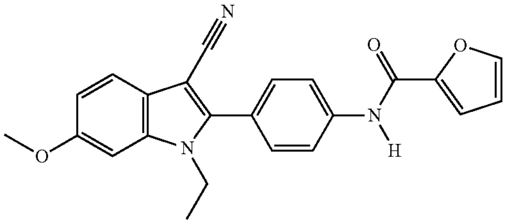
804
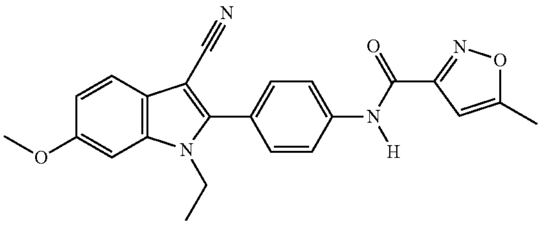
-continued
806
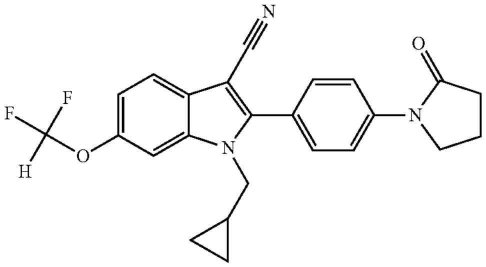
807
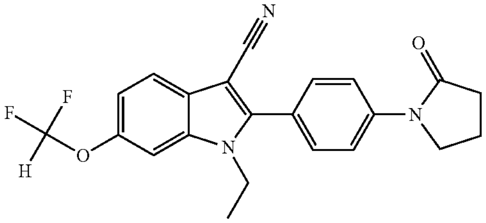
808
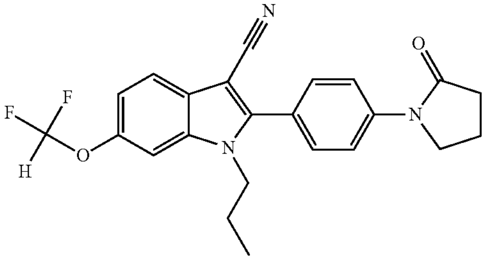
809
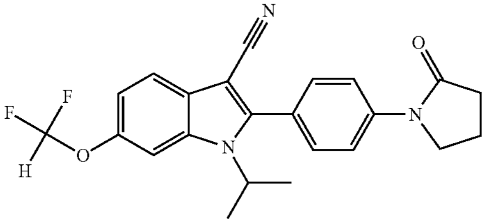
810
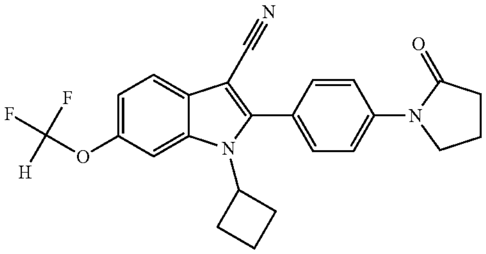
811
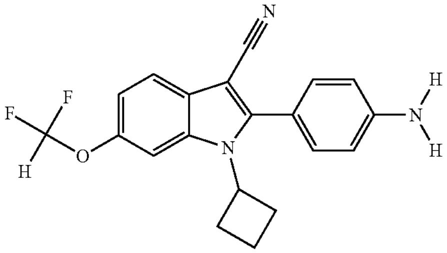

-continued
812
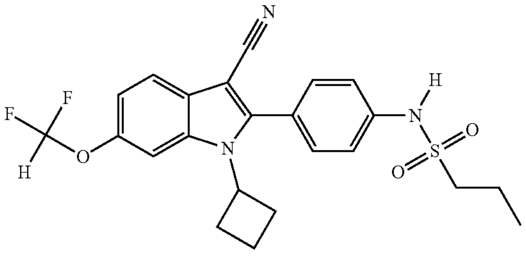
813
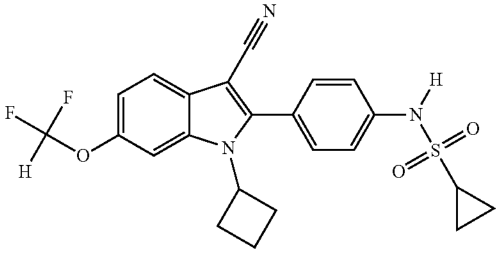
814
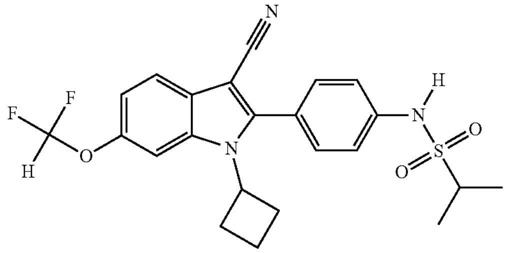
815
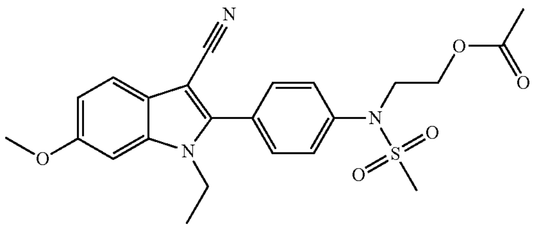
816
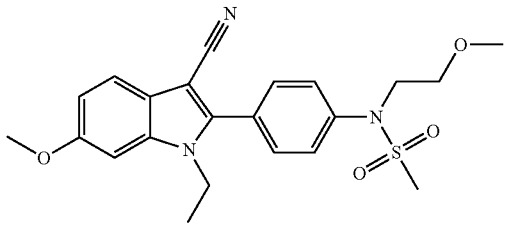
817
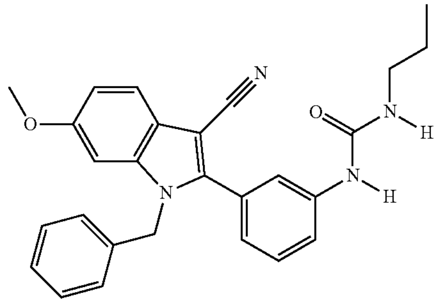
-continued
818
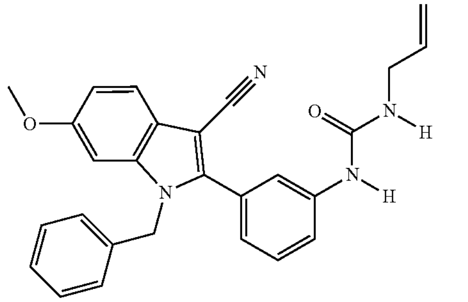
819
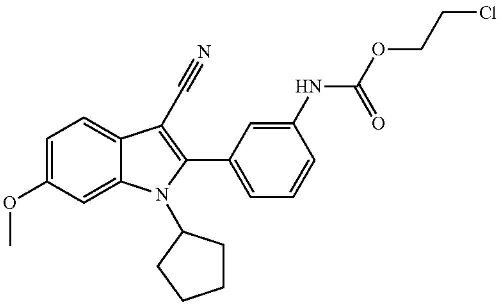
820
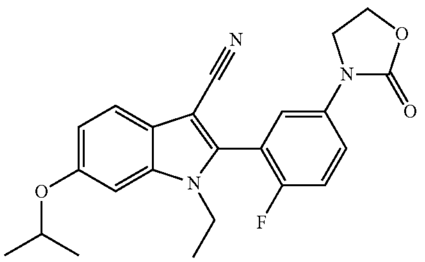
821
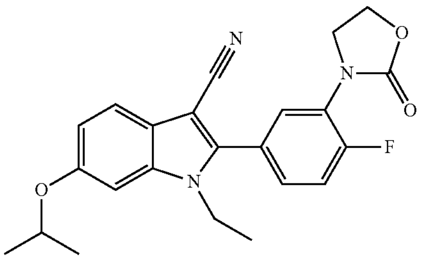
822
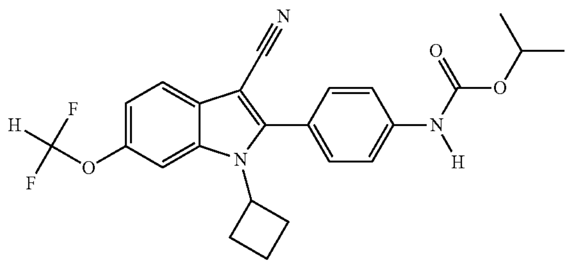

-continued
823
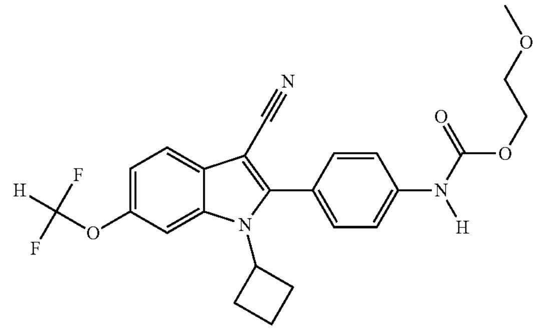
824
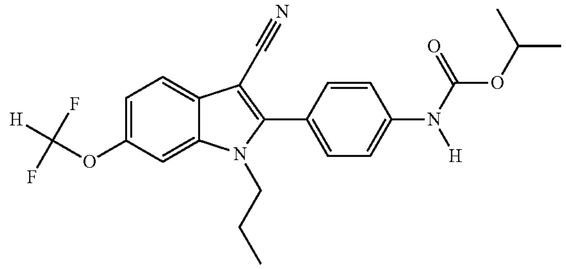
825
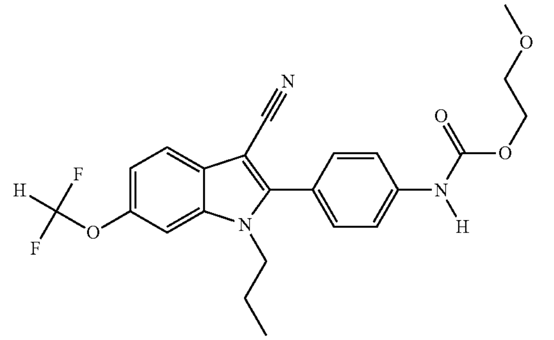
826
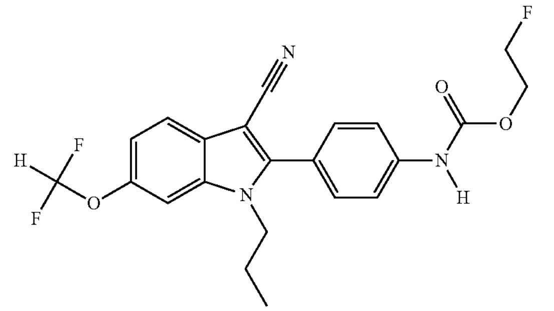
827
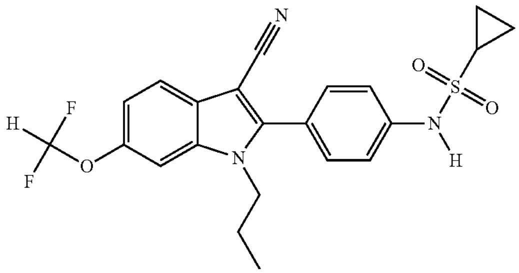
-continued
828
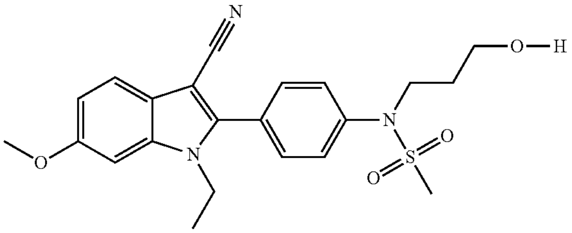
829
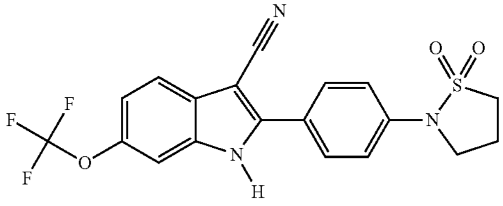
830
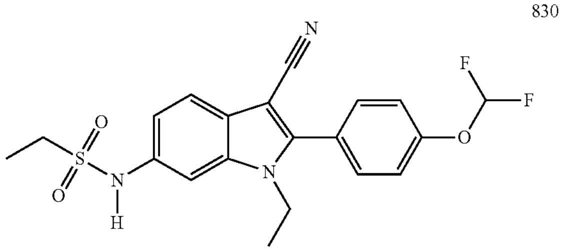
831
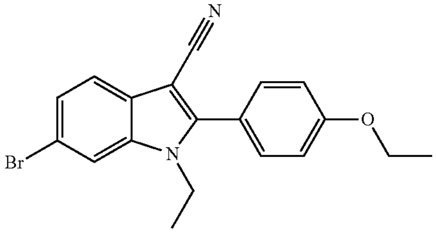
832
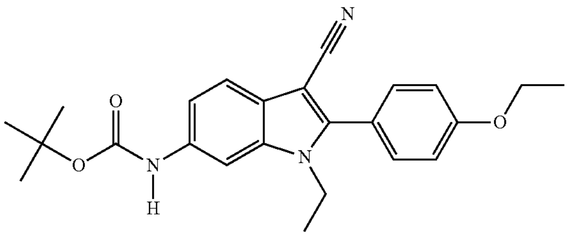
833
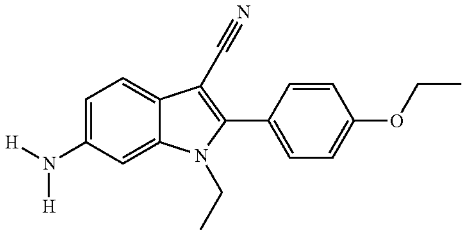

-continued
834
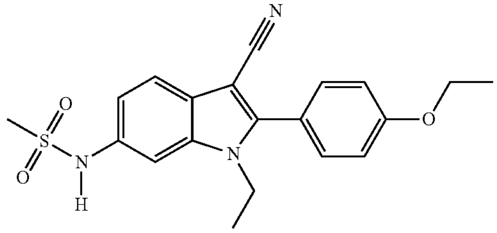
835
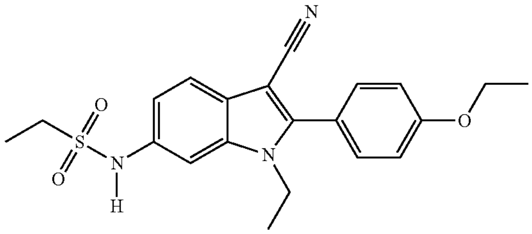
836
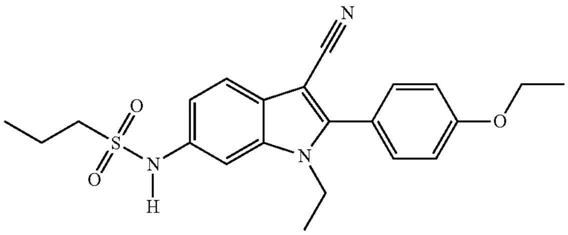
837
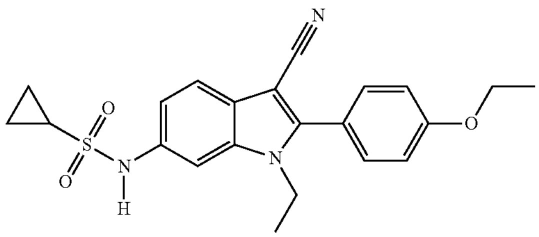
838
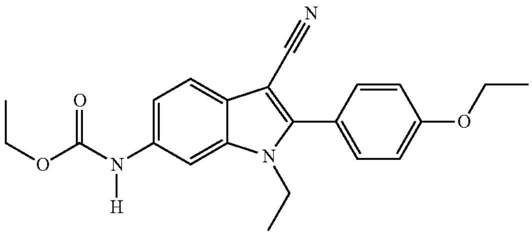
839
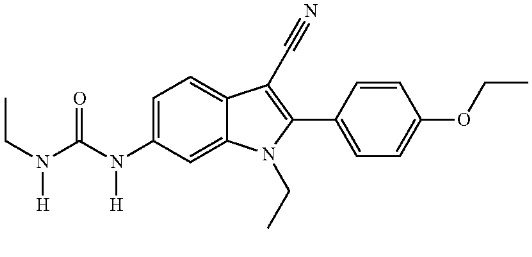
-continued
840
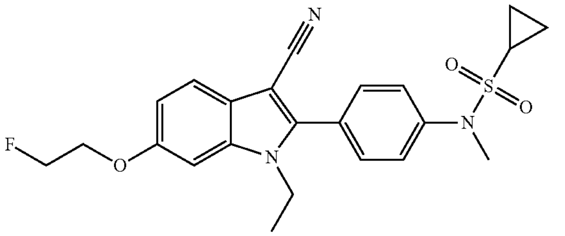
844
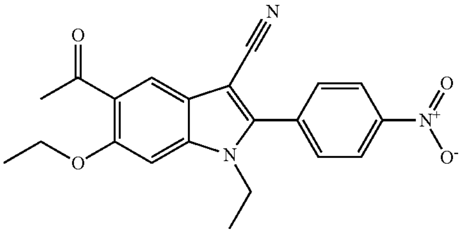
845
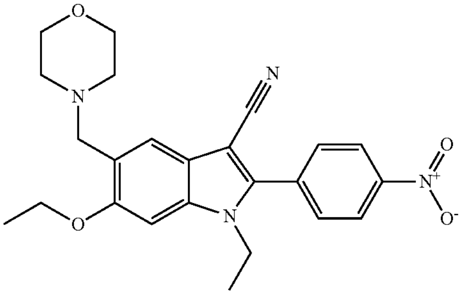
846
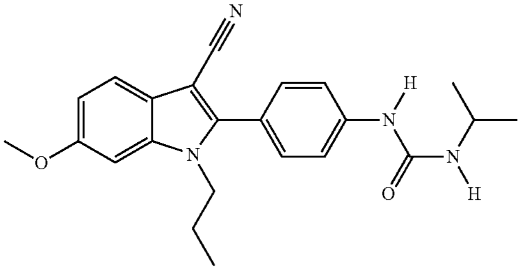
847
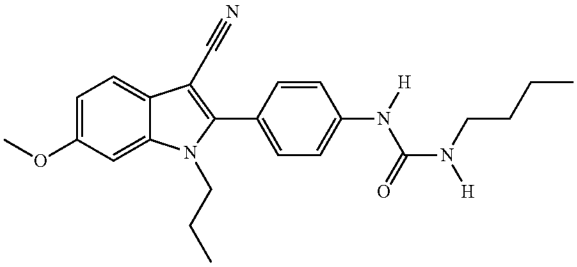

-continued
848
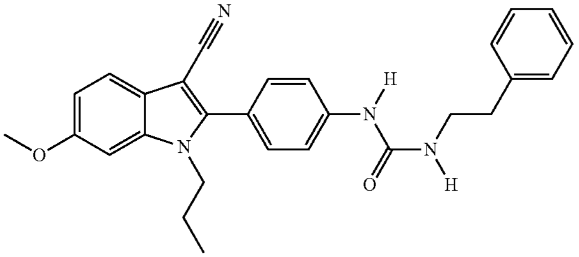
849
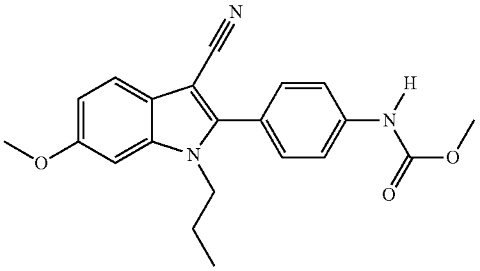
850
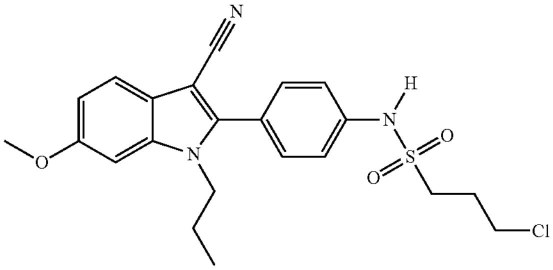
851
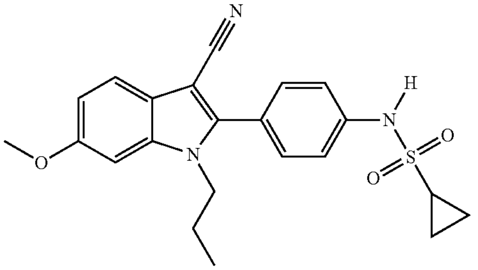
852
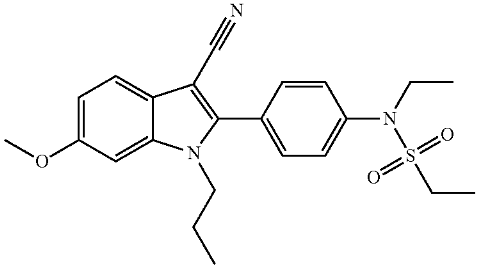
-continued
853
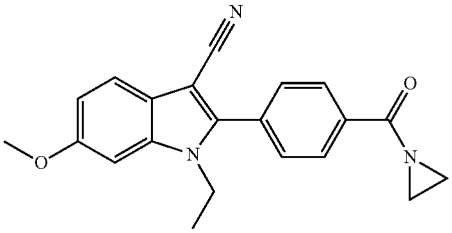
854
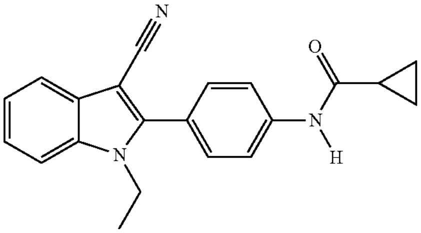
855
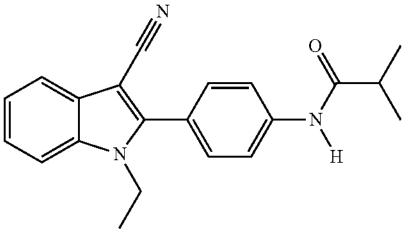
856
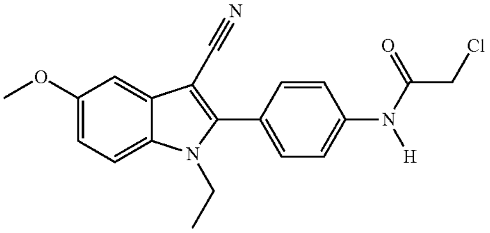
857
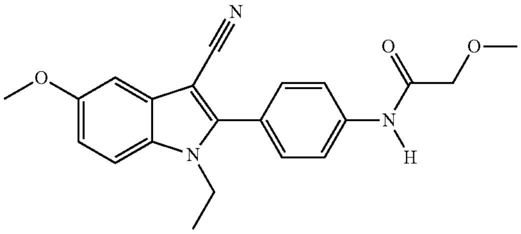
858
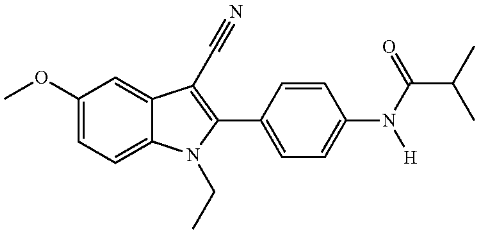

-continued

859

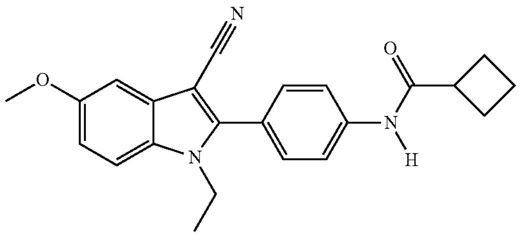

860

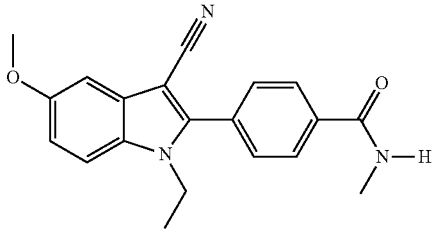

861

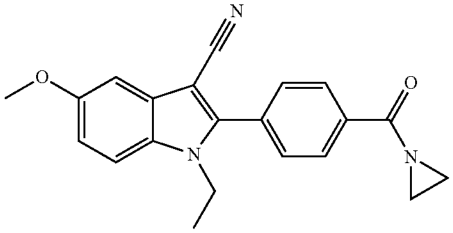

862

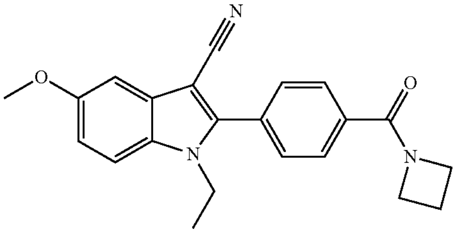

863

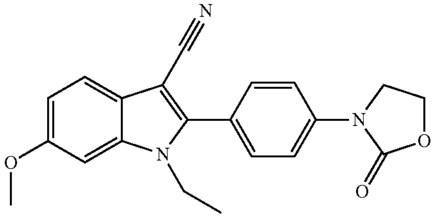

864

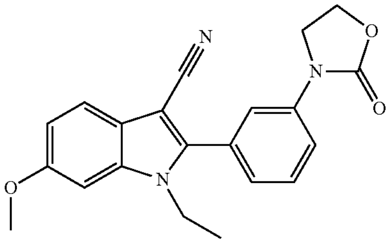

or a pharmaceutically acceptable salt thereof.

9. A pharmaceutical composition comprising a compound of claim 1 or a pharmaceutically acceptable salt thereof and one or more pharmaceutically acceptable excipients.

10. A pharmaceutical composition comprising a compound of claim 2 or a pharmaceutically acceptable salt thereof and one or more pharmaceutically acceptable excipients.

11. A pharmaceutical composition comprising a compound of claim 8 or a pharmaceutically acceptable salt thereof and one or more pharmaceutically acceptable excipients.

12. A compound of Formula (I):

(I)

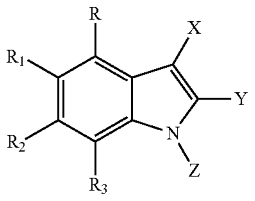

wherein:

X is:

-cyano;

Y is:

-aryl substituted with one or more of the following:

—$C_1$ to $C_6$ alkoxy, optionally substituted with:

—$C_1$ to $C_6$ alkoxy,

-hydroxy,

-one or more halogen substituents,

-5 or 6 membered heterocycle, optionally substituted with:

—$C_1$ to $C_6$ alkyl, or

-hydroxy,

-amino optionally substituted with one or more $C_1$ to $C_6$ alkyl substituents, —$NR_iSO_2R_x$, where $R_x$ is $C_1$ to $C_6$ alkyl and $R_i$ is:

-hydrogen,

—$C_1$ to $C_6$ alkyl,

—$COR_x$, where $R_x$ is as defined above,

—$C_1$ to $C_6$ haloalkyl, or

—$C_1$ to $C_6$ haloalkoxy,

—$NR_jCOR_k$, where $R_k$ is:

—$C_1$ to $C_6$ alkyl,

-hydrogen, or

-amino optionally substituted with one or more $C_1$ to $C_6$ alkyl substituents, and $R_j$ is:

-hydrogen,

—$C_1$ to $C_6$ alkyl,

—$COR_x$, where $R_x$ is as defined above,

—$C_1$ to $C_6$ haloalkyl, or

—$C_1$ to $C_6$ haloalkoxy,

—$N{=}N{=}^{+}{=}N^{-}$, or

—$COR_1$, where $R_1$ is 5 or 6 membered heterocycle optionally substituted with hydroxy, -amino optionally substituted with one or more $C_1$ to $C_6$ alkyl substituents, -nitro, —$C_1$ to $C_6$ alkyl, optionally substituted with:

—$NHSO_2R_x$, where $R_x$ is as defined above, or

—$NR_xSO_2R_x$, where $R_x$ is as defined above,

—$C_1$ to $C_6$ haloalkoxy,

-halogen,

-hydroxy,

—$COOR_x$, where $R_x$ is as defined above,

—$COR_m$, where $R_m$ is:

-amino optionally substituted with:

(i) -cyclopropyl, cyclobutyl, cyclopentyl, or cyclohexyl, or
(ii) one or more $C_1$ to $C_6$ alkyl substituents, where the $C_1$ to $C_6$ alkyl substituents are optionally substituted with: -hydroxy
-5 or 6 membered heterocycle,
-amino optionally substituted with one or more $C_1$ to $C_6$ alkyl substituents,
—$C_1$ to $C_6$ alkoxy,
-3 to 7 membered heterocycle, optionally substituted with $C_1$ to $C_6$ alkyl, optionally substituted with di-$C_1$ to $C_6$ alkyl-amino,
—$NHR_n$, where $R_n$ is:
—$CH_2CONH_2$, or
-aryl optionally substituted with:
—$C_1$ to $C_6$ alkyl,
-one or more halogen substituents,
-nitro, or
-one or more $C_1$ to $C_6$ alkoxy substituents,
—$NR_oCOR_p$, where $R_p$ is:
—$C_1$ to $C_6$ alkyl optionally substituted with:
-halogen,
—$C_1$ to $C_6$ alkoxy, or
-aryl,
-cyclopropyl,
-cyclobutyl,
-cyclopentyl,
-cyclohexyl,
-5 or 6 membered heterocycle,
-aryl, optionally substituted with halogen,
-5 or 6 membered heteroaryl optionally substituted with one or more $C_1$ to $C_6$ alkyl substituents,
-hydrogen,

- 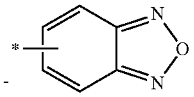 or 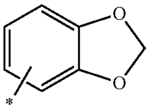, and where $R_o$ is:
-hydrogen,
—$C_1$ to $C_6$ alkyl,
—$COR_x$, where $R_x$ is as defined above,
—$C_1$ to $C_6$ haloalkyl, or
—$C_1$ to $C_6$ haloalkoxy,
—$NR_qCONR_qR_r$, where $R_q$ is:
-hydrogen,
—$C_1$ to $C_6$ alkyl,
—$C_1$ to $C_6$ haloalkyl,
—$C_1$ to $C_6$ haloalkoxy, or
—$COR_x$, where $R_x$ is as defined above,
and where $R_r$, is:
-aryl optionally substituted with:

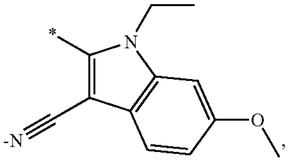,

—$C_1$ to $C_6$ alkyl,
—$C_1$ to $C_6$ haloalkyl,
—$OR_s$, where $R_s$ is aryl, or
—$COOR_x$, where $R_x$ is as defined above,
—$C_1$ to $C_6$ alkyl optionally substituted with one or more of the following:
-halogen,
—$C_2$ to $C_6$ alkenyl,
-aryl, or
—$COOR_x$, where $R_x$ is as defined above,
—$COOR_x$, where $R_x$ is as defined above,
-cyclopropyl, cyclobutyl, cyclopentyl, or cyclohexyl,
—$NR_tCOOR_u$, where $R_u$, is:
—$C_1$ to $C_{12}$ alkyl, optionally substituted with:
-aryl optionally substituted with $C_1$ to $C_6$ alkyl or $C_1$ to $C_6$ alkoxy,
—$C_2$ to $C_6$ alkenyl,
—$C_1$ to $C_6$ alkoxy,
—$C_2$ to $C_6$ alkynyl,
-halogen,
-5 or 6 membered heterocycle,
-cyclopropyl,
-cyclobutyl,
-cyclopentyl, or
-cyclohexyl,
-aryl, optionally substituted with:
—$C_1$ to $C_6$ alkoxy,
-halogen, or
—$C_1$ to $C_6$ alkyl,
-5 or 6 membered heterocycle,
-cyclopropyl, cyclobutyl, cyclopentyl, or cyclohexyl, wherein cyclopropyl, cyclobutyl, cyclopentyl or cyclohexyl are optionally substituted with one or more $C_1$ to $C_6$ alkyl substituents,
and $R_t$ is:
-hydrogen,
—$C_1$ to $C_6$ alkyl,
—$COR_x$, where $R_x$ is as defined above,
—$C_1$ to $C_6$ haloalkyl, or
—$C_1$ to $C_6$ haloalkoxy,
—$NR_vSO_2R_w$, where $R_v$ is:
-hydrogen,
—$COR_x$, where $R_x$ is as defined above, or
—$C_1$ to $C_6$ alkyl, optionally substituted with:
-halogen,
—$COR_x$, where $R_x$ is as defined above,
—$OCOR_x$, where $R_x$ is as defined above,
-hydroxyl, or
—$C_1$ to $C_6$ alkoxy,
and where $R_w$ is:
—$C_1$ to $C_6$ alkyl optionally substituted with:
-halogen,
—$C_1$ to $C_6$ haloalkyl,
-aryl, or
-5 or 6 membered heterocycle,
-cyclopropyl,
-cyclobutyl,
-cyclopentyl,
-cyclohexyl,
—$C_2$ to $C_6$ alkenyl,
—$C_1$ to $C_6$ alkyl- or di-$C_1$ to $C_6$ alkyl-amino optionally substituted with halogen,
-5 or 6 membered heterocycle, or
-5 or 6 membered heteroaryl optionally substituted with:
—$C_1$ to $C_6$ alkyl,
-5 or 6 membered heterocycle, or

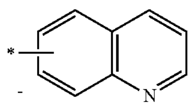

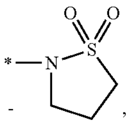,
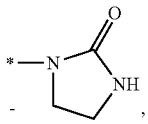,
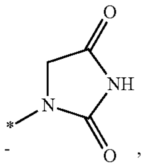,
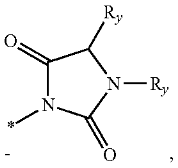, optionally substituted with $C_1$ to $C_6$ alkyl, where $R_y$ is $C_1$ to $C_6$ alkyl or hydrogen,

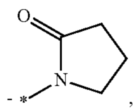,
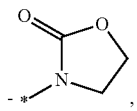,
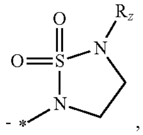, where $R_z$, is hydrogen or $C_1$ to $C_6$ alkyl, optionally substituted with aryl, —$SR_x$, where $R_x$ is as defined above, —$SO_2R_{aa}$, where $R_{aa}$ is:

—$C_1$ to $C_6$ alkyl,

-amino,

—$C_1$ to $C_6$ alkyl- or di-$C_1$ to $C_6$ alkyl-amino optionally substituted with hydroxy or —$COOR_x$, where $R_x$ is as defined above, -5 or 6 membered heteroaryl, -cyclopropylamino, cyclobutylamino, cyclopentylamino, or cyclohexylamino, -aryl, or —$NHR_{bb}$, where $R_{bb}$ is:

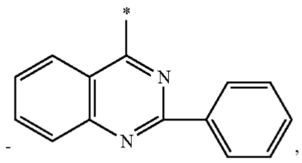,
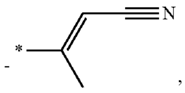,

—C(=S)$NH_2$, or

—$PO(OR_x)_2$, where $R_x$ is as defined above;

Z is:

—$C_1$ to $C_6$ alkyl optionally substituted with:

—$C_1$ to $C_6$ alkoxy,

-one or more halogen substituents, or

-aryl;

—$C_2$ to $C_6$ alkenyl;

-aryl optionally substituted with $C_1$ to $C_6$ alkoxy or one or more $C_1$ to $C_6$ alkyl substituents;

—$COOR_x$, where $R_x$ is as defined above;

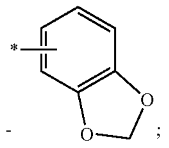;

-cyclopropyl;

-cyclobutyl;

-cyclopentyl;

-cyclohexyl;

-cyclopropylmethyl;

-cyclobutylmethyl; or -cyclopentylmethyl;

R is hydrogen, halogen or $C_1$ to $C_6$ alkoxy;

$R_1$ is:

-hydrogen;

-hydroxy;

-halogen;

—$C_1$ to $C_6$ haloalkyl;

-nitro;

-5 or 6 membered heteroaryl;

-5 or 6 membered heterocycle;

—$C_1$ to $C_6$ alkoxy optionally substituted with:

-one or more halogen substituents,

-aryl, or

-5 or 6 membered heterocycle;

-aryl optionally substituted with $C_1$ to $C_6$ alkoxy;

—COR, where $R_x$ is as defined above;

—$C_1$ to $C_6$ alkyl optionally substituted with di-$C_1$ to $C_6$ alkyl-amino or 5 or 6 membered heterocycle;

-cyclopropyl;

-cyclobutyl;

-cyclopentyl; or

-cyclohexyl;

and wherein when $R_2$ is unsubstituted methoxy, then $R_1$ is hydrogen;

$R_2$ is:

-nitro;

-hydrogen;

-halogen;

-hydroxy;

—$C_1$ to $C_6$ alkyl, optionally substituted with one or more halogen substituents;

-cyclopropyl;

-cyclobutyl;

-cyclopentyl;

-cyclohexyl;

-amino;

—$C_1$ to $C_6$ alkoxy optionally substituted with:

-one or more halogen substituents,

—$OCOR_x$, where $R_x$ is as defined above,

-di-$C_1$ to $C_6$ alkyl-amino optionally substituted with $C_1$ to $C_6$ alkoxy, -5 or 6 membered heterocycle optionally substituted with $C_1$ to $C_6$ alkyl, -5 or 6 membered heteroaryl, or -aryl;

—$COOR_x$, where $R_x$ is as defined above;

—$C_1$ to $C_6$ haloalkyl;

-amide optionally substituted with:

-hydroxy, or

-aryl;

-5 or 6 membered heteroaryl;

—$OCOR_x$, where $R_x$ is as defined above;

—$NHCOR_{jj}$, where $R_{jj}$ is:

—$C_1$ to $C_6$ alkoxy, or

-amino optionally substituted with one or more $C_1$ to $C_6$ alkyl substituents;

—$OR_{kk}$, where $R_{kk}$ is 5 to 6 membered heteroaryl;

—$NHSO_2R_x$, where $R_x$ is as defined above;

—$NHSO_2$cyclopropyl;

—$NHSO_2$cyclobutyl;

—$NHSO_2$cyclopentyl; or —$NHSO_2$cyclohexyl;

and wherein when $R_1$ is unsubstituted methoxy, then $R_2$ is hydrogen; and $R_3$ is:

-hydrogen; or

—$CH_2OCOR_x$, where $R_x$ is as defined above;

or a pharmaceutically acceptable salt thereof.

13. The compound of claim 12, wherein

Y is:

-aryl substituted with one or more of the following:

—$C_1$ to $C_6$ alkoxy

-nitro,

—$C_1$ to $C_6$ alkyl

-halogen;

and

Z is:

—$C_1$ to $C_6$ alkyl optionally substituted with:

—$C_1$ to $C_6$ alkoxy,

-one or more halogen substituents, or

-aryl.

14. A pharmaceutical composition comprising a compound of claim 12 or a pharmaceutically acceptable salt thereof and one or more pharmaceutically acceptable excipients.

* * * * *